US012692482B2

(12) United States Patent
Erickson et al.

(10) Patent No.: US 12,692,482 B2
(45) Date of Patent: Jul. 28, 2026

(54) **METHODS AND SYSTEMS FOR THE RAPID DETECTION OF *LISTERIA* USING INFECTIOUS AGENTS**

(71) Applicant: Laboratory Corporation of America Holdings, Burlington, NC (US)

(72) Inventors: Stephen Erickson, White Bear Township, MN (US); Jose S. Gil, Winnetka, CA (US); Matthew J. Brown, Burlington, NC (US); Minh Mindy Bao Nguyen, Shoreview, MN (US); Wendy Hahn, Hugo, MN (US)

(73) Assignee: Laboratory Corporation of America Holdings, Burlington, NC (US)

( * ) Notice: Subject to any disclaimer, the term of this patent is extended or adjusted under 35 U.S.C. 154(b) by 1042 days.

(21) Appl. No.: 17/665,343

(22) Filed: Feb. 4, 2022

(65) Prior Publication Data

US 2022/0243181 A1     Aug. 4, 2022

Related U.S. Application Data

(60) Provisional application No. 63/145,772, filed on Feb. 4, 2021.

(51) Int. Cl.
| | |
|---|---|
| *C12N 7/00* | (2006.01) |
| *C12N 15/86* | (2006.01) |
| *C12Q 1/70* | (2006.01) |

(52) U.S. Cl.
CPC .............. *C12N 7/00* (2013.01); *C12N 15/86* (2013.01); *C12Q 1/70* (2013.01); *C12N 2795/10121* (2013.01); *C12N 2795/10131* (2013.01); *C12N 2795/10143* (2013.01); *C12N 2795/10221* (2013.01); *C12N 2795/10231* (2013.01); *C12N 2795/10243* (2013.01)

(58) Field of Classification Search
None
See application file for complete search history.

(56) References Cited

U.S. PATENT DOCUMENTS

| | | |
|---|---|---|
| 2017/0044502 A1 | 2/2017 | Koeris et al. |
| 2018/0274004 A1 | 9/2018 | Koeris et al. |
| 2020/0239860 A1 | 7/2020 | Erickson et al. |
| 2020/0399614 A1 | 12/2020 | Gil et al. |

FOREIGN PATENT DOCUMENTS

| | | | | |
|---|---|---|---|---|
| JP | 2016517687 A | 6/2016 | | |
| JP | 2016521996 A | 7/2016 | | |
| WO | WO-2017011309 A1 * | 1/2017 | .............. | C12N 7/00 |
| WO | 2020257502 A1 | 12/2020 | | |

OTHER PUBLICATIONS

2017 U.S. Food and Drug Administration Bacteriological Analytical Manual, Chapter 10 "Detection of Listeria monocytogenes in Foods and Environmental samples, and Enumeration of Listeria monocytogenes in Foods".
Altschul, S., et al., "Basic Local Alignment Search Tool," *J. Mol. Biol.* 215:403-410 (1990).
Altschul, S., et al., "Gapped BLAST and PSI-BLAST: a new generation of protein database search programs," *Nucl. Acids Res.* 25:3389-3402 (1997).
Altschul, S. et al., "Protein database searches using compositionally adjusted substitution matrices," *FEBS J.* 272:5101-5109 (2005).
Bruinsma, S. et al., "Bead-linked transposomes enable a normalization-free workflow for NGS library preparation," *BMC Genomics* 19:722 (2018), 16 pages.
Ellis, E. and Delbrück, M., The Growth of Bacteriophage, *J. Gen. Physiol.* 22:365-384 (1939).
Fokine, A. and Rossmann, M., "Molecular architecture of tailed double-stranded DNA phages," *Bacteriophage* 4:e28281 (2014), 22 pages.
Habann, M., et al., "*Listeria* phage A511, a model for the contractile tail machineries of SP01-related bacteriophages," *Mol. Microbiol.* 92(1):84-99 (2014).
Kim, J., et al., "Host Ranges of *Listeria*-Specific Bacteriophages from the Turkey Processing Plant Environment in the United States," Appl. Environ. Microbiol. 74(21):6623-6630 (2008).
Klumpp, J. et al., "The Terminally Redundant, Nonpermuted Genome of *Listeria* Bacteriophage A511: a Model for the SPO1-Like Myoviruses of Gram-Positive Bacteria," *J. Bacteriol.* 190(17):5753-5765 (2008).
Lavysh, D. et al., "The genome of AR9, a giant transducing *Bacillus* phage encoding two multisubunit RNA polymerases," *Virology* 495:185-196 (2016).
Loessner, M. and Busse, M., "Bacteriophage Typing of *Listeria* Species," *Appl. Environ. Microbiol.* 56(6):1912-1918 (1990).
Loessner, M. and Scherer, S., "Organization and Transcriptional Analysis of the *Listeria* Phage A511 Late Gene Region Comprising the Major Capsid and Tail Sheath Protein Genes cps and tsh," *J. Bacteriol.* 177(22):6601-6609 (1995).
Murray, D. et al., "Localization of Biologically Important Regions on Toxic Shock Syndrome Toxin 1," *Infect. Immun.* 65(1):371-374 (1996).
Nguyen, M. et al., "Accurate and sensitive detection of Salmonella in foods by engineered bacteriophages," *Sci. Rep.* 10:17463 (2020), 13 pages.
Orsi, R. and Wiedmann, M., "Characteristics and distribution of *Listeria* spp., including *Listeria* species newly described since 2009," *Appl. Microbiol. Biotechnol.* 100:5273-5287 (2016).

(Continued)

*Primary Examiner* — Nicole Kinsey White
(74) *Attorney, Agent, or Firm* — Kilpatrick Townsend & Stockton LLP

(57)     ABSTRACT

Disclosed herein are methods and systems for rapid detection of microorganisms such as *Listeria* spp. in a sample. A genetically modified bacteriophage is also disclosed which comprises an indicator gene in the late gene region. The specificity of the bacteriophage, such as *Listeria*-specific bacteriophage, allows detection of a specific microorganism, such as *Listeria* spp. and an indicator signal may be amplified to optimize assay sensitivity.

25 Claims, 9 Drawing Sheets

Specification includes a Sequence Listing.

(56) References Cited

OTHER PUBLICATIONS

Park, S.F. and Stewart, G.S., "High-efficiency transformation of Listeria monocytogenes by electroporation of penicillin-treated cells," *Gene* 94(1):129-132 (1990).

Reagin, M.J. et al., "TempliPhi: A Sequencing Template Preparation Procedure That Eliminates Overnight Cultures and DNA Purification," *J. Biomol. Tech.* 14(2):143-148 (2003).

Serrano-Heras, G. et al., "Phase 29 protein p56 prevents viral DNA replication impairment caused by uracil excision activity of uracil-DNA glycosylase," *Proc. Natl. Acad. Sci. USA* 105(49):19044-19049 (2008).

Tokman, J.I et al., "Temperature Significantly Affects the Plaquing and Adsorption Efficiencies of *Listeria* Phages," *Front. Microbiol.* 7:631 (2016), 10 pages.

Uchiyama, J. et al., "Intragenus generalized transduction in *Staphylococcus* spp. by a novel giant phage," *ISME J.* 8:1949-1952 (2014).

Weigele, P. and Raleigh, E., "Biosynthesis and Function of Modified Bases in Bacteria and Their Viruses," *Chem. Rev.* 116:12655-12687 (2016).

Yuan, Y. and Gao, M., "Jumbo Bacteriophages: An Overview," *Front. Microbiol.* 8:403 (2017), 9 pages.

Yuan, Y. and Gao, M., "Proteomic Analysis of a Novel *Bacillus* Jumbo Phage Revealing Glycoside Hydrolase As Structural Component," *Front. Microbiol.* 7:745 (2016), 11 pages.

European Application No. 22705674.4, Office Action mailed on Jan. 21, 2025, 2 pages.

European Application No. 22705674.4, Office Action mailed on Oct. 9, 2024, 3 pages.

European Application No. 22705674.4, Office Action mailed on Sep. 23, 2024, 3 pages.

European Application No. 22705674.4, Office Action mailed on Aug. 18, 2025, 6 pages.

Erickson et al., Isolation and Engineering of a Listeria Grayi Bacteriophage, Nature Scientific Reports, vol. 11, No. 1, Sep. 23, 2021, 12 pages.

Meile et al., Engineered Reporter Phages for Rapid Bioluminescence-Based Detection and Differentiation of Viable Listeria Cells, Applied and Environmental Microbiology, vol. 85, No. 11, May 19, 2020, pp. 1-14.

International Application No. PCT/US2022/015345, International Preliminary Report on Patentability mailed on Aug. 17, 2023, 13 pages.

International Application No. PCT/US2022/015345, International Search Report and Written Opinion mailed on Jul. 15, 2022, 19 pages.

International Application No. PCT/US2022/015345, Invitation to Pay Additional Fees and, Where Applicable, Protest Fee mailed on May 24, 2022, 5 pages.

Japanese Application No. 2023-547210, Office Action mailed on Jan. 16, 2026, 14 pages (10 pages of English Translation and 4 pages of original document).

* cited by examiner

| 20HR ENRICHMENT | | | | |
|---|---|---|---|---|
| Sponge | Listeria CFU | Challenge CFU | RLU | Confirmation Plating @ 24HR Enrichment |
| Surface Swab #1 | 100 | 0 | 624152 | POS |
| Surface Swab #2 | 100 | 0 | 147 | NEG |
| Surface Swab #3 | 100 | 0 | 311263 | POS |
| Surface Swab #4 | 100 | 1000 | 111906 | POS |
| Surface Swab #5 | 100 | 1000 | 286374 | POS |
| Surface Swab #6 | 100 | 1000 | 223923 | POS |
| Surface Swab #7 | 1000 | 0 | 2585576 | POS |
| Surface Swab #8 | 1000 | 0 | 5865588 | POS |
| Surface Swab #9 | 1000 | 0 | 12006347 | POS |
| Surface Swab #10 | 1000 | 10,000 | 263787 | POS |
| Surface Swab #11 | 1000 | 10,000 | 324328 | POS |
| Surface Swab #12 | 1000 | 10,000 | 388401 | POS |
| Negative Control | 0 | 0 | 259 | NEG |
| Positive Control | 10 | 0 | 41635196 | POS |

FIG. 6

SEQUENCE LISTING

<160> NUMBER OF SEQ ID NOS: 7

<210> SEQ ID NO 1
<211> LENGTH: 223580
<212> TYPE: DNA
<213> ORGANISM: Artificial Sequence
<220> FEATURE:
<223> OTHER INFORMATION: WT bacteriophage LPJP1

<400> SEQUENCE: 1

```
ccagttgagt ttgacgaaaa agcatgtctt ctacatctac cggtacatct gaaatatctt      60
tcttacattt actacatgtt aatccatgaa ttgcataaga aataccatat ttatcagatt     120
gctcactaat catttcacta agactcttca tgtcactaac ttcaagatta ctaatgatct     180
taagaatttg ttctgggttt gttacttta caaatttaag ttctccagtt ttttccaatc     240
tatctaggtc aggaaccatt attttttag tgaataaaat tagatcaata taatctctaa     300
cttcatcata gctttcaggt ttaatatatg atagtaatgt taatttatct tttagtgaag     360
gtatttgaat atcgaatacc attttactta acggcatttg ggaacgagtg atcttattta     420
ctgctgaata cttttaatg acgcttggat ctttaactgt atcagtaatt tgttttaaac     480
gagaatatgt ttcttcattc ttaacaacaa taagattctc attataagct ttaacattcc     540
tcataacgtt tccacatgat ccacacttaa tatcaaaaga agttccacgt gggaatgttt     600
```

```
gacagaatag tccgtaaatt aaagtatcta gatcatagat agatgtaatg tcaatgaatg    660
tatcccaatc taatttacct agtgtagtgg aattaatttt actaaagtat gtttgatatt    720
gacgtaatgt agattcatat gcagaagcgg tgcttgatga gatagaaagc atatcattca    780
tacgtagact ctctacatga gcaatatatg ctgattgatt taatgtaact tgataagtag    840
ggcttcctgt taatgcatat ttaaatttat caaaattaat atctttaaat ttatcttcat    900
catcaataat taatgagtcg atatctttta aattatcaat ttttgcttta tcaagaatat    960
ctttaactga gtctttttta ggttcttgtt taatttcagt taatgtttca tctacttgta    1020
mgttgttaat attttcttga ttaattgggt ctttaatagg aatctcatca cttggttctt    1080
caaaaattcc tttaatctct tcttcttctt ttttctcatt atcaggaaca tcatcaggta    1140
ttggatttcc atctaaaggc tcaatgtctg atggattata cgcaaattgt tcttcatttt    1200
cttgtgattt ttgttcatat tgatattgtt gagtcattgc ttgttcggta ttttcatttt    1260
ctccagtatt attcgttact gaggaatctt cttctttctg gtaaacatca atacctgtac    1320
cagagagaga taagttagga tcaatattct cttctttttt agcttcttca gattttctac    1380
gttgctctgc ttctagaaat aattttgcta catgttgagg atcttcacct actacttggg    1440
catgtaacat tgctatttct agatcgctca tcttttttatc gggaatatta atatttgtag    1500
gaatattgtt attttcatta ttatctgatt ttaataccat tgtatatttt acctccacat    1560
aatttatatt attttttaatt atacattatt tttgatacag ttgtatttgt tttattattg    1620
tatccatata ataatccaaa gtttagatta gtagtagtat tagaatctac taaattaata    1680
tctatataaa acgtatttac atttacgttt gaattactag aaagaacgtt tttaacattt    1740
tgtatattaa tctttacaac gatatcttga tgtacaatat atgattctat ttgattttca    1800
attttacttt gaagttctaa tctagtttcc ktatccaaga tttcatataa atataatccg    1860
ataccgatgc ccatattagg ttggttcggg tacgttcctt gctctattat aattaaattt    1920
tggatctgtt gtgctaatgc ttctaggttt tctcttaata ttggttgatt gaagtcatcc    1980
ctctctagta taacttcagg tctgaatgat atatttgatt catccgcttt aaagtctgcc    2040 ataatttttca ccactttcta tttaaagtat tctataaaaa tcaatagctt ttaattataa    2100
ttatatgttg cagtaaaaat taacatttta aaaaattatt tgtgaacaat attatatata    2160
agtttagaaa aatttttttc tgggtttata taatacttaa atatcactaa attgtttaaa    2220
atactcgggt tgtagttcac attgttgact aaccatttaa ataatataat tacatttagt    2280
gatattatac atatctttca tcataacatt attctaaaaa ataatgttat gatgaatatt    2340
gttttaatga acatatactt attatagata tattaatgca gaaagaagtg aatattttga    2400
aacaatttaa atgtccatat gacagaaaga tatttgtaaa taaaaaggca ttatatgatt    2460
atatggaaaa gaattattca gatcaattaa atggactatc tccggctaat gcttatttta    2520
atatcaagta taacaaaaca catggtagat gtattgtatg cggtaagaat acaccattta    2580
acgaaactac tgaaaagtat gatcgtttat gttcagataa atgtaaaatt aaatatagaa    2640
agcagtttgt agagagaatg aaaaaagttc acggaacaga tactctatta agagatcctg    2700
aaatgcagaa aagaatgtta gctaatcgta aaattgcagg agtatatacg tggtctgatg    2760
gtagtaaatt taaatatgtg ggtagttatg agaaagatgc gttagaatat atggataaga    2820
tattaggatt tcactctaag gatattattg ttccttctcc aataatcttt gattatacgc    2880
ttgatggtaa aaaacatttc tatataccag atatatttat tgttcctttc aacatrgtgg    2940
tagaagtaaa aggtactaac aatcattacc aaactaggga tagacgtact gaagatgcta    3000
```

-continued

```
aggataaagc ggttcttaag acaaagtatc gttatgcaaa attagttgac aagaaatatg    3060
acaagttcaa tgacattatt gagaatctta aagaatcaaa ggacgataaa gtccgttaat    3120
ataaataaaa ttttaaaccc tcatttcaat aatatattat aattaagata atgtatatta    3180
tcatattgaa atgaggggat tttattggaa aataagaaac gtaaattctt ggcactgtgt    3240
ggaattagtg gttcgggtaa gaattctgtt gaatctatac ttgatggtta ttatgataat    3300
gttaatggag tgtttttaa aaaactaaat caagtaacaa ctaggaatat tcgaaatact    3360
gatgaattta atagtggaat atatagtttt ataactatag atatttataa tctaataaaa    3420
gaaaatctca ttggaaaaac agttatcgat aataaatatt attatggtac gcttgatact    3480
agtactacag atggttgtat taatactatt attgtcaatg caaaaggatt atctaatctt    3540
aagaatgatc ttaataataa gtatggtgaa gataactatg acctatttgt attgcagatt    3600
gctaataata ctcctgtgga aagaagaaat agagacgcag aatttatcag aggtgaatat    3660
aatgatttaa aaggattgtc taacgcaact cttataaaata atcctagtaa atggttaact    3720
gtctctgacg taattaactg tcttaagaaa gaaggttttt tggatacatg acattagtta    3780
gtcatactaa gttatatgaa aaaacaaatt atcgtaataa aagaattagc tatattaaaa    3840
atacgttgat tactgagttt gatataaaaa gtgctggtct aaatattcta tatgaaatgg    3900
aatatttaga ccaaaatcaa tatgaaaaat tattatcaat ggaaaagtat gaaagaaacr    3960
ttacaatcgg aaagatatta aggtctaata aagaaatgaa tgaagcatta tcatttggtt    4020
tttcagaagc gagaagatta ttttttcgaat taaatcaaat tgatgattca gaattattat    4080
ctattaagaa ggatgcaata tttcttatag gtagaaataa tataaatatt aacggtaatg    4140
tttctgaatt tataaaattt agaccaaaga aatcttatac aacgtttgtt gaagtgttag    4200
accgagaaca ctatttgaac tttgaaagcg aagaaataat ttatgatatt aaaggatact    4260
ctagtgatat taaagatatt cataatgaat atttattaaa ggatcttctt aatgtaatga    4320
agtttgatta tgttaatgat aaagatagaa tatttgaata tttagcagtt cttaaggatg    4380
acctaattaa atatagactt ccagtatcat actataatga tattaaagta ggaaaatata    4440
ttgtagaaat gggtaacgca ttatttgatc tagataatat taatgataat attaagcaat    4500
attgcctgtt gtctaataat cttagtttta ttttaaatct aatcaataag actctttcat    4560 aaaaaaaaa taaataatat attaaggtaa cgatcattaa tttgatmgtt acctcttttt    4620 tttttttct atgatccata atatactata tatttacaga ttttattttc ttgtcaatcg    4680
ttaatgatac ttcagtcatg ataagcataa tcttgctcat aacatattcc tcaatatgtt    4740
cttctgaaat gatggtagaa accctatatt ttaagtcact agacattctt tctacaactt    4800
cattagtaca tgatataaca gattcttcaa attcatctgt agttgtatcg atatctatat    4860
catcactaag ttcactctga tcttcatcaa tagatgtttc agtagtcgca gtattttcta    4920
catattcatt tccttcattg tcatactgaa tattcatacc attaattgca gtaacttcac    4980
ttaatctagg aagtattcta tcaatacttt cagcaattaa attattcttt actatccata    5040
tgctaatatc aataagaata tctaattcct ttagtgcttt ttcaccatca atattattat    5100
gcatcattct attattacgg ttagatttaa taatcaatct tccaataatt atatgtgtaa    5160
taaatataat tattagtatt gaaggtactg taatgtaaaa taaatttgta gtcatcaaat    5220
aaacttcccc tattcattta ttatttatat ataattattc atactaaaaa cttgaatttt    5280
attttcttct aagaaagata caacttcctg agaattatca tattcttcta aataatatac    5340
```

-continued

```
tttagatatt cctgaagcaa taatcgtttt ggcacaatta aagcatggtg aatgagtaat    5400
aaacattcga tgcgccttct gtatttccag agtttctagc caccttagat attgcgttta    5460
tttctgcatg tatttcatat tttaatgacc atttatgatg aatttccata tcttcacata    5520
aataaaattt ctttccttga ctttcaatat aataatcttt gcgacaaatg aaatacgatt    5580
gtgaagtata ccataatcct tctttcttta tgaatatatc attacagtta gcgtatccac    5640
taggggttcc attaattcct gaagatataa tggagttatt cttaacaata atgcaggaga    5700
ctttctttgc agagcattta cttatttctg acattcttat tgcaatattc ataaagttta    5760
cttcgtttgt cgtaaatagt catccatatt attatcttca ttatctataa atatatctac    5820
caagatatgg ccactgatct tattctaatt ataataaatt atttgaaatg atgcattgtt    5880
taaatacttt taattttccg aatgttaatg ttaatatcaa cacgatttat aaaattgtca    5940
atttctgtat ctgtattaga gaacatattt tcaaagatat caaactttat aattcgataa    6000
aagctatctt gacttatata atgtgcaata ttattaacaa tattatcatt atctgtaaga    6060
taaagatact tcacaacaag actaagcgtt gttaatatta gtctgtatat ttcttttata    6120
cgataatcgt ttatattttt atctataatt aacgtatcat atgattctgt ctggaagtta    6180
aatttatatg tttcttgaga atttactttc ttcatcaaac taattataga tactgcgttt    6240
gatggcattt ttttcacttt tggaaatatc aattctttat tatttattct tcttttgta     6300 tcttttatta attcatcaat aaattttgaa aattcggcat tatataactc atcattactt    6360
agatccatat ttttttgtag ttcaatatac attttaaatt ctagttccaa tctatttaat    6420
atatgaactt catgctttga taataagtta atatataata cgtttattgt aggaaattta    6480
atattggatt tatcatcagt atctatatca gtggattcta tatagtatga tgagggtgaa    6540
atataatttt tatatttata catatgcgta tatgagtaaa taactaattc attagtatac    6600
gtaaaattca ttaaattatc attatcataa ttatccactt caatatagtt gtttattatt    6660 gcatctttc gactgattaa cgatctttct ttattatatt tgtgcattat aaaagagata     6720
tatctattat tatttatata attagatgaa tcgataaaca tgtcatattc ttgtaattct    6780
tcaaaacata gttctaaaat atttgcaagc aatatttgaa ttatatttct attatctttt    6840
attttattat aaccataata attttttgtga cttatcatag gaatatctga aaatatgatg   6900
taattttcag aagtaagaaa aaaattagaa ttatttaaat cattgaagat accagtaatt    6960
ttactgatat cttcaagact tatatttta aatttttcat agttccataa atttctcact     7020
ttaatattat ggttagcatc agtatagaaa tatttagtat caatattcat taactaatca    7080
ctatccttat ataatatttt agtatcgata tttacttttg ttttttaaagt taacgtctct   7140 tactgttcct ggaggattat tgattgataa tcctgcatta ttattacttt ctgtaagaag    7200
ccagatagta tatcctttag gtttcttaca atcaagcgta ttctcaccaa aaccatccgt    7260
aataataata ttaatatctg atcgaatatt ttcattaata tatttaattg gagcagtcaa    7320
tgtagttcca ccataagcag ttctttcaaa tttacgtaat ctatctttct tagataacgg    7380
atatacatca tgaaccattg tatcaaagtg aattacatat agtttacttt taatatttga    7440
aataatctga cgaatttgat caaaagccaa agccacttct tcgtcactca ttgatcctga    7500
catggtcgat agctacggta attttagatt cacattcgac attcttccta ataagtcacc    7560
acgatctggc attcttctat ttctacgcag attagttctt ttataaggaa ctttttaaaga   7620 accaatcttc gtacgtaaga tttgttgcca aggaataact ttttccttat taatattttc    7680
tagaaattta ttaatagaaa caggaactga tccggctaaa gatagtcgtt caatagtatt    7740
```

-continued

```
ttcgatattt tgttttattg aacgttgaat gtcttcttca gaataatcgc cgttttttcca    7800 ttttgagtga gaagaattag cactattatt catgttaatg cgtatctttc ttaccttctg    7860
aatctaattc attacctaga tcattttcat cttttccgta ttcatgagat ttgccagtat    7920
taccattaga agaaccttct tcttcatttt cgctgtcatt atctccacca ttatcagtat    7980
cagatgaatc atcatcatta ttcccacttt gattacttgg cattccatta ttattttgac    8040
cgcttttatt attttcatta gcttctaata atgcatccat atagtattca aaagatttat    8100
ctttttccaa atccttatta ttagttaaca ttcttacata atctagtgta atagaacctt    8160
ctggaatatc atcaatatat tgattaatag aacaatccat agcaatattt gccatatgca    8220
tgaagtcttg attttttacta atcgacttat tcttcaatat cggaaaatat gattatttga    8280
aatatgaagt aattcatgag taataactgc aatgaattct cgatcattaa acattaaaat    8340
tttatatgga tttagatata atgtaaatgt atctttaaat gtattttcag catagctaac    8400
tgctgccgga gcaaagttcg gatcatgaac aacttcttta atcatattaa ttgtaaatag    8460
agcaaagaat ttgtcatcat taatgttatc actaattaaa ttagtgaatg ttaacttaat    8520
atatgcttca aatgcttttt ctaacttttt tgaagcttca agaggtaaaa gcttctcctt    8580
accataatat tcaagaagaa acttttttaa ttcttttcta gtcatactat tagaattata    8640
attatctaaa gtaggcatta atatcctcca ccgatctaat tattttaaac ggtttactaa    8700
ttttttgatt gattgcgata tattcatcat attgataaac tctgttatag aaatcatctg    8760
cagtattatt tacgagtcta attaacattg caaaagtact catgataact tcttcttctc    8820
ccaaagtatc tacaaattta atatagttcg cagtcattct atctaaatct tttttatttt    8880
ttactcgttt actatcgtta cccatttcac gaacaacata attaattaca taacgactaa    8940
gtagtgtttt acgtaagttt gtttcctctt taatttgggt caatagtttt tcatctttag    9000
ataagtttgg gttatcgata atcaattcag ctcggatcat agggtttgtt ttgtctttta    9060
ggaaattaaa gaataatgaa gtagctttcg aacctagatt accttcaaac actgcacgta    9120
gtttatgact aatagatact gtatcttctg ggaattgttt catatgttca taatacgcat    9180
cagaactacg tttccatgaa cgtggagtag gtgacttacc taatgcttga attttctaca    9240
aatgacagca actcaggatt tgttgcaata aattcagaaa tatcttcatg aatgtttggt    9300
cgaatatata gtggagtaga agtatttgca tctacatatt caaattcttg aatagcccaa    9360
tctaaccatt cttctggatc tggatctagt ctaagatctg taaataggtt atgtagggca    9420
tagttcattg tgtttacttg ataatcaata ccgtcactgt tttcatctgt aggatttcct    9480
gcagtaataa tatataattc ttctggaaga gagtattgat gaattctccg atcaagaata    9540
atattcatta actcttgttg aacagctaaa tctgaacggt taagttcatc gataaatagt    9600
aatggaattt ttccattatc tgcaatctta tatagtttac caattgtact atgaatagta    9660
tattcatttt ctttaggttg ttcttcattt ttaaaccatg ttttgatatt tgtaagttta    9720
aatttatttt taggttctgc aatatgaggg atactgttaa tttctccttc tttaagtaag    9780
ttaccatcaa gcttaacaaa ctcaattaag tcaccatttc tttcattata acgttcaaca    9840
aataattaag ccaaactaga ttttacgatc cctgcatgac cttcaataaa tggtacgctt    9900
cctgaagcta ccactacgcc tactacatct aacaagtctg acattttcat aaataaattc    9960
caccaatcta tattttttat tttattacta atttataata tatatttata aattatttat   10020
aattgtgtat atcacgctac taattttggt taatgtttct tcaaggttta aaaatgaaga   10080
```

```
actttcttat catcatttt atacttctaa tgcaagattg tcaaatctat gattatattc     10140
aataaagtga ggaagtaatt cttctggaat atatcgattt cttttttgatg tacctttttt     10200 aaatgaatta gtagtatgtc ctttaaccca cgtaaaatta aattcatatt gagaagaact     10260
attattaata atatttacta ataacttcca catctcagca ttctttactg gtgttcctga     10320
actactcatc cagtttcgat taatccatcc agtcatatat tctgtaatac ctctgataac     10380
gtattgacta tctgaaacaa cactaatatt aaacttttct ttattaccat tcttataatt     10440
atctctcata atatgcgcta ttccataaat aacggctaat aattcatttt ggttaattgt     10500
tgaatcatga aaagatcttt taatactgta tagcgtatta aattcggtgt cagtaatata     10560
gcatccaaat cctccataca taggcttact ggggtctttc ctaccattat taaagctact     10620
tgcatccgta aataaatata tgtaatttgt attatcgttg tccaatatat tttcactccc     10680
acgtttagtt atttctttc gcctatattc tattattgta attctagaat aaaaaattaa     10740
ttataataaa caatataata taagcacttc tataagaaag gtctgatatt tatgaaagtt     10800
ccaaataaga atataataaa tgatattata gataaggaac tagaagaaaa taaaacattt     10860
gtagtagata ctaatgaatt tgatactgag aatatgatca atagtgttgt tcctagtgaa     10920
gaaaaattta ataaagctat tgaaaaaatt attcgtaagt ctaatgaata tcgtagatat     10980
atcggaatac tgaaaaataa tattgatcta acttcttgta aattttttgaa acgtgttgat     11040 gtttctgaaa taagaagagt taatattgaa atgcatcatt acccatttac tctctatgac     11100
atcgtatcta tgcatcgaga acgtatcaag caagatttag gtgaattta ttcatatgat     11160 acattcacaa ttgcagaaaa tattatgaaa atgcactatg agaataaaat cggtattgta     11220
cctttatcat atactgctca tgaattagct cattccggaa aactagttat tcctcttaat     11280
aaagattatg tctttggtaa ctggcaagaa ttagaaaaag aagatattat tattacagat     11340
agtatgcgaa agcaactaga agtattagaa caaatgacaa atagtattga gtctggaagc     11400
cttaactcaa acgaagatct atttagtaat attcagactg taatcaatat gaaaagttct     11460
ggaataccaa ataagattat aaaggaaaaa tcaatcattg aggatattaa taatcctgaa     11520
actgatgaag atataatata ataaaaatcc cttaacgtat aataatacta tacgttaagg     11580
gatataatgt tatattatga ttttttgcca ttaacttgat ctaataactt atatatgaat     11640
aattctttat atactttctg atctctatta tatttatcaa tagttgcttt ttcatcatca     11700
gaaataactt ctgtactaaa gtctttaact ttaataacca tatctaactc tgtgtttaaa     11760
gattctgatt ttaatacgat atggaataaa tttatgaatt tagtattttc accttcaata     11820
aattcataat tatctaataa agaaattttc ttatcaacat cagaagaact aaatattttt     11880
ccaaagaaat catcaatata ttgattaatt gatagtttaa taatttcttc ttcactataa     11940 ttttattag ttggaatatc ctgagtgtac caaattttt gaattttatc atggagcaat     12000
acattaaata cgcccggaga atttaccata atattgctaa caacaaagct aatactaaac     12060
gtatatacct ttggcttagt ttctaattta tcatctgagt tacatgatcc ttctgatgaa     12120
gtaaagttat aaaatgtatt aaattctttt acaaactgag catataatct ttcaataaaa     12180
ttatcttcaa aaggtccaaa atctgtactt aatggaagtt caaggtctcc actctccatt     12240
aaattaattg cttcttgaat tgattcaatt aatatatcaa tcttactatt tacttcatta     12300
tcaatacgat cagttacacc tttcggacca tagatattta acgtcatata ttcattattg     12360
ttatcattct tattaagtac gtcatatgtt acactagtaa taacttcaca attacgtgaa     12420
aaatccaatt ctttatcagt gatatcatct aaatctttga tatcaccaat aattcttaaa     12480
```

-continued

```
ctaatagcat cctcaatatt aggcatccta attccacatc catttctttt tatttgataa   12540
taatttatta ataaataaat ataatttttt acattcattt acaagattat acattccta    12600 taactatgat atattcaata gttatgggga atgtatttat aattaattag tgcattgtat   12660
taatatattg tatatacgat gaagcgttat cctttattac attatcatgt tgtcttattt   12720
catatttcgt taacatgata ttaatgaaga tataagttat aataaagaat atataactaa   12780
gtattaatag ttttaataat agtttatttt tagttcgatt atcttggttt tcatcagtat   12840
ctatattttt tcttaaattc ttcattaaaa agtcccccctt ttattctata tattatattg   12900
ttttttaata aaagcgtaat aaacgaatat atagacatat attataatta tgataaaata   12960
ataaataata taaagaaaag gatgatatta taatgaaaaa atttgtacaa gtattattag   13020
taggagttct attagcagta gcagtaacaa ttgtaactat taacgttaca gaaagtaata   13080
acggtacaat gcaaaaagaa ttattaccaa aagtaatttt aaatagacaa tagtataatt   13140
actactattg tctatttttt tttttagttg attaagaata ttttatcata atctagatta   13200
tcgttgaatt ctaaaaagaa gtccccaaca ttacttactg tacattttct aatagaagat   13260
actccttcat ctattggtgt agtcttattt acttctagct ccatactatt atcactataa   13320
actcaggata gatattttcc aagaatagat aacttctaca ttttcttcat ttaatacttt   13380
ttgtatcatg tataagtgat atatattgtc atcatccctc ttcatatcgt ttgggaagat   13440
gtatccaata gttttatcat tcttatcaaa ataaaaattt tccacaataa attctttgac   13500
aagattagta ttcagtaatt caatagcgtt atttaagaaa tcttgtctaa ataaacctaa   13560
attatgaata ttgatttcta gcatattata atccacacct ttttctttttt tctttttaaga  13620 tattaattca ttattaagat aaatgtttac actaaagtca tctttagaag tattatttat   13680
ttctaacgta ataatgtaat cattgttagc actataaaag atgtattctt ttatataccct  13740 aaaattatgt tgtttatcaa taaatgaatc aatcgtgttt gatgtaatat cccccttata   13800
atctttgata taattcttat caaaatatat ttttgcttta tatatctttt ctttaatata   13860
ttcaaaagat tctttgttat ctgcagtaat tgtaacttga ttatttagaa atttgttata   13920
atcaatatta agtatattta cttcattatg attataacaa acgttccatg cagtaaatat   13980
ttcttttgaa ataaactcaa aaatattatt atccccactg ttattcataa taaatttccc   14040
ccgatatatt tatttgatat agtaagtttt attctaatat ttatttaagt ttataatgat   14100
atattataga tatggcaaat atataatata tattttaatt tttcattaac aatattttaa   14160
ggaataagga gtgctgatta atgtatagat atatacgtac aaacggttct atgcgaaata   14220
aattgaaaga aatgaatatt gataagaatg acagtatctt tgaaaatact gttaagatta   14280
ttaatgaatt aataaatcat ttctattcaa taagtgaagt atttaacttc atagaaaaag   14340
aaaatattca tatcaataat gaagtgatgc aatatttaag ttctgatgaa ttttataaat   14400
ctgcatatac ttcgaaaata atgatgaaga atcatatgtc taaacattca tttattcgca   14460
tgataaaaaa tgaattgtgt tatcgtaata ttagttttat ttttaatgat tcattattta   14520
ctaatgatga tattgccacg ataatagtta ggaatgatct agctgaaata ccatttgata   14580
ttatggttaa ggaaaatcca ttaagcttga aagattttaa gaagacttta agatataata   14640
atttaaatga tcatgaaaaa tctattttag aattacgtaa tatttaaatt tattaagaaa   14700
aaaaaaagat aactattgta attttaatag ttatcttttt ttcggatcat agaaatattt   14760
tatatattat ataggataat catattatat atctttaatg atgataatct gttggctaat   14820
```

-continued

```
tctggacttc ttttctctaa tgaatagata tcgatagctt caataagatt aattacttta   14880
ataaatccta gatttcgata tcttttattt attaaaacaa aattaagtaa ttctatgaat   14940
tgtattaatc tttcagcatg atacaacgat tttattttat attttttcttc aacatcagcg   15000 agatctaatc catattcttt gtagtaattt ttctttaata gcggcttcat cctacgtatc   15060
atgatactaa tatatctatt aagttcatta taggtagttt tagtattctt atacactgcc   15120 atttttatgag tttttaaagta gttatataag taatctatta tatcattaaa gaaatattcg   15180
tttgcataaa taatctttat aaaactagac tttggcataa taatatctaa tattttaggg   15240
ttaatcgtaa tccgagtatt ttcaacccctt gataagaatt taatatatgt ttcagttata   15300
aatttatata caacttctga ttcaatatta aactttttcac aaaaattaca tatgacatca   15360
ttgatatcat acttattatc acaacagaag acgtaagacg aaattgtata caataatata   15420
tattcagtat tattattatt actatgacta atattatcat ataaatcact tatcatgatc   15480
atcatatttt caggtttaat atcatataaa tagaatatat tttgatagta tgataatatt   15540 tgttgactt tacgtttatt attctttaat aagtacgtaa taatattcat aggtaataat   15600
gtaaccgatt ccgtatcttt tttatctaat gccctattat tacctaagta tgataagata   15660
tcgataatat caccaaagtt agaaatatca ttgtatatat ctagtatact ttcaatgttt   15720
tcatttaatg acattggttg taatttatat ttatacgtta tcataatttg tcacctgtat   15780
tcttttcaat gatatttcta attttattat tagtatattc atcatttgag taaattctag   15840
gtaatatctt tggtttattc ttattagaag gaagattatc aattattgaa aaaattgata   15900
ttactttatt aataatattt ataatattgg tatttttaga tttcaataac ttattaatgt   15960
catatgataa taattcatta tcactatcaa acttcttata gaatgtaaaa ccgtacatat   16020
taatattatt ttctagtaat attaacgtat ccataatatt attatatctt acgtcatcca   16080
atttatctga atactccgtt ctcataacaa agcttattac tttaacaata aaatcaacta   16140
cgttatattt attttttatat ctacgatata ttctaggata attgaatata gaattgataa   16200
aagttgtatc tttatacgtt atataggata ctgatataga agggtctccg gtatcaataa   16260
ttctagtaat attttcatat tcatcatcaa ttatattatc attgttaaga tattttaaca   16320
atatatattc aatatatagt aaattcatat ttaaaaaagg atctaatata cattgaattt   16380
cattaaaatt tttaatattt atatcatatc cctcatacat tataatattt tcgataaacc   16440
ttgatttttc agtgcgagaa taatctttaa ttttacaaat attattttttt gttaagagac   16500 atttatactt cattgtattg ttattaataa ccatatccct aaaaatttct tttgtatctt   16560
ttgtaggttg atctacatat ttagaaaatt tacgattaaa atcaattgta tcccttaatg   16620
attttggatt ataggttcgt gaattaattt ctaaatattc ttgaatgtct gtattaattg   16680
atatactatt tgtcacgcta tatcacgtcc tatcatttat tatatgctta acaaattaat   16740 tcggctttc attaacttac ataattcatc tattcgttta atattattaa gagtgttctt   16800
tcttattaat gaattatgat tatccgcact aacattatct tcatatcttc taaataattc   16860
ataattatta ttagtataat ctatagaatc caaaatttta atacgtgcat tattttttac   16920
gctagtcatt ttattattat taaaattaat atataagttt aataattcaa aaataatgga   16980
tattctatca atactgcttt caaataatat tagatcatct ttattgttaa aattaagata   17040
tctagatatt cttaatgcac tatgagggtc tattccgata atactgttaa ttgctttttt   17100
actattaagt attatatctt tctgattatc tgtaaaaaat ttagaataac cactaccata   17160
tattgtattg aatattttag ccattgatga tttactaata aatttttttaa aatgtttatc   17220
```

-continued

```
atcaatatct ctaacgccat atatcgcaca gaatagattg gttgaatata gattcatttt   17280
gtcaatcata gttaaatatt cattatctgt aattgtagaa gattctgaaa tgcatgtttt   17340 aaactttca gatatcctat ttcttatacc gaagtcagga tcatcgtcat tggatatatt    17400
gttatatgtg tcaaatagtc taaaaataat ttttctaatg tatgaagagt ttatttgtaa   17460
attactacta gtatacttat acttcttact agatggtgat ataataaagt caattaaatc    17520
gtcaaacagt acactataca tggaattatt attgataaat gaatcatata atttgtcaat    17580
attcttctta gtaattatat aattactata attcatactt cttttcgtat atatatgatt    17640
aatattaaca tattgagtat tatccataaa agtactaaac agtttattgt atattacgct    17700
tgacctaata ctatatttaa acataatgta atcctttctt aaatattaat gtccttaata    17760
taatgacgta ataattcctc ggatattcct agttccttag acattacttc aataggtttg    17820
ttaagattct tttcaatata gtctgttata tattgttctg aactacgtga attacctacc    17880
ttaatatcag tagtacttaa tggcatttta aacccaatag ttcttgggtt agtaattttt    17940
tcatattcgg gaactggatc attcttaata atatggtctg gtagtttcat attatgtttt    18000
tctaggctac aattatccaa tcttttaagt ttatctaatg attcattagt aatgataatc    18060
attagatcgt ttctacttag gtctactgac atttcttttca cattttcatc ataaagtagt    18120
gtagacatat gactaataat atcatgtgaa ttttccaatg taatattttg atccatatat    18180
tttctaatat attcgactaa ttttttctgc atattccgat tccaccaatc tatattattt    18240
attagagatt atacgtatat ccattcaatt gttaggttgt ttagaattac cttcatttag    18300
ttttatattt aatacatatt gaatattgtt tcctttatta aatttaatgt aatacttagt    18360
catatcacca gtagtattat taataagtct aattgaatag gatttcttac tatgtttatt    18420
aatatgagta tatagattat cttcatcctc tataatgata ttctttctg taaagtaatc    18480 taatatagat tctattcgtt ttaatttatt catccttatc gataataata tcgataagga    18540
tgagaataat atagttaaca tgataaatat aatcatatat ccatcgttcc ttccatatct    18600
attttatgga cattcattaa agtaaatatca tacttttaa cttcaatatc aattgcagta    18660
tagtttacca taaatgtata tcgattcttt ccaattttac taagactatt atatatctgg    18720
attgaatatt cacggatatt tggagaagtt attatattcg tattcatttt attatcatat    18780
tcagttaatt tatcaataat tgagtatgat aacatgattt ttttatgtac aatagatctg    18840
tacactattg agactataaa gattataatc ataatcgata ataataatat catttaaaca    18900
tcctttctta tatagattta tttaattttt tgattactga tatacacaac ttctttaaag    18960
tcttcatcat atactaattc aaatttatcg ttattgtaga aaaaagtgta tgtattatga    19020
gtcctattta aagatcttc acagtgatat aacagatctt taaatacatt ttccggattt     19080
acataagatt cctccataac attttcatat ccagaaagaa ttaaataatt tctaatgtct    19140
ggatagactt tttccttaag aaactttgga tccattcttt ttctaaattc agccccaaga    19200
atataatcat ttatagaatc cattatctta tcaataatta aaaatccgat taacactaaa    19260
agtaatactc ctacaatatt aaataataac ataaatttat cactatcctt ttctttttat    19320
atatatataa aaatcgatat cactccatta tagtaacaat tattggagtg atatcgattt    19380
aattttaagt tatatactaa gaattatttc gtgagataaa tatttcttag tataatgaaa    19440
taaacatgct ttagactaat aataagataa attgtcaagg ggaatttgat ctttatacat    19500
tattttcatt taataacaag tttatttata attctaatta ttatatcaga attataaatat   19560
```

-continued

```
attattaaaa tgtaactata aatttttata attatacatt gataatcata tctacattaa   19620 tattttttctg ttgaatcatt agattagaat tctttaatgt attattaatt ttattaatat   19680
ttaggttatc cgactcaata tatttgttga taaatacatc aatgtatgct tttggattat   19740
tcattgaatt aataatcgta tcttccatat tatcaatagg tttaggagat atgaccatat   19800
tgataataga tgacatttca ttagtcattc ccgcttcaat agtaatctta tcaaatatat   19860
ttttttcatc tttccataag gtattatcaa tattcatttt attaatattg aattcttcta   19920
aaatgaaaca attgttttct aatacatctt ttatttcatg agttagagtg ataacgtttc   19980
ttaaccaaaa ggaacactgt ttattaagtt cttctagaat tacattcttt tgagatatat   20040
tttcccttaa ttcatcaata tccttggtgt agttatcata tctattttta tataaattat   20100
attcatccat attggattct tctaatttta tatccataat ttcagaaaca gcattttttg   20160
catctataaa tttagatatc aatttttcag atcgattaat agtgaaacca ttaaaatatt   20220
cttttgcctt actattaata cataaatatg tatcatatag gaaattaata gttttttgtc   20280
tattttccct tagcgtatta agatcttgt tattcaatga ttttctaaat ttaactgcta   20340
attcataatc attatcgata tttgtaccttt cagtgctgat gatattataa taagtagtag   20400 tattctttt taaaggttta ttgataatat ttaactgaaa tgttctaatt tccttcatac   20460
ttactcccac caccattatt atctaaatat ttatcatact aataatatta tctaattttt   20520
cacttttaac aatattttca tttaatacta aaacatcatt tatatatgga aaacattctg   20580
taatgtgttt aattataaat tctgacgtaa tagatctttg attcattagt acttctttat   20640
gatttaattt ataccagtat atttcaataa agtcaattga caacttttgt cttcttgata   20700 taatatcccca acaatcatca tcaatatata ctgatataag ttcatatagc gttttttcat   20760
caagattagc ataatagata ttcttcttca tatattggga aaactttatt aagaattcct   20820
tactatagtt acaatgcata acaatatgac tatcccaagg aataaaatct atattttgag   20880
agtattcttc aattgtcatg tgtttgtata tactatgatc aatatattcc caaaatattt   20940
tagtttggtt tttagtaata aatttcatat acattttatt atatttcacc cgataactaa   21000
atctaaacca ttcaggatca tttatatctt ctttttttagt catatcaaga ttaaataaga   21060
ccccaataaa taatcttagt tgatttataa atcgacctttt atacgtgtcc attatattca   21120
agttattctt ttcctttctt aatataatta tattccattt atatattaac tatttatttt   21180
atacatatta aaacccaata gatatatagt aaatatctat tgggttagtg ttttattcag   21240
agatcttaac tgtacatact aatggattat gctgtaattc actaactaat ttaggaatag   21300
ttgtaagttt atatctaata gatggatttt gtttttcttc ttccaatata ctaatcgatt   21360
catgaattcg aataatttct tcacgactaa ttggtttaac aaatattgca ggcttaccag   21420
tattaatatt gattccctca ataatattca tttcatcatg acttgataag taacccacaa   21480
taatcttaat attttttaaa tctttatacg ttaatcttgt ttctaataat gaatcatctt   21540
tcattacgca taaacttccc ttccagttta agttttattt tatataatta ttagttaaac   21600
tagtatataa aaaattaaac tgaattatag aataatttat ttaaaagaat ataacgtacc   21660
tttcatatca ttataataac tatatttaat cgatttaaat ttatccatac tattgaagaa   21720
gataaattcc ggagtatctt tcttaggagg atagtttaca atatcaataa tatgagcgat   21780
aacttgcata tccatatcgg tatatttaat attagatagt tttgttttttg atcgatttac   21840 tgtagttttt ctagtccttt tatcaatgta aatagtaatt tcttcgggat tttcagtaag   21900
ttcttcatga attatattga gaaaatttac cgcttgaaga tacggtacta gcgatatttc   21960
```

-continued

```
cattgtacta ttaaagtttt cttcattact tttagagttg atcatatttt taatattttt    22020
tagtttacct attgttttta acattataat ttccaccttt aattatttat ttgttgttat    22080
catattaata aaaaatgtat agtcgataaa attagaccca ttgtctctaa taattttttac   22140 atcatctttta aaattaacat attctttaat aaaatcgaga ttatgggttt ttcctttaat   22200
cgattttgag tcaatatcgt taattgcaag atttcttata acgtatggac tatctttaga   22260
atcataatac aagttatgga ttctaagaat aaatatacta ttatataaat tttctttttaa   22320 gaaagataaa ctttcagtga atcctaattc atgagtctta tcattatatc cagtaatatg   22380
accagtgctg acatgtccat tactatggat aatttcaact ttattattaa ttaatgattc   22440
aatattcgtt tcgtttgtat acttatcaaa aatagtatga ttagacgcat tataaatatt   22500
aatattcata tcgtcatcaa ttgtataaat atatttttttt gagataagtt tatcgagaat  22560
taattttaat gtattttttc ttaatttaaa taaacgctct tttagataac atactttatc   22620
aatatccgga tacttttctt ttagtgaata atctttattg atagtattaa cgtcaatata   22680
tgatatgtat tcaatataat gaagattaat aatatcatta tcattaaatg atgttaattt   22740 cttttttaatt gtagtgatat tcattacttc atagtaaata tcattattaa tcttttctttt  22800 taaactaata atcaatatttt cctcagactt atcatttgta aataagaaac ctaaattgct   22860
catagcactt tcaataaaag aaatattatt atccatttag atttacaccc tttctaatct    22920
atatattcat tatagttaat gcatctttaa atttttgatc ttcattcata tatttaatta   22980
agtatggatg ttctttaaat tcattatcat acttagttaa tttattatag tatctaataa    23040 taaattttttt tggtaagttt tcttgacttc tcgatatttt gaaccataaa ttagcattat   23100
ctaagggtac agtgcttagt atatattcaa ttgatactat tggtaattgg tatcttgaaa    23160
tagtcattat aattgtgtgc aagtcaaaat attctatata ttttagtatt acgcttaatt   23220
ctaatttatg gtttgaaacg ataatataat tccagaataa ttttggagca tatttatcaa   23280
gagaaataat attatctatt gttacatcat actcaatatc gtattgagag aatattaatt   23340
ctgcagttat attttcccaa attttagtat taatatctat actgtctgca tacttaataa    23400
atagattaat atcgtacagt aatagtttat aattatatcc tatggaaaaa tctatattgt   23460
caagaatatt aggattattt ctcgatatat ctaatattct attgcatatt tcaggaatat   23520
tgtgatcata tttatatgag ttaaattgag attcaataaa agaagggtag taattttcttt   23580 caccagtatc atactttttta tcaatatcta taactaattt aattatatcg attttttcat   23640 tcttttttaga aataataatt tttcttatat cttcgttact aataggctcg gtatcagttc   23700
tagacataat attctaacaa tcctttctat tattaaaaaa taaaatctga gactataatt   23760
gatcatatag tctcagaaat attttatatt aatcttctaa attattattt aatatattca   23820
tagacatatt aaaaatactt cttgaacgtt taccgatacg atttattgtt ttttcagata   23880
tatttaaata atctttaaat tttatcggaa aatacttgag gtacatagaa atttgttctg   23940
gattatcaat aatattgtta tcaatgatag ttcgaacaac agtataaatt tgaccattaa   24000
gtaattcgtc aatagttgtt tggatcgtat gcttgaataa ttcatccttt cttaaatgtt   24060
gatgatcttt atactccatt ttcattctaa ctttaatata aggatcgtta taatcttgat   24120
gatcattaac tagagattca ggatgaaata tttcattaaa taatttaata tcgtcatttt   24180
ttccatattt tataataata tttgtaatta ataatctcga aatttcacca atttcattat   24240
aaggaatttc tgattcttca aatttttaatg tataattaat ttctttttaaa tactcattat  24300
```

-continued

```
agtatcggta tttataatta gatgttaatg caagagaagt tacaaagtta agattatttt   24360
gataacttcc tactaatcta acttcattat aaaatacatt atcctttata agttgattaa   24420
tgattttata atatctttgc attaatacat taaacttatc ggtactacaa ttttttggtt   24480
tagtaattga tttaattaat gattgttggg tattaattaa attttccatt tcgctaaagt   24540
ctgaaagaac aaacttgtca ggatcaatat tctttaataa gttatacgca tacattagag   24600
tattaacaat atcgtaatca ctacaagaat aaatatggtt atttcgcata aaattatact   24660
tgaattcatc actaatttca gtaatttggt atggaatacc gttattaaga aatgaagtta   24720
taatgtgttt aacttcttga actggtgaac cggaattaaa taatttttca atacatttaa   24780
ttccgtgata actgaattct aagtcatcta tatcattaca atagttcttt ttaggaacaa   24840
ttgaattctt cgtaatattc ttatgaatat tacgaaattc cctatgaaga tctttaaagt   24900
tctttttgaa tgtatcatta ttactagttt cttttaaatt agcataaatc ttaattgtat   24960
tattcattat ttatcaatcc tttaatatat ttttatttt caatattaac tttaaattct   25020
attccttgat ctaccatatc ataatcaata tcagcaactc gaccaacgct gataatatat   25080
tgcttgtaca attcagtatc tttaagatta tgaccaagat atgcagtatc atatctgtca   25140
ctttcaatct ctcctggact atattgaaca ttggagatcg ggttatcatt tagatctttt   25200
aatacgttat attctttacg atcagtatca aaaagcctat tcattgaacc ttcaaaagct   25260
acttcaccat cactaaaatt ttctatgatg aacttactgt taagaaatat agtgagtcag   25320
ttgttctaac tttatcatta gggtcaaaat tagatggttt tgggtcatta tcaaacttaa   25380
cccctttatt aggaataata tccatacgaa ctagagctac tgtataatca gtggcttgta   25440
ctggtccgat tgtaaacaca taattttcag gagaattaac gataactgtc ataataattt   25500
tataatcatt atcattagtt accctatagt ctcctacctc tgtaagttca tattcttctt   25560
cttttttgtt ttcataaggg gtttaagttc ttgtattttt gattgaactg aatctttgtt   25620
aacatgatta ctatcattat ttaatacaaa ataaataact actgataacc ctattaataa   25680
tactacaaat attaatattt ttttcatttg aaagttcctc cgttttctag attttttattg   25740 attttatata ttactttttaa acctttagca aatcttttag attttacatc tttcatacta   25800
attacattac ttttcttagc tacttttttta attttcataa ttgatccatc ctttatattt   25860
tatttaatca ttattataat atattaatga aaattatatt attacgctaa aaaaaaaaaa   25920
atccgtaata ctcataaaag agtattacgg gaatatttat attatttaaa atctttcaca   25980
tatatgaaaa ccatgatcag tggctaattt ataatcaaag tttaatccta gattcattaa   26040
ataaaactta tcagcttctt ccttactgaa tgtattgatt aatgtttcta gtgacatatg   26100
acattcttta tcataatcat aagtttcgca agaagcatca tgatatatct catcaaagta   26160
accttgatga ataagacttt caatatcatc accgaaatta tttgcgtcac cactataata   26220
tattactttt tcatcaacct taataatata tccatacgtc ataatgctcg gagaatgtcc   26280
aacagatact gctttttattt gaacgttaga gtcaatatga taaaattcat attcttcaat   26340
aaattgtatt ttataatcta cgtctgcatg aacatcatta atctttaata aattaacgat   26400
attttcacca tatgataaaa atagattaac ttttatatta tgaatatgtt taaagtatct   26460
aataaatgtt ggtaaggaac ctatacggtc agcgtgagta tgagtaataa ttacattaat   26520
gctatcaaaa ttctttatca tactatccat aaaataatca tcaattaata tatcaaacac   26580
catacttcca caatcaataa gataaaaatt gttattatta ataaagtatg cagacgtatt   26640
tcctaattct gtattaaatt catttccggt tcctataaaa tttagtaaat tattatacat   26700
```

-continued

```
tttatatacc gcctttattt tttttttttta ttattttttc taaaaaaata ttggatattg  26760
tcatttattt gacaatatcc aataaaataa ggaaagtgta aactagttag aatattacac  26820
ttttagacga aagagtaata tggagataac aactagtcgt acgggattag agatagttat  26880
atttaggcat aagatttacc taaatataat atattattat ccaaaatatt aattttttat  26940
ttttacagtt tacgcatata aatcttcatt ataagcgtat tgaattcttt attgtatgaa  27000
ttaatatccg taatattata attatgacca ataagattat cattgttaat attagaatta  27060
tatacgctaa ttgcattatt atataatgct tctaattcat cataatttttc taataaacta  27120 tacttgtaat gtatatatac aaagttactt ataatcatat cgataaattt tgaatcgata  27180
tttgcaaaat atattttact agaattagat ataagcgttg gtattgtaaa attaccatga  27240
tacatttcag cattaaaata attcttctta catatttcat aaataacagt atcgtcatta  27300
ctatttagat attcattata cgtcatatta ataaaatttg caagattgat tggttctgtt  27360
ttgatatttg aatagacgat attattatat gatttataat cgtgtagcgt agatcgtaat  27420
acattttcag taattacact attactacga gaaaaatttt ctttatattg aaagtacttt  27480
tcaatattaa ttcttaagca attattaact tcttctagat tagatctaga ttcattattc  27540
gaagtatcaa taatatcttc cttaatataa tttcgcagac ttttctcatc aggattatta  27600
tgtaatatat ctactataat aatcgcagtt ttaattagta tatccgtaga ttttttatcc  27660
gatctatttc caaaattaat aatatttctt aagaaataaa ttaatatctt tggatcatag  27720
ttatacatat tatatatcat gctgacaaat atattgttaa ttccaattct tccattaaga  27780
atatgttcta taaaataata atacttattt gtagaatctt cattatattt attattagca  27840
atatacgctg attggttgga tacacgaata aagcttgaat ataatgcaga gatataacta  27900
ttattaaaat aaatagttgg aacgatatta caaaagaaat cagctaattc tttaatatct  27960
ataatattta gtatagattt tttataatac ttcataaatt cttttggcgt atattggaga  28020
ttatcaatct tgatctttttc agtgtcaaac ataagagcgt gggactcatt tataaaatata  28080 ttaaaatcat atatatttga agtgaatata tcttttagga aactatattt atctttgatt  28140
aatgaataca ttgtatttct aatcatattt tgaaaatata taattcgtag attattactt  28200
tttttagtat tgtcagaatc gactaatgat ttaatttctt tataatattt tgatagatta  28260
gatttggaaa aagtttcgtt aaattcttta caatcatcta aaaatttgtt atatacttta  28320
tcgacaagat cactattact gatttcatga gtatcatatt tatttttttat tttatcgata  28380 gaattttcgt cataataaat tctatcgata aaactactaa ttatcggcat gttgatgtat  28440
cacttctttc cattgatata gtgcataatg tcaatatgta acaaaatgct cttactctga  28500
tctctactgg cattacaata atcaaattca tgctgataat gatccaataa cattaatgca  28560
tagttatatt gattttggat gatgcttgaa atattattac ttaatttata ttctaaatat  28620
tcaataatat ttagaacttc attgtcaata ggattaattt tttcataatt atttaataag  28680
taatgatata cattttttata aatttcgaca gaatcattac ttatttgaat gtcattatttt  28740 attgaaaaac aaaataacga attaaaatca ttaggatcaa ttaatagttt ttctaaaata  28800
atcttagtct tttcactttc tttatattca atccatctta cagggatata ttcagctctc  28860
tgcatgctaa tgagagattt aaataactta attgaatttt tctttttcttg caaactatat  28920 ttactaaaaa tataatttat catattttct acaaaaagat taattctacc aatagtatgg  28980
tttactgtag ccatgtttgt tccttcaata atatgatctt tactgctaac attaataata  29040
```

-continued

```
aacattcttt atcatccttc actgttttat tttattcaca ttattataat atatacttat  29100
cttattagta aaaaagaac tatcacattt tattatgtaa tagttcttct atggattaat   29160
tgatgaatta atttctgtac tattatttat tcggttaatt ttatcttcta aagatatcaa   29220
cctaataaca tttttttttt tatttgtcat ataaaataaa tcactctttt attcataatt   29280
attctattat catatgcact tctttataag atatatttat agaaactgta tattaataac   29340
agtttctata ttaatgatag tttaacttta tcaaagatgt ttctatgatt aagagaattc   29400
ttaataaggt cattaatagt tatatttatg tggtaaggtt ttacattatc ttctgcatta   29460
taaatctgta aatttatatt gtatccattt actataaatt tataatatac cgaaacatat   29520
tctcttgtta ctggttgctt aaaacggtca gacgtaaaag tataattaaa tgtataagaa   29580
tcaatataac cattattagt tgataaatca ctgatattat aagtatattc atcgatgtct   29640
gatgggtcaa gatctgtatt atttctaata aattcataga tcatactttt taggatttcc   29700
gatagatatg tgatagttaa tattgaagaa ctaaatcttt tactattaaa tttttctttt   29760
atattgtaag tattatcatt atattcaata tcttttgatg gaatattata attagatgta   29820
aacatttcgt taaatgtttt tcgttcttca gaagttaatt catttaatgt tttaattaat   29880
tctttgtcat tatataataa aaatgaatta attatatggt acgtaatatt cccattaaca   29940
tgtaaaggtt tacttaaaaa tcctagagat tttaccatta gataatttcc tttctttttt   30000
tttttaatat taattttaga tattatacat tttaattcta tcataatatt tgatattcta   30060
cttctttcct ttatacttat atggattcaa gaatcatttt atcatatatt ttcatatgtt   30120
tcccacaatc aaataataga tcaatcatat taatattttt gttaaaaatt ttatcattaa   30180
tgaaaaaatc aatatctaat tcattgctat ctttatccat actaaattta attttgtcag   30240
aaataaatgt aaatttagta taaggatgat aattctccat aaatttatat tcgggtatat   30300
cttgaattct tattagggca gagacttcaa attttaatat taatgctaaa aatttcttaa   30360
agaaattaga ttctagtata ttccagacgc caaaaatatc attctctcga tatttactaa   30420
aactaaatat acgctctaag ttatcaatca tttccatatt atttagtttt gtcaattttt   30480
cttctaagtc atcataaatc tcaaatattt gtacaatatc attttgattt gtttcgaaaa   30540
tatacataga tactatttcc tcatacacgc tattatctat gtatggaata aatgaatttt   30600
tagctgaatc tttaatctgt tttatatttt tcatgtatac cattccttc attctttaat    30660 ttcaagaata ttatgtggga agatatcaat taaagatacc ttcccacata atatatgtaa   30720
cgattgttta gtacaacata tcactatatt tattcataat attctttgta aatatataaa   30780
ggacttgttc aaattcaata tcggtcaaac ataatttacc gtaggcttga cgattacaaa   30840
atgatgagat agttgataat gaattaccat gaaaaaccat tctttcaagc actctgtttt   30900
gattgtcatt aagcttatca tattttttctt gggaagtgat cattttatga gtcatactta   30960
atagatcgcc ttctaaagta ttagggaaaa cataattacc ttcagaattt aaaataaaaat  31020 ggttaaatcg atttaatatt tcttttttgat aattttcttt tgttttattc aacactatta   31080 aaaccccccat aaccaattag aattatttat atactatata tttatttatt agtatatcaa   31140 tttatttga gtaatatgga aaaaattatt ttaaaatccc taaataaaca tataagttta    31200
cttaaggatc atagatattt ttaattcttt attttattaa atactttta atttattaat    31260 atcaattaat ttctttttca tactttcagg taatatttca tcatgatact ttaatattaa   31320
aggaatattt aatttatcaa tatacgtatc aataaattct agtgatatat cttgacattt   31380
gctaataata tcccaattaa ctttatcttg aaactcaata ataaagtctt ctgataatgt   31440
```

```
ctggtaccaa ctaataaagt accaatctaa agaatctttg aatctacgaa taaaatcttc   31500
tgataatttc tgttgtgaac taatattata ccaatctaat tcatcttgga acctttcaat   31560
aaattcttct gataatgtct cgatacctac tgatgctaaa ccagtttaat ttatcttgaa   31620
acttttcaat gaattcttct gataactctt gatgtatgct gatgctagac cagtttaatt   31680
tatcttgaaa cttttcgata aattcttcgg ataatttctg ttgtgaacta atattatacc   31740
aatctatttt atcctgaaac ttctcaatga attcttctga taatgtctga ttcctactga   31800
catgattcct attaatggtt atttttccat aaataagtat accacctttt tgctatatac   31860
ttttaatttt aataatttct ttatgtttat taataaatta tcgtgataca ttttgaatcg   31920
attcaatata atgccaattt actttattct gaaacttctc aataaacttt tccgaaaatt   31980
tctgttctct actgatataa ctccaattta ctttatcttg aaattttttcg atgaattctt   32040 ctgatagttt ttggtcagac gatatatagt cccaatctac tttatcttga aactcttcga   32100
tgaatttttc ggataatctc tgatatatac taatatgctt ccaattaact ttatcttgaa   32160
attttctaat taattcttct gataatttct ggcataaacc aatataatgc caatctactt   32220
tatcctgaaa cttctcaatg aattcttcgg ataatttata atattcagag atactacacc   32280
aattaacttt atcctgaaac ttttcaataa actgctcaga taatttctga tatgaactaa   32340
tattgtacca aactacttta tcctgatatt tagaaataaa attttctgat aagttctttt   32400
gatccctact aatattgtac caaactactt tatcttgaaa ctcttcaata aactgctcag   32460
ataatgtctg ataccaacta atattgtacc aattaacttt attctgatat ttagaaataa   32520
aattttctga taagttcttt tgatccttac taatataata ccaatctact ttatcctgaa   32580
acttttcaat gaattcttct gataattttt gatgtgagct aatatatttc caatctactt   32640
tatcctgaaa cttttcaatg aattcttcgg ataatttttt cttccaacta atctcagtcc   32700
aatctacttt tactgaatca tcaacgatta ttttatccat agataatatt acatcctttc   32760 tttttttcact atatactttt taatttatca atagcaatca atttatccat tgtttcttca   32820
gatagtgtat cttcgtatct atatattaga tatttaacgt ataatttatg catatatcta   32880
ataatgaatt cttccgataa ttcttgatgc atactaatag ctttccaatt aattttatcc   32940
tgaaactctt caataaaatt ttcagacaat gtctgatatt tgctaatttc attccaatct   33000
accatatcct gacagttacg aataaaatct tctgataagt ctcgaactga cgaagaagca   33060
tgccgccaat taacattttc tggaaatttt agaataaggt cattagatac atttctattt   33120
aagcaaaaat aatcccaaca tatcttatct tgaaatttgg caataaatga ttcactattt   33180
aatttctgat gcatactgat ttcattccaa ttaactctat cctgaaactc ttcaatgaat   33240
tcttctgata gttttggtc agacgatata tattgccaat taactttatc ttgatattta   33300
cgaataaatt tttccgataa tttttggtat tgacttataa tatcccagtt taatttatct   33360
tgatatttaa tgataaactt ttcaggcaat tcttcattat atgcaatata ttcccagtta   33420
ggttcaacag taaaattata ttttttcatta tacttcatag gaaaccctct ttcttttaag   33480
ctattatata ttcttcatta tagtaatatt agtcagctta tctatagttt tctgagataa   33540 cgagtttta tgaatttcaa gtacgaattc aatatccaag caatgaatat tcctaagaat   33600
aaaatcatct gacaatttct ggtattggat aataaaatcc cagtacactt tatttccaaa   33660
attttcaatg aattcttctg ataattttttg atattgggaa atattatacc aattaactct   33720
atcttgaaac tcaataataa agtcttctga taatgtctgg taccaactaa tttcattcca   33780
```

-continued

```
atctactata ttctgacaat tacgaataag atcttctgat agcttttggt ttatactgat   33840
gtagtaccaa ttaactctat cctgaaactt aataataaat gaatcagata attcctgaaa   33900
tatactaata tatttccaat taaccatgtc ttgatattta tggataagtt tttctgataa   33960
tttctgtttt atactaataa agtcccaatc taatttgtct tgaaaagtat caataaattt   34020
ttcattcaac attatgttct tagatatgta tgtccaatca attttatcat catttatgtt   34080
aatatcatta gttttaatgt actcgttaat attcataaat tataaccacc ttatttttct   34140
tctatatgta taatatataa ttttaattta tgttagatgt ataaaaaaaa ggaaatgcgt   34200
atttaataaa tgtataattc ctatataatt attatattat ataagaatta tacatttagt   34260
agttatatat gtcttaatgc atcaatttcc tctaatctat ttatgaattc tttagataat   34320
gattctgaat tattatttat tattgaacta atcgatactt tatcaatatg attattaata   34380
aattcttctg ataattgttg ctctccacta ataacgttcc aattaacttt atcttgaaat   34440
ttatcaataa aagattccga taatgtctga tatctactaa tatagtacca actaagttta   34500
tcttgaaatt tctcaatgaa ttcttctgat aattgttgat ctgtactaat aacatcccag   34560
tctactttat cctgatattt acgaataaat ttttccgata atatttggta ttgacttata   34620
atatcccagt ttaatttatc ttgaaatttc tcaatgaatt cttctgataa tttctgttgt   34680
gaactaataa tgtaccaatc tattttatct tggaaccttt caatgaattc ttctgataat   34740
tttcgatacc tgctgatgct agaccagttt aatttatctt ggaacttctc aatgaattcc   34800
tcagataatt cttgatgtat actgatgcta gaccagttta atttatcttg gaacttctca   34860
atgaattcct cagataactt ttgatttcta ctaatatcat accaatctaa tttatttttc   34920
agattattaa taaaatcttt atcatctaag ttttttatttt tcataagtat atcaatcctt   34980
tatactaata tttaaacatg tcttaattta ttaatttctt ttaatttatc tacaaattct   35040
ttagataatg attttgaatt gtattgtagt aatgcttcaa gatttaattt atttagatat   35100
ttatggataa atgtcttaga taacttttgg tttctactaa tagactccca gtttaattta   35160
tcctgaaact taatgataaa ttcttctgat aatacttgac atgcaccaat atattgccag   35220
ttaatcctat tttggaactt ctcaatgaat tcttctgata attgttgctc ttcactaata   35280
acgtcccaat caattttatc ttgaaattta tcaataaaag tttcagataa tttttggaac   35340
cgactaatta agtaccaatt tacattactc tgaaactctt caataaattc ttctgataac   35400
ttttgatgtt cacagattaa aagccaattt acattactct gaaatttacg aatagattct   35460
tcagataatt tttgagatcg actaacttga ctccagatta atttattttg aaacttacta   35520
ataaattctc ctgacagttt ttcacattga gatatataat accaatccaa tttatcttgg   35580
aacttctcga taaactcttc agataatttt tgatatgtta caataaaatc ccagtcaaca   35640
gtattctgaa acttatcaat aaaagtttca gataattttt gatatatgct gatataaaac   35700
caattaactt tatcttggaa ttcttcgatg aattcttctg atagtttttg gtatatactg   35760
atatttgacc atactacttt atcttggaat tttctaataa agtcttcaga taatgtacgt   35820
ttttcacata ataacccccca attaatcttt tcggggaatt cacttataaa ctcttcggtt   35880
aggtttttat tccacataaa agtataccat tccttctcta taaagatatt tagatacttt   35940
ttattttatt aatttgaatt agtttatttta acaattgagg tgataataat tctgaattgt   36000
actgtattag gtgttcaata tttaatttat ttaaatgatt atagataaac ttctcagata   36060 attttttgata tctgctaata taatcccaat taacttttatc ttggaactta atgataaagt   36120
tttctgatag tttttttgatat tgacttgtag catcccaatc aagcttattc tgaaaatcag   36180
```

-continued

```
tgatgaattc ttccgataat atttgatatt gactaacatc ctcccaatca tttatcatat   36240
cttgaaactt aatgataaag ttttctgaca atttatgata aattacgact aagtaccaat   36300
taagtttata tctaaatttt tcgatgaatt cttctgataa ttttttgatct ccactaatag   36360 tatgccaatc aatattgtcc tgaagttctt cgatgaattc ttcggataat tcttgatatt   36420
cactaatatt aatccaatta actttatctt taaatctagc aataaagtct tctgataatt   36480
tctgatattg gcttatatta taccaatcta cattgttttg aaattcttca ataaagtctt   36540
ccgataattc ttgatatcga ctaataaatat cccattttaa attattctgg aatttacgga   36600
taaagtcttc cgataattct tgatatcgac taataaatatc ccattttaca ttattctgga   36660
atttgcgaat aaagtcttct gataatttct gatattcact aatattagtc cagtcaactt   36720
tatcttgaaa ttcgataata aatttctttg atagttttg atgtttagaa atactgtgcc   36780
aatttacttt atcttgaaac tcacggataa attttttccga taattttttga tatttactaa   36840 cgtctgtcca tctaataata tcttgatatt cacggataaa atcttcaggc aacttaacac   36900
atgataccgt agtataccaa tcataaccaa acctttcaag tgttacgtga cttatattat   36960
tattgactgt ttccatagta cttaattcct cctataatat cattttttaat cttattaaga   37020 aattagacca agttaatatc taattttttg aagtataaat taataaattc ctctaatagt   37080
tttatgaaaa taaaatatat tctcagtata tttattatgt gaaaaatcag cacatattca   37140
tcatatcatt aataatacgc tttctctctt tttttgatac aatgtaatac gtgttatcaa   37200
tataattaaa ttctttaata aaatcttccg ataatatttg atatcgactt ataaatatccc   37260 agtttacatt atcttgaaac tcatggataa aatcttcaga taattttttgg tacatactaa   37320 tataatccca atctactttta tcctgaaatt ctctaataga gtcttctgac aatctttgat   37380
atatgctaat attttcccag tctacattat cttggaattc ttcagataat ttttgatacc   37440
ttgaagattg atacaaattt gtaattttat tatattcaat attaatatca ttgttatatt   37500
tgatatcgct atcatgatta tcattattat ttagtgataa cacatgattt ttatctttta   37560
taacattatc atattttgga atatacaata ttaagggatc attattacta ttatcatcta   37620 gatttttttga aatttcaata ttagcggaat tagatttaat tttatcaata tatactttat   37680
ttctaaattc tataataaac ttttttggata gtttttgcga attggataat ttttgtgaaa   37740
atataagatg ttcccaatat aattccgatt catattttct tataaattct tcagacaatc   37800
ctctggttct atcaatcatg ttccaattta aattatatgg attaagttcg acaatctctt   37860
cgacagtata ataacaatta atatccataa taatccctca tttcatttat tattttaata   37920
tatgatgcat ttatacatta taattataat atatatttat cctataagtt ataaaaaaaa   37980
aaatcaaacg tgatatataa tgattatcac gtttgatatg taattatttt ttaagaatgt   38040
ttaatagtct tagagaatat tctaaatatt tagattgatt ttttacattg taagttatta   38100
ataataataa tgaagagaga aggaacagat ctcctgattt acaataatct ttttgatatt   38160
ttccatacat tacattacat ttcaatagcg ttaataagat ctaattctgc aataagctga   38220
cttactcggt gatctgatag attttttccta ttttgaattt cttgttcttt tgcttcatct   38280
aaaatattat ttaatgctaa cataattcta tctaatagaa ccatcgattc cttataaact   38340
tttacagaat tttcacgatt tttaagaata tttattaaat tactgagact taattcatac   38400
tgtcttattt cttcgccatg attattgatt tttgtaagtt caagtttttgc aataaataac   38460 cgaataatat caatattcct atccctatta tccattaata gaattatatt ttttagattt   38520
```

-continued

```
tcgcaaatac catcaactga taccattata tttcaccttc tattctactt ttagtaaaca   38580
tattaagtgc ttctaattca ttattgatca tttccaaatt tacttcttgt aaattctttt   38640
ctttcattaa tttaatttgt tcttgatttt ctttttcttt ttctacagat ttagtaatta   38700
cttcttcaat cttaacaagt aatgaattta ctgttgtata tacttcatct gaaaatattg   38760
cactattttc atttaagtgt ccaataatta tatcatttat gcttgataaa cttaatctaa   38820
ttttatcatg tgtatggata ttgtatttta atagattaga tacttttttg tttttcatta   38880
atgaattaat agttcttctt aatcgattat tatagttttt atctttaaag tattgaatat   38940
actcgatatt tttattaatg aatttaataa aatcaatagc gtccatatcc ggaatatatt   39000
tttcagttga ataaattatt gcattatcat tattattttt atatcttagt gagtttgatc   39060
tagttaagtg cctatttata tatctaagat catttgtagc ttgatctatt tcactgaaat   39120
taacggaatc atctcttaca atatctttat agtcacgaag tattaaatat cctgaactaa   39180
taataccttt agttaaatga ttattttaa tgcgcatata agtctcaata ttatttttaa   39240
taatattgag gcaactttgg atatttaatg aatcaatatt atttaaacta atatattcga   39300
tttcattaaa caatttagac aattctttac ttctagataa attttctgaa agtaaaaatt   39360
tatctaaaag atcatcattc ttattatttt ttattttaat aaatttaaac attcgatcac   39420
catccagtta attattataa ttcttttctaa tctttgttat ataaatttat tatcatttcg   39480
aaaattcaga tatttctcaa ttctctgatc ttaactaatt tacgctttat tttattagat   39540
attagtttat catgtgatat caatagatca atatctaatt tcttgaagaa tatattaatg   39600
aattcttctg ataaattttc acaatatata gatttgccct tccagttgat tgtactatta   39660
ttttcaatag ataagtatta atcttcagtt agatcaataa tatcttcaag atgtgaacca   39720
aaagtagaat agtctattaa ccatatttct tttaatgggt cttcttcaag aaagattgca   39780
atatcttttg catgtttctt aattttatcc acaatataat tatacgttcg atcagcacca   39840
ctaggattct taatggatct tagaaaaacg tcatcataag attcagtttc aataatatga   39900
tatccttcat aagtttttatt tccttttttgt aacgtcaccg atcttaatac acttttttcga  39960 gtttctttaa tgccaattag gtcagctaaa ttaattactt cttttttatt cagatcaatt   40020
ccattttcta gtacaaaagg aactggttgt aggttctcgt attcctcatc atcaatatca   40080
cttagtgaat taatatattc taaagcatca ttatatgatt taaataccttt atgtttattc   40140 ttttccgtat tagtaatttt atatttgatt gtcatagacc atcaatccct tcatttagtt   40200 aattttttatt tttaaattct agtttaatat tattactctg aaccttacgt aaatacgata   40260
atatcgaatt caccttttact ttccatacat cattcacaac agaaagtatt tgcttcatcc   40320
gataatatat ctgattatta ttatcgatgg caagaattat actcatatgc tgagcctgaa   40380
ttaccttatc aatcgtaata atatcgtaca agttctttc atttctactt ttaattaatt   40440
cttcgccatc attatactta attggtctta tcttcataag ttcactaaca gatttaataa   40500
tttcagacgt atttatacat tccatattat cattcaaaat ttctttttaaa tattgaatat   40560 tattatctgt ctgcttaata ttatttaata agtatacttc atattctgcg ataataaata   40620
aaatatcctt atatttttca cgaacagtac taatctcacg attatttcga atattatagt   40680
cactatcaat attggacatc attctcataa tagtatcaga ttttttcttca atataattaa   40740 tatacgtttc attatatgcg taacgtataa tatcctttga tacttggtta tttattgact   40800
gaagtttatg cgatatttca aagatctcta ttttacgatt aactacgtca taatatattt   40860
cttgagcttc tttcttttta tccagtgata agcttgaata cgtaggaact ttatcataca   40920
```

-continued

```
tagcaggatg tatatacaat atattatctc ctttcattat tattattatt gttgatttat   40980
taaatatata ttaataatat atatgcattt ttataataaa gtttaatatt attccctaat   41040
acaagaattt acatttatct tgtattaggg aacaaattta tttattttga tctatattaa   41100
taaaatataa tacccaaaaa gaccatatta acccaaagat gattattaaa aatctaaaaa   41160
ttaatgaatc tataagcaat cctaatataa ttaatattag tgacattatg gttaaaatca   41220
ttaatactat ttctttatga tctttttaata agttaaatat tttttttcata ataaaacccc   41280 cattataata taataattaa atgtataaaa aaattaaatc ataaaattta atttatgtaa   41340
cttgttaggg gagaacgagt tacgtcgtat ctcttgcgtt atcaacaata tttatagttg   41400
ttcataaata ttatgacttt tgtattttgc atttttgtta tttccaataa ttgttatata   41460
gttttggtat attaatctat atattatttc atcattacaa tagaaccaac cttatagtaa   41520
aaattatata taaagaataa aaaatctata taatttacct tcggtataag gattgttaca   41580
tagaaggaaa gatctacata ttttttattaa aaagcatata tggatttata gttaagtcag   41640
aaccaaccct atagtaaaaa ttatattaat aattatattt tattatgagt ttaatgcttc   41700
gttgtaagaa tctttacatg cacggataaa ttatagttaa ttgttatgta taatatatcc   41760
aagcatgtaa ggtttcttag attattttta tttttttatta ttttaataac taataaagat   41820
attaaactta atttatttcg ttatatataa tattaaagta attatttatc tatatgattt   41880
acttctataa ctttaatttc tagttctgaa acttcttcgt gttttctgaa tactgatgca   41940
gtatttcttg taacgtatat tttatgtttt ccgggaatcc attcaatatt gattttaaga   42000
ttatcctgaa tcattttaat gagcgttagt ctactagctt tatttactaa ttcgccccaa   42060
aggtaatatt cattataacc attattccta agaatgtcta attcttttttt tgataaatttg   42120 tattttgttt cataagttat ttccatgatt tattaattat ccacctttat ttattatttt   42180
taaagatcaa taatgttatc tagatgtaaa gattctttat ctaatgaatt attatcgata   42240
atatagttaa ttcttgattt aacgatgacg tcagttattc tcttaatttc tttaatgcag   42300
gcactatata attcattctt gtctattttt gttatctttaa aggtaagatc ttcaagcttt   42360
tcgtaatcaa ttggttgttc acgtccatac ataatccaac ttgtatatcc actacttact   42420
ttttttcttt tcagtatttc agtgttatag taatttgtga tggtagaaaa atatttttgc   42480 cttttttcttt taatactttt aaagtatatt ttgttgtctg aatgaacgca gaattttaag   42540
ttaaatgaat tgttaataag aacttcaaaa tctaaatcat ctaataccat ttaataattc   42600
attcctttca tttatttaat tgtttatgc tccaaagaat atctgatttt aagtcttcta   42660
ggaattttac cgtactaata atagtgtttt cgtgtaagta atcttttttct agtatcattc   42720 tttctttata tatttcaatt aattggaata atctttcttt atgtttagaa agataagcat   42780
aacctaagat ttctgctgag aagacgatat attcatcatt caaattatca attctttttt   42840
gagacagatt attatcattt ttataagacg tcataatttc agagattaga tcataatata   42900
agttacttaa tacttttatt gtcttttcta ttaacctatt aaattttttct gctttttcttt   42960 cttgaattaa aataatcgta tcattaatag cattattata ggaatattct tcattgctgt   43020
aaagatatgt tttctttttta tcttctaatt tcttttctat ttccttaata gtattgattt   43080 gtattttttat actattaatt gaatcatcat cgctgattgg gatattgtcc atcttttttaa   43140 taagagacgt atccgttttt aaataattat ctttagtatc aatcgctacc ttattaccat   43200
ctaattcttt tattataccct tcttttgtaa cgccattatg cattacttttt acacgttcac   43260
```

-continued

```
ctatctcaaa cttttccatc attttcaccc cacatctatt tcttcaatag gaactgcaaa   43320
ttgccaataa cgctcatctg atgactttat ttgttctttt gttaacttag tagtaaaccc   43380
agatgatatt tgaaaaggaa taagttgtct ttttgcaaac ataccactta cgcctgtaga   43440
agggtttatc gctagatata aataatcatt aacttttttta gaaacatttt tatcccattt   43500
cagttcatta ttttcaataa attgaacttg ttcgtctatt tcgaatttca taaatatgat   43560
ttcttaaatt aattattttt tcactaatag tcttatcaat attaataata ttatttttct   43620 tcttttttaaa aaacatattc accattcctt taacttattc attctttaat tttttgttaa   43680
ttgaatcttt actaatattt cgaataattt ctagttcatc agataatata tcatcaatag   43740
tattattctt agatattta atattttat ccatatcttt atatacttcg aatattttag   43800
agaaatcgtt atagatagta attaatattt ctttaatttt ttcatacata gatttggtaa   43860 ttattcctttc agtctcttga ccaatattaa taataatatt gtaaatatta ttaattgtat   43920
caatatactg ggagagttct tcagtgaatt cattttttttg ttgatttaat attgacatat   43980
tatcagactt aataagtatt ttatcgatta tatctaaaag tttaacatga taattagttt   44040
taccatttac acccattaca taatcatata acggtttaga tctattaata tttctcgtcaa   44100 tttcattatc tgataatcta tcgtagttat acaaacgata tccacctttt tttaatatat   44160 tataccttt tacatatgga tgagatttat taatattaat tttgaaatca tatactatat   44220
ttttaatact aaatttatca tacataatct gatactcata actaatagta gaacgttctc   44280
ggatgtagta tttttttatcc ataaagatat tatcaaagta ttcataatat tcttggggtg   44340
aaggtagttt gtctgtagta atttgaatta ttgatacctt atgaattgat tcaactaagg   44400
tattaataat ttgctttctt aatttgatta attcattatc gatagttata accgattctg   44460
tatctgataa ttcatcagta atcacatctt caggttcttc attatttatt ttttttatgtg   44520 atttttctttt aaaaaacatg ttcatcattc cttttctata atatttatttt aatttattaa   44580 taacaataaa gtttttttctt tagtaactat ctttttaaaa tattagttta tcattacagg   44640
aataactaat ttaatagtta ttcctgtaat aattttttctt ttaatttata tcttcgtata   44700
taataagata ctgaatcatt tttcatatga acattggttg agatttcaga gatagttgct   44760
tttggattct ttttttagata ttctaagata ctattgattc ttgaattagt agaatcatca   44820 tcactattttc gaatacctttt aattttttcga ttatatttaa tattattctt tttaatatat   44880
gactgaattg tgtgatattc tacattaaaa tgttttgcaa tttctgtcat tgttaaattc   44940
ggattttctt caataaattt ggataatcct tcaattttta cttttattttt cggaccaata   45000 ccttttttac ttacatatgg tagatcatat tttttaatct tttcccttaa tgtatttgga   45060
acatagtaaa ttttttcaga taattcatta actgataatt cgggattttt cataatgata   45120
tttcttagat attcttttttc ctgaatttga tctttagaaa gtttttttgat cattatatat   45180 accttctttg ttatataatt tttctacttt tattaattcg tctaatataa ttattaattg   45240
tagatacatt tgcattaaaa tgtttagcaa tcttgcttgc tgtagcttca ggatatttta   45300
tcataaaatt aataatttca ttatcatcaa acattttatc caccctttta ctttttatagg   45360 ggatattgtt tctttttaatt gtattaccaa taaatgactt tgatacataa aagtgtttttg   45420 caattttatc taatgttaag tcaggattat cgctaatata tttagaaagg tcgttaatat   45480 tgataaatatc ttcataaata acagtatcgt tatcataatt atattgcata ttatattcct   45540
taatatattt acggatggtt ggtgcagagt aaccagttcc tgatgcaatt ttctttattg   45600
aatgagtagg gttactatta atatattctt taataatatt aggatctact tttttcaaaa   45660
```

-continued

```
ctttattcac aacactttca ttttatttag tattcttctt ttccttagca aagtatgcaa  45720
ttagtatgta tattatcata gatattaatg ttattatatc taagacatat tcattaatag  45780
ttattgcatt atggtgtatt ccatataaga atgtatatat tgtggtatac acattattga  45840
atataaggat tattagaggt atatacctca ttttataacg aagtttatat agggatactt  45900
catgactact atatagtaat aatccaataa gaagattagc cgttaatgct aatgtatatg  45960 ttatttttc agacaatact tcattagtag taaataaatt tattgtaaga aatataatca  46020
taaagaatat aaataagctt gttattagtc tagttcgaat atcaattttt tcattattaa  46080
tacacgatat atagactaat aaaaagatta caagatttgt tagtaacata taataataat  46140
cctactttcc atatacttat aagaagaatc cccattaata aaggattctt cttataatct  46200
aaatttattt tacatatact ttatatgatt caagtaattt attttttcttt gatagtttag  46260 tattgataag ttttctgaaa aataactttg tgttgaaaga gatttgcgtt aattctgttt  46320
tatcttcacc aaaattagtg ctttcgtaag atgcggctga tttaattaca ccccttattaa  46380 taagattttc ttcagaatat gtagataatt taccgttatt accaatcata actacaaatt  46440
caattgattc atcaatattg ccgataaaat gttttaaatt ttcaataaaa attcttttt  46500 cattaaatgt tctaagtcta cgttttctat caatttcaat aataaatgct ttcggtttct  46560
ttttgatatt attaaatagt ttaataatat cttctttaat aaattttaga ttagtatcac  46620
tggtgatata gtattgtaag taatattctt cagattttaa attatttact tttttggtaa  46680
tatcataaaa agtagtagtt tcaattaatg gaataaatata gttacttttta atactcgtga  46740 tagcagtatt aataccagtg acatctttat cgccaatcac aattgttttt ttattcttct  46800
tagcaaattt ttctagatta tcaatcattc ttgagaaatc agttttctta gtttttttat  46860
tagatcttaa caaacttgca acatttaaca tatagtttac catcctttt attttttagg  46920 tttttttattt acaaacagta gaataataat ggcaacgcca attccaataa ttgcaggaag  46980 taaatctttta aatatatcca tgtcgaatca cctttatat tttatttttt gtatacatat  47040
tccgtatcat aattttcaat aataagtta acagttccat gagaaactcc aagagatctt  47100
gcaatcttag caattgaaaa ttcaggatgt tccattataa tattattaac agattctata  47160 atttttttcat tagttaaaga attattagac atattaactt ggttatacgt tgcgatacta  47220
aatttatatt cttcaaatag actaataata tattcttcgg agaatcctgt atcttcagat  47280
aatcttgctg gagtcataat atcattactg tctaatacaa ttttacttaa tctttttaaag  47340 tctgataatc gtgtatcaat cttcatatct gaaatgctca tttttttgaag tctaatagat  47400 gaaatatctt ttccttcttc tttcataatt cttctaatag ttgattttgc aattgaaaat  47460
tcaacattac attttttcagc aatttctaat attgtcattt caggattatt acgataagta  47520
taaataatat ctttagtcat cttactaaat ttatcattat gctcataagt ttctcttctc  47580 tctcttctt gtcttcttct actttctgca cttgttaaaa cattttgact cattaccatg  47640
ataatcttcc acccttttta attaatttaa taaattgtat taatataaga ttataaagta  47700
tatctatgat agtttaaatt aaatatattg taatcgttta tcacatgcct gaattacaat  47760
agcatcccat aaagcattat gtttatcttc atttactatg acattaatat attcactagc  47820
aaattcttca cgattaatat ccggatcaat attttttagtt ctaaatactg tagaaatatc  47880
ataatagtac atgtcaacaa attctggaat taatgtagca tctttttcctt tattaattag  47940 atccacaaat aacatccaat cgtatgccat taagtcacta acaaatacta gtttttcaga  48000
```

-continued

```
actatgctta gcattatatg ataaccattc gataatttta tcagaaactt catctttagt   48060
tccatatact atagttgtct tagcattatc cgattttgat gctaatgcgt catgtttgtt   48120
aaaaaatcga agtttaggaa taacattatc attcacccaa acacttgatt tcgttgtatc   48180
aaaattagat acttccgcat aaaatagtct accgtacgta tctaccattc caatactaat   48240
taggtcggca tcttttgtta aatttgtaaa ttctgtatca aaatatatct tattatccat   48300
aatgtaccaa ctttctttaa tttgtctata tatttctcaa tataatactt gataagaaat   48360
tattgaattc ttttattaat cgatctagcg ccttatcatt aagtaatgaa tttatattta   48420
taaatatgga ttgattatca ataaatttat tgatatcttt tatatctata acaattaaga   48480
acttaccatt atcatcttta tataaagaac tattgattga ttctaatttt ttatttatat   48540
ataacatttt accatcaaca ataaatttag ggttagtata cactaattga aacataccat   48600
tagaacattt cgattcaata ggtaaatatt tatacatctt atattcatct atagatataa   48660
tatcaataat gcatgtaaac aaatatcttt taatgatttt tcacccctat aatttataat   48720
tttgatacta taaaataaat atcatattta taaataatta ttattctaaa aaaataaaaa   48780
attcgattaa tgatatatga catatcatta atcgaatata atctatttaa gtatagatac   48840
tgttacgtta gatgtcccac tagaacctat ttgcgattta tcaattaata aatcaatttt   48900
attcccaata attgcgcttc ccgtatcaca tgctttagcg ataaatgaat taccattagg   48960
atatgtaatt cttaaaatac tgttcattgg aattactgat gtatctacag ctacaatacg   49020
atgaccttct ggagaataaa tagtgttact cactttagtt ccattagcag taattcctgt   49080
gcttggagta taatcatccc caaccgcata tactgtcata cgaaaagaac caatttttct   49140
gtatgaagaa ttttctttag ttgaaacatt ccgtacagtt tttttatttt ttactttatg   49200
acctttgttt aattttaatt tcttgataag tttaatatta tcattcttaa tattttttaat   49260 aattgtatct ttatctttaa ttttctttgt aagttctttt atatcagtag acattttatt   49320
acttttatta acaatatttt cattttgttc ttctagatta ttattgattt tattctgttt   49380
taatattaat ttttcctgac tttggatcat atggtttaga ttagattgat gaatcgtttg   49440
aaatgctgtt aacgatagta gtagaattac gataattgat acgcatgtag ttttaatatt   49500
cattcgattc aatttctttt tcttatgcat agattcctcc atttctatta taacattaat   49560
actatttgct atagtaaaat tatatatcaa aaaaccgtag tatattatta ttgttttaat   49620
atactacggt ttcttatttt attttatatt attttttaaa caatattact aagaattttt   49680
ggcgtttttt ccacaaaata aatttcatct gaattgatct caatgatatt ggcaattagt   49740
tttctaataa atccaacaat attactgata tggataattt tattttcgtt aagaattgag   49800
aagttatcta gtaatccatt aacttttaga ttgatatatg aatatgattc tttatcaata   49860
taaaattcaa taaggtcgga atcgataatc ctaacattaa ctatattata caaatttgct   49920
ttgtttttac tattaatgtc actaataagt ttatcataat catctttatc cggagtatga   49980
aaataatatg gatttaaaag attaataaaa ttgatctgat attctttttcc taaaatatta   50040 aaaactaatc cattttttttc tgaaaattta gttgtaagaa ctttatctat aatcactttc   50100
tgttccattt aaaccacact cctataccat attattagta ttaataactt attgtattaa   50160
gttattataa aatacccaat acgttaaata ataaacgtat tgggagtatt aatactaata   50220
attattgaat tctatctttta attacaacta ttgttttatg gaaattacta acaaatttaa   50280
tatttgtgtc ataatattta tttctaatat tattagggat gtgaccaata atatcactat   50340
aaatagtatc aatagtctta tcgatatttt caatatccgt atatacataa tgagataagt   50400
```

-continued

```
tatttacaat aatttttcca atatcaatat attcattttc aaacatatta gtatattctt   50460
caggacgtag taaattccta aatagatttt caatattatt aataattaca tcaatatttt   50520
catcattaat aatatcatcg atatcattat taataataat atcaacaatt tcatctacat   50580
aataattaac attgtctttt tgattttcag taataccgat taatccatca acttgctcta   50640
ctttacctgg attatcatca tagatattac tatccattga tgttgaaacg ttatccattt   50700
cattaacgct tgaatcttct ttattcctac cactaaataa cttattaaat aatttcttaa   50760
acatacaaat ctctcctttt atactatatt ttactattat tataatatat aaataaaaaa   50820
atgattaaat tagtatatct ccaatcaatt tatattttga ttagagatat actaattatt   50880
tttaacttat ataatcatcg atatttattt ctttaagttt aatcgacata tcatgaaatg   50940
ctttatattg ataggtaatt ttttgaagtt atctccaaat tttcccccaa tccaaaccgt   51000
acgtgagact ttcatctcat acggctttcc atctactagg aatctaaacc taatctgtta   51060
tgtatctttc ttttagtag actaaggact ttccctaatt tatatttcta taaatattat   51120
cggtatctta tcctcgcttt caatccaaat aaaatttcag ttatagtcca gattagactt   51180
tccgagaaat aagtattata ttaatacttt tggatcttcc catgtttcta tagacttagg   51240
tttattatat aacttaggac ttttctagac catatatctt acttcttaac atgataagct   51300
aataaggtta ttatcaatga ttaataacta ttagaagata tatttataca ttactgtata   51360
ggattaagtc attatagaaa attagttaaa tctatccata ttatactacc caaaccaaga   51420
tatcttatcc tttttaatta aaaggacaat cttcttgact tcatccagct tcacacatag   51480
taattacttg ctatgcatgt ggaatattat tttcaggaaa atcttagaat ctttgttatc   51540
taagtccttg atcagtctat aaattaaatt atataaaaat ataattccta caatccctca   51600
tattaaaata atgatttctg tagaacatgt cacaccattg ataatccagt taatgcattc   51660
ccaataccat tcgcaattag cccaacattc ttaattccca tttgatagta tagttcgcct   51720
gcacatttat tacagatatg ttcagactta cagtataatg gactacgcat ttcaacattc   51780
ttattaataa atttaccttt attttcttcg gtaatttgcg ttaatttatc accgtctttt   51840
acataacgag taataaataa attaatatta ttatttgtaa gtgtaatatt taaatatttt   51900
ttagatttac aatcacttcc atgatcgcca agaattattg actgaaatgc agtggcaagt   51960
tttttcgctt catatccacc atcttgagta ccaatagcac gacttgcact agcacttgta   52020
ataatttctg catattgata tagttcgtca ggaggaatac catcgtctag tgaagccata   52080
ctaactcgaa catcatttgg gtccgcataa cttttagtta cacctctagc taccgctgtt   52140
tgtttaaagt tattattaaa acttccacgg cttccactat cataaatatc catatcggaa   52200
gcatctttaa gaatatcatg ggataatgtt aataattctt tttctatttt agatacagta   52260
acaatatccc cagaatcaat tgcctttta tgcttaacaa tcagttcttc tttacgagat   52320
tttacttgag gaggagtcat cattaaagtt gtactaagtg atgttgcaat gaatttagtt   52380
ataccaaagc ccagccattg catcttatca atataattac taaaatcagc tacagtaatt   52440
ttatcttcta ataagagagt acttaattgt ttatctaact tactaatagc cccaccatcc   52500
attggatgat taatatatcc aatatatctt cctaattttg catcaataat taataggtta   52560
aagatatatc gacctactgt agtagtaatt ttatctttat taaaatgaat atttgattct   52620
aattcaaaat aatcacttgg gtcaaacttt gcatcttcat ttttggtata tgcaaataat   52680
tcttgtaatt tttccatagt gatatcattc tctgaaagat taagaatctc aatctttcta   52740
```

-continued

```
gcatcactaa tctttttacc tttatatgct ttttgcaact atattcacat cctttataaa   52800
ttatatcctt taatataaat aaatgttcta ttagataata aaattgttag gatcatagaa   52860
aaaaaaaaat ataacctaga tatctaggtt atatttctta atataatctg accataaaga   52920
attaatactt tccttatctt gaacgcttat tatgtctttt aattcaattt tattatttc    52980 ttcaaagtat atatacgata atatactgga gattgcatca taaccttgtt catccgtatt   53040
aatataaacg ttatcatcat taccataatc cataaatgta ttatatgatc tttttgattt    53100
tatttgtact ggttgatgat taattactac gtctgttcca ttcctatcta aatatgcaga   53160
acattccatc caaaatttaa ttttcttttt attaaatata ttctgaactt ttcctagaat   53220
tcccattact gcaatttctg catagtgacc ttcattaagc attggtggca gtttatcaat   53280
acattttccg ttgaatcctt cttttcttgc ttggttctta taatagttca attcatttaa   53340
attaatatac atcgtaatat tccccacta atcgtattat ttatagtatt attattttt     53400 cacaattctt acatttggtt cgataaattt aataaaacaa aatttcattg atagctttat   53460
aatagtatat gtagttgcaa tcataaatac aatattaatg aatatattat tgtcatagtt   53520
ccacaatact acgtttgaag caataattaa tagaatggtc agtattaccg ttatcataat   53580
tgagataaag atcttgttta ctatacgatt attcatatca tttccctacc ttacttttac   53640
tttttataaa catgtctact ttattacgag aatccaagta ttcagagaac tgatcgatga   53700
aaagatttat tgatatgtta tatgttaagt atgagaatga aatcgatact aataagtcta   53760
ggtaaatatt attatttcta aaacatactt cattaataaa aagaaaccat aatgatgacg   53820
taataataat attaaatatt actttggtga taagatttct aaataattta tcactagaat   53880
agatacttag tatactttcc tctctctcaa aattaaatat agccattaca gttcttaaca   53940 tatttttct acttttaatt tcgatattct taattaaaaa gttgcataag aataacactg   54000
ctttatttat gtacattata taatcaaccc ttcttttttt tatttaatca ttattataat   54060
atatcattaa aacttgtatt attacatttt ttataaatta gagggatatg acaagttata   54120
tgtcatatcc ctctaataaa tataatttat gctacgtaaa taatatattc catttcaata   54180
tttgtagata atccacttaa tgagatagaa tcaaaagtca atcttgatcc acaactaatg   54240
ttttcataag agttttagt ttcattgtat ctacctaacc ataaacataa ttcattgatc   54300
attccaccac gacattcact agggtcgata gttaatgata gactatatga aacttctcca   54360
gtaaatgtat taatattcca acctttagaa ttaccaaaag gttttgaatt tgtagcacca   54420
ttaaatcgtt taccataata ttttacagta ccatccggat cagcttgtgg taaataatat   54480 ttcattttt gttcatcagt aagctctttt acaatagagg gattatcttg agtttcagta   54540
tcattatcct tatcagggtc tactgtaata aaaggaaatt tttgagctaa tccattatca   54600
ttaaattttg gagcaactgg agtgaatgga ctagcattaa tatccgcccc tccttctcct   54660
actgagaata gacagattga tcttgcagga tcatagactt cgttgtatgt tgatggatgt   54720
ttttctttta ataatgcttc cattacaaat acacgagttc tttgtaaaat taaattatct   54780
tgaatattga ttacttgttt tgtatctgca ttacggaaaa taacttttcc tcgaattcct   54840
ttatctgaat ctgcagtacc aatattatct tcaaaaattt cttgaatgtt attatcttta   54900
gacataatgt ggattacact tcctattcat ttattttata gatatcgatc ttaatcattt   54960
gatttaataa ataattatc actaaacgtt atattatcat caagacgttt tgttaagttt   55020
aaactatgag aatcaattat agaaatataa tccctaaata gtattccacc tatttagtg   55080 acatccatgg tatcaaacaa tcttatactg ttatccattt tactatcaaa cttataaata   55140
```

-continued

```
gaactactat aaactgtatc gatagtatag gatttaaata cttttatgag gatataaata  55200
tatgatttta cataatcaga tagaccaatc gtattatttt gagttaagaa atcatattcc  55260
cctagattta aatgattatc aatactttca acaagttcaa atattctttc acgatatata  55320
tcatctttac ttaatgaatc aatatcgtat atattaatat ctacttctgt atagaaatat  55380
aagtttggat cattatcttt taagtaatct gtaaacgtat tatattttga gaaaatatcc  55440
atatttaaat catttgtaaa tttttcattc cataatttat taaacaaact atatagttta  55500
taatcatttg tattaataat tgtttcttct aagtcttccc ttagtttttc attatatcgg  55560 tatattttg cgaagtcatt catagtatat cttctttat tattgactat ttcatcatat  55620
gaaccaaaaa catctataaa taccgataaa ttcttatagt ttattagctg ttttcgataa  55680
atatattcat tgactgaaat agcttcatca atagctgaag gaatcatatc aataactttt  55740
ctaaagttct caatagtttt atttcgatta tatatatcga aaacggtact taacctgtta  55800
ataccaagct tatttataaa gtctcgcatt tcagacatta ttaccacgtt gtccatacca  55860
aactggaata tcttatcagt actaatatat ttaatatcta cctgataatt aacaaatctt  55920
gatagtaatt gtttcaatag actatattcc gatattatag acattgatat ttttctattt  55980
ttatcaagaa gaatattcat taagtattct aatccatcat aaatattacc attcttaatg  56040
tgattttcta atttcttaga accgttaata ctttggatgt attctgaagt gaactgcatt  56100 tggtttggt aaactattga agaattatac attgctacaa tactatcaaa atcttggtct  56160
atatctaagt caaatccttt caacttaaat cgatttagat aacccataat attttcccat  56220
tctcgtactc tgaattttcg tttattccag aaaagatatt ttcttaatga aataataata  56280
tcatttacat ttttatcaat atcatatccg taggtatgtt ctaagaatgg aatttttcta  56340
attttatcag accaattcat tctttttaat accagtgtta ttaatgcaac aatagcatca  56400
aatatatgaa tttcactatc agagatattg cggttattaa atttaaagtc aatattctca  56460
agattaacta cttttgaagc ttcttgatag gtaatattat tatcactagc atatttattg  56520
attattgctc tattttttaat ttctaggtca tttaataatc cataaaagta tgataattgt  56580
ttcgaattat taatcagatc aagaacaata tcgactgaaa tatactttgt atttataata  56640
ttgaatgatt gttctagtat attttttcttt tcagctcgcc aatagggatc accttcagta  56700
attgcgtcat aatctaccct aggatgaagc gaaaaattta attcttcatc aataggaact  56760
ttatagaatt ctagtgagtc atcaccgcct agattatttt tcttagcaag catataccta  56820
tttatctgta cattatcaaa agagaaaaga ttctttatga cattgaatac atcattatct  56880
cccttgttac taatcatttc atttatgaat cgataaattc ttcgttgata atttactgga  56940
acagaatcaa aataatctaa tccccatgat ataaatccat tttttaattt ttttctatca  57000
taagtatcaa tattaaagta tccttccata gtcttattaa tataacgcat tatagtcata  57060
aatattagat attctcgata tacttcacga ttatatgttt gattactaaa tgcttcagta  57120
aacgtaacat ttaggaaata attaatcgat tcatagtaag cttcattaaa taaactttta  57180
tgccatttat ctaatgtatt actagtttct ttaagtatat agaaatcttt tgctcttctt  57240
gctgaagcat aatcaatatt atatcgatta aataaatctt tataataagg gtttgattca  57300
ttatatcctt taatgatatt tgattttttct gattctgaaa gttccgaatc actatcatat  57360
atagcactta aatatctact agaatttaat agtgatgaag gagtttcatt tgcttctgcc  57420
aattgagtat ccttaattac tagtccacga gcataattta taacatcttt tatttcatta  57480
```

-continued

```
atatcctagt ctttaaatgc attataaaaa taatatggtg tatattttct taacatctct   57540
tctttaaatt cattgaccaa ttaaaaacgc caccattcta ttattatttt tatattataa   57600
agagttgttc ataagttata atatcttttt agttttgata tagaaacaat atactatata   57660
ttaaaataaa gttagggtga tttatatatg aatattaaaa aaataaataa gaataaaaca   57720
gtaagtaata ttgtatctat cagtaaagat ggaaatataa ttcttaagga taagaattat   57780
acaagtgata attttttaga ctcattctat ataaagtcac tggatagtaa atctatgaat   57840
aaatttataa aaaatataga atcattaatt cgaacatcat tagagtattc tagatatatt   57900
gggtatttat ctacagttca aaatatcaat acagatgcaa ttatggcaaa tattaattct   57960
gatgatgcca gtctagagtt tcatcattat ccatttactc tttatgatat tgtagaaatt   58020
gttataaata aaaatattgc attacaagaa aattttacat caatatctat agctagggaa   58080
gttttaaaat tacattatga taatatgata ggattatcta gagtcagtag aacggtacat   58140
caattagctc atgccggcga aattttttatt ccattagata gtatatttgg aagggttaat   58200
gatgttcgtt aatgattttt atgaatatat ttatcaagaa cacattatta cgtataataa   58260
gattattgaa atttataata ataagaatta tgataatgat ataacaaaat aattttttagt   58320 tatatattat aattaaaata ataactatta taggtggcga ttatatgaaa aaaggaatag   58380
acgattatat taataaatat ataagtgatg atccagagac tcaaaaagaa atagatctca   58440
ttgtaagtaa aataaatgat tttaataata attgtattga attgatgaat gatgaaaata   58500
tgatctgtga agaaaatatt attaatggta ccattaatga agttaaagac attctattaa   58560
cgttatcaaa tacatttaca tctgtttata tggcgaacag agttattgaa aatattgaat   58620
tatttataaa tggtgaaaat gacgaagagc ttcatgaata tatttatata atgcaagatt   58680
caattgaaga ttttgatgat attcctttat atgacaaaac gttattgtct gaagcgatta   58740
ataccattca gcgagcagaa tttctaaata tgatactcaa agaaatacat atctcaatat   58800
atttagaaaa aacactgaaa ttattaaacg atattatgga ttataatagt gataatttgc   58860
cttatgatat gtctatagaa attaatgcat tactgatgag ttctgagtat acattatcag   58920
ttatattaag tcaatttaat catattataa ctaagtcata tactaaatat ctaaagatcg   58980
ttgacattat ctaattttaa acctaatacc ataattttat ggtattaggt taattttttt   59040
ttttattttt taaggtttaa actacctagc acatttgttt ctttatttct aattctttca   59100
tcaacagtat ttaataattt taaattacca taaattacta ctgcataggt tttattttct   59160
tccggatttt ttgtttttaac aattaattta tcaaaatcaa cagaatattc atcttctgta   59220
agcattctgt tatttgcaaa tatttttact tcaatacatt tatccatatt tccattattt   59280
ttttcaattt ctttagcaac acgaattagt cctgaagaca ttattgattt aatatccaat   59340
tcatcatatg ctacattaaa gtcaggaata aattctgaga aatataagat ttgctttttca   59400 ttaagagttg gaggtattaa atcttttttga gttataatat taaacttaaa tgtatcacta   59460
ttatctattt ctggaatatc ttttataata ttttcgtttc gcatttctaa aataaatgat   59520
cccggcatcc ataattctgc agtcattgca tatcgcactt cagaataaga attgattaga   59580
ttattcatta ttttttgaga atttgctaat tctggatatc ttaacatgat atttgcagga   59640
tactcgcaca tataggtagg attatttgta gacatattta ttttttctat aattgggttt   59700
agtgaatgag ataataaata ttcacgtaat ttatctttat cttcttcatt atcaaaatct   59760
aaacctaata cattacatat attcaatata aatgataatg gtatttcata aggtattcta   59820
atatcattaa ggtaatttac tccgttattc tcaaaattct gatttaagaa atttaagtta   59880
```

```
ttccaagcag aaagttcact agggagtttc atgtatatat caaaacgtaa ttttatccga   59940
ttaggaatat aaaaaatacg aatatcattt tcatgatctt caaataccat tttgtattct   60000
ttgtgtttat tacgattttt tatataaatat tgatgagtag accaaaaagg taatatatca   60060
ataaatgtat cacctaactc aaatttaggg gagattccaa tgtatggttt aggcatatca   60120
gtaaataacc ctttaccatt actaaaatta gtcgaattta atgattcacc gatatatacc   60180
tttttaaaat atttaggtgg aaatttgctt ataaaatagt ttgatatgaa tgatgatacg   60240
ccactaataa cattatgtat agatggacta gcagtacata atgctacact attattatat   60300
tcagatcttg caggatctaa cataagagaa tcacgccttt ctatataatg ttgttcacaa   60360
aacaaaaaac ccctattact atagttatat agtaataggg taaaagatca gagattgtgg   60420
gatctctaaa agtgtgaagt acagaaagca tatacaatag gttaaaaaat aaaaggttaa   60480
aaaaatccta tcgtataata tattatttag aaaattacgc ttaaaaaaat aatattatct   60540
ctaggtactg atgctcgaat tgtatacatg tttgaaatga tgaatttatc aaagtcgaaa   60600
tcttctccaa caatttcttc aaactcttca tttcctctaa taaatttatt aatgataata   60660 gtagtttttat taataatttc gttagtcaag ataacctgta cttttttctac atatttattc   60720 atgtttttat catcattttg attttttaact tcaggaaaat tttcattttc cggtttattt   60780
agttttaata caaattcagg attatcctta ttaataaaga ttcttgaatt attatctttta   60840 aaatcaactt tttctgattc atcaataatt tttcttaatt cattaactaa attttcttta   60900
ccgataaaac taataatgtt atttcggata gcaatttctt ttctgagttt aatcagtttt   60960
tcatcatcaa tcatctcatt tagtctttttc tcattttcat tataaatcat cttgtatttt   61020
cttcccttct aattcctttt caggattata tgttaattca ctattaatttt cattatttt   61080 aattttcatt gcaagatcta atatgtcatc atctagtgtt tttttaagtt ctttacttat   61140
gcgtatattt tttgaatttg ggttttctttt aaatcttatt attagatttg tttctggatg   61200
agtattataa cgtttttcag atattaaccg atatacttga ttatcatctt tccatagtat   61260
tttatttaat aagtccatta atgtttttttg ataattatcg atatctggtt ttttaattct   61320
tttttcctga tttgtcaaca ttagatatat tttataaagg ctatttccaa actttgttgg   61380
aatattacta aatatggatt ctaattctat tggaccttca aaagcgtttt cattaaaagg   61440
tattttattc ttatgaactg aattatattc gtttatagat ttaattaata ttttttcgaaa   61500 ttcatttttta tacccaccta atggatcgta tgtgctacca atgatattaa atctatgtcg   61560
ttgatacggt aatatttccc tatcaatatt aaatatgtatt tcattttttat caaatttaat   61620 gatatctata tttgcattta agatatacat cttaaaattt ctcgattttg gttttttaat   61680
ttttatatcc aaaggttttt cttcaccatt aggaataggg cttttttttca ttactgcttc   61740 tcacctccaa aagtattagt atataaataa ttattattca ataattataa ttttttaaag   61800
taaaaatata ctcatatcaa tcattttaat atatcacgat atatgataat taattaattg   61860
atatgagtat ataagttata taaaatactg atgccattat taatattaat gcagttacta   61920
tataatatat taactgcatt attttgcttt tcagatctat ttattctaaa cgtcatattc   61980
atatgacgtt ctatttcttt aaataattta tccataaagt tttcaatatc agaagtagtt   62040
ttcttaatgg gtttaatttc tttaattatt tcattagtat atttattcgt ttcatctgct   62100
tgttctttaa ttgcatttaa aacagcatca gtttttcttct tatgtgcttc aaattcttct   62160
tttgtaatat attttttcttt atcaatatat ttatcgttat cttttctttt aaatatcctt   62220
```

-continued

```
tttagtagtg cagtgaactt ttccatcatc cttaaaccca ccttattttt attttaataa   62280
aaggtcgggt acgatattaa tagctgaaac aattatacca ctcagagcag gtaacaatgc   62340
taaccatatt ttatttctgc tttcactatt atctaattta tgactatgtg ataattgtgt   62400
tgtttcaaga ttccctattc gttcatctga agattttgta aatgaatcta tttttgtcct   62460
agtttcattt ttaacttcct cgatatttga attaaatctt tcaccaagat catcaatttt   62520
attaaaaatt tgacttgaga aatcatcaaa ttttttctta atattatcta cattttgact   62580
tattttagca atctctatat ttgtatcatt tagtttgtt gaattttcat cagttttctt   62640
cttaatatct gaagtagttt gattatagtt gtcgataaaa agtttaaatt catttctgga   62700
aactagttct ttttctgagt tatttgccaa aacctcaccc ccccagttat agtagccata   62760
ccgttaaata ccgatatgat taatagacgg ttaaagtttg acttaatgag agtatttgta   62820
tcgtttactg cagaagcata aattatccat gctattgttg caaagaaaca tgatatcgct   62880
attataatat atctagaggg tttcttataa gatataaacg ccgatataat gagtaatgaa   62940
ccagtaacaa caaagatata tgaccatata attatgggaa atacccctatt taacataata   63000 tatgtttcag aagtaagtaa tacactagat tcggcaatat taaaactgat tcccgtactt   63060
aatgataata atcctaatag gattaataga gattgttcca tcaaaagaat ataattaaat   63120
tcattcataa attttttaat tatattttc attataataa acaatccttt cagaaaatat   63180
caatagcact tacccgattt aataattcat tccactgagc ttcagtcgga aatccattat   63240 cacctttttgc acctttaaga ctagctaacc attcagcttc agttccacta aatccagatg   63300
cttttgctag gtcgtaagca gacttaccgt tatcaccagt gcttccttta tcgcctttat   63360 cacctttttgc gcctttaata ctagctaacc attgagttaa tgtaccgtta aatccatcag   63420
caactgctaa gtagtaagca gacttaccgt tatcaccatt atcacctttt gcgcctttaa   63480
gactagctaa ccattcagct tcagttccac taaatccagc taattttgct agttcgtaag   63540
cagacttacc gttatctcca gtgcttcctt tatcgccttt tgcaccttta atactaacta   63600
accattcggc ttcagttcca ctaaagccgg ctaattttgc tagttcgtaa gcagaattac   63660
cgttatcacc agtgcttcct ttatcgcctt tgtcgccttt tgcaccttta agactagcta   63720
accattcggc ttcagttcca ctaaatccat ctaattttgc tagatcgtaa gcagacttac   63780
cctcttcacc atcaactccg ggatcaccct ttggtccacg gtcactatcg gaaacggtat   63840
catctacgat atcttcatta ggtttatgat agttaacttg agatatttca tcaatattac   63900
taattacatt agtaactctt cccgcttcag aatacgttaa tacaagttca tcacgatcat   63960
attttaatgt accactacgt ttaatatctt ttactagtac tcgatgatct gagtatattg   64020
atgtgattat tatttcattt ttgttatgtc tatcgatgta ttcttctatt ctatatccta   64080
tagccatttt attatatcat ccctttcgta taaagaaacc tttatataat tttttgtttt   64140
atatattgga gttctaaata taaaaattat tatgatttgt atatattaat aacatctata   64200
attctaagct gtgcttcttg atataattta ttcttccaat cttcacctaa gtcaataatt   64260
ttattttttg gtaatgtttc tagtaattca atcttatttt cacgtatatc ggtagtaatt   64320
acatcattat cgtcatatac ggttaatgat ttataattat atttataaaa tgataattct   64380
ataaatctac ctatatcgtt tatattattt tttcctataa ctactaattt aggtatcata   64440
taatcattat aatcaacttc aatagcatta tcgttatcaa tatattcaat agttgtatga   64500
attttatcat cttcagtaat tacttctgga agattatatg gtttaatact gaagtcaaaa   64560
ccatattttt cagaatagtt atacgtatct gtaatattaa cagaatagtt tcgtattcct   64620
```

-continued

```
tcattttgaa ttgaattaat atcgtctata ttattaaata aataaatatt atcaatattt  64680
ggtagttcta aataatgata attattgaat tctctttcta gtactgtttc actaaagaac  64740
attgaatcaa aaagataatc atcatcattg ttagaagtaa taataaacgt attaatacct  64800
ttattaagtt taattttatt agcatattcg taaacatttg tttgttcatt ataaatgctt  64860
aatcgatcat gagatatacc ttgactatta tatttatacg tatatgacaa tccgttaata  64920
tttacttttg cattacgatt atatttatca ctaggattat atccagtaat atatacatat  64980
ttctcaatat cattttctag gttaatctta aattcgatat tacctttatt tatctttact  65040
aatttattag ataataagtt attataagta ttatcaacaa tctctgaagt attatcatca  65100
tttactgttt ttaatgaaga tgataattca tatcctgtaa tatttccatt aatttttata  65160
ggatcgatga aatgattata tattggaaca tggttaataa ttgctttttct aagaactaaa  65220 atattaaaat ctacattttt tgtatttcta ggttgacctg actttaataa tatttcttca  65280
atataatcat tatggtcagc attaataata ttattgttga tttgattctg agtatacata  65340
ctatactgtt taggagttat atcttgccat acattcttgt tattaccatt agttgttaaa  65400
cttctttcaa tattattaat aaagattgaa gatgttttag atgtcagatt attacttccc  65460
atatataccg tcatattgta attattcatt tcaggaataa atatcttcat tcttaaatac  65520
ccatcttcta atcgaacata acccttttcca aaatatttta aatagtcaga agtcattcgt  65580
gatccagaag ttttagtatc ttcatattca aatattgttc catcataaca ttcatataca  65640
taagtaccgt cagctagtat agacggatat atgactccat cattattgat ataaccatga  65700
gtaatgatat cctgatcaaa aataatatct tttggatagt gtggatgaca ataacactct  65760
ccattacaat tacacccatt atcacagtca tcatcatcgt catcaccatt attaggtgga  65820
gtaaatttat tattaatgta atttaccatt gttatactgg taggatcaac aatactttga  65880
acttttccat tcttatcagt aaaatttatt ttaaaatctt tatgttctaa taagccatca  65940
tgattaatat ctttaattaa tgtcttaaca ttagaatcga ttgatgtaat atcaattaat  66000
cctgagttat gatcatcaat catttcttca atacgataaa ctttcatatt ttgtttcacc  66060
tactatccgt ttaatattat attgttatct taaaaatttt aggacttttt gacctattcc  66120
atatttaata tctttaaatt tattatctaa tgacctaaat gataaaactt ggactgctct  66180
atccctagtc atcaacaagt ttgtttttaat acgtttcatt aggtttaatt catcataacg  66240
cattcctgcc atacactcaa tatatgatgt taatccaata ttatatctta attgcttaat  66300
acgcttagaa gccattaggt taggatataa gtcacgtact tgcatagata cggttacttc  66360
acgaggaaag ttttcagcag tccatgtttg ttcttcgcca cgaaccatat ttattgatga  66420
tattacgcca cattcacatt caaatcttcc tggacaagac attctaacca agaaaggttg  66480
tttataacta taatatgcgt cttgtaacgg taaacctaat accagtaaag atacaaatgg  66540
tacatataca taattgaata tcgctctagg atctccataa ggagtataga atctaaattc  66600
taaattatac gatctatcga aagtagagtt tgaccataag tctggatagt ataactgaga  66660
accatctaga tttcagtaa acgcaccaac taagctaccc aataccggaa ttgtttcaat  66720
aacgtctgtt atcatatcct tgattccatc agtaatagca cccaataatc ctccgccgcc  66780
aattcaggca agagttttat tttctctaat ttcagcctgt ttactattag attcactagc  66840
taaagaagac tgagaataat cattagatga actttctgat acgctggttg atttatttgc  66900
atagaaagca atgccgtagt tatcaccatt attatatttta ctaaaatcga aaacaccttc  66960
```

-continued

```
taatcccata gaatgatata tatagcttag tattgtttgt acatatcgat aatactcttc   67020
gtaattttgt ttaaacgata taaatcttcc atcactaaac ttatttgcat taatcattgg   67080
aaagacatta tcttcaattt tctctccaat accgaaaaga ttaaaagtgt ttcctgacat   67140
actaccaaat aatttcttat ttagtctagg ttttccggga gtaataaata ttactggtag   67200
atcattttcg aatgtatttc ggtacactct agagtttgca tcatctaatg gaccatattt   67260
aagtggcata cctaataccc ttatattatc tttaccatat gaagcatcaa acgtatctat   67320
tttagtattt ccaaaagcat taatagtttc tcccattgca ttgacatata gaccttcatt   67380
attaacttgt gaagggtcaa tatcatcttc ttgcattagt gtgtctccct caactccact   67440
gtctggtttt acaatataaa aatcatcatc tgaatccgta ttattattag aattttattt   67500
acttactaaa tcaggcatat tttcaccact ttcaaaataa attttccttg agaccaaatt   67560
taatacattt atggtctcaa ggaaataaaa tttaatatcc cgctaatata ggagttatac   67620
tattaggatc aagtttaaag cttggttgat ctaatttatt atctctatca tttttatgat   67680
catttctagt ttgtttttaag atgttattcg tttcattagt taagttatta ttagttgctt   67740
ctagtctact aatatttcta atttcacgaa ttaaatcact caatttgctg atagaatctt   67800
tatcattctt atcaattaat ttatacatct tatcgagaat atgatttact tttttaagtt   67860
catcatattt ttctttatca tattggtaag gtttattagg tttagcggaa cttccattag   67920
atccattttt accattagaa ccgttagcac cattagatcc gttttttacct ccggaaccat   67980 tctttccacc gccgttaggt ttagcggaac ttccattaga tccgtttttta ccattaaaac   68040 cgttagaacc attaccatta gaagaaccac tagaaccagg actattatct ccagaatatc   68100
aacccttaga gccaccactt ttagaaggtt cagcggttgc tgaagttgaa ttactaccat   68160
ctttaccatt agagaagtct tcattatctc cttttagacc gtattcttta gcatatttac   68220
tgttaatacg atcaccgata gctttctttt cttcttcagt tagtttaaag ttagctcttg   68280 attttttgttc ttcagtttct tcattaactt ctccagtacc agacagttct gcactaccat   68340
cagcagtacc tccagtgttt ccactaactc taccaaatcc tactaatcta ccaaaccaat   68400
ctgcaggcat atttaatgca tcactacgaa tgtttacacc tttactagat tcagcattga   68460
tcattttccc ttcactgata taaatacccta cgtgggaaat agaaccatct gggtttgctg   68520
agaagaatat caaatcacca atagatagtt catctttttt aattctttta gtagcttttat   68580 attgttctct agaagtacgt ggaagtttct taccgacaga attgtatgca ttcataacta   68640
gactagaaca gtcaaaggtc ttagttttac ctaaaccaga acttggtccc attgagtatg   68700
gagtaccgat atacttctta gcatattcta cgtctttata tcctatagat tgtccgtcag   68760
ttttatcaga acttccatta ttggacatta cagaacctaa attacttcca atatctttac   68820
tggtattttt attttctttta ctagacgata cttttttggtt tgtaagatct tttagttttg   68880
caccctcttc tttagcacgt cttcttaatc ccgcttcttg attggttcct gcatattgac   68940
ccatatattg acttaatctt tgtttttgga ctaaatcaat aatttgattg tctgatagtt   69000
tactaatatt ttttctggct aatgcacgtt taaatagact agttgcacct ccagcaccat   69060
gctgtactga agcacttaaa attaattctt gaatacctct agatcgacca cttaaatcag   69120
ttcccagtgc tttatttatt ttagctagtc ctggattata gaagtctttt tggaagtatt   69180
cttgttgtgc ttcaccaaat gctttatttt gtcctaattt tttccaagaa gcatcaaagc   69240
tagatgaacc tggagaacca ctaagctttt tagcaaggtc tggatgagct gatcctaacc   69300
atttaacaaa attagccagt gatcctttag tagatgataa ttggtaaata ccgtaagatt   69360
```

-continued

```
taccgccggc atctccaacc ccactagaga tatatcccgc accactaaag tcttctttac   69420
cagtttcata aaatctggct actgaaccaa agtcttttga aagattcttt ccagctccgg   69480
aaccgccaga gtttccacca gtcgatgcag catttgcatt aacgctacct aatccttta    69540 caatatcttt taatttatca gtaattgatg agaagaaatt gcttatttta ccccatactg   69600
atttagatgg tttatttgga tcaaatccat tttccgccat attatataat gctgcaaccg   69660
gagtaagact gaataaagat ttagcaaatg atttaggatt ctttttcata tcttgaccta   69720
ctctagatga cattaattta ctgtattcag aacccatatt cataaccatt cctaatggag   69780
tagcatctaa aaagtcttta aacttacttt gttctttacc atctttacct ttatcatctt   69840 tcttttttctt tctagcatca ttgaattttt cagcaatacc cattggagtt aatccgtaat   69900
agtgcatctt taatcttatt tttacgttct tcggattttt tctctttatc attctttttc   69960 ttttctttt cagctttatc acctttaatt aaatccccaa tagaaggtaa tttaggagtg   70020
cttgcagatt tacctgattt agcactcgac attccttta caattgatcc tactaatata   70080
gaacctaata ttgctgcacc gccaacagct aatgccggtc cggcaattgg aattccagat   70140
actaatgata gtaatgccct tccaccattt cctgcaatcc taagagctga tgagattcca   70200
gatactaatt tttctctggt tgcattaaat attgcagttc ctctttcagt aacagttcta   70260
aatgcttcag tttcacctag acttttcatt cgaaacatca ttcgagcaat tattcctttt   70320
ttactttctg cggattctag tgcaatatct ttagttgctg aagccattct cattttagct   70380
attagatttt cagttttttc acgaatggaa ttgattgtac ccattggatc ttttactgat   70440
gaaacaattg atcctccaac tttttttagca gtatccatag caagaccgcc tgcattttg   70500 accattacac caaattttgt atctttaacc attccccata cagatccggc tgcattaatg   70560
gctccagata tagtatcttg gttaataata ttatcgggtt caccgctaat gatatcacct   70620
ttagttttat tattaaacat attcatacga tctttggttt tcttgatttt atcttgcata   70680
gaatgatact tggatacaat tgaactacct agtttacttg aaggattttt aaatgccgag   70740
cttgcatctt taattttggt tctagagcca taatcctcac cgactgaaat atctaagata   70800
tttacagggt cgcttgcgtc aggagtaaca tcttgaccat tcgcatttt tacaaaatca   70860 ctcctaaggt ctgatacgct tgatgcaata attgacagat accctagttt cttagatataY   70920 tctaskraga atawwtmtcy wctymryatm mttwtmawta wwtcyastaa gaatgcarma   70980
ttagaatcta tgatasmgtk rakcwrkwat cgtcatmayg agtwatattw mmkrtasttt   71040
cattatcaaa taatccaaat aatgcatttt ttactgatcc tagaggagtc tctgcttgta   71100
aatatctttg accttttact tgtgtcttaa gaacatttct tgaaaaagtt gcactattac   71160
catctataat ctgtgataat ttttcataga tgtctccatc aaacatgtct ttgttattat   71220
ctaatgcagt actgttttta atattatttt tagataattt gataatagta tctttaatat   71280
tatcattatc gattcctgct tcactcatca tagattctaa tgttgcattc ttactagatt   71340
tatttaaaag tatgctgagt ggagatttat tctccgtaga gattgctcta tccattccag   71400
aattaaagtt atctttagct ttactaggat ctaaccattt tccactctta taatcatata   71460 ctaattttg acctgaagaa gcttctagca ttttttgctaa ataacctgga attaccgtat   71520
taatagtatt atgagtttga gcatcaaagt taacaggtct gtctgctgaa actctagcca   71580
tagagcttac ttttcctaga ttagcaggac caaattgtcg attgagtgaa gtcattagtg   71640
gattttcacc aaagatttc ttaaattgac cactaatgat actttcgtca ccttcaacaa   71700
```

```
gattacctag tgctgaatgt attttttccgc caactttacc attgggatta gttcgattaa   71760
gcgtaccttt aaccattctg tcaattaatc tttctttatt ttggaatggt ccaatttcac   71820
cagtagataa tctttcaata gtgtcatata ttgatgcagg tatatttgat acattcttat   71880
caaaataatt ttttactcta tctcttgcat atctatttgc tcgttcatta atattttttag   71940 agatagaatt ttttgcattt ttaagtaagt ctttagcgct tgcatttcca gaatttagac   72000
tactaagttt aaacattgat gatgttattt tacctattcc aaatatacca gaaagcatat   72060
catccattag acccacatta ttgatacttg ctttagcgct tgcttgagat attctattca   72120
ttttttctaa taatgtagta gatttagaag attgctcgat taattgtgaa tagaatttga   72180
tatttgtttg attcatttta tttaaggtat tatttaacgt agaaaatcct cttgtattta   72240
ccccaactac tgaacttgct gatacaatag tagattcaac aattttatca atattttgtt   72300
cttcatttac atcttcatta ttgatatgat cattattatc ttgaggagat tcggtatcaa   72360
taataacttc agagttaacg cttgaagtat tacttgattt tcgattcatt ttatttaatg   72420
atctacttag tatatctaac gtgtttttac cataagcttc aatacccaaa ttatcttggt   72480
tcattgaatt atttgaagtt ctattattct tactttccag tttatcgtct aaatctttag   72540
atatacttcg gtatatatta ttagcagaca tattggatgc aggaattcga ttatttcctt   72600
ttccccaatt tttattacct ttattcatat tgtcaatata tttacttccc tctttaaaag   72660
tgctatcaat acttttatct gccattctag tgtctcacca actttcatat gtagagatta   72720
aatcgcatta ttaatcttct tatatattaa tgtttaagaa tagtaaaaat ctgataactt   72780
tagaaaaaaa aaaaataacc atatagagat aatatctcta tatggtaaat ataatttaaa   72840
gatcaatatt aaattgtgat ttttcagtta taagagtatt taattcttcc gcactatatt   72900
tactataacg tttatttata gtactgctaa tatattttaa aatataaact agatttaata   72960
atacgctaaa tcttcttaat tctttttcat ctttagataa ttcttttagt tttttatgat   73020
attttctttc aggatattgc ctgcgaatat taaggaaaag tatttctgaa attacatcat   73080
taaatttatc tatttgaagc ttagtttttat attcgctagg tagttcttct agaataatct   73140
ttttaaaatg atccttgttt agattataat ctacaataag atgagtaatg actgaaccaa   73200
tatataaata tatatccata atttctaaga tagctaattt ttcattatcc atagattgat   73260
tgtttacttc atataaatat tcttgtactt cttccattat ctgagggtaa aatctttcta   73320
gcattttaca ttctgtttct tctggaaatt tatacttaga tatcatatgt ttttgatttt   73380
caataagatt ttcatagag aatgagaaac tattgttttc ttccgtaata attgatttaa   73440
ctttataagc caaatttaca acacccacaa tctgtttatt tataagtatt attatctaaa   73500
agggtcttgg tattaatcta aattccttaa tatcttcttc agtattaaga ttaaattcaa   73560
tttcccactt attttttattt aatattttttc gaatattata gtcaaaaaag aattcggcag   73620
tatctataaa atttcctaaa atacttgttc taaagttata cgtaaaagat tttccaataa   73680
taatcttttg atttatactg gtcggtattt tccaaattcc attgatatca attctgaaaa   73740
gattatctgg atcatagtaa atattagaaa aataatctaa tattgtttta atatcaccta   73800
tatttctatt ataaggaata atgctttttct tagttttctt atggataatt tttaatatac   73860
cgtcataatt ttttgtttcc ataagcgaca tgcctttcaa ttaattttat taataattta   73920
tttttgaaaa ctgattttttt agatataaat ttattctaat attagagttt tgtattgaat   73980
gagttagatc tatgatattc tcattactat taccagaatt atttagtaca tttataaattc   74040 ttagtaagtt ttgttgactt tcaggagtta ccttcatact catatcatta attatattat   74100
```

-continued

```
aatctaaact ttcttttgac atattaatat caatagaatc aataatatta atattttcta    74160
aagatatatc tttcattctt ttattatcct caatatccga tataatataa ctaagataga    74220
atattgtccg tagttgattt attcggtaag tattttatat atgaatgttt ggatacgtta    74280
tcatgaatgg tggttcaatc ttatctttat atttaacatt attattgaat atttcatcaa    74340
tcttataaac aatatcctga tacattcccc tatacattat gtctttattg taacaaacac    74400
tggaatagta tactaaatat acatttataa ttaaaaacga aaaaatattt atcattagaa    74460
acatttttat ttcatgaata ttataataat ttataaatgt actaaaatta aaagatacta    74520
gtagtataca agtattaata gctactaggt ataaaggatt cttataaata atcttaccaa    74580
tagtaataaa tttatatttc tttaacaatt tagatcactt ccatttcttt atatgacgtg    74640
aatatattat tgtatagaaa aaatataaat gtacaataaa tattatagtg caggtagtta    74700
tatctataat aaaataaata taactaccta cactgattcc ccgatttaac taatacaata    74760
ataaaaaatt gttattgttg tctatgttgt ttgtatttct cttcaaactc agaagtgtat    74820
gattcattta gtttggagat atcataatct ttaccgtcat ctccagtgaa cgtaccatcc    74880
ccattatctg ttccacgaat cttatcataa ttcattacgc ttgcaaacat acgagttcct    74940
ggcatacaca atgtttcagt ttcacggact ttaccaatat gagcatttgt tttcttacgt    75000
gaaaatccag tagaacctac acgaactctt agtccatttt taagagtctc atctaagata    75060
tccccaaagg cggtaatcat atcaaatact tttcgtttag aaagatcatc ttcactaaaa    75120
gatccatcag caatcagttt atcataaaga agatttactt gatcgtcctt aatcaacata    75180
tctaattttt caccactatc tgtcttttga tcaataagtt tattaagagt tagatattca    75240
cgagattctt ttggtttctc ttctttttttc tttttagatt ctttttttagg tttatcctct    75300 tttttatctt ttgttgaatc tttcttgact gatttagtag ttttagattt ttctttaggt    75360
tcaacttttt ctttattaac tacttcttct gaagaaatct tagtaggttc actttcttca    75420
ctagttttta ccactggttt aacaacacgt ttcttgggtg tttcttcttt agctttactt    75480
tttaccactg gaactacttt tttattaagt tcaactttttt cttcactaac tgcttcttct    75540
gaagaaggtt taactgtact ctttcttact gctcttttta ccataggacg aacgactttc    75600
ttcttttctt ctgccattta atttaccacc tttaatttat tttttgaaat attattaaat    75660
tagttattga ataaaaataa tctttttaatt cttaacttta tttaatatat accctatttt    75720
atattaatgt aactacctta ttgccaacga tatttaacaa tatttcacgt ttataatata    75780
tacttataat ataggtttaa attttaattt tttaaagaaa aattttcata acatattaat    75840
attaaaaatt atattaattt gattttctta tgggactccg atgggactcg caaaatctgg    75900
actgagccta gactccttat taagatgctt attaatggac tttactattt taaatcgaat    75960
tccaacgttt gttaaaaggt ggacaaatag agggtaaaga gcttgcggta tagtagacga    76020
tggtctcact gtagatgtaa gtaagtttgt aaagattctt tattatttta cgttttattc    76080 ttttttttact tcccacactt gaagagtgtt taaaaggggg gttgggggggt ttattgttag    76140 tttaatttttt tcataaataa ttttaaaata aaaattattt ttattaaaaa ataatttaga    76200
gtgggtgctg gaatttcagc gctccgcact tcattccgat aataaacaaa ccgagaacct    76260
gaagttgagt attgtatcca attatcctta atatcaaaga atgtttataa taagtaatat    76320
acagtaatta aataataaat attgtatata ggaaatatag tatgaatatt attcaatata    76380
ataattaatg atttgataaa tactttaata taaaaagtat ttatcagtat aatatctaat    76440
```

-continued

```
caatataaat attcaataat taataaaatt ttaagttaga tattaaatat tatattaata    76500
ttagaatagt ataataaata ttaaatatta gaaatatcta ataattatta catataaggt    76560
atatagtatt tcaattatat tagtattaat aagtttttatc aatataattt aaataacaat   76620
tctatatact gaatgaataa aaataattat tcagagagga gagtatactt ttgttatata    76680
tcagtgacct aaagaagtat agattatata aaggtaataa gcttaatggt attaataagt    76740
taagtgaaaa taaagatcca aataaaggtc aattaatatt acatttagga aataatgata    76800
cagatattat cagtttcttt aattcaagaa tatttaagaa taatctattc aaaagttatt    76860
ctacagctag aagatataga actaataata aacgaaaaat gtatattaaa gatcttaaag    76920
aacattttgc aaagataaag aaagaaacaa aagttacatt atttactaaa gtaaattata    76980
aacagtttaa gggtaataac ttagtatatg atattacaga tcaatataat attgaaattg    77040
aatcaattaa taataaaaag aatggtttaa tggtttctaa taactttata aagttattag    77100
aaaaatctct gttggaagaa tatgatgata cagtattatt aattaatatg aatacattga    77160
acgtagatat ggatgatata ttcaatatta ctaagtctac tcatccacta acagttattg    77220
attttattat taaaaagaaa ttggatatta gtaacttaat tgacaagaat ataacaattg    77280
ttgtatttaa tcctaataac agattatttt atagttatcc attaactaca gaattatatc    77340
ctaaaagaca gatcatcaat caaagatcta aatcactaat taatttggaa gttaatgaaa    77400
ttgaaagcaa tgatgagatg agtaatattc cagacattaa tgatattgat gatgctaaaa    77460
gacaactagg taataatatg aggttaggtc gattaaggtc tagaagtaag atacctgtta    77520
gtatagacaa ttctgaagta agtaataatt cttcacaaga agactcaata acaactaaaa    77580
aattagatga tattgataaa gctaatgaaa taaatgataa ggttgaagaa attattaccc    77640
ttactagtga taatacttta ttatcttcag aagctaaaaa acaattatat acaatagctc    77700
aagatgaaat taaaaataat aaagatttag ttaagatgga tagtgctaaa gttgtctcta    77760
ttcttaatcg taatgaagaa ttcaatagaa tagtttcaat gtcttataga tcatttaata    77820
ttggtggatc gaacgcaaaa gagcttgcaa gaacagcagc actacaaaaa agacagaatg    77880
aaatccttaa tgataaaaat atttcgaatg tattagctca tgcaaatgat aaaatgattg    77940
ataaaggaat tattaaatca aataatatta atgatgaaac attatcagaa ctttctgtaa    78000 actctttttga taagagttac attgagaaac aatttaatgc cgatattatt aatgtgttaa    78060
aatcatttaa cgataatgag gatattagcg tattcatctc agacatatct tctgaagact    78120
cttcagactt tcagacaaag aaaactacat taaacgttaa gcttaaagat actaaaggca    78180
ttaatcataa actatcatta gatattccta agatatataa cggtagatat atgatggtta    78240
acggtagtaa aaaaatacta acaaacagt tactgttaaa acctgtagta aaaactgcac     78300
cggacacagt acaaataact actaactaca ataaaatgtt tgttaagaga tttggtagaa    78360
aagatactcc aatgttagct tctatcaaag aaatctttaa taaatttaaa attgaagatc    78420
atcttctttc tggtaaaaac attaaatatt ctttaggtaa ttcattatta gttaactcaa    78480
aatatctaac ttcagtagaa tacaataata tttctaatta tttactaagc tttagttctg    78540
gtaaagatta ttacaatttt aaccaaaagt tattattaga attcattgat aatgatgata    78600
aacttaattc actagaatat gattctacgt tatatttccc agtaggatat acttcagata    78660
aaagtaaact tatcttagca aatttttaaag attatcacgt ttattataaa ggtgcaacta    78720
ataattatga atttgtagaa gaaagtttaa gtagaatgat attactaaat attttgtatga    78780 atgttgatga tgaggttgct aagtttattg ataagggaat taaagcaaat gataaactaa    78840
```

-continued

```
catatacacg agtaaatatc attaataaaa caattcctct aataatatta ttgtcatatg   78900
agaatggatt aatcaataca ttgaatcgat ataatattga ctttgaagta ttagattcca   78960
atcctaaact aaagattact gataataaag ttaaacttaa atttaaggat aaatatttgg   79020
tatatgataa tacactaata agaaattcat tattattgtc aggtcttcat ataatggata   79080
ttaatgaata taacttagat gaaatggaaa ccaaagaacc atatttagat ttattccaag   79140
aattgtttaa tagtcggaat gtagctaaag gtattcataa tgcattatct ctcgctattg   79200
atcctatcac caaagaagtt ttagaagatc tgggattacc aactaatata tttgatgtct   79260
tattgtattc aaatacatta ttagaagata tgtcttataa tactcctaat gatatgaatg   79320
tctatcgaat tcgtggggca gagcaaatct ctggtatgat ttataagata attgctgaat   79380
catacaagaa ctataaggat tctctaaatt caagaaatag tgctactaga attactgtac   79440
caaaggacat tcttataaag actcttatgg agagtcatac ggtagaggaa aattctgaat   79500
taaacccaac attagaagtt gaagttagtg gtaaagtatc ttataaagga ccaaatggtc   79560
ttaacttaag tcaaggttat actcctgcag ttcgttcata tgaccgttct atgaaaggaa   79620
tattgtcgat gatatcacca gacagtagta agattggtga agttcgtcaa ttaagttata   79680
atcctgcaat agttagtact cgtggatatt tagatgtaga tgctttaaac ggtaatgaat   79740
ctacaagcct atattctcct tctgaacttt taaataactt tacaagctta catgctgatc   79800
caccacgtat atctatgcaa gtaactcaac aaaaacattt actaacaaca agagtcaata   79860
gtaaaccgct tatcggtact ggtgtagaaa aatcattagc atatcaaata tctgatactt   79920
ttgctactaa agctaaatat gatggtaaag tagataagat agatactgtt aataatttaa   79980
tgatggtttc ttacgataac ggtaaaaaag atatcattga tattggagtt gtaatgaata   80040
aaaactccgg tggaggattc tttttagcac aatctaaaga tattatgttt aaagaaggtc   80100
aaaagttcaa gaatggagaa attcttgcaa agaatcctaa cttctttatt ggtgataagc   80160
aaggtgaaat atcatatgct attggtaaac tttctaaagt agctttagct ccattagacg   80220
gaacttatga agatagttct atgatatcat catctatgtc agaggatatg acttctaaaa   80280
ttacaatgaa aaaagattta gtgttaggta cttcggcaaa cttatcttat attgtaaaag   80340
aaggtcaaaa cgttaagact ggagattcat tagctgtatt tgaaaatgaa tttgatgatg   80400
attctataaa tcagctatta aatactattg gtgataaatt tgaagaagaa atccaagaaa   80460
tatctaataa agttgtaaaa tcaaagtata ctggggtagt ccagaagatt aatatttatt   80520
ataatcgaga gattgatgaa ttttcttctt cattacaaaa gttaattaaa gcttatattt   80580
ctaaatatga aaagaaaaat aagataatct cagattatat gaaagatagc gatattgata   80640
tatcatatga tatgaatatt cctagtatta ctaaaatgga ttcagataag attaagggta   80700
atgatgtaga tggattatta attgaattct atattgaata tgaggataat ttaagtactg   80760
gtgataaagt aacatattat acggcactta aaacggttat atctgacgta ttcccagaag   80820
gtgaagaacc ttttgcagaa tcagacccag aagaacatat tgaagcagta ttgtctccat   80880
tatctgttat ttctcgtatg actcaagacg tttatctaac attatatact aacaaagcat   80940
taatcaatct gaaaaaacaa attggtgaaa tgttaaaata actcactctt gagagaaaca   81000
tattaatatt atagatgtga aggttgcttt gtgcagcttt cgcatctata atttctatca   81060
agaaagttgg tgaaactagt gggtaagtta gtatcaaata ataataacgg gaataatgta   81120
agtcctatag aaaaagatat tgtaaataac tatataggta gttatattga aggtactagt   81180
```

-continued

```
gcatatagta aactattaga aaatgctccc aattttgtta cctattactc taaaaatact   81240
agatcatcta atgaagatcc gggtcttgga ggaactgttg aatacgtagg ttcagaatct   81300
tcactattat ataacaaaat aaagaatttt ccagtatttt ccgttaatga aataaatcct   81360
acttttaatt ttgaagaagg cgtaggactg gatactgaat tagaaagtca agcaatagta   81420
ctacctaaaa ctattatacc tttacctgat gattatttga cattttcata tcatgaaaaa   81480
ggatatgagt attttaagac atatcgaatt aataatgttt ctacttcttc aataggtagt   81540
aacacctact attcaataac ttttattaat gatcctatag atataaggat tcttgaagaa   81600
agacaagtag ataaaactta tagatttgtt tatgaaaatg taggtactac tgataaagta   81660
attatagaag aagatgacat attattaatt gataaaattg aaaagatatg tggagatatt   81720
aatgaaagat atattaataa tttctacaat tcacagttag gtattttatt atacgaaaat   81780
ctagatgaaa gtttattata tagtcctaat cttcattatt ttataaataa gaatcaggta   81840
tttataaata atcgaacttt catgagaaac gtatatatag aagatataac aaaagtgaag   81900
ctgaaagatt ataacaaatc tttatttagc attattgata atggttataa taacattaat   81960
atgtcttatc aatatataac tagggttttg gaaaataata ttctaaagaa aactaggggt   82020
ctttatgttg aagatttaga aattattgga tctagttgta atattaaaat tccgagaact   82080
acgattcata attatttttc agtagatatt aatgatttga taaataacta tgatggcgta   82140
gactcgttaa atggtataga tgcgataaca tcaattataa caatttattt agaacaacca   82200
gaacaattaa gtattaatac gttatttaat ttagtttcta aattaaatta tgatgactat   82260
tcaatcagta attatttctt tataccatgc gtattatcca ttataaatat aattactaat   82320
aaaaattact atacattctg aagaagtata gaactgagag gaacgtgaat ataaatgttt   82380
aagaaaatag aagaaaaaat ccatcaaaga aatatgggaag ttgaagctag taaaattgta   82440
agtgaagaat tagaagttgt tgaaccagaa gaagaaaaaa ttattgcagt acctaatact   82500
tctgaaaaca atgaagtttt gggtaatcca gaacaagatc ctgaaattgg tcaatttatc   82560
gatagcactg atgaatacga tgatgaagaa gatgcattga ttgatgcttt agaagataaa   82620
aatgacgatg aaggtttaga cggtattgtt gataaagata atgaagaaaa acctgtagaa   82680
acttctgaag ttacatttag tgaatctaaa gatgataaaa aagaagataa gaaagatgag   82740
gacgaaaaag aagattctga agatgaagac aacgatgaat ctgaggaagc tgaagaagaa   82800
gatggtgatg atgagtctga acttgaagaa ggaatcagtt ccatgttctc tggaattttt   82860
gacatcaatg aagaaattga agatgatact aataatattt taaatacact aatcagcgaa   82920
gaagaagata tctttattaa agatgaagaa gacgaaaaag atgatgaacc tattgaaatt   82980
gattttattg gtgatgatga aaaagatcaa gaagataaag aaatcgaaga atctgatact   83040
gattatctta aaaaagaata tctaggtgaa acaatactta ataaaatctt cgacaaataa   83100
tactgttaac ataatattat taagggtata taaaatataa attatataaa ggatgtgtat   83160
ttcaaaatgc caaaagttgt tataaaagat aataaatttg tatttggttt aggtaaagga   83220
ccatttaata atccagttga gattagtgat gaactttac gtaaattaaa aatctctgga   83280
tatacggtaa ttgaagtaaa tgatcgtcat atcgtatatg aaactccaaa taatgaagaa   83340
aaagctgaag aagttaaaga agatcctaaa gaagaactac accaagaaga agagtctgat   83400
gaatccgtag aagctactgc aactgaagaa gaaataaaag acgaagaaca tcaagaagaa   83460
tctaatgaag aaaaaaccga atcatctaaa gaatctgata acgaaaaagt tgaagatgat   83520
agtgatgaag aagatttcaa atcaatgaag gttgatgaac ttaaagaaat tctagaagaa   83580
```

-continued

```
cgtggaattg aattcaaagc taatgatact aaaaaagttc tcctttcaaa attaggtgta   83640
agtgaataat attttatat tatattgata ggtctacttg ttgaaattat agcaagtaga   83700 cctattttt tcgattatta taagttagat aagaggtgtt tatgtgtgcc aaaagtaatt   83760
atattaaata ataaatatat accagatatt ggtagtggtc caatactaga accaattgaa   83820
atcagtaatg aaaaatacca ttatctaata gataatggtt ttaatatata tcagatagac   83880
gataatgaag atattatgat tgatccatcc ataactacca tattgaaagg taaagttaag   83940
tcagtatatg gaatgtttca tgcagatcag aaaaaacttg attcactatt aatgtttaat   84000
agaacaagca tatcttcatt aaaaaatgtt aatactaaga gtattacaga aaataataat   84060
ataatatatt ggaaatcaat agataccgat attgcatatg taaattctga cggttatatt   84120
gctgcaaaag aaaatggtta cacaatagtt actggttttg attcaaataa tacgcttaaa   84180
gcaataatgt tcataacggt aatacctaaa cttccaatat tacccaatga tattaatgtt   84240
aatttagaaa gctatatgga acttaataga tatgcagaat ttcaatactt agttgaatta   84300
cttcctagcg aagtagataa taataaagta agtattacat caaataatat acaaattgca   84360
actattgatg aaaagaataa aagaattatt gctgaagaac ctggatatgc tgttattaat   84420
gttaagagtg cagaaaaccc tgaagtatct catagtacgt tgctaaaagt ttttcctaat   84480
gatgatagga ataatccttc taatataaat gtaaatattc cggacgagat tacaattaag   84540
gttggagagg aaattccctt tgaagtaaaa attactcctg agtcggctaa taatctagga   84600
tatatgtctt tctcatcaaa agttggaatt gtatctttat tagataataa ccatattctt   84660
ggtaatagta ttggcgtagc aaccataact attgtatcga ataaaatatc atcattatat   84720
aaagaaatac gagttaatgt tgaagcacca gaccctaatg atattattgt aaatttaact   84780
gaagtatcta ttgagaaagg tcagactaga gggtttaatg taacagttct tccaatatca   84840
gctaatgaca gaacttacag taatagttct ttaaatgaaa atattgcgac tgtaactcag   84900
aataatatta ttaccggagt taatattggg gacacaaaag taagaataac atctaataaa   84960
aagcctgaat tatttaggga tattatcgtg catgttactc caccaagccc taaagatatt   85020
atgactgatc ttccagacga gattacaatt actgataccg aaactagaaa ttttacagtt   85080
caaattcttc ctgaagatac atttaacaac aaatatgata tggaagtaac aattccggat   85140
attattgatc ttgataaaga aaatttatca tttaaaggta aaaagatagg tgtaactaat   85200
ttaagaattt tttcacagta taaccatgat attttaaa atgttaaaat taatgtagta   85260
ccaagtccat tacctgatcc gacatctttt aaagttattc gtagagatac tggggaagaa   85320
ttaaaaaatg gagatactgt acctagtaat aaagatatac tttttgatgt tatagtttta   85380
ccagaaaatg ccaatgataa aagtyatata gtatcatctt cagacgtaac gattgcaaaa   85440
gttaacttaa attctataat aggagtttct cctggtcaag ttaatattag aataacatta   85500
aacaaagttt caacaatatt taaagtattt caacttaata ttgaagaacc tgttcctaca   85560
ttaattgata ttgatgtacc aagcaatatt actgtacaaa ctatgcaaac acgtaatttc   85620
actgcaacta tatatcctga aaatactcca taccaaaatt tcttaacatc tgttgaaaat   85680
cctgatatag taactatttt agataataca aatccaaaaa tacgtacgat taaaggaata   85740
aaacaaggtg taactaaggt taaagtgtat tccgaatttg atccaacaat atttaaagaa   85800
attaacgtta cagtagttaa tcctaatcct agttcaatag aagtttctcc aagaagtatt   85860
tcaatgttat taaatgaaac taaagaattg gatattaatg tattgccaga atatgctaat   85920
```

-continued

```
gatagaacat acactattaa acaaacaggc ttaggtatgg tttctattaa tggaaataag   85980
attactggtg tgttaaaagg aaatgtaaga ttagatatta tatctaacaa agtaagttct   86040
cttggaacta cggtatatgt tactgttgat aatcctgacc ctgaagatat gattgtcgat   86100
atacctgacg agatcgatat caatgtagat gaaagaagaa attttggtat aacatttgtt   86160
ccagaaatag ttagtgatga ttctattatt ataacatcat ctaattctag tattgctata   86220
ggtagtgctg tacaaaaatt tattaatgga gtttctgttg gtactgcaac attaactatt   86280
agatctaata aagtagctac tttatttaaa gaagttatcg taaatgttca tgaagataga   86340
cctgacccaa caagtatcaa tgttggaact aatccgctta ctttagaatt aggtactaca   86400
actccaataa atattgcata tgaaccagaa attaatagtg gtggtaaaat aattgatgat   86460
tattccacat caaacactat tattagaatg gatcaattta aaaattcaat acaagctatt   86520
cgactaggat ctactagtat taaatatact tctgaaagat ttccaaatat tacaaatacg   86580
tctaaatatt acagttattc ctcctagacc aaaaagtatt agtgataact tttcatataa   86640
taattcttta aatgttaatg aagcaacaaa taaatcgtta attgttagct ttttaccaag   86700
cacggcggta aacattggat acaatgtagt tattgatgat ccaactgttt tattatttaa   86760
tacaaactct aagaaatttg aagcattaaa agaaggagag actatcgtta aggtggtatc   86820
tactgataat tcttctctat ttgtagaaca taaatttaaa gttaataaaa atattattat   86880
cgatgacggt ggtaacggta aagatgatga tggtaatgaa gttatagttc caaaatcaat   86940
aacgtcagat atagtcactg aaatgatagt cgataagaac tatcgggtaa acgtaacagt   87000
tttaccagat aatgctattg ataaaggttt tgaagttata actagcgata ataatgcgtt   87060
taatatagtt caaaacagtg gatcatattt tactattaaa tcattggttt ctggaatgta   87120
taatattacg ttgcaatcta cattaaatcc taatataagc gtatcttatg atatcgtgtc   87180
aggcactgaa gatgaattac atccaatctt accagaaaca ataaatatta taaatgctac   87240
tgatgaaatg actgtagatg aaggtacatc tatgaatttg gatatacaag ttctaccaga   87300
aaattcaact aataaaaatg taactggtta cagtagtaat gaagaattag caactatacc   87360
taataataaa actataagtt ttattaaaga aggttcagta gacattacaa ttacatcaaa   87420
taaagtacct acattaagta aaacaattca ctttattatt aaaaaacccg accctaagag   87480
aattgaaatt aatgcaccca acgcagtaac tttaaatatc ggtgagtcta aagaatatct   87540
gataagtgta attcctgaaa atagtattga taaagaatat atttcagaaa cactagattc   87600
tagtattgtt actactaatg gaaaaaatat tattaaagcg gttaaagaag gaaacactac   87660
aattgtgttt aggtctaaaa cttttccaga tatatttaca cgacttaatg ttattgttct   87720
tcctcctgaa ccgaatgaaa taattgtatc tccatccaat gaaacaatta atatgattaa   87780
gcttgatgaa ttagtatttg atgtaacgat taatccttca aacgcaatcg atttaacata   87840
taagattgag tcaagtgata ctaatattgt aaaaattaaa aatcaagata cagtggttgc   87900
agtaaatccc ggagaagcaa acgtgactat atcgtctaga cagaatgcta atctaaaagt   87960
tattaaaaag attattgtaa ctgcgcctga cccagaatct atagatgtta ttggtttttgg   88020 accagacgaa acaatgatta caaattcaac aactaagtcc gttaatttta tagtcaatcc   88080
ggctaatgct aaagtatcta actttacagt agtatcttct agtgattcgg tacaaattaa   88140
tattccggat caaacaaaat atggatttac tgtaaaacct gttaaagagg gtaatgcaat   88200
tatcactatc caattatcat cattcccaga tattatttac aatattaatg taagggtgaa   88260
taaccctgat cctgaaagca taactgcagg gataactaat cctccaaata tgccttctgg   88320
```

-continued

```
aaatattcca ggaaaaggaa ttgctatagg agagaaggtt gtattaaatg ctaagatact   88380
acctgaatat gctaatgata taacttactc aattagtagt agcgataatg atgtctttga   88440
ggttcgagat gatggaattt atgcattaaa agccggaaca tctaaagtta gggtattctc   88500
taataaagtt ccaacaatat ttaaagaatt tgatttagaa tgtctaggta ataatgttag   88560
tgatattgaa ctggatattc agtcaccatt caatatggtc gttggtaata cgaaacaaat   88620
aagtataaat attcttccta ctgatgctat tgataagagg tatcagctta aaacagatga   88680
cgctaatatt gtatcggtat tagataataa tacaatacga gctatatctc tctggggtaa   88740
atggtgaagg atttacgaat atacgaataa tatctttacg taataattct gtggttaaag   88800
taatacgagt taatgtagaa aacttaacgc ctcaaagtat tgatcttgtt ccatctggac   88860
ccatagaaat atattcatta acatcaacta catttaatgc atatgtaaga ccagacactg   88920
taattgatag ggatacggta gttagtagtt cagacatttc aatagctacg gttcaacaat   88980
catatataac tgaaggtggc ataaaaatta ctagagttac agtaaatgca cttaaatctg   89040
gaaatgttaa tattcgtgta tcatctaata attatagaaa tatttttaag atgattaata   89100
taaatattat tgacccagat ccggaatcaa ttactgtaac tccattaaca ataaatatgg   89160
ctcaagatac atctactaat tttaatgtaa atattcttcc agagaatgct aatgatagaa   89220
catttaatac tgagattgca gatcctacaa ttgtttctgt taatggaaat acaattactg   89280
gtcttaaaac aggaacgact acagttaaag tatcttcaaa taaaatacca tcattaaata   89340
agacaatcac agtcaatgtg agtcttccta atgtaaataa aattgagatt actactgcat   89400
tagttgcggg aacagttaat actgtatatg agggcgagtc ttatccattt cttattaagt   89460
tattgccaga agttgctgca gataaatcat ttacgataaa atattctgct aatgctgata   89520
tgtctggtac tgctgattac tcatttaatt ttggatatcg taatgattca ttaaatccat   89580
cactatatat atcagctaca agttcatcta gatatgttcc acctttgtt agatatattc   89640 aagtggtttc agctaatgga attacctcgg atatatatgg tctaagtgtt gtacttaaac   89700
ctatatataa aatggatagt acatttacat tttataatga tcagtaagct tctgctaaaa   89760
ctactatatc ttttgatagt actaatccta attctgaaaa ttatgtaatt aatgcctatg   89820
ccggaacaac agctagagac cctaatatta atactgttaa tttatatcct cttgaagcaa   89880
aagatacaaa tttaacagtt actataagtg atcctacaaa agcatcatat aatagtacaa   89940
ctaagacttt tacagctctt caatatgata ctgaaactac tgcaaagatt gcatccacaa   90000
ctagccctga tgtatttgta attgttaaga ttaaatgtat gagatctaga ataacgtctg   90060
tacaagttac aggtcagaat ggattaagat atagtactgg cgatgtcttt ggaatagtag   90120
taacaactgg tccagaaggt gctattgata caaatgatta tacattatct tcaagtaatg   90180
atactattat atcaataaat aatgaaacta gaactggagt tgctttaaag gcaggttcat   90240
caactattac cgcattattt aataaagccg gcgtatcaaa tagtgctaga tttactatat   90300
ctgacgtact tcccacttca gtaggtatta ctgaccctcc aggaggttct gagctaatta   90360
ttggaagatc ctatccgata actccaagtg tattgccgac taatacaact aataaagcgg   90420
taacctattc tggaaataat tcaagttatt taacattgtc taaaataaat aatattgatt   90480
atattaatgt gttgggtaaa attgcaacaa atacacctat aactattcga tcagttgcta   90540
gtacgggaat ttacagtaca gttcaatata agactgcgta tgaatacca acaagcattg   90600 atatatccaa aattaatgac tcatataatt taactgaaac aattgactta tctactttga   90660
```

-continued

```
taaatataat tccatcaaat accgataatg ataataatta tacaataaca actcaagata   90720
ccgataaaat aaatattgat ggtaagaaat taacatttat taaagatggt agtgcaacta   90780
ttacagtaac tcataataga aataatattt ccgttaataa attgattaat attgtatata   90840
atgattcaat taaaccgaat attgtatttta ctacttcaaa tattatcata aataataatg   90900
aatttgatat taaaaataat attactaaag atttaacact agatgaatac ctcattactg   90960
gtgatcttaa tggttggaga tataatggca ataagaagtt ttcagatagt ggagattttc   91020
aaattaaatt taattatcct attaatatgc ttgaatttga aagtattaat gatcaatttt   91080
caagtgaatt tatgtataat ttaaataatc cggattctaa agttgatcca ccccaatatg   91140
ttgaccttga taggggtagt gatttgatta atgatcgatt atttagtata ttagatacgt   91200
ataccatttc ttcatattat aataaacgaa gaagtactag tggtaatgaa agtcaatcat   91260
atattgtaag cgcttcacca gtaataaata atatatctcc tgcaggagaa tatttttata   91320
aagtctatgt aaagaatgat cctaataatt atattattat tagaattaat atcggtattc   91380
atggatcaaa acaatccagt aatttgatat ataatggata tcctactctc attagtccag   91440
tatcaatatc tactgatgat aatataaact atgaacttaa agtacagctg tatttaagat   91500
ctaagtggtt gagtggggac aaatcacctt tattatttaa taatgagtta attactcatc   91560
gattaatgct tgattcttca tataataata aaataaatat taatggtatt gaatataata   91620
acattagtga ttttattgaa attgataata gaattattaa tcgaataagt agactaggtg   91680
taaatcgtgt aaatactatt accaatactg tcgcatctat tgatagtgtg gtcgcagcat   91740
atccggacag ggtaagttat tttattaaaa gaaatcctac taaaaatgaa gaatttagta   91800
tggatataag attagtaagt attgaggatt cgaatatcaa aattccagta acttatacat   91860
tcactacaat taataaataa ttctttcaaa gaagcatatg ataagattct tgaaaagaag   91920
attaaaaaaa aaaaaaaaat aaatctccca taacctatta atttaggtta tgggagattt   91980
tatgattatt tattaaacag atcatcaata ttattagtat cgatatcttc ttgagtttct   92040
tcctcatcat cttcatctaa cggtacaaaa ttgataactg gtttatatcc taatgccttt   92100
gcaatatctg atagactgga ataagatgtc gcacctttt tccgtagtct gtaaaagata   92160
ttagaagctc ttccttcatt attaggatta tcaagatcaa acttttcaaa gaattcttca   92220
aatgttttac cttttttcacc ctgctcatta atgaattctg cagtaattaa tgctaattct   92280
gtttgatttt caatagaatc cacatcaata tgcaatggac cagttaattt ctttcgttta   92340
gatttctcag aaggatcttt agaagccttg atcatactat ctttcttatc taatttatcc   92400
atatttacat tatttagttt tgaaaataga tcatcggaca cgagaatttc acctcattta   92460
ttattcatat tagaaatcca tatcatcatt agaaatttct tcagaagcac caatctcagt   92520
tgattttgca attaatgatt taagatcttt tgatccacca ctagcttgga taatttctgt   92580
atccacatct tctgtttgtt tatctgcaac ttttttctag gatgatttaa agttactacc   92640
actattatta ctgttattaa atgtagaact tacatttta ggttcagtgg ttgtatcatt   92700
ttgtgataga ttgttatcat aaggatgttg agttgcgttt ggattctttc tagttactcg   92760
attactattg aatccaccac ttgtgtttcc tgaacgattg aatggagttg ttgatgtagg   92820
tctattaaat ccaccagtgt ttggacgttg actaaatgaa ccactattat tagattgacc   92880
ttgagaataa tttcctccgc ccaaaatatt aataacgtga tctaatttat tttctacagt   92940
atataatttc gcttgaattt tctggaactc ttgtagaata taaagatcaa tattattaat   93000
acaatcaatc atattgaata attgtagtgt agttagttct actgaatatt catcgccatt   93060
```

-continued

```
tacgcataaa ataaatcctg gataagtagt atcatcatta cgatgaatga ttgaaggata   93120
gattaataat tttttacctt gaccaccaaa ctctggagag aaccattgtg gtaattctgg   93180
aagatcccat acacgattac ctgaattatt accttcaata atttcattag caacttggtt   93240
catatatgat tttaatgttt catgatgagc ctgactaact acaacattct cacgaacgct   93300
ttgattagtt tcaggattaa atcgactata atcaaaacgt aaaaacaccg ttgcgctgtt   93360
ttgaatacta gttaacgttt gaacatcgga atatcgatct gaagtgtatt ctcttgcata   93420
ttcagcatcc ctacgtttat cattagttga tgttttatta cctagtaata aagaactttc   93480
tagtttaaaa ttgaaagcac taaatagcgt tagaccatga gattctactg gattaaaatt   93540
tgacaaaata tgattcctcc taataatttt atatattaca ataatataat atatgattat   93600
aatttatttt aaatgattat tcatttgtat cttgatttaa tgataatgca gtaagtctgg   93660
aaagcttact aacaaactga cttcgtataa ttgatgagta caatgcttct tcaggaacat   93720
taaacatttc accaatctta ctgatactgt cacctgaagt ataatctaag aattgatata   93780
cactaaaaat attgataggt tcaggaatga tatattctgg aattactgga atttttatttt   93840 taaataagaa agctttatct aagaaatgaa tccaatctat tggattatct acccaaaaaa   93900
gtattttatt ttttcctgaa ttagaaagct ctaataacaa tgattcaata ttattgtata   93960
ttgttgcatc ttcatctttc ataattctaa tatttttgtt agcatcataa gtataaatct   94020
tttcaacatt attcgctagt tgattattat atactttcat actatcttct tgggatatag   94080
ctgtagcaat atcgtaattt gtaaattcat aatagtaatt agatattaca ccttctgctt   94140
cttctacacc caaacacata ttcatgatgt tagatgacgt actagaccca tctaacatac   94200
atgataagta aatatttaca atcttagttc tttccatatt ttacccatcc ttatttaatt   94260 cttttttgttt tttcatttct ttattataga atatatcatg agttaataaa aatttgaaat   94320
taagttcaga attaatacta ttgataatat ctttaatact tttattaata actgcagggt   94380
ttgttaaatc ttcaagaatt ttcttttccc taatatcatt attaatagtt aaagacatat   94440
caagtagatc gtttttaatt ttatgatatt tttcaaattt aagtttacga tgtctataga   94500
aaaaaccatc actattattt tcactataca tctttaagaa tgatgcatat ttattaaata   94560
agtcttccct ttgaatttta atttcacctt tttggagttc taaaatttca atagaccttt   94620
taatatggtt attaattttt ctaagttgag ttaattcaat atcaataatc tctgtaacaa   94680
gatcaaaatt tacaattccg ataatattac cgtcaatatt aatattaaat ctaagaatat   94740
taaagtcttc tgaaattttta gcaccaatta atgaaaagat atcttcatca tactgtccag   94800
tattaacatt ctttgttaaa gaatatataa aatctttctt aatacgattc acaatcgtat   94860
taaagatatt tttactagcg attaattctt caatgaattt tgaaggattt gtttctgaga   94920
gggaataacg atcgttagat gcatacaaaa ttttcaccac tttccgctat ataatttcca   94980
atttagattc aataatttct ttacatcttt tacgataaat tttctttctt ttagttaatt   95040
gacgtttaca ttcatcaaaa cctgtatcaa tgacatcaaa gtatagacat tctttatttt   95100
ttaccttacg taaacgaccc ataatttgta tcaacccttc ttcagaacca gaaggtacag   95160
tatttactaa tactcgtaaa gattgttcat ctaaaccttt accgaaagat ttatccgtag   95220
taacaataat atcttttttca aacgcagtag attttttcatc tttaggaacg tctgaataaa   95280
atctacttac cgatatatcc cacttattat tttcaatttc tactaagaaa tcttggtaga   95340
aagcattaac cataatctta ttttttaaata agattgcagt ctttctttta ttcttacctt   95400
```

-continued

```
tatcaaagat aatatcgaag ataatctgat aaatatagtt ataatattca tcatgctttt    95460
tatcaataat atactgagaa tagcttggta cattaaatcc ataacctttta gatttctttc    95520 taatttcaac taaatcttca ttactaggtt tagtatctat tttacaaatg attgttctaa    95580
tgtatctatc actatcacta actacagtag agaattttgg aacgttcata tacatattct    95640
gataaacttt attttcaata ggattagatc tactaggagt cgcagttaaa tataatgatg    95700
gacagtcata agtagaatca atattaaata cagaaatata ttcaacgtga gcttcatcat    95760
aaactttaat tgatattcca attcgattaa ataactttac aaccctatca ggatcagact    95820
gaattaattg gttaacagtc ttgtgaatag ataaaaagaa tttatactta gatatatcac    95880
gtttagtcat cttttctaat ttttcaatag attctattcc tgaataataa taaatattat    95940
ctaatgatac gtctgtatat tcactaattc tatccttcca ctgttctaat aatgatttca    96000
tatcaataaa gataattggt actgctttga ttttattaat ataattaata gcacaaaaag    96060
ttttcccttc accagtcttt aacgataaaa acttttgata ataattatta tcatcattaa    96120
gaaaattcat tgcatcttct tgaatttttat ttttaggttt atatttcatt ttaaaattat    96180
ttttcctaag aatattttta tttctttttat cattaatatg aatattaaca ttttgtcttc    96240
ttcttaagtt actagataaa gaatcaatat caataccaga aggaaatatt gctttatcat    96300
catctatctt gtatgcttta aaatcatact taaaccattt agcattccat acagaaagac    96360
tattttctac agcactagcc attttttcgc tatagttatt aataactatc cttgttggat    96420
aaatatcaag atccattcat atatcacacc tttattagtt taaaatcaat agaatgtatt    96480
atataactaa ataatacatt ctattgatat attttaattt aatattcttt aaagaataag    96540
tgaggaaaag attcaaagaa attaatatgg ttaagttctt caggactttc agcatctgta    96600
gcattaataa tgtaaccaaa aatagggact tttgaagtga tataatattt accttctttta    96660 aatggaccaa ctgtcttttg acatttatcc attaaatata attcaccatc taactggtat    96720
cctactgaaa gtttatcacc tagttcatac attgataaaa aatcggtatt attaataaat    96780
tctgtaaatt cttttggatt attggtatat cgtctgattc taaatttatt ttcatctgga    96840
atattatcta aactaataat aaatctattt ttttctactt cttcggaatc aattaaatta    96900
tctttgtcca tattcatata tctatatatc tcccttataa ataaaattat ctaaatacccc   96960 tatcgaattc agattcaaca tctttaccaa aaagatcatt ataactatct gtcttaaatt    97020
gtttttcaat attttgatat aatagtgaca ttgcaggact tttcttaccg ataagtattg    97080
catcacttac attatatata ttatattttg gtaattcttc agcattagca aattcggttc    97140
tatcattatt ttctagactt accatttccc ttacaatagt ttctacatgt acagaatcaa    97200
tcattgttcc tgaatccact aataagttta caatttcttg tacaatgata gaataatcat    97260
tatttgatac atttctaata aaatgatttt tttctaagat atctttaatc tttagaagtg    97320
ggtctgcaat accatcattt tccacaataa tattaaacat atattcatta tcaggcatat    97380
attttaatga gaatacataa ttatttgtgg aattatcata atactgttca atatcatccg    97440
caatctcatt aggaataatt aagcttaatg gagtgtcaat tctaatctga gtgtctttcc    97500 taccttaac atagattgtt cttgtttgat atttattctt ttcagagtct tcatttttcca    97560 taagatcatc tttatgaata tagattgttt cattatcaga aataggacta accttatctt    97620
caaataattg aaacttagat aagaaatctt tagaccagtt agcatcctta ataataactt    97680
ctaataaatg ctttgttgat aagatttttt gtgttaatgg attagtaagt tctaaagttg    97740
cagcagttcc tactttaatg tgtttattaa tcttttctaa tcttccataa catctaggac    97800
```

-continued

```
atataccttt tgaatgtgcg catgttattg gactaaatat cttaatatct ttaccaataa  97860
gatgtgtatc attcttagtt attacggtag ttttattagt atcttcatca tacatccaac  97920
gatgattata tagtgataac atgtctttat ctctaaatatg aatattaata taatgagaag  97980
tgttacaact atctacatta ttttcatctt tgtgaagttc tttatcttgt ggatcaatat  98040
ctaatgtgta tattactgaa tcttcagtta atatagatat ctttcggtta gtatatccag  98100
actgttttac ttgatccttt gcagtgataa ttgcttttct accacctact gcatcaataa  98160
agaattctgt tacatttta attccccctta caaaagaact attaattgga gtagtaataa  98220
ctttaccata tagatcgggc ttataaccaa ttaatccaaa attttgatta aattgtttta  98280
tattaattcc tgcacccgac atgattaaat ctctagtaat attatctta tcttctttaa  98340 taatttgaat cattttatct ttgttttctg caattttttg attatttgtt ccaatatcat  98400
cttttaattc tggatcaagt tcgaattcta aagttttctt aaattcttca tttctatcca  98460
taatatcgat tatatcaaat aaactataag tcactccgct ctgatataat acgttttgag  98520
tactaaatat tgatagttca tctactgacc acgcaatatc tttttttaatc aattttatct  98580 tttcatcact aatatcataa ttataaattt tgttaataat cttatcataa aatacattat  98640
gaagattaac attataatta ccctttttcat tacaatcttt taagataaat gtaaactctt  98700
cggtaaattc ttcttccaaa ctcttaaaag gtttttgccaa aataaacgtt gttaataaat  98760
ttgacctaga tatttttgat gttccaaatt gtaaaatttc tctacgagaa tccacatctt  98820
ctacaatttt ctttcctaat tcatcaatct tcgaataata cttagtatca tcatgaagaa  98880
ttgaattaaa taaagataga tctaatactg tactcaatat cctccacaca atcctttctg  98940
taatatattt aaccacaaat atataatata taattgtaag ataatttaat aatcacaaac  99000
ctatattatg attctaacag aatatttcat tgttgtaaat taaaattaac tttttatctt  99060
atgaaactta atgtggatca tagaaaattt aaactatcaa taaaaatata tattatatat  99120
ttgcgaataa aatcccctat catataatta taacacaaat ttatatgata ggggaaataa  99180
attatttatc ttcgactttt ttagattctg atttagcttt acgtttttct ccgaattcac  99240
gaagtttttg ttttcctttg cttgcatact taagttgaat tgctcggcga gtttctcggc  99300
gcaacttaga atatttaacg tatttacggt aaagtggatc atttgcttct ttagcggaaa  99360
ttaatactgc ttgagtatat aaacgtttct tagcggtacg tttatctaaa cgaacaatat  99420
tggcttcttc tagatagctt aaagattctt ccaaagtttg cattgaactt tcttcattat  99480
tataattaaa aaatgtatct ttcatattga ttaagcatcc ctttctctaa ataaaatggt  99540
ttaataatta tatgtttatc aattcaatgc agaaaaaata ataatttatt tttattcgtt  99600
aataatgttt tatattatat aaaatataga aaggaaagat aatttatgta tagtttttag  99660
tagtaatatt ctctttaatt atataaaaaa taaaattggt ggtgtattgt ttatatgaag  99720
attgaagaaa aagaacgtga aatgaaacat attggttaca tgaagatatt acttaatgtt  99780
gctaaagaag aatttccaga tatggaagaa gatgtattaa aagaaaagat taaaaatatt  99840
gtaaaggata acatgaaaaa tccaaaagca atgattgatg atcgtgaaac aacattatta  99900
ggattagaca aatttatcgt aactgagaaa cctatcatta ctggtttttgg atcaatgtat  99960 ttaactcatg ataagtttga taatctatta gcaaaattgg ttgaatatat tatcaaaact 100020
cgtaaagttt ataaaaataa aatgttcgaa cacgttaatg atgatgatca aacactgaga 100080
aatatgtatg atatgtatca acgtaccatg aagatcctag cgaactcatt ttacggatca 100140
```

```
ttgatccaaa gtagctttat tttgtataat ccgatatctg gtccgtcagt tacttattct 100200
ggtgttgata ttatcactac tgcactaaat aattttgaga aattcttagc aaataatatc 100260
tattttagaa atgtagatga tattattgta tatatgaata atattaaatc tgaaaattat 100320
agtatggata aagttaaatt taaacaatcc cgtagtaaag atcagattat tgattatttta 100380 tttgataaga cagataatta tatggatgaa gatagaatat tattgatgac aatgatgaat 100440
aattatacgg atgaagattt acttaagctt tattataaaa ataacttcat tgatttatta 100500
aaagaatctg atattgcaga taattatttt aaagaaattc taagttgcta tgaatttact 100560
gatccaaacg atcctcctgc taaagttatc tccactaatg aaatttgtac tattaaagga 100620
aaagataacg gtaaaattaa agttaaatta tctaatggtg aaatttctct agaagatcct 100680
agtaatattt tagattatag ggaaaaatta gataatttat ggaatattat tagaaatatt 100740
gtattctaca attatcaaga tttctatcgt atggaaaatt ctgaagaaag attaagaaaa 100800
acagtgctcg tggttaatgt atagccacac ttatatagta atatataggt taaaaattct 100860
attaattgct ggaaaatcct aaagcttatt taactacaac ggaatcagta atgataaacg 100920
tgaatgttgt cgaaagactg aaaaaaataaa taagattaat acatggtgaa ataaaagtac 100980
tataatatat agtatcctaa atattaatta taatggatga tcagcagcag tatttcttta 101040
agattataaa tgaaagaaaa aagaaatgtt gttcaacgac tatcaaaaga ttattatata 101100
aataataatt tagtagagta gagccaagct tttgggttag tatttaagag atattatctt 101160
aatgtaaaac tattaaatcg aaaaatagaa ttatcctta gtaaggataa agatatagtc 101220
tgttctttaa ggaaatctta aagaagttca taagagaact gcataagaat tagcgcactt 101280
atgtgaacac gaaagtgata ccgactcaaa cttcttgtat ctcaatcact ttgtcgattt 101340
attctcagaa atttatccag atattacgat gaaagaaaat gataaatcta ttgtatctgc 101400
cattaatact attatgtata ttgttactga atgtattaat gaaacgtatt acaagtatgg 101460
aatggaactc ggtattccag aagataaacg tggactaatt aatatgaaga atgaatttct 101520
atataaacgt ttaatgctaa cagacgctca aaagaattat gctggcgtaa ttttaatgca 101580
agaaggaaat attcttcaga ctcctaagat tgatattaaa ggattagcaa ttaagaagac 101640
aaatacgaat aaacatgtac gtgaagaatt ttcaggaatt cttaaagatg tcattcttga 101700
atcagataag attgatggtt ctgaatttat tactagatat aagaatctag aaaaagaaat 101760
tcgaagatct ttaatgaata gtgaaatcac atttactctc cctagaactg caaatattaa 101820
agaaaactac gtagcaccat atacgcaagc accatacaaa ggtgtattag tatggaacac 101880
attatatcct gataaagaaa ttaacttacc aaacaaagtt aatcttatca agctaaatat 101940
tgaaactttt gatgatattg aaagtaaaac taatgatcaa gatctaattg aacgatttaa 102000
gaaagtttat gaagatgagg aattgacaaa aaaaggaatt acttatattg ctattgaagc 102060
agaacaaaaa catattcctg aagaaatcat tccatttatt gacatacctg aaatggttaa 102120
gactcatgta tcatcaggat ccaaactaat gacgtcatta ggattcaatc cattagtaat 102180
taatggatca ttattcccaa caaatattat taacttttaa tgaaagtagg aaatctattg 102240
gaaaatttaa atattgatat gaatgatcca accaagaaaa aacatattgt ggtagattgt 102300
gatgaagtat tatgcaatat ttcaccaaaa tggacatact taatacatca agaaaaagac 102360
tattttggta aatatatgaa tcttattgat aattttgata ttgatctgca ttataatatg 102420
gttttatcta gaaataagtt ttatctaaat cagtggttaa ttaaagatga atcatatacg 102480
aattatagtg aagacgaaat ggatgaagta ttaagacgta tgatgatgct ttatgaaact 102540
```

-continued

```
gaagattact atgataactt aaaaccaaat cctattgtag agtcattagc attatcgatt 102600
cgtcaaccta ttttagatag aatatctatt gtaacaagaa caaacgctaa aaatcttaag 102660
tctaaagaaa gatttcttaa gaattgtttt caaggtgtta tgaataaagt tgatatatac 102720
tttgtagaaa atgatgaaaa taagtctgat attattaaag acttaggtga cggtattgca 102780
gctatatatg aagatgaagt taaaaatatt gtagacattt tagataactg taataatctt 102840
gataaaagct taatatatgt acctagttat ggatataata acgctaacct tgatttatat 102900
actaaagcag aagaaaaagg aactcaatta agatattatt catattaaag gatgtggact 102960
tattatgtat aatggtaatt atgatataag tctatatgaa tatttaaaaa gtaaacttaa 103020
agtatgctat atcacaagca aaaggatga  aactgttata cgttgtcctt tttgcggtga 103080
ttctgcaaaa aatcagtatt ctgcacactt atatataaat aataaaccac cttataaata 103140
ttattgtcaa aaatgtaatt caaatggaat atttaatgat aagatactta ataatctaaa 103200 tattttttgat gcaaaactaa atcaacaact taaagtatca tacgaaaaat tcattaaaga 103260
tgcaggaata aaatatggaa aatcatttc  atcactattt aatatggatg aaacggacat 103320
tcttccaaat aactttggaa tgttagaatt aagaaaaata aaatactatg aagatagatt 103380
gggaataaaa ctcaatgatg aattattaat taagtataga attattctta atcttagtga 103440
ttatatggaa aataataaaa ttccaataaa acaagacaaa tggtatattg aaaaattaaa 103500
aatgattaat gataattaca ttatattctt atctaatgac aagaatgtta ttaactgcag 103560
aaatataaca aatgttactg aaaaaaagaa acgtcatatt aaaatgagac tatttgaaga 103620
ttttactgat gaaagtagaa gtttttactc aataaagaat aatatatctc ttgataaatc 103680
tttatacaat attcatttaa cagagggtat atctgatatt atatccgtgc atcataatat 103740
atttaaagat caggaaaata ataatgatat ttttatatct agtaatggta agggttataa 103800
ttcggtatta caatatttat tatcaattgg gattacaaac gcaaatatta atatatatgg 103860
tgattcagat gttaatcgta attattataa tagattaaag tataatttac tagctaaata 103920 taatgggggtt aatctctatt ttaatattgc taaggatcct tatggtaatg gatttaaaga 103980
ctttggcgta agatctgaaa atgtagaatt aagtaaaagc attaagattt ctttctaact 104040
taatggatca tagaaatttt ctaaaaaaaa aaaagaccct aatagatatt atatctatta 104100
gggttatatt tatttaatta ttcttttttt aattgataag gatacacatt aatatatttta 104160 ctatctaata aatcatacac attaattaac cgaccataca tattaatctt tgaaattacc 104220
acatcgtgaa ttttttcctaa agaatcaata atataaaaat cttttcctac aataatattt 104280
ctattataaa tttctttcat gaattcatct aatgaatttt ggtctaattc agtattatac 104340
atattaatca tttatatttc cttctttctt tttttttta  atatatttttc catttcatga 104400 taaggtatat tcattataat tgatacatca ttagtactat aattatcatc tagatatttta 104460 tctattaatc tttttctttc agagatgcat ttattttttag cagtataatg atcatactgt 104520
cggttagcac ttttaagttc tttaaagaat aaactattat tgttaatata tttttttaata 104580 ttagatttat ctactgataa ttcattagct aatgaataaa cactgctgat attcttctta 104640
ttgataatat caagaatata tgataaacga gaaattcttt taactatcaa attgcaatct 104700
ttaacttcca tattaaaaat aatatctaca tattttttcc atgatggagg attatcgata 104760
gatgtagttt tattatttaa tagtgaatta agatatatga caatatcttt atttaatttg 104820 gtattatttta tgatatcatc atattttcct tcatcataat tacgttctat atattttgta 104880
```

-continued

```
aggtatttta ttttttcatc atcaagacta aaatatgtca tatatttctt aaagaaagta 104940
tttaacttta atttagtata tcttcttcga atattaaaac cataaacaaa cacattagtt 105000
actgtggtat ctatatcttc cataacagta ttaactttaa tattattatt aacagtatta 105060
actttaatat tattattctt aataaaatta ttcatgttct ttatttcatc gatagtatta 105120
atgataatat ttctagacaa taattcttct tttttaaaat tattaataac ttctgtatta 105180
tttaaagata aaatgaaggc atttttcatc tttttaatat tatttctaat aactttatta 105240
attatattta tatcaacact ataagttttt gattttatgt tattaaatat atctaggtta 105300
gtaataatat ctttttttagt agataatttt agataagtgt tgattataaa ttcatctata 105360
tctttaggat atataaatata caatgcatca accataacct tattatcata gataagttta 105420
attttaattg ataattcttt ttctagaata ttaatacaat tttcactaat tgatgtctta 105480
gtattaattt ttttaccata atggtagtca tttcgtatat cacatattat tgaatgttct 105540
agattagtaa ttatataaat tttattatat aattctttat tattctttat aatattatta 105600
acactataaa tataaccaac gccaatatca taaaatatat ccatatttgt aacaaaagaa 105660
aatttctttt ttaactgatt atatgacttg ataatattct tttcaatact atcagtactt 105720
ccatcattaa atatcaattt attatccttt agatattctt taaatgaatc taatatagta 105780
ttatagttat ctagattctt attgagtact aaagatataa tatcaatgtc attcattttt 105840
cgatagttct taatactttt gacaatactt ttctttgttg gaatttttat attgttcttt 105900
atatttaatt catttattgt attaaatggt atattacagt ataataatat atcatctaaa 105960
cttaaatttt caataaaaat taattgaata aattcattat agttgatgta attatttta 106020 actttatttt cttcagtaat tcgtattcct tttaacatgg aataaagctt tgactgatca 106080
taactaaatc ctgatagttc agagatttct tctaaggtta ctttattagg attaagttta 106140
ttaatattat ttaggataat attatcaaca atcttagctt ctgagatatt tttgttcttc 106200
ttattatttt tagtttttatt atcataacta attttcattt ttttatcaaa tagaccggat 106260
tcatcaatat atagatttac tacacctact ggaactttat atttcataca tattgacttt 106320
aaatcaaaat tatcattaag atatgtacta tctatttcat gttttaattc ctcgctaatt 106380
cttaacatct agttattcca ccttttaaat attattaaag aaaaggataa tgaaaataaa 106440
tttcattatc catataatta caatgcaata atcaagtttg ttttagctct agtaattcca 106500
gtgtataatt gttgatgata tatgctctta ttatatattt catcaaacag taatacatta 106560
tcatattccg atccctgtga tttatatacg gttgttgcat aaccaaactt aaacttatta 106620
atgataacat gtgattcttc aaaaatattt cttcgaagaa ttaatgactt atacatttca 106680
ttttcataaa tttgatcatc attagttatt ccatccgtaa aatataatgc atctacatgc 106740
aatctattat agattccagt atctgatgaa aatgtaggtt taaagtctaa ttcaaaagta 106800
tccaaccttt tcttatattc atagatattt tccacataac cgataatacc atttgttaaa 106860
tactgttgtg atccattatc ttcatacatt tctaaccagt tattcttaag acatattaat 106920
ttttcaccaa catatggaaa tggtgaattc aaattaagta tatttttttct aataagagag 106980 tttatcctat caacagttat attttttgaa gctagaattt gatctgcgcc agtatacata 107040
tcatagtcta catctttttt attaataatc attacatttt catcgatagg accaattctt 107100
aatctatttt tcttacgaac ttcattagct aaccatataa ttggattatc cagtgcttgc 107160
cttaatggtt catctaggaa gatatctggt ctttttcatat atttattaat tccaccttta 107220
actggtggaa gctgcatcgg gtctccaatc ataatgattg ggacgttaaa tgtaattagt 107280
```

-continued

```
tcttcaatca ttgaatctgt aaccatacta ccttcgtcta caataattaa tttaatattt 107340
tttgaaatac tttctttttt aataaagtta aacttattct tttttttcatc ataaactaca 107400 ttatacatta acctatgaat tgttgaagtg ttattattcc ctttcctatt aagaacatta 107460
gtagcggttc cagtatatgc agaatatact acctgttcat cgtttaaatt gattgccgaa 107520
gttataaatt ttataattgt acttttacct gttccggcta atcctgctat tgtaaaaact 107580
tttttaatat ctttattcca ccattcaact gctcgcataa caacctcttc ttgtttgttt 107640
gttagcgtaa taatactcat tatatacacc gctttctatc cattttattt actataattt 107700
tttattaaca ttataaatta ctttttcatt aatataatat ataattaaaa atttatacaa 107760
ctttctaaca taacattata atagtaaata atggcggtga taaaatgtca atgagagata 107820
tgaatggaaa tcgtattatg gactcattta gcttcgataa agagtatgaa ggaatagtat 107880
tagataataa cgattttgac gataaactat ttattaaagt atatatctct gaattgttta 107940
ttaatgatat tcctgagaag gttatcgata ttaatgaaaa tattgatcat actaaaataa 108000
ttaataataa taaaataaat tttaaaaaat ctgtagtaca taataattat ttgaagtgct 108060
atccaatcat atataataat atgaatcttg atataatgaa accaaaaata ggttcaaaag 108120
ttattgtcaa atttattaat ggtaatccaa aattgccata ttatgagaat aaaggatatt 108180
atacagatat tattatacca attcctcccg aaattataga tcctcctact gatccatcca 108240
ctagtgatga ttatacttct tttggatact atagaatgat taaacttact aatccggcta 108300
tgattggtcg agatatacta aaaatccaaa agaaattaaa gactcttggg tatacattca 108360
ctattgatac actagacggt atatatgatt taagaatgtt gaattatata aaagattttc 108420
aatctaaaaa taaactaagt gtagatggac agattggtcc aattacgttt agaacaatta 108480
tgcgtaaaaa tatataattt ttaaattcga acatatattt atagtaagat agtttactat 108540
aaatatattt aattggggtg gaaattttta tggaacaagt aacttctgga ctattaattt 108600
tgacagtatt atccgtagta attcagtatt tagttgaaag aattaaagat atttttccaa 108660
caaaagttat ggataaacta gcaaactatg ttaatcctgc tttctggtct ttaattgtat 108720
ctcttcctat tgcttttggt ataaatattg atttatttgc aattatcggt tataaatatgc 108780 atccaacatg gcttgcaaca ttatttactg gttttgcatt gagtggtaga gcaactggta 108840
ttaatgaact tattaaatca ttaagtgctg ttaaaactaa taattttact caagcagatt 108900
cggtaaaaaa tactgatgaa gaagaaatta aagttgtcgc taaatctaaa aaataatata 108960
tatccctata gtgtataatt gcactatagg gaatttttatt tactaaaatt ataaaataca 109020
taataaaata acattaaaat atatttacat taatatacag aaatggatga ttaaatatga 109080
aatatccgat acgtgaggat catagaaaaa gagtcaagac aaattacatt attattactc 109140
atgctaataa tcttataaaa aggggaacac atataaataa tgcattgagg cagagaactt 109200
ttaaatacac ttggggaata tggcaagaat atttaatgac tcacgttaat aaaagatatt 109260
taccaatgca ttatttttatt gaattaattg ataaagatta tgcagtattg aagggtcttt 109320
ctgaccataa accttcttac tttattaatg atttagtaga cgaaggtgta ataaaatatg 109380
tttaccgaga ttcgatatta atagtcattg gagataattt tagtataaat aatcctgata 109440
ctagaatgat tgatcattta gcaactaaag ttattcttcc attaatgaaa acgtataatt 109500
taagttggaa taaaatacaa ttttttgatg agtgtttaac tgactcattt attaataata 109560
ttgataatga tgaaataaaa tataaattacg aatatgaacc aatgtctatg tttgatatga 109620
```

-continued

```
gtattctaag aaatgcagta cttagatata aatcataaat ataaaataat aattataagt 109680
attgtgtggt gataattgga aatggataat aatcaaagac ataagaatag aaattttttt 109740
aatataatga taattataaa tattgtaatt attgttataa taattgtatc ttcagtatat 109800
ctatatatac atataaaattc aggaaacagt tattcaaaag aaacatatgc taaagtgaat 109860
aatgtgtata tgacatatga taatgaagat aaggatatac aagtaagaat tggtaaaaag 109920
aaactaataa tatttaataa tggtaaaatt aaagagatta tatttaataa ttttgaagta 109980
tcagtatatg atgaatatac tttaatatac atttctggag ataatgatga agttagtatt 110040
tctgtagaca atgataaaga ttccatttct gatatagtca taaataatca aagtttaata 110100
gaataattat atagatatat agaagtgtgg aaagaaggtt acaatatatg ctcatattaa 110160
aaatgagaac tgacaaaaaa gtagactata aaaaattatg gtttataaaa cttcatagaa 110220
aattaaatat tgaaattcat tataaatatag aggaaaatgg attctactat attgataata 110280
ataaaacatt aaaacttaaa aaagatttt caagaacaat tagtatgatt cttgatatta 110340
agaaaagatt caattcgttt aatactgaaa tggatataat tgataataat attaatatgt 110400
atcttaatga cgttataaat aactttgaaa aagaagaaat gctaagaatt atactaggaa 110460
cttcggaata taatgtgaag aatctatata atgatcttac tgaattagga attaatattg 110520
atccagactt attatatgta aatttatata aaaatacaaa acattccgaa tataatgatg 110580
aaataaagaa tacatttaaa agaatttgat aacctgaata ctaataatta aaatagtatt 110640
caggttatca atttttatcg agcaaaaaat attttttttcc ttcttgaatg ttttaaggca 110700
ccaatgcgca ttttttcaac tagttcttct ttcttatttt ttccatcagc tagatcttca 110760
ataaataatt ctatactgcc atacgttgtt tgaatatttt gaaagcgatg tctaatttga 110820
tataatgatt cttgagtatc atatagacat aattgcataa aatgttcttg aagatttact 110880
ggtatgctgt caaaatgttc actatgaact gcgtttgcat atactagaat tccgtttaat 110940
gtatattggg gagcaatttc aatttggttt ggatgaataa accggaatgt tgaaggattt 111000
atttgacctt gaatgttact catcatctga ttttcaaata aacttccaga accagaacca 111060
gctctaggag ttcctccgat aattgcacta ttactactat acatatctaa tccaattaca 111120
cgattaatat ttaatacgga agtctctgta tctaaataat aacgattctc atatcccgga 111180
acaagatctt tattaaatac tcggatttct tcaattcttg ggaaatactt actaaacgta 111240
atcaaacttt ctgatcttat tccactaaga atttcttcat gagaaagttc taattgtgta 111300
aatttatatc ctaattttcg ttctaagaat cgataacct ctgtaggatt aatcatttag 111360
ttatcactat ccttccaata ataaaaatac aataccactt cctaaattta attaagaagt 111420
ggtatatttt aaaacatatc ttgtatatat ttgcttaaat cacgtttaat ttcttcttcg 111480
agataaatcc ggatagtttc gtttgattgt ttaatactta atgtttgatc ttcagtaaga 111540
gttactgaac cattctctag attcatagat atacctaatg attctgctaa tgaatataca 111600
ttttcagatt ttttagtaac aaactctaat aattcagaaa cttgataagg aactacttta 111660
cctgaaagat tatatgagtt tgagcttgct gcttctaaca atccttgata atcttctgag 111720
aagtcttcat taatccggtg agtcatatat gagtttggat gggatggaat aacaacccaa 111780
tcatagcagc aaatcattaa aggtgaatga actcgttgat acttcccatc aggcttaata 111840
atattaccaa taccacgcat ggagaatgct gcctttgatc cttgattaat caaacctttc 111900
atgtctctac ctacagatgt atctgcagtt tcaactcgtc caattaatcg attcccatca 111960
aacttagctt cagttacaat atgcgaaata ttgcgttgat caatatataa ttgtctacga 112020
```

-continued

```
ttatcagtat ttaatggatg acctgcttct ccaaagaatg ttctattttt aattttttcc 112080
tgaacaattg ggttttgtat tgcttcatca attgcacgtc tatcataaat acggtttttt 112140
tgttctggtg catcagcttc ttgcaactca gtctcgaata atacattatt aagtgtttta 112200
tctataattt tcggtttaga ttcagtgacc gattccatta taatataacc tttttcttca 112260
gtcataatag taatacacgt cctttcttag tatataaata aaatttataa taaaatgttt 112320
gattagataa ttattttttt aaacaactta tttataaaata ttcttttat cattttgat 112380 aaaatatgtt ttaaatttaa agaatattaa attataaaat aaaatgataa ggtgggaaat 112440
ataaaatgcc aaaaacttt ttagatgtaa tccttgaaga tgcagacgca tttgaagcta 112500
gtaaatctgt tgaagtggtt gataaaaata ctactgaacc tgaagtagtc gctaaagatg 112560
aaaaagctga tgtagaagaa caaaaagaag tatgtgacga aaaagaaaaa gctattgaaa 112620
aagaaaaaga agaatatact aatgatgcag aagttgaaat tactagtgac gtttcattaa 112680
tgaataatgt tgctgataaa ttagatagtg gtatgtctat tgaagaatca ttcaattctc 112740
taatcgaggt taatctagtt aagaatgaat ttaaaaacat gggcttgact tctgaagaaa 112800
ttaatcttct tgctgaagat gcttctaaag aaagaaaagg aattatacgt ggattggcta 112860
aaaaaatcgg tatcgatgat agcggtaatg ttgatgctcg taaatatgtt aatgctcgta 112920
aaaaattagg cgtaaaacaa attactgccg cagtaacttc tacggttgct gcaagtgctg 112980
ctgctggagc tagtagctat tatattgaaa catcaaaaag taaaagcgaa actgttaaag 113040
gtggaatctt ttcaggttta actgtaggat tggtcgtagg ttattgggtt tcccttttct 113100
catttgtagt tactattttg caaagtgcta aagttaaagg tcaaatgaaa agtgatccat 113160
ctatcttaag aaatgctctt gctgaaaata aaaaagattt agctgaagtt gtatcttcta 113220
tgtctaaagt taaagaagat gctaaagcaa ccaagcaatt agaacgtatt caaaaagctt 113280
tacttcgtga aaaatccaaa ttattgaaat tgcaagaaaa attaaataca aaataagtta 113340
tatatgatct caattctgat taatttcaga attgagattt atttaaacat tattatataa 113400
gaaaatatat attggtggtg atttcaattg catctagatg aggaaagtat tagatacgct 113460
ataaaattta cagaatcttt agaaaaaaat gattttgaat atggtcaaac aattcgtgaa 113520
gaaattcaaa atgaaaataa ttcatctcaa ataaaaaata ttatgaatat gctcaatatt 113580
aaaaatccaa atactattac tgttgaagaa tatttaaaga tacgtagaaa aattaaattt 113640
tcgggtctta ttggattctt agcaggtctc ggaggaagcg taatgtttac ttcagatatt 113700
attataaata atgatcggct tagagacgat cctcaaaata gaggagtcgc taatagaaat 113760
aatcgtagta agctaagtat gcttaagtca accttatttg ctttagtttc ggcttttggt 113820
tcatttgctt tatcagtatt atatagtaag agcgttaaga aaacttcagt agctaatcca 113880
tcaatagtta gaagtttatt agctattaat gcaaatgact taagaatggt agaaaaagca 113940
aataatagtg tagttactaa gtctgactta aaatatatac gtagaataga acgaatatta 114000
attagggaaa aaagggatct attaaaattg caagcatacg ttataaagaa aaataaatga 114060
aagaagtgaa aatttttatg gaatataatg atgtattttt agaatattta aattctgaag 114120
aagataatat tgaaaatatg gaagaattcc tatcaagcta cattggaatt aaaccaagat 114180
atcttgaaat tagacctact gtatttagtg aaacaagaat tactaatgat ggtattagtg 114240
atgaagaaga taatagcgaa gaatctgatc gtaaaagatc tactgatgaa gtaaaaaaga 114300
ttagtagaga agtaatggaa aaagataaga aaaagaatct taatccacaa aataaagcaa 114360
```

-continued

```
aaattgcaac tattaaacgt gaaatggaaa aatcgattaa aatggatcca aatagtcttg 114420
gtaatgatac taaacttaaa agacttatgc gtgtaggaat tacaatgtta gtttctttcg 114480
ggattatttt tgctcctgca gttggtgtct taataaagat tattgctctt atcggagtag 114540
ctgctactgc aaaacacgtt aatcgtaaaa aattggaaaa tactattata ttactaatgg 114600
ataaaattaa atatattgaa gatgaaatgg aaaaagcatc agacaatcct aaaaagaaat 114660
atgaattaac aagagtaaaa cgagaactcc aaagaacact tatgaagtat cagtctagac 114720
ttcggaattt ccattaatat atgatttgta taagcgatgt tgcaaaggag gtactattat 114780
attgaaagat gatttcttta attatttatt tgaagcagat gatccagaag aaataagtaa 114840
tattgatcct aatgaagata atactgaaaa taataacgag gatactcctt ctaatgaaga 114900
aagtttacca aacgaaaata gtgatgaaaa tgatttagaa aaggatccag aaatagaaga 114960
acctgataat gaagaagaaa tagaacctaa tgaaaatgaa gacccgaata ataatttacg 115020
tataaaggaa atattatttg agaatttctc tggacttaaa aatgcaatta aacgattatt 115080
tactgacatt gaatcggtaa tacatatcgt aaaatcatat gattctaata atgataatca 115140
taatttagaa aatactgtgg atggaatatc tgaaaaagga tatgacattt taaataaaat 115200
tcaaacatta caaaatggtg taattcttaa tatatcaaac gataaattaa aaatcatata 115260
taatgaatta gaaaatcaag taagtgatat tattaaggaa tattcaaata aagttgatgt 115320
aaagttgaaa aacaagtatt aataatataa acaatttaat ataaaaattt taatttattt 115380
ctatgtaagt ttcgtttatt acttttttaa agtaagaatg atgaacaatt atatataaat 115440
aatttataat attattttta taatctataa ttttatataa gaaaaggaga gaaattaaat 115500
tatgcgtaat tttaaacgta ttacaaagac taatacagat tcttttagta ctcatctaag 115560
cgaaactcaa gactatttcg ctaatactaa aggaacaaat attactggac aagatatcgc 115620
tgcaattata gtgaatgaac aatattttga tgagtatgca actcgtctat tagaaggttt 115680
cgatgctgac cttagtgaag aactaggtgt tcttttagaa aacactcgta gcaacattat 115740
ggaatccttg ggtggaatta ctccatttgc ttcactttca atgcctgttt tggttaaact 115800
ttgggctcgt ttgtctatgg taaatgctat tcctactact cctgttacta ctcctgcatt 115860
tgtagtacca actatcaaac catatactat tggtccagat ggtgaaaaat actacctacc 115920
agaagctatt aatactattc ctgaacactt tgtaagtctt cgtcaactta agaagatat 115980 cactattact ggtggtcgtc tttctgacta tgatctattt acaggtgtat caactgctga 116040
ccgtgctaaa ggtgatcaag tagaccgtaa attccaaatt gttgcaggaa catggtctga 116100
ttcttataat gtcgctgatg ctgctcttgg cgaatatgaa cttaaaggtc aagctcttaa 116160
aatggatatt catggtaata tctttggtaa agtaacatat actactgatg gtaatggtgc 116220
tactaatgaa gatactatta tgggacatgt tgatgttgaa aaaggtcgtt tagatttaac 116280
ttctctttct ggtaaattga ctgagttcaa aattcaaggt ttcgtttctt ctgaaatgca 116340
tactggtaca actcaagttg gttttgatgt tgatgatcgt acaatcaaca ttggtactgc 116400
tccacatatc gaaggtatcc tacctatcga atccgtacaa gatagtaaag ctatgtatga 116460
tattgatgca gcagctgtta ttgttgatac aatgtctgct acttctgcac aaaaagttga 116520
tactgacttg attgaattct tgttacgttc ttatgaaggt actaatgctg cttatcataa 116580
aactttcgat gtacatccaa atggtggata caacatgcat ccgcatgaat ggcgccgtgg 116640
tattcgtgac gttattgact ggatgtctca agcaatgaaa aatgattaca aaacttatga 116700
tgcttacttt gtaattgttg gtaatccaat tgacactcaa ttgattcctg acattgaatg 116760
```

-continued

```
ggaattccaa ggagctactg atgaagttgc gggaattaac gtttcttata gcgttggtgc 116820
ttcttctaca gttaaccgtt ataaagttgt ttcttctgac ttagtacctg ctggagatct 116880
attaatcttt gcagttccta ctcgtgaaga cttcaaaact tacgaatact acccatacac 116940
tttcaatatc gttaataatt acaacaatgc tgttaaccaa agcgttccta acattatgct 117000
ttctcgccgt tatacagttg aagaatttgt tccaattatc ggtaaagtta caattaaaaa 117060
caacgatgca actcaatacg ctcgttaata aatattatga acctttcaga gaccttttgg 117120
tttctgaaag gttattattt ataaaaattt aaattggcgg tgcaaccatg catattgatt 117180
atggtattga aaagaatata tcaaagtact tacatgaaga attactaact gaagatatct 117240
ataatcatcc tttattaaaa aagattgatg atgaatttca gaaaatatta gatgaagata 117300
atattaatga tactaaacta ccagtaacat catataaaaa aattcaaaat ataattaaat 117360
atgtctcaac tatatttaat ataaatttaa ttataacgat tgataacgat aatatcctta 117420
cttatggaat gatgacattt attccggtta aaaatctaac aaagatatct aataatataa 117480
agaagattgt acttcaacca aaaactggtt ttgaatatat taaaactgaa gttattgaaa 117540
ttaaaataca gaaaaaatta atatctttca ttaaggatcc aaacttactt ataagaaata 117600
ataaagttcc aaaaaattat actcctagtg gaagaatatt gaccagtata cttcttcatg 117660
aagtaggtca tcatatattc attggatttg aaattaagaa atctattaaa aatgataaac 117720 tttttttcaat taacggtggt aatggtaaag aaataactat acctagtaat gttaataata 117780
ataaatatgt attaacaagc actatattat ctatattaac gttaagtatt tctatgcata 117840
gttatatgag aagtgaatac aatgcggata acctaccaat acaatatggt tatggtaaag 117900
aagtatttta ttttttcagaa ttaatggaaa tattagaaaa acaaaaaaga aattcaattc 117960
tattaaagat taaaggattt ctaatgtttg gtaaagataa ttattataat cgtaaaataa 118020
agaatcaagt aattattatg atgaaaaaag aattaaataa tgataataat agtcctaaag 118080
ataaggaaat tattatagat aatttaaaaa ctatagaaaa tcttgaatag ataatgtggt 118140
ataacttatt aattaataag ttataccatt aatacgcaag taactattaa ttataataaa 118200
ataaagaaat tgtggtgata aaagtatgct taagattaat attaaagata atcctgaact 118260
taaaaagaat attacttcaa aaaataaaaa actctttat gatttcaata caaataatca 118320
atctttccta gaattagcta ttgaattaaa aagattggga atcagaaata ataagttaca 118380
tttagtttta tatgataaga gtctttccgg agtagatccg tatgacccga acttaactga 118440
taacgtaaag gcaagaattg ttaaagagag cattattaat ttttggtact ttattaggga 118500
agtagttcgt attccagttc caggatcttc agtccatttt gctattcata gagggaacct 118560
tgcaatgtgt ttctgtttat aaataatttt aaataccgta ttaatgttac ctcgacaaca 118620
ttataagaca tatagtgctg taggtttttta tttatggatt gaattattag taggtagaaa 118680
ctatcaaatg atctttttcac ataaatcatt aacggatagt attgccaatc taaaaagatt 118740
gacggctcta tttgaactat taccgacata tatgactgaa cctatcttaa atagtaagaa 118800
tgataagaat gctgaaacta tttttaacaat tgactcaata aataatacca ttaggacaat 118860
tggtccaagc acagatattg cttcagcaga taagtcaggt taacttaatt tttcggcttg 118920
actataaaac ttttttttaatt gctggaacat ccttaagtct attaaactac aacgtaactg 118980
gtaacggtaa gcgtgaatgt ttgaaaatta atagaattgg acaatcagca gccaagcttc 119040
caatgattat tggatgaagg ttcaacgact atcgaaaggg taaatttata ttttaaattt 119100
```

-continued

```
agaactgagt agagtagagc caagacaaaa atttgcaagt ttacttggtt agtaattaag 119160
tgacattaac ttaatgtaat tctattaaat cgaaacggaa agtatagaat aaaaataaat 119220
atatattata ataatgatga gataatttat atcttcttta attaagatta ttaaagaggt 119280
gattattatg gtaagaaaaa acacagaatt tgatctagtt aatagaatat cacaaaaatt 119340
cagtaataat gaatttacct atattgaagg gtttaataga atgatagata aatgtagatt 119400
taaatgtaat aattgtggaa atgataatta ttatacttcg ccatccatat tattggataa 119460
aaataaatct atatactgta atctatgtaa tcctgcaact ttacgaaaaa attcatttat 119520
ggataatgtt aataaaaatt acactgtttt agaaaaacct aaaaataata aacaaaatat 119580
atctgtaaag tgtaatttat gtgatttcat atttaaaaca aggtcacaat atttaacagc 119640
tatggacaaa cctagtaaaa ctcgaaattt gtgtcctaaa tgtaatgcat caaattctga 119700
aaaaatattt gcaaaatttc ttgattctca aaatattaat tatgaaatgc agaaaaagtt 119760
taaagaatgt atcggtatta ataatagagt cactccattt gatttttata tagattcaat 119820
gaatctaatt gttgaaattg atggaaaaca acacgattca ttaaaatatg cattccatag 119880
agatattaaa gaatatgaaa gaactgttgc taatgacaat attaaaaata atttttgtag 119940
tgaaaataat attggattaa tacgtttaag atataaattgc aaaagtaaag aaattgaatt 120000
catggaatca attattgatg caaaatatat tccaaacgta aaattatcca taaatgcaaa 120060
tcttattaaa tattagatat aaatctcatc aattataat tctgactctt caaataaaat 120120
ttggagagtt tattattttt aggttttct ataaagatat agtctatggg gagagaaatc 120180
tcttaaactt gttatattct aagcgaggaa tgaccgttgt atgcgccgta atgagtttat 120240
aaaaactcta atcaattttg agaataacgg aatgatagat agcaaataat cttgaaacgt 120300
tatatctaat actcctacat gcatatattt attaaacgga ctatatgtgt gaagttaggt 120360
gaagtcagtt gaaccactcc cctataacgg gaaacttaag tattatatac taagagtgta 120420
tagactggga tgcgttataa tatggtaagg atattctta aaagaattag acgaatcaat 120480
gaattaaaac cgttaaaaat taatctaaca ggttaatgaa tactaatagg gatgagtaag 120540
tgagcggtta tgaaaatcct atttaagtta tgctcttaaa ttattattag tgcggtagag 120600
ttggtaccta agttataact atgctatcaa aattgaaaag gtggaaacta ggaagatcgt 120660
aaagatgttt aatgtctgat ctaataaata ggaaatgatt tatgaatctt agtggcagca 120720
gcctgtagta gtgatgaagc tcttgtaatg agagtggagt gaaggggcat agtcagagat 120780
tatattaacc aaaataatctt tgatggaacg ctgtatacga tgaaagtcgt acgtacagtg 120840
tgaagtgggg gaaaatccgg agataaatttc aaaggattac ctatcactat ccgttaatat 120900
ggttagatga atatgcgttt ttaaaatata atgatacggt atttaaagca atgcgccctg 120960
cttttacaga agcaagtaaa gctgcaagca tgaatgatac tccgtattca atacttatta 121020
caacaacgcc tagtaattta gattccgatg aaggaaattc atgttataat cttatacaaa 121080
atgcagctag gtttgatgaa aagatgtatg attggtacta tcagtttggt ccagaatacc 121140
ttcaatcata cttggataaa aactctggta atgatttat atatattgaa tttagttata 121200
aagaattagg taaagatgat gaatggttag agagtcagat tcgggcaatg ttaggtgata 121260
gacttaaggt taagattgaa ttattattag aatgggtttc tagtagtgaa gattcaatct 121320
ttagtgaaga tattattgaa tctcttgaag gtaatattat aaaaagggaa aattatgcag 121380
gatccatata tttatgtgat ggaacatata aactagatgt tattaaaaat cctataaact 121440
tattaactaa aacatacgtt atatcaatag atattgccgg aggattaggt aaagataata 121500
```

-continued

```
ccgttgtaac cgttattgat ccagtagacc ttaatacggt aatggtattt caaaataata 121560
aaattactgt tccggaatta gaagatcttg ttactgatct agtgttaaat tatattccaa 121620
acgcagtagt tattccagaa cgaaactatg gtggggaaca actgattgat tatattatta 121680
aacataattt aatatctaaa aatctttttt atgtaacaaa acaaataact actgaaaaga 121740
caatcttaca agaaaataat gtttttagaa aaagaagtaa taaagttaga aaagaaaaaa 121800
gggtatatgg tatatataca acaactaaga ctcgtgatat aatgattaat actatccttc 121860
caatgattgt ttatgaaaga cccgaattgg taaataatgc ttccttattt aatgatatta 121920
aaacgctaga aagaaaaaga aatggtaaga ttgaacataa gtcaaatcgc catgatgata 121980
atttattttc atatctggta ggattatatg cactattata tgaacactcg atcagtaggt 122040
ttgtggatat tattgataaa cccgagttaa ataaggaaga tgaattagtt gataccgtaa 122100
taatacgggt caacatcgtt taactagttc tcaaaaagca tcaagaacta ttaataattt 122160
aagaaaagtt agtaaaaaac caacaagcaa atcaattatt aatgcatcaa tgaatataaa 122220
taacgaagat tctagtatta ataattctat gagtaaaaaa ccacgaagag gactaaattt 122280
agtccgaaaa tataataaaa aataaattaa ttttttatat actatcctaa aaaatattat 122340
ataataatta aatataattg attggaagtg gaaattttat tatggttatg ttaaatgcaa 122400
ctgtaaatga agaatataaa cgtgaaaacg taaatgaaat tattacaaat attagtgagg 122460
atattatgat tgataatatc ttatctcaaa taaatgatac tgatattcag gatctttctg 122520
aagtaagaaa atcattcttt gaatactttg aagaacgtta taactttgtt aagaaaaatt 122580
ataacgatga tgatgaagca atgcaaaatt gccgagaagt ctttgatgat attttaaatc 122640
aaattattaa agcaatctct gaaaaataca gttttgatct tttctttttca gatatcctat 122700 tattcgatac aaaagtagaa attactaaaa gtctatatta tttctttgtc atcaatattc 122760
gggaaaatat tgaaaatatg atttattatt ttatcatgaa aaatagaaaa acattagtaa 122820
aaatgtttaa cactattagt aaagaagaaa gaaagaattt aagctatatt aatcttagtt 122880
ctgcaatcaa taatgattat acgacaatga tatatcattt aagcatgatt attgataata 122940
ttgaaattcc tactaatgaa gatattattg aattaatggt tgaagataat tcatatgaac 123000
tttataacta cgtaactgtt aatacattag ttcttacaaa tttctgcgaa gtaaattata 123060
atgaaaactt ttactcaatc tttctagata ttattaagaa ttctccaatt attgtaagaa 123120
atgttagaaa ctcacttatt gactcattaa aataatatta attaccctat ccttaaataa 123180
tttaaggata gggtttttatt taaacaattt tttataagaa atatttaaag aagggagacg 123240
ttaatggttg actaaaaaga tgagcagttt agaccgaatt aaagattcac ttattttttaa 123300 aggtgaaata ttagatatat acttaccaaa atctaatttt gataaaaatc tatcaacgta 123360
taatggtgaa tatataaata ctatgggtat cttttcattc attgaaaaga aagctggacc 123420
tgaagataaa acaactaaag gaactttacg taaactagaa ttacctaata tgattgactt 123480
tcaatacgat tcaagttatt cttttaaggg aaaattatcg gatgaattac cctctgacac 123540
atacgaagtt tttcgactta ctacaggaaa tcaatttatt gcaaatgtat ttacagaaca 123600
aaatgcttct aatgttaaaa aatttatatc ggctcttcat ggtggtaata ttccgagttc 123660
agtatcttat gataatatta ttaaactata cttagatact ttatcaatta ataaagttag 123720
tttacgtagt ccatcagtaa tttatgaatt gattatctcc gaattatgta ggtatagtaa 123780
agatattaat gaacctttta gaaagattat tgcttcaaaa aataatatta gtccctatat 123840
```

-continued

```
gtatacaaat attaatctta agaaattacc atcaatcaat tctacttttg cggcacttag 123900
ttttgaaaat ccaaatcaag caattattga cagtattaat aagaatatca atggtgaaaa 123960
agagaatgaa tctcctattg aaaggactat taaatactaa tattttaaaa caataaaata 124020
taatcttaat aagatgattt attttttatgt ttattaagtt ttttataaaa aagattataa 124080
tgaaaggaat gaattataaa tatggctaat gatgcaagtt tgacacaact acatccatca 124140
gtttcatccg ttatcaatgc aaatcagtct aattttctta catctaatgg tgtagttact 124200
ctatttgctg cagacacctt tgctaaaggt aaagatggtg caattgattt tgttagtact 124260
aaagatgaat ttatttttaa atacggtact ccagattatt ccaaatacgg tcaatcagct 124320
tataatattg tagagtggtt agaaaatgga ggtcaagcat ttgtcctacg tcttcttcct 124380
gatgatgcta ccttctctca tgcaattctg aatgtacaaa gtaaagttgt atctcaaggt 124440
aaaaatgttt taactactgc aggagaattg gttaaattag atgatgttca tctacgtcct 124500
actactgctt ttattaagaa aaataatcgt gataagaata tgttgatgtc tgaattgaca 124560
aaaactcgtt ctgatgagaa tactgttgat ggttatacaa ataactttgt attgctagta 124620
tatccagaag gtcgtggaga agcttacaat aatttaggtt tccgtatgac tcttaatggt 124680
tctttcgatt cagcagtaaa tagttctcgt gtttataact tcgaagtaat tcaatatgat 124740
tctgaatcta atatgactgt agttgaagga ccattttatg tatctttcga tcgtactgca 124800
atctcagctt ctggggaatc tatgtttatt gaagatgtta ttaatcgcta ttctaaacac 124860
gttaattgtg aatttaatga agaaaacttt aaccgtttga ctaaatctat taatcctaat 124920
gttaacccag gacatattga tattcttact ggtaaatcta aagttcttcc ttctggtaaa 124980
gctgaaacag tttattccga aattactcgt gataacgaag atattcatat ttcattacaa 125040
aaatataatg ctcgtggaga actagtaact cagaatggta atgctgtgct taatattcca 125100
gaccctacgg atactgttga agcagcattg attagtttag ataatggatt acgtgaaaat 125160
atttacaatc tagactctaa taaacttgct tacatgaaag aacaattccc taaactaaaa 125220
actgatagtt ctagcgaatt taaattggct atgaatcaaa ttatcaatgt tccaggagat 125280
gattctcaac ctaaaacagg tgaagtggtt acgcttatta ataataactt tgattcatct 125340
aatcctagca gtctttatag taaatacctt attgctaaag aagcttatat tagtgaagat 125400
agtgatgaaa atctttctgc agtattatca tacgtagatc gtttgtctga agtattgaag 125460
tctcaattta ttgattattc tactaaaatg aatgcttctt atacattaac tcttcataat 125520
tcaccaaatc ctcaacttcc ggcacaatat gcgcttgaac ttaactcttt gactgatctt 125580
cttaataaga aagatcaaat caatatcttt acagttgagc atcaaggtaa actatttgat 125640
attcaagaaa caatcactaa atatcgttta ggtactgtta gtggaagtta tttggaagga 125700
ttgtcattaa tcctaaacaa tgttgagaat gaaattaaat atgtatatga aagcttactt 125760
ccagtagcat acaatggtta tcaaaatgta cctgtagaga tttctgataa atttgattca 125820
tcaaaaccag aaagcattac aagtcgttat aaccgtatct tagatcttca aagtgatatg 125880
caatcaggaa ttattgacaa tacagcaact aatcgtgatg aaatcacttc agtagctaat 125940
gatattacta ttgatctatt ggatgttatt aatgaagtta cattcacttc tagcactaca 126000
aatattgaaa gtgcatgtac aacttcagta tctcatattc tagataatat cgtttctttc 126060
cattctgcag ttcttacaat gattacacct caaggtactt atgactttga tgcaatcatt 126120
tctaatgcta gaactcaaat tgaaactgaa atttctaaag tttctacatc taactctaaa 126180
ttctttaata caaatctaat tgactttttct aatccaatta aacttctttt gggttctgat 126240
```

-continued

```
ggttcattta cttatgaccc agataattta tctgaaagac gtgcttctat taaacaatgg 126300
ttaattaaag catatagtgg atcagttgat tctgatctat tgaataaaga taaatatcca 126360
attgatatca ttttggatgc aaaatatgat agtgatgtaa aagccgctat cggtagtttg 126420
gcagccaata ttcgccgaga tttccaattc tttgcggatg atgcgggtgg ttcatttagt 126480
tcttctccag tagattctct atcatggaga cagacttctg cattcaatat tagttctctt 126540
aacgtttcaa tattctctca agatttaact tactatgatg aatatactgg taaagatatt 126600
cgcttcaccg ctccttatca actagcaagt aagattcctt acaacgcagt acaatacgga 126660
ttgcaatatc ctttagctgg accacgtaga ggtctaatta gtggtcataa agctatttct 126720
tgggttccta atgaagctga aaaagaaaaa ctatatattg ctaaaatcaa ttatattgaa 126780
caagatacta gacgtactaa atttggttca caatccacta cagaaactgg ttatggtgca 126840
ttatctaata ttaataatgt atttactatt cttaaaatgg aacgtgatgc taaagaactt 126900
gtatctagtt accaatttga attcaatgat gaagaaacta aagattctct ttatactgaa 126960
ttgaattctt acctatctaa atatacaagt gaccgtagct gtgagtctgt tgtagctact 127020
gttagtgctt ctgactatga taaacaacaa cgtatcatta aagtaaatat ttctgttaag 127080
tttaacggaa ttattgaacg tgttcaatta agcttcgatg tagctaatta atactacaat 127140
atttctaact agaggtaaat aatttatact tattttattt atctctagta tttattataa 127200
acaattatta cttataagag aggatgacaa acataatgct aaaaccgggt tctagtgcta 127260
gagtctttga taatgactta gctaaaggta aaagcttttt taccggatca atgaatacac 127320
aagaacttca gtttgatcca tttgttacag gatatgcatt tatcctttgg actaaagttc 127380
ctacttgggt tgaaaaatca ttcccaggat tccgtagcca aactcaaaag aattttaaag 127440
aattctcagg aatttcagat atggaactac aaactgctga atatacgcat acttttaata 127500
acaatgctta tcgtttttaat agtggtatta ctaaaaacaa tactgagttt actctaagac 127560
atcaagaatt ctcaggtaat ccaattacaa atatgtataa cttatgggtt tctggtatca 127620
gtgatccaca aactggtatt gctacttatc ctaaagaata taatatggag tatgctgcta 127680
agaatcatac aggggaactt ctatatattg ttactcgtcc tgacgtaaat aacgtagaac 127740
gtaataatat tgaaaaagca ttcttctata cagcagttat gcctactcgt attgcattaa 127800
atcattttaa ctatacttta ggtactcatg atggtgctga agttgaaatg ccatttgcag 127860
gaaacttgca tattggtcca ttagttgatg attatgctaa agaaatgtta cgtaaaacat 127920
actcctttaa cgctcaaggt atgtttaacc ctcaagatgg ttcaattgct ggtgaaaata 127980
ttgctgtatt taatgataat gcaggagtta ctggttctgg tctaggagat atctaattaa 128040
attaaatacc tatcactata ttaatttatg gtgataggta ttttatattt taatttttta 128100
gagaaattat agatatctaa caataatata taaatgtatt tggttgtgaa tctttattat 128160
ttaaaataat tttttaaata ttagaataac aatataatat aattttactt ctacgtgtcg 128220
gtatgcaagc tggttaaagc agacggactg taactccgtt tcgaaagatt cgaaggttca 128280
aatccttccc ggcacatctt tatggaaagt tgtctgagtg gtttaaggtc tcggtcttga 128340
aaaccgatga acgtttatag cgttccgtgg gttcgaatcc cacactttcc tctttttatat 128400 tatggacttt taaagtttag tggctttaag agtcagccaa ttgtttgttt ttctttctt 128460 attccatatt tactttaggg atatatctta aggggttttt gatatatccc actccttttg 128520
acgtgtagct caatggtaga gcatctgact gttaatcaga cggttgcaag ttcgagtctt 128580
```

-continued

```
gccacgtcag cttattttat taatacctta taattaatta ataccttata attaattaat 128640
ataaggtatt aataatccta atacggttct ttagctcagt tggttagagc agacggctca 128700
taaccgtccg gtcgatggtt cgagtccatc aagaaccatt tctctaaaaa agattatata 128760
gagaacagta atattaaatt cagtaatctt attctaagtt aatatgtata tattaataag 128820
atgataatta aagaaattaa ttattgctga ataatattaa atttcttaat aaatagatca 128880
attaacttaa aaaatatcat aacgatcctt tttaaaacca caccttcaaa aaccatgtat 128940
atgattgatc tatttaatga agtcaaaagt attcttgtat cctcctaata tatgaatatt 129000
taaccatttt tttttttttt tttgcaagtt tatattggtt cttgcaaact cttttttcac 129060
gtattatctc ttaaatgagg taatacgtgt ttttattata aaaataaata tatattaaa 129120 tgatgattaa aataatatat agattggatt gatgagacga tggcatacaa tattgataac 129180
gtaagggaaa ctaaggcaaa ggtattaaga acggcaatta attctctgat tgctagatat 129240
tatgaatcta atgatccaaa tactgcacta gagtatttgg agacagctgc taaaatggag 129300
gaatttgttg agaatgacaa ttataattat ttattagatt ataatatgaa gagtacccat 129360
ctagttagac gagtgactag tattgataca aatctcaata aatcagaaac aaatgttgga 129420
aaacaaaaga ttagatgtat gtatgaaaga gaaaagtctg catatattta taatatcaaa 129480
aacaagaaag ttgaaagtgt ttatagaaat aataagaata tttctaagat caataaacca 129540
aactttaatg aagatgatat tgcattaatg cgtaagattc ttgattccga agagggtagt 129600
gctatacata gaaatcttat tggttcttat gtatacaatc atcgaattgg taaatgtgga 129660
gtgattgtcg gaattactaa agcgcatatg tattatacac ttagtgataa gcataataat 129720
actaaaacta atgataccaa gtttgttgtg agatatctag acaatactat gaacaacaaa 129780
caaacatcta ttggtatctg gcgtgctact aaatgttcat ttagtaaaga aatttcggac 129840
tttgcaacat attatactag ttcagaaagt acggaagagt atgataaaga atatgttatt 129900
aattcaatga atcgtctata tgaaattgag aagaattata ctcataaatt ctttgataca 129960
ggactaaaga tttaaagaat attaacgcta atcatccaat aataaggatg attagcgtta 130020
tttttttttt tttttaattt tttctagata cgtttattgc cttcataact atcttatagg 130080
aatcatatgc tatcttttca ggaattacgt ttgaatattt attatggaca tccactaatt 130140
tcttacgtag ttcttcatcg ctagtattaa taattagctt ctgaaacatt ccaaagatac 130200
tcatatgttc tcgtaatcca ctattactag aattatatat taccttatta aattcgatct 130260
tttttacttt attagatcgg caatattcat tatcaatatt ttctaatagt ttattaaggt 130320
cactaatagt ctttatacct tttattttac taatatcttt atgatattca gatatagatg 130380
cgtatatatt attttttagaa aatatactta tctcatcttt attaaaatgt ttgtttaaac 130440
catcttgatt tataatatta attccattcc gaatattttc tttatttcga ctaataattt 130500
cagtaatagt actttgtcta tctttatgtt tctcaataag attttttact ttacgtaata 130560
ttgattcatt aatttgtgat tctaataaat ctttaatata attattatcc atatctatat 130620
atcacctttg tctttacgat tatatttata gaattctatc aattcaagag aaagatcacc 130680
aaaaatagct tgcattgaaa ttccaccatt gatatttaca ttttccatat ccttaaagtt 130740
tattagtggg ttaaggtaat cataattatt attattatct gcaataaata ctcgaattct 130800
attatttttt ttaataacct taattaattt actatcaaag ttataatcat aggtatctat 130860
agttttaata tataacgtag gatcatcttt aaatatatta cgtttagttc catagaattg 130920
atctatttct ttaaatccgt tcgaagcaat atttcctaca gctacagaaa agctattata 130980
```

-continued

```
tggtggtaga ttactatttg tactatcact tttaataaag aatccataac cagaattatc 131040
attcttattg tagtcgagag caaataatat cgctccgccc ttagatggtg aagtatgttt 131100
tagtttaaat gtgataatat attcgtctgg taaagttaaa tttgtactat acatattttt 131160
ccaaatatta ttctttgttt cgttatccct tgaactttta ataatcactg gattagattt 131220
aattttaaca ttattttgaa ttgtttctat aattctacca ttattatatg atggattatt 131280
tgtgataatt tcactaccgt ttatttcttg tatggttgga tgaaaatata ttccttcaaa 131340
agaatcttta gggaaaattt taacaccttt atcatctatt gtcttataat tatataatag 131400
gtttatatta taccatccag aggaaggaac tgtgaaacta gtatatgaat cattatttga 131460
atagctctta atattaatag attttgtttt gatatatgca gtagtatcct tttttgcatt 131520
aattataaca ttaaccgtaa tttttttcaat acttattgat ttacttttaa taatacccaa 131580
cttaaggtaa ctattctttt tattagtatt aaaaatatct gatcttggat gtaatgtagt 131640
tacgctttca gtagtactgt ctgtataagt aataatcatt tcataaccca tactatcaat 131700
atcatcatta ttaaaactac ttgagtactc taaatttgta aagaataatc tattatcttt 131760
aatacgatta atatctcgat agttatttac tgagtcagca gtaaaattta ccgatataat 131820
attattcttt cctttttttta ttgtactatc aagaacatgc acatacctac cttgatcttc 131880
atcataagaa acaaatgttc cattatacga atttacaaac ttatcaagat tatcatctct 131940
aaaatcgctt aataattcca tttcattagg attaaaatct ttattaatat ttacaatatt 132000
ttttgcagta tcaaggttat ttatcattaa tcgtacattt ccactaaagt tgttggtcaa 132060
tccatatttt ttacttttat ctaagtatat tttacctgta aatgatttag tataacctttt 132120 tttaaaatag tatgatggta tactagttag acctttatca tctaacgtaa aaggatctac 132180
atatcgacca tcattatctg taactttacc catttcaaca tctattgatg ctagattata 132240
gtttgcattt aatatttcat ctttattatc tgaaaaatca ggaactgtat gccatggaat 132300
tgtttcattg atatcagtac ctaataaatc ttttgatttt tcatttaatg gatgtaacat 132360
atgttttttt acatatcttg gactttgtac ggttgatttc atatttttttt cctgattaat 132420 aattttattg attgtattta gaatagtatc agggaatact ttaattgttt tcttattaaa 132480
tttttcaaca gtatccatat cattaacaaa cattaataag taccataagt cagttgtttc 132540
atataattcc tcagatacat attccggtct ataaaattgg ttttccgata tatcataatc 132600
aattaagttt gatttaaaaa tattttcata cttttttaac aatggaaaac ctaatactat 132660
ctttccttct aataaataaa agttagatat attactaagc aatatttttat taacgtttat 132720 tgaatttatt ccaccaacta agtcaacaaa tcttgaacta tctaaactat ttctagaatt 132780
atctactact accaaaatat attcaccact tttcaaattt cattatataa ttatatgtta 132840
ctatattctt ttttatcaaa aaaaaaaaa aatgccatag tatattatgt aatatactat 132900
ggcataataa atgttacatc attggatcat tattatcttc agaactattt ttaatattag 132960
atatatttaa cttatcttta gttaaatctt gatttgtttc gttaaataat gtatcaaact 133020
tagtccaatc aagagtagac atatatattt ctgaagctaa tttttttccta aacaatcttt 133080 tcttattatc ggtatcctca ttttgttctg actctgtgaa ataattacct acaataaaat 133140
ctattgtctg tgaaatatta ttaatttgtt cattaacatt agcaatattc ataaatactg 133200
gtgtagggaa attaatagtg atttcttcaa tttttacttc atcttggttt tcgttataat 133260 cttttttcatc atttgttttg ttcttatctt tacgatctcg ttcaccatac tcataacgat 133320
```

-continued

```
atagctcttg aattatctta gtaaagaatt tactaaacgt ttcttgatat ccaataactc 133380
ttcgaacaaa attactattc tgcattgata gatttcttgc aaaatcaact tcattagtag 133440
catcaatata attaattgga acacctgttc cattaactgc cgatttctgt aagaattcta 133500
agaaatcatc attaatatca gcttgtatac ctggaataac atcaatatcg aaaggcttat 133560
ctccattaac tgttggaata aatgcttctt ctgtagcacc taaagtttta agcatagtag 133620
atacactatt tccgggacca atactatcca ttgaaaattc agtagtcttt aaatctcgga 133680
taagttcttc aatagttccc tcaatatcag aatccatatc agactctacg taatatactc 133740
ttctatctct accttgatta attttttacca ttaaatttgt aattaatgta gaaagataca 133800 tttttaggaaa aaatagacta ttatttaatc tagatacacc atactcgcta gtgctatcta 133860
aaggtagatg atacacctga tttggttcta agaatgttat agatatatct ttattgataa 133920
tatagtcttc tctgaccaat ctatatatta catctttaaa atcttggtta tcttctaaaa 133980
agtctttaga tattttatca ctaattcctt ttacaaatat atcagtaatt atcttgtatt 134040
tttcattact agtcactcct gaaccactct gatttgatct agagttataa tacattgtaa 134100
tatctccatt aacactagaa gatccttgtg gggcattacc gttaagagtt cctgcaatag 134160
tacctaatat tgaactacct ttaaatgaat tattgctacc attcttttca atatacacgt 134220
atcctaaaca tactccatca atagatattt taatgatatc ttccggacta aatattttta 134280
agtaagatcc ggtaatattt agattttgaa tgtctttaga tttttttactt gcttttcgag 134340 attcagatac aagatttaga gggtctttat aatattttac atttttagat atagactcat 134400
atacctcatt agcagtactt tctactaaaa tcttttcaat atctttagga ttactttttag 134460 aaaatctttt tccatttttta atattagatg atttaaattc aatattttca tcattcataa 134520
cactttcaat aagattttca atatttctat gatccacgtt aaaagattca tttagatcat 134580
cttcttcaga atcaataaag agattattgg tatctaattc attaaattca tcttcagaaa 134640
gaatactttt aaattggctt tctagatcgg taaccatgat aaacagatca ccctcaatta 134700
atgtattccg aatagaattt cgaataactg tatttagatt atatttatca atcaacttag 134760
acatattacc attgaattct tttttatccg tctcccctaa ggtagtattt tcattattat 134820
aatagtatga tattgattgt tttgttacat cgtctggaga cataatagaa tctacatacg 134880 tatcaaatagc tgtacccaat tccggaaaat actgagatat tagtctaaaa tcatcatatc 134940
tttgccatct tagttttttct tcagcaaact ctcctgatga gaaactactt tcaactttttt 135000 ccttaaaata attgttgtat atatcagaac tttttttatt tttcgtattt ttcattccag 135060
tattcttaac tttatctctc tgtatgtcgg agataaatatc aattatactt cttcctgaac 135120
tgttattatt accgtttctt cgtttaatct tatttaacat atcatgaaga ttacttaatt 135180
tatcttttgg tatatctttc tggttcataa taccgtatag atttttaata atgtttgcat 135240
tatctgccat taaacttatc cacctttcta aattgatgaa aaaaaaaaa tatcatagga 135300 aaaaatttcc ctatgatatt cactaatatt tatttcatat ctacgaatat atatgattgt 135360
tccataatat aagtatcatt acaaacttca attacaagca tttttaatga tgaatccttg 135420
ttatgattaa agcataatat atttatagat ggatgtttac tatatactac tggaatataa 135480
tcactaaatt tttcttcttt atattttca tatgcttcat taatatcttt tggatagttc 135540
aatgatccga gattatcctt aatatttgta aaataaggta tttcagtaaa ttggtctata 135600
tcgacaatta atggttcagg attctttttta cgaatatact taaagccttt gataaattta 135660
gttgatacgg taacactaat ataatcatct aattcaggtt taatcatatc atcatggata 135720
```

-continued

```
ataatattat tattatcatt tttatcaata actattgaga atgtatattt attgtcaaat 135780
tcaagtaatt ttattacatc atcatcacta agcgttatct ttggaatatt taatgaattt 135840
tcactaaaag aatctaatac aggaacaata tgatcattat acgcattaat atcttttct 135900 tctaaatacc atttaataaa aaagtctgat tgtctaataa actttatata gttatcgtta 135960
tagtctattt ctatagagac aattttatct gatttatttt tacgcatttc aaaaaattct 136020
atcatatgaa tagaaaatgt attcttttgc ataaaatcat ttactgtttt cattatacct 136080
tttttatcta gttttcttte aataaaagta gcattgatat actttggtag ttgtttttagt 136140 agtgcgtcat cgtttagtga gggaaatgca aaaccattat taaaaatcaa cctatcccca 136200
acattaagta cattcctaaa ttgatctacc atttcttcaa tagaaactac aatttttttga 136260 gcttcattag gatcatctac aataactta ttattttctt caatatacaa ctataattca 136320
cctacttctt gcatacttc agaatctatt gattctctaa tcatacccaa agcatcttta 136380
atatttggta gattataata tttaatgcaa aattgtaaag ggttattact attataatca 136440
tcaataaatg attctgtaat attcttatta ccttgtttaa aagtaatatt tccgataaga 136500
ctttcaggac taatatttaa cgccataata atatgagggt atagtgcagt taagtcaata 136560
tcggttacat tatcgaaaat catatttgat tttttaccca taatatcaat accgattgga 136620
tgaacttttg atgagtctgc tacaaacgca cctttaattt ttccatcaat cttaggatat 136680
aatgaactat gattattact aattacaaac ccaccattat tataaaagat ttctgtaagg 136740
tttcttaagc atattgtttt cttaagtgct tttgttattc gagtatgtgt taacgaacta 136800
atttgataaa ttagatctaa gaatttagtt gcttttttcga tcatcattaa gagaactgta 136860
tcctgaatgt tatatagaat gaatttatag tagttttttaa tatatacgtt agtgatgtct 136920
ccgtcaccct cttcaaactc atccttttgc atccctactt ctttttttcacc tatgtcgttc 136980 aatttgtaag agtctaagac tcccatagat agcgataggt aagtatttga tattatctcc 137040 aactttttccc ccgcttcaca ccgtacgtga gactttcacc tcatacggcg ttccatcact 137100
cagtttatat tgtcaccgat atattaatga caataactag tcgttaacta agttttcttaa 137160 tttagttagt tgtgtttttat ttaccccggt aggaaaatca gtactatagt gaattagatt 137220
atgtgaataa acagacagta atacaagatt atcaaaacta tttgacccac cttttgatct 137280 cggctttta tgatgtataa ctaagttatc tattcctatt ttatataatg gtatattagt 137340
gataggatcc ttcttctgtt ttttaaccag accgggaata tacattttat accttatatt 137400
gggaaaatta gaactatttg taagcatatt aataaatttt aatattaact catcgttgtt 137460
cttagttttc ataataggcg tccaatactg tttatttatg agataatctt tagtattttt 137520
actggattgt ttccgccaca tccatgtatt aaatataatg tctttatact tataaatttc 137580
agtatcaggt ttcttataca tttgactttg tcgactccaa ctatataaaa ttccgttaac 137640
taagttaata taagcttgca tattagtaac taaattaaaa ttatatatag ttcccaatat 137700
aatagacatt accttttgat aatgaccttt tctcagttca gaccttaata attttttctg 137760
attataccaa aacttactaa gatttttaaa tgagatcatc acatgtccac ttgcaaatcg 137820
catatactta aaacctacaa agttaattac aaagtcctga ccttctttga taatgatttc 137880
actagtttta ttccagttta aagaaacttg atgttttgta caccaagaat ctaaaacagg 137940
tttaaatctt tctacatccc aaggattcgg actaattatt ataaaatcat cagcataacg 138000
aatcattctt atctgcattc gattaccaac ggttttcaaa tattgatctt tacctttttcg 138060
```

-continued

```
cctataatat gacatattat aaaacttatt ataaggatgt gttttgtgaa attcagatcc 138120
attagaaata gcctcattat acatgtttaa gtcattgact aagatttcta gatcatgtaa 138180
taaaacgtta gctagtatag gaccaagtat agaaccttga gctaaaccaa tcccttgata 138240
ctttgtgtct ttagtatcta tagacataag aaactttata gatcttagta gttgcgtatc 138300
tctaattttg tgattatacc ttaatttatc aagtactata tctaaattaa tagtatcaaa 138360
atacttagat aaatcacaat ctagtactga tccattcttt atttctttag tgttatttac 138420
taaagctgac atggcatgtt gagttgagag attacgtcta aaaccataag aatcaggata 138480
aaattgatat tccaaaatag gttctaaaat attaagaata cattgttgtg ctattcgatc 138540
taatatatta gttattccaa gagttctaaa cgaaccatcc tcttttggaa tgtcaacaag 138600
tcttgaatat agttttatat caccttttat tcgtttcaat aataggcttt taatatcttt 138660
gtaatcttgt tttagtaaat catctaaagt ttgaccatct ggtcccggag tatttcttcc 138720
atcattagac attatccgtt taatagcata ttgaatatta ctatctttaa taatatatct 138780
agataaatgc gtaaaagatg gtttaccatt taaaacatca ttatacaatt ttatttggat 138840
tttattgaaa tcaaaatata tagaatgtaa acttttgtg tctatattaa cacaccttct 138900
tacaaaatca agctctgaat ataaatcagg caattatata tcattgtttt gagtgacttt 138960
gggctttccc attaatgata cattacatat catattatcg gtttctaccc aaactttcag 139020
tctgtattca tttaacttca ccgtgactag cagctaaacc gttaaattaa taatataaaa 139080
ttatctacag accttcccac gttccctaca tcatagaata tagtatactt aggttcttcc 139140
tctaggctct gtgtgattat agaaataatc tggttcccat tatataccat ccatctacgc 139200
aacaaacaat acgtatttgg aacacaagtt tactagcatt tctactagca catacctgta 139260
cattcagaag ttcgtcagtc ttaaaagaca tactaaccat atatacctcc acccgaccca 139320
tttgagagga ttgtttaccc tttcgtcaac ttaatgttac gctctaagtt agccgtcttc 139380
acccagcttc acacataaat atcactactt atgcatgtgg gagtattagt gtacatctga 139440
tataacttta gggagttata tagtgtattt gatgtagagt tattcaatat tattataata 139500
ctgaacttta gacacgccta tgtgtatcat agactttctc taaaaacatg tcgcacgctt 139560
attgatattg gcatataacg ccatttgatc taaatatgtt gtatatccag ctacttcata 139620
tatggaagac ttatctgcag gattattgtg ttttcatcc attttatgat atacatattt 139680
atatttaaaa tcatcaggac acattaattc ttcaggaatc gcattattct ttagaattcg 139740
attatatatt gtgataaagt caaaatcagc attccacgca ctagcaaagt caggtcgatg 139800
aacttcattg atataatgaa agaaatcact aattaaatca atttctttat catattcata 139860
aatattaaac gttaagtcta aattatattc tttatatttg ttttttagtt catccaataa 139920
tttagtttta tccaacattg cgtctttata accatcatga tcatatttta atgcaaaagt 139980
ttcaacagta agattccatt catttacaag tgtaataata ttaatcggag cttctgcttt 140040
cttttgatct ggaaatccaa taatattttg agtatctact tcgatatcgt aaaaagattt 140100
ctttagtcca aaaagattat tatcaggagc atgtttttct aaataacgat gaatataatt 140160
atcttcaata ttcttatcag aaccatgaat tcgataatct aaatgcattt ttttaagatt 140220
tcttctatca cgaaaatctt cagacttcat aatattatca tagaatattt ttacgctagg 140280
atcttttaac tctgtagcaa tacttttaaa tatatctctg ttataacatc ttacttgcct 140340 tacttttttct ttatcaatat agtttcttac aacattatct tgaaattccg gtttagtaat 140400
ataataatcc atcattggtt tttcaataat atgatgtttt tttgtaccgt cctcttcttt 140460
```

-continued

```
agtgaccata ataagtttat caaaattatc tactgcacca gaatttcttg catctttctg 140520
gtttaaatat gttgtcttaa ttagttgacc caaaatatac accaccatct aaatttatat 140580
aattccttgt tatttttatt ttataaaatt atattctagt aagattaatg atatcaataa 140640
ctttgttata tccatcgaat ttaaataaat cttttctact tataataata tctttatcta 140700
gatttttagc atatttaaga aagaatctca tatccatatc atgataagta ctaatcattt 140760 cccattttt agaataattt ttaggattat tcttcatatg cctatcaata aatttagtgg 140820 ataattttt ttcttttaaa catgtttaaa ttaaaattat tacttttct accgtttatt 140880 attgataaca gttttcttc actaatatta ttattttccg ccattacttc tttttgtct 140940 aacggtacat ttttgaaatc taatttatct ttattataag ccaataattt actattttta 141000
ctaataagat caatatattc atcatccatg aaaactgatg cgtttgttat aaagtttaca 141060
gtatcgttaa atacatatat ttttctta ttagatgtat cactactact attatattta 141120
catatagtat ttattagata cttaatagat ttaatactat taagagtatc atattccgca 141180
atacggaaca tatatttaaa tacataggaa atataaccaa tactaagata atcaatattt 141240
aacattaacg tatctatgaa actgcataag actttattaa tattcatatt atttttcata 141300
tgacttgact tgatcattag attaagatga ataataggtt ccacatcttc gctttttatat 141360 gatttataat attcaaaaat ttgcggtata atataatcgc ataaaaattc ttcatctata 141420
ttcgaattag ataaaataaa atttatatta tcgtatgaat attccatata gtcacgaaat 141480
aatattctaa ttatagaact attaaattcc ataactgacc gcactgaaag ataagaattt 141540
ttactattta ctatcttatc aatattcttt ataaatatat gattaggtat tttcatttca 141600
taataatcta tattatcaaa attttttata ataaagtcaa tcatcttatc agatattcgg 141660
tgtccgtaaa atgatactaa atctttgata aattcttcgc tgtattcata catatattta 141720
tctaattctt cgttcggtat acttatataa ttatctgtaa atcttaatag tttatcacccc 141780 aaattcccat tactaggatc aatttctatt gtaagtttct tcaatatact taccaacctt 141840
tctataatta tactagcttt agatcaatta cgctttttc aaattcattt aaatgtttag 141900
accaattgaa tgatacttct ttatacctat taatttcatc aatagtcatt aagtttattg 141960
tattaaaatc cagcgatatc aatgaaaata ctttattctt taatgaaccg ataacatttg 142020
tatttataag tatattataa atttcataat atttttaga tatatcttta ttcatttgta 142080
atgaattttc actaataaaa tttccactat ctgatatcac ataatcaata aatactgtat 142140
catttattat attaaatata ctaaccggat cagatatgtc acgcattata ttagtcaata 142200
tagattcaat atgtgaatta tcattattac ctttattata ctgatataat aaaggtaata 142260
tttctaaaac aaatatagtt ctcttagact tccataatgg aggcttattt aagtataatg 142320
atacttggaa tttatcatcg atatcataat aattcttttt tagtaaatct ataaatgata 142380
taatgaattc atcattatca ataatctta gtgatttaat tatattatca tataagttta 142440 atttttaat tatcttcatg cttaattcaa tatttttaat tctaagtatg ttcattataa 142500
tattgtctga atttgattta aatatacata gacttagaat ttttatataa tggaatatat 142560
acatataata tcacgcttcc taatcattct tgcttttcat tatcgattac taaactatga 142620
ttttctaaag aacttagcca tggatcatag atattattga atctttcttt atcgctaata 142680
tctttagtaa atatatttaa gaatgatttt tgatatttct tatcattatc aaaccatgaa 142740
gatataaact cttttccact ttctttactt aattcagtta atgtagtata tacttggatt 142800
```

-continued

```
gcaaagaaag aacttaatcc tactgcatca acatctaaat cattatgtga atcgttatca 142860
ataataatat agcgattatc atcaacagga gtatacttat tcagtgcaat cttttgaaac 142920
tcaattttaa tattaccatt aaaactatat tcaccatcaa tataattgtt aataatataa 142980
aaactatttg taataagttc ctcaatacat ttatcagctt cagcaataat taattcatta 143040
ctatattttt gtaaatcttc atagtttttga attcctaagg atttaagtct tacagcaata 143100
aatccttcag taattccaga taaagagatt aaaaattttg caggattcaa tgaatatact 143160
aatttattag tattattctc agtaataatt tcaatactat atggaatttc catatatcgt 143220
tcagaatttt cagtatatgt gttactgtct tcatcagtaa ccacccattt ttttctagtt 143280
cttctattaa ttctagaaat tttatttttc atttcaccta cattattgct gttatttaag 143340
ctgatattta ctaagatagt ttttacatta tcgtgagaat taataattct aaagtcataa 143400
ttattttttc gaagatcact tgtaactttc ggtaattcat tatttttaac atctaatttt 143460
acgctaaaca tttttatcat ccattctatt tttattttaa caataattcg actactaata 143520
ttaatattag tagtcgatat aatttatttt tctgcattaa aaataatagt tttattttcc 143580
ataaatacag tatcttcaat atcaatgctt ggattcttcg ttaaaattaa atccacgtca 143640
gaagtatgga attcatcatt atggctaatc acaaatattt gttccatatt taaataatct 143700
gtttgtagat ccaatacttc cataaactta cgtctattat ttgtatctaa tgtagcatca 143760
acttcgtcta aatatataat gttataccct gaagatacgg tttcaatcat tgacaatgat 143820
aatgataaac tagtgattgc agtttcacct tgagaactta acttaatatc tgaaagatca 143880
gttccgttat ctttaaagac ccttataaag aaatcttttt cagtgatatc aaaacgtata 143940
ctaaatgatt caccgtaagc aacttttaat aagttatttg tatcagacgc aatctttta 144000 agataattat caataaatat taatggaata cctttcttag gatctaatga ttctttaata 144060
gttttaaagt catcatatac ttttttcaata ctagatagtt tatcggtaat atttgttgca 144120
atattaagtc ttttttcatt atcttctaat ttattcttaa cttcagataa tgcgttatta 144180
ttaatattga tagacgtttc agtattattt aatagatcat tattatttttc taatgttttt 144240 agtctggatg taatatcatt ataaactgaa tcgtatactt cttttttatt aagaatactt 144300
tcatagtttg atctcagatc tttaagaata ttcagtatat ccaatcgttt agatactgtt 144360
ttaatattct tatcatattg atctattgat tcattattat ctttaatact tgaagataat 144420
ttttcttctt ccaaagtact agatttcaat agttcttcat actcattata tgattcacgc 144480
atgatattgt aattttcaat agaccctta atattatcaa taagattgga tactttgtct 144540
cggttgttga tattattaat tagatcaata tataaattag gtagttttac aagactattt 144600
tcaatatgat cacggtttgg taaaaataag tcatcctcat ttaaattaat aatgcttgca 144660
atattacgaa tattattaaa tttaggtaga acttcttgac gatatttatc aaaatattta 144720
ataatatttg acaaattact gatattatta ttagtttcta ttcgatcttt ttctaaatta 144780
cttaaggtat tttctaattc atccaactta ggatattcat tctctttata ttctaaagca 144840
atttgaataa aaggacaact atcaatatta catgcttcag gtcttctatc tagtgttgtt 144900
agtaaattag atctactatt aatatcacta atattttat tgacttccag aatttgagat 144960
tcgatatcat tcattttgga atcattagat ttaaacatac ttagataata ttcgtagttg 145020
tcaaaagtaa tattatcgtc ttcaaagtaa gtactttcat ccatactcat aagatttctt 145080
agagagtcca gaagattacc agtttgatga atactattat acatattatt gtcattcata 145140
atagattcaa cattttccat actagtttca ttcaataaag aatttatatt cttattaact 145200
```

-continued

```
tcagtcagat attcttcatt tttttctaat tcgtcataat acttttcagg attaaattct 145260
ttaaacgaat atattttatt acggtaaaga ctaatatttt ccctaatttt ctttaatcgg 145320
tcttcagaat cagtattttt ttcctttaat gaatttctcg atgtttcttc tttgattaat 145380
ttttctgtaa attgttgatg tttattataa atatcatcac ttgtatattt ttctaatgct 145440
ggaaattgag aatatatatt ctgtaatcct tggtaagatt catcaagact cgtattaatt 145500
gtattaatag tattattaaa ttggtcaatc gatttattaa tatctatttc atcaataggt 145560
agatttagtt catttaattt ttctttaata aaagaactat ccatatcaat attatattta 145620
gtaattgttc tttgttcgtt taaacgttct ttttcagatt ctaatgattt aatattattg 145680
gttaattctt ctttattttc ttttatagta ttaatatcat catacttaga aagatcagaa 145740
tttaatgtct taagattttt atctaaaaaa gataatttat ctttaataac attaaatctt 145800
tctaaataat catccataga aggtataaac ttatataaat aatccttacg ttcggcagtt 145860
ttataatcaa taaagttatt catattatta cctaatctag caactgtcat ataatcttta 145920
gtaattccaa gctcagtact tacaatttct tcaaaccac gaattccacc attttcattt 145980
aattccgtac cattcttaga aataaatgac ttattatgag aagaattatc accataataa 146040
tgtttaataa tatacttatc attataatta atataatgaa tttctttata tcctttagta 146100
tctggaataa taatgttatt tctagagtca tttgtaccac ggtaaggatt caatgcggaa 146160
agaataactg ttttaccaga accattagaa ccaattaaca taattatttt atttttagaa 146220
tgggagaaat caatttcaat tgactctttt cccattccag catatattcc gataaagttt 146280 actaattta aatatgttat tttcaagata tcacatcttt ctaattattt aatcttttct 146340
agacaaacta aaactaaatt taatcttatt actagcggca ttataaataa agtttgtaat 146400
tacatcgtta ggagattcat tattcttttt acatgactta acaaaatctt cataaatatc 146460
atatctacaa tttagtaata gcgtttcagg aatgaaatca atgatttcca tattctgaat 146520
attcatttct tcagtaatac cattattatc aatataattt agtataaata attcaataag 146580
attataatca gagttatta agattcctga ataaattaga tctttttcac gattagtata 146640
attatcaata tacttcttag gaataataac cctaatattt tttctaggtt tatcaaaaat 146700
aactaaattg atctttgtat tatcatgacc aaaaagatta ttagatttt cataatctac 146760 aacttctgta aattgctgat atgacttaca atgataacag ttaattgttt tgatatgatc 146820
aaccgcttta ttgatcgata cttttctttg aatcattact ttattaccac aattgttaca 146880
tattagagta catggttttg tattatataa tgaatttgcg ttattttttg tcatgagaaa 146940
tcacccattc atccataaca ctaatataat ctttattctt aatatctaga aattcattat 147000
ataatttatc aaaatctgga taaaattctt ctttttttact tttaacacga ttaataacat 147060
cattataatt tggtgaaaat aatagatctc gaatatccct aagactatga tacggcaaat 147120 tttcttttctt tacgctatta tacattactt gtgccatgtt catacttctt tcatgattat 147180 aatcaattt tcgaataatt ccaaattttc tagtcttcaa atcaaagcaa accatatttc 147240
gaatatgatt attgtactta gtactatata acatatcttc tttaacttgt tctgaaataa 147300
aatcattagt tgttagttta ataggtgctt ctaaatcttt tctatccact acaattttat 147360 tttttttcaga ttgataataa ttatatacgc cataagaatc atttttacca taattcgaga 147420
tagttctaat attaaaaacc gctcttaata ataaattatc agtactgcta aattcatatg 147480
ataactgtaa attgaaatct cttgcatttt tttccacatc tgaagcaaac tttaaaaatt 147540
```

-continued

```
ttagagcttc accactaata tatgatgtag tagtttatc  tctagcttca ttatatctat 147600
ttaagtttgc attaattgtg gatctaatta tctttgataa tgtaccattt acatcattta 147660
cattaaaatt tttcatgaaa atctctccat tctatttttt ataaatattc ataattgaga 147720
ataattcttt tatttcttaa atcactaata cgatcaatat tgattcctaa tcggttacag 147780
tgttctaagc ttgaaagaat tctaatatct ttattgattg attcgatatc ttttattgta 147840
gtattttctt ttctggaagc atataataaa attgattcag ggtcatttga aaagatattt 147900
tgattgatcc atctattata tcgattatta ataatattgg acgttgtatt cacagtagta 147960
atagattctt tggaatcaat atttcttaca ataccctactc tttttttgtgg agaattataa 148020 gtaaaaacaa tatcgttact aatactttct ggagaaacta ttctgctatt attaacagta 148080
aatttactat tagttctacg tgttaataat ttataactat tccgtttatt tacgttataa 148140
tctaaatcat cactaatctg aaatgataca tatgaaatta atccaccaat attattaaac 148200
gcaggaatta ataagagatc actatattca gatgaaatct ttcttacgtt attatcaata 148260
cgtcttttaa ttgtttctaa tgctgaaatc atttcccctt tagcgtataa tttataatac 148320
tgcttaataa gaatgttaat aaatttgatt gtttctttaa tttcagttgt aggaattaat 148380
aaattatgat aattattatt cctataagtt tttcttttctt taatactagt tgacattaaa 148440
aatcatcctt tcaaaattat tattataatg actatgtaat attgacataa attaattctc 148500
atgtcattac atagtcatta taataatata taaatatagt taaagttgaa aggtaatttt 148560
ttattcttct atttctacat aactgaattc tgaattatca gagaatatta cgcctacttc 148620
attatcgtct tcatcataaa gagattcaat tattcggtta ttagctaaat atgaatcaat 148680
tacttcatta ttcatttcat tagaagagta tactgtttga tcttcatcta agaatattgg 148740
ttctgaagta ttaatatcta cgcacattac atatccaata ctttctaaat agtccacaaa 148800
gttctcggaa tcatcttcaa caattaccac agattcagtc ttttttccctt tttcgttaac 148860 cgatttttta gcatcattat tcttaatagc atttagtctt tcttcaatga gtttatcata 148920
atcttgttct tcaacttcat tttcattatc ttcgttatta tcattttcta agttttcatc 148980
tacaactttt tgaaggtctt ttcggtttgt atttaataat tcatttacaa ttcctttaat 149040
aattaaactt tgatccccat taatatcgct gtctttatta ttaatattgt attctttaat 149100
cttaatatct gccattttaa ctttaagatc cgacattgct ttaattaatt gcatcttcat 149160
tgtcttaaga ctaatcaggt tagatgtctg gtccgtaaca aaccttgggt ctgtcttcat 149220
tctagaattt tgtgccttac ttcccctatc aaaataacct tcagaataag tatataattc 149280
atcaatagat gataattctt ttttaagcat attatattca tcaataagtt ctggatctat 149340
tgaaaattta ggtttatttt gttcttccat atatttaatt tcacctacct attttgtaag 149400
agtatatagt gataatactg cttcattacc aactttactt atcgattcac cttgttggga 149460
taatatattt gttttttgcat taatcaattg atctgcttct ttatttgctt cagcactgaa 149520
taccccacga attgaaagcg tatccccatc ataatcagca cctagagcag cagttaatga 149580
gttattaata actaatgaat cagtaaaata attttctgct actggatagt ctggaaaaat 149640
gattggatag ttttccagat atctatcttc aattttttcga tattcagtat cattagtgct 149700
tagcacaaca atctttgaag ggaagatgct ttgataatta tctactggat atcgagtaca 149760
atacacatgt ttatcagaag taatatcaat agctgcaata tacaataaat ctgttattgt 149820
aaagtttcta tcaagatcag tatgaaatac ttctactgga tattcattac ctttgtcgtc 149880
tttaaccgta attgctttaa atctagcagg tatattctta ataaagttac ttactaactt 149940
```

-continued

```
attaatatct ttatcggtaa attgattttt tacattatca ataaagacat cttcaccttt 150000
tttattcttt acatttgaaa attcttcaat atggatatca ataaagtcat taatatattt 150060
tacaaagaat ggaaagaata atgcacatac ctgacttaat ggaatgccta cggtcccaaa 150120
ttttatttct gtatcgtccc atctatttgt gtttgatcta ggagcagaga ttactgatct 150180
agttgcataa tcaatggatt ttcctaatag acccctatgc actaagccgt tcttaccaga 150240
aatatagtcg ataaatgttt tatatacgtc atatataatt gtctgcattt gagattcggt 150300
atttgttcgg acaaagctaa acgatgattc accatctaga ctagaaccaa aacgaattag 150360
tttagcgtat agatcattaa tctcatctac gtctgctatt cttccggctt ttgatgtgtt 150420
tggattgaag tctcttaaga atgggggaat aacgataaat ttatttataa ataatgtatc 150480
tttatcaaat ttttcaataa tatttagttt actatcacgt tgtaaacttt ctgttttttt 150540
gaatgataat ttttcaaaat tattgtataa gaaacttaca ccggtttctc cgtttacatc 150600
atcctcaact agttgaccat ctttaatggt aaaatatttt aaaccactaa tacattcttc 150660
aattctttta tctaaagata tgattaattt atatactact gggtgaaata ttctggtatt 150720
taaatcaata tatgcaaact gatttgatct cgatttagac ccgatttctc caaatatttc 150780
ataactaaac aatccatctt cagtaggata attcgattga ttaaaaaata ttgggtttgt 150840
tatttttggt aagttatttt gttttactac attatcgata tctaacaaat ttattttcaa 150900
agataaacaa ccacctttct tttttaggta tcacatttta agatataata aatatttgtt 150960
taataatagt ataagtattt aattaaatgc aaggatctta gaaaaaaaaa aataagagaa 151020
taatatgtca ttatattatt ctcttatata ctgatttgtc tagtgaatca atattcttta 151080
atgatattat tatttataag ataacttaca ataatatcga tatcaatggc aaaattttct 151140
ttatcataaa tatctttatt taaagatgta tattcaatac atttactgat gatatcatct 151200
ttactgtata atgatttatc cttattcatt acaatccaga tgatatctac attatttgaa 151260
gtattttcaa aatttccatt attattcaaa tcaattaaca ttttaagaat aataacaatg 151320
tatttaataa attcatttac aatgtgacca ttagtaataa tatcattatt ataataatgt 151380
tgttcgtata tttcataact ttcattagat tcaatttcat taataacaat ctttctaggg 151440
tttagtactt ctagtgaaaa tacatccaat aaaaattcta gtctttttatt taatacatgc 151500 cgattaattc ttgaattctg ttgttgatga ttctgaagat caatattata atattgtttt 151560
atcaagttat aaataatatc tacagaggta gtatgaattt tatttcttga aaatttttca 151620
ttttttcgat atttatatag gtaacttaaa acttttgcat aactgtcatc aacaacagtc 151680
ttatttttac atacaatatc ttttaattca gatgagctaa ttgttaacga taacatataa 151740 tataccccctt ttctttatag ttttattttta atcaatacaa aacacttaga catatctaaa 151800
tggatatcat gaatattata ctcagataag gattttacaa tatgatctac aataatgtgc 151860
atttcattat cacttaagta ttttttatta tttttctag ataatagatt aatctttaat 151920
gtaaataaat ttttatagaa atattttgaa gatttaaata attctgtatt aattgattct 151980
tctaaatatt gcacataact attatttaat aattttttag tattaactgt catatatatt 152040
tgatctttat taaaattaat tttatttttta aaatctttaa gtttcataat catagaataa 152100
taaatccatc cattcgtatt tttatttaat gaataaaata ctcaactaac ataagagtta 152160
gttgagtata tatcctagtt atttagtaaa tatgcagctt gtaaagtatc tttatcaaga 152220
ccataatccc tattaaagtc tccattatta acactaatta ttaaattaga aggttttatc 152280
```

-continued

```
ttttcaaatt ctttaacttg ttcttttgaa aataatgcaa taatatttaa tacgtcacca 152340
tcatagtctc cacctaatcc ggcaagaaca ttattacata ggcttagtgt tttatccgaa 152400 atatccttt taactttggc aatattcatt aataagatac ttgaagtgga tattgaagga 152460
tttcgattta gtataatata taaaccacct tcagttttat taatcaattc ttccatataa 152520
cgatacattt ttttattaaa tgtattttta gtatctatat ggaattttttc agcttccact 152580 aaagaaatat tctctgaagt tgaaataaga ttaattaatg gacccttata taattcgtga 152640
aaagtaatat aattcatata tacttcatcc attttacata atgggtctgg agatataacg 152700
tttcttgcag agtagttaat tcgagtacct aaaatctgtt tacgaattgt tcctctttta 152760
cctttaatat tatttttaat aatactatct acaattttta acacgtcaat ctgtactcga 152820
tactgtaatt ttaacttctg aattttaata tcttcataga tttcttcatc actattgaca 152880
atatctttta acatatttgt atgattgatt aagaaattgt agtcattatt tatttcagaa 152940
agccgaaata gattttctga agcaattaac tgagccggtc tcaatttagg actaaatatt 153000
ggtaagcagt caataaacaa taatccttca aaataccaac ggataaatacg tttatattct 153060 aatgaatttt tctgtttttgt atcaacatac ttttggagta attcaataaa tctttcttta 153120
aattcatcca aaccgatatt ccgatcctca aattcttcat gctcactacc ttcttcatct 153180
tctaaatcaa caatatttcc atttgcatca atacgcttat tatacataat catatcaata 153240
aatttagtac catcaaataa tttgattaat cgatcaaaca taataggatt aactacatag 153300
ttattcttaa aatctacata accgaagtta tcaatattat ccctttcaac ttcaggacca 153360
tagatttctt cagaaaatat tccatcaata gaatatttct tttctttttt tgttactggt 153420
tcatggttag taataatttt atcttgttca attaattccc taaaatcgat aatccgtact 153480
ctagtcaaaa gtaatcaagc atcctttcta acaccttta ggcttttatc atattcacga 153540
ttaatcatta catccacata tgaataattc ttagcttccg cttcagatat ctcttcttct 153600
gagaatcctg agttgtagat tgttctttct tcaacaatat tatcaataat atcctttttc 153660
tttttattaa attttgtaat aatcttctga tagaaggagg ttttactgat aaatgcagag 153720
atcactgtaa aaacaattat tgtaatcata atacattcaa aaataatagt aaacatttcc 153780
atcaccattc tttatttatt ttttttattaa tcatcataat cagttaagaa accttcaata 153840
tcaggtttct tttcaaagaa gaatgttcct gaattatttg gatcatattt cttacagaaa 153900
ggtactacgg taaaagaact tccagggtct cctgaactag tacttactaa atcgatcttt 153960
ccaacaaagc ttggataaat acccctagcg cttactgata atccattagc tgttgcagat 154020
tgtggaccct ttacagaacc ttttagataa cgagtaaata gatccataga attaacatta 154080
tttgagaatc ttactaattc gctgttagga atattattta ctaagtaatc ttctttaata 154140
ttgctaaata gtgtttttaa tttacttaca ttattatttt ttggtccaac taagcgatat 154200
ccgcctttgg ataatttttg agttagatca taaaatagat attcattaac ccttaaacgt 154260
ttattggata aagagtgatt atctactttt aaaatattgt aatagtttgt aatcatattt 154320
ctaacaatcg cataaatatc ttctttatct tctgaacgta atcttaaatt ggatcgagtt 154380
gtattatcta gtaaacgttc aaaggaggat aagatagata tagctttatc aaaagtcatt 154440
gaattattat ttgtaaatac cgaacctagt tttctcttcc aataatcaga atcaaaagat 154500
ttttcataat caattcgatt atatttaaat agatctacta aggttgcaat taatgttgca 154560
ttagattttt gatcgctttc aatccattct cgattaactt ttaatgcaat acttttttgtc 154620 aactggaaga agtaatattc tggactagta atatcatgat cttcagtttt aacgatttct 154680
```

-continued

```
acataattat gaatattaaa gtatcttaga gtttcaacta caccttttcc tgcaaaatag 154740
tagttcatta catttacagt tttcttaaat aatagtgtca ttaacgctct agtttttaat 154800
ggttcaccat tattaaaacg ttcatcaata tcagatagta caaccttttt acccttaatc 154860
ttgattggca taaacattgt tttcaataca ataattccat cattagtacg ataatactcg 154920
gagtcattca tttggaatac tgggaaaaat tcatttccgt taattaagaa gtattgttga 154980
tctaataatt cagggaataa tagtttaatt tcttttttgga ttgtttcttt tccatcagaa 155040
agttccattg taactttaat tctaataaat ctagattcct cgatattaac ggttggatgg 155100
ttaatctttc tagcttttacc tttttttattt tctttctttt cttcagtaac ttgtttttctt 155160 tccttataga ttttccgatc tgtatcaatt tcacatttaa caaaacgaat accttctaca 155220
aattcaagtc ctttaaaaac atcttcaact aattttggta agtttctttt agatctaaag 155280
aagatcactt cctcattaaa tggagctttt tcttccattt tattttgaag atcattaaag 155340
agttttcttg acaagtttgg cacaaacaaa caactccaat caaaatttat tttataaatt 155400
tttatatcgt ataaaaacaa ttaactatta ttagataaaa atttgttttt atataaaaat 155460
aaaaatttaa ggatgtgtat atactatgtt gagaaacggt gaagaatttt ttaatgaatg 155520
gtctgaaaga tcaggaatac ctaaatatga attaaaacgt caatggaata ttatggtaga 155580
aatggttatg gatagcatca tggaagaaga ttttaccaaa acagtattac caagcatagg 155640
cgcttttgaa actattgtta aacctccata tattgctaga gatcctagaa atgaaaaagt 155700
tgttattgca caagttagga agcgaattaa ttttagaata tatcgcagat ttaaaaaaat 155760
agtaacagga ttgttataat tttcgtaata cagatattta tttctgtatt acgaaaatct 155820
ttttaattgt tatttctttt aataatctgt ttttcaatat aaattctatc ttcttgagat 155880
agtccattat atatttcttc taaagattca atatcttcat tatcattaat taatacatca 155940
atatacctat ctaagatttc tttaggtaca ttagttttta aattattgat attatatgat 156000
aaattgatct tagaattagt aaatttatta tcaacaatct ttacacttaa ctgatttcca 156060
tcattactaa tattgatgct tgaattagta cttttcacttg taatattaag ttcaatactt 156120
tttaatattt tgttaattat atttaaatcc aagttaaaac atcctttcta ttcttatata 156180
ttgtacattt atataatata taagaataat attagttgat gaatcgagat ttagcttctt 156240
cgatagtcat aatttctttt tgcatttcct tagctttaac aatttttgaa gaagtggatt 156300
ctttatcttt acaaactaca atatcagttt ttgaagatac gctacctgta actttatgac 156360
cgagtaattc taatttctgt ttaaattcat tatcccgaat tcctgtaaaa acaataactt 156420
tagattcttc agaagcatta ttagataatt cttgtttaat agattttagt ttaaattcat 156480
taatcaagaa tatcaattct tcttcattat tcgagatacc gtttagtaat ttttctgcct 156540
taatatctga aaatccttca atattaataa tatcttcttt cttaggtaaa gatccatttta 156600 caaagaattc gttaattact tcttccaaga tatattcctt acagaatagt ttagagtttt 156660
caatacctaa tccttcaata cctaatgaac caagaatttg ataatcatat agatcacgtt 156720
tgttattaat tgcattcttg atattatcta gtgattttct acctaaccct tcaataaagt 156780
tatcatcaat actatcataa tctatactat ataagtctgt gattgaagtc cataatttat 156840
tttcatataa tttactaata gtagatttgt caataccttt aatggctagt ttatcaagat 156900
agttagatat ctttccaata acgtttccag aacattctgg attattacag tatgcaaagg 156960
tttgattatc attaataact acactttctt gctgacatac gggacaatat ttggtaaatt 157020
```

-continued

```
tgtcaggaat aatatctttg ttatgatcac tatctacttt atcaatatat gttagtgtat 157080
cattcctata ttgtactaaa atttctgaac caatacctaa acctaattct tccgctcttg 157140
caaaattatg gagactttgt tttgtatgcg tacttccatt tgaaaatgta actggttcaa 157200
aatgtactaa tttagtaatt cgtgaaaaay yasswawkws wtasctaaar tcagtamtmc 157260
acaytwttyk wytgywswta rrstasyyta wswrcarwmr aawartgtkr wgtacykwtw 157320
kkagyyatym mtwrggtgat ttttcacgaw wwtcgtcatc taaaatttca acgacaaatac 157380 catcaatcat aaatccatag ttatatcgat tattaataac ttcattatag aaatcattaa 157440
attcttcaat gactttttct actgaattac tttcactagt aatactgaat tcttaaccga 157500
ttaaactatt tgatcctaag atattaaaac tattatctcg tttagataat gtaatttcga 157560
atggataatt atcttcatcg aggaatttaa tatctagagg gacaagagtt aagaatttag 157620
agaatttatg agcatcgtcc ctacctaata ttccagaggt tgcggatcgt ggattaacat 157680
aattattctt tgtataatca tttaactttt ctaaattatc atacgtaata ataacttcat 157740
ttctaattgc gaaaggtagt ttgatatcat attcttgtaa aggatcttta gcgatgctct 157800
taaatacatt agtgagatct aacccgatac cgtctttttcc acgagtatac gccttatcaa 157860
actttccatc tttaaaagta gtaactactg aattcccatc aaactttaat gtaaatagga 157920
atgtcgggaa cttagaaaaa ggtttaagct tattaatcat tccttgaatt acttttggaa 157980
aatcattaat atctttacat ttaaataatg ttcctgtcag attttttatat tcatgcttca 158040 tattaagaat acctttatcc gttttcggta atgatcctac aatttcttca ccagttaatt 158100
gtaagtattg ttgatataat tggtcatatt caagatcaga cataattact gtatctgtat 158160
tataatacat gcttgatgca ttttctaaat attctttttac taaattatat ttatcatgtt 158220
ctttactgtc taaaattctt tttgattctg tataatccac atttttcaat atccacactt 158280
ctttctatat tattatttaa tattaatctt ttttccatta atggtaatat agttatattc 158340
actgttataa gatacattta taatgtccat atcagcatca tatacttcat ctatttcttt 158400
ttcatcaaca tatatttttc cattgtctaa ttttatttca tataatccat cacttataac 158460
tataacatta tctatctttt tattataagt tttagatttc ttaccatcaa tatatatttc 158520
accatctttt aataacacat ttaaaccatt attatatata ttggcatttc tattttgagg 158580
aagagtttta tgttgatgaa aaatattatt atatactttt ttaattttat ttatcacatc 158640
atcacaacct tatttaatct taagatatat cctatcacac tataaaaatg tgataggata 158700 cttttttattt attttttatac ttattaatat caaactagtc tttattattg gtatattcat 158760
taagcatgga ttcaatatct tcatcactta attttttcgat attatcaaaa tcatttttat 158820
aatctggatc agtattaatt tcaacaccta tagatttaaa atatgaattg ataatttttat 158880 tattattact aatagtgtct gatttcttag gtaatttaat gtcaaaagga tttccgagaa 158940
gttgagcttt tactaaatta cttctatctt cagtattatt tgaataagca tcagttaatc 159000
tttcaatagg ttctaaagat cctactaatc ctgaattggt atattccatt tccaattacc 159060
ttcacataga ttcgcaattt ctatgcagtt ctcttatgaa cttctctaag tttccttaga 159120
agttgagact atatctttat cttatttaaa atttctttttt gtttttaagat acttcccatt 159180 tcgcctgtca tttgcttaca gactacatca atagtcgttg aactttcttc caataattgt 159240
tggaagctta gctgctgatt atccattata attgatactt aggaatatta tatttatacc 159300
agaatataat atcttttttat ctcaccatat atcattccaa ttattttttc tatctttcga 159360
taacattcac gcttatcatt actgattgcg ttttagttaa ttggactttta ggagtttcca 159420
```

-continued

```
gcaattaaag aaattttcat catatatcac tatataatgc ggcaaaattt accgactcta 159480
attggagtat tattagtaac attatcagaa tttttcatat ctttagtttt tgttggaaga 159540
ttctggaagt tagtattacc ttcactacga atagatgttt tttcaatagg ctcatgttta 159600
agtctaagca tatatagttg acccatttca ataggcttac taattccact tagtttataa 159660
cgatcgatat tgaatttatc acgaatatct ttaagtttaa aaatatccat atcattccag 159720
aatggtgtaa attgaatata aattccattc tttatagtat cttctagata atgatcctta 159780
tcgctatcac ttaattgatc atatatactg attaatgatt tatacatatt ttcatcaata 159840
gacttaatat attcagataa taaattaaac ttttcttcac gactatccat atgttccatt 159900
cgatatcgaa taacttgaga catcatattg aatgtatgtt caaatgattg tgaaggattt 159960
aatcggttat taacgccaaa aggattaaga ataatatccg ctctattttc taggcaagaa 160020
tctttatcaa actcctcacc atcaatagtt tcaattacag gcatttcttc gtccggaaga 160080
attaatccaa taattccttt attaccatat cgaccagtta gttttgaacc tttcacaaga 160140
ggaattcttt ctaagattgt aaataccgct acaatacggt caaacactct tccctcagac 160200
tgaaatttat ttgcaggatc attaaatgct gcaatcttat tataaaatgc agataaatca 160260
ctactgatat tatttctttt actagataca ataggtttta aatattctac aacttcagag 160320
taatattttg agatagaaat atattcattg tacatctgat gattatattt ttgagatcgt 160380
aacttatcaa gactttcgtt attataaata tcaatgtcaa taacaatacc ttcagcatgt 160440
tttactgtgt cagtagcaaa gatctttctt aaattgacat ctttcatact gaatcccata 160500
tcattataat taattcgacg aattcccatt aacttaccat ctttaatttc ttcaccaata 160560
ctaggaaaag ttctatatga ttcatcatcg ccatatagat ttaatagtac atcattggta 160620
tttagattga tcttaacttt ctttattaaa taggaagcca tcttttgagc agtactctca 160680
gaaacaacaa tagagtcttc atttgtgaat cctttgtatg gaatatatac cgcattgaga 160740
tttttaccat actgaaagtt catatcttcg tcataatttt gatctcgata aattactttg 160800
ttttcaaatt cttcattttc attgatatta tcaattactt cattattgaa ttttagtcca 160860
aagtgttctg ttaaatgttt tgcttctttt cgttctacaa tatgatagag ttcttcttct 160920
tcattaaata atattgccgt gtaattaaat ttattcttgt aaaatttttt aagaagtttc 160980
catctaccat caagcttttt atatccagta gaatatttac ctacttgatt ttcaaaacca 161040
gtaaaaacta atggtggatc agcttgttcc aattgaatat tttgacttaa atgagaagta 161100
aacatttgtg acctattaga gttagtctta tctaagtttg gaatgagtaa tgtttcggct 161160
aagaaatcaa atttaccttt atatttttca tcattaatct ctgttaaatc caaagtataa 161220
ccacactttc tttttttttt taatatacta atctatccat tatataagag ttattatatt 161280
atacgcttat tggatagatt agtacttgta attattaaga tttatttatc attttctttt 161340
tcgatttcaa ttaaattcat gtcagagtca tagtatcttc catctgaacc aacccaaata 161400
tcttcatctt tattaacgca gtcaataaga gtaacaatat tatcattctt ggtagatttt 161460
ggaattgttt taaacacttg attttcacca taagcgtcaa aagcatttct aaattcttca 161520
ttagtattat atagtgtaac aaaatcttta cgtttaaatt taacgtctgg aagagtagga 161580
atagagtatc ctccttgcgg tgaaccatct aatagtttat tatctttaag ataagcaaac 161640
agtgaaatac cgttagagaa tccattaagt tgatcaaaaa cagaattaaa tgagtatcct 161700
gaagccgaaa tacgggactt aacaattagt ccatcaactt ctaaaccttt atatccagtt 161760
```

-continued

```
tcctcttcct taacattttt acccggattc aatttaacaa atgtattaga taaatatcca 161820
aaggcagaac cacctggaat agcttcatca atctttagat gattcagcga agctttagtc 161880
ttaactactg gattaatttc aatcttagta gtaatatgat taatcgcaaa taacatgata 161940
tttgcttttt ctaatgcact tgagccaatt aatcgtttaa tcatctgatt attgtatttt 162000
gcttgtgctg ttgcagacat ctgtccactc atcttttctt cttcactgat gtctttagta 162060
tacatagcag caatagaatc taagataata attgtcggat cgaactcata aattggttta 162120
cctgtaattg gatctaattt acctgtatca tgtttaagtt tatcgcccct gctaagtttc 162180
tctttttcaa taattttac taaaccataa agagtttctg tcgatattcc tgaattaaga 162240
agattatact tttcaagaat cttttcatca tcccacccag taatattttt aatacgagct 162300
aatgatccgg catgctcata atctagatga taaatttcag aattttcata acgatcaaca 162360
atattacatg caatttgttg aattaatgtt gatttaccag acccggattt acctacaatg 162420
gtaaataatt taccggcatc taatcccatc attaattctc ccttactatc ataacttgct 162480
aactttgcat caatctgact gaaacccgtt ctataagttt cagtaaaatt tttggattca 162540
cctaatccat cttcaataa ctcttttta acttcatctg taattaatcc catcatttta 162600
cttcctcctt agatatcata cattataaat cattgttatt acaataaaat aatttttat 162660 ttataataac atcatactac aacattccct tcagtatttt tattttaaca tattttgac 162720 gtaaagtgga gataatttt tacatcataa tttattataa aatgctataa tgaagattat 162780
acttcttcat tatagcatca ttaattctaa tacttagata atattaattt aacaacatcg 162840
tcagtattta tcatttcaaa ttttgacata ttatcaatat aatcacgtag tttatcagta 162900
tcaatcaaat tacaataatc atttctttt acaatgtctg taactatttg tctaaatcta 162960
gtgtctgata tgattacatt tacatctttt ataaatgtat caatgaaaat ttttattgta 163020 tttttgcaa tattagcttt atcaacatca aatattttat cgataatttt atcaatcttg 163080
aatgcataaa aaagtaacat ttcatagttc atatcaggta atttattttt tgcatacata 163140
ataaatactt cgatagggtc tcgctcaatt tcttcagttt ttaataataa ttcataaata 163200
tagtctcgga tagatattcg agataaagct tcttgcattt gattaataaa gactgaagtg 163260
ttatctaatg atatttttc taatattgtg attagttcac ttgcctgttc atcaactaat 163320
cttttataaa tagtattatc acgcatatta tcttcctgaa ttatcttaaa ttcatttaca 163380
aaagtcaaaa atattcctcc tttcttcaat agtaaataat cacaaatata taatatatat 163440
ttattattga atttttaagat cgtttatatt tgagatgttt tcttctttaa catcagcaaa 163500
atctaaatta aatgtatcgg aatcatctag taaatcatta tcaattcctg caccagtaag 163560
aaattgggat acggtattta acgtacgctt atcattaatg cttcccggta aatcttgtaa 163620
tgaagtatat ccatacattg caatattttt atacattgta gattttgcgt cttgtgagtc 163680
cgctctaggg cttaagaatt cttttaatgc atatttagcg tcaatagcac ttaatgcaat 163740
agtttctaag tcactgatcc gtgcaatctt atcttcgttt gttacttggt tggttcttaa 163800
actacgttta ctaatatcta atgagtaggt attctttttc gataaggttt gttatactga 163860
taggtaaaga tatactataa acgtattctt tttcccccag tccaaaccgt acgtgagact 163920
ttcatctcat acggctttcc atcaaattta tttcattact tagaataaat acttaataaa 163980
taactattct aattaatgaa aattagattt gactaagaac tttctctcca ctatttatta 164040
tcatagcttc atcgatactt cattctctct tactccctat aaataggta tcaaacgttc 164100 cctttaaatt aggtatataa atgtacttag gatccacctg ttatttataa caatacttac 164160
```

-continued

```
atataagtat aatatgacaa cctattagtc atattagcta ataaagacta caattttatt 164220
tcgcctatta taaatcatta aagtgattcg tattcctatc catatacatc taccctaacc 164280
gctataagta ttattagcga cttcatccag cttcacacat attaattact caatatgcat 164340
gtggaatatc attaatagca attcatgact attatttagg ttagtcacag cttattcatt 164400
taaagagtta attatatacg catatataat catgcaatcc tcaatatttt tacatatctt 164460
tctgcataac gtttcgcacg tagtctcctt acgggaagat aacctaatgg tactggatat 164520
ctagttctta atggattatc tttatttcca tcatgacgat aatagatata ttcttctaat 164580
ggtacattca taaagtctag tgtttcttta atatctatca gttttggttc atttttattc 164640
ggtaatactt ctaaatagaa attatcatca ccattagtaa atttttttcat atacgataaa 164700 aattgttcgt cactcatttt atcgtaaata tctttatact ttttagcatt agaaccagtt 164760
ttatctaatt tattgaatac gtcaataata tacttttgaa ttttatttct tttttgttta 164820
ttattagata cttcttcatt taattctacc gattcattga gattatcttt tgtatccata 164880
taatatactg ataatatttt aaataaatta atcgaattat cttcagaaat atcatacttc 164940
ttaatgtttt tatctttaaa aggaaacttg tcaatactga attcaataat ctttagacca 165000
tctagatcac ggttatcgta cttatcagta tataacttag aaagataatt tgaactaatt 165060
tccctaattt gagaagtatt tgataatcta atagattcag gataaccaaa ctcaggataa 165120
taattaaata atacataact atcattttct ttgtaataag gaagactaat ataatctatt 165180
aattctttat tttttttcatt atatagaccc attatcataa gttttgtaaa aggttgaatg 165240
tttcttagta ttaagtaaat aatagtatta ataacattac tattcaactt gtgataatca 165300
gtaagagtat cactatactt gatgatattg aatagactca tttttatact actattataa 165360
cttcgattat tatcattaag tatagattca atatacttaa tgatatcttc tttattatta 165420
atatcatttc taaatataat atccattata taatcattaa aatcaatttt tgtaatatca 165480
ataaccgaat cctcatcaat agatattact cttttatata atgatgataa tgggtatctt 165540
acaataccag aacgggtata tttagtaatt gataataatg agggatgaga tattaactga 165600 tctaattta tagatggata taatttactt tctgaatccc tgagtttaaa taattcaata 165660
ccataagttc tcataatggt cataaatacg cttactaatt gaatttctct tatagttgtt 165720
ttatttcctt ctgcacttct aattattaga tcattatcca agtattgatt ataatcttta 165780
atcttatcag agaaagtatt aaactgatct ataatattaa tattattttt atcataatat 165840
ataggaaact caattacctc tgtaaacata tcaatattct ttaacttctt ttcaaaattg 165900
gatgtaaact cagatacttc cattttttca tcgttataat caattccaaa tattctagaa 165960
ttatcatgac tatctattaa cgcaattta cttagtctat ctttagcaga acctattacc 166020
ctatcaataa ttaatgtaac ttctaattta catttatcct ctgaaggact attatcaaaa 166080
ggtatatatt cattattatc tagcattaat gcattatctg taaattttct ttcattccct 166140
aggtactcat tatattttt attcatataa ttatccaact ataattcact tcctttatat 166200
tattcactgg tatatctata tgtttatatt actagttatt aaaatctttt atcaaaaaaa 166260
aaaaaaatat taattattaa atacatagta tataacaatt tatttgttat atactatgta 166320 tcttttttc cttacattat attgattaga aatttaaacc taaccagtat ctagcaaaca 166380
tagatttata tgaaactaaa tctacaataa atattgatac gaaaataacc aatgataaag 166440
caattaccca agataagaat acaattactt tcttagataa attaagatta agtaatctt 166500
```

-continued

```
cttcaaatct ttttagtgta aaatttttca tgttatcttc taagaataat aagattgtaa 166560
tgcattttaa tagttcatta aagattccca caattttgtt actaccatta tttttattta 166620
ctattactgt ttgttttttcc actttctcca cactcctaat attattattt tcattttata 166680
aattaaaaag ttaacctatc atcaggataa taaaaatatc caatgatagg ttaactcgtt 166740
tttctctata tttaaataat atttaaacta ttaaaaatta taatcaatct cagacttttg 166800
aaattcagct ttcattcgtt ttagttcttc tttatcaata tttttttctg acctaatagt 166860
agtacctgtt ggcactttta tattagtaat cattttgcct tgaactgtta ggataatatt 166920
taaagtaatc aatataagag ccaagagcaa taatgaacca ataataaaag atgaaatata 166980
tctatctact ttctttacat cttctttatg tttactctgg ttggatttat atttcgtact 167040
aagattatcc attcttattt tcacttccat tcattttata ttagtaatat aatttatcta 167100
tattacataa tgataatata taaacaaaat atgggttatt acgcttttat aaaaatttat 167160
agttaatgta taataatatt atatattttg gatcatagaa aaatatatat gctttataag 167220
tatatattat aaatttgtag taaaataatt aattatggag gattaatatg aaagaatctt 167280
taaagtttaa tgtcaaggaa gtaagaattc ttagcaaaat cgcatctaat gaatatgcta 167340
atgaggaaag tcggtatgaa agcttttttat ctaaattgga aacatttaat aactttcgtt 167400
caggattttt atatctgtat ctaaagaatc tttcagaaag tggattaact aaacaagaat 167460
ctttaaataa ggctattgat aaatatgtca ataattcaa taagatttag aataatggca 167520
gatatttatt gtaataataa atttatcaat gttgaagaat tagagttcac tggaacgaac 167580
gaaagtaacg caaggaaaca attaactggt taccttaata gactaacaag agaaaataat 167640
aatggtagat atacagctaa gaatattaat ataatatccca ttaaatcccca atttcaaaac 167700 aatattgaaa atcaagaaca actaaatctt tttagtaatg atattaatga tgatttataa 167760
tctaagtaaa tcatcattaa ttatctttaa taaattatga aagtagtgat atttttttgg 167820
ctaaattaaa gaaaagcaaa agacgagtat cctttgaaac aattgttaaa agggttattg 167880
aaaaacattt tcttgaaaag tatgataaag cagaactaga tttagataac gaggaaacgt 167940
atcaaatcgg gttaggttct attgatattg ataaatacaa tatcaatcct gatgatttcg 168000
aaacctctgg aatttattat tacagtaaag ggaaaatatc tttagataaa gattcatctc 168060
ctttacgaac aatgaatgtt aatgtaggaa ctgttaagcc tttatatgac gtaatatatg 168120
aaattgaaat tatttcaagg gtagaaccag aaaattaataa tttaacagta ttaggatatt 168180
ttattaaaga atagatatgg atggtgaaat aacattgaca agaacttatt ctggtgaaga 168240
tattgatgtt ttagagggtc tagaggctat tcaggttaga ccggatatgt atgtaggaag 168300
ttcagatgaa acagtcaatc atcttgttaa agaagcaatt gataatggtg tagatgaatt 168360
tcttaataat tttggaacaa aggttattgt tgacttagat actgaagaaa atattattac 168420
agttattgat gatggtcgag gattacctac tgacattcat cctaaaaaga aaattccaac 168480
aatgcaagta ttgttatcag aagtacattc tggtgcaaaa ttccgtaaag attctttttaa 168540 agtttctagt ggtaagaatg gcgttggtat taaagctgtt aatgcattgt ctgaatatct 168600
ccgagtaatt tctattaggg aaggatacca atattcaatg gaattctcta atggtaaagt 168660
tactaaagaa tttaagaaag aaaagcaaaa agaatacaaa gatatcaagc atggaacaat 168720
tattgcattt aagcctaatg gagaaattat cgataattat gacaaatttg atccagaatt 168780
cattaaagat aattttagaaa agcgtgcata cagtaatgct aatcttaaat taatctataa 168840
agaaaaaggt aaagaagtag ctacgtatca tcatgagaat ggtattcgag actatatcac 168900
```

-continued

```
aattcttaat aataatcctt ttactagtaa tcattattat aaagaagaat tagaaaacgg 168960
cgacttatac gaagtaactt ttggatatag taactcttca gacgaaaata tctatagttt 169020
tgttaatgga ttgaaaactg ctcgtggtac gcatgaaacc ggattcaaaa tggcacttac 169080
aaacttaatg actaattata ttaagaataa taaaatgttg ccaaaaaata tgcaagctaa 169140
ggctattacg ggtgaagata ttcgttctgg attagtatgc gttattaatc ttaagttgca 169200
aaaaacatca tacaggtcac aaactaaaga tgaattatca aaccctgaag tttctggtat 169260
tattaagcgg attacaaatt cagcagtaaa agatattatg gatacaaacc ctagtgaatt 169320
taaaaaggta tgtagtcgta ttattgattt tgctaaagga agaattaatg cttctaaata 169380
tcgtgaaaag attgttaaag atacgaataa tcttacatta agttctaaat tttcagattg 169440
cctttctaag gatccttctg aaagagaaat ctttctatgt gaaggagact ctgcaagctc 169500
tggaattaaa gaattcagaa tctctcaaac tcaggcagta ttcccattaa aaggtaaacc 169560
taagaactct tatggtcttt ctagtaaaag tttattaggt aatgatgaat ttaataatat 169620
cattaagatt atttttggta ctaatgatat taaaaatatt gattatgata aagtccgata 169680
tcataaaatc atctttactg cagactcaga tactgatgga ttacacatta attcattatt 169740
agggttattc ttttatacgc attttaaaga attatttgat agaggatata tttatatcgc 169800
aatgccacct aaatatagta cttatgataa tgtttctaag aaatttattt actttaagaa 169860
tgataaagaa ttaaatactt ttaaattcaa taacattaag aaacgtatta agcttagtga 169920
tgatagtgaa tttaaattaa aagactttat taataatatg agcgaatatc aaaatcagta 169980
caatattgtt aaacagaata ataataatat ttccgatagc gttattgata cattcttatt 170040
acatggtcat gaaagtaatt cctttattga aaagatcctt ctagatagga ataactacag 170100
attcagtaag aataaaaacg gaaatattat tggaatgcac gataatgctt ggcatgatat 170160
taatattgac ttattaaata atgatattag tcgtattaag aaagttatga gcattagcga 170220
cttgtttgaa tttacagata ccaaaacaaa tgaaatttat agtaatgtaa cattaaaatt 170280
tcttatggat tatatcaata gtaaatttac gtataaactt aactatttta agggtcttgg 170340
tgaagcaaat cctgaagaat tgtttgatac taccattgat cctgaaaaac gtgatttaat 170400
tcaggttagg attgatcctg aaaatgaaga atcaacccaa gaaattacag atatattctt 170460
taaaaataat tcaactcaaa gaaaagaata tgtaaatagt tggtttaata ttaaataaaa 170520
ttttatacaa ttcgggtatt acttagagtt aatcccgaat tgtataatta aattaaaata 170580
aaggtggttc atacttttgg ctattattca aaaacaactt gtaaatattc atgaagaaaa 170640
tatggaagaa tactttgttg aaatacttac tagtcgttca attccagata ttaatgattc 170700
attaaaaccc agtcaacgaa gaattattta ttctatgaat aaagatcgaa gatttagtaa 170760
tttaccattt actaaatctg caatgatcgt aggttctgca ttaatgattc atgcccatgg 170820
tgacgcatca ttatacaata ctgcagtaaa tttaactcgt aaattttcta acatgcaacc 170880
attagttgaa ggtcacggat cttttggtaa cgtatatgat cctagacctg ctcaaatgag 170940
atatactcaa atgcgactaa ataagtttag tgaagaagtt ttactagata atattaatga 171000
taactgcgtt gatttcgtac catccttatga tgaatctgaa ttagaacctg tcgttctccc 171060
atcaaaaatt ccaatgattc ttatcaatgg ttcttttggt attggtggag catatcgttc 171120
atttattccc cctcataatc caaaaaatgt tattaattat acaattgatt atatcaaaaa 171180
tccaaataaa tctgaagaat cattaattaa agataatgaa ttatatccga gtttccctct 171240
```

-continued

```
aggtggtatt ttagataata aagatattat taaaaaatat acgactggtg aaggaaaatt 171300
ggttctacgt gcaaagatta ttaaggatga aaataaatct actcttacca ttgtacaatt 171360
accatacatg aaaactcaag atatcattat tgaaaatata caagaagcag ttaaaaaaga 171420
atacattaaa gatattaaag gtattgataa tggttctgag cgtggtaaga ttaaacttat 171480
tattaaatgt tttaagggaa cagacctaaa cgtagtagaa agtcaattat ataagcatac 171540
cggattgcaa agtacgttac cattaagctt tgtattagta gatcaaggtg actttaaaaa 171600
atataatgga attaaacata ttatttctga ttgggttgaa tttagaagaa caactattcg 171660
aagaattaaa acgaacctta ttagtaaact tgaaagaagg attcatatat tagaaggatt 171720
actaaaagta ttagatccaa aagtattaac aaaacttatt aaattaattc gtgaaggaaa 171780
tagtcgtgat ggaattaaac taagtattca agataagttt gatttatctg tagaacaagc 171840
tgaatatatt gttgaaatga agatctatcg actaagtaat attggtatta atgatacaaa 171900
aaatgaatta gctgataaaa tgagggaatt tgacgatcaa tccgaattta tgaaagatcc 171960
tagtcgtatc gataaatata ttattgatga actacaatca atcagtaaat ctaaaaatct 172020
tcgtaatgac tttgaaataa ctacttatga tgataaatatg aatgaattgg atatagaatc 172080
cctgattcca gacgaaaatt atacgattgt tgctacaaag ggaaactata tcaagaaatt 172140
catttcagaa atgaaagtac aaaaacgtgg cggtaaagga attaatatcg gcaaacttaa 172200
agataatgat attcctttag gaattatctc tgctaatagt aaagacaata ttttatttat 172260
tacagataaa ggtaagattt ataactataa atgttataaa ttaccaaacg cttctagtat 172320
taagacgcta ggtaataata tttctaatct tattaaaaag gaaaagttag tatcgatttt 172380
tagctttact gatgatcaat aaataatga taaaaattgc ttattagtaa gtactattgg 172440
taataatatt aagttagtat caatgaccga actaaaaagt atgaatgaat ctggattaat 172500
tttatctaaa cttaaagata atgatgaagt aacaagtgtt aaattagtag acattactga 172560
atctagtaat gtaattggta tcacttctga aggtatggtt attcgttacag acatctcaaa 172620 tattccagtt attaaaagaa ctacacaagg tagtaaccta tttaataata aatatattac 172680
agaaagtaat aaacttgtat cggtatctct agaaacaaaa aatactactg gtctgtatat 172740
tattactaaa tcaggattat ctaaacgtgt aaagattgat gaattcagta aatatcctag 172800
aagggtaaaa ggtgtaatgg ggattaatct aaaagatact gatgataaag ttgtatctat 172860
ggaaacttat gaaaatgtag atgaccataa tcttatcatt atctcaaatc agaaagcaat 172920
ttccatacct cttagtgata tttctgagta taagagacct gcaaaaggac taacacttca 172980
gaagcttgaa gatgacaact atattattga ttcatgctta atttagtatt agagggtaag 173040
ccattgttta ttgatggctt atcttttttt tttttcattt atatataaaa attaaccttt 173100
tatataacaa tattatatac tattgaaagg ttgtggaaaa taaatggcaa aagaacttat 173160
tttagatgtt tctcatcatc aagatcccaa taactttaac tgggctaaac ttaaagatga 173220
aatcgatcta atactaattc gtgtacaata tggatcaaat actattgacc gtcaatacaa 173280
gaaatttgtt gagcttgctg aaaaacataa aattccttt ggtcactatg cttatggtgt 173340
atttgttagt tctaaagatg cagtagttga agctaataac ttttttaaaac gtggtgatag 173400 tgaagctact gtatggattt tagatgtaga atccgacact attgagtcat gtaaaaattc 173460
tcctctaggt gaagcttctc aagcatttat cgatactctt agcaaagccg gaaagaaaac 173520 tggttttttac tatgaacatc ttatattgga aaatatggtt tagataatgt taaagctgat 173580
ttccgctgga tgccacgcta tggaaaaaat gatggtactt tatcaggaag tgctaaacct 173640
```

-continued

```
gatatttctt gtgatttatg gcaatatact agtactggta agctaaaatc atattccggt 173700
agtgctttag acttaagtat tcttaatggt aagaaggata ttaaatactt tacaggtaaa 173760
gcatcatcaa ataaaccatc cactgttaaa ccatctaagc cttctaaacc tagtgattca 173820
aaagatactg taaaaactac tagttattat gttactgcaa ctaaacttaa tattcgtcaa 173880
aaacctgatg ctgatagtaa atctttagga acattggatc ataatgatcg tgttcaagtt 173940
atttcaatta gtaaaggttg ggcaaaatta aaatccggta gtaaagaagt atatgtttct 174000
gaaaaatata tttctaaaaa agcaaaatca aataaaccga aaccagtaac cactaagact 174060
tatacagtcg taaaaggga tactctttct ggtattggca aaaaacttgg aaaagattgg 174120
aaagcattag cttctaaaaa taatattaaa ggtccagctt acgtaattaa accaggacaa 174180
aaaattaaat attaaatatt ttattcacca tacaaacaga tcattatatt tagtgatcac 174240
atatgtttgt atggtgatct ttttaagaaa gagggtttga aaagttgact aaacaatcaa 174300
tattattaaa tagttttgaa gaaaaaattg aacaggcatt taaaaatagt agtaatgtaa 174360
ataaattagt aaaaattgta agtcaatata ttgataaaaa tagtgatata ttaaatcata 174420
atacacctac atatcgacta gtgtttgctc gtgaaggata tgatgctgaa gttatatatg 174480
atatagttaa tatatatcct gaagaaatta aagaagttat ttcacaacta acatttattc 174540
gaaaagaatg gaaagtaacc aatgaaccct tttcggtatt aatgacttta attattcgat 174600
attttcattt aaaaaataat cgtagagcat tgcaatctgc aataatgtat ctttcattat 174660
cattttattc atcgttacat tttagatcat ttagatatga accgaacgat aatattatgc 174720
agtatacaat taaccgtgta agtaataaat tctactttaa acagtacggt acagtattta 174780
aagcacttaa tgctactgct gacaaagcag atatgaatct taaaaactct ttaaaaaaga 174840
atgatgacga attaattatt gcatatatga catccctaag aagtcgtctt gcaaaccaat 174900
taactacttt tgcccaagag tttttataaag accatgcagc taataattat ttaaataagg 174960
tatcggatgt ttatgatgac gaaaaccata ttgaaaatac aaatgtttct ggaattgtga 175020
tgtcacaaac tagtaaagta tctcttaact tttatcaatc tagacttaat gaaaaatata 175080
ttatgatatc tgcatctact tctaaagtta cggctaatgc agtaagaaat acattagaag 175140
atgttaagga acatgaacga gaaaaagtgg aaacgattat tcgtaataca atatcaatat 175200
atttaaatga tcgaaaaaat tcggtaaact caatcggatc acagaaattt atcaattatt 175260
gtattggaat atatacaaaa agtaatacaa aagaaaaatt ggtattagaa ataaaatcaa 175320
tattaaacta tttcttaaaa gaatactgtg ataaatataa cagtactgat agggaagcta 175380
ctaagaataa ttatcgtaaa gctgtatttc tttactttat attcttaatc agtgcaaata 175440
actaaaaaaa aaaaatatta aagaatatat ccatataacc aataataggt tatatggata 175500
tatttttatt gcttatttaa atttcttcag tatccctttt tattaattca tttacttttt 175560
ctgatataaa tatagtggat attcccattg aaatcattgt aatcagcata agtgttaata 175620
acgctaaaat taaaatttgc ataataatca ttataaccat cctttttaaat tttattttc 175680 aattacagta cttgtaatat taccatcagt atcgactcca gtcattacag tgtatgtatt 175740
aactacagca ccatctgcaa atacgccatc agttcctta gatttacaa atacaatgta 175800 tgtatgttcc ccatgaggac ccatttgttc attgtcttct gtaatatcat aatataaatt 175860
actagtatta atatttccat attttttaga tacaattgaa gctagatctt cattagataa 175920
tgttgttgac atatatactt gttgataatt atttagatca acttttttac tatttttac 175980
```

-continued

```
ttgttctttc atttcgctta atttactttg tttataatct actttatcaa tagataatgt 176040
ttttgattta gtgttatatt taaccgtttt atctttaata ttgaaaataa gatttccatt 176100
tttatcatct ttagattgat atttgtcaaa tttatcattc aatactacat tatcatctac 176160
atgaccgatt tcaacgctag tataactacc taatactaaa tgatctttag ttaattttac 176220
atatccttga gtatcttcat tataatattc cccagtaact gtattgatat ctggagtctt 176280
ttctttttta attgttactt tcttttcttt tttcttattt tctttagaag gagttttagt 176340
ttcaattttc ttaacgtcat tatctttctt tacaaaagta taattggttg acacaatccc 176400
aacaaatatt ccaagggcaa tagctacagt aataattcca gttagtatta atttcttttt 176460
catgttgatc catcctttc tttttttttt tatttaaatg tctaataccg aatagctaat 176520
cgatattaga cataattgaa aatttattat ttttattaat ttttttatta attaaatttt 176580
gaattttaat aacttctttt ttaaattcta agtttctatc atctatacct tggataactt 176640
tatcaaattg attatatcca ataatattta catatccttc tagaccagaa cctttttatat 176700 ccttataact ggatataata aatgattttg cattactttt tacatataaa tttgaattat 176760
atgaattatt agtttttcta attttaatat atgatgatac cattttctta acttgttttt 176820
cattcacaaa taatactttta tatttatcat tgatatatac ttcttcagga ataattcttc 176880
tttctaacat gtatggaaca ctttttattaa atgtaatttc tgatgtatca ttattataaa 176940
taatattatc atctttacga atattaatat atttatcaat atcttttaca gtatgaactg 177000
cagataactt atcgaaatta atatcaaatt tttccatata aatataaata tctagttcac 177060
cgctaatata tttaccgtta tcatgtgtga ttatagatac ggtagttttc gtagttccat 177120
taaattcaga tgtttcgata ttatgcgtat taagaattat atacttaaga ttattattat 177180
ataatttttt gatctgtaaa aataagtcat ttacactata cattagcata atagttaata 177240
ccaacttcca ttattaattt ttaatactag gataatatct attaatttag atattatcct 177300
agtgatattt tattaatctt caaatacaac gaatccgtag atattaattg gatcttctac 177360
ttcagtaatt acactaaatg tatttccatt agcaccacca ttatcttcta ctacataacc 177420
actgtgaccc atcacttcag taatattatt atcctgtagt tctttcatct taccatcatc 177480
aaaaaagtca ggatcaattt catccacccc taatgtataa ctttctgaaa tgactacatc 177540
tacaccatac acttttttaa tttttttccgt taatttactt acgtctaatg acataataaa 177600
cacttcctta ttatttattt tatttcatga ttataatata tatttgtaaa tgtctttatt 177660
acggattaat cgatattctt ttccttcaat agtatttata tttaatgaca taggattaat 177720
atgtggatgt aatactacac gtttataact gaatacctga ttcataagtt caataatatt 177780
gtcagcatca aaattatcgt ttatatattc aatactgtat ataatatttt tatgcattga 177840
aacatttaaa ccaacatcaa tattattctt atctaaatat tctttgatta gattaagtct 177900
atttacgata tcatattggt ctggaaaaca gttcattaaa tggcttgccc ttccttgaat 177960
attttcttca attatcataa tttcttttat ttgttctatt atattatcca actaattcac 178020
taccttcttt taatatattt gataattctt tataatattt tccttccaat gtagtaataa 178080
tattatcatc attgtctaga aatattaatg agaatatctg gcaactattt cttgcaataa 178140
ataatttatt aacttttttca ccttttttcta agaatgtatt aagtttaata tcataatact 178200
tataataaag acttcgcata atccaaccaa tatcacgttc ttcttgaata tataatgtat 178260
catcataatc tggaataata tctaattcat atatttttc tgaatcatca taattgtatg 178320
aactaaactt atgttcacta ttaattaagg tatgtggtct atcaaaataa catttatcct 178380
```

-continued

```
ctagtattgt acgattaata tcattacgta aatatcctaa gaatatcttt ttataatgag 178440
tattattagt aatccaatcc gaaataatac taaaatcatt attatttaat aactggtttg 178500
attcaatatt atccattatt aaacaaatat ctatagtttt tgtttcttga ttgaatattc 178560
caatttccca tacaaaacta aaccagatct tttttacccat atatccagtc aatattcctg 178620
caagaggatt ctctagagat atttttacta aaggtgcagc caatccatta ggagtgaaac 178680
aacattttgt tttaacgcca atattcatta tttcatcaac atctttagaa aagtaaataa 178740
atttattact atgattattg gatatattca ttttagattc agatacatta tattttgtac 178800
ctgcacgagc caataataca ttattgatat atttattcat ttccttataa tttaggtcag 178860
attttcgaat tacttcataa ttcataaaag gtaataattt aataaactta tcattattat 178920
atttagataa tgaactttga agaaaattat atgcttcatc aatataatta ctatttactt 178980
ttttatttgt aatatattta ttagtaactt tattaggaaa ttcactaaca aatcgatgaa 179040
tggatatatt attgactacg catttatttta aaatattcat taactgttca tatgaaaata 179100
aattaaacat acgatataaa ccatttttct ttttatattt aacaaattgt atgtcaaata 179160
attcaggttc taatttatta tcaagattat tattgtacca gtccttaata agctttatca 179220
tcttatacat tctttttttta ccaaacttat catgcaaaaa cagtatttca tgttctaatt 179280
taaaatcagt aattgaagca ccaataccaa tatttaattg atgtaatttt tcaattattt 179340
taatttcatt atagatttca ctgtcaattt gagaaagtga aagtacatct ttatataagg 179400
atgcaatata ttcttcatat agtacattat tattcttcaa tttttttcatc accacgcttt 179460 atagattcaa atatattaat atacttatca tataattttc taaattttcc agtttcatca 179520
atatgcaaat agtatgacat cttaccaagt aattcataat catcataata acaagatccg 179580
gttttcatat atgaatataa gttattacgc atatcatcat acttttctga acttaatgtt 179640
aattgatttt tatgatttat cgtaatccca gtaatattac gcatattccc tttaagatag 179700
acagttttac tatcattaat tttaaattta tcattatata tcttgaatgc ctgattacat 179760
atcttaatga taaatttttt attaaatagt ttattattgt caatatttgt tgaaaaagta 179820
atatcatccg aatatgaaga acaaattatt ccatatttat ggaatatggt ttgtatatga 179880
ttaataatat ctaccataat aatattcgat attacgccag aaactggatt acctagaaac 179940
attttatcat tttcatcaac aaaacctttc tttatagtat ccatatattt atcagtaacg 180000
ccatggaata atagtaatat gaatctacta ttaattaatt tccaatcaat actaggaaaa 180060
taattagata tatctacttt aataatatat ttattattaa ggtgcattaa tgcattatct 180120
tttatagata catttttttcg ataagccata atatttggat atttcaagtt tgatattttt 180180
ctatctaatc ttttatcgag gatcttagaa atttctttta atgtattttt aatttttata 180240
tttggatcaa taacttcacg ttctttacca ttttttttcta tcttgatttt cttaaataat 180300
tcaatattat tgtcctctaa gtctttaatg atacaatata actgaattat ttctagagac 180360
attcttcttt ttaataataa ttttatatca ctggcatatt tactttttaag tttataaatt 180420 agatatttac tattactaat tttagagttg ggatataata atatatatcc tttacttact 180480
gatacaagag gtgtagatga aaaagatcta tacatactaa agaattcact atattccctc 180540
agctcaatag aattctctaa taaatatttt ttactatagt taaaatctat actgttggat 180600
gtcttataat aattcataat cttaattaat aagtcataac tatccttaaa tagtatatta 180660
tttagctgaa ctaacttttt ttctgaatta tcaaatcttg atattatttt aatatcttta 180720
```

-continued

```
tcatatggat aaaagatccc tttattagtt aaaattctta atggattctt actaattatt 180780
aataaatcat tcaatattta tcttcacctt tcttttttatt gttttcaaaa aaatttaaaa 180840
tgaccgaaca ttctttatac taataatgta taaagaatgt tcggctagta tattttagat 180900
agatgtatac ttttactact caaatataat aatacaaatt atgttagtac gaatatacag 180960
tataccgcac gcgctgagtg cggtatacta acacgcaacc gaaatctatg aggtgcgtgt 181020
tagtataatt aatattacag agaatagtgt taagtgtttg aatgcatatt aacgatacgt 181080
taatgcttat caaatattaa atgatatatt gagaaaaact aatattatat tgatagctta 181140
atatacatct attaaaacca aaattatatt atattattta cataaaataa taatttttta 181200
ttatatataa aatcaaaaaa caggaattta ttgaccgggg tccgaataat gtcgatttat 181260
cgcatgaatg gacccgaagc aataaattgc atgtataatg gaaataattt tttgactagt 181320
gacgattaca tcacatatta atcattttat atataatata ttaacttata aattgtaaaa 181380
tccaagaaat ttatgaaacc gcagctcacg tcccgagtaa tttataactc agaaatgtga 181440
gctgctggtt ttactaaatg ataatgatag agacttttt gattagtgaa gattacatca 181500
catattaatc attttacaat ttataattac gtaaattaaa taatattttg atttactgat 181560
tattaatcag tctaaaatat tccttcaata taatgatata tacttaaaat ttaagtaaac 181620
tttaaaagca tatatttgag aaggatactt ataattaata gtaaattgta gaatctaaac 181680
aaaagaattc agcacttcat tcgtacctga cgtaactagt aaggcaggta cggaaaggat 181740
gtggaattac tttaataatg atagaaactt ttttgattag tgacgattac atcacatatt 181800
aatcattcta caatatacaa taaatattaa aatttaagta agatttaaaa tcagtgaaaa 181860
gatttgtgag atgtcggatc ggatcgagaa atacttgtat gaagcgatca gatactctga 181920
tatcaaacaa tcaataaaat acgacatata ttgattagtg acgattacat cacatattaa 181980
tcattttata tctacttaaa tttataaatt aataataatt tttgcatctt ctttaatatt 182040
aacactttcc ggtctagaag ttttttagaga agttctatca ttaaatcgag tatctttaat 182100
aaattctaat ccatcaatat taattctttt cataaactgt ttagaatttt cattaaatga 182160
tgatgaaata tatttaatgt cattatcaat aataaatttc tttagatctt caaaaatata 182220
cttaatactt gaggtaattt ttttattaaa tggaattaca atgtcttcaa tatacaataa 182280
tttactatgg gtatccgtat taaagcttct attgttaaat tgaacgctct cattttccgg 182340
atcataacca taaatattag atattaaata tccataaata tcattgttat cattacgaat 182400
aatatatgat ggagacttca ttttcctagc aattttcttt aattcagaaa tatcgctatc 182460
ttgtttccaa acattctttt caacgtataa cattctattg aaccaacccg gtgatgcctt 182520
ttcaataata acttcactat atggagaata ttttttaata atatctttat tatcagaacc 182580
aatatattta atattatttt tacgatctaa taccgtaaat acatatcttg agtcgtcaaa 182640
tgatgaatat ctattgaagt tattttcata acaaattagc ccttcactag aagatcttaa 182700
tctctgagta tatgaaactt tataaattact attaatatca ttacgtaaat atcctaaata 182760
tattttattg tagtctgaat taatatcaag ccagttaata atatattcat attcattcat 182820
gtctaaactt tttgacgatt caatattatc tagaattaaa ttggtttcat atgatttagt 182880
atcttcatta tattcaacaa tctcccatac aaaactaaac cacgtttttag tatcaaaaac 182940 gccctcaaga atccctgcga ttggactttc aatagcgggt tttaataatg attttgcagc 183000
accgtctggt ctgaaacaac ataatgtacg gaaaccaatt gaattaatgt ctactttttc 183060
tttagtaaat ttaatcatat cattatattt actatcgtca aatagcattt caccattaga 183120
```

-continued

```
agtttcccca taggataatc ctttttttgc gttatcaata atattaacat actttcttag 183180
atcactaata tttttagatt ccctaacacc ttgataatta atatagttta atagcttaag 183240
aaagtcttta cttttataaa ttcttttaat atatgctaat atcgtatcaa tatatgtttc 183300
atcatcatcc agtctttcta ttgcagtctt tggaaaattc tcgataaagt tatgaagatc 183360
tattttattt tcagaattac ccttattata tgcatatgag acaaaattaa gaagtttagt 183420
tgcattatca tatgagattc gaattaataa tgaatttaat ttacttccat aattactatt 183480
tttttcttta agatttgata tagtaaagtt actagtatac ttatccttaa acatttttgg 183540
attaatacct aaatgtgact cagatataag atctgtaatt tggtaaacat cctttaattg 183600
tttaacaggt tctactagat tgatattact tcttaaatca ttatttaatt tatttgttat 183660
ttctaaatcc atattaaatt catacttatt aatgcgatca ctgagaatac tatcttcgca 183720
tgataacatt agcttcataa tattgattgc ttttttctga ctgttatata atgcggatag 183780
atatattaat gcactagtaa gtctttcact attgattaat aaaaattctg gaggaataac 183840
tctaaatctt ccaatgtcat gtaaagaagt aatattattt attacctgta atagatcaga 183900
attatccatt gtatagttaa atttagaaca atagtctaga aaattagaga atatttcatt 183960
taattcgttt agataatttt tcatcatcta tattattgta gttgtcatat aaatacatat 184020
tatgattcac ttccttattt attaatcaac tttaggttca ttaattaatt ttaatttaat 184080
taacgtattt tgatattcat ttacgagatt ttccatttta ttagtattat cgatataacg 184140
ataataacta attctacctt taagttcatt aaatgtcatt gaaatattat taatattatt 184200
tttattctta gataatttaa agaaaatagt ctttagtagt ctatacattt tcctatctaa 184260
tgtacattga tcattgtgat taattcgaat ccctgtaatt cttcttttgt tattcgacat 184320
tttaatagtt ttttcatctt taatagataa attactataa ttatatactt caaatgcctt 184380
attaagaatg aacttcaaat attttctatt aaagaattca cttttctcgt ttgatgaaaa 184440
agtaatatca tctgcataaa tagagaatgt aataccacta tcaattaata cattttttaag 184500 atattttgcc acattactca ttaacaagtt tgataatgat ccagaagcag gattcccctg 184560
atataatcca ccagtctctg gattaataaa gatttctttg aataacgtat ccattactga 184620
atctttatta ttcttcttct taaaattttc tttacctaac actaataatt taaagtactt 184680
actaatatct tcatatctac aattatcaaa gaatgaagca atatccattt taataatata 184740
tttattattt ttatgaacta atgcgttatc tagtatacct tttttctttt gataagcaaa 184800
taaatgtttt tcaacacctt tattagataa ttgagtttct aacattccat taaagatatt 184860
attaaatttt ctactaatat ctttaatatc attatgtgga gcatagatat ctctaatttt 184920
tgtaccttga ttaatcttga aatgttgata taatttttca ttattattct gaattaatat 184980
tctggttaat agtaactcta gtaataatgg tttattattt ggttgatctg gcgatatact 185040
tatatctaat aaatatttaa tcattttaat catttcttta tcatctgtga ttttataaat 185100
attatattta ttgtatatat catttgtatt tgtaataata tagagataac catcattcat 185160
ttcaatatat ctatgagata tattgagatt tctataggat aattttatac tgatattatt 185220
aataaactct gtaattaaag ttttatcata agtaacaact ggtaaatcgg gatatccttc 185280
attaatacaa atttcatcat ttgagagcag atcataagtc ttaataattt tttctatatt 185340
ttctagatga atgtcattaa attcctcgtt attttcaaat ttattatttt cttctagata 185400
tgatatatct tttattgatt gaatcaattt attacggata ttatatttaa ctaatttagc 185460
```

-continued

```
taataccttt ttatcagaaa taatattctt tttcattcga atatctattt ctgatacaat 185520
ctctccattt atatcgatta atacattatc gattaatatt agtgatagca aatactgtca 185580
cacctttcct ttaattatta aattattact acataaattt actatttaat attcattata 185640
tgatcccacc tatttatttt attttacatt ttaataatat ataaataaaa tttaaataaa 185700
tattcccgat atctctataa taggagatat cgggaatata ttttatttag ttacagttac 185760 gttaatttt cttttcatgg aagtaaaaga ttcaggaaca acggtaataa ttgtttcacc 185820
ttcacttacg ccaataagtt tagatggatt attctcatcc actttaacga gttcttcacc 185880
tttttctaga attatcagaa ccttatcact aacgagatta tcaggagtca tagttccgat 185940
aatatcttta ctttcgcctt cttttatagt aagatcttca tctacgctaa aactttctgg 186000
tttggtaatt ctatcgttaa ttacagatat tacgtctata gtatcaatag gtgtatacca 186060
cgaagaaact tgtcctgcaa tacctcttga ttcatctact acttcatcat aaatgataca 186120
accgcttaca tcatcatacg taagtcgatg tccaaaagct cttgatggaa aaatttgaga 186180
ttgggatgtt gttacaattg tggagattaa tagtggatca gataaatcat tatgacgatc 186240
gataaatcct tttacagttt caatagctat cattttttatt attcattcct ctctatttta 186300
acgaatattt tttctgcgat taaattcagc ttcctctttc tttttcattaa ggattgttag 186360 atgagtatct attctatctt gctttgcttc cttatcactt ttaaaagtat tattgttaat 186420
aatactttca ctaaatacgt ttggatgaga tatattgctt ttttcattaa atccatcatt 186480
gaagaaaata ctttcatcaa tatttttatt atccatattt ataaacatcc tttcctacat 186540
gattataaac cttcaaagaa cttccacata ttctcatcaa cttctccagt aataaccata 186600
ttagatacca tttgtatttt tcttacatta ttataagtat ccttatcata tattcctgaa 186660
acactagttg ttgtaattgc aaatttacgt ttattatcat ttatctttgt ttgaataaat 186720
aatacgtctg gtccttccat aagaggatta ctatatttaa gaactcttgt aaattcaaca 186780
ataagcgtat caataatatt tttccatgtt atgggtccaa caattccatc ttcagtaaga 186840
ttatttgaat gttgaaatga tttaacaata gtttcagtag aactatcata agaaccagta 186900
acctcaatat catatcttag ttttgaaagt ttattttgaa gcgtaataat atcgtcacct 186960
atcatcattg gtgatttata actaagcatt cgatgatagt ttgaatagtc tttaatatca 187020
tttaatgcaa ttatcaattc attaattta tcaaagtctt ctttcttcat tctaccatca 187080
acttctagat taaatgtttt ttggaatatt cttaccgagt tatatgtgta taaatcatag 187140
ataccattac gaatagtgat tgggatatta atcatagata aatatatttg taataatta 187200 acgtcattac cgataactgg tttttctgga tcatagtaga attccctttt accaaaacta 187260
taagaaacag ttcctgcagg attgtctaca tacatcggta gaataataga aagaatttgg 187320
gaacgaagaa cattcatatc aactaatgat cctagattac tatattttgc ataatattca 187380
tttaatgaat gaatgtttct aatatttcga tatcgaccac taatattagc acatagattc 187440
tctagagata catattggct ttgagttagg tctttaatct ccgtatttcc ttcaagacat 187500
ataaagattt tactagaaga tactggatca gtattatcaa tgagttcaat atctttttcca 187560 gcaatatttt cattaagata catttttccgc attagtaagt caatattaca aggtaatgct 187620
ctttcgggtc tacctgaaat aatatcccct tttttagtaa tataataatg gaatgcaaac 187680
atctttaatc ctaacccttt atgaattgat tctaatgtat cataatccat actaatatta 187740
tgacaatcta aaataactat atttgatgga ttattcttgt atataagatc ttttaccggg 187800
tcaggagttg tatctacata gttctcatca gtattagcat ccagtaaaga taacatgtat 187860
```

-continued

```
gatatatgac ttccccacat attattccat tgttttccat ctactgaaaa agttcccgct 187920
aaatcatttt gatcataaga accgcttctt gtaaatttat ttaagtatct taaacaacgg 187980
tttaataatg aatacgtagt agatatttca atagtgtcat ttatgatatt taaataacgg 188040
atacacgact ctgcaagaat gcttgcataa taggtattat ctctagcact gtttggttca 188100
tatacactat taaattttgt gattatccct ttattttcag agttccatat agtattaata 188160
gattttataa atttcataat gatattattt acattattat ttacgtaacc ttttcaaga 188220 agtctaatta atgaattaat gatattatat tgaaactctc cccaatctcc tctttgatct 188280
aaaccttccc acctaaaact attagatgaa atatcaaaga taggtttaaa gaaaccttct 188340
acaccttttt cattataata ttcttttttga gatcgatcta aaatatcaat aagtttagtt 188400
aattcattaa tcattccaag gtcatataat acttctggtt tttgataacc tagatatatg 188460
tcatcgttcc aactatcaag cttattatta atagttgtta ttgagttagg tagcattata 188520
tttttcatat tattagaata attatcaacg ctttcgatat aatcgatatt tataatacta 188580
ggaatatctt tttcctttc aatataaaac ttattaaatg tacgatctaa tgaataattt 188640
aataatgatc cgatatattg aagctcaatg aaagaagaag taaccttact tttaaatatt 188700
gctttggtta atggaaattt aacagatttt ccatcagtat taaaattaac tttaatacta 188760
ttaaataaat caactgattt aggaagattt aatttccatt ctacattatt actatcatag 188820
atatataaat caattccatc actagcacga tagcgaattg tagggtttgt ttttgtattt 188880
cgactaaaag gaataaccat gtttgaccaa ccatcataag aaccattatc attactttct 188940
tcattaatcg taaaggtagc tttaatacta ttccgagttt catcatcagt agatttcact 189000
tcaataattt cagaaatact attcggagaa ctctctgcaa tatataatga ttcttcagga 189060
agattaaaat tatcccagat tacttcacgg taatctttta acatttcagg agtcaatcaa 189120
tatttattaa attcattatc ttttacattc gtcttataga atccaatatt atgatcttta 189180
tcttcaataa taaattttaa tactttatca ttatcggttt taattctaga ttctatatat 189240
gaaatatctt taagcgtaaa taatttattt acgccaaaat gaatatcttg attaattgag 189300
attgaattta gtataacatt tccattagta tcatcacgat aaattaatac agaatctgaa 189360
ctatctttat taataaaaga gccactatca gataatggat ccaaattatt tatttcagaa 189420
gtgatccatc taggtttaat tggcatatct aatataaatt taatagtatc ttttgtaata 189480
tcccttgccc tcatccattt actattcggt aaaatatcat aaagattact ataacattca 189540
taagaaagca ataaactttc aatactgcat atattttat taggatccag agtatgccaa 189600
taatttgtag gatcatattt ctgattagat ttaataaagt tatcattatc taattgagta 189660
tatactagta atagcgtgct gttaacatct ttatcttcta atacaatcct tacagtatta 189720
tctttacgga tataatactc ttcaatatca tagcttatac ctataatatt agaagccgga 189780
ttattttcat cacttaattt agaaccaaaa tctctaacac taaataattt tttaaaattg 189840
ctatccgtac taaaaattgc aataccatta acaaattctg ccgattcatt caatattaat 189900
ttttcagaat taaagggttc cgatgcatta tatgtaaaat gaggaaccca taaattatct 189960
tgagaaaaac tagttggaac atcatttgga tataaggtat caatggttgc attcatcgta 190020
gattctatta attctaagga tatacttacg ccagaattat actgatatat aagtgaatta 190080
atatattgaa actgcgaagt agatgttcct gaattaatat taatataatc aaataagtaa 190140 tcttcttta tataatttaa tctagacatt gaattaagat ttatagataa tggactagtg 190200
```

-continued

```
tttttttgtat ttgcacttac aaatttatta tattcagata tccatttttct aatatctttt 190260 aaatgaacat ctaatttctt ttcagaaaga tattttgtca aatttatcac cgccattcat 190320
attataacat tttgtttaat atcaatttaa cttttttaccc aacctttagt attattatat 190380
ttatatttaa ctgtagtaat tttagtttca ttaataactt tcttaagacc taatcttaat 190440
acaagtgaat ccctattaat aatattccgt gcagaaacat atctaacttg ttttgtaatg 190500
aatggaattg ttcgttgaac tgtagagaat ggactacttg agttgtctct actctttggt 190560
aatctttgaa gattatcaga gttaagcgta gatattcgat taagaccagt aggatcgatc 190620
ttccattttt tacttttacc accaagatta acttttttgtc gccacgttgc agatcctcca 190680
ccatacttaa cgctcgggtt aggtgaaaat ccattagacg atgtagtaaa tgtagtttta 190740
gacgcaaatc ctgaaggact ttcatataat ggcattagta aattagatgg acttctaatg 190800
tatccaatag tatttgcagg actgcttgtt gttccagtta atggcaatcc ttcaaacata 190860
tcccatgata aatatctatt cgatattcta gttccagtag ttttatttac tttattatag 190920
aatcctcgat aaaatacacc agtaccttca gtaacactat attttttcaag agttagagga 190980 tcaattgccg aaccttgata gaaccaatca gaaaatctag atcttaatcc aacacaagca 191040
tctacatatt ggctttctga agtataattc gaactagagt agttaaataa tcttcgatcc 191100
caacgacaat catatgcagt tttttcatat gatacacttt tttgtaattg cattgttcct 191160
gaaaaacttc ccatttttaat taatttctga tttacttcat ccataagtgt tttaatatta 191220
ttccatatct gtaataattc agtattctta ctattcgcat cattactaaa tgcttcagtc 191280
aatgaattat tactaaggtt attgaatata tcaatctgac tttgtattaa gtcattatat 191340
tgtcctaagt ctagtccgtc taattgtaat gatatatcac ctaattggtt tacattattc 191400
ttacttattt tacctagata tactgttttg agtcgggcag actccatatc agaaaaaata 191460
tctaaacttg tatcaaatat ttcttcttgt ttattatata tttcattata tatattatat 191520
aaattattaa tctttccagg tattacattc tttcttaatt ttataccttc catatcattc 191580
tctaggaaat caataatatt ttctctaaga actttagtaa ttggtattgg taagttaata 191640
ccttcctctg taacgtatat gtcatgttct actagatcaa ctaataactc tccagtcttc 191700
agagtattaa aatattttttg aagatagtct tgatacgaca ttggtatata aatatatctt 191760
gacattaaaa ttacaccacc attattatat aatatgttta aatgttattg atttaaccttt 191820 tttattactt atcttccctt tagtcttatt tactaatgaa gttacccatg aatcatatgt 191880
tgattgaaat gcactagaat ctacatttttt ctcaacagta gtatatcttg atctcatatt 191940
agttaaatca gttccagttt tagtcttata accttttata aagttgtata gatatgttaa 192000
ttcagataat cttctttgta ttgaaaatat tccaggaagc ttttctacta cttttggaat 192060
aattgttgcg ataatatcta caaaactcca tatatctacg gtattttgtc tgatttgatt 192120
ttccaatgta tttaatattg caatgatctg agctaataat tctttaagac cgttcattcg 192180
attatataaa tcatttgttt cagataattt tgtctgatag agtgcttcca aattagatat 192240
ctctgtttct aatagagtaa taatgctctt aagagtagag actaggtact tctgtgaaaa 192300
taactcacct tcaatatcct ttgtagctga ttgatcatta acaattaaat gaccagtacg 192360
agtatttact aaaagttctg aatctttcga ttccagttta gttttttcag ttaatggctg 192420
aacgtacaat ctatatgtca taacttatta tcacttccat atcatttttta aatttaagtt 192480 agcagttgat atattaatta taccaactgc taactatatt agaaacttgt aataatatttt 192540 acaagcttag tatagaatcc ttcatgttta tctttgaatg cattatattt agttgttaat 192600
```

-continued

```
atcttttat tagcttcgat ttcaacgctt cgtagattgt aatagtttct accaagatta 192660
tcaattactg tagtatatag atcggcataa tctaataaat catttcttaa tttagtaata 192720
ttagtactta gattcattag cttattatag tttgttaaga aagacccatc tacattattt 192780
gtaatacttg ttatcttatt acgaatatca gtaatatcgg aagtagtttt atcaacttca 192840
gcttttaatg catcaacctg agtttttaaa ttatttattc caccaacaac tgcatctaca 192900
aaaggtttta atagatcatt attactgtca atttcagata aattatctct taaccaagat 192960
aattgatttt tatatagatt tgttacttta aatatatcat atataactgt tgagtttaat 193020
gataataagt tatttaattc ttttgtaatt tcaataattt cataactacc agtatcagaa 193080
tttttcgtat tagatacaac ggatatattt ccagtatgtt catcaataat cagttctcca 193140
ggaaatctaa atagatcatt ttctcgacta aacggaatta atacatttcg atcaagatct 193200
actggaagat tataattctc agtaacatta ttatcatgat caataattcc gctagagtaa 193260
ttatttacat caatataata ataagaacta ttatacatat tatttgactg ttttctagcg 193320
gtaatgatta gtcgatatat accatttaca ctactgatat tctttaataa tgggtcacct 193380
atattgatga ttgaattatt aagtgaagca gtatatacaa ctcccggttc tttattaata 193440
atatccaata caaaagttga atcaatatta ataatttttc catgactaat attcttagca 193500
attggttttg aaggaggtat ggtatcaata gtgatagttt tagatgaaga tgaactttta 193560
ccatttaact tactagtagc ttttacattt aatgtaaatt ttctaataga tttaacgtaa 193620
ttatagttct taataggatc acctagagta tactggtaaa ccatttattg taatttcata 193680
ggtacacatt gggattctta caatattagg aatgatcaaa ctatttgtaa ggtttcctga 193740
attatctgga atattaatta ctggtaaatc tggtactgta acatttaaca tgtctgacgt 193800
aatttctaaa ttattttcaa gaatcatatc attatccatt atttttctag cagtgatgat 193860
gcagggttca gtaattataa atggaccagt atactctttc caagaattgt taatagaagt 193920
cttatacagt ttacttttaa tgtgttctct ttcagactca ataaatacat attcaataga 193980
aatattatat gactcggaat aatatttttt atcattataa tctattcttg gtggagtata 194040
aatataattc ttaacaatat taaatttaaa tgtagtataa cttaacgtat aattatgtct 194100
atctgtaaat actgctaaga attcatgagt ccctcccgaa gtgaatgttg aaccagaagt 194160
ataattgttt ccatcaatat aacaattaag cgtataattt gaattattat tcattacagt 194220
gattgttata tcatcagcac actgagatat atctgcagaa ctcacatcaa aaggagttaa 194280
tggtttagat gatgatattg atattgacgg attaactgga actgtagttt gatccattcc 194340
agtagtatta atagtctgag ttgccattaa tttatgtgaa gaatcagaaa cattagtgat 194400
attacttcca gaaactcagc taatcgtaac atcatcatgt aaatggtttc tagttgatgt 194460
agcatatctg tataatttaa tagtagaatc aaaaaatatc ggcatattat agttaggcat 194520
aataaatttt ttcttaccat tataatccat aacatacata ctattatctt tatcaatttt 194580
actatcaggc ttaagaacaa tatcattaaa taatggatta gtatcactag atactgaatc 194640
atgatatata acagtactaa taatatctcc aacttgttct ggtataataa ctacgtttac 194700
ggaaatctgt actacatctg aatctacacc attgctaaca ttaatatcta gattataatc 194760
tccttcatct ttaaatgata atttttagttt tggatcattc gtattagtgt ctaatggtgt 194820
agcggtatat gttttttgaag gatcatcagt atctgtaaca ctataggtat acgatgaatc 194880
tttttcaata tgaattataa tatcaattga tccatcccca ttagtaatac tatctactat 194940
```

-continued

```
aggtaagatt aatgttgcat tatcatcagc aataactgag aaaattaaat cttcaggggg 195000
attaatcgta tttataaaat taacaatcat taattcgtct gaattgaata gtttatttat 195060
atcgattttt cgataaatat taatctcagt atcagtctca tatagcccta gatatgtgag 195120
cattgtatct gaaacgtaat cgttaacctc tataacgtca ccatcatcat tagttaccgt 195180
tatattagta gattcctgta agtcatttac taattcattc acatatactt taaacgtata 195240
ctgatcggta cctttagtta gtttaatata tacgtcatta tcttctgcaa ttgttattga 195300
agttggtaat gatatactaa acatgttata attatttgag tctattgtaa tgtcattatc 195360
agtaccatta atatttagtt taccattata aattccagta ccttcaacgt gatatactcc 195420
agtaatatta gaatcgccaa tattaaatgt atcaatagat aattgtatat tttcacttct 195480
aactactagt actttctgat tatctgcaac taatataccc tttgagttgt atatcttaaa 195540
tgatatctca tccgtatctg aagatattcc tgtactagat gttattttca tcattttatc 195600
atttttcgta ttactaaatt tagtaacagt tgatgtagtt tcaacaccat taatatacat 195660
aataatatta tctaattcac ccttatactt agcaataatc tcagttggat tatttccatt 195720
aaagaagaaa ggataaaagt ctactgcagt ataatcaata tttattgcaa ccttatcatt 195780
aaatgtatct acactgtctg gatcatctga gtcttttggt atagatggtt catatgtgtc 195840
actatatttt acaataggat ctataaagtt ggtatataat cctgcaattg aatcattctt 195900
gacaataggt atattttcat ttctgattga tgtgtatgtt gatggaatat ctactctata 195960
aacatcaata ttagtaccat acgcagaagt atgtctaatc gagtctgaat tgtaaagata 196020
tttattaata ttcgatttat cgatatatcc actgaaaaca tatatatctg aaaattcatc 196080
catattgaga gtatattccg ttaccgtatc actaataaaa tcttcatctt ctgatattga 196140
ttgaaatgat tcaattaagc tttcttgaag atcattaata aaatcttcgt tagatagatc 196200
atcgtcatcg ccaatagttg aagcacttaa catagtgata ttattcttac caatagaacc 196260
ttttacaact gaaccattac ctcctccaat aatctgcgat atattattat ttacattaaa 196320
tgataaatta cttacatctt ttggtaatct aattgcttta tataggaaat tatcatttat 196380
tccttgagtt agtataaata gttgatataa tatactagaa tcatcagaat aatcagaagt 196440
tcctccaaaa tcattttcaa taataaccct aaatttcagt tgagttaatc cattatatgc 196500
atttgtacta ttattaaaat cttcgtctcc agtaataaat cttactctac taccgttacc 196560
gcctgtgggt gctgtacttt gtaatgtaaa gactttattg gtagtactcc aattactcca 196620
ttgatccgat ctttcatctt taaccgaata ttctagatat actttgttag ccccaaatga 196680
tggaattgaa cttataaaat ctttataata cttttccataa ttactaaagt atgttatatc 196740
tgcaggtcta gaatataatg gattaatacc gttatcaata aagaaaggat ttacattatc 196800
tatcttaatt ggatttggtt taatcccttt catatcataa ttcattttaa aataaaattt 196860
acgtggatca actaatgatt tattagttaa atcgttaaac gcttctattg ttaattcaaa 196920
tactttatta tgataattat tatatactgc gtttggatta tcgcttgcca atgacaaagt 196980
atatcctgac gtattctctt tataaaactt cttaagatct ggattattaa gtgctttat 197040 attatatcga taaattactg gtcgaccagt tgaatcattt acccctgaaa aactaaaggt 197100
ataattaagc ttatttgctt cactagtgtt tgcaggaatc actgtaggat tatttggatc 197160
attactcata aatgttaaaa atgatcgatc ttcatttaac atactagcag tagtaactat 197220
ccccagtgcg ctcttactaa tatttattac gtttggcata ttagaaagat tattaaacac 197280
ttcagtatta tccggatcaa tattatcact atatgatagt actgtattaa ttttagtttc 197340
```

-continued

```
atctgaaaaa taaaatggat caatatcaag ataatataaa tctccaactt tagtatcata 197400
gttatcttta gataatctaa attcgtgtaa actactctgc gttgttactt ggaaaataat 197460
atcaacaaaa gcagaatctt ccgtaccatt aatattttta tttttctaatt ttccaaaaat 197520 agagaaaccg ttctgatctc caactataga ctcatttcct tccgtaccgg actcaacttc 197580
tatatttgtg tatgttaatg cttctccata tggattctct acaaagaatg ttctagcaat 197640
tccataatct gcaggagtcc aactttgtat gaattgtatt aattgttctc tagtatgtgc 197700
tattactgtc aagaaatttc accacctata tttataactt cttataatta atagtttaaa 197760
aatccatact aagaaatatt taattcctta gtatggacga tatttttata ttatcggatc 197820
aataatatcc gcttcaggat catagatttt ttgaggattc atatccaaaa taatattctg 197880
actaatatat ttgttattta tttcttcaga atctaatgaa atatcccaac ttaatagatc 197940
attattatta caattaataa tagttttcc acgttgacgc atatagtcca ttagaattaa 198000
tttccggata ctacctctag aattatcatt tgttattcca gtcaatatat caaaattact 198060
agtttgtctt acgttatagt atgaatgata gtaattatcg tttaaattca ttttatcata 198120
cttataccaa tctaatatta atttaagttg agtatgatca tcgtagctaa atctaatcat 198180
tacatttatt aatggatcag cataatcaat aatttgaata cttttaccat taagtatttt 198240
tactttacta gaatctattc ttaaattatt aacgtaaact gtaaatgtgc ctttaataaa 198300
tattactgaa tcgtcatcta aactgaatac atctgttgtt ccttcagccg gcttactaaa 198360
agttcttata tagttggagt tttcattaag aagatttatt tcgatagtag atgtttttagg 198420 tacaatgctt ttaaaaacaa ttaatgacgg aatagattca aagtcaggat caataatggt 198480
ataatcaatt ccaggatata atgttaatcc atcgatatta atatcgatat cttcaggatt 198540
actattaatg tttgtaaaaa tatttgaatc atcatctaac gtagcaaatg gtaaacaatc 198600
aatatcatat tcatttaagt ctaattgatt gtagtataac gagccactat ttgtaccact 198660
agtcaaaaga tgtatttcgg taccttcatc catataagat gaaccatata cgataagtct 198720
tactgtatta tattcaggtt caatcttaat ataataattg tatgggttaa ttcttctaaa 198780
gaaattccaa gttttcttct taataaagac tcttaattgt gaaggagtaa ttcccgttgg 198840
taatgcaaca tccgttaata gtataccagt agttcctaac atattagttt gatcttcaaa 198900
cgtattatca attatatgag tcttaattgt tttctcggat tcaacaatct tacgtttatt 198960
accagagaca attacttcat atttatcctg aagactagaa ttcccatcta aaacatcatt 199020
agcatcattc acatcaatat attctttaat aaatcttgaa ggcatgtatg catatatttt 199080
tccatctaaa ctatcttgtt gcttaatcga tttacggaaa atatgtttac cattaataaa 199140
tatatcagat attaatgaat tttgtttctt ttcatatgaa ccatattccg aagtaaaatc 199200
aatataacca tactgagatt catcattaat aaaattattt ataaacggat cttttgtaac 199260
ttttatttta gagttatcca acttagtttc aaatgaatta tgtcccattg tctctataaa 199320
taatgtttta ttaccttgtt ctaattcatt aactaatgat ttttcaatca tccgaatatc 199380
attgtctgta ttcttatata agatatcagt aacatttctt ggatcaatat ccatttggaa 199440
tgttttagtc tctataagtt gttctgaatt agtattaaat atactaaagg ttatatcttt 199500
attgggggtg aaattaagtt catcaatctg taatcgatag tactttctt ctaattctgg 199560 aagatcgtct ggtttataat atacacgttg ataattatca ttaccaatga tattaattaa 199620
gtagcttgaa acatcatcat tactctcaga agaagagaat atcatatttt taatctttac 199680
```

-continued

```
agtaagctta taataatctt cgattctttt aaaattatta atgatgatag tctttccatc 199740
aatagttatt gtcattatat attcggatga taataaatat cttagtctaa aatagattga 199800
tccgttcaga tagtatgcat tcttatatag aattttatat ataatgtctt ctggagtggc 199860
ttgaatattt ttattagaat atctaacatc taaatcttca ttaagaacag tatatctaat 199920
catatcattt cctaaaggta gcattaattc tgataatact gtttctttat catcaaaagg 199980
aatatacata ttggcacttt ggtttgcttc aggaaatatc ctactaatag agttcgatct 200040
atagtttaga gaaacattat agttactttt atctacaata tctaaactat gcattaaatt 200100
aacatgaaca tttaagaaaa atttactatt tgtactatta ttaaaactgc gtttttctat 200160
ccatgtataa tcaatactta aatcaggaag atattctaat ttatagaatg tggtatctct 200220
actagaatta ttaacaataa caaatagatt ggttgctaca atattttctg gatagttatc 200280
taactgaata ttttcaataa tatttcgctt agtattaatt aatactaatt gattcatact 200340
atccataaga ataatataat ttttaaccag tactacttta tcaatattat ttctaacgtt 200400
tgctaaccat gttttattcg tcaagttatt attagcatac ttaaaactat atatatttcc 200460
actatatgat gatacgtata atgtagattt atcactatca tatatcataa aattatttgt 200520
cgataatatt ttatcattat aatctgtctg acttaatgat actttttcta caatagagtt 200580
atctacagac ttaataatat taatattaaa actatctttt aattctagtc ctataaatat 200640
tgtaaagtcg atattattcg attcaggaat gatttcaaaa ccagaaataa aatatgaagc 200700
ggtatacaac acttttgttg tattcgttat agtatttact agtataatat gttgatacgt 200760
ggagtagtat ataaaatcat taacaatcct taattgattt actaattcat actcatatgg 200820
agaagtatta gttattttat ttatagttcc tgagatatta tacattccag tagttgtatt 200880
tctactaaaa gatacataac tgataccatt cttatgaaac atatatatct tattatcgat 200940
aactgtaaaa tcgattactt cctcattaat atcaaatgaa cctacttttt ctccagtacc 201000
aaagtctttt ataatatcaa ttcgattctt aatagaaccg gtaggatatt tatataatct 201060
gaatagttct tctaaatata tacacattgc aggcatatat cctgaattag catatgatat 201120
agaatgaaat aagtctaacc tattacgttt ttgatattta tctaatatat tcccattcaa 201180
tgttatagtc aatactttca ccatctttct tttacaatta taaggaatcg agaataaaat 201240
atcccgattc ccaatttatt taaataagac ttgaaaaact tgtaaatgtt tttagagaga 201300
atttacctaa tgtattttcg ataattgctt ctcgattaag gttagcgctt atagatgatg 201360
acattaccat atgcataaat gcaggaaggt aatcaatagc taatacagta gagtctccat 201420
acattcttac ataattctct aaataagagc gtacttgtaa tttctctaaa cctttattt 201480 tcttgaggtt atcaaaaagt gtaaagatgt ctttatatag ttccttctcg cttagattaa 201540
atccttcttc catttcttta attaaagata atgaagaacc attaaagcaa gctttatagg 201600
caatatcgtc tattgtatta ttataattct ttttagccat tgctaataga taaaactttg 201660
atagaataaa ggatacaaag tctgatttaa aatcatttag gttaatgaa aacattttat 201720 caaatatctt tgaacctagt ctagaatatg caatagatga attttcatt aattcagtat 201780 tacttgtaaa tcgattccaa tttccattta attcataagt aatcattgct tgttgcatta 201840
gtccgaataa tgttttttggt tggatttctc cacctgcatt agtgtatcgt gaaacatcaa 201900
ctaatacgtc acgttgattg ttatatcttc tttcaaatac aatcaagtat gatggaaatt 201960
tatttgattt atttgatata ggaatgattt ttccagagtt atataaccca acaacttat 202020 ttttagtagg ataattaatt cgtctattaa taatatttat atttgatct aatacatctt 202080
```

-continued

```
tagataaaac atctttacta gtgtttattt tattaagttt tattttaaga tcatgctgaa 202140
aattagatgt attgaaaatg gcggaatcac ttaattgtac cattatttca ctttcccttc 202200
aattaattta tatgatatta atttgttcaa tatattaaca ttttttacat ttatatatta 202260
taaattcgta taatggaaat ataataaaat tttcagttta tcggttaaaa tattattata 202320
ttataaaata aatgtgataa ggatggatta tattatgagt gataaaaaaa tgcttaaagt 202380
aggatttctt agcccaaatg atgataggat tcgttttaaa gaagtagatt tttcgaatag 202440
tgaatcttat gataaagaaa ttgtgagtgt tattagtcct accggaaata ttgatgcagg 202500
aatcatgaat cttaatgaag atttagaaat tcataacttc ttaattttat ttgataatga 202560
aatgtcaaca aataaaggag aatataattt tacacattca attagtcctc tttttggtga 202620
agttgctttt gtaaaattcg gttatactgg ggataaatatg gaaccagtaa gcatgttaga 202680
tgatgaagct gaggttctca gtgatattat ttatcaagaa aaaacttctg atcgagcaat 202740
tgaatttaaa gaaaaaattc ttgaagaagt aagaatttac ggtaaagatg gattttttacg 202800 taaatataat gaaagtattg aagaggcgca aaaaatgtat gaagataatt tttcagaaga 202860
agaagaaaaa taattaagaa tggatggtgg attataattg tctaatataa acgtagttag 202920
tattgcagat ttacatttttg gctaagaaag atgatagtcg actaatgaat gaattaacaa 202980
caatatttat tccacagatt aagaatattc atgaatctga taaaattgat ttgattgtta 203040
ttgctggaga tctatttgac cgtattctta agtttgatga agttggtgga aaattagtat 203100 tgaatttttat gcaagaactt attgaatgga caaataaaaa taatatttat tttcgaatta 203160
ttcagggaac taaaactcat gactataatc aattagctgt gtttagaaaa gcagaagttg 203220
ataattataa tttttaaaatt tatgaaacgg tatataatga aaaattgact atcaatgaaa 203280
aagaatttaa tattttatat ttacctgaag aatatcctga agatatgaat gattattata 203340
aagaattctt tgatgttcaa gaaaatacgt atgatatgat tttcggtcat ggaatgatcg 203400
attttgtagc tttcactggt tatgaagatg atactgaaaa aattgtaaag aaagcaccag 203460
tatttgttgc ggatgactta attaaaatta caaaaggacc aatatgtttt ggacatattc 203520
acgactatca tgaatataaa aaacaaatat attattcagg ttcattctcc agatattctc 203580
atggcgatac tatggataaa ggatatttat atattaagtt aaacagtgaa gatacttctg 203640
aatatgaaat tagtttctat gttaatgaat tagctccaac atatgccact attgatttag 203700
ataaaatcaa atatgataat atggaagatt tagcatcatt aattaatgat agtcgtgaag 203760
aatatgactt cattcgaatt aaatcaacaa ataataatga tagttctatt gtaagaaaag 203820
ttattgaaaa tagtcctaat attaaagtta ctttaaagaa taagaataac gaagaacaac 203880
aagttgattc taaatggaac ttcattcttg atagagagct tgatactgac gactctataa 203940
agaaatttat taaaattaaa tatgataaag atatcgatat tagtaagatt aaagcaattc 204000
ttaatccaga gattgaagat attgatgata ttattaagaa tatttatgat aagaaaaaat 204060
aattaataat ctttattaag aagtgaatta tgaaaggaat gtttcattgt gccatttatg 204120
gataatagcg aacgtacaag agtctttaga tctagaatgg atgaatcttc tcaacaagaa 204180
tttccattaa agatttccgt atcatactta tttagtttag caagatatgt ggtatatcca 204240
agtaaactta tcactagaac taatttacgg aatttagata cattattatc agcagtcgat 204300
attgatagat cttatttaga aaatgaagta atggaaaaga atgcatttat attcttaaga 204360
gaaattaacc gtgtattatt acatcaacaa tcaacaatag aaacattgtt tgattatatt 204420
```

-continued

```
gatgatgaat taaaagatag agaaatctct gaagatgctc ttcaagaatg tgtaaacaat 204480
attgcaatgg tgtttgatga taatttcatt cttgatgata gtgaaatatt aagcttaaca 204540
aactatgtag aatccagatt aaagattatg gcactatatc gtcaacgtga tagaatggaa 204600
ggtattttag aattaatcaa aatgaataaa tctccaaacg aaattaatac tgaatttaaa 204660
gattttgtta cgcagaatgc attacaatta agaaagattg aaacgaataa tcgaagttca 204720
atggacgata ttatgtttag cagagataat gatcgatcag tagattcact agactctact 204780
attagacaat taagaagtcc tagtaataaa ttattaacag gatatagtaa gtttaatgaa 204840
atgattaatg gtggtttaga ggatggtcga ctttatttac tcttcggcgt tcctaaatca 204900
tttaagtctg gtgttatgtt aaatattgga atgtcagtat gtcataataa cgcaggattt 204960
aagacaaaag atcctaataa agaaccaacc gttgtttatt tatctcaaga aaatacaatt 205020
atagaaacag tagaacgatt atatgaatat attactggta ctagtattaa tgaatcacaa 205080
gctactacgc aagatgtttt agaattaatc atgcaatata cgtatgattg tactggtatt 205140
tatttaaaaa ttatgtatag accaaataaa agtattgata caagttatct atataatatt 205200
tatgatgagc ttaatgaaga aggtaaagaa tgcatcttta tgattcaaga ttatactcga 205260
agaattagac cttctgaagg gcaaaatcaa gatattcgga tacaactcgg taatatatct 205320
gatgagttct gtacgtttgc taaggaaaaa ggtatccctg taatgtcggc gggacaatta 205380
aaccgtaatg caaatgaaat tgtagaggat gctcttgtta agaatcgttc agactttatt 205440
aataagttag gtcgccatca tattgcagag tctgcaatgt tacttgaaaa tgctgattat 205500
ggaattatca ttggtcgaca agattatctt ccagagggtg aagacgaaat taatcgcaaa 205560
agttatatgt catttaaact tattgcttct cgtgggaaaa ataaggataa agatagcaat 205620
atgttctctc aaccttttga aaatggattt aaaattgcag aagatattaa tctagctgaa 205680
ccattagcaa aattaagaat taatgaacaa cagtctcaac aagatatgga aaatagtgct 205740
gacgaagtaa ttacttcaag aactcctaga tataacagta ctagtaaatc tagtagtata 205800
gttccgggaa tcaatactgg taagagacga acaaatcttt catcaacagc attattacaa 205860
gaagatgata ttccgttcta aataatatta ataacctaac atcctttttt atagggatgt 205920
taggttaatt tttttttttt agatagattc ggctttttga cgtaatttac taaaatcgat 205980
attaaacatt ttaagtgtat tcatactttc tagtatagta taagatataa tagattctac 206040
aattgtcatt tctgcaatat cttctttttt agattctgat agatccatat tttccattac 206100
gtatgataag cgttcttcac taattttcat atataatgat ttttcatctt taacttctac 206160
attattttca ttgcatttat caacaaagtt tttgtatttc ttctcataat caattacatt 206220
gataacttta tcttcaatta cgtttactgc agattcaatt aatgatttct cctcatcatg 206280
gatagaagat acaatatctc caacttggtc aaatgataat ttctcttcat ttacataatg 206340
actgactttt gtcttaacaa gacttaataa gtcaccaaag gcaccatgct cttgaatatt 206400
gattgattta ttttctacaa tagtattaaa agcattaata cattcattat aaatataatc 206460
aacattccct tgttttttgaa cttcatcaat aggaatagct cggtatacaa tacttccaaa 206520
taatgttgga gctacttctt cagcatgttc attaattcga ttttcctttt gaaccatctt 206580
ttcacgttct tcagcttcac gctgaaccgt aatagacgtt gttcgtagta atttactctt 206640
gttttccata tctaaatttt cttgtaatgc ttttcttct tctttcttt tacggaaata 206700 ttcagtacgt gcattatttt cttctctaag atttcttgaa ctttcaccaa agatactaag 206760
tcttgacatt aattttcact ctcctataat ttttgctata ttaatttgtt tgataagtta 206820
```

-continued

```
tattagctac atgctcatat tttttaccta gattgatagt agtgacttta ccattactat 206880
ctgtcgtttc tacaatatta tcagaaagtg ttttcttaat attgatatat tcaggaacat 206940
attcaatgat ttcttgtttt gagagatcat taatatttct tgcattgtta aggatttttt 207000
gatatttatt agatatcttt tcatcataat taccacttaa accgttatat tcaatatagc 207060
taatgatcgc aaattcttct tctaacaatc ttaatagatt agatataggt acgattccat 207120
cagtattaca ggcttcaata aagtcggaaa taaatttctt aattgataag tcatcattat 207180
cattaacggc ttcatatgtg tgaatagtta aatcaattag catgtcaatg cgagtaataa 207240
gatcatactt aacactatct ccatccactt cagtatttaa gtaataatat ttagatggtt 207300
cccaactatt ataaaatttc atatcaattg tagtattatt ttccagttta ggataacat 207360 tgcttaatat agtgatatac gattcaatta atgtatataa ataactatat tcatatataa 207420
aatattgtaa actaatgagc ggtatcattt caacttttaaa atccttattt gcgtcactaa 207480
cgtttgaagc acctactcta gttactgtac ttgtcataat actagaaaga ttacgatata 207540
actttacggt agaattagta gttactgata atgccaatac ataattatca atatttctat 207600
tagcatctgg aaactcatca tcaaacaatt caatttcatt attattcttt gtaccaacag 207660
tcttatatga attatctta taaagaattc cgatcttaat atatagatct tcatcaataa 207720
atacattatc tagaacatca ccattttcat catatagcga gtttgataat gataataatc 207780
ctttattaaa tttacgatta gttgataatt ttgcagtata agtagactct gcttgttctg 207840
gattttcacg ttcaaattca aagtaaccat acttcttatt agagttttt gacattaaga 207900 tacctcgtac gcaaatacgt ttatctaagt cgcctatcgt ttcattactg tttagatcaa 207960
acttaatagt ataagtatcg gaatccaaag tagattcaaa atcatgaatt tttgttatat 208020
taagtttatt gataatcatt gttgtaggaa ttaagttatt aagataactg tatgatgtat 208080
cgaatgtttc atcaatatcc agtttataat atttagcact taatacagga tcaatatcta 208140
ttttaactaa gaatggatta gtatatacaa gcgtattttt atcattaata gatttttttaa 208200 tatcatcagt atatccatcg ggaagatgtt tatatttttt atcaatataa tcatactgaa 208260
ttaatgaatg ttccggaatt acatatccat taatatcgtc acctaacagt tgatctgtaa 208320
aatatttctt agagaaagtt acactacttg cagtatttgt aggaataacc tttttatcat 208380
tatcacgtaa taataaaaat gcattatata aacgctgaag aacatcattt cgcttttttca 208440 taaagtttat tgatgagtca tttaagcttg atgctcgatc aatatttcgg aaatagatat 208500
ctaagtcagt atccataatt aaattatctc taccgagagc agtttcaata attttgtctt 208560
tcataccgct agtacttagt ttatcattac ctcctgaagc agaggtaata ggaactactg 208620
ttgtgagcat cttttgaaaag ttattacttg ctgaattagt aaagttaaat aatacttctc 208680
catcaaaagt aaagtttcct tcagaacctt ttgtagttaa tatctcaatg gttatcttac 208740
tattatatct aggtctaaag ttattaacta atgaagaaaa agatatctgt aatttattat 208800
catcaacaaa cgtataataa cagaatttct catcaggatt agaaggatta aaggtattat 208860
taaagtatgc gtttaatttt acttttttcgc ccatatacgt ataatatata ttgaatcctg 208920
ccaattgatc gtcaaactct gcagtataga ataaattatc actaatatct tcagacaata 208980
tatcaaagtc aaaagaacta ctttgaactt ggtaaatatc taaatttaga tacatatact 209040
tttcaccatc aaagatagat tgataaactt ttatctcagg aatactaagt tcaatatatg 209100
ggaatgtact tacttcatca ataagatatc tagctgtaat cgtataatca ttattctgat 209160
```

-continued

```
tttgtttcat taatatttgt acgtcataag gtaactggaa tttaaattta cccacagaaa 209220
attcaaattc tcgatctaat atgatctgat aagtttaag agctttaact ttgatatatt 209280
gatcttcgat aatttcttcc cttaatggag aatttattaa atcctcttta cgtataacca 209340
tattaactaa catatgagaa gggtttgata gtactaatgg tacgttatat aattttgcat 209400
aattgaagat actatctggg aatgatgcac tatttaagaa gtgttcatca tacagtacat 209460
tacgattata taccgagttt ttaacctcat gggctgcaat ttcattaaag tatccaaaga 209520
aaccagtttt taataagttt aatgcagcat tatttccttc agaaccagta gcaatatttg 209580
tatcatcaat attaaaatat gtgcttgcca ttttaagcca atgttcatgt acgtcatatg 209640
acgtttgatt tactttaact actgaacttg tatcttcttt agcattcttc ataaaagaag 209700
gtacatctgt tatatcgttt ggattatttt tatttgccat ttattctcac gcccaatcac 209760
tatttaatta tccaatacaa atttgagttt atattttttc ttttcattat caccatagtt 209820
ttcaagaact actgcaggtc tatctaattt tgttaggtct aagtctgtaa aaaagtcatt 209880
atatttctta gcagatcctg gagaagtact atatataata ctttctgaat ctttactaga 209940
cgctaatact ggagagtcta atgatactga attaaagtcc attaatattg cgggatccat 210000
atcttcttta tatgaataag catagttaaa acttaactga gcgatatctt ttgaagctcc 210060
aatatcacta ttcattacgt catatggaac atttgttggt gaacatccag tgtatttagt 210120
atagtataat atcgtttcca taacaaaatc taataaaaag taatatatgg aacttgtata 210180
atcaatatat cgattcataa atacttgtgg attaggtttc atttgtcctc tagatactgc 210240
ttcaatatag tcagtccata atttatgaat ctgtagtatt gtactatttt tatcttcttc 210300
aaaagtaacg ctagtttcat cagctactac actattaata aatggtccag gaagtaattg 210360
cttgtgacca taaacgtttt cattaacttc tttagtaata gtagatattc ctttaagtga 210420
catgttaata aatctattag ttaacggttt tatgaaagaa ctatttgaac catatataga 210480
tcctccgcca gtcttactgg ttgcgttccc accataatta agcatattta atatttcagg 210540
gcgattatcc ctcatatatt gaaaaaaaga attcacattt atattttaat ccgttaagtt 210600
aagtttggga gtagtaacaa ataccatagg gaatgcttta accatcggtt catttcttaa 210660
gctattttcc aatctatatg gattaaaata tttattctca tttatattat aattccctat 210720
aatctttttt ctaattttcg tctgacttttg acaaaagttt tcaccaactt tcatattaag 210780
atcctagtat gttataaatt attgttaatg tatgcatgaa aatattaatt tatattttat 210840
ttatatatta taaattcgta atagatatag tgatcatcct tatagagtaa gtttaataat 210900
taatattaag aaaaatgatt tatattactg tccatattaa ataaaatatg acctcacacc 210960
agtaatataa attctgtaaa attatttggc ttaactctat cagcgctata taaattgaaa 211020
tcatgcatat cggagaatat taaataattc ttagggttag tcgatacagt gagaaactat 211080
atctattaaa aaatattatt gtcttacatg ggggcgttct tatgtgctat atgattgaat 211140
aaaaagaaaa aatatgattt agaaaaaaca gtaataatac ttcttagtat tattaataag 211200
atcctatact gaataaaatt gaggtatatg aaagcgctca taggattatt tattaaagat 211260
tattagagtc acatttcaat taattgatct gtgactctaa taatctttat ttaatttttt 211320
ttttttataa cgcttcctat gataaaacaa taaaatataa agtaatatta attaggtcat 211380
ctaaattgaa aaggagagag cgtaaatgtc aaaaagcgta ttgctaaatt tgacttcact 211440
ctttggtgaa gtagttctta gtaaaaaagg acaatctgaa ttagataaaa gttataaaga 211500
attagttaaa aataaatctg ctagtaatag ttatctaaat acaattaaag gaaaagcaga 211560
```

```
atctgctatt atgcaatttc ctttagtaat ttctaataat atatctatcg gagtttttaga 211620 tggtattcgt agaaatattg aaattgaacg tgctacggag ttcagattag tattgtctaa 211680
cgaaccagta caaaatgtta caactaatgc ggaattcatg aataaatatc acactaactt 211740
tagtcttgga gaagatattt cttcagcaca taatgaattc aatcaagagt ctaaatatat 211800
ggaagaaaaa ttagaaatgc gttcacttaa tgattttaca agatctcgtc aatatcttag 211860
agaagaaggc gaacaagatt ttgttaatgc taagattgat aaggataaag aagaaatgag 211920
tagagttgaa agaagaattc agaattctcg tatagtttct gatcgaaatg caatctctcc 211980
attaattgta aacagtccta ttacttatag tatttctaaa gtctttaata atgatggaaa 212040
agaaattaag gttgatcctc caaaaattat tgaaggtcaa attcgttttg gaattaaagc 212100
ggtatctcat ttagttaata gcgaagatat tgtattttat cttggcgatg ccgctagacg 212160
tagtaatttc ttagcaaaag tagttcggtt tacttctggc gagcttaagt ttggtaagga 212220
tttaattcta gcaagtgaac gtaataaacg tttagtacat gaccgtaaag gttctggtgc 212280
tatttggaga aacatgaatt atatttctga actgaataat attcgtgcca atgtaggcaa 212340
tgtaaataaa atgcaagtac ctactattac tttagcaatt agtaaagaag aagtagattc 212400
tattgcagaa aagacaggaa tcaattttat cgataatcct aacgctacag aacgtttgtt 212460
taaagaattt tacttattag acttcatgat cattgatgaa ctaaatgaag tagcatacaa 212520
atttaatcgt actggaaaaa catatgaccg tttttagccta cgttctttag agatttcagg 212580
atctactgaa agtcagttaa agaaacctat ggaattcagt caattaaata aaatgattaa 212640
ctctatgaga aaataagaaa ggataggtga ataattcaat gcgtggattt aataatcgtt 212700
taaaaaataa accaacatct tctaaagatg ccttacaaca gttattagtt gagagtggcg 212760
gattagaaat gaataaatat aaaattacttt ctgaagaagg taaaattggt attagtgacc 212820
gagtgttaat tactcttatg aaatcaatta aaccaaaatt agaaaaaccg gtatttaagg 212880
atattactaa gtctaaaggt gatattacta aatataaagc ttatgatgat ctagaaaaag 212940
tattaaataa agttcgttcc gttatttcaa acagttctaa acctgtagat aaagacgtta 213000
aagaaaatat gtcaagctta gatactgttt atgattttgt tattcgtgaa aaagatgcat 213060
ttatgcgtgg atttagtaat aaagattctt tagtaatgtc attatatgta tcttgtgttt 213120
cggttattgc agaaggatca ttagtaatgt ttacagatgc tttagaacct acttccgata 213180
actttggaaa tattacaatt aatgttaaag atcgtccgaa atcaatgaat aagagtttat 213240
ttattggact aagacaattt tctgatatgg ttaatgctaa aaaattaaaa gatattatta 213300
aaggtggaca aattaactta gaagaagaac taggtgaaag ctttgttgga tctctttcag 213360
tattgggtaa attctttaat aaagtagcag atagtatgga tgatgctaaa gaaaaagccc 213420
atgatgatgc agattctcca aaaggtgaag atagtgcaat gattcgattc ttcaaatcaa 213480
ataaatttga taaagcatcg gacgttactc gtaagattgg taatcgagta attctaccga 213540
ttgttgcatt attattagta tgtatgttta ttcgccttgt agtatttatt atttatcgta 213600
ctcgtgtaaa cgttgcagac aatcttcgta gtgctgctga agttattgat gagaactcta 213660
ttcgaattca agataaaaat gtacgtgaac gacaagaaaa gtctgctaaa ctattccgta 213720
aactagcgga taaagtagat gtagacttta atgtggcaga ctctggtgct gataaggata 213780
ttcgtcaaca agatgaatta atggctaaag gtgcagatga tatgattagt tcatatcaaa 213840
ataatgctaa cgagtttggt atctaaaaaa aaaatatccc tatacattct aaaattgaat 213900
```

-continued

```
gtataggat  atatattatg  aaattttacg  taatataatt  tgaccaccat  tatcagtagt  213960
attattactt  ttagttgaaa  atatttccgt  cattttaaga  acctgataat  caccattata  214020
tttattataa  tattcagaat  caaacgttat  agtgaatttt  ttaaaacagt  catcgatatt  214080
tatatccata  ttattaaaac  taaatcttag  tatggtatta  ttttcagtta  tttgtttagt  214140
atattcctgt  agattttat  tatcatattt  attttcatat  acaattgttt  tattaatagt  214200
accatttcta  tccttaatac  tatctatttg  ataactgtct  ttttctaaac  ctatcatgtc  214260
acgattaaaa  ataatattat  ttgtaccata  taattctgca  tacaactcag  tctgatccat  214320
aataacaaca  ctattaatct  tagtattaat  atacttatca  gttattccat  ttaattgatt  214380
agtttcacta  taagtaccca  tgatattctg  gtcttcagga  ttagcattaa  ctggtatttt  214440
aacgtctata  cgtatatttc  cagactcaac  tatttccata  gaagacattg  gagtaattac  214500
taatttatta  tatgacataa  acacttttag  actatcatta  tatattccgt  aagcattatt  214560
aatgtggcta  atattagtta  gaatatttcc  gggtattaag  gctaattgat  cgtatatttt  214620
ttgattgtct  ggagaagata  gatatgttct  tactggaaga  agagttaata  atctagtaat  214680
gacttcagta  acattagtat  ttgaatatat  accgctagta  ttatatttat  taatagatag  214740
acatatttca  gggacgcata  aacattcaaa  ttcttcatac  tggtaatttg  tatctgttgt  214800
atcttgggtt  aatctatcac  taatattaat  cgccctctta  tcaataataa  gcggctttag  214860
aataatatct  ccgagaaata  tatcattaat  atatgagttg  gcagtatccg  catcaatgga  214920
tgaagctcct  aaacttacta  caaatttctc  agaatcttct  tgtaaactta  ccataacaga  214980
tactggtaat  ttatagacta  atgatatcag  tggcattta  taattttgaa  aatcaatatc  215040
gattttagtt  aatcgaatat  attcagaagc  atcaaacata  tttccatctg  agaataagaa  215100
cttactacgt  agattaaaag  tttttttagt  tatacgagaa  taatccattt  attatttttc  215160
acatccattt  cattcattca  atatagtaat  atgtttattt  attaaaataa  atttataaga  215220
atatattata  ataatagatt  ataatatatt  tagggagttg  tttatatgga  ttacggaaat  215280
tattttggct  atgatacaga  aaatatcgaa  aagattatga  actcaaagaa  agttaaatat  215340
acaaaactca  tgtcaatggt  aaagaattat  gtaacgaggg  aatctattgg  caagaatgta  215400
aatatctata  ttgatatgaa  tactatttta  aagcagatat  ataataagga  taatattgaa  215460
atctttaatc  atttaaagag  tgataaacgt  ttatttatta  ctgctgaaat  tataaatatt  215520
attggtcact  atagacattt  cttttcttca  agattgaaaa  tgtatactac  gttttattta  215580
tttacttctt  ttgaaaaatc  atcatatcat  acaaatatat  atcctgatta  tcgtaaagaa  215640
tattacgaaa  aaagattggg  tgatagagat  tttgtttttt  caaatattaa  taagattatt  215700
aaggataata  tgaatatcgt  taagaagatt  ttaaagtatg  taccaaacgc  atatttgatt  215760
aatacaaaag  ataatgatcc  ttcattagta  cctacttatt  tattaaatga  taatcgtttt  215820
actttagata  ccgacttgaa  tattattatt  agcaatgata  aactttttcag  acaagattta  215880 ttatataggg  ataatacgct  tatcttagaa  attaaaggaa  aagataataa  acgacttatc  215940
gcttatgagg  acgttatcaa  tactattgta  gatagtacta  aaggtaaaag  ggtttattca  216000
gactataact  tattaacaga  atccattaca  cttctggatc  ctcttgtaaa  gaataaagaa  216060
tataatatta  attcaattaa  acgaactagt  gaaatgaaag  cactagacat  tattgaaaaa  216120
ggtattaatg  ataatattat  ttcttcacaa  agctattatg  acgtagatga  agcatataat  216180
gatttagctt  tttatcttgg  tgaaaataat  gaggatgaat  ttaaaagaaa  tatgtcaatc  216240
gttaatcata  aaaattgcaat  gtcacatact  tttaaagatt  tagaacacgt  tatactttcc  216300
```

-continued

```
caaataattg atctagagga tgatagagga ttaatggaat tgaatgataa gttctttca 216360 aaatatccta ttgttatgga ctatcttggt gaaagtttct atgatccgag ataaaaaaa 216420 aaaatatccc taatgctaat attacttagc attagggact tattatatac ttattttttt 216480
tttttagact gatttaataa attcaataat ttccattgac attaaaactt tatccatatc 216540
ttcgataaat acttcattat cattttcatc aatatacata aaatcataat tatatgaggt 216600
tgataatgac atgataaagt tttcacgttg aactagatca ataatactgt catactcagt 216660
aagaacttct ccatagcttt ctgatgttac gatcttatta ttaatcttat tactaatgcg 216720
atttcttttt ccagaaggaa tagttttact tagtagaact ttgggtaaaa gtttatagtt 216780 attctttca agttctctaa tcatcgcaac tagtaatact agtactctgg gttcacggaa 216840
gttcttaatg gcaaatcttt ttgcaaagta catattcata agtgaaattt ggaattcgtt 216900
taaatgttta acattactac ttaaacgtac aatttcttca ttagtaatat tatattttta 216960
gatagagtct ctcacatact tatcgataga tgcatcatta ataacgcttg acatttcatt 217020
atgtttatgg tactgaatta aagaaaattt atcattctca tctagatcgt catctgaact 217080
agaaatcttg attactttga attgtagtgc ataattagaa cggaaagcat attcaatctt 217140
tcttttaata actacgtcta aatacgatat tgatgattta ttaatagaaa gtttgcatat 217200
aattgtacgt ataatttcat cggtaatttt ttggtttaat atgtcttcat ctacagatat 217260
attttgcaag aagtaccaga taactttatc tttgtataac gtcttttaa tacgtggttc 217320 aacaattttg ctaatcttag taagaatatt aatccctttt ttattactaa aatagcgatt 217380
aattaattta aaagtcttta agaatagttg ttcattgtaa ggcttatttt tagcattacc 217440
tgaagtaata agatattcac atatagtagg aattaacaaa cgttgcatga ttgcagaacg 217500
gattagtact ttatttgatt catcagttac ttgtagttca ggaacaattt tatcagagtt 217560
agttctacta taatcatcta atgaaatcgt atatgtagaa tcaactactg catcaatagc 217620
ttgtaataac ttatcaaatt taataaaatc ttcgaaatct tcaataaatt tactttcagt 217680
ataatcttca tccataaaca tgtttacttt aaaatttaat agtttatagg caatttcagg 217740
aacttcattt aaaaagtagt ttaaatcatt gtaaataata tgatagatat ttgaataaat 217800
tgcttgatga atattatatt caaataactt ttctttaccc tctaaattag cattctctaa 217860
aatagaagca aagtctacaa ctatcttttt gggatgagca tagttatctt ctgtaatata 217920
agttgtaatg tctttacgat gttcaacttt ttcaatagtt accatttcgt ttggatcatt 217980
ctcactttta ggtaaagata cagttacttc tttttaatcct tcaatagata tatacttatt 218040 tttttaactta aactcttcct tcacactatt accccctaact tttgtgttat cagacgttat 218100
tgtcactcaa aaacaccaac cattctcttt ttatttttat taataatata attgggatga 218160
gattaatttt tcatcatata catatcaacc tttcttattt atatatacta taccacactt 218220
atatataata tataattgaa aagttattaa cgtttattaa tagatgttct acgagattta 218280
gattttttat tacgatcaaa gatactttgt ttcttaggtt tatcgatatt tttattttta 218340
ggttttcctt tacttctaat atcttttatc ttcttgttat gaagtcttct attcttataa 218400
cgctcaattt caacaagctt tctttctgaa gcgggtatat ttctagatac ttgtattttg 218460
tcaataggtt ttaatctttc taatgaggga aatgttaata gattattctt ttctagatat 218520
ataagggcaa aataaacact tttttcaaat ccataaattt ggtttgggtt tcttacttta 218580
ggttcatcta ctaaagattt aatactcatt ttattcttaa gccaatcaat aatcaaacca 218640
```

-continued

```
tctcgattat aaatatatcc atacgtaaac ataaagttag gattattact atagaaactg 218700
atatgcgagt ttagaataga aacgtttgta ttatttttgt ctattttaat tactacgtca 218760
taaaccattt tttctwywmt awacgtykca kawsrrwtty tawakwmata rtmcwaactt 218820
tatstttacr tmtkkawata yttmtamwck aratggttts awtmttgatt rgcttwwkwa 218880
tamaatgagt attaaatcgg tcatacatat tggcgataat catatcccgc ctagctaatc 218940
ctgcagaacc ttttcctgaa gggtttttgca taaactgttt tacagtgatc atttctaata 219000 tacacccct atttattaat tataacataa ttttttgtta aatttaaaat aaactttttt 219060
attttaaaaa attattaacc cctaacgtga atgataacta tcacgttagg gtcaacttta 219120
ttataagcta attcgaatat attgattact tgtaaccagt aatccaatta ctgaaaatga 219180
tgctctcata atctgaatat ccgtcattac cgagttgata atctttgttt cagagtcagg 219240
aacatatttc ttttctttaa gatcataaat cattttattg ttaatacaac tctcaacagt 219300
ttcatatact tcttcatcgc taaataattg agagttcttt aatacaattg catatgtttc 219360
tttaaatgca gaatatacta gttgtaacaa tactttatct acttcagtta aactttcttc 219420
attatcaata atatctttaa ttacttttgg aattgaaata tttcctcccg gaatataacc 219480
gtaatctaaa gcagatctac atgcaaagat agaatcttcc aagagatatt tacgagtatc 219540
acgttccaat tcagatttac caccaataaa taacgtagct actttagaaa gtaatctagc 219600
tttacgattc tctaatttaa agatttcaga atctacacct ttttgatata cgtctaaatt 219660
ctttaaatct tgaatattaa ggtcaattaa ttcaattcga gcatctaatt cttcttgatg 219720
atactctccc ttaataaatt gagttgatcc accagtcatc gttactgttt cacaacgacc 219780
aatatgttca ccataaaatt gagcgttatt tgttttactt aagataaata agtcttcaaa 219840
accttcttta cctttttag tattaatctg agttcctaag tatattgcta agtcttcgaa 219900
ttcttcttta cgagttctag cgggaaagtc tgtagctgca atttctaggg atactctggt 219960
attattgatc ttttgaatct tcataaagtc aataaaattcc gttctatatt ccttcgcaac 220020
aataactaga cttttaccat taccgcatac ctgaccaata agatgggcaa agaaatcaat 220080
atccgtctta tctaaacatg aatcagtaat aaatacataa ggttctttga acattgcttc 220140 aatcttatt ggtttatttg caaagatagg gtcaacatac ccacgactag tttcaatacc 220200
atttacaatt tcaaatgtat cctcttcaga agtagattta tctaaataaa taaatcctcg 220260
tttaccaatt tgtttataga tattataaat aatatttccg tctttttcat cattgttgtt 220320
agatacggtt gcaatattac ggagaatctc aaagttatct tcattaatag gaattgattt 220380 ttctttttaat ttcttttcaa tcagttcacc aacattatt aatgaattaa tgatttcttt 220440
cttaggaagc ttacctaaga attgtgaacg atcattaacc attggttcta attgattata 220500
taattcatta ctaaccacta ctgaagaagt tgatccatca ccaacctctt gcactaatga 220560
tcttgaaata gtcttaatat tattcagaaa agtagtacta atagtattgt taaaacgaat 220620
cttgtctaaa attgtgaatc catctttaga gatcttagaa ccatataaat tatcttctag 220680
aatagttgta gatccataat atcctaagga tttagaaaga atatcactaa tactattaag 220740
tgtttcttta gcaatttttt gatatacttc atcagaaatt acattgcttt ctacaatatc 220800
aattttttcc ttaggttcaa gaattcttga aatttgatct ttaataatat tgctcataca 220860
cttttccacg ctgctatata aattagtgaa tttaatttaa ttcacaagaa tttaatcaac 220920
ttcgtcaaca agtttcttat aaattcacaa aaagtgaaaa tacagaggaa aactctctta 220980
agttataatg ggtttagcca acccttctg catatatttt taaattacat gcagaattat 221040
```

-continued

```
aatctctatc catcacttca ttacattgat cacatgtata taatctatcc gaaagtttca 221100 ttttttttatc attttctttt ttatatcaac aacaactaca aatttgagtt gatggaaacc 221160
atctatctgc aataattaag gtatttccat ataaaatact tttatattgt aattgaactt 221220
taaaacgata aaataaagac cgtgatatag atttagatat ttttcggtta gataacattc 221280
ctttaacatt taaatcttct atacatatag tgtgataatt tttaataacg taagaagtaa 221340
acttatgcag ccaatcatct tgtatatttt gtattttcaa ataaatattt tgaagtttga 221400
ttttcacttt attatattta ttcgaattat tgactttct agacaagatt ttttggtata 221460
aagaaatttt cttatataat ggaattaaat tttttaaagg actattaaat cggtgatttt 221520
cttcacttat atcaaaatga ccaatatttg catcaattcc aactgtcgga agattttgat 221580
ttgaatgata catactatca tcagtatcaa tacagaaaga agcaaaatac tgatttgctc 221640
tttttgtaat tgtacatatt ttaatatcac cattaaatcg tatcgattca gacatttta 221700 caccatattt aaatttaggt aaaaataatc gattattaat aatccttatt gtactttcgg 221760
cttttcgatt aatcgtaaat gaacttttg cttttcgttt attttgaat ttaggtttac 221820 ctgaattaga tgtaaaaaat ctcttccaac catatgccat attttacaa gtattatcaa 221880 aaatatttgg gggaaaatta tcccattcag gtttcaattt cctttatat tcgtctcgca 221940 cttttcgttc attaggttta ttgccgttaa tgtacatttc attccatata ttcaaagaca 222000
cattatatga atatcttgaa taattgaaaa aatctttaaa ttgtaactgc attgtttgt 222060 taggatagat tctgattttt tgacttatta tcatctaaat catcccttaa agttttttta 222120
tattttcgta atccgtataa tcggctagaa aatacatgaa taattgtcat aagatcatca 222180
actagttctt tttcaggaga agaactttct aaattaatta cagttagtgt tgttccatta 222240
actttacatc tttcttcaat aagttcaaaa ccaaaacgag ttagtcgatc tttatatgtt 222300
ataataagtt ctgatacttc tttgtttct atcatgtcaa ttaattttaa aaaattcttt 222360
cgtttaaaat taattccgga tgcaatatct gaaagataaa tattaacagg ttttccacta 222420
ttaactgaaa atgtttcaat agattgtcgt tggttttcaa gttctttctt ttggttacta 222480
gttgaaactc gataatatgc tacaatttt ctttttctt caggtttgat attattagtt 222540
agttcaaaat aatcatcaac catttcgtca gtataatact ttaggcgtcc ttttcgaata 222600
ggtttaatta tttttttcctt ttctaatgtt tctagttttt tctttgatat acgtaatttc 222660
attctaaatt catcagaacg cataaccatt taaaacacac tccttttaa tttatattat 222720 attgttacat taaaatataa attaaagtga aaaagagtga aactagatga tattcataat 222780
aagtcggcta aattaaattc ttattataat tcccaatttt gtgtttccac attggttaaa 222840
tagcaggact atatcataac ctataatatt ataggtccct cgtacttccc tttcggtact 222900
ctacttgctt cgtatagata tctcaatcta tcttattcac catataggtg ttacatttat 222960
tatttgcttt cgatagtctc tgaacgttca cccatcaagt gggagcttcg ctgctagatt 223020
ttccattagt ccacccttag cactacgttt tctaaggttc acattattac ttcacttaga 223080
cactgatagg ttttatttca gcttaggtaa tcttaaagag ttttttctgt ctttcgactg 223140
cattcacgct taccgttacc agttacgttg tagcccttta agctttagga gtttacaagc 223200
aattcacaag gtttcgcata catctttaca gatatatggg agttttgaat acaggttaat 223260
ttaatttata ttttaaacta aactcatta aaatcaatta aaccattact gcttctttc 223320 tccactttt tattttatta taattgaaag tacattgtca ttttcaataa tacaatcgaa 223380
```

-continued

```
ttcttcgata aaggtataca tcttaatata atctttacat gaatcaagat caatataatt 223440
attaaatttt aaggatactt ttttaaattg tctaatttct tcatctttgg aagtattgtt 223500
aaatcctttg atgatattaa atgaaaattt ctcttcaaga tcatatagta gtaaattaag 223560
ctttaatccg aattcagaat                                            223580

<210> SEQ ID NO 2
<211> LENGTH: 224658
<212> TYPE: DNA
<213> ORGANISM: Artificial Sequence
<220> FEATURE:
<223> OTHER INFORMATION: LPJP1.NL Recombinant Bacteriophage

<400> SEQUENCE: 2
tgacgaaaaa gcatgtcttc tacatctacc ggtacatctg aaatatcttt cttacattta      60
ctacatgtta atccatgaat tgcataagaa ataccatatt tatcagattg ctcactaatc     120
atttcactaa gactcttcat gtcactaact tcaagattac taatgatctt aagaatttgt     180
tctgggtttg ttacttttac aaatttaagt tctccagttt tttccaatct atctaggtca     240
ggaaccatta ttttttttagt gaataaaatt agatcaatat aatctctaac ttcatcatag     300
ctttcaggtt taatatatga tagtaatgtt aatttatctt ttagtgaagg tatttgaata     360
tcgaatacca ttttacttaa cggcatttgg gaacgagtga tcttatttac tgctgaatac     420
tttttaatga cgcttggatc tttaactgta tcagtaattt gttttaaacg agaatatgtt     480
tcttcattct taacaacaat aagattctca ttataagctt taacattcct cataacgttt     540
ccacatgatc cacacttaat atcaaaagaa gttccacgtg ggaatgtttg acagaatagt     600
ccgtaaatta aagtatctag atcatagata gatgtaatgt caatgaatgt atcccaatct     660
aatttaccta gtgtagtgga attaatttta ctaaagtatg tttgatattg acgtaatgta     720
gattcatatg cagaagcggt gcttgatgag atagaaagca tatcattcat acgtagactc     780
tctacatgag caatatatgc tgattgattt aatgtaactt gataagtagg gcttcctgtt     840
aatgcatatt taaatttatc aaaattaata tctttaaatt tatcttcatc atcaataatt     900
aatgagtcga tatcttttaa attatcaatt tttgctttat caagaatatc tttaactgag     960
tcttttttag gttcttgttt aatttcagtt aatgtttcat ctacttgtac gttgttaata    1020 tttttcttgat taattgggtc tttaatagga atctcatcac ttggttcttc aaaaattcct    1080
ttaatctctt cttcttcttt tttctcatta tcaggaacat catcaggtat tggatttcca    1140
tctaaaggct caatgtctga tggattatac gcaaattgtt cttcatttc ttgtgatttt    1200 tgttcatatt gatattgttg agtcattgct tgttcggtat tttcattttc tccagtatta    1260
ttcgttactg aggaatcttc ttctttctgg taaacatcaa tacctgtacc agagagagat    1320
aagttaggat caatattctc ttctttttta gcttcttcag attttctacg ttgctctgct    1380
tctagaaata attttgctac atgttgagga tcttcaccta ctacttgggc atgtaacatt    1440
gctatttcta gatcgctcat ctttttatcg ggaatattaa tatttgtagg aatattgtta    1500
ttttcattat tatctgattt taataccatt gtatatttta cctccacata atttatatta    1560
tttttaatta tacattattt ttgatacagt tgtatttgtt ttattattgt atccatataa    1620
taatccaaag tttagattag tagtagtatt agaatctact aaattaatat ctatataaaa    1680
cgtatttaca tttacgtttg aattactaga aagaacgttt ttaacatttt gtatattaat    1740
ctttacaacg atatcttgat gtacaatata tgattctatt tgattttcaa ttttactttg    1800
aagttctaat ctagtttccg tatccaagat ttcatataaa tataatccga taccgatgcc    1860
```

-continued

```
catattaggt tggttcgggt acgttccttg ctctattata attaaatttt ggatctgttg    1920
tgctaatgct tctaggtttt ctcttaatat tggttgattg aagtcatccc tctctagtat    1980
aacttcaggt ctgaatgata tatttgattc atccgcttta aagtctgcca taattttcac    2040
cactttctat ttaaagtatt ctataaaaat caatagcttt taattataat tatatgttgc    2100
agtaaaaatt aacattttaa aaaattattt gtgaacaata ttatatataa gtttagaaaa    2160
atttttttct gggtttatat aatacttaaa tatcactaaa ttgtttaaaa tactcgggtt    2220
gtagttcaca ttgttgacta accatttaaa taatataatt acatttagtg atattataca    2280
tatctttcat cataacatta ttctaaaaaa taatgttatg atgaatattg ttttaatgaa    2340
catatactta ttatagatat attaatgcag aaagaagtga atattttgaa acaatttaaa    2400
tgtccatatg acagaaagat atttgtaaat aaaaaggcat tatatgatta tatggaaaag    2460
aattattcag atcaattaaa tggactatct ccggctaatg cttattttaa tatcaagtat    2520
aacaaaacac atggtagatg tattgtatgc ggtaagaata caccatttaa cgaaactact    2580
gaaaagtatg atcgtttatg ttcagataaa tgtaaaatta aatatagaaa gcagtttgta    2640
gagagaatga aaaaagttca cggaacagat actctattaa gagatcctga aatgcagaaa    2700
agaatgttag ctaatcgtaa aattgcagga gtatatacgt ggtctgatgg tagtaaattt    2760
aaatatgtgg gtagttatga gaaagatgcg ttagaatata tggataagat attaggattt    2820
cactctaagg atattattgt tccttctcca ataatctttg attatacgct tgatggtaaa    2880
aaacatttct atataccaga tatatttatt gttcctttca acatggtggt agaagtaaaa    2940
ggtactaaca atcattacca aactagggat agacgtactg aagatgctaa ggataaagcg    3000
gttcttaaga caaagtatcg ttatgcaaaa ttagttgaca agaaatatga caagttcaat    3060
gacattattg agaatcttaa agaatcaaag gacgataaag tccgttaata aaaataaaat    3120 tttaaacccct catttcaata atatattata attaagataa tgtatattat catattgaaa    3180
tgagggattt ttattggaaa ataagaaacg taaattcttg gcactgtgtg gaattagtgg    3240
ttcgggtaag aattctgttg aatctatact tgatggttat tatgataatg ttaatggagt    3300 gtttttaaa aaactaaatc aagtaacaac taggaatatt cgaaatactg atgaatttaa    3360
tagtggaata tatagttta taactataga tatttataat ctaataaaag aaaatctcat    3420
tggaaaaaca gttatcgata ataaatatta ttatggtacg cttgatacta gtactacaga    3480
tggttgtatt aatactatta ttgtcaatgc aaaaggatta tctaatctta agaatgatct    3540
taataataag tatggtgaag ataactatga cctatttgta ttgcagattg ctaataatac    3600
tcctgtggaa agaagaaata gagacgcaga atttatcaga ggtgaatata atgatttaaa    3660
aggattgtct aacgcaactc ttataaataa tcctagtaaa tggttaactg tctctgacgt    3720
aattaactgt cttaagaaag aaggttttt ggatacatga cattagttag tcatactaag    3780
ttatatgaaa aaacaaatta tcgtaataaa agaattagct atattaaaaa tacgttgatt    3840
actgagtttg atataaaaag tgctggtcta aatattctat atgaaatgga atatttagac    3900
caaaatcaat atgaaaaatt attatcaatg gaaaagtatg aaagaaacgt tacaatcgga    3960
aagatattaa ggtctaataa agaaatgaat gaagcattat catttggttt ttcagaagcg    4020
agaagattat ttttcgaatt aaatcaaatt gatgattcag aattattatc tattaagaag    4080
gatgcaatat ttcttatagg tagaaataat ataaatatta acggtaatgt ttctgaattt    4140 ataaaatttta gaccaaagaa atcttataca acgtttgttg aagtgttaga ccgagaacac    4200
```

```
tatttgaact ttgaaagcga agaaataatt tatgatatta aaggatactc tagtgatatt    4260
aaagatattc ataatgaata tttattaaag gatcttctta atgtaatgaa gtttgattat    4320
gttaatgata aagatagaat atttgaatat ttagcagttc ttaaggatga cctaattaaa    4380
tatagacttc cagtatcata ctataatgat attaaagtag gaaaatatat tgtagaaatg    4440
ggtaacgcat tatttgatct agataatatt aatgataata ttaagcaata ttgcctgttg    4500
tctaataatc ttagtttat tttaaatcta atcaataaga ctctttcata aaaaaaaaat    4560
aaataatata ttaaggtaac gatcattaat ttgatcgtta cctcttttt ttttttctat    4620 gatccataat atactatata tttacagatt ttattttctt gtcaatcgtt aatgatactt    4680
cagtcatgat aagcataatc ttgctcataa catattcctc aatatgttct tctgaaatga    4740
tggtagaaac cctatatttt aagtcactag acattctttc tacaacttca ttagtacatg    4800
atataacaga ttcttcaaat tcatctgtag ttgtatcgat atctatatca tcactaagtt    4860
cactctgatc ttcatcaata gatgtttcag tagtcgcagt attttctaca tattcatttc    4920
cttcattgtc atactgaata ttcataccat taattgcagt aacttcactt aatctaggaa    4980
gtattctatc aatactttca gcaattaaat tattctttac aatccgtatg ctaatatcaa    5040
taagaatatc taattccttt agtgctttt caccatcaat attattatgc atcattctat    5100
tattacggtt agatttaata atcaatcttc caataattat atgtgtaata aatataatta    5160
ttagtattga aggtactgta atgtaaaata aatttgtagt catcaaataa acttcccta    5220 ttcatttatt atttatatat aattattcat actaaaaact tgaattttat tttcttctaa    5280
gaaagataca acttcctgag aattatcata ttcttctaaa taatatactt tagatattcc    5340
tgaagcaata atcgttttgg cacaattaaa gcatggtgaa tgagtaataa acattgatgc    5400
gccttctgta tttccagagt ttctagccac cttagatatt gcgtttattt ctgcatgtat    5460
ttcatatttt aatgaccatt tatgatgaat ttccatatct tcacataaat aaaatttctt    5520
tccttgactt tcaatataat aatctttgcg acaaatgaat tccggatgtg aagtatacca    5580
taatccttct ttctttatga atatatcatt acagttagcg tatccactag gggttccatt    5640
aattcctgaa gatataatgg agttattctt aacaataatg caggagactt tctttgcaga    5700
gcatttactt atttctgaca ttcttattgc aatattcata aagtttactt cgtttgtcgt    5760
aatatagtca tccatattat tatcttcatt atctataaat atatctacca ctatataacc    5820
accgatctta ttctaattat aataaattat ttgaaatgat gcattgttta aatactttta    5880
attttccgaa tgttaatgtt aatatcaaca cgatttataa aattgtcaat ttctgtatct    5940
gtattagaga acatattttc aaagatatca aactttataa ttcgataaaa gctatcttga    6000
cttatataat gtgcaatatt attaacaata ttatcattat ctgtaagata aagatacttc    6060
acaacaagac taagcgttgt taatattagt ctgtatattt cttttatacg ataatcgttt    6120
atatttttat ctataattaa cgtatcatat gattctgtct ggaagttaaa tttatatgtt    6180
tcttgagaat ttactttctt catcaaacta attatagata ctgcgtttga tggcattttt    6240
ttcacttttg gaaatatcaa ttctttatta tttattcttc tttttgtatc ttttattaat    6300
tcatcaataa attttgaaaa ttcggcatta tataactcat cattacttag atccatattt    6360
ttttgtagtt caatatacat tttaaattct agttccaatc tatttaatat atgaacttca    6420
tgctttgata ataagttaat atataatacg tttattgtag gaaatttaat attggatta    6480 tcatcagtat ctatatcagt ggattctata tagtatgatg agggtgaaat ataatttta    6540 tatttataca tatgcgtata tgagtaaata actaattcat tagtatacgt aaaattcatt    6600
```

-continued

```
aaattatcat tatcataatt atccacttca atatagttgt ttattattgc atcttttcga    6660
ctgattaacg atctttcttt attatatttg tgcattataa aagagatata tctattatta    6720
tttatataat tagatgaatc gataaacatg tcatattctt gtaattcttc aaaacatagt    6780
tctaaaatat ttgcaagcaa tatttgaatt atatttctat tatcttttat tttattataa    6840
ccataataat ttttgtgact tatcatagga atatctgaaa atatgatgta attttcagaa    6900
gtaagaaaaa aattagaatt atttaaatca ttgaagatac cagtaatttt actgatatct    6960
tcaagactta tattttttaaa ttttttcatag ttccataaat ttctcacttt aatattatgg    7020
ttagcatcag tatagaaata tttagtatca atattcatta actaatcact atccttatat    7080
aatattttag tatcgatatt tacttttgtt tttaaagtta acgtctctta ctgttcctgg    7140
aggattattg attgataatc ctgcattatt attactttct gtaagaagcc agatagtata    7200
tcctttaggt ttcttacaat caagcgtatt ctcaccaaaa ccatccgtaa taataatatt    7260
aatatctgat cgaatatttt cattaatata tttaattgga gcagtcaatg tagttccacc    7320
ataagcagtt ctttcaaatt tacgtaatct atctttctta gataacggat atacatcatg    7380
aaccattgta tcaaagtgaa ttacatatag tttacttttaa atatttgaaa taatctgacg    7440
aatttgatca aaagcccaag ccacttcttc gtcactcatt gatcctgaca tgtcgatagc    7500
tacggtaatt ttagattcac gatccggcat tcttcctaat aagtcaccac gatctggcat    7560
tcttctattt ctacggagat tagttctttt ataaggaact tttaaagaac caatcttcgt    7620
acgtaagatt tgttgccaag gaataacttt ttccttatta atattttcta gaaatttatt    7680
aatagaaaca ggaactgatc cggctaaaga tagtcgttca atagtatttt cgatattttg    7740
ttttattgaa cgttgaatgt cttcttcaga ataatcgccg ttttccatt ttgagtgaga    7800 agaattagca ctattattca tgttaatgcg ttctttctta ccttctgaat ctaattcatt    7860
acctagatca ttttcatctt ttccgtattc atgagatttg ccagtattac cattagaaga    7920
accttcttct tcattttcgc tgtcattatc tccaccatta tcagtatcag atgaatcatc    7980
atcattattc ccactttgat tacttggcat tccattatta ttttgaccgc tttattatt    8040 ttcattagct tctaataatg catccatata gtattcaaaa gatttatctt tttccaaatc    8100
cttattatta gttaacattc ttacataatc tagtgtaata gaaccttctg gaatatcatc    8160
aatatattga ttaatagaac aatccatagc aatatttgcc atatgcatga agtcttgatt    8220
tttactaatc gccatattct tatatcggaa aatatgatta tttgaaatat gaagtaattc    8280
atgagtaata actgcaatga attctcgatc attaaacatt aaaattttat atggatttag    8340
atataatgta aatgtatctt taaatgtatt ttcagcatag ctaactgctg ccggagcaaa    8400
gttcggatca tgaacaactt ctttaatcat attaattgta aatagagcaa agaatttgtc    8460
atcattaatg ttatcactaa ttaaattagt gaatgttaac ttaatatatg cttcaaatgc    8520
tttttctaac ttttttgaag cttcaagagg taaaagcttc tccttaccat aatattcaag    8580
aagaaacttt tttaattctt ttctagtcat actattagaa ttataattat ctaaagtagg    8640
cattaatatc ctccaccgat ctaattattt taaacgttta ctaatttttt gattgattgc    8700
gatatattca tcatattgat aaactctgtt atagaaatca tctgcagtat tatttacttg    8760
tcgattaaac attgcaaaag tactcatgat aacttcttct tctcccaaag tatctacaaa    8820
tttaatatag ttcgcagtca ttctatctaa atctttttta tttttactc gtttactatc    8880 gttacccatt tcacgaacaa cataattaat tacataacga ctaagtagtg ttttacgtaa    8940
```

-continued

```
gtttgtttcc tctttaattt gggtcaatag ttttttcatct ttagataagt ttgggttatc     9000
gataatcaat tcagctcgga tcatagggtt tgttttgtct tttaggaaat taaagaataa     9060
tgaagtagct ttcgaaccta gattaccttc aaacactgca cgtagtttat gactaataga     9120
tactgtatct tctgggaatt gtttcatatg ttcataatac gcatcagaac tacgtttcca     9180
tgaacgtgga gtaggtgact tacctaagct tgaactatct acaaatgaca gcaactcagg     9240
atttgttgca ataaattcag aaatatcttc atgaatgttt ggtcgaatat atagtggagt     9300
agaagtattt gcatctacat attcaaattc ttgaatagcc caatctaacc attcttctgg     9360
atctggatct agtctaagat ctgtaaatcg gtcacgtagg gcatagttca ttgtgtttac     9420
ttgataatca ataccgtcac tgttttcatc tgtaggattt cctgcagtaa taatatataa     9480
ttcttctgga agagagtatt gatgaattct ccgatcaaga ataatattca ttaactcttg     9540
ttgaacagct aaatctgaac ggttaagttc atcgataaat agtaatggaa ttttttccatt    9600 atctgcaatc ttatatagtt taccaattgt actatgaata gtatattcat tttctttagg     9660
ttgttcttca ttttttaaacc atgttttgat atttgtaagt ttaaatttat ttttaggttc     9720
tgcaatatga gggataccgg taatttctcc ttctttaagt aagttaccat caagcttaac     9780
aaactcaatt aagtcaccat ttcttttcatt ataacgttca acaaataatt cagccaaact     9840
agattttccg atccctgcat gaccttcaat aaatggtacg cttcctgaag ctaccactac     9900
gcctactaca tctaacaagt ctgacatttt cataaataaa ttccaccaat ctatatttt      9960 tattttatta ctaatttata atatatattt ataaattatt tataattgtg tttgtcgcag     10020
tactaatttt ggttaatgtt tcttcaaggt ttaaaaatac tttcttatca tcatttttttg     10080 cttctaatgc aagatcgtca catcgctgat tatattcaat aaagtgaggt agtaattctt     10140
ctggaatatg tcgatttctt tttgatgtac cttttttaaa tgaattagta gtatgtcctt     10200
taacccacgt aaaattaaat tcatattgag aagaactatt attaataata tttactaata     10260
acttccacat ctcagcattc tttactggtg ttcctgaact actcatccag tttcgattaa     10320
tccatccagt catatattct gtaatacctc tgataacgta ttgactatct gaaacaacac     10380
taatattaaa cttttctttta ttaccattct tataattatc tctcataata tgcgctattc    10440
cataaataac ggctaataat tcattttggt taattgttga atcatgaaaa gatctttttaa    10500 tactgtatag cgtattaaat tcggtgtcag taatatagca tccaaatcct ccatacatag     10560
gcttactggg gtctttccta ccattattaa agctacttgc atccgtaaat aaatatatgt     10620
aatttgtatt atcgttgtcc aatatatttt cactcccacg tttagttatt tctttttcgcc    10680 tatattctat tattgtaatt ctagaataaa aaattaatta taataaacaa tataatataa     10740
gcacttctat aagaaaggtc tgatatttat gaaagttcca aataagaata taataaatga     10800
tattatagat aaggaactag aagaaaataa aacatttgta gtagatacta atgaatttga     10860
tactgagaat atgatcaata gtgttgttcc tagtgaagaa aaatttaata aagctattga     10920
aaaaattatt cgtaagtcta atgaatatcg tagatatatc ggaatactga aaaataatat     10980
tgatctaact tcttgtaaat ttttgaaacg tgttgatgtt tctgaaataa gaagagttaa     11040
tattgaaatg catcattacc catttactct ctatgacatc gtatctatgc atcgagaacg     11100
tatcaagcaa gatttaggtg aatttttattc atatgataca ttcacaattg cagaaaatat     11160
tatgaaaatg cactatgaga ataaaatcgg tattgtacct ttatcatata ctgctcatga     11220
attagctcat tccggaaaac tagttattcc tcttaataaa gattatgtct ttggtaactg     11280
gcaagaatta gaaaaagaag atattattat tacagatagt atgcgaaagc aactagaagt     11340
```

-continued

```
attagaacaa atgacaaata gtattgagtc tggaagcctt aactcaaacg aagatctatt   11400
tagtaatatt cagactgtaa tcaatatgaa aagttctgga ataccaaata agattataaa   11460
ggaaaaatca atcattgagg atattaataa tcctgaaact gatgaagata taatataata   11520
aaaatccctt aacgtataat aatactatac gttaagggat ataatgttat attatgattt   11580
tttgccatta acttgatcta ataacttata tatgaataat tctttatata ctttctgatc   11640
tctattatat ttatcaatag ttgctttttc atcatcagaa ataacttctg tactaaagtc   11700
tttaacttta ataaccatat ctaactctgt gtttaaagat tctgatttta atacgatatg   11760
gaataaattt atgaatttag tattttcacc ttcaataaat tcataattat ctaataaaga   11820
aattttctta tcaacatcag aagaactaaa tattttttcca aagaaatcat caatatattg   11880
attaattgat agtttaataa tttcttcttc actataattt ttattagttg gaatatcctg   11940
agtgtaccaa atttttttgaa ttttatcatg gagcaataca ttaaatacgc ccggagaatt   12000
taccataata ttgctaacaa caaagctaat actaaacgta tataccttg gcttagtttc   12060 taatttatca tctgagttac atgatccttc tgatgaagta aagttataaa atgtattaaa   12120
ttcttttaca aactgagcat ataatctttc aataaaatta tcttcaaaag gtccaaaatc   12180
tgtacttaat ggaagttcaa ggtctccact ctccattaaa ttaattgctt cttgaattga   12240
ttcaattaat atatcaatct tactatttac ttcattatca atacgatcag ttacaccttt   12300
cggaccatag atatttaacg tcatatattc attattgtta tcattcttat taagtacgtc   12360
atatgttaca ctagtaataa cttcacaatt acgtgaaaaa tccaattctt tatcagtgat   12420
atcatctaaa tctttgatat caccaataat tcttaaacta atagcatcct caatattagg   12480
catcctaatt ccacatccat ttcttttat ttgataataa tttattaata aataaatata   12540
attttttaca ttcatttaca agattataca ttccctataa ctatgatata ttcaatagtt   12600
atagggaatg tatttataat taattagtgc attgtattaa tatattgtat atacgatgaa   12660
gcgttatcct ttattacatt atcatgttgt cttatttcat atttcgttaa catgatatta   12720
atgaagatat aagttataat aaagaatata taactaagta ttaatagttt taataatagt   12780
ttatttttag ttcgattatc ttggtttttca tcagtatcta tattttttct taaattcttc   12840
attaaaaagt ccccctttta ttctatatat tatattgttt tttaataaaa gcgtaataaa   12900
cgaatatata gacatatatt ataattatga taaaataataa aataatataa agaaaaggat   12960
gatattataa tgaaaaaatt tgtacaagta ttattagtag gagttctatt agcagtagca   13020
gtaacaattg taactattaa cgttacagaa agtaataacg gtacaatgca aaaagaatta   13080
ttaccaaaag aaattttaaa tagacaatag tataattact actattgtct attttttttt   13140
tttagttgat taagaatatt ttatcataat ctagattatc gttgaattct aaaaagaagt   13200
ccccaacatt acttactgta cattttctaa tagaagatac tccttcatct attggtgtag   13260
tattatttac ttctagcgcc atactattat cactataaac tcggatagat attttccaag   13320
aatagataac ttctacattt tcttcattta atactttttg tatcatgtat aagtgatata   13380
tattgtcatc atccctcttc atatcgtttg ggaagatgta tccaatagtt ttatcattct   13440
tatcaaaata aaaattttcc acaataaatt ctttgacaag attagtattc agtaattcaa   13500
tagcgttatt taagaaatct tgtctaaata aacctaaatt atgaatattg atttctagca   13560
tattataatc cacaccttt tcttttttct tttaagatat taattcatta ttaagataaa   13620
tgtttacact aaagtcatct ttagaagtat tatttatttc taacgtaata atgtaatcat   13680
```

-continued

```
tgttagcact ataaaagatg tattcttta tatacctaaa attatgttgt ttatcaataa    13740
atgaatcaat cgtgtttgat gtaatatccc ccttataatc tttgatataa ttcttatcaa    13800
aatatatttt tgctttatat atcttttctt taatatattc aaaagattct ttgttatctg    13860
cagtaattgt aacttgatta tttagaaatt tgttataatc aatattaagt atatttactt    13920
cattatgatt ataacaaacg ttccatgcag taaatatttc ttttgaaata aactcaaaaa    13980
tattattatc cccactgtta ttcataataa atttcccccg atatatttat ttgatatagt    14040 aagtttt att ctaatattta tttaagttta taatgatata ttatagatat ggcaaatata    14100
taatatatat tttaattttt cattaacaat atttaagga ataaggagtg ctgattaatg    14160
tatagatata tacgtacaaa cggttctatg cgaaataaat tgaaagaaat gaatattgat    14220
aagaatgaca gtatctttga aaatactgtt aagattatta atgaattaat aaatcatttc    14280
tattcaataa gtgaagtatt taacttcata gaaaaagaaa atattcatat caataatgaa    14340
gtgatgcaat atttaagttc tgatgaattt tataaatctg catatacttc gaaaataatg    14400
atgaagaatc atatgtctaa acattcattt attcgcatga taaaaaatga attgtgttat    14460
cgtaatatta gttttatttt taatgattca ttatttacta atgatgatat tgccacgata    14520
atagttagga atgatctagc tgaaatacca tttgatatta tggttaagga aaatccatta    14580
agcttgaaag attttaagaa gactttaaga tataataatt taaatgatca tgaaaaatct    14640
attttagaat tacgtaatat ttaaatttat taagaaaaaa aaaagataac tattgtaatt    14700
ttaatagtta tcttttttc ggatcataga aatattttat atattatata ggataatcat    14760
attatatatc tttaatgatg ataatctgtt ggctaattct ggacttcttt tctctaatga    14820
atagatatcg atagcttcaa taagattaat tactttaata aatcctagat ttcgatatct    14880
tttatttatt aaaacaaaat taagtaattc tatgaattgt attaatcttt cagcatgata    14940
caacgatttt attttatatt tttcttcaac atcagcgaga tctaatccat attctttgta    15000 gtaattttc tttaatagcg gcttcatcct acgtatcatg atactaatat atctattaag    15060
ttcattatag gtagttttag tattcttata cactgccatt ttatgagttt taaagtagtt    15120
atataagtaa tctattatat cattaaagaa atattcgttt gcataaataa tctttataaa    15180
actagacttt ggcataataa tatctaatat tttagggtta atcgtaatcc gagtattttc    15240
aacccttgat aagaatttaa tatatgtttc agttataaat ttatatacaa cttctgattc    15300
aatattaaac ttttcacaaa aattacatat gacatcattg atatcatact tattatcaca    15360
acagaagacg taagacgaaa ttgtatacaa taatatatat tcagtattat tattattact    15420
atgactaata ttatcatata aatcacttat catgatcatc atatttcag gtttaatatc    15480 atataaatag aatatatttt gatagtatga taatatttgt tgacttttac gtttattatt    15540
ctttaataag tacgtaataa tattcatagg taataatgta accgattccg tatcttttt    15600 atctaatgcc ctattattac ctaagtatga taagatatcg ataatatcac caaagttaga    15660
aatatcattg tatatatcta gtatactttc aatgtttca tttaatgaca ttggttgtaa    15720
tttatattta tacgttatca taatttgtca cctgtattct tttcaatgat atttctaatt    15780
ttattattag tatattcatc atttgagtaa attctaggta atatctttgg tttattctta    15840
ttagaaggaa gattatcaat tattgaaaaa attgatatta ctttattaat aatatttata    15900
atattggtat ttttagattt caataactta ttaatgtcat atgataataa ttcattatca    15960
ctatcaaact tcttatagaa tgtaaaaccg tacatattaa tattattttc tagtaatatt    16020
aacgtatcca taatattatt atatcttacg tcatccaatt tatctgaata ctccgttctc    16080
```

-continued

```
ataacaaagc ttattacttt aacaataaaa tcaactacgt tatatttatt tttatatcta  16140
cgatatattc taggataatt gaatatagaa ttgataaaag ttgtatcttt atacgttata  16200
taggatactg atatagaagg gtctccggta tcaataattc tagtaatatt ttcatattca  16260
tcatcaatta tattatcatt gttaagatat tttaacaata tatattcaat atatagtaaa  16320
ttcatattta aaaaggatc taatatacat tgaatttcat taaaattttt aatatttata  16380
tcatatccct catacattat aatattttcg ataaaccttg atttttcagt gcgagaataa  16440
tctttaattt tacaaatatt atttttgtt aagagacatt tatacttcat tgtattgtta  16500
ttaataacca tatccctaaa aatttctttt gtatcttttg taggttgatc tacatattta  16560
gaaaatttac gattaaaatc aattgtatcc cttaatgatt ttggattata ggttcgtgaa  16620
ttaatttcta aatattcttg aatgtctgta ttaattgata tactatttgt cacgctatat  16680
cacgtcctat catttattat atgcttaaca aattaattcg gcttttcatt aacttacata  16740
attcatctat tcgtttaata ttattaagag tgttctttct tattaatgaa ttatgattat  16800
ccgcactaac attatcttca tatcttctaa ataattcata attattatta gtataatcta  16860
tagaatccaa aattttaata cgtgcattat tttttacgct agtcatttta ttattattaa  16920
aattaatata taagtttaat aattcaaaaa taatggatat tctatcaata ctgctttcaa  16980
ataatattag atcatcttta ttgttaaaat taagatatct agatattctt aatgcactat  17040
gagggtctat tccgataata ctgttaattg cttttttact attaagtatt atatctttct  17100
gattatctgt aaaaaattta gaataaccac taccatatat tgtattgaat attttagcca  17160
ttgatgattt actaataaat tttttaaaat gtttatcatc aatatctcta acgccatata  17220
tcgcacagaa tagattggtt gaatatagat tcattttgtc aatcatagtt aaatattcat  17280
tatctgtaat tgtagaagat tctgaaatgc atgtttttaaa cttttcagat atcctatttc  17340
ttataccgaa gtcaggatca tcgtcattgg atatattgtt atatgtgtca aatagtctaa  17400
aaataatttt tctaatgtat gaagagttta tttgtaaatt actactagta tacttatact  17460
tcttactaga tggtgatata ataaagtcaa ttaaatcgtc aaacagtaca ctatacatgg  17520
aattattatt gataaatgaa tcatataatt tgtcaatatt cttcttagta attatataat  17580
tactataatt catacttctt ttcgtatata tatgattaat attaacatat tgagtattat  17640
ccataaaagt actaaacagt ttattgtata ttacgcttga cctaatacta tatttaaaca  17700
taatgtaatc ctttcttaaa tattaatgtc cttaatataa tgacgtaata attcctcgga  17760
tattcctagt tccttagaca ttacttcaat aggtttgtta agattctttt caatatagtc  17820
tgttatatat tgttctgaac tacgtgaatt acctacctta atatcagtag tacttaatgg  17880
cattttaaac ccaatagttc ttgggttagt aatttttttca tattcgggaa ctggatcatt  17940
cttaataata tggtctggta gtttcatatt atgtttttct aggctacaat tatccaatct  18000
tttaagttta tctaatgatt cattagtaat gataatcatt agatcgtttc tacttaggtc  18060
tactgacatt tctttcacat tttcatcata aagtagtgta gacatatgac taataatatc  18120
atgtgaattt tccaatgtaa tattttgatc catatatttt ctaatatatt cgactaattt  18180
tttctgcata ttccgattcc accaatctat attatttatt agagattata cgtatatcca  18240
ttcaattgtt aggttgttta gaattacctt catttagttt tatatttaat acatattgaa  18300
tattgtttcc tttattaaat ttaatgtaat acttagtcat atcaccagta gtattattaa  18360
taagtctaat tgaataggat ttcttactat gtttattaat atgagtatat agattatctt  18420
```

-continued

```
catcctctat aatgatattc ttttctgtaa agtaatctaa tatagattct attcgtttta  18480
atttattcat ccttatcgat aataatatcg ataaggatga gaataatata gttaacatga  18540
taaatataat catatatcca tcgttccttc catatctatt ttatggacat tcattaaagt  18600
aatatcatac tttttaactt caatatcaat tgcagtatag tttaccataa atgtatatcg  18660
attctttcca attttactaa gactattata tatctggatt gaatattcac ggatatttgg  18720
agaagttatt atattcgtat tcattttatt atcatattca gttaatttat caataattga  18780
gtatgataac atgatttttt tatgtacaat agatctgtac actattgaga ctataaagat  18840
tataatcata atcgataata ataatatcat ttaaacatcc tttcttatat agatttattt  18900 aatttttttga ttactgatat acacaacttc tttaaagtct tcatcatata ctaattcaaa  18960
tttatcgtta ttgtagaaaa aagtgtatgt attatgagtc ctatttaaag atctttcaca  19020
gtgatataac agatctttaa atacattttc cggatttaca taagattcct ccataacatt  19080
ttcatatcca gaaagaatta aataatttct aatgtctgga tagactttt ccttaagaaa  19140 ctttggatcc attctttttc taaattcagc cccaagaata taatcattta tagaatccat  19200
tatcttatca ataattaaaa atccgattaa cactaaaagt aatactccta caatattaaa  19260
taataacata aatttatcac tatccttttc ttttttatata tatataaaaa tcgatatcac  19320
tccattatag taacaattat tggagtgata tcgatttaat tttaagttat atactaagaa  19380
ttatttcgtg agataaatat ttcttagtat aatgaaataa acatgcttta gactaataat  19440
aagataaatt gtcaaggga atttgatctt tatacattat tttcatttaa taacaagttt  19500
atttataatt ctaattatta tatcagaatt ataaatatt attaaaatgt aactataaat  19560
ttttataatt atacattgat aatcatatct acattaatat ttttctgttg aatcattaga  19620
ttagaattct ttaatgtatt attaattta ttaatattta ggttatccga ctcaatatat  19680
ttgttgataa atacatcaat gtatgctttt ggattattca ttgaattaat aatcgtatct  19740
tccatattat caataggttt aggagatatg accatattga taatagatga catttcatta  19800
gtcattcccg cttcaatagt aatcttatca aatatatttt tttcatcttt ccataaggta  19860 ttatcaaatat tcattttatt aatattgaat tcttctaaaa tgaaacaatt gttttctaat  19920
acatctttta tttcatgagt tagagtgata acgtttctta accaaaagga acactgttta  19980
ttaagttctt ctagaattac attctttttga gatatatttt cccttaattc atcaatatcc  20040
ttggtgtagt tatcatatct attttttatat aaattatatt catccatatt ggattcttct  20100
aattttatat ccataatttc agaaacagca tttttttgcat ctataaattt agatatcaat  20160
ttttcagatc gattaatagt gaaaccatta aaatattctt ttgccttact attaatacat  20220
aaatatgtat catataggaa attaaatagtt ttttgtctat tttcccttag cgtattaaga  20280
tctttgttat tcaatgattt tctaaattta actgctaatt cataatcatt atcgatattt  20340
gtaccttcag tgctgatgat attataataa gtagtagtat tctttttttaa aggtttattg  20400 ataatattta actgaaatgt tctaatttcc ttcatactta ctcccaccac cattattatc  20460
taaatattta tcatactaat aatattatct aattttttcac ttttaacaat attttcattt  20520
aatactaaaa catcatttat atatggaaaa cattctgtaa tgtgtttaat tataaattct  20580
gacgtaatag atctttgatt cattagtact tctttatgat ttaatttata ccagtatatt  20640
tcaataaagt caattgacaa cttttgtctt cttgatataa tatcccaaca atcatcatca  20700
atatatactg atataagttc atatagcgtt ttttcatcaa gattagcata atagatattc  20760
ttcttcatat attgggaaaa ctttattaag aattccttac tatagttaca atgcataaca  20820
```

-continued

```
atatgactat cccaaggaat aaaatctata ttttgagagt attcttcaat tgtcatgtgt   20880
ttgtatatac tatgatcaat atattcccaa aatattttag tttggttttt agtaataaat   20940
ttcatataca ttttattata tttcacccga taactaaatc taaaccattc aggatcattt   21000
atatcttctt ttttagtcat atcaagatta aataagaccc caataaataa tcttagttga   21060
tttataaatc gccctttata cgtgtccatt atattcaagt tattcttttc ctttcttaat   21120
ataattatat tccatttata tattaactat ttattttata catattaaaa cccaatagat   21180
atatagtaaa tatctattgg gttagtgttt tattcagaga tcttaactgt acatactaat   21240
ggattatgct gtaattcact aactaattta ggaatagttg taagtttata tctaatagat   21300
ggattttgtt tttcttcttc caatatacta atcgattcat gaattcgaat aatttcttca   21360
cgactaattg gtttaacaaa tattgcaggc ttaccagtat taatattgat tccctcaata   21420
atattcattt catcatgact tgataagtaa cccacaataa tcttaatatt ttttaaatct   21480
ttatacgtta atcttgtttc taataatgaa tcatctttca ttacgcataa acttcccttc   21540
cagtttaagt tttattttat ataattatta gttaaactag tatataaaaa attaaactga   21600
attatagaat aatttattta aaagaatata acgtaccttt catatcatta taataactat   21660
atttaatcga tttaaattta tccatactat tgaagaagat aaattccgga gtatctttct   21720
taggaggata gtttacaata tcaataatat gagcgataac ttgcatatcc atatcggtat   21780
atttaatatt agatagtttt gtttttgatc gatttactgt agtttttcta gtccttttat   21840
caatgtaaat agtaatttct tcgggatttt cagtaagttc ttcatgaatt atattgagaa   21900
aatttaccgc ttcaagatac ggttctagcg atgtttccat tgtactatta aagttttctt   21960
cattactttt agagttgatc atatttttaa tattttttag tttacctatt gtttttaaca   22020
ttataatttc cacctttaat tatttatttg ttgttatcat attaataaaa aatgtatagt   22080
cgataaaatt agacccattg tctctaataa tttttacatc atctttaaaa ttaacatatt   22140
ctttaataaa atcgagatta tgggtttttc ctttaatcga ttttgagtca atatcgttaa   22200
ttgcaagatt tcttataacg tatggactat ctttagaatc ataatacaag ttatggattc   22260
taagaataaa tatactatta tataaatttt cttttaagaa agataaactt tcagtgaatc   22320
ctaattcatg agtcttatca ttatatccag taatatgacc agtgctgaca tgtccattac   22380
tatggataat ttcaacttta ttattaatta atgattcaat attcgtttcg tttgtatact   22440
tatcaaaaat agtatgatta gacgcattat aaatattaat attcatatcg tcatcaattg   22500
tataaatata tttttttgag ataagtttat cgagaattaa ttttaatgta tttttttctta   22560 atttaaataa acgctctttt agataacata ctttatcaat atccggatac ttttctttta   22620
gtgaataatc tttattgata gtattaacgt caatatatga tatgtattca atataatgaa   22680
gattaataat atcattatca ttaaatgatg ttaatttctt tttaattgta gtgatattca   22740
ttacttcata gtaaatatca ttattaatct tttctttttaa actaataatc aatatttcct   22800
cagacttatc atttgtaaat aagaaaccta aattgctcat agcactttca ataaaagaaa   22860
tattattatc catttagatt tacacccttt ctaatctata tattcattat agttaatgca   22920
tctttaaatt tttgatcttc attcatatat ttaattaagt atggatgttc tttaaattca   22980
ttatcatact tagttaattt attatagtat ctaataataa attttttttgg taagttttct   23040 tgacttctcg atattttgaa ccataaatta gcattatcta agggtacagt gcttagtata   23100
tattcaattg attctattgg taattggtat cttgaaatag tcattataat tgtgtgcaag   23160
```

-continued

```
tcaaaatatt ctatatattt tagtattacg cttaattcta atttatggtt tgaaacgata   23220
atataattcc agaataattt tggagcatat ttatcaagag aaataatatt atctattgtt   23280
acatcatact caatatcgta ttgagagaat attaattctg cagttatatt ttcccaaatt   23340
ttagtattaa tatctatact gtctgcatac ttaataaata gattaatatc gtacagtaat   23400
agtttataat tatatcctat ggaaaaatct atattgtcaa gaatattagg attatttctc   23460
gatatatcta atattctatt gcatatttca ggaatattgt gatcatattt atatgagtta   23520
aattgagatt caataaaaga agggtagtaa ttttcttcac cagtatcata cttttttatca   23580 atatctataa ctaatttaat tatatcgatt ttttcattct ttttagaaat aataattttt   23640
cttatatctt cgttactaat aggctcggta tcagttctag acataatatt ctaacaatcc   23700
tttctattat taaaaaataa aatctgagac tataattgat catatagtct cagaaatatt   23760
ttatattaat cttctaaatt attatttaat atattcatag acatattaaa aatacttctt   23820
gaacgtttac cgatacgatt tattgttttt tcagatatat ttaaataatc tttaaatttt   23880
atcggaaaat acttgaggta catagaaatt tgttctggat tatcaataat attgttatca   23940
atgatagttc gaacaacagt ataaatttga ccattaagta attcgtcaat agttgtttgg   24000
atcgtatgct tgaataattc atcctttctt aaatgttgat gatctttata ctccatttc   24060 attctaactt taatataagg atcgttataa tcttgatgat cattaactag agattcagga   24120
tgaaatattt cattaaataa tttaatatcg tcattttttc catattttat aataatattt   24180
gtaattaata atctcgaaat ttcaccaatt tcattataag gaatttctga ttcttcaaat   24240
tttaatgtat aattaatttc ttttaaatac tcattatagt atcggtattt ataattagat   24300
gttaatgcaa gagaagttac aaagttaaga ttattttgat aacttcctac taatctaact   24360
tcattataaa atacattatc ctttataagt tgattaatga ttttataata tctttgcatt   24420
aatacattaa acttatcggt actacaattt tttggtttag taattgattt aattaatgat   24480
tgttgggtat taattaaatt ttccatttcg ctaaagtctg aaagaacaaa cttgtcagga   24540
tcaatattct ttaataagtt atacgcatac attagagtat taacaatatc gtaatcacta   24600
caagaataaa tatggttatt tcgcataaaa ttatacttga attcatcact aatttcagta   24660
atttggtatg gaataccgtt attaagaaat gaagttataa tgtgtttaac ttcttgaact   24720
ggtgaaccgg aattaaataa ttttttcaata catttaattc cgtgataact gaattctaag   24780
tcatctatat cattacaata gttcttttta ggaacaattg aattcttcgt aatattctta   24840
tgaatattac gaaattccct atgaagatct ttaaagttct ttttgaatgt atcattatta   24900
ctagtttctt ttaaattagc ataaatctta attgtattat tcattatta tcaatccttt   24960 aatatatttt tattttttcaa tattaacttt aaattctatt ccttgatcta ccatatcata   25020
atcaatatca gcaactcgac caacgctgat aatatattgc ttgtacaatt cagtatcttt   25080
aagattatga ccaagatatg cagtatcata tctgtcactt tcaatctctc ctggactata   25140
ttgaacattg gagatcgggt tatcatttag atctttaat acgttatatt ctttacgatc   25200
agtatcaaaa agcctattca ttgaaccttc aaaagctact tcaccatcac taaaattttg   25260
tacggatgaa cttactgtta agaaatatag tgagtcagtt gttctaactt tatcattagg   25320
gtcaaaatta gatggttttg ggtcattatc aaacttaacc cctttattag gaataatatc   25380
catacgaact agagctactg tataatcagt ggcttgtact ggtccgattg taaacacata   25440
attttcagga gaattaccga taactgtcat aataatttta taatcattat cattagttac   25500
cctatagtct cctacctctg taagttcata ttcttcttct tttttggttt tcataagagg   25560
```

```
tttaagttct tgtattttg attgaactga atctttgtta acatgattac tatcattatt   25620
taatacaaaa taaataacta ctgataaccc tattaataat actacaaata ttaatatttt   25680
tttcatttga aagttcctcc gttttctaga tttttattga ttttatatat tacttttaaa   25740
cctttagcaa atcttttaga ttttacatct ttcatactaa ttacattact tttcttagct   25800
acttttttaa ttttcataat tgatccatcc tttatatttt atttaatcat tattataata   25860
tattaatgaa aattatatta ttacgctaaa aaaaaaaaaa tccgtaatac tcataaaaga   25920
gtattacggg aatatttata ttatttaaaa tctttcacat atatgaaaac catgatcagt   25980
ggctaattta taatcaaagt ttaatcctag attcattaaa taaaacttat cagcttcttc   26040
cttactgaat gtattgatta atgtttctag tgacatatga cattctttat cataatcata   26100
agtttcgcaa gaagcatcat gatatatctc atcaaagtaa ccttgatgaa taagactttc   26160
aatatcatca ccgaaattat ttgcgtcacc actataatat attactttt catcaacctt   26220 aataatatat ccatacgtca taatgctcgg agaatgtcca acagatactg cttttatttg   26280
aacgttagag tcaatatgat aaaattcata ttcttcaata aattgtattt tataatctac   26340
gtctgcatga acatcattaa tctttaataa attaacgata ttttcaccat atgataaaaa   26400
tagattaact tttatattat gaatatgttt aaagtatcta ataaatgttg gtaaggaacc   26460
tatacggtca gcgtgagtat gagtaataat tacattaatg ctatcaaaat tctttatcat   26520
actatccgta aaataatcat caattaatat atcaaacacc atacttccac aatcaataag   26580
ataaaaattg ttattattaa taaagtatgc agacgtattt cctaattctg tattaaattc   26640
atttccggtt cctataaaat ttagtaaatt attatacatt ttatataccg cctttatttt   26700
ttttttttat tattttttct aaaaaaatat tggatattgt catttatttg acaatatcca   26760
ataaaataag gaaagtgtaa actagttaga atattacact tttagacgaa agagtaatat   26820
ggagataaca actagtcgta cgggattaga gatagttata tttaggcata agatttacct   26880
aaatataata tattattatc caaaatatta attttttatt tttacagttt acgcatataa   26940
atcttcatta taagcgtatt gaattcttta ttgtatgaat taatatccgt aatattataa   27000
ttatgaccaa taagattatc attgttaata ttagaattat atacgctaat tgcattatta   27060
tataatgctt ctaattcatc ataattttct aataaactat acttgtaatg tatatataca   27120
aagttactta taatcatatc gataaatttt gaatcgatat ttgcaaaata tattttacta   27180
gaattagata taagcgttgg tattgtaaaa ttaccatgat acatttcagc attaaaataa   27240
ttcttcttac atatttcata aataacagta tcgtcattac tatttagata ttcattatac   27300
gtcatattaa taaaatttgc aagattgatt ggttctgttt tgatatttga atagacgata   27360
ttattatatg atttataatc gtgtagcgta gatcgtaata cattttcagt aattacacta   27420
ttactacgag aaaaatttt tttatattga aagtacttt caatattaat tcttaagcaa   27480
ttattaactt cttctagatt agatctagat tcattattcg aagtatcaat aatatcttcc   27540
ttaatataat ttcgcagact tttctcatca ggattattat gtaatatatc tactataata   27600
atcgcagttt taattagtat atccgtagat ttttatccg atctatttcc aaaattaata   27660
atatttctta agaaataaat taatatcttt ggatcatagt tatacatatt atatatcatg   27720
ctgacaaata tattgttaat tccaattctt ccattaagaa tatgttctat aaaataataa   27780
tacttatttg tagaatcttc attatattta ttattagcaa tatacgctga ttggttggat   27840
acacgaataa agcttgaata taatgcagag atataactat tattaaaata aatagttgga   27900
```

-continued

```
acgatattac aaaagaaatc agctaattct ttaatatcta taatatttag tatagatttt   27960
ttataatact tcataaattc ttttggcgta tattggagat tatcaatctt gatcttttca   28020
gtgtcaaaca taagagcgtg ggactcattt ataaatatat taaaatcata tatatttgaa   28080
gtgaatatat cttttaggaa actatattta tctttgatta atgaatacat tgtatttcta   28140
atcatatttt gaaaatatat aattcgtaga ttattacttt ttttagtatt gtcagaatcg   28200
actaatgatt taatttcttt ataatatttt gatagattag atttggaaaa agtttcgtta   28260
aattctttac aatcatctaa aaatttgtta tatactttat cgacaagatc actattactg   28320
atttcatgag tatcatattt attttttatt ttatcgatag aattttcgtc ataataaatt   28380
ctatcgataa aactactaat tatcggcatg ttgatgtatc acttcttttcc attgatatag  28440 tgcataatgt caatatgtaa caaaatgctc ttactctgat ctctactggc attacaataa   28500
tcaaattcat gctgataatg atccaataac attaatgcat cgttatattg attttggatg   28560
atgcttgaaa tattattact taatttatat tctaaatatt caataatatt tagaacttca   28620
ttgtcaatag gattaatttt ttcataatta tttaataagt aatgatatac atttttataa   28680
atttcgacag aatcattact tatttgaatg tcattattta ttgaaaaaca aaataacgaa   28740
ttaaaatcat taggatcaat taatagtttt tctaaaataa tcttagtctt ttcactttct   28800
ttatattcaa tccatcttac agggatatat tcagctctct gcatgctaat gagagattta   28860
aataacttaa ttgaattttt cttttcttgc aaactatatt tactaaaaat ataatttatc   28920
atattttcta caaaaagatt aattctacca atagtatggt ttactgtagc catgtttgtt   28980
ccttcaataa tatgatcttt actgctaaca ttaataataa acattcttta tcatccttca   29040
ctgtttattt ttattcacat tattataata tatacttatc ttattagtaa aaaaagaact   29100
atcacatttt attatgtaat agttcttcta tggattaatt gatgaattaa tttctgtact   29160
attatttatt cggttaattt tatcttctaa agatatcaac ctaataacat ttttttttttt  29220 atttgtcata taaaataaat cactctttta ttcataatta ttctattatc atatgcactt   29280
ctttataaga tatatttata gaaactgtat attaataaca gtttctatat taatgatagt   29340 ttaacttttat caaagatgtt tctatgatta agagaattct taataaggtc attaatagtt   29400
atatttatgt ggtaaggttt tacattatct tctgcattat aaatctgtaa atttatattg   29460
tatccattta ctataaattt ataatatacc gaaacatatt ctcttgttac tggttgctta   29520
aaacggtcag acgtaaaagt ataattaaat gtataagaat caatataacc attattagtt   29580
gataaatcac tgatattata agtatattca tcgatgtctg atgggtcaag atctgtatta   29640
tttctaataa attcatagat catactttt aggatttccg atagatatgt gatagttaat   29700
attgaagaac taaatctttt actattaaat ttttctttta tattgtaagt attatcatta   29760
tattcaatat ctttttgatgg aatattataa ttagatgtaa acatttcgtt aaatgttttt   29820
cgttcttcag aagttaattc atttaatgtt ttaattaatt ctttgtcatt atataataaa   29880
aatgaattaa ttatatggta cgtaatattc ccattaacat gtaaaggttt acttaaaaat   29940
cctagagatt ttaccattag ataatttcct ttctttttttt ttttaatatt aatttttagat 30000 attatacatt ttaattctat cataaatattt gatattctac ttctttcctt tatacttata   30060
tggattcaag aatcatttta tcatatattt tcatatgttt cccacaatca aataatagat   30120
caatcatatt aatattttttg ttaaaaatttt tatcattaat gaaaaaatca atatctaatt   30180
cattgctatc tttatccata ctaaatttaa ttttgtcaga aataaatgta aatttagtat   30240
aaggatgata attctccata aatttatatt cgggtatatc ttgaattctt attagggcag   30300
```

-continued

```
agacttcaaa ttttaatatt aatgctaaaa atttcttaaa gaaattagat tctagtatat   30360
tccagacgcc aaaaatatca ttctctcgat atttactaaa actaaatata cgctctaagt   30420
tatcaatcat ttccatatta tttagttttg tcaatttttc ttctaagtca tcataaatct   30480
caaatatttg tacaatatca ttttgatttg tttcgaaaat atacatagat actatttcct   30540
catacacgct attatctatg tatggaataa atgaattttt agctgaatct ttaatcggtt   30600
ttatattttt catgtatacc attcctttca ttctttaatt tcaagaatat tatgtgggaa   30660
gatatcaatt aaagatacct tcccacataa tatatgtaac gattgtttag tacaacatat   30720
cactatattt attcataata ttctttgtaa atatataaag gacttgttca aattcaatat   30780
cggtcaaaca taatttaccg taggcttgac gattacaaaa tgatgagata gttgataatg   30840
aattaccatg aaaaaccatt ctttcaagca ctctgttttg attgtcatta agcttatcat   30900 attttttcttg ggaagtgatc atttatgag tcatacttaa tagatcgcct tctaaagtat   30960
tagggaaaac ataattacct tcagaattta aataaaaatg gttaaatcga tttaatattt   31020
ctttttgata attttctttt gttttattca acactattaa aaccccccata accaattaga   31080 attatttata tactatatat ttatttatta gtatatcaat ttattttgag taatatggaa   31140
aaaattattt taaaatccct aaataaacat ataagtttac ttaaggatca tagatatttt   31200
taattcttta ttttattaaa tactttttaa tttattaata tcaattaatt tcttttttcat   31260 actttcaggt aatatttcat catgatactt taatattaaa ggaatattta atttatcaat   31320
atacgtatca ataaattcta gtgatatatc ttgacatttg ctaataatat cccaattaac   31380
tttatcttga aactcaataa taaagtcttc tgataatgtc tggtaccaac taataaagta   31440
ccaatctaaa gaatctttga atctacgaat aaaatcttct gataatttct gttgtgaact   31500
aatattatac caatctaatt catcttggaa cctttcaata aattcttctg ataattctcg   31560
atacctactg atgctaaacc agtttaattt atcttgaaac ttttcaatga attcttctga   31620
taactcttga tgtatgctga tgctagacca gtttaattta tcttgaaact tttcgataaa   31680
ttcttcggat aatttctgtt gtgaactaat attataccaa tctattttat cctgaaactt   31740
ctcaatgaat tcttctgata atgtctgatt cctactgaca tgattcctat taatggttat   31800 ttttttccata aataagtata ccacctttt gctatatact ttttaattta ataatttctt   31860
tatgtttatt aataaattct cgtgatacat tttgaatcga ttcaatataa tgccaattta   31920
ctttattctg aaacttctca ataaactttt ccgataattt ctgttctcta ctgatataac   31980
tccaatttac tttatcttga aatttctcga tgaattcttc tgatagtttt tggtcagacg   32040
atatatagtc ccaatctact ttatcttgaa actcttcgat gaatttttcg gataatctct   32100
gatatatact aatatgcttc caattaactt tatcttgaaa ttttctaatt aattcttctg   32160
ataatttctg gcataaacca atataatgcc aatctacttt atcctgaaac ttctcaatga   32220
attcttcgga taatttataa tattcagaga tactacacca attaacttta tcctgaaact   32280
tttcaataaa ctgctcagat aatttctgat acgcactaat attgtaccaa actactttat   32340
cctgatattt agaaataaaa ttttctgata agttcttttg atccctacta atattgtacc   32400
aaactacttt atcttgaaac tcttcaataa actgctcaga taatgtctga taccaactaa   32460
tattgtacca attaacttta ttctgatatt tagaaataaa attttctgat aagttctttt   32520
gatccttact aatataatac caatctactt tatcctgaaa cttttcaatg aattcttcgg   32580 ataattttttg atgtgagcta ataaatttcc aatctacttt atcctgaaac ttttcaatga   32640
```

-continued

```
attcttcgga taattttttc ttccaactaa tctcagtcca atctactttt actgaatcat   32700
caacgattat tttatccata gataatatta catcctttct tttttcacta tatacttttt   32760
aatttatcaa tagcaatcaa tttatccatt gtttcttcag atagtgtatc ttcgtatcta   32820
tatattagat atttaacgta taatttatgc atatatctaa taatgaattc ttccgataat   32880
tcttgatgca tactaatagc tttccaatta attttatcct gaaactcttc aataaaattt   32940
tcagacaatg tctgatattt gctaatttca ttccaatcta ccatatcctg acagttacga   33000
ataaaatctt ctgataagtc tcgaactgac gaagaagcat gccgccaatt aacattttct   33060
ggaaatttta gaataaggtc attagataca tttctattta agcaaaaata atcccaacat   33120
atcttatctt gaaatttggc aataaatgat tcactattta atttctgatg catactgatt   33180
tcattccaat taactctatc ctgaaactct tcaatgaatt cttctgatag ttttttggtca   33240 gacgatatat attgccaatt aactttatct tgatattcac gaataaattt ttccgataat   33300
ttttggtatt gacttataat attccagttt aatttatctt gatatttaat gataaacttt   33360
tcaggcaatt cttcattata tgcaatatat tcccagttag gttcaacagt aaaattatat   33420
ttttcattat acttcatagg aaaccctctt tctttttaagc tattatatat tcttcattat   33480
agtaatatta gtcagcttat ctatagtttt ctgagataac gagtttttat gaatttcaag   33540
tacgaattca atatccaagc aatgaatatt cctaagaata aaatcatctg acaatttctg   33600
gtattggata ataaaatccc agtacacttt atttccaaaa ttttcaatga attcttctga   33660
taatttttga tattgggaaa tattatacca attaactcta tcttgaaact caataataaa   33720
gtcttctgat aatgtctggt accaactaat ttcattccaa tctactatat tctgacaatt   33780
acgaataaga tcttctgata gcttttggtt tatactgatg tagtaccaat taactctatc   33840
ctgaaactta ataataaatg aatcagataa ttcctgaaat atactaatat atttccaatt   33900
aaccatgtct tgatatttat ggataagttt ttctgataat ttctgtttta tactaataaa   33960
gtcccaatct aatttgtctt taaaagtatc aataaatttt tcattcaaca ttatgttctt   34020
agatatgtat gtccaatcaa ttttatcatc atttatgtta atatcattag ttttaatgta   34080
ctcgttaata ttcataaatt ataaccacct tattttttctt ctatatgtat aatatataat   34140
tttaatttat gttagatgta taaaaaaaag gaaatgcgta tttaataaat gtataattcc   34200
tatataatta ttatattata taagaattat acatttagta gttatatatg tcttaatgca   34260
tcaatttcct ctaatctatt tatgaattct ttagataatg attctgaatt attatttatt   34320
attgaactaa tcgatacttt atcaatatga ttattaataa attcttctga taattgttgc   34380
tctccactaa taacgttcca attaacttta tcttgaaatt tatcaataaa agattccgat   34440
aatgtctgat atctactaat atagtaccaa ctaagtttat cttgaaattt ctcaatgaat   34500
tcttctgata attgttgatc tgtactaata acatcccagt ctactttatc ctgatattca   34560
cgaataaatt tttccgataa tatttggtat tgacttataa tatcccagtt taatttatct   34620
tgaaatttct caatgaattc ttctgataat ttctgttgtg aactaataat gtaccaatct   34680
attttatctt ggaacctttc gatgaattct tctgataatt ttcgatacct gctgatgcta   34740
gaccagttta atttatcttg gaacttctca atgaattcct cagataattc ttgatgtata   34800
ctgatgctag accagtttaa tttatcttgg aacttctcaa tgaattcctc agataacttt   34860
tgatttctac taatatcata ccaatctaat ttatttttca gattattaat aaaatctttta   34920 tcatctaagt ttttatttttt cataagtata tcaatccttt atactaatat ttaaacatgt   34980
cttaatttat taatttctttt taatttatct acaaattctt tagataatga ttttgaattg   35040
```

-continued

```
tattgtagta atgcttcaag atttaattta tttagatatt tatggataaa tgtcttagat   35100 aactttggt ttctactaat agactcccag tttaatttat cctgaaactt aatgataaat    35160
tcttctgata atacttgaca tgcaccaata tattgccagt taatcctatt ttggaacttc   35220
tcaatgaatt cttctgataa ttgttgctct tcactaataa cgtcccaatc aattttatct   35280
tgaaatttat caataaaagt ttcagataat ttttggaacc gactaattaa gtaccaattt   35340
acattactct gaaactcttc aataaattct tctgataact tttgatgttc acagattaaa   35400
agccaattta cattactctg aaatttacga atagattctt cagataattt ttgagatcga   35460
ctaacttgac tccagattaa tttattttga aacttactaa taaattctcc tgacagtttt   35520
tgacattgag atatataata ccaatccaat ttatcttgga acttctcgat aaactcttca   35580
gataattttt gatatgttac aataaaatcc cagtcaacag tattctgaaa cttatcaata   35640
aaagtttcag ataatttttg atatatgctg atataaaacc aattaacttt atcttggaat   35700
tcttcgatga attcttctga tagttttttgg tatatactga tatttgacca tactactttta   35760 tcttggaatt ttctaataaa gtcttcagat aatgtacgtt tttcacataa taacccccaa   35820
ttaatctttt cggggaattc gcttataaac tcttcggtta ggttttttatt ccacataaaa   35880 gtataccatt ccttctctat aaagatattt agatacttttt tattttatta atttgaatta   35940
gtttatttaa caattgaggt gataataatt ctgaattgta ctgtattagg tgttcaatat   36000
ttaatttatt taaatgatta tagataaact tctcagataa ttttttgatat ctgctaatat   36060 aatcccaatt aactttatct tggaacttaa tgataaagtt ttctgatagt ttttgatatt   36120
gacttgtagc atcccaatca agcttattct gaaaatcagt gatgaattct tccgataata   36180
tttgatattg actaacatcc tcccaatcat ttatcatatc ttgaaactta atgataaagt   36240
tttctgacaa tttatgataa attacgacta agtaccaatt aagtttatat ctaaattttt   36300
cgatgaattc ttctgatagt ttttggtatc cgctaatagt atgccaatca atattgtcct   36360
gaagttcttc gatgaattct tcggataatt cttgatattc actaatatta atccaattaa   36420
ctttatcttt aaatctagca ataaagtctt ctgataattt ctgatattgg cttatattat   36480
accaatctac attgttttga aattcttcaa taaagtcttc cgataattct tgatatcgac   36540
taataatatc ccatttttaaa ttattctgga atttgcgaat aaagtcttcc gataattctt   36600
gatatcgact aataatatcc catttacat tattctggaa tttgcgaata aagtcttctg   36660
ataatttctg atattcacta atattagtcc agtcaacttt atcttgaaat tcgataataa   36720
atttctttga tagtttttga tgtttagaaa tactgtgcca atttactttta tcttgaaact   36780 cacggataaa ttttttccgat aatttttgat atttactaac gtctgtccat ctaataatat   36840
cttgatattc acggataaaa tcttcaggca acttaacaca tgataccgta gtataccaat   36900
cataaccaaa cctttcaagt gttacgtgac ttatattatt attgactgtt tccatagtac   36960
ttaattcctc ctataatatc attttttaatc ttattaagaa attagaccaa gttaatatct   37020
aattttttga agtataaatt aataaattcc tctaatagtt ttatgaaaat aaaatatatt   37080
ctcagtatat ttattatgtg aaaaatcagc acatattcat catatcatta ataatacgct   37140
ttctctcttt ttttgataca atgtaatacg tgttatcaat ataattaaat tctttaataa   37200
aatcttccga taatatttga tatcgactta taatatccca gtttacatta tcttgaaact   37260
catggataaa atcttcagat aatttttggt acatactaat ataatcccaa tctactttat   37320
cctgaaattc tctaatagag tcttctgaca atctttgata tatgctaata ttttcccagt   37380
```

-continued

```
ctacattatc ttggaattct tcagataatt tttgatacct tgaagattga tacaaatttg   37440
taattttatt atattcaata ttaatatcat tgttatattt gatatcgcta tcatgattat   37500
cattattatt tagtgataac acatgatttt tatcttttat aacattatca tattttggaa   37560
tatacaatat taagggatca ttattactat tatcatctag attttttgaa atttcaatat   37620
tagcggaatt agatttaatt ttatcaatat atactttatt tctaaattct ataataaact   37680
ttttggatag tttttgcgaa ttggataatt tttgtgaaaa tataagatgt tcccaatata   37740
attccgattc atattttctt ataaattctt cagacaatcc tctggttcta tcaatcatgt   37800
tccaatttaa attatatgga ttaagttcga caatctcttc gacagtataa taacaattaa   37860
tatccataat aatccctcat ttcatttatt attttaatat atgatgcatt tatacattat   37920
aattataata tatatttatc ctataagtta taaaaaaaaa aatcaaacgt gatatataat   37980
gattatcacg tttgatatgt aattattttt taagaatgtt taatagtctt agagaatatt   38040
ctaaatattt agattgattt tttacattgt aagttattaa taataataat gaagagagaa   38100
ggaacagatc tcctgattta caataatctt tttgatattt tccatacatt acattacatt   38160
tcaatagcgt taataagatc taattctgca ataagctgac ttactcggtg atctgataga   38220
tttttcctat tttgaatttc ttgttctttt gcttcatcta aaatattatt taatgctaac   38280
ataattctat ctaatagaac catcgattcc ttataaactt ttacagaatt ttcacgattt   38340
ttaagaatat ttattaaatt actgagactt aattcatact gtcttatttc ttcgccatga   38400
ttattgattt ttgtaagttc aagttttgca ataaataacc gaataatatc aatattccta   38460
tccctattat ccattaatag aattatattt tttagatttt cgcaaatacc atcaactgat   38520
accattatat ttcaccttct attctacttt tagtaaacat attaagtgct tctaattcat   38580
tattgatcat ttccaaattt acttcttgta aattctttttc tttcattaat ttaatttgtt   38640 cttgatttttc ttttttctttt tctacagatt tagtaattac ttcttcaatc ttaacaagta   38700
atgaatttac tgttgtatat acttcatctg aaaatattgc actattttca tttaagtgtc   38760
caataattat atcatttatg cttgataaac ttaatctaat tttatcatgt gtatggatat   38820
tgtattttaa tagattagat actttttttgt ttttcattaa tgaattaata gttcttctta   38880
atcgattatt atagttttta tctttaaagt attgaatata ctcgatattt ttattaatga   38940
atttaataaa atcaatagcg tccatatccg gaatatattt ttcagttgaa taaattattg   39000
cattatcatt attattttta tatcttagtg agtttgatct agttaagtgc ctatttatat   39060
atctaagatc atttgtagct tgatctattt cactgaaatt aacggaatca tctcttacaa   39120
tatctttata gtcacgaagt attaaatatc ctgaactaat aataccttta gttaaatgat   39180
tatttttaat gcgcatataa gtctcaatat tattttttaat aatattgagg caactttgga   39240
tatttaatga atcaatatta tttaaactaa tatattcgat ttcattaaac aatttagaca   39300
attctttact tctagataaa ttttctgaaa gtaaaaattt atctaaaaga tcatcattct   39360 tattatttt tattttaata aatttaaaca ttcgatcacc atccagttaa ttattataat   39420
tctttctaat ctttgttata taaatttatt atcatttcga aaattcagat atttctcaat   39480
tctctgatct taactaattt acgctttatt ttattagata ttagtttatc atgtgatatc   39540
aatagatcaa tatctaattt cttgaagaat atattaatga attcttctga taaattttca   39600
caatatatag atttgccctt ccagttgatt gtactattat tttcaataga taagtattaa   39660
tcttcagtta gatcaataat atcttcaaga tgtgaaccaa aagtagaata gtctattaac   39720
catatttctt ttaatgggtc ttcttcaaga aagattgcaa tatcttttgc atgtttctta   39780
```

-continued

```
attttatcca caatataatt atacgttcga tcagcaccac taggattctt aatggatctt   39840
agaaaaacgt catcataaga ttcagtttca ataatatgat atccttcata agtttttattt  39900 ccttttttgta acgtcaccga tcttaataca cttttttcgag tttctttaat gccaattagg  39960
tcagctaaat taattacttc ttttttattc agatcaattc cattttctag tacaaaagga   40020
actggttgta ggttctcgta ttcctcatca tcaatatcac ttagtgaatt aatatattct   40080
aaagcatcat tatatgattt aaataccttta tgtttattct tttccgtatt agtaatttta   40140
tatttgattg tcatagacca tcaatccctt catttagtta attttttattt ttaaattcta   40200 gtttaatatt attactctga accttacgta aatacgataa tatcgaattc acctttactt   40260
tccatacatc attcacaaca gaaagtattt gcttcatccg ataatatatc tgattattat   40320
tatcgatggc aagaattata ctcatatgct gagcctgaat taccttatca atcgtaataa   40380
tatcgtacaa gtttctttca tttctacttt taattaattc ttcgccatca ttatacttaa   40440
ttggtcttat cttcataagt tcactaacag atttaataat ttcagacgta tttatacatt   40500
ccatattatc attcaaaatt tcttttaaat attgaatatt attatctgtc tgcttaatat   40560
tatttaataa gtatacttca tattctgcga taataaataa aatatcctta tatttttcac   40620
gaacagtact aatctcacga ttatttcgaa tattatagtc actatcaata ttggacatca   40680
ttctcataat agtatcagat ttttcttcaa tataattaat atacgtttca ttatatgcgt   40740
aacgtataat atcctttgat acttggttat ttattgactg aagtttatgc gatatttcaa   40800
agatctctat tttacgatta actacgtcat aatatatttc ttgagcttct ttcttttttat   40860 ccagtgataa gcttgaatac gtaggaactt tatcatacat agcaggatgt atatacaata   40920
tattatctcc tttcattatt attattattg ttgatttatt aaatatatat taataatata   40980
tatgcatttt tataataaag tttaatatta ttccctaata caagaattta catttatctt   41040
gtattaggga acaaatttat ttattttgat ctatattaat aaaatataat acccaaaaag   41100
accatattaa cccaaagatg attattaaaa atctaaaaat taatgaatct ataagcaatc   41160
ctaatataat taatattagt gacattatgg ttaaaatcat taatactatt tctttatgat   41220 ctttttaataa gttaaatatt tttttcataa taaaaccccc attataatat aataattaaa   41280
tgtataaaaa aattaaaatca taaaatttaa tttatgtaac ttgttagggg agaacgagtt  41340
acgtcgtatc tcttgcgtta tcaacaatat ttatagttgt tcataaatat tatgacttt   41400 gtattttgca tttttgttat ttccaataat tgttatatag ttttggtata ttaatctata   41460
tattatttca tcattacaat agaaccaacc ttatagtaaa aattatatat aaagaataaa   41520
aaatctatat aatttacctt cggtataagg attgttacat agaaggaaag atctacatat   41580
ttttattaaa aagcatatat ggatttatag ttaagtcaga accaaccta tagtaaaaat   41640 tatattaata attatatttt attatgagtt taatgcttcg ttgtaagaat ctttacatgc   41700
acggataaat tatagttaat tgttatgtat aatatatcca agcatgtaag gtttcttaga   41760
ttatttttat ttttttattat tttaataact aataaagata ttaaacttaa tttatttcgt   41820
tatatataat attaaagtaa ttatttatct atatgattta cttctataac tttaatttct   41880
agttctgaaa cttcttcgtg ttttctgaat actgatgcag tatttcttgt aacgtatatt   41940
ttatgttttc cgggaatcca ttcaatattg attttaagat tatcctgaat cattttaatg   42000
agcgttagtc tactagcttt atttactaat tcgccccaaa ggtaatattc attataacca   42060
ttattcctaa gaatgtctaa ttctttttttt gataatttgt attttgtttc ataagttatt   42120
```

-continued

```
tccatgattt attaattatc cacctttatt tattatttt aaagatcaat aatgttatct   42180
agatgtaaag attctttatc taatgaatta ttatcgataa tatagttaat tcttgattta   42240
acgatgacgt cagttattct cttaatttct ttaatgcagg cactatataa ttcattcttg   42300 tctattttg ttatctttaa ggtaagatct tcaagctttt cgtaatcaat tggttgttca   42360
cgtccataca taatccaact tgtatatcca ctacttactt ttttctttt cagtatttca   42420 gtgttatagt aatttgtgat ggtagaaaaa tattttgcc tttttctttt aatactttta   42480
aagtatattt tgttgtctga atgaacgcag aattttaagt taaatgaatt gttaataaga   42540
acttcaaaat ctaaatcatc taataccatt taataattca ttcctttcat ttatttaatt   42600
gttttatgct ccaaagaata tctgatttta agtcttctag gaattttacc gtactaataa   42660
tagtgttttc gtgtaagtaa tcttttttcta gtatcattct ttcttatat atttcaatta   42720 attggaataa tctttcttta tgtttagaaa gataagcata acctaagatt tctgctgaga   42780
agacgatata ttcatcattc aaattatcaa ttctttttg agacagatta ttatcatttt   42840
tataagacgt cataatttca gagattagat cataatataa gttacttaat acttttattg   42900
tcttttctat taacctatta aattttctg cttttcttc ttgaattaaa ataatcgtat   42960
cattaatagc attattatag gaatattctt cattgctgta aagatatgtt ttcttttat   43020 cttctaatt cttttctatt tccttaatag tattgatttg tatttttata ctattaattg   43080
aatcatcatc gctgattggg atattgtcca tctttttaat aagagacgta tccgttttta   43140
aataattatc tttagtatca atcgctacct tattaccatc taattctttt attatacctt   43200
cttttgtaac gccattatgc attactttta cacgttcacc tatctcaaac ttttccatca   43260
ttttcacccc acatctattt cttcaatagg aactgcaaat tgccaataac gctcatctga   43320
tgactttatt tgttctttg ttaacttagt agtaaaccca gatgatattt gaaaaggaat   43380
aagttgtctt tttgcaaaca taccacttac gcctgtagaa gggtttatcg ctagatataa   43440
ataatcatta actttttag aaacattttt atcccatttc agttcattat tttcaataaa   43500
ttgaacttgt tcgtctattt cgaatttcat aaatatgatt tcttaaatta attatttttt   43560
cactaatagt cttatcaata ttaataaatat tattttctt ctttttaaaa aacatattca   43620
ccattccttt aacttattca ttctttaatt ttttgttaat tgaatctta ctaatatttc   43680 gaataatttc tagttcatca gataatatat catcaaatagt attattctta gatatttaa   43740 tatttttatc catatctta tatacttcga atattttaga gaaatcgtta tagatagtaa   43800
ttaatatttc tttaattttt tcatacatag atttggtaat tattccttca gtctcttgac   43860
caatattaat aataatattg taaatattat taattgtatc aatatactgg gagagttctt   43920
cagtgaattc attttttgt tgatttaata ttgacatatt atcagactta ataagtattt   43980
tatcgattat atctaaaagt ttaacatgat aattagtttt accatttaca cccattacat   44040
aatcatataa cggtttagat ctattaatat tttcgtcaat ttcattatct gataatctat   44100
cgtagttata caaacgatat ccacctttt ttaatatatt ataccttttt acatatggat   44160
gagatttatt aatattaatt ttgaaatcat atactatatt tttaatacta aatttatcat   44220
acataatctg atactcataa ctaatagtag aacgttctcg gatgtagtat tttttatcca   44280
taaagatatt atcaaagtat tcataatatt cttggggtga aggtagtttg tctgtagtaa   44340
tttgaattat tgatacctta tgaattgatt caactaaggt attaataatt tgctttctta   44400
atttgattaa ttcattatcg atagttataa ccgattctgt atctgataat tcatcagtaa   44460
tcacatcttc aggttcttca ttatttattt ttttatgtga ttttctttta aaaaacatgt   44520
```

-continued

```
tcatcattcc ttttctataa tatttattta atttattaat aacaataaag tttttttctt  44580
agtaactatc tttttaaaat attagtttat cattacagga ataactaatt taatagttat  44640
tcctgtaata attttttcttt taatttatat cttcgtatat aataagatac tgaatcattt  44700
ttcatatgaa cattggttga gatttcagag atagttgctt ttggattctt ttttagatat  44760
tctaagatac tattgattct tgaattagta gaatcatcat cactatttcg aatacctttaa  44820 attttcgat tatatttaat attattcttt ttaatatatg actgaattgt gtgatattct  44880
acattaaaat gttttgcaat ttctgtcatt gttaaattcg gattttcttc aataaatttg  44940
gataatcctt caattttttac ttttattttc ggaccaatac ctttttttact tacatatggt  45000 agatcatatt ttttaatctt ttcccttaat gtatttggaa catagtaaat tttttcagat  45060
aattcattaa ctgataattc gggatttttc ataatgatat ttcttagata ttcttttttcc  45120 tgaatttgat ctttagaaag tttttttgatc attatatata ccttctttgt tatataattt  45180
ttctactttt attaattcgt ctaatataat tattaattgt agatacattt gcattaaaat  45240
gtttagcaat cttgcttgct gtagcttcag gatattttat cataaaatta ataatttcat  45300
tatcatcaaa cattttatcc accctttttac ttttatagggg gatattgttt cttttaattg  45360
tattaccaat aaatgacttt gatacataaa agtgttttgc aattttatct aatgttaagt  45420
caggattatc gctaatatat ttagaaaggt cgttaatatt gataatatct tcataaataa  45480
cagtatcgtt atcataatta tattgcatat tatattcctt aatatatta cggatggttg  45540 gtgcagagta accagttcct gatgcaattt tctttattga atgagtaggg ttactattaa  45600
tatattcttt aataatatta ggatctactt ttttcaaaac tttattcaca acactttcat  45660
tttatttagt attcttcttt tccttagcaa agtatgcaat tagtatgtat attatcatag  45720
atattaatgt tattatatct aagacatatt cattaatagt tattgcatta tggtgtattc  45780
catataagaa tgtatatatt gtggtataca cattattgaa tataaggatt attagaggta  45840
tatacctcat tttataacga agtttatata gggatacttc atgactacta tatagtaata  45900
atccaataag aagattagcc gttaatgcta atgtatatgt tattttttca gacaatactt  45960
cattagtagt aaataaattt attgtaagaa atataatcat aaagaatata aatacgcttg  46020
ttattagtct agttcgaata tcaattttttt cattattaat acacgatata tagactaata  46080
aaaagattac aagatttgtt agtaacatat aataataatc ctactttcca tatacttata  46140
agaagaatcc ccattaataa aggattcttc ttataatcta aatttatttt acatatactt  46200
tatatgattc aagtaattta ttttttctttg atagtttagt attgataagt tttctgaaaa  46260
ataactttgt gttgaaagag atttgcgtta attctgtttt atcttcacca aaattagtgc  46320
tttcgtaaga tgcggctgat ttaattacac ccctattaat aagatttttct tcagaatatg  46380 tagataattt accgttatta ccaatcataa ctacaaattc aattgattca tcaatattgc  46440
cgataaaatg ttttaaattt tcaataaaaa ttctttttttc attaaatgtt ctaagtctac  46500
gttttctatc aatttcaata ataaatgctt tcggtttctt tttgatatta ttaaatagtt  46560 taataaatatc ttctttaata aattttagat tagtatcact ggtgatatag tattgtaagt  46620
aatattcttc agattttaaa ttatttactt ttttggtaat atcataaaaa gtagtagttt  46680
caattaatgg aataatatag ttacttttaa tactcgtgat agcagtatta ataccagtga  46740
catctttatc gccaatcaca attgtttttt tattcttctt agcaaatttt tctagattat  46800
caatcattct tgagaaatca gttttcttag ttttttttatt agatcttaac aaacttgcaa  46860
```

-continued

```
catttaacat atagtttacc atcctttta tttttaggt tttttattta caaacagtag   46920
aataataatg gcaacgccaa ttccaataat tgcaggaagt aaatctttaa atatatccat   46980
gtcgaatcac cttttatatt ttattttttg tatacatatt ccgtatcata attttcaata   47040
ataagtttaa cagttccatg agaaactcca agagatcttg caatcttagc aattgaaaat   47100
tcaggatgtt ccattataat attattaaca gattctataa ttttttcatt agttaaagaa   47160
ttattagaca tattaacttg gttatacgtt gcgatactaa atttatattc ttcaaataga   47220
ctaataatat attcttcgga gaatcctgta tcttcagata atcttgctgg agtcataata   47280
tcattactgt ctaatacaat tttacttaat ctttttaaagt ctgataatcg tgtatcaatc   47340
ttcatatctg aaatgctcat tttttgaagt ctaatagatg aaatatcttt tccttcttct   47400
ttcataattc ttctaatagt tgattttgca attgaaaatt caacattaca ttttttcagca   47460 atttctaata ttgtcatttc aggattatta cgataagtat aaataatatc tttagtcatc   47520
ttactaaatt tatcattatg ctcataagtt tctcttctct ctcttctttg tcttcttcta   47580
ctttctgcac ttgttaaaac attttgactc attaccatga taatcttcca cccttttttaa   47640 ttaatttaat aaattgtatt aatataagat tataaagtat atctatgata gtttaaatta   47700
aatatattgt aatcgtttat cacatgcctg aattacaata gcatcccata aagcattatg   47760
tttatcttca tttactatga cattaatata ttcactagca aattcttcac gattaatatc   47820
cggatcaata tttttagttc taaatactgt agaaatatca taatagtaca tgtcaacaaa   47880
ttctggaatt aatgtagcat ctttttccttt attaattaga tccacaaata acatccaatc   47940
gtatgccatt aagtcactaa caaatactag ttttttcagaa ctatgcttag cattatatga   48000
taaccattcg ataattttat cagaaacttc atctttagtt ccatatacta tagttgtctt   48060
agcattatcc gattttgatg ctaatgcgtc atgtttgtta aaaaatcgaa gtttaggaat   48120
aacattatca ttcacccaaa cacttgattt cgttgtatca aaattagata cttccgcata   48180
aaatagtcta ccgtacgtat ctaccattcc aatactaatt aggtcggcat cttttgttaa   48240
atttgtaaat tctgtatcaa aatatatctt attatccata atgtaccaac tttcttttaat   48300 ttgtctatat atttctcaat ataatacttg ataagaaatt attgaattct tttattaatc   48360
gatctagcgc cttatcatta agtaatgaat ttatatttat aaatatggat tgattatcaa   48420
taaatttatt gatatctttt atatctataa caattaagaa cttaccatta tcatctttat   48480
ataaagaact attgattgat tctaattttt tatttatata taacatttta ccatcaacaa   48540
taaatttagg gttagtatac actaattgaa acataccatt agaacatttc gattcaatag   48600
gtaaatattt atacatctta tattcatcta tagatataat atcaataatg catgtaaaca   48660
aatatctttt aatgattttt caccctata atttataatt ttgatactat aaaataaata   48720
tcatatttat aaataattat tattctaaaa aaataaaaaa ttcgattaat gatatatgac   48780
atatcattaa tcgaatataa tctatttaag tatagatact gttacgttag atgtcccact   48840
agaacctatt tgcgatttat caattaataa atcaatttta ttcccaataa ttgcgcttcc   48900
cgtatcacat gctttagcga taaatgaatt accattagga tatgtaattc ttaaaatact   48960
gttcattgga attactgatg tatctacagc tacaatacga tgaccttctg gagaataaat   49020
agtgttactc actttagttc cattagcagt aattcctgtg cttggagtat aatcatcccc   49080
aaccgcatat actgtcatac gaaaagaacc aattttttctg tatgaagaat tttctttagt   49140
tgaaacattc cgtacagttt ttttatttttt tactttatga cctttgttta attttaattt   49200
cttgataagt ttaatattat cattcttaat atttttaata attgtatctt tatctttaat   49260
```

```
tttctttgta agttctttta tatcagtaga cattttatta cttttattaa caatattttc   49320
attttgttct tctagattat tattgatttt attctgtttt aatattaatt tttcctgact   49380
ttggatcata tggtttagat tagattgatg aatcgtttga aatgctgtta acgatagtag   49440
tagaattacg ataattgata cgcatgtagt tttaatattc attcgattca atttcttttt   49500
cttatgcata gattcctcca tttctattat aacattaata ctatttgcta tagtaaaatt   49560
atatatcaaa aaaccgtagt atattattat tgttttaata tactacggtt tcttatttta   49620
ttttatatta ttttttaaac aatattacta agaattttg gcgttttttc cacaaaataa    49680
atttcatctg aattgatctc aatgatattg gcaattagtt ttttaataaa tccaacaata   49740
ttactgatat ggataatttt atttttcgtta agaattgaga agttatctag taatccatta   49800
acttttagat tgatatatga atatgattct ttatcaatat aaaattcaat aaggtcggaa   49860
tcgataatcc taacattaac tatattatac aaatttgctt tgttttttact attaatgtca   49920 ctaataagtt tatcataatc atctttatcc ggagtatgaa aataatatgg atttaaaaga   49980
ttaataaaat tgatctgata ttcttttcct aaaatattaa aaactaatcc attttttttct   50040 gaaaatttag ttgtaagaac tttatctata atcactttct gttccattta aaccacactc   50100
ctataccata ttattagtat taataactta ttgtattaag ttattataaa atacccaata   50160
cgttaaataa taaacgtatt gggagtatta atactaataa ttattgaatt ctatctttaa   50220
ttacaactat tgttttatgg aaaattactaa caaatttaat atttgtgtca taatatttat   50280
ttctaatatt attagggatg tgaccaataa tatcactata aatagtatca atagtcttat   50340
cgatattttc aatatccgta tatacataat gagataagtt atttacaata atttttccaa   50400
tatcaatata ttcattttca aacatattag tatattcttc aggacgtagt aaattcctaa   50460
atagattttc aatattatta ataattacat caatattttc atcattaata atatcatcga   50520
tatcattatt aataataata tcaacaattt catctacata ataattaaca ttgtcttttt   50580
gattttcagt aataccgatt aatccgtcaa cttgctctac tttacctgga ttatcatcat   50640
agatattact atccattgat gttgaaacgt tatccatttc attaacgctt gaatcttctt   50700
tattcctacc actaaataac ttattaaaata atttcttaaa catacaaatc tctcctttta   50760
tactatattt tactattatt ataatatata aataaaaaaa tgattaaatt agtatatctc   50820
caatcaattt atattttgat tagagatata ctaattattt ttaacttata taatcatcga   50880
tatttatttc tttaagtttta atcgacatat catgaaatgc tttatattga taggtaattt   50940
tttgaagtta tctccaaatt ttcccccaat ccaaaccgta cgtgagactt tcatctcata   51000
cggctttcca tctactagga atctaaacct aatctgttat gtatctttct ttttagtaga   51060
ctaaggactt tccctaattt atatttctat aaatattatc ggtatcttat cctcgctttc   51120
aatccaaata aaatttcagt tatagtccag attagacttt ccgagaaata agtattatat   51180
taatactttt ggatcttccc atgtttctat agacttaggt ttattatata acttaggact   51240
tttctagacc atatatctta cttcttaaca tgataagcta ataaggttat tatcaatgat   51300
taataactat tagaagatat atttatacat tactgtatag gattaagtca ttatagaaaa   51360
ttcgttaaat ctatccatat tatactaccc aaaccaagat atcttatcct ttttaattaa   51420
aaggacaatc ttcttgactt catccagctt cacacatagt aattacttgc tatgcatgtg   51480
gaatattatt ttcaggaaaa tcttagaatc tttgttatct aagtccttga tcagtctata   51540
aattaaatta tataaaaata taattcctac aatccctcat attaaaataa tgatttctgt   51600
```

-continued

```
agaacatgtc acaccattga taatccagtt aatgcattcc caataccatt cgcaattagc   51660
ccaacattct taattcccat ttgatagtat agttcgcctg cacatttatt acagatatgt   51720
tcagacttac agtataatgg actacgcatt tcaacattct tattaataaa tttaccttta   51780
ttttcttcgg taatttgcgt taatttatca ccgtctttta cataacgagt aataaataaa   51840
ttaatattat tatttgtaag tgtaatattt aaatattttt tagatttaca atcacttcca   51900
tgatcgccaa gaattattga ctgaaatgca gcggcaagtt ttttcgcttc atatccacca   51960
tcttgagtac caatagcacg acttgcacta gcacttgtaa taatttctgc atattgatat   52020
agttcgtcag gaggaatacc atcgtctagt gaagccatac taactcgaac atcatttggg   52080
tccgcataac ttttagttac acctctagct accgctgttt gtttaaagtt attattaaaa   52140
cttccacggc ttccactatc ataaatatcc atatcggaag catctttaag aatatcatgg   52200
gataatgtta ataattcttt ttctatttta gatacagtaa caatatcccc agaatcaatt   52260 gccttttat gcttaacaat cagttcttct ttacgagatt ttacttgagg aggagtcatc   52320
attaaagttg tactaagtga tgttgcaatg aatttagtta taccaaagcc cagccattgc   52380
atcttatcaa tataattact aaaatcagct acagtaattt tatcttctaa taagagagta   52440
cttaattgtt tatctaactt actaatagcc ccaccatcca ttggatgatt aatatatcca   52500
atatatcttc ctaattttgc atcaataatt aataggttaa agatatatcg acctactgta   52560
gtagtaattt tatctttatt aaaatgaata tttgattcta attcaaaata atcacttggg   52620
tcaaactttg catcttcatt tttggtatat gcaaataatt cttgtaattt ttccatagtg   52680
atatcattct ctgaaagatt aagaatctca atctttctag catcactaat cttttttacct   52740 ttatatgctt tttgcaacta tattcacatc ctttataaat tatatccttt aatataaata   52800
aatgttctat tagataataa aattgttagg atcatagaaa aaaaaaaata taacctagat   52860
atctaggtta tatttcttaa tataatctga ccataaagaa ttaatacttt ccttatcttg   52920
aacgcttatt atgtcttta attcaatttt attattttct tcaaagtata tatacgataa   52980
tatactggag attgcatcat aaccttgttc atccgtatta atataaacgt tatcatcatt   53040
accataatcc ataaatgtat tatatgatct tttgatttt atttgtactg gttgatgatt   53100
aattactacg tctgttccat tcctatctaa atatgcagaa cattccatcc aaaatttaat   53160
tttcttttta ttaaatatat tctgaacttt tcctagaatt cccattactg caatttctgc   53220
atagtgacct tcattaagca ttggtggcag tttatcaata cattttccgt tgaatccttc   53280
ttttcttgct tggttcttat aatagttcaa ttcatttaaa ttaatataca tcgtaatatt   53340
cccccactaa tcgtattatt tatagtatta ttattttttc acaattctta catttggttc   53400
gataaattta ataaaacaaa atttcattga tagctttata atagtatatg tagttgcaat   53460
cataaataca atattaatga atatattatt gtcatagttc cacaatacta cgtttgaagc   53520
aataattaat agaatggtca gtattaccgt tatcataatt gagataaaga tcttgtttac   53580
tatacgatta ttcatatcat ttccctacct tacttttact ttttataaac atgtctactt   53640
tattacgaga atccaagtat tcagagaact gatcgatgaa aagatttatt gatatgttat   53700
atgttaagta tgagaatgaa atcgatacta ataagtctag gtaaatatta ttatttctaa   53760
aacatacttc attaataaaa agaaaccata atgatgacgt aataataata ttaaatatta   53820
ctttggtgat aagatttcta aataatttat cactagaata gatacttagt atactttcct   53880
ctctctcaaa attaaatata gccattacag ttccttaacat attttttcta cttttaattt   53940
cgatattctt aattaaaaag ttgcataaga ataacactgc tttatttatg tacattatat   54000
```

```
aatcaaccct tctttttttt atttaatcat tattataata tatcattaaa acttgtatta   54060 ttacatttt tataaattag agggatatga caagttatat gtcatatccc tctaataaat   54120
ataatttatg ctacgtaaat aatatattcc atttcaatat ttgtagataa tccacttaat   54180
gagatagaat caaaagtcaa tcttgatcca caactaatgt tttcataaga gtttttagtt   54240
tcattgtatc tacctaacca taaacataat tcattgatca ttccaccacg acattcacta   54300
gggtcgatag ttaatgatag actatatgaa acttctccag taaatgtatt aatattccaa   54360
cctttagaat taccaaaagg ttttgaattt gtagcaccat taaatcgttt accataatat   54420
tttacagtac catccggatc agcttgtggt aaataatatt tcatttttg ttcatcagta   54480 agctctttta caatagaggg attatcttga gtttcagtat cattatcctt atcagggtct   54540
actgtaataa aaggaaattt ttgagctaat ccattatcat taaattttgg agcaactgga   54600
gtgaatggac tagcattaat atccgcccct ccttctccta ctgagaatag acagattgat   54660
cttgcaggat catagacttc gttgtatgtt gatggatgtt tttctttaa taatgcttcc   54720 attacaaata cacgagttct ttgtaaaatt aaattatctt gaatattgat tacttgtttt   54780
gtatctgcat tacggaaaat aacttttcct cgaattcctt tatctgaatc tgcagtacca   54840
atattatctt caaaaatttc ttgaatgtta ttatctttag acataatgtg gattacactt   54900
cctattcatt tattttatag atatcgatct taatcatttg atttaataaa taatttatca   54960
ctaaacgtta tattatcatc aagacgtttt gttaagttta aactatgaga atcaattata   55020
gaaatataat ccctaaatag tattccacct attttagtga catccatggt atcaaacaat   55080
cttatactgt tatccatttt actatcaaac ttataaatag aactactata aactgtatcg   55140
atagtatagg atttaaatac ttttatgagg atataaatat atgattttac ataatcagat   55200
agaccaatcg tattattttg agttaagaaa tcatattccc ctagatttaa atgattatca   55260
atactttcaa caagttcaaa tattctttca cgatatatat catctttact taatgaatca   55320
atatcgtata tattaatatc tacttctgta tagaaatata agtttggatc attatctttt   55380
aagtaatctg taaacgtatt atattttgag aaaatatcca tatttaaatc atttgtaaat   55440
ttttcattcc ataatttatt aaacaaacta tatagttat aatcatttgt attaataatt   55500
gtttcttcta agtcttccct tagtttttca ttatatcggt atattttgc gaagtcattc   55560 atagtatatc ttcttttatt attgactatt tcatcatatg aaccaaaaac atctataaat   55620
accgataaat tcttatagtt tattagctgt tttcgataaa tatattcatt gactgaaata   55680
gcttcatcaa tagctgaagg aatcatatca ataacttttc taaagttctc aatagtttta   55740
tttcgattat atatatcaaa aacggtactt aacctgttaa taccaagctt atttataaag   55800
tctcgcattt cagacattat taccacgttg tccataccaa actggaatat cttatcagta   55860
ctaatatatt taatatctac ctgataatta acaaatcttg atagtaattg tttcaataga   55920
ctatattccg atattataga cattgatatt tttctatttt tatcaagaag aatattcatt   55980
aagtattcta atccatcata aatattacca ttcttaatgt gattttctaa tttcttagaa   56040
ccgttaatac tttggatgta ttctgaagtg aactgcattt ggttttggta aactattgaa   56100
gaattataca ttgctacaat actatcaaaa tcttggtcta tatctaagtc aaatcctttc   56160
aacttaaatc gatttagata acccataata ttttcccatt ctcgtactct gaattttcgt   56220
ttattccaga aaagatattt tcttaatgaa ataataatat catttacatt tttatcaata   56280
tcatatccgt aggtatgttc taagaatgga attttttctaa ttttatcaga ccaattcatt   56340
```

-continued

```
cttttttaata ccagtgttat taatgcaaca atagcatcaa atatatgaat ttcactatca   56400
gagatattgc ggttattaaa tttaaagtca atattctcaa gattaactac ttttgaagct   56460
tcttgatagg taatattatt atcactagca tatttattga ttattgctct attttttaatt   56520 tctaggtcat ttaataatcc ataaaagtat gataattgtt tcgaattatt aatcagatca   56580
agaacaatat cgactgaaat atactttgta tttataatat tgaatgattg ttctagtata   56640 ttttttctttt cagctcgcca atagggatca ccttcagtaa ttgcgtcata atctaccta   56700 ggatgaagcg aaaaatttaa ttcttcatca ataggaactt tatagaattc tagtgagtca   56760
tcaccgccta gattattttt cttagcaagc atataccctat ttatctgtac attatcaaaa   56820
gagaaaagat tctttatgac attgaataca tcattatctc ccttgttacg aatcatttca   56880
tttattaatc gataaattct tcgttgataa tttactggaa cagaatcaaa ataatctaat   56940
ccccatgata taaatccatt tttttaattttt tttctatcat aagtatcaat attaaagtat   57000
ccttccatag tcttattaat ataacgcatt atagtcataa atattagata ttctcgatat   57060
acttcacgat tatatgtttg attactaaat gcttcagtaa acgtaacatt taggaaataa   57120
ttaatcgatt catagtaagc ttcattaaat aaacttttat gccatttatc taatgtatta   57180
ctagtttctt taagtatata gaaatctttt gctcttcttg ctgaagcata atcaatatta   57240
tatcgattaa ataaatcttt ataataaggg tttgattcat tatatccttt aatgatattt   57300 gattttctg attctgaaag ttccgaatca ctatcatata tagcacttaa atatctacta   57360
gaatttaata gtgatgaagg agtttcattt gcttctgcca attgagtatc cttaattact   57420
agtccacgag cataatttat aacatcttttt atttcattaa tatccgagtc tttaaatgca   57480
ttataaaaat aatatggtgt atattttctt aacatctctt ctttaaattc attgaccaat   57540
taaaaacgcc accattctat tattattttt atattataaa gagttgttca taagttataa   57600 tatctttttta gttttgatat agaaacaata tactatatat taaaataaag ttagggtgat   57660
ttatatatga atattaaaaa aataaataag aataaaacag taagtaatat tgtatctatc   57720
agtaaagatg gaaatataat tcttaaggat aagaattata caagtgataa tttttttagac   57780 tcattctata taaagtcact ggatagtaaa tctatgaata aatttataaa aaatatagaa   57840
tcattaattc gaacatcatt agagtattct agatatattg ggtatttatc tacagttcaa   57900
aatatcaata cagatgcaat tatggcaaat attaattctg atgatgccag tctagagttt   57960
catcattatc catttactct ttatgatatt gtagaaattg ttataaataa aaatattgca   58020
ttacaagaaa atttttacatc aatatctata gctagggaag ttttaaaatt acattatgat   58080
aatatgatag gattatctag agtcagtaga acggtacatc aattagctca tgccggcgaa   58140
atttttattc cattagatag tatatttgga agggttaatg atttcgttaa tgattttttat   58200 gaatatattt atcaagaaca cattattacg tataataaga ttattgaaat ttataataat   58260
aagaattatg ataatgatat aacaaaataa tttttagtta tatattataa ttaaaataat   58320
aactattata ggtggcgatt atatgaaaaa aggaatagac gattatatta ataaatatat   58380
aagtgatgat ccagagactc aaaaagaaat agatctcatt gtaagtaaaa taaatgattt   58440
taataataat tgtattgaat tgatgaatga tgaaaatatg atctgtgaag aaaatatttat   58500 taatggtacc attaatgaag ttaaagacat tctattaacg ttatcaaata catttacatc   58560
tgtttatatg gcgaacagag ttattgaaaa tattgaatta tttataaatg gtgaaaatga   58620
cgaagagctt catgaatata tttatataat gcaagattca attgaagatt ttgatgtatat   58680 tcctttatat gacaaaacgt tattgtctga agcgattaat accattcagc gagcagaatt   58740
```

-continued

```
tctaaatatg atactcaaag aaatacatat ctcaatatat ttagaaaaaa cactgaaatt   58800
attaaacgat attatggatt ataatagtga taatttgcct tatgatatgt ctatagaaat   58860
taatgcatta ctgatgagtt ctgagtatac attatcagtt atattaagtc aatttaatca   58920
tattataact aagtcatata ctaaatatct aaagatcgtt gacattatct aattttaaac   58980
ctaataccat aattttatgg tattaggtta attttttttt ttatttttta aggtttaaac   59040
tacctagcac atttgtttct ttatttctaa ttctttcatc aacagtattt aataatttta   59100
aattaccata aattactact gcataggttt tattttcttc cggatttttt gttttaacaa   59160
ttaatttatc aaaatcaaca gaatattcat cttctgtaag cattctgtta tttgcaaata   59220
tttttacttc aatacattta tccatatttc cattattttt ttcaatttct ttagcaacac   59280
gaattagtcc tgaagacatt attgatttaa tatccaattc atcatatgct acattaaagt   59340
caggaataaa ttctgagaaa tataagattt gcttttcatt aagagttgga ggtattaaat   59400 cttttttgagt tataatatta aacttaaatg tatcactatt atctatttct ggaatatctt   59460
ttataatatt ttcgtttcgc atttctaaaa taaatgatcc cggcatccat aattctgcag   59520
tcattgcata tcgcacttca gaataagaat tgattagatt attcattatt ttttgagaat   59580
ttgctaattc tggatatctt aacatgatat ttgcaggata ctcgcacata taggtaggat   59640
tatttgtaga catatttatt ttttctataa ttgggtttag tgaatgagat aataaatatt   59700
cacgtaattt atctttatct tcttcattat caaaatctaa acctaataca ttacatatat   59760
tcaatataaa tgataatggt atttcataag gtattctaat atcattaagg taatttactc   59820
cgttattctc aaaattctga tttaagaaat ttaagttatt ccaagcagaa agttcactag   59880
ggagtttcat gtatatatca aaacgtaatt ttatccgatt aggaatataa aaaatacgaa   59940
tatcattttc atgatcttca aataccattt tgtattcttt gtgtttatta cgattttta   60000 tataatattg atgagtagac caaaaaggta atatatcaat aaatgtatca cctaactcaa   60060 atttaggga gattccaatg tatggtttag gcatatcagt aaataacccct ttaccattac   60120 taaaattagt cgaatttaat gattcaccga tatataccott tttaaaatat ttaggtggaa   60180
atttgcttat aaaaatagttt gatatgaatg atgatacgcc actaataaca ttatgtatag   60240
atggactagc agtacataat gctacactat tattatattc agatcttgca ggatctaaca   60300
taagagaatc acgcctttct atataatgtt gttcacaaaa caaaaaaccc ctattactat   60360
agttatatag taatagggta aaagatcaga gattgtggga tctctaaaag tgtggagtac   60420
agaaagcata tacaataggt taaaaaataa aaggttaaaa aaatcctatc gtataatata   60480
ttatttagaa aattacgctt aaaaaaataa tattatctct aggtactgat gctcgaattg   60540
tatacatgtt tgaaatgatg aatttatcaa agtcgaaatc ttctccaaca atttcttcaa   60600
actcttcatt tcctctaata aatttattaa tgataatagt agttttatta ataatttcgt   60660
tagtcaagat aacctgtact ttttctacat atttattcat gtttttatca tcattttgat   60720
ttttaacttc aggaaaattt tcattttccg gtttatttag ttttaataca aattcaggat   60780
tatccttatt aataaagatt cttgaattat tatctttaaa atcaacttttt tctgattcat   60840 caataatttt tcttaattca ttaactaaat tttctttacc gataaaacta ataatgttat   60900
ttcggatagc aatttcttttt ctgagtttaa tcagttttttc atcatcaatc atctcattta   60960
gtcttttctc attttcatta taaatcatct tgtattttct tcccttctaa ttcctttttca   61020 ggattatatg ttaattcact attaatttca ttattttttaa ttttcattgc aagatctaat   61080
```

-continued

```
atgtcatcat ctagtgtttt tttaagttct ttacttatgc gtatattttt tgaatttggg    61140
ttttctttaa atcttattat tagatttgtt tctggatgag tattataacg tttttcagat    61200
attaaccgat atacttgatt atcatctttc catagtattt tatttaataa gtccattaat    61260
gttttttgat aattatcgat atctggtttt ttaattcttt tttcctgatt tgtcaacatt    61320
agatatattt tataaaggct atttccaaac tttgttggaa tattactaaa tatggattct    61380
aattctattg gaccttcaaa agcgtttttca ttaaaaggta ttttattctt atgaactgaa    61440
ttatattcgt ttatagattt aattaatatt tttcgaaatt catttttata cccacctaat    61500
ggatcgtatg tgctaccaat gatattaaat ctatgtcgtt gatacggtaa tatttcccta    61560
tcaatattaa tatgtatttc attttttatca aatttaatga tatctatatt tgcatttaag    61620
atatacatct taaaatttct cgatttttggt tttttaattt ttatatccaa aggtttttct    61680
tcaccattag gaataggtct ttttttcatt actgcttctc acctccaaaa gtattagtat    61740
ataaataatt attattcaat aattataatt ttttaaagta aaaatatact catatcaatc    61800
attttaatat atcacgatat atgataatta attaattgat atgagtatat aagttatata    61860
aaatactgat gccattatta atattaatgc agttactata taatatatta acgcattatt    61920
ttgcttttca gatctattta ttctaaacgt catattcata tgacgttcta tttctttaaa    61980
taatttatcc ataaagtttt caatatcaga agtagttttc ttaatgggtt taatttcttt    62040
aattatttca ttagtatatt tattcgtttc atctgcttgt tctttaattg catttaaaac    62100
agcatcagtt ttcttcttat gtgcttcaaa ttcttctttt gtaatatatt tttctttatc    62160
aatatattta tcgttatctt ttctttttaaa tatccttttt agtagtgcag tgaacttttc    62220
catcatcctt aaacccacct tattttatt ttaataaaag gtcgggtacg atattaatag    62280
ctgaaacaat tataccactc agagcaggta acaatgctaa ccatatttta tttctgcttt    62340
cactattatc taatttatga ctatgtgata attgtgttgt ttcaagattc cctattcgtt    62400
catctgaaga ttttgtaaat gaatctattt ttgtcctagt ttcatttttta acttcctcga    62460 tatttgaatt aaatctttca ccaagatcat caatttatt aaaaatttga cttgagaaat    62520
catcaaattt ttctttaata ttatctacat tttgacttat tttagcaatc tctatatttg    62580
tatcatttag ttttgttgaa ttttcatcag ttttcttctt aatatctgaa gtagtttgat    62640
tatagttgtc gataaaaagt ttaaattcat ttctggaaac tagttctttt tctgagttat    62700
ttgccaaaac ctcacccccc cagttatagt agccataccg ttaaataccg atatgattaa    62760
tagacggtta aagtttgact taatgagagt atttgtatcg tttactgcag aagcataaat    62820
tatccatgct attgttgcaa agaaacatga tatcgctatt ataatatatc tagagggttt    62880
cttataagat ataaacgccg atataatgag taatgaacca gtaacaacaa agatatatga    62940
ccatataatt atgggaaata ccctatttaa cataatatat gtttcagaag taagtaatac    63000
actagattcg gcaatattaa aactgattcc cgtacttaat gataataatc ctaataggat    63060
taatagagat tgttccatca aaagaatata attaaattca ttcataaatt ttttaattat    63120 attttttcatt ataataaaca atcctttcag aaaatattat accatatact tataattaaa    63180
atatatggta taattattct caattaataa atttatacaa attattcgga tggtggtgaa    63240
tctaatttag cttcaatagc acttacccga tttaataatt cattccactg agcttcagtc    63300
ggaaatccat tatcaccttt tgcacctttta agactagcta accattcagc ttcagttcca    63360
ctaaatccag atgctttttgc taggtcgtaa gcagacttac cgttatcacc agtgcttcct    63420
ttatcgcctt tatcaccttt tgcgccttta atactagcta accattgagt taatgtaccg    63480
```

```
ttaaatccat cagcaactgc taagtcgtaa gcagacttac cgttatcacc attatcacct   63540
tttgcgcctt taagactagc taaccattca gcttcagttc cactaaatcc agctaatttt   63600
gctagttcgt aagcagactt accgttatct ccagtgcttc ctttatcacc ttttgcacct   63660
ttaatactaa ctaaccattc ggcttcagtt ccactaaagc cggctaattt tgctagttcg   63720
taagcagaat taccgttatc accagtgctt cctttatcgc ctttgtcgcc ttttgcacct   63780
ttaagactag ctaaccattc ggcttcagtt ccactaaatc catctaattt tgctagatcg   63840
taagcagact taccctcttc accatcaact ccgggatcac cctttggtcc acggtcacta   63900
tcggaaacgg tatcatctac gatatcttca ttaggtttat gatagttaac ttgagatatt   63960
tcatcaatat tactaattac attagtaact cttcccgctt cagaatacgt taatacaagt   64020
tcatcacgat catattttaa tgtaccacta cgtttaatat cttttactag tactcgatga   64080
tctgagtata ttgatgtgat tattatttca ttttttgttat gtctatcgat gtattcttct   64140
attctatatc ctatagccat tttattatat catccctttc gtataaagaa acctttatat   64200 aatttttttgt tttatatatt ggagttctaa atataaaaat tattatgatt tgtatatatt   64260
aataacatct ataattctaa gctgtgcttc ttgatataat ttattcttcc aatcttcacc   64320
taagtcaata attttatttt ttggtaatgt ttctagtaat tcaatcttat tttcacgtat   64380
atcggtagta attacatcat tatcgtcata tacggttaat gatttataat tatatttata   64440
aaatgataat tctataaatc tacctatatc gtttatatta tttttttccta taactactaa   64500 tttaggtatc atataatcat tataatcaac ttcaatagca ttatcgttat caatatattc   64560
aatagttgta tgaattttat catcttcagt aattacttct ggaagattat atggtttaat   64620
actgaagtca aaaccatatt tttcagaata gttatacgta tctgtaatat taacagaata   64680
gtttcgtatt ccttcatttt gaattgaatt aatatcgtct atattattaa ataaataaat   64740
attatcaata tttggtagtt ctaaataatg ataattattg aattctcttt ctagtactgt   64800
ttcactaaag aacattgaat caaaaagata atcatcatca ttgttagaag taataataaa   64860
cgtattaata cctttattaa gtttaatttt attagcatat tcgtaaacat ttgtttgttc   64920
attataaatg cttaatcgat catgagatat accttgacta ttatatttat acgtatatga   64980
caatccgtta atatttactt ttgcattacg attatatttta tcactaggat tatatccagt   65040
aatatataca tatttctcaa tatcattttc taggttaatc ttaaattcga tattacctttt   65100 atttatcttt actaatttat tagataataa gttattataa gtattatcaa caatctctga   65160
agtattatca tcatttactg ttttttaatga agatgataat tcatatcctg taatatttcc   65220
attaattttt ataggatcga tgaaatgatt atatattgga acatggttaa taattgcttt   65280
tctaagaact aaaatattaa aatctacatt ttttgtattt ctaggttgac ctgactttaa   65340
taatatttct tcaatataat cattatggtc agcattaata atattattgt tgatttgatt   65400
ctgagtatac atactatact gtttaggagt tatatcttgc catacattct tgttattacc   65460
attagttgtt aaacttcttt caatattatt aataaagatt gaagatgttt tagatgtcag   65520
attattactt cccatatata ccgtcatatt gtaattattc atttcaggaa taaatatctt   65580
cattcttaaa tacccatctt ctaatcgaac ataacccttt ccaaaatatt ttaaatagtc   65640
agaagtcatt cgtgatccag aagtttttagt atcttcatat tcaaatattg ttccatcata   65700
acattcatat acataagtac cgtcagctag tatagacgga tatatgactc catcattatt   65760
gatataacca tgagtaatga tatcctgatc aaaaataata tcttttggat agtgtggatg   65820
```

-continued

```
acaataacac tctccattac aattacaccc attatcacag tcatcatcat cgtcaccacc   65880
attattaggt ggagtaaatt tattattaat gtaatttacc attgttatac tggtaggatc   65940
aacaatactt tgaactttc cattcttatc agtaaaattt attttaaaat ctttatgttc   66000
taataagcca tcacgattaa tatctttaat taatgtctta acattagaat cgattgatgt   66060
aatatcaatt aatcctgagt tatgatcatc aatcatttct tcaatacgat aaactttcat   66120
attttgtttc acctactatc cgtttaatat tatattgtta tcttaaaaat tttaggactt   66180
tttgacctat tccatattta atatctttaa atttattatc taatgaccta aatgataaaa   66240
cttggactgc tctatcccta gtcatcaaca agtttgtttt aatacgtttc attaggttta   66300
attcatcata acgcattcct gccatacact caatatatga tgttaatcca atattatatc   66360
ttaattgctt aatacgctta gaagccatta ggttaggata taagtcacgt acttgcatag   66420
atacggttac ttcacgagga aagttttcag cagtccatgt ttgttcttcg ccacgaacca   66480
tatttattga tgatattacg ccacattcac attcaaatct tcctggacaa gacattctaa   66540
ccaagaaagg ttgtttataa ctataatatg cgtcttgtaa cggtaaacct aataccagta   66600
aagatacaaa tggtacatat acataattga atatcgctct aggatctcca taaggagtat   66660
agaatctaaa ttctaaatta tacgatctat cgaaagtaga gtttgaccat aagtctggat   66720
agtataactg agaaccatct agattttcag taaacgcacc aactaagcta cccaataccg   66780
gaattgtttc aataacgtct gttatcatat ccttgattcc atcagtaata gcacccaata   66840
atcctccgcc gccaattccg gcaagagttt tattttctct aatttcagcc tgtttactat   66900
tagattcact agctaaagaa gactgagaat aatcattaga tgaactttct gatacgctgg   66960
ttgatttatt tgcatagaaa gcaatgccgt agttatcacc attattatat ttactaaaat   67020
cgaaaacacc ttctaatccc atagaatgat atatatagct tagtattgtt tgtacatatc   67080
gataatactc ttcgtaattt tgtttaaacg atataaatct tccatcacta aacttatttg   67140
cattaatcat tggaaagaca ttatcttcaa ttttctctcc aataccgaaa agattaaaag   67200
tgtttcctga catactacca aataatttct tatttagtct aggttttccg ggagtaataa   67260
atattactgg tagatcattt tcgaatgtat ttcggtacac tctagagttt gcatcatcta   67320
atggaccata tttaagtggc atacctaata cccttatatt atctttacca tatgaagcat   67380
caaacgtatc tattttagta tttccaaaag cattaatagt ttctcccatt gcattgacat   67440
atagaccttc attattaact tgtgaagggt caatatcatc ttcttgcatt agtgtgtctc   67500
cctcaactcc actgtctggt tttacaatat aaaaatcatc atctgaatcc gtattattat   67560 tagaatttt attacttact aaatcaggca tattttcacc actttcaaaa taaatttcc   67620 ttgagaccaa atttaataca tttatggtct caaggaaata aaatttaata tcccgctaat   67680
ataggagtta tactattagg atcaagttta aagcttggtt gatctaattt attatctcta   67740 tcattttat gatcatttct agtttgtttt aagatgttat tcgtttcatt agttaagtta   67800
ttattagttg cttctagtct actaatattt ctaatttcac gaattaaatc actcaatttg   67860
ctgatagaat ctttatcatt cttatcaatt aatttataca tcttatcgag aatatgattt   67920
acttttttaa gttcatcata ttttttcttta tcatattggt aaggtttatt aggtttagcg   67980
gaacttccat tagatccatt tttaccgtta gaaccgttag caccattaga tccgtttta   68040 cctccggaac cattctttcc accgccgtta ggtttagcgg aacttccatt agatccgttt   68100
ttaccattaa aaccgttaga accattacca ttagaagaac cactagaacc aggactatta   68160
tctccagaat atccacccttt agagccacca cttttagaag gttcagcggt tgctgaagtt   68220
```

-continued

```
gaattactac catctttacc attagagaag tcttcattat ctcctttag accgtattct    68280 ttagcatatt tactgttaat acgatcaccg atagctttct tttcttcttc agttagttta    68340
aagttagctc ttgattttg ttcttcagtt tcttcattaa cttctccagt accagacagt    68400
tctgcactac catcagcagt acctccagtg tttccactaa ctctaccaaa tcctactaat    68460
ctaccaaacc aatctgcagg catatttaat gcatcactac gaatgtttac acctttacta    68520
gattcagcat tgatcatttt cccttcactg atataaatac ctacgtggga aatagaacca    68580
tctgggtttg ctgagaagaa tatcaaatca ccaatagata gttcatcttt tttaattctt    68640
ttagtagctt tatattgttc tctagaagta cgtggaagtt tcttaccgac agaattgtat    68700
gcattcataa ctagactaga acagtcaaag gtcttagttt tacctaaacc agaacttggt    68760
cccattgagt atggagtacc gatatacttc ttagcatatt ctacggcttt atatcctata    68820
gattgtccgt cagttttatc agaacttcca ttattggaca ttacagaacc taaattactt    68880
ccaatatctt taccggtatt tttattttct ttactagacg atactttttg gtttgtaaga    68940
tcttttagtt ttgcaccctc ttctttagca cgtcttctta atcccgcttc ttgattggtt    69000
cctgcatatt gacccatata ttgacttaat cttttgtttt ggactaaatc aataatttga    69060
ttgtctgata gtttactaat attttttccg gctaatgcac gtttaaatag actagttgca    69120
cctccagcac catgctgtac tgaagcactt aaaattaatt cttgaatacc tctagatcga    69180
ccacttaaat cagttcccag tgctttattt attttagcta gtcctggatt atagaagtct    69240
ttttggaagt attcttgttg tgcttcacca aatgctttat tttgtcctaa tttttttccaa    69300 gaagcatcaa agctagatga acctggagaa ccactaagct ttttagcaag gtctggatga    69360
gctgatccta accatttaac aaaattagcc agtgatcctt tagtagatga taattggtaa    69420
ataccgtaag atttaccgcc ggcatctcca accccactag agatatatcc cgcaccacta    69480
aagtcttctt taccagtttc ataaaatctg gctactgaac caaagtcttt tgaaagattc    69540
tttccagctc cggaaccgcc agagtttcca ccagtcgatg cagcatttgc attaacgcta    69600
cctaatcctt ttacaatatc tttttaattta tcagtaattg atgagaagaa attgcttatt    69660
ttaccccata ctgatttaga tggtttattt ggatcaaatc cattttccgc catattatat    69720
aatgctccaa ccggagtaag actgaataaa gatttagcaa atgatttagg attcttttttc    69780 atatcttgac ctactctaga tgacattaat ttactgtatt cagaacccat attcataacc    69840
attcctaatg gagtagcatc taaaaagtct ttaaacttac tttgttcttt accatcttta    69900
cctttatcat ctttcttttt ctttctagca tcattgaatt tttcagcaat acccattgga    69960
gttaatccgt atagtgcatc tttaatctta ttttttacgtt cttcggattt tttctcttta    70020
tcattctttt tcttttctttt ttcagctttta tcacctttaa ttaaatcccc aatagaaggt    70080
aatttaggag tgcttgcaga tttacctgat ttagcactcg acattccttt tacaattgat    70140
cctactaata tagaacctaa tattgctgca ccgccaacag ctaatgccgg tccggcaatt    70200
ggaattccag atactaatga tagtaatgcc cttccaccat ttcctgcaat cctaagagct    70260
gatgagattc cagatactaa ttttttctctg gttgcattaa atattgcagt tcctctttca    70320
gtaacagttc taaatgcttc agtttcacct agacttttca ttcgaaacat cattcgagca    70380
attattcctt ttttactttc tgcggattct agtgcaatat ctttagttgc tgaagccatt    70440
ctcattttag ctattagatt ttcagttttt tcacgaatgg aattgattgt acccattgga    70500 tctttttactg atgaaacaat tgatcctcca actttttttag cagtatccat agcaagaccg    70560
```

-continued

```
cctgcatttt tgaccattcc accaaatttt gtatctttaa ccattcccca tacagatccg   70620
gctgcattaa tggctccaga tatagtatct tggttaataa tattatcggg ttcaccgcta   70680
atgatatcac ctttagtttt attattaaac atattcatac gatctttggt tttcttgatt   70740
ttatcttgca tagaatgata cttggataca attgaactac ctagtttact tgaaggattt   70800
ttaaatgccg agcttgcatc tttaattttg gttctagagc cataatcctc accgactgaa   70860
ctatcgatat ttacagggtc gcttgcgtca ggagtaacat cttgaccatt cgcatttttt   70920
acaaaatcac tcctaaggtc tgatacgctt gatgcaataa ttgacagata ccctagtttc   70980
ttagatattt cagtaagaat atttatcttc ttcatatcat tatcattatt tccacttgca   71040
gaattatatg ataccgttga tctattatcg tcatcacgag ttatatttcc tgtagtttca   71100
ttatcaaata atccaaataa tgcatttttt actgatccta gaggagtctc tgcttgtaaa   71160
tatctttgac cttttacttg tgtcttaaga acatttcttg aaaaagttgc actattacca   71220
tctataatct gtgataattt ttcatagatg tctccatcaa acatgtcttt gttattatct   71280
aatgcagtac ggttttttgat attattttta gataatttga taatagtatc tttaatatta   71340
tcattatcga ttcctgcttc actcatcata gattctaatg ttgcattctt actagattta   71400
tttaaaagta tgctgagtgg agatttattc tccgtagaga ttgctctatc cattccagaa   71460
ttaaagttat ctttagcttt actaggatct aaccattttc cactcttata atcatatact   71520
aatttttgac ctgaagaagc ttctagcatt tttgctaaat aacctggaat taccgtatta   71580
atagtattat gagtttgagc atcaaagtta acaggtctgt ctgctgaaac tctagccata   71640
gagcttactt ttcctagatt agcaggacca aattgtcgat tgagtgaagt cattagtgga   71700
ttttcaccaa agattttctt aaattgacca ctaatgatac tttcgtcacc ttcaacaaga   71760
ttacctagtg ctgaatgtat ttttccgcca actttaccat tgggattagt tcgattaagc   71820
gtacctttaa ccattctgtc aattaatctt tctttatttt ggaatggtcc aatttcacca   71880
gtagataatc tttcaatagt gtcatatatc gatgcaggta tatttgatac attcttatca   71940
aaataatttt ttactctatc tcttgcatat ctatttgctc gttcattaat atttttagag   72000
atagaatttt ttgcattttt aagtaagtct ttagcgcttg catttccaga atttagacta   72060
ctaagtttaa acattgatga tgttatttta cctattccaa atataccaga aagcatatca   72120
tccattagac ccacattatt gatacttgct ttagcgcttg cttgagatat tctattcatt   72180
ttttctaata atgtagtaga tttagaagat tgctcgatta attgtgaata gaatttgata   72240
tttgtttgat tcattttatt taaggtatta tttaacgtag aaaatcctct tgtatttacc   72300
ccaactactg aacttgctga tacaatagta gattcaacaa ttttatcaat attttgttct   72360
tcatttacat cttcattatt gatatgatca ttattatctt gaggagattc ggtatcaata   72420
ataacttcag agttaacgct tgaagtatta cttgattttc gattcatttt atttaatgat   72480
ctacttagta tatctaacgt gtttttacca taagcttcaa tacccaaatt atcttggttc   72540
attgaattat ttgaagttct attattctta ctttccagtt tatcgtctaa atctttagat   72600
atacttcggt atatattatt agcagacata ttggatgcag gaattcgatt atttcctttt   72660
ccccaatttt tattaccttt attcatattg tcaatatatt tacttccctc tttaaaagtg   72720
ctatcaatac ttttatctgc cattctagtg tctcaccaac tttcatatgt agagattaaa   72780
tcgcattatt aatcttctta tatattaatg tttaagaata gtaaaaatct gataacttta   72840
gaaaaaaaaa aaataaccat atagagataa tatctctata tggtaaatat aatttaaaga   72900
tcaatattaa attgtgattt ttcagttata agagtatta attcttccgc actatattta   72960
```

-continued

```
ctataacgtt tatttatagt actgctaata tattttaaaa tataaactag atttaataat   73020
acgctaaatc ttcttaattc tttttcatct ttagataatt cttttagttt tttatgatat   73080
tttctttcag gatattgcct gcgaatatta aggaaaagta tttctgaaat tacatcatta   73140
aatttatcta tttgaagctt agtttatat tcgctaggta gttcttctag aataatcttt   73200
ttaaaatgat ccttgtttag attataatct acaataagat gagtaatgac tgaaccaata   73260
tataaatata tatccataat ttctaagata gctaattttt cattatccat agattgattg   73320
tttacttcat ataaatattc ttgtacttct tccattatct gagggtaaaa tctttctagc   73380
attttacatt ctgtttcttc tggaaattta tacttagata tcatatgttt ttgattttca   73440
ataagatttt ctatagagaa tgagaaacta ttgttttctt ccgtaataat tgatttaact   73500
ttataagcca aatttacaac acccacaatc tgtttattta taagtattat tatctaaaag   73560
ggtcttggta ttaatctaaa ttccttaata tcttcttcag tattaagatt aaattcaatt   73620
tcccacttat ttttatttaa tatttttcga atattatagt caaaaaagaa ttcggcagta   73680
tctataaaat ttcctaaaat acttgttcta aagttatacg taaaagattt tccaataata   73740
atcttttgat ttatactggt cggtattttc caaattccat tgatatcaat tctgaaaaga   73800
ttatctggat catagtaaat attagaaaaa taatctaata ttgtttttaat atcacctata   73860 tttctattat aaggaataat gcttttctta gttttcttat ggataatttt taatataccg   73920
tcataatttt ttgtttccat aagcgacatg cctttcaatt aattttatta ataatttatt   73980
tttgaaaact gatttttttag atataaattt attctaatat tagagttttg tattgaatga   74040
gttagatcta tgatattctc attactatta ccagaattat ttagtacatt tataattctt   74100
agtaagtttt gttgactttc aggagttacc ttcatactca tatcattaat tatattataa   74160
tctaaacttt cttttgacat attaatatca atagaatcaa taatattaat attttctaaa   74220
gatatatctt tcattctttt attatcctca atatccgata taatataact aagatagaat   74280
attgtccgta gttgatttat tcggtaagta ttttttataat gaatgtttgg atacgttatc   74340
atgaatggtg gttcaatctt atctttatat ttaacattat tattgaatat ttcatcaatc   74400
ttataaacaa tatcctgata cattcccta tacattatgt ctttattgta acaaacactg   74460
gaatagtata ctaaatatac atttataatt aaaaacgaaa aaatatttat cattagaaac   74520 attttttattt catgaatatt ataataattt ataaatgtac taaaattaaa agatactagt   74580
agtatacaag tattaatagc tactaggtat aaaggattct tataaataat cttaccaata   74640
gtaataaatt tatatttctt taacaattta gatcacttcc atttctttat atgacgtgaa   74700
tatattattg tatagaaaaa atataaatgt acaataaata ttatagtgca ggtagttata   74760
tctataataa aataaatata actacctaca ctgattcccc gatttaacta atacaataat   74820
aaaaaattgt tattgttgtc tatgttgttt gtatttctct tcaaactcag aagtgtatga   74880
ttcatttagt ttggagatat cataatcttt accgtcatct ccagtgaacg taccatcccc   74940
attatctgtt ccacgaatct tatcataatt cattacgctt gcaaacatac gagttcctgg   75000
catacacaat gtttcagttt cacggacttt accaatatga gcatttgttt tcttacgtga   75060
aaatccagta gaacctacac gaactcttag tccatttta agagtctcat ctaagatatc   75120
cccaaaggcg gtaatcatat caaatacttt tcgtttagaa agatcatctt cactaaaaga   75180
tccatcagca atcagtttat cataaagaag atttacttga tcgtccttaa tcaacatatc   75240 taattttttca ccactatctg tcttttgatc aataagttta ttaagagtta gatattcacg   75300
```

-continued

```
agattctttt ggtttctctt cttttttctt tttagattct tttttaggtt tatcctcttt   75360
tttatctttt gttgaatctt tcttgactga tttagtagtt ttagattttt ctttaggttc   75420 aacttttct ttattaacta cttcttctga agaaatctta gtaggttcac tttcttcact    75480
agtttttacc actggtttaa caacacgttt cttgggtgtt tcttctttag ctttactttt   75540
taccactgga actacttttt tattaagttc aacttttct tcactaactg cttcttctga    75600
agaaggttta actgtactct ttcttactgc tctttttacc ataggacgaa cgactttctt   75660
cttttcttct gccatttaat ttaccaccct taatttatt tttgaaatat tattaaatta    75720
gttattgaat aaaaataatc ttttaattct taactttatt taatatatac cctatttat    75780 attaatgtaa ctaccttatt gccaacgata tttaacaata tttcacgttt ataatatata   75840
cttataatat aggtttaaat tttaatttt taaagaaaaa ttttcataac atattaatat    75900
taaaaattat attaatttga ttttcttatg ggactccgat gggactcgca aaatctggac   75960
tgagcctaga ctccttatta agatgcttat taatggactt tactatttta aatcgaattc    76020
caacgtttgt taaaaggtgg acaaatagag ggtaaagagc ttgcggtata gtagacgatg   76080
gtctcactgt agatgtaagt aagtttgtaa agattcttta ttattttacg ttttattctt    76140
tttttacttc ccacacttga agagtgttta aaaggggggt tggggggttt attgttagtt   76200
taattttttc ataaataatt ttaaaataaa aattattttt attaaaaaat aatttagagt   76260
gggtgctgga atttcagcgc tccgcacttc attccgataa taaacaaacc gagaacctga   76320
agttgagtat tgtatccaat tatccttaat atcaaagaat gtttataata agtaatatac    76380
agtaattaaa taataaatat tgtatatagg aaatatagta tgaatattat tcaatataat   76440
aattaatgat ttgataaata ctttaatata aaaagtattt atcagtataa tatctaatca   76500
atataaatat tcaataatta ataaaatttt aagttagata ttaaatatta tattaatatt   76560
agaatagtat aataaatatt aaatattaga aatatctaat aattattaca tataaggtat   76620
atagtatttc aattatatta gtattaataa gttttatcaa tataatttaa ataacaattc   76680
tatatactga atgaataaaa ataattattc agagaggaga gtatacttt gttatatatc     76740 agtgacctaa agaagtatag attatataaa ggtaataagc ttaatggtat taataagtta   76800
agtgaaaata aagatccaaa taaaggtcaa ttaatattac atttaggaaa taatgataca   76860
gatattatca gtttctttaa ttcaagaata tttaagaata atctattcaa aagttattct   76920
acagctagaa gatatagaac taataataaa cgaaaaatgt atattaaaga tcttaaagaa   76980
cattttgcaa agataaagaa agaaacaaaa gttacattat ttactaaagt aaattataaa   77040
cagtttaagg gtaataactt agtatatgat attacagatc aatataatat tgaaattgaa   77100
tcaattaata ataaaaagaa tggtttaatg gtttctaata actttataaa gttattagaa   77160
aaatctctgt tggaagaata tgatgataca gtattattaa ttaatatgaa tacattgaac   77220
gtagatatgg atgatatatt caatattact aagtctactc atccactaac agttattgat   77280
tttattatta aaagaaatt ggatattagt aacttaattg acaagaatat aacaattgtt    77340
gtatttaatc ctaataacag attattttat agttatccat taactacaga attatatcct   77400
aaaagacaga tcatcaatca aagatctaaa tcactaatta atttggaagt taatgaaatt   77460
gaaagcaatg atgagatgag taatattcca gacattaatg atattgatga tgctaaaaga   77520
caactaggta ataatatgag gttaggtcga ttaaggtcta gaagtaagat acctgttagt   77580
atagacaatt ctgaagtaag taataattct tcacaagaag actcaataac aactaaaaaa   77640
ttagatgata ttgataaagc taatgaaata aatgataagg ttgaagaaat tattacccctt   77700
```

-continued

```
actagtgata atactttatt atcttcagaa gctaaaaaac aattatatac aatagctcaa    77760
gatgaaatta aaaataataa agatttagtt aagatggata gtgctaaagt tgtctctatt    77820
cttaatcgta atgaagaatt caatagaata gtttcaatgt cttatagatc atttaatatt    77880
ggtggatcga acgcaaaaga gcttgcaaga acagcagcac tacaaaaaag acagaatgaa    77940
atccttaatg ataaaaatat ttcgaatgta ttagctcatg caaatgataa aatgattgat    78000
aaaggaatta ttaaatcaaa taatattaat gatgaaacat tatcagaact ttctgtaaac    78060
tcttttgata agagttacat tgagaaacaa tttaatgccg atattattaa tgtgttaaaa    78120
tcatttaacg ataatgagga gattagcgta ttcatctcag acatatcttc tgaagactct    78180
tcagactttc agacaaagaa aactacatta aacgttaagc ttaaagatac taaaggcgtt    78240
aatcataaac tatcattaga tattcctaag atatataacg gtagatatat gatggttaac    78300
ggtagtaaaa aaatactaac aaaacagtta ctgttaaaac ctgtagtaaa aactgcaccg    78360
gacacagtac aaataactac taactacaat aaaatgtttg ttaagagatt tggtagaaaa    78420
gatactccaa tgttagcttc tatcaaagaa atctttaata aatttaaaat tgaagatcat    78480
cttctttctg gtaaaaacat taaatattct ttaggtaatt cattattagt taactcaaaa    78540
tatctaactt cagtagaata caataatatt tctaattatt tactaagctt tagttctggt    78600
aaagattatt acaattttaa ccaaaagtta ttattagaat tcattgataa tgatgataaa    78660
cttaattcac tagaatatga ttctacgtta tatttcccag taggatatac ttcagataaa    78720
agtaaactta tcttagcaaa ttttaaagat tatcacgttt attataaagg tgcaactaat    78780
aattatgaat ttgtagaaga aagtttaagt agaatgatat tactaaatat tttgatgagt    78840
gttgatgatg aggttgctaa gtttattgat aagggaatta aagcaaatga taaactaaca    78900
tatacacgag taaatatcat taataaaaca attcctctaa taatattatt gtcatatgag    78960
aatggattaa tcaatacatt gaatcgatat aatattgact ttgaagtatt agattccaat    79020
cctaaactaa agattactga taataaagtt aaacttaaat ttaaggataa atatttggta    79080
tatgataata cactaataag aaaattcatta ttattgtcag gtcttcatat aatggatatt    79140
aatgaatata acttagatga aatggaaacc aaagaaccat atttagattt attccaagaa    79200
ttgtttaata gtcggaatgt agctaaaggt attcataatg cattatctct cgctattgat    79260
cctatcacca aagaagtttt agaagatctg ggattaccaa ctaatatatt tgatgtctta    79320
ttgtattcaa atacattatt agaagatatg tcttataata ctcctaatga tatgaatgtc    79380
tatcgaattc gtggggcaga gcaaatctct ggtatgattt ataagataat tgctgaatca    79440
tacaagaact ataaggattc tctaaattca agaaatagtg ctactagaat tactgtacca    79500
aaggacattc ttataaagac tcttatggag agtcctacgg tagaggaaaa ttctgaatta    79560
aacccaacat tagaagttga agttagtggt aaagtatctt ataaaggacc aaatggtctt    79620
aacttaagtc aaggttatac tcctgcagtt cgttcatatg accgttctat gaaaggaata    79680
ttgtcgatga tatcaccaga cagtagtaag attggtgaag ttcgtcaatt aagttataat    79740
cctgcaatag ttagtactcg tggatattta gatgtagatg ctttaaacgg taatgaatct    79800
acaagcctat attctccttc tgaactttta aataacttta caagcttaca tgctgatcca    79860
ccacgtatat ctatgcaagt aactcaacaa aaacatttac taacaacaag agtcaatagt    79920
aaaccgctta tcggtactgg tgtagaaaaa tcattagcat atcaaatatc tgatacttttt    79980 gctactaaag ctaaatatga tggtaaagta gataagatag atactgttaa taatttaatg    80040
```

-continued

```
atggtttctt acgataacgg taaaaaagat atcattgata ttggagttgt aatgaataaa   80100
aactccggtg gaggattctt tttagcacaa tctaaagata ttatgtttaa agaaggtcaa   80160
aagttcaaga atggagaaat tcttgcaaag aatcctaact tctttattgg tgataagcaa   80220
ggtgaaatat catatgctat tggtaaactt tctaaagtag ctttagctcc attagacgga   80280
acttatgaag atagttctat gatatcatca tctatgtcag aggatatgac ttctaaaatt   80340
acaatgaaaa aagatttagt gttaggtact tcggcaaact tatcttatat tgtaaaagaa   80400
ggtcaaaacg ttaagactgg agattcatta gctgtatttg aaaatgaatt tgatgatgat   80460
tctataaatc agctattaaa tactattggt gataaatttg aagaagaaat ccaagaaata   80520
tctaataaag ttgtaaaatc aaagtatact ggggtagtcc agaagattaa tatttattat   80580
aatcgagaga ttgatgaatt ttctccttca ttacaaaagt taattaaagc ttatatttct   80640
aaatatgaaa agaaaaataa gataatctca gattatatga aagatagcga tattgatata   80700
tcatatgata tgaatattcc tagtattact aaaatggatt cagataagat taagggtaat   80760
gatgtagatg gattattaat tgaattctat attgaatatg aggataattt aagtactggt   80820
gataaagtaa catattatac ggcacttaaa acggttatat ctgacgtatt cccagaaggt   80880
gaagaacctt ttgcagaatc agacccagaa gaacatattg aagcagtatt gtctccatta   80940
tctgttattt ctcgtatgac tcaagacgtt tatctaacat tatatactaa caaagcatta   81000
atcaatctga aaaacaaat tggtgaaatg ttaaaataac tcactcttga gagaaacata   81060
ttaatattat agatgtgaag gttgctttgt gcagctttcg catctataat ttctatcaag   81120
aaagttggtg aaactagtgg gtaagttagt atcaaataat aataacggga ataatgtaag   81180
tcctatagaa aaagatattg taaataacta tataggtagt tatattgaag gtactagtgc   81240
atatagtaaa ctattagaaa atgctcccaa ttttgttacc tattactcta aaaatactag   81300
atcatctaat gaagatccgg gtcttggagg aacggttgaa tacgtaggtt cagaatcttc   81360
actattatat aacaaaataa agaattttcc agtattttcc gttaatgaaa taaatcctac   81420
ttttaatttt gaagaaggcg taggactgga tactgaatta gaaagtcaag caatagtact   81480
acctaaaact attataccttt tacctgatga ttatttgaca ttttcatatc atgaaaaagg   81540
atatgagtat tttaagacat atcgcattaa taatgtttct acttcttcaa taggtagtaa   81600
cacctactat tcaataactt ttattaatga tcctatagat ataaggattc ttgaagaaag   81660
acaagtagat aaaacttatc gatttgttta tgaaaatgta ggtactactg ataaagtaat   81720
tatagaagaa gatgacatat tattaattga taaaattgaa aagatatgtg gagatattaa   81780
tgaaagatat attaataatt tctacaattc acagttaggt attttattat acgaaaatct   81840
agatgaaagt ttattatata gtcctaatct tcattatttt ataaataaga atcaggtatt   81900
tataaataat cgaactttca tgagaaacgt atatatagaa gatataacaa aagtgaagct   81960
gaaagattaa aacaaatctt tatttagcat tattgataat ggttataata acattaatat   82020
gtcttatcaa tatataacta gggttttgga aaataatatt ctaaagaaaa ctaggggtct   82080
ttatgttgaa gatttagaaa ttattggatc tagttgtaat attaaaattc gagaactac   82140 gattcataat tattttttcag tagatattaa tgatttgata aataactatg atggcgtaga   82200
ctcgttaaat ggtatagatg cgataacatc aattataaca atttatttag cacaaccaga   82260
acaattaagt attaatacgt tatttaattt agtttctaaa ttaaattatg atgactattc   82320
aatcagtaat tatttctttta taccatgcgt attatccatt ataaatataa ttactaataa   82380
aaaaattact atacattctg aagaagtata gaactgagag gaacgtgaat ataaatgttt   82440
```

-continued

```
aagaaaatag aagaaaaaat ccatcaaaga aatatggaag ttgaagctag taaaattgta  82500
agtgaagaat tagaagttgt tgaaccagaa gaagaaaaaa ttattgcagt acctaatact  82560
tctgaaaaca atgaagtttt gggtaatcca gaacaagatc ctgaaattgg tcaatttatc  82620
gatagcactg atgaatacga tgatgaagaa gatgcattga ttgatgcttt agaagataaa  82680
aatgacgatg aaggtttaga cggtattgtt gataaagata atgaagaaaa acctgtagaa  82740
acttctgaag ttacatttag tgaatctaaa gatgataaaa aagaagataa gaaagatgag  82800
gacgaaaaag aagattctga agatgaagac aacgatgaat ctgaggaagc tgaagaagaa  82860
gatggtgatg atgagtctga acttgaagaa ggaatcagtt ccatgttctc tggaattttt  82920
gacatcaatg aagaaattga agatgatact aataatattt taaatacact aatcagcgaa  82980
gaagaagata tctttattaa agatgaagaa gacgaaaaag atgatgaacc tattgaaatt  83040
gattttattg gtgatgatga aaaagatcaa gaagataaag aaatcgaaga atctgatact  83100
gattatctta aaaaagaata tctaggtgaa acaatactta ataaaatctt cgacaaataa  83160
tactgttaac ataatattat taagggtata taaaatataa attatataaa ggatgtgtat  83220
ttcaaaatgc caaaagttgt tataaaagat aataaatttg tatttggttt aggtaaagga  83280
ccatttaata atccagttga gattagtgat gaactttac gtaaattaaa aatctctgga  83340
tatacggtaa ttgaagtaaa tgatcgtcat atcgtatatg aaactccaaa taatgaagaa  83400
aaagctgaag aagttaaaga agatcctaaa gaagaactac accaagaaga agagtctgat  83460
gaatccgtag aagctactgc aactgaagaa gaaaataaag acgaagaaca tcaagaagaa  83520
tctaatgaag aaaaaaccga atcatctaaa gaatctgata acgaaaaagt tgaagatgat  83580
agtgatgaag aagatttcaa atcaatgaag gttgatgaac ttaaagaaat tctagaagaa  83640
cgtggaattg aattcaaagc taatgatact aaaaaagttc tcctttcaa attaggtgta  83700 agtgaataat atttttatat tatattgata ggtctacttg ttgaaattat agcaagtaga  83760
cctatttttt tcgattatta taagttagat aagaggtgtt tatgtgtgcc aaaagtaatt  83820
atattaaata ataaatatat accagatatt ggtagtggtc caatactaga accaattgaa  83880
atcagtaatg aaaaatacca ttatctaata gataatggtt ttaatatata tcagatagac  83940
gataatgaag atattatgat tgatccatcc ataactacca tattgaaagg taaagttaag  84000
tcagtatatg gaatgtttca tgcagatcag aaaaaacttg attcactatt aatgtttaat  84060
agaacaagca tatcttcatt aaaaaatgtt aatactaaga gtattacaga aaataataat  84120
ataatatatt ggaaatcaat agataccgat attgcatatg taaattctga cggttatatt  84180
gctgcaaaag aaaatggttc cacaatagtt actggttttg attcaaataa tacgcttaaa  84240
gcaataatgt tcataacggt aatacctaaa cttccaatat tacccaatga tattaatgtt  84300
aatttagaaa gctatatgga acttaataga tatgcagaat ttcaatactt agttgaatta  84360
cttcctagcg aagtagataa taataaagta agtattacat caaataatat acaaattgca  84420
actattgatg aaaagaataa aagaattatt gctgaagaac ctggatatgc tgttattaat  84480
gttaagagtg cagaaaaccc tgaagtatct catagtacgt tgctaaaagt ttttcctaat  84540
gatgatagga ataatccttc taatataaat gtaaatattc cggacgagat tacaattaag  84600
gttggagagg aaattccctt tgaagtaaaa attactcctg agtcggctaa taatctagga  84660
tatatgtctt tctcatcaaa cgttggaatt gtatctttat tagataataa ccatattctt  84720
ggtaatagta ttggcgtagc aaccataact attgtatcga ataaaatatc atcattatat  84780
```

-continued

```
aaagaaatac gagttaatgt tgaagcacca gaccctaatg atattattgt aaatttaact    84840
gaagtatcta ttgagaaagg tcagactaga gggtttaatg taacagttct tccaatatca    84900
gctaatgaca gaacttacag taatagttct ttaaatgaaa atattgcgac tgtaactcag    84960
aataatatta ttaccggagt taatattggg gacacaaaag taagaataac atctaataaa    85020
aagcctgaat tatttaggga tattatcgtg catgttactc cgccaagccc taaagatatt    85080
atgactgatc ttccagacga gattacaatt actgataccg aaactagaaa ttttacagtt    85140
caaattcttc ctgaagatac atttaacaac aaatatgata tggaagtaac aattccggat    85200
attattgatc ttgataaaga aaatttatca tttaaaggta aaaagatagg tgtaactaat    85260
ttaagaattt tttcacagta taaccatgat attttttaaaa atgttaaaat taatgtagta    85320
ccaagtccat tacctgatcc gacatctttt aaagttattc gtagagatac tggggaagaa    85380
ttaaaaaatg gagatactgt acctagtaat aaagatatac tttttgatgt tatagtttta    85440
ccagaaaatg ccaatgataa aagttatata gtatcatctt cagacgtaac gattgcaaaa    85500
gttaacttaa attctataat aggagtttct ccgggtcaag ttaatattag aataacatta    85560
aacaaagttt caacaatatt taaagtattt caacttaata ttgaagaacc tgttcctaca    85620
ttaattgata ttgatgtacc aagcaatatt actgtacaaa ctatgcaaac acgtaatttc    85680
actgcaacta tatatcctga aaatactcca taccaaaatt tcttaacatc tgttgaaaat    85740
cctgatatag taactatttt agataataca aatccaaaaa tacgtacgat taaaggaata    85800
aaacaaggtg taactaaggt taaagtgtat tccgaatttg atccaacaat atttaaagaa    85860
attaacgtta cagtagttaa tcctaatcct agttcaatag aagtttctcc aagaagtatt    85920
tcaatgttat taaatgaaac taaagaattg gatattaatg tattgccaga atatgctaat    85980
gatagaacat acactattaa acaaacaggc ttaggtatgg tttctattaa tggaaataag    86040
attactggtg tgttaaaagg aaatgtaaga ttagatatta tatctaacaa agtaagttct    86100
cttggaacta cggtatatgt tactgttgat aatcctgacc ctgaagatat gattgtcgat    86160
atacctgacg agatcgatat caatgtagat gaaagaagaa attttggcgt aacatttgtt    86220 ccagaaaatag ttagtgatga ttctattatt ataacatcat ctaattctag tattgctata    86280
ggtagtgctg tacaaaaatt tattaatgga gtttctgttg gtactgcaac attaactatt    86340
agatctaata aagtagctac tttatttaaa gaagttatcg taaatgttca tgaagataga    86400
cctgacccaa caagtatcaa tgttggaact aatccgctta ctttagaatt aggtactaca    86460
actccaataa atattgcata tgaaccagaa attaatagtg gtggtaaaat aattgatgat    86520
tattccacat caaacactat tattagaatg gatcaattta aaaattcaat acaagctatt    86580
cgactaggat ctactagtat taaatatact tctgaaagat ttccaaatat tacaaatacg    86640
ctaaatatta cagttattcc tcctagacca aaaagtatta gtgataactt ttcatataat    86700
aattctttaa atgttaatga agcaacaaat aaatcgttaa ttgttagctt tttaccaagc    86760
acggcggtaa acattggata caatgtagtt attgatgatc caactgtttt attatttaat    86820
acaaactcta agaaatttga agcattaaaa gaaggagaga ctatcgttaa ggtggtatct    86880
actgataatt cttctctatt tgtagaacat aaatttaaag ttaataaaaa tattattatc    86940
gatgacggtg gtaacggtaa agatgatgat ggtaatgaag ttatagttcc aaaatcaata    87000
acgtcagata tagtcactga aatgatagtc gataagaact atcgggtaaa cgtaacagtt    87060
ttaccagata atgctattga taaaggtttt gaagttataa ctagcgataa taatgcgttt    87120
aatatagttc aaaaacagtgg atcatatttt actattaaat cattggtttc tggaatgtat    87180
```

-continued

```
aatattacgt tgcgatctac attaaatcct aatataagcg tatcttatga tatcgtgtca   87240
ggcactgaag atgaattaca tccaatctta ccagaaacaa taaatattat aaatgctact   87300
gatgaaatga ctgtagatga aggtacatct atgaatttag atatacaagt tctaccagaa   87360
aattcaacta ataaaaatgt aactggttac agtagtaatg aagaattagc aactatacct   87420
aataataaaa ctataagttt tattaaagaa ggttcagtag acattacaat tacatcaaat   87480
aaagtaccta cattaagtaa aacaattcac tttattatta aaaaacccga ccctaagaga   87540
attgaaatta atgcacccaa cgcagtaact ttaaatatcg gtgagtctaa agaatatctg   87600
ataagtgtaa ttcctgaaaa tagtattgat aaagaatata tttcagaaac actagattct   87660
agtattgtta ctactaatgg aaaaaatatt attaaagcgg ttaaagaagg aaacactaca   87720
gttgtgttta ggtctaaaac ttttccagat atatttacac gacttaatgt tattgttctt   87780
cctcctgaac cgaatgaaat aattgtatct ccatccaatg aaacaattaa tatgattaag   87840
cttgatgaat tagtatttga tgtaacgatt aatccctcaa acgcaatcga tttaacatat   87900
aagattgagt caagtgatac taatattgta aaaattaaaa atcaagatac agtggttgca   87960
gtaaatcccg gagaagcaaa cgtgactata tcgtctagac ggaatgctaa tctaaaagtt   88020
attaaaaaga ttattgtaac tgcgcctgac ccagaatcta tagatgttat tggttttgga   88080
ccagacgaaa caatgattac aaattcaaca actaagtccg ttaattttat agtcaatccg   88140
gctaatgcta aagtatctaa cttttacagta gtatcttcta gtgattcggt acaaattaat   88200
attccggatc aaacaaaata tggatttact gtaaaacctg ttaaagaggg taatgcaatt   88260
atcactatcc aattatcatc attcccagat attatttaca atattaatgt aagggtgaat   88320
aaccctgatc ctgaaagcat aactgcaggg ataactaatc ctccaaatat gccttctgga   88380
aatattccag gaaaaggaat tgctatagga gagaaggttg tattaaatgc taagatacta   88440
cctgaatatg ctaatgatat aacttactca attagtagta gcgataatga tgtctttgag   88500
gttcgagatg atggaattta tgcattaaaa gccggaacat ctaaagttag ggtattctct   88560
aataaagttc caacaatatt taaagaattt gatttagaat gtctaggtaa taatgttagt   88620
gatattgaac tggatattca gtcaccattc aatatggtcg ttggtaatac gaaacaaata   88680
agtataaata ttcttcctac tgatgctatt gataagaggt atcagcttaa aacagatgac   88740
gctaatattg tatcggtatt agataataat acaatacgag ctatatctcc tggggtaaat   88800
ggtgaaggat ttacgaatat acgaataata tctttacgta ataattctgt ggttaaagta   88860
atacgagtta atgtagaaaa cttaacgcct caaagtattg atcttgttcc atctggaccc   88920
atagaaatat attcattaac atcaactaca tttaatgcat atgtaagacc agacacggta   88980
attgataggg atacggtagt tagtagttca gacatttcaa tagctacggt tcaacaatca   89040
tatataactg aaggtggcat aaaaattact agagttaccg taaatgcact taaatctgga   89100
aatgttaata ttcgtgtatc atctaataat tatagaaata tttttaagat gattaatata   89160
aatattattg acccagatcc ggaatcaatt actgtaactc cattaacaat aaatatggct   89220
caagatacat ctactaattt taatgtaaat attcttccag agaatgctaa tgatagaaca   89280
tttaatactg agattgcaga tcctacaatt gtttctgtta atggaaatac aattactggt   89340
cttaaaacag gaacgactac agttaaagta tcttcaaata aaataccatc attaaataag   89400
acaatcacag tcaatgtgag tcttcctaat gtaaataaaa ttgagattac tactgcatta   89460
gttgcgggaa cagttaatac tgtatatgag ggcgagtctt atccatttct tattaagtta   89520
```

-continued

```
ttgccagaag ttgctgcaga taaatcattt acgataaaat attctgctaa tgctgatatg  89580
tctggtactg ctgattactc atttaatttt gggtatcgta atgattcatt aaatccatca  89640
ctatatatat cagctacaag ttcatctaga tatgttccac cttttgttag atatattcaa  89700
gtggtttcag ctaatggaat tacctcggat atatatggtc taagtgttgt acttaaaccg  89760
atatataaaa tggatagtac atttacattt tataatgatc agtacgcttc tgctaaaact  89820
actatatctt ttgatagtac taatcctaat tctgaaaatt atgtaattaa tgcctatgcc  89880
ggaacaacag ctagagaccc taatattaat actgttaatt tatatcctct tgaagcaaaa  89940
gatacaaatt taacagttac tataagtgat cctacaaaag catcatataa tagtacaact  90000
aagactttta ccgctcttca atatgatact gaaactactg caaagattgc atccacaact  90060
agccctgatg tatttgtaat tgttaagatt aaatgtatga gatctagaat aacgtctgta  90120
caagttacag gtcagaatgg attaagatat agtactggcg atgtctttgg aatagtagta  90180
acaactggtc cagaaggtgc tattgataca aatgattata cattatcttc aagtaatgat  90240
actattatat caataaataa tgaaactaga actggagttg ctttaaaggc aggttcatca  90300
actattaccg cattatttaa taaagccggc gtatcaaata gtgctagatt tactatatct  90360
gacgtacttc ccacttcagt aggtattact gaccctccag gaggttctga gctaattatt  90420
ggaagatcct atccgataac tccaagtgta ttgccgacta atacaactaa taaagcggta  90480
acctattctg gaaataattc aagttattta acattgtcta aaataaataa tattgattat  90540
attaatgtgg tgggtaaaat tgcaacaaat acacctataa ctattcgatc agttgctagt  90600
acgggaattt acagtacagt tcaatataag actgcgtatg aatacccaac aagcattgat  90660
atatccaaaa ttaatgactc atataattta actgaaacaa ttgacttatc tactttgata  90720
aatataattc catcaaatac cgataatgat aataattata caataacaac tcaagatacc  90780
gataaaataa atattgatgg taagaaatta acatttatta aagatggtag tgcaactatt  90840
acagtaactc ataatagaaa taatatttcc gttaataaat tgattaatat tgtatataat  90900
gattcaatta aaccgaatat tgtatttact acttcaaata ttatcataaa taataatgaa  90960
tttgatatta aaaataatat tactaaagat ttaacactag atgaatacct cattactggt  91020
gatcttaatg gttggagata taatggcaat aagaagtttt cagatagtgg agattttcaa  91080
attaaattta attatcctat taatatgctt gaatttgaaa gtattaatga tcaattttca  91140
agtgaattta tgtataattt aaataatccg gattctaaag ttgatccacc ccaatatgtt  91200
gaccttgata ggggtagtga tttgattaat gatcgattat ttagtatatt agatacgtat  91260
accatttctt catattataa taaacgaaga agtactagtg gtaatgaaag tcaatcatat  91320
attgtaagcg cttcaccagt aataaataat atatctcctg caggagaata tttttataaa  91380
gtctatgtaa agaatgatcc taataattat attattatta gaattaatat cggtattcat  91440
ggatcaaaac aatccagtaa tttgatatat aatggatatc ctactctcat tagtccagta  91500
tcaatatcta ctgatgataa tataaactat gaacttaaag tacagctgta tttaagatct  91560
aagtggttga gtggggacaa atcacctta ttatttaata atgagttaat tactcatcga  91620
ttaatgcttg attcttcata taataataaa ataaatatta atggtattga atataataac  91680
attagtgatt ttattgaaat tgataataga attattaatc gaataagtag actaggtgta  91740
aatcgtgtaa atactattac cgatactgtc gcatctattg atagtgtggt cgcagcatat  91800
ccggacaggg taagttattt tattaaaaga aatcctacta aaaatgaaga atttagtatg  91860
gatataagat tagtaagtat tgaggattcg aatatcaaaa ttccagtaac ttatacattc  91920
```

-continued

```
actacaatta ataaataatt ctttcaaaga agcatatgat aagattcttg aaaagaagat   91980
taaaaaaaaa aaaaaaaata aatctcccat aacctattaa tttaggttat gggagatttt   92040
atgattattt attaaacaga tcatcaatat tattagtatc gatatcttct tgagtttctt   92100
cctcatcatc ttcatctaac ggtacaaaat tgataactgg tttatatcct aatgcctttg   92160
caatatctga tagactggaa taagatgtcg cacctttttt ccgtagtctg taaaagatat   92220
tagaagctct tccttcatta ttaggattat caagatcaaa cttttcaaag aattcttcaa   92280
atgttttacc tttttcaccc tgctcattaa tgaattctgc agtaattaat gctaattctg   92340
tttgattttc aatagaatcc acatcaatat gcaatggacc agttaatttc tttcgtttag   92400
atttctcaga aggatcttta gaagccttga tcatactatc tttcttatct aatttatcca   92460
tatttacatt atttagtttt gaaaatagat catcggacac gagaatttca cctcatttat   92520
tattcatatt agaaatccat atcatcatta gaaatttctt cagaagcacc aatctcagtt   92580
gattttgcaa ttaatgattt aagatctttt gatccaccac tagcttggat aatttctgta   92640
tccacatctt ctgtttgttt atctgcaact tttttctcgg atgatttaaa gttactacca   92700
ctattattac tgttattaaa tgtagaactt acatttttag gttcagtggt tgtatcattt   92760
tgtgatagat tgttatcata aggatgttga gttgcgtttg gattctttct agttactcga   92820
ttactattga atccaccact tgtgtttcct gaacgattga atggagttgt tgatgtaggt   92880
ctattaaatc caccagtgtt tggacgttga ctaaatgaac cactattatt agattgacct   92940
tgagaataat ttcctccgcc caaaatatta ataacgtgat ctaatttatt ttctacagta   93000
tataatttcg cttgaatttt ctggaactct tgtagaatat aaagatcaat attattaata   93060
caatcaatca tattgaataa ttgtagtgta gttagttcta ctgaatattc atcgccattt   93120
acgcataaaa taaatcctgg ataagtagta tcatcattac gatgaatgat tgaaggatag   93180
attaataatt ttttaccttg accaccaaac tctggagaga accattgtgg taattctgga   93240
agatcccata cacgattacc tgaattatta ccttcaataa tttcattagc aacttggttc   93300
atatatgatt ttaatgtttc atgatgagcc tgactaacta caacattctc acgaacgctt   93360
tgattagttt caggattaaa tcgactataa tcaaaacgta aaaacaccgt tgcgctgttt   93420
tgaatactag ttaacgtttg aacatcggaa tatcgatctg aagtgtattc tcttgcatat   93480
tcagcatccc tacgtttatc attagttgat gttttattac ctagtaataa agaacttct   93540 agtttaaaat tgaaagcact aaatagcgtt agaccatgag attctactgg attaaaattt   93600
gacaaaatat gattcctcct aataatttta tatattacaa taatataata tatgattata   93660
atttatttta aatgattatt catttgtatc ttgatttaat gataatgcag taagtctgga   93720
aagcttacta acaaactgac ttcgtataat tgatgagtac aatgcttctt caggaacatt   93780
aaacatttca ccaatcttac tgatactgtc acctgaagta taatctaaga attgatatac   93840
actaaaaata ttgataggtt caggaatgat atattctgga attactggaa ttttattttt   93900
aaataagaaa gctttatcta agaaatgaat ccaatctatt ggattatcta cccaaaaaag   93960
tattttattt tttcctgaat tagaaagctc taataacaat gattcaatat tattgtatat   94020
tgttgcatct tcatctttca taattctaat attttttgtta gcatcataag tataaatctt   94080
ttcaacatta ttcgctagtt gattattata tactttcata ctatcttctt gggatatagc   94140
tgtagcaata tcgtaatttg taaattcata atagtaatta gatattacac cttctgcttc   94200
ttctacaccc aaacacatat tcatgatgtt agatgacgta ctagacccat ctaacataca   94260
```

-continued

```
tgataagtaa atatttacaa tcttagttct ttccatattt tacccatcct tatttaattc   94320
tttttgtttt ttcatttctt tattatagaa tatatcatga gttaataaaa atttgaaatt   94380
aagttcagaa ttaatactat tgataatatc tttaatactt ttattaataa ctgcagggtt   94440
tgttaaatct tcaagaattt tcttttccct aatatcatta ttaatagtta aagacatatc   94500
aagtagatcg tttttaattt tatgatattt ttcaaattta agtttacgat gtctatagaa   94560
aaaaccatca ctattatttt cactatacat ctttaagaat gatgcatatt tattaaataa   94620
gtcttccctt tgaattttaa tttcaccttt ttggagttct aaaatttcaa tagacctttt   94680
aatatggtta ttaattttc taagttgagt taattcaata tcaataatct ctgtaacaag    94740
atcaaaattt acaattccga taatattacc gtcaatatta atattaaatc taagaatatt   94800
aaagtcttct gaaattttag caccaattaa tgaaaagata tcttcatcat actgtccagt   94860
attaacattc tttgttaaag aatatataaa atctttctta atacgattca caatcgtatt    94920
aaagatattt ttactagcga ttaattcttc aatgaatttt gaaggatttg tttctgagag   94980
ggaataacga tcgttagatg catacaaaat tttcaccact ttccgctata taatttccaa   95040
tttagattca ataatttctt tacatctttt acgataaatt ttctttcttt tagttaattg    95100
acgtttacat tcatcaaaac ctgtatcaat gacatcaaag tatagacatt ctttattttt   95160
taccttacgt aaacgaccca taatttgtat caacccttct tcagaaccag aaggtacagt   95220
atttactaat actcgtaaag attgttcatc taaacctttta ccgaaagatt tatccgtagt   95280
aacaataata tcttttttcaa acgcagtaga ttttttcatct ttaggaacgt ctgaataaaa   95340
tctacttacc gatatatccc acttattatt ttcaatttct actaagaaat cttggtagaa   95400
agcattaacc ataatcttat ttttaaataa gattgcagtc tttcttttat tcttacctttt   95460 atcaaagata atatcgaaga taatctgata aatatagtta taatattcat catgcttttt   95520
atcaataata tactgagaat agcttggtac attaaatcca taacctttag atttctttct   95580
aatttcaact aaatcttcat tactaggttt agtatctatt ttacaaatga ttgttctaat   95640
gtatctatca ctatcactaa ctacagtaga gaattttgga acgttcatat acatattctg    95700
ataaacttta ttttcaatag gattagatct actaggagtc gcagttaaat ataatgatgg    95760
acagtcataa gtagaatcaa tattaaatac agaaatatat tcaacgtgag cttcatcata   95820
aactttaatt gatattccaa ttcgattaaa taactttaca accctatcag gatcagactg    95880
aattaattgg ttaacagtct tgtgaataga taaaaagaat ttatacttag atatatcacg    95940
tttagtcatc ttttctaatt tttcaataga ttctattcct gaaataatat aaatattatc   96000
taatgatacg tctgtatatt cactaattct atccttccac tgttctaata atgatttcat   96060
atcaataaag ataattggta ctgctttgat tttattaata taattaatag cacaaaaagt    96120
tttcccttca ccagtcttta acgataaaaa cttttgataa taattattat catcattaag    96180
aaaattcatt gcatcttctt gaattttatt tttaggttta tatttcattt taaaattatt   96240
tttcctaaga atatttttat ttcttttatc attaatatga atattaacat tttgtcttct   96300
tcttaagtta ctagataaag aatcaatatc aataccagaa ggaaatattg ctttatcatc   96360
atctatcttg tatgctttaa aatcatactt aaaccattta gcattccata cagaaagact   96420
attttctaca gcactagcca ttttttcgct atagttatta ataactatcc ttgttggata   96480 aaatatcaaga tccattcata tatcacacct ttattagttt aaaatcaata gaatgtatta   96540
tataactaaa taatacattc tattgatata ttttaattta atattctta aagaataagt    96600 gaggaaaaga ttcaaagaaa ttaatatggt taagttcttc aggactttca gcatctgtag   96660
```

-continued

```
cattaataat gtaaccaaaa atagggactt ttgaagtgat ataatattta ccttctttaa   96720
atggaccaac tgtcttttga catttatcca ttaaatataa ttcaccatct aactggtatc   96780
ctactgaaag tttatcacct agttcataca ttgataaaaa atcggtatta ttaataaatt   96840
ctgtaaattc ttttggatta ttggtatatc gtctgattct aaatttattt tcatctggaa   96900
tattatctaa actaataata aatctatttt tttctacttc ttcggaatca attaaattat   96960
ctttgtccat attcatatat ctatatatct cccttataaa taaaattatc taaataccct   97020
atcgaattca gattcaacat ctttaccaaa aagatcatta taactatctg tcttaaattg   97080
tttttcaata ttttgatata atagtgacat tgcaggactt ttcttaccga taagtattgc   97140
atcacttaca ttatatatat tatattttgg taattcttca gcattagcaa attcggttct   97200
atcattattt tctagactta ccatttccct tacaatagtt tctacatgta cagaatcaat   97260
cattgttcct gaatccacta ataagtttac aatttcttgt acaatgatag aataatcatt   97320
atttgataca tttctaataa aatgattttt ttctaagata tctttaatct ttagaagtgg   97380
gtctgcaata ccatcatttt ccacaataat attaaacata tattcattat caggcatata   97440
ttttaatgag aatacataat tatttgtgga attatcataa tactgttcaa tatcatccgc   97500
aatctcatta ggaataatta agcttaatgg agtgtcaatt ctaatctgag tgtctttcct   97560
acctttaaca tagattgttc ttgtttgata tttattcttt tcagagtctt catttttccat   97620 aagatcatct ttatgaatat agattgtttc attatcagaa ataggactaa ccttatcttc   97680
aaataattga aacttagata agaaatcttt agaccagtta gcatccttaa taataacttc   97740
taataaatgc tttgttgata agattttttg tgttaatgga ttagtaagtt ctaaagttgc   97800
agcagttcct actttaatgt gtttattaat cttttctaat cttccataac atctaggaca   97860
tatacctttt gaatgtgcgc atgttattgg actaaatatc ttaatatctt taccaataag   97920
atgtgtatca ttcttagtta ttacggtagt tttattagta tcttcatcat acatccaacg   97980
atgattatat agtgataaca tgtctttatc tctaatatga atattaatat aatgagaagt   98040
gttacaacta tctacattat tttcatcttt gtgaagttct ttatcttgtg gatcaatatc   98100
taatgtgtat attactgaat cttcagttaa tatagatatc tttcggttag tatatccaga   98160
ctgttttact tgatcctttg cagtgataat tgcttttcta ccacctactg catcaataaa   98220
gaattctgtt acatttttaa ttccccttac aaaagaacta ttaattggag tagtaataac   98280
tttaccatat agatcgggct tataaccaat taatccaaaa ttttgattaa attgtttat   98340 attaattcct gcacccgaca tgattaaatc tctagtaata ttatctttat cttctttaat   98400
aatttgaatc attttatctt tgttttctgc aatttttttga ttatttgttc caatatcatc   98460
ttttaattct ggatcaagtt cgaattctaa agttttctta aattcttcat ttctatccat   98520
aatatcgatt atatcaaata aactataagt cactccgctc tgatataata cgttttgagt   98580
actaaatatt gatagttcat ctactgacca cgcaatatct tttttaatca attttatctt   98640
ttcatcacta atatcataat tataaatttt gttaataatc ttatcataaa atacattatg   98700
aagattaaca ttataattac ccttttcatt acaatctttt aagatataatg taaactcttc   98760 ggtaaattct tcttccaaac tcttaaaagg ttttgccaaa ataaacgttg ttaataaatt   98820
tgacctagat attttttgatg ttccaaattg taaaatttct ctacgagaat ccacatcttc   98880
tacaattttc tttcctaatt catcaatctt cgaataatac ttagtatcat catgaagaat   98940
tgaattaaat aaagatagat ctaatactgt actcaatatc ctccacacaa tcctttctgt   99000
```

-continued

```
aatatattta accacaaata tataatatat aattgtaaga taatttaata atcacaaacc  99060
tatattatga ttctaacaga atatttcatt gttgtaaatt aaaattaact ttttatctta  99120
tgaaacttaa tgtggatcat agaaaattta aactatcaat aaaaatatat attatatatt  99180
tgcgaataaa atcccctatc atataattat aacacaaatt tatatgatag gggaaataaa  99240
ttatttatct tcgactttt tagattctga tttagcttta cgttttctc cgaattcacg  99300 aagtttttgt tttcctttgc ttgcatactt aagttgaatt gctcggcgag tttctcggcg  99360
caacttagaa tatttaacgt atttacggta aagtggatca tttgcttctt tagcggaaat  99420
taatactgct tgagtatata aacgtttctt agcggtacgt ttatctaaac gaacaatatt  99480
ggcttcttct agatagctta aagattcttc caaagtttgc attgaacttt cttcattatt  99540
ataattaaaa aatgtatctt tcatattgat taagcatccc tttctctaaa taaaatggtt  99600
taataattat atgtttatca attcaatgca gaaaaaataa taatttattt ttattcgtta  99660
ataatgtttt atattatata aaatatagaa aggaaagata atttatgtat agtttttagt  99720
agtaatattc tctttaatta tataaaaaat aaaattggtg gtgtattgtt tatatgaaga  99780
ttgaagaaaa agaacgtgaa atgaaacata ttggttacat gaagatatta cttaatgttg  99840
ctaaagaaga atttccagat atggaagaag atgtattaaa agaaaagatt aaaaatattg  99900
taaaggataa catgaaaaat ccaaaagcaa tgattgatga tcgtgaaaca acattattag  99960
gattagacaa atttatcgta actgagaaac ctatcattac tggttttgga tcaatgtatt 100020
taactcatga taagtttgat aatctattag caaaattggt tgaatatatt atcaaaactc 100080
gtaaagttta taaaaataaa atgttcgaac acgttaatga tgatgatcaa acactgagaa 100140
atatgtatga tatgtatcaa cgtaccatga agatcctagc gaactcattt tacggatcat 100200
tgatccaaag tagctttatt ttgtataatc cgatatctgg tccgtcagtt acttattctg 100260
gtgttgatat tatcactact gcactaaata attttgagaa attcttagca aataatatct 100320
attttagaaa tgtagatgat attattgtat atatgaataa tattaaatct gaaaattata 100380
gtatggataa agttaaattt aaacaatccc gtagtaaaga tcagattatt gattatttat 100440
ttgataagac agataattat atggatgaag atagaatatt attgatgaca atgatgaata 100500
attatacgga tgaagattta cttaagcttt attataaaaa taacttcatt gatttattaa 100560
aagaatctga tattgcagat aattattta aagaaattct aagttgctat gaatttactg 100620
atccaaacga tcctcctgct aaagttatct ccactaatga aatttgtact attaaaggaa 100680
aagataacgg taaaattaaa gttaaattat ctaatggtga aatttctcta gaagatccta 100740
gtaatatttt agattatagg gaaaaattag ataatttatg gaatattatt agaaatattg 100800
tattctacaa ttatcaagat ttctatcgta tggaaaattc tgaagaaaga ttaagaaaaa 100860
cagtgctcgt ggttaatgta tagccacact tatatagtaa tatataggtt aaaaattcta 100920
ttaattgctg gaaaatccta aagcttattt aactacaacg gaatcagtaa tgataaacgt 100980
gaatgttgtc gaaagactga aaaaataaat aagattaata catggtgaaa taaaagtact 101040
ataatatata gtatcctaaa tattaattat aatggatgat cagcagcagt atttctttaa 101100
gattataaat gaaagaaaaa agaaatgttg ttcaacgact atcaaaagat tattatataa 101160
ataataattt agtagagtag agccaagctt ttgggttagt atttaagaga tattatctta 101220
atgtaaaact attaaatcga aaaatagaat tatcctttag taaggataaa gatatagtct 101280
gttctttaag gaaatcttaa agaagttcat aagagaactg cataagaatt agcgcactta 101340
tgtgaacacg aaagtgatac cgactcaaac ttcttgtatc tcaatcactt tgtcgattta 101400
```

-continued

```
ttctcagaaa tttatccaga tattacgatg aaagaaaatg ataaatctat tgtatctgcc 101460
attaatacta ttatgtatat tgttactgaa tgtattaatg aaacgtatta caagtatgga 101520
atggaactcg gtattccaga agataaacgt ggactaatta atatgaagaa tgaatttcta 101580
tataaacgtt taatgctaac agacgctcaa aagaattatg ctggcgtaat tttaatgcaa 101640
gaaggaaata ttcttcagac tcctaagatt gatattaaag gattagcaat taagaagaca 101700
aatacgaata aacatgtacg tgaagaattt tcaggaattc ttaaagatgt cattcttgaa 101760
tcagataaga ttgatggttc tgaatttatt actagatata agaatctaga aaaagaaatt 101820
cgaagatctt taatgaatag tgaaatcaca tttactctcc ctagaactgc aaatattaaa 101880
gaaaactacg tagcaccata tacgcaagca ccatacaaag gtgtattagt atggaacaca 101940
ttatatcctg ataaagaaat taacttacca aacaaagtta atcttatcaa gctaaatatt 102000
gaaacttttg atgatattga aagtaaaact aatgatcaag atctaattga acgatttaag 102060
aaagtttatg aagatgagga attgacaaaa aaaggaatta cttatattgc tattgaagca 102120
gaacaaaaac atattcctga agaaatcatt ccatttattg acatacctga aatggttaag 102180
actcatgtat catcaggatc caaactaatg acgtcattag gattcaatcc attagtaatt 102240
aatggatcat tattcccaac aaatattatt aactttttaat gaaagtagga aatctattgg 102300
aaaatttaaa tattgatatg aatgatccaa ccaagaaaaa acatattgtg gtagattgtg 102360
atgaagtatt atgcaatatt tcaccaaaat ggacatactt aatacatcaa gaaaaagact 102420
attttggtaa atatatgaat cttattgata attttgatat tgatctgcat tataatatgg 102480
ttttatctag aaataagttt tatctaaatc agtggttaat taaagatgaa tcatatacga 102540
attatagtga agacgaaatg gatgaagtat taagacgtat gatgatgctt tatgaaactg 102600
aagattacta tgataactta aaaccaaatc ctattgtaga gtcattagca ttatcgattc 102660
gtcaacctat tttagataga atatctattg taacaagaac aaacgctaaa aatcttaagt 102720
ctaaagaaag atttcttaag aattgttttc aaggtgttat gaataaagtt gatatatact 102780
ttgtagaaaa tgatgaaaat aagtctgata ttattaaaga cttaggtgac ggtattgcag 102840
ctatatatga agatgaagtt aaaaatattg tagacatttt agataactgt aataatcttg 102900
ataaaagctt aatatatgta cctagttatg gatataataa cgctaacctt gatttatata 102960
ctaaagcaga agaaaaagga actcaattaa gatattattc atattaaagg atgtggactt 103020
attatgtata atggtaatta tgatataagt ctatatgaat atttaaaaag taaacttaaa 103080
gtatgctata tcacaagcaa aaaggatgaa actgttatac gttgtccttt ttgcggtgat 103140
tctgcaaaaa atcagtattc tgcacactta tatataaata ataaaccacc ttataaatat 103200
tattgtcaaa aatgtaattc aaatggaata tttaatgata agatacttaa taatctaaat 103260 attttttgatg caaaactaaa tcaacaactt aaagtatcat acgaaaaatt cattaaagat 103320
gcaggaataa aatatggaaa atcattttca tcactattta atatggatga aacggacatt 103380
cttccaaata actttggaat gttagaatta agaaaaataa aatactatga agatagattg 103440
ggaataaaac tcaatgatga attattaatt aagtatagaa ttattcttaa tcttagtgat 103500
tatatggaaa ataataaaat tccaataaaa caagacaaat ggtatattga aaaattaaaa 103560
atgattaatg ataattacat tatattctta tctaatgaca agaatgttat taactgcaga 103620
aatataacaa atgttactga aaaaaagaaa cgtcatatta aaatgagact atttgaagat 103680
tttactgatg aaagtagaag tttttactca ataaagaata atatatctct tgataaatct 103740
```

-continued

```
ttatacaata ttcatttaac agagggtata tctgatatta tatccgtgca tcataatata 103800
tttaaagatc aggaaaataa taatgatatt tttatatcta gtaatggtaa gggttataat 103860
tcggtattac aatatttatt atcaattggg attacaaacg caaatattaa tatatatggt 103920
gattcagatg ttaatcgtaa ttattataat agattaaagt ataatttact agctaaatat 103980
aatggggtta atctctattt taatattgct aaggatcctt atggtaatgg atttaaagac 104040
tttggcgtaa gatctgaaaa tgtagaatta agtaaaagca ttaagatttc tttctaactt 104100
aatggatcat agaaattttc taaaaaaaaa aaagaccta atagatatta tatctattag 104160
ggttatattt atttaattat tcttttttta attgataagg atacacatta atatatttac 104220
tatctaataa atcatacaca ttaattaacc gaccatacat attaatcttt gaaattacca 104280
catcgtgaat ttttcctaaa gaatcaataa tataaaaatc ttttcctaca ataatatttc 104340
tattataaat ttctttcatg aattcatcta atgaattttg gtctaattca gtattataca 104400
tattaatcat ttatatttcc ttctttcttt tttttttta atatatttc catttcatga 104460 taaggtatat tcattataat tgatacatca ttagtactat aattatcatc tagatattta 104520
tctattaatc ttttctttc agagatgcat ttatttttag cagtataatg atcatactgt 104580
cggttagcac ttttaagttc tttaaagaat aaactattat tgttaatata tttttaata 104640 ttagatttat ctactgataa ttcattagct aatgaataaa cactgctgat attcttctta 104700
ttgataatat caagaatata tgataaacga gaaattcttt taactatcaa attgcaatct 104760
ttaacttcca tattaaaaat aatatctaca tattttttcc atgatggagg attatcgata 104820
gatgtagttt tattatttaa tagtgaatta agatatatga caatatcttt atttaatttg 104880
gtattattta tgatatcatc atattttcct tcatcataat tacgttctat atattttgta 104940
aggtatttta tttttttcatc atcaagacta aaatatgtca tatatttctt aaagaaagta 105000 tttaactttta atttagtata tcttcttcga atattaaaac cataaacaaa cacattagtt 105060 actgtgggtat ctatatcttc cataacagta ttaactttaa tattattatt aacagtatta 105120
actttaatat tattattctt aataaaatta ttcatgttct ttatttcatc gatagtatta 105180 atgataaatat ttctagacaa taattcttct ttttttaaaat tattaataac ttctgtatta 105240
tttaaagata aaatgaaggc attttttcatc ttttttaatat tatttctaat aactttatta 105300
attatattta tatcaacact ataagttttt gattttatgt tattaaaatat atctaggtta 105360 gtaataatat cttttttagt agataatttt agataagtgt tgattataaa ttcatctata 105420
tctttaggat atataatata caatgcatca accataacct tattatcata gataagttta 105480 atttttaattg ataattcttt ttctagaata ttaatacaat tttcactaat tgatgtctta 105540
gtattaattt ttttaccata atggtagtca tttcgtatat cacatattat tgaatgttct 105600
agattagtaa ttatataaat tttattatat aattcttttat tattctttat aatattatta 105660
acactataaa tataaccaac gccaatatca taaaatatat ccatatttgt aacaaaagaa 105720
aatttctttt ttaactgatt atatgacttg ataatattct tttcaatact atcagtactt 105780
ccatcattaa atatcaattt attatccttt agatattctt taaatgaatc taatatagta 105840
ttatagttat ctagattctt attgagtact aaagatataa tatcaatgtc attcattttt 105900
cgatagttct taatacttttt gacaatactt ttctttgttg gaattttat attgttcttt 105960 atatttaatt catttattgt attaaatggt atattacagt ataataatat atcatctaaa 106020
cttaaatttt caataaaaat taattgaata aattcattat agttgatgta attatttta 106080 actttatttt cttcagtaat tcgtattcct tttaacatgg aataaagctt tgactgatca 106140
```

-continued

```
taactaaatc ctgatagttc agagatttct tctaaggtta ctttattagg attaagttta 106200
ttaatattat ttaggataat attatcaaca atcttagctt ctgagatatt tttgttcttc 106260
ttattatttt tagttttatt atcataacta attttcattt ttttatcaaa tagaccggat 106320
tcatcaatat atagatttac tacacctact ggaactttat atttcataca tattgacttt 106380
aaatcaaaat tatcattaag atatgtacta tctatttcat gttttaattc ctcgctaatt 106440
cttaacatct agttattcca ccttttaaat attattaaag aaaaggataa tgaaaataaa 106500
tttcattatc catataatta caatgcaata atcaagtttg ttttagctct agtaattcca 106560
gtgtataatt gttgatgata tatgctctta ttatatattt catcaaacag taatacatta 106620
tcatattccg atccctgtga tttatatacg gttgttgcat aaccaaactt aaacttatta 106680
atgataacat gtgattcttc aaaaatattt cttcgaagaa ttaatgactt atacatttca 106740
ttttcataaa tttgatcatc attagttatt ccatccgtaa aatataatgc atctacatgc 106800
aatctattat agattccagt atctgatgaa aatgtaggtt taaagtctaa ttcaaaagta 106860
tccaaccttt tcttatattc atagatattt tccacataac cgataatacc atttgttaaa 106920
tactgttgtg atccattatc ttcatacatt tctaaccagt tattcttaag acatattaat 106980
ttttcaccaa catatggaaa tggtgaattc aaattaagta tattttttct aataagagag 107040
tttatcctat caacagttat attttttgaa gctagaattt gatctgcgcc agtatacata 107100
tcatagtcta catctttttt attaataatc attacatttt caccgatagg accaattctt 107160
aatctatttt tcttacgaac ttcattagct aaccatataa ttggattatc cagtgcttgc 107220
cttaatggtt catctaggaa gatatctggt cttttcatat atttattaat tccacccttta 107280 actggtggaa gctgcatcgg gtctccaatc ataatgattg ggacgttaaa tgtaattagt 107340
tcttcaatca ttgaatctgt aaccatacta ccttcgtcta caataattaa tttaatattt 107400
tttgaaatac tttctttttt aataaagtta aacttattct ttttttcatc ataaactaca 107460
ttatacatta acctatgaat tgttgaagtg ttattattcc ctttcctatt aagaacatta 107520
gtagcggttc cagtatatgc agaatatact acctgttcat cgtttaaatt gattgccgaa 107580
gttataaatt ttataattgt acttttacct gttccggcta atcctgctat tgtaaaaact 107640 ttttttaatat ctttattcca ccattcaact gctcgcataa caacctcttc ttgtttgttt 107700
gttagcgtaa taatactcat tatatacacc gctttctatc cattttattt actataatttt 107760 tttattaaca ttataaatta cttttttcatt aatataatat ataattaaaa atttatacaa 107820
ctttctaaca taacattata atagtaaata atggcggtga taaaatgtca atgagagata 107880
tgaatggaaa tcgtattatg gactcattta gcttcgataa agagtatgaa ggaatagtat 107940
tagataataa cgattttgac gataaactat ttattaaagt atatatctct gaattgttta 108000
ttaatgatat tcctgagaag gttatcgata ttaatgaaaa tattgatcat actaaaataa 108060
ttaataataa taaaataaat tttaaaaaat ctgtagtaca taataattat ttgaagtgct 108120
atccaatcat atataataat atgaatcttg atataatgaa accaaaaata ggttcaaaag 108180
ttattgtcaa atttattaat ggtaatccaa aattgccata ttatgagaat aaaggatatt 108240
atacagatat tattatacca attcctcccg aaattataga tcctcctact gatccatcca 108300
ctagtgatga ttatacttct tttggatact atagaatgat taaacttact aatccggcta 108360
tgattggtcg agatatacta aaaatccaaa agaaattaaa gactcttggg tatacattca 108420
ctattgatac actagacggt atatatgatt taagaatgtt gaattatata aaagattttc 108480
```

-continued

```
aatctaaaaa taaactaagt gtagatggac agattggtcc aattacgttt agaacaatta 108540
tgcgtaaaaa tatataattt ttaaattcga acatatattt atagtaagat agtttactat 108600
aaatatattt aattggggtg gaaattttta tggaacaagt aacttctgga ctattaattt 108660
tgacagtatt atccgtagta attcagtatt tagttgaaag aattaaagat atttttccaa 108720
caaaagttat ggataaacta gcaaactatg ttaatcctgc tttctggtct ttaattgtat 108780
ctcttcctat tgcttttggt ataaatattg atttatttgc aattatcggt tataatatgc 108840
atccaacatg gcttgcaaca ttatttactg gtttttgcatt gagtggtgga gcaactggta 108900
ttaatgaact tattaaatca ttaagtgctg ttaaaactaa taattttact caagcagatt 108960
cggtaaaaaa tactgatgaa gaagaaatta aagttgtcgc taaatctaaa aaataatata 109020
tatccctata gtgtataatt gcactatagg gaattttatt tactaaaatt ataaaataca 109080
taataaaata acattaaaat atatttacat taatatacag aaatggatga ttaaatatga 109140
aatatccgat acgtgaggat catagaaaaa gagtcaagac aaattacatt attattactc 109200
atgctaataa tcttataaaa aggggaacac atataaataa tgcgttaagg cagagaactt 109260
ttaaatacac ttggggaata tggcaagaat atttaatgac tcacgttaat aaaagatatt 109320
taccaatgca ttattttatt gaattaattg ataaagatta tgcagtattg aagggtcttt 109380
ctgaccataa accttcttac tttattaatg atttagtaga cgaaggtgta ataaaatatg 109440
tttaccgaga ttcgatatta atagtcattg gagataattt tagtataaat aatcctgata 109500
ctagaatgat tgatcattta gcaactaaag ttattcttcc attaatgaaa acgtataatt 109560
taagttggaa taaaatacaa tttttgatg agtgtttaac tgactcattt attaataata 109620
ttgataatga tgaaataaaa tataattacg aatatgaacc aatgtctatg tttgatatga 109680
gtattctaag aaatgcagta cttagatata aatcataaat ataaaataat aattataagt 109740
attgtgtggt gataattgga aatggataat aatcaaagac ataagaatag aaatttttt 109800 aatataatga taattataaa tattgtaatt attgttataa taattgtatc ttcagtatat 109860
ctatatatac atataaattc aggaaacagt tattcaaaag aaacatatgc taaagtgaat 109920
aatgtgtata tgacatatga taatgaagat aaggatatac aagtaagaat tggtaaaaag 109980
aaactaataa tatttaataa tggtaaaatt aaagagatta tatttaataa tttttgaagta 110040 tcagtatatg atgaatatac tttaatatac atttctggag ataatgatga agttagtatt 110100
tctgtagaca atgataaaga ttccatttct gatatagtca taaataatca aagtttaata 110160
gaataattat atagatatat agaagtgtgg aaagaaggtt acaatatatg ctcatattaa 110220
aaatgagaac tgacaaaaaa gtagactata aaaaattatg gtttataaaa cttcatagaa 110280
aattaaatat tgaaattcat tataatatag aggaaaatgg attctactat attgataata 110340
ataaaacatt aaaacttaaa aaagattttt caagaacaat tagtatgatt cttgatatta 110400
agaaaagatt caattcgttt aatactgaaa tggatataat tgataataat attaatatgt 110460
atcttaatga cgttataaat aactttgaaa aagaagaaat gctaagaatt atactaggaa 110520
cttcggaata taatgtgaag aatctatata atgatcttac tgaattagga attaatattg 110580
atccagactt attatatgta aatttatata aaaatacaaa acattccgaa tataatgatg 110640
aaataaagaa tacatttaaa agaatttgat aacctgaata ctaataatta aaatagtatt 110700
caggttatca attttttatcg agcaaaaaat atttttttcc ttcttgaatg ttttaaggca 110760
ccaatgcgca tttttttcaac tagttcttct ttcttatttt ttccatcagc tagatcttca 110820
ataaataatt ctatactgcc atacgttgtt tgaatatttt gaaagcgatg tctaatttga 110880
```

-continued

```
tataatgatt cttgagtatc atatagacat aattgcataa aatgttcttg aagatttact 110940
ggtatgctgt caaaatgttc actatgaact gcgtttgcat atactagaat tccgtttaat 111000
gtatattggg gagcaatttc aatttggttt ggatgaataa accggaatgt tgaaggattt 111060
atttgacctt gaatgttact catcatctga ttttcaaata aacttccaga accagaacca 111120
gctctaggag ttcctccgat aattgcacta ttactactat acatatctaa tccaattaca 111180
cgattaatat ttaatacgga agtctctgta tctaaataat aacgattctc atatcccgga 111240
acaagatctt tattaaatac tcggatttct tcaattcttg ggaaatactt actaaacgta 111300
atcaaacttt ctgatcttat tccactaaga atttcttcat gagaaagttc taattgtgta 111360
aatttatatc ctaattttcg ttctaagaat cgaataacct ctgtaggatt aatcatttag 111420
ttatcactat ccttccaata ataaaaatac aataccactt cctaaattta attaagaagt 111480
ggtatatttt aaaacatatc ttgtatatat ttgcttaaat cacgtttaat ttcttcttcg 111540
agataaatcc ggatagtttc gtttgattgt ttaatactta atgtttgatc ttcagtaaga 111600
gttactgaac cattctcgag attcatagat atacctaatg attctgctaa tgaatataca 111660
ttttcagatt ttttagtaac aaactctaat aattcagaaa cttgataagg aactacttta 111720
cctgaaagat tatatgagtt tgagcttgct gcttctaaca atccttgata atcttctgag 111780
aagtcttcat taatccggtg agtcatatat gagtttggat gggatggaat aacaacccaa 111840
tcatagcagc aaatcattaa aggtgaatga actcgttgat acttcccatc aggcttaata 111900
atattaccaa taccacgcat ggagaatgct gcctttgatc cttgattaat caaacctttc 111960
atgtctctac ctacagatgt atctgcagtt tcaactcgtc caattaatcg attcccatca 112020
aacttagctt cagttacaat atgcgaaata ttgcgttgat caatatataa ttgtctacga 112080
ttatcagtat ttaatggatg acctgcttct ccaaagaatg ttctattttt aatttttcc 112140 tgaacaattg ggttttgtat tgcttcatca attgcacgtc tatcataaat acggttatta 112200
cggttaggtg catcagcttc ttgcaactca gtctcgaata atacattatt aagtgtttta 112260
tctataattt tcggtttaga ttcagtgacc gattccatta taatataacc tttttcttca 112320
gtcataatag taatacacgt cctttcttag tatataaata aaatttataa taaaatgttt 112380
gattagataa ttatttttt aaacaactta ttataaaata ttcttttat catttttgat 112440 aaaatatgtt ttaaatttaa agaatattaa attataaat aaaatgataa ggtgggaaat 112500
ataaaatgcc aaaaacttt ttagatgtaa tccttgaaga tgcagacgca tttgaagcta 112560
gtaaatctgt tgaagtggtt gataaaaata ctactgaacc tgaagtagtc gctaaagatg 112620
aaaaagctga tgtagaagaa caaaaagaag tatgtgacga aaaagaaaaa gctattgaaa 112680
aagaaaaaga agaatatact aatgatgcag aagttgaaat tactagtgac gtttcattaa 112740
tgaataatgt tgctgataaa ttagatagtg gtatgtctat tgaagaatca ttcaattctc 112800
taatcgaggt taatctagtt aagaatgaat ttaaaaacat gggcttgact tctgaagaaa 112860
ttaatcttct tgctgaagat gcttctaaag aaagaaaagg aattatacgt ggattggcta 112920
aaaaaatcgg tatcgatgat agcggtaatg ttgatgctcg taaatatgtt aatgctcgta 112980
aaaaattagg cgtaaaacaa attactgccg cagtaacttc tacggttgct gcaagtgctg 113040
ctgctggagc tagtagctat tatattgaaa catcaaaaag taaaagcgaa actgttaaag 113100
gtggaatctt ttcaggttta actgtaggat tggtcgtagg ttattgggtt tcccttttct 113160
catttgtagt tactattttg caaagtgcta aagttaaagg tcaaatgaaa agtgatccat 113220
```

-continued

```
ctatcttaag aaatgctctt gctgaaaata aaaaagattt agctgaagtt gtatcttcta 113280
tgtctaaagt taaagaagat gctaaagcaa ccaagcaatt agaacgtatt caaaaagctt 113340
tacttcgtga aaaatccaaa ttattgaaat tgcaagaaaa attaaataca aaataagtta 113400
tatatgatct caattctgat taatttcaga attgagattt atttaaacat tattatataa 113460
gaaaatatat attggtggtg atttcaattg catcttgatg aggaaagtat tagatacgct 113520
ataaaattta cagaatcttt agaaaaaaat gattttgaat atggtcaaac aattcgtgaa 113580
gaaattcaaa atgaaaataa ttcatctcaa ataaaaaata ttatgaatat gctcaatatt 113640
aaaaatccaa atactattac tgttgaagaa tatttaaaga tacgtagaaa aattaaattt 113700
tcgggtctta ttggattctt agcaggtctc ggaggaagcg taatgtttac ttcagatatt 113760
attataaata atgatcggct tagagacgat cctcaaaata gaggagtcgc taatagaaat 113820
aatcgtagta agctaagtat gcttaagtca accttatttg ctttagtttc ggcttttggt 113880
tcatttgctt tatcagtatt atatagtaag agcgttaaga aaacttcagt agctaatcca 113940
tcaatagtta gaagtttatt agctattaat gcaaatgact taagaatggt agaaaaagca 114000
aataatagtg tagttactaa gtctgactta aaatatatac gtagaataga acgaatatta 114060
attagggaaa aaagggatct attaaaattg caagcatacg ttataaagaa aaataaatga 114120
aagaagtgaa aatttttatg gaatataatg atgtattttt agaatattta aattctgaag 114180
aagataatat tgaaaatatg gaagaattcc tatcaagcta cattggaatt aaaccaagat 114240
atcttgaaat tagacctact gtatttagtg aaacaagaat tactaatgat ggtattagtg 114300
atgaagaaga taatagcgaa gaatctgatc gtaaagatc tactgatgaa gtaaaaaaga 114360
ttagtagaga agtaatggaa aaagataaga aaaagaatct taatccacaa aataaagcaa 114420
aaattgcaac tattaaacgt gaaatggaaa aatcgattaa aatggatcca aatagtcttg 114480
gtaatgatac taaacttaaa agacttatgc gtgtaggaat tacaatgtta gtttctttcg 114540
ggattatttt tgctcctgca gttggtgtct taataaagat tattgctctt atcggagtag 114600
ctgctactgc aaaacacgtt aatcgtaaaa aattggaaaa tactattata ttactaatgg 114660
ataaaattaa atatattgaa gatgaaatgg aaaaagcatc agacaatcct aaaaagaaat 114720
atgaattaac aagagtaaaa cgagaactcc aaagaacact tatgaagtat cagtctagac 114780
ttcggaattt ccattaatat atgatttgta taagcgatgt tgcaaaggag gtactattat 114840
attgaaagat gatttcttta attatttatt tgaagcagat gatccagaag aaataagtaa 114900
tattgatcct aatgaagata atactgaaaa taataacgag gatactcctt ctaatgaaga 114960
aagtttacca aacgaaaata gtgatgaaaa tgatttagaa aaggatccag aaatagaaga 115020
acctgataat gaagaagaaa tagaacctaa tgaaaatgaa gacccgaata taaatttacg 115080
tataaaggaa atattatttg agaatttctc tggacttaaa aatgcaatta aacgattatt 115140
tactgacatt gaatcggtaa tacatatcgt aaaatcatat gattctaata atgataatca 115200
taatttagaa aatactgtgg atggaatatc tgaaaaagga tatgacattt taaataaaat 115260
tcaaacatta caaaatggtg taattcttaa tatatcaaac gataaattaa aaatcatata 115320
taatgaatta gaaaatcaag taagtgatat tattaaggaa tattcaaata aagttgatgt 115380
aaagttgaaa aacaagtatt aataatataa acaatttaat ataaaaattt taatttattt 115440
ctatgtaagt ttcgtttatt acttttttaa agtaagaatg atgaacaatt atatataaat 115500
aatttataat attattttta taatctataa ttttatataa gaaaaggaga gaaattaaat 115560
tatgcgtaat tttaaacgta ttacaaagac taatacagat tctttttagta ctcatctaag 115620
```

-continued

```
cgaaactcaa gactatttcg ctaatactaa aggaacaaat attactggac aagatatcgc 115680
tgcaattata gtgaatgaac aatattttga tgagtatgca actcgtctat tagaaggttt 115740
cgatgctgac cttagtgaag aactaggtgt tcttttagaa aacactcgta gcaacattat 115800
ggaatccttg ggtggaatta ctccatttgc ttcactttca atgcctgttt tggttaaact 115860
ttgggctcgt ttgtctatgg taaatgctat tcctactact cctgttacta ctcctgcatt 115920
tgtagtacca actatcaaac catatactat tggtccagat ggtgaaaaat actacctacc 115980
agaagctatt aatactattc ctgaacactt tgtaagtctt cgtcaactta aagaagatat 116040
cactattact ggtggtcgtc tttctgacta tgatctattt acaggtgtat caactgctga 116100
ccgtgctaaa ggtgatcaag tagaccgtaa attccaaatt gttgcaggaa catggtctga 116160
ttcttataat gtcgctgatg ctgctcttgg cgaatatgaa cttaaaggtc aagctcttaa 116220
aatggatatt catggtaata tctttggtaa agtaacatat actactgatg gtaatggtgc 116280
tactaatgaa gatactatta tgggacatgt tgatgttgaa aaaggtcgtt tagatttaac 116340
ttctctttct ggtaaattga ctgagttcaa aattcaaggt ttcgtttctt ctgaaatgca 116400
tactggtaca actcaagttg gttttgatgt tgatgatcgt acaatcaaca ttggtactgc 116460
tccacatatc gaaggtatcc tacctatcga atccgtacaa gatagtaaag ctatgtatga 116520
tattgatgca gcagctgtta ttgttgatac aatgtctgct acttctgcac aaaaagttga 116580
tactgacttg attgaattct tgttacgttc ttatgaaggt actaatgctg cttatcataa 116640
aactttcgat gtacatccaa atggtggata caacatgcat ccgcatgaat ggcgccgtgg 116700
tattcgtgac gttattgact ggatgtctca agcaatgaaa aatgattaca aaacttatga 116760
tgcttacttt gtaattgttg gtaatccaat tgacactcaa ttgattcctg acattgaatg 116820
ggaattccaa ggagctactg atgaagttgc gggaattaac gtttcttata gcgttggtgc 116880
ttcttctaca gttaaccgtt ataaagttgt ttcttctgac ttagtacctg ctggagatct 116940
attaatcttt gcagttccta ctcgtgaaga cttcaaaact tacgaatact acccatacac 117000
tttcaatatc gttaataatt acaacaatgc tgttaaccaa agcgttccta acattatgct 117060
ttctcgccgt tatacagttg aagaatttgt tccaattatc ggtaaagtta caattaaaaa 117120
caacgatgca actcaatacg ctcgttaaat agagtataaa ttctattcag tttcgtatat 117180
taatactagt agataggagg tgtttcgaat ggtcttcaca ctcgaagatt tcgttgggga 117240
ctggcgacag acagccggct acaacctgga ccaagtcctt gaacagggag gtgtgtccag 117300
tttgtttcag aatctcgggg tgtccgtaac tccgatccaa aggattgtcc tgagcggtga 117360
aaatgggctg aagatcgaca tccatgtcat catcccgtat gaaggtctga gcggcgacca 117420
aatgggccag atcgaaaaaa ttttaaggt ggtgtaccct gtggatgatc atcactttaa 117480
ggtgatcctg cactatggca cactggtaat cgacggggtt acgccgaaca tgatcgacta 117540
tttcggacgg ccgtatgaag gcatcgccgt gttcgacggc aaaaagatca ctgtaacagg 117600
gaccctgtgg aacggcaaca aaattatcga cgagcgcctg atcaacccg acggctccct 117660 gctgttccga gtaaccatca acggagtgac cggctggcgg ctgtgcgaac gcattctggc 117720
gtaataaata ttatgaacct ttcagagacc ttttggtttc tgaaaggtta ttatttataa 117780
aaatttaaat tggcggtgca accatgcata ttgattatgg tattgaaaag aatatatcaa 117840
agtacttaca tgaagaatta ctaactgaag atatctataa tcatcctta ttaaaaaaga 117900 ttgatgatga atttcagaaa atattagatg aagataatat taatgatact aaactaccag 117960
```

-continued

```
taacatcata taaaaaaatt caaaatataa ttaaatatgt ctcaactata tttaatataa 118020
atttaattat aacgattgat aacgataata tccttactta tggaatgatg acatttattc 118080
cggttaaaaa tctaacaaag atatctaata atataaagaa gattgtactt caaccaaaaa 118140
ctggttttga atatattaaa actgaagtta ttgaaattaa aatacagaaa aaattaatat 118200
ctttcattaa ggatccaaac ttacttataa gaaataataa agttccaaaa aattatactc 118260
ctagtggaag aatattgacc agtatacttc ttcatgaagt aggtcatcat atattcattg 118320
gatttgaaat taagaaatct attaaaaatg ataaactttt ttcaattaac ggtggtaatg 118380
gtaaagaaat aactatacct agtaatgtta ataataataa atatgtatta acaagcacta 118440
tattatctat attaacgtta agtatttcta tgcatagtta tatgagaagt gaatacaatg 118500
cggataacct accaatacaa tatggttatg gtaaagaagt attttatttt tcagaattaa 118560
tggaaatatt agaaaaacaa aaaagaaatt caattctatt aaagattaaa ggatttctaa 118620
tgtttggtaa agataattat tataatcgta aaataaagaa tcaagtaatt attatgatga 118680
aaaaagaatt aaataatgat aataatagtc ctaaagataa ggaaattatt atagataatt 118740
taaaaactat agaaaatctt gaatagataa tgtggtataa cttattaatt aataagttat 118800
accattaata cgcaagtaac tattaattat aataaaataa agaaattgtg gtgataaaag 118860
tatgcttaag attaatatta aagataatcc tgaacttaaa aagaatatta cttcaaaaaa 118920
taaaaaactc ttttatgatt tcaatacaaa taatcaatct ttcctagaat tagctattga 118980
attaaaaaga ttgggaatca gaaataataa gttacattta gttttatatg ataagagtct 119040
ttccggagta gatccgtatg acccgaactt aactgataac gtaaaggcaa gaattgttaa 119100
agagagcatt attaattttt ggtactttat tagggaagta gttcgtattc cagttccagg 119160
atcttcagtc cattttgcta ttcatagagg gaaccttgca atgtgtttct gtttattaaa 119220
taatttaaat accgtattaa tgttacctcg acaacattat aagacatata gtgctgtagg 119280
tttttattta tggattgaat tattagtagg tagaaactat caaatgatct tttcacataa 119340
atcattaacg gatagtattg ccaatctaaa aagattgacg gctctatttg aactattacc 119400
gacatatatg actgaaccta tcttaaatag taagaatgat aagaatgctg aaactatttt 119460
aacaattgac tcaataaata ataccattag gacaattggt ccaagcacag atattgcttc 119520
agcagataag tcaggttaac ttaatttttc ggcttgacta taaaactttt ttaattgctg 119580
gaacatcctt aagtctatta aactacaacg taactggtaa cggtaagcgt gaatgtttga 119640
aaattaatag aattggacaa tcagcagcca agcttccaat gattattgga tgaaggttca 119700
acgactatcg aaagggtaaa tttatatttt aaatttagaa ctgagtagag tagagccaag 119760
acaaaaattt gcaagtttac ttggttagta attaagtgac attaacttaa tgtaattcta 119820
ttaaatcgaa acggaaagta tagaataaaa ataaatatat attataataa tgatgagata 119880
atttatatct tctttaatta agattattaa agaggtgatt attatggtaa gaaaaaacac 119940
agaatttgat ctagttaata gaatatcaca aaaattcagt aataatgaat ttacctatat 120000
tgaagggttt aatagaatga tagataaatg tagatttaaa tgtaataatt gtggaaatga 120060 taatattat acttcgccat ccatattatt ggataaaaat aaatctatat actgtaatct 120120
atgtaatcct gcaactttac gaaaaaattc atttatggat aatgttaata aaaattacac 120180 tgtttttagaa aaacctaaaa ataataaaca aaatatatct gtaaagtgta atttatgtga 120240
tttcatattt aaaacaaggt cacaatattt aacagctatg gacaaaccta gtaaaactcg 120300
aaatttgtgt cctaaatgta atgcatcaaa ttctgaaaaa atatttgcaa aatttcttga 120360
```

-continued

```
ttctcaaaat attaattatg aaatgcagaa aaagtttaaa gaatgtatcg gtattaataa 120420
tagagtcact ccatttgatt tttatataga ttcaatgaat ctaattgttg aaattgatgg 120480
aaaacaacac gattcattaa aatatgcatt ccatagagat attaaagaat atgaaagaac 120540
tgttgctaat gacaatatta aaaataattt ttgtagtgaa aataatattg gattaatacg 120600
tttaagatat aattgcaaaa gtaaagaaat tgaattcatg gaatcaatta ttgatgcaaa 120660
atatattcca aacgtaaaat tatccataaa tgcaaatctt attaaatatt agatataaat 120720
ctcatcaatt tataattctg actcttcaaa taaaatttgg agagtttatt tttttttttt 120780
ttctataaag atatagtcta tggggagaga aatctcttaa acttgttata ttctaagcga 120840
ggaatgaccg ttgtatgcgc cgtaatgagt ttataaaaac tctaatcaat tttgagaata 120900
acggaatgat agatagcaaa taatcttgaa acgttatatc taatactcct acatgcatat 120960
atttattaaa cggactatat gtgtgaagtt aggtgaagtc agttgaacca ctcccctata 121020
acggaaaact taagtattat atactaagag tgtatagact gggatgcgtt ataatatggt 121080
aaggatattc tttaaaagaa ttagacgaat caatgaatta aaaccgttaa aaattaatct 121140
aacaggttaa tgaatactaa tagggatgag taagtgagcg gttatgaaaa tcctatttaa 121200
gttatgctct taaattatta ttagtgcggt agagttggta cctaagttat aactatgcta 121260
tcaaaattga aaaggtggaa actaggaaga tcgtaaagat gtttaatgtc tgatctaata 121320
aataggaaat gatttatgaa tcttagtggc agcagcctgt agtagtgatg aagctcttgt 121380
aatgagagtg gagtgaaggg gcatagtcag agattatatt aaccaaataa tctttgatgg 121440
aacgctgtat acgatgaaag tcgtacgtac agtgtgaagt gggggaaaat ccggagataa 121500
tttcaaagga ttacctatca ctatccgtta atatggttag atgaatatgc gtttttaaaa 121560
tataatgata cggtatttaa agcaatgcgc cctgctttta cagaagcaag taaagctgca 121620
agcatgaatg atactccgta ttcaatactt attacaacaa cgcctagtaa tttagattcc 121680
gatgaaggaa attcatgtta taatcttata caaaatgcag ctaggtttga tgaaaagatg 121740
tatgattggt actatcagtt tggtccagaa taccttcaat catacttgga taaaaactct 121800
ggtaatgatt ttatatatat tgaatttagt tataaagaat taggtaaaga tgatgaatgg 121860
ttagagagtc agattcgggc aatgttaggt gatagactta aggttaagat tgaattatta 121920
ttagaatggg tttctagtag tgaagattca atctttagtg aagatattat tgaatctctt 121980
gaaggtaata ttataaaaag ggaaaattat gcaggatcca tatatttatg tgatggaaca 122040
tataaactag atgttattaa aaatcctata aacttattaa ctaaaacata cgttatatca 122100
atagatattg ccggaggatt aggtaaagat aataccgttg taaccgttat tgatccagta 122160
gaccttaata cggtaatggt atttcaaaat aataaaatta ctgttccgga attagaagat 122220
cttgttactg atctagtgtt aaattatatt ccaaacgcag tagttattcc agaacgaaac 122280
tatggtgggg aacaactgat tgattatatt attaaacata atttaatatc taaaaatctt 122340 tttttatgtaa caaaacaaat aactactgaa aagacaatct tacaagaaaa taatgttttt 122400
agaaaaagaa gtaataaagt tagaaaagaa aaaagggtat atggtatata tacaacaact 122460
aagactcgtg atataatgat taatactatc cttccaatga ttgtttatga aagacccgaa 122520
ttggtaaata atgcttcctt atttaatgat attaaaacgc tagaaagaaa aagaaatggt 122580
aagattgaac ataagtcaaa tcgccatgat gataatttat tttcatatct ggtaggatta 122640
tatgcactat tatatgaaca ctcgatcagt aggtttgtgg atattattga taaacccgag 122700
```

-continued

```
ttaaataagg aagatgaatt agttgatagc ggtaataata cgggtcaaca tcgtttaact 122760
agttctcaaa aagcatcaag aactattaat aatttaagaa aagttagtaa aaaaccaaca 122820
agcaaatcaa ttattaatgc atcaatgaat ataaataacg aagattctag tattaataat 122880
tctatgagta aaaaccacg aagaggacta aatttagtcc gaaatataaa taaaaaataa 122940
attaattttt tatatactat cctaaaaaat attatataat aattaaatat aattgattgg 123000
aagtggaaat tttattatgg ttatgttaaa tgcaactgta aatgaagaat ataaacgtga 123060
aaacgtaaat gaaattatta caaatattag tgaggatatt atgattgata atatcttatc 123120
tcaaataaat gatactgata ttcaggatct ttctgaagta agaaaatcat tctttgaata 123180
ctttgaagaa cgttataact ttgttaagaa aaattataac gatgatgatg aagcaatgca 123240
aaattgccga gaagtctttg atgatatttt aaatcaaatt attaaagcaa tctctgaaaa 123300
atacagtttt gatcttttct tttcagatat cctattattc gatacaaaag tagaaattac 123360
taaaagtcta tattatttct ttgtcatcaa tattcgggaa aatattgaaa atatgattta 123420 ttatttatc atgaaaaata gaaaaacatt agtaaaaatg tttaacacta ttagtaaaga 123480
agaaagaaag aatttaagct atattaatct tagttctgca atcaataatg attatacgac 123540
aatgatatat catttaagca tgattattga taatattgaa attcctacta atgaagatat 123600
tattgaatta atggttgaag ataattcata tgaactttat aactacgtaa ctgttaatac 123660
attagttctt acaaatttct gcgaagtaaa ttataatgaa aacttttact caatctttct 123720
agatattatt aagaattctc caattattgt aagaaatgtt agaaactcac ttattgactc 123780
attaaaataa tattaattac cctatcctta aataatttaa ggatagggtt ttatttaaac 123840 aatttttat aagaaatatt taaagaaggg agacgttaat ggttgactaa aaagatgagc 123900
agtttagacc gaattaaaga ttcacttatt tttaaaggtg aaatattaga tatatactta 123960
ccaaaatcta attttgataa aaatctatca acgtataatg gtgaatatat aaatactatg 124020
ggtatctttt cattcattga aaagaaagct ggacctgaag ataaaacaac taaaggaact 124080
ttacgtaaac tagaattacc taatatgatt gactttcaat acgattcaag ttattctttt 124140
aagggaaaat tatcggatga attaccctct gacacatacg aagttttttcg acttactaca 124200 ggaaatcaat ttattgcaaa tgtatttaca gaacaaaatg cttctaatgt taaaaaattt 124260
atatcggctc ttcatggtgg taatattccg agttcagtat cttatgataa tattattaaa 124320
ctatacttag atactttatc aattaataaa gttagtttac gtagtccatc agtaatttat 124380
gaattgatta tctccgaatt atgtaggtat agtaaagata ttaatgaacc ttttagaaag 124440
attattgctt caaaaaataa tattagtccc tatatgtata caaatattaa tcttaagaaa 124500
ttaccatcaa tcaattctac tttttgcggca cttagttttg aaaatccaaa tcaagcaatt 124560
attgacagta ttaataagaa tatcaatggt gaaaaagaga atgaatctcc tattgaaagg 124620
actattaaat actaatattt taaaacaata aaatataatc ttaataagat gatttatttt 124680
tatgtttatt aagttttta taaaaaagat tataatgaaa ggaatgaatt ataaatatgg 124740
ctaatgatgc aagtttgaca caactacatc catcagtttc atccgttatc aatgcaaatc 124800
agtctaattt tcttacatct aatggtgtag ttactctatt tgctgcagac acctttgcta 124860
aaggtaaaga tggtgcaatt gatttttgtta gtactaaaga tgaatttatt tttaaatacg 124920
gtactccaga ttattccaaa tacggtcaat cagcttataa tattgtagag tggttagaaa 124980
atggaggtca agcatttgtc ctacgtcttc ttcctgatga tgctaccttc tctcatgcaa 125040
ttctgaatgt acaaagtaaa gttgtatctc aaggtaaaaa tgtttttaact actgcaggag 125100
```

-continued

```
aattggttaa attagatgat gttcatctac gtcctactac tgcttttatt aagaaaaata 125160
atcgtgataa gaatatgttg atgtctgaat tgacaaaaac tcgttctgat gagaatactg 125220
ttgatggtta tacaaataac tttgtattgc tagtatatcc agaaggtcgt ggagaagctt 125280
acaataattt aggtttccgt atgactctta atggttcttt cgattcagca gtaaatagtt 125340
ctcgtgttta taacttcgaa gtaattcaat atgattctga atctaatatg actgtagttg 125400
aaggaccatt ttatgtatct ttcgatcgta ctgcaatctc agcttctggg gaatctatgt 125460
ttattgaaga tgttattaat cgctattcta aacacgttaa ttgtgaattt aatgaagaaa 125520
actttaaccg tttgactaaa tctattaatc ctaatgttaa cccaggacat attgatattc 125580
ttactggtaa atctaaagtt cttccttctg gtaaagctga aacagtttat tccgaaatta 125640
ctcgtgataa cgaagatatt catatttcat tacaaaaata taatgctcgt ggagaactag 125700
taactcagaa tggtaatgct gtgcttaata ttccagaccc tacggatact gttgaagcag 125760
cattgattag tttagataat ggattacgtg aaaatattta caatctagac tctaataaac 125820
ttgcttacat gaaagaacaa ttccctaaac taaaaactga tagttctagc gaatttaaat 125880
tggctatgaa tcaaattatc aatgttccag gagatgattc tcaacctaaa acaggtgaag 125940
tggttacgct tattaataat aactttgatt catctaatcc tagcagtctt tatagtaaat 126000
accttattgc taaagaagct tatattagtg aagatagtga tgaaaatctt tctgcagtat 126060
tatcatacgt agatcgtttg tctgaagtat tgaagtctca atttattgat tattctacta 126120
aaatgaatgc ttcttataca ttaactcttc ataattcacc aaatcctcaa cttccggcac 126180
aatatgcgct tgaacttaac tctttgactg atcttcttaa taagaaagat caaatcaata 126240
tctttacagt tgagcatcaa ggtaaactat ttgatattca agaaacaatc actaaatatc 126300
gtttaggtac tgttagtgga agttatttgg aaggattgtc attaatccta aacaatgttg 126360
agaatgaaat taaatatgta tatgaaagct tacttccagt agcatacaat ggttatcaaa 126420
atgtacctgt agagatttct gataaatttg attcatcaaa accagaaagc attacaagtc 126480
gttataaccg tatcttagat cttcaaagtg atatgcaatc aggaattatt gacaatacag 126540
caactaatcg tgatgaaatc acttcagtag ctaatgatat tactattgat ctattggatg 126600
ttattaatga agttacattc acttctagca ctacaaatat tgaaagtgca tgtacaactt 126660
cagtatctca tattctagat aatatcgttt ctttccattc tgcagttctt acaatgatta 126720
cacctcaagg tacttatgac tttgatgcaa tcatttctaa tgctagaact caaattgaaa 126780
ctgaaatttc taaagtttct acatctaact ctaaattctt taatacaaat ctaattgact 126840
tttctaatcc aattaaactt cttttgggtt ctgatggttc atttacttat gacccagata 126900
atttatctga aagacgtgct tctattaaac aatggttaat taaagcatat agtggatcag 126960
ttgattctga tctattgaat aaagataaat atccaattga tatcattttg gatgcaaaat 127020
atgatagtga tgtaaaagcc gctatcggta gtttggcagc caatattcgc cgagatttcc 127080
aattctttgc ggatgatgcg ggtggttcat ttagttcttc tccagtagat tctctatcat 127140
ggagacagac ttctgcattc aatattagtt ctcttaacgt ttcaatattc tctcaagatt 127200
taacttacta tgatgaatat actggtaaag atattcgctt caccgctcct tatcaactag 127260
caagtaagat tccttacaac gcagtacaat acggattgca atatccttta gctggaccac 127320
gtagaggtct aattagtggt cataaagcta tttcttgggt tcctaatgaa gctgaaaaag 127380
aaaaactata tattgctaaa atcaattata ttgaacaaga tactagacgt actaaatttg 127440
```

-continued

```
gttcacaatc cactacagaa actggttatg gtgcattatc taatattaat aatgtattta 127500
ctattcttaa aatggaacgt gatgctaaag aacttgtatc tagttaccaa tttgaattca 127560
atgatgaaga aactaaagat tctctttata ctgaattgaa ttcttaccta tctaaatata 127620
caagtgaccg tagctgtgag tctgttgtag ctactgttag tgcttctgac tatgataaac 127680
aacaacgtat cattaaagta aatatttctg ttaagtttaa cggaattatt gaacgtgttc 127740
aattaagctt cgatgtagct aattaatact acaatatttc taactagagg taaataattt 127800
atacttattt tatttatctc tagtatttat tataaacaat tattacttat aagagaggat 127860
gacaaacata atgctaaaac cgggttctag tgctagagtc tttgataatg acttagctaa 127920
aggtaaaagc ttttttaccg gatcaatgaa tacacaagaa cttcagtttg atccatttgt 127980
tacaggatat gcatttatcc tttggactaa agttcctact tgggttgaaa aatcattccc 128040
aggattccgt agccaaactc aaaagaattt taaagaattc tcaggaattt cagatatgga 128100
actacaaact gctgaatata cgcatacttt taataacaat gcttatcgtt ttaatagtgg 128160
tattactaaa aacaatactg agtttactct aagacatcaa gaattctcag gtaatccaat 128220
tacaaatatg tataacttat gggtttctgg tatcagtgat ccacaaactg gtattgctac 128280
ttatcctaaa gaatataata tggagtatgc tgctaagaat catacagggg aacttctata 128340
tattgttact cgtcctgacg taaataacgt agaacgtaat aatattgaaa aagcattctt 128400
ctatacagca gttatgccta ctcgtattgc attaaatcat tttaactata ctttaggtac 128460
tcatgatggt gctgaagttg aaatgccatt tgcaggaaac ttgcatattg gtccattagt 128520
tgatgattat gctaaagaaa tgttacgtaa aacatactcc tttaacgctc aaggtatgtt 128580
taaccctcaa gatggttcaa ttgctggtga aaatattgct gtatttaatg ataatgcagg 128640
agttactggt tctggtctag gagatatcta attaaattaa atacctatca ctatattaat 128700
ttatggtgat aggtatttta tattttaatt ttttagagaa attatagata tctaacaata 128760
atatataaat gtatttggtt gtgaatcttt attatttaaa ataatttttt aaatattaga 128820
ataacaatat aatataattt tacttctacg tgtcggtatg caagctggtt aaagcagacg 128880
gactgtaact ccgtttcgaa agattcgaag gttcaaatcc ttcccggcac atctttatgg 128940
aaagttgtct gagtggttta aggtctcggt cttgaaaacc gatgaacgtt tatagcgttc 129000
cgtgggttcg aatcccacac tttcctcttt tatattatgg acttttaaag tttagtggct 129060
ttaagagtca gccaattgtt tgttttttct tctttattcc atatttactt tagggatata 129120
tcttaagggg tttttgatat atcccactcc ttttgacgtg tagctcaatg gtagagcatc 129180
tgactgttaa tcagacggtt gcaagttcga gtcttgccac gtcagcttat tttattaata 129240
ccttataatt aattaatacc ttataattaa ttaatataag gtattaataa tcctaatacg 129300 gttcttagc tcagttggtt agagcagacg gctcataacc gtccggtcga tggttcgagt 129360
ccatcaagaa ccatttctct aaaaaagatt atatagagaa cagtaatatt aaattcagta 129420
atcttattct aagttaatat gtatatatta ataagatgat aattaaagaa attaattatt 129480
gctgaataat attaaatttc ttaataaata gatcaattaa cttaaaaaat atcataacga 129540
tcctttttaa aaccacacct tcaaaaacca tgtatatgat tgatctattt aatgaagtca 129600
aaagtattct tgtatcctcc taatatatga atatttaacc atttttttt tttttttgc 129660 aagtttatat tggttcttgc aaactctttt ttcacgtatt atctcttaaa tgaggtaata 129720 cgtgtttta ttataaaaat aaatatatat tataatgatg attaaaataa tatatagatt 129780
ggattgatga gacgatggca tacaatattg ataacgtaag ggaaactaag gcaaaggtat 129840
```

-continued

```
taagaacggc aattaattct ctgattgcta gatattatga atctaatgat ccaaatactg 129900
cactagagta tttggagaca gctgctaaaa tggaggaatt tgttgagaat gacaattata 129960
attatttatt agattataat atgaagagta cccatctagt tagacgagtg actagtattg 130020
atacaaatct caataaatca gaaacaaatg ttggaaaaca aaagattaga tgtatgtatg 130080
aaagagaaaa gtctgcatat atttataata tcaaaaacaa gaaagttgaa agtgtttata 130140
gaaataataa gaatatttct aagatcaata aaccaaactt taatgaagat gatattgcat 130200
taatgcgtaa gattcttgat tccgaagagg gtagtgctat acatagaaat cttattggtt 130260
cttatgtata caatcatcga attggtaaat gtggagtgat tgtcggaatt actaaagcgc 130320
atatgtatta tacacttagt gataagcata ataatactaa aactaatgat accaagtttg 130380
ttgtgagata tctagacaat actatgaaca acaaacaaac atctattggt atctggcgtg 130440
ctactaaatg ttcatttagt aaagaaattt cggactttgc aacatattat actagttcag 130500
aaagtacgga agagtatgat aaagaatatg ttattaattc aatgaatcgt ctatatgaaa 130560
ttgagaagaa ttatactcat aaattctttg atacaggact aaagatttaa agaatattaa 130620
cgctaatcat ccaataataa ggatgattag cgttattttt tttttttta attttttcta 130680 gatacgttta ttgccttcat aactatctta taggaatcat atgctatctt ttcaggaatt 130740
acgtttgaat atttattatg gacatccact aatttcttac gtagttcttc atcgctagta 130800
ttaataatta gcttctgaaa cattccaaag atactcatat gttctcgtaa tccactatta 130860
ctagaattat atattacctt attaaattcg atctttttta ctttattaga tcggcaatat 130920
tcattatcaa tattttctaa tagtttatta aggtcactaa tagtctttat acctttattt 130980
ttactaatat ctttatgata ttcagatata gatgcgtata tattattttt agaaaatata 131040
cttatctcat ctttattaaa atgtttgttt aaaccatctt gatttataat attaattcca 131100
ttccgaatat tttctttatt tcgactaata atttcagtaa tagtactttg tctatcttta 131160
tgtttctcaa taagattttt tactttacgt aatattgatt cattaatttg tgattctaat 131220
aaatctttaa tataattatt atccatatct atatatcacc tttgtcttta cgattatatt 131280
tatagaattc tatcaattca agagaaagat caccaaaaat agcttgcatt gaaattccac 131340
cattgatatt tacattttcc atatccttaa agtttattag tgggttaagg taatcataat 131400
tattattatt atctgcaata aatactcgaa ttctattatt ttttttaata accttaatta 131460
atttactatc aaagttataa tcataggtat ctatagtttt aatatataac gtaggatcat 131520
ctttaaatat attacgttta gttccataga attgatctat ttctttaaat ccgttcgaag 131580
caatatttcc tacagctaca gaaacgctat tatatggtgg tagattacta tttgtactat 131640
cacttttaat aaagaatcca taaccagaat tatcattctt attgtagtcg agagcaaata 131700
atatcgctcc gcccttagat ggtgaagtat gttttagttt aaatgtgata atatattcgt 131760
ctggtaaagt taaatttgta ctatacatat ttttccaaat attattcttt gtttcgttat 131820
cccttgaact tttaataatc actggattag atttaatttt aacattattt tgaattgttt 131880
ctataattct accattatta tatgatggat tatttgtgat aatttcacta ccgtttattt 131940
cttgtatggt tggatgaaaa tatattcctt caaaagaatc tttagggaaa attttaacac 132000
ctttatcatc tattgtctta taattatata ataggtttat attataccat ccagaggaag 132060
gaactgtgaa actagtatat gaatcattat ttgaatagct cttaatatta atagattttg 132120
ttttgatata tgcagtagta tccttttttg cattaattat aacattaacc gtaatttttt 132180
```

-continued

```
caatacttat tgatttactt ttaataatac ccaacttaag gtaactattc tttttattag 132240
tattaaaaat atctgatctt ggatgtaatg tagttacgct ttcagtagta ctgtctgtat 132300
aagtaataat catttcataa cccatactat caatatcatc attattaaaa ctacttgagt 132360
actctaaatt tgtaaagaat aatctattat ctttaatacg attaatatct cgatagttat 132420
ttactgagtc agcagtaaaa tttaccgata taatattatt ctttcctttt tttattgtac 132480
tatcaagaac atgcacatac ctaccttgat cttcatcata agaaacaaat gttccattat 132540
acgaatttac aaacttatca agattatcat ctctaaaatc gcttaataat tccatttcat 132600
taggattaaa atctttatta atatttacaa tattttttgc agtatcaagg ttatttatca 132660
ttaatcgtac atttccacta aagttgttgg tcaatccata tttttttactt ttatctaagt 132720 atattttacc tgtaaatgat ttagtataac ctttttttaaa atagtatgat ggtatactag 132780
ttagaccttt atcatctaac gtaaaaggat ctacatatcg accatcatta tctgtaactt 132840
tacccatttc aacatctatt gatgctagat tatagtttgc atttaatatt tcatctttat 132900
tatctgaaaa atcaggaact gtatgccatg gaattgtttc attgatatca gtacctaata 132960 aatctttttga ttttttcattt aatggatgta acatatgttt ttttacatat cttggacttt 133020
gtacggttga tttcatattt ttttcctgat taataatttt attgattgta tttagaatag 133080
tatcagggaa tactttaatt gttttcttat taaatttttc aacagtatcc atatcattaa 133140
caaacattaa taagtaccat aagtcagttg tttcatataa ttcctcagat acatattccg 133200
gtctataaaa ttggttttcc gatatatcat aatcaattaa gtttgattta aaaatatttt 133260
catacttttt taacaatgga aaacctaata ctatctttcc ttctaataaa taaaagttag 133320
atatattact aagcaatatt ttattaacgt ttattgaatt tattccacca actaagtcaa 133380
caaatcttga actatctaaa ctatttctag aattatctac tactaccaaa atatattcac 133440
cacttttcaa atttcattat ataattatat gttactatat tctttttttat caaaaaaaaa 133500 aaaaaatgcc atagtatatt atgtaatata ctatggcata ataaatgtta catcattgga 133560
tcattattat cttcagaact attttttaata ttagatatat ttaacttatc tttagttaaa 133620
tcttgatttg tttcgttaaa taatgtatca aacttagtcc aatcaagagt agacatatat 133680
atttctgaag ctaatttttt cctaaacaat cttttcttat tatcggtatc ctcattttgt 133740
tctgactctg tgaaataatt acctacaata aaatctattg tctgtgaaat attattaatt 133800
tgttcattaa cattagcaat attcataaat actggtgtag ggaaattaat agtgatttct 133860
tcaattttta cttcatcttg gttttcgtta taatcttttt catcatttgt tttgttctta 133920
tctttacgat ctcgttcacc atactcataa cgatatagct cttgaattat cttagtaaag 133980
aatttactaa acgtttcttg atatccaata actcttcgaa caaaattact attctgcatt 134040
gatagatttc ttgcaaaatc aacttcatta gtagcatcaa tataattaat tggaacacct 134100
gttccattaa ctgccgattt ctgtaagaat tctaagaaat catcattaat atcagcttgt 134160 ataccetggaa taacatcaat atcgaaaggc ttatctccat taactgttgg aatataatgct 134220 tcttctgtag cacctaaagt tttaagcata gtagatacac tatttccggg accaatacta 134280
tccattgaaa attcagtagt ctttaaatct cggataagtt cttcaatagt tccctcaata 134340
tcagaatcca tatcagactc tacgtaatat actcttctat ctctaccttg attaattttt 134400
accattaaat ttgtaattaa tgtagaaaga tacattttag caaaaaatag actattattt 134460
aatctagata caccatactc gctagtgcta tctaaaggta gatgatacac ctgatttggt 134520
tctaagaatg ttatagatat atctttattg ataatatagt cttctctgac caatctatat 134580
```

-continued

```
attacatctt taaaatcttg gttatcttct aaaaagtctt tagatatttt atcactaatt 134640 cctttacaa atatatcagt aattatcttg tatttttcat tactagtcac tcctgaacca 134700
ctctgatttg atctagagtt ataatacatt gtaatatctc cattaacact agaagatcct 134760 tgtgggcat taccgttaag agttcctgca atagtaccta atattgaact acctttaaat 134820
gaattattgc taccattctt ttcaatatac acgtatccta aacatactcc atcaatagat 134880
attttaatga tatcttccgg actaaatatt tttaagtaag atccggtaat atttagattt 134940
tgaatgtctt tagatttttt acttgctttt cgagattcag atacaagatt tagagggtct 135000
ttataatatt ttacattttt agatatagac tcatatacct cattagcagt actttctact 135060
aaaatctttt caatatcttt aggattactt ttagaaaatc tttttccatt tttaatatta 135120
gatgatttaa attcaatatt ttcatcattc ataacacttt caataagatt ttcaatattt 135180
ctatgatcca cgttaaaaga ttcatttaga tcatcttctt cagaatcaat aaagagatta 135240
ttggtatcta attcattaaa ttcatcttca gaaagaatac ttttaaattg gctttctaga 135300
tcggtaacca tgataaacag atcaccctca attaatgtat tccgaataga atttcgaata 135360 actgtatttta gattatattt atcaatcaac ttagacatat taccattgaa ttcttttttta 135420 tccgtctccc ctaaggtagt attttcatta ttataatagt atgatattga ttgttttgtt 135480
acatcgtctg gagacataat agaatctaca tacgtatcaa tagctgtacc caattccgga 135540
aaatactgag atattagtct aaaatcatca tatctttgcc atcttagttt ttcttcagca 135600
aactctcctg atgagaaact actttcaact ttttccttaa aataattgtt gtatatatca 135660
gaactttttt tattttttcgt attttttcatt ccagtattct taactttatc tctctgtatg 135720
tcggagataa tatcaattat acttcttcct gaactgttat tattaccgtt tcttcgttta 135780
atcttattta acatatcatg aagattactt aatttatctt ttggtatatc tttctggttc 135840
ataataccgt atagatttt attaacgttt gcattatctg ccattaaact tatccacctt 135900
tctaaattga tgaaaaaaaa aaatatcata ggaaaaaatt tccctatgat attcactaat 135960
atttatttca tatctacgaa tatatatgat tgttccataa tataagtatc attacaaact 136020
tcaattacaa gcattttaa tgatgaatcc ttgttatgat taaagcataa tatatttata 136080
gatggatgtt tactatatac tactggaata taatcactaa attttttcttc tttatatttt 136140 tcatatgctt cattaatatc ttttggatag ttcaatgatc cgagattatc cttaatattt 136200
gtaaaataag gtatttcagt aaattggtct atatcgacaa ttaatggttc aggattcttt 136260
ttacgaatat acttaaagcc tttgataaat ttagttgata cggtaacact aatataatca 136320
tctaattcag gtttaatcat atcatcatgg ataataatat tattattatc atttttatca 136380
ataactattg agaatgtata tttattgtca aattcaagta attttattac atcatcatca 136440
ctaagcgtta tctttggaat atttaatgaa ttttcactaa aagaatctaa tacaggaaca 136500
atatgatcat tatacgcatt aatatctttt tcttctaaat accatttaat aaaaaagtct 136560
gattgtctaa taaactttat atagttatcg ttatagtcta tttctataga gacaatttta 136620
tctgatttat ttttacgcat ttcaaaaaat tctatcatat gaatagaaaa tgtattcttt 136680
tgcataaaat catttactgt tttcattata ccttttttat ctagtttttct ttcaataaaa 136740 gtagcattga tatactttgg tagttgtttt agtagtgcgt catcgtttag tgagggaaat 136800
gcaaaaccat tattaaaaat caacctatcc ccaacattaa gtacattcct aaattgatct 136860
accatttctt caatagaaac tacaattttt tgagcttcat taggatcatc tacaataact 136920
```

-continued

```
ttattatttt cttcaatata caactataat tcacctactt cttgcatact ttcagaatct 136980
attgattctc gaatcatacc caaagcatct ttaatatttg gtagattata atatttaatg 137040
caaaattgta aagggttatt actattataa tcatcaataa atgattctgt aatattctta 137100
ttaccttgtt taaaagtaat atttccgata agactttcag gactaatatt taacgccata 137160
ataatatgag ggtatagtgc agttaagtca atatcggtta cattatcgaa aatcatattt 137220 gatttttac ccataatatc aataccgatt ggatgaactt ttgatgagtc tgctacaaac 137280
gcacctttaa ttttttccatc aatcttagga tataatgaac tatgattatt actaattaca 137340
aacccaccat tattataaaa gatttctgta aggtttctta agcatattgt tttcttaagt 137400
gcttttgtta ttcgagtatg tgttaacgaa ctaatttgat aaattagatc taagaattta 137460
gttgcttttt cgatcatcat taagagaact gtatcctgaa tgttatatag aatgaattta 137520
tagtagtttt taatatatac gttagtgatg tctccgtcac cctcttcaaa ctcatccttt 137580
tgcatcccta cttctttttc acctatgtcg ttcaatttgt aagagtctaa gactcccata 137640
gatagcgata ggtaagtatt tgatattatc tccaactttt cccccgcttc acaccgtacg 137700
tgagactttc acctcatacg gcgttccatc actcagttta tattgtcacc gatatattaa 137760
tgacaataac tagtcgttaa ctaagtttct taatttagtt agttgtgttt tatttacccc 137820
ggtaggaaaa tcagtactat agtgaattag attatgtgaa taaacagaca gtaatacaag 137880
attatcaaaa ctatttgacc cacctttga tctcggcttt ttatgatgta taactaagtt 137940
atctattcct attttatata atggtatatt agtgatagga tccttcttct gtttttttaac 138000 cagaccggga agatacattt tataccttat attgggaaaa ttagaactat ttgtaagcat 138060
attaataaat tttaatatta actcatcgtt gttcttagtt ttcataatag gcgtccaata 138120
ctgtttattt atgagataat ctttagtatt tttactggat tgtttccgcc acatccatgt 138180
attaaatata atgtctttat acttataaat ttcagtatca ggtttcttat acatttgact 138240
ttgtcgactc caactatata aaattccgtt aactaagtta atataagctt gcatattagt 138300
aactaaatta aaattatata tagttcccaa tataatagac attaccttttt gataatgacc 138360 ttttctcagt tcagacctta ataatttttt ctgattatac caaaacttac taagattttt 138420
aaatgagatc atcacatgtc cacttgcaaa tcgcatatac ttaaaaccta caaagttaat 138480
tacaaagtcc tgaccttctt tgataatgat ttcactagtt ttattccagt ttaaagaaac 138540
ttgatgtttt gtacaccaag aatctaaaac aggtttaaat cttttctacat cccaaggatt 138600 cggactaatt attataaaat catcagcata acgaatcatt cttatctgca ttcgattacc 138660
aacggttttc aaatattgat ctttacctttt tcgcctataa tatgacatat tataaaactt 138720
attataagga tgtgttttgt gaaattcaga tccattagaa atagcctcat tatacatgtt 138780
taagtcattg actaagattt ctagatcatg taataaaacg ttagctagta taggaccaag 138840
tatagaacct tgagctaaac caatcccttg atactttgtg tctttagtat ctatagacat 138900
aagaaacttt atagatctta gtagttgcgt atctctaatt ttgtgattat accttaattt 138960
atcaagtact atatctaaat taatagtatc aaaatactta gataaatcac aatctagtac 139020
tgatccattc tttatttctt tagtgttatt tactaaagct gacatggcat gttgagttga 139080
gagattacgt ctaaaaccat aagaatcagg ataaaattga tattccaaaa taggttctaa 139140
aatattaaga atacattgtt gtgctattcg atctaatata ttagttattc caagagttct 139200
aaacgaacca tcctcttttg gaatgtcaac aagtcttgaa tatggtttta tatcacctttt 139260 tattcgtttc aataataggc ttttaatatc tttgtaatct tgtttttagta aatcatctaa 139320
```

```
agtttgacca tctggtcccg gagtatttct tccatcatta gacattatcc gtttaatagc 139380
atattgaata ttactatctt taataatata tctagataaa tgcgtaaaag atggtttacc 139440
atttaaaaca tcattataca attttatttg gattttattg aaatcaaaat atatagaatg 139500
taaacttttt gtgtctatat taacacacct tcttacaaaa tcaagctctg aatataaatc 139560
aggcaattat atatcattgt tttgagtgac tttgggcttt cccattaatg atacattaca 139620
tatcatatta tcggtttcta cccaaacttt cagtctgtat tcatttaact tcaccgtgac 139680
tagcagctaa accgttaaat taataatata aaattatcta cagaccttcc cacgttccct 139740
acatcataga atatagtata cttaggttct tcctctaggc tctgtgtgat tatagaaata 139800
atctggttcc cattatatac catccatcta cgcaacaaac aatacgtatt tggaacacaa 139860
gtttactagc atttctacta gcacatacct gtacattcag aagttcgtca gtcttaaaag 139920
acatactaac catatatacc tccacccgac ccatttgaga ggattgttta ccctttcgtc 139980
aacttaatgt tacgctctaa gttagccgtc ttcacccagc ttcacacata aatatcacta 140040
cttatgcatg tgggagtatt agtgtacatc tgatataact ttagggagtt atatagtgta 140100
tttgatgtag agttattcaa tattattata atactgaact ttagacacgc ctatgtgtat 140160
catagacttt ctctaaaaac atgtcgcacg cttattgata ttggcatata acgccatttg 140220
atctaaatat gttgtatatc cagctacttc atatatggaa gacttatctg caggattatt 140280
gtgtttttca tccattttat gatatacata tttatattta aaatcatcag gacacattaa 140340
ttcttcagga atcgcattat tctttagaat tcgattatat attgtgataa agtcaaaatc 140400
agcattccac gcactagcaa agtcaggtcg atgaacttca ttgatataat gaaagaaatc 140460
actaattaaa tcaatttctt tatcatattc ataaatatta aacgttaagt ctaaattata 140520
ttctttatat ttgtttttta gttcatccaa taatttagtt ttatccaaca ttgcgtcttt 140580
ataaccatca tgatcatatt ttaatgcaaa agtttcaaca gtaagattcc attcatttac 140640
aagtgtaata atattaatcg gagcttctgc tttcttttga tctggaaatc caataatatt 140700
ttgagtatct acttcgatat cgtaaaaaga tttctttagt ccaaaaagat tattatcagg 140760
agcatgtttt tctaaataac gatgaatata attatcttca atattcttat cagaaccatg 140820
aattcgataa tctaaatgca ttttttttaag atttcttcta tcacgaaaat cttcagactt 140880
cataatatta tcatagaata tttttacgct aggatctttt aactctgtag caatactttt 140940
aaatatatct ctgttataac atcttacttg ccttactttt tctttatcaa tatagtttct 141000
tacaacatta tcttgaaatt ccggtttagt aatataataa tccatcattg gttttttcaat 141060 aatatgatgt ttttttgtac cgtcctcttc tttagtgacc ataataagtt tatcaaaatt 141120
atctactgca ccagaatttc ttgcatcttt ctggtttaaa tatgttgtct taattagttg 141180
acccaaaata tacaccacca tctaaatttta tataattcct tgttatttttt attttataaa 141240 attatattct agtaagatta atgatatcaa taactttgtt atatccatcg aatttaaata 141300 aatctttttct acttataata atatctttat ctagattttt agcatattta agaaagaatc 141360
tcatatccat atcatgataa gtactaatca tttcccattt tttagaataa ttttttaggat 141420 tattcttcat atgcctatca ataaatttag tggataattt ttttctttta aacatgttta 141480
aattaaaatt attacttttt ctaccgttta ttattgataa cagttttttct tcactaatat 141540 tattattttc cgccattact tcttttttgt ctaacggtac atttttgaaa tctaatttat 141600
ctttattata agccaataat ttactatttt tactaataag atcaatatat tcatcatcca 141660
```

-continued

```
tgaaaactga tgcgtttgtt ataaagttta cagtatcgtt aaatacatat attttttctt 141720
tattagatgt atcactacta ctattatatt tacatatagt atttattaga tacttaatag 141780
atttaatact attaagagta tcatattccg caatacggaa catatattta aatacatagg 141840
aaatataacc aatactaaga taatcaatat ttaacattaa cgtatctatg aaactgcata 141900
agactttatt aatattcata ttatttttca tatgacttga cttgatcatt agattaagat 141960
gaataatagg ttccacatct tcgcttttat atgatttata atattcaaaa atttgcggta 142020
taatataatc gcataaaaat tcttcatcta tattcgaatt agataaaata aaatttatat 142080
tatcgtatga atattccata tagtcacgaa ataatattct aattatagaa ctattaaatt 142140
ccataactga ccgcactgaa agataagaat ttttactatt tactatctta tcaatattct 142200
ttataaatat atgattaggt attttcattt cataataatc tatattatca aaatttttta 142260
taataaagtc aatcatctta tcagatattc ggtgtccgta aaatgatact aaatctttga 142320
taaattcttc gctgtattca tacatatatt tatctaattc ttcgttcggt atacttatat 142380
aattatctgt aaatcttaat agtttatcac ccaaattccc attactagga tcaatttcta 142440
ttgtaagttt cttcaatata cttaccaacc tttctataat tatactagct ttagatcaat 142500
tacgcttttt tcaaattcat ttaaatgttt agaccaattg aatgatactt ctttatacct 142560
attaatttca tcaatagtca ttaagtttat tgtattaaaa tccagcgata tcaatgaaaa 142620
tactttattc tttaatgaac cgataacatt tgtatttata agtatattat aaatttcata 142680 atattttta gatatatctt tattcatttg taatgaattt tcactaataa aatttccact 142740
atctgatatc acataatcaa taaatactgt atcatttatt atattaaata tactaaccgg 142800
atcagatatg tcacgcatta tattagtcaa tatagattca atatgtgaat tatcattatt 142860
acctttatta tactgatata ataaaggtaa tatttctaaa acaaatatag ttctcttaga 142920
cttccataat ggaggcttat ttaagtataa tgatacttgg aatttatcat cgatatcata 142980
ataattcttt tttagtaaat ctataaatga tataatgaat tcatcattat caataatctt 143040
tagtgattta attatattat catataagtt taattttta attatcttca tgcttaattc 143100 aatatttta attctaagta tgttcattat aatattgtct gaatttgatt taaatataca 143160
tagacttaga attttatat aatggaatat atacatataa tatcacgctt cctaatcatt 143220 cttgctttc attatcgatt actaaactat gattttctaa agaacttagc catggatcat 143280
agatattatt gaatctttct ttatcgctaa tatctttagt aaatatattt aagaatgatt 143340
tttgatattt cttatcatta tcaaaccatg aagatataaa ctcttttcca ctttcttac 143400 ttaattcagt taatgtagta tatacttgga ttgcaaagaa agaacttaat cctactgcat 143460
caacatctaa atcattatgt gaatcgttat caataataat atagcgatta tcatcaacag 143520
gagtatactt attcagtgca atcttttgaa actcaatttt aatattacca ttaaaactat 143580
attcaccatc aatataattg ttaataatat aaaaactatt tgtaataagt tcctcaatac 143640
atttatcagc ttcagcaata attaattcat tactatattt ttgtaaatct tcatagtttt 143700
gaattcctaa ggatttaagt cttacagcaa taaatccttc agtaattcca gataaagaga 143760
ttaaaaattt tgcaggattc aatgaatata ctaatttatt agtattattc tcagtaataa 143820
tttcaatact atatggaatt tccatatatc gttcagaatt ttcagtatat gtgttactgt 143880
cttcatcagt aaccacccat ttttttctag ttcttctatt aattctagaa attttatttt 143940
tcatttcacc tacattattg ctgttatta agctgatatt tactaagata gtttttttcat 144000 tatcgtgaga attaataatt ctaaagtcat aattattttt tcgaagatca cttgtaactt 144060
```

-continued

```
tcggtaattc attattttta acatctaatt ttacgctaaa catttttatc atccattcta 144120
tttttatttt aacaataatt cgactactaa tattaatatt agtagtcgat ataatttatt 144180
tttctgcatt aaaaataata gtttattttt ccataaatac agtatcttca atatcaatgc 144240
ttggattctt cgttaaaatt aaatccacgt cagaagtatg gaattcatca ttatggctaa 144300
tcacaaatat ttgttccata tttaaataat ctgtttgtag atccaatact tccataaact 144360
tacgtctatt atttgtatct aatgtagcat caacttcgtc taaatatata atgttatacc 144420
ctgaagatac ggtttcaatc attgacaatg ataatgataa actagtgatt gcagtttcac 144480
cttgagaact taacttaata tctgaaagat cagttccgtt atctttaaag acccttataa 144540
agaaatcttt ttcagtgata tcaaaacgta tactaaatga ttcaccgtaa gcaactttta 144600
ataagttatt tgtatcagac gcaatctttt aagataatt atcaataaat attaatggaa 144660
tacctttctt aggatctaat gattctttaa tagtttaaa gtcatcatat acttttttcaa 144720 tactagatag tttatcggta atatttgttg caatattaag tctttttttca ttatcttcta 144780 atttattctt aacttcagat aatgcgttat tattaatatt gatagacgtt tcagtattat 144840
ttaatagatc attattattt tctaatgttt ttagtctgga tgtaatatca ttataaactg 144900
aatcgtatac ttctttttta ttaagaatac tttcatagtt tgatctcaga tctttaagaa 144960
tattcagtat atccaatcgt ttagatactg ttttaatatt cttatcatat tgatctattg 145020
attcattatt atctttaata cttgaagata attttttcttc ttccaaagta ctagatttca 145080
atagttcttc atactcatta tatgattcac gcatgatatt gtaattttca atagaccctt 145140
taatattatc aataagattg gatactttgt ctcggttgtt gatattatta attagatcaa 145200
tatataaatt aggtagtttt acaagactat tttcaatatg atcacggttt ggtaaaaata 145260
agtcatcctc atttaaatta ataatgcttg caatattacg aatattatta aatttaggta 145320
gaacttcttg acgatattta tcaaaatatt taataatatt tgacaaatta ctgatattat 145380
tattagtttc tattcgatct tttttctaaat tacttaaggt attttctaat tcatccaact 145440
taggatattc attctctta tattctaaag caatttgaat aaaaggacaa ctatcaatat 145500
tacatgcttc aggtcttcta tctagtgttg ttagtaaatt agatctacta ttaatatcac 145560
taatattttt attgacttcc agaatttgag attcgatatc attcattttg gaatcattag 145620
atttaaacat acttagataa tattcgtagt tgtcaaaagt aatattatcg tcttcaaagt 145680
aagtactttc atccatactc ataagatttc ttagagagtc cagaagatta ccagtttgat 145740
gaatactatt atacatatta ttgtcattca taatagattc aacatttttcc atactagttt 145800 cattcaataa agaatttata ttcttattaa cttcagtcag atattcttca ttttttttcta 145860 attcgtcata atacttttca ggattaaatt ctttaaacga agatattta ttacggtaaa 145920 gactaatatt ttccctaatt ttctttaatc ggtcttcaga atcagtattt ttttcctta 145980 atgaatttct cgatgtttct tctttgatta attttttctgt aaattgttga tgtttattat 146040
aaatatcatc acttgtatat ttttctaatg ctggaaattg agaatatata ttctgtaatc 146100
cttggtaaga ttcatcaaga ctcgtattaa ttgtattaat agtattatta aattggtcaa 146160
tcgatttatt aatatctatt tcatcaatag gtagatttag ttcatttaat ttttctttaa 146220
taaaagaact atccatatca atattatatt tagtaattgt tctttgttcg tttaaacgtt 146280 cttttttcaga ttctaatgat ttaatattat tggttaattc ttctttattt tcttttatag 146340
tattaatatc atcatactta gaaagatcag aatttaatgt cttaagattt ttatctaaaa 146400
```

-continued

```
aagataattt atctttaata acattaaatc tttctaaata atcatccata gaaggtataa 146460
acttatataa ataatcctta cgttcggcag ttttataatc aataaagtta ttcatattat 146520
tacctaatct agcaactgtc atataatctt tagtaattcc aagctcagta cttacaattt 146580
cttcaaaacc acgaattcca ccattttcat ttaattccgt accattctta gaaataaatg 146640
acttattatg agaagaatta tcaccataat aatgtttaat aatatactta tcattataat 146700 taatataat aatttcttta tatcctttag tatctggaat aataatgtta tttctagagt 146760
catttgtacc acggtaagga ttcaatgcgg aaagaataac tgttttacca gaaccattag 146820
aaccaattaa cataattatt ttatttttag aatgggagaa atcaatttca attgactctt 146880
ttcccattcc agcatatatt ccgataaagt ttactaattt taaatatgtt attttcaaga 146940
tatcacatct ttctaattat ttaatctttt ctagacaaac taaaactaaa tttaatctta 147000
ttactagcgg cattataaat aaagtttgta attacatcgt taggagattc attattcttt 147060
ttacatgact taacaaaatc ttcataaata tcatatctac aatttagtaa tagcgtttca 147120
ggaatgaaat caatgattc catattctga atattcattt cttcagtaat accattatta 147180
tcaatataat ttagtataaa taattcaata agattataat cagagttatt taagattcct 147240
gaataaatta gatcttttc acgattagta taattatcaa tatacttctt aggaataata 147300
accctaatat tttttctagg tttatcaaaa ataactaaat tgatctttgt attatcatga 147360
ccaaaaagat tattagattt ttcataatct acaacttctg taaattgctg atatgactta 147420
caatgataac agttaattgt tttgatatga tcaaccgctt tattgatcga tacttttctt 147480
tgaatcatta ctttattacc acaattgtta catattagag tacatggttt tgtattatat 147540
aatgaatttg cgttattttt tgtcatgaga aatcacccat tcatccataa cactaatata 147600
atctttattc ttaatatcta gaaattcatt atataattta tcaaaatctg gataaaattc 147660
ttctttttta cttttaacac gattaataac atcattataa tttggtgaaa ataatagatc 147720
tcgaatatcc ctaagactat gatacggcaa attttctttc tttacgctat tatacattac 147780
ttgtgccatg ttcatacttc tttcatgatt ataatcaatt tttcgaataa ttccaaattt 147840
tctagtcttc aaatcaaagc aaaccatatt tcgaatatga ttattgtact tagtactata 147900
taacatatct tctttaactt gttctgaaat aaaatcatta gttgttagtt taataggtgc 147960
ttctaaatct tttctatcca ctacaatttt attttttttca gattgataat aattatatac 148020
gccataagaa tcatttttac cataattcga gatagttcta atattaaaaa ccgctcttaa 148080
taataaatta tcagtactgc taaattcata tgataactgt aaattgaaat ctcttgcatt 148140
tttttccaca tctgaagcaa actttaaaaa ttttagagct tcaccactaa tatatgatgt 148200
agtagtttta tctctagctt cattatatct atttaagttt gcattaattg tggatctaat 148260
tatctttgat aatgtaccat ttacatcatt tacattaaaa tttttcatga aaatctctcc 148320
attctatttt ttataaatat tcataattga gaataattct tttatttctt aaatcactaa 148380
tacgatcaat attgattcct aatcggttac agtgttctaa gcttgaaaga attctaatat 148440
ctttattgat tgattcgata tcttttattg tagtattttc ttttctggaa gcatataata 148500
aaattgattc agggtcattt gaaaagatat tttgattgat ccatctatta tatcgattat 148560
taataatatt ggacgttgta ttcacagtag taatagattc tttggaatca atatttctta 148620
caatacctac tctttttttgc ggagaattat aagtaaaaac aatatcgtta ctaatacttt 148680
ctggagaaac tattctgcta ttattaacag taaatttact attagttcta cgtgttaata 148740
atttataact attccgttta tttacgttag aatctaaatc atcactaatc tgaaatgata 148800
```

-continued

```
catatgaaat taatccacca atattattaa acgcaggaat taataagaga tcactatatt 148860
cagatgaaat ctttcttacg ttattatcaa tacgtctttt aattgtttct aatgctgaaa 148920
tcgtttcccc tttagcgtat aatttataat actgcttaat aagaatgtta ataaatttga 148980
ttgtttcttt aatttcagtt gtaggaatta ataaattatg ataattatta ttcctataag 149040
tttttctttc tttaatacta gttgacatta aaaatcatcc tttcaaaatt attattataa 149100
tgactatgta atattgacat aaattaattc tcatgtcatt acatagtcat tataataata 149160
tataaatata gttaaagttg aaaggtaatt ttttattctt ctatttctac ataactgaat 149220
tctgaattat cagagaatat tacgcctact tcattatcgt cttcatcata aagagattca 149280
attattcggt tattagctaa atatgaatca attacttcat tattcatttc attagaagag 149340
tatactgttt gatcttcatc taagaatatt ggttctgaag tattaatatc tacgcacatt 149400
acatatccaa tactttctaa atagtccgca aagttctcgg aatcatcttc aacaattacc 149460
acagattcag tctttttccc tttttcgtta accgatttt tagcatcatt attcttaata 149520
gcatttagtc tttcttcaat gagtttatca taatcttgtt cttcaacttc attttcatta 149580
tcttcgttat tatcattttc taagtttttca tctacaactt tttgaaggtc ttttcggttt 149640
gtatttaata attcatttac aattcctta ataattaaac tttgatcccc attaatatcg 149700
ctgtctttat tattaatatt gtattcttta atcttaatat ctgccatttt aactttaaga 149760
tccgacattg ctttaattaa ttgcatcttc attgtcttaa gactaatcag gttagatgtc 149820
tggtccgtaa caaaccttgg gtctgtcttc attctagaat tttgtgcctt acttcccta 149880 tcaaaataac cttcagaata agtatataat tcatcaatag atgataattc ttttttaagc 149940
atattatatt catcaataag ttctggatct attgaaaatt taggtttatt ttgttcttcc 150000
atatatttaa tttcacctac ctattttgta agagtatata gtgataatac tgcttcatta 150060
ccaactttac gtatcgattc accttgttgg gataatatat ttgttttgc attaatcaat 150120 tgatctgctt ctttatttgc ttcagcactg aatacccac gaattgaaag cgtatcccca 150180
tcataatcag cacctagagc agcagttaat gagttattaa taactaatga atcagtaaaa 150240
taattttctg ctactggata gtctggaaaa atgattggat agtttccag atatctatct 150300 tcaatttttc gatattcagt atcattagtg cttagcacaa caatctttga agggaagatg 150360
ctttgataat tatctactgg atatcgagta caatacacat gtttatcaga agtaaatca 150420 atagctgcaa tatacaataa atctgttatt gtaaagtttc tatcaagatc agtatgaaat 150480
acttctactg gatattcatt acctttgtcg tctttaaccg taattgcttt aaatctagca 150540
ggtatattct taataaagtt acttactaac ttattaatat ctttatcggt aaattgattt 150600
tttacattat caataaagac atcttcacct tttttattct ttacatttga aaattcttca 150660
atatggatat caataaagtc attaatatat tttacaaaga atggaaagaa taatgcacat 150720
acctgactta atggaatgcc tacggtccca aattttattt ctgtatcgtc ccatctattt 150780
gtgtttgatc taggagcaga gattactgat ctagttgcat aatcaatgga ttttcctaat 150840
agacccctat gcactaagcc gttcttacca gaaatatagt cgataaatgt tttatatacg 150900
tcatatataa ttgtctgcat ttgagattcg gtatttgttc ggacaaagct aaacgatgat 150960
tcaccatcta gactagaacc aaaacgaatt agtttagcgt atagatcatt aatctcatct 151020
acgtctgcta ttcttccggc ttttgatgtg tttggattga agtctcttaa gaatggggga 151080
ataacgataa atttatttat aaataatgta tctttatcaa attttttcaat aatatttagt 151140
```

-continued

```
ttactatcac gttgtaaact ttctgttttt ttgaatgata attttttcaaa attattgtat 151200 aagaaactta caccggtttc tccgtttaca tcatcctcaa ctagttgacc atctttaatg 151260
gtaaaatatt ttaaaccact aatacattct tcaattcttt tatctaaaga tatgattaat 151320
ttatatacta ctgggtgaaa tattctggta tttaaatcaa tatatgcaaa ctgatttgat 151380
ctcgatttag acccgatttc tccaaatatt tcataactaa acaatccatc ttcagtagga 151440
taattcgatt gattaaaaaa tattgggttt gttattttttg gtaagttatt ttgtttttact 151500 acattatcga tatctaacaa atttatttttc aaagataaac aaccacctttt ctttttttagg 151560 tatcacattt taagatataa taaatatttg tttaataata gtataagtat ttaattaaat 151620
gcaaggatct tagaaaaaaa aaaataagag aataatatgt cattatatta ttctcttata 151680
tactgatttg tctagtgaat caatattctt taatgatatt attatttata agataactta 151740
caataatatc gatatcaatg gcaaaatttt ctttatcata aatatcttta tttaaagatg 151800
tatattcaat acatttactg atgatatcat ctttactgta taatgattta tccttattca 151860
ttacaatcca gatgatatct acattatttg aagtattttc aaaatttcca ttattattca 151920
aatcaattaa catttttaaga ataataacaa tgtatttaat aaattcattt acaatgtgac 151980
cattagtaat aaatatcatta ttataataat gttgttcgta tatttcataa ctttcattag 152040
attcaatttc attaataaca atctttctag ggtttagtac ttctagtgaa aatacatcca 152100
ataaaaattc tagtctttta tttaatacat gccgattaat tcttgaattc tgttgttgat 152160
gattctgaag atcaatatta taatattgtt ttatcaagtt ataaataata tctacagagg 152220
tagtatgaat tttatttctt gaaaatttttt cattttttcg atatttatat aggtaactta 152280 aaactttttgc ataactgtca tcaacaccag tcttattttt acatacaata tcttttaatt 152340
cagatgagct aattgttaac gataacatat aatatacccc ttttctttat agtttttattt 152400 taatcaatac aaaacactta gacatatcta aatggatatc atgaatatta tactcagata 152460
aggattttac aatatgatct acaataatgt gcatttcatt atcacttaag tattttttttat 152520 tattttttct agataataga ttaatcttta atgtaaataa attttttatag aaatattttttg 152580 aagatttaaa taattctgta ttaattgatt cttctaaata ttgcacataa ctattattta 152640
ataatttttt agtattaact gtcatatata tttgatcttt attaaaatta attttattttt 152700 taaaatcttt aagtttcata atcatagaat aataaatcca tccattcgta tttttttatttta 152760 atgaataaaa tactcaacta acataagagt tagttgagta tatatcctag ttatttagta 152820
aatatgcagc ttgtaaagta tctttatcaa gaccataatc cctattaaag tctccattat 152880
taacactaat tattaaaatta gaaggtttta tctttttcaaa ttctttaact tgttcttttttg 152940 aaaataatgc aataatattt aatacgtcac catccatagtc tccacctaat ccggcaagaa 153000
cattattaca taggcttagt gttttatccg aaatatcctt tttaactttg gcaatattca 153060
ttaataagat acttgaagtg gatattgaag gatttcgatt tagtataata tataaaccac 153120
cttcagtttt attaatcaat tcttccatat aacgatacat ttttttttatta aatgtatttt 153180 tagtatctat atggaatttt tcagcttcca ctaaagaaat attctctgaa gttgaaataa 153240
gattaattaa tggacccttta tataattcgt gaaaagtaat ataattcata tatacttcat 153300
ccattttaca taatgggtct ggagatataa cgtttcttgc agagtagtta attcgagtac 153360
ctaaaatctg tttacgaatt gttcctcttt tacctttaat attattttta ataatactat 153420
ctacaatttt taacacgtca atctgtactc gatactgtaa ttttaacttc tgaattttaa 153480
tatcttcata gatttcttca tcactattga caatatcttt taacatattt gtatgattga 153540
```

-continued

```
ttaagaaatt gtagtcatta tttatttcag aaagccgaaa tagattttct gaagcaatta 153600
actgagccgg tctcaattta ggactaaata ttggtaagca gtcaataaac aataatcctt 153660
caaaatacca acggataata cgtttatatt ctaatgaatt tttctgtttt ggatcaacat 153720
acttttggag taattcaata aatctttctt taaattcatc caaaccgata ttccgatcct 153780
caaattcttc atgctcacta ccttcttcat cttctaaatc aacaatattt ccatttgcat 153840
caatacgctt attatacata atcatatcaa taaatttagt accatcaaat aatttgatta 153900
atcgatcaaa cataatagga ttaactacat agttattctt aaaatctaca taaccgaagt 153960
tatcaatatt atcccttttca acttcaggac catagatttc ttcagaaaat attccatcaa 154020
tagaatattt cttttctttt tttgttactg gttcatggtt agtaataatt ttatcttgtt 154080
caattaattc cctaaaatcg ataatccgta ctctagtcaa aagtaatcaa gcatcctttc 154140
taacaccttt taggctttta tcatattcac gattaatcat tacatccaca tatgaataat 154200
tcttagcttc cgcttcagat atctcttctt ctgagaatcc tgagttgtag attgttcttt 154260
cttcaacaat attatcaata atatccttttt tcttttttatt aaattttgta ataatcttct 154320
gatagaagga ggttttactg ataaatgcag agatcactgt aaaaacaatt attgtaatca 154380
taatacattc aaaaataata gtaaacattt ccatcaccat tctttattta ttttttttatt 154440 aatcatcata atcagttaag aaaccttcaa tatcaggttt cttttcaaag aagaatgttc 154500
ctgaattatt tggatcatat ttcttacaga aaggtactac ggtaaaagaa cttccagggt 154560
ctcctgaact agtacttact aaatcgatct ttccaacaaa gcttggataa atacccctag 154620
cgcttactga taatccatta gctgttgcag attgtggacc ctttacagaa cctttttagat 154680 aacgagtaaa tagatccata gaattaacat tatttgagaa tcttactaat tcgctgttag 154740
gaatattatt tactaagtaa tcttctttaa tattgctaaa tagtgttttt aatttactta 154800
cattattatt ttttggtcca actaagcgat atccgcctttt ggataatttt tgagttagat 154860
cataaaatag atattcatta acccttaaac gtttattgga taaagagtga ttatctactt 154920
ttaaaatatt gtaatagttt gtaatcatat ttctaacaat cgcataaata tcttctttat 154980
cttctgaacg taatcttaaa ttggatcgag ttgtattatc tagtaaacgt tcaaaggagg 155040
ataagataga tatagcttta tcaaaagtca ttgaattatt atttgtaaat accgaaccta 155100
gttttctctt ccaataatca gaatcaaaag attttttcata atcaattcga ttatatttaa 155160
atagatctac taaggttgca attaatgttg cattagattt ttgatcgctt tcaatccatt 155220
ctcgattaac ttttaatgca atacttttttg tcaactggaa gaagtaatat tctggactag 155280
taatatcatg atcttcagtt ttaacgattt ctacataatt atgaatatta aagtatctta 155340
gagtttcaac tacaccttttt cctgcaaaat agtagttcat tacatttaca gttttcttaa 155400
ataatagtgt cattaacgct ctagttttta atggttcacc attattaaaa cgttcatcaa 155460
tatcagatag tacaaccttt ttaccccttaa tcttgattgg cataaacatt gttttcaata 155520
caataattcc atcattagta cgataatact cggagtcatt catttggaat actgggaaaa 155580
attcatttcc gttaattaag aagtattgtt gatctaataa ttcagggaat aatagtttaa 155640 tttcttttttg gattgtttct tttccatcag aaagttccat tgtaacttta attctaataa 155700
atctagattc ctcgatatta acggttggat ggttaatctt tctagcttta cctttttttat 155760 tttcttttctt ttcttcagta acttgttttc tttccttata gattttccga tctgtatcaa 155820
tttcacattt aacaaaacga ataccttcta caaattcaag tcctttaaaa acatcttcaa 155880
```

-continued

```
ctaattttgg taagttttct ttagatctaa agaagatcac ttcctcatta aatggagctt 155940
tttcttccat tttattttga agatcattaa agagtttttct tgacaagttt ggcacaaaca 156000
aacaactcca atcaaaattt attttataaa tttttatatc gtataaaaac aattaactat 156060
tattagataa aaatttgttt ttatataaaa ataaaaattt aaggatgtgt atatactatg 156120
ttgagaaacg gtgaagaatt ttttaatgaa tggtctgaaa gatcaggaat acctaaatat 156180
gaattaaaac gtcaatggaa tattatggta gaaatggtta tggatagcat catggaagaa 156240
gattttacca aaacagtatt accaagcata ggcgcttttg aaactattgt taaacctcca 156300
tatattgcta gagatcctag aaatgaaaaa gttgttattg cacaagttag gaagcgaatt 156360 aatttttagaa tatatcgcag atttaaaaaa atagtaacag gattgttata attttcgtaa 156420
tacagatatt tatttctgta ttacgaaaat ctttttaatt gttatttctt ttaataatct 156480 gttttttcaat ataaattcta tcttcttgag atagtccatt atatatttct tctaaagatt 156540
caatatcttc attatcatta attaatacat caatatacct atctaagatt tctttaggta 156600
cattagtttt taaattattg atattatatg ataaattgat cttagaatta gtaaatttat 156660
tatcaacaat ctttacactt aactgatttc catcattact aatattgatg cttgaattag 156720
tactttcact tgtaatatta agttcaatac tttttaatat tttgttaatt atatttaaat 156780
ccaagttaaa acatcctttc tattcttata tattgtacat ttatataata tataagaata 156840
atattagttg atgaatcgag atttagcttc ttcgatagtc ataatttctt tttgcatttc 156900 cttagctttta acaatttttg aagaagtgga ttctttatct ttacaaacta caatatcagt 156960
ttttgaagat acgctacctg taactttatg accgagtaat tctaatttct gtttaaattc 157020
attatcccga attcctgtaa aaacaataac tttagattct tcagaagcat tattagataa 157080
ttcttgttta atagatttta gtttaaattc attaatcaag aatatcaatt cttcttcatt 157140
attcgagata ccgtttagta attttttctgc cttaatatct gaaaatcctt caatattaat 157200
aatatcttct ttcttaggta aagatccatt tacaaagaat tcgttaatta cttcttccaa 157260
gatatattcc ttacagaata gtttagagtt ttcaatacct aatccttcaa tacctaatga 157320
accaagaatt tgataatcat atagatcacg tttgttatta attgcattct tgatattatc 157380
tagtgatttt ctacctaacc cttcaataaa gttatcatca atactatcat aatctatact 157440
atataagtct gtgattgaag tccataattt attttcatat aatttactaa tagtagattt 157500
gtcaatacct ttaatggcta gtttatcaag atagttagat atctttccaa taacgtttcc 157560
agaacattct ggattattac agtatgcaaa ggttttgatta tcattaataa ctacactttc 157620
ttgctgacat acgggacaat atttggtaaa tttgtcagga ataatatctt tgttatgatc 157680
actatctact ttatcaatat atgttagtgt atcattccta tattgtacta aaatttctga 157740
accaatacct aaacctaatt cttccgctct tgcaaaatta tggagacttt gtttttgtatg 157800 cgtacttcca tttgaaaatg taactggttc aaaatgtact aatttagtaa ttcgtgaaaa 157860
atcacctaat tgatagctaa aatcagtaat aacacttttt ttctgttcat agggtagttt 157920
aactgcaatc gaataatgtg gagtaccttt aggagtcatt cctagttttt cacgataatc 157980
gtcatctaaa atttcaacga caataccatc aatcataaat ccatagttat atcgattatt 158040
aataacttca ttatagaaat cattaaattc ttcaatgact ttttctactg aattactttc 158100
actagtaata ctgaattctg aaccgattaa actatttgat cctaagatat taaaactatt 158160 atctcgtttta gataatgtaa tttcgaatgg ataattatct tcatcgagga atttaatatc 158220
tagagggaca agagttaaga atttagagaa tttatgagca tcgtccctac ctaatattcc 158280
```

-continued

```
agaggttgcg gatcgtggat taacataatt attctttgta taatcattta acttttctaa 158340
attatcatac gtaataataa cttcatttct aattgcgaaa ggtagtttga tatcatattc 158400
ttgtaaagga tctttagcga tgctcttaaa tacattagtg agatctaacc cgataccgtc 158460
ttttccacga gtatacgcct tatcaaactt tccatcttta aaagtagtaa ctactgaatt 158520
cccatcaaac tttaatgtaa ataggaatgt cgggaactta gaaaaaggtt taagcttatt 158580
aatcattcct tgaattactt ttggaaaatc attaatatct ttacatttaa ataatgttcc 158640
tgtcagattt ttatattcat gcttcatatt aagaatacct ttatccgttt tcggtaatga 158700
tcctacaatt tcttcaccag ttaattgtaa gtattgttga tataattggt catattcaag 158760
atcagacata attactgtat ctgtattata atacatgctt gatgcatttt ctaaatattc 158820
ttttactaaa ttatatttat catgttcttt actgtctaaa attctttttg attctgtata 158880
atccacattt ttcaatatcc acacttcttt ctatattatt atttaatatt aatctttttt 158940
ccattaatgg taatatagtt atattcactg ttataagata catttataat gtccatatca 159000
gcatcatata cttcatctat ttctttttca ttaacatata tttttccatt gtctaatttt 159060
atttcatata atccatcact tataactata acattatcta tcttttttatt ataagtttta 159120 gatttcttac catcaatata tatttcacca tcttttaata acacatttaa accattatta 159180
tatatattgg catttctatt ttgaggaaga gtttttatgtt gatgaaaaat attattatat 159240
acttttttaa ttttatttat cacatcatca caaccttatt taatcttaag atatatccta 159300
tcacactata aaaatgtgat aggatacttt ttatttatt ttatacttat taatatcaaa 159360 cgagtctttta ttattggtat attcattaag catggattca atatcttcat cacttaattt 159420
ttcgatatta tcaaaatcat ttttataatc tggatcagta ttaatttcaa cacctataga 159480
tttaaaatat gaattgataa ttttattatt attactaata gtgtctgatt tcttaggtaa 159540
tttaatgtca aaaggatttc cgagaagttg agcttttact aaattacttc tatcttcagt 159600
attatttgaa taagcatcag ttaatctttc aataggttct aaagatccta ctaatcctga 159660
attggtatat tccatttcca attaccttca catagattcg caatttctat gcagttctct 159720
tatgaacttc tctaagtttc cttagaagtt gagactatat ctttatctta tttaaaattt 159780 cttttttgttt taagatactt cccatttcgc ctgtcatttg cttacagact acatcaatag 159840
tcgttgaact ttcttccaat aattgttgga agcttagctg ctgattatcc attataattg 159900
atacttagga atattatatt tataccagaa tataatatct ttttatctca ccatatatca 159960
ttccaattat ttttttctatc tttcgataac attcacgctt atcattactg attgcgtttt 160020
agttaattgg actttaggag tttccagcaa ttaaagaaat tttcatcata tatcactata 160080
taatgcggca aaatttaccg actctaattg gagtattatt agtaacatta tcagaatttt 160140
tcatatcttt agttttttgtt ggaagattct ggaagttagt attaccttca ctacgaatag 160200 atgtttttttc aataggctca tgtttaagtc taagcatata tagttgaccc atttcaatag 160260
gcttactaat tccacttagt ttataacgat cgatattgaa tttatcacga atatctttaa 160320
gtttaaaaat atccatatca ttccagaatg gtgtaaattg aatataaatt ccattcttta 160380
tagtatcttc tagataatga tccttatcgc tatcacttaa ttgatcatat atactgatta 160440
atgatttata catattttca tcaatagact aatatatattc agataataaa ttaaacttttt 160500 cttcacgact atccatatgt tccattcgat atcgaataac ttgagacatc atattgaatg 160560
tatgttcaaa tgattgtgaa ggatttaatc ggttattaac gccaaaagga ttaagaataa 160620
```

-continued

```
tatccgctct attttctagg caagaatctt tatcaaactc ctcaccatca atagtttcaa 160680
ttacaggcat ttcttcgtcc ggaagaatta atccaataat tcctttatta ccatatcgac 160740
cagttagttt tgaacctttc acaagaggaa ttctttctaa gattgtaaat accgctacaa 160800
tacggtcaaa cactcttccc tcagactgaa atttatttgc aggatcatta aatgctgcaa 160860
tcttattata aaatgcagat aaatcactac tgatattatt tcttttacta gatacaatag 160920
gttttaaata ttctacaact tcagagtaat attttgagat agaaatatat tcattgtaca 160980
tctgatgatt atatttttga gatcgtaact tatcaagact ttcgttatta taaatatcaa 161040
tgtcaataac aataccttca gcatgtttta ctgtgtcagt agcaaagatc tttcttaaat 161100
tgacatcttt catactgaat cccatatcat tataattaat tcgacgaatt cccattaact 161160
taccatcttt aatttcttca ccaatactag gaaaagttct atatgattca tcatcgccat 161220
atagatttaa tagtacatca ttggtattta gattgatctt aactttcttt attaaatagg 161280
aagccatctt ttgagcagta ctctcagaaa caacaataga gtcttcattt gtgaatcctt 161340
tgtatggaat atataccgca ttgagatttt taccatactg aaagttcata tcttcgtcat 161400
aattttgatc tcgataaatt actttgtttt caaattcttc attttcattg atattatcaa 161460
ttacttcatt attgaatttt agtccaaagt gttctgttaa atgttttgct tctttttcgtt 161520 ctacaatatg atagagttct tcttcttcat taaataatat tgccgtgtaa ttaaatttat 161580
tcttgtaaaa tttttttaaga agtttccatc taccatcaag cttttttatat ccagtagaat 161640 atttacctac ttgattttca aaaccagtaa aaactaatgg tggatcagct tgttccaatt 161700
gaatattttg acttaaatga gaagtaaaca tttgtgacct attagagtta gtcttatcta 161760
agtttggaat gagtaatgtt tcggctaaga aatcaaattt acctttatat ttttcatcat 161820
taatctctgt taaatccaaa gtataaccac actttctttt ttttttttaat atactaatct 161880 atccattata taagagttat tatattatac gcttattgga tagattagta cttgtaatta 161940
ttaagattta tttatcattt tcttttttcga tttcaattaa attcatgtca gagtcatagt 162000
atcttccatc tgaaccaacc caaatatctt catctttatt aacgcagtca ataagagtaa 162060
caatattatc attcttggta gattttggaa ttgtttttaaa cacttgattt tcaccataag 162120
cgtcaaaagc atttctaaat tcttcattag tattatatag tgtaacaaaa tctttacgtt 162180
taaatttaac gtctggaaga gtaggaatag agtatcctcc ttgcggtgaa ccatctaata 162240
gtttattatc tttaagataa gcaaacagtg aaataccgtt agagaatcca ttaagttgat 162300
caaaaacaga attaaatgag tatcctgaag ccgaaatacg ggacttaaca attagtccat 162360
caacttctaa acctttatat ccagtttcct cttccttaac attttttaccc ggattcaatt 162420 taacaaatgt attagataaa tatccaaagg cagaaccacc tggaatagct tcatcaatct 162480
ttagatgatt cagcgaagct ttagtcttaa ctactggatt aatttcaatc ttagtagtaa 162540
tatgattaat cgcaaataac atgatatttg cttttttctaa tgcacttgag ccaattaatc 162600
gtttaatcat ctgattattg tattttgctt gtgctgttgc agacatctgt ccactcatct 162660
tttcttcttc actgatgtct ttagtataca tagcagcaat agaatctaag ataataattg 162720
tcggatcgaa ctcataaatt ggtttacctg taattggatc taatttacct gtatcatgtt 162780
taagtttatc gccctgcta agtttctctt tttcaataat ttttactaaa ccataaagag 162840
tttctgccga tattcctgaa ttaagaagat tatactttc aagaatcttt tcatcagccc 162900
acccagtaat attttttaata cgagctaatg atccggcatg ctcataatct agatgataaa 162960
tttcagaatt ttcataacga tcaacaatat tacatgcaat ttgttgaatt aatgttgatt 163020
```

-continued

```
taccagaccc ggatttacct acaatggtaa ataatttacc ggcatctaat cccatcatta 163080
attctccctt actatcataa cttgctaact ttgcatcaat ctgactgaaa cccgttctat 163140
aagtttcagt aaaatttttg gattcaccta atccatcttt caataactct tttttaactt 163200
catctgtaat taatcccata catttacttc ctccttagat atcatacatt ataaatcatt 163260
gttattacaa taaaataatt ttttatttat aataacatca tactacaaca ttcccttcag 163320
tatttttatt ttaacatatt tttgacgtaa agtggagata atttttttaca tcataattta 163380 ttataaaatg ctataatgaa gattatactt cttcattata gcatcattaa ttctaatact 163440
tagataatat taatttaaca acatcgtcag tatttatcat ttcaaatttt gacatattat 163500
caatataatc acgtagttta tcagtatcaa tcaaattaca ataatcattt cttttttacaa 163560 tgtctgtaac tatttgtcta aatctagtgt ctgatgat tacatttaca tcttttataa 163620
atgtatcaat gaaaatttt attgtatttt ttgcaatatt agctttatca acatcaaata 163680
ttttatcgat aattttatca atcttgaatg cataaaaaag taacatttca tagttcatat 163740
caggtaattt atttttttgca tacataataa atacttcgat agggtctcgc tcaatttctt 163800 cagttttttaa taataattca taaatatagt ctcggataga tattcgagat aaagcttctt 163860
gcatttgatt aataaagact gaagtgttat ctaatgatat ttttttctaat attgtgatta 163920 gttcacttgc ctgttcatca actaatcttt tataaatagt attatcacgc atattatctt 163980
cctgaattat cttaaattca tttacaaaag tcaaaaatat tcctcctttc ttcaatagta 164040
aataatcaca aatatataat atatatttat tattgaattt taagatcgtt tatatttgag 164100 atgtttttctt cttttaacatc agcaaaatct aaattaaatg tatcggaatc atctagtaaa 164160
tcattatcaa ttcctgcacc agtaagaaat tgggatacgg tatttaacgt acgcttatca 164220
ttaatgcttc ccggtaaatc ttgtaatgaa gtatatccat acattgcaat atttttatac 164280
attgtagatt ttgcgtcttg tgagtccgct ctagggctta agaattcttt taatgcatat 164340
ttagcgtcaa tagcacttaa tgcaatagtt tctaagtcac tgatccgtgc aatcttatct 164400
tcgtttgtta cttggttggt tcttaaacta cgtttactaa tatctaatga gtaggtattc 164460 ttttttcgata aggtttgtta tactgatagg taaagatata ctataaacgt attctttttc 164520
ccccagtcca aaccgtacgt gagactttca tctcatacgg ctttccatca aatttattttc 164580 attacttaga ataaatactt aataaataac tattctaatt aatgaaaatt agatttgact 164640
aagaactttc tctccactat ttattatcat agcttcatcg atacttcatt ctctcttact 164700
ccctataaat agggtatcaa acgttcccct taaattaggt atataaatgt acttaggatc 164760
cacctgttat ttataacaat acttacatat aagtataata tgacaaccta ttagtcatat 164820
tagctaataa agactacaat tttatttcgc ctattataaa tcattaaagt gattcgtatt 164880
cctatccata tacatctacc ctaaccgcta taagtattat tagcgacttc atccagcttc 164940
acacatatta attactcaat atgcatgtgg aatatcatta atagcaattc atgactatta 165000
tttaggttag tcacagctta ttcatttaaa gagttaatta tatacgcata tataatcatg 165060
caatcctcaa tattttttaca tatctttctg cataacgttt cgcacgtagt ctccttacgg 165120
gaagataacc taatggtact ggatatctag ttcttaatgg attatcttta tttccatcat 165180
gacgataata gatatattct tctaatggta cattcataaa gtctagtgtt tctttaatat 165240
ctatcagttt tggttcattt ttattcggta atacttctaa atagaaatta tcatcaccat 165300
tagtaaattt tttcatatac gataaaaaatt gttcgtcact cattttatcg taaatatctt 165360
```

-continued

```
tatacttttt agcattagaa ccagttttat ctaatttatt gaatacgtca ataatatact 165420
tttgaatttt atttcttttt tgtttattat tagatacttc ttcatttaat tctaccgatt 165480
cattgagatt atcttttgta tccatataat atactgataa tattttaaat aaattaatcg 165540
aattatcttc agaaatatca tacttcttaa tgtttttatc tttaaaagga aacttgtcaa 165600
tactgaattc aataatcttt agaccatcta gatcacggtt atcgtactta tcagtatata 165660
acttagaaag ataatttgaa ctaatttccc taatttgaga agtatttgat aatcaatag 165720 attcaggata accaaactca ggataataat taaataatac ataactatca ttttctttgt 165780
aataaggaag actaatataa tctattaatt ctttattttt ttcattatat agacccatta 165840
tcataagttt tgtaaaaggt tgaatgtttc ttagtattaa gtaaataata gtattaataa 165900
cattactatt caacttgtga taatcagtaa gagtatcact atacttgatg atattgaata 165960
gactcatttt tatactacta ttataacttc gattattatc attaagtata gattcaatat 166020
acttaatgat atcttcttta ttattaatat catttctaaa tataatatcc attatataat 166080
cattaaaatc aatttttgta atatcaataa ccgaatcctc atcaatagat attactcttt 166140
tatataatga tgataatggg tatcttacaa taccagaacg ggtatattta gtaattgata 166200
ataatgaggg atgagatatt aactgatcta attttataga tggatataat ttactttctg 166260
aatccctgag tttaaataat tcaataccat aagttctcat aatggtcata aatacgctta 166320
ctaattgaat ttctcttata gttgttttat ttccttctgc acttctaatt attagatcat 166380
tatccaagta ttgattataa tctttaatct tatcagagaa agtattaaac tgatctataa 166440
tattaatatt atttttatca taatatatag gaaactcaat tacctctgta aacatatcaa 166500
tattctttaa cttcttttca aaattggatg taaactcaga tacttccatt ttttcatcgt 166560
tataatcaat tccaaatatt ctagaattat catgactatc tattaacgca attttactta 166620
gtctatcttt agcagaacct attaccctat caataattaa tgtaacttct aatttacatt 166680
tatcctctga aggactatta tcaaaaggta tatattcatt attatctagc attaatgcat 166740
tatctgtaaa ttttctttca ttccctaggt actcattata ttttttattc atataattat 166800
ccaactataa ttcacttcct ttatattatt cactggtata tctatatgtt tatattacta 166860
gttattaaaa tcttttatca aaaaaaaaaa aaatattaat tattaaatac atagtatata 166920
acaatttatt tgttatatac tatgtatctt ttttttcctta cattatattg attagaaatt 166980
taaacctaac cagtatctag caaacataga tttatatgaa actaaatcta caataaatat 167040
tgatacgaaa ataaccaatg ataaagcaat tacccaagat aagaatacaa ttactttctt 167100
agataaatta agattaagta atctttcttc aaatcttttt agtgtaaaat ttttcatgtt 167160
atcttctaag aataataaga ttgtaatgca ttttaatagt tcattaaaga ttcccacaat 167220
tttgttacta ccattatttt tatttactat tactgtttgt ttttccactt tctccacact 167280
cctaatatta ttattttcat tttataaatt aaaaagttaa cctatcatca ggataataaa 167340
aatatccaat gataggttaa ctcgtttttc tctatattta ataatatttt aaactattaa 167400
aaattataat caatctcaga cttttgaaat tcagctttca ttcgttttag ttcttcttta 167460
tcaatatttt tttctgacct aatagtagta cctgttggca cttttatatt agtaatcatt 167520
ttgccttgaa ctgttaggat aatatttaaa gtaatcaata taagagccaa gagcaataat 167580
gaaccaataa taaaagatga aatatatcta tctactttct ttcatcttc tttatgttta 167640 ctctggttgg atttatattt cgtactaaga ttatccattc ttattttcac ttccattcat 167700
tttatattag taatataatt tatctatatt acataatgat aatatataaa caaaatatgg 167760
```

-continued

```
gttattacgc ttttataaaa atttatagtt aatgtataat aatattatat attttggatc 167820
atagaaaaat atatatgctt tataagtata tattataaat ttgtagtaaa ataattaatt 167880
atggaggatt aatatgaaag aatctttaaa gtttaatgtc aaggaagtaa gaattcttag 167940
caaaatcgca tctaatgaat atgctaatga ggaaagtcgg tatgaaagct ttttatctaa 168000
attggaaaca tttaataact ttcgttcagg attttttatat ctgtatctaa agaatctttc 168060
agaaagtgga ttaactaaac aagaatcttt aaataaggct attgataaat atgtcaaata 168120
attcaataag atttagaata atggcagata tttattgtaa taataaattt atcaatgttg 168180
aagaattaga gttcactgga acgaacgaaa gtaacgcaag gaaacaatta actggttacc 168240
ttaatagact aacaagagaa aataataatg gtagatatac agctaagaat attaatataa 168300
tacccattaa atcccaattt caaaacaata ttgaaaatca agaacaacta aatctttta  168360 gtaatgatat taatgatgat ttataatcta agtaaatcat cattaattat ctttaataaa 168420
ttatgaaagt agtgatattt ttttggctaa attaaagaaa agcaaaagac gagtatcctt 168480
tgaaacaatt gttaaaaggg ttattgaaaa acattttctt gaaaagtatg ataaagcaga 168540
actagattta gataacgagg aaacgtatca aatcgggtta ggttctattg atattgataa 168600
atacaatatc aatcctgatg atttcgaaac ctctggaatt tattattaca gtaaagggaa 168660
aatatcttta gataaagatt catctccttt acgaacaatg aatgttaatg taggaactgt 168720
taagccttta tatgacgtaa tatatgaaat tgaaattatt tcaagggtag aaccagaaat 168780
taataattta acagtattag gatattttat taaagaatag atatggatgg tgaaataaca 168840
ttgacaagaa cttattctgg tgaagatatt gatgtttag agggtctaga ggctattcag  168900
gttagaccgg atatgtatgt aggaagttca gatgaaacag tcaatcatct tgttaaagaa 168960
gcaattgata atggtgtaga tgaatttctt aataattttg gaacaaaggt tattgttgac 169020
ttagatactg acgaaaatat tattacagtt attgatgatg gtcgaggatt acctactgac 169080
attcatccta aaaagaaaat tccaacaatg caagtattgt tatcagaagt acattctggt 169140
gcaaaattcc gtaaagattc ttttaaagtt tctagtggta agaatggcgt tggtattaaa 169200
gctgttaatg cattgtctga atatctccga gtaatttcta ttagggaagg ataccaatat 169260
tcaatggaat tctctaatgg taaagttact aaagaattta agaaagaaaa gcaaaaagaa 169320
tacaaagata tcaagcatgg aacaattatt gcatttaagc ctaatggaga atttatcgat 169380
aattatgaca aatttgatcc cgaattcatt aaagataatt tagaaaagcg tgcatacagt 169440
aatgctaatc ttaaattaat ctataaagaa aaaggtaaag aagtagctac gtatcatcat 169500
gagaatggta ttcgagacta tatcacaatt cttaataata atccttttac tagtaatcat 169560
tattataaag aagaattaga aaacggcgac ttatacgaag taacttttgg atatagtaac 169620
tcttcagacg aaaaatatcta tagttttgtt aatggattga aaactgctcg tggtacgcat 169680
gaaaccggat tcaaaatggc acttacaaac ttaatgacta attatattaa gaataataaa 169740
atgttgccaa aaaatatgca agctaaggct attacgggtg aagatattcg ttctggatta 169800
gtatgcgtta ttaatcttaa gttgcaaaaa acatcataca ggtcacaaac taaagatgaa 169860
ttatcaaacc ctgaagtttc tggtattatt aagcggatta caaattcagc agtaaaagat 169920
attatggata caaaccctag tgaatttaaa aaggtatgta gtcgtattat tgattttgct 169980
aaaggaagaa ttaatgcttc taaatatcgt gaaaagattg ttaaagatac gaataatctt 170040
acattaagtt ctaaattttc agattgcctt tctaaggatc cttctgaaag agaaatcttt 170100
```

-continued

```
ctatgtgaag gagactctgc aagctctgga attaaagaat tcagaatctc tcaaactcag 170160
gcagtattcc cattaaaagg taaacctaag aactcttatg gtctttctag taaaagttta 170220
ttaggtaatg atgaatttaa taatatcatt aagattattt ttggtactaa tgatattaaa 170280
aatattgatt atgataaagt ccgatatcat aaaatcatct ttactgcaga cgcagatact 170340
gatggattac acattaattc attattaggg ttattctttt atacgcattt taaagaatta 170400
tttgatagag gatatattta tatcgcaatg ccacctaaat atagtactta tgataatgtt 170460
tctaagaaat ttatttactt taagaatgat aaagaattaa atacttttaa attcaataac 170520
attaagaaac gtattaagct tagtgatgat agtgaattta aattaaaaga ctttattaat 170580
aatatgagcg aatatcaaaa tcagtacaat attgttaaac agaataataa taatatttcc 170640
gatagcgtta ttgatacatt cttattacat ggtcatgaaa gtaattcctt tattgaaaag 170700
atccttctag ataggaataa ctacagattc agtaagaata aaaacggaaa tattattgga 170760
atgcacgata atgcttggca tgatattaat attgacttat taaataatga tattagtcgt 170820
attaagaaag ttatgagcat tagcgacttg tttgaattta cagataccaa aacaaatgaa 170880
atttatagta atgtaacatt aaaatttctt atggattata tcaatagtaa atttacgtat 170940
aaacttaact attttaaggg tcttggtgaa gcaaatcctg aagaattgtt tgatactacc 171000
attgatcctg aaaaacgtga tttaattcag gttaggattg atcctgaaaa tgaagaatca 171060
acccaagaaa ttacagatat attctttaaa aataattcaa ctcaaagaaa agaatatgta 171120
aatagttggt ttaatattaa ataaaatttt atacaattcg ggtattactt agagttaatc 171180
ccgaattgta taattaaatt aaaataaagg tggttcatac ttttggctat tattcaaaaa 171240
caacttgtaa atattcatga agaaaatatg gaagaatact ttgttgaaat acttactagt 171300
cgttcaattc cagatattaa tgattcatta aaacccagtc aacgaagaat tatttattct 171360
atgaataaag atcgaagatt tagtaattta ccatttacta aatctgcaat gatcgtaggt 171420
tctgcattaa tgattcatgc ccatggtgac gcatcattat acaatactgc agtaaattta 171480
actcgtaaat tttctaacat gcaaccatta gttgaaggtc acggatcttt tggtaacgta 171540
tatgatccta gacctgctca aatgagatat actcaaatgc gactaaataa gtttagtgaa 171600
gaagttttac tagataatat taatgataac tgcgttgatt tcgtaccatc ttatgatgaa 171660
tctgaattag aacctgtcgt tctcccatca aaaattccaa tgattcttat caatggttct 171720
tttggtattg gtggagcata tcgttcattt attccccctc ataatccaaa aaatgttatt 171780
aattatacaa ttgattatat caaaaatcca aataaatctg aagaatcatt aattaaagat 171840
aatgaattat atccgagttt ccctctaggt ggtattttag ataataaaga tattattaaa 171900
aaatatacga ctggtgaagg aaaattggtt ctacgtgcaa agattattaa ggatgaaaat 171960
aaatctactc ttaccattgt acaattacca tacatgaaaa ctcaagatat cattattgaa 172020
aatatacaag aagcagttaa aaaagaatac attaaagata ttaaaggtat tgataatggt 172080
tctgagcgtg gtaagattaa acttattatt aaatgtttta agggaacaga cctaaacgta 172140
gtagaaagtc aattatataa gcataccgga ttgcaaagta cgttaccatt aagctttgta 172200
ttagtagatc aaggtgactt taaaaaatat aatggaatta aacatattat ttctgattgg 172260
gttgaattta gaagaacaac tattcgaaga attaaaacga accttattag taaacttgaa 172320
agaaggattc atatattaga aggattacta aaagtattag atccaaaagt attaacaaaa 172380
cttattaaat taattcgtga aggaaatagt cgtgatggaa ttaaactaag tattcaagat 172440
aagtttgatt tatctgtaga acaagctgaa tatattgttg aaatgaagat ctatcgacta 172500
```

-continued

```
agtaatattg gtattaatga tacaaaaaat gaattagctg ataaaatgag ggaatttgac 172560
gatcaatccg aatttatgaa agatcctagt cgtatcgata aatatattat tgatgaacta 172620
caatcaatca gtaaatctaa aaatcttcgt aatgactttg aaataactac ttatgatgat 172680
aatatgaatg aattggatat cgaatccctg attccagacg aaaattatac gattgttgct 172740
acaaagggaa actatatcaa gaaattcatt tcagaaatga aagtacaaaa acgtggcggt 172800
aaaggaatta atatcggcaa acttaaagat aatgatattc ctttaggaat tatctctgct 172860
aatagtaaag acaatatttt atttattaca gataaaggta agatttataa ctataaatgt 172920
tataaattac caaacgcttc tagtattaag acgctaggta ataatatttc taatcttatt 172980
aaaaaggaaa agttagtatc gattattagc gttactgatg atcaattaaa taatgataaa 173040
aattgcttat tagtaagtac tattggtaat aatattaagt tagtatcaat gaccgaacta 173100
aaaagtatga atgaatctgg attaatttta tctaaactta aagataatga tgaagtaaca 173160
agtgttaaat tagtagacat tactgaatct agtaatgtaa ttggtatcac ttctgaaggt 173220
atggttattc gtacagacat ctcaaatatt ccagttatta aaagaactac acaaggtagt 173280
aacctattta ataataaata tattacagaa agtaataaac ttgtatcggt atctctagaa 173340
acaaaaaata ctactggtct gtatattatt actaaatcag gattatctaa acgtgtaaag 173400
attgatgaat tcagtaaata tcctagaagg gtaaaaggtg taatggggat taatctaaaa 173460
gatactgatg ataaagttgt atctatggaa acttatgaaa atgtagatga ccataatctt 173520
atcattatct caaatcagaa agcaatttcc atacctctta gtgatatttc tgagtataag 173580
agacctgcaa aaggactaac acttcagaag cttgaagatg acaactatat tattgattca 173640
tgcttaattt agtattagag ggtaagccat tgtttattga tggcttatct tttttttttt 173700
ttcatttata tataaaaatt aacctttttat ataacaatat tatatactat tgaaaggttg 173760
tggaaaataa atggcaaaag aacttatttt agatgtttct catcatcaag atcccaataa 173820
ctttaactgg gctaaactta aagatgaaat cgatctaata ctaattcgtg tacaatatgg 173880
atcaaatact attgaccgtc aatacaagaa atttgttgag cttgctaaaa aacataaaat 173940
tccttttggt cactatgctt atggtgtatt tgttagttct aaagatgcag tagttgaagc 174000
taataacttt ttaaaacgtg gtgatagtga agctactgta tggatttttag atgtagaatc 174060 cgacactatt gagtcatgta aaaattctcc tctaggtgaa gcttctcaag catttatcga 174120
tactcttagc aaagccggaa agaaaactgg tttttactat gaacatcgtt atattggaaa 174180 atatggtttta gataatgtta aagctgattt ccgctggatg ccacgctatg gaaaaaatga 174240 tggtactttta tcaggaagtg ctaaacctga tatttcttgt gatttatggc aatatactag 174300
tactggtaag ctaaaatcat attccggtag tgctttagac ttaagtattc ttaatggtaa 174360
gaaggatatt aaatacttta caggtaaagc atcatcaaat aaaccatcca ctgttaaacc 174420
atctaagcct tctaaaccta gtgattcaaa agatactgta aaaactacta gttattatgt 174480
tactgcaact aaacttaata ttcgtcaaaa acctgatgct gatagtaaat ctttaggaac 174540
attggatcat aatgatcgtg ttcaagttat ttcaattagt aaaggttggg caaaattaaa 174600
atccggtagt aaagaagtat atgtttctga aaaatatatt tctaaaaaag caaatcaaa 174660 taaaccgaaa ccagtaacca ctaagactta tacagtcgta aaaggggata ctctttctgg 174720
tattggcaaa aaacttggaa aagattggaa agcattagct tctaaaaata atattaaagg 174780
tccagcttac gtaattaaac caggacaaaa aattaaatat taaatatttt attcaccata 174840
```

-continued

```
caaacagatc attatattta gtgatcacat atgtttgtat ggtgatcttt ttaagaaaga 174900
gggtttgaaa agttgactaa acaatcaata ttattaaata gttttgaaga aaaaattgaa 174960
caggcattta aaaatagtag taatgtaaat aaattagtaa aaattgtaag tcaatatatt 175020
gataaaaata gtgatatatt aaatcataat acacctacat atcgactagt gtttgctcgt 175080
gaaggatatg atgctgaagt tatatatgat atagttaata tatatcctga agaaattaaa 175140
gaagttattt cacaactaac atttattcga aaagaatgga aagtaaccaa tgaacccttt 175200
tcggtattaa tgactttaat tattcgatat tttcatttaa aaaataatcg tagagcattg 175260
caatctgcaa taatgtatct ttcattatca ttttattcat cgttacattt tagatcattt 175320
agatatgaac cgaacgataa tattatgcag tatacaatta accgtgtaag taataaattc 175380
tactttaaac agtacggtac agtatttaaa gcacttaatg ctactgctga caaagcagat 175440
atgaatctta aaaactcttt aaaaaagaat gatgacgaat taattattgc atatatgaca 175500
tccctaagaa gtcgtcttgc aaaccaatta actacttttg cccaagagtt ttataaagac 175560
catgcagcta ataattattt aaataaggta tcggatgttt atgatgacga aaaccatatt 175620
gaaaatacaa atgtttctgg aattgtgatg tcacaaacta gtaaagtatc tcttaacttt 175680
tatcaatcta gacttaatga aaaatatatt atgatatctg catctacttc taaagttacg 175740
gctaatgcag taagaaatac attagaagat gttaaggaac atgaacgaga aaaagtggaa 175800
acgattattc gtaatacaat atcaatatat ttaaatgatc gaaaaaattc ggtaaactca 175860
atcggatcac agaaatttat caattattgt attggaatat atacaaaaag taatacaaaa 175920
gaaaaattgg tattagaaat aaaatcaata ttaaactatt tcttaaaaga atactgtgat 175980
aaatataaca gtactgatag ggaagctact aagaataatt atcgtaaagc tgtatttctt 176040
tactttatat tcttaatcag tgcaaataac taaaaaaaaa aaatattaaa gaatatatcc 176100
atataaccaa taataggtta tatggatata tttttattgc ttatttaaat ttcttcagta 176160
tcccttttta ttaattcatt tactttttct gatataaata tagtggatat tcccattgaa 176220
atcattgtaa tcagcataag tgttaataac gctaaaatta aaatttgcat aataatcatt 176280
ataaccatcc ttttaaattt tatttttcaa ttacagtact tgtaatatta ccatcagtat 176340
cgactccagt cattacagtg tatgtattaa ctacagcacc ctctgcaaat acgccatcag 176400
ttcctttaga ttttacaaat acaatgtatg tatgttcccc atgaggaccc atttgttcat 176460
tgtcttctgt aatatcataa tataaattac tagtattaat atttccatat tttttagata 176520
caattgaagc tagatcttca ttagataatg ttgttgacat atatacttgt tgataattat 176580
ttagatcaac ttttttacta ttttttactt gttctttcat ttcgcttaat ttactttgtt 176640
tataatctac tttatcaata gataatgttt ttgatttagt gttatattta accgttttat 176700
ctttaatatt gaaaataaga tttccatttt tatcatcttt agattgatat ttgtcaaatt 176760
tatcattcaa tactacatta tcatctacat gaccgatttc aacgctagta taactaccta 176820
atactaaatg atctttagtt aattttacat atccttgagt atcttcatta taatattccc 176880
cagtaactgt attgatatct ggagtctttt cttttttaat tgttactttc ttttctttt 176940 tcttattttc tttagaagga gttttagttt caatttct aacgtcatta tctttcttta 177000
caaaagtata attggttgac acaatcccaa caaatattcc aagggcaata gctacagtaa 177060
taattccagt tagtattaat ttcttttca tgttgatcca tccttttctt ttttttttta 177120
tttaaatgtc taataccgaa tagctaatcg atattagaca taattgaaaa tttattattt 177180
ttattaattt ttttattaat taaattttga attttaataa cttctttttt aaattctaag 177240
```

```
tttctatcat ctataccttg gataaccttta tcaaattgat tatatccaat aatatttaca 177300
tatccttcta gaccagaacc ttttatatcc ttataactgg atataataaa tgattttgca 177360 ttactttta catataaatt tgaattatat gaattattag tttttctaat tttaatatat 177420
gatgatacca ttttcttaac ttgtttttca ttcacaaata atactttata tttatcattg 177480
atatatactt cttcaggaat aattcttctt tctaacatgt atggaacact tttattaaat 177540
gtaatttctg atgtatcatt attataaata atattatcat ctttacgaat attaatatat 177600
ttatcaatat cttttacagt atgaactgca gataacttat cgaaattaat atcaaatttt 177660
tccatataaa tataaatatc tagttcaccg ctaatatatt taccgttatc atatgtgatt 177720
atagatacgg tagttttcgt agttccatta aattcagatg tttcgatatt atgcgtatta 177780
agaattatat acttaagatt attattatat aattttttga tctgtaaaaa taagtcattt 177840
acactataca ttagcataat agttaatacc aacttccatt attaattttt aatactagga 177900
taatatctat taatttagat attatcctag tgatatttta ttaatcttca aatacaacga 177960
atccgtagat attaattgga tcttctactt cagtaattac actaaatgta tttccattag 178020
caccaccatt atcttctact acataaccac tgtgacccat cacttcagta atattattat 178080
cctgtagttc tttcatctta ccatcatcaa aaaagtcagg atcaatttca tccacccta 178140 atgtataact ttctgaaatg actacatcta caccatacac ttttttaatt ttttccgtta 178200
atttacttac gtctaatgac ataataaaca cttccttatt atttatttta tttcatgatt 178260
ataatatata tttgtaaatg tctttattac ggattaatcg atattctttt ccttcaatag 178320
tatttatatt taatgacata ggattaatat gtggatgtaa tactacacgt ttataactga 178380
atacctgatt cataagttca ataatattgt cagcatcaaa attatcgttt atatattcaa 178440
tactgtatat aatattttta tgcattgaaa catttaaacc aacatcaata ttattcttat 178500
ctaaatattc tttgattaga ttaagtctat ttacgatatc atattggtct ggaaaacagt 178560
tcattaaatg gcttgccctt ccttgaatat tttcttcaat tatcataatt tctttatttt 178620
gttctattat attatccaac taattcacta ccttcttta atatatttga taattcttta 178680 taatatttc cttccaatgt agtaataata ttatcatcat tgtctagaaa tattaatgag 178740
aatatctggc aactatttct tgcaataaat aatttattaa cttttcacc tttttctaag 178800 aatgtattaa gtttaatatc ataatactta taataaagac ttcgcataat ccaaccaata 178860
tcacgttctt cttgaatata taatgtatcg tcataatctg gaataatatc taattcatat 178920 atttttctg aatcatcata attgtatgaa ctaaacttat gttcactatt aattaaggta 178980
tgtggtctat caaaataaca tttatcctct agtattgtac gattaatatc attacgtaaa 179040
tatcctaaga atatctttt ataatgagta ttattagtaa tccaatccga aataatacta 179100
aaatcattat tatttaataa ctggtttgat tcaatattat ccattattaa acaaatatct 179160
atagtttttg tttcttgatt gaatattcca atttcccata caaaactaaa ccagatcttt 179220
ttacccatat atccagtcaa tattcctgca agaggattct ctagagatat ttttactaaa 179280
ggtgcagcca atccattagg agtgaaacaa cattttgttt taacgccaat attcattatt 179340
tcatcaacat ctttagaaaa gtaaataaat ttattactat gattattgga tatattcatt 179400
ttagattcag atacattata ttttgtacct gcacgagcca ataatacatt attgatatat 179460
ttattcattt ccttataatt taggtcagat tttcgaatta cttcataatt cataaaaggt 179520
aataatttaa taaacttatc attattatat ttagataatg aactttgaag aaaattatat 179580
```

-continued

```
gcttcatcaa tataattact atttactttt ttatttgtaa tatatttatt agtaacttta 179640
ttaggaaatt cactaacaaa tcgatgaatg gatatatta tgactacgca tttatttaaa 179700
atattcatta actgttcata tgaaaataaa ttaaacatac gatataaacc atttttcttt 179760
ttatatttaa caaattgtat gtcaaataat tcaggttcta atttattatc aagattatta 179820
ttgtaccagt ccttaataag ctttatcatc ttatacattc ttttttttacc aaacttatca 179880 tgcaaaaaca gtatttcatg ttctaattta aaatcagtaa ttgaagcacc aataccaata 179940
tttaattgat gtaattttc aattatttta atttcattat agatttcact gtcaatttga 180000
gaaagtgaaa gtacatcttt atataaggat gcaatatatt cttcatatag tacattatta 180060
ttcttcaatt ttttcatcac cacgctttat agattcaaat atattaatat acttatcata 180120
taattttcta aattttccag tttcatcaat atgcaaatag tatgacatct taccaagtaa 180180
ttcataatca tcataataac aagatccggt tttcatatat gaatataagt tattacgcat 180240
atcatcatac ttttctgaac ttaatgttaa ttgattttta tgatttatcg taatcccagt 180300
aatattacgc atattcccctt taagatagac agttttacta tcattaattt taaatttatc 180360
attatatatc ttgaatgcct gattacatat cttaatgata aattttttat taaatagttt 180420
attattgtca atatttgttg aaaaagtaat atcatccgaa tatgaagaac aaattattcc 180480
atatttatgg aatatggttt gtatatgatt aataatatct accataataa tattcgatat 180540
tacgccagaa actggattac ctagaaacat tttatcattt tcatcaacaa aacctttctt 180600
tatagtatcc atatatttat cagtaacgcc atggaataat agtaatatga atctactatt 180660
aattaatttc caatcaatac taggaaaata attagatata tctactttaa taatatattt 180720
attattaagg tgcattaatg cattatcttt tatagataca ttttttcgat aagccataat 180780
atttggatat ttcaagtttg atatttttct atctaatctt ttatcgagga tcttagaaat 180840
ttcttttaat gtatttttaa ttttttatatt tggatcaata acttcacgtt ctttaccatt 180900
tttttctatc ttgattttct aaaataattc aatattattg tcctctaagt ctttaatgat 180960
acaatataac tgaattattt ctagagacat tcttcttttt aataataatt ttatatcact 181020
ggcatattta cttttaagtt tataaattag atatttacta ttactaattt tagagttggg 181080
atataataat atatatcctt tacttactga tacaagaggt gtagatgaaa aagatctata 181140
catactaaag aattcactat attccctcag ctcaatagaa ttctctaata aatatttttt 181200
actatagtta aaatctatac tgttggatgt cttataataa ttcataatct taattaataa 181260
gtcataacta tccttaaata gtatattatt tagctgaact aacttttttt ctgaattatc 181320
aaatcttgat attattttaa tatctttatc atatggataa aagatccctt tattagttaa 181380
aattcttaat ggattcttac taattattaa taaatcattc aatatttatc ttcaccttttc 181440 ttttattgt tttcaaaaaa atttaaaatg accgaacatt ctttatacta ataatgtata 181500
aagaatgttc ggctagtata tttttagatag atgtatactt ttactactca aatataataa 181560
tacaaattac gttagtacga atatacagta taccgcacgc gctgagtgcg gtatactaac 181620
acgcaaccga aatctatgag gtgcgtgtta gtataattaa tattacagag aatagtgtta 181680
agtgtttgaa tgcatattaa cgatacgtta atgcttctca aatattaaat gatatattga 181740
gaaaaactaa tattatattg atagcttaat atacatctat taaaaccaaa attatattat 181800
attatttaca taaaataata attttttatt atatataaaa tcaaaaaaca ggaatttatt 181860
gaccggggtc cgaataatgt cgattttatcg catgaatgga cccgaagcaa taaattgcat 181920
gtataatgga aataattttt tgactagtga cgattacatc acatattaat cattttatat 181980
```

-continued

```
ataatatatt aacttataaa ttgtaaaatc caagaaattt atgaaaccgc agctcacgtc 182040
ccgagtaatt tataactcgg aaatgtgagc tgctggtttt actaaatgat aatgatagag 182100
acttttttga ttagtgacga ttacatcaca tattaatcat tttacaattt ataattacgt 182160
aaattaaata atattttgat ttactgatta ttaatcagtc taaaatattc cttcaatata 182220
atgatatata cttaaaattt aagtaaactt taaaagcata tatttgagaa ggatacttat 182280
aattaatagt aaattgtaga atctaaacaa aagaattcag cacttcattc gtacctgacg 182340
taactagtaa ggcaggtacg gaaaggatgt ggaattactt taataatgat agaaactttt 182400
ttgattagtg acgattacat cacatattaa tcattctaca atatacaata aatattaaaa 182460
tttaagtaag atttaaaatc agtgaaaaga tttgtgagat gtcggatcgg atcgagaaat 182520
acttgtatga agcgatcaga tactctgata tcaaacaatc aataaaatac gacatatatt 182580
gattagtgac gattacatca catattaatc attttatatc tacttaaatt tataaattaa 182640
taataatttt tgcatcttct ttaatattaa cactttccgg tctagaagtt tttagagaag 182700
ttctatcatt aaatcgagta tctttaataa attctaatcc atcaatatta attctttttca 182760 taaactgttt agaattttca ttaaatgatg atgaaatata tttaatgtca ttatcaataa 182820
taaatttctt tagatcttca aaaatatact taatacttga ggtaattttt ttattaaatg 182880
gaattacaat gtcttcaata tacaataatt tactatgggt atccgtatta aagcttctat 182940
tgttaaattg aacgctctca tttttccggat cataaccata aatattagat attaaatatc 183000
cataaatatc attgttatca ttacgaataa tatatgatgg agacttcatt ttcctagcaa 183060
ttttctttaa ttcagaaata tcgctatctt gtttccaaac attctttttca acgtataaca 183120 ttctattgaa ccaacccggt gatgcctttt caataataac ttcactatat ggagaatatt 183180
ttttaataat atctttatta tcagaaccaa tatatttaat attattttta cgatctaata 183240
ccgtaaatac atatcttgag tcgtcaaatg atgaatatct attgaagtta ttttcataac 183300
aaattagccc ttcactagaa gatcttaatc tctgagtata tgaaacttta taattactat 183360
taatatcatt acgtaaatat cctaaatata tttttattgta gtctgaatta atatcaagcc 183420
agttaataat atattcatat tcattcatgt ctaaactttt tgacgattca atattatcta 183480
gaattaaatt ggtttcatat gatttagtat cttcattata ttcaacaatc tcccatacaa 183540
aactaaacca cgttttagta tcaaaaacgc cctcaagaat ccctgcgatt ggactttcaa 183600
tagcgggttt taataatgat tttgcagcac cgtctggtct gaaacaacat aatgtacgga 183660
aaccaattga attaatgtct actttttctt tagtaaattt aatcatatca ttatatttac 183720
tatcgtcaaa tagcatttca ccattagaag tttccccata ggataatcct ttttttgcgt 183780
tatcaataat attaacatac tttccttgat cactaatatt tttagattcc ctaacacctt 183840
gataattaat atagtttaat agcttaagaa agtctttact tttataaatt cttttaatat 183900
atgctaatat cgtatcaata tatgtttcat catcatccag tctttctatt gcagtctttg 183960
gaaaattctc gataaagtta tgaagatcta tttttatttttc agaattaccc ttattatatg 184020
catatgagac aaaattaaga agtttagttg cattatcata tgagattcga attaataatg 184080
aatttaattt acttccataa ttactatttt tttctttaag atttgatata gtaaagttac 184140
tagtatactt atccttaaac attttttggat taatacctaa atgtgactca gatataagat 184200
ctgtaatttg gtaaacatcc tttaattgtt taacaggttc tactagattg atattacttc 184260
ttaaatcatt atttaatttta tttgttattt ctaaatccat attaaaattca tacttattaa 184320
```

-continued

```
tgcgatcact gagaatacta tcttcgcatg ataacattag cttcataata ttgattgctt 184380
ttttctgact gttatataat gcggatagat atattaatgc actagtaagt ctttcactat 184440
tgattaataa aaattctgga ggaataactc taaatcttcc aatgtcatgt aaagaagtaa 184500
tattatttat tacctgtaat agatcagaat tatccattgt atagttaaat ttagaacaat 184560
agtctagaaa attagagaat atttcattta ttcgtttaga taattttttca tcatctatat 184620 tattgtagtt gtcatataaa tacatattat gattcacttc cttatttatt aatcaacttt 184680
aggttcatta attaattttta atttaattaa cgtattttga tattcattta cgagattttc 184740
cattttatta gtattatcga tataacgata ataactaatt ctacctttaa gttcattaaa 184800
tgtcattgaa atattattaa tattattttt attcttagat aatttaaaga aaatagtctt 184860
tagtagtcta tacattttcc tatctaatgt acattgatca ttgtgattaa ttcgaatccc 184920
tgtaattctt cttttgttat tcgacatttt aatagttttt tcatctttaa tagataaatt 184980
actataatta tatacttcaa atgccttatt aagaatgaac ttcaaatatt ttctattaaa 185040
gaattcactt ttctcgtttg atgaaaaagt aatatcatct gcataaatag agaatgtaat 185100
accactatca attaatacat ttttaagata ttttgccaca ttactcatta acaagtttga 185160
taatgatcca gaagcaggat tcccctgata taatccacca gtctctggat taataaagat 185220
ttctttgaat aacgtatcca ttactgaatc tttattattc ttcttcttaa aattttcttt 185280
acctaacact aataatttaa agtacttact aatatcttca tatctacaat tatcaaagaa 185340
tgaagcaata tccattttaa taatatattt attatttta tgaactaatg cgttatctag 185400 tataccttt ttcttttgat aagcaaataa atgtttttca acacctttat tagataaattg 185460 agtttctaac attccattaa agatattatt aaattttcta ctaatatctt taatatcatt 185520
atgtggagca tagatatctc taattttttgt accttgatta atcttgaaat gttgatataa 185580
tttttcatta ttattctgaa ttaatattct ggttaatagt aactctagta ataatggttt 185640
attatttggt tgatctggcg atatacttat atctaataaa tatttaatca ttttaatcat 185700
ttctttatca tctgtgattt tataaatatt atatttattg tatatatcat ttgtatttgt 185760
aataatatag agataaccat cattcatttc aatatatcta tgagatatat tgagatttct 185820
ataggataat tttatactga tattattaat aaactctgta attaaagttt tatcataagt 185880
aacaactggt aaatcgggat atccttcatt aatacaaatt tcatcatttg agagcagatc 185940
ataagtctta ataattttttt ctatattttc tagatgaatg tcattaaatt cctcgttatt 186000
ttcaaattta ttatttttctt ctagatatga tatatctttt attgattgaa tcaatttatt 186060
acggatatta tatttaacta atttagctaa tacctttta tcagaaataa tattcttttt 186120
cattcgaata tctatttctg atacaatctc tccatttata tcgattaata cattatcgat 186180
taatattagt gatagcaaat actgtcacac ctttccttta attattaaat tattactaca 186240
taaatttact atttaatatt cattatatga tcccacctat ttatttatt ttacatttta 186300 ataatatata aataaaattt aaataaatat tcccgatatc tctataatag gagatatcgg 186360
gaatatattt tatttagtta cagttacgtt aattttttctt ttcatggaag taaaagattc 186420
aggaacaacg gtaataattg tttcaccttc acttacgcca ataagtttag atggattatt 186480
ctcatccact ttaacgagtt cttcaccttt ttctagaatt atcagaacct tatcactaac 186540
gagattatca ggagtcatag ttccgataat atctttactt tcgccttctt ttatagtaag 186600
atcttcatct acgctaaaac tttctggttt ggtaattcta tcgttaatta cagatattac 186660
gtctatagta tcaataggtg tataccacga agaaacttgt cctgcaatac ctcttgattc 186720
```

-continued

```
atctactact tcatcataaa tgatacaacc gcttacatca tcatacgtaa gtcgatgtcc 186780
aaaagctctt gatggaaaaa tttgagattg ggatgttgtt acaattgtgg agattaatag 186840
tggatcagat aaatcattat gacgatcgat aaatcctttt acagtttcaa tagctatcat 186900
ttttattatt cattcctctc tattttaacg aatatttttt ctgcgattaa attcagcttc 186960
ctctttcttt tcattaagga ttgttagatg agtatctatt ctatcttgct ttgcttcctt 187020 atcacttttta aaagtattat tgttaataat actttcacta aatacgtttg gatgagatat 187080 attgctttt tcattaaatc catcattgaa gaaaatactt tcatcaatat ttttattatc 187140
catatttata aacatccttt cctacatgat tataaacctt caaagaactt ccacatattc 187200
tcatcaactt ctccagtaat aaccatatta gataccattt gtatttttct tacattatta 187260
taagtatcct tatcatatat tcctgaaaca ctagttgttg taattgcaaa tttacgttta 187320
ttatcattta tctttgtttg aataaataat acgtctggtc cttccataag aggattacta 187380
tatttaagaa ctcttgtaaa ttcaacaata agcgtatcaa taatatttttt ccatgttatg 187440 ggtccaacaa ttccatcttc agtaagatta tttgaatgtt gaaatgattt aacaatagtt 187500
tcagtagaac tatcataaga accagtaacc tcaatatcat atcttagttt tgaaagttta 187560
ttttgaagcg taataatatc gtcacctatc atcattggtg atttataact aagcattcga 187620
tgatagtttg aatagtcttt aatatcattt aatgcaatta tcaattcatt aattttatca 187680
aagtcttctt tcttcattct accatcaact tctagattaa atgttttttg gaatattctt 187740
accgagttat atgtgtataa atcatagata ccattacgaa tagtgattgg gatattaatc 187800
atagataaat atatttgtaa taatttaacg tcattaccga taactggttt ttctggatca 187860
tagtagaatt ccctttttacc aaaactataa gaaacagttc ctgcaggatt gtctacatac 187920
atcggtacaa taatagaaag aatttgggaa cgaagaacat tcatatcaac taatgatcct 187980
agattactat attttgcata atattcattt aatgaatgaa tgtttctaat atttcgatat 188040
cgaccactaa tattagcaca tagattctct agagatacat attggctttg agttaggtct 188100
ttaatctccg tatttccttc aagacatata aagattttac tagaagatac tggatcagta 188160
ttatcaatga gttcaatatc ttttccagca atatttttcat taagatacat tttccgcatt 188220
agtaagtcaa tattacaagg taatgctctt tcgggtctac ctgaaataat atcccctttt 188280
ttagtaatat aataatggaa tgcaaacatc tttaatccta acccttttatg aattgattct 188340 aatgtatcat aatccatact aatattacga caatctaaaa taactatatt tgatggatta 188400
ttcttgtata taagatcttt taccgggtca ggagttgtat ctacatagtt ctcatcagta 188460
ttagcatcca gtaaagataa catgtatgat atatgacttc cccacatatt attccattgt 188520
tttccatcta ctgaaaaagt tcccgctaaa tcattttgat cataagaacc gcttcttgta 188580 aatttatttta agtatcttaa acaacggttt aataatgaat acgtagtaga tatttcaata 188640
gtgtcattta tgatatttaa ataacggata cacgactctg caagaatgct tgcataatag 188700
gtattatctc tagcactgtt tggttcatat acactattaa attttgtgat tatcccttta 188760
ttttcagagt tccatatagt attaatagat tttataaatt tcataatgat attatttaca 188820
ttattattta cgtaacctttt ttcaagaagt ctaattaatg aattaatgat attatattga 188880
aactctcccc aatctcctct ttgatctaaa ccttcccacc taaaactatt agatgaaata 188940
tcaaagatag gttaaagaa accttctaca cctttttcat tataatattc tttttgagat 189000
cgatctaaaa tatcaataag tttagttaat tcattaatca ttccaaggtc atataaatact 189060
```

```
tctggttttt gataaacctag atatatgtca tcgttccaac tatcaagctt attattaata 189120
gttgttattg agttaggtag cattatattt ttcatattat tagaataatt atcaacgctt 189180
tcgatataat cgatatttat aatactagga atatcttttt cctttttcaat ataaaactta 189240 ttaaatgtac gatctaatga ataatttaat aatgatccga tatattgaag ctcaatgaaa 189300
gaagaagtaa ccttactttt aaatattgct ttggttaatg gaaatttaac agattttcca 189360
tcagtattaa aattaacttt aatactatta aataaatcaa ctgatttagg aagatttaat 189420
ttccattcta cattattact atcatagata tataaatcaa ttccatcact agcacgatag 189480
cgaattgtag ggtttgtttt tgtatttcga ctaaaaggaa taaccatgtt tgaccaacca 189540
tcataagaac cattatcatt actttcttca ttaatcgtaa aggtagcttt aatactattc 189600
cgagtttcat catcagtaga tttcacttca ataatttcag aaatactatt cggagaactc 189660
tctgcaatat ataatgattc ttcaggaaga ttaaaattat cccagattac ttcacggtaa 189720
tcttttaaca tttcaggagt caatcgatat ttattaaatt cattatcttt tacattcgtc 189780
ttatagaatc caatattatg atctttatct tcaataataa attttaatac tttatcatta 189840
tcggttttaa ttctagattc tatatatgaa atatctttaa gcgtaaataa tttatttacg 189900
ccaaaatgaa tatcttgatt aattgagatt gaatttagta taacatttcc attagtatca 189960
tcacgataaa ttaatacaga atctgaacta tctttattaa taaaagagcc actatcagat 190020
aatggatcca aattatttat ttcagaagtg atccatctag gttaattgg catatctaat 190080 ataaatttaa tagtatcttt tgtaatatcc cttgccctca tccatttact attcggtaaa 190140
atatcataaa gattactata acattcataa gaaagcaata aactttcaat actgcatata 190200
tttttattag gatccagagt atgccaataa tttgtaggat catatttctg attagattta 190260
ataaagttat cattatctaa ttgagtatat actagtaata gcgtgctgtt aacatcttta 190320
tcttctaata caatccttac agtattatct ttacggatat aatactcttc aatatcatag 190380 cttatacccta taatattaga agccggatta ttttcatcac ttaatttaga accaaaatct 190440
ctaacactaa ataattttttt aaaattgcta tccgtactaa aaattgcaat accattaaca 190500
aattctgccg attcattcaa tattaatttt tcagaattaa agggttccga tgcattatat 190560
gtaaaatgag gaacccataa attatcttga gaaaaactag ttggaacatc atttggatat 190620
aaggtatcaa tggttgcatt catcgtagat tctattaatt ctaaggatat acttacgcca 190680
gaattatact gatatataag tgaattaata tattgaaact gcgaagtaga tgttcctgaa 190740
ttaatattaa tataatcaaa taagtaatct tcttttttatat aatttaatct agacattgaa 190800
ttaagattta tagataatgg actagtgttt tttgtatttg cacttacaaa tttattatat 190860
tcagatatcc attttctaat atcttttaaa tgaacatcta atttctttttc agaaagatat 190920 tttgtcaaat ttatcaccgc cattcatatt ataacatttt gtttaatatc aatttaactt 190980
tttacccaac ctttagtatt attatattta tatttaactg tagtaatttt agtttcatta 191040
ataactttct taagacctaa tcttaataca agtgaatccc tattaataat attccgtgca 191100
gaaacatatc taacttgttt tgtaatgaat ggaattgttc gttgaactgt agagaatgga 191160
ctacttgagt tgtctctact ctttggtaat cttttgaagat tatcagagtt aagcgtagat 191220
attcgattaa gaccagtagg atcgatcttc cattttttac ttttaccacc aagattaact 191280
ttttgtcgcc acgttgcaga tcctccacca tacttaacgc tcgggttagg tgaaaatcca 191340
ttagacgatg tagtaaatgt agtttttagac gcaaatcctg aaggactttc atataatggc 191400
attagtaaat tagatggact tctaatgtat ccaatagtat ttgcaggact gcttgttgtt 191460
```

-continued

```
ccagttaatg gcaatccttc aaacatatcc catgataaat atctattcga tattctagtt 191520
ccagtagttt tatttacttt attatagaat cctcgataaa atacaccagt accttcagta 191580
acactatatt tttcacgagt tagaggatca attgccgaac cttgatagaa ccaatcagaa 191640
aatctagatc ttaatccaac acaagcatct acatattggc tttctgaagt ataattcgaa 191700
ctagagtagt taaataatct tcgatcccaa cgacaatcat atgcagtttt ttcatatgat 191760
acactttttt gtaattgcat tgttcctgaa aaacttccca ttttaattaa tttctgattt 191820
acttcatcca taagtgtttt aatattattc catatctgta ataattcagt attcttacta 191880
ttcgcatcat tactaaatgc ttcagtcaat gaattattac taaggttatt gaatatatca 191940
atctgacttt gtattaagtc attatattgt cctaagtcta gtccgtctaa ttgtaatgat 192000
atatcaccta attggtttac attattctta cttattttac ctagatatac tgttttgagt 192060
cgggcagact ccatatcaga aaaaatatct aaacttgtat caaatatttc ttcttgttta 192120
ttatatattt cattatatat attatataaa ttattaatct ttccaggtat tacattcttt 192180
cttaatttta taccttccat atcattctct aggaaatcaa taatattttc tctaagaact 192240
ttagtaattg gtattggtaa gttaatacct tcctctgtaa cgtatatgtc atgttctact 192300
agatcaacta ataactctcc agtcttcaga gtattaaaat atttttgaag atagtcttga 192360
tacgacattg gtatataaat atatcttgac attaaaatta caccaccatt attatataat 192420
atgtttaaat gttattgatt taaccttttt attacttatc ttcccttag tcttatttac 192480 taatgaagtt acccatgaat catatgttga ttgaaatgca cgagaatcta catttttctc 192540
aacagtagta tatcttgatc tcatattagt taaatcagtt ccagttttag tcttataacc 192600
ttttataaag ttgtatagat atgttaattc agataatctt ctttgtattg aaaatattcc 192660
aggaagcttt tctactactt ttggaataat tgttgcgata atatctacaa aactccatat 192720
atctacggta ttttgtctga tttgattttc caatgtattt aatattgcaa tgatctgagc 192780
taataattct ttaagaccgt tcattcgatt atataaatca tttgtttcag ataattttgt 192840
ctgatagagt gcttccaaat tagatatctc tgtttctaat agagtaataa tgctcttaag 192900
agtagagact aggtacttct gtgaaaataa ctcaccttca atatcctttg tagctgattg 192960
atcattaaca attaaatgac cagtacgagt atttactaaa agttctgaat ctttcgattc 193020
cagtttagtt ttttcagtta atggctgaac gtacaatcta tatgtcataa cttattatca 193080
cttccatatc atttttaaat ttaagttagc agttgatata ttaattatac caactgctaa 193140
ctatattaga aacttgtaat aatatttaca agcttagtat agaatccttc atgtttatct 193200
ttgaatgcat tatatttagt tgttaatatc tttttattag cttcgatttc aacgcttcgt 193260
agattgtaat agtttctacc aagattatca attactgtag tatatagatc ggcataatct 193320
aataaatcat ttcttaattt agtaatatta gtacttagat tcattagctt attatagttt 193380
gttaagaaag acccatctac attatttgta atacttgtta tcttattacg aatatcagta 193440
atatcggaag tagtttatc aacttcagct tttaatgcat caacctgagt ttttaaatta 193500
tttattccac caacaactgc gtctacaaaa ggttttaata gatcattatt actgtcaatt 193560
tcagataaat tatctcttaa ccaagataat tgattttat atagatttgt tactttaaat 193620
atatcatata taactgttga gtttaatgat aataagttat ttaattcttt tgtaatttca 193680
ataatttcat aactaccagt atcagaattt ttcgtattag atacaacgga tatatttcca 193740
gtatgttcat caataatcag ttctccagga aatctaaata gatcattttc tcgactaaac 193800
```

-continued

```
ggaattaata catttcgatc aagatctact ggaagattat aattctcagt aacattatta 193860
tcatgatcaa taattccgct agagtaatta tttacatcaa tataataata agaactatta 193920
tacatattat ttgactgttt tctagcggta atgattagtc gatatatacc atttacacta 193980
ctgatattct ttaataatgg gtcacctata ttgatgattg aattattaag tgaagcagta 194040
tatacaactc ccggttcttt attaataata tccaatacaa aagttgaatc aatattaata 194100 attttttccat gactaatatt cttagcaatt ggttttgaag gaggtatggt atcaatagtg 194160 atagtttttag atgaagatga acttttacca tttaacttac tagtagcttt tacatttaat 194220
gtaaattttc taatagattt aacgtaatta tagttcgtaa taggatcacc tagagtatac 194280
ggtaaaccat ttattgtaat ttcataggta cacattggga ttcttacaat attaggaatg 194340
atcaaactat ttgtaaggtt tcctgaatta tctggaatat taattactgg taagtctggt 194400
actgtaacat ttaacatgtc tgacgtaatt tctaaattat tttcaagaat catatcatta 194460
tccattattt ttctagcagt gatgatgcag ggttcagtaa ttataaatgg accagtatac 194520
tctttccaag aattgttaat agaagtctta tacagtttac ttttaatgtg ttctctttca 194580
gactcaataa atacatattc aatagaaata ttatatgact cggaataata tttttttatca 194640 ttataatcta ttcttggtgg agtataaata taattcttaa caatattaaa tttaaatgta 194700
gtataactta acgtataatt atgtctatct gtaaatactg ctaagaattc atgagtccct 194760
cccgaagtga atgttgaacc agaagtataa ttgtttccat caatataaca attaagcgta 194820
taatttgaat tattattcat tacagtgatt gttatatcat cagcacactg agatatatct 194880
gcagaactca catcaaaagg agttaatggt ttagatgatg atattgatat tgacggatta 194940
actggaactg tagtttgatc cattccagta gtattaatag tctgagttgc cattaattta 195000
tgtgaagaat cagaaacatt agtgatatta cttccagaaa ctccgctaat cgtaacatca 195060
tcatgtaaat ggtttctcgt tgatgtagca tatctgtata atttaatagt agaatcaaaa 195120
aatatcggca tattatagtt aggcataata aattttttct taccattata atccataaca 195180
tacatactat tatctttatc aattttacta tcaggcttaa gaacaatatc attaaataat 195240
ggattagtat cactagatac tgaatcatga tatataacag tactaataat atctccaact 195300
tgttctggta taataactac gtttacggaa atctgtacta catctgaatc tacgccattg 195360
ctaacattaa tatctagatt ataatctcct tcatctttaa atgataattt tagttttgga 195420
tcattcgtat tagtgtctaa tggtgtagcg gtatatgttt ttgaaggatc atcagtatct 195480
gtaacactat aggtatacga tgaatctttt tcaatatgaa ttataatatc aattgatcca 195540
tccccattag taatactatc tactataggt aagattaatg ttgcattatc atcagcaata 195600
actgagaaaa ttaaatcttc aggggggatta atcgtattta taaaattaac aatcattaat 195660
tcgtctgaat tgaatagttt atttatatcg attttttcgat aaatattaat ctcagtatca 195720
gtctcatata gccctagata tgtgagcatt gtatctgaaa cgtaatcgtt aacctctata 195780
acgtcaccat catcattagt taccgttata ttagtagatt cctgtaagtc atttactaat 195840
tcattcacat atactttaaa cgtatactga tcggtacctt tagttagttt aatatatacg 195900
tcattatctt ctgcaattgt tattgaagtt ggtaatgata tactaaacat gttataatta 195960
tttgagtcta ttgtaatgtc attatcagta ccattaatat ttagtttacc attataaatt 196020
ccagtacctt caacgtgata tactccagta atattagaat cgccaatatt aaatgtatca 196080
atagataatt gtatattttc acttctaact actagtactt tctgattatc tgcaactaat 196140
ataccctttg agttgtatat cttaaatgat atctcatccg tatctgaaga tattcctgta 196200
```

-continued

```
ctagatgtta ttttcatcat tttatcattt ttcgtattac taaatttagt aacagttgat 196260
gtagtttcaa caccattaat atacataata atattatcta attcaccctt atacttagca 196320
ataatctcag ttggattatt tccattaaag aagaaaggat aaaagtctac tgcagtataa 196380
tcaatattta ttgcaacctt atcattaaat gtatctacac tgtctggatc atctgagtct 196440
tttggtatag agggttcata tgtgtcacta tattttacaa taggatctat aaagttggta 196500
tataatcctg caattgaatc attcttgaca ataggtatat tttcatttct gattgatgtg 196560
tatgttgatg gaatatctac tctataaaca tcaatattag taccatacgc agaagtatgt 196620
ctaatcgagt ctgaattgta aagatattta ttaatattcg atttatcgat atatccactg 196680
aaaacatata tatctgaaaa ttcatccata ttgagagtat attccgttac cgtatcacta 196740
ataaaatctt catcttctga tattgattga aatgattcaa ttaagctttc ttgaagatca 196800
ttaataaaat cttcgttaga tagatcatcg tcatcgccaa tagttgaagc acttaacata 196860
gtgatattat tcttaccaat agaacctttt acaactgaac cattacctcc gccaataatc 196920
tgcgatatat tattatttac attaaatgat aaattactta catcttttgg taatctaatt 196980
gctttatata ggaaattatc atttattcct tgagttagta taaatagttg atataatata 197040
ctagaatcat cagaataatc agaagttcct ccaaaatcat tttcaataat aaccctaaat 197100
ttcagttgag ttaatccatt atacgcattt gtactattat taaaatcttc gtctccagta 197160
ataaatctta ctctactacc gttaccgcct gtgggtgctg tactttgtaa tgtaaagact 197220
ttattggtag tactccaatt actccattga tccgatcttt catctttaac cgaatattct 197280
agatatactt tgttagcccc aaatgatgga attgaactta taaaatcttt ataatacttt 197340
ccataattac taaagtatgt tatatctgca ggtctagaat ataatggatt aataccgtta 197400
tcaataaaga aaggatttac attatctatc ttaattggat ttggtttaat ccctttcata 197460
tcataattca ttttaaaata aaatttacgt ggatcaacta atgatttatt agttaaatcg 197520
ttaaacgctt ctattgttaa ttcaaatact ttattatgat aattattata tactgcgttt 197580
ggattatcgc ttgccaatga caaagtatat cctgacgtat tctctttata aaacttctta 197640
agatctggat tattaagtgc ttttatatta tatcgataaa ttactggtcg accagttgaa 197700
tcatttaccc ctgaaaaact aaaggtataa ttaagcttat ttgcttcact agtgtttgca 197760
ggaatcactg taggattatt tggatcatta ctcataaatg ttaaaaatga tcgatcttca 197820
tttaacatac tagcagtagt aactatcccc ggtgcgctct tactaatatt tattacgttt 197880
ggcatattag aaagattatt aaacacttca gtattatccg gatcaatatt atcactatat 197940
gatagtactg tattaatttt agtttcatct gaaaaataaa atggatcaat atcaagataa 198000
tataaatctc caactttagt atcatagtta tctttagata atctaaattc gtgtaaacta 198060
ctctgcgttg ttacttggaa aataatatcg acaaaagcag aatcttccgt accattaata 198120
tttttatttt ctaattttcc aaaaatagag aaaccgttct gatctccaac tatagactca 198180
tttccttccg taccggactc aacttctata tttgtgtatg ttaatgcttc tccatatgga 198240
ttctctacaa agaatgttct agcaattcca taatctgcag gagtccaact ttgtatgaat 198300
tgtattaatt gttctctagt atgtgctatt actgtcaaga aatttcacca cctatattta 198360
taacttctta taattaatag tttaaaaatc catactaaga aatatttaat tccttagtat 198420
ggacgatatt tttatattat cggatcaata atatccgctt caggatcata gattttttga 198480
ggattcatat ccaaaataat attctgacta atatatttgt tatttatttc ttcagaatct 198540
```

-continued

```
aatgaaatat cccaacttaa tagatcatta ttattacaat taataatagt ttttccacgt 198600
tgacgcatat agtccattag aattaatttc cggatactac ctctagaatt atcatttgtt 198660
attccagtca atatatcaaa attactagtt tgtcttacgt tatagtatga atgatagtaa 198720
ttatcgttta aattcatttt atcatactta taccaatcta atattaattt aagttgagta 198780
tgatcatcgt agctaaatct aatcattaca tttattaatg gatcagcata atcaataatt 198840
tgaatacttt taccattaag tatttttact ttactagaat ctattcttaa attattaacg 198900
taaactgtaa atgtgccttt aataaatatt actgaatcgt catctaaact gaatacatct 198960
gttgttcctt cagccggctt actaaaagtt cttatatagt tggagttttc attaagaaga 199020
tttatttcga tagtagatgt tttaggtaca atgctttaa aaacaattaa tgacggaata 199080
gattcaaagt caggatcaat aatggtataa tcaattccag gatataatgt taatccatcg 199140
atattaatat cgatatcttc aggattacta ttaatgtttg taaaaatatt tgaatcatca 199200
tctaacgtag caaatggtaa acaatcaata tcatattcat ttaagtctaa ttgattgtag 199260
tataacgagc cactatttgt accactagtc aaaagatgta tttcggtacc ttcatccata 199320
taagatgaac catatacgat aagtcttact gtattatatt caggttcaat cttaatataa 199380
taattgtatg ggttaattct tctaaagaaa ttccaagttt tcttcttaat aaagactctt 199440
aattgtgaag gagtaattcc cgttggtaat gcaacatccg ttaatagtat accagtagtt 199500
cctaacatat tagtttgatc ttcaaacgta ttatcaatta tatgagtctt aattgttttc 199560
tcggattcaa caatcttacg tttattacca gagacaatta cttcatattt atccggaaga 199620
ctagaattcc catctaaaac atcattagca tcattcacat caatatattc tttaataaat 199680
cttgaaggca tgtatgcata tattttcca tctaaactat cttgttgctt aatcgattta 199740
cggaaaatat gtttaccatt aataaatata tcagatatta atgaattttg tttctttttca 199800 tatgaaccat attccgaagt aaaatcaata taaccatact gagattcatc attaataaaa 199860
ttatttataa acggatcttt tgtaactttt attttagagt tatccaactt agttccaaat 199920
gaattatgtc ccattgtctc tataaataat gttttattac cttgttctaa ttcattaact 199980 aatgatttt caatcatccg aatatcattg tctgtattct tatataagat atcagtaaca 200040
tttcttggat caatatccat ttggaatgtt ttagtctcta taagttgttc tgaattagta 200100
ttaaatatac taaaggttat atctttattg ggggtgaaat taagttcatc aatctgtaat 200160
cgatagtact tttcttctaa ttctggaaga tcgtctggtt tataatatac acgttgataa 200220
ttatcattac caatgatatt aattaagtcg cttgaaacat catcattact ctcagaagaa 200280
gagaatatca tatttttaat ctttacagta agcttataat aatcttcgat tcttttaaaa 200340
ttattaatga tgatagtctt tccatcaata gttattgtca ttatatattc ggatgataat 200400
aaatatctta gtctaaaata gattgatccg ttcagatagt atgcattctt atatagaatt 200460
ttatatataa tgtcttctgg agtggcttga atatttttat tagaatatct aacatctaaa 200520
tcttcattaa gaacagtata tctaatcata tcatttccta aaggtagcat taattctgat 200580
aatactgttt ctttatcatc aaaaggaata tacatattgg cactttggtt tgcttcagga 200640
aatatcctac taatagagtt cgatctatag tttagagaaa cattatagtt acttttatct 200700
acaatatcta aactatgcat taaattaaca tgaacattta agaaaaattt actatttgta 200760
ctattattaa aactgcgttt ttctatccat gtataatcaa tacttaaatc aggaagatat 200820
tctaatttat agaatgtggt atctctacta gaattattaa caataacaaa tagattggtt 200880
gctacaatat tttctggata gttatctaac tgaatatttt caataatatt tcgcttagta 200940
```

```
ttaattaata ctaattgatt catactatcc ataagaataa tataattttt aaccagtact 201000
actttatcaa tattatttct aacgtttgct aaccatgttt tattcgtcaa gttattatta 201060
gcatacttaa aactatatat atttccacta tatgatgata cgtataatgt agatttatca 201120
ctatcatata tcataaaatt atttgtcgat aatattttat cattataatc tgtctgactt 201180
aatgatactt tttctacaat agagttatct acagacttaa taatattaat attaaaacta 201240
tcttttaatt ctagtcctat aaatattgta aagtcgatat tattcgattc aggaatgatt 201300
tcaaaaccag aaataaaata tgaagcggta tacaacactt ttgttgtatt cgttatagta 201360
tttactagta taatatgttg atacgtggag tagtatataa aatcattaac aatccttaat 201420
tgatttacta attcatactc atatggagaa gtattagtta ttttatttat agttcctgag 201480
atattataca ttccagtagt tgtatttcta ctaaaagata cataactgat accattctta 201540
tgaaacatat atatcttatt atcgataact gtaaaatcga ttacttcctc attaatatca 201600
aatgaaccta ctttttctcc agtaccaaag tcttttataa tatcaattcg attcttaata 201660
gaaccggtag gatatttata taatctgaat agttcttcta aatatataca cattgcaggc 201720
atatatcctg aattagcata tgatatagaa tgaaataagt ctaacctatt acgtttttga 201780
tatttatcta atatattccc attcaatgtt atagtcaata ctttcaccat ctttctttta 201840
caattataag gaatcgagaa taaaatatcc cgattcccaa tttatttaaa taagacttga 201900
aaaacttgta aatgttttta gagagaattt acctaatgta ttttcgataa ttgcttctcg 201960
attaaggtta gcgcttatag atgatgacat taccatatgc ataaatgcag gaaggtaatc 202020
aatagctaat acagtagagt ctccatacat tcttacataa ttctctaaat aagagcgtac 202080
ttgtaatttc tctaaacctt ttattttctt gaggttatca aaaagtgtaa agatgtcttt 202140
atatagttcc ttctcgctta gattaaaatcc ttcttccatt tctttaatta aagataatga 202200
agaaccatta aagcaagctt tataggcaat atcgtctatt gtattattat aattcttttt 202260
agccattgct aatagataaa actttgatag aataaaggat acaaagtctg atttaaaatc 202320
atttaggttt aatgaaaaca ttttatcaaa tatctttgaa cctagtctag aatatgcaat 202380
agatgaattt ttcattaatt cagtattact tgtaaatcga ttccaatttc catttaattc 202440
ataagtaatc attgcttgtt gcattagtcc gaataatgtt tttggttgga tttctccacc 202500
tgcattagtg tatcgtgaaa catcaactaa tacgtcacgt tgattgttat atcttctttc 202560
aaatacaatc aagtatgatg gaaatttatt tgatttattt gatataggaa tgattttttcc 202620 agagttatat aacccaacaa ctttattttt agtaggataa ttaattcgtc tattaataat 202680
atttatattt tgatctaata catctttaga taaaacatct ttactagtgt ttattttatt 202740
aagttttatt ttaagatcat gctgaaaatt agatgtattg aaaatggcgg aatcacttaa 202800
ttgtaccatt atttcacttt cccttcaatt aatttatatg atattaattt gttcaatata 202860
ttaacatttt ttacatttat atattataaa ttcgtataat ggaaatataa taaaattttc 202920
agtttatcgg ttaaaatatt attatattat aaaataaatg tgataaggat ggattatatt 202980
atgagtgata aaaaaatgct taaagtagga tttcttagcc caaatgatga taggattcgt 203040
tttaaagaag tagattttttc gaatagtgaa tcttatgata aagaaattgt gagtgttatt 203100
agtcctaccg gaaatattga tgcaggaatc atgaatctta atgaagattt agaaattcgt 203160
aacttcttaa ttttatttga taatgaaatg tcaacaaata aaggagaata taattttaca 203220
cattcaatta gtcctctttt tggtgaagtt gcttttgtaa aattcggtta tactggggat 203280
```

-continued

```
aatatggaac cagtaagcat gttagatgat gaagctgagg ttctcagtga tattatttat 203340
caagaaaaaa cttctgatcg agcaattgaa tttaaagaaa aaattcttga agaagtaaga 203400
atttacggta aagatggatt tttacgtaaa tataatgaaa gtattgaaga ggcgcaaaaa 203460
atgtatgaag ataatttttc agaagaagaa gaaaaataat taagaatgga tggtggatta 203520
taattgtcta atataaacgt agttagtatt gcagatttac attttggtaa gaaagatgat 203580
agtcgactaa tgaatgaatt aacaacaata tttattccac agattaagaa tattcatgaa 203640
tctgataaaa ttgatttgat tgttattgct ggagatctat ttgaccgtat tcttaagttt 203700
gatgaagttg gtggaaaatt agtattgaat tttatgcaag aacttattga atggacaaat 203760
aaaaataata tttattttcg aattattcag ggaactaaaa ctcatgacta taatcaatta 203820
gctgtgttta gaaaagcaga agttgataat tataatttta aaatttatga aacggtatat 203880
aatgaaaaat tgactatcaa tgaaaaagaa tttaatattt tatatttacc tgaagaatat 203940
cctgaagata tgaatgatta ttataaagaa ttctttgatg ttcaagaaaa tacgtatgat 204000
atgattttcg gtcatggaat gatcgatttt gtagctttca ctggttatga agatgatact 204060
gaaaaaattg taaagaaagc accagtattt gttgcggatg acttaattaa aattacaaaa 204120
ggaccaatat gttttggaca tattcacgac tatcatgaat ataaaaaaca aatatatttat 204180 tcaggttcat tctccagata ttctcatggc gatactatgg ataaaggata tttatatatt 204240
aagttaaaca gtgaagatac ttctgaatat gaaattagtt tctatgttaa tgaattagct 204300
ccaacatatg ccactattga tttagataaa atcaaatatg ataatatgga agatttagca 204360
tcattaatta atgatattcg tgaagaatat gacttcattc gaattaaatc aacaaataat 204420
aatgatagtt ctattgtaag aaaagttatt gaaaatagtc ctaatattaa agttacttta 204480
aagaataaga ataacgaaga acaacaagtt gattctaaat ggaacttcat tcttgataga 204540
gagcttgata ctgacgactc tataaagaaa tttattaaaa ttaaatatga taaagatatc 204600
gatattagta agattaaagc aattcttaat ccagagattg aagatattga tgatattatt 204660
aagaatattt atgataagaa aaaataatta ataatctttta ttaagaagtg aattatgaaa 204720
ggaatgtttc attgtgccat ttatggataa tagcgaacgt acaagagtct ttagatctag 204780
aatggatgaa tcttctcaac aagaatttcc attaaagatt tccgtatcat acttatttag 204840
tttagcaaga tatgtggtat atccaagtaa acttatcact agaactaatt tacggaattt 204900
agatacatta ttatcagcag tcgatattga tagatcttat ttagaaaatg aagtaatgga 204960
aaagaatgca tttatattct taagagaaat taaccgtgta ttattacatc aacaatcaac 205020
aatagaaaca ttgtttgatt atattgatga tgaattaaaa gatagagaaa tctctgaaga 205080
tgctcttcaa gaatgtgtaa acaatattgc aatggtgttt gatgataatt tcattcttga 205140
tgatagtgaa atattaagct aacaaaacta tgtagaatcc agattaaaga ttatggcact 205200
atatcgtcaa cgtgatagaa tggaaggtat tttagaatta atcaaaatga ataaatctcc 205260
aaacgaaatt aatactgaat ttaaagattt tgttacgcag aatgcattac aattaagaaa 205320
gattgaaacg aataatcgaa gttcaatgga cgatattatg tttagcagag ataatgatcg 205380
atcagtagat tcactagact ctactattag acaattaaga agtcctagta ataaattatt 205440
aacaggatat agtaagttta atgaaatgat taatggtggt ttagaggatg gtcgacttta 205500
tttactcttc ggcgttccta aatcatttaa gtctggtgtt atgttaaata ttggaatgtc 205560
agtatgtcat aataacgcag gatttaagac aaaagatcct aataaagaac caccgttgt 205620 ttatttatct caagaaaata caattataga aacagtagaa cgattatatg aatatattac 205680
```

-continued

```
tggtactagt attaatgaat cacaagctac tacgcaagat gttttagaat taatcatgca 205740
atatacgtat gattgtactg gtatttattt aaaaattatg tatagaccaa ataaaagtat 205800
tgatacaagt tatctatata atatttatga tgagcttaat gaagaaggta aagaatgcat 205860
ctttatgatt caagattata ctcgaagaat tagaccttct gaagggcaaa atcaagatat 205920
tcggatacaa ctcggtaata tatctgatga gttctgtacg tttgctaagg aaaaaggtat 205980
ccctgtaatg tcggcgggac aattaaaccg taatgcaaat gaaattgtag aggatgctct 206040
tgttaagaat cgttcagact ttattaataa gttaggtcgc catcatattg cagagtctgc 206100
aatgttactt gaaaatgctg attatggaat tatcattggt cgacaagatt atcttccaga 206160
gggtgaagac gaaattaatc gcaaaagtta tatgtcattt aaacttattg cttctcgtgg 206220
gaaaaataag gataaagata gcaatatgtt ctctcaacct tttgaaaatg gatttaaaat 206280
tgcagaagat attaatctag ctgaaccatt agcaaaatta agaattaatg aacaacagtc 206340
tcaacaagat atggaaaata gtgctgacga agtaattact tcaagaactc ctagatataa 206400
cagtactagt aaatctagta gtatagttcc gggaatcaat actggtaaga gacgaacaaa 206460
tctttcatca acagcattat tacaagaaga tgatattccg ttctaaataa tattaataac 206520
ctaacatcct tttttatagg gatgttaggt taattttttt tttttagata gattcggctt 206580
tttgacgtaa tttactaaaa tcgatattaa acattttaag tgtattcata ctttctagta 206640
tagtataaga tataatagat tctacaattg tcatttctgc aatatcttct tttttagatt 206700
ctgatagatc catattttcc attacgtatg ataagcgttc ttcactaatt ttcatatata 206760 atgattttc atctttaact tctacattat tttcattgca tttatcaaca aagtttttgt 206820
atttcttctc ataatcaatt acattgataa ctttatcttc aattacgttt actgcagatt 206880
caattaatga tttctcctca tcatggatag aagatacaat atctccaact tggtcaaatg 206940
ataatttctc ttcatttaca taatgactga cttttgtctt aacaagactt aataagtcac 207000
caaaggcacc atgctcttga atattgattg atttattttc tacaatagta ttaaaagcat 207060
taatacattc attataaata taatcaacat tcccttgttt ttgaacttca tcaataggaa 207120
tagctcggta tacaatactt ccaaataatg ttggagctac ttcttcagca tgttcattaa 207180
ttcgattttc cttttgaacc atcttttcac gttcttcagc ttcacgctga accgtaatag 207240
acgttgttcg tagtaatTta ctcttgtttt ccatatctaa attttcttgt aatgcttttt 207300
cttcttcttt cttttttacgg aaatattcag tacgtgcatt attttcttct ctaagatttc 207360
ttgaactttc accaaagata ctaagtcttg acattaattt tcactctcct ataattttttg 207420 ctatattaat ttgtttgata agttatatta gctacatgct catatttttt acctagattg 207480
atagtagtga ctttaccatt actatctgtc gtttctacaa tattatcaga aagtgttttc 207540
ttaatattga tatattcagg aacatattca atgatttctt gttttgagag atcattaata 207600
tttcttgcat tgtttaaggat ttttttgatat ttattagata tcttttcatc ataattacca 207660
cttaaaccgt tatattcaat atagctaatg atcgcaaatt cttcttctaa caatcttaat 207720
agattagata taggtacgat tccatcagta ttacaggctt caataaagtc ggaaataaat 207780
ttcttaattg ataagtcatc attatcatta acggcttcat atgtgtgaat agttaaatca 207840
attagcatgt caatgcgagt aataagatca tacttaacac tatctccatc cacttcagta 207900
tttaagtaat aatatttaga tggtccccaa ctattataaa atttcatatc aattgtagta 207960
ttattttcca gtttaggaat aacattgctt aatatagtga tatacgattc aattaatgta 208020
```

-continued

```
tataaataac tatattcata tataaaatat tgtaaactaa tgagcggtat catttcaact 208080
ttaaaatcct tatttgcgtc actaacgttt gaagcaccta ctctagttac tgtacttgtc 208140
ataatactag aaagattacg atataacttt acggtagaat tagtagttac tgataatgcc 208200
aatacataat tatcaatatt tctattagca tctggaaact catcatcaaa caattcaatt 208260
tcattattat tctttgtacc aacagtctta tatgaattat ctttataaag aattccgatc 208320
ttaatatata gatcttcatc aataaataca ttatctagaa catcaccatt ttcatcatat 208380
agcgagtttg ataatgataa taatcctta ttaaatttac gattagttga taattttgca 208440
gtataagtag actctgcttg ttctggattt tcacgttcaa attcaaagta accatacttc 208500
ttattagagt tttttgacat taagatacct cgtacgcaaa tacgtttatc taagtcgcct 208560
atcgtttcat tactgtttag atcaaactta atagtatacg tatcggaatc caaagtagat 208620
tcaaaatcat gaattttttgt tatattaagt ttattgataa tcattgttgt aggaattaag 208680
ttattaagat aactgtatga tgtatcgaat gtttcatcaa tatccagttt ataatattta 208740
gcacttaata caggatcaat atctatttta actaagaatg gattagtata tacaagcgta 208800
tttttatcat taatagattt tttaatatca tcagtatatc catcgggaag atgtttatat 208860
tttttatcaa tataatcata ctgaattaat gaatgttccg gaattacata tccattaata 208920
tcgtcaccta acagttgatc tgtaaaatat ttcttagaga aagttacact acttgcagta 208980
tttgtaggaa taacctttt atcattatca cgtaataata aaaatgcatt atataaacgc 209040
tgaagaacat catttcgctt tttcataaag tttattgatg agtcatttaa gcttgatgct 209100
cgatcaatat ttcggaaata gatatctaag tcagtatcca taattaaatt atctctaccg 209160
agagcagttt caataatttt gtctttcata ccgctagtac ttagtttatc attacctcct 209220
gaagcagagg taataggaac tactgttgtg agcatctttg aaaagttatt acttgctgaa 209280
ttagtaaagt taaataatac ttctccatca aaagtaaagt ttccttcaga accttttgta 209340
gttaatatct caatggttat cttactatta tatctaggtc taaagttatt aactaatgaa 209400
gaaaaagata tctgtaattt attatcatca acaaacgtat aataacagaa tttctcatca 209460
ggattagaag gattaaaggt attattaaag tatgcgttta attttacttt ttcgcccata 209520
tacgtataat atatattgaa tcctgccaat tgatcgtcaa actctgcagt atagaataaa 209580
ttatcactaa tatcttcaga caatatatca aagtcaaaag aactactttg aacttggtaa 209640
atatctaaat ttagatacat atacttttca ccatcaaaga tagattgata aactttttatc 209700 tcaggagtac taagttcaat atatgggaat gtacttactt catcaataag atatctagct 209760
gtaatcgtat aatcattatt ctgattttgt ttcattaata tttgtacgtc ataaggtaac 209820
tggaatttaa atttacccac agaaaattca aattctcgat ctaatatgat ctgataagtt 209880
ttaagagctt taacttcgat atattgatct tcgataattt cttcccttaa tggagaattt 209940
attaaatcct ctttacgtat aaccatatta actaacatat gagaagggt tgatagtact 210000 aatggtacgt tatataattt tgcataattg aagatactat ctgggaatga tgcactattt 210060
aagaagtgtt catcatacag tacattacga tgatataccg agttttaac ctcatgggct 210120 gcaatttcat taaagtatcc aaagaaacca gttttaata agtttaatgc agcattattt 210180
ccttcagaac cagtagcaat atttgtatca tcaatattaa aatatgtgct tgccattta 210240 agccaatgtt catgtacgtc atatgacgtt tgatttactt taactactga acttgtatct 210300
tctttagcat tcttcataaa agaaggtaca tctgttatat cgtttggatt attttttattt 210360 gccatttatt ctcacgccca atcactattt aattatccaa tacaaatttg agtttatatt 210420
```

-continued

```
ttttctttc attatcacca tagttttcaa gaactactgc aggtctatct aattttgtta 210480
ggtctaagtc tgtaaaaaag tcattatatt tcttagcaga tcccggagaa gtactatata 210540
taatactttc tgaatcttta ctagacgcta atactggaga gtctaatgat actgaattaa 210600
agtccattaa tattgcggga tccatatctt ctttatatga atacgcatag ttaaaactta 210660
actgagcgat atcttttgaa cctccaatat cactattcat tacgtcatat ggaacatttg 210720
ttggtgaaca tccagtgtat ttagtatagt ataaatatcgt ttccatatca aaatctaata 210780
aaaagtaata tatggaactt gtataatcaa tatatcgatt cataaatact tgtggattag 210840
gtttcatttg tcctctagat actgcttcaa tatagtcagt ccataattta tgaatctgta 210900
gtattgtact atttttatct tcttcaaaag ttacgctagt ttcatcagct actacactat 210960
taataaatgg tccaggaagt aattgcttgt gaccataaaa cgtttcatta acttctttag 211020
taatagtaga tattcctta agtgacatgt taataaatct attagttaac ggtttatga 211080 aagaactatt tgaaccatat atagatcctc cgccagtctt actggttgcg ttcccaccat 211140
aattaagcat atttaatatt tcagggcgat tatccctcat atattgaaaa aaagaattca 211200
catttatatt ttcatccgtt aagttaagtt ttggagtagt aacaaatacc atagggaatg 211260
ctttaaccat cggttcattt cttaagctat tttccaatct atatggatta aaatatttat 211320
tctcatttat attataattc cctataatct tttttctaat ttcgtctgac tttgacaaaa 211380
gttttcacca actttcatat taagatccta gtatgttata aattattgtt aatgtatgca 211440
tgaaaatatt aatttatatt ttatttatat attataaatt cgtaatagat atagtgatca 211500
tccttataga gtaagtttaa taattaatat taagaaaaat gatttatatt actgtccata 211560
ttaaataaaa tatgacctca caccagtaat ataaattctg taaaattatt tggcttaact 211620
ctatcagcgc tatataaatt gaaatcatgc atatcggaga atattaaata attcttaggg 211680
ttagtcgata cagtgagaaa ctatatctat taaaaaatat tattgtctta catgggggcg 211740
ttcttatgtg ctatatgatt gaataaaaag aaaaaatatg atttagaaaa aacagtaata 211800
atacttctta gtattattaa taagatccta tactgaataa aattgaggta tatgaaagcg 211860
ctcataggat tatttattaa agattattag agtcacattt cattaattga tctgtgactc 211920
taataatctt tatttaattt ttttttttta taacgcttcc tatgataaaa caataaaata 211980
taaagtaata ttaattaggt catctaaatt gaaaaggaga gagcgtaaat gtcaaaaagc 212040
gtattgctaa atttgacttc actctttggt gaagtagttc ttagtaaaaa aggacaatct 212100
gaattagata aaagttataa agaattagtt aaaaataaat ctgctcgtaa tagttatcta 212160
aatacaatta aaggaaaagc agaatctgct attatgcaat ttcctttagt aatttctaat 212220
aatatatcta tcggagtttt agatggtatt cgtagaaata ttgaaattga acgtgctacg 212280
gagttcggat tagtattgtc taacgaacca gtacaaaatg ttacaactaa tgcggaattc 212340
atgaataaat atcacactaa ctttagtctt ggagaagata tttcttcagc acataatgaa 212400
ttcaatcaag agtctaaata tatggaagaa aaattagaaa tgcgttcact taatgatttt 212460
acaagatctc gtcaatatct tagagaagaa ggcgaacaag attttgttaa tgctaagatt 212520
gataaggata aagaagaaat gagtgagagtt gaaagaagaa ttcagaattc tcgtatagtt 212580
tctgatcgaa atgcaatctc tccattaatt gtaaacagtc ctattactta tagtatttct 212640 aaagtctta ataatgatgg aaaagaaatt aaggttgatc ctccaaaaat tattgaaggt 212700
caaattcgtt ttggaattaa agcggtatct catttagtta atagcgaaga tattgtatttt 212760
```

-continued

```
tatcttggcg atgccgctag acgtagtaat ttcttagcaa aagtagttcg gtttacttct 212820
ggcgagctta agtttggtaa ggatttaatt ctagcaagcg aacgtaataa acgtttagta 212880
catgaccgta aaggttctgg tgctatttgg agaaacatga attatatttc tgaactgaat 212940
aatattcgtg ccaatgtagg caatgtaaat aaaatgcaag tacctactat tactttagca 213000
attagtaaag aagaagtaga ttctattgca gaaaagacag gaatcaattt tatcgataat 213060
cctaacgcta cagaacgttt gtttaaagaa ttttacttat tagacttcat gatcattgat 213120
gaactaaatg aagtagcata caaatttaat cgtactggaa aaacatatga ccgttttagc 213180
ctacgttctt tagagatttc aggatctact gaaagtcagt taaagaaacc tatggaattc 213240
agtcaattaa ataaaatgat taactctatg agaaaataag aaaggatagg tgaataattc 213300
aatgcgtgga tttaataatc gtttaaaaaa taaaccaaca tcttctaaag atgccttaca 213360
acagttatta gttgagagtg gcggattaga aatgaataaa tataaattac tttctgaaga 213420
aggtaaaatt ggtattagtg accgagtgtt aattactctt atgaaatcaa ttaaaccaaa 213480
attagaaaaa ccggtattta aggatattac taagtctaaa ggtgatatta ctaaatataa 213540
agcttatgat gatctagaaa aagtattaaa taaagttcgt tccgttattt caaacagttc 213600
taaacctgta gataaagacg ttaaagaaaa tatgtcaagc ttagatactg tttatgattt 213660
tgttattcgt gaaaaagatg catttatgcg tggatttagt aataaagatt ctttagtaat 213720
gtcattatat gtatcttgtg tttcggttat tgcagaagga tcattagtaa tgtttacaga 213780
tgctttagaa cctacttccg ataactttgg aaatattaca attaatgtta aagatcgtcc 213840
gaaatcaatg aataagagtt tatttattgg actaagacaa ttttctgata tggttaatgc 213900
taaaaaatta aaagatatta ttaaaggtgg acaaattaac ttagaagaag aactaggtga 213960
aagctttgtt ggatctcttt cagtattggg taaattcttt aataaagtag cagatagtat 214020
ggatgatgct aaagaaaaag cccatgatga tgcagattct ccaaaaggtg aagatagtgc 214080
aatgattcga ttcttcaaat caaataaatt tgataaagca tcggacgtta ctcgtaagat 214140
tggtactcga gtaattctac cgattgttgc attattatta gtatgtatgt ttattcgcct 214200
tgtagtattt attatttatc gtactcgtgt aaacgttgca gacaatcttc gtagtgctgc 214260
tgaagttatt gatgagaact ctattcgaat tcaagataaa aatgtacgtg aacgacaaga 214320
aaagtctgct aaactattcc gtaaactagc ggataaagta gatgtagact ttaatgtggc 214380
agactctggt gctgataagg atattcgtca acaagatgaa ttaatggcta aaggtgcaga 214440
tgatatgatt agttcatatc aaaataatgc taacgagttt ggtatctaaa aaaaaatatc 214500
cctatacatt ctaaaattga atgtataggg atatatatta tgaaatttta cgtaatataa 214560
tttgaccacc attatcagta gtattattac ttttagttga aaatatttcc gtcattttaa 214620
gaacctgata atcaccatta tatttattat aatattcaga atcaaacgtt atagtgaatt 214680
ttttaaaaca gtcatcgata tttatatcca tattattaaa actaaatctt agtatggtat 214740
tattttcagt tattcgttta gtatattcct gtagattttt attatcatat ttattttcat 214800
atacaattgt tttattaata gtaccatttc tatccttaat actatctatt tgataactgt 214860 cttttttctaa acctatcatg tcacgattaa aaataatatt atttgtacca tataattctg 214920
catacaactc agtctgatcc ataataacaa cactattaat cttagtatta atatacttat 214980
cagttattcc atttaattga ttagtttcac tataagtacc catgatattc tggtcttcag 215040
gattagcatt aactggtatt ttaacgtcta tacgtatatt tccggactca actatttcca 215100
tagaagacat tggagtaatt actaatttat tatatgacat aaacactttt agactatcat 215160
```

-continued

```
tatatattcc gtaagcatta ttaatgtggc taatattagt tagaatattt ccgggtatta 215220
aggctaattg atcgtatatt tttttgattgt ctggagaaga tagatatgtt cttactggaa 215280
gaagagttaa taatctagta atgacttcag taacattagt atttgaatat ataccgctag 215340
tattatattt attaatagat agacatattt cagggacgca taaacattca aattcttcat 215400
actggtaatt tgtatctgtt gtatcttggg ttaatctatc actaatatta atcgccctct 215460
tatcaataat aagcggcttt agaataatat ctccgagaaa tatatcatta atatatgagt 215520
tggtagtatc cgcatcaatg gatgaagctc ctaaacttac tacaaatttc tcagaatctt 215580
cttgtaaact taccataaca gatactggta atttatagac taatgatatc agtggcattt 215640
tataattttg aaaatcaata tcgattttag ttaatcgaat atattcagaa gcatcaaaca 215700
tatttccatc tgagaataag aacttactac gtagattaaa agtttttttta gttatacgag 215760 aataatccat ttattatttt tcacatccat ttcattcatt caatatagta atatgtttat 215820
ttattaaaat aaatttataa gaatatatta taataataga ttataatata tttagggagt 215880
tgtttatatg gattacggaa attattttgg ctatgataca gaaaatatcg aaaagattat 215940
gaactcaaag aaagttaaat atacaaaact catgtcaatg gtaaagaatt atgtaacgag 216000
ggaatctatt ggcaagaatg taaatatcta tattgatatg aatactattt taaagcagat 216060
atataataag gataatattg aaatctttaa tcatttaaag agtgataaac gtttatttat 216120
tactgctgaa attataaata ttattggtca ctatagacat ttctttttctt caagattgaa 216180 aatgtatact acgttttatt tatttacttc ttttgaaaaa tcatcatatc atacaaatat 216240
atatcctgat tatcgtaaag aatattacga aaaaagattg ggtgatagag attttgtttt 216300
ttcaaatatt aataagatta ttaaggataa tatgaatatc gttaagaaga tttttaaagta 216360 tgtaccaaac gcatatttga ttaatacaaa agataatgat ccttcattag tacctactta 216420
tttattaaat gataatcgtt ttactttaga taccgacttg aatattatta ttagcaatga 216480 taaactttttc agacaagatt tattatatag ggataatacg cttatcttag aaattaaagg 216540
aaaagataat aaacgactta tcgcttatga ggacgttatc aatactattg tagatagtac 216600
taaaggtaaa agggtttatt cagactataa cttattaaca gaatccatta cacttctgga 216660
tcctcttgta aagaataaag aatataatat taattcaatt aaacgaacta gtgaaatgaa 216720
agcactagac attattgaaa aaggtattaa tgataatatt atttcttcac aaagctatta 216780
tgacgtagat gaagcatata atgatttagc ttttttatctt ggtgaaaata atgaggatga 216840
atttaaaaga aatatgtcaa tcgttaatca taaaattgca atgtcacata cttttaaaga 216900
tttagaacac gttatacttt cccaaataat tgatctagag gatgatagag gattaatgga 216960
attgaatgat aagttctttt caaaatatcc tattgttatg gactatcttg gtgaaagttt 217020
ctatgatccg agataaaaaa aaaaatatcc ctaatgctaa tattacttag cattagggac 217080
ttattatata cttattttttt ttttttagac tgatttaata aattcaataa tttccattga 217140
cattaaaact ttatccatat cttcgataaa tacttcatta tcattttcat caatatacat 217200
aaaatcataa ttatatgagg ttgataatga catgataaag ttttcacgtt gaactagatc 217260
aataatactg tcatactcag taagaacttc tccatagctt tctgatgtta cgatcttatt 217320
attaatctta ttactaatgc gatttctttt tccagaagga atagtttac ttagtagaac 217380 tttgggtaaa agtttatagt tattcttttc aagttctcta atcatcgcaa ctagtaatac 217440
tagtactctg ggttcacgga agttcttaat ggcaaatctt tttgcaaagt acatattcat 217500
```

-continued

```
aagtgaaatt tggaattcgt ttaaatgttt aacattacta cttaaacgta caatttcttc 217560
attagtaata ttatattttt cgatagagtc tctcacatac ttatcgatag atgcatcatt 217620
aataacgctt gacatttcat tatgtttatg gtactgaatt aaagaaaatt tatcattctc 217680
atctagatcg tcatctgaac tagaaatctt gattactttg aattgtagtg cataattaga 217740
acggaaagca tattcaatct ttcttttaat aactacgtct aaatacgata ttgatgattt 217800
attaatagaa agtttgcata taattgtacg tataatttca tcggtaattt tttggtttaa 217860
tatgtcttca tctacagata tattttgcaa gaagtaccag ataactttat ctttgtataa 217920 cgtctttta atacgtggtt caacaatttt gctaatctta gtaagaatat taatcccttt 217980
ttgattacta aaatagcgat taattaattt aaaagtcttt aagaatagtt gttcattgta 218040
aggcttattt ttagcattac ctgaagtaat aagatattca catatagtag gaattaacaa 218100
acgttgcatg attgcagaac ggattagtac tttatttgat tcatcagtta cttgtagttc 218160
aggaacaatt ttatcagagt tagttctact ataatcatct aatgaaatcg tatatgtaga 218220
atcaactact gcatcaatag cttgtaataa cttatcaaat ttaataaaat cttcgaaatc 218280
ttcaataaat ttactttcag tataatcttc atccataaac atgtttactt taaaatttaa 218340
tagtttatag gcaatttcag gaacttcatt taaaaagtag tttaaatcat tgtaaataat 218400
atgatagata tttgaataaa ttgcttgatg aatattatat tcaaataact tttctttacc 218460
ctctaaatta gcattctcta aaatagaagc aaagtctaca accatctttt tgggatgagc 218520
atagttatct tctgtaatat aagttgtaat gtctttacga tgttcaactt tttcaatagt 218580
taccatttcg tttggatcat tctcactttt aggtaaagat acagttactt cttttaatcc 218640
ttcaatagat atatacttat tttttaactt aaactcttcc ttcacactat tacccctaac 218700
ttttgtgtta tcagacgtta ttgtcactca aaaacaccaa ccattctctt tttatttta 218760 ttaataatat aattgggatg agattaattt ttcatcatat acatatcaac ctttcttatt 218820
tatatatact ataccacact tatatataat atataattga aaagttatta acgtttatta 218880
atagatgttc tacgagattt agattttta ttacgatcaa agatactttg tttcttaggt 218940
ttatcgatat ttttattttt aggttttcct ttacttctaa tatctttat cttcttgtta 219000 tgaagtcttc tattcttata acgctcaatt tcaacaagct ttctttctga agcgggtata 219060
tttctagata cttgtatttt gtcaataggt tttaatcttt ctaatgaggg aaatgttaat 219120
agattattct tttctagata tataagggca aaataaacac ttttttcaaa tccataaatt 219180
tggtttgggt ttcttacttt aggttcatct actaaagatt taatactcat tttattctta 219240
agccaatcaa taatcaaacc atctcgatta taaatatatc catacgtaaa cataaagtta 219300
ggattattac tatagaaact gatatgcgag tttagaatag aaacgtttgt attatttttg 219360
tctattttaa ttactacgtc ataaaccatt ttttcttcaa tatacgtttc agaaggaatt 219420
ttaaatacat agtacaaact atcttcatct ttaaatactt ctacactaaa caatctttta 219480 gctttttat acagagtatt aaatcggtca tacatattgg cgataatcat atcccgccta 219540
gctaatcctg cagaaccttt tcctgaaggg ttttgcataa actgttttac agtgatcatt 219600
tctaatatac acccctat tattaattat aacataattt tttgttaaat ttaaaataaa 219660
cttttttatt ttaaaaaatt attaacccct aacgtgaatg ataactatca cgttagggtc 219720
aactttatta taagctaatt cgaatatatt gattacttgt aaccagtaat ccaattactg 219780
aaaatgatgc tctcataatc tgaatatccg tcattaccga gttgataatc tttgtttcag 219840
agtcaggaac atatttctt tctttaagat cataaatcat tttattgtta atacaactct 219900
```

```
caacagtttc atatacttct tcatcgctaa ataattgaga gttctttaat acaattgcat 219960
atgtttcttt aaatgcagaa tatactagtt gtaacaatac tttatctact tcagttaaac 220020
tttcttcatt atcaataata tctttaatta cttttggaat tgaaatattt cctcccggaa 220080
tataaccgta atctaaagca gatctacatg caaagataga atcttccaag agatatttac 220140
gagtatcacg ttccaattca gatttaccac caataaataa cgtagctact ttagaaagta 220200
atctagcttt acgattctct aatttaaaga tttcagaatc tacacctttt tgatatacgt 220260
ctaaattctt taaatcttga atattaaggt caattaattc aattcgagca tctaattctt 220320
cttgatgata ctctccctta ataaattgag ttgatccacc agtcatcgtt actgtttcac 220380
aacgaccaat atgttcacca taaaattgag cgttatttgt tttacttaag ataaataagt 220440
cttcaaaacc ttctttacct tttttagtat taatctgagt tcctaagtat attgctaagt 220500
cttcgaattc ttctttacga gttctagcgg gaaagtctgt agctgcaatt tctagggata 220560
ctctggtatt attgatcttt tgaatcttca taaagtcaat aaattccggt ctatattcct 220620
tcgcaacaat aactagactt ttaccattac cgcatacctg accaataaga tgggcaaaga 220680
aatcaatatc cgtcttatct aaacatgaat cagtaataaa tacataaggt tctttgaaca 220740
ttgcttcaat cttatttggt ttatttgcaa agatagggtc aacataccca cgactagttt 220800
caataccatt tacaatttca aatgtatcct cttcagaagt agatttatct aaataaataa 220860
atcctcgttt accaatttgt ttatagatat tataaataat atttccgtct ttttcatcat 220920
tgttgttaga tacggttgca atattacgga gaatctcaaa gttatcttca ttaataggaa 220980
ttgatttttc ttttaatttc ttttcaatca gttcaccaac attatttaat gaattaatga 221040
tttctttctt aggaagctta cctaagaatt gtgaacgatc attaaccatt ggttctaatt 221100
gattatataa ttcattacta accactactg aagaagttga tccatcacca acctcttgca 221160
ctaatgatct tgaaatagtc ttaatattat tcagaaaagt agtactaata gtattgttaa 221220
aacgaatctt gtctaaaatt gtgaatccat ctttagagat cttagaacca tataaattat 221280
cttctagaat agttgtagat ccataatatc ctaaggattt agaaagaata tcactaatac 221340
tattaagtgt ttctttagca atttttttgat atacttcatc agaaattaca ttgctttcta 221400
caatatcaat tttttcctta ggttcaagaa ttcttgaaat ttgatcttta ataatattgc 221460
tcatacactt ttccacgctg ctatataaat tagtgaattt aatttaattc acaagaattt 221520
aatcaacttc gtcaacaagt ttcttataaa ttcacaaaaa gtgaaaatac agaggaaaac 221580
tctcttaagt tataatgggt ttagccaacc ctttctgcat atattttaa attacatgca 221640 gaattataat ctctatccat cacttcatta cattgatcac atgtatataa tctatccgaa 221700
agtttcattt ttttatcatt ttcttttta tatccacaac aactacaaat ttgagttgat 221760
ggaaaccatc tatctgcaat aattaaggta tttccatata aaatactttt atattgtaat 221820
tgaactttaa aacgataaaa taaagaccgt gatatagatt tagatatttt tcggttagat 221880
aacattcctt taacatttaa atcttctata catatagtgt gataattttt aataacgtaa 221940
gaagtaaact tatgcagcca atcatcttgt atattttgta ttttcaaata aatattttga 222000
agtttgattt tcactttatt atatttattc gaattattga cttttctaga caagattttt 222060
tggtataaag aaattttctt atataatgga attaaatttt ttaaaggact attaaatcgg 222120
tgattttctt cacttatatc aaaatgacca atatttgcat caattccaac tgtcggaaga 222180
ttttgatttg aatgatacat actatcatca gtatcaatac agaaagaagc aaaatactga 222240
```

-continued

```
tttgctcttt ttgtaattgt acatattta atatcaccat taaatcgtat cgattcagac 222300 attttttacac catatttaaa tttaggtaaa aataatcgat tattaataat ccttattgta 222360
ctttcggctt ttcgattaat cgtaaatgaa cttttttgctt ttcgtttatt tttgaattta 222420
ggtttacctg aattagatgt aaaaaatctc ttccaaccat atgccatatt tttacaagca 222480
ttatcaaaaa tatttggggg aaaattatcc cattcaggtt tcaatttcct tttatattcg 222540
tctcgcactt ttcgttcatt aggtttattg ccgttaatgt acatttcatt ccatatattc 222600
aaagacacat tatatgaata tcttgaataa ttgaaaaaat ctttaaattg taactgcatt 222660
gttttgttag gatagattct gatttttttga cttattatca tctaaatcat cccttaaagt 222720
ttttttatat tttcgtaatc cgtataatcg gctagaaaat acatgaataa ttgtcataag 222780
atcatcaact agttctttt caggagaaga actttctaaa ttaattacag ttagtgttgt 222840
tccattaact ttacatcttt cttcaataag ttcaaaacca aaacgagtta gtcgatcttt 222900
atatgttata ataagttctg atacttcttg gttttctatc atgtcaatta attttaaaaa 222960
attctttcgt ttaaaattaa ttccggatgc aatatctgaa agataaatat taacaggttt 223020
tccactatta actgaaaatg tttcaataga ttgtcgttgg ttttcaagtt ctttcttttg 223080
gttactagtt gaaactcgat aatatgctac aatttttctt ttttcttcag gtttgatatt 223140
attagttagt tcaaaataat catcaaccat ttcgtcagta taatacttta ggcgtccttt 223200
tcgaataggt ttaattattt tttccttttc taatgtttct agtttttct ttgatatacg 223260 taatttcatt ctaaattcat cagaacgcat aaccatttaa aacacactcc tttttaattt 223320
atattatatt gttacattaa aatataaatt aaagtgaaaa agagtgaaac tagatgatat 223380
tcataataag tcggctaaat taaattctta ttataattcc caattttgtg tttccacatt 223440
ggttaaatag caggactata tcataaccta taatattata ggtccctcgt acttcccttt 223500
cggtactcta cttgcttcgt atagatatct caatctatct tattcaccat ataggtgtta 223560
catttattat ttgctttcga tagtctctga acgttcaccc atcaagtggg agcttcgctg 223620
ctagattttc cattagtcca cccttagcac tacgttttct aaggttcaca ttattacttc 223680
acttagacac tgataggttt tatttcagct taggtaatct taaagagttt tttctgtctt 223740
tcgactgcat tcacgcttac cgttaccagt tacgttgtag ccctttaagc tttaggagtt 223800
tacaagcaat tcacaaggtt tcgcatacat ctttacagat atatgggagt tttgaataca 223860
ggttaattta atttatattt taaactaaac tcatttaaaa tcaattaaac cattactgct 223920 tctttttctcc actttttttat tttattataa ttgaaagtac attgtcattt tcaataatac 223980
aatcgaattc ttcgataaag gtatacatct taatataatc tttacatgaa tcaagatcaa 224040
tataattatt aaattttaag gatacttttt taaattgtct aatttcttca tctttggaag 224100
tattgttaaa tcctttgatg atattaaatg aaaatttctc ttcaagatca tatagtagta 224160
aattaagctt taatccgaat tcagaatgct taagtgaatc ataataattg tcttcatcat 224220
aatccccatt cttttcggta agtttattat aaaatttaaa attatcggta ttaatattca 224280 ttaaacttttc accacgcttt cttaatttgc cataataact caactggact attagtatttt 224340 accatttatc ggacttagat atccatggtc tggtttacct gttgtatttt cattaggaga 224400
agaagaggtt cctccattat agagatttct cagttcagct tcttgccttt tatgtttttc 224460
agcaatatcc tcttctttaa cttctctaag tcctaataat agatacattt cagtgttcat 224520
gatatcgttt agacttaatt taccttcaaa taactctaat aaatatagta tatctttaga 224580
atcattcaat actttctttt cgataatcat tgaaccacta ctatttttct catctactgc 224640
```

-continued tgaagctcca gttgagtt                                                 224658

<210> SEQ ID NO 3
<211> LENGTH: 48
<212> TYPE: DNA
<213> ORGANISM: Artificial Sequence
<220> FEATURE:
<223> OTHER INFORMATION: Primer sequence

<400> SEQUENCE: 3
aggaaacagc tatgacatga ttacgttatc ataaaacttt cgatgtac                 48

<210> SEQ ID NO 4
<211> LENGTH: 33
<212> TYPE: DNA
<213> ORGANISM: Artificial Sequence
<220> FEATURE:
<223> OTHER INFORMATION: Primer sequence

<400> SEQUENCE: 4
atttatactc tatttaacga gcgtattgag ttg                                 33

<210> SEQ ID NO 5
<211> LENGTH: 506
<212> TYPE: DNA
<213> ORGANISM: Artificial Sequence
<220> FEATURE:
<223> OTHER INFORMATION: Upstream HR Flank 1

<400> SEQUENCE: 5
ggtaccatgt acatccaaat ggtggataca acatgcatcc gcatgaatgg cgccgtggta    60
ttcgtgacgt tattgactgg atgtctcaag caatgaaaaa tgattacaaa acttatgatg    120
cttactttgt aattgttggt aatccaattg acactcaatt gattcctgac attgaatggg    180
aattccaagg agctactgat gaagttgcgg gaattaacgt ttcttatagc gttggtgctt    240
cttctacagt taaccgttat aaagttgttt cttctgactt agtacctgct ggagatctat    300
taatctttgc agttcctact cgtgaagact tcaaaactta cgaatactac ccatacactt    360
tcaatatcgt taataattac aacaatgctg ttaaccaaag cgttcctaac attatgcttt    420
ctcgccgtta tacagttgaa gaatttgttc caattatcgg taaagttaca attaaaaaca    480
acgatgcaac tcaatacgct cgttaa                                         506

<210> SEQ ID NO 6
<211> LENGTH: 506
<212> TYPE: DNA
<213> ORGANISM: Artificial Sequence
<220> FEATURE:
<223> OTHER INFORMATION: Downstream HR Flank 2

<400> SEQUENCE: 6
taaatattat gaacctttca gagacctttt ggtttctgaa aggttattat ttataaaaat    60
ttaaattggc ggtgcaacca tgcatattga ttatggtatt gaaaagaata tatcaaagta    120
cttacatgaa gaattactaa ctgaagatat ctataatcat cctttattaa aaaagattga    180
tgatgaattt cagaaaatat tagatgaaga taatattaat gatactaaac taccagtaac    240
atcatataaa aaaattcaaa atataattaa atatgtctca actatattta atataaattt    300
aattataacg attgataacg ataatatcct tacttatgga atgatgacat ttattccggt    360
taaaaatcta acaaagatat ctaataatat aaagaagatt gtacttcaac caaaaactgg    420

-continued

```
ttttgaatat attaaaactg aagttattga aattaaaata cagaaaaaat taatatcttt      480
cattaaggat ccaaacttac gtcgac                                          506

<210> SEQ ID NO 7
<211> LENGTH: 60
<212> TYPE: DNA
<213> ORGANISM: Artificial Sequence
<220> FEATURE:
<223> OTHER INFORMATION: Promoter 3

<400> SEQUENCE: 7
atagagtata aattctattc agtttcgtat attaatacta gtagatagga ggtgtttcga       60
```

METHODS AND SYSTEMS FOR THE RAPID DETECTION OF *LISTERIA* USING INFECTIOUS AGENTS

RELATED APPLICATIONS

This application claims priority to U.S. provisional patent application No. 63/145,772 filed on Feb. 4, 2021. The disclosure of U.S. provisional patent application No. 63/145,772, is incorporated by reference in its entirety herein. The disclosures of U.S. application Ser. Nos. 13/773,339, 14/625,481, 15/263,619, 15/409,258, and 16/905,607 are hereby incorporated by reference in their entirety herein.

FIELD OF THE INVENTION

This invention relates to compositions, methods, systems, and kits for the detection of microorganisms using infectious agents.

SEQUENCE LISTING

The instant application contains a Sequence Listing which has been submitted via EFSWeb and is hereby incorporated by reference in its entirety. Said ASCII copy, created on May 30, 2026, is named 1291928 PhDx 2021-02-US ST25, and is 585,727 bytes in size.

BACKGROUND

There is a strong interest in improving speed and sensitivity for detection of bacteria, viruses, and other microorganisms in biological, food, water, and clinical samples. Microbial pathogens can cause substantial morbidity among humans and domestic animals, as well as immense economic loss. Also, detection of microorganisms is a high priority for the Food and Drug Administration (FDA) and Centers for Disease Control (CDC), as well as the United States Department of Agriculture (USDA), given outbreaks of life-threatening or fatal illness caused by ingestion of food contaminated with certain microorganisms, e.g., *Listeria* spp., *Salmonella* spp., or *Staphylococcus* spp.

In particular, *Listeria* spp. are known to cause the potentially serious infection, listeriosis. *Listeria* spp., such as *L. monocytogenes*, are typically transmitted through ingestion of contaminated food products. *L. monocytogenes* is a gram-positive bacterium commonly associated with contamination of food products, including but not limited to, milk, seafood, poultry, and meat. Food-borne illnesses, such as listeriosis, can be prevented by detecting contaminated foods prior to consumer availability.

Traditional microbiological tests for the detection of bacteria rely on non-selective and selective enrichment cultures followed by plating on selective media and further testing to confirm suspect colonies. Such procedures can require as long as seven days. For examples, traditional tests for the detection of *Listeria* spp. in food products are complex and time consuming requiring 24-48 hour enrichment periods followed by additional lengthy testing with a total time for detection ranging from 5-7 days. A variety of rapid methods have been investigated and introduced into practice to reduce the time requirement. However, these methods have drawbacks. For example, polymerase chain reaction (PCR) tests, which also include an amplification step and therefore are capable of both very high sensitivity and selectivity; are economically limited to a small sample size. With dilute bacterial suspensions, most small subsamples will be free of cells and therefore purification and/or lengthy enrichment steps are still required.

The time required for traditional biological enrichment is dictated by the growth rate of the target bacterial population of the sample, by the effect of the sample matrix, and by the required sensitivity. Due to the time required for cultivation, these methods can take up to eight days, depending upon the organism to be identified and the source of the sample. This lag time is generally unsuitable as the contaminated food, water, or other product may have already made its way into livestock or humans. In addition, increases in antibiotic-resistant bacteria and biodefense considerations make rapid identification of bacterial pathogens in water, food and clinical samples critical priorities worldwide.

Therefore, there is a need for more rapid, simple, and sensitive detection and identification of microorganisms, such as bacteria and other potentially pathogenic microorganisms.

SUMMARY

Embodiments of the invention comprise compositions, methods, systems, and kits for the detection of microorganisms such as *Listeria* spp. The invention may be embodied in a variety of ways.

In some aspects, the invention comprises a recombinant bacteriophage comprising an indicator gene inserted into a late gene region of a bacteriophage genome. In some embodiments the recombinant bacteriophage is a genetically modified *Listeria*-specific bacteriophage genome. In certain embodiments the recombinant bacteriophage comprises a genetically modified bacteriophage genome derived from a bacteriophage that specifically recognizes *Listeria* spp. In some embodiments, the bacteriophage used to prepare the recombinant bacteriophage specifically infects one or more *Listeria* spp. In an embodiment, the recombinant bacteriophage can distinguish *Listeria* spp. in the presence of other types of bacteria. In some embodiments the recombinant bacteriophage specifically recognizes *Listeria monocytogenes*. In some embodiments the recombinant bacteriophage specifically recognizes *Listeria grayi*.

In some embodiments of recombinant indicator bacteriophage, the indicator gene can be codon-optimized and can encode a soluble protein product that generates an intrinsic signal or a soluble enzyme that generates signal upon reaction with substrate. Some recombinant bacteriophage further comprise an untranslated region upstream of a codon-optimized indicator gene, wherein the untranslated region includes a bacteriophage late gene promoter and a ribosomal entry site. In some embodiments, the indicator gene is a luciferase gene. The luciferase gene can be a naturally occurring gene, such as *Oplophorus* luciferase, Firefly luciferase, Lucia luciferase, or Renilla luciferase, or it can be a genetically engineered gene such as NANO-LUC®.

Also disclosed herein are methods for preparing a recombinant indicator bacteriophage. Some embodiments include selecting a wild-type bacteriophage that specifically infects a target pathogenic bacterium; preparing a homologous recombination plasmid/vector comprising an indicator gene; transforming the homologous recombination plasmid/vector into target pathogenic bacteria; infecting the transformed target pathogenic bacteria with the selected wild-type bacteriophage, thereby allowing homologous recombination to occur between the plasmid/vector and the bacteriophage genome; and isolating a particular clone of recombinant bacteriophage. In some embodiments the selected wild-type bacteriophage is a *Listeria*-specific bacteriophage.

In some embodiments, preparing a homologous recombination plasmid/vector includes determining the natural nucleotide sequence in the late region of the genome of the selected bacteriophage; annotating the genome and identifying the major capsid protein gene of the selected bacteriophage; designing a sequence for homologous recombination downstream of the major capsid protein gene, wherein the sequence comprises a codon-optimized indicator gene; and incorporating the sequence designed for homologous recombination into a plasmid/vector. The step of designing a sequence can include inserting a genetic construct comprising an untranslated region, including a phage late gene promoter and ribosomal entry site, upstream of the codon-optimized indicator gene. In some embodiments, the phage late gene promoter is an exogenous promoter, different from any endogenous promoter in the phage genome. Thus, in some methods, the homologous recombination plasmid comprises an untranslated region including a bacteriophage late gene promoter and a ribosomal entry site upstream of the codon-optimized indicator gene.

Some embodiments of the invention are compositions that include a recombinant indicator bacteriophage as described herein. For example, compositions can include one or more wild-type or genetically modified infectious agents (e.g., bacteriophages) and one or more indicator genes. In some embodiments, the compositions, methods, systems and kits of the invention may comprise a cocktail of at least one recombinant bacteriophage for use in detection of microorganisms such as *Listeria* spp. In certain instances, the cocktail compositions is able to detect *L. grayi*.

In some embodiments, the invention comprises a method for detecting a microorganism of interest in a sample comprising the steps of incubating the sample with a recombinant bacteriophage that infects the microorganism of interest, wherein the recombinant bacteriophage comprises an indicator gene inserted into a late gene region of the bacteriophage such that expression of the indicator gene during bacteriophage replication following infection of host bacteria results in a soluble indicator protein product, and detecting the indicator protein product, wherein positive detection of the indicator protein product indicates that the microorganism of interest is present in the sample.

In some embodiments of methods for preparing recombinant indicator bacteriophage, the wild-type bacteriophage is a *Listeria* spp.-specific bacteriophage and the target pathogenic bacterium is *Listeria* spp. In some embodiments, isolating a particular clone of recombinant bacteriophage comprises a limiting dilution assay for isolating a clone that demonstrates expression of the indicator gene.

Other aspects of the invention include methods for detecting bacteria, such as *Listeria* spp. in a sample, including steps of incubating the sample with a recombinant bacteriophage derived from *Listeria*-specific bacteriophage and detecting an indicator protein product produced by the recombinant bacteriophage, wherein positive detection of the indicator protein product indicates that *Listeria* spp. is present in the sample.

*Listeria* spp. are gram positive rod shaped bacteria that are ubiquitous in soil, water, and in several animals intended for consumption. *Listeria* spp. can grow at wide temperature and pH ranges and can tolerate high concentrations of sodium chloride allowing for a greater ability to contaminate food during processing. In humans, *Listeria monocytogenes* is of particular concern as the causative agent of Listeriosis. Listeriosis is usually caused by eating food that has been contaminated with *L. monocytogenes*. It is estimated that 1,600 people get Listeriosis each year, resulting in about 260 deaths. The infection is most likely to sicken pregnant women and their newborns, adults aged 65 or older, and people with weakened immune systems. Most concerning are infections occurring in pregnant women were the infection can lead to miscarriage, still birth, premature delivery, or even life-threating infections such as sepsis or meningitis in the newborn In some embodiments, the invention includes methods for the detection of *Listeria* spp. using a recombinant bacteriophage derived from a bacteriophage that targets *Listeria* spp. The sample can be a food or water sample. In some embodiments, samples include environmental samples (e.g., sponges and swabs of surfaces or equipment for bacterial monitoring in factories and other processing facilities).

In some embodiments of methods for detecting bacteria, the sample is first incubated in conditions favoring growth for an enrichment period of 24 hours or less, 23 hours or less, 22 hours or less, 21 hours or less, 20 hours or less, 19 hours or less, 18 hours or less, 17 hours or less, 16 hours or less, 15 hours or less, 14 hours or less, 13 hours or less, 12 hours or less, 11 hours or less, 10 hours or less, or 9 hours or less, 8 hours or less, 7 hours or less, 6 hours or less, 5 hours or less, 4 hours or less, 3 hours or less, or 2 hours or less. In some embodiments, the sample is not enriched prior to detection. In some embodiments, the total time to results is less than 26 hours, 25 hours, 24 hours, 23 hours, 22 hours, 21 hours, 20 hours, 19 hours, 18 hours, 17 hours, 16 hours, 15 hours, 14 hours, 13 hours, 12 hours, 11 hours, 10 hours, 9 hours, 8 hours, 7 hours, 6 hours, 5 hours, 4 hours, 3 hours or 2 hours. In some embodiments, the ratio of signal to background generated by detecting the indicator is at least 2.0 or at least 2.5 or at least 3.0. In some embodiments, the method detects as few as 1, 10, 15, 20, 30, 40, 50, 60, 70, 80, 90, or 100 of the specific bacteria in a sample of a standard size for the food safety industry.

Additional embodiments include systems and kits for detecting *Listeria* spp., wherein the systems or kits include a recombinant bacteriophage derived from *Listeria*-specific bacteriophage. Some embodiments further include a substrate for reacting with an indicator to detect the soluble protein product expressed by the recombinant bacteriophage. These systems or kits can include features described for the bacteriophage, compositions, and methods of the invention. In still other embodiments, the invention comprises non-transient computer readable media for use with methods or systems according to the invention.

BRIEF DESCRIPTION OF THE FIGURES

The present invention may be better understood by referring to the following non-limiting figures.

FIG. 5A shows detection of *Listeria* in sponges spiked at <1 CFU spike/10 mL. FIG. 5B shows detection of *Listeria* in sponges spiked at <1 CFU spike/90 mL.

FIG. 6 shows data from embodiments of a *Listeria* detection assay using recombinant bacteriophage specific for *Listeria* to detect *Listeria* in environmental surface swab sponge samples.

FIG. 7A depicts LPJP1's large icosahedral head and long straight tail. FIG. 7B depicts LPJP1's contractile outer tail sheath.

DETAILED DESCRIPTION OF THE INVENTION

Figure 1:
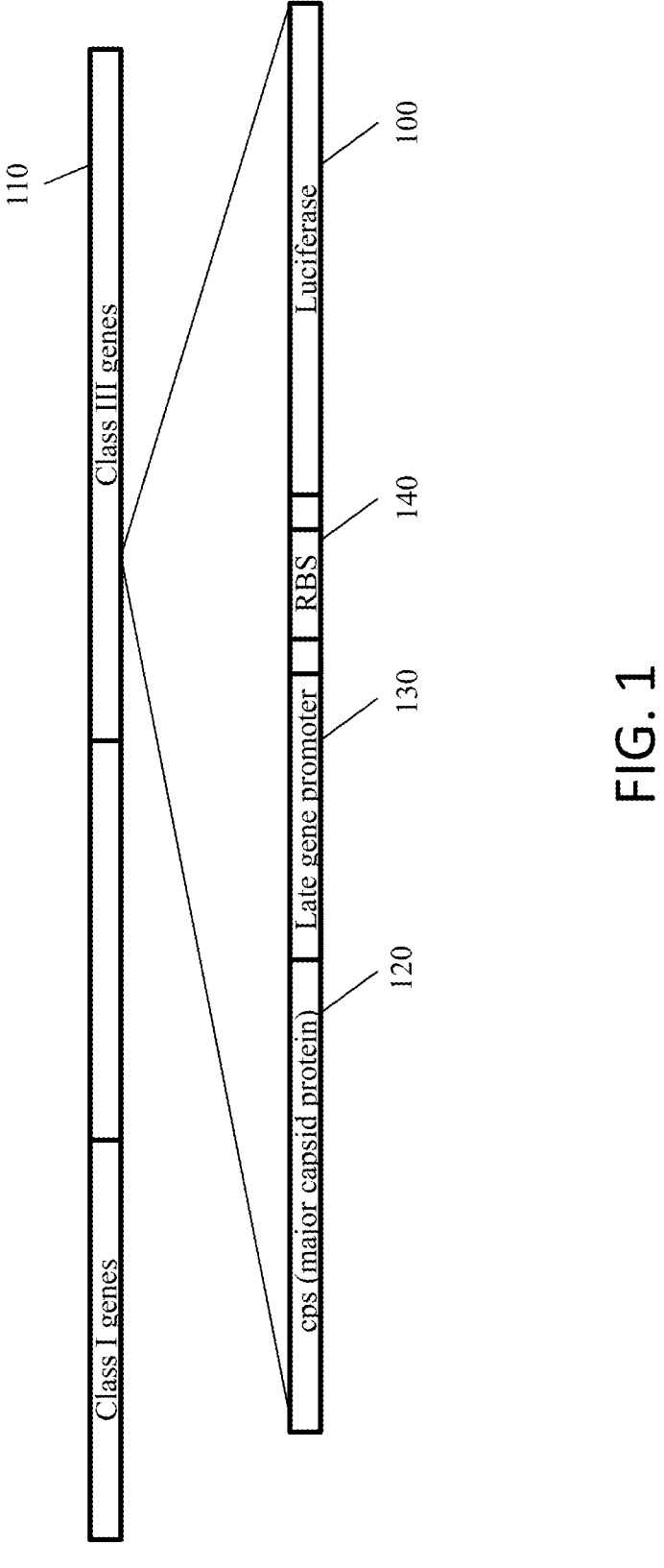
FIG. 1 depicts an indicator phage construct according to an embodiment of the invention illustrating insertion of a genetic construct comprising a luciferase gene, a bacteriophage late gene promoter, and a ribosomal binding site (RBS) inserted into the late (class III) region of a bacteriophage. The promoter depicted is in addition to and separate from the endogenous late gene promoter upstream of the endogenous late genes, such as the gene for major capsid protein (MCP).

Disclosed herein are compositions, methods and systems that demonstrate surprising sensitivity for detection of a microorganism of interest, such as *Listeria* spp., in test samples (e.g., biological, food, water, and environmental samples). Detection can be achieved in a shorter timeframe than was previously thought possible using genetically modified infectious agents in assays performed with minimal enrichment times during which microorganisms could potentially multiply. Also surprising is the success of using a potentially high multiplicity of infection (MOI), or high concentrations of plaque forming units (PFU), for incubation with a test sample. Such high phage concentrations (PFU/mL) were previously purported to be detrimental in bacterium detection assays, as they were purported to cause "lysis from without." However, a high concentration of phage can facilitate finding, binding, and infecting a low number of target cells.

The compositions, methods, systems and kits of the invention may comprise infectious agents for use in detection of microorganisms such as *Listeria* spp. In certain embodiments, the invention may comprise a composition comprising a recombinant bacteriophage having an indicator gene inserted into a late gene region of the bacteriophage. In certain embodiments, expression of the indicator gene during bacteriophage replication following infection of a host bacterium results in production of a soluble indicator protein product. In certain embodiments, the indicator gene may be inserted into a late gene (i.e., class III) region of the bacteriophage. The bacteriophage can be derived from *Listeria* spp.-specific bacteriophage, or another wild-type or engineered bacteriophage. In some embodiments, the recombinant bacteriophage is constructed from at least one of LPJP1, LMA4, LMA8, A511, P70, LP-ES1, and LP-ES3 bacteriophages.

In some embodiments, the compositions, methods, systems and kits of the invention may comprise a cocktail of at least one recombinant bacteriophage for use in detection of microorganisms such as *Listeria* spp.

In some aspects, the invention comprises a method for detecting a microorganism of interest. The method may use an infectious agent for detection of the microorganism of interest such as a *Listeria* spp. For example, in certain embodiments, the microorganism of interest is *Listeria* spp. and the infectious agent is a bacteriophage that specifically infects a *Listeria* spp. Thus, in certain embodiments, the method may comprise detection of a bacterium of interest in a sample by incubating the sample with a recombinant bacteriophage that infects the bacterium of interest. In certain embodiments, the recombinant bacteriophage comprises an indicator gene. The indicator gene may, in certain embodiments, be inserted into a late gene region of the bacteriophage such that expression of the indicator gene during bacteriophage replication following infection of host bacteria results in production of an indicator protein product. The method may comprise detecting the indicator protein product, wherein positive detection of the indicator protein product indicates that the bacterium of interest is present in the sample. In some embodiments, the indicator protein is soluble.

In certain embodiments, the invention may comprise a system. The system may contain at least some of the compositions of the invention. Also, the system may comprise at least some of the components for performing the method. In certain embodiments, the system is formulated as a kit. Thus, in certain embodiments, the invention may comprise a system for rapid detection of a microorganism of interest such as *Listeria* spp. in a sample, comprising: A component for incubating the sample with an infectious agent specific for the microorganism of interest, wherein the infectious agent comprises an indicator moiety; and a component for detecting the indicator moiety. In yet other embodiments, the invention comprises software for use with the methods or systems.

Thus, some embodiments of the present invention solve a need by using bacteriophage-based methods for amplifying a detectable signal indicating the presence of bacteria. In certain embodiments as few as 10 bacteria are detected. The principles applied herein can be applied to the detection of a variety of microorganisms. Because of numerous binding sites for an infectious agent on the surface of a microorganism, the capacity to produce progeny during infection, and the potential for high level expression of an encoded indicator moiety, the infectious agent or an indicator moiety can be more readily detectable than the microorganism itself. In this way, embodiments of the present invention can achieve tremendous signal amplification from even a single infected cell.

Aspects of the present invention utilize the high specificity of binding agents that can bind to particular microorganisms, such as the binding component of infectious agents, as a means to detect and/or quantify the specific microorganism in a sample. In some embodiments, the present invention utilizes the high specificity of infectious agents such as bacteriophage.

In some embodiments, detection is achieved through an indicator moiety associated with the binding agent specific for the microorganism of interest. For example, an infectious agent may comprise an indicator moiety, such as a gene encoding a soluble indicator. In some embodiments the indicator may be encoded by the infectious agent, such as a bacteriophage, and the bacteriophage is designated an indicator phage.

Some embodiments of the invention disclosed and described herein utilize the discovery that a single microorganism is capable of binding specific recognition agents, such as phage. Following infection and replication of the phage, progeny phage may be detected via an indicator moiety expressed during phage replication. This principle allows amplification of indicator signal from one or a few cells based on specific recognition of microorganism surface receptors. For example, by exposing as few as 10 bacteria cells to a plurality of phage, thereafter allowing amplification of the phage and high-level expression of an encoded indicator gene product during replication, the indicator signal is amplified such that the bacteria are detectable.

Embodiments of the methods and systems of the invention can be applied to detection and quantification of a variety of microorganisms (e.g., bacteria) in a variety of circumstances, including but not limited to detection of pathogens from food, water, and commercial samples. The methods of the present invention provide high detection sensitivity and specificity rapidly. In some embodiments detection is possible within a single replication cycle of the bacteriophage, which is unexpected.

Definitions

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures used in connection with, and techniques of, cell and tissue culture, molecular biology, immunology, microbiology, genetics and protein and nucleic acid chemistry and hybridization described herein are those well-known and commonly used in the art. Known methods and techniques are generally performed according to conventional methods well known in the art and as described in various general and more specific references that are discussed throughout the present specification unless otherwise indicated. Enzymatic reactions and purification techniques are performed according to manufacturer's specifications, as commonly accomplished in the art or as described herein. The nomenclatures used in connection with the laboratory procedures and techniques described herein are those well-known and commonly used in the art.

The following terms, unless otherwise indicated, shall be understood to have the following meanings:

As used herein, the terms "a", "an", and "the" can refer to one or more unless specifically noted otherwise.

The use of the term "or" is used to mean "and/or" unless explicitly indicated to refer to alternatives only or the alternatives are mutually exclusive, although the disclosure supports a definition that refers to only alternatives and "and/or." As used herein "another" can mean at least a second or more.

Throughout this application, the term "about" is used to indicate that a value includes the inherent variation of error for the device, the method being employed to determine the value, or the variation that exists among samples.

The term "solid support" or "support" means a structure that provides a substrate and/or surface onto which biomolecules may be bound. For example, a solid support may be an assay well (i.e., such as a microtiter plate or multi-well plate), or the solid support may be a location on a filter, an array, or a mobile support, such as a bead or a membrane (e.g., a filter plate, latex particles, paramagnetic particles, or lateral flow strip).

The term "binding agent" refers to a molecule that can specifically and selectively bind to a second (i.e., different) molecule of interest. The interaction may be non-covalent, for example, as a result of hydrogen bonding, van der Waals interactions, or electrostatic or hydrophobic interactions, or it may be covalent. The term "soluble binding agent" refers to a binding agent that is not associated with (i.e., covalently or non-covalently bound) to a solid support.

As used herein, an "analyte" refers to a molecule, compound or cell that is being measured. The analyte of interest may, in certain embodiments, interact with a binding agent. As described herein, the term "analyte" may refer to a protein or peptide of interest. An analyte may be an agonist, an antagonist, or a modulator. Or, an analyte may not have a biological effect. Analytes may include small molecules, sugars, oligosaccharides, lipids, peptides, peptidomimetics, organic compounds and the like.

The term "detectable moiety" or "detectable biomolecule" or "reporter" or "indicator" or "indicator moiety" refers to a molecule that can be measured in a quantitative assay. For example, an indicator moiety may comprise an enzyme that may be used to convert a substrate to a product that can be measured. An indicator moiety may be an enzyme that catalyzes a reaction that generates bioluminescent emissions (e.g., luciferase). Or, an indicator moiety may be a radioisotope that can be quantified. Or, an indicator moiety may be a fluorophore. Or, other detectable molecules may be used.

As used herein, "bacteriophage" or "phage" includes one or more of a plurality of bacterial viruses. In this disclosure, the terms "bacteriophage" and "phage" include viruses such as mycobacteriophage (such as for TB and paraTB), mycophage (such as for fungi), mycoplasma phage, and any other term that refers to a virus that can invade living bacteria, fungi, mycoplasma, protozoa, yeasts, and other microscopic living organisms and uses them to replicate itself. Here, "microscopic" means that the largest dimension is one millimeter or less. Bacteriophages are viruses that have evolved in nature to use bacteria as a means of replicating themselves. A phage does this by attaching itself to a bacterium and injecting its DNA (or RNA) into that bacterium, and inducing it to replicate the phage hundreds or even thousands of times. This is referred to as phage amplification.

As used herein, "late gene region" refers to a region of a viral genome that is transcribed late in the viral life cycle. The late gene region typically includes the most abundantly expressed genes (e.g., structural proteins assembled into the bacteriophage particle). Late genes are synonymous with class III genes and include genes with structure and assembly functions. For example, the late genes (synonymous with class III,) are transcribed in phage T7, e.g., from 8 minutes after infection until lysis, class I (e.g., RNA polymerase) is early from 4-8 minutes, and class II from 6-15 minutes, so there is overlap in timing of II and III. A late promoter is one that is naturally located and active in such a late gene region.

As used herein, "culturing for enrichment" refers to traditional culturing, such as incubation in media favorable to propagation of microorganisms, and should not be confused with other possible uses of the word "enrichment," such as enrichment by removing the liquid component of a sample to concentrate the microorganism contained therein, or other forms of enrichment that do not include traditional facilitation of microorganism propagation. Culturing for enrichment for periods of time may be employed in some embodiments of methods described herein.

As used herein "recombinant" refers to genetic (i.e., nucleic acid) modifications as usually performed in a laboratory to bring together genetic material that would not otherwise be found. This term is used interchangeably with the term "modified" herein.

As used herein "RLU" refers to relative light units as measured by a luminometer (e.g., GLOMAX® 96) or similar instrument that detects light. For example, the detection of the reaction between luciferase and appropriate substrate (e.g., NANOLUC® with NANO-GLO®) is often reported in RLU detected.

As used herein "time to results" refers to the total amount of time from beginning of sample incubation to generated result. Time to results does not include any confirmatory testing time. Data collection can be done at any time after a result has been generated.

Samples

Each of the embodiments of the methods and systems of the invention can allow for the rapid detection and quantification of microbes in a sample. For example, methods according to the present invention can be performed in a shortened time period with superior results.

Bacterial cells detectable by the present invention include, but are not limited to, bacterial cells that are food or water borne pathogens.

Samples may be liquid, solid, or semi-solid. Samples may be swabs of solid surfaces. Samples may include environmental materials, such as water samples, or the filters from air samples or aerosol samples from cyclone collectors. Samples may be of vegetables, meat, fish, poultry, peanut butter, processed foods, powdered infant formula, powdered milk, teas, starches, eggs, milk, cheese, or other dairy products.

In some embodiments, samples may be used directly in the detection methods of the present invention, without preparation, concentration, or dilution. For example, liquid samples, including but not limited to, milk and juices, may be assayed directly. Samples may be diluted or suspended in solution, which may include, but is not limited to, a buffered solution or a bacterial culture medium. A sample that is a solid or semi-solid may be suspending in a liquid by mincing, mixing or macerating the solid in the liquid. A sample should be maintained within a pH range that promotes bacteriophage attachment to the host bacterial cell. A sample should also contain the appropriate concentrations of divalent and monovalent cations, including but not limited to $Na^+$, $Mg^{2+}$, and $Ca^{2+}$. Preferably a sample is maintained at a temperature that maintains the viability of any pathogen cells contained within the sample.

In some embodiments of the detection assay, the sample is maintained at a temperature that maintains the viability of any pathogen cell present in the sample. For example, during steps in which bacteriophages are attaching to bacterial cells, it is preferable to maintain the sample at a temperature that facilitates bacteriophage attachment. During steps in which bacteriophages are replicating within an infected bacterial cell or lysing such an infected cell, it is preferable to maintain the sample at a temperature that promotes bacteriophage replication and lysis of the host. Such temperatures are at least about 25 degrees Celsius (C), more preferably no greater than about 35 degrees C., most preferably about 30 degrees C.

Assays may include various appropriate control samples. For example, control samples containing no bacteriophages or control samples containing bacteriophages without bacteria may be assayed as controls for background signal levels.

Indicator Bacteriophage

As described in more detail herein, the compositions, methods, systems and kits of the invention may comprise infectious agents for use in detection of pathogenic microorganisms. In certain embodiments, the invention comprises a recombinant indicator bacteriophage, wherein the bacteriophage genome is genetically modified to include an indicator or reporter gene. In some embodiments, the invention may include a composition comprising a recombinant bacteriophage having an indicator gene incorporated into the genome of the bacteriophage.

A recombinant indicator bacteriophage can include a reporter or indicator gene. In certain embodiments of the infectious agent, the indicator gene does not encode a fusion protein. For example, in certain embodiments, expression of the indicator gene during bacteriophage replication following infection of a host bacterium results in a soluble indicator protein product. In certain embodiments, the indicator gene may be inserted into a late gene region of the bacteriophage. Late genes are generally expressed at higher levels than other phage genes, as they code for structural proteins. The late gene region may be a class III gene region and may include a gene for a major capsid protein.

Some embodiments include designing (and optionally preparing) a sequence for homologous recombination downstream of the major capsid protein gene. Other embodiments include designing (and optionally preparing) a sequence for homologous recombination upstream of the major capsid protein gene. In some embodiments, the sequence comprises a codon-optimized reporter gene preceded by an untranslated region. The untranslated region may include a phage late gene promoter and ribosomal entry site.

In some embodiments, an indicator bacteriophage is derived from *Listeria*-specific phage. In some embodiments, the selected wild-type bacteriophage or cocktail of wild-type bacteriophages is capable of infecting at least one target *Listeria* spp. In some embodiments, the wild-type bacteriophage is mutated to expand the host range of the wild-type bacteriophage. *Listeria* species are ubiquitous in the environment and are often found in water, sewage and soil.

In some embodiments, the selected wild-type bacteriophage or cocktail of wild-type bacteriophages is capable of infecting one or more, two or more, or three or more target *Listeria* spp. In certain instances the target species of *Listeria* is selected from *L. monocytogenes, L. ivanovii, L. innocua*, and *L. grayi*. *Listeria grayi* is a Gram-positive bacterial species, consisting of two genetically related subspecies: *L. grayi* subsp. *grayi* and *L. grayi* subsp. *murrayi*. Although typically classified as non-pathogenic, *L. grayi* has been associated with severe disease in rare cases involving immunocompromised individuals (Todeschini, et al., A case of *Listeria murray/grayi* bacteremia in a patient with advanced Hodgkin's disease. *Eur J Clin Microbiol Infect Dis* 1998, 17, 808-810; Rapose, et al., *Transpl Infect Dis* 2008, 10, 434-436; Salimnia, et al., *Listeria grayi*: vancomycin-resistant, gram-positive rod causing bacteremia in a stem cell transplant recipient. *Transpl Infect Dis* 2010, 12, 526-528). *L. grayi* shares a number of important characteristics with the food-borne pathogen, *L. monocytogenes*, including motility and growth at refrigerated temperatures (Orsi, R. H.; Wiedmann, M. Characteristics and distribution of *Listeria* spp., including *Listeria* species newly described since 2009. *Appl Microbiol Biotechnol* 2016, 100, 5273-5287). These shared features have allowed this and other non-pathogenic *Listeria* species to serve as useful tools in food safety. One particular example of this can be seen in *Listeria* environmental monitoring programs (Tompkin, R. B. Control of *Listeria monocytogenes* in the food-processing environment. *J Food Prot* 2002, 65, 709-725). If any viable *Listeria* species are detected during sampling, preventative intervention allows the elimination of permissive growth conditions in an effort to preempt contamination with pathogenic species, particularly *L. monocytogenes*.

Hundreds of *Listeria* phages have been described over the years and the deficiency in lytic phage appears unique to the *L. grayi* species. For example, previous work developing a bacteriophage typing system for *Listeria* species revealed that none of the 16 typing phage could lyse *L. grayi* (Loessner, M. J.; Busse, M. *Appl Environ Microbiol* 1990, 56, 1912-1918). Additionally, studies isolating *Listeria*-specific phage from food processing plants found phage capable of lysing all tested *Listeria* species except for *L. grayi* (Kim, et al., Host ranges of *Listeria*-specific bacteriophages from the turkey processing plant environment in the United States. *Appl Environ Microbiol* 2008, 74, 6623-6630). The lack of reported lytic phages for this species could have indicated a unique phage resistance mechanism or simply imply that such a phage was incredibly rare or challenging to isolate.

In some embodiments, the selected wild-type bacteriophage is from the Caudovirales order of phages. Caudovirales are an order of tailed bacteriophages with double-stranded DNA (dsDNA) genomes. Each virion of the Caudovirales order has an icosahedral head that contains the viral genome and a flexible tail. The Caudovirales order comprises five bacteriophage families: Myoviridae (long contractile tails), Siphoviridae (long non-contractile tails), Podoviridae (short non-contractile tails), Ackermannviridae, and Herelleviridae. The term myovirus can be used to describe any bacteriophage with an icosahedral head and a long contractile tail, which encompasses bacteriophages within both the Myoviridae and Herelleviridae families. In some embodiments, the selected wild-type bacteriophage is a member of the Myoviridae family such as, *Listeria* phage B054, *Listeria* phage LipZ5, *Listeria* phage PSU-VKH-LP041, and *Listera* phage WIL-2. In other embodiments, the selected wild-type bacteriophage is a member of the family Herelleviridae. The genus *Pecentumvirus*, under the family Herelleviridae includes bacteriophages such as *Listeria* phage LMSP-25, *Listeria* phage LMTA-148, *Listeria* phage LMTA-34, *Listeria* phage LP-048, *Listeria* phage LP-064, *Listeria* phage LP-083-2, *Listeria* phage LP-125, *Listeria* virus P100, *Listeria* phage List-36, *Listeria* phage WIL-1, *Listeria* phage vB LmoM_AG20, and *Listeria* virus A511. LMA4 and LMA8 are also likely in the genus *Pecentumvirus*, under the family Herelleviridae. In other embodiments, the selected wild-type bacteriophage is LMA4 or LMA8.

In some embodiments, the host range of the selected wild-type bacteriophage is expanded prior to construction of the recombinant bacteriophage. For example, WT A511 bacteriophages are not capable of infecting the 3A serotype of *Listeria* monocytogenes. In some embodiments, the host range of bacteriophage using the methods described in US 2020/0399614, which is incorporated in its entirety herein. For example, in some embodiments, a mutant bacteriophage with a an expanded host-range is produced using a method comprising: (i) preparing a series of first co-culture mixtures of varying ratios comprising a host bacterial strain and a target-host bacterial strain; (ii) adding a phage strain to each of the first co-culture mixtures; (iii) incubating the first co-culture mixtures and the phage strain under bacterial culture conditions; (iv) collecting a phage lysate from each of the plurality of first-co-cultures; (v) pooling the phage lysates from each of the plurality of first co-cultures; (vi) assaying phage lysates to determine if the bacteria host-range has expanded; and (vii) isolating a mutant phage with expanded host-range. In certain instances the selected wild-type bacteriophage is LP-ES3 (A511-3A), which is derived from wild-type bacteriophage, A511, but has been adapted to be capable of infecting serotype 3A of *Listeria* monocytogenes. In some embodiments, the mutant bacteriophage comprises a mutation in a gene encoding the tail receptor. In some embodiments, the mutation is a single nucleotide polymorphism. In certain instances, mutant bacteriophage comprising a mutation in a gene encoding the tail receptor are capable of infecting serotype 3A of *Listeria* monocytogenes.

In still other embodiments, the selected wild-type bacteriophage is a member of the family Ackermannviridae. In still other embodiments, the selected wild-type bacteriophage is a member of the family Siphoviridae, which includes *Listeria* phages A006, A118, A500, B025, LP-026, LP-030-2, LP-030-3, LP-037, LP-101, LP-110, LP-114, P35, P40, P70, PSA, vB_LmoS_188, and vB_Lmos_293. In other embodiments, the selected wild-type bacteriophage is LP-ES1. LP-ES1 is also likely in the genus *Homburgvirus*, under the family Siphoviridae. LP-ES1 is capable of infecting *L. innocua*. In certain embodiments, the selected wild-type bacteriophage is capable of infecting *L. innocua*.

In some embodiments, the selected wild-type bacteriophage is a jumbo or giant bacteriophage. Jumbo phages are prokaryotic viruses with genomes greater than 200 kbp in length. Compared with smaller phage, jumbo phages are rarely described and the vast majority (greater than 95%) of these phages recognize Gram-negative bacteria, with only a few recognizing Gram-positive species, primarily within the genus *Bacillus* (Yuan, Y.; Gao, M. Jumbo Bacteriophages: An Overview. *Front Microbiol* 2017, 8, 403). The majority of identified jumbo phages belong to the order Caudovirales. They have a head with icosahedral symmetry and a tail. The majority of the genes in a jumbo phage are functionally unassigned. These phages are able to create highly complex virions compared to those of phages with smaller genomes. Some genomes have novel host infection strategies.

Many *Listera* phages are not species-dependent but are specific for one or more serovars. Broad host range *Listera* phage, such as A511, can infect multiple serovars by binding to conserved substituents of cell wall teichoic acids (WTAs). Other Gram-positive jumbo phage, such as PBS1 of *Bacillus*, appear to recognize active host flagella. *L. grayi* is the only motile species of the *Listeria* sensu lato group. Additionally, the flagellar antigens of *L. grayi* have previously been found to be unique compared to all other species. Although the regulation of flagella in *L. grayi* is poorly described, it is worth noting that flagellar expression in *L. monocytogenes* is typically suppressed at 37° C. Thus, in some embodiments, the bacteriophage is specific for a flagellar antigen of a bacteria of interest. In certain instances, the bacteriophage is specific for a conserved substituent of WTAs of a bacteria of interest.

In some embodiments, an indicator bacteriophage is derived from *Listeria*-specific phage. An indicator bacteriophage may be constructed from a *Pecentumvirus, Tequatravirus*, ViI, *Kuttervirus, Homburgvirus*, LPJP1, LMTA-94, LMA4, LMA8, P70, LP-ES1, LP-ES3 or another bacteriophage having a genome with at least 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% homology to *Listeria* phage LPJP1, LMTA-94, P70, T7, T7-like, T4, T4-like, *Listeria* spp.-specific bacteriophage, ViI, or ViI-like (*Kuttervirus*, per GenBank/NCBI) bacteriophages. In other embodiments, the selected wild-type bacteriophage is LPJP1, LP-ES1, LP-ES3, LMA4 or LMA8. In some embodiments, the indicator phage is derived from a bacteriophage that is highly specific for a particular pathogenic microorganism. The genetic modifications may avoid deletions of wild-type genes and thus the modified phage may remain more similar to the wild-type infectious agent than many commercially available phage. Environmentally derived bacteriophage may be more specific for bacteria that are found in the environment and as such, genetically distinct from phage available commercially.

In some embodiments, the recombinant bacteriophage is constructed using the WT bacteriophage LPJP1 (SEQ ID NO: 1). In certain embodiments recombinant bacteriophage is constructed using a WT bacteriophage having SEQ ID NO:1 or at least 95, 90, 85, 80, or 75% homology to SEQ ID NO:1.

In another aspect of the invention, a cocktail composition comprises at least one type of recombinant bacteriophage. In some embodiments, the cocktail composition comprises at least one type of recombinant bacteriophage constructed from LPJP1, LMA4, LMA8, A511, P70, LP-ES1, and LP-ES3. In other embodiments, the cocktail composition comprises at least one type of recombinant bacteriophage constructed from LPJP1, LMA8, LP-ES1, and LP-ES3. In some embodiments, the bacteriophage cocktail is capable of infecting *L. monocytogenes*. In certain embodiments, the bacteriophage cocktail is capable of infecting at least 1, 2, 3, 4, 5, 6, 7, 8, 9, 10, 11, 12, or 13 or more serovars of *L. monocytogenes*. In some embodiments, the bacteriophage cocktail is capable of infecting at least one of serovars 1/2a, 1/2b, 1/2c, 3a, 3b, 3c, 4a, 4b, 4c, 4d, 4e, 6a, and 6c of the species *L. monocytogenes*.

In some embodiments, the cocktail composition comprises ate leat one recombinant bacteriophage capable of infecting *L. innocua*. LP-ES1, likely in the genus *Homburgvirus*, under the family Siphoviridae, is capable of infecting *L. innocua*.

Figure 7:
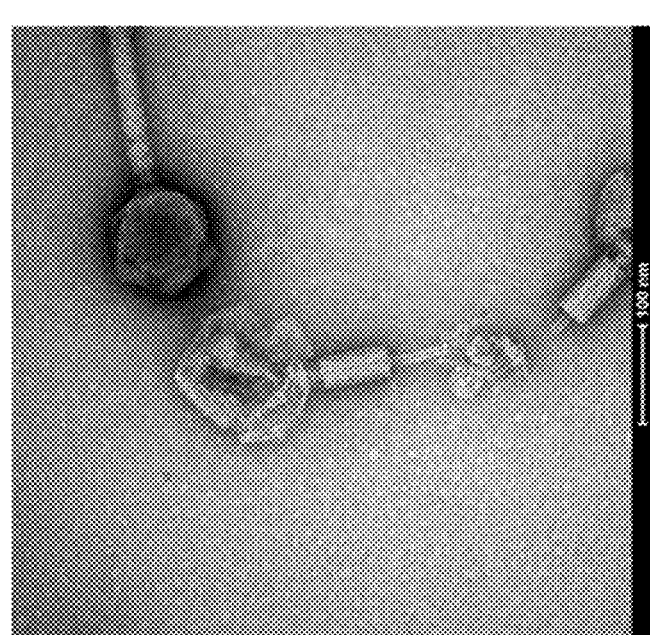
FIG. 7 depicts phage morphology visualized by transmission electron microscopy.
Figure 7:

Although phages have been found for most *Listeria* species, phages targeting *L. grayi* have thus far remained elusive. In some embodiments, the bacteriophage cocktail, comprises a recombinant bacteriophage capable of detecting *L. grayi*. The *L. grayi*-specific phage LPJP1 was isolated from farm silage. TEM revealed that LPJP1 was morphologically similar to the dsDNA Myoviridae family, with a large icosahedral head, a long straight tail, and a contractile outer tail sheath (FIG. 7A,B). LPJP1 is a jumbo phage displaying a genome with only limited homology to available viral DNA sequences. Jumbo phages are tailed bacteriophages with genomes larger than 200 kbp having both a large phage virion and large genome size. Jumbo phages are difficult to isolate. Top hits by BLAST analysis were other jumbo phages, specifically those that infect another Gram-positive genus, *Bacillus*. Poor sequence homology among jumbo phages has been previously described and genome annotation is often underwhelming due to the significant occurrence of genes of unknown function. The paucity of jumbo phage in Gram-positive genera besides *Bacillus* has resulted in speculation that this could indicate a unique property of *Bacillus* or alternatively, that phage targeting other Gram-positive genera simply remained to be discovered. To date, only one example of a jumbo phage infecting a Gram-positive genus outside of *Bacillus* had been reported. The *Staphylococcus* phage S6, although not fully sequenced, was originally described as a giant myophage with an approximate genome size of 270 kbp. Surprisingly, LPJP1 appears to not only be the first identified *L. grayi* phage, but also the first jumbo phage infecting the *Listeria* genus. In some embodiments, the phage is a jumbo phage. In certain instances, the jumbo phage is specific for *Listeria*. In some embodiments, the jumbo phage is specific for *L. grayi*.

Moreover, phage genes thought to be nonessential may have unrecognized function. For example, an apparently nonessential gene may have an important function in elevating burst size such as subtle cutting, fitting, or trimming functions in assembly. Therefore, deleting genes to insert an indicator may be detrimental. Most phages can package DNA that is a few percent larger than their natural genome. Thus a bacteriophage with a larger genome size may be advantageous. In some embodiments, the bacteriophage is a jumbo bacteriophages. In some embodiments, the jumbo bacteriophage has a genome that is at least 200, 225, 250, 275, 300, 325, 350, 375, 400, 425, 450, 475, 500, 525, or 550 kbp in length.

In some instances, a jumbo bacteriophage may not be available for a particular bacteria of interest. With this consideration a smaller indicator gene may be a more appropriate choice for modifying a bacteriophage, especially one with a smaller genome. OpLuc and NANOLUC® proteins are only about 20 kDa (approximately 500-600 bp to encode), while FLuc is about 62 kDa (approximately 1,700 bp to encode). Moreover, the reporter gene should not be expressed endogenously by the bacteria (i.e., is not part of the bacterial genome), should generate a high signal to background ratio, and should be readily detectable in a timely manner. In some embodiments, the indicator gene is a luciferase. In other embodiments, the indicator gene is an active subunit of a luciferase. Promega's NANOLUC® is a modified *Oplophorus gracilirostris* (deep sea shrimp) luciferase. In some embodiments, NANOLUC® combined with Promega's NANO-GLO®, an imidazopyrazinone substrate (furimazine), can provide a robust signal with low background.

In some indicator phage embodiments, the indicator gene can be inserted into an untranslated region to avoid disruption of functional genes, leaving wild-type phage genes intact, which may lead to greater fitness when infecting non-laboratory strains of bacteria. Additionally, including stop codons in all three reading frames may help to increase expression by reducing read-through, also known as leaky expression. This strategy may also eliminate the possibility of a fusion protein being made at low levels, which would manifest as background signal (e.g., luciferase) that cannot be separated from the phage.

An indicator gene may express a variety of biomolecules. The indicator gene is a gene that expresses a detectable product or an enzyme that produces a detectable product. For example, in one embodiment the indicator gene encodes a luciferase enzyme. Various types of luciferase may be used. In alternate embodiments, and as described in more detail herein, the luciferase is one of *Oplophorus* luciferase, Firefly luciferase, *Lucia* luciferase, *Renilla* luciferase, or an engineered luciferase. In some embodiments, the luciferase gene is derived from *Oplophorus*. In some embodiments, the indicator gene is a genetically modified luciferase gene, such as NANOLUC®.

Thus, in some embodiments, the present invention comprises a genetically modified bacteriophage comprising a non-bacteriophage indicator gene in the late (class III) gene region. In some embodiments, the non-native indicator gene is under the control of a late promoter. Using a viral late gene promoter ensures the reporter gene (e.g., luciferase) is not only expressed at high levels, like viral capsid proteins, but also does not shut down like endogenous bacterial genes or even early viral genes.

In some embodiments, the late promoter is a *Pecentumvirus, Tequatravirus, Homburgvirus*, or *Kuttervirus* promoter, or another phage promoter similar to that found in the selected wild-type phage, i.e., without genetic modification. The late gene region may be a class III gene region, and the bacteriophage may be derived from *Listera* phage LMTA-94, P70, A511, LP-ES1, LP-ES3, LMA4, LMA8, *Pecentumvirus, Tequatravirus, Homburgvirus, Kuttervirus*, T7, T4, T4-like, ViI, *Listeria* spp.-specific bacteriophage, or another wild-type bacteriophage having a genome with at least 70, 75, 80, 85, 90 or 95% homology to LMTA-94, LMA4, LMA8, *Pecentumvirus, Tequatravirus, Homburgvirus, Kuttervirus*, T7, T4, ViI, or *Listeria*-specific bacteriophage. The *Pecentumvirus* late gene promoter is distinct from the T4 or *Tequatravirus* promoter, as it consists of not only the −10 region, but also a −35 region. This −35 region differs from the standard −35 region found in most bacterial promoters.

Genetic modifications to infectious agents may include insertions, deletions, or substitutions of a small fragment of nucleic acid, a substantial part of a gene, or an entire gene. In some embodiments, inserted or substituted nucleic acids comprise non-native sequences. A non-native indicator gene may be inserted into a bacteriophage genome such that it is under the control of a bacteriophage promoter. Thus, in some embodiments, the non-native indicator gene is not part of a fusion protein. That is, in some embodiments, a genetic modification may be configured such that the indicator protein product does not comprise polypeptides of the wild-type bacteriophage. In some embodiments, the indicator protein product is soluble. In some embodiments, the invention comprises a method for detecting a bacterium of interest comprising the step of incubating a test sample with such a recombinant bacteriophage.

In some embodiments, expression of the indicator gene in progeny bacteriophage following infection of host bacteria results in a free, soluble protein product. In some embodiments, the non-native indicator gene is not contiguous with a gene encoding a structural phage protein and therefore does not yield a fusion protein. Unlike systems that employ a fusion of a detection moiety to the capsid protein (i.e., a fusion protein), some embodiments of the present invention express a soluble indicator or reporter (e.g., soluble luciferase). In some embodiments, the indicator or reporter is ideally free of the bacteriophage structure. That is, the indicator or reporter is not attached to the phage structure. As such, the gene for the indicator or reporter is not fused with other genes in the recombinant phage genome. This may greatly increase the sensitivity of the assay (down to a single bacterium), and simplify the assay, allowing the assay to be completed in two hours or less for some embodiments, as opposed to several hours due to additional purification steps required with constructs that produce detectable fusion proteins. Further, fusion proteins may be less active than soluble proteins due, e.g., to protein folding constraints that may alter the conformation of the enzyme active site or access to the substrate. If the concentration is 1,000 bacterial cells/mL of sample, for example, less than four hours of infection may be sufficient for the detection of the target bacterium.

Moreover, fusion proteins by definition limit the number of the moieties attached to subunits of a protein in the bacteriophage. For example, using a commercially available system designed to serve as a platform for a fusion protein would result in about 415 copies of the fusion moiety, corresponding to the about 415 copies of the gene 10B capsid protein in each T7 bacteriophage particle. Without this constraint, infected bacteria can be expected to express many more copies of the detection moiety (e.g., luciferase) than can fit on the bacteriophage. Additionally, large fusion proteins, such as a capsid-luciferase fusions, may inhibit assembly of the bacteriophage particle, thus yielding fewer bacteriophage progeny. Thus a soluble, non-fusion indicator gene product may be preferable.

In some embodiments, the indicator phage encodes a reporter, such as a detectable enzyme. The indicator gene product may generate light and/or may be detectable by a color change. Various appropriate enzymes are commercially available, such as alkaline phosphatase (AP), horseradish peroxidase (HRP), or luciferase (Luc). In some embodiments, these enzymes may serve as the indicator moiety. In some embodiments, Firefly luciferase is the indicator moiety. In some embodiments, *Oplophorus* luciferase is the indicator moiety. In some embodiments, NANO-LUC® is the indicator moiety. Other engineered luciferases or other enzymes that generate detectable signals may also be appropriate indicator moieties.

In some embodiments, the use of a soluble detection moiety eliminates the need to remove contaminating parental phage from the lysate of the infected sample cells. With a fusion protein system, any bacteriophage used to infect sample cells would have the detection moiety attached, and would be indistinguishable from the daughter bacteriophage also containing the detection moiety. As detection of sample bacteria relies on the detection of a newly created (de novo synthesized) detection moiety, using fusion constructs requires additional steps to separate old (parental) moieties from newly created (daughter bacteriophage) moieties. This may be accomplished by washing the infected cells multiple times, prior to the completion of the bacteriophage life cycle, inactivating excess parental phage after infection by physical or chemical means, and/or chemically modifying the parental bacteriophage with a binding moiety (such as biotin), which can then be bound and separated (such as by Streptavidin-coated Sepharose beads). However, even with all these attempts at removal, parental phage can remain when a high concentration of parental phage is used to assure infection of a low number of sample cells, creating background signal that may obscure detection of signal from infected cell progeny phage.

By contrast, with the soluble detection moiety expressed in some embodiments of the present invention, purification of the parental phage from the final lysate is unnecessary, as the parental phage do not have any detection moiety attached. Thus any detection moiety present after infection must have been created de novo, indicating the presence of an infected bacterium or bacteria. To take advantage of this benefit, the production and preparation of parental phage may include purification of the phage from any free detection moiety produced during the production of parental bacteriophage in bacterial culture. Standard bacteriophage purification techniques may be employed to purify some embodiments of phage according to the present invention, such as sucrose density gradient centrifugation, cesium chloride isopycnic density gradient centrifugation, HPLC, size exclusion chromatography, and dialysis or derived technologies (such as Amicon brand concentrators—Millipore, Inc.). Cesium chloride isopycnic ultracentrifugation can be employed as part of the preparation of recombinant phage of the invention, to separate parental phage particles from contaminating luciferase protein produced upon propagation of the phage in the bacterial host. In this way, the parental recombinant bacteriophage of the invention is substantially free of any luciferase generated during production in the bacteria. Removal of residual luciferase present in the phage stock can substantially reduce background signal observed when the recombinant bacteriophage are incubated with a test sample.

In some embodiments of modified bacteriophage, the late promoter (class III promoter, e.g., from *Pecentumvirus, Homburgvirus*, T7, T4, ViI, or LMA4/8) has high affinity for RNA polymerase of the same bacteriophage that transcribes genes for structural proteins assembled into the bacteriophage particle. These proteins are the most abundant proteins made by the phage, as each bacteriophage particle comprises dozens or hundreds of copies of these molecules. The use of a viral late promoter can ensure optimally high level of expression of the luciferase detection moiety. The use of a late viral promoter derived from, specific to, or active under the original wild-type bacteriophage the indicator phage is derived from (e.g., a *Pecentumvirus, Homburgvirus*, T4, T7, ViI, or LMA4/8 late promoter with a *Pecentumvirus*, T4, T7-, ViI-, or LMA-based system) can further ensure optimal expression of the detection moiety. The use of a standard bacterial (non-viral/non-bacteriophage) promoter may in some cases be detrimental to expression, as these promoters are often down-regulated during bacteriophage infection (in order for the bacteriophage to prioritize the bacterial resources for phage protein production). Thus, in some embodiments, the phage is preferably engineered to encode and express at high level a soluble (free) indicator moiety, using a placement in the genome that does not limit expression to the number of subunits of a phage structural component.

Compositions of the invention may comprise one or more wild-type or genetically modified infectious agents (e.g., bacteriophages) and one or more indicator genes. In some embodiments, compositions can include cocktails of different indicator phages that may encode and express the same or different indicator proteins. In some embodiments, the cocktail of bacteriophage comprises at least two different types of recombinant bacteriophages.

Methods of Preparing Indicator Bacteriophage

Embodiments of methods for making indicator bacteriophage begin with selection of a wild-type bacteriophage for genetic modification. Some bacteriophage are highly specific for a target bacterium. This presents an opportunity for highly specific detection.

Thus, the methods of the present invention utilize the high specificity of binding agents, associated with infectious agents that recognize and bind to a particular microorganism of interest as a means to amplify a signal and thereby detect low levels of a microorganism (e.g., a single microorganism) present in a sample. For example, infectious agents (e.g., bacteriophage) specifically recognize surface receptors of particular microorganisms and thus specifically infect those microorganisms. As such, these infectious agents may be appropriate binding agents for targeting a microorganism of interest.

Some embodiments of the invention utilize the specificity of binding and high-level genetic expression capacity of recombinant bacteriophage for rapid and sensitive targeting to infect and facilitate detection of a bacterium of interest. In some embodiments, a *Listeria*-specific bacteriophage is genetically modified to include a reporter gene. In some embodiments the late gene region of a bacteriophage is genetically modified to include a reporter gene. In some embodiments, a reporter gene is positioned downstream of the major capsid gene. In other embodiments, a reporter gene is positioned upstream of the major capsid gene. In some embodiments, the inserted genetic construct further comprises its own exogenous, dedicated promoter to drive expression of the indicator gene. The exogenous promoter is in addition to any endogenous promoter in the phage genome. As bacteriophage produce polycistronic mRNA transcripts, only a single promoter is required upstream of the first gene/cistron in the transcript. Conventional recombinant constructs only use the endogenous bacteriophage promoter to drive inserted genes. In contrast, addition of an additional promoter upstream of the reporter gene and ribosomal binding site may increase gene expression by acting as a secondary initiation site for transcription. The complicated and compact genomes of viruses often have overlapping genes in different frames, sometimes in two different directions.

Some embodiments of methods for preparing a recombinant indicator bacteriophage include selecting a wild-type bacteriophage that specifically infects a target pathogenic bacterium such as *Listeria* spp.; preparing a homologous recombination plasmid/vector that comprises an indicator gene; transforming the homologous recombination plasmid/vector into target pathogenic bacteria; infecting the transformed target pathogenic bacteria with the selected wild-type bacteriophage, thereby allowing homologous recombination to occur between the plasmid/vector and the bacteriophage genome; and isolating a particular clone of recombinant bacteriophage.

Various methods for designing and preparing a homologous recombination plasmid are known. Various methods for transforming bacteria with a plasmid are known, including heat-shock, F pilus-mediated bacterial conjugation, electroporation, and other methods. Various methods for isolating a particular clone following homologous recombination are also known. Some method embodiments described herein utilize particular strategies.

Thus, some embodiments of methods for preparing indicator bacteriophage include the steps of selecting a wild-type bacteriophage that specifically infects a target pathogenic bacterium; determining the natural sequence in the late region of the genome of the selected bacteriophage; annotating the genome and identifying the major capsid protein gene of the selected bacteriophage; designing a sequence for homologous recombination adjacent to the major capsid protein gene, wherein the sequence comprises a codon-optimized reporter gene; incorporating the sequence designed for homologous recombination into a plasmid/vector; transforming the plasmid/vector into target pathogenic bacteria; selecting for the transformed bacteria; infecting the transformed bacteria with the selected wild-type bacteriophage, thereby allowing homologous recombination to occur between the plasmid and the bacteriophage genome; determining the titer of the resulting recombinant bacteriophage lysate; and performing a limiting dilution assay to enrich and isolate the recombinant bacteriophage. Some embodiments comprise further repeating the limiting dilution and titer steps, following the first limiting dilution assay, as needed until the recombinant bacteriophage represent a detectable fraction of the mixture. For example, in some embodiments the limiting dilution and titer steps can be repeated until at least $\frac{1}{30}$ of the bacteriophage in the mixture are recombinant before isolating a particular clone of recombinant bacteriophage. A ratio of 1:30 recombinant: wild-type is expected, in some embodiments, to yield an average of 3.2 transducing units (TU) per 96 plaques (e.g., in a 96-well plate). The initial ratio of recombinant to wild-type phage may be determined by performing limiting dilution assays based on the TCID50 (tissue culture infectious dose 50%) as previously described in U.S. application Ser. No. 15/409,258. By Poisson distribution, a 1:30 ratio generates a 96% chance of observing at least one TU somewhere in the 96 wells.

FIG. 1 depicts a schematic representation of the genomic structure of a recombinant indicator bacteriophage of the invention. For the embodiment depicted in FIG. 1, the detection moiety is encoded by a luciferase gene 100 inserted within the late (class III) gene region 110, which is expressed late in the viral life cycle. Late genes are generally expressed at higher levels than other phage genes, as they code for structural proteins. Thus, in the embodiment of the recombinant phage depicted in FIG. 1, the indicator gene (i.e., luciferase) is inserted into the late gene region, just after the gene for major capsid protein (cps) 120, and is a construct comprising the luciferase gene 100. In some embodiments, the construct depicted in FIG. 1 may include stop codons in all 3 reading frames to ensure luciferase is not incorporated into the cps gene product through creation of a fusion protein. Also as depicted in FIG. 1, the construct may comprise an additional, dedicated late promoter 130 to drive transcription and expression of the luciferase gene. The construct also comprises a ribosome binding site (RBS) 140. This construct ensures soluble luciferase is produced such that expression is not limited to the number of capsid proteins inherent in the phage display system.

As noted herein, in certain embodiments, it may be preferred to utilize infectious agents that have been isolated from the environment for production of the infectious agents of the invention. In this way, infectious agents that are specific to naturally derived microorganisms may be generated.

Figure 2:
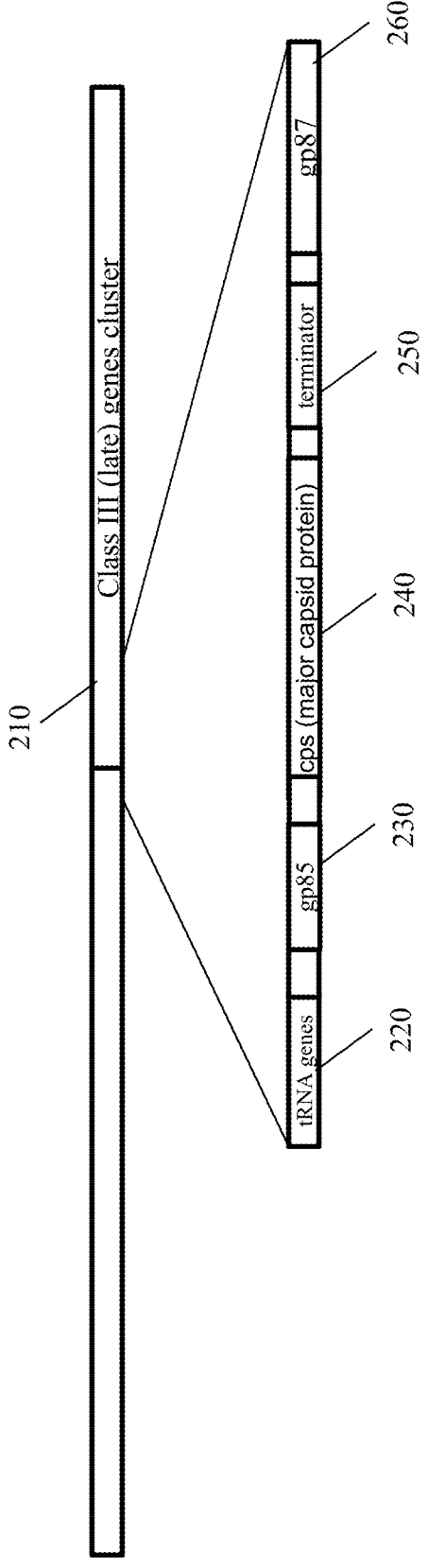
FIG. 2 shows the genome of bacteriophage LMA4, a myovirus (related to *Listeria* phage LMTA-94) which was obtained from sewage. A hypothetical gene homologous to the putative prohead protease p85protein is upstream of cps, the major capsid gene within the late gene region, consisting of structural genes, which code for virion proteins. Following the cps, is a transcriptional terminator, followed by a homolog to the LMTA-94 tail sheath protein (tsh). As these virion proteins are expressed at a very high level, any genes inserted into this region can be expected to have similar expression levels, as long as late gene promoters and/or other similar control elements are used.

For example, FIG. 2 shows the genome of bacteriophage LMA4, a wild-type bacteriophage that specifically infects *Listeria* spp. As discussed in the Examples, the Major Capsid Protein (cps) 240 and various other structural genes are within the late gene region 210, consisting of structural genes, which code for virion proteins. Genes coding for tRNA 220 represent genomic sequence adjacent to, but outside of the late gene region. A hypothetical gene homologous to the putative prohead protease of *Listera* phage LMTA-94 230 is upstream of cps 240, consisting of structural genes, which code for virion proteins. Other late genes depicted are homologs to *Listera* phage LMTA-94's putative Major Capsid Protein (cps) 240, followed by a transcriptional terminator 250, and a homolog to *Listera* phage LMTA-94 Tail Sheath Protein (tsh) 260. As these virion proteins are expressed at a very high level, any genes inserted into this region can be expected to have similar expression levels, as long as late gene promoters and/or other similar control elements are used.

There are numerous known methods and commercial products for preparing plasmids. For example, PCR, site-directed mutagenesis, restriction digestion, ligation, cloning, and other techniques may be used in combination to prepare plasmids. Synthetic plasmids can also be ordered commercially (e.g., GeneWiz). Cosmids can also be employed, or the CRISPR/CAS9 system could be used to selectively edit a bacteriophage genome. Some embodiments of methods of preparing a recombinant indicator bacteriophage include designing a plasmid that can readily recombine with the wild-type bacteriophage genome to generate recombinant genomes. In designing a plasmid, some embodiments include addition of a codon-optimized reporter gene, such as a luciferase gene. Some embodiments further include addition of elements into the upstream untranslated region. For example, in designing a plasmid to recombine with the *Listeria*-specific bacteriophage genome, an upstream untranslated region can be added between the sequence encoding the C-terminus of the gp23/Major Capsid Protein and the start codon of the NANOLUC® reporter gene. The untranslated region can include a promoter, such as a T4, *Tequatravirus, Homburgvirus*, T7, T7-like, *Pecentumvirus, Listeria*-specific bacteriophage, ViI, or *Kuttervirus* promoter. The untranslated region can also include a Ribosomal Entry/Binding Site (RBS), also known as a "Shine-Dalgarno Sequence" with bacterial systems. Either or both of these elements, or other untranslated elements, can be embedded within a short upstream untranslated region made of random sequences comprising about the same GC content as rest of the phage genome. The random region should not include an ATG sequence, as that will act as a start codon.

Figure 3:
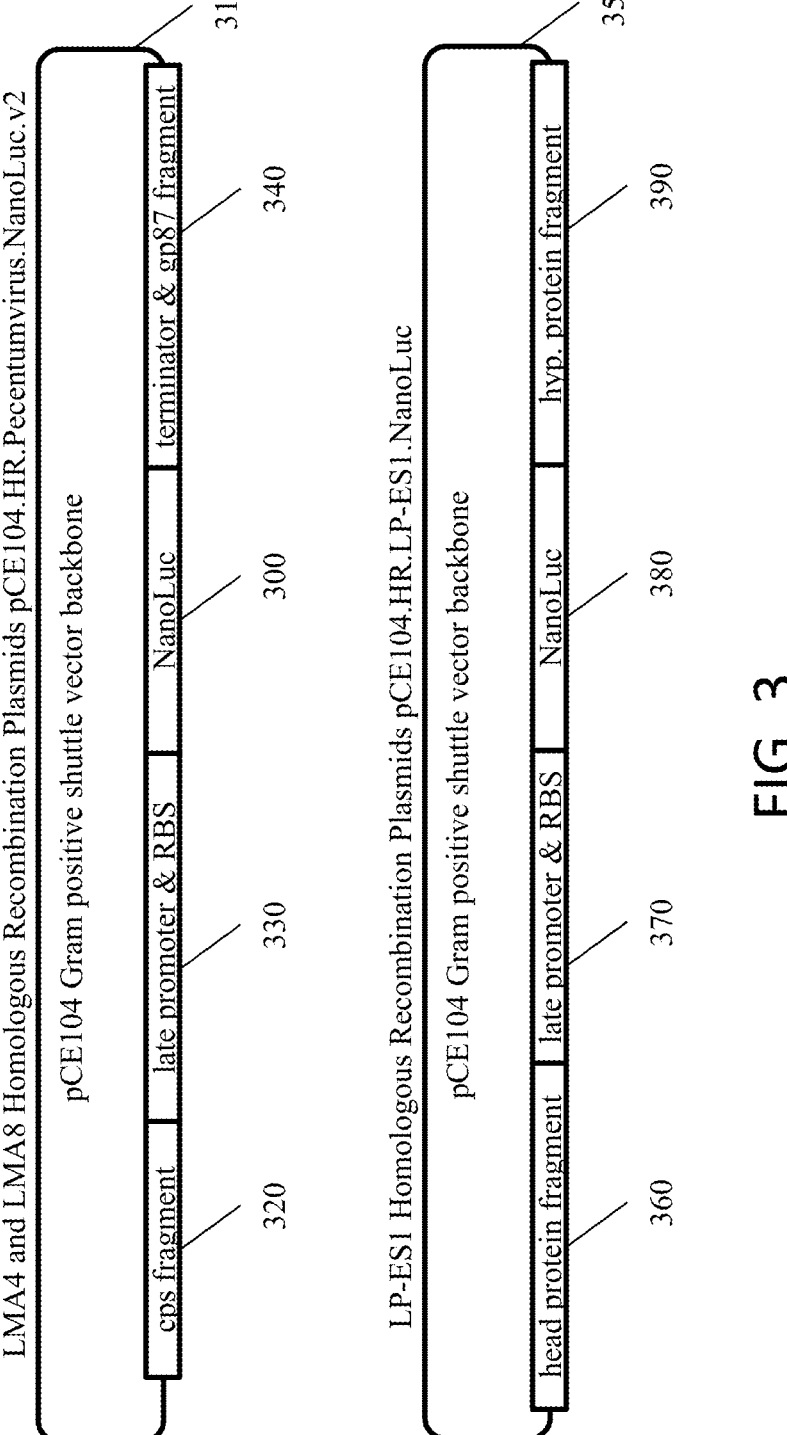
FIG. 3 shows two homologous recombination plasmid construct designs carrying the luciferase gene used to construct the recombinant phages with approximately several hundred basepairs of matching phage sequence upstream and downstream of the insertion site to promote homologous recombination. NANOLUC® luciferase is inserted into a pCE104 Gram positive shuttle vector plasmid backbone with an upstream untranslated region containing a dedicated phage late gene promoter and Ribosomal Entry Site. pCE104.HR.A511.NanoLuc.v2 was used to construct recombinants for the *Pecentumviruses* A511, LMA4 and LMA8. pCE104.HR.LP-ES1.NanoLuc was used to construct the *Homburvirus* LP-ES1. Each construct consisted of 500 bp of homologous sequence consisting of a fragment of the Major Capsid Protein gene (cps) followed by a late gene promoter, which was added in addition to the endogenous late gene promoter upstream of the major capsid protein in the phage genome, the luciferase gene, and approximately 258 bp of downstream matching sequence for homologous recombination for pCE104.HR.A511.NanoLuc.v2 and 500 bp of downstream for pCE104.HR.LP-ES1.NanoLuc. All recombinants used a P100virus late gene promoter instead of the T4 late gene promoter.

The compositions of the invention may comprise various infectious agents and/or indicator genes. For example, FIG. 3 shows a homologous recombination plasmid construct used in making the indicator phage specific for *Listeria* spp. Constructs were made and used in recombination with *Listeria* spp. phage LMA4, *Listeria* spp. phage LMA8, *Listeria* spp. phage LP-ES3, *Listeria* spp. phage LP-ES1 or other *Listeria*-specific phages to generate recombinant bacteriophage of the invention. The construct in FIG. 3 shows a general schematic for the recombination plasmid used for homologous recombination insertion of the NANOLUC® luciferase into both *Listeria* spp. *Pecentumvirus* phages LMA4 and LMA8, each with 500 bp of upstream and downstream homologous sequence: homologous recombination plasmid pCE104.HR.*Listeria*Phage.NANOLUC.v2. *Pecentumvirus*.NANOLUC.v2 and the recombination plasmid used for homologous recombination insert of the NANOLUC® luciferase into *Listeria* spp. *Homburgvirus* phage LP-ES1, pCE104.HR.LP-ES1.NanoLuc In certain embodiments a plasmid is designated pCE104.HR.*Pecentumvirus*.NanoLuc.v2. The detection/indicator moiety is encoded by the NANOLUC® reporter gene 300. The insert, represented by the series of rectangles, is in the Gram positive shuttle vector, pCE104 310. The upstream homologous recombination region consists of 500 bp of the major capsid protein C-terminal fragment 320. A *Pecentumvirus* late promoter consensus sequence & Shine-Dalgarno Ribosomal Entry/Binding Site within the 5' untranslated region 330. The codon-optimized NANO-LUC® reporter gene 300 follows immediately after. The endogenous transcriptional terminator comes next, along with the untranslated region (UTR) and hypothetical protein N-Terminal fragment consisting of the downstream homologous recombination 340 are at the end of the Homologous Recombination region.

The Major Capsid Protein fragment is a part of a structural gene that encodes a virion protein. As these virion proteins are expressed at a very high level, any genes inserted into this region can be expected to have similar expression levels, as long as late gene promoters and/or other similar control elements are used.

In some embodiments, indicator phage according to the invention comprise *Listeria*-specific bacteriophage genetically engineered to comprise a reporter gene such as a luciferase gene. For example, an indicator phage can be *Listeria* spp.-specific bacteriophage wherein the genome comprises the sequence of the NANOLUC® gene. A recombinant *Listeria*-specific NANOLUC® bacteriophage genome may further comprise a consensus promoter of *Pecentumvirus*, T4, T7, *Listeria*-specific, ViI, LMA4, or LMA8 bacteriophage or another late promoter. In further embodiments, the promoter is an exogenous promoter. Insertion of an exogenous promoter to drive expression of an indicator gene is advantageous in that expression is not limited by the expression of other phage proteins (e.g., the major capsid protein).

Thus, in the embodiment of the recombinant phage generated as a result of the recombination, the indicator gene (i.e., NANOLUC®) is inserted into the late gene region, just downstream of the gene encoding the major capsid protein, and thus creates recombinant bacteriophage genomes comprising the NANOLUC® gene. The construct may additionally comprise the consensus promoter of *Listera* phage LMTA-94, T4, T7, *Listeria*-specific bacteriophage, ViI, or another late promoter or another suitable promoter to drive transcription and expression of the luciferase gene. The construct may also comprise a composite untranslated region synthesized from several UTRs. This construct ensures soluble luciferase is produced such that expression is not limited to the number of capsid proteins inherent in the phage display system.

Recombinant phage generated by homologous recombination of a plasmid designed for recombination with the wild-type phage genome can be isolated from a mixture comprising a very small percentage (e.g., 0.005%) of total phage genomes. Following isolation, large scale production may be performed to obtain high titer recombinant indicator phage stocks appropriate for use in the *Listeria* spp. detection assay. Furthermore, cesium chloride isopycnic density gradient centrifugation may be used to separate phage particles from contaminating luciferase protein to reduce background.

NANOLUC®-expressing phage have repeatedly been found to exhibit impressive diagnostic sensitivity and robust signal production across multiple genera. Some jumbo phages have recently been described to form a novel nucleus-like proteinaceous shell upon infection, which protects phage DNA from host defense mechanisms and could conceivably interfere with genetic engineering. Despite this possibility, a NANOLUC®-expressing recombinant, LPJP1.NL was successfully generated using standard homologous recombination methods. LPJP1.NL produced substantial RLU from limited bacterial burdens without enrichment, requiring only a single log phase *L. grayi* bacterium to yield a detectable signal after a 4 h infection. As expected, signal increased proportionally with bacterial burden. Overall, LPJP1.NL is both the first jumbo phage reporter and the first phage reporter capable of detecting *L. grayi*. The success of LPJP1.NL highlights the untapped potential of jumbo phage in phage-based diagnostics.

Methods of Using Infectious Agents for Detecting *Listeria* spp.

As noted herein, in certain embodiments, the invention may comprise methods of using infectious particles for detecting microorganisms. The methods of the invention may be embodied in a variety of ways.

In an embodiment, the invention may comprise a method for detecting a bacterium of interest in a sample comprising the steps of: incubating the sample with bacteriophage that infects the bacterium of interest, wherein the bacteriophage comprises an indicator gene such that expression of the indicator gene during bacteriophage replication following infection of the bacterium of interest results in production of a soluble indicator protein product; and detecting the indicator protein product, wherein positive detection of the indicator protein product indicates that the bacterium of interest is present in the sample. In certain instances, the invention comprises a method for detecting *Listeria* spp. in a sample comprising: incubating the sample with a cocktail composition comprising at least one *Listeria*-specific recombinant bacteriophage; and detecting an indicator protein product produced by the recombinant bacteriophage, wherein positive detection of the indicator protein product indicates that *Listeria* spp. is present in the sample.

In certain instances, the recombinant bacteriophage or cocktail of recombinant bacteriophages are capable of detecting one or more target species of *Listeria*. In some embodiments, the target species of *Listeria* is selected from *L. monocytogenes, L. ivanovii, L. innocua*, and *L. grayi*. In certain embodiments, the bacteriophage or cocktail of recombinant bacteriophages is capable of infecting at least 1, 2, 3, 4, 5, 6, or 7 or more serovars of *L. monocytogenes*. In some embodiments, the bacteriophage cocktail is capable of infecting at least one of serovars 1/2a, 1/2b, 1/2c, 3a, 3b, 3c, 4d, 4d, 4e, and 7 of the species *L. monocytogenes*.

In some embodiments, at least one type of recombinant bacteriophage is constructed from LMA4, LMA8, A511, P70, LP-ES1, and LP-ES3. In other embodiments, at least one type of recombinant bacteriophage is constructed from LMA8, LP-ES1, and LP-ES3. In embodiments, the recombinant bacteriophage is cpable of infecting one or more of *L. innocua, L. grayi, L. monocytogenes* serovar 3A.

In certain embodiments, the assay may be performed to utilize a general concept that can be modified to accommodate different sample types or sizes and assay formats. Embodiments employing recombinant bacteriophage of the invention (i.e., indicator bacteriophage) may allow rapid detection of specific bacterial strains such as *Listeria* spp., with total assay times under 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12, 12.5, 13.0, 13.5, 14.0, 14.5, 15.0, 15.5, 16.0, 16.5, 17.0, 17.5, 18.0, 18.5, 19.0, 19.5, 20.0, 21.0, 21.5 22.0, 22.5, 23.0, 23.5, 24.0, 24.5 25.0, 25.5, or 26.0 hours, depending on the sample type, sample size, and assay format. For example, the amount of time required may be somewhat shorter or longer depending on the strain of bacteriophage and the strain of bacteria to be detected in the assay, type and size of the sample to be tested, conditions required for viability of the target, complexity of the physical/chemical environment, and the concentration of "endogenous" non-target bacterial contaminants.

The bacteriophage (e.g., T7, T4, P70 P100, A511, LP-ES3, LP-ES1, LMA4 or LMA8 phage) may be engineered to express a soluble luciferase during replication of the phage. Expression of luciferase is driven by a viral capsid promoter (e.g., the bacteriophage *Pecentumvirus* or T4 late promoter), yielding high expression. Parental phage are prepared such that they are free of luciferase, so the luciferase detected in the assay must come from replication of progeny phage during infection of the bacterial cells. Thus, there is generally no need to separate out the parental phage from the progeny phage.

Figure 4:
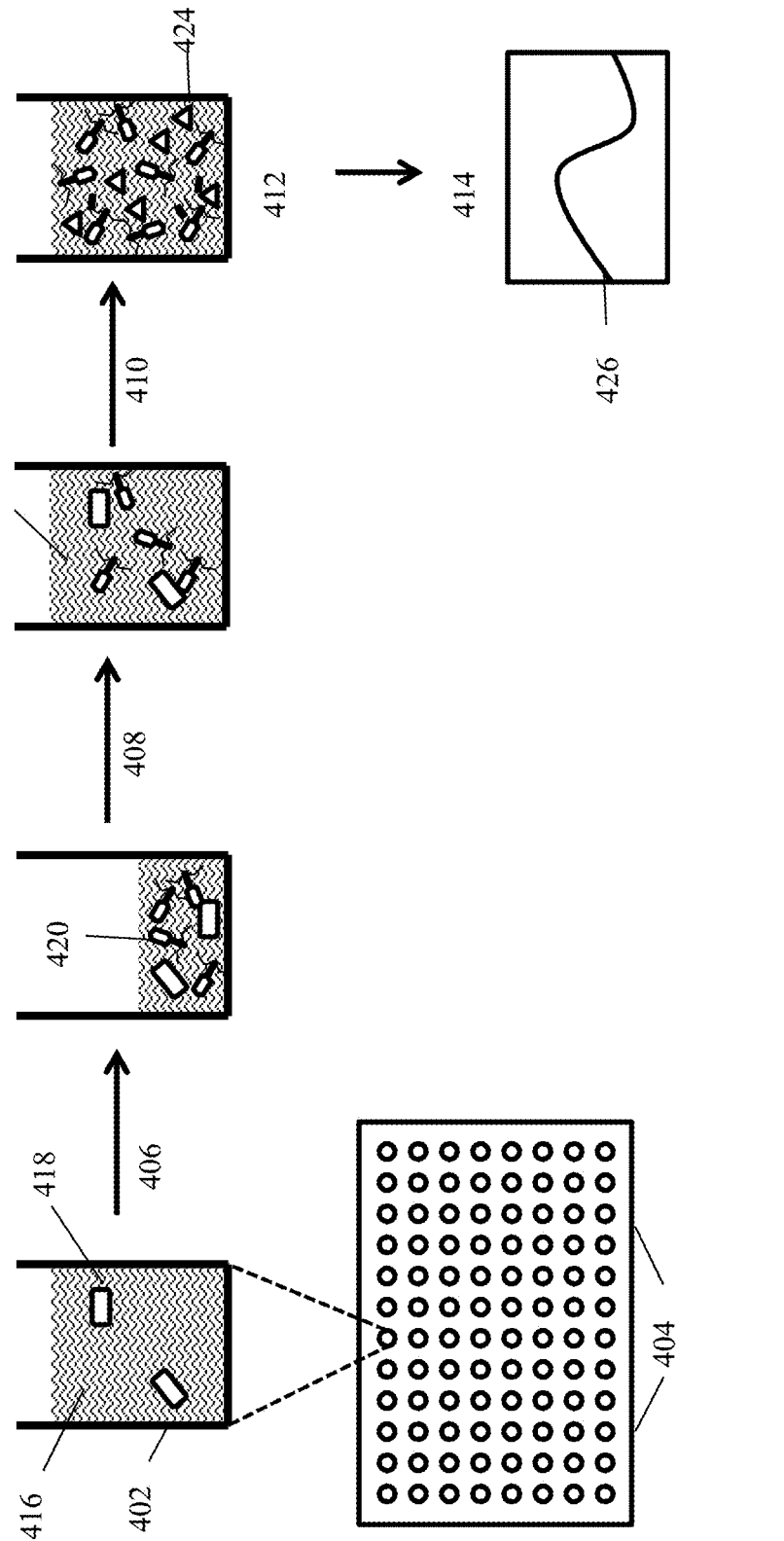
FIG. 4 depicts a filter plate assay for detecting bacteria of interest using a modified bacteriophage according to an embodiment of the invention where bacteria and recombinant phage are incubated on filter plates and after generation of progeny bacteriophage the indicator protein is detected directly without removal of the incubation medium.

FIG. 4 depicts a filter plate assay for detecting *Listeria* using a modified bacteriophage according to an embodiment of the invention. Briefly, samples 416 that include a bacterium of interest 418 may be added to wells 402 of a multi-well filter plate 404 and spun 406 to concentrate the samples by removal of liquid from the sample. Genetically modified phage 420 are added to wells and incubated with additional media added for enough time sufficient for adsorption 408 followed by infection of target bacteria and advancement of the phage life cycle 410 (e.g., ~240 minutes). Finally, luciferase substrate is added and reacts with any luciferase present 424. The resulting emission is measured in a luminometer 414 which detects luciferase activity 426.

In some embodiments, enrichment of bacteria in the sample is not needed prior to testing. In some embodiments, the sample may be enriched prior to testing by incubation in conditions that encourage growth. In such embodiments, the enrichment period can be 1, 2, 3, 4, 5, 6, 7, 8, 9, 10, 11, 12, 13, 14, 15, 16, 17, 18, 19, 20, 21, 22, 23, or 24 hours or longer, depending on the sample type and size.

In some embodiments, the indicator bacteriophage comprises a detectable indicator moiety, and infection of a single pathogenic cell (e.g., bacterium) can be detected by an amplified signal generated via the indicator moiety. Thus the method may comprise detecting an indicator moiety produced during phage replication, wherein detection of the indicator indicates that the bacterium of interest is present in the sample.

In an embodiment, the invention may comprise a method for detecting a bacterium of interest in a sample comprising the steps of: incubating the sample with a recombinant bacteriophage that infects the bacterium of interest, wherein the recombinant bacteriophage comprises an indicator gene inserted into a late gene region of the bacteriophage such that expression of the indicator gene during bacteriophage replication following infection of host bacteria results in production of a soluble indicator protein product; and detecting the indicator protein product, wherein positive detection of the indicator protein product indicates that the bacterium of interest is present in the sample. In some embodiments, the amount of indicator moiety detected corresponds to the amount of the bacterium of interest present in the sample.

As described in more detail herein, the methods and systems of the invention may utilize a range of concentrations of parental indicator bacteriophage to infect bacteria present in the sample. In some embodiments the indicator bacteriophage are added to the sample at a concentration sufficient to rapidly find, bind, and infect target bacteria that are present in very low numbers in the sample, such as ten cells. In some embodiments, the phage concentration can be sufficient to find, bind, and infect the target bacteria in less than one hour. In other embodiments, these events can occur in less than two hours, or less than three hours, or less than four hours, following addition of indicator phage to the sample. For example, in certain embodiments, the bacteriophage concentration for the incubating step is greater than $1 \times 10^5$ PFU/mL, greater than $1 \times 10^6$ PFU/mL, or greater than $1 \times 10^7$ PFU/mL.

In certain embodiments, the recombinant infectious agent may be purified so as to be free of any residual indicator protein that may be generated upon production of the infectious agent stock. Thus, in certain embodiments, the recombinant bacteriophage may be purified using cesium chloride isopycnic density gradient centrifugation prior to incubation with the sample. When the infectious agent is a bacteriophage, this purification may have the added benefit of removing bacteriophage that do not have DNA (i.e., empty phage or "ghosts").

In some embodiments of the methods of the invention, the microorganism may be detected without any isolation or purification of the microorganisms from a sample. For example, in certain embodiments, a sample containing one or a few microorganisms of interest may be applied directly to an assay container such as a spin column, a microtiter well, or a filter and the assay is conducted in that assay container. Various embodiments of such assays are disclosed herein.

Aliquots of a test sample may be distributed directly into wells of a multi-well plate, indicator phage may be added, and after a period of time sufficient for infection, a lysis buffer may be added as well as a substrate for the indicator moiety (e.g., luciferase substrate for a luciferase indicator) and assayed for detection of the indicator signal. Some embodiments of the method can be performed on filter plates. Some embodiments of the method can be performed with or without concentration of the sample before infection with indicator phage.

For example, in many embodiments, multi-well plates are used to conduct the assays. The choice of plates (or any other container in which detecting may be performed) may affect the detecting step. For example, some plates may include a colored or white background, which may affect the detection of light emissions. Generally speaking, white plates have higher sensitivity but also yield a higher background signal. Other colors of plates may generate lower background signal but also have a slightly lower sensitivity. Additionally, one reason for background signal is the leakage of light from one well to another, adjacent well. There are some plates that have white wells but the rest of the plate is black. This allows for a high signal inside the well but prevents well-to-well light leakage and thus may decrease background. Thus the choice of plate or other assay vessel may influence the sensitivity and background signal for the assay.

Methods of the invention may comprise various other steps to increase sensitivity. For example, as discussed in more detail herein, the method may comprise a step for washing the captured and infected bacterium, after adding the bacteriophage but before incubating, to remove excess parental bacteriophage and/or luciferase or other reporter protein contaminating the bacteriophage preparation.

In some embodiments, detection of the microorganism of interest may be completed without the need for culturing the sample as a way to increase the population of the microorganisms. For example, in certain embodiments the total time required for detection is less than 28.0 hours, 27.0 hours, 26.0 hours, 25.0 hours, 24.0 hours, 23.0 hours, 22.0 hours, 21.0 hours, 20.0 hours, 19.0 hours, 18.0 hours, 17.0 hours, 16.0 hours, 15.0 hours, 14.0 hours, 13.0 hours, 12.0 hours, 11.0 hours, 10.0 hours, 9.0 hours, 8.0 hours, 7.0 hours, 6.0 hours, 5.0 hours, 4.0 hours, 3.0 hours, 2.5 hours, 2.0 hours, 1.5 hours, or less than 1.0 hour. Minimizing time to result is critical in food and environmental testing for pathogens.

In contrast to assays known in the art, the method of the invention can detect individual microorganisms. Thus, in certain embodiments, the method may detect as few as 10 cells of the microorganism present in a sample. For example, in certain embodiments, the recombinant bacteriophage is highly specific for *Listeria* spp. In an embodiment, the recombinant bacteriophage can distinguish *Listeria* spp. in the presence of other types of bacteria. In certain embodiments, the recombinant bacteriophage can be used to detect a single bacterium of the specific type in the sample. In certain embodiments, the recombinant bacteriophage detects as few as 2, 3, 4, 5, 6, 7, 8, 9, 10, 15, 20, 30, 40, 50, 60, 70, 80, 90, or 100 of the specific bacteria in the sample.

Thus, aspects of the present invention provide methods for detection of microorganisms in a test sample via an indicator moiety. In some embodiments, where the microorganism of interest is a bacterium, the indicator moiety may be associated with an infectious agent such as an indicator bacteriophage. The indicator moiety may react with a substrate to emit a detectable signal or may emit an intrinsic signal (e.g., fluorescent protein). In some embodiments, the detection sensitivity can reveal the presence of as few as 50, 40, 30, 20, 10, 5, or 2 cells of the microorganism of interest in a test sample. In some embodiments, even a single cell of the microorganism of interest may yield a detectable signal. In some embodiments, the bacteriophage is a *Pecentumvirus, Tequatravirus, Homburgvirus,* or *Kuttervirus* bacteriophage. In some embodiments, the recombinant bacteriophage is derived from *Listeria*-specific bacteriophage. In certain embodiments, a recombinant *Listeria*-specific bacteriophage is highly specific for *Listeria* spp.

In some embodiments, the indicator moiety encoded by the infectious agent may be detectable during or after replication of the infectious agent. Many different types of detectable biomolecules suitable for use as indicator moieties are known in the art, and many are commercially available. In some embodiments the indicator phage comprises an enzyme, which serves as the indicator moiety. In some embodiments, the genome of the indicator phage is modified to encode a soluble protein. In some embodiments, the indicator phage encodes a detectable enzyme. The indicator may emit light and/or may be detectable by a color change in an added substrate. Various appropriate enzymes are commercially available, such as alkaline phosphatase (AP), horseradish peroxidase (HRP), or luciferase (Luc). In some embodiments, these enzymes may serve as the indicator moiety. In some embodiments, Firefly luciferase is the indicator moiety. In some embodiments, *Oplophorus* luciferase is the indicator moiety. In some embodiments, NANO-LUC® is the indicator moiety. Other engineered luciferases or other enzymes that generate detectable signals may also be appropriate indicator moieties.

Thus, in some embodiments, the recombinant bacteriophage of the methods, systems or kits is prepared from wild-type *Listeria*-specific bacteriophage. In some embodiments, the indicator gene encodes a protein that emits an intrinsic signal, such as a fluorescent protein (e.g., green fluorescent protein or others). The indicator may emit light and/or may be detectable by a color change. In some embodiments, the indicator gene encodes an enzyme (e.g., luciferase) that interacts with a substrate to generate signal. In some embodiments, the indicator gene is a luciferase gene. In some embodiments, the luciferase gene is one of *Oplophorus* luciferase, Firefly luciferase, Renilla luciferase, External Gaussia luciferase, Lucia luciferase, or an engineered luciferase such as NANOLUC®, Rluc8.6-535, or Orange Nano-lantern.

Detecting the indicator may include detecting emissions of light. In some embodiments, a luminometer may be used to detect the reaction of indicator (e.g., luciferase) with a substrate. The detection of RLU can be achieved with a luminometer, or other machines or devices may also be used. For example, a spectrophotometer, CCD camera, or CMOS camera may detect color changes and other light emissions. Absolute RLU are important for detection, but the signal to background ratio also needs to be high (e.g., >2.0, >2.5, or >3.0) in order for single cells or low numbers of cells to be detected reliably.

In some embodiments, the indicator phage is genetically engineered to contain the gene for an enzyme, such as a luciferase, which is only produced upon infection of bacteria that the phage specifically recognizes and infects. In some embodiments, the indicator moiety is expressed late in the viral life cycle. In some embodiments, as described herein, the indicator is a soluble protein (e.g., soluble luciferase) and is not fused with a phage structural protein that limits its copy number.

Thus in some embodiments utilizing indicator phage, the invention comprises a method for detecting a microorganism of interest comprising the steps of capturing at least one sample bacterium; incubating the at least one bacterium with a plurality of indicator phage; allowing time for infection and replication to generate progeny phage and express soluble indicator moiety; and detecting the progeny phage, or preferably the indicator, wherein detection of the indicator demonstrates that the bacterium is present in the sample.

For example, in some embodiments the test sample bacterium may be captured by binding to the surface of a plate, or by filtering the sample through a bacteriological filter (e.g., 0.45 µm pore size spin filter or plate filter). In an embodiment, the infectious agent (e.g., indicator phage) is added in a minimal volume to the captured sample directly on the filter. In an embodiment, the microorganism captured on the filter or plate surface is subsequently washed one or more times to remove excess unbound infectious agent. In an embodiment, a medium (e.g., Luria-Bertani (LB) Broth, Buffered Peptone Water (BPW) or Tryptic Soy Broth or Tryptone Soy Broth (TSB), Brain Heart Infusion (BHI) Buffered *Listeria* Enrichment Broth (BLEB) University of Vermont (UVM) Broth, or Fraser Broth) may be added for further incubation time, to allow replication of bacterial cells and phage and high-level expression of the gene encoding the indicator moiety. However, a surprising aspect of some embodiments of testing assays is that the incubation step with indicator phage only needs to be long enough for a single phage life cycle. The amplification power of using bacteriophage was previously thought to require more time, such that the phage would replicate for several cycles. A single replication cycle of indicator phage can be sufficient to facilitate sensitive and rapid detection according to some embodiments of the present invention.

In some embodiments, aliquots of a test sample comprising bacteria may be applied to a spin column and after infection with a recombinant bacteriophage and an optional washing to remove any excess bacteriophage, the amount of soluble indicator detected will be proportional to the amount of bacteriophage that are produced by infected bacteria.

Soluble indicator (e.g., luciferase) released into the surrounding liquid upon lysis of the bacteria may then be measured and quantified. In an embodiment, the solution is spun through the filter, and the filtrate collected for assay in a new receptacle (e.g., in a luminometer) following addition of a substrate for the indicator enzyme (e.g., luciferase substrate). Alternatively, the indicator signal may be measured directly on the filter.

In various embodiments, the purified parental indicator phage does not comprise the detectable indicator itself, because the parental phage can be purified before it is used for incubation with a test sample. Expression of late (Class III) genes occurs late in the viral life cycle. In some embodiments of the present invention, parental phage may be purified to exclude any existing indicator protein (e.g., luciferase). In some embodiments, expression of the indicator gene during bacteriophage replication following infection of host bacteria results in a soluble indicator protein product. Thus, in many embodiments, it is not necessary to separate parental from progeny phage prior to the detecting step. In an embodiment, the microorganism is a bacterium and the indicator phage is a bacteriophage. In an embodiment, the indicator moiety is soluble luciferase, which is released upon lysis of the host microorganism.

Thus, in an alternate embodiment, the indicator substrate (e.g., luciferase substrate) may be incubated with the portion of the sample that remains on a filter or bound to a plate surface. Accordingly, in some embodiments the solid support is a 96-well filter plate (or regular 96-well plate), and the substrate reaction may be detected by placing the plate directly in the luminometer.

For example, in an embodiment, the invention may comprise a method for detecting *Listeria* spp. comprising the steps of: infecting cells captured on a 96-well filter plate with a plurality of parental indicator phage capable of expressing luciferase upon infection; washing excess phage away; adding BHI broth and allowing time for phage to replicate and lyse the specific *Listeria* spp. target (e.g., 60-240 minutes); and detecting the indicator luciferase by adding luciferase substrate and measuring luciferase activity directly in the 96-well plate, wherein detection of luciferase activity indicates that the *Listeria* spp. is present in the sample.

In another embodiment, the invention may comprise a method for detecting *Listeria* spp. comprising the steps of: infecting cells in liquid solution or suspension in a 96-well plate with a plurality of parental indicator phage capable of expressing luciferase upon infection; allowing time for phage to replicate and lyse the specific *Listeria* spp. target (e.g., 60-240 minutes); and detecting the indicator luciferase by adding luciferase substrate and measuring luciferase activity directly in the 96-well plate, wherein detection of luciferase activity indicates that the *Listeria* spp. is present in the sample. In such an embodiment no capturing step is necessary. In some embodiments, the liquid solution or suspension may be a consumable test sample, such as a vegetable wash. In some embodiments, the liquid solution or suspension may be a vegetable wash fortified with concentrated Luria-Bertani (LB) Broth, Buffered Peptone Water (BPW) or Tryptic Soy Broth or Tryptone Soy Broth (TSB), Brain Heart Infusion (BHI) Buffered *Listeria* Enrichment Broth (BLEB) University of Vermont (UVM) Broth, or Fraser Broth. In some embodiments, the liquid solution or suspension may be bacteria diluted in BHI Broth.

In some embodiments, lysis of the bacterium may occur before, during, or after the detection step. Experiments suggest that infected unlysed cells may be detectable upon addition of luciferase substrate in some embodiments. Presumably, luciferase may exit cells and/or luciferase substrate may enter cells without complete cell lysis. Thus, for embodiments utilizing the spin filter system, where only luciferase released into the lysate (and not luciferase still inside intact bacteria) is analyzed in the luminometer, lysis is required for detection. However, for embodiments utilizing filter plates or 96-well plates with sample in solution or suspension, where the original plate full of intact and lysed cells is directly assayed in the luminometer, lysis is not necessary for detection.

In some embodiments, the reaction of indicator moiety (e.g., luciferase) with substrate may continue for 60 minutes or more, and detection at various time points may be desirable for optimizing sensitivity. For example, in embodiments using 96-well filter plates as the solid support and luciferase as the indicator, luminometer readings may be taken initially and at 10- or 15-minute intervals until the reaction is completed.

Surprisingly, high concentrations of phage utilized for infecting test samples have successfully achieved detection of very low numbers of a target microorganism in a very short timeframe. The incubation of phage with a test sample in some embodiments need only be long enough for a single phage life cycle. In some embodiments, the bacteriophage concentration for this incubating step is greater than $7\times10^6$, $8\times10^6$, $9\times10^6$, $1.0\times10^7$, $1.1\times10^7$, $1.2\times10^7$, $1.3\times10^7$, $1.4\times10^7$, $1.5\times10^7$, $1.6\times10^7$, $1.7\times10^7$, $1.8\times10^7$, $1.9\times10^7$, $2.0\times10^7$, $3.0\times10^7$, $4.0\times10^7$, $5.0\times10^7$, $6.0\times10^7$, $7.0\times10^7$, $8.0\times10^7$, $9.0\times10^7$, or $1.0\times10^8$ PFU/mL.

Success with such high concentrations of phage is surprising because the large numbers of phage were previously associated with "lysis from without," which killed target cells and thereby prevented generation of useful signal from earlier phage assays. It is possible that the clean-up of prepared phage stocks described herein helps to alleviate this problem (e.g., clean-up by cesium chloride isopycnic density gradient ultracentrifugation), because in addition to removing any contaminating luciferase associated with the phage, this clean-up may also remove ghost particles (particles that have lost DNA). The ghost particles can lyse bacterial cells via "lysis from without," killing the cells prematurely and thereby preventing generation of indicator signal. Electron microscopy demonstrates that a crude phage lysate (i.e., before cesium chloride clean-up) may have greater than 50% ghosts. These ghost particles may contribute to premature death of the microorganism through the action of many phage particles puncturing the cell membrane. Thus ghost particles may have contributed to previous problems where high PFU concentrations were reported to be detrimental. Moreover, a very clean phage prep allows the assay to be performed with no wash steps, which makes the assay possible to perform without an initial concentration step. Some embodiments do include an initial concentration step, and in some embodiments this concentration step allows a shorter enrichment incubation time.

Some embodiments of testing methods may further include confirmatory assays. A variety of assays are known in the art for confirming an initial result, usually at a later point in time. For example, the samples can be cultured (e.g., selective chromogenic plating), and PCR can be utilized to confirm the presence of the microbial DNA, or other confirmatory assays can be used to confirm the initial result.

In certain embodiments, the methods of the present invention combine the use of a binding agent (e.g., antibody) to purify and/or concentrate a microorganism of interest such as *Listeria* spp. from the sample in addition to detection with an infectious agent. For example, in certain embodiments, the present invention comprises a method for detecting a microorganism of interest in a sample comprising the steps of: capturing the microorganism from the sample on a prior support using a capture antibody specific to the microorganism of interest such as *Listeria* spp.; incubating the sample with a recombinant bacteriophage that infects *Listeria* spp. wherein the recombinant bacteriophage comprises an indicator gene inserted into a late gene region of the bacteriophage such that expression of the indicator gene during bacteriophage replication following infection of host bacteria results in a soluble indicator protein product; and detecting the indicator protein product, wherein positive detection of the indicator protein product indicates that *Listeria* spp. is present in the sample.

In some embodiments synthetic phage are designed to optimize desirable traits for use in pathogen detection assays. In some embodiments bioinformatics and previous analyses of genetic modifications are employed to optimize desirable traits. For example, in some embodiments, the genes encoding phage tail proteins can be optimized to recognize and bind to particular species of bacteria. In other embodiments the genes encoding phage tail proteins can be optimized to recognize and bind to an entire genus of bacteria, or a particular group of species within a genus. In this way, the phage can be optimized to detect broader or narrower groups of pathogens. In some embodiments, the synthetic phage may be designed to improve expression of the reporter gene. Additionally and/or alternatively, in some instances, the synthetic phage may be designed to increase the burst size of the phage to improve detection.

In some embodiments, the stability of the phage may be optimized to improve shelf-life. For example, enzybiotic solubility may be increased in order to increase subsequent phage stability. Additionally and/or alternatively phage thermostability may be optimized. Thermostable phage better preserve functional activity during storage thereby increasing shelf-life. Thus, in some embodiments, the thermostability and/or pH tolerance may be optimized.

In some embodiments the genetically modified phage or the synthetically derived phage comprises a detectable indicator. In some embodiments the indicator is a luciferase. In some embodiments the phage genome comprises an indicator gene (e.g., a luciferase gene or another gene encoding a detectable indicator).

Systems and Kits of the Invention

In some embodiments, the invention comprises systems (e.g., automated systems or kits) comprising components for performing the methods disclosed herein. In some embodiments, indicator phage are comprised in systems or kits according to the invention. Methods described herein may also utilize such indicator phage systems or kits. Some embodiments described herein are particularly suitable for automation and/or kits, given the minimal amount of reagents and materials required to perform the methods. In certain embodiments, each of the components of a kit may comprise a self-contained unit that is deliverable from a first site to a second site.

In some embodiments, the invention comprises systems or kits for rapid detection of a microorganism of interest in a sample. The systems or kits may in certain embodiments comprise a component for incubating the sample with an infectious agent specific for the microorganism of interest, wherein the infectious agent comprises an indicator moiety and a component for detecting the indicator moiety. In some embodiments of both the systems and the kits of the invention, the infectious agent is a recombinant bacteriophage that infects the bacterium of interest, and the recombinant bacteriophage comprises an indicator gene inserted into a late gene region of the bacteriophage as the indicator moiety such that expression of the indicator gene during bacteriophage replication following infection of host bacteria results in a soluble indicator protein product. Some systems further comprise a component for capturing the microorganism of interest on a solid support.

In other embodiments, the invention comprises a method, system, or kit for rapid detection of a microorganism of interest in a sample, comprising an infectious agent component that is specific for the microorganism of interest, wherein the infectious agent comprises an indicator moiety, and a component for detecting the indicator moiety. In some embodiments, the bacteriophage is a *Tequatravirus*, ViI, *Kuttervirus, Homburgvirus, Pecentumvirus,* or *Listeria* spp.-specific bacteriophage. In one embodiment, the recombinant bacteriophage is derived from *Listeria* spp.-specific bacteriophage. In certain embodiments, the recombinant bacteriophage is highly specific for a particular bacterium. For example, in certain embodiments, the recombinant bacteriophage is highly specific for *Listeria* spp. In an embodiment, the recombinant bacteriophage can distinguish *Listeria* spp. in the presence of other types of bacteria. In certain embodiments, a system or kit detects as few as 1, 10, 15, 20, 30, 40, 50, 60, 70, 80, 90, or 100 specific bacteria in the sample.

In certain embodiments, the systems and/or kits may further comprise a component for washing the captured microorganism sample. Additionally or alternatively, the systems and/or kits may further comprise a component for determining amount of the indicator moiety, wherein the amount of indicator moiety detected corresponds to the amount of microorganism in the sample. For example, in certain embodiments, the system or kit may comprise a luminometer or other device for measuring a luciferase enzyme activity.

In some systems and/or kits, the same component may be used for multiple steps. In some systems and/or kits, the steps are automated or controlled by the user via computer input and/or wherein a liquid-handling robot performs at least one step.

Thus in certain embodiments, the invention may comprise a system or kit for rapid detection of a microorganism of interest in a sample, comprising: a component for incubating the sample with an infectious agent specific for the microorganism of interest, wherein the infectious agent comprises an indicator moiety; a component for capturing the microorganism from the sample on a solid support; a component for washing the captured microorganism sample to remove unbound infectious agent; and a component for detecting the indicator moiety. In some embodiments, the same component may be used for steps of capturing and/or incubating and/or washing (e.g., a filter component). Some embodiments additionally comprise a component for determining the amount of the microorganism of interest in the sample, wherein the amount of indicator moiety detected corresponds to the amount of microorganism in the sample. Such systems can include various embodiments and subembodiments analogous to those described above for methods of rapid detection of microorganisms. In an embodiment, the microorganism is a bacterium and the infectious agent is a bacteriophage. In a computerized system, the system may be fully automated, semi-automated, or directed by the user through a computer (or some combination thereof).

In some embodiments, the system may comprise a component for isolating the microorganism of interest from the other components in the sample.

In an embodiment, the invention comprises a system or kit comprising components for detecting a microorganism of interest comprising: a component for isolating at least one microorganism from other components in the sample; a component for infecting at least one microorganism with a plurality of a parental infectious agent; a component for lysing at least one infected microorganism to release progeny infectious agents present in the microorganism; and a component for detecting the progeny infectious agents, or with greater sensitivity, a soluble protein encoded and expressed by the infectious agent, wherein detection of the infectious agent or a soluble protein product of the infectious agent indicates that the microorganism is present in the sample. The infectious agent may comprise *Listeria*-specific NANOLUC® bacteriophage carrying the NANOLUC® indicator gene.

The systems or kits may comprise a variety of components for detection of progeny infectious agents. For example, in an embodiment, the progeny infectious agent (e.g., bacteriophage) may comprise an indicator moiety. In an embodiment, the indicator moiety in the progeny infectious agent (e.g., bacteriophage) may be a detectable moiety that is expressed during replication, such as a soluble luciferase protein.

In other embodiments, the invention may comprise a kit for rapid detection of a microorganism of interest in a sample, the system comprising: a component for incubating the sample with an infectious agent specific for the microorganism of interest, wherein the infectious agent comprises an indicator moiety; a component for capturing the microorganism from the sample on a solid support; a component for washing the captured microorganism sample to remove unbound infectious agent; and a component for detecting the indicator moiety. In some embodiments, the same component may be used for steps of capturing and/or incubating and/or washing. Some embodiments additionally comprise a component for determining amount of the microorganism of interest in the sample, wherein the amount of indicator moiety detected corresponds to the amount of microorganism in the sample. Such kits can include various embodiments and subembodiments analogous to those described above for methods of rapid detection of microorganisms. In an embodiment, the microorganism is a bacterium and the infectious agent is a bacteriophage.

In some embodiments, the kit or system comprises (1) *Listeria* recombinant phage cocktail, (2) lysis buffer, (3) assay buffer, (4) luciferase substrate, (5) 96 well plate, (6) plate sealing tape, and (7) package instructions. In some embodiments the kit or system comprises two or more of the components enumerated above, or substantially similar alternatives (e.g., 384-well plate or any other configuration/ container).

In some embodiments, a kit may comprise a component for isolating the microorganism of interest from the other components in the sample.

These systems and kits of the invention include various components. As used herein, the term "component" is broadly defined and includes any suitable apparatus or collections of apparatuses suitable for carrying out the recited method. The components need not be integrally connected or situated with respect to each other in any particular way. The invention includes any suitable arrangements of the components with respect to each other. For example, the components need not be in the same room. But in some embodiments, the components are connected to each other in an integral unit. In some embodiments, the same components may perform multiple functions.

Computer Systems and Computer Readable Media

The system, as described in the present technique or any of its components, may be embodied in the form of a computer system. Typical examples of a computer system include a general-purpose computer, a programmed microprocessor, a microcontroller, a peripheral integrated circuit element, and other devices or arrangements of devices that are capable of implementing the steps that constitute the method of the present technique.

A computer system may comprise a computer, an input device, a display unit, and/or the Internet. The computer may further comprise a microprocessor. The microprocessor may be connected to a communication bus. The computer may also include a memory. The memory may include random access memory (RAM) and read only memory (ROM). The computer system may further comprise a storage device. The storage device can be a hard disk drive or a removable storage drive such as a floppy disk drive, optical disk drive, etc. The storage device can also be other similar means for loading computer programs or other instructions into the computer system. The computer system may also include a communication unit. The communication unit allows the computer to connect to other databases and the Internet through an I/O interface. The communication unit allows the transfer to, as well as reception of data from, other databases. The communication unit may include a modem, an Ethernet card, or any similar device which enables the computer system to connect to databases and networks such as LAN, MAN, WAN and the Internet. The computer system thus may facilitate inputs from a user through input device, accessible to the system through I/O interface.

A computing device typically will include an operating system that provides executable program instructions for the general administration and operation of that computing device, and typically will include a computer-readable storage medium (e.g., a hard disk, random access memory, read only memory, etc.) storing instructions that, when executed by a processor of the server, allow the computing device to perform its intended functions. Suitable implementations for the operating system and general functionality of the computing device are known or commercially available, and are readily implemented by persons having ordinary skill in the art, particularly in light of the disclosure herein.

The computer system executes a set of instructions that are stored in one or more storage elements, in order to process input data. The storage elements may also hold data or other information as desired. The storage element may be in the form of an information source or a physical memory element present in the processing machine.

The environment can include a variety of data stores and other memory and storage media as discussed above. These can reside in a variety of locations, such as on a storage medium local to (and/or resident in) one or more of the computers or remote from any or all of the computers across the network. In a particular set of embodiments, the information may reside in a storage-area network ("SAN") familiar to those skilled in the art. Similarly, any necessary files for performing the functions attributed to the computers, servers, or other network devices may be stored locally and/or remotely, as appropriate. Where a system includes computing devices, each such device can include hardware elements that may be electrically coupled via a bus, the elements including, for example, at least one central processing unit (CPU), at least one input device (e.g., a mouse, keyboard, controller, touch screen, or keypad), and at least one output device (e.g., a display device, printer, or speaker). Such a system may also include one or more storage devices, such as disk drives, optical storage devices, and solid-state storage devices such as random access memory ("RAM") or read-only memory ("ROM"), as well as removable media devices, memory cards, flash cards, etc.

Such devices also can include a computer-readable storage media reader, a communications device (e.g., a modem, a network card (wireless or wired), an infrared communication device, etc.), and working memory as described above. The computer-readable storage media reader can be connected with, or configured to receive, a computer-readable storage medium, representing remote, local, fixed, and/or removable storage devices as well as storage media for temporarily and/or more permanently containing, storing, transmitting, and retrieving computer-readable information. The system and various devices also typically will include a number of software applications, modules, services, or other elements located within at least one working memory device, including an operating system and application programs, such as a client application or Web browser. It should be appreciated that alternate embodiments may have numerous variations from that described above. For example, customized hardware might also be used and/or particular elements might be implemented in hardware, software (including portable software, such as applets), or both. Further, connection to other computing devices such as network input/output devices may be employed.

Non-transient storage media and computer readable media for containing code, or portions of code, can include any appropriate media known or used in the art, including storage media and communication media, such as but not limited to volatile and non-volatile, removable and non-removable media implemented in any method or technology for storage and/or transmission of information such as computer readable instructions, data structures, program modules, or other data, including RAM, ROM, EEPROM, flash memory or other memory technology, CD-ROM, digital versatile disk (DVD) or other optical storage, magnetic cassettes, magnetic tape, magnetic disk storage or other magnetic storage devices, or any other medium which can be used to store the desired information and which can be accessed by the a system device. Based on the disclosure and teachings provided herein, a person of ordinary skill in the art will appreciate other ways and/or methods to implement the various embodiments.

A computer-readable medium may comprise, but is not limited to, an electronic, optical, magnetic, or other storage device capable of providing a processor with computer-readable instructions. Other examples include, but are not limited to, a floppy disk, CD-ROM, DVD, magnetic disk, memory chip, ROM, RAM, SRAM, DRAM, content-addressable memory ("CAM"), DDR, flash memory such as NAND flash or NOR flash, an ASIC, a configured processor, optical storage, magnetic tape or other magnetic storage, or any other medium from which a computer processor can read instructions. In one embodiment, the computing device may comprise a single type of computer-readable medium such as random access memory (RAM). In other embodiments, the computing device may comprise two or more types of computer-readable medium such as random access memory (RAM), a disk drive, and cache. The computing device may be in communication with one or more external computer-readable mediums such as an external hard disk drive or an external DVD or Blu-Ray drive.

As discussed above, the embodiment comprises a processor which is configured to execute computer-executable program instructions and/or to access information stored in memory. The instructions may comprise processor-specific instructions generated by a compiler and/or an interpreter from code written in any suitable computer-programming language including, for example, C, C++, C#, Visual Basic, Java, Python, Perl, JavaScript, and ActionScript (Adobe Systems, Mountain View, Calif.). In an embodiment, the computing device comprises a single processor. In other embodiments, the device comprises two or more processors. Such processors may comprise a microprocessor, a digital signal processor (DSP), an application-specific integrated circuit (ASIC), field programmable gate arrays (FPGAs), and state machines. Such processors may further comprise programmable electronic devices such as PLCs, programmable interrupt controllers (PICs), programmable logic devices (PLDs), programmable read-only memories (PROMs), electronically programmable read-only memories (EPROMs or EEPROMs), or other similar devices.

The computing device comprises a network interface. In some embodiments, the network interface is configured for communicating via wired or wireless communication links. For example, the network interface may allow for communication over networks via Ethernet, IEEE 802.11 (Wi-Fi), 802.16 (Wi-Max), Bluetooth, infrared, etc. As another example, network interface may allow for communication over networks such as CDMA, GSM, UMTS, or other cellular communication networks. In some embodiments, the network interface may allow for point-to-point connections with another device, such as via the Universal Serial Bus (USB), 1394 FireWire, serial or parallel connections, or similar interfaces. Some embodiments of suitable computing devices may comprise two or more network interfaces for communication over one or more networks. In some embodiments, the computing device may include a data store in addition to or in place of a network interface.

Some embodiments of suitable computing devices may comprise or be in communication with a number of external or internal devices such as a mouse, a CD-ROM, DVD, a keyboard, a display, audio speakers, one or more microphones, or any other input or output devices. For example, the computing device may be in communication with various user interface devices and a display. The display may use any suitable technology including, but not limited to, LCD, LED, CRT, and the like.

The set of instructions for execution by the computer system may include various commands that instruct the processing machine to perform specific tasks such as the steps that constitute the method of the present technique. The set of instructions may be in the form of a software program. Further, the software may be in the form of a collection of separate programs, a program module with a larger program or a portion of a program module, as in the present technique. The software may also include modular programming in the form of object-oriented programming. The processing of input data by the processing machine may be in response to user commands, results of previous processing, or a request made by another processing machine.

While the present invention has been disclosed with references to certain embodiments, numerous modifications, alterations and changes to the described embodiments are possible without departing from the scope and spirit of the present invention, as defined in the appended claims. Accordingly, it is intended that the present invention not be limited to the described embodiments, but that it have the full scope defined by the language of the following claims, and equivalents thereof.

EXAMPLES

Results depicted in the following examples demonstrate detection of a low number of cells, as few as 1 *Listeria* bacteria, in a shortened time to results.

Example 1

Creation and Isolation of Indicator Phage from *Listeria*-Specific Bacteriophage Indicator Phage *Listeria*-specific LMA4.NANOLUC, LMA8.NANOLUC, and other *Listeria* bacteriophages were created through homologous recombination using procedures as previously described. See FIGS. 1-3 which depict and describe recombinant *Listera* phages derived from LMA4 and LMA8.

The genomic sequences of these phage were obtained through whole genome sequencing using the Illumina MiSeq system with de novo sequence assembly. Based on previously known and annotated genomes of related phage, the late gene regions and Major Capsid Protein genes were located on the new phage genomes. Plasmids were designed and synthesized to insert NANOLUC® along with the appropriate late gene promoter and ribosomal binding site, flanked by approximately 200-500 bp of matching phage sequence to promote homologous recombination.

Target bacteria were transformed with the Homologous Recombination Plasmids under appropriate antibiotic selection and infected with their respective wild-type phage to allow for homologous recombination with the plasmid. Following homologous recombination to generate the recombinant bacteriophage genomes, a series of titer and enrichment steps was used to isolate specific recombinant bacteriophages that express NANOLUC® as previously described.

Finally, large-scale production was performed to obtain high titer stocks appropriate for use in the *Listeria* spp. detection assays. Cesium chloride isopycnic density gradient centrifugation may be used to separate phage particles from contaminating luciferase protein to reduce background. In other embodiments, sucrose isopycnic density gradient centrifugation may be used to separate phage particles from contaminating luciferase protein to reduce background.

Example 2

Inoculated Sponge Sample—Sponge Assay for *Listeria*

EZ Reach polyurethabe sponge samplers were pre-wetted with Dey/Engley Broth and spiked with <1 CFU of *Listeria monocytogenes*, which was diluted from an overnight culture or with 100 CFU challenge bacteria (Cronobacter sakazakii).

The handle of the sponge was broken off and the sponge was placed into medium in a bag. Buffered *Listeria* Enrichment Broth (BLEB) (Remel) medium (10 or 90 mL) was added to cover as much of the sponge as possible. The sponge was then gently massaged to release bacteria into the medium and enrichment followed at 35° C. for 16-18 hours or 24 hours. After enrichment, sponges were gently massaged/squeezed to remove the liquid and were then moved away from the medium in the bag. The bag was then gently massaged to mix the contents. 150 µl aliquots were transferred to a 96-well plate. The sponge was then placed into the medium for further enrichment at 35° C., if necessary.

Sponge samples were tested with *Listera* phage cocktail following 1-hour and 4-hour infection. Briefly, phage reagent (10 µl) was added to samples and the samples incubated at 30° C. for 1 hour or 4 hours. Finally, 65 µl of Luciferase Master Mix reagent was added to each well and gently mixed by pipetting up and down. Samples were read (i.e., luminescence detected) on a luminometer (GloMax96) instrument 3 minutes after substrate addition. Sponges/swabs were placed back into the bag/tube and enrichment continued at 35° C. for a total of 24 hours. Optionally, aliquots may be taken and further enriched and tested again.

Figure 5:
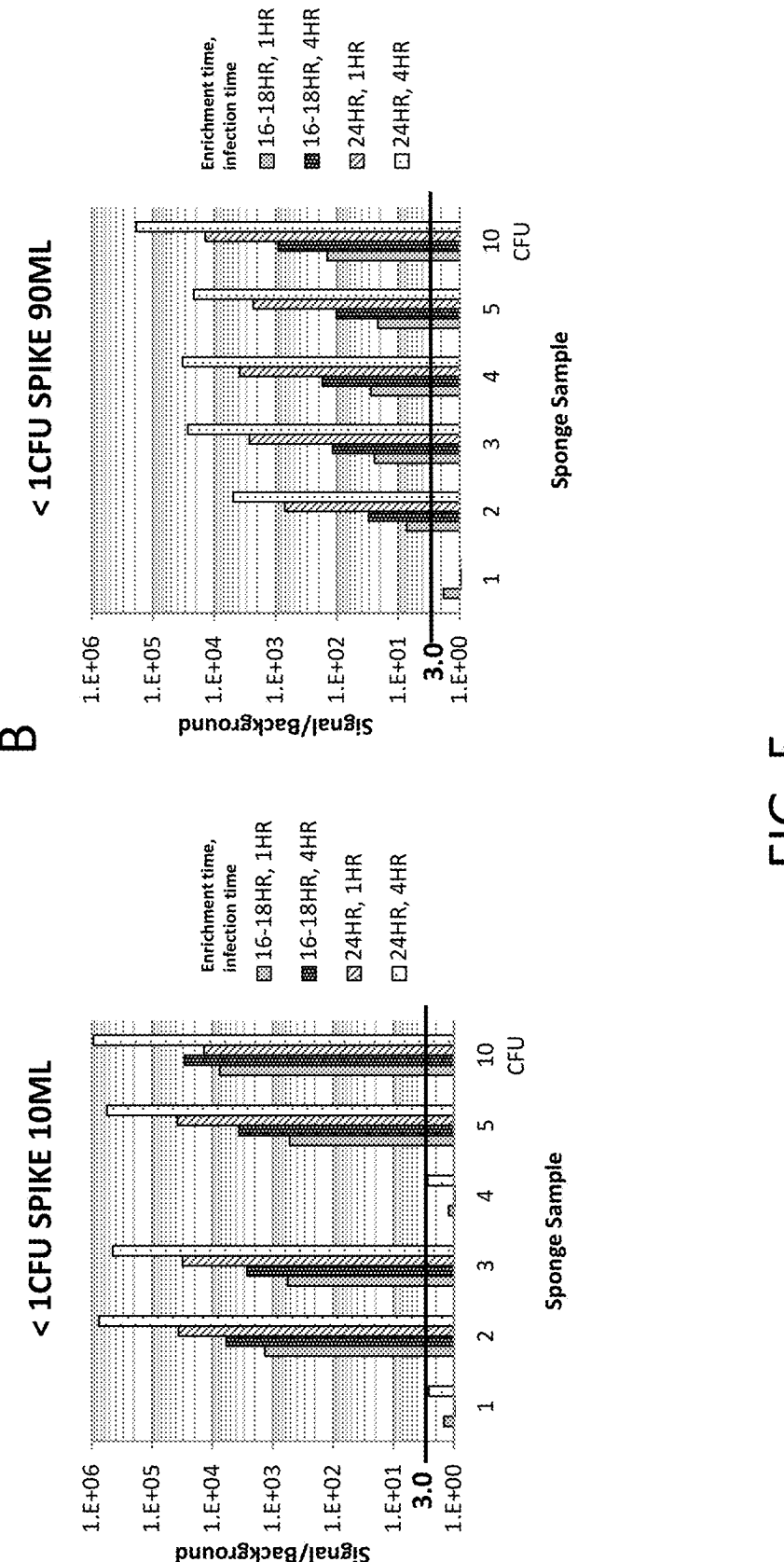
FIG. 5 shows data from embodiments of a *Listeria* detection assays using recombinant bacteriophage specific for *Listeria* to detect *Listeria* in spiked sponges.

Results are shown in FIG. 5. A signal to background ratio (S/B) greater than 3 was considered positive. The background level was determined to be 100 RLU based on prior phage characterizations. These experiments indicate that the *Listeria* Phage Assay can detect a 1 CFU spike of *L. monocytogenes* ATCC 19115 following 16-18 hours of enrichment and 1 hour of infection. FIG. 5A (10 mL medium) shows that sponge samples 1 and 4 were negative for detection of *Listeria* (i.e., S/B <3.0). Sponge samples 2, 3, 5, and the 10 CFU control were all positive for all enrichment and infection times. FIG. 5B (90 mL medium) shows that sponge 1 was negative for detection of *Listeria* while all other samples had positive detection. These data indicate that sponges with 10 mL of added medium generated a better signal with higher relative S/B than samples with 90 mL added medium.

Thus the experiment demonstrates it is possible to detect 1 CFU spike from an overnight culture with all the conditions tried (i.e., 16-18 hr enrichment—1 hr infection, 16-18 hr enrichment—4 hr infection, 24 hr enrichment—1 hr infection, and 24 hr enrichment—4 hr infection.

Example 3

Environmental Surface Sample—Sponge Assay for *Listeria*

Stainless steel surfaces were inoculated with the indicated number of cells in medium. Cells were allowed dry onto the surface and kept at room temperature for 18-24 hours before being swabbed with EZ Reach polyurethane sponge samplers were pre wet with Letheen medium (World BioProducts). *Listeria monocytogenes* 19115 was used as the target and *Staphylococcus aureus* 12600 was used as the challenge strain.

The handle of the sponge was broken off and the sponge was placed back into medium in the bag. Buffered *Listeria* Enrichment Broth (BLEB) (Remel) medium (20 mL) was added to cover as much of the sponge in medium as possible. The sponge was gently massaged to release bacteria into the medium and enrichment followed at 35° C. for 20 hours. After enrichment, sponges were gently massaged, squeezed to remove the liquid, and then moved away from the medium in the bag. The bag was gently massaged to mix the contents. 150 µl aliquots were transferred to a 96-well plate. The sponge was replaced into the medium and incubated at 35° C. if further enrichment was necessary.

Sponge samples were tested with *Listera* phage cocktail following 1-hour and 4-hour infection. Briefly, phage reagent (10 μl) was added to samples and incubated at 30° C. for 4 hours. Finally, 65 μl of Luciferase Master Mix reagent was added to each well and gently mixed by pipetting up and down. Samples were read (i.e., luminescence detected) on a GloMax96 instrument 3 minutes after substrate addition.

Phage reagent (10 μl) was added to samples and incubated at 30° C. for 4 hours. Finally 65 μl of Luciferase Master Mix reagent was added to each well and gently mixed by pipetting up and down. Samples were read (i.e., luminescence detected) on a GloMax96 instrument 3 minutes (180 seconds) after substrate addition.

FIG. 6 shows the RLU generated from the stainless steel surface swabs. Samples generating RLU>300 were considered positive. These data show that the *Listeria* Phage Assay can detect a 100 CFU surface inoculation of *L. monocytogenes* with a 20-hour enrichment and 4 hours of infection in the presence of a non-*Listeria* bacteria present at a 10-fold greater CFU level than the target *Listeria* bacteria. Sample 2 and the negative control were negative for detection of *L. monocytogenes*. All other samples, including the positive control, were positive. Compared to the spiked sponge experiments, the swabs of stainless steel required longer enrichment period and a higher CFU level for positive detection. This can be attributed to several variables, including increased injury to surface inoculated cells as compared to those from an overnight culture. Surface inoculated cells typically have significant loss of viability. Also, recovery of cells form a surface with sponges can be highly variable.

Example 4

Bacteriophage Isolation, Purification, and High Titer Stock Preparation

The *Listeria grayi* bacteriophage LPJP1 was isolated from silage collected from a Wisconsin farm. 3 g of silage was added to 30 mL of BHI media and allowed to diffuse at 2-8° C. for 72 h. To remove bacteria and debris, this solution was centrifuged at 4700×g for 10 min and the supernatant passed through a 0.45 μm filter followed by a 0.2 μm filter (Nalgene, Rochester, NY, USA). As an initial assessment to determine phage presence, a spot test was performed using a standard overlay method (Gratia, A., *Ann. Inst. Pasteur* 1936, 57, 652-676). Briefly, 100 of a log phase culture of the *L. grayi* strain (ATCC 19120) was mixed with 3 mL of melted 0.5% (w/v) semi-solid BHI agar and then poured evenly atop BHI agar plates to form a lawn. Once the semi-solid agar solidified, plates were spotted with 5 μL of the filtered supernatant and incubated overnight at 30° C. As spot testing yielded promising results, isolation of single plaques was pursued using a modification of the above overlay method. 100 μL of a log phase culture, 100 μL of diluted filtered supernatant, and 3 mL of melted semi-solid was poured atop a BHI agar plate and incubated overnight at 30° C. Individual plaques were then isolated by picking them with a pipette tip and resuspending them in 1 mL BHI media. This process of single plaque isolation, dilution, and plating was serially repeated five times to ensure a pure culture of a single phage.

High titer phage stocks were generated from broth lysates as described previously (Nguyen, et al. *Sci Rep* 2020, 10, 17463). Briefly, a log phase culture of *L. grayi* (ATCC 19120) was infected at a multiplicity of infection (MOI) of 0.05 and incubated statically for 5 min to facilitate bacteriophage adsorption. Infected cells were diluted into fresh BHI media and incubated at 30° C. with shaking at 225 rpm until lysis was visually apparent. To remove debris, the lysate was clarified by centrifugation. The supernatant was centrifuged to pellet phage and this pellet was resuspended in TMS Buffer (50 mM Tris-HCl pH 7.8, 10 mM MgCl2, and 300 mM NaCl). Resuspended phage were treated with RNase and DNase I before being further purified using a sucrose density gradient (10-30%) and ultimately being resuspended in SM buffer (50 mM Tris-HCl pH 7.5, 8 mM MgSO4·7H2O, 100 mM NaCl, and 0.01% (w/v) gelatin). This method frequently yielded stock solutions with a titer around $1.5\times1011$ plaque forming units (pfu) per mL.

Figure 9:
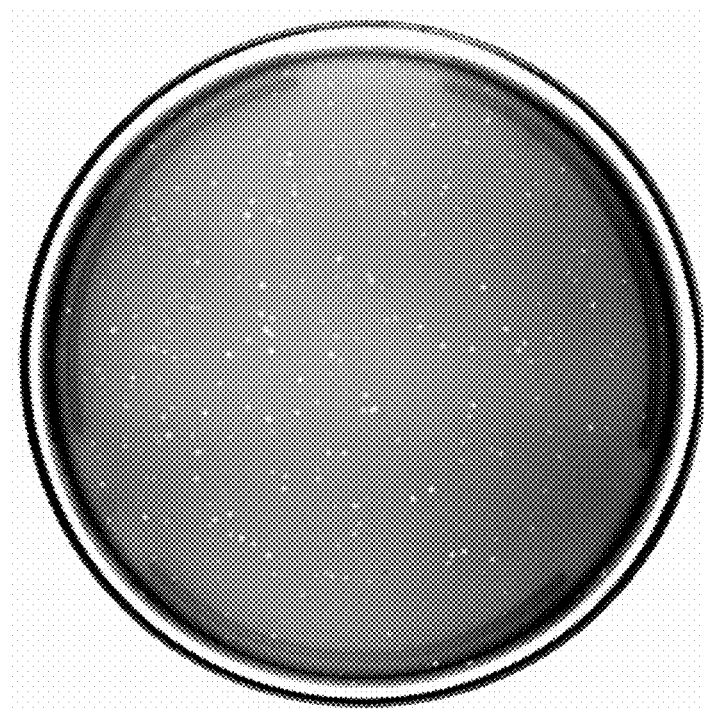
FIG. 9 depicts plaque formation by LPJP1 on *L. grayi* (ATCC 19120). LPJP1 was diluted, mixed with overnight culture and 0.5% semi-solid BHI agar, and poured evenly atop BHI agar plates. Plates were imaged after overnight incubation at 30° C.

LPJP1 formed small clear plaques at 30° C. on the *L. grayi* strain ATCC 19120 (FIG. 9). Interestingly, plaques were not observed at 37° C. The mechanism behind this phenotype is not fully understood but is consistent with temperature-dependent plaque formation observed with other *Listera* phages. A one-step growth curve on LPJP1 revealed a burst size of approximately 50 to 60 pfu with cycle time of roughly 60 min. To our knowledge, LPJP1 is the first published phage capable of lysing and forming plaques on *L. grayi*.

Transmission electron microscopy was used to confirm phage presence and determine the morphology of LPJP1. Microscopy revealed the presence of a large icosahedral head, non-flexible long straight tail, and contractile outer tail sheath (FIG. 7A,B). These characteristics match the morphology of the Myoviridae family of dsDNA phage (Fokine and Rossmann, Bacteriophage 2014).

Example 5

Bacteriophage Characterization (Burst Size, Replication Cycle Time, and Microscopy)

To calculate the burst size and replication cycle time of LPJP1, a standard one-step growth curve was performed using the *L. grayi* strain ATCC 19120, as described previously (Ellis and Delbruck, *Journal of General Physiology* 1939, 22, 365-384).

Transmission electron microscopy (TEM) of LPJP1 was performed as described previously (Nguyen, et al., *Sci Rep* 2020, 10, 17463). Briefly, 400 mesh grids coated with a thin carbon film were glow discharged, floated on purified high titer phage stock, and subsequently stained with 2% uranyl acetate. A Technai G2 Spirit BioTWIN with an accelerating voltage set at 30 kV was used for image capture.

Example 6

Bacteriophage DNA Isolation, Sequencing, and PCR

To isolate phage DNA, $6\times10^{10}$ pfu/mL were first heated at 95° C. for 2 min and then allowed to cool to room temperature. Sodium dodecyl sulfate (SDS), ethylenediaminetetracetic acid (EDTA), and proteinase K were added to a final concentration of 0.1% SDS, 5 mM EDTA, and 53 μg/mL proteinase K. This mixture was incubated for 1 h at 50° C. before performing three rounds of phenol/chloroform extractions, serially separating the aqueous phase. After the addition of 0.1 volumes of 3 M sodium acetate and 2.5 volumes of ethanol to this phase, DNA was precipitated at −80° C. Precipitated DNA was pelleted and washed twice with 70% ethanol. Washed DNA was pelleted once again, air dried, and finally resuspended in 10 mM Tris-HCL pH 8.0.

Phage DNA was quantified using absorbance at 260 nm on a NanoDrop (Thermo Fisher Scientific, Waltham, MA, USA) and sent to Laragen Inc. (Los Angeles, CA, USA) for sequencing. Laragen Inc. quantified dsDNA using a Qubit dsDNA HS assay kit (Thermo Fisher Scientific, Waltham, MA, USA) and performed library preparation using the Nextera DNA Flex library prep (Illumina, San Diego, CA, USA). When successful library preparation was achieved, samples underwent MiSeq whole genome sequencing (Illumina, San Diego, CA, USA) and contig assembly. When indicated, DNA was amplified prior to sequencing using a Illustra TempliPhi DNA amplification kit (Cytiva, Marlborough, MA, USA) according to manufacturer's instructions. Amplified DNA was quantified and submitted for sequencing, as described above. Genome assemblies obtained from Laragen Inc. were examined for homology to other viruses using the Basic Local Alignment Search Tool (BLAST) (BLASTN, limited to viruses (taxid:10239)) (Altschul, et al, *Nucleic Acids Res* 1997, 25, 3389-3402; Altschul, et al., *J Mol Biol* 1990, 215, 403-410).

Polymerase chain reaction (PCR) was performed using either the Q5 hot start high-fidelity DNA polymerase or the Q5U hot start high-fidelity DNA polymerase (New England BioLabs, Ipswich, MA, USA). DNA templates were either native phage DNA or TempliPhi-amplified DNA prepared as described above. To ensure elements of the TempliPhi reaction did not interfere with PCR, amplified DNA was cleaned up using a Monarch PCR and DNA cleanup kit (New England BioLabs, Ipswich, MA, USA). PCR was performed using 2 ng of DNA, either amplified or native, and either the Q5 or Q5U polymerase, as per manufacturer's instructions. Primers were (5'-AGGAAACAGCTATGA-CATGATTACGTTATCATAAAACTTTCGATGTAC-3' (SEQ ID NO: 3)) and (5'-ATT TATACTCTATT-TAACGAGCGTATTGAGTTG-3' (SEQ ID NO: 4)) and were obtained from Eurofins Genomics (Louisville, KY, USA). PCR reactions were assessed using gel electrophoresis. Half of each reaction was mixed with GelPilot DNA loading dye (Qiagen, Hilden, Germany) and loaded onto a 1% agarose gel (Bio-Rad Laboratories, Hercules, CA, USA) in standard Tris-acetate-EDTA (TAE) buffer. For size comparison, O'GeneRuler 1 kb plus DNA ladder (Thermo Fisher Scientific, Waltham, MA, USA) was added to flanking wells. SYBR DNA Gel Strain (Invitrogen, Carlsbad, CA, USA) was included in the gel to allow visualization of results. The gel was electrophoresed for 100 Vh while submerged in TAE buffer. Gel imaging was performed using the Gel Doc EZ system and ImageLab (version 6.0.1) software (Bio-Rad, Hercules, CA, USA).

Figure 8:
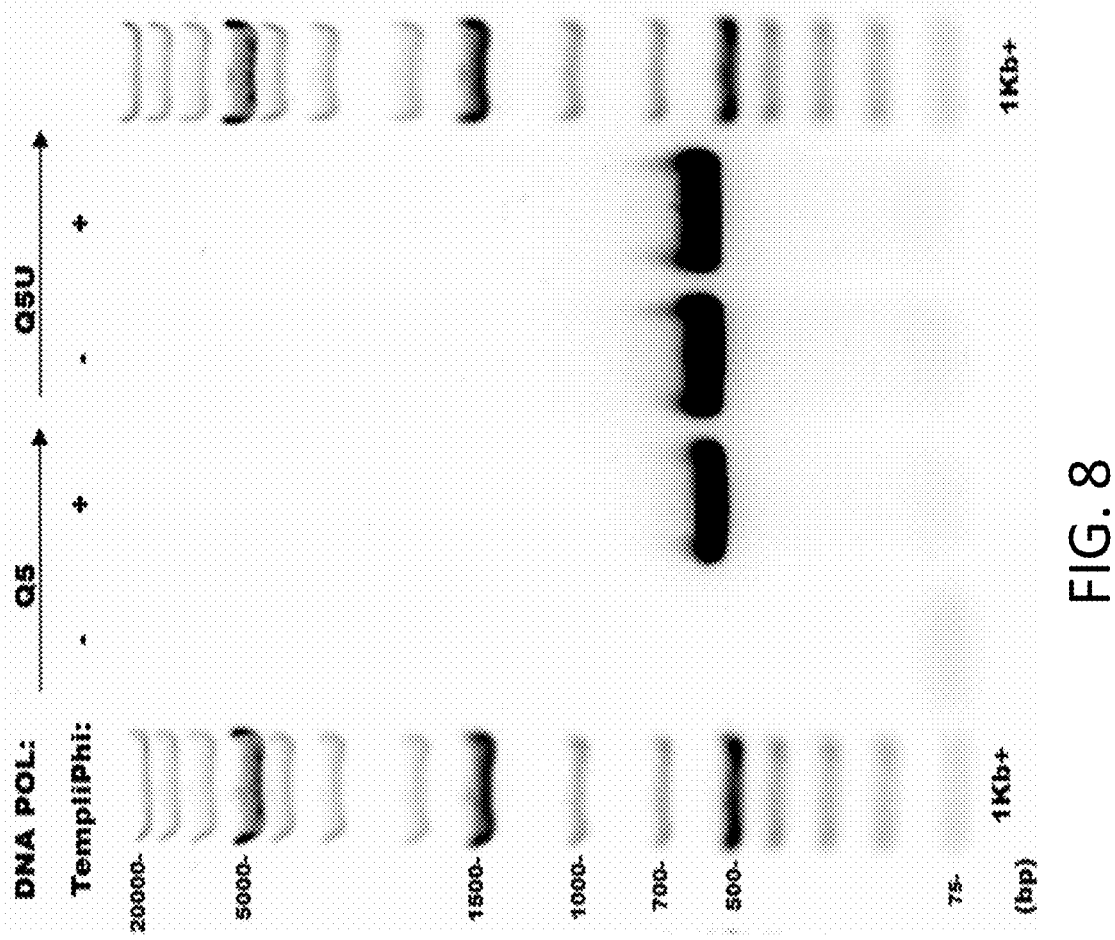
FIG. 8 depicts gel electrophoresis of PCR-amplified LPJP1 DNA. Flanking lanes 1 and 6 contain O'GeneRuler 1 kb plus DNA ladder. Lanes 2 through 5 contain the PCR amplification of either native LPJP1 DNA (lanes 2 and 4) or TempliPhi-treated LPJP1 DNA (lanes 3 and 5) using either the Q5 DNA polymerase (lanes 2 and 3) or the uracil-tolerant Q5U DNA polymerase (lanes 4 and 5).

The success of library preparation only after DNA amplification with the phi29 bacteriophage polymerase could indicate the presence of modified base pairs, such as uracil, in the genome of LPJP1. This hypothesis was further supported with PCR. In particular, DNA isolated from LPJP1 could only be directly amplified when an uracil-tolerant polymerase, such as Q5U, was used (FIG. 8). Importantly, modified base pairs are also found in several other jumbo phage, including those displaying limited homology to LPJP1. In particular, the genomes of the *Bacillus* jumbo phages AR9 and PBS1 and the *Staphylococcus* phage S6 were found to contain deoxyuridine in place of thymidine (Lavysh, et al., *Virology* 2016, 495, 185-196; Uchiyama, et al., *ISME J* 2014, 8, 1949-1952; Takahashi and Marmur, *Nature* 1963, 197, 794-795). Furthermore, AR9 library preparation was performed following DNA amplification using the uracil-tolerant polymerase, KAPA HiFi Uracil+. The benefit of DNA amplification using an uracil-tolerant polymerase is clear. Thus, while it is possible that LPJP1 represents an exceptionally rare phage, it is equally likely that such jumbo phages have been overlooked due to technical limitations and challenges.

Example 7

Design and Engineering of Luciferase Reporter Phage Recombinants

Homologous recombination was used to insert a late gene promoter and NANOLUC® downstream of the predicted major capsid protein to create a NANOLUC®-expressing recombinant of LPJP1. No predicted genes are anticipated to be disrupted following recombination at this site. A predicted major capsid protein was identified in LPJP1 by manual screening of possible open reading frames in the LPJP1 genome assembly. This prediction was supported by homology observed using BLAST (BLASTP) (Altschul, et al., *Nucleic Acids Res* 1997, 25, 3389-3402; Altschul, et al., *FEBS J* 2005, 272, 5101-5109). A shuttle vector containing homology flanks to mediate recombination, a late gene promoter, and NANOLUC® sequence was designed as follows. The upstream flank begins with a KpnI restriction site followed by 500 bp of homology upstream of the insertion site. The insertion site was immediately after predicted major capsid protein of LPJP1. Following this flank, a promoter was added containing −10 and −35 elements from A511's major capsid protein (a late gene) sequence and an A511 consensus ribosome binding site sequence (Loessner and Scherer, *J Bacteriol* 1995, 177, 6601-6609; Klumpp, et al., *J Bacteriol* 2008, 190, 5753-5765). NANOLUC® coding sequence was added following this promoter. The downstream flank contained 500 bp of homology downstream of the target insertion site and was followed by a SalI restriction site. Sequences for both flanks and the promoter are provided (Table 1). The sequence of NANOLUC® has been previously described. These sequences were synthesized and inserted between the KpnI and SalI restriction sites of the multiple cloning site in the previously described shuttle vector pCE104 (Murray, et al., 1. *Infect Immun* 1996, 64, 371-374).

TABLE 1

| DNA Sequences Used in Homologous Recombination (HR) | |
|---|---|
| Feature | DNA Sequence |
| Upstream HR Flank[1] | GGTACCATGTACATCCAAATGGTGGATACAACATGCATCCGCATGAATGGCGCCGTGGTATT CGTGACGTTATTGACTGGATGTCTCAAGCAATGAAAAATGATTACAAAACTTATGATGCTTA CTTTGTAATTGTTGGTAATCCAATTGACACTCAATTGATTCCTGACATTGAATGGGAATTCCA AGGAGCTACTGATGAAGTTGCGGGAATTAACGTTTCTTATAGCGTTGGTGCTTCTTCTACAGT TAACCGTTATAAAGTTGTTTCTTCTGACTTAGTACCTGCTGGAGATCTATTAATCTTTGCAGTT CCTACTCGTGAAGACTTCAAAACTTACGAATACTACCCATACACTTTCAATATCGTTAATAAT |

TABLE 1-continued

DNA Sequences Used in Homologous Recombination (HR)

| Feature | DNA Sequence |
|---|---|
| | TACAACAATGCTGTTAACCAAAGCGTTCCTAACATTATGCTTTCTCGCCGTTATACAGTTGAA GAATTTGTTCCAATTATCGGTAAAGTTACAATTAAAAACAACGATGCAACTCAATACGCTCG TTAA |
| Downstream HR Flank[2] | TAAATATTATGAACCTTTCAGAGACCTTTTGGTTTCTGAAAGGTTATTATTTATAAAAATTTA AATTGGCGGTGCAACCATGCATATTGATTATGGTATTGAAAAGAATATATCAAAGTACTTAC ATGAAGAATTACTAACTGAAGATATCTATAATCATCCTTTATTAAAAAAGATTGATGATGAA TTTCAGAAAATATTAGATGAAGATAATATTAATGATACTAAACTACCAGTAACATCATATAA AAAAATTCAAAATATAATTAAATATGTCTCAACTATATTTAATATAAATTTAATTATAACGAT TGATAACGATAATATCCTTACTTATGGAATGATGACATTTATTCCGGTTAAAAATCTAACAA AGATATCTAATAATATAAAGAAGATTGTACTTCAACCAAAAACTGGTTTTGAATATATTAAA ACTGAAGTTATTGAAATTAAAATACAGAAAAAATTAATATCTTTCATTAAGGATCCAAACTT ACGTCGAC |
| Promoter[3] | ATAGAGTATAAATTCTATTCAGTTTCGTATATTAATACTAGTAGATAGGAGGTGTTTCGA |

[1]Upstream homologous recombination flank consists of a KpnI restriction site (underlined) and 500 bp of homology immediately upstream of desired insertion site (predicted major capsid protein)
[2]Downstream homologous recombination flank consists of 500 bp of homology immediately downstream of desired insertion site, followed by a SalI restriction site (underlined)
[3]Key elements of the promoter sequence used are underlined. -35 (ATAGAGTA) and -10 (TATATT) elements are from the late gene major capsid protein sequence of A511, while the ribosome binding site used (AGGAGGTG) is the reported A511 consensus sequence.

ATCC 19120, the *L. grayi* strain used during isolation of LPJP1, was also selected as a host for recombination. Electrocompetent ATCC 19120 was generated using a modification of a previously described method (Park, S. F.; Stewart, G. S. High-efficiency transformation of *Listeria monocytogenes* by electroporation of penicillin-treated cells. *Gene* 1990, 94, 129-132). 10 µg/mL of Penicillin G (Thermo Fisher Scientific, Waltham, MA, USA) was added to a log phase culture of ATCC 19120 and incubated for 1 h at 37° C. with shaking (225 rpm). Treated cultures were then chilled on ice for 30 min, pelleted, and washed three times with cold SMP (272 mM sucrose, 1 mM MgCl2, 7 mM Sodium phosphate pH 6.8). Cells were pelleted a final time and resuspended in 1 mL of cold SMP. 100 µL aliquots were frozen and stored at −80° C. until use. 100 ng of homologous recombination plasmid DNA was added to thawed electrocompetent cells, incubated on ice for 15 min, and transferred to a 0.2 cm cuvette. Electroporation was carried out using a MicroPulser electroporation apparatus (Bio-Rad Laboratories, Hercules, CA, USA) with voltage of 2.5 kV and a 2.8 msec time constant. Electroporated cells were recovered in fresh BHI for 2 h at 30° C. before being plated on BHI agar plates containing 5 µg/mL erythromycin sulfate (Alfa Aesar, Haverhill, MA, USA). Plates were incubated at 37° C. for 24 h before being examined for transformants.

Erythromycin-resistant colonies were picked, grown up BHI containing 5 µg/mL erythromycin sulfate, and infected with varying amounts of LPJP1 equivalent to MOIs of 0.01 to 0.1. Infections were incubated for 4.5 h at 30° C. with 225 rpm shaking. To remove debris and intact bacteria, samples were centrifuged for 2 min at 6,800×g and the supernatant passed through a 0.45 µm filter. This solution was transferred to a 100 kDa pore protein concentrator PES column (Pierce Biotechnology, Rockford, IL) and buffer exchanged with TMS. Potential phage recombinants were identified from this reaction. Briefly, enrichment of limiting dilutions followed by screening for luciferase production was used to improve the likelihood of finding a recombination event. When found to be positive, these enrichments were plated to isolate single plaques on semi-solid agar, as described above. Candidate plaques were picked, mixed with diluted cultures of ATCC 19120, and evaluated for NANOLUC® production. Single plaque isolation, dilution, and plating was serially performed five times to establish a pure NANO-LUC®-expressing recombinant, called LPJP1.NL. Using the same preparation method described above, high titer stocks of LPJP1.NL were made and sent for genome sequencing. Analysis of the assembled genome of LPJP1.NL verified that the homologous recombination occurred as desired, inserting the promoter and NANOLUC® downstream of the predicted major capsid protein.

Example 8

Limit of Detection of LPJP1.NL

The limit of detection of LPJP1.NL in *L. grayi* was determined as follows. A log phase culture ($OD_{600}$ of 0.1 to 0.5) of the *L. grayi* strain ATCC 19120 was diluted in BHI media to achieve 10 to 100,000 CFU/mL. 100 µL of each bacterial dilution or BHI media was added to at least six replicate wells on a 96-well plate. Each well was infected with 10 µL of LPJP1.NL at $1.2×10^7$ pfu/mL and the infection was allowed to proceed for 4 h at 30° C. At the end of the infection, 65 µL of a luciferase detection solution was added to each well. The luciferase detection solution consisted of 50 µL of NanoGlo buffer, 15 µL of *Renilla lysis* buffer, and 1 of NanoGlo substrate (Promega Corp., Madison, WI, USA). A GloMax Navigator luminometer (Promega Corp., Madison, WI, USA), set to a 3 min wait time and 1 sec integration, was used to detect light production. Using this method, relative light units (RLU) values were obtained for each well and averaged among replicates.

When indicated, the above protocol was modified to determine the effect of infection temperature in signal production. Bacteria were prepared and infected as described above with the following exception. For each burden, two wells were infected with LPJP1.NL. One set of wells was infected for 4 h at 30° C., while the other set was infected for 4 h at 37° C. RLU values were obtained using a luciferase detection solution as described above.

NANOLUC®-expressing bacteriophage typically yield robust signal following infection of even a few bacterial cells. In order to evaluate the sensitivity of LPJP1.NL for *L. grayi*, the limit of detection of this recombinant reporter was determined. LPJP1.NL was allowed to infect 0 to 10,000

CFU of *L. grayi* for 4 h at 30° C. After addition of substrate, NANOLUC® production in each sample was quantified using a luminometer. Infection of *L. grayi* with LPJP1.NL yielded an easily detectable signal over media background and increased proportionally with CFU (Table 2). Background from media and reporter alone was a minimal 96 RLU while a single CFU of *L. grayi* was sufficient to achieve an average RLU signal of twice this amount. As expected, variation between replicate wells was noted when low bacterial burdens were tested. Overall, these results indicate that LPJP1.NL is a sensitive reporter capable of producing a signal over background from a single CFU of *L. grayi* after a 4 h infection.

TABLE 2

Limit of Detection of LPJP1NL in *L. grayi*

| Detected Cells [1] | Replicate Wells | Avg. RLU [2] | SD [3] | % CV [4] | S/B [5] |
|---|---|---|---|---|---|
| 0 | 6 | 96 | 6 | 6 | 1.0 |
| 1 | 10 | 191 | 135 | 71 | 2.0 |
| 2 | 10 | 553 | 327 | 59 | 5.8 |
| 5 | 10 | 1012 | 474 | 47 | 10.6 |
| 10 | 10 | 2565 | 1055 | 41 | 26.9 |
| 100 | 10 | 24,056 | 2463 | 10 | 251.9 |
| 1000 | 6 | 264,210 | 24,637 | 9 | 2766.6 |
| 10,000 | 6 | 4,414,026 | 322,722 | 7 | 46,220.2 |

[1] Log phase cultures of *L. grayi* (ATCC 19120) were diluted to the indicated burden and infected with LPJP1.NL for 4 h at 30° C.
[2] Average (Avg.) Relative Light Units (RLU) across replicate wells.
[3] Standard Deviation (SD)
[4] Coefficient of Variation (CV)
[5] Signal over background (S/B) was calculated by dividing the Avg. RLU for each condition by the Avg. RLU of background (0 cells).

Previous concerns over the phenomenon of temperature-dependent plaque formation with *Listera* phages and the implications on phage reporters have been raised (Tokman, J. I., et al., *Front Microbiol* 2016, 7, 631). Since LPJP1 shared this phenotype, an experiment was carried out to determine the role of temperature during infection on the signal production of LPJP1.NL. Minimal differences were noted between the RLU obtained from a 4 h infection at 30° C. or 37° C. and both temperatures yielded comparable results across all burdens (Table 3). In spite of the lack of plaque formation at 37° C., the robust signal from LPJP1.NL at this temperature suggests that phage DNA was injected successfully. These results suggest that, while higher temperatures may prohibit plaque formation in many *Listera* phage, increased temperatures do not impede the production of signal from *Listera* phage reporters.

TABLE 3

Comparison of Limit of Detection After 30° C. or 37° C. Infection

| Detected Cells [1] | RLU-30° C. [2] | RLU-37° C. [2] |
|---|---|---|
| 0 | 89 (Neg.) | 88 (Neg.) |
| 1 | 248 (Pos.) | 909 (Pos.) |
| 2 | 821 (Pos.) | 966 (Pos.) |
| 5 | 1692 (Pos.) | 2926 (Pos.) |
| 10 | 2155 (Pos.) | 2893 (Pos.) |
| 100 | 24,407 (Pos.) | 34,156 (Pos.) |
| 1000 | 250,905 (Pos.) | 391,186 (Pos.) |
| 10,000 | 5,940,865 (Pos.) | 5,546,562 (Pos.) |

[1] Log phase cultures of *L. grayi* (ATCC 19120) were diluted to the indicated burden and infected with LPJP1.NL for 4 h at 30° C. or 37° C.
[2] Relative Light Units (RLU) are provided. Positive (Pos.) and negative (Neg.) detection was determined for each sample using a threshold of 190 RLU, approximately twice media background.

Example 9

Genome Sequencing and Engineering of LPJP1

LPJP1 was sequenced in order to determine suitable siters for inserting a genetic construct. Initial attempts to sequence the genome of this phage were unsuccessful. Despite obtaining sufficient DNA quantity and quality, library preparation using bead-lined transposomes (Illumina, San Diego, CA, USA) could not be achieved, failing at DNA amplification. This library preparation method is generally considered to be quite robust, demonstrating resistance to poor DNA quality and productivity with various DNA quantities (Bruinsma, S. et al. *BMC Genomics* 2018, 19, 722). One possible explanation for this failure is the presence of modified DNA base pairs, which have been observed to serve a number of functions in some bacteriophage (Weigele, P. et al. *Chem Rev* 2016, 116, 12655-12687). In particular, the presence of deaminated base pairs, such as uracil or hypoxanthine, in DNA templates can inhibit commercial high-fidelity proofreading archaeal polymerases (Fogg, M J et al., *Nat Struct Biol* 2002, 9, 922-927; Russell, H. J. et al, *Nucleic Acids Res* 2009, 37, 7603-7611). DNA preparations of LPJP1 were amplified using the TempliPhi DNA amplification kit, which utilizes the Phi29 bacteriophage polymerase capable of reading past uracil-containing DNA (Reagin, M. J. et al., *J Biomol Tech* 2003, 14, 143-148; Serrano-Heras, G. et al. *Proc Natl Acad Sci USA* 2008, 105, 19044-19049). Library preparation was successfully completed using PCR-amplified DNA of LPJP1. Further support of both the presence of modified base pairs in LPJP1 and the ability to overcome this with the TempliPhi kit was obtained using the assembled sequence. Primers were designed to amplify an approximately 550 bp region within the LPJP1 genome. PCR amplification was performed using equivalent amounts of either native LPJP1 DNA or TempliPhi-treated LPJP1 DNA. The reaction was performed using either the Q5 polymerase or the uracil-tolerant Q5U polymerase. When these reactions were analyzed by gel electrophoresis, a distinct band of the expected size was observed with native DNA and the Q5U polymerase and TempliPhi-treated DNA with both polymerases (FIG. 8). A clear difference was observed between the uracil-sensitive Q5 polymerase and the uracil-tolerant Q5U polymerase on native phage DNA. Importantly, the failure of the Q5 polymerase in PCR was specific to native DNA and TempliPhi-treated DNA could be effectively amplified by both polymerases. These results support the hypothesis that LPJP1 contains modified base pairs.

Assembly of LPJP1 sequences revealed a large genome, 223,580 bp in length. This crosses the threshold of 200,000 bp to be considered a jumbo phage (Hendrix, R. W. *Curr Top Microbiol Immunol* 2009, 328, 229-240). Two interesting sequence features were identified. First, LPJP1 had minimal homology to available viral nucleotide sequences when using BLAST. The top three matches by query coverage were phage vB_BpuM-BpSP (8% query coverage, 67% identity), phage PBS1 (6% query coverage, 66% identity), and phage AR9 (6% query coverage, 66% identity). Of note, all three of these genomes are from jumbo phage infecting *Bacillus* (Yuan, Y. et al. *Front Microbiol* 2016, 7, 745; Lavysh, D. et al. *Virology* 2016, 495, 185-196). Secondly, LPJP1 has an abnormally low GC content (25.9%) when compared to its host *L. grayi* (41.6%). Interestingly, this GC content discrepancy is also shared by the previously mentioned jumbo phage vB_BpuM-BpSP (25.9%) compared to 41.2% for its *B. pumilus* host, and jumbo phage PBS1 (27.7%) and AR9 (27.8%) compared to 43.5% for their *B.*

*subtilis* host. These basic features indicate that LPJP1 has homology, albeit limited, to jumbo phages capable of infecting another Gram-positive genus, *Bacillus*.

Manual examination of potential open reading frames in LPJP1 revealed a candidate major capsid protein. BLAST analysis of this protein sequence indicated homology with the precursor of major head subunit protein of the *Bacillus* jumbo phage AR9 as a top hit (97% query coverage, 40.5% identity). Amino acid homology was also observed with the structural protein sp46 precursor of both the jumbo phage *Bacillus* vB_BpuM-BpSP (99% query coverage, 36.4% identity) and the Yersinia jumbo phage phiR1-37 (98% query coverage, 30.3% identity). Homologous recombination was used then to mediate insertion of a late gene promoter and the NANOLUC® luciferase immediately downstream of the coding sequence for this candidate major capsid protein. Insertion of this sequence was not predicted to disrupt any phage genes. A recombinant NANOLUC®-expressing LPJP1, referred hereafter as LPJP1.NL (SEQ ID NO: 2) was isolated, purified, and confirmed using genome sequencing.

```
SEQ ID NO: 1 LP-JP1 Genome Sequence >2020-01-17 LP-JP1 reassembled v1 (223,580 bp)
CCAGTTGAGTTTGACGAAAAAGCATGTCTTCTACATCTACCGGTACATCTGAAATATCTTTCTTACATT
TACTACATGTTAATCCATGAATTGCATAAGAAATACCATATTTATCAGATTGCTCACTAATCATTTCAC
TAAGACTCTTCATGTCACTAACTTCAAGATTACTAATGATCTTAAGAATTTGTTCTGGGTTTGTTACTTT
TACAAATTTAAGTTCTCCAGTTTTTTCCAATCTATCTAGGTCAGGAACCATTATTTTTTTAGTGAATAAA
ATTAGATCAATATAATCTCTAACTTCATCATAGCTTTCAGGTTTAATATATGATAGTAATGTTAATTTAT
CTTTTAGTGAAGGTATTTGAATATCGAATACCATTTTACTTAACGGCATTTGGGAACGAGTGATCTTAT
TTACTGCTGAATACTTTTTAATGACGCTTGGATCTTTAACTGTATCAGTAATTTGTTTTAAACGAGAAT
ATGTTTCTTCATTCTTAACAACAATAAGATTCTCATTATAAGCTTTAACATTCCTCATAACGTTTCCACA
TGATCCACACTTAATATCAAAAGAAGTTCCACGTGGGAATGTTTGACAGAATAGTCCGTAAATTAAAG
TATCTAGATCATAGATAGATGTAATGTCAATGAATGTATCCCAATCTAATTTACCTAGTGTAGTGGAAT
TAATTTTACTAAAGTATGTTTGATATTGACGTAATGTAGATTCATATGCAGAAGCGGTGCTTGATGAGA
TAGAAAGCATATCATTCATACGTAGACTCTCTACATGAGCAATATATGCTGATTGATTTAATGTAACTT
GATAAGTAGGGCTTCCTGTTAATGCATATTTAAATTTATCAAAATTAATATCTTTAAATTTATCTTCATC
ATCAATAATTAATGAGTCGATATCTTTTAAATTATCAATTTTTGCTTTATCAAGAATATCTTTAACTGAG
TCTTTTTTAGGTTCTTGTTTAATTTCAGTTAATGTTTCATCTACTTGTAMGTTGTTAATATTTTCTTGATT
AATTGGGTCTTTAATAGGAATCTCATCACTTGGTTCTTCAAAAATTCCTTTAATCTCTTCTTCTTCTTTTT
TCTCATTATCAGGAACATCATCAGGTATTGGATTTCCATCTAAAGGCTCAATGTCTGATGGATTATACG
CAAATTGTTCTTCATTTTCTTGTGATTTTTGTTCATATTGATATTGTTGAGTCATTGCTTGTTCGGTATTT
TCATTTTCTCCAGTATTATTCGTTACTGAGGAATCTTCTTCTTTCTGGTAAACATCAATACCTGTACCAG
AGAGAGATAAGTTAGGATCAATATTCTCTTCTTTTTTTAGCTTCTTCAGATTTTCTACGTTGCTCTGCTTC
TAGAAATAATTTTGCTACATGTTGAGGATCTTCACCTACTACTTGGGCATGTAACATTGCTATTTCTAG
ATCGCTCATCTTTTTATCGGGAATATTAATATTTGTAGGAATATTGTTATTTTCATTATTATCTGATTTT
AATACCATTGTATATTTTACCTCCACATAATTTATATTATTTTTAATTATACATTATTTTTGATACAGTT
GTATTTGTTTTATTATTGTATCCATATAATAATCCAAAGTTTAGATTAGTAGTAGTATTAGAATCTACTA
AATTAATATCTATATAAAACGTATTTACATTTACGTTTGAATTACTAGAAAGAACGTTTTTAACATTTT
GTATATTAATCTTTACAACGATATCTTGATGTACAATATATGATTCTATTTGATTTTCAATTTTACTTTG
AAGTTCTAATCTAGTTTCCKTATCCAAGATTTCATATAAATATAATCCGATACCGATGCCCATATTAGG
TTGGTTCGGGTACGTTCCTTGCTCTATTATAATTAAATTTTGGATCTGTTGTGCTAATGCTTCTAGGTTT
TCTCTTAATATTGGTTGATTGAAGTCATCCCTCTCTAGTATAACTTCAGGTCTGAATGATATATTTGATT
CATCCGCTTTAAAGTCTGCCATAATTTTCACCACTTTCTATTTAAAGTATTCTATAAAAATCAATAGCTT
TTAATTATAATTATATGTTGCAGTAAAAATTAACATTTTAAAAAATTATTTGTGAACAATATTATATAT
AAGTTTAGAAAAATTTTTTTCTGGGTTTATATAATTACTTAAATATCACTAAATTGTTTAAAATACTCGG
GTTGTAGTTCACATTGTTGACTAACCATTTAAATAATATAATTACATTTAGTGATATTATACATATCTTT
CATCATAACATTATTCTAAAAAATAATGTTATGATGAATATTGTTTTAATGAACATATACTTATTATAG
ATATATTAATGCAGAAAGAAGTGAATATTTTGAAACAATTTAAATGTCCATATGACAGAAAGATATTT
GTAAATAAAAAGGCATTATATGATTATATGGAAAAGAATTATTCAGATCAATTAAATGGACTATCTCC
GGCTAATGCTTATTTTAATATCAAGTATAACAAAACACATGGTAGATGTATTGTATGCGGTAAGAATA
CACCCATTTAACGAAACTACTGAAAAGTATGATCGTTTATGTTCAGATAAATGTAAAATTAAATATAGA
AAGCAGTTTGTAGAGAGAATGAAAAAAGTTCACGGAACAGATACTCTATTAAGAGATCCTGAAATGC
AGAAAAGAATGTTAGCTAATCGTAAAATTGCAGGAGTATATACGTGGTCTGATGGTAGTAAATTTAAA
TATGTGGGTAGTTATGAGAAAGATGCGTTAGAATATATGGATAAGATATTAGGGATTTCACTCTAAGGA
TATTATTGTTCCTTCTCCAATAATCTTTGATTATACGCTTGATGGTAAAAAACATTTCTATATACCAGAT
ATATTTATTGTTCCTTTCAACATRGTGGTAGAAGTAAAAGGTACTAACAATCATTACCAAACTAGGGAT
AGACGTACTGAAGATGCTAAGGATAAAGCGGTTCTTAAGACAAAGTATCGTTATGCAAAATTAGTTGA
CAAGAAATATGACAAGTTCAATGACATTATTGAGAATCTTAAAGAATCAAAGGACGATAAAGTCCGTT
AATATAAATAAAATTTTAAACCCTCATTTCAATAATATATTATAATTAAGATAATGTATATTATCATAT
TGAAATGAGGGGATTTTATTGGAAAATAAGAAACGTAAATTCTTGGCACTGTGTGGAATTAGTGGTTC
GGGTAAGAATTCTGTTGAATCTATACTTGATGGTTATTATGATAATGTTAATGGAGTGTTTTTAAAAA
ACTAAATCAAGTAACAACTAGGAATATTCGAAATACTGATGAATTTAATAGTGGAATATATAGTTTTA
TAACTATAGATATTTATAATCTAATAAAAGAAAATCTCATTGGAAAAACAGTTATCGATAATAAATAT
TATTATGGTACGCTTGATACTAGTACTACAGATGGTTGTATTAATACTATTATTGTCAATGCAAAAGGA
TTATCTAATCTTAAGAATGATCTTAATAATAAGTATGGTGAAGATAACTATGACCTATTTGTATTGCAG
ATTGCTAATAATACTCCTGTGGAAAGAAGAAATAGAGACGCAGAATTTATCAGAGGTGAATATAATG
ATTTAAAAGGATTGTCTAACGCAACTCTTATAAATAATCCTAGTAAATGGTTAACTGTCTCTGACGTAA
TTAACTGTCTTAAGAAAGAAGGTTTTTTGGATACATGACATTAGTTAGTCATACTAAGTTATATGAAAA
AACAAATTATCGTAATAAAAGAATTAGCTATATTAAAAATACGTTGATTACTGAGTTTGATATAAAAA
GTGCTGGTCTAAATATTCTATATGAAATGAAATATTTAGACCAAAATCAATATGAAAAATTATTATCA
ATGGAAAAGTATGAAAGAAACRTTACAATCGGAAAGATATTAAGGTCTAATAAAGAAATGAATGAAG
CATTATCATTTGGTTTTTCAGAAGCGAGAAGATTATTTTTCGAATTAAATCAAATTGATGATTCAGAAT
TATTATCTATTAAGAAGGATGCAATATTTCTTATAGGTAGAAATAATATAAATATTAACGGTAATGTTT
CTGAATTTATAAAATTTAGACCAAAGAAATCTTATACAACGTTTGTTGAAGTGTTAGACCGAGAACAC
TATTTGAACTTTGAAAGCGAAGAAATAATTTATGATATTAAAGGATACTCTAGTGATATTAAAGATAT
TCATAATGAATATTTATTAAAGGATCTTCTTAATGTAATGAAGTTTGATTATGTTAATGATAAAGATAG
AATATTTGAATATTTAGCAGTTCTTAAGGATGACCTAATTAAATATAGACTTCCAGTATCATACTATAA
TGATATTAAAGTAGGAAAATATATTGTAGAAATGGGTAACGCATTATTTGATCTAGATAATATTAATG
ATAATATTAAGCAATATTGCCTGTTGTCTAATAATCTTAGTTTTATTTTAAATCTAATCAATAAGACTCT
```

-continued

```
TTCATAAAAAAAAAATAAATAATATATTAAGGTAACGATCATTAATTTGATMGTTACCTCTTTTTTTTT
TTTTCTATGATCCATAATATACTATATATTTACAGATTTTATTTTCTTGTCAATCGTTAATGATACTTCA
GTCATGATAAGCATAATCTTGCTCATAACATATTCCTCAATATGTTCTTCTGAAATGATGGTAGAAACC
CTATATTTTAAGTCACTAGACATTCTTTCTACAACTTCATTAGTACATGATATAACAGATTCTTCAAATT
CATCTGTAGTTGTATCGATATCTATATCATCACTAAGTTCACTGTCATCTTCATCAATAGATGTTTCAGT
AGTCGCAGTATTTTCTACATATTCATTTCCTTCATTGTCATACTGAATATTCATACCATTAATTGCAGTA
ACTTCACTTAATCTAGGAAGTATTCTATCAATACTTTCAGCAATTAAATTATTCTTTACTATCCATATGC
TAATATCAATAAGAATATCTAATTCCTTTAGTGCTTTTTCACCATCAATATTATTATGCATCATTCTATT
ATTACGGTTAGATTTAATAATCAATCTTCCAATAATTATATGTGTAATAAAATATAATTATTAGTATTGA
AGGTACTGTAATGTAAAATAAATTTGTAGTCATCAAATAAACTTCCCCTATTCATTTATTATTTATATA
TAATTATTCATACTAAAAACTTGAATTTTATTTTCTTCTAAGAAAGATACAACTTCCTGAGAATTATCA
TATTCTTCTAAATAATATACTTTAGATATTCCTGAAGCAATAATCGTTTTGGCACAATTAAAGCATGGT
GAATGAGTAATAAACATTCGATGCGCCTTCTGTATTTCCAGAGTTTCTAGCCACCTTAGATATTGCGTT
TATTTCTGCATGTATTTCATATTTTAATGACCATTTATGATGAATTTCCATATCTTCACATAAATAAAAT
TTCTTTCCTTGACTTTCAATATAATAATCTTTGCGACAAATGAAATACGATTGTGAAGTATACCATAAT
CCTTCTTTCTTTATGAATATATCATTACAGTTAGCGTATCCACTAGGGGTTCCATTAATTCCTGAAGATA
TAATGGAGTTATTCTTAACAATAATGCAGGAGACTTTCTTTGCAGAGCATTTACTTATTTCTGACATTC
TTATTGCAATATTCATAAAGTTTTACTTCGTTTGTCGTAAATAGTCATCCATATTATTATCTTCATTATCT
ATAAATATATCTACCAAGATATGGCCACTGATCTTATTCTAATTATAATAAATTATTTGAAATGATGCA
TTGTTTAAATACTTTTAATTTTCCGAATGTTAATGTTAATATCAACACGATTTATAAAATTGTCAATTTC
TGTATCTGTATTAGAGAACATATTTTCAAAGATATCAAACTTTATAATTCGATAAAAGCTATCTTGACT
TATATAATGTGCAATATTATTAACAATATTATCATTATCTGTAAGATAAAGATACTTCACAACAAGACT
AAGCGTTGTTAATATTAGTCTGTATATTTCTTTTATACGATAATCGTTTATATTTTTATCTATAATTAAC
GTATCATATGATTCTGTCTGGAAGTTAAATTTATATGTTTCTTGAGAATTTACTTTCTTCATCAAACTAA
TTATAGATACTGCGTTTGATGGCATTTTTTTCACTTTTGGAAATATCAATTCTTTATTATTTATTCTTCTT
TTTGTATCTTTTATTAATTCATCAATAAATTTTGAAAATTCGGCATTATATAACTCATCATTACTTAGAT
CCATATTTTTTTGTAGTTCAATATACATTTTAAATTCTAGTTCCAATCTATTTAATATATGAACTTCATG
CTTTGATAATAAGTTAATATATAATACGTTTATTGTAGGAAATTTAATATTGGATTTATCATCAGTATC
TATATCAGTGGATTCTATATAGTATGATGAGGGTGAAATATAATTTTTATATTTATACATATGCGTATA
TGAGTAAATAACTAATTCATTAGTATACGTAAAATTCATTAAATTATCATTATCATAATTATCCACTTC
AATATAGTTGTTTATTATTGCATCTTTTCGACTGATTAACGATCTTTCTTTATTATATTTGTGCATTATA
AAAGAGATATATCTATTATTATTTATATAATTAGATGAATCGATAAACATGTCATATTCTTGTAATTCT
TCAAAACATAGTTCTAAAATATTTGCAAGCAATATTTGAATTATATTTCTATTATCTTTTATTTTATTAT
AACCATAATAATTTTTGTGACTTATCATAGGAATATCTGAAAATATGATGTAATTTTCAGAAGTAAGA
AAAAAATTAGAATTATTTAAATCATTGAAGATACCAGTAATTTTACTGATATCTTCAAGACTTATATTT
TTAAATTTTTCATAGTTCCATAAATTTCTCACTTTAATATTATGGTTAGCATCAGTATAGAAATATTTAG
TATCAATATTCATTAACTAATCACTATCCTTATATAATATTTTAGTATCGATATTTACTTTTGTTTTTAA
AGTTAACGTCTCTTACTGTTCCTGGAGGATTATTGATTGATAATCCTGCATTATTATTACTTTCTGTAAG
AAGCCAGATAGTATATCCTTTAGGTTTCTTACAATCAAGCGTATTCTCACCAAAACCATCCGTAATAAT
AATATTAATATCTGATCGAATATTTTCATTAATATATTTAATTGGAGCAGTCAATGTAGTTCCACCATA
AGCAGTTCTTTCAAATTTACGTAATCTATCTTTCTTAGATAACGGATATACATCATGAACCATTGTATC
AAAGTGAATTACATATAGTTTACTTTTAATATTTGAAATAATCTGACGAATTTGATCAAAAGCCAAAG
CCACTTCTTCGTCACTCATTGATCCTGACATGGTCGATAGCTACGGTAATTTTAGATTCACATTCGACA
TTCTTCCTAATAAGTCACCACGATCTGGCATTCTTCTATTCTACGCAGATTAGTTCTTTTATAAGGAAC
TTTTAAAGAACCAATCTTCGTACGTAAGATTTGTTGCCAAGGAATAACTTTTTCCTTATTAATATTTTCT
AGAAATTTATTAATAGAAACAGGAACTGATCCGGCTAAAGATAGTCGTTCAATAGTATTTTCGATATT
TTGTTTTATTGAACGTTGAATGTCTTCTTCAGAATAATCGCCGTTTTCCATTTTGAGTGAGAAGAATTA
GCACTATTATTCATGTTAATGCGTATCTTTCTTACCTTCTGAATCTAATTCATTACCTAGATCATTTTCA
TCTTTTCCGTATTCATGAGATTTGCCAGTATTACCATTAGAAGAACCTTCTTCTTCATTTTCGCTGTCAT
TATCTCCACCATTATCAGTATCAGATGAATCATCATCATTATTCCCACTTTGATTACTTGGCATTCCATT
ATTATTTTGACCGCTTTTATTATTTTCATTAGCTTCTAATAATGCATCCATATAGTATTCAAAAGATTTA
TCTTTTTCCAAATCCTTATTATTAGTTAACATTCTTACATAATCTAGTGTAATAGAACCTTCTGGAATAT
CATCAATATATTGATTAATAGAACAATCCATAGCAATATTTGCCATATGCATGAAGTCTTGATTTTTAC
TAATCGACTTATTCTTCAATATCGGAAAATATGATTATTTGAAATATGAAGTAATTCATGAGTAATAAC
TGCAATGAATTCTCGATCATTAAACATTAAAATTTTATATGGATTTAGATATAATGTAAATGTATCTTT
AAATGTATTTTCAGCATAGCTAACTGCTGCCGGAGCAAAGTTCGGATCATGAACAACTTCTTTAATCAT
ATTAATTGTAAATAGAGCAAAGAATTTGTCATCATTAATGTTATCACTAATTAAATTAGTGAATGTTAA
CTTAATATATGCTTCAAATGCTTTTTCTAACTTTTTTGAAGCTTCAAGAGGTAAAAGCTTCTCCTTACCA
TAATATTCAAGAAGAAACTTTTTTAATTCTTTTCTAGTCATAATTAGAATTATAATTATCTAAAGTA
GGCATTAATATCCTCCACCGATCTAATTATTTTAAACGGTTTACTAATTTTTTGATTGATTGCGATATAT
TCATCATATTGATAAACTCTGTTATAGAAATCATCTGCAGTATTATTTACGAGTCTAATTAACATTGCA
AAAGTACTCATGATAACTTCTTCTTCTCCCAAAGTATCTACAAATTTAATATAGTTCGCAGTCATTCTA
TCTAAATCTTTTTTATTTTTTACTCGTTTACTATCGTTACCCATTTCACGAACAACATAATTAATTACAT
AACGACTAAGTAGTGTTTTACGTAAGTTTGTTTCCTCTTTAATTTGGGTCAATAGTTTTTCATCTTTAGA
TAAGTTTGGGTTATCGATAATCAATTCAGCTCGGATCATAGGGTTTGTTTTGTCTTTTAGGAAATTAAA
GAATAATGAAGTAGCTTTCGAACCTAGATTACCTTCAAACACTGCACGTAGTTTATGACTAATAGATA
CTGTATCTTCTGGGAATTGTTTCATATGTTCATAATACGCATCAGAACTACGTTTCCATGAACGTGGAG
TAGGTGACTTACCTAATGCTTGAATTTTCTACAAATGACAGCAACTCAGGATTTGTTGCAATAAATTCA
GAAATATCTTCATGAATGTTTGGTCGAATATATAGTGGAGTAGAAGTATTTGCATCTACATATTCAAAT
TCTTGAATAGCCCAATCTAACCATTCTTCTGGATCTGGATCTAGTCTAAGATCTGTAAATAGGTTATGT
AGGGCATAGTTCATTGTGTTTACTTGATAATCAATACCGTCACTGTTTTCATCTGTAGGATTTCCTGCA
GTAATAATATATAATTCTTCTGGAAGAGAGTATTGATGAATTCTCCGATCAAGAATAATATTCATTAAC
TCTTGTTGAACAGCTAAATCTGAACGGTTAAGTTCATCGATAAAGTAATGGAATTTTTCCATTATCT
GCAATCTTATATAGTTTACCAATTGTACTATGAATAGTATATTCATTTTCTTTAGGTTGTTCTTCATTTTT
AAACCATGTTTTGATATTTGTAAGTTTAAATTTATTTTTAGGTTCTGCAATATGAGGGATACTGTTAATT
TCTCCTTCTTTAAGTAAGTTACCATCAAGCTTAACAAACTCAATTAAGTCACCCATTTCTTTCATTATAAC
GTTCAACAAATAATTAAGCCAAACTAGATTTTACGATCCCTGCATGACCTTCAATAAATGGTACGCTTC
CTGAAGCTACCACTACGCCTACTACATCTAACAAGTCTGACATTTTCATAAATAAATTCCACCAATCTA
TATTTTTTATTTTATTACTAATTTATAATATATATTTATAAATTATTTATAATTGTGTATATCACGCTACT
```

```
AATTTTGGTTAATGTTTCTTCAAGGTTTAAAAATGAAGAACTTTCTTATCATCATTTTTATACTTCTAAT
GCAAGATTGTCAAATCTATGATTATATTCAATAAAGTGAGGAAGTAATTCTTCTGGAATATATCGATTT
CTTTTTGATGTACCTTTTTTAAATGAATTAGTAGTATGTCCTTTAACCCACGTAAAATTAAATTCATATT
GAGAAGAACTATTATTAATAATATTTACTAATAACTTCCACATCTCAGCATTCTTTACTGGTGTTCCTG
AACTACTCATCCAGTTTCGATTAATCCATCCAGTCATATATTCTGTAATACCTCTGATAACGTATTGAC
TATCTGAAACAACACTAATATTAAACTTTTCTTTATTACCATTCTTATAATTATCTCTCATAATATGCGC
TATTCCATAAATAACGGCTAATAATTCATTTTGGTTAATTGTTGAATCATGAAAAGATCTTTTAATACT
GTATAGCGTATTAAATTCGGTGTCAGTAATATAGCATCCAAATCCTCCATACATAGGCTTACTGGGGTC
TTTCCTACCATTATTAAAGCTACTTGCATCCGTAAATAAATATATGTAATTTGTATTATCGTTGTCCAAT
ATATTTTCACTCCCACGTTTAGTTATTTCTTTTCGCCTATATTCTATTATTGTAATTCTAGAATAAAAAA
TTAATTATAATAAACAATATAATATAAGCACTTCTATAAGAAAGGTCTGATATTTATGAAAGTTCCAA
ATAAGAATATAATAAATGATATTATAGATAAGGAACTAGAAGAAAATAAAACATTTGTAGTAGATAC
TAATGAATTTGATACTGAGAATATGATCAATAGTGTTGTTCCTAGTGAAGAAAAATTTAATAAAGCTA
TTGAAAAAATTATTCGTAAGTCTAATGAATATCGTAGATATATCGGAATACTGAAAAATAATATTGAT
CTAACTTCTTGTAAATTTTTGAAACGTGTTGATGTTTCTGAAATAAGAAGAGTTAATATTGAAATGCAT
CATTACCCATTTACTCTCTATGACATCGTATCTATGCATCGAGAACGTATCAAGCAAGATTTAGGTGAA
TTTTATTCATATGATACATTCACAATTGCAGAAAATATTATGAAAATGCACTATGAGAATAAAATCGG
TATTGTACCTTTATCATATACTGCTCATGAATTAGCTCATTCCGGAAAACTAGTTATTCCTCTTAATAAA
GATTATGTCTTTGGTAACTGGCAAGAATTAGAAAAAGAAGATATTATTATTACAGATAGTATGCGAAA
GCAACTAGAAGTATTAGAACAAATGACAAATAGTATTGAGTCTGGAAGCCTTAACTCAAACGAAGAT
CTATTTAGTAATATTCAGACTGTAATCAATATGAAAAGTTCTGGAATACCAAATAAGATTATAAAGGA
AAAATCAATCATTGAGGATATTAATAATCCTGAAACTGATGAAGATATAATATAATAAAAATCCCTTA
ACGTATAATAATACTATACGTTAAGGGATATAATGTTATATTATGATTTTTTGCCATTAACTTGATCTA
ATAACTTATATATGAATAATTCTTTATATACTTTCTGATCTCTATTATATTTATCAATAGTTGCTTTTTCA
TCATCAGAAATAACTTCTGTACTAAAGTCTTTAACTTTAATAACCATATCTAACTCTGTGTTTAAAGAT
TCTGATTTTAATACGATATGGAATAAATTTATGAATTTAGTATTTTCACCTTCAATAAATTCATAATTAT
CTAATAAAGAAATTTTCTTATCAACATCAGAAGAACTAAATATTTTTCCAAAGAAATCATCAATATATT
GATTAATTGATAGTTTAATAATTTCTTCTTCACTATAATTTTTATTAGTTGGAATATCCTGAGTGTACCA
AATTTTTTGAATTTTATCATGGAGCAATACATTAAATACGCCCGGAGAATTTACCATAATATTGCTAAC
AACAAAGCTAATACTAAACGTATATACCTTTGGCTTAGTTTCTAATTTATCATCTGAGTTACATGATCC
TTCTGATGAAGTAAAGTTATAAAATGTATTAAATTCTTTTACAAACTGAGCATATAATCTTTCAATAAA
ATTATCTTCAAAAGGTCCAAAATCTGTACTTAATGGAAGTTCAAGGTCTCCACTCTCCATTAAATTAAT
TGCTTCTTGAATTGATTCAATTAATATATCAATCTTACTATTTACTTCATTATCAATACGATCAGTTACA
CCTTTCGGACCCATAGATATTTAACGTCATATATTCATTATTGTTATCATTCTTATTAAGTACGTCATATG
TTACACTAGTAATAACTTCACAATTACGTGAAAAATCCAATTCTTTATCAGTGATATCATCTAAATCTT
TGATATCACCAATAATTCTTAAACTAATAGCATCCTCAATATTAGGCATCCTAATTCCACATCCATTTC
TTTTTATTTGATAATAATTTATTAATAAATAAATATAATTTTTTACATTCATTTACAAGATTATACATTC
CCTATAACTATGATATATTCAATAGTTATAGGGAATGTATTTATAATTAATTAGTGCATTGTATTAATA
TATTGTATATACGATGAAGCGTTATCCTTTATTACATTATCATGTTGTCTTATTTCATATTTCGTTAACA
TGATATTAATGAAGATATAAGTTATAATAAAGAATATATAACTAAGTATTAATAGTTTTAATAATAGTT
TATTTTTAGTTCGATTATCTTGGTTTTCATCAGTATCTATATTTTTTCTTAAATTCTTCATTAAAAAGTCC
CCCTTTTATTCTATATATTATATTGTTTTTTAATAAAAGCGTAATAAACGAATATATAGACATATATTAT
AATTATGATAAAATAATAAATAATATAAAGAAAAGGATGATATTATAATGAAAAAATTTGTACAAGT
ATTATTAGTAGGAGTTCTATTAGCAGTAGCAGTAACAATTGTAACTATTAACGTTACAGAAAGTAATA
ACGGTACAATGCAAAAAGAATTATTACCAAAAGTAATTTTAAATAGACAATAGTATAATTACTACTAT
TGTCTATTTTTTTTTTTAGTTGATTAAGAATATTTTATCATAATCTAGATTATCGTTGAATTCTAAAAAG
AAGTCCCCAACATTACTTACTGTACATTTTCTAATAGAAGATACTCCTTCATCTATTGGTGGTAGTCTTAT
TTACTTCTAGCTCCATACTATTATCACTATAAACTCAGGATAGATATTTTCCAAGAATAGATAACTTCT
ACATTTTCTTCATTTAATACTTTTTGTATCATGTATAAGTGATATATATTGTCATCATCCCTCTTCATATC
GTTTGGGAAGATGTATCCAATAGTTTTATCATTCTTATCAAAATAAAAATTTTCCACAATAAATTCTTT
GACAAGATTAGTATTCAGTAATTCAATAGCGTTATTTAAGAAATCTTGTCTAAATAAACCTAAATTATG
AATATTGATTTCTAGCATATTATAATCCACACCTTTTTCTTTTTTCTTTTAAGATATTAATTCATTATTAA
GATAAATGTTTACACTAAAGTCATCTTTAGAAGTATTATTTATTTCTAACGTAATAATGTAATCATTGT
TAGCACTATAAAAGATGTATTCTTTTATATACCTAAAATTATGTTGTTTATCAATAAATGAATCAATCG
TGTTTGATGTAATATCCCCCTTATAATCTTTGATATAATTCTTATCAAATATATTTTTTGCTTTATATAT
CTTTTCTTTAATATATTCAAAAGATTCTTTGTTATCTGCAGTAATTGTAACTTGATTATTTAGAAATTTG
TTATAATCAATATTAAGTATATTTACTTCATTATGATTATAACAAACGTTCCATGCAGTAAATATTTCTT
TTGAAATAAACTCAAAAATATTATTATCCCCACTGTTATTCATAATAAATTTCCCCCGATATATTTATTT
GATATAGTAAGTTTTATTCTAATATTTATTTAAGTTTATAATGATATATTATAGATATGGCAAATATAT
AATATATATTTTAATTTTTCATTAACAATATTTTAAGGAATAAGGAGTGCTGATTAATGTATAGATATA
TACGTACAAACGGTTCTATGCGAAATAAATTGAAAGAAATGAATATTGATAAGAATGACAGTATCTTT
GAAAATACTGTTAAGATTATTAATGAATTAATAAATCATTTCTATTCAATAAGTGAAGTATTTAACTTC
ATAGAAAAAGAAAATATTCATATCAATAATGAAGTGATGCAATATTTAAGTTCTGATGAATTTTATAA
ATCTGCATATACTTCGAAAATAATGATGAAGAATCATATGTCTAAACATTCATTTATTCGCATGATAAA
AAATGAATTGTGTTATCGTAATATTAGTTTTATTTTTAATGATTCATTATTTACTAATGATGATATTGCC
ACGATAATAGTTAGGAATGATCTAGCTGAAATACCATTTGATATTATGGTTAAGGAAAATCCATTAAG
CTTGAAAGATTTTAAGAAGACTTTAAGATATAATAATTTAAATGATCATGAAAAATCTATTTTAGAATT
ACGTAATATTTAAATTTATTAAGAAAAAAAAAAGATAACTATTGTAATTTTAATAGTTATCTTTTTTTC
GGATCATAGAAATATTTTATATATTATATAGGATAATCATATTATATATCTTTAATGATGATAATCTGT
TGGCTAATTCTGGACTTCTTTTCTCTAATGAATAGATATCGATAGCTTCAATAAGATTAATTACTTTAAT
AAATCCTAGATTTCGATATCTTTTATTTATTAAAACAAAATTAAGTAATTCTATGAATTGTATTAATCTT
TCAGCATGATACAACGATTTTATTTTATATTTTTCTTCAACATCAGCGAGATCTAATCCATATTCTTTGT
AGTAATTTTCTTTAATAGCGGCTTCATCCTACGTATCATGATACTAATATATCTATTAAGTTCATTATA
GGTAGTTTTAGTATTCTTATACACTGCCATTTTATGAGTTTTAAAGTAGTTATATAAGTAATCTATTATA
TCATTAAAGAAATATTCGTTTGCATAAATAATCTTTATAAAACTAGACTTTGGCATAATAATATCTAAT
ATTTTAGGGTTAATCGTAATCCGAGTATTTTCAACCCTTGATAAGAATTTAATATATGTTTCAGTTATA
AATTTATATACAACTTCTGATTCAATATTAAACTTTTCACAAAAATTACATATGACATCATTGATATCA
TACTTATTATCACAACAGAAGACGTAAGACGAAATTGTATACAATAATATATATTCAGTATTATTATTA
TTACTATGACTAATATTATCATATAAATCACTTATCATGATCATCATATTTTCAGGTTTAATATCATATA
```

```
AATAGAATATATTTTGATAGTATGATAATATTTGTTGACTTTTACGTTTATTATTCTTTAATAAGTACGT
AATAATATTCATAGGTAATAATGTAACCGATTCCGTATCTTTTTTATCTAATGCCCTATTATTACCTAAG
TATGATAAGATATCGATAATATCACCAAAGTTAGAAATATCATTGTATATATCTAGTATACTTTCAATG
TTTTCATTTAATGACATTGGTTGTAATTTATATTTATACGTTATCATAATTTGTCACCTGTATTCTTTTCA
ATGATATTTCTAATTTTATTATTAGTATATTCATCATTTGAGTAAATTCTAGGTAATATCTTTGGTTTAT
TCTTATTAGAAGGAAGATTATCAATTATTGAAAAAATTGATATTACTTTTATTAATAATATTTATAATAT
TGGTATTTTTAGATTTCAATAACTTATTAATGTCATATGATAATAATTCATTATCACTATCAAACTTCTT
ATAGAATGTAAAACCGTACATATTAATATTATTTTCTAGTAATATTAACGTATCCATAATATTATTATA
TCTTACGTCATCCAATTTATCTGAATACTCCGTTCTCATAACAAAGCTTATTACTTTAACAATAAAATC
AACTACGTTATATTTATTTTTATATCTACGATATATTCTAGGATAATTGAATATAGAATTGATAAAAGT
TGTATCTTTATACGTTATATAGGATACTGATATAGAAGGGTCTCCGGTATCAATAATTCTAGTAATATT
TTCATATTCATCATCAATTATATTATCATTGTTAAGATATTTTAACAATATATATTCAATATATAGTAAA
TTCATATTTAAAAAAGGATCTAATATACATTGAATTTCATTAAAATTTTAATATTTATATCATATCCCT
CATACATTATAATATTTTCGATAAACCTTGATTTTTCAGTGCGAGAATAATCTTTAATTTTACAAATATT
ATTTTTTGTTAAGAGACATTTATACTTCATTGTATTGTTATTAATAACCATATCCCTAAAAATTTCTTTT
GTATCTTTTGTAGGTTGATCTACATATTTAGAAAATTTACGATTAAAATCAATTGTATCCCTTAATGATT
TTGGATTATAGGTTCGTGAATTAATTTCTAAATATTCTTGAATGTCTGTATTAATTGATATACTATTTGT
CACGCTATATCACGTCCTATCATTTATTATATGCTTAACAAATTAATTCGGCTTTTCATTAACTTACATA
ATTCATCTATTCGTTTAATATTATTAAGAGTGTTCTTTCTTATTAATGAATTATGATTATCCGCACTAAC
ATTATCTTCATATCTTCTAAATAATTCATAATTATTATTAGTATAATCTATAGAATCCAAAATTTTAATA
CGTGCATTATTTTTTACGCTAGTCATTTTATTATTATTAAAATTAATATATAAGTTTAATAATTCAAAAA
TAATGGATATTCTATCAATACTGCTTTCAAATAATATTAGATCATCTTTATTGTTAAAATTAAGATATCT
AGATATTCTTAATGCACTATGAGGGTCTATTCCGATAATACTGTTAATTGCTTTTTTACTATTAAGTATT
ATATCTTTCTGATTATCTGTAAAAAATTTAGAATAACCACTACCATATATTGTATTGAATATTTTAGCC
ATTGATGATTTACTAATAAATTTTTTAAAATGTTTATCATCAATATCTCTAACGCCATATATCGCACAG
AATAGATTGGTTGAATATAGATTCATTTTGTCAATCATAGTTAAATATTCATTATCTGTAATTGTAGAA
GATTCTGAAATGCATGTTTTAAACTTTTCAGATATCCTATTTCTTATACCGAAGTCAGGATCATCGTCA
TTGGATATATTGTTATATGTGTCAAATAGTCTAAAAATAATTTTTCTAATGTATGAAGAGTTTATTTGT
AAATTACTACTAGTATACTTATACTTCTTACTAGATGGTGATATAATAAAGTCAATTAAATCGTCAAAC
AGTACACTATACATGGAATTATTATTGATAAATGAATCATATAATTTGTCAATATTCTTCTTAGTAATT
ATATAATTACTATAATTCATACTTCTTTTCGTATATATATGATTAATATTAACATATTGAGTATTATCCA
TAAAAGTACTAAACAGTTTATTGTATATTACGCTTGACCTAATACTATATTTAAACATAATGTAATCCT
TTCTTAAATATTAATGTCCTTAATATAATGACGTAATAATTCCTCGGATATTCCTAGTTCCTTAGACATT
ACTTCAATAGGTTTGTTAAGATTCTTTTCAATATAGTCTGTTATATATTGTTCTGAACTACGTGAATTAC
CTACCTTAATATCAGTAGTACTTAATGGCATTTTAAACCCAATAGTTCTTGGGTTAGTAATTTTTTCATA
TTCGGGAACTGGATCATTCTTAATAATATGGTCTGGTAGTTTCATATTATGTTTTTCTAGGCTACAATTA
TCCAATCTTTTAAGTTTATCTAATGATTCATTAGTAATGATAATCATTAGATCGTTTCTACTTAGGTCTA
CTGACATTTCTTTCACATTTTCATCATAAAGTAGTGTAGACATATGACTAATAATATCATGTGAATTTT
CCAATGTAATATTTTGATCCATATATTTTCTAATATATTCGACTAATTTTTTCTGCATATTCCGATTCCA
CCAATCTATATTATTTATTAGAGATTATACGTATATCCATTCAATTGTTAGGTTGTTTAGAATTACCTTC
ATTTAGTTTTATATTTAATACATATTGAATATTGTTTCCTTTATTAAATTTAATGTAATACTTAGTCATA
TCACCAGTAGTATTATTAATAAGTCTAATTGAATAGGATTTCTTACTATGTTTATTAATATGAGTATAT
AGATTATCTTCATCCTCTATAATGATATTCTTTTCTGTAAAGTAATCTAATATAGATTCTATTCGTTTTA
ATTTATTCATCCTTATCGATAATAATATCGATAAGGATGAGAATAATATAGTTAACATGATAAATATA
ATCATATATCCATCGTTCCTTCCATATCTATTTTATGGACATTCATTAAAGTAATATCATACTTTTTAAC
TTCAATATCAATTGCAGTATAGTTTACCATAAATGTATATCGATTCTTTCCAATTTTACTAAGACTATTA
TATATCTGGATTGAATATTCACGGATATTTGGAGAAGTTATTATATTCGTATTCATTTTATTATCATATT
CAGTTAATTTATCAATAATTGAGTATGATAACATGATTTTTTTATGTACAATAGATCTGTACACTATTG
AGACTATAAAGATTATAATCATAATCGATAATAATAATATCATTTAAACATCCTTTCTTATATAGATTT
ATTTAATTTTTTGATTACTGATATACACAACTTCTTTAAAGTCTTCATCATATACTAATTCAAATTTATC
GTTATTGTAGAAAAAAGTGTATGTATTATGAGTCCTATTTAAAGATCTTTCACAGTGTATAACAGATC
TTTAAATACATTTTCCGGATTTACATAAGGATTCCTCCATAACATTTTCATATCCAGAAAGAATTAAATA
ATTTCTAATGTCTGGATAGACTTTTTCCTTAAGAAACTTTGGATCCATTCTTTTTCTAAATTCAGCCCCA
AGAATATAATCATTTATAGAATCCATTATCTTATCAATAATTAAAAATCCGATTAACACTAAAAGTAAT
ACTCCTACAATATTAAATAATAACATAAATTTATCACTATCCTTTTCTTTTTATATATATATAAAAATCG
ATATCACTCCATTATAGTAACAATTATTGGAGTGATATCGATTTAATTTTAAGTTATATACTAAGAATT
ATTTCGTGAGATAAATATTCTTAGTATAATGAAATAAACATGCTTTAGACTAATAATAAGATAAATTG
TCAAGGGGAATTTGATCTTTATACATTATTTTCATTTAATAACAAGTTTATTTATAATTCTAATTATTAT
ATCAGAATTATAATATATTATTAAAATGTAACTATAAATTTTTATAAATTACATTGATAATCATATCT
ACATTAATATTTTTCTGTTGAATCATTAGATTAGAATTCTTTAATGTATTATTAATTTTATTAATATTTA
GGTTATCCGACTCAATATATTTGTTGATAAATACATCAATGTATGCTTTTGGATTATTCATTGAATTAAT
AATCGTATCTTCCATATTATCAATAGGTTTAGGAGATATGACCATATTGATAATAGATGACATTTCATT
AGTCATTCCCGCTTCAATAGTAATCTTATCAAATATATTTTTTTCATCTTTCCATAAGGTATTATCAATA
TTCATTTTATTAATATTGAATTCTTCTAAAATGAAACAATTGTTTTCTAATACATCTTTTATTTCATGAG
TTAGAGTGATAACGTTTCTTAACCAAAAGGAACACTGTTTATTAAGTTCTTCTAGAATTACATTCTTTT
GAGATATATTTTCCCTTAATTCATCAATATCCTTGGTGTAGTTATCATATCTATTTTTATATAAATTATA
TTCATCCATATTGGATTCTTCTAATTTTATATCCATAATTTCAGAAACAGCATTTTTTGCATCTATAAAT
TTAGATATCAATTTTTCAGATCGATTAATAGTGAAACCATTAATTCTTTTGCCTTACTATTAATAC
ATAAATATGTATCATATAGGAAATTAATAGTTTTTTGTCTATTTTCCCTTAGCGTATTAAGATCTTTGTT
ATTCAATGATTTTCTAAATTTAACTGCTAATTCATAATCATTATCGATATTTGTACCTTCAGTGCTGATG
ATATTATAATAAGTAGTAGTATTCTTTTTTAAAGGTTTATTGATAATATTTAACTGAAATGTTCTAATTT
CCTTCATACTTACTCCCACCACCATTATTATCTAAATATTTATCATACTAATAATATTATCTAATTTTTC
ACTTTTAACAATATTTTCATTTAATACTAAAACATCATTTATATATGGAAACATTCTGTAATGTGTTTA
ATTATAAATTCTGACGTAATAGATCTTTGATTCATTAGTACTTCTTTATGATTTAATTTATACCAGTATA
TTTCAATAAAGTCAATTGACAACTTTTGTCTTCTTGATATAATATCCCAACAATCATCATCAATATATA
CTGATATAAGTTCATATAGCGTTTTTTCATCAAGATTAGCATAATAGATATTCTTCTTCATATATTGGG
AAAACTTTATTAAGAATTCCTTACTATAGTTACAATGCATAACAATATGACTATCCCAAGGAATAAAA
TCTATATTTTGAGAGTATTCTTCAATTGTCATGTGTTTGTATATACTATGATCAATATATTCCCAAAATA
TTTTAGTTTGGTTTTTTAGTAATAAATTTCATATACATTTTATTATATTTCACCCGATAACTAAATCTAAA
```

-continued

```
CCATTCAGGATCATTTATATCTTCTTTTTTAGTCATATCAAGATTAAATAAGACCCCAATAAATAATCT
TAGTTGATTTATAAATCGACCTTTATACGTGTCCATTATATTCAAGTTATTCTTTTCCTTTCTTAATATA
ATTATATTCCATTTATATATTAACTATTTATTTTATACATATTAAAACCCAATAGATATATAGTAAATAT
CTATTGGGTTAGTGTTTTATTCAGAGATCTTAACTGTACATACTAATGGATTATGCTGTAATTCACTAA
CTAATTTAGGAATAGTTGTAAGTTTATATCTAATAGATGGATTTTGTTTTTCTTCTTCCAATATACTAAT
CGATTCATGAATTCGAATAATTTCTTCACGACTAATTGGTTTAACAAATATTGCAGGCTTACCAGTATT
AATATTGATTCCCTCAATAATATTCATTTCATCATGACTTGATAAGTAACCCACAATAATCTTAATATT
TTTTAAATCTTTATACGTTAATCTTGTTTCTAATAATGAATCATCTTTCATTACGCATAAACTTCCCTTC
CAGTTTAAGTTTTATTTTATATAATTATTAGTTAAACTAGTATATAAAAAATTAAACTGAATTATAGAA
TAATTTATTTAAAAGAATATAACGTACCTTTCATATCATTATAATAACTATATTTAATCGATTTAAATTT
ATCCATACTATTGAAGAAGATAAATTCCGGAGTATCTTTCTTAGGAGGATAGTTTACAATATCAATAAT
ATGAGCGATAACTTGCATATCCATATCGGTATATTTAATATTAGATAGTTTTGTTTTTGATCGATTTACT
GTAGTTTTTCTAGTCCTTTTATCAATGTAAATAGTAATTTCTTCGGGATTTTCAGTAAGTTCTTCATGAA
TTATATTGAGAAAATTTACCGCTTGAAGATACGGTACTAGCGATATTTCCATTGTACTATTAAAGTTTT
CTTCATTACTTTTAGAGTTGATCATATTTTTAATATTTTTTAGTTTACCTATTGTTTTTAACATTATAATT
TCCACCTTTAATTATTTATTTGTTGTTATCATATTAATAAAAAATGTATAGTCGATAAAATTAGACCCA
TTGTCTCTAATAATTTTTACATCATCTTTAAAATTAACATATTCTTTAATAAAATCGAGATTATGGGTTT
TTCCTTTAATCGATTTTGAGTCAATATCGTTAATTGCAAGATTTCTTTATAACGTATGGACTATCTTTAGA
ATCATAATACAAGTTATGGATTCTAAGAATAAATATACTATTATATAAATTTTCTTTTAAGAAAGATAA
ACTTTCAGTGAATCCTAATTCATGAGTCTTATCATTATATCCAGTAATATGACCAGTGCTGACATGTCC
ATTACTATGGATAATTTCAACTTTATTATTAATTAATGATTCAATATTCGTTTCGTTTGTATACTTATCA
AAAATAGTATGATTAGACGCATTATAAATATTAATATTCATATCGTCAATTGTATAAATATATTTT
TTTGAGATAAGTTTATCGAGAATTAATTTTAATGTATTTTTTCTTAATTTAAATAAACGCTCTTTTAGAT
AACATACTTTATCAATATCCGGATACTTTTCTTTTAGTGAATAATCTTTATTGATAGTATTAACGTCAAT
ATATGATATGTATTCAATATAATGAAGATTAATAAATATCATTATCATTAAATGATGTTAATTTCTTTTTA
ATTGTAGTGATATTCATTACTTCATAGTAAATATCATTATTAATCTTTTCTTTTAAACTAATAATCAATA
TTTCCTCAGACTTATCATTTGTAAATAAGAAACCTAAATTGCTCATAGCACTTTCAATAAAAGAAATAT
TATTATCCATTTAGATTTACACCCTTTCTAATCTATATATTCATTATAGTTAATGCATCTTTAAATTTTTG
ATCTTCATTCATATATTTAATTAAGTATGGATGTTCTTTAAATTCATTATCATACTTAGTTAATTTATTA
TAGTATCTAATAATAAATTTTTTTGGTAAGTTTTCTTGACTTCTCGATATTTTGAACCATAAATTAGCAT
TATCTAAGGGTACAGTGCTTAGTATATATTCAATTGATACTATTGGTAATTGGTATCTTGAAATAGTCA
TTATAATTGTGTGCAAGTCAAAATATTCTATATATTTTAGTATTACGCTTAATTCTAATTTATGGTTTGA
AACGATAATATAATTCCAGAATAATTTTGGAGCATATTTATCAAGAGAAATAATATTATCTATTGTTAC
ATCATACTCAATATCGTATTGAGAGAATATTAATTCTGCAGTTATATTTTCCCAAATTTTAGTATTAAT
ATCTATACTGTCTGCATACTTAATAAATAGATTAATATCGTACAGTAATAGTTTATAATTATATCCTAT
GGAAAAATCTATATTGTCAAGAATATTAGGATTATTTCTCGATATATCTAATATTCTATTGCATATTTC
AGGAATATTGTGATCATATTTATATGAGTTAAATTGAGATTCAATAAAAGAAGGGTAGTAATTTTCTTC
ACCAGTATCATACTTTTTATCAATATCTATAACTAATTTAATTATATCGATTTTTTCATTCTTTTTAGAA
ATAATAATTTTTCTTATATCTTCGTTACTAATAGGCTCGGTATCAGTTCTAGCACATAATAATTCTAACAAT
CCTTTCTATTATTAAAAAATAAAATCTGAGCTATAATTGATCATATAGTCTCAGAAATATTTTATATT
AATCTTCTAAATTATTATTTAATATATTCATAGACATATTAAAAATACTTCTTGAACGTTTACCGATAC
GATTTATTGTTTTTTCAGATATATTTAAATAATCTTTAAATTTTATCGGAAAATACTTGAGGTACATAG
AAATTTGTTCTGGATTATCAATAATATTGTTATCAATGATAGTTCGAACAACAGTATAAATTTGACCAT
TAAGTAATTCGTCAATAGTTGTTTGGATCGTATGCTTGAATAATTCATCCTTTCTTAAATGTTGATGATC
TTTATACTCCATTTTCATTCTAACTTTAATATAAGGATCGTTATAATCTTGATGATCATTAACTAGAGAT
TCAGGATGAAATATTTCATTAAATAATTTAATATCGTCATTTTTTTCCATATTTTATAATAATATTTGTAA
TTAATAATCTCGAAATTTCACCAATTTCATTATAAGGAATTTCTGATTCTTCAAATTTTAATGTATAATT
AATTTCTTTTAAATACTCATTATAGTATCGGTATTTATAATTAGATGTTAATGCAAGAGAAGTTACAAA
GTTAAGATTATTTTGATAACTTCCTACTAATCTAACTTCATTATAAAATACATTATCCTTTATAAGTTGA
TTAATGATTTTATAATATCTTTGCATTAATACATTAAACTTATCGGTACTACAATTTTTTGGTTTAGTAA
TTGATTTAATTAATGATTGTTGGGTATTAATTAAATTTTCCATTTCGCTAAAGTCTGAAAGAACAAACT
TGTCAGGATCAATATTCTTTAATAAGTTATACGCATACATTAGAGTATTAACAATATCGTAATCACTAC
AAGAATAAATATGGTTATTTCGCATAAAATTATACTTGAATTCATCACTAATTTCAGTAATTTGGTATG
GAATACCGTTATTAAGAAATGAAGTTATAATGTGTTTAACTTCTTGAACTGGTGAACCGGAATTAAAT
AATTTTTCAATACATTTAATTCCGTGATAACTGAATTCTAAGTCATCTATATCATTACAATAGTTCTTTT
TAGGAACAATTGAATTCTTCGTAATATTCTTATGAATATTACGAAATTCCCTATGAAGATCTTTAAAGT
TCTTTTTGAATGTATCATTATTACTAGTTTCTTTTAAATTAGCATAAATCTTAATTGTATTATTCATTATT
TATCAATCCTTTAATATATTTTTATTTTTCAATATTAACTTTAAATTCTATTCCTTGATCTACCATATCAT
AATCAATATCAGCAACTCGACCAACGCTGATAATATATTGCTTGTACAATTCAGTATCTTTAAGATTAT
GACCAAGATATGCAGTATCATATCTGTCACTTTCAATCTCTCCTGGACTATATTGAACATTGGAGATCG
GGTTATCATTTAGATCTTTTAATACGTTATATTCTTTACGATCAGTATCAAAAAGCCTATTCATTGAACC
TTCAAAAGCTACTTCACCATCACTAAAATTTTCTATGATGAACTTACTGTTAAGAAATATAGTGAGTCA
GTTGTTCTAACTTTATCATTAGGGTCAAAATTAGATGGTTTTGGGTCATTATCAAACTTAACCCCTTTAT
TAGGAATAATATCCATACGAACTAGAGCTACTGTATAATCAGTGGCTTGTACTGGTCCGATTGTAAAC
ACATAATTTTCAGGAGAATTAACGATAACTGTCATAATAATTTTATAATCATTATCATTAGTTACCCTA
TAGTCTCCTACCTCTGTAAGTTCATATTCTTCTTCTTTTTTGTTTTCATAAGGGGTTTAAGTTCTTGTATT
TTTGATTGAACTGAATCTTTGTTAACATGATTACTATCATTATTTAATACAAAATAAATAACTACTGAT
AACCCTATTAATAATACTACAAATATTAATATTTTTTTCATTTGAAAGTTCCTCCGTTTTCTAGATTTTT
ATTGATTTTATATATTACTTTTAAACCTTTAGCAAATCTTTTAGATTTTACATCTTTCATACTAATTACA
TTACTTTTCTTAGCTACTTTTTTAATTTTCATAATTGATCCATCCTTTATATTTTATTTAATCATTATTAT
AATATATTAATGAAAATTATATTATTACGCTAAAAAAAAAAAAAATCCGTAATACTCATAAAGAGTAT
TACGGGAATATTTATATTATTTAAAATCTTTCACATATATGAAAACCATGATCAGTGGCTAATTTATAA
TCAAAGTTTAATCCTAGATTCATTAAATAAAACTTATCAGCTTCTTCCTTACTGAATGTATTGATTAAT
GTTTCTAGTGACATATGACATTCTTTATCATAATCATAAGTTTCGCAAGAAGCATCATGATATATCTCA
TCAAAGTAACCTTGATGAATAAGACTTTCAATATCATCACCGAAATTATTTGCGTCACCACTATAATAT
ATTACTTTTTCATCAACCTTAATAATATATCCATACGTCATAATGCTCGGAGAATGTCCAACAGATACT
GCTTTTATTTGAACGTTAGAGTCAATATGATAAAATTCATATTCTTCAATAAATTGTATTTTATAATCTA
CGTCTGCATGAACATCATTAATCTTTAATAAATTAACGATATTTTCACCATATGATAAAAATAGATTAA
CTTTTATATTATGAATATGTTTAAAGTATCTAATAAATGTTGGTAAGGAACCTATACGGTCAGCGTGAG
```

-continued

```
TATGAGTAATAATTACATTAATGCTATCAAAATTCTTTATCATACTATCCATAAAATAATCATCAATTA
ATATATCAAACACCATACTTCCACAATCAATAAGATAAAAATTGTTATTATTAATAAAGTATGCAGAC
GTATTTCCTAATTCTGTATTAAATTCATTTCCGGTTCCTATAAAATTTAGTAAATTATTATACATTTTAT
ATACCGCCTTTATTTTTTTTTTTTATTATTTTTTCTAAAAAAATATTGGATATTGTCATTTATTTGACAAT
ATCCAATAAAATAAGGAAAGTGTAAACTAGTTAGAATATTACACTTTTAGACGAAAGAGTAATATGGA
GATAACAACTAGTCGTACGGGATTAGAGATAGTTATATTTAGGCATAAGATTTACCTAAATATAATAT
ATTATTATCCAAAATATTAATTTTTTATTTTTACAGTTTACGCATATAAATCTTCATTATAAGCGTATTG
AATTCTTTATTGTATGAATTAATATCCGTAATATTATAATTATGACCAATAAGATTATCATTGTTAATAT
TAGAATTATATACGCTAATTGCATTATTATATAATGCTTCTAATTCATCATAATTTTCTAATAAACTATA
CTTGTAATGTATATATACAAAGTTACTTATAATCATATCGATAAATTTTGAATCGATATTTGCAAAATA
TATTTTACTAGAATTAGATATAAGCGTTGGTATTGTAAAATTACCATGATACATTTCAGCATTAAAATA
ATTCTTCTTACATATTTCATAAATAACAGTATCGTCATTACTATTTAGATATTCATTATACGTCATATTA
ATAAAATTTGCAAGATTGATTGGTTCTGTTTTGATATTTGAATAGACGATATTATTATATGATTTATAA
TCGTGTAGCGTAGATCGTAATACATTTTCAGTAATTACACTATTACTACGAGAAAAATTTTCTTTATAT
TGAAAGTACTTTTCAATATTAATTCTTAAGCAATTATTAACTTCTTCTAGATTAGATCTAGATTCATTAT
TCGAAGTATCAATAATATCTTCCTTAATATAATTTCGCAGACTTTTCTCATCAGGATTATTATGTAATAT
ATCTACTATAATAATCGCAGTTTTAATTAGTATATCCGTAGATTTTTTATCCGATCTATTTCCAAAATTA
ATAATATTTCTTAAGAAATAAATTAATATCTTTGGATCATAGTTATACATATTATATATCATGCTGACA
AATATATTGTTAATTCCAATTCTTCCATTAAGAATATGTTCTATAAAATAATAATACTTATTTGTAGAA
TCTTCATTATATTTATTATTAGCAATATACGCTGATTGGTTGGATACACGAATAAAGCTTGAATATAAT
GCAGAGATATAACTATTATTAAAATAAATAGTTGGAACGATATTACAAAAGAAATCAGCTAATTCTTT
AATATCTATAATATTTAGTATAGATTTTTTATAATACTTCATAAATTCTTTTGGCGTATATTGGAGATTA
TCAATCTTGATCTTTTCAGTGTCAAACATAAGAGCGTGGGACTCATTTATAAATATATTAAAATCATAT
ATATTTGAAGTGAATATATCTTTTAGGAAACTATATTTATCTTTGATTAATGAATACATTGTATTTCTAA
TCATATTTTGAAAATATATAATTCGTAGATTATTACTTTTTTTAGTATTGTCAGAATCGACTAATGATTT
AATTTCTTTAATATTTTGATAGATTAGATTTGGAAAAAGTTTCGTTAAATTCTTTACAATCATCTAAA
AATTTGTTATATACTTTATCGACAAGATCACTATTACTGATTTCATGAGTATCATATTTATTTTTTATTT
TATCGATAGAATTTTCGTCATAATAAATTCTATCGATAAAACTACTAATTATCGGCATGTTGATGTATC
ACTTCTTTCCATTGATATAGTGCATAATGTCAATATGTAACAAAATGCTCTTACTCTGATCTCTACTGG
CATTACAATAATCAAATTCATGCTGATAATGATCCAATAACATTAATGCATAGTTATATTGATTTTGGA
TGATGCTTGAAATATTATTACTTAATTTATATTCTAAATATTCAATAATATTTAGAACTTCATTGTCAAT
AGGATTAATTTTTTCATAATTATTTAATAAGTAATGATATACATTTTTATAAATTTCGACAGAATCATT
ACTTATTTGAATGTCATTATTTATTGAAAAACAAAATAACGAATTAAAATCATTAGGATCAATTAATA
GTTTTTCTAAAATAATCTTAGTCTTTTCACTTTCTTTATATTCAATCCATCTTACAGGGATATATTCAGC
TCTCTGCATGCTAATGAGAGATTTAAATAACTTAATTGAATTTTTCTTTTCTTGCAAACTATATTTACTA
AAAATATAATTTATCATATTTTCTACAAAAAGATTAATTCTACCAATAGTATGGTTTACTGTAGCCATG
TTTGTTCCTTCAATAATATGATCTTTACTGCTAACATTAATAATAAACATTCTTTATCATCCTTCACTGT
TTTATTTTATTCACATTATTATAATATATACTTATCTTATTAGTAAAAAAAGAACTATCACATTTTATTA
TGTAATAGTTCTTCTATGGATTAATTGATGAATTAATTTCTGTACTATTATTTATTCGGTTAATTTTATC
TTCTAAAGATATCAACCTAATAACATTTTTTTTTTATTTGTCATATAAAATAAATCACTCTTTTATTCA
TAATTATTCTATTATCATATGCACTTCTTTATAAGATATATTTATAGAAACTGTATATTAATAACAGTTT
CTATATTAATGATAGTTTAACTTTATCAAAGATGTTTCTATGATTAAGAGAATTCTTAATAAGGTCATT
AATAGTTATATTTATGTGGTAAGGTTTTACATTATCTTCTGCATTATAAATCTGTAAATTTATATTGTAT
CCATTTACTATAAATTTATAATATACCGAAACATATTCTCTTGTTACTGGTTGCTTAAAACGGTCAGAC
GTAAAAGTATAATTAAATGTATAAGAATCAATATAACCATTATTAGTTGATAAATCACTGATATTATA
AGTATATTCATCGATGTCTGATGGGTCAAGATCTGTATTATTTCTAATAAATTCATAGATCATACTTTTT
AGGATTTCCGATAGATATGTGATAGTTAATATTGAAGAACTAAATCTTTTACTATTAAATTTTTCTTTTA
TATTGTAAGTATTATCATTATATTCAATATCTTTTGATGGAATATTATAATTAGATGTAAACATTTCGTT
AAATGTTTTTCGTTCTTCAGAAGTTAATTCATTTAATGTTTTAATTAATTCTTTGTCATTATATAATAAA
AATGAATTAATTATATGGTACGTAATATTCCCATTAACATGTAAAGGTTTACTTAAAAATCCTAGAGAT
TTTACCATTAGATAATTTCCTTTCTTTTTTTTTTAATATTAATTTTAGATATTAATACATTTTAATTCTAT
CATAATATTTGATATTCTACTTCTTTCCTTTATACTTATATGGATTCAAGAATCATTTTATCATATATTTT
CATATGTTTCCCACAATCAAATAATAGATCAATCATATTAATTATTTTTGTTAAAAATTTTATCATTAAT
GAAAAAATCAATATCTAATTCATTGCTATCTTTATCCATACTAAATTTAATTTTGTCAGAAATAAATGT
AAATTTAGTATAAGGATGATAATTCTCCATAAATTTATATTCGGGTATATCTTGAATTCTTATTAGGGC
AGAGACTTCAAATTTTAATATTAATGCTAAAAATTTCTTAAAGAAATTAGATTCTAGTATATTCCAGAC
GCCAAAAATATCATTCTCTCGATATTTACTAAAACTAAATATACGCTCTAAGTTATCAATCATTTCCAT
ATTATTTAGTTTTGTCAATTTTTCTTCTAAGTCATCATAAATCTCAAATATTTGTACAATATCATTTTGA
TTTGTTTCGAAAATATACATAGATACTATTTCCTCATACACGCTATTATCTATGTATGGAATAAATGAA
TTTTTAGCTGAATCTTTAATCTGTTTTATATTTTTCATGTATACCATTCCTTTCATTCTTTAATTTCAAGA
ATATTATGTGGGAAGATATCAATTAAAGATACCTTCCCACATAATATATGTAACGATTGTTTAGTACAA
CATATCACTATATTTATTCATAATATTCTTTGTAAATATATAAAGGACTTGTTCAAATTCAATATCGGTC
AAACATAATTTACCGTAGGCTTGACGATTACAAAATGATGAGATAGTTGATAATGAATTACCCATGAAA
AACCATTCTTTCAAGCACTCTGTTTTGATTGTCATTAAGCTTATCATATTTTTCTTGGGAAGTGATCATT
TTATGAGTCATACTTAATAGATCGCCTTCTAAAGTATTAGGGAAAACATAATTACCTTCAGAATTTAAA
TAAAAATGGTTAAATCGATTTAATATTTCTTTTTGATAATTTTCTTTTGTTTTATTCAACACTATTAAAA
CCCCCATAACCAATTAGAATTATTTATATACTATATATTTATTTATTAGTATATCAATTTATTTTGAGTA
ATATGGAAAAAATTATTTTAAAATCCCTAAATAAACATATAAGTTTACTTAAGGATCATAGATATTTTT
AATTCTTTATTTTATTAAATACTTTTTAATTTATTAATATCAATTAATTTCTTTTTCATACTTTCAGGTAA
TATTTCATCATGATACTTTAATATTAAAGGAATATTTAATTTATCAATATACGTATCAATAAATTCTAG
TGATATATCTTGACATTTGCTAATAATATCCCAATTAACTTTATCTTGAAACTCAATAATAAAGTCTTCT
GATAATGTCTGGTACCAACTAATAAAGTACCAATCTAAAGAATCTTTGAATCTACGAATAAAATCTTC
TGATAATTTCTGTTGTGAACTAATATTATACCAATCTAATTCATTTGGAACCTTTCAATAAATTTCTTCT
GATAATGTCTCGATACCTACTGATGCTAAACCAGTTTAATTTATCTTGAAACTTTTCAATGAATTCTTCT
GATAACTCTTGATGTATGCTGATGCTAGACCAGTTTAATTTATCTTGAAACTTTTCGATAAATTCTTCG
GATAATTTCTGTTGTGAACTAATATTATACCAATCTATTTTATCCTGAAACTTCTCAATGAATTCTTCTG
ATAATGTCTGATTCCTACTGACATGATTCCTATTAATGGTTATTTTTCCATAAATAAGTATACCACCTTT
TTGCTATATACTTTTTAATTTAATAATTTCTTTATGTTTATTAATAAATTATCGTGTACACATTTTGAATC
GATTCAATATAATGCCAATTTACTTTATTCTGAAACTTCTCAATAAACTTTTCCGAAAATTTCTGTTCTC
```

-continued

```
TACTGATATAACTCCAATTTACTTTATCTTGAAATTTTTCGATGAATTCTTCTGATAGTTTTTGGTCAGA
CGATATATAGTCCCAATCTACTTTATCTTGAAACTCTTCGATGAATTTTTCGGATAATCTCTGATATATA
CTAATATGCTTCCAATTAACTTTATCTTGAAATTTTCTAATTAATTCTTCTGATAATTTCTGGCATAAAC
CAATATAATGCCAATCTACTTTATCCTGAAACTTCTCAATGAATTCTTCGGATAATTTATAATATTCAG
AGATACTACACCAATTAACTTTATCCTGAAACTTTTCAATAAACTGCTCAGATAATTTCTGATATGAAC
TAATATTGTACCAAACTACTTTATCCTGATATTTAGAAATAAAATTTTCTGATAAGTTCTTTTGATCCCT
ACTAATATTGTACCAAACTACTTTATCTTGAAACTCTTCAATAAACTGCTCAGATAATGTCTGATACCA
ACTAATATTGTACCAATTAACTTTATTCTGATATTTAGAAATAAAATTTTCTGATAAGTTCTTTTGATCC
TTACTAATATAATACCAATCTACTTTATCCTGAAACTTTTCAATGAATTCTTCTGATAATTTTTGATGTG
AGCTAATATATTTCCAATCTACTTTATCCTGAAACTTTTCAATGAATTCTTCGGATAATTTTTTCTTCCA
ACTAATCTCAGTCCAATCTACTTTTACTGAATCATCAACGATTATTTTATCCATAGATAATATTACATCC
TTTCTTTTTTCACTATATACTTTTTAATTTATCAATAGCAATCAATTTATCCATTGTTTCTTCAGATAGTG
TATCTTCGTATCTATATATTAGATATTTAACGTATAATTTATGCATATATCTAATAATGAATTCTTCCGA
TAATTCTTGATGCATACTAATAGCTTTCCAATTAATTTTATCCTGAAACTCTTCAATAAAATTTTCAGAC
AATGTCTGATATTTGCTAATTTCATTCCAATCTACCATATCCTGACAGTTACGAATAAAATCTTCTGAT
AAGTCTCGAACTGACGAAGAAGCATGCCGCCAATTAACATTTTCTGGAAATTTTAGAATAAGGTCATT
AGATACATTTCTATTTAAGCAAAAATAATCCCAACATATCTTATCTTGAAATTTGGCAATAAATGATTC
ACTATTTAATTTCTGATGCATACTGATTTCATTCCAATTAACTCTATCCTGAAACTCTTCAATGAATTCT
TCTGATAGTTTTTGGTCAGACGATATATATTGCCAATTAACTTTATCTTGATATTTACGAATAAATTTTT
CCGATAATTTTTGGTATTGACTTATAATATCCCAGTTTAATTTATCTTGATATTTAATGATAAACTTTTC
AGGCAATTCTTCATTATATGCAATATATTCCCAGTTAGGTTCAACAGTAAAATTATATTTTTCATTATA
CTTCATAGGGAAACCCTCTTTCTTTTAAGCTATTATATATTCTTCATTATAGTAATATTAGTCAGCTTATC
TATAGTTTTCTGAGATAACGAGTTTTTATGAATTTCAAGTACGAATTCAATATCCAAGCAATGAATATT
CCTAAGAATAAAATCATCTGACAATTTCTGGTATTGGATAATAAAATCCCAGTACACTTTATTTCCAAA
ATTTTCAATGAATTCTTCTGATAATTTTTGATATTGGGAAATATTATACCAATTAACTCTATCTTGAAAC
TCAATAATAAAGTCTTCTGATAATGTCTGGTACCAACTAATTTCATTCCAATCTACTATATTCTGACAA
TTACGAATAAGATCTTCTGATAGCTTTTGGTTTATACTGATGTAGTACCAATTAACTCTATCCTGAAAC
TTAATAATAAATGAATCAGATAATTCCTGAAATATACTAATATATTTCCAATTAACCATGTCTTGATAT
TTATGGATAAGTTTTTCTGATAATTTCTGTTTTATACTAATAAAGTCCCAATCTAATTTGTCTTGAAAAG
TATCAATAAATTTTTCATTCAACATTATGTTCTTAGATATGTATGTCCAATCAATTTTATCATCATTTAT
GTTAATATCATTAGTTTTAATGTACTCGTTAATATTCATAAATTATAACCACCTTATTTTTCTTCTATAT
GTATAATATATAATTTTAATTTATGTTAGATGTATAAAAAAAAGGAAATGCGTATTTAATAAATGTATA
ATTCCTATATAATTATTATATTATATAAGAATTATACATTTAGTAGTTATATATGTCTTAATGCATCAAT
TTCCTCTAATCTATTTATGAATTCTTTAGATAATGATTCTGAATTATTATTTATTATTGAACTAATCGAT
ACTTTATCAATATGATTATTAATAAATTCTTCTGATAATTGTTGCTCTCCACTAATAACGTTCCAATTAA
CTTTATCTTGAAATTTATCAATAAAGATTCCGATAATGTCTGATATCTACTAATATAGTACCAACTAA
GTTTATCTTGAAATTTCTCAATGAATTCTTCTGATAATTGTTGATCTGTACTAATAACATCCCAGTCTAC
TTTATCCTGATATTTACGAATAAATTTTTCCGATAATATTTGGTATTGACTTATAATATCCCAGTTTAAT
TTATCTTGAAATTTCTCAATGAATTCTTCTGATAATTTCTGTTGTGAACTAATAATGTACCAATCTATTT
TATCTTGGAACCTTTCAATGAATTCTTCTGATAATTTTCGATACCTGCTGATGCTAGACCAGTTTAATTT
ATCTTGGAACTTCTCAATGAATTCCTCAGATAATTCTTGATGTATACTGATGCTAGACCAGTTTAATTT
ATCTTGGAACTTCTCAATGAATTCCTCAGATAACTTTTGATTTCTACTAATATCATACCAATCTAATTTA
TTTTTCAGATTATTAATAAAATCTTTATCATCTAAGTTTTTATTTTTCATAAGTATATCAATCCTTTATAC
TAATATTTAAACATGTCTTAATTTATTAATTTCTTTTAATTTATCTACAAATTCTTTAGATAATGATTTT
GAATTGTATTGTAGTAATGCTTCAAGATTTAATTTATTTAGATATTTATGGATAAATGTCTTAGATAAC
TTTTGGTTTCTACTAATAGACTCCCAGTTTAATTTATCCTGAAACTTAATGATAAAATTCTTCTGATAATA
CTTGACATGCACCAATATATTGCCAGTTAATCCTATTTTGGACTTCTCAATGAATTCTTCTGATAATTG
TTGCTCTTCACTAATAACGTCCCAATCAATTTTATCTTGAAATTTATCAATAAAAGTTTCAGATAATTTT
TGGAACCGACTAATTAAGTACCAATTTACATTACTCTGAAACTCTTCAATAAATTCTTCTGATAACTTT
TGATGTTCACAGATTAAAAGCCAATTTACATTACTCTGAAATTTACGAATAGATTCTTCAGATAATTTT
TGAGATCGACTAACTTGACTCCAGATTAATTTATTTTGAAACTTACTAATAAATTCTCCTGACAGTTTTT
CACATTGAGATATATAATACCAATCCAATTTATCTTGGAACTTCTCGATAAACTCTTCAGATAATTTTT
GATATGTTACAATAAAATCCCAGTCAACAGTATTCTGAAACTTATCAATAAAAGTTTCAGATAATTTTT
GATATATGCTGATATAAAACCAATTAACTTTATCTTGGAATTCTTCGATGAATTCTTCTGATAGTTTTTG
GTATATACTGATATTTGACCATACTACTTTATCTTGGAATTTTCTAATAAAGTCTTCAGATAATGTACGT
TTTTCACATAATAACCCCCCAATTAATCTTTTCGGGGAATTCACTTATAAACTCTTCGGTTAGGTTTTTAT
TCCACATAAAAGTATACCATTCCTTCTCTATAAAGATATTTAGATACTTTTTTATTTTATTAATTTGAATT
AGTTTATTTAACAATTGAGGTGATAATAATTCTGAATTGTACTGTATTAGGTGTTCAATATTTAATTTAT
TTAAATGATTATAGATAAACTTCTCAGATAATTTTTGATATCTGACTAATAATCCCAATTAACTTTTATC
TTGGAACTTAATGATAAAGTTTTCTGATAGTTTTTGATATTGACTTGTAGCATCCCAATCAAGCTTATTC
TGAAAATCAGTGATGAATTCTTCCGATAATATTTGATATTGACTAACATCCTCCCAATCATTTATCATA
TCTTGAAACTTAATGATAAAGTTTTCTGACAATTTATGATAAATTACGACTAAGTACCAATTAAGTTTA
TATCTAAATTTTTCGATGAATTCTTCTGATAATTTTTGATCTCCACTAATAGTATGCCAATCAATATTGT
CCTGAAGTTCTTCGATGAATTCTTCGGATAATTCTTGATATTCACTAATATTAATCCAATTAACTTTATC
TTTAAATCTAGCAATAAAGTCTTCTGATAATTTCTGATATTGGCTTATATTATACCAATCTACATTGTTT
TGAAATTCTTCAATAAAGTCTTCCGATAATTCTTGATATCGACTAATAATATCCCATTTTAAATTATTCT
GGAATTTACGGATAAAGTCTTCCGATAATTCTTGATATCGACTAATAATATCCCATTTTACATTATTCT
GGAATTTGCGAATAAAGTCTTCTGATAATTTCTGATATTCACTAATATTAGTCCAGTCAACTTTATCTT
GAAATTCGATAATAAATTTCTTTGATAGTTTTTGATGTTTAGAAATACTGTGCCAATTTACTTTATCTTG
AAACTCACGGATAAATTTTTCCGATAATTTTTGATATTTACTAACGTCTGTCCATCTAATAATATCTTGA
TATTCACGGATAAAATCTTCAGGCAACTTAACACATGATACCGTAGTATACCAATCATAACCAAACCT
TTCAAGTGTTACGTGACTTATATTATTATTGACTGTTTCCATAGTACTTAATTCCTCCTATAATATCATT
TTTAATCTTATTAAGAAATTAGACCAAGTTAATATCTAATTTTTTGAAGTATAAATTAATAAATTCCTC
TAATAGTTTTATGAAAATAAAATATATTCTCAGTATATTTATTATGTGAAAAATCAGCACATATTCATC
ATATCATTAATAATACGCTTTCTCTCTTTTTTTGATACAATGTAATACGTGTTATCAATATAATTAAATT
CTTTAATAAAATCTTCCGATAATATTTGATATCGACTTATATATCCCAGTTTACATTATCTTGAAACTC
ATGGATAAAATCTTCAGATAATTTTTGGTACATACTAATATAATCCCAATCTACTTTATCCTGAAATTC
TCTAATAGAGTCTTCTGACAATCTTTGATATATGCTAATATTTTCCCAGTCTACATTATCTTGGAATTCT
TCAGATAATTTTTGATACCTTGAAGATTGATACAAATTTGTAATTTTATTATATTCAATATTAATATCAT
```

```
TGTTATATTTGATATCGCTATCATGATTATCATTATTATTTAGTGATAACACATGATTTTTATCTTTTAT
AACATTATCATATTTTGGAATATACAATATTAAGGGATCATTATTACTATTATCATCTAGATTTTTTGA
AATTTCAATATTAGCGGAATTAGATTTAATTTTATCAATATATACTTTATTTCTAAATTCTATAATAAAC
TTTTTGGATAGTTTTTGCGAATTGGATAATTTTTGTGAAAATATAAGATGTTCCCAATATAATTCCGATT
CATATTTTCTTATAAATTCTTCAGACAATCCTCTGGTTCTATCAATCATGTTCCAATTTAAATTATATGG
ATTAAGTTCGACAATCTCTTCGACAGTATAATAACAATTAATATCCATAATAATCCCTCATTTCATTTA
TTATTTTAATATATGATGCATTTATACATTATAATTATAATATATATTTATCCTATAAGTTATAAAAAAA
AAAATCAAACGTGATATATAATGATTATCACGTTTGATATGTAATTATTTTTTAAGAATGTTTAATAGT
CTTAGAGAATATTCTAAATATTTAGATTGATTTTTTTACATTGTAAGTTATTAATAATAATAATGAAGAG
AGAAGGAACAGATCTCCTGATTTACAATAATCTTTTTGATATTTTCCATACATTACATTACATTTCAAT
AGCGTTAATAAGATCTAATTCTGCAATAAGCTGACTTACTCGGTGATCTGATAGATTTTTCCTATTTTG
AATTTCTTGTTCTTTTGCTTCATCTAAAATATTATTTAATGCTAACATAATTCTATCTAATAGAACCATC
GATTCCTTATAAACTTTTACAGAATTTTCACGATTTTTAAGAATATTTATTAAATTACTGAGACTTAATT
CATACTGTCTTATTTCTTCGCCATGATTATTGATTTTTGTAAGTTCAAGTTTTGCAATAAATAACCGAAT
AATATCAATATTCCTATCCCTATTATCCATTAATAGAATTATATTTTTTAGATTTTCGCAAATACCATCA
ACTGATACCATTATATTTCACCTTCTATTCTACTTTTAGTAAACATATTAAGTGCTTCTAATTCATTATT
GATCATTTCCAAATTTACTTCTTGTAAATTCTTTTCTTTCATTAATTTAATTTGTTCTTGATTTTCTTTTTC
TTTTTCTACAGATTTAGTAATTACTTCTTCAATCTTAACAAGTAATGAATTTACTGTTGTATATACTTCA
TCTGAAAATATTGCACTATTTTCATTTAAGTGTCCAATAATTATATCATTTATGCTTGATAAACTTAATC
TAATTTTATCATGTGTATGGATATTGTATTTTAATAGATTAGATACTTTTTTGTTTTTCATTAATGAATT
AATAGTTCTTCTTAATCGATTATTATAGTTTTTATCTTTAAAGTATTGAATATACTCGATATTTTTATTA
ATGAATTTAATAAAATCAATAGCGTCCATATCCGGAATATATTTTTCAGTTGAATAAATTATTGCATTA
TCATTATTATTTTTATATCTTAGTGAGTTTGATCTAGTTAAGTGCCTATTTATATATCTAAGATCATTTG
TAGCTTGATCTATTTCACTGAAATTAACGGAATCATCTCTTACAATATCTTTATAGTCACGAAGTATTA
AATATCCTGAACTAATAATACCTTTAGTTAAATGATTATTTTTAATGCGCATATAAGTCTCAATATTAT
TTTTAATAATATTGAGGCAACTTTGGATATTTAATGAATCAATATTATTTAAACTAATATATTCGATTTC
ATTAAACAATTTAGACAATTCTTTACTTCTAGATAAATTTTCTGAAAGTAAAAATTTATCTAAAAGATC
ATCATTCTTATTATTTTTTATTTTAATAAATTTAAACATTCGATCACCATCCAGTTAATTATTATAATTC
TTTCTAATCTTTGTTATATAAATTTATTATCATTTCGAAAATTCAGATATTTCTCAATTCTCTGATCTTA
ACTAATTTACGCTTTATTTTATTAGATATTAGTTTATCATGTGATATCAATAGATCAATATCTAATTTCT
TGAAGAATATATTAATGAATTCTTCTGATAAATTTTCACAATATATAGATTTGCCCTTCCAGTTGATTG
TACTATTATTTTCAATAGATAAGTATTAATCTTCAGTTAGATCAATAATATCTTCAAGATGTGAACCAA
AAGTAGAATAGTCTATTAACCATATTTCTTTTAATGGGTCTTCTTCAAGAAAGATTGCAATATCTTTTG
CATGTTTCTTAATTTTATCCACAATATAATTATACGTTCGATCAGCACCACTAGGATTCTTAATGGATCT
TAGAAAAACGTCATCATAAGATTCAGTTTCAATAATATGATATCCTTCATAAGTTTTATTTCCTTTTTGT
AACGTCACCGATCTTAATACACTTTTTCGAGTTTCTTTAATGCCAATTAGGTCAGCTAAATTAATTACTT
CTTTTTTATTCAGATCAATTCCATTTTCTAGTACAAAAGGAACTGGTTGTAGGTTCTCGTATTCCTCATC
ATCAATATCACTTAGTGAATTAATATATTCTAAAGCATCATTATATGATTTAAATACCTTATGTTTATTC
TTTTCCGTATTAGTAATTTTATATTTGATTGTCATAGACCATCAATCCCTTCATTTAGTTAATTTTTATTT
TTAAATTCTAGTTTAATATTATTACTCTGAACCTTACGTAAATACGATAATATCGAATTCACCTTTACTT
TCCATACATCATTCACAACAGAAAGTATTTGCTTCATCCGATAATATATCTGATTATTATTATCGATGG
CAAGAATTATACTCATATGCTGAGCCTGAATTACCTTATCAATCGTAATAATATCGTACAAGTTTCTTT
CATTTCTACTTTTAATTAATTCTTCGCCATCATTATACTTAATTGGTCTTATCTTCATAAGTTCACTAAC
AGATTTAATAATTTCAGACGTATTTATACATTCCATATTATCATTCAAAATTTCTTTTAAATATTGAATA
TTATTATCTGTCTGCTTAATATTATTTAATAAGTATACTTCATATTCTGCGATAATAAATAAAATATCCT
TATATTTTTCACGAACAGTACTAATCTCACGATTATTTCGAATATTATAGTCACTATCAATATTGGACA
TCATTCTCATAATAGTATCAGATTTTTCTTCAATATAATTAATATACGTTTCATTATATGCGTAACGTAT
AATATCCTTTGATACTTGGTTATTTATTGACTGAAGTTTATGCGATATTTCAAAGATCTCTATTTTACGA
TTAACTACGTCATAATATATTTCTTGAGCTTCTTTCTTTTTATCCAGTGATAAGCTTGAATACGTAGGAA
CTTTATCATACATAGCAGGATGTATATACAATATATTATCTCCTTTCATTATTATTATTATTGTTGATTT
ATTAAATATATTAATAATATATGCATTTTTATAATAAAGTTTAATATTATTCCCTAATACAAGAA
TTTACATTTATCTTGTATTAGGGAACAAATTTATTTATTTTGATCTATATTAATAAAATATAATACCCAA
AAAGACCATATTAACCCAAAGATGATTATTAAAAATCTAAAAATTAATGAATCTATAAGCAATCCTAA
TATAATTAATATTAGTGACATTATGGTTAAAATCATTAATACTATTTCTTTATGATCTTTTAATAAGTTA
AATATTTTTTCATAATAAAACCCCCATTATAATAATTAAAATTAAATTGTAATAAAAAATTAAATCATAA
AATTTAATTTATGTAACTTGTTAGGGGAGAACGAGTTACGTCGTATCTCTTGCGTTATCAACAATATTT
ATAGTTGTTCATAAATATTATGACTTTTGTATTTTGCATTTTTGTTATTTCCAATAATTGTTATATAGTTT
TGGTATATTAATCTATATATTATTTCATCATTACAATAGAACCAACCTTATAGTAAAAATTATATATAA
AGAATAAAAAATCTATATAATTTACCTTCGGTATAAGGATTGTTACATAGAAGGAAAGATCTACATAT
TTTTATTAAAAAGCATATATGGATTTATAGTTAAGTCAGAACCAACCCTATAGTAAAAATTATATTAAT
AATTATATTTTATTATGAGTTTAATGCTTCGTTGTAAGAATCTTTACATGCACGGATAAATTATAGTTA
ATTGTTATGTATAATATATCCAAGCATGTAAGGTTTCTTAGATTATTTTTATTTTTTATTATTTTAATAA
CTAATAAAGTATATTAAAACTTAATTTATTTCGTTATATAATTAAAGTAATTATTTTATCTATATGATT
TACTTCTATAACTTTAATTTCTAGTTCTGAAACTTCTTCGTGTTTTCTGAATACTGATGCAGTATTTCTT
GTAACGTATATTTTATGTTTTCCGGGAATCCATTCAATATTGATTTTAAGATTATCCTGAATCATTTTAA
TGAGCGTTAGTCTACTAGCTTTATTTACTAATTCGCCCCAAAGGTAATATTCATTATAACCATTATTCCT
AAGAATGTCTAATTCTTTTTTTTGATAATTTGTATTTTGTTTCATAAGTTATTTCCATGATTTATTAATTAT
CCACCTTTATTTATTATTTTTAAAGATCAATAATGTTATCTAGATGTAAAGATTCTTTATCTAATGAATT
ATTATCGATAATATAGTTAATTCTTGATTTAACGATGACGTCAGTTGATTCTCTTAATTTCTTTAATGCAG
GCACTATATAATTCATTCTTGTCTATTTTTGTTATCTTTAAGGTAAGATCTTCAAGCTTTTCGTAATCAA
TTGGTTGTTCACGTCCATACATAATCCAACTTGTATATCCACTACTTACTTTTTTTTCTTTTCAGTATTTCA
GTGTTATAGTAATTTGTGATGGTAGAAAAATATTTTTGCCTTTTTCTTTTAATACTTTTAAAGTATATTT
TGTTGTCTGAATGAACGCAGAATTTTAAGTTAAAATGAATTGTTAAAATCAAAATCTAAATCAT
CTAATACCATTTAATAATTCATTCCTTTCATTTATTTAATTGTTTTATGCTCAAAGAATATCTGATTTT
AAGTCTTCTAGGAATTTTACCGTACTAATAATAGTGTTTTCGTGTAAGTAATCTTTTTCTAGTATCATTC
TTTCTTTATATATTTCAATTAATTGGAATAATCTTTCTTTATGTTTAGAAAGATAAGCATAACCTAAGAT
TTCTGCTGAGAAGACGATATATTCATCATTCAAATTATCAATTCTTTTTTGAGACAGATTATTATCATTT
TTATAAGACGTCATAATTTCAGAGATTAGATCATAATATAAGTTACTTAATACTTTTATTGTCTTTTCTA
TTAACCTATTAAATTTTTCTGCTTTTTCTTCTTGAATTAAAAATAATCGTATCATTAATAGCATTATTATA
```

-continued

```
GGAATATTCTTCATTGCTGTAAAGATATGTTTTCTTTTTATCTTCTAATTTCTTTTCTATTTCCTTAATAG
TATTGATTTGTATTTTTATACTATTAATTGAATCATCATCGCTGATTGGGATATTGTCCATCTTTTTAAT
AAGAGACGTATCCGTTTTTAAATAATTATCTTTAGTATCAATCGCTACCTTATTACCATCTAATTCTTTT
ATTATACCTTCTTTTGTAACGCCATTATGCATTACTTTTACACGTTCACCTATCTCAAACTTTTCCATCA
TTTTCACCCCACATCTATTTCTTCAATAGGAACTGCAAATTGCCAATAACGCTCATCTGATGACTTTATT
TGTTCTTTTGTTAACTTAGTAGTAAACCCAGATGATATTTGAAAAGGAATAAGTTGTCTTTTTGCAAAC
ATACCACTTACGCCTGTAGAAGGGTTTATCGCTAGATATAAATAATCATTAACTTTTTTAGAAACATTT
TTATCCCATTTCAGTTCATTATTTTCAATAAATTGAACTTGTTCGTCTATTTCGAATTTCATAAATATGA
TTTCTTAAATTAATTATTTTTTCACTAATAGTCTTATCAATATTAATAATATTATTTTTCTTCTTTTTAAA
AAACATATTCACCATTCCTTTAACTTATTCATTCTTTAATTTTTTGTTAATTGAATCTTTACTAATATTTC
GAATAATTTCTAGTTCATCAGATAATATATCATCAATAGTATTATTCTTAGATATTTTAATATTTTTATC
CATATCTTTATATACTTCGAATATTTTAGAGAAATCGTTATAGATAGTAATTAATATTTCTTTAATTTTT
TCATACATAGATTTGGTAATTATTCCTTCAGTCTCTTGACCAATATTAATAATAATATTGTAAATATTAT
TAATTGTATCAATATACTGGGAGAGTTCTTCAGTGAATTCATTTTTTTGTTGATTTAATATTGACATATT
ATCAGACTTAATAAGTATTTTATCGATTATATCTAAAAGTTTAACATGATAATTAGTTTTACCATTTAC
ACCCATTACATAATCATATAACGGTTTAGATCTATTAATATTTTCGTCAATTTCATTATCTGATAATCTA
TCGTAGTTATACAAACGATATCCACCTTTTTTTAATATATTATACCTTTTTACATATGGATGAGATTTAT
TAATATTAATTTTGAAATCATATACTATATTTTTAATACTAAATTTATCATACATAATCTGATACTCATA
ACTAATAGTAGAACGTTCTCGGATGTAGTATTTTTTATCCATAAAGATATTATCAAAGTATTCATAATA
TTCTTGGGGTGAAGGTAGTTTGTCTGTAGTAATTTGAATTATTGATACCTTATGAATTGATTCAACTAA
GGTATTAATAATTTGCTTTCTTAATTTGATTAATTCATTATCGATAGTTATAACCGATTCTGTATCTGAT
AATTCATCAGTAATCACATCTTCAGGTTCTTCATTATTTATTTTTTATGTGTGATTTTCTTTTAAAAAACA
TGTTCATCATTCCTTTTCTATAATATTTATTTAATTTATTAATAACAATAAAGTTTTTTCTTTAGTAACTA
TCTTTTTAAAATATTAGTTTATCATTACAGGAATAACTAATTTAATAGTTATTCCTGTAATAATTTTTCT
TTTAATTTATATCTTCGTATATAATAAGATACTGAATCATTTTTTCATATGAACATTGGTTGAGATTTCAG
AGATAGTTGCTTTTGGATTCTTTTTTAGATATTCTAAGATACTATTGATTCTTGAATTAGTAGAATCATC
ATCACTATTTCGAATACCTTTAATTTTTCGATTATATTTAATATTATTCTTTTTAATATATGACTGAATT
GTGTGATATTCTACATTAAAATGTTTTGCAATTTCTGTCATTGTTAAATTCGGATTTTCTTCAATAAATT
TGGATAATCCTTCAATTTTTACTTTTATTTTCGGACCAATACCTTTTTTACTTACATATGGTAGATCATA
TTTTTTAATCTTTTCCCTTAATGTATTTGGAACATAGTAAATTTTTTCAGATAATTCATTAACTGATAAT
TCGGGATTTTTCATAATGATATTTCTTAGATATTCTTTTTCCTGAATTTGATCTTTAGAAAGTTTTTTGAT
CATTATATATACCTTCTTTGTTATATAATTTTTCTACTTTTATTAATTCGTCTAATATAATTATTAATTGT
AGATACATTTGCATTAAAATGTTTAGCAATCTTGCTTGCTGTAGCTTCAGGATATTTTATCATAAAATT
AATAATTTCATTATCATCAAACATTTTATCCACCCTTTTACTTTTATAGGGGATATTGTTTCTTTTAATT
GTATTACCAATAAATGACTTTGATACATAAAGTGTTTTGCAATTTTATCTAATGTTAAGTCAGGATTA
TCGCTAATATATTTAGAAAGGTCGTTAATATTGATAATATCTTCATAAATAACAGTATCGTTATCATAA
TTATATTGCATATTATATTCCTTAATATATTTACGGATGGTTGGTGCAGAGTAACCAGTTCCTGATGCA
ATTTTCTTTATTGAATGAGTAGGGTTACTATTAATAATATTCTTTAATAATATTAGGATCTACTTTTTTCA
AAACTTTATTCACAACACTTTCATTTTATTTAGTATTCTTCTTTTCCTTAGCAAAGTATGCAATTAGTAT
GTATATTATCATAGATATTAATGTTATTATATCTAAGACATATTCATTAATAGTTATTGCATTATGGTGT
ATTCCATATAAGAATGTATATATTGTGGTATACACATTATTGAATATAAGGATTATTAGAGGTATATAC
CTCATTTTATAACGAAGTTTATATAGGGATACTTCATGACTACTATATAGTAATAATCCAATAAGAAGA
TTAGCCGTTAATGCTAATGTATATGTTATTTTTTCAGACAATACTTCATTAGTAGTAAATAAATTTATTG
TAAGAAATATAATCATAAAGAATATAAATAAGCTTGTTATTAGTCTAGTTCGAATATCAATTTTTTCAT
TATTAATACACGATATATAGACTAATAAAAAGATTACAAGATTTGTTAGTAACATATAATAATAATCC
TACTTTCCATATACTTATAAGAAGAATCCCCATTAATAAAGGATTCTTCTTATAATCTAAATTTATTTTA
CATATACTTTATATGATTCAAGTAATTTATTTTTCTTTGATAGTTTAGATTATCAATCATTCTTGAGAAATC
AGTTTTCTTAGTTTTTTTATTAGATCTTAACAAACTTGCAACATTTAACATATAGTTTACCATCCTTTTT
ATTTTTTAGGTTTTTTATTTACAAACAGTAGAATAATAATGGCAACGCCAATTCCAATAATTGCAGGAA
GTAAATCTTTAAATATATCCATGTCGAATCACCTTTTATATTTTATTTTTTGTACACATATTCCGTATCA
TAATTTTCAATAATAAGTTTAACAGTTCCATGAGAAACTCCAAGAGATCTTGCAATCTTAGCAATTGAA
AATTCAGGATGTTCCATTATAATATTATTAACAGATTCTATAATTTTTTCATTAGTTAAAGAATTATTAG
ACATATTAACTTGGTTATACGTTGCGATACTAAATTTATATTCTTCAAATAGACTAATAATATATTCTTC
GGAGAATCCTGTATCTTCAGATAATCTTGCTGGAGTCATAATATCATTACTGTCTAATACAATTTTACT
TAATCTTTTAAAGTCTGATAATCGTGATCAATCTTCATATCTGAAATGCTCATTTTTTGAAGTCTAATA
GATGAAATATCTTTTCCTTCTTCTTTCATAATTCTTCTAATAGTTGATTTTGCAATTGAAAATTCAACAT
TACATTTTTCAGCAATTTCTAATATTGTCATTTCAGGATTATTACGATAAGTATAAATAATATCTTTAGT
CATCTTACTAAATTTATCATTATGCTCATAAGTTTCTCTTCTCTCTCTTCTTTGTCTTCTTCTACTTTCTG
CACTTGTTAAAACATTTTGACTCATTACCATGATAATCTTCCACCCTTTTTAATTAATTTAATAAATTGT
ATTAATAAGATTATAAAGTATATCTATGATAGTTTAAATTAAATATATTGTAATCGTTTATCACATG
CCTGAATTACAATAGCATCCCATAAAGCATTATGTTTATCTTCATTTACTATGACATTAATATATTCACT
AGCAAATTCTTCACGATTAATATCCGGATCAATATTTTTAGTTCTAAATACTGTAGAAATATCATAATA
GTACATGTCAACAAATTCTGGAATTAATGTAGCATCTTTTCCTTTATTAATTAGATCCACAAATAACAT
CCAATCGTATGCCATTAAGTCACTAACAAATACTAGTTTTTCAGAACTATGCTTAGCATTATATGATAA
CCATTCGATAATTTTATCAGAAACTTCATCTTTAGTTCCATATACTATGGTGTCTTAGCATTATCCGAT
TTTGATGCTAATGCGTCATGTTTGTTAAAAAAATCGAAGTTTAGGAATAACATTATCATTCACCCAAACA
CTTGATTTCGTTGTATCAAAATTAGATACTTCCGCATAAAATAGTCTACCGTACGTATCTACCATTCCA
ATACTAATTAGGTCGGCATCTTTTGTTAAATTTGTAAATTCTGTATCAAAATATATCTTATTATCCATAA
TGTACCAACTTTCTTTAATTTGTCTATATATTTCTCAATATAATACTTGATAAGAAATTATTGAATTCTT
TTATTAATCGATCTAGCGCCTTATCATTAAGTAATGAATTTATATTTATAAATATGGATTGATTATCAA
TAAATTTATTGATATCTTTTATATCTATAACAATTAAGAACTTACCATTATCATCTTTATATAAAGAACT
```

-continued

```
ATTGATTGATTCTAATTTTTTATTTATATATAACATTTTACCATCAACAATAAATTTAGGGTTAGTATAC
ACTAATTGAAACATACCATTAGAACATTTCGATTCAATAGGTAAATATTTATACATCTTATATTCATCT
ATAGATATAATATCAATAATGCATGTAAACAAATATCTTTTAATGATTTTTCACCCCTATAATTTATAA
TTTTGATACTATAAAATAAATATCATATTTATAAATAATTATTATTCTAAAAAAATAAAAAATTCGATT
AATGATATATGACATATCATTAATCGAATATAATCTATTTAAGTATAGATACTGTTACGTTAGATGTCC
CACTAGAACCTATTTGCGATTTATCAATTAATAAATCAATTTTATTCCCAATAATTGCGCTTCCCGTATC
ACATGCTTTAGCGATAAATGAATTACCATTAGGATATGTAATTCTTAAAATACTGTTCATTGGAATTAC
TGATGTATCTACAGCTACAATACGATGACCTTCTGGAGAATAAATAGTGTTACTCACTTTAGTTCCATT
AGCAGTAATTCCTGTGCTTGGAGTATAATCATCCCCAACCGCATATACTGTCATACGAAAAGAACCAA
TTTTTCTGTATGAAGAATTTTCTTTAGTTGAAACATTCCGTACAGTTTTTTTATTTTTTACTTTATGACCT
TTGTTTAATTTTAATTTCTTGATAAGTTTAATATTATCATTCTTAATATTTTTAATAATTGTATCTTTATC
TTTAATTTTCTTTGTAAGTTCTTTTATATCAGTAGACATTTTATTACTTTTATTAACAATATTTTCATTTT
GTTCTTCTAGATTATTATTGATTTTATTCTGTTTTAATATTAATTTTTCCTGACTTTGGATCATATGGTTT
AGATTAGATTGATGAATCGTTTGAAATGCTGTTAACGATAGTAGTAGAATTACGATAATTGATACGCA
TGTAGTTTTAATATTCATTCGATTCAATTTCTTTTTCTTATGCATAGATTCCTCCATTCTATTATAACAT
TAATACTATTTGCTATAGTAAAATTATATATCAAAAAACCGTAGTATATTATTATTGTTTTAATATACT
ACGGTTTCTTATTTTATTTTATATTATTTTTTAAACAATATTACTAAGAATTTTTGGCGTTTTTTCCACAA
AATAAATTTCATCTGAATTGATCTCAATGATATTGGCAATTAGTTTTCTAATAAATCCAACAATATTAC
TGATATGGATAATTTTATTTTCGTTAAGAATTGAGAAGTTATCTAGTAATCCATTAACTTTTAGATTGA
TATATGAATATGATTCTTTATCAATATAAAATTCAATAAGGTCGGAATCGATAATCCTAACATTAACTA
TATTATACAAATTTGCTTTGTTTTTACTATTAATGTCACTAATAAGTTTATCATAATCATCTTTATCCGG
AGTATGAAAATAATATGGATTTAAAAGATTAATAAAATTGATCTGATATTCTTTTCCTAAAATATTAAA
AACTAATCCATTTTTTTCTGAAAATTTAGTTGTAAGAACTTTATCTATAATCACTTTCTGTTCCATTTAA
ACCACACTCCTATACCATATTATTAGTATTAATAACTTATTGTATTAAGTTATTATAAAATACCCAATA
CGTTAAATAATAAACGTATTGGGAGTATTAATACTAATAATTATTGAATTCTATCTTTAATTACAACTA
TTGTTTTATGGAAATTACTAACAAATTTAATATTTGTGTCATAATATTTATTTCTAATATTATTAGGGAT
GTGACCAATAATATCACTATAAATAGTATCAATAGTCTTATCGATATTTTCAATATCCGTATATACATA
ATGAGATAAGTTATTTACAATAATTTTTCCAATATCAATATATTCATTTTCAAACATATTAGTATATTCT
TCAGGACGTAGTAAATTCCTAAATAGATTTTCAATATTATTAATAATTACATCAATATTTTCATCATTA
ATAATATCATCGATATCATTATTAATAATAATATCAACAATTTCATCTACATAATAATTAACATTGTCT
TTTTGATTTTCAGTAATACCGATTAATCCATCAACTTGCTCTACTTTACCTGGATTATCATCATAGATAT
TACTATCCATTGATGTTGAAACGTTATCCATTTCATTAACGCTTGAATCTTCTTTATTCCTACCACTAAA
TAACTTATTAAATAATTTCTTAAACATACAAATCTCTCCTTTTATACTATATTTTACTATTATTATAATA
TATAAATAAAAAAATGATTAAATTAGTATATCTCCAATCAATTTATATTTTGATTAGAGATATACTAAT
TATTTTTAACTTATATAATCATCGATATTTATTTCTTTAAGTTTAATCGACATATCATGAAATGCTTTAT
ATTGATAGGTAATTTTTTGAAGTTATCTCCAAATTTTCCCCCAATCCAAACCGTACGTGAGACTTTCAT
CTCATACGGCTTTCCATCTACTAGGAATCTAAACCTAATCTGTTATGTATCTTTCTTTTTAGTAGACTAA
GGACTTTCCCTAATTTATATTTCTATAAAATATTATCGGTATCTTATCCTCGCTTTCAATCCAAATAAAAT
TTCAGTTATAGTCCAGATTAGACTTTCCGAGAAATAAGTATTATATTAATACTTTTGGATCTTCCCATG
TTTCTATAGACTTAGGTTTATTATATAACTTAGGACTTTTCTAGACCATATATCTTACTTCTTAACATGA
TAAGCTAATAAGGTTATTATCAATGATTAATAACTATTAGAAGATATATTTATACATTACTGTATAGGA
TTAAGTCATTATAGAAAATTAGTTAAATCTATCCATATTATACTCACCCAAACCAAGATATCTTATCCTT
TTTAATTAAAAGGACAATCTTCTTGACTTCATCCAGCTTCACACATAGTAATTACTTGCTATGCATGTG
GAATATTATTTTCAGGAAAATCTTAGAATCTTTGTTATCTAAGTCCTTGATCAGTCTATAAATTAAATT
ATATAAAAATATAATTCCTACAATCCCTCATATTAAAATAATGATTTCTGTAGAACATGTCACACCATT
GATAATCCAGTTAATGCATTCCCAATACCATTCGCAATTAGCCCAACATTCTTAATTCCCATTTGATAG
TATAGTTCGCCTGCACATTTATTACAGATATGTTCAGACTTACAGTAATGGACTACGCATTTCAACA
TTCTTATTAATAAATTTACCTTTATTTTCTTCGGTAAATTGCGTTAATTTATCACCGTCTTTTACATAACG
AGTAATAAATAAATTAATATTATTATTTGTAAGTGTAATATTTAAATATTTTTTAGATTTACAATCACTT
CCATGATCGCCAAGAATTATTGACTGAAATGCAGTGGCAAGTTTTTTCGCTTCATATCCACCATCTTGA
GTACCAATAGCACGACTTGCACTAGCACTTGTAATAATTTCTGCATATTGATATAGTTCGTCAGGAGGA
ATACCATCGTCTAGTGAAGCCATACTAACTCGAACATCATTTGGGTCCGCATAACTTTTAGTTACACCT
CTAGCTACCGCTGTTTGTTTAAAGTTATTATTAAAACTTCCACGGCTTCCACTATCATAAATATCCATAT
CGGAAGCATCTTTAAGAATATCATGGGATAATGTTAATAATTCTTTTTCTATTTTAGATACAGTAACAA
TATCCCCAGAATCAATTGCCTTTTTATGCTTAACAATCAGTTCTTCTTTTACGAGATTTTACTTGAGGAGG
AGTCATCATTAAAGTTGTACTAAGTGATGTTGCAATGAATTTAGTTATACCAAAGCCCAGCCATTGCAT
CTTATCAATATAATTACTAAAATCAGCTACAGTAATTTTATCTTCTAATAAGAGAGTACTTAATTGTTT
ATCTAACTTACTAATAGCCCCACCATCCATTGGATGATTAATATATCCAATATATCTTCCTAATTTTGC
ATCAATAATTAATAGGTTAAAGATATATGACCTACTGTAGTAGTAATTTATCTTTATTAAAATGAAT
ATTTGATTCTAATTCAAAATAATCACTTGGGTCAAACTTTGCATCTTCATTTTTGGTATATGCAAATAAT
TCTTGTAATTTTTCCATAGTGATATCATTCTCTGAAAGATTAAGAATCTCAATCTTTCTAGCATCACTAA
TCTTTTTACCTTTATATGCTTTTTGCAACTATATTCACATCCTTTATAAATTATATCCTTTAATATAAATA
AATGTTCTATTAGATAATAAAATTGTTAGGATCATAGAAAAAAAAAAAATATAACCTAGATATCTAGGT
TATATTTCTTAATATAATCTGACCATAAAGAATTAATACTTTCCTTATCTTGAACGCTTATTATGTCTTT
TAATTCAATTTTATTATTTTCTTCAAAGTATATATACGATAATATACTGGAGATTGCATCATAACCTTGT
TCATCCGTATTAATATAAACGTTATCATCATTACCATAATCCATAAATGTATTATATGATCTTTTTGATT
TTATTTGTACTGGTTGATGATTAATTACTACGTCTGTTCCATTCCTATCTAAATATGCAGAACATTCCAT
CCAAAATTTAATTTTCTTTTTATTAAAATATATTCTGAACTTTTCCTTAGAATTCCCATTACTGCAATTTCT
GCATAGTGACCTTCATTAAGCATTGGTGGCAGTTTATCAATACATTTTCCGTTGAATCCTTCTTTTCTTG
CTTGGTTCTTATAATAGTTCAATTCATTTAAATTAATATACATCGTAATATTCCCCCACTAATCGTATTA
TTTATAGTATTATTATTTTTTCACAATTCTTACATTTGGTTCGATAAATTTAATAAAACAAAATTTCATT
GATAGCTTTATAATAGTATATGTAGTTGCAATCATAAATACAATATTAATGAATATATTATTGTCATAG
TTCCACAATACTACGTTTGAAGCAATAATTAATAGAATGGTCAGTATTACCGTTATCATAATTGAGATA
AAGATCTTGTTTACTATACGATTATTCATATCATTTCCCTACCTTACTTTTTTACTTTTTTATAAACATGTCT
ACTTTATTACGAGAATCCAAGTATTCAGAGAACTGATCGATGAAAAGATTTATTGATATGTTATATGTT
AAGTATGAGAATGAAATCGATACTAATAAGTCTAGGTAAATATTATTATTTCTAAAACATACTTCATTA
ATAAAAAGAAACCATAATGATGACGTAATAATAATATTAAATATTACTTTGGTGATAAGATTTCTAAA
TAATTATCACTAGAATAGATACTTAGTATACCTTTCCTCTCTCTCAAAATTAAATATAGCCATTACAGT
TCTTAACATATTTTTTCTACTTTTAATTTCGATATTCTTAATTAAAAAGTTGCATAAGAATAACACTGCT
```

-continued

```
TTATTTATGTACATTATATAATCAACCCTTCTTTTTTTTATTTAATCATTATTATAATATATCATTAAAAC
TTGTATTATTACATTTTTTATAAATTAGAGGGATATGACAAGTTATATGTCATATCCCTCTAATAAATA
TAATTTATGCTACGTAAATAATATATTCCATTTCAATATTTGTAGATAATCCACTTAATGAGATAGAAT
CAAAAGTCAATCTTGATCCACAACTAATGTTTTCATAAGAGTTTTTAGTTTCATTGTATCTACCTAACC
ATAAACATAATTCATTGATCATTCCACCACGACATTCACTAGGGTCGATAGTTAATGATAGACTATATG
AAACTTCTCCAGTAAATGTATTAATATTCCAACCTTTAGAATTACCAAAAGGTTTTGAATTTGTAGCAC
CATTAAATCGTTTACCATAATATTTTACAGTACCATCCGGATCAGCTTGTGGTAAATAATATTTCATTTT
TTGTTCATCAGTAAGCTCTTTTACAATAGAGGGATTATCTTGAGTTTCAGTATCATTATCCTTATCAGG
GTCTACTGTAATAAAAGGAAATTTTTGAGCTAATCCATTATCATTAAATTTTGGAGCAACTGGAGTGA
ATGGACTAGCATTAATATCCGCCCCTCCTTCTCCTACTGAGAATAGACAGATTGATCTTGCAGGATCAT
AGACTTCGTTGTATGTTGATGGATGTTTTTCTTTTAATAATGCTTCCATTACAAATACACGAGTTCTTTG
TAAAATTAAATTATCTTGAATATTGATTACTTGTTTTGTATCTGCATTACGGAAAATAACTTTTCCTCGA
ATTCCTTTATCTGAATCTGCAGTACCAATATTATCTTCAAAAATTTCTTGAATGTTATTATCTTTAGACA
TAATGTGGATTACACTTCCTATTCATTTATTTTATAGATATCGATCTTAATCATTTGATTTAATAAATAA
TTTATCACTAAACGTTATATTATCATCAAGACGTTTTGTTAAGTTTAAACTATGAGAATCAATTATAGA
AATATAATCCCTAAATAGTATTCCACCTATTTTAGTGACATCCATGGTATCAAACAATCTTATACTGTT
ATCCATTTTACTATCAAACTTATAAATAGAACTACTATAAACTGTATCGATAGTATAGGATTTAAATAC
TTTTATGAGGATATAAATATATGATTTTACATAATCAGATAGACCAATCGTATTATTTTGAGTTAAGAA
ATCATATTCCCCTAGATTTAAATGATTATCAATACTTTCAACAAGTTCAAATATTCTTTCACGATATAT
ATCATCTTTACTTAATGAATCAATATCGTATATATTAATATCTACTTCTGTATAGAAATATAAGTTTGG
ATCATTATCTTTTAAGTAATCTGTAAACGTATTATATTTTGAGAAAATATCCATATTTAAATCATTTGTA
AATTTTTCATTCCATAATTTATTAAACAAACTATATAGTTTATAATCATTTGTATTAATAATTGTTTCTT
CTAAGTCTTCCCTTAGTTTTTCATTATATCGGTATATTTTTGCGAAGTCATTCATAGTATATCTTCTTTTA
TTATTGACTATTTCATCATATGAACCAAAAACATCTATAAATACCGATAAATTCTTATAGTTTATTAGC
TGTTTTCGATAAATATATTCATTGACTGAAATAGCTTCATCAATAGCTGAAGGAATCATATCAATAACT
TTTCTAAAGTTCTCAATAGTTTTATTTCGATTATATATATCGAAAACGGTACTTAACCTGTTAATACCA
AGCTTATTTATAAAGTCTCGCATTTCAGACATTATTACCACGTTGTCCATACCAAACTGGAATATCTTA
TCAGTACTAATATATTTAATATCTACCTGATAATTAACAAATCTTGATAGTAATTGTTTCAATAGACTA
TATTCCGATATTATAGACATTGATATTTTTCTATTTTTATCAAGAAGAATATTCATTAAGTATTCTAATC
CATCATAAATATTACCATTCTTAATGTGATTTTCTAATTTCTTAGAACCGTTAATACTTTGGATGTATTC
TGAAGTGAACTGCATTTGGTTTTGGTAAACTATTGAAGAATTATACATTGCTACAATACTATCAAAATC
TTGGTCTATATCTAAGTCAAATCCTTTCAACTTAAATCGATTTAGATAACCCATAATATTTTCCCATTCT
CGTACTCTGAATTTTCGTTTATTCCAGAAAAGATATTTTCTTAATGAAATAATAATATCATTTACATTTT
TATCAATATCATATCCGTAGGTATGTTCTAAGAATGGAATTTTTCTAATTTTATCAGACCAATTCATTCT
TTTTAATACCAGTGTTATTAATGCAACAATAGCATCAAATATATGAATTTCACTATCAGAGATATTGCG
GTTATTAAATTTAAAGTCAATATTCTCAAGATTAACTACTTTTGAAGCTTCTTGATAGGTAATATTATT
ATCACTAGCATATTTATTGATTATTGCTCTATTTTTAATTTCTAGGTCATTTAATAATCCATAAAAGTAT
GATAATTGTTTCGAATTATTAATCAGATCAAGAACAATATCGACTGAAATATACTTTGTATTTATAATA
TTGAATGATTGTTCTAGTATATTTTTCTTTTCAGCTCGCCAATAGGGATCACCTTCAGTAATTGCGTCAT
AATCTACCCTAGGATGAAGCGAAAAATTTAATTCTTCATCAATAGGAACTTTATAGAATTCTAGTGAG
TCATCACCGCCTAGATTATTTTTCTTAGCAAGCATATACCTATTTATCTGTACATTATCAAAAGAGAAA
AGATTCTTTATGACATTGAATACATCATTATCTCCCTTGTTACTAATCATTTCATTTATGAATCGATAAA
TTCTTCGTTGATAATTTACTGGAACAGAATCAAAATAATCTAATCCCCATGATATAAATCCATTTTTTA
ATTTTTTTCTATCATAAGTATCAATATTAAAGTATCCTTCCATAGTCTTATTAATATAACGCATTATAGT
CATAAATATTAGATATTCTCGATATACTTCACGATTATATGTTTGATTACTAAATGCTTCAGTAAACGT
AACATTTAGGAAATAATTAATCGATTCATAGTAAGCTTCATTAAATAAACTTTTATGCCATTTATCTAA
TGTATTACTAGTTTCTTTAAGTATATAGAAATCTTTTGCTCTTGTTGCTGCTGAGACATAATCAATATTATAT
CGATTAAATAAATCTTTATAATAAGGGTTTGATTCATTATATCCTTTAATGATATTTGATTTTTCTGATT
CTGAAAGTTCCGAATCACTATCATATATAGCACTTAAATATCTACTAGAATTTAATAGTGATGAAGGA
GTTTCATTTGCTTCTGCCAATTGAGTATCCTTAATTACTAGTCCACGAGCATAATTTATAACATCTTTTA
TTTCATTAATATCCTAGTCTTTAAATGCATTATAAAAATAATATGGTGTATATTTTCTTAACATCTCTTC
TTTAAATTCATTGACCAATTAAAAAACGCCACCATTCTATTATTATTTTTTATATTATAAAGAGTTGTTCAT
AAGTTATAATATCTTTTTAGTTTTGATATAGAACAATATACTATATATTAAAATAAAGTTAGGGTGAT
TTATATATGAATATTAAAAAAATAAATAAGAATAAAACAGTAAGTAATATTGTATCTATCAGTAAAGA
TGGAAATATAATTCTTAAGGATAAGAATTATACAAGTGATAATTTTTTAGACTCATTCTATATAAAGTC
ACTGGATAGTAAATCTATGAATAAATTTATAAAAAAATATAGAATCATTAATTCGAACATCATTAGAGT
ATTCTAGATATATTGGGTATTTATCTACAGTTCAAAATATCAATACAGATGCAATTATGGCAAATATTA
ATTCTGATGATGCCAGTCTAGAGTTTCATCATTATCCATTTACTCTTTATGATATTGTAGAAATTGTTAT
AAATAAAAATATTGCATTACAAGAAAATTTTACATCAATATCTATAGCTAGGGAAGTTTTAAAATTAC
ATTATGATAATATGATAGGATTATCTAGAGTCAGTAGAACGGTACATCAATTAGCTCATGCCGGCGAA
ATTTTTATTCCATTAGATAGTATATTTGGAAGGGTTAATGATGTTCGTTAATGATTTTTATGAATATATT
TATCAAGAACACATTATTACGTATAATAAGATTATTGAAATTTATAATAATAAGAATTATGATAATGA
TATAACAAAATAATTTTTAGTTATATATTATAATTAAAATAATAACTATTATAGGTGGCGATTATATGA
AAAAAGGAATAGACGATTATATTAATAAATATATAAGTGATGATCCAGAGACTCAAAAAGAAATAGA
TCTCATTGTAAGTAAAATAAATGATTTTAATAATAATTGTATTGAATTGATGAATGATGAAAATATGAT
CTGTGAAGAAATATTATTAATGGTACCATTAATGAAGTTAAAGACATTCTATTAACGTTATCAAATA
CATTTACATCTGTTTATATGGCGAACAGAGTTATTGAAAATATTGAATTATTTATAAATGGTGAAAATG
ACGAAGAGCTTCATGAATATATTTATATAATGCAAGATTCAATTGAAGATTTTGATGATATTCCTTTAT
ATGACAAAACGTTATTGTCTGAAGCGATTAATACCCATTCAGCGAGCAGAATTTCTAAATATGATACTC
AAAGAAATACATATCTCAATATATTTAGAAAAAACACTGAAATTATTAAACGATATTATGGATTATAA
TAGTGATAATTTGCCTTATGATATGTCTATAGAAATTAATGCATTACTGATGAGTTCTGAGTATACATT
ATCAGTTATATTAAGTCAATTTAATCATATTATAACTAAGTCATATACTAAATATCTAAAGATCGTTGA
CATTATCATTTTAAACCTAATACCATAATTTTATGGTATTAGGTTAATTTTTTTTTTTTTTATTTTTTAAGG
TTTAAACTACCTAGCACATTTGTTTCTTTATTTCTAATTCTTTCATCAACAGTATTTAATAATTTTAAATT
ACCATAAATTACTACTGCATAGGTTTTATTTTCTTCCGGATTTTTTGTTTTAACAATTAATTTATCAAAA
TCAACAGAATATTCATCTTCTGTAAGCATTCTGTTATTTGCAAATATTTTTACTTCAATACATTTATCCA
TATTTCCATTATTTTTTTCAATTTCTTTAGCAACACGAATTAGTCCTGAAGACATTATTGATTTAATATC
CAATTCATCATATGCTACATTAAAGTCAGGAATAAATTCTGAGAAATATAAGATTTGCTTTTCATTAAG
AGTTGGAGGTATTAAATCTTTTTGAGTTATAATATTAAACTTAAATGTATCACTATTATCTATTTCTGGA
```

```
ATATCTTTTATAATATTTTCGTTTCGCATTTCTAAAATAAATGATCCCGGCATCCATAATTCTGCAGTCA
TTGCATATCGCACTTCAGAATAAGAATTGATTAGATTATTCATTATTTTTTGAGAATTTGCTAATTCTGG
ATATCTTAACATGATATTTGCAGGATACTCGCACATATAGGTAGGATTATTTGTAGACATATTTATTTT
TTCTATAATTGGGTTTAGTGAATGAGATAATAAATATTCACGTAATTTATCTTTATCTTCTTCATTATCA
AAATCTAAACCTAATACATTACATATATTCAATATAAATGATAATGGTATTTCATAAGGTATTCTAATA
TCATTAAGGTAATTTACTCCGTTATTCTCAAAATTCTGATTTAAGAAATTTAAGTTATTCCAAGCAGAA
AGTTCACTAGGGAGTTTCATGTATATATCAAAACGTAATTTTATCCGATTAGGAATATAAAAAATACG
AATATCATTTTCATGATCTTCAAATACCATTTTGTATTCTTTGTGTTTATTACGATTTTTTATATAATATT
GATGAGTAGACCAAAAAGGTAATATATCAATAAATGTATCACCTAACTCAAATTTAGGGGAGATTCCA
ATGTATGGTTTAGGCATATCAGTAAATAACCCTTTACCATTACTAAAATTAGTCGAATTTAATGATTCA
CCGATATATACCTTTTTAAAATATTTAGGTGGAAATTTGCTTATAAAATAGTTTGATATGAATGATGAT
ACGCCACTAATAACATTATGTATAGATGGACTAGCAGTACATAATGCTACACTATTATTATATTCAGAT
CTTGCAGGATCTAACATAAGAGAATCACGCCTTTCTATATAATGTTGTTCACAAAACAAAAAACCCCT
ATTACTATAGTTATATAGTAATAGGGTAAAAGATCAGAGATTGTGGGATCTCTAAAAGTGTGAAGTAC
AGAAAGCATATACAATAGGTTAAAAAATAAAAGGTTAAAAAAATCCTATCGTATAATATATTATTTAG
AAAATTACGCTTAAAAAAATAATATTATCTCTAGGTACTGATGCTCGAATTGTATACATGTTTGAAATG
ATGAATTTATCAAAGTCGAAATCTTCTCCAACAATTTCTTCAAACTCTTCATTTCCTCTAATAAATTTAT
TAATGATAATAGTAGTTTTATTAATAATTTCGTTAGTCAAGATAACCTGTACTTTTTCTACATATTTATT
CATGTTTTTATCATCATTTTGATTTTTAACTTCAGGAAAATTTTCATTTTCCGGTTTATTTAGTTTTAATA
CAAATTCAGGATTATCCTTATTAATAAAGATTCTTGAATTATTATCTTTAAAATCAACTTTTTCTGATTC
ATCAATAATTTTTCTTAATTCATTAACTAAATTTTCTTTACCGATAAAACTAATAATGTTATTTCGGATA
GCAATTTCTTTTCTGAGTTTAATCAGTTTTTCATCATCAATCATCTCATTTAGTCTTTTCTCATTTTCATT
ATAAATCATCTTGTATTTTCTTCCCTTCTAATTCCTTTTCAGGATTATATGTTAATTCACTATTAATTTCA
TTATTTTTAATTTTCATTGCAAGATCTAATATGTCATCATCTAGTGTTTTTTTAAGTTCTTTACTTATGCG
TATATTTTTTGAATTTGGGTTTTCTTTAAATCTTATTATTAGATTTGTTTCTGGATGAGTATTATAACGTT
TTTCAGATATTAACCGATATACTTGATTATCATCTTTCCATAGTATTTTATTTAATAAGTCCATTAATGT
TTTTTGATAATTATCGATATCTGGTTTTTTAATTCTTTTTTCCTGATTTGTCAACATTAGATATATTTTAT
AAAGGCTATTTCCAAACTTTGTTGGAATATTACTAAATATGGATTCTAATTCTATTGGACCTTCAAAAG
CGTTTTCATTAAAAGGTATTTTATTCTTATGAACTGAATTATATTCGTTTATAGATTTAATTAATATTTT
TCGAAATTCATTTTTATACCCACCTAATGGATCGTATGTGCTAACAATGATATTAAATCTATGTCGTTG
ATACGGTAATATTTCCCTATCAATATTAATATGTATTTCATTTTTATCAAATTTAATGATATCTATATTT
GCATTTAAGATATACATCTTAAAATTTCTCGATTTTGGTTTTTTAATTTTTATATCCAAAGGTTTTTCTTC
ACCATTAGGAATAGGTCTTTTTTTCATTACTGCTTCTCACCTCCAAAAGTATTAGTATATAAATAATTAT
TATTCAATAATTATAATTTTTAAAGTAAAAATATACTCATATCAATCATTTTAATATATCACGATATA
TGATAATTAATTAATTGATATGAGTATATAAGTTATATAAAATACTGATGCCATTATTAATATTAATGC
AGTTACTATATAATATATTAACTGCATTATTTTGCTTTTCAGATCTATTTATTCTAAACGTCATATTCAT
ATGACGTTCTATTTCTTTAAATAATTTATCCATAAAGTTTTCAATATCAGAAGTAGTTTTCTTAATGGGT
TTAATTTCTTTAATTATTTCATTAGTATATTTATTCGTTTCATCTGCTTGTTCTTTAATTGCATTTAAAAC
AGCATCAGTTTTCTTCTTATGTGCTTCAAATTCTTCTTTTGTAATATATTTTTCTTTATCAATATATTTAT
CGTTATCTTTTCTTTTAAATATCCTTTTTAGTAGTGCAGTGAACTTTTCCATCATCCTTAAACCCACCTT
ATTTTTATTTTAATAAAAGGTCGGGTACGATATTAATAGCTGAAACAATTATACCACTCAGAGCAGGT
AACAATGCTAACCATATTTTATTTCTGCTTTCACTATTATCTAATTTATGACTATGTGATAATTGTGTTG
TTTCAAGATTCCCTATTCGTTCATCTGAAGATTTTGTAAATGAATCTATTTTTGTCCTAGTTTCATTTTTA
ACTTCCTCGATATTTGAATTAAATCTTTCACCAAGATCATCAATTTTATTAAAAATTTGACTTGAGAA
TCATCAAATTTTTCTTTAATATTATCTACATTTTGACTTATTTTAGCAATCTCTATATTTGTATCATTTAG
TTTTGTTGAATTTTCATCAGTTTTCTTCTTAATATCTGAAGTAGTTTGATTATAGTTGTCGATAAAAGT
TTAAATTCATTTCTGGAACTAGTTCTTTTTCTGAGTTATTTGCCAAAACCTCACCCCCCCAGTTATAGT
AGCCATACCGTTAAATACCGATATGATTAATAGACGGTTAAAGTTTGACTTAATGAGAGTATTTGTATC
GTTTACTGCAGAAGCATAAATTATCCATGCTATTGTTGCAAAGAAACATGATATCGCTATTATAATATA
TCTAGAGGGTTTCTTATAAGATATAAACGCCGATATAATGAGTAATGAACCAGTAACAACAAAGATAT
ATGACCATATAATTATGGGAAATACCCTATTTAACATAATATATGTTTCAGAAGTAAGTAATACACTA
GATTCGGCAATATTAAAACTGATTCCCGTACTTAATGATAATAATCCTAATAGGATTAATAGAGATTGT
TCCATCAAAAGAATATAATTAAATTCATTCATAAATTTTTTAATTATATTTTTCATTATAATAAACAATC
CTTTCAGAAAATATCAATAGCACTTACCCGATTTAATAATTCATTCCACTGAGCTTCAGTCGGAAATCC
ATTATCACCTTTTGCACCTTTAAGACTAGCTAACCATTCAGCTTCAGTTCCACTAAATCCAGATGCTTTT
GCTAGGTCGTAAGCAGACTTACCGTTATCACCAGTGCTTCCTTTATCGCCTTTATCACCTTTTGCGCCTT
TAATACTAGCTAACCATTGAGTTAATGTACCGTTAAATCCATCAGCAACTGCTAAGTAGTAAGCAGAC
TTACCGTTATCACCATTATCACCTTTTGCGCCTTTAAGACTAGCTAACCATTCAGCTTCAGTTCCACTAA
ATCCAGCTAATTTTGCTAGTTCGTAAGCAGACTTACCGTTATCTCCAGTGCTTCCTTTATCGCCTTTGC
ACCTTTAATACTAACTAACCATTCGGCTTCAGTTCCACTAAAGCCGGCTAATTTTGCTAGTTCGTAAGC
AGAATTACCGTTATCACCAGTGCTTCCTTTATCGCCTTTGTCGCCTTTTGCACCTTTAAGACTAGCTAAC
CATTCGGCTTCAGTTCCACTAAATCCATCTAATTTTGCTAGATCGTAAGCAGACTTACCCTCTTCACCA
TCAACTCCGGGATCACCCTTTGGTCCACGGTCACTATCGGAAACGGTATCATCTACGATATCTTCATTA
GGTTTATGATAGTTAACTTGAGATATTTCATCAATATTACTAATTACATTAGTAACTCTTCCCGCTTCAG
AATACGTTAATACAAGTTCATCACGATCATATTTTAATGTACCACTACGTTTAATATCTTTTACTAGTA
CTCGATGATCTGAGTATATTGATGTGATTATTATTTCATTTTTGTTATGTCTATCGATGTATTCTTCTATT
CTATATCCTATAGCCATTTTATTATATCATCCCTTTCGTATAAAGAAACCTTTATATAATTTTTTGTTTT
ATATATTGGAGTTCTAAATATAAAAATTATTATGATTTGTATATATTAATAACATCTATAATTCTAAGC
TGTGCTTCTTGATATAATTTATTCTTCCAATCTTCACCTAAGTCAATAATTTTATTTTTTGGTAATGTTTC
TAGTAATTCAATCTTATTTTCACGTATATCGGTAGTAATTACATCATTATCGTCATATACGGTTAATGAT
TTATAATTATATTTATAAAATGATAATTCTATAAATCTACCTATATCGTTTATATTATTTTTTCCTATAA
CTACTAATTTAGGTATCATATAATCATTATAATCAACTTCAATAGCATTATCGTTATCAATATATTCAA
TAGTTGTATGAATTTTATCATCTTCAGTAATTACTTCTGGAAGATTATATGGTTTAATACTGAAGTCAA
AACCATATTTTTCAGAATAGTTATACGTATCTGTAATATTAACAGAATAGTTTCGTATTCCTTCATTTTG
AATTGAATTAATATCGTCTATATTATTAAATAAATAAATATTATCAATATTTGGTAGTTCTAAATAATG
ATAATTATTGAATTCTCTTTCTAGTACTGTTTCACTAAAGAACATTGAATCAAAAAGATAATCATCATC
ATTGTTAGAAGTAATAATAAACGTATTAATACCTTTATTAAGTTTAATTTTTATTAGCATATTCGTAAAC
ATTTGTTTGTTCATTATAAATGCTTAATCGATCATGAGATATACCTTGACTATTATATTTATACGTATAT
GACAATCCGTTAATATTTACTTTTGCATTACGATTATATTTATCACTAGGATTATATCCAGTAATATATA
```

-continued

```
CATATTTCTCAATATCATTTTCTAGGTTAATCTTAAATTCGATATTACCTTTATTTATCTTTACTAATTTA
TTAGATAATAAGTTATTATAAGTATTATCAACAATCTCTGAAGTATTATCATCATTTACTGTTTTTAATG
AAGATGATAATTCATATCCTGTAATATTTCCATTAATTTTTATAGGATCGATGAAATGATTATATATTG
GAACATGGTTAATAATTGCTTTTCTAAGAACTAAAATATTAAAATCTACATTTTTTGTATTTCTAGGTT
GACCTGACTTTAATAATATTTCTTCAATATAATCATTATGGTCAGCATTAATAATATTATTGTTGATTTG
ATTCTGAGTATACATACTATACTGTTTAGGAGTTATATCTTGCCATACATTCTTGTTATTACCATTAGTT
GTTAAACTTCTTTCAATATTATTAATAAAGATTGAAGATGTTTTAGATGTCAGATTATTACTTCCCATAT
ATACCGTCATATTGTAATTATTCATTTCAGGAATAAATATCTTCATTCTTAAATACCCATCTTCTAATCG
AACATAACCCTTTCCAAAATATTTTAAATAGTCAGAAGTCATTCGTGATCCAGAAGTTTTAGTATCTTC
ATATTCAAATATTGTTCCATCATAACATTCATATACATAAGTACCGTCAGCTAGTATAGACGGATATAT
GACTCCATCATTATTGATATAACCATGAGTAATGATATCCTGATCAAAAATAATATCTTTTGGATAGTG
TGGATGACAATAACACTCTCCATTACAATTACACCCATTATCACAGTCATCATCATCGTCATCACCATT
ATTAGGTGGAGTAAATTTATTATTAATGTAATTTACCATTGTTATACTGGTAGGATCAACAATACTTTG
AACTTTTCCATTCTTATCAGTAAAATTTATTTTAAAATCTTTATGTTCTAATAAGCCATCATGATTAATA
TCTTTAATTAATGTCTTAACATTAGAATCGATTGATGTAATATCAATTAATCCTGAGTTATGATCATCA
ATCATTTCTTCAATACGATAAACTTTCATATTTTGTTTCACCTACTATCCGTTTAATATTATATTGTTATC
TTAAAAATTTTAGGACTTTTTGACCTATTCCATATTTAATATCTTTAAATTTATTATCTAATGACCTAAA
TGATAAAACTTGGACTGCTCTATCCCTAGTCATCAACAAGTTTGTTTTAATACGTTTCATTAGGTTTAAT
TCATCATAACGCATTCCTGCCATACACTCAATATATGATGTTAATCCAATATTATATCTTAATTGCTTA
ATACGCTTAGAAGCCATTAGGTTAGGATATAAGTCACGTACTTGCATAGATACGGTTACTTCACGAGG
AAAGTTTTCAGCAGTCCATGTTTGTTCTTCGCCACGAACCATATTTATTGATGATATTACGCCACATTC
ACATTCAAATCTTCCTGGACAAGACATTCTAACCAAGAAAGGTTGTTTATAACTATAATATGCGTCTTG
TAACGGTAAACCTAATACCAGTAAAGATACAAATGGTACATATACATAATTGAATATCGCTCTAGGAT
CTCCATAAGGAGTATAGAATCTAAATTCTAAATTATACGATCTATCGAAAGTAGAGTTTGACCATAAG
TCTGGATAGTATAACTGAGAACCATCTAGATTTTCAGTAAACGCACCAACTAAGCTACCCAATACCGG
AATTGTTTCAATAACGTCTGTTATCATATCCTTGATTCCATCAGTAATAGCACCCAATAATCCTCCGCC
GCCAATTCAGGCAAGAGTTTTATTTTCTCTAATTTCAGCCTGTTTACTATTAGATTCACTAGCTAAAGA
AGACTGAGAATAATCATTAGATGAACTTTCTGATACGCTGGTTGATTTATTTGCATAGAAAGCAATGC
CGTAGTTATCACCATTATTATATTTACTAAAATCGAAAACACCTTCTAATCCCATAGAATGATATATAT
AGCTTAGTATTGTTTGTACATATCGATAATACTCTTCGTAATTTTGTTTAAACGATATAAATCTTCCATC
ACTAAACTTATTTGCATTAATCATTGGAAAGACATTATCTTCAATTTTCTCTCCAATACCGAAAAGATT
AAAAGTGTTTCCTGACATACTACCAAATAATTTCTTATTTAGTCTAGGTTTTCCGGGAGTAATAAATAT
TACTGGTAGATCATTTTCGAATGTATTTCGGTACACTCTAGAGTTTGCATCATCTAATGGACCATATTT
AAGTGGCATACCTAATACCCTTATATTACTCTTTACCATATGAAGCATCAAACGTATCTATTTTAGTATT
TCCAAAAGCATTAATAGTTTCTCCCATTGCATTGACATATAGACCTTCATTATTAACTTGTGAAGGGTC
AATATCATCTTCTTGCATTAGTGTGTCTCCCTCAACTCCACTGTCTGGTTTTACAATATAAAAATCATCA
TCTGAATCCGTATTATTATTAGAATTTTTATTACTTACTAAATCAGGCATATTTTCACCACTTTCAAAAT
AAATTTTCCTTGAGACCAAATTTAATACATTTATGGTCTCAAGGAAATAAAATTTAATATCCCGCTAAT
ATAGGAGTTATACTATTAGGATCAAGTTTAAAGCTTGGTTGATCTAATTTATTATCTCTATCATTTTTAT
GATCATTTCTAGTTTGTTTTAAGATGTTATTCGTTTCATTAGTTAAGTTATTATTAGTTGCTTCTAGTCTA
CTAATATTTCTAATTTCACGAATTAAATCACTCAATTTGCTGATAGAATCTTTATCATTCTTATCAATTA
ATTTATACATCTTATCGAGAATATGATTTACTTTTTTAAGTTCATCATATTTTTCTTTATCATATTGGTA
AGGTTTATTAGGTTTAGCGGAACTTCCATTAGATCCATTTTTACCATTAGAACCGTTAGCACCATTAGA
TCCGTTTTTACCTCCGGAACCATTCTTTCCACCGCCGTTAGGTTTAGCGGAACTTCCATTAGATCCGTTT
TTACCATTAAAACCGTTAGAACCATTACCATTAGAAGAACCACTAGAACCAGGACTATTATCTCCAGA
ATATCAACCCTTAGAGCCACCACTTTTAGAAGGTTCAGCGGTTGCTGAAGTTGAATTACTACCATCTTT
ACCATTAGAGAAGTCTTCATTATCTCCTTTTAGACCGTATTCTTTAGCATATTTACTGTTAATACGATCA
CCGATAGCTTTCTTTTCTTCTTCAGTTAGTTTAAAGTTAGCTCTTGATTTTTGTTCTTCAGTTTCTTCATT
AACTTCTCCAGTACCAGACAGTTCTGCACTACCATCAGCAGTACCTCCAGTGTTTCCACTAACTCTACC
AAATCCTACTAATCTACCAAACCAATCTGCAGGCATATTTAATGCATCACTACGAATGTTTACACCTTT
ACTAGATTCAGCATTGATCATTTTCCCTTCACTGATATAAATACCTACGTGGGAAATAGAACCATCTGG
GTTTGCTGAGAAGAATATCAAATCACCAATAGATAGTTCATCTTTTTTAATTCTTTTAGTAGCTTTATAT
TGTTCTCTAGAAGTACGTGGAAGTTTCTTACCGACAGAATTGTATGCATTCATAACTAGACTAGAACA
GTCAAAGGTCTTAGTTTTACCTAAACCAGAACTTGGTCCCATTGAGTATGGAGTACCGATATACTTCTT
AGCATATTCTACGTCTTTATATCCTATAGATTGTCCGTCAGTTTATCAGAACTTCCATTATTGGACATT
ACAGAACCTAAATTACTTCCAATATCTTTACTGGTATTTTTATTTTCTTTACTAGACGATACTTTTTGGT
TTGTAAGATCTTTTAGTTTTGCACCCTCTTCTTTAGCACGTCTTCTTAATCCCGCTTCTTGATTGGTTCCT
GCATATTGACCCATATATTGACTTAATCTTTGTTTTTGGACTAAATCAATAATTTGATTGTCTGATAGTT
TACTAATATTTTTCTGGCTAATGCACGTTTAAATAGACTAGTTGCACCTCCAGCACCATGCTGTACTG
AAGCACTTAAAATTAATTCTTGAATACCTCTAGATCGACCACTTAAATCAGTTCCCAGTGCTTTATTTA
TTTTAGCTAGTCCTGGATTATAGAAGTCTTTTTGGAAGTATTCTTGTTGTGCTTCACCAAATGCTTTATT
TTGTCCTAATTTTTTCCAAGAAGCATCAAAGCTAGATGAACCTGGAGAACCACTAAGCTTTTTAGCAA
GGTCTGGATGAGCTGATCCTAACCATTTAACAAAATTAGCCAGTGATCCTTTAGTAGATGAATATTGGT
AAATACCGTAAGATTTACCGCCGGCATCTCCAACCCCACTAGAGATATATCCCGCACCACTAAAGTCT
TCTTTACCAGTTTCATAAAATCTGGCTACTGAACCAAAGTCTTTTGAAAGATTCTTTCCAGCTCCGGAA
CCGCCAGAGTTTCCACCAGTCGATGCAGCATTTGCATTAACGCTACCTAATCCTTTTACAATATCTTTT
AATTTATCAGTAATTGATGAGAAGAAATTGCTTATTTTACCCCATACTGATTTAGATGGTTTATTTGGA
TCAAATCCATTTTCCGCCATATTATATAATGCTGCAACCGGAGTAAGACTGAATAAAGATTTAGCAAA
TGATTTAGGATTCTTTTTCATATCTTGACCTACTCTAGATGACATTAATTTACTGTATTCAGAACCCATA
TTCATAACCATTCCTAATGGAGTAGCATCTAAAAAGTCTTTAAACTTACTTTGTTCTTTACCATCTTTAC
CTTTATCATCTTTCTTTTTCTTTCTAGCATCATTGAATTTTTCAGCAATACCCATTGGAGTTAATCCGTA
ATAGTGCATCTTTAATCTTATTTTTACGTTCTTCGGATTTTTTCTCTTTATCATTCTTTTTCTTTTCTTTTT
CAGCTTTATCACCTTTAATTAAATCCCCAATAGAAGGTAATTTAGGATGCTTGCAGATTTACCTGATT
TAGCACTCGACATTCCTTTTACAATTGATCCTACTAATATAGAACCTAATATTGCTGCACCGCCAACAG
CTAATGCCGGTCCGGCAATTGGAATTCCAGATACTAATGATAGTAATGCCCTTCCACCCATTTCCTGCAA
TCCTAAGAGCTGATGAGATTCCAGATACTAATTTTTCTCTGGTTGCATTAAATATTGCAGTTCCTCTTTC
AGTAACAGTTCTAAATGCTTCAGTTTCACCTAGACTTTTCATTCGAAACATCATTCGAGCAATTATTCC
TTTTTTACTTTCTGCGGATTCTAGTGCAATATCTTTAGTTGCTGAAGCCATTCTCATTTTAGCTATTAGA
TTTTCAGTTTTTTCACGAATGGAATTGATTGTACCCATTGGATCTTTTACTGATGAAACAATTGATCCTC
```

```
CAACTTTTTTAGCAGTATCCATAGCAAGACCGCCTGCATTTTTGACCATTACACCAAATTTTGTATCTTT
AACCATTCCCCATACAGATCCGGCTGCATTAATGGCTCCAGATATAGTATCTTGGTTAATAATATTATC
GGGTTCACCGCTAATGATATCACCTTTAGTTTTATTATTAAACATATTCATACGATCTTTGGTTTTCTTG
ATTTTATCTTGCATAGAATGATACTTGGATACAATTGAACTACCTAGTTTACTTGAAGGATTTTTAAAT
GCCGAGCTTGCATCTTTAATTTTGGTTCTAGAGCCATAATCCTCACCGACTGAAATATCTAAGATATTT
ACAGGGTCGCTTGCGTCAGGAGTAACATCTTGACCATTCGCATTTTTTACAAAATCACTCCTAAGGTCT
GATACGCTTGATGCAATAATTGACAGATACCCTAGTTTCTTAGATATYTCTASKRAGAATAWWTMTCY
WCTYMRYATMMTTWTMAWTAWWTCYASTAAGAATGCARMATTAGAATCTATGATASMGTKRAKCW
RKWATCGTCATMAYGAGTWATATTWMMKRTASTTTCATTATCAAATAATCCAAATAATGCATTTTTT
ACTGATCCTAGAGGAGTCTCTGCTTGTAAATATCTTTGACCTTTTACTTGTGTCTTAAGAACATTTCTTG
AAAAAGTTGCACTATTACCATCTATAATCTGTGATAATTTTTCATAGATGTCTCCATCAAACATGTCTT
TGTTATTATCTAATGCAGTACTGTTTTTAATATTATTTTTAGATAATTTGATAATAGTATCTTTAATATT
ATCATTATCGATTCCTGCTTCACTCATCATAGATTCTAATGTTGCATTCTTACTAGATTTATTTAAAAGT
ATGCTGAGTGGAGATTTATTCTCCGTAGAGATTGCTCTATCCATTCCAGAATTAAAGTTATCTTTAGCT
TTACTAGGATCTAACCATTTTCCACTCTTATAATCATATACTAATTTTTTGACCTGAAGAAGCTTCTAGC
ATTTTTGCTAAATAACCTGGAATTACCGTATTAATAGTATTATGAGTTTGAGCATCAAAGTTAACAGGT
CTGTCTGCTGAAACTCTAGCCATAGAGCTTACTTTTCCTAGATTAGCAGGACCAAATTGTCGATTGAGT
GAAGTCATTAGTGGATTTTCACCAAAGATTTTCTTAAATTGACCACTAATGATACTTTCGTCACCTTCA
ACAAGATTACCTAGTGCTGAATGTATTTTTCCGCCAACTTTACCATTGGGATTAGTTCGATTAAGCGTA
CCTTTAACCATTCTGTCAATTAATCTTTCTTTATTTTGGAATGGTCCAATTTCACCAGTAGATAATCTTT
CAATAGTGTCATATATTGATGCAGGTATATTTGATACATTCTTATCAAAATAATTTTTTACTCTATCTCT
TGCATATCTATTTGCTCGTTCATTAATATTTTTAGAGATAGAATTTTTTGCATTTTTAAGTAAGTCTTTA
GCGCTTGCATTTCCAGAATTTAGACTACTAAGTTTAAACATTGATGATGTTATTTTACCTATTCCAAAT
ATACCAGAAAGCATATCATCCATTAGACCCACATTATTGATACTTGCTTTAGCGCTTGCTTGAGATATT
CTATTCATTTTTTCTAATAATGTAGTAGATTTAGAAGATTGCTCGATTAATTGTGAATAGAATTTGATA
TTTGTTTGATTCATTTTATTTAAGGTATTATTTAACGTAGAAAATCCTCTTGTATTTACCCCAACTACTG
AACTTGCTGATACAATAGTAGATTCAACAATTTTATCAATATTTTGTTCTTCATTTACATCTTCATTATT
GATATGATCATTATTATCTTGAGGAGATTCGGTATCAATAATAACTTCAGAGTTAACGCTTGAAGTATT
ACTTGATTTTCGATTCATTTTATTTAATGATCTACTTAGTATATCTAACGTGTTTTTACCATAAGCTTCA
ATACCCAAATTATCTTGGTTCATTGAATTATTTGAAGTTCTATTATTCTTACTTTCCAGTTTATCGTCTA
AATCTTTAGATATACTTCGGTATATATTATTAGCAGACATATTGGATGCAGGAATTCGATTATTTCCTT
TTCCCCAATTTTTATTACCTTTATTCATATTGTCAATATATTTACTTCCCTCTTTAAAAGTGCTATCAATA
CTTTTATCTGCCATTCTAGTGTCTCACCAACTTTCATATGTAGAGATTAAATCGCATTATTAATCTTCTT
ATATATTAATGTTTAAGAATAGTAAAAATCTGATAACTTTAGAAAAAAAAAAAATAACCATATAGAGA
TAATATCTCTATATGGTAAATATAATTTAAAGATCAATATTAAATTGTGATTTTTCAGTTATAAGAGTA
TTTAATTCTTCCGCACTATATTTACTATAACGTTTATTTATAGTACTGCTAATATATTTTAAAATATAAA
CTAGATTTAATAATACGCTAAATCTTCTTAATTCTTTTTCATCTTTAGATAATTCTTTTAGTTTTTTTATGA
TATTTTCTTTCAGGATATTGCCTGCGAATATTAAGGAAAAGTATTTCTGAAATTACATCATTAAATTTA
TCTATTTGAAGCTTAGTTTTATATTCGCTAGGTAGTTCTTCTAGAATAATCTTTTTAAAATGATCCTTGT
TTAGATTATAATCTACAATAAGATGAGTAATGACTGAACCAATATATAAATATATATCCATAATTTCTA
AGATAGCTAATTTTTCATTATCCATAGATTGATTGTTTACTTCATATAAATATTCTTGTACTTCTTCCAT
TATCTGAGGGTAAAATCTTTCTAGCATTTTACATTCTGTTTCTTCTGGAAATTTATACTTAGATATCATA
TGTTTTTGATTTTCAATAAGATTTTCTATAGAGAATGAGAAACTATTGTTTTCTTCCGTAATAATTGATT
TAACTTTATAAGCCAAATTTACAACACCCACAATCTGTTTATTTATAAGTATTATTATCTAAAAGGGTC
TTGGTATTAATCTAAATTCCTTAATATCTTCTTCAGTATTAAGATTAAATTCAATTTCCCACTTATTTTT
ATTTAATATTTTTCGAATATTATAGTCAAAAAGAATTCGGCAGTATCTATAAAATTTCCTAAAATACT
TGTTCTAAAGTTATACGTAAAAGATTTTCCAATAATAATCTTTTGATTTTATACTGGTCGGTATTTTCCAA
ATTCCATTGATATCAATTCTGAAAAGATTATCTGGATCATAGTAAATATTAGAAAAATAATCTAATATT
GTTTTAATATCACCTATATTTCTATTATAAGGAATAATGCTTTTCTTAGTTTTCTTATGGATAATTTTTA
ATATACCGTCATAATTTTTTGTTTCCATAAGCGACATGCCTTTCAATTAATTTTATTAATAATTTATTTT
TGAAAACTGATTTTTTAGATATAAATTTATTCTAATATTAGGTTTGTATTGAATGAGTTAGATCTAT
GATATTCTCATTACTATTACCAGAATTATTTAGTACATTTATAATTCTTAGTAAGTTTTGTTGACTTTCA
GGAGTTACCTTCATACTCATATCATTAATTATATTATAATCTAAACTTTCTTTTGACATATTAATATCAA
TAGAATCAATAATATTAATATTTTCTAAAGATATATCTTTCATTCTTTTATTATCCTCAATATCCGATAT
AATATAACTAAGATAGAATATTGTCCGTAGTTGATTTATTCGGTAAGTATTTTTATAATGAATGTTTGG
ATACGTTATCATGAATGGTGGTTCAATCTTATCTTTATATTTAACATTATTATTGAATATTTCATCAATC
TTATAAACAATATCCTGATACATTCCCCTATACATTATGTCTTTATTGTAACAAACACTGGAATAGTAT
ACTAAATATACATTTATAATTAAAAACGAAAAAATATTTATCATTAGAAACATTTTTATTTCATGAATA
TTATAATAATTTATAAATGTACTAAAATTAAAAGATACTAGTAGTATACAAGTATTAATAGCTACTAG
GTATAAAGGATTCTTATAAATAATCTTACCAATAGTAATAAATTTATATTTCTTTAACAATTTAGATCA
CTTCCATTTCTTTATATGACGTGAATATATTATTGTATAGAAAAAATATAAATGTACAATAAATATTAT
AGTGCAGGTAGTTATATCTATAATAAAATAAATATAACTACCTACACTGATTCCCCGATTTAACTAATA
CAATAATAAAAAATTGTTATTGTTGTCTATGTTGTTTGTATTTCTCTTCAAACTCAGAAGTGTATGATTC
ATTTAGTTTGGAGATATCATAATCTTTACCGTCATCTCCAGTGAACGTACCATCCCCATTATCTGTTCCA
CGAATCTTATCATAATTCATTACGCTTGCAAACATACGAGTTCCTGGCATCACAATGTTTCAGTTTCA
CGGACTTTACCAATATGAGCATTTGTTTTCTTACGTGAAAATCCAGTAGAACCTACACGAACTCTTAGT
CCATTTTTAAGAGTCTCATCTAAGATATCCCCAAAGGCGGTAATCATATCAAATACTTTTCGTTTAGAA
AGATCATCTTCACTAAAAGATCCATCAGCAATCAGTTTATCATAAAGAAGATTTACTTGATCGTCCTTA
ATCAACATATCTAATTTTTCACCACTATCTGTCTTTTGATCAATAAGTTTATTAAGAGTTAGATATTCAC
GAGATTCTTTTGGTTTCTCTTCTTTTTTCTTTTTAGATTCTTTTTAGGTTTATCCTCTTTTTTATCTTTTG
TTGAATCTTTCTTGACTGATTTAGTAGTTTTAGATTTTTCTTTAGGTTCAACTTTTTCTTTATTAACTACT
TCTTCTGAAGAAATCTTAGTAGGTTCACTTTCTTCACTAGTTTTTACCACTGGTTTAACAACACGTTTCT
TGGGTGTTTTCTTCTTTAGCTTTACTTTTTACCACTGGAACTACTTTTTTATTAAGTTCAACTTTTTCTTCA
CTAACTGCTTCTTCTGAAGAAGGTTTAACTGTACTCTTTCTTACTGCTCTTTTTACCATAGGACGAACGA
CTTTCTTCTTTTCTTCTGCCATTTAATTTACCACCTTTAATTTATTTTTTGAAATATTATTAAATTAGTTA
TTGAATAAAAATAATCTTTTAATTCTTAACTTTATTTAATATATACCCTATTTTATATTAATGTAACTAC
CTTATTGCCAACGATATTTAACAATATTTCACGTTTATAATATATACTTATAATATAGGTTTAAATTTTA
ATTTTTTAAAGAAAAATTTTCATAACATATTAATATTAAAAATTATATTAATTTGATTTTCTTATGGGAC
TCCGATGGGACTCGCAAAATCTGGACTGAGCCTAGACTCCTTATTAAGATGCTTATTAATGGACTTTAC
```

```
TATTTTAAATCGAATTCCAACGTTTGTTAAAAGGTGGACAAATAGAGGGTAAAGAGCTTGCGGTATAG
TAGACGATGGTCTCACTGTAGATGTAAGTAAGTTTGTAAAGATTCTTTATTATTTTACGTTTTATTCTTT
TTTTACTTCCCACACTTGAAGAGTGTTTAAAAGGGGGGTTGGGGGGTTTATTGTTAGTTTAATTTTTTC
ATAAATAATTTTAAAATAAAAATTATTTTTATTAAAAAATAATTTAGAGTGGGTGCTGGAATTTCAGCG
CTCCGCACTTCATTCCGATAATAAACAAACCGAGAACCTGAAGTTGAGTATTGTATCCAATTATCCTTA
ATATCAAAGAATGTTTATAATAAGTAATATACAGTAATTAAATAATAAATATTGTATATAGGAAATAT
AGTATGAATATTATTCAATATAATAATTAATGATTTGATAAATACTTTAATATAAAAAGTATTTATCAG
TATAATATCTAATCAATATAAATATTCAATAATTAATAAAATTTTAAGTTAGATATTAAATATTATATT
AATATTAGAATAGTATAATAAATATTAAATATTAGAAATATCTAATAATTATTACATATAAGGTATAT
AGTATTTCAATTATATTAGTATTAATAAGTTTTATCAATATAATTTAAATAACAATTCTATATACTGAA
TGAATAAAAATAATTATTCAGAGAGGAGAGTATACTTTTGTTATATATCAGTGACCTAAAGAAGTATA
GATTATATAAAGGTAATAAGCTTAATGGTATTAATAAGTTAAGTGAAAATAAAGATCCAAATAAAGGT
CAATTAATATTACATTTAGGGAAATAATGATACAGATATTATCAGTTTCTTTAATTCAAGAATATTTAAG
AATAATCTATTCAAAAGTTATTCTACAGCTAGAAGATATAGAACTAATAATAAACGAAAAATGTATAT
TAAAGATCTTAAAGAACATTTTGCAAAGATAAAGAAAGAAACAAAAGTTACATTATTTACTAAAGTAA
ATTATAAACAGTTTAAGGGTAATAACTTAGTATATGATATTACAGATCAATATAATATTGAAATTGAA
TCAATTAATAATAAAAAGAATGGTTTAATGGTTTCTAATAACTTTATAAAGTTATTAGAAAAATCTCTG
TTGGAAGAATATGATGATACAGTATTATTAATTAATATGAATACATTGAACGTAGATATGGATGATAT
ATTCAATATTACTAAGTCTACTCATCCACTAACAGTTATTGATTTTATTATTAAAAAGAAATTGGATAT
TAGTAACTTAATTGACAAGAATATAACAATTGTTGTATTTAATCCTAATAACAGATTATTTTATAGTTA
TCCATTAACTACAGAATTATATCCTAAAAGACAGATCATCAATCAAAGATCTAAATCACTAATTAATTT
GGAAGTTAATGAAATTGAAAGCAATGATGAGATGAGTAATATTCCAGACATTAATGATATTGATGATG
CTAAAAGACAACTAGGTAATAATATGAGGTTAGGTCGATTAAGGTCTAGAAGTAAGATACCTGTTAGT
ATAGACAATTCTGAAGTAAGTAATAATTCTTCACAAGAAGACTCAATAACAACTAAAAAATTAGATGA
TATTGATAAAGCTAATGAAATAAATGATAAGGTTGAAGAAATTATTACCCTTACTAGTGATAATACTT
TATTATCTTCAGAAGCTAAAAAACAATTATATACAATAGCTCAAGATGAAATTAAAAATTAAAAATAAAGAT
TTAGTTAAGATGGATAGTGCTAAAGTTGTCTCTATTCTTAATCGTAATGAAGAATTCAATAGAATAGTT
TCAATGTCTTATAGATCATTTAATATTGGTGGATCGAACGCAAAAGAGCTTGCAAGAACAGCAGCACT
ACAAAAAAGACAGAATGAAATCCTTAATGATAAAAATATTTCGAATGTATTAGCTCATGCAAATGATA
AAATGATTGATAAAGGAATTATTAAATCAAATAATATTAATGATGAAACATTATCAGAACTTTCTGTA
AACTCTTTTGATAAGAGTTACATTGAGAAACAATTTAATGCCGATATTATTAATGTGTTAAAATCATTT
AACGATAATGAGGATATTAGCGTATTCATCTCAGACATATCTTCTGAAGACTCTTCAGACTTTCAGACA
AAGAAAACTACATTAAACGTTAAGCTTAAAGATACTAAAGGCATTAATCATAAACTATCATTAGATAT
TCCTAAGATATATAACGGTAGATATATGATGGTTAACGGTAGTAAAATAACTAACAAAACAGTTAC
TGTTAAAACCTGTAGTAAAAACTGCACCGGACACAGTACAAATAACTACTAACTACAATAAAATGTTT
GTTAAGAGATTTGGTAGAAAAGATACTCCAATGTTAGCTTCTATCAAAGAAATCTTTAATAAATTTAA
AATTGAAGATCATCTTCTTTCTGGTAAAAACATTAAATATTCTTTAGGTAATTCATTATTAGTTAACTC
AAAATATCTAACTTCAGTAGAATACAATAATATTTCTAATTATTTACTAAGCTTTAGTTCTGGTAAAGA
TTATTACAATTTTAACCAAAAGTTATTATTAGAATTCATTGATAATGATGATAAACTTAATTCACTAGA
ATATGATTCTACGTTATATTTCCCAGTAGGATATACTTCAGATAAAAGTAAACTTATCTTAGCAAATTT
TAAAGATTATCACGTTTATTATAAAGGTGCAACTAATAATTATGAATTTGTAGAAGAAAGTTTAAGTA
GAATGATATTACTAAATATTTTGATGAATGTTGATGATGAGGTTGCTAAGTTTATTGATAAGGGAATTA
AAGCAAATGATAAACTAACATATACACGAGTAAATATCATTAATAAAACAATTCCTCTAATAATATTA
TTGTCATATGAGAATGGATTAATCAATACATTGAATCGATATAATATTGACTTTGAAGTATTAGATTCC
AATCCTAAACTAAAGATTACTGATAATAAAGTTAAACTTAAATTTAAGGATAAATATTTGGTATATGA
TAATACACTAATAAGAAATTCATTATTATTGTCAGGTCTTCATATAATGGATATTAATGAATATAACTT
AGATGAAATGGAAACCAAAGAACCATATTTAGATTTATTCCAAGAATTGTTTAATAGTCGGAATGTAG
CTAAAGGTATTCATAATGCATTATCTCTCGCTATTGATCCTATCACCAAAGAAGTTTTAGAAGATCTGG
GATTACCAACTAATATATTTGATGTCTTATTGTATTCAAATACATTATTAGAAGATATGTCTTATAATA
CTCCTAATGATATGAATGTCTATCGAATTCGTGGGGCAGAGCAAATCTCTGGTATGATTTATAAGATA
ATTGCTGAATCATACAAGAACTATAAGGATTCTCTAAATTCAAGAAATAGTGCTACTAGAATTACTGT
ACCAAAGGACATTCTTATAAAGACTCTTATGGAGAGTCATACGGTAGAGGAAAATTCTGAATTAAACC
CAACATTAGAAGTTGAAGTTAGTGGTAAAGTATCTTATAAAGGACCAAATGGTCTTAACTTAAGTCAA
GGTTATACTCCTGCAGTTCGTTCATATGACCGTTCTATGAAAGGAATATTGTCGATGATATCACCAGAC
AGTAGTAAGATTGGTGAAGTTCGTCAATTAAGTTATAATCCTGCAAATAGTTAGTACTCGTGGATATTTA
GATGTAGATGCTTTAAACGGTAATGAATCTACAAGCCTATATTCTCCTTCTGAACTTTTAAATAACTTT
ACAAGCTTACATGCTGATCCACCACGTATATCTATGCAAGTAACTCAACAAAAACATTTACTAACAAC
AAGAGTCAATAGTAAACCGCTTATCGGTACTGGTGTAGAAAAATCATTAGCATATCAAATATCTGATA
CTTTTGCTACTAAAGCTAAATATGATGGTAAAGTAGATAAGATAGATACTGTTAATAATTTAATGATG
GTTTCTTACGATAACGGTAAAAAAGATATCATTGATATTGGAGTTGTAATGAATAAAAACTCCGGTGG
AGGATTCTTTTTAGCACAATCTAAAGATATTATGTTTAAAGAAGGTCAAAAGTTCAAGAATGGAGAAA
TTCTTGCAAAGAATCCTAACTTCTTTATTGGTGATAAGCAAGGTGAAATATCATATGCTATTGGTAAAC
TTTCTAAAGTAGCTTTAGCTCCATTAGACGGAACTTATGAAGATAAGTTCTATGATATCATCATCTATGT
CAGAGGATATGACTTCTAAAATTACAATGAAAAAAGATTTAGTGTTAGGTACTTCGGCAAACTTATCT
TATATTGTAAAAGAAGGTCAAAACGTTAAGACTGGAGATTCATTAGCTGTATTTGAAAATGAATTTGA
TGATGATTCTATAAATCAGCTATTAAATACTATTGGTGATAAATTTGAAGAAGAAATCCAAGAAATAT
CTAATAAAGTTGTAAAATCAAAGTATACTGGGGTAGTCCAGAAGATTAATATTTATTATAATCGAGAG
ATTGATGAATTTTCTTCTTCATTACAAAAGTTAATTAAAGCTTAATATTCTAAATATGAAAAGAAAAAT
AAGATAATCTCAGATTATATGAAAGATAGCGATATTGATATATCATATGATATGAATATTCCTAGTATT
ACTAAAATGGATTCAGATAAGATTAAGGGTAATGATGTAGATGGATTATTAATTGAATTCTATATTGA
ATATGAGGATAATTTAAGTACTGGTGATAAAGTAACATATTATACGGCACTTAAAACGGTTATATCTG
ACGTATTCCCAGAAGGTGAAGAACCTTTTGCAGAATCAGACCCAGAAGAACATATTGAAGCAGTATTG
TCTCCATTATCTGTTATTTCTCGTATGACTCAAGACGTTTATCTAACATTATATACTAACAAAGCATTAA
TCAATCTGAAAAAACAAATTGGTGAAATGTTAAAATAACTCACTCTTGAGAGAAACATATTAATATTA
TAGATGTGAAGGTTGCTTTGTGCAGCTTTCGCATCTATAATTTCTATCAAGAAAGTTGGTGAAACTAGT
GGGTAAGTTAGTATCAAATAATAATAACGGGAATAATGTAAGTCCTATAGAAAAGATATTGTAAATA
ACTATATAGGTAGTTATATTGAAGGTACTAGTGCATATAGTAAACTATTAGAAAATGCTCCCAATTTTG
TTACCTATTACTCTAAAAATACTAGATCATCTCAATGAAGATCCGGGTCTTGGAGGAACTGTTGAATAC
GTAGGTTCAGAATCTTCACTATTATATAACAAAATAAAGAATTTTCCAGTATTTTCCGTTAATGAAATA
```

-continued

```
AATCCTACTTTTAATTTTGAAGAAGGCGTAGGACTGGATACTGAATTAGAAAGTCAAGCAATAGTACT
ACCTAAAACTATTATACCTTTACCTGATGATTATTTGACATTTTCATATCATGAAAAAGGATATGAGTA
TTTTAAGACATATCGAATTAATAATGTTTCTACTTCTTCAATAGGTAGTAACACCTACTATTCAATAAC
TTTTATTAATGATCCTATAGATATAAGGATTCTTGAAGAAAGACAAGTAGATAAAACTTATAGATTTGT
TTATGAAAATGTAGGTACTACTGATAAAGTAATTATAGAAGAAGATGACATATTATTAATTGATAAAA
TTGAAAAGATATGTGGAGATATTAATGAAAGATATATTAATAATTTCTACAATTCACAGTTAGGTATTT
TATTATACGAAAATCTAGATGAAAGTTTATTATATAGTCCTAATCTTCATTATTTTATAAATAAGAATC
AGGTATTTATAAATAATCGAACTTTCATGAGAAACGTATATATAGAAGATATAACAAAAGTGAAGCTG
AAAGATTATAACAAATCTTTATTTAGCATTATTGATAATGGTTATAATAACATTAATATGTCTTATCAA
TATATAACTAGGGTTTTGGAAAATAATATTCTAAAGAAAACTAGGGGTCTTTATGTTGAAGATTTAGA
AATTATTGGATCTAGTTGTAATATTAAAATTCCGAGAACTACGATTCATAATTATTTTTCAGTAGATAT
TAATGATTTGATAAATAACTATGATGGCGTAGACTCGTTAAATGGTATAGATGCGATAACATCAATTA
TAACAATTTATTTAGAACAACCAGAACAATTAAGTATTAATACGTTATTTAATTTAGTTTCTAAATTAA
ATTATGATGACTATTCAATCAGTAATTATTTCTTTATACCATGCGTATTATCCATTATAAATATAATTAC
TAATAAAAATTACTATACATTCTGAAGAAGTATAGAACTGAGAGGAACGTGAATATAAATGTTTAAGA
AAATAGAAGAAAAATCCATCAAAGAAATATGGAAGTTGAAGCTAGTAAAATTGTAAGTGAAGAATT
AGAAGTTGTTGAACCAGAAGAAGAAAAATTATTGCAGTACCTAATACTTCTGAAAACAATGAAGTTT
TGGGTAATCCAGAACAAGATCCTGAAATTGGTCAATTTATCGATAGCACTGATGAATACGATGATGAA
GAAGATGCATTGATTGATGCTTTAGAAGATAAAAATGACGATGAAGGTTTAGACGGTATTGTTGATAA
AGATAATGAAGAAAAACCTGTAGAAACTTCTGAAGTTACATTTAGTGAATCTAAAGATGATAAAAAA
GAAGATAAGAAAGATGAGGACGAAAAAGAAGATTCTGAAGATGAAGCAACGATGAATCTGAGGAA
GCTGAAGAAGAAGATGGTGATGATGAGTCTGAACTTGAAGAAGGAATCAGTTCCATGTTCTCTGGAAT
TTTTGACATCAATGAAGAAATTGAAGATGATACTAATAATAATTTTAAATACACTAATCAGCGAAGAAG
AAGATATCTTTATTAAAGATGAAGAAGACGAAAAAGATGATGAACCTATTGAAATTGATTTTATTGGT
GATGATGAAAAAGATCAAGAAGATAAAGAAATCGAAGAATCTGATACTGATTATCTTAAAAAAGAAT
ATCTAGGTGAAACAATACTTAATAAAATCTTCGACAAATAATACTGTTAACATAATATTATTAAGGGT
ATATAAAATATAAATTATATAAAGGATGTGTATTTCAAAATGCCAAAAGTTGTTATAAAAGATAATAA
ATTTGTATTTGGTTTAGGTAAAGGACCATTTAATAATCCAGTTGAGATTAGTGATGAACTTTTACGTAA
ATTAAAAATCTCTGGATATACGGTAATTGAAGTAAATGATCGTCATATCGTATATGAAACTCCAAATA
ATGAAGAAAAAGCTGAAGAAGTTAAAGAAGATCCTAAAGAAGAACTACACCAAGAAGAAGAGTCTG
ATGAATCCGTAGAAGCTACTGCAACTGAAGAAGAAAATAAAGACGAAGAACATCAAGAAGAATCTAA
TGAAGAAAAAACCGAATCATCTAAAGAATCTGATAACGAAAAGTTGAAGATGATAGTGATGAAGAA
GATTTCAAATCAATGAAGGTTGATGAACTTAAAGAAATTCTAGAAGAACGTGGAATTGAATTCAAAGC
TAATGATACTAAAAAAGTTCTCCTTTCAAAATTAGGTGTAAGTGAATAATATTTTTATATTATATTGAT
AGGTCTACTTGTTGAAATTATAGCAAGTAGACCTATTTTTTTCGATTATTATAAGTTAGATAAGAGGTG
TTTATGTGTGCCAAAAGTAATTTATATTAAATAATAAATATATACCAGATATTGGTAGTGGTCCAATACT
AGAACCAATTGAAATCAGTAATGAAAAATACCATTATCTAATAGATAATGGTTTTAATATATATCAGA
TAGACGATAATGAAGATATTATGATTGATCCATCCATAACTACCATATTGAAAGGTAAAGTTAAGTCA
GTATATGGAATGTTTCATGCAGATCAGAAAAAACTTGATTCACTATTAATGTTTAATAGAACAAGCAT
ATCTTCATTAAAAAATGTTAATACTAAGAGTATTACAGAAAATAATAATATAATATATTGGAAATCAA
TAGATACCGATATTGCATATGTAAATTCTGACGGTTATATTGCTGCAAAAGAAAATGGTTACACAATA
GTTACTGGTTTTGATTCAAATAATACGCTTAAAGCAATAATGTTCATAACGGTAATACCTAAACTTCCA
ATATTACCCAATGATATTAATGTTAATTTAGAAAGCTATATGGAACTTAATAGATATGCAGAATTTCAA
TACTTAGTTGAATTACTTCCTAGCGAAGTAGATAATAATAAAGTAAGTATTACATCAAATAATATACA
AATTGCAACTATTGATGAAAAGAATAAAAGAATTATTGCTGAAGAACCTGGATATGCTGTTATTAATG
TTAAGAGTGCAGAAAACCCTGAAGTATCTCATAGTACGTTGCTAAAAGTTTTTCCTAATGATGATAGG
AATAATCCTTCTAATATAAATGTAAATATTCCGGACGAGATTCAATTAAGGTTGGAGAGGAAATTCC
CTTTGAAGTAAAAATTACTCCTGAGTCGGCTAATAATCTAGGATATATGTCTTTCTCATCAAAAGTTGG
AATTGTATCTTTATTAGATAATAACCATATTCTTGGTAATAGTATTGGCGTAGCAACCATAACTATTGT
ATCGAATAAAATATCATCATTATATAAAGAAATACGAGTTAATGTTGAAGCACCAGACCCTAATGATA
TTATTGTAAATTTAACTGAAGTATCTATTGAGAAAGGTCAGACTAGAGGGTTTAATGTAACAGTTCTTC
CAATATCAGCTAATGACAGAACTTACAGTAATAGTTCTTTAAATGAAAATATTGCGACTGTAACTCAG
AATAATATTATTACCGGAGTTAATATTGGGGACACAAAGTAAGAATAACATCTAATAAAAAGCCTGA
ATTATTTAGGGATATTATCGTGCATGTTACTCCACCAAGCCCTAAAGATATTATGACTGATCTTCCAGA
CGAGATTACAATTACTGATACCGAAACTAGAAATTTTACAGTTCAAATTCTTCCTGAAGATACATTTAA
CAACAAATATGATATGGAAGTAACAATTCCGGATATTATTGATCTTGATAAAGAAAATTTATCATTTA
AAGGTAAAAAGATAGGTGTAACTAATTTAAGAATTTTTTCACAGTATAACCATGATATTTTTAAAAAT
GTTAAAATTAATGTAGTACCAAGTCCATTACCTGATCCGACATCTTTTAAAGTTATTCGTAGAGATACT
GGGGAAGAATTAAAAAATGGAGATACTGTACCTAGTAATAAAGATAACTTTTTTGATGTTATAGTTTTT
ACCAGAAAATGCCAATGATAAAAGTTATATAGTATCATCTTCAGACGTAACGATTGCAAAAGTTAACT
TAAATTCTATAATAGGAGTTTCTCCTGGTCAAGTTAATATTAGAATAACATTAAACAAAGTTTCAACAA
TATTTAAAGTATTTCAACTTAATATTGAAGAACCTGTTCCTACATTAATTGATATTGATGTACCAAGCA
ATATTACTGTACAAACTATGCAAACACGTAATTTCACTGCAACTATATATCCTGAAAATACTCCATACC
AAAATTTCTTAACATCTGTTGAAAATCCTGATATAGTAACTATTTTAGATAATACAAATCCAAAAATAC
GTACGATTAAAGGAATAAAACAAGGTGTAACTAAGGTTAAAGTGTATTCCGAATTTGATCCAACAATA
TTTAAAGAAATTAACGTTACAGTAGTTAATCCTAATCCTAGTTCAATAGAAGTTTCTCCAAGAAGTATT
TCAATGTTATTAAATGAAACTAAAGAATTGGATATTAATGTATTGCCAGAATATGCTAATGATAGAAC
ATACACTATTAAACAAACAGGCTTAGGTATGGTTTCTATTAATGGAAATAAGATTACTGGTGTGTTAA
AAGGAAATGTAAGATTAGATATTATATCTAACAAAGTAAGTTCTCTTGGAACTACGGTATATGTTACT
GTTGATAATCCTGACCCTGAAGATATGATTGTCGATATACCTGACGAGATCGATATCAATGTAGATGA
AAGAAGAAATTTTGGTATAACATTTGTTCCAGAAATAGTTAGTGATGATTCTATTATTATAACATCATC
TAATTCTAGTATTGCTATAGGTAGTGCTGTACAAAAATTTATTAATGGAGTTTCTGTTGGTACTGCAAC
ATTAACTTATTAGATCTAATAAAGTAGCTACTTTATTTAAAGAAGTTATCGTAAATGTTCATGAAGATAG
ACCTGACCCAACAAGTATCAATGTTGGAACTAATCCGCTTACTTTAGAATTAGGTACTACAACTCCAAT
AAATATTGCATATGAACCAGAATTAATAGTGGTGGTAAAATAATTGATGATTATTCCACATCAAACA
CTATTATTAGAATGGATCAATTTAAAAAATTCAATACAAGCTATTCGACTAGGATCTACTAGTATTAAAT
ATACTTCTGAAAGATTTCCAAATATTACAAATACGTCTAAATATTACAGTTATTCCTCCTAGACCAAAA
AGTATTAGTGATAACTTTTCATATAATAATTCTTTAAATGTTAATGAAGCAACAAATAAATCGTTAATT
GTTAGCTTTTTACCAAGCACGGCGGTAAACATTGGATACAATGTAGTTATTGATGATCCAACTGTTTTA
```

```
TTATTTAATACAAACTCTAAGAAATTTGAAGCATTAAAAGAAGGAGAGACTATCGTTAAGGTGGTATC
TACTGATAATTCTTCTCTATTTGTAGAACATAAATTTAAAGTTAATAAAAATATTATTATCGATGACGG
TGGTAACGGTAAAGATGATGATGGTAATGAAGTTATAGTTCCAAATCAATAACGTCAGATATAGTCA
CTGAAATGATAGTCGATAAGAACTATCGGGTAAACGTAACAGTTTTACCAGATAATGCTATTGATAAA
GGTTTTGAAGTTATAACTAGCGATAATAATGCGTTTAATATAGTTCAAAACAGTGGATCATATTTTACT
ATTAAATCATTGGTTTCTGGAATGTATAATATTACGTTGCAATCTACATTAAATCCTAATATAAGCGTA
TCTTATGATATCGTGTCAGGCACTGAAGATGAATTACATCCAATCTTACCAGAAACAATAAATATTAT
AAATGCTACTGATGAAATGACTGTAGATGAAGGTACATCTATGAATTTAGATATACAAGTTCTACCAG
AAAATTCAACTAATAAAAATGTAACTGGTTACAGTAGTAATGAAGAATTAGCAACTATACCTAATAAT
AAAACTATAAGTTTTATTAAAGAAGGTTCAGTAGACATTACAATTACATCAAATAAAGTACCTACATT
AAGTAAAACAATTCACTTTATTATTAAAAAACCCGACCCTAAGAGAATTGAAATTAATGCACCCAACG
CAGTAACTTTAAATATCGGTGAGTCTAAAGAATATCTGATAAGTGTAATTCCTGAAAATAGTATTGAT
AAAGAATATATTTCAGAAACACTAGATTCTAGTATTGTTACTACTAATGGAAAAAATATTATTAAAGC
GGTTAAAGAAGGAAACACTACAATTGTGTTTAGGTCTAAAACTTTTCCAGATATATTTACACGACTTA
ATGTTATTGTTCTTCCTCCTGAACCGAATGAAATAATTGTATCTCCATCCAATGAAACAATTAATATGA
TTAAGCTTGATGAATTAGTATTTGATGTAACGATTAATCCTTCAAACGCAATCGATTTAACATATAAGA
TTGAGTCAAGTGATACTAATATTGTAAAAATTAAAAATCAAGATACAGTGGTTGCAGTAAATCCCGGA
GAAGCAAACGTGACTATATCGTCTAGACAGAATGCTAATCTAAAAGTTATTAAAAAGATTATTGTAAC
TGCGCCTGACCCAGAATCTATAGATGTTATTGGTTTTGGACCAGACGAAACAATGATTACAAATTCAA
CAACTAAGTCCGTTAATTTTATAGTCAATCCGGCTAATGCTAAAGTATCTAACTTTACAGTAGTATCTT
CTAGTGATTCGGTACAAATTAATATTCCGGATCAAACAAAATATGGATTTACTGTAAAACCTGTTAAA
GAGGGTAATGCAATTATCACTATCCAATTATCATCATTCCCAGATATTATTTTACAATATTAATGTAAGG
GTGAATAACCCTGATCCTGAAAGCATAACTGCAGGGATAACTAATCCTCCAAATATGCCTTCTGGAAA
TATTCCAGGAAAAGGAATTGCTATAGGAGAGAAGGTTGTATTAAATGCTAAGATACTACCTGAATATG
CTAATGATATAACTTACTCAATTAGTAGTAGCGATAATGATGTCTTTGAGGTTCGAGATGATGGAATTT
ATGCATTAAAAGCCGGAACATCTAAAGTTAGGGTATTCTCTAATAAAGTTCCAACAATATTTAAAGAA
TTTGATTTAGAATGTCTAGGTAATAATGTTAGTGATATTGAACTGGATATTCAGTCACCATTCAATATG
GTCGTTGGTAATACGAAACAAATAAGTATAAATATTCTTCCTACTGATGCTATTGATAAGAGGTATCA
GCTTAAAACAGATGACGCTAATATTGTATCGGTATTAGATAATAATACAATACGAGCTATATCTCTCTG
GGGTAAATGGTGAAGGATTTACGAATATACGAATAATATCTTTACGTAATAATTCTGTGGTTAAAGTA
ATACGAGTTAATGTAGAAAACTTAACGCCTCAAAGTATTGATCTTGTTCCATCTGGACCCATAGAAAT
ATATTCATTAACATCAACTACATTTAATGCATATGTAAGACCAGACACTGTAATTGATAGGGATACGG
TAGTTAGTAGTTCAGACATTTCAATAGCTACGGTTCAACAATCATATATAACTGAAGGTGGCATAAAA
ATTACTAGAGTTACAGTAAATGCACTTAAATCTGGAAATGTTAATATTCGTGTATCATCTAATAATTAT
AGAAATATTTTTAAGATGATTAATATAAATATTATTGACCCAGATCCGGAATCAATTACTGTAACTCCA
TTAACAATAAATATGGCTCAAGATACATCTACTAATTTTAATGTAAATATTCTTCCAGAGAATGCTAAT
GATAGAACATTTAATACTGAGATTGCAGATCCTACAATTGTTTCTGTTAATGGAAATACAATTACTGGT
CTTAAAACAGGAACGACTACAGTTAAAGTATCTTCAAATAAAATACCATCATTAAATAAGACAATCAC
AGTCAATGTGAGTCTTCCTAATGTAAATAAAATTGAGATTACTACTGCATTAGTTGCGGGAACAGTTA
ATACTGTATATGAGGGCGAGTCTTATCCATTTCTTATTAAGTTATTGCCAGAAGTTGCTGCAGATAAAT
CATTTACGATAAAATATTCTGCTAATGCTGATATGTCTGGTACTGCTGATTACTCATTTAATTTTGGATA
TCGTAATGATTCATTAAATCCATCACTATATATATCAGCTACAAGTTCATCTAGATATGTTCCACCTTTT
GTTAGATATATTCAAGTGGTTTCAGCTAATGGAATTACCTCGGATATATATGGTCTAAGTGTTGTACTT
AAACCTATATATAAAATGGATAGTACATTTACATTTTATAATGATCAGTAAGCTTCTGCTAAAACTACT
ATATCTTTTGATAGTACTAATCCTAATTCTGAAAATTATGTAATTAATGCCTATGCCGGAACAACAGCT
AGAGACCCTAATATTAATACTGTTAATTTATATCCTCTTGAAGCAAAAGATACAAATTTAACAGTTACT
ATAAGTGATCCTACAAAAGCATCATATAATAGTACAACTAAGACTTTTACAGCTCTTCAATATGATACT
GAAACTACTGCAAAGATTGCATCCACAACTAGCCCTGATGTGTATTTGTAATTGTTAAGATTAAATGTATG
AGATCTAGAATAACGTCTGTACAAGTTACAGGTCAGAATGGATTAAGATATAGTACTGGCGATGTCTT
TGGAATAGTAGTAACAACTGGTCCAGAAGGTGCTATTGATACAAATGATTATACATTATCTTCAAGTA
ATGATACTATTATATCAATAAATAATGAAACTAGAACTGGAGTTGCTTTAAAGGCAGGTTCATCAACT
ATTACCGCATTATTTAATAAAGCCGGCGTATCAAATAGTGCTAGATTTACTATATCTGACGTACTTCCC
ACTTCAGTAGGTATTACTGACCCTCCAGGAGGTTCTGAGCTAATTATTGGAAGATCCTATCCGATAACT
CCAAGTGTATTGCCGACTAATACAACTAATAAAGCGGTAACCTATTCTGGAAATAATTCAAGTTATTT
AACATTGTCTAAAATAAATAATATTGATTATATTAATGTGTTGGGTAAAATTGCAACAAATACACCTAT
AACTATTCGATCAGTTGCTAGTACGGGAATTTACAGTACAGTTCAATATAAGACTGCGTATGAATACC
CAACAAGCATTGATATATCCAAAATTAATGACTCATATAATTTAACTGAAACAATTGACTTATCTACTT
TGATAAATATAATTCCATCAAATACCGATAATGATAATAATTATACAATAACAACTCAAGATACCGAT
AAAATAAATATTGATGGTAAGAAATTAACATTTATTAAAGATGGTAGTGCAACTATTACAGTAACTCA
TAATAGAAATAATATTTCCGTTAATAAATTGATTAATATTGTATATAATGATTCAATTAAACCGAATAT
TGTATTTACTACTTCAAATATTATCATAAATAATAATGAATTTGATATTAAAAATAATATTACTAAAGA
TTTAACACTAGATGAATACCTCATTACTGGTGATCTTAATGGTTGGAGATATAATGGCAATAAGAAGT
TTTCAGATAGTGGAGATTTTCAAATTAAATTTAATTATCCTATTAAATATGCTTGAATTTGAAAGTATTA
ATGATCAATTTTCAAGTGAATTTATGTATAATTTAAATAATCCGGATTCTAAAGTTGATCCACCCCAAT
ATGTTGACCTTGATAGGGGTAGTGATTTGATTAATGATCGATTATTTGTATATATTAGATACGTATACCA
TTTCTTCATATTATAATAAACGAAGAAGTACTAGTGGTAATGAAAGTCAATCATATATTGTAAGCGCTT
CACCAGTAATAAATAATATATCTCCTGCAGGAGAATATTTTTATAAAGTCTATGTAAAGAATGATCCT
AATAATTATATTATTATTAGAATTAATATCGGTTATTCATGGATCAAAACAATCCAGTAATTTGATATAT
AATGGATATCCTACTCTCATTAGTCCAGTATCAATATCTACTGATGATAATATAAACTATGAACTTAAA
GTACAGCTGTATTTAAGATCTAAGTGGTTGAGTGGGGACAAATCACCTTTATTATTTAATAATGAGTTA
ATTACTCATCGATTAATGCTTGATTCTTCATATAATAATAAAATAAATATTAATGGTATTGAATATAAT
AACATTAGTGATTTTATTGAAATTGATAATAGAATTATTAATCGAATAAGTAGACTAGGTGTAAATCG
TGTAAATACTATTACCAATACTGTCGCATCTATTGATAGTGTGGTCGCAGCATATCCGGACAGGGTAA
GTTATTTTATTAAAAGAAATCCTACTAAAAATGAAGAATTTAGTATGGATATAAGATTAGTAAGTATT
GAGGATTCGAATATCAAAATTCCAGTAACTTATACATTCACTACAATTAATAAATAATTCTTTCAAAGA
AGCATATGATAAGATTCTTGAAAAGAAGATTAAAAAAAAAAAAAAAATAAATCTCCCATAACCTATT
AATTTAGGTTATGGGAGATTTTATGATTATTTATTAAACAGATCATCAATATTATTAGTATCGATATCT
TCTTGAGTTTCTTCCTCATCATCTTCATCTAACGGTACAAAATTGATAACTGGTTTATATCCTAATGCCT
TTGCAATATCTGATAGACTGGAATAAGATGTCGCACCTTTTTTCCGTAGTCTGTAAAAGATATTAGAAG
```

-continued

```
CTCTTCCTTCATTATTAGGATTATCAAGATCAAACTTTTCAAAGAATTCTTCAAATGTTTTACCTTTTTC
ACCCTGCTCATTAATGAATTCTGCAGTAATTAATGCTAATTCTGTTTGATTTTCAATAGAATCCACATC
AATATGCAATGGACCAGTTAATTTCTTTCGTTTAGATTTCTCAGAAGGATCTTTAGAAGCCTTGATCAT
ACTATCTTTCTTATCTAATTTATCCATATTTACATTATTTAGTTTTGAAAATAGATCATCGGACACGAGA
ATTTCACCTCATTTATTATTCATATTAGAAATCCATATCATCATTAGAAATTTCTTCAGAAGCACCAAT
CTCAGTTGATTTTGCAATTAATGATTTAAGATCTTTTGATCCACCACTAGCTTGGATAATTTCTGTATCC
ACATCTTCTGTTTGTTTATCTGCAACTTTTTTCTAGGATGATTTAAAGTTACTACCACTATTATTACTGT
TATTTAAATGTAGAACTTACATTTTTAGGTTCAGTGGTTGTATCATTTTGTGATAGATTGTTATCATAAG
GATGTTGAGTTGCGTTTGGATTCTTTCTAGTTACTCGATTACTATTGAATCCACCACTTGTGTTTCCTGA
ACGATTGAATGGAGTTGTTGATGTAGGTCTATTAAATCCACCAGTGTTTGGACGTTGACTAAATGAAC
CACTATTATTAGATTGACCTTGAGAATAATTTCCTCCGCCCAAAATATTAATAACGTGATCTAATTTAT
TTTCTACAGTATATAATTTCGCTTGAATTTTCTGGAACTCTTGTAGAATATAAAGATCAATATTATTAAT
ACAATCAATCATATTGAATAATTGTAGTGTAGTTAGTTCTACTGAATATTCATCGCCATTTACGCATAA
AATAAATCCTGGATAAGTAGTATCATCATTACGATGAATGATTGAAGGATAGATTAATAATTTTTTACC
TTGACCACCAAACTCTGGAGAGAACCATTGTGGTAATTCTGGAAGATCCCATACACGATTACCTGAAT
TATTACCTTCAATAATTTCATTAGCAACTTGGTTCATATATGATTTTAATGTTTCATGATGAGCCTGACT
AACTACAACATTCTCACGAACGCTTTGATTAGTTTCAGGATTAAATCGACTATAATCAAAACGTAAAA
ACACCGTTGCGCTGTTTTGAATACTAGTTAACGTTTGAACATCGGAATATCGATCTGAAGTGTATTCTC
TTGCATATTCAGCATCCCTACGTTTATCATTAGTTGATGTTTTATTACCTAGTAATAAAGAACTTTCTAG
TTTAAAATTGAAAGCACTAAATAGCGTTAGACCATGAGATTCTACTGGATTAAAATTTGACAAAATAT
GATTCCTCCTAATAATTTTATATATTACAATAATATAATATATGATTATAATTTATTTTAAATGATTATT
CATTTGTATCTTGATTTAATGATAATGCAGTAAGTCTGGAAAGCTTACTAACAAACTGACTTCGTATAA
TTGATGAGTACAATGCTTCTTCAGGAACATTAAACATTTCACCAATCTTACTGATACTGTCACCTGAAG
TATAATCTAAGAATTGATATACACTAAAAATATTGATAGGTTCAGGAATGATATATTCTGGAATTACT
GGAATTTTATTTTTAAATAAGAAAGCTTTATCTAAGAAATGAATCCAATCTATTGGATTATCTACCCAA
AAAAGTATTTTATTTTTTCCTGAATTAGAAAGCTCTAATAACAATGATTCAATATTATTGTATATTGTTG
CATCTTCATCTTTCATAATTCTAATATTTTTGTTAGCATCATAAGTATAAATCTTTTCAACATTATTCGC
TAGTTGATTATTATATACTTTCATACTATCTTCTTGGGATATAGCTGTAGCAATATCGTAATTTGTAAAT
TCATAATAGTAATTAGATATTACACCTTCTGCTTCTTCTACACCCAAACACATATTCATGATGTTAGAT
GACGTACTAGACCCATCTAACATACATGATAAGTAAATATTTTACAATCTTAGTTCTTTCCATATTTTAC
CCATCCTTATTTAATTCTTTTTGTTTTTTCATTTCTTTATTATAGAATATATCATGAGTTAATAAAAATTT
GAAATTAAGTTCAGAATTAATACTATTGATAATATCTTTAATACTTTTATTAATAACTGCAGGGTTTGT
TAAATCTTCAAGAATTTTCTTTTCCCTAATATCATTATTAATAGTTAAAGACATATCAAGTAGATCGTTT
TTAATTTTATGATATTTTTCAAATTTAAGTTTACGATGTCTATAGAAAAAACCATCCATATTTATTTTCAC
TATACATCTTTAAGAATGATGCATATTTATTTAAATAAGTCTTCCCTTTGAATTTTAATTTCACCTTTTTG
GAGTTCTAAAATTTCAATAGACCTTTTAATATGGTTATTAATTTTTCTAAGTTGAGTTAATTCAATATCA
ATAATCTCTGTAACAAGATCAAAATTTACAATTCCGATAATATTACCGTCAATATTAATATTAAATCTA
AGAATATTAAAGTCTTCTGAAATTTTAGCACCAATTAATGAAAAGATATCTTCATCATACTGTCCAGTA
TTAACATTCTTTGTTAAAGAATATATAAAATCTTTCTTAATACGATTCACAATCGTATTAAAGATATTTT
TACTAGCGATTAATTCTTCAATGAATTTTGAAGGATTTGTTTCTGAGAGGGAATAACGATCGTTAGATG
CATACAAAATTTTCACCACTTTCCGCTATATAATTTCCAATTTAGATTCAATAATTTCTTTACATCTTTT
ACGATAAATTTTCTTTCTTTTAGTTAATTGACGTTTACATTCATCAAAACCTGTATCAATGACATCAAA
GTATAGACATTCTTTATTTTTTACCTTACGTAAACGACCCATAATTTGTATCAACCCTTCTTCAGAACCA
GAAGGTACAGTATTTACTAATACTCGTAAAGATTGTTCATCTAAACCTTTACCGAAAGATTTATCCGTA
GTAACAATAATATCTTTTTCAAACGCAGTAGATTTTTCATCTTTAGGAACGTCTGAATAAAATCTACTT
ACCGATATATCCCACTTATTATTTTCAATTTCTACTAAGAAATCTTGGTAGAAAGCATTAACCATAATC
TTATTTTTAAATAAGATTGCAGTCTTTCTTTTATTCTTACCTTTATCAATAATATCGAAGATAATCT
GATAAATATAGTTATAATATTCATCATGCTTTTTATCAATAATATACTGAGAATAGCTTGGTACATTAA
ATCCATAACCTTTAGATTTCTTTCTAATTTCAACTAAATCTTCATTACTAGGTTTAGTATCTATTTTACA
AATGATTGTTCTAATGTATCTATCACTATCACTAACTACAGTAGAGAATTTTGGAACGTTCATATACAT
ATTCTGATAAACTTTATTTTCAATAGGATTAGATCTACTAGGAGTCGCAGTTAAATATAATGATGGACA
GTCATAAGTAGAATCAATATTTAAATACAGAAATATATTCAACGTGAGCTTCATCATAAACTTTAATTG
ATATTCCAATTCGATTAAATAACTTTACAACCCTATCAGGATCAGACTGAATTAATTGGTTAACAGTCT
TGTGAATAGATAAAAAGAATTTATACTTAGATATATCACGTTTAGTCATCTTTTCTAATTTTTCAATAG
ATTCTATTCCTGAAATAATATAAATATTATCTAATGATACGTCTGTATATTCACTAATTCTATCCTTCCA
CTGTTCTAATAATGATTTCATATCAATAAAGATAATTGGTACTGCTTTGATTTTTATTAATATAATTAATA
GCACAAAAGTTTTCCCTTCACCAGTCTTTAACGATAAAAACTTTTGATAATAATTATTATCATCATTA
AGAAAATTCATTGCATCTTCTTGAATTTTATTTTTAGGTTTATATTTCATTTTAAAATTATTTTTCCTAAG
AATATTTTTATTTCTTTTATCATTAATATGAATATTAACATTTTGTCTTCTTCTTAAGTTACTAGATAAA
GAATCAATATCAATACCAGAAGGAAATATTGCTTTATCATCATCTATCTTGTATGCTTTAAAATCATAC
TTAAACCATTTAGCATTCCATACAGAAAGACTATTTCTACAGCACTAGCCATTTTTTCGCTATAGTTA
TTAATAACTATCCTTGTTGGATAAATATCAAGATCCATTCATATATCACACCTTTATTAGTTTAAAATC
AATAGAATGTATTATATAACTAAATAATACATTCTATTGATATATTTTAATTTAATATTCTTTAAAGAA
TAAGTGAGGAAAAGATTCAAAGAAATTAATATGGTTAAGTTCTTCAGGACTTTCAGCATCTGTAGCAT
TAATAATGTAACCAAAAATAGGGACTTTTGAAGTGATATAATATTTACCTTCTTTAAATGGACCAACTG
TCTTTTGACATTTATCCATTAAATATAATTCACCATCTAACTGGTATCCTACTGAAAGTTTATCACCTAG
TTCATACATTGATAAAAAATCGGTATTATTAATAAATTCTGTAAATTCTTTTGGATTATTGGTATATCGT
CTGATTCTAAATTTATTTTCATCTGGAATATTATCTAAACTAATAATAAATCTATTTTTTTCTACTTCTTC
GGAATCAATTAAATTATCTTTGTCCATATTCATATATCTATATATCTCCCTTATAAATAAAATTATCTAA
ATACCCTATCGAATTCAGATTCAACATCTTTACCAAAAAGATCATTATAACTATCTGTCTTAAATTGTT
TTTCAATATTTTGATATAATAGTGACATTGCAGGACTTTTCTTACCGATAAGTATTGCATCACTTACATT
ATATATATTATATTTTGGTAATTCTTCAGCATTAGCAAATTCGGTTCTATCATTATTTTCTAGACTTACC
ATTTCCCTTACAATAGTTTCTACATGTACAGAATCAATCGTTCCTGAATCCACTAATAAGTTTACA
ATTTCTTGTACAATGATAGAATAATCATTATTTGATACATTTCTAATAAAATGATTTTTTTCTAAGATAT
CTTTAATCTTTAGAAGTGGGTCTGCAATACCATCATTTTCCACAATAATATTAAACATATATTCATTAT
CAGGCATATATTTTAATGAGAATACATAATTATTTGTGGAATTATCATAATACTGTTCAATATCATCCG
CAATCTCATTAGGAATAATTAAGCTTAATGGAGTGTCAATTCTAATCTGAGTGTCTTTCCTACCTTTAA
CATAGATTGTTCTTGTTTGATATTTATTCTTTTCAGAGTCTTCATTTTCCATAAGATCATCTTTATGAAT
ATAGATTGTTTCATTATCAGAAATAGGACTAACCTTATCTTCAAATAATTGAAACTTAGATAAGAAATC
```

```
TTTAGACCAGTTAGCATCCTTAATAATAACTTCTAATAAATGCTTTGTTGATAAGATTTTTTGTGTTAAT
GGATTAGTAAGTTCTAAAGTTGCAGCAGTTCCTACTTTAATGTGTTTATTAATCTTTTCTAATCTTCCAT
AACATCTAGGACATATACCTTTTGAATGTGCGCATGTTATTGGACTAAATATCTTAATATCTTTACCAA
TAAGATGTGTATCATTCTTAGTTATTACGGTAGTTTTATTAGTATCTTCATCATACATCCAACGATGATT
ATATAGTGATAACATGTCTTTATCTCTAATATGAATATTAATATAATGAGAAGTGTTACAACTATCTAC
ATTATTTTCATCTTTGTGAAGTTCTTTATCTTGTGGATCAATATCTAATGTGTATATTACTGAATCTTCA
GTTAATATAGATATCTTTCGGTTAGTATATCCAGACTGTTTTACTTGATCCTTTGCAGTGATAATTGCTT
TTCTACCACCTACTGCATCAATAAAGAATTCTGTTACATTTTTAATTCCCCTTACAAAAGAACTATTAA
TTGGAGTAGTAATAACTTTACCATATAGATCGGGCTTATAACCAATTAATCCAAAATTTTGATTAAATT
GTTTTATATTAATTCCTGCACCCGACATGATTAAATCTCTAGTAATATTATCTTTATCTTCTTTAATAAT
TTGAATCATTTTATCTTTGTTTTCTGCAATTTTTTGATTATTTGTTCCAATATCATCTTTTAATTCTGGAT
CAAGTTCGAATTCTAAAGTTTTCTTAAATTCTTCATTTCTATCCATAATATCGATTATATCAAATAAACT
ATAAGTCACTCCGCTCTGATATAATACGTTTTGAGTACTAAATATTGATAGTTCATCTACTGACCACGC
AATATCTTTTTTAATCAATTTTATCTTTTCATCACTAATATCATAATTATAAATTTTGTTAATAATCTTAT
CATAAAATACATTATGAAGATTAACATTATAATTACCCTTTTCATTACAATCTTTTAAGATAAATGTAA
ACTCTTCGGTAAATTCTTCTTCCAAACTCTTAAAAGGTTTTGCCAAAATAAACGTTGTTAATAAATTTG
ACCTAGATATTTTGATGTTCCAAATTGTAAAATTTCTCTACGAGAATCCACATCTTCTACAATTTTCTT
TCCTAATTCATCAATCTTCGAATAATACTTAGTATCATCATGAAGAATTGAATTAAATAAAGATAGATC
TAATACTGTACTCAATATCCTCCACACAATCCTTTCTGTAATATATTTAACCACAAATATATAATATAT
AATTGTAAGATAATTTAATAATCACAAACCTATATTATGATTCTAACAGAATATTTCATTGTTGTAAAT
TAAAATTAACTTTTTATCTTATGAAACTTAATGTGGATCATAGAAAATTTAAACTATCAATAAAAATAT
ATATTATATATTTGCGAATAAAATCCCCTATCATATAATTATAACACAAATTTATATGATAGGGGAAAT
AAATTATTTATCTTCGACTTTTTTAGATTCTGATTTAGCTTTACGTTTTTCTCCGAATTCACGAAGTTTTT
GTTTTCCTTTGCTTGCATACTTAAGTTGAATTGCTCGGCGAGTTTCTCGGCGCAACTTAGAATATTTAAC
GTATTTACGGTAAAGTGGATCATTTGCTTCTTTAGCGGAAATTAATACTGCTTGAGTATATAAACGTTT
CTTAGCGGTACGTTTATCTAAACGAACAATATTGGCTTCTTCTAGATAGCTTAAAGATTCTTCCAAAGT
TTGCATTGAACTTTCTTCATTATTATAATTAAAAAATGTATCTTTCATATTGATTAAGCATCCCTTTCTC
TAAATAAAATGGTTTAATAATTATATGTTTATCAATTCAATGCAGAAAAAATAATAATTTATTTTTATT
CGTTAATAATGTTTTATATTATATAAAAATATAGAAAGGAAAGATAATTTATGTATAGTTTTTAGTAGTA
ATATTCTCTTTAATTATATAAAAAAATAAAATTGGTGGTGTATTTGTTTATATGAAGATTGAAGAAAAAG
AACGTGAAATGAAACATATTGGTTACATGAAGATATTACTTAATGTTGCTAAAGAAGAATTTCCAGAT
ATGGAAGAAGATGTATTAAAAGAAAAGATTAAAAATATTGTAAAGGATAACATGAAAAATCCAAAAG
CAATGATTGATGATCGTGAAACAACATTATTAGGATTAGACAAATTTATCGTAACTGAGAAACCTATC
ATTACTGGTTTTGGATCAATGTATTTAACTCATGATAAGTTTGATAATCTATTAGCAAAATTGGTTGAA
TATATTATCAAAACTCGTAAAGTTTATAAAAATAAAATGTTCGAACACGTTAATGATGATGATCAAAC
ACTGAGAAATATGTATGATATGTATCAACGTACCATGAAGATCCTAGCGAACTCATTTTACGGATCAT
TGATCCAAAGTAGCTTTATTTTGTATAATCCGATATCTGGTCCGTCAGTTACTTATTCTGGTGTTGATAT
TATCACTACTGCACTAAATAATTTTGAGAAATTCTTAGCAAATAATCATCTATTTTAGAAATGTAGATGA
TATTATTGTATATATGAATAATATTAAATCTGAAAATTATAGTATGGATAAAGTTAAATTTAAACAATC
CCGTAGTAAAGATCAGATTATTGATTATTTATTTGATAAGACAGATAATTATATGGATGAAGATAGAA
TATTATTGATGACAATGATGAATAATTATACGGATGAAGATTTACTTAAGCTTTATTATAAAAATAACT
TCATTGATTTATTAAAAGAATCTGATATTGCAGATAATTATTTTAAAGAAATTCTAAGTTGCTATGAAT
TTACTGATCCAAACGATCCTCCTGCTAAAGTTATCTCCACTAATGAAATTTGTACTATTAAAGGAAAAG
ATAACGGTAAAATTAAAGTTAAATTATCTAATGGTGAAATTTCTCTAGAAGATCCTAGTAATATTTTAG
ATTATAGGGAAAAATTAGATAATTTATGGAATATTATTAGAAATATTGTATTCTACAATTATCAAGATT
TCTATCGTATGGAAAATTCTGAAGAAAGATTAAGAAAAACAGTGCTCGTGGTTAATGTATAGCCACAC
TTATATAGTAATATATAGGTTAAAAATTCTATTAATTGCTGGAAAATCCTAAAGCTTATTTAACTACAA
CGGAATCAGTAATGATAAACGTGAATGTTGTCGAAAGACTGAAAAAATAAATAAGATTAATACATGG
TGAAATAAAAGTACTATAATATATAGTATCCTAAATATTAATTATAATGGATGATCAGCAGCAGTATT
TCTTTAAGATTATAAATGAAAGAAAAAAGAAATGTTGTTCAACGACTATCAAAAGATTATTATATAAA
TAATAATTTAGTAGAGTAGAGCCAAGCTTTTGGGTTAGTATTTAAGAGATATTATCTTAATGTAAAACT
ATTAAATCGAAAAATAGAATTATCCTTTAGTAAGGATAAAGATATAGTCTGTTCTTTAAGGAAATCTT
AAAGAAGTTCATAAGAGAACTGCATAAGAATTAGCGCACTTATGTGAACACGAAAGTGATACCGACT
CAAACTTCTTGTATCTCAATCACTTTGTCGATTTATTCTCAGAAATTTATCCAGATATTACGATGAAAG
AAAATGATAAATCTATTGTATCTGCCATTAATACTATTATGTATATTGTTACTGAATTTAATGAAA
CGTATTACAAGTATGGAATGGAACTCGGTATTCCAGAAGATAAACGTGGACTAATTAATATGAAGAAT
GAATTTCTATATAAACGTTTAATGCTAACAGACGCTCAAAAGAATTATGCTGGCGTAATTTTAATGCA
AGAAGGAAATATTCTTCAGACTCCTAAGATTGATATTAAAGGATTAGCAATTAAGAAGACAAATACGA
ATAAACATGTACGTGAAGAATTTTCAGGAATTCTTAAAGATGTGCATTCTTGAATCAGATAAGATTGAT
GGTTCTGAATTTATTACTAGATATAAGAATCTAGAAAAAGAAATTCGAAGATCTTTAATGAATAGTGA
AATCACATTTACTCTCCCTAGAACTGCAAATATTAAAGAAAACTACGTAGCACCATATACGCAAGCAC
CATACAAAGGTGTATTAGTATGGAACACATTATATCCTGATAAAGAAATTAACTTACCAAACAAAGTT
AATCTTATCAAGCTAAATATTGAAACTTTTGATGATATTGAAAGTAAAACTAATGATCAAGATCTAATT
GAACGATTTAAGAAAGTTTATGAAGATGAGGAATTGACAAAAAAAGGAATTACTTATATTGCTATTGA
AGCAGAACAAAAACATATTCCTGAAGAAATCATTCCATTTATTGACATACCTGAAATGGTTAAGACTC
ATGTATCATCAGGATCCAAACTAATGACGTCATTAGGATTCAATCCATTAGTAATTAATGGATCATTAT
TCCCAACAAATATTATTAACTTTTAATGAAAGTAGGAAATCTATTGGAAAATTTAAATATTGATATGA
ATGATCCAACCAAGAAAAAACATATTGTGGTAGATTGTGATGAAGTATTATGCAATATTTCACCAAAA
TGGACATACTTAATACATCAAGAAAAAGACTATTTTGGTAAATATATGAATCTTATTGATAATTTTGAT
ATTGATCTGCATTATAATATGGTTTTATCTAGAAATAAGTTTTATCTAAATCAGTGGTTAATTAAAGAT
GAATCATATACGAATTATAGTGAAGACGAAATGGATGAAGTATTAAGACGTATGATGATGCTTTATGA
AACTGAAGATTACTATGATAACTTAAAACCAAATCCTATTGTAGAGTCATTAGCATTATCGATTCGTCA
ACCTATTTTAGATAGAATATCTATTGTAACAAGAACAAACGCTAAAAATCTTAAGTCTAAAGAAAGAT
TTCTTAAGAATTGTTTTCAAGGTGTTATGAATAAAGTTGATATATACTTTGTAGAAAATGATGAAAATA
AGTCTGATATTATTAAAGACTTAGGTGACGGTATTGCAGCTATATATGAAGATGAAGTTAAAAATATT
GTAGACATTTTAGATAACTGTAATAATCTTGATAAAAGCTTAATATATGTACCTAGTTATGGATATAAT
AACGCTAACCTTGATTTATATACTAAAGCAGAAGAAAAAGGAACTCAATTAAGATATTATTCATATTA
AAGGATGTGGACTTATTATGTATAATGGTAATTATGATATAAGTCTATATGAATATTTAAAAAGTAAA
CTTAAAGTATGCTATATCACAAGCAAAAAGGATGAAACTGTTATACGTTGTCCTTTTTGCGGTGATTCT
```

-continued

```
GCAAAAAATCAGTATTCTGCACACTTATATATAAATAATAAACCACCTTATAAATATTATTGTCAAAA
ATGTAATTCAAATGGAATATTTAATGATAAGATACTTAATAATCTAAATATTTTTGATGCAAAACTAAA
TCAACAACTTAAAGTATCATACGAAAAATTCATTAAAGATGCAGGAATAAAATATGGAAAATCATTTT
CATCACTATTTAATATGGATGAAACGGACATTCTTCCAAATAACTTTGGAATGTTAGAATTAAGAAAA
ATAAAATACTATGAAGATAGATTGGGAATAAAACTCAATGATGAATTATTAATTAAGTATAGAATTAT
TCTTAATCTTAGTGATTATATGGAAAATAATAAAATTCCAATAAAACAAGACAAATGGTATATTGAAA
AATTAAAAATGATTAATGATAATTACATTATATTCTTATCTAATGACAAGAATGTTATTAACTGCAGAA
ATATAACAAATGTTACTGAAAAAAAGAAACGTCATATTAAAATGAGACTATTTGAAGATTTTACTGAT
GAAAGTAGAAGTTTTTACTCAATAAAGAATAATATATCTCTTGATAAATCTTTATACAATATTCATTTA
ACAGAGGGTATATCTGATATTATATCCGTGCATCATAATATATTTAAAGATCAGGAAAATAATAATGA
TATTTTTATATCTAGTAATGGTAAGGGTTATAATTCGGTATTACAATATTTATTATCAATTGGGATTAC
AAACGCAAATATTAATATATATGGTGATTCAGATGTTAATCGTAATTATTATAATAGATTAAAGTATA
ATTTACTAGCTAAATATAATGGGGTTAATCTCTATTTTAATATTGCTAAGGATCCTTATGGTAATGGAT
TTAAAGACTTTGGCGTAAGATCTGAAAATGTAGAATTAAGTAAAAGCATTAAGATTTCTTTCTAACTTA
ATGGATCATAGAAATTTTCTAAAAAAAAAAAAAGACCCTAATAGATATTATATCTATTAGGGTTATATT
TATTTAATTATTCTTTTTTTAATTGATAAGGATACACATTAATATATTTACTATCTAATAAATCATACAC
ATTAATTAACCGACCATACATATTAATCTTTGAAATTACCACATCGTGAATTTTTCCTAAAGAATCAAT
AATATAAAAATCTTTTCCTACAATAATATTTCTATTATAAATTTCTTTCATGAATTCATCTAATGAATTT
TGGTCTAATTCAGTATTATACATATTAATCATTTATATTTCCTTCTTTCTTTTTTTTTTTAATATATTTCC
ATTTCATGATAAGGTATATTCATTATAATTGATACATCATTAGTACTATAATTATCATCTAGATATTTAT
CTATTAATCTTTTTCTTTCAGAGATGCATTTATTTTTTAGCAGTATAATGATCATACTGTCGGTTAGCACT
TTTAAGTTCTTTAAAGAATAAACTATTATTGTTAATATATTTTTAATATTAGATTTATCTACTGATAAT
TCATTAGCTAATGAATAAACACTGCTGATATTCTTCTTATTGATAATATCAAGAATATATGATAAACGA
GAAATTCTTTTAACTATCAAATTGCAATCTTTAACTTCCATATTAAAAATAATATCTACATATTTTTCC
ATGATGGAGGATTATCGATAGATGTAGTTTTATTATTTAATAGTGAATTAAGATATATGACAATATCTT
TATTTAATTTGGTATTATTTATGATATCATCATATTTTCCTTCATCATAATTACGTTCTATATATTTTGTA
AGGTATTTTATTTTTTCATCATCAAGACTAAAATATGTCATATATTTCTTAAAGAAAGTATTTAACTTTA
ATTTAGTATATCTTCTTCGAATATTAAAACCATAAACAAACACATTAGTTACTGTGGTATCTATATCTT
CCATAACAGTATTAACTTTAATATTATTATTAACAGTATTAACTTTAATATTATTATTCTTAATAAAATT
ATTCATGTTCTTTATTTCATCGATAGTATTAATGATAATATTTCTAGACAATAATTCTTCTTTTTTAAAA
TTATTAATAACTTCTGTATTATTTAAAGATAAAATGAAGGCATTTTTCATCTTTTTAATATTATTTCTAA
TAACTTTATTAATTATATTTATATCAACACTATAAGTTTTTGATTTTATGTTATTAAATATATCTAGGTT
AGTAATAATATCTTTTTTAGTAGATAATTTTAGATAAGTGTTGATTATAAATTCATCTATATCTTTAGGA
TATATAATATACAATGCATCAACCATAACCTTATTATCATAGATAAGTTTAATTTTAATTGATAATTCT
TTTTCTAGAATATTAATACAATTTTCACTAATTGATGTCTTAGTATTAATTTTTTTACCATAATGGTAGT
CATTTCGTATATCACATATTATTGAATGTTCTAGATTAGTAATTATATAAATTTTATTATATAATTCTTT
ATTATTCTTTATAATATTATTAACACTATAAATATAACCAACGCCAATATCATAAAATATATCCATATT
TGTAACAAAAGAAAATTTCTTTTTTAACTGATTATATGACTTGATAATATTCTTTTCAATACTATCAGTA
CTTCCATCATTAAATATCAATTTATTATCCTTTAGATATTCTTTAAATGAATCTAATATAGTATTATAGT
TATCTAGATTCTTATTGAGTACTAAAGATATAATATCAATGTCATTCATTTTTCGATAGTTCTTAATACT
TTTGACAATACTTTTCTTTGTTGGAATTTTTATATTGTTCTTTATATTTAATTCATTTATTGTATTAAATG
GTATATTACAGTATAATAATATATCATCTAAACTTAAATTTTCAATAAAAATTAATTGAATAAATTCAT
TATAGTTGATGTAATTATTTTTAACTTTATTTTCTTCAGTAATTCGTATTCCTTTTAACATGGAATAAAG
CTTTGACTGATCATAACTAAATCCTGATAGTTCAGAGATTTCTTCTAAGGTTACTTTATTAGGATTAAG
TTTATTAATATTATTTAGGATAATATTATCAACAATCTTAGCTTCTGAGATATTTTTGTTCTTCTTATTAT
TTTTAGTTTTATTATCATAACTAATTTTCATTTTTTTATCAAATAGACCGGATTCATCAATATATAGATT
TACTACACCTACTGGAACTTTATATTTCATACATATTGACTTTAAATCAAAATTATCATTAAGATATGT
ACTATCTATTTCATGTTTTAATTCCTCGCTAATTCTTAACATCTAGTTATTCCACCTTTTAAATATTATTA
AAGAAAAGGATAATGAAAATAAATTTCATTATCCATATAATTACAATGCAATAATCAAGTTTGTTTTA
GCTCTAGTAATTCCAGTGTATAATTGTTGATGATATATGCTCTTATTATATATTTCATCAAACAGTAAT
ACATTATCATATTCCGATCCCTGTGATTTATATACGGTTGTTGCATAACCAAACTTAAACTTATTAATG
ATAACATGTGATTCTTCAAAAATATTTCTTCGAAGAATTAATGACTTATACATTTCATTTTCATAAATTT
GATCATCATTAGTTATTCCATCCGTAAAATATAATGCATCTACATGCAATCTATTATAGATTCCAGTAT
CTGATGAAAATGTAGGTTTAAAGTCTAATTCAAAAGTATCCAACCTTTTCTTATATTCATAGATATTTT
CCACATAACCGATAATACCATTTGTTAAATACTGTTGTGATCCATTATCTTCATACATTTCTAACCAGTT
ATTCTTAAGACATATTAATTTTTCACCAACATATGGAAATGGTGAATTCAAATTAAGTATATTTTTTCT
AATAAGAGAGTTTATCCTATCAACAGTTATATTTTTTGAAGCTAGAATTTGATCTGCGCCAGTATACAT
ATCATAGTCTACATCTTTTTTATTAATAATCATTACATTTTCATCGATAGGACCAATTCTTAATCTATTT
TTCTTACGAACTTCATTAGCTAACCATATAATTGGATTATCCAGTGCTTGCCTTAATGGTTCATCTAGG
AAGATATCTGGTCTTTTCATATATTTATTAATTCCACCTTTAACTGGTGGAAGCTGCATCGGGTCTCCA
ATCATAATGATTGGGACGTTAAATGTAATTAGTTCTTCAATCATTGAATCTGTAACCATACTACCTTCG
TCTACAATAATTAATTTAATATTTTTTGAAATACTTTCTTTTTTAATAAAGTTAAACTTATTCTTTTTTTC
ATCATAAACTACATTATACATTAACCTATGAATTGTTGAAGTGTTATTATTCCCTTTCCTATTAAGAAC
ATTAGTAGCGGTTCCAGTATATGCAGAATATACTACCTGTTCATCGTTTAAATTGATTGCCGAAGTTAT
AAATTTTATAATTGTACTTTTACCTGTTCCGGCTAATCCTGCTATTGTAAAAACTTTTTTAATATCTTTA
TTCCACCATTCAACTGCTCGCATAACAACCTCTTCTTGTTTGTTTGTTAGCGTAATAATACTCATTATAT
ACACCGCTTTCTATCCATTTTATTTACTATAATTTTTTATTAACATTATAAATTACTTTTTCATTAATATA
ATATATAATTAAAAAATTTATACAACTTTCTAACATAACATTATTAAATAATTGGCGGTGATAAA
ATGTCAATGAGAGATATGAATGGAAATCGTATTATGGACTCATTTAGCTTCGATAAAGAGTATGAAGG
AATAGTATTAGATAATAACGATTTTGACGATAAACTATTTATTAAAGTATATATCTCTGAATTGTTTAT
TAATGATATTCCTGAGAAGGTTATCGATATTAATGAAAATATTGATCATACTAAAATAATTAATAATA
ATAAAATAAATTTTAAAAAATCTGTAGTACATAATAATTATTTGAAGTGCTATCCAATCATATATAATA
ATATGAATCTTGATATAATGAAACCAAAAATAGGTTCAAAAGTTATTGTCAAATTTATTAATGGTAAT
CCAAAATTGCCATATTATGAGAATAAAGGATATTATACAGATATTATTATACCAATTCCTCCCGAAATT
ATAGATCCTCCTACTGATCCATCCACTAGTGATGATTATACTTCTTTTGGATACTATAGAATGATTAAA
CTTACTAATCCGGCTATGATTGGTCGAGATATACTAAAAATCCAAAAGAAATTAAAGACTCTTGGGTA
TACATTCACTATTGATACACTAGACGGTATATATGATTTAAGAATGTTGAATTATATAAAAGATTTTCA
ATCTAAAAATAAACTAAGTGTAGATGGACAGATTGGTCCAATTACGTTTAGAACAATTATGCGTAAAA
ATATATAATTTTTAAATTCGAACATATATTTATAGTAAGATAGTTTACTATAAATATATTTAATTGGGG
```

-continued

```
TGGAAATTTTTATGGAACAAGTAACTTCTGGACTATTAATTTTGACAGTATTATCCGTAGTAATTCAGT
ATTTAGTTGAAAGAATTAAAGATATTTTTCCAACAAAAGTTATGGATAAACTAGCAAACTATGTTAAT
CCTGCTTTCTGGTCTTTAATTGTATCTCTTCCTATTGCTTTTGGTATAAATATTGATTTATTTGCAATTAT
CGGTTATAATATGCATCCAACATGGCTTGCAACATTATTTACTGGTTTTGCATTGAGTGGTAGAGCAAC
TGGTATTAATGAACTTATTAAATCATTAAGTGCTGTTAAAACTAATAATTTTACTCAAGCAGATTCGGT
AAAAAATACTGATGAAGAAGAAATTAAAGTTGTCGCTAAATCTAAAAAATAATATATATCCCTATAGT
GTATAATTGCACTATAGGGAATTTTATTTACTAAAATTATAAAATACATAATAAAATAACATTAAAAT
ATATTTACATTAATATACAGAAATGGATGATTAAATATGAAATATCCGATACGTGAGGATCATAGAAA
AAGAGTCAAGACAAATTACATTATTATTACTCATGCTAATAATCTTATAAAAAGGGGAACACATATAA
ATAATGCATTGAGGCAGAGAACTTTTAAATACACTTGGGGAATATGGCAAGAATATTTAATGACTCAC
GTTAATAAAAGATATTTACCAATGCATTATTTTATTGAATTAATTGATAAAGATTATGCAGTATTGAAG
GGTCTTTCTGACCATAAACCTTCTTACTTTATTAATGATTTAGTAGACGAAGGTGTAATAAAATATGTT
TACCGAGATTCGATATTAATAGTCATTGGAGATAATTTTAGTATAAATAATCCTGATACTAGAATGATT
GATCATTTAGCAACTAAAGTTATTCTTCCATTAATGAAAACGTATAATTTAAGTTGGAATAAAATACA
ATTTTTTGATGAGTGTTTAACTGACTCATTATTAATAATATTGATAATGATGAAATAAAATATAATTA
CGAATATGAACCAATGTCTATGTTTGATATGAGTATTCTAAGAAATGCAGTACTTAGATATAAATCAT
AAATATAAAATAATAATTATAAGTATTGTGTGGTGATAATTGGAAATGGATAATAATCAAAGACATAA
GAATAGAAATTTTTTAATATAATGATAATTATAAATATTGTAATTATTGTTATAATAATTGTATCTTCA
GTATATCTATATATACATATAAATTCAGGAAACAGTTATTCAAAAGAAACATATGCTAAAGTGAATAA
TGTGTATATGACATATGATAATGAAGATAAGGATATACAAGTAAGAATTGGTAAAAAGAAACTAATA
ATATTTAATAATGGTAAAATTAAAGAGATTATATTTAATAATTTTGAAGTATCAGTATATGATGAATAT
ACTTTAATATACATTTCTGGAGATAATGATGAAGTTAGTATTTCTGTAGACAATGATAAAGATTCCATT
TCTGATATAGTCATAAATAATCAAAGTTTAATAGAATAATTATATAGATATATAGAAGTGTGGAAAGA
AGGTTACAATATATGCTCATATTAAAAATGAGAACTGACAAAAAGTAGACTATAAAAAATTATGGTT
TATAAAACTTCATAGAAAATTAAATATTGAAATTCATTATAATATAGAGGAAAATGGATTCTACTATA
TTGATAATAATAAAACATTAAAACTTAAAAAAGATTTTTCAAGAACCAATTAGTATGATTCTTGATATTA
AGAAAAGATTCAATTCGTTTAATACTGAAATGGATATAATTGATAATAATATTAATATGTATCTTAATG
ACGTTATAAATAACTTTGAAAAGAAGAAATGCTAAGAATTATACTAGGAACTTCGGAATATAATGTG
AAGAATCTATATAATGATCTTACTGAATTAGGAATTAATATTGATCCAGACTTATTATATGTAAATTTA
TATAAAAATACAAAACATTCCGAATATAATGATGAAATAAAGAATACATTTAAAAGAATTTGATAACC
TGAATACTAATAATTAAAATAGTATTCAGGTTATCAATTTTTATCGAGCAAAAAATATTTTTTTCCTTCT
TGAATGTTTTAAGGCACCAATGCGCATTTTTTCAACTAGTTCTTCTTTCTTATTTTTTCCATCAGCTAGA
TCTTCAATAAATAATTCTATACTGCCATACGTTGTTTGAATATTTTGAAAGCGATGTCTAATTTGATAT
AATGATTCTTGAGTATCATATAGACATAATTGCATAAAATGTTCTTGAAGATTTACTGGTATGCTGTCA
AAATGTTCACTATGAACTGCGTTTGCATATACTAGAATTCCGTTTAATGTATATTGGGGAGCAATTTCA
ATTTGGTTTGGATGAATAAACCGGAATGTTGAAGGATTTATTTGACCTTGAATGTTACTCATCATCTGA
TTTTCAAATAAACTTCCAGAACCAGAACCAGCTCTAGGAGTTCCTCCGATAATTGCACTATTACTACTA
TACATATCTAATCCAATTACACGATTAATATTTAATACGGAAGTCTCTGTATCTAAATAATAACGATTC
TCATATCCCGGAACAAGATCTTTATTAAATACTCGGATTTCTTCAATTCTTGGGAAATACTTACTAAAC
GTAATCAAACTTTCTGATCTTATTCCACTAAGAATTTCTTCATGAGAAAGTTCTAATTGTGTAAATTTAT
ATCCTAATTTTCGTTCTAAGAATCGAATAACCTCTGTAGGATTAATCATTTAGTTATCACTATCCTTCCA
ATAATAAAAATACAATACCACTTCCTAAATTTAATTAAGAAGTGGTATATTTTAAAACATATCTTGTAT
ATATTTGCTTAAATCACGTTTAATTTCTTCTTCGAGATAAATCCGGATAGTTTCGTTTGATTGTTTAATA
CTTAATGTTTGATCTTCAGTAAGAGTTACTGAACCATTCTCTAGATTCATAGATATACCTAATGATTCT
GCTAATGAATATACATTTTCAGATTTTTTAGTAACAAACTCTAATAATTCAGAAACTTGATAAGGAACT
ACTTTACCTGAAAGATTATATGAGTTTGAGCTTGCTGCTTCTAACAATCCTTGATAATCTTCTGAGAAG
TCTTCATTAATCCGGTGAGTCATATATGAGTTTGGATGGGATGGAATAACAACCCAATCATAGCAGCA
AATCATTAAAGGTGAATGAACTCGTTGATACTTCCCATCAGGCTTAATAATATTACCAATACCACGCAT
GGAGAATGCTGCCTTTGATCCTTGATTAATCAAACCTTTCATGTCTCTACCTACAGATGTATCTGCAGT
TTCAACTCGTCCAATTAATCGATTCCCATCAAACTTAGCTTCAGTTACAATATGCGAAATATTGCGTTG
ATCAATATATAATTGTCTACGATTATCAGTATTTAATGGATGACCTGCTTCTCCAAAGAATGTTCTATT
TTTAATTTTTTCCTGAACAATTGGGTTTTGTATTGCTTCATCAATTGCACGTCTATCATAAATACGGTTT
TTTTGTTCTGGTGCATCAGCTTCTTGCAACTCAGTCTCGAATAATACATTATTAAGTGTTTTATCTATAA
TTTTCGGTTTAGATTCAGTGACCGATTCCATTATAATATAACCTTTTTCTTCAGTCATAATAGTAATACA
CGTCCTTTCTTAGTATATAAATAAAATTTATAATAAAATGTTTGATTAGATAATTATTTTTTTAAACAAC
TTATTATAAAATATTCTTTTTATCATTTTTGATAAAATATGTTTTAAATTTAAAGAATATTAAATTATAA
AATAAAATGATAAGGTGGGAAATAAAAATGCCAAAAACTTTTTTAGATGTAATCCTTGAAGATGCAG
ACGCATTTGAAGCTAGTAAATCTGTTGAAGTGGTTGATAAAAATACTACTGAACCTGAAGTAGTCGCT
AAAGATGAAAAAGCTGATGTAGAAGAACAAAAAGAAGTATGTGACGAAAAAGAAAAAGCTATTGAA
AAAGAAAAAGAAGAATATACTAATGATGCAGAAGTTGAAATTACTAGTGACGTTTCATTAATGAATA
ATGTTGCTGATAAATTAGATAGTGGTATGTCTATTGAAGAATCATTCAATTCTCTAATCGAGGTTAATC
TAGTTAAGAATGAATTTAAAAACATGGGCTTGACTTCTGAAGAAATTAATCTTCTTGCTGAAGATGCTT
CTAAAGAAAGAAAAGGAATTATACGTGGATTGGCTAAAAAATCGGTATCGATGATAGCGGTAATGT
TGATGCTCGTAAATATGTTAATGCTCGTAAAAAAATTAGGCGTAAAACAAATTACTGCCGCAGTAACTT
CTACGGTTGCTGCAAGTGCTGCTGCTGGAGCTAGTAGCTATTATATTGAAACATCAAAAAGTAAAAGC
GAAACTGTTAAAGGTGGAATCTTTTCAGGTTTAACTGTAGGATTGGTCGTAGGTTATTGGGTTTCCCTT
TTCTCATTTGTAGTTACTATTTTGCAAAGTGCTAAAGTTAAAGGTCAAATGAAAGTGATCCATCTATC
TTAAGAAATGCTCTTGCTGAAAATAAAAAAGATTTAGCTGAAGTTGTATCTTCTATGTCTAAAGTTAAA
GAAGATGCTAAAGCAACCAAGCAATTAGAACGTATTCAAAAAGCTTTACTTCGTGAAAAATCCAAATT
ATTGAAATTGCAAGAAAAATTAAATACAAAATAAGTTATATATGATCTCAATTCTGATTAATTTCAGA
ATTGAGATTTATTTAAACATTATTATATAAGAAAATATATATTGGTGGTGATTTCAATTGCATCTAGAT
GAGGAAAGTATTAGATACGCTATAAAATTTACAGAATCTTTAGAAAAAAATGATTTTGAATATGGTCA
AACAATTCGTGAAGAAATTCAAAATGAAAATAATTCATCTCAAATAAAAAAATATTATGAATATGCTCA
ATATTAAAAAATCCAAATACTATTACTGTTGAAGAATATTTAAAGATACGTAGAAAAATTAAATTTTCG
GGTCTTATTGGATTCTTAGCAGGTCTCGGAGGAAGCGTAATGTTTACTTCAGATATTATTATAAATAAT
GATCGGCTTAGAGACGATCCTCAAAATAGAGGGAGTCGCTAATAGAAATAATCGTAGTAAGCTAAGTAT
GCTTAAGTCAACCTTATTTGCTTTAGTTTCGGCTTTTGGTTCATTTGCTTTATCAGTATTATATAGTAAG
AGCGTTAAGAAACTTCAGTAGCTAATCCATCAATAGTTAGAAGTTTATTAGCTATTAATGCAAATGA
CTTAAGAATGGTAGAAAAAGCAAATAATAGTGTAGTTACTAAGTCTGACTTAAAATATATACGTAGAA
```

-continued

```
TAGAACGAATATTAATTAGGGAAAAAAAGGGATCTATTAAAATTGCAAGCATACGTTATAAAGAAAAA
TAAATGAAAGAAGTGAAAATTTTTATGGAATATAATGATGTATTTTTAGAATATTTAAATTCTGAAGA
AGATAATATTGAAAATATGGAAGAATTCCTATCAAGCTACATTGGAATTAAACCAAGATATCTTGAAA
TTAGACCTACTGTATTTAGTGAAACAAGAATTACTAATGATGGTATTAGTGATGAAGAAGATAATAGC
GAAGAATCTGATCGTAAAAGATCTACTGATGAAGTAAAAAAGATTAGTAGAGAAGTAATGGAAAAAG
ATAAGAAAAAGAATCTTAATCCACAAAATAAAGCAAAAATTGCAACTATTAAACGTGAAATGGAAAA
ATCGATTAAAATGGATCCAAATAGTCTTGGTAATGATACTAAACTTAAAAGACTTATGCGTGTAGGAA
TTACAATGTTAGTTTCTTTCGGGATTATTTTTGCTCCTGCAGTTGGTGTCTTAATAAAGATTATTGCTCT
TATCGGAGTAGCTGCTACTGCAAAACACGTTAATCGTAAAAAATTGGAAAATACTATTATATTACTAA
TGGATAAAATTAAATATATTGAAGATGAAATGGAAAAAGCATCAGACAATCCTAAAAAGAAATATGA
ATTAACAAGAGTAAAACGAGAACTCCAAAGAACACTTATGAAGTATCAGTCTAGACTTCGGAATTTCC
ATTAATATATGATTTGTATAAGCGATGTTGCAAAGGAGGTACTATTATATTGAAAGATGATTTCTTTAA
TTATTTATTTGAAGCAGATGATCCAGAAGAAATAAGTAATATTGATCCTAATGAAGATAATACTGAAA
ATAATAACGAGGATACTCCTTCTAATGAAGAAAGTTTACCAAACGAAAATAGTGATGAAAATGATTTA
GAAAAGGATCCAGAAATAGAAGAACCTGATAATGAAGAAGAAATAGAACCTAATGAAAATGAAGAC
CCGAATAATAATTTACGTATAAAGGAAATATTATTTGAGAATTTCTCTGGACTTAAAAATGCAATTAA
ACGATTATTTACTGACATTGAATCGGTAATACATATCGTAAAATCATATGATTCTAATAATGATAATCA
TAATTTAGAAAATACTGTGGATGGAATATCTGAAAAAGGATATGACATTTTAAATAAAATTCAAACAT
TACAAAATGGTGTAATTCTTAATATATCAAACGATAAATTAAAAATCATATATAATGAATTAGAAAAT
CAAGTAAGTGATATTATTAAGGAATATTCAAATAAAGTTGATGTAAAGTTGAAAAACAAGTATTAATA
ATATAAACAATTTAATATAAAAATTTTAATTTATTTCTATGTAAGTTTCGTTTATTACTTTTTTAAAGTA
AGAATGATGAACAATTATATATAAAATAATTTATAATATTATTTTTATAATCTATAATTTTATATAAGAA
AAGGAGAGAAATTAAATTATGCGTAATTTTAAACGTATTACAAAGACTAATACAGATTCTTTTAGTAC
TCATCTAAGCGAAACTCAAGACTATTTCGCTAATACTAAAGGAACAAATATTACTGGACAAGATATCG
CTGCAATTATAGTGAATGAACAATATTTTGATGAGTATGCAACTCGTCTATTAGAAGGTTTCGATGCTG
ACCTTAGTGAAGAACTAGGTGTTCTTTTTAGAAAACACTCGTAGCAACATTATGGAATCCTTGGGTGGA
ATTACTCCATTTGCTTCACTTTCAATGCCTGTTTTGGTTAAACTTTGGGCTCGTTTGTCTATGGTAAATG
CTATTCCTACTACTCCTGTTACTACTCCTGCATTTGTAGTACCAACTATCAAACCATATACTATTGGTCC
AGATGGTGAAAAATACTACCTACCAGAAGCTATTAATACTATTCCTGAACACTTTGTAAGTCTTCGTCA
ACTTAAAGAAGATATCACTATTACTGGTGGTCGTCTTTCTGACTATGATCTATTTACAGGTGTATCAAC
TGCTGACCGTGCTAAAGGTGATCAAGTAGACCGTAAATTCCAAATTGTTGCAGGAACATGGTCTGATT
CTTATAATGTCGCTGATGCTGCTCTTGGCGAATATGAACTTAAAGGTCAAGCTCTTAAAATGGATATTC
ATGGTAATATCTTTGGTAAAGTAACATATACTACTGATGGTAATGGTGCTACTAATGAAGATACTATTA
TGGGACATGTTGATGTTGAAAAAGGTCGTTTAGATTTAACTTCTCTTTCTGGTAAATTGACTGAGTTCA
AAATTCAAGGTTTCGTTTCTTCTGAAATGCATACTGGTACAACTCAAGTTGGTTTTGATGTTGATGATC
GTACAATCAACATTGGTACTGCTCCACATATCGAAGGTATCCTTACCTATCGAATCCGTACAAGATAGT
AAAGCTATGTATGATATTGATGCAGCAGCTGTTATTGTTGATACAATGTCTGCTACTTCTGCACAAAAA
GTTGATACTGACTTGATTGAATTCTTGTTACGTTCTTATGAAGGTACTAATGCTGCTTATCATAAAACTT
TCGATGTACATCCAAATGGTGGATACAACATGCATCCGCATGAATGGCGCCGTGGTATTCGTGACGTT
ATTGACTGGATGTCTCAAGCAATGAAAAATGATTACAAAACTTATGATGCTTACTTTGTAATTGTTGGT
AATCCAATTGACACTCAATTGATTCCTGACATTGAATGGGAATTCCAAGGAGCTACTGATGAAGTTGC
GGGAATTAACGTTTCTTATAGCGTTGGTGCTTCTTCTACAGTTAACCGTTATAAAGTTGTTTCTTCTGAC
TTAGTACCTGCTGGAGATCTATTAATCTTTGCAGTTCCTACTCGTGAAGACTTCAAAACTTACGAATAC
TACCCATACACTTTCAATATCGTTAATAATTACAACAATGCTGTTAACCAAAGCGTTCCTAACATTATG
CTTTCTCGCCGTTATACAGTTGAAGAATTTGTTCCAATTATCGGTAAAGTTACAATTAAAAACAACGAT
GCAACTCAATACGCTCGTTAATAAATATTATGAACCTTTCAGAGACCTTTTGGTTTCTGAAAGGTTATT
ATTTATAAAAATTTAAATTGGCGGTGCAACCATGCATATTGATTATGGTATTGAAAAGAATATATCAA
AGTACTTACATGAAGAATTACTAACTGAAGATATCTATAATCATCCTTTATTAAAAAAAGATTGATGAT
GAATTTCAGAAAATATTAGATGAAGATAATATTAATGATACTAAACTACCAGTAACATCATATAAAAA
AATTCAAAATATAATTAAATATGTCTCAACTATATTTAATATAAATTTAATTATAACGATTGATAACGA
TAATATCCTTACTTATGGAATGATGACATTTATTCCGGTTAAAAATCTAACAAAGATATCTAATAATAT
AAAGAAGATTGTACTTCAACCAAAAACTGGTTTTGAATATATTAAAACTGAAGTTATTGAAATTAAAA
TACAGAAAAAATTAATATCTTTCATTAAGGATCCAAACTTACTTATAAGAAATAATAAAGTTCCAAAA
AATTATACTCCTAGTGGAAGAATATTGACCAGTATACTTCTTCATGAAGTAGGTCATCATATATTCATT
GGATTTGAAATTAAGAAATCTATTAAAAATGATAAACTTTTTTCAATTAACGGTGGTAATGGTAAAGA
AATAACTATACCTAGTAATGTTAATAATAATAAATATGTATTAACAAGCACTATATTATCTATATTAAC
GTTAAGTATTTCTATGCATAGTTATATGAGAAGTGAATACAATGCGGATAACCTACCAATACAATATG
GTTATGGTAAAGAAGTATTTTATTTTTCAGAATTAATGGAAATATTAGAAAAACAAAAAAGAAATTCA
ATTCTATTAAAGATTAAAGGATTTCTAATGTTTGGTAAAGATAATTTTTATTATTATAATCGTAAAATAAAGAAT
CAAGTAATTATTATGATGAAAAAAGAATTAAATAATGATAATAATAGTCCTAAAGATAAGGAAATTAT
TATAGATAATTTAAAAACTATAGAAAATCTTGAATAGATAATGTGGTATAACTTATTAATTAATAAGTT
ATACCATTAATACGCAAGTAACTATTAATTATAATAAAATAAAGAAATTGTGGTGATAAAGTATGCT
TAAGATTAATATTAAAGATAATCCTGAACTTAAAAAGAATATTACTTCAAAAAATAAAAAACTCTTTT
ATGATTTCAATACAAATAATCAATCTTTCCTAGAATTAGCTATTGAATTAAAAAGATTGGGAATCAGA
AATAATAAGTTACATTTAGTTTTATATGATAAGAGTCTTTCCGGAGTAGATCCGTATGACCCGAACTTA
ACTGATAACGTAAAGGCAAGAATTGTTAAAGAGAGCATTATTAATTTTTGGTACTTTATTAGGGAAGT
AGTTCGTATTCCAGTTCCAGGATCTTCAGTCCATTTTGCTATTCATAGAGGGAACCTTGCAATGTGTTT
CTGTTTATTAAATAATTTAAATACCGTATTAATGTTACCTCGACAACATTATAAGACTATAGTGCTGT
AGGTTTTTATTTATGGATTGAATTATTAGTAGGTAGAAACTATCAAATGATCTTTTCACATAAATCATT
AACGGATAGTATTGCCAATCTAAAAAGATTGACGGCTCTATTTGAACTATTACCGACATATATGACTG
AACCTATCTTAAATAGTAAGAATGATAAGAATGCTGAAACTATTTTAACCAATTGACTCAATAAATAAT
ACCATTAGGACAATTGGTCCAAGCACAGATATTGCTTCAGCAGATAAGTCAGGTTAACTTAATTTTTCG
GCTTGACTATAAAACTTTTTTAATTGCTGGAACATCCTTAAGTCTATTAAACTACAACGTAACTGGTAA
CGGTAAGCGTGAATGTTTGAAAATTAATAGAATTGGACAATCAGCAGCCAAGCTTCCAATGATTATTG
GATGAAGGTTCAACGACTATCGAAAGGGTAAATTTATATTTTAAATTTAGAACTGAGTAGAGTAGAGC
CAAGACAAAAATTTGCAAGTTTACTTGGTTAGTAATTAAGTGACATTAACTTAATGTAATTCTATTAAA
TCGAAACGGAAAGTATAGAATAAAAAATAAATATATATTATAATAATGATGAGATAATTTATATCTTCT
TTAATTAAGATTATTAAAGAGGTGATTATTATGGTAAGAAAAAACACAGAATTTGATCTAGTTAATAG
AATATCACAAAAAATTCAGTAATAATGAATTTACCTATATTGAAGGGTTTAATAGAATGATAGATAAAT
```

```
GTAGATTTAAATGTAATAATTGTGGAAATGATAATTATTATACTTCGCCATCCATATTATTGGATAAAA
ATAAATCTATATACTGTAATCTATGTAATCCTGCAACTTTACGAAAAAATTCATTTATGGATAATGTTA
ATAAAAATTACACTGTTTTAGAAAAACCTAAAAATAATAAACAAAATATATCTGTAAAGTGTAATTTA
TGTGATTTCATATTTAAAACAAGGTCACAATATTTAACAGCTATGGACAAACCTAGTAAAACTCGAAA
TTTGTGTCCTAAATGTAATGCATCAAATTCTGAAAAAATATTTGCAAAATTTCTTGATTCTCAAAATAT
TAATTATGAAATGCAGAAAAAGTTTAAAGAATGTATCGGTATTAATAATAGAGTCACTCCATTTGATT
TTTATATAGATTCAATGAATCTAATTGTTGAAATTGATGGAAAACAACACGATTCATTAAAATATGCAT
TCCATAGAGATATTAAAGAATATGAAAGAACTGTTGCTAATGACAATATTAAAAATAATTTTTGTAGT
GAAAATAATATTGGATTAATACGTTTAAGATATAATTGCAAAAGTAAAGAAATTGAATTCATGGAATC
AATTATTGATGCAAAATATATTCCAAACGTAAAATTATCCATAAATGCAAATCTTATTAAATATTAGAT
ATAAATCTCATCAATTTATAATTCTGACTCTTCAAATAAAATTTGGAGAGTTTATTATTTTTAGGTTTTT
CTATAAAGATATAGTCTATGGGGAGAGAAATCTCTTAAACTTGTTATATTCTAAGCGAGGAATGACCG
TTGTATGCGCCGTAATGAGTTTATAAAAACTCTAATCAATTTTGAGAATAACGGAATGATAGATAGCA
AATAATCTTGAAACGTTATATCTAATACTCCTACATGCATATATTTATTAAACGGACTATATGTGTGAA
GTTAGGTGAAGTCAGTTGAACCACTCCCCTATAACGGGAAACTTAAGTATTATATACTAAGAGTGTAT
AGACTGGGATGCGTTATAATATGGTAAGGATATTCTTTAAAAGAATTAGACGAATCAATGAATTAAAA
CCGTTAAAAATTAATCTAACAGGTTAATGAATACTAATAGGGATGAGTAAGTGAGCGGTTATGAAAAT
CCTATTTAAGTTATGCTCTTAAATTATTATTAGTGCGGTAGAGTTGGTACCTAAGTTATAACTATGCTA
TCAAAATTGAAAAGGTGGAAACTAGGAAGATCGTAAAGATGTTTAATGTCTGATCTAATAAATAGGA
AATGATTTATGAATCTTAGTGGCAGCAGCCTGTAGTAGTGATGAAGCTCTTGTAATGAGAGTGGAGTG
AAGGGGCATAGTCAGAGATTATATTAACCAAATAATCTTTGATGGAACGCTGTATACGATGAAAGTCG
TACGTACAGTGTGAAGTGGGGGAAAATCCGGAGATAATTTCAAAGGATTACCTATCACTATCCGTTAA
TATGGTTAGATGAATATGCGTTTTTAAAATATAATGATACGGTATTTAAAGCAATGCGCCCTGCTTTTA
CAGAAGCAAGTAAAGCTGCAAGCATGAATGATACTCCGTATTCAATACTTATTACAACAACGCCTAGT
AATTTAGATTCCGATGAAGGAAATTCATGTTATAATCTTATACAAAATGCAGCTAGGTTTGATGAAAA
GATGTATGATTGGTACTATCAGTTTGGTCCAGAAATACCTTCAATCATACTTGGATAAAAAACTCTGGTAA
TGATTTTATATATATTGAATTTAGTTATAAAGAATTAGGTAAAGATGATGAATGGTTAGAGAGTCAGA
TTCGGGCAATGTTAGGTGATAGACTTAAGGTTAAGATTGAATTATTATTAGAATGGGTTTCTAGTAGTG
AAGATTCAATCTTTAGTGAAGATATTATTGAATCTCTTGAAGGTAATATTATAAAAAGGGAAAATTAT
GCAGGATCCATATATTTATGTGATGGAACATATAAACTAGATGTTATTAAAAATCCTATAAACTTATTA
ACTAAAACATACGTTATATCAATAGATATTGCCGGAGGATTAGGTAAAGATAATACCGTTGTAACCGT
TATTGATCCAGTAGACCTTAATACGGTAATGGTATTTCAAAATAATAAAATTACTGTTCCGGAATTAGA
AGATCTTGTTACTGATCTAGTGTTAAATTATATTCCAAACGCAGTAGTTATTCCAGAACGAAACTATGG
TGGGGAACAACTGATTGATTATATTATTAAACATAATTTAATATCTAAAAATCTTTTTTATGTAACAAA
ACAAATAACTACTGAAAAGACAATCTTACAAGAAAATAATGTTTTTAGAAAAAGAAGTAATAAAGTT
AGAAAAGAAAAAAGGGTATATGGTATATATACAACAACTAAGACTCGTGATATAATGATTAATACTAT
CCTTCCAATGATTGTTTATGAAAGACCCGAATTGGTAAATAATGCTTCCTTATTTAATGATATTAAAAC
GCTAGAAAGAAAAAGAAATGGTAAGATTGAACATAAGTCAAATCGCCATGATGATAATTTATTTTCAT
ATCTGGTAGGATTATATGCACTATTATATGAACACTCGATCAGTAGGTTTGTGGATATTATTGATAAAC
CCGAGTTAAATAAGGAAGATGAATTAGTTGATACCGTAATAATACGGGTCAACATCGTTTAACTAGTT
CTCAAAAAGCATCAAGAACTATTAATAATTTAAGAAAAGTTAGTAAAAAACCAACAAGCAAATCAAT
TATTAATGCATCAATGAATATAAATAACGAAGATTCTAGTATTAATAATTCTATGAGTAAAAAACCAC
GAAGAGGACTAAATTTAGTCCGAAAATATAATAAAAAATAAATTAATTTTTTATATACTATCCTAAAA
AATATTATATAATAATTAAATATAATTGATTGGAAGTGGAAATTTTATTATGGTTATGTTAAATGCAAC
TGTAAATGAAGAATATAAACGTGAAAACGTAAATGAAATTATTACAAATATTAGTGAGGATATTATGA
TTGATAATATCTTATCTCAAATAAATGATACTGATATTCAGGATCTTTCTGAAGTAAGAAAATCATTCT
TTGAATACTTTGAAGAACGTTATAACTTTGTTAAGAAAAATTATAACGATGATGATGAAGCAATGCAA
AATTGCCGAGAAGTCTTTGATGATATTTTAAATCAAATTATTAAAGCAATCTCTGAAAAATACAGTTTT
GATCTTTTCTTTTCAGATATCCTATTATTCGATACAAAGTAGAAATTACTAAAAGTCTATATTATTTCT
TTGTCATCAATATTCGGGAAAATATTGAAAATATGATTTATTATTTTATCATGAAAAATAGAAAAACAT
TAGTAAAAATGTTTAACACTATTGTAAAGAAGAAAGAAAGAAATTAAGCTATATTAATCTTAGTTCT
GCAATCAATAATGATTATACGACAATGATATATCATTTAAGCATGATTATTGATAATATTGAAATTCCT
ACTAATGAAGATATTATTGAATTAATGGTTGAAGATAATTCATATGAACTTTATAACTACGTAACTGTT
AATACATTAGTTCTTACAAATTTCTGCGAAGTAAATTATAATGAAAACTTTTACTCAATCTTTCTAGAT
ATTATTAAGAATTCTCCAATTATTGTAAGAAATGTTAGAAACTCACTTATTGACTCATTAAAATAATAT
TAATTACCCTATCCTTAAATAATTTAAGGATAGGGTTTTATTTAAACAATTTTTATAAGAAATATTTA
AAGAAGGGAGACGTTAATGGTTGACTAAAAAGATGAGCAGTTTAGACCGAATTAAAGATTCACTTATT
TTTAAAGGTGAAATATTAGATATATACTTACCAAAATCTAATTTTGATAAAAATCTATCAACGTATAAT
GGTGAATATATAAATACTATGGGTATCTTTTCATTCATTGAAAAGAAAAGCTGGACCTGAAGATAAAAC
AACTAAAGGAACTTTACGTAAACTAGAATTACCTAATATGATTGACTTTCAATACGATTCAAGTTATTC
TTTTAAGGGAAAATTATCGGATGAATTACCCTCTGACACATACGAAGTTTTTCGACTTACTACAGGAA
ATCAATTTATTGCAAATGTATTTACAGAACAAAATGCTTCTAATGTTAAAAAATTTATATCGGCTCTTC
ATGGTGGTAATATTCCGAGTTCAGTATCTTATGATAATATTATTAAACTATACTTAGATACTTTATCAA
TTAATAAAGTTAGTTTACGTAGTCCATCAGTAATTTATGAATTGATTATCTCCGAATTATGTAGGTATA
GTAAAGATATTAATGAACCTTTTAGAAAGATTATTGCTTCAAAAAATAATATTAGTCCCTATATGTATA
CAAATATTAATCTTAAGAAATTACCATCAATCAATTCTACTTTTGCGGCACTTAGTTTTGAAAATCCAA
ATCAAGCAATTATTGACAGTATTAATAAGAATATCAATGGTGAAAAAGAGAATGAATCTCCTATTGAA
AGGACTATTAAAATACTAATATTTTAAAACAATAAAATATAATCTTAAGATGATTTATTTTTATGGTT
TATTAAGTTTTTTATAAAAAAGATTATAATGAAAGGAATGAATTATAAATATGGCTAATGATGCAAGT
TTGACACAACTACATCCATCAGTTTCATCCGTTATCAATGCAAATCAGTCTAATTTTCTTACATCTAAT
GGTGTAGTTACTCTATTTGCTGCAGACACCTTTGCTAAAGGTAAAGATGGTGCAATTGATTTTGTTAGT
ACTAAAGATGAATTTATTTTTAAATACGGTACTCCAGATTATTCCAAATACGGTCAATCAGCTTATAAT
ATTGTAGAGTGGTTAGAAAATGGAGGTCAAGCATTTGTCCTACGTCCTCTTTCCTGATGATGCTACCTTC
TCTCATGCAATTCTGAATGTACAAAGTAAAGTTGTATCTCAAGGTAAAAATGTTTTAACTACTGCAGG
AGAATTGGTTAAATTAGATGATGTTCATCTACGTCCTACTACTGCTTTTATTAAGAAAAATAATCGTGA
TAAGAATATGTTGATGTCTGAATTGACAAAAACTCGTTCTGATGAGAATACTGTTGATGGTTATACAA
ATAACTTTGTATTGCTAGTATATCCAGAAGGTCGTGGAGAAGCTTACAATAATTTAGGTTTCCGTATGA
CTCTTAATGGTTCTTTCGATTCAGCAGTAAATAGTTCTCGTGTTTATAACTTCGAAGTAATTCAATATG
ATTCTGAATCTAATATGACTGTAGTTGAAGGACCATTTTATGTATCTTTCGATCGTACTGCAATCTCAG
```

```
CTTCTGGGGAATCTATGTTTATTGAAGATGTTATTAATCGCTATTCTAAACACGTTAATTGTGAATTTA
ATGAAGAAAACTTTAACCGTTTGACTAAATCTATTAATCCTAATGTTAACCCAGGACATATTGATATTC
TTACTGGTAAATCTAAAGTTCTTCCTTCTGGTAAAGCTGAAACAGTTTATTCCGAAATTACTCGTGATA
ACGAAGATATTCATATTTCATTACAAAAATATAATGCTCGTGGAGAACTAGTAACTCAGAATGGTAAT
GCTGTGCTTAATATTCCAGACCCTACGGATACTGTTGAAGCAGCATTGATTAGTTTAGATAATGGATTA
CGTGAAAATATTTACAATCTAGACTCTAATAAACTTGCTTACATGAAAGAACAATTCCCTAAACTAAA
AACTGATAGTTCTAGCGAATTTAAATTGGCTATGAATCAAATTATCAATGTTCCAGGAGATGATTCTCA
ACCTAAAACAGGTGAAGTGGTTACGCTTATTAATAATAACTTTGATTCATCTAATCCTAGCAGTCTTTA
TAGTAAATACCTTATTGCTAAAGAAGCTTATATTAGTGAAGATAGTGATGAAAATCTTTCTGCAGTATT
ATCATACGTAGATCGTTTGTCTGAAGTATTGAAGTCTCAATTTATTGATTATTCTACTAAAATGAATGC
TTCTTATACATTAACTCTTCATAATTCACCAAATCCTCAACTTCCGGCACAATATGCGCTTGAACTTAA
CTCTTTGACTGATCTTCTTAATAAGAAAGATCAAATCAATATCTTTACAGTTGAGCATCAAGGTAAACT
ATTTGATATTCAAGAAACAATCACTAAATATCGTTTAGGTACTGTTAGTGGAAGTTATTTGGAAGGATT
GTCATTAATCCTAAACAATGTTGAGAATGAAATTAAATATGTATATGAAAGCTTACTTCCAGTAGCAT
ACAATGGTTATCAAAATGTACCTGTAGAGATTTCTGATAAATTTGATTCATCAAAACCAGAAAGCATT
ACAAGTCGTTATAACCGTATCTTAGATCTTCAAAGTGATATGCAATCAGGAATTATTGACAATACAGC
AACTAATCGTGATGAAATCACTTCAGTAGCTAATGATATTACTATTGATCTATTGGATGTTATTAATGA
AGTTACATTCACTTCTAGCACTACAAAATATTGAAAGTGCATGTACAACTTCAGTATCTCATATTCTAGA
TAATATCGTTTCTTTCCATTCTGCAGTTCTTACAATGATTACACCTCAAGGTACTTATGACTTTGATGCA
ATCATTTCTAATGCTAGAACTCAAATTGAAACTGAAATTTCTAAAGTTTCTACATCTAACTCTAAATTC
TTTAATACAAATCTAATTGACTTTTCTAATCCAATTAAACTTCTTTTGGGTTCTGATGGTTCATTTACTT
ATGACCCAGATAATTTATCTGAAAGACGTGCTTCTATTAAACAATGGTTAATTAAAGCATATAGTGGA
TCAGTTGATTCTGATCTATTGAATAAAGATAAATATCCAATTGATATCATTTTGGATGCAAAATATGAT
AGTGATGTAAAAGCCGCTATCGGTAGTTTGGCAGCCAATATTCGCCGAGATTTCCAATTCTTTGCGGAT
GATGCGGGTGGTTCATTTAGTTCTTCTCCAGTAGATTCTCTATCATGGAGACAGACTTCTGCATTCAAT
ATTAGTTCTCTTAACGTTTCAATATTCTCTCAAGATTTAACTTACTATGATGAATATACTGGTAAAGAT
ATTCGCTTCACCGCTCCTTATCAACTAGCAAGTAAGATTCCTTACAACGCAGTACAATACGGATTGCAA
TATCCTTTAGCTGGACCACGTAGAGGTCTAATTAGTGGTCATAAAGCTATTTCTTGGGTTCCTAATGAA
GCTGAAAAGAAAAACTATATATTGCTAAAATCAATTATATTGAACAAGATACTAGACGTACTAAATT
TGGTTCACAATCCACTACAGAAACTGGTTATGGTGCATTATCTAATATTAATAATGTATTTACTATTCT
TAAAATGGAACGTGATGCTAAAGAACTTGTATCTAGTTACCAATTTGAATTCAATGATGAAGAAACTA
AAGATTCTCTTTATACTGAATTGAATTCTTACCTATCTAAATATACAAGTGACCGTAGCTGTGAGTCTG
TTGTAGCTACTGTTAGTGCTTCTGACTATGATAAACAACAACGTATCATTAAAGTAAATATTTCTGTTA
AGTTTAACGGAATTATTGAACGTGTTCAATTAAGCTTCGATGTAGCTAATTAATACTACAATATTTCTA
ACTAGAGGTAAATAATTTATACTTATTTTATTTATCTCTAGTATTTATTATAAACAATTATTACTTATAA
GAGAGGATGACAAACATAATGCTAAAACCGGGTTCTAGTGCTAGAGTCTTTGATAATGACTTAGCTAA
AGGTAAAAGCTTTTTTACCGGATCAATGAATACACAAGAACTTCAGTTTGATCCATTTGTTACAGGATA
TGCATTTATCCTTTGGACTAAAGTTCCTACTTGGGTTGAAAAATCATTCCCCAGGATTCCGTAGCCAAAC
TCAAAAGAATTTTAAAGAATTCTCAGGAATTTCAGATATGGAACTACAAACTGCTGAATATACGCATA
CTTTTAATAACAATGCTTATCGTTTTAATAGTGGTATTACTAAAAACAATACTGAGTTTACTCTAAGAC
ATCAAGAATTCTCAGGTAATCCAATTACAAATATGTATAACTTATGGGTTTCTGGTATCAGTGATCCAC
AAACTGGTATTGCTACTTATCCTAAAGAATATAATATGGAGTATGCTGCTAAGAATCATACAGGGGAA
CTTCTATATATTGTTACTCGTCCTGACGTAAATAACGTAGAACGTAATAATATTGAAAAAGCATTCTTC
TATACAGCAGTTATGCCTACTCGTATTGCATTAAATCATTTTAACTATACTTTAGGTACTCATGATGGT
GCTGAAGTTGAAATGCCATTTGCAGGAAACTTGCATATTGGTCCATTAGTTGATGATTATGCTAAAGA
AATGTTACGTAAAACATACTCCTTTAACGCTCAAGGTATGTTTAACCCTCAAGATGGTTCAATTGCTGG
TGAAAATATTGCTGTATTTAATGATAATGCAGGAGTTACTGGTTCTGGTCTAGGAGATATCTAATTAAA
TTAAATACCTATCACTATATTAATTTATGGTGATAGGTATTTTATATTTTAATTTTTTAGAGAAATTATA
GATATCTAACAATAATATATAAATGTATTTGGTTGTGAATCTTTATTATTTAAAATAATTTTTTAAATAT
TAGAATAACAATATAATATAATTTTACTTCTACGTGTCGGTATGCAAGCTGGTTAAAGCAGACGGACT
GTAACTCCGTTTCGAAAGATTCGAAGGTTCAAATCCTTCCCGGCACATCTTTATGGAAAGTTGTCTGAG
TGGTTTAAGGTCTCGGTCTTGAAAACCGATGAACGTTTATAGCGTTCCGTGGGTTCGAATCCCACACTT
TCCTCTTTTATATTATGGACTTTTAAAGTTTAGTGGCTTTAAGAGTCAGCCAATTGTTTGTTTTTCTTTCT
TTATTCCATATTTACTTTAGGGATATATCTTAAGGGGTTTTTGATATATCCCACTCCTTTTGACGTGTAG
CTCAATGGTAGAGCATCTGACTGTTAATCAGACGGTTGCAAGTTCGAGTCTTGCCACGTCAGCTTATTT
TATTAATACCTTATAATTAATTAATACCTTATAATTAATTAATATAAGGTATTAATAATCCTAATACGG
TTCTTTAGCTCAGTGGTTAGAGCAGACGGCTCATAACCGTCCGGTCGATGGTTCGAGTCCATCAAGA
ACCATTTCTCTAAAAAAGATTATATAGAGAACAGTAATATTAAATTCAGTAATCTTATTCTAAGTTAAT
ATGTATATATTAATAAGATGATAATTAAAGAAATTAATTATTGCTGAATAATATTAAATTTCTTAATAA
ATAGATCAATTAACTTAAAAAAATATCATAACGATCCTTTTTAAAACCACACCTTCAAAAACCATGTAT
ATGATTGATCTATTTAATGAAGTCAAAAGTATTCTTGTATCCTCCTAATATATGAATATTTAACCATTTT
TTTTTTTTTTTTTGCAAGTTTATATTGGTTCTTGCAAACTCTTTTTTTCACGTATTATCTCTTAAATGAGGT
AATACGTGTTTTTATTATAAAAATAAAATATATATTATAATGATGATTAAAATAATATAATAGATTGGATT
GATGAGACGATGGCATACAATATTGATAACGTAAGGGAAACTAAGGCAAAGGTATTAAGAACGGCAA
TTAATTCTCTGATTGCTAGATATTATGAATCTAATGATCCAAATACTGCACTAGAGTATTGGAGACAG
CTGCTAAAATGGAGGAATTTGTTGAGAATGACAATTATAATTATTTATTAGATTATAATATGAAGAGT
ACCCATCTAGTTAGACGAGTGACTAGTATTGATACAAATCTCAATAAATCAGAAACAAATGTTGGAAA
ACAAAAGATTAGATGTATGTATGAAAGAGAAAAGTCTGCATATATTTATAATATCAAAAACAAGAAA
GTTGAAAGTGTTTATAGAAATAATAAGAATATTTCTAAGATCAATAAAACCAAACTTTAATGAAGATGA
TATTGCATTAATGCGTAAGATTCTTGATTCCGAAGAGGGTAGTGCTATACATAGAAATCTTATTGGTTC
TTATGTATACAATCATCGAATTGGTAAATGTGGAGTGATTGTCGGAATTACTAAAGCGCATATGTATTA
TACACTTAGTGATAAGCATAATAATACTAAAACTAATGATACCAAGTTTGTTGTGAGATATCTAGACA
ATACTATGAACAACAAACAAACATCTATTGGTATCTGGCGTGCTACTAAATGTTCATTTAGTAAAGAA
ATTTCGGACTTTGCAACATATTATACTAGTTCAGAAAGTACGGAAGAGTATGATAAAGAATATGTTAT
TAATTCAATGAATCGTCTATATGAAATTGAGAAGAATTATACTCATAAATTCTTTGATACAGGACTAA
AGATTTAAAGAATATTAACGCTAATCATCCAATAATAAGGATGATTAGCGTTATTTTTTTTTTTTTTTAA
TTTTTTCTAGATACGTTTATTGCCTTCATAACTATCTTATAGGAATCATATGCTATCTTTTCAGGAATTA
CGTTTGAATATTTATTATGGACATCCACTCAATTTCTTACGTAGTTCTTCATCGCTAGTATTAATAATTAG
CTTCTGAAACATTCCAAAGATACTCATATGTTCTCGTAATCCACTATTACTAGAATTATATATTACCTT
```

-continued

```
ATTAAATTCGATCTTTTTTACTTTATTAGATCGGCAATATTCATTATCAATATTTTCTAATAGTTTATTA
AGGTCACTAATAGTCTTTATACCTTTTATTTTACTAATATCTTTATGATATTCAGATATAGATGCGTATA
TATTATTTTTAGAAAATATACTTATCTCATCTTTATTAAAATGTTTGTTTAAACCATCTTGATTTATAAT
ATTAATTCCATTCCGAATATTTCTTTATTTCGACTAATAATTTCAGTAATAGTACTTTGTCTATCTTTAT
GTTTCTCAATAAGATTTTTTACTTTACGTAATATTGATTCATTAATTTGTGATTCTAATAAATCTTTAAT
ATAATTATTATCCATATCTATATATCACCTTTGTCTTTACGATTATATTTATAGAATTCTATCAATTCAA
GAGAAAGATCACCAAAAATAGCTTGCATTGAAATTCCACCATTGATATTTACATTTTCCATATCCTTAA
AGTTTATTAGTGGGTTAAGGTAATCATAATTATTATTATTATCTGCAATAAATACTCGAATTCTATTATT
TTTTTTAATAACCTTAATTAATTTACTATCAAAGTTATAATCATAGGTATCTATAGTTTTAATATATAAC
GTAGGATCATCTTTAAATATATTACGTTTAGTTCCATAGAATTGATCTATTTCTTTAAATCCGTTCGAAG
CAATATTTCCTACAGCTACAGAAAAGCTATTATATGGTGGTAGATTACTATTTGTACTATCACTTTTAA
TAAAGAATCCATAACCAGAATTATCATTCTTATTGTAGTCGAGAGCAAATAATATCGCTCCGCCCTTAG
ATGGTGAAGTATGTTTTAGTTTAAATGTGATAATATATTCGTCTGGTAAAGTTAAATTTGTACTATACA
TATTTTTCCAAATATTATTCTTTGTTTCGTTATCCCTTGAACTTTTAATAATCACTGGATTAGATTTAATT
TTAACATTATTTTGAATTGTTTCTATAATTCTACCATTATTATATGATGGATTATTTGTGATAATTTCAC
TACCGTTTATTTCTTGTATGGTTGGATGAAAATATATTCCTTCAAAAGAATCTTTAGGGAAAATTTTAA
CACCTTTATCATCTATTGTCTTATAATTATATAATAGGTTTATATTATACCATCCAGAGGAAGGAACTG
TGAAACTAGTATATGAATCATTATTTGAATAGCTCTTAATATTAATAGATTTTGTTTTGATATATGCAG
TAGTATCCTTTTTTGCATTAATTATAACATTAACCGTAATTTTTTCAATACTTATTGATTTACTTTTAATA
ATACCCAACTTAAGGTAACTATTCTTTTTATTAGTATTAAAAATATCTGATCTTGGATGTAATGTAGTT
ACGCTTTCAGTAGTACTGTCTGTATAAGTAATAATCATTTCATAACCCATACTATCAATATCATCATTA
TTAAAACTACTTGAGTACTCTAAATTTGTAAAGAATAATCTATTATCTTTAATACGATTAATATCTCGA
TAGTTATTTACTGAGTCAGCAGTAAAATTTACCGATATAATATTATTCTTTCCTTTTTTTATTGTACTAT
CAAGAACATGCACATACCTACCTTGATCTTCATCATAAGAAACAAATGTTCCATTATACGAATTTACA
AACTTATCAAGATTATCATCTCTAAAATCGCTTAATAATTCCATTTCATTAGGATTAAAATCTTTATTA
ATATTTACAATATTTTTTGCAGTATCAAGGTTATTTATCATTAATCGTACATTTCCACTAAAGTTGTTGG
TCAATCCATATTTTTTACTTTTATCTAAGTATATTTTACCTGTAAATGATTTAGTATAACCTTTTTTAAA
ATAGTATGATGGTATACTAGTTAGACCTTTATCATCTAACGTAAAAGGATCTACATATCGACCATCATT
ATCTGTAACTTTACCCATTTCAACATCTATTGATGCTAGATTATAGTTTGCATTTAATATTTCATCTTTA
TTATCTGAAAAATCAGGAACTGTATGCCATGGAATTGTTTCATTGATATCAGTACCTAATAAATCTTTT
GATTTTTCATTTAATGGATGTAACATATGTTTTTTTTTACATATCTTGGACTTTGTACGGTTGATTTCATAT
TTTTTTCCTGATTAATAATTTTATTGATTGTATTTAGAATAGTATCAGGGAATACTTTAATTGTTTTCTT
ATTAAATTTTTCAACAGTATCCATATCATTAACAAACATTAATAAGTACCATAAGTCAGTTGTTTCATA
TAATTCCTCAGATACATATTCCGGTCTATAAAATTGGTTTTCCGATATATCATAATCAATTAAGTTTGA
TTTAAAAATATTTTCATACTTTTTTAACAATGGAAAACCTAATACTATCTTTCCTTCTAATAAATAAAA
GTTAGATATATTACTAAGCAATATTTTATTAACGTTTATTGAATTTATTCCACCAACTAAGTCAACAAA
TCTTGAACTATCTAAACTATTTCTAGAATTATCTACTACTACCAAAATATATTCACCACTTTTCAAATTT
CATTATATAATTATATGTTACTATATTCTTTTTTATCAAAAAAAAAAAAAAATGCCATAGTATATTATG
TAATATACTATGGCATAATAAATGTTACATCATTGGATCATTATTATCTTCAGAACTATTTTTAATATTA
GATATATTTAACTTATCTTTAGTTAAATCTTGATTTGTTTCGTTAAATAATGTATCAAACTTAGTCCAAT
CAAGAGTAGACATATATATTTCTGAAGCTAATTTTTTCCTAAACAATCTTTTCTTATTATCGGTATCCTC
ATTTTGTTCTGACTCTGTGAAATAATTACCTACAATAAAATCTATTGTCTGTGAAATATTATTAATTTGT
TCATTAACATTAGCAATATTCATAAATACTGGTGTAGGGAAATTAATAGTGATTTCTTCAATTTTTACT
TCATCTTGGTTTTCGTTATAATCTTTTTCATCATTTGTTTTGTTCTTATCTTTACGATCTCGTTCACCATA
CTCATAACGATATAGCTCTTGAATTATCTTAGTAAAGAATTTACTAAACGTTTCTTGATATCCAATAAC
TCTTCGAACAAAATTACTATTCTGCATTGATAGATTTCTTGCAAAATCAACTTCATTAGTAGCATCAAT
ATAATTAATTGGAACACCTGTTCCATTAACTGCCGATTTCTGTAAGAATTCTAAGAAATCATCATTAAT
ATCAGCTTGTATACCTGGAATAACATCAATATCGAAAGGCTTATCTCCATTAACTGTTGGAATAAATGC
TTCTTCTGTAGCACCTAAAGTTTTAAGCATAGTAGATACACTATTTCCGGGACCAATACTATCCATTGA
AAATTCAGTAGTCTTTAAATCTCGGATAAGTTCTTCAATAGTTCCCTCAATATCAGAATCCATATCAGA
CTCTACGTAATATACTCTTCTATCTCTACCTTGATTAATTTTTACCATTAAATTTGTAATTAATGTAGAA
AGATACATTTTAGGAAAAAATAGACTATTATTTAATCTAGATACACCATACTCGCTAGTGCTATCTAAA
GGTAGATGATACACCTGATTTGGTTCTAAGAATGTTATAGATATATCTTTATTGATAATATAGTCTTCT
CTGACCAATCTATATATTACATCTTTAAAATCTTGGTTATCTTCTAAAAAGTCTTTAGATATTTTATCAC
TAATTCCTTTTACAAATATATCAGTAATTATCTTGTATTTTTCCATTAGTCACTCCTGAACCACTCTG
ATTTGATCTAGAGTTATAATACATTGTAATATCTCCATTAACACTAGAAGATCCTTGTGGGGCATTACC
GTTAAGAGTTCCTGCAATAGTACCTAATATTGAACTACCTTTAAATGAATTATTGCTACCATTCTTTTC
AATATACACGTATCCTAAACATACTCCATCAATAGATATTTTAATGATATCTTCCGGACTAAATATTTT
TAAGTAAGATCCGGTAATATTTAGATTTTGAATGTCTTTAGATTTTTTACTTGCTTTTCGAGATTCAGAT
ACAAGATTTAGAGGGTCTTTATAATATTTTACATTTTTAGATATAGACTCATATACCTCATTAGCAGTA
CTTTCTACTAAAATCTTTTCAATATCTTTAGGATTACTTTTAGAAAATCTTTTTCCATTTTTAATATTAG
ATGATTTAAATTCAATATTTTCATCATTCATAACACTTTCAATAAGATTTTCAATATTTCTATGATCCAC
GTTAAAAGATTCATTTAGATCATCTTCTTCAGAATCAATAAAGAGATTATTGGTATCTAATTCATTAAA
TTCATCTTCAGAAAGAATACTTTTTAAATTGGCTTTCTAGATCGGTAACCATGATAAACAGATCACCCTC
AATTAATGTATTCCGAATAGAATTTCGAATAACTGTATTTAGATTATATTTATCAATCAACTTAGACAT
ATTACCATTGAATTCTTTTTTTATCCGTCTCCCCTAAGGTAGTATTTTCATTATTATAATAGTATGATATT
GATTGTTTTGTTACATCGTCTGGAGACATAATAGAATCTACATACGTATCAATAGCTGTACCCAATTCC
GGAAAATACTGAGATATTAGTCTAAAATCATCATATCTTTGCCATCTTAGTTTTTCTTCAGCAAACTCT
CCTGATGAGAAACTACTTTCAACTTTTTCCTTAAAATAATTGTTGTATATATCAGAACTTTTTTTATTTT
TCGTATTTTTCATTCCAGTATTCTTAACTTTATCTCTCTGTATGTCGGAGATAATATCAATTATACTTCTT
CCTGAACTGTTATTATTACCGTTTCTTCGTTTAATCTTATTTAACATATCATGAAGATTACTTAATTTAT
CTTTTGGTATATCTTTCTGGTTCATAATACCGTATAGATTTTTAATAATGTTTGCATTATCTGCCATTAA
ACTTATCCACCTTTCTAAATTGATGAAAAAAAAAAAAATATCATAGGGAAAAATTTCCCTATGATATTC
ACTAATATTTATTTCATATCTACGAATATATATGATTGTTCCATAATATAAGTATCATTACAAACTTCA
ATTACAAGCATTTTTAATGATGAATCCTTGTTATGATTAAAGCATAATATATTTATAGATGGATGTTTA
CTATATACTACTGGAATATAATCACTAAATTTTTCTTCTTTATATTTTTCATATGCTTCATTAATATCTTT
TGGATAGTTCAATGATCCGAGATTATCCTTAATATTTGTAAAATAAGGTATTTCAGTAAATTGGTCTAT
ATCGACAATTAATGGTTCAGGATTCTTTTTTACGAATATACTTAAAGCCTTTGATAAATTTAGTTGATAC
GGTAACACTAATATAATCATCTAATTCAGGTTTAATCATATCATCATGGATAATAATATTATTATTATC
```

```
ATTTTTATCAATAACTATTGAGAATGTATATTTATTGTCAAATTCAAGTAATTTTATTACATCATCATCA
CTAAGCGTTATCTTTGGAATATTTAATGAATTTTCACTAAAAGAATCTAATACAGGAACAATATGATCA
TTTATACGCATTAATATCTTTTTCTTCTAAATACCATTTAATAAAAAAGTCTGATTGTCTAATAAACTTTA
TATAGTTATCGTTATAGTCTATTTCTATAGAGACAATTTTATCTGATTTATTTTTACGCATTTCAAAAAA
TTCTATCATATGAATAGAAAATGTATTCTTTTGCATAAAATCATTTACTGTTTTCATTATACCTTTTTTA
TCTAGTTTTCTTTCAATAAAAGTAGCATTGATATACTTTGGTAGTTGTTTTAGTAGTGCGTCATCGTTTA
GTGAGGGAAATGCAAAACCATTATTAAAAATCAACCTATCCCCAACATTAAGTACATTCCTAAATTGA
TCTACCATTTCTTCAATAGAAACTACAATTTTTTGAGCTTCATTAGGATCATCTACAATAACTTTATTAT
TTTCTTCAATATACAACTATAATTCACCTACTTCTTGCATACTTTCAGAATCTATTGATTCTCTAATCAT
ACCCAAAGCATCTTTAATATTTGGTAGATTATAATATTTAATGCAAAATTGTAAAGGGTTATTACTATT
ATAATCATCAATAAATGATTCTGTAATATTCTTATTACCTTGTTTAAAAGTAATATTTCCGATAAGACT
TTCAGGACTAATATTTAACGCCATAATAATATGAGGGTATAGTGCAGTTAAGTCAATATCGGTTACATT
ATCGAAAATCATATTTGATTTTTTACCCATAATATCAATACCGATTGGATGAACTTTTGATGAGTCTGC
TACAAACGCACCTTTAATTTTTCCATCAATCTTAGGATATAATGAACTATGATTATTACTAATTACAAA
CCCACCATTATTATAAAAGATTTCTGTAAGGTTTCTTAAGCATATTGTTTTCTTAAGTGCTTTTGTTATT
CGAGTATGTGTTAACGAACTAATTTGATAAATTAGATCTAAGAATTTAGTTGCTTTTTCGATCATCATT
AAGAGAACTGTATCCTGAATGTTATATAGAATGAATTTATAGTAGTTTTTAATATATACGTTAGTGATG
TCTCCGTCACCCTCTTCAAACTCATCCTTTTGCATCCCTACTTCTTTTTCACCTATGTCGTTCAATTTGTA
AGAGTCTAAGACTCCCATAGATAGCGATAGGTAAGTATTTGATATTATCTCCAACTTTTCCCCCGCTTC
ACACCGTACGTGAGACTTTCACCTCATACGGCGTTCCATCACTCAGTTTATATTGTCACCGATATATTA
ATGACAATAACTAGTCGTTAACTAAGTTTCTTAATTTAGTTAGTTGTGTTTTATTTACCCCGGTAGGAA
AATCAGTACTATAGTGAATTAGATTATGTGAATAAACAGACAGTAATACAAGATTATCAAAACTATTT
GACCCACCTTTTGATCTCGGCTTTTTATGATGTATAACTAAGTTATCTATTCCTATTTTATATAATGGTA
TATTAGTGATAGGATCCTTCTTCTGTTTTTTAACCAGACCGGGAATATACATTTTATACCTTATATTGGG
AAAATTAGAACTATTTGTAAGCATATTAATAAATTTTAATATTAACTCATCGTTGTTCTTAGTTTTCATA
ATAGGCGTCCAATACTGTTTATTTATGAGATAATCTTTAGTATTTTTACTGGATTGTTTCCGCCACATCC
ATGTATTAAATATAATGTCTTTATACTTATAAATTTCAGTATCAGGTTTCTTATACATTTGACTTTGTCG
ACTCCAACTATATAAAATTCCGTTAACTAAGTTAATATAAGCTTGCATATTAGTAACTAAATTAAAATT
ATATATAGTTCCCAATATAATAGACATTACCTTTTGATAATGACCTTTTCTCAGTTCAGACCTTAATAA
TTTTTTCTGATTATACCAAAACTTACTAAGATTTTTAAATGAGATCATCACATGTCCACTTGCAAATCG
CATATACTTAAAACCTACAAAGTTAATTACAAAGTCCTGACCTTCTTTGATAATGATTTCACTAGTTTT
ATTCCAGTTTAAAGAAACTTGATGTTTTGTACACCAAGAATCTAAAACAGGTTTAAATCTTTCTACATC
CCAAGGATTCGGACTAATTATTATAAAAATCATCAGCATAACGAATCATTCTTATCTGCATTCGATTACC
AACGGTTTTCAAATATTGATCTTTACCTTTTCGCCTATAATATGACATATTAAAACTTATTATAAGG
ATGTGTTTTGTGAAATTCAGATCCATTAGAAATAGCCTCATTATACATGTTTAAGTCATTGACTAAGAT
TTCTAGATCATGTAATAAAACGTTAGCTAGTATAGGACCAAGTATAGAACCTTGAGCTAAACCAATCC
CTTGATACTTTGTGTCTTTAGTATCTATAGACATAAGAAACTTTATAGATCTTAGTAGTTGCGTATCTCT
AATTTTGTGATTATACCTTAATTTATCAAGTACTATATCTAAATTAATAGTATCAAAATACTTAGATAA
ATCACAATCTAGTACTGATCCATTCTTTATTTCTTTAGTGTTATTTACTAAAGCTGACATGGCATGTTGA
GTTGAGAGATTACGTCTAAAACCATAAGAATCAGGATAAAATTGATATTCCAAAATAGGTTCTAAAAT
ATTAAGAATACATTGTTGTGCTATTCGATCTAATATATTAGTTATTCCAAGAGTTCTAAACGAACCATC
CTCTTTTGGAATGTCAACAAGTCTTGAATATAGTTTTATATCACCTTTTATTCGTTTCAATAATAGGCTT
TTAATATCTTTGTAATCTTGTTTTAGTAAATCATCTAAAGTTTGACCATCTGGTCCCGGAGTATTTCTTC
CATCATTAGACATTATCCGTTTAATAGCATATTGAATATTACTATCTTTAATAATATATCTAGATAAAT
GCGTAAAAGATGGTTTACCATTTAAAACATCATTATACAATTTTATTTGGATTTTATTGAAATCAAAAT
ATATAGAATGTAAACTTTTTGTGTCTATATTAACACACCTTCTTACAAAATCAAGCTCTGAATATAAAT
CAGGCAATTATATATCATTGTTTTGAGTGACTTTGGGCTTTCCCATTAATGATACATTACATATCATATT
ATCGGTTTCTACCCAAACTTTCAGTCTGTATTCATTTAACTTCACCGTGACTAGCAGCTAAACCGTTAA
ATTAATAATATAAAATTATCTACAGACCTTCCCACGTTCCCTACATCATAGAATATAGTATACTTAGGT
TCTTCCTCTAGGCTCTGTGTGATTATAGAAATAATCTGGTTCCCATTATATACCATCCATCTACGCAAC
AAACAATACGTATTTGGAACACAAGTTTACTAGCATTTCTACTAGCACATACCTGTACATTCAGAAGTT
CGTCAGTCTTAAAAGACATACTAACCATATATACCTCCACCCGACCCATTTGAGAGGATTGTTTACCCT
TTCGTCAACTTAATGTTACGCTCTAAGTTAGCCGTCTTCACCCAGCTTCACACATAAATATCACTACTT
ATGCATGTGGGAGTATTAGTGTACATCTGATATAACTTTAGGGAGTTATATAGTGTATTTGATGTAGAG
TTATTCAATATTATTATAATACTGAACTTTAGACACGCCTATGTGTATCATAGACTTTCTCTAAAAACA
TGTCGCACGCTTATTGATATTGGCATATAACGCCATTTGATCTAAATATGTTGTATATCCAGCTACTTC
ATATATGGAAGACTTATCTGCAGGATTATTGTGTTTTTCATCCATTTTATGATATACATATTTATATTTA
AAATCATCAGGACACATTAATTCTTCAGGAATCGCATTATTCTTTAGAATTCGATTATATATTGTGATA
AAGTCAAAATCAGCATTCCACGCACTAGCAAAGTCAGGTCGATGAACTTCATTGATATAATGAAAGAA
ATCACTAATTAAATCAATTTCTTTATCATATTCATAAATATTAAACGTTAAGTCTAAATTATATTCTTTA
TATTTGTTTTTTAGTTCATCCAATAATTTAGTTTTATCCAACATTGCGTCTTTATAACCATCATGATCAT
ATTTTAATGCAAAAGTTTCAACAGTAAGATTCCATTCATTTACAAGTGTAATAATATTAATCGGAGCTT
CTGCTTTCTTTTGATCTGGAAATCCAATAATATTTTGAGTATCTACTTCGATATCGTAAAAAGATTTCTT
TAGTCCAAAAAGATTATTATCAGGAGCATGTTTTTCTAAATAACGATGAATATAATTATCTTCAATATT
CTTATCAGAACCATGAATTCGATAATCTAAATGCATTTTTTTAAGATTTCTTCTATCACGAAAATCTTC
AGACTTCATAATATTATCATAGAATATTTTTACGCTAGGATCTTTTAACTCTGTAGCAATACTTTTAAAT
ATATCTCTGTTATAACATCTTACTTGCCTTACTTTTTCTTTATCAATATAGTTTCTTACAACATTATCTTG
AAATTCCGGTTTAGTAATATAATAATCCATCATTGGTTTTTCAAGTAATGATGTTTTTTTGTACCGTCC
TCTTCTTTAGTGACCATAATAAGTTTATCAAAATTATCTACTGCACCAGAATTTCTTGCATCTTTCTGGT
TTAAATATGTTGTCTTAATTAGTTGACCCAAAATATACACCACCATCTAAATTTATATAATTCCTTGTTA
TTTTTATTTTATAAAATTATATTCTAGTAAGATTAATGATATCAATAACTTTGTTATATCCATCGAATTT
AAATAAATCTTTTCTACTTATAATAATATCTTTATCTAGATTTTTAGCATATTTAAGAAAGAATCTCATA
TCCATATCATGATAAGTACTAATCATTTCCCATTTTTTAGAATAATTTTAGGATTATTCTTCATATGCC
TATCAATAAATTTAGTGGATAATTTTTTTTCTTTTAAACATGTTTAAATTAAAATTATTACTTTTTCTAC
CGTTTATTATTGATAACAGTTTTTCTTCACTAATATTATTATTTTCCGCCATTACTTCTTTTTTGTCTAAC
GGTACATTTTGAAATCTAATTTATCTTTATTATAAGCCAATAATTTACTATTTTTACTAATAAGATCAA
TATATTCATCATCCATGAAAACTGATGCGTTTGTTATAAAGTTTACAGTATCGTTAAATACATATATTT
TTTCTTTATTAGATGTATCACTACTACTATTATATTTACATATAGTATTTATTAGATACTTAATAGATTT
AATACTATTAAGAGTATCATATTCCGCAATACGGAACATATATTTAAATACATAGGAAATATAACCAA
```

```
TACTAAGATAATCAATATTTAACATTAACGTATCTATGAAACTGCATAAGACTTTATTAATATTCATAT
TATTTTTCATATGACTTGACTTGATCATTAGATTAAGATGAATAATAGGTTCCACATCTTCGCTTTTATA
TGATTTATAATATTCAAAAATTTGCGGTATAATATAATCGCATAAAAATTCTTCATCTATATTCGAATT
AGATAAAATAAAATTTATATTATCGTATGAATATTCCATATAGTCACGAAATAATATTCTAATTATAGA
ACTATTAAATTCCATAACTGACCGCACTGAAAGATAAGAATTTTTACTATTTACTATCTTATCAATATT
CTTTATAAATATATGATTAGGTATTTTCATTTCATAATAATCTATATTATCAAAATTTTTTATAATAAAG
TCAATCATCTTATCAGATATTCGGTGTCCGTAAAATGATACTAAATCTTTGATAAATTCTTCGCTGTATT
CATACATATATTTATCTAATTCTTCGTTCGGTATACTTATATAATTATCTGTAAATCTTAATAGTTTATC
ACCCAAATTCCCATTACTAGGATCAATTTCTATTGTAAGTTTCTTCAATATACTTACCAACCTTTCTATA
ATTATACTAGCTTTAGATCAATTACGCTTTTTTCAAATTCATTTAAATGTTTAGACCAATTGAATGATAC
TTCTTTATACCTATTAATTTCATCAATAGTCATTAAGTTTATTGTATTAAAATCCAGCGATATCAATGAA
AATACTTTATTCTTTAATGAACCGATAACATTTGTATTTATAAGTATATTATAAATTTCATAATATTTTT
TAGATATATCTTTATTCATTTGTAATGAATTTTCACTAATAAAATTTCCACTATCTGATATCACATAATC
AATAAATACTGTATCATTTATTTATATTAAATATACTAACCGGATCAGATATGTCACGCATTATATTAGT
CAATATAGATTCAATATGTGAATTATCATTATTACCTTTATTATACTGATATAATAAAGGTAATATTTC
TAAAACAAATATAGTTCTCTTAGACTTCCATAATGGAGGCTTATTTAAGTATAATGATACTTGGAATTT
ATCATCGATATCATAATAATTCTTTTTTAGTAAATCTATAAATGATATAATGAATTCATCATTATCAAT
AATCTTTAGTGATTTAATTATATTATCATATAAGTTTAATTTTTTAATTATCTTCATGCTTAATTCAATA
TTTTTAATTCTAAGTATGTTCATTATAATATTGTCTGAATTTGATTTAAATATACATAGACTTAGAATTT
TTATATAATGGAATATATACATATAATATCACGCTTCCTAATCATTCTTGCTTTTCATTATCGATTACTA
AACTATGATTTTCTAAAGAACTTAGCCATGGATCATAGATATTATTGAATCTTTCTTTATCGCTAATAT
CTTTAGTAAATATATTTAAGAATGATTTTTGATATTTCTTATCATTATCAAACCATGAAGATATAAACT
CTTTTCCACTTTCTTTACTTAATTCAGTTAATGTAGTATATACTTGGATTGCAAAGAAAGAACTTAATCC
TACTGCATCAACATCTAAATCATTATGTGAATCGTTATCAATAATAATATAGCGATTATCATCAACAGG
AGTATACTTATTCAGTGCAATCTTTTGAAACTCAATTTTAATATTACCATTAAAACTATATTCACCATC
AATATAATTGTTAATAATATAAAAACTATTTGTAATAAGTTCCTCAATACATTTATCAGCTTCAGCAAT
AATTAATTCATTACTATATTTTTGTAAATCTTCATAGTTTTGAATTCCTAAGGATTTAAGTCTTACAGCA
ATAAATCCTTCAGTAATTCCAGATAAAGAGATTAAAAATTTTGCAGGATTCAATGAATATACTAATTT
ATTAGTATTATTCTCAGTAATAATTTCAATACTATATGGAATTTCCATATATCGTTCAGAATTTTCAGTA
TATGTGTTACTGTCTTCATCAGTAACCACCCATTTTTTTCTAGTTCTTCTATTAATTCTAGAAATTTTATT
TTTCATTTCACCTACATTATTGCTGTTATTTAAGCTGATATTTACTAAGATAGTTTTTACATTATCGTGA
GAATTAATAATTCTAAAGTCATAATTATTTTTTCGAAGATCACTTGTAACTTTCGGTAATTCATTATTTT
TAACATCTAATTTTACGCTAAACATTTTTATCATCCATTCTATTTTTATTTTAACAATAATTCGACTACT
AATATTAATATTAGTAGTCGATATAATTTATTTTTCTGCATTAAAAATAAATAGTTTTATTTTCCATAAAT
ACAGTATCTTCAATATCAATGCTTGGATTCTTCGTTAAAATTAAATCCACGTCAGAAGTATGGAATTCA
TCATTATGGCTAATCACAAATATTTGTTCCATATTTAAATAATCTGTTTGTAGATCCAATACTTCCATAA
ACTTACGTCTATTATTTGTATCTAATGTAGCATCAACTTCGTCTAAATATATAATGTTATACCCTGAAG
ATACGGTTTCAATCATTGACAATGATAATGATAAACTAGTGATTGCAGTTTCACCTTGAGAACTTAACT
TAATATCTGAAAGATCAGTTCCGTTATCTTTAAAGACCCTTATAAAGAAATCTTTTTCAGTGATATCAA
AACGTATACTAAATGATTCACCGTAAGCAACTTTTAATAAGTTATTTGTATCAGACGCAATCTTTTTAA
GATAATTATCAATAAATATTAATGGAATACCTTTCTTAGGATCTAATGATTCTTTAATAGTTTTAAAGT
CATCATATACTTTTTCAATACTAGATAGTTTATCGGTAATATTTGTTGCAATATTAAGTCTTTTTTCATT
ATCTTCTAATTTATTCTTAACTTCAGATAATGCGTTATTATTAATATTGATAGACGTTTCAGTATTATTT
AATAGATCATTATTATTTTTCTAATGTTTTTAGTCTGGATGTAATATCATTATAAACTGAATCGTATACTT
CTTTTTTATTAAGAATACTTTCATAGTTTGATCTCAGATCTTTAAGAATATTCAGTATATCCAATCGTTT
AGATACTGTTTTAATATTCTTATCATATTGATCTATTGATTCATTATTATCTTTAATACTTGAAGATAAT
TTTTCTTCTTCCAAAGTACTAGATTTCAATAGTTCTTCATACTCGTTTATATGATTCACGCATGATATTGT
AATTTTCAATAGACCCTTTAATATTATCAATAAGATTGGATACTTTGTCTCGGTTGTTGATATTATTAAT
TAGATCAATATATAAATTAGGTAGTTTTACAAGACTATTTTCAATATGATCACGGTTTGGTAAAAATAA
GTCATCCTCATTTAAATTAATAATGCTTGCAATATTACGAATATTATTAAATTTAGGTAGAACTTCTTG
ACGATATTTATCAAAATATTTAATAATATTTGACAAATTACTGATATTTATTATTAGTTTCTATTCGATCT
TTTTCTAAATTACTTAAGGTATTTTCTAATTCATCCAACTTAGGATATTCATTCTCTTTATATTCTAAAG
CAATTTGAATAAAAGGACAACTATCAATATTACATGCTTCAGGTCTTCTATCTAGTGTTGTTAGTAAAT
TAGATCTACTATTAATATCACTAATATTTTTATTGACTTCCAGAATTTGAGATTCGATATCATTCATTTT
GGAATCATTAGATTTAAACATACTTAGATAATATTCGTAGTTGTCAAAAGTAATATTATCGTCTTCAAA
GTAAGTACTTTCATCCATACTCATAAGATTTCTTAGAGAGTCCAGAAGATTACCAGTTTGATGAATACT
ATTATACATATTATTGTCATTCATAATAGATTCAACATTTTCCATACTAGTTTCATTCAATAAAGAATTT
ATATTCTTATTAACTTCAGTCAGATATTCTTCATTTTTTTCTAATTCGTCATAATACTTTTCAGGATTAA
ATTCTTTAAACGAATATATTTTATTACGGTAAAGACTAATATTTTCCCTAATTTTCTTTAATCGGTCTTC
AGAATCAGTATTTTTTTCCTTTAATGAATTTCTCGATGTTTCTTCTTTGATTAATTTTTTCTGTAAATTGTT
GATGTTTATTATAAATATCATCACTTGTATATTTTTCTAATGCTGGAAATTGAGAATATATATTCTGTAA
TCCTTGGTAAGATTCATCAAGACTCGTATTAATTGTATTAATAGTATTATTAAATTGGTCAATCGATTT
ATTAATATCTATTTCATCAATAGGTAGATTTAGTTCATTTAATTTTTCTTTAATAAAAGAACTATCCATA
TCAATATTATATTTAGTAATTGTTCTTTGTTCGTTTAAACGTTCTTTTTCAGATTCTAATGATTTAATATT
ATTGGTTAATTCTTCTTTATTTTCTTTTATAGTATTAATATCATCATACTTAGAAAGATCAGAATTTAAT
GTCTTAAGATTTTTATCTAAAAAAGATAATTTATCTTTAATAACATTAAATCTTTCTAAATAATCATCC
ATAGAAGGTATAAACTTATATAAATAATCCTTACGTTCGGCAGTTTTATAATCAATAAAGTTATTCATA
TTATTACCTAATCTAGCAACTGTCATATAATCTTTAGTAATTCCAAGCTCAGTACTTACAATTTCTTCAA
AACCACGAATTCCACCATTTTCATTTAATTCCGTACCATTCTTAGAAATAAATGACTTATTATGAGAAG
AATTATCACCATAATAATGTTTAATAATATACTTATCATTATAATTAATATAATGAATTTCTTTATATCC
TTTAGTATCTGGAATAATAATGTTATTTCTAGAGTCATTTGTACCACGGTAAGGATTCAATGCGGAAAG
AATAACTGTTTTACCAGAACCATTAGAACCAATTAACATAATTATTTTATTTTTAGAATGGGAGAAATC
AATTTCAATTGACTCTTTTCCCATTCCAGCATATATTCCGATAAAGTTTACTAATTTTAAATATGTTATT
TTCAAGATATCACATCTTTCTAATTATTTAATCTTTTCTAGACAAACTAAAACTAAATTTAATCTTATTA
CTAGCGGCATTATAAATAAAGTTTGTAATTACATCGTTAGGAGATTCATTATTCTTTTTACATGACTTA
ACAAAATCTTCATAAATATCATATCTACAATTTAGTAATAGCGTTTCAGGAATGAAATCAATGATTTCC
ATATTCTGAATATTCATTTCTTCAGTAATACCATTATTATCAATATAATTTAGTATAAATAATTCAATAA
GATTATAATCAGAGTTATTTAAGATTCCTGAATAAATTAGATCTTTTTCACGATTAGTATAATTATCAA
TATACTTCTTAGGAATAATAACCCTAATATTTTTTCTAGGTTTATCAAAAATAACTAAATTGATCTTTGT
```

```
ATTATCATGACCAAAAAGATTATTAGATTTTTCATAATCTACAACTTCTGTAAATTGCTGATATGACTT
ACAATGATAACAGTTAATTGTTTTGATATGATCAACCGCTTTATTGATCGATACTTTTCTTTGAATCATT
ACTTTATTACCACAATTGTTACATATTAGAGTACATGGTTTTGTATTATATAATGAATTTGCGTTATTTT
TTGTCATGAGAAATCACCCATTCATCCATAACACTAATATAATCTTTATTCTTAATATCTAGAAATTCA
TTATATAATTTATCAAAATCTGGATAAAATTCTTCTTTTTTACTTTTAACACGATTAATAACATCATTAT
AATTTGGTGAAAATAATAGATCTCGAATATCCCTAAGACTATGATACGGCAAATTTTCTTTCTTTACGC
TATTATACATTACTTGTGCCATGTTCATACTTCTTTCATGATTATAATCAATTTTTCGAATAATTCCAAA
TTTTCTAGTCTTCAAATCAAAGCAAACCATATTTCGAATATGATTATTGTACTTAGTACTATATAACAT
ATCTTCTTTAACTTGTTCTGAAATAAAATCATTAGTTGTTAGTTTAATAGGTGCTTCTAAATCTTTTCTA
TCCACTACAATTTTATTTTTTTCAGATTGATAATAATTATATACGCCATAAGAATCATTTTTACCATAAT
TCGAGATAGTTCTAATATTAAAAACCGCTCTTAATAATAAATTATCAGTACTGCTAAATTCATATGATA
ACTGTAAATTGAAATCTCTTGCATTTTTTTCCACATCTGAAGCAAACTTTAAAAATTTTAGAGCTTCAC
CACTAATATATGATGTAGTAGTTTTATCTCTAGCTTCATTATATCTATTTAAGTTTGCATTAATTGTGGA
TCTAATTATCTTTGATAATGTACCATTTACATCATTTACATTAAAATTTTTCATGAAAATCTCTCCATTC
TATTTTTTATAAATATTCATAATTGAGAATAATTCTTTTATTTCTTAAATCACTAATACGATCAATATTG
ATTCCTAATCGGTTACAGTGTTCTAAGCTTGAAAGAATTCTAATATCTTTATTGATTGATTCGATATCTT
TTATTGTAGTATTTTCTTTTCTGGAAGCATATAATAAAATTGATTCAGGGTCATTTGAAAAGATATTTT
GATTGATCCATCTATTATATCGATTATTAATAATATTGGACGTTGTATTCACAGTAGTAATAGATTCTTT
GGAATCAATATTTCTTACAATACCTACTCTTTTTTGTGGAGAATTATAAGTAAAAACAATATCGTTACT
AATACTTTCTGGAGAAACTATTCTGCTATTATTAACAGTAAATTTACTATTAGTTCTACGTGTTAATAA
TTTATAACTATTCCGTTTATTTACGTTATAATCTAAATCATCACTAATCTGAAATGATACATATGAAATT
AATCCACCAATATTATTAAACGCAGGAATTAATAAGAGATCACTATATTCAGATGAAATCTTTCTTAC
GTTATTATCAATACGTCTTTTAATTGTTTCTAATGCTGAAATCATTTCCCCTTTAGCGTATAATTTATAA
TACTGCTTAATAAGAATGTTAATAAATTTGATTGTTTCTTTAATTTCAGTTGTAGGAATTAATAAATTAT
GATAATTATTATTCCTATAAGTTTTTCTTTCTTTAATACTAGTTGACATTAAAAATCATCCTTTCAAAAT
TATTATTATAATGACTATGTAATATTGACATAAATTAATTCTCATGTCATTAACATAGTCATTATAATAA
TATATAAATATAGTTAAAGTTGAAAGGTAATTTTTTATTCTTCTATTTCTACATAACTGAATTCTGAATT
ATCAGAGAATATTACGCCTACTTCATTATCGTCTTCATCATAAAGAGATTCAATTATTCGGTTATTAGC
TAAATATGAATCAATTACTTCATTATTCATTTCATTAGAAGAGTATACTGTTTGATCTTCATCTAAGAA
TATTGGTTCTGAAGTATTAATATCTACGCACATTACATATCCAATACTTTCTAAATAGTCCACAAAGTT
CTCGGAATCATCTTCAACAATTACCACAGATTCAGTCTTTTTCCCTTTTTCGTTAACCGATTTTTTAGCA
TCATTATTCTTAATAGCATTTAGTCTTTCTTCAATGAGTTTATCATAATCTTGTTCTTCAACTTCATTTTC
ATTATCTTCGTTATTATCATTTTCTAAGTTTTCATCTACAACTTTTTGAAGGTCTTTTCGGTTTGTATTTA
ATAATTCATTTACAATTCCTTTAATAATTAAACTTTGATCCCCATTAATATATCGCTGTCTTTATTATTAAT
ATTGTATTCTTTAATCTTAATATCTGCCATTTTAACTTTAAGATCCGACATTGCTTTAATTAATTGCATC
TTCATTGTCTTAAGACTAATCAGGTTAGATGTCTGGTCCGTAACAAACCTTGGGTCTGTCTTCATTCTA
GAATTTTGTGCCTTACTTCCCCTATCAAAATAACCTTCAGAATAAGTATATAATTCATCAATAGATGAT
AATTCTTTTTAAGCATATTATATTCATCAATAAGTTCTGGATCTATTGAAAATTTAGGTTTATTTTGTT
CTTCCATATATTTAATTTCACCTACCTATTTTGTAAGAGTATATAGTGATAATACTGCTTCATTACCAAC
TTTACTTATCGATTCACCTTGTTGGGATAATATATTTGTTTTTGCATTAATCAATTGATCTGCTTCTTTAT
TTGCTTCAGCACTGAATACCCCACGAATTGAAAGCGTATCCCCATCATAATCAGCACCTAGAGCAGCA
GTTAATGAGTTATTAATAACTAATGAATCAGTAAAATAATTTTCTGCTACTGGATAGTCTGGAAAAAT
GATTGGATAGTTTTCCAGATATCTATCTTCAATTTTTCGATATTCAGTATCATTAGTGCTTAGCACAACA
ATCTTTGAAGGGAAGATGCTTTGATAATTATCTACTGGATATCGAGTACAATACACATGTTTATCAGAA
GTAATATCAATAGCTGCAATATACAATAAATCTGTTATTGTAAAGTTTCTATCAAGATCAGTATGAAAT
ACTTCTACTGGATATTCATTACCTTTGTCGTCTTTAACCGTAATTGCTTTAAATCTAGCAGGTATATTCT
TAATAAAGTTACTTACTAACTTATTAATATCTTTATCGGTAAATTGATTTTTTTACATTATCAATAAAGAC
ATCTTCACCTTTTTTATTCTTTACATTTGAAAATTCTTCAATATGGATATCAATAAAGTCATTAATATAT
TTTACAAAGAATGGAAAGAATAATGCACATACCTGACTTAATGGAATGCCTACGGTCCCAAATTTTAT
TTCTGTATCGTCCCATCTATTTGTGTTTGATCTAGGAGCAGAGATTACTGATCTAGTTGCATAATCAAT
GGATTTTCCTAATAGACCCCTATGCACTAAGCCGTTCTTACCAGAAATATAGTCGATAAATGTTTTATA
TACGTCATATATAATTGTCTGCATTTGAGATTCGGTATTTGTTCGGACAAAGCTAAACGATGATTCACC
ATCTAGACTAGAACCAAAACGAATTAGTTTAGCGTATAGATCATTAATCTCATCTACGTCTGCTATTCT
TCCGGCTTTTGATGTGTTTGGATTGAAGTCTCTTAAGAATGGGGGAATAACGATAAATTTATTTATAAA
TAATGTACTTTTATCAAATTTTTCAATAATATTTAGTTTACTATCACGTTGTAAACTTTCTGTTTTTTTGA
ATGATAATTTTTCAAAATTATTGTATAAGAAACTTACACCGGTTTCTCCGTTTACATCATCCTCAACTA
GTTGACCATCTTTAATGGTAAAATATTTTAAACCACTAATACATTCTTCAATTCTTTTTATCTAAAGATAT
GATTAATTTATATACTACTGGGTGAAATATTCTGGTATTTAAATCAATATATGCAAACTGATTTGATCT
CGATTTAGACCCGATTTCTCCAAATATTTCATAACTAAACAATCCATCTTCAGTAGGATAATTCGATTG
ATTAAAAAATATTGGGTTTGTTATTTTTGGTAAGTTATTTTGTTTTACTACATTATCGATATCTAACAAA
TTTATTTTCAAAGATAAACAACCACCTTTCTTTTTTAGGTATCACATTTTAAGATATAATAAATATTTGT
TTAATAATAGTATAAGTATTTAATTAAATGCAAGGATCTTAGAAAAAAAAAATAAGAGAATAATATG
TCATTATATTATTCTCTTATATACTGATTTGTCTAGTGAATCAATATTCTTTAATGATATTATTATTTATA
AGATAACTTACAATAATATCGATATCAATGGCAAAATTTTCTTTATCATAAATATCTTTATTTAAAGAT
GTATATTCAATACATTTACTGATGATATCATCTTTACTGTATAATGATTTATCCTTATTCATTACAATCC
AGATGATATCTACATTATTTGAAGTATTTTCAAAATTTCCATTATTATTCAAATCAATTAACATTTTAAG
AATAATAACAATGTATTTAATAAATTCATTTACAATGTGACCATTAGTAATAATATCATTATTATAATA
ATGTTGTTCGTATATTTCATAACTTTCATTAGATTCAATTTCATTAATAACAATCTTTCTAGGGTTTAGT
ACTTCTAGTGAAAATACATCCAATAAAAATTCTAGTCTTTTATTTAATACATGCCGATTAATTCTTGAA
TTCTGTTGTTGATGATTCTGAAGATCAATATTATAATATTGTTTTATCAAGTTATAAATAATATCTACAG
AGGTAGTATGAATTTTATTTCTTGAAAATTTTTCATTTTTTCGATATTTATATAGGTAACTTAAAACTTT
TGCATAACTGTCATCAACAACAGTCTTATTTTTACATACAATATCTTTTAATTCAGATGAGCTAATTGTT
AACGATAACATATAATATACCCCTTTTCTTTATAGTTTTATTTTAATCAATACAAAACACTTAGACATA
TCTAAATGGATATCATGAATATTATACTCAGATAAGGATTTTACAATATGATCTACAATAATGTGCATT
TCATTATCACTTAAGTATTTTTTATTATTTTTTCTAGATAATAGATTAATCTTTAATGTAAATAAATTTTT
ATAGAAATATTTTGAAGATTTAAATAATTCTGTATTAATTGATTCTTCTAAATATTGCACATAACTATT
ATTTAATAATTTTTTAGTATTAACTGTCATATATATTTGATCTTTATTAAAATTAATTTTATTTTTAAAAT
CTTTAAGTTTCATAATCATAGAATAATAAATCCATCCATTCGTATTTTTATTTAATGAATAAAATACTC
AACTAACATAAGAGTTAGTTGAGTATATATCCTAGTTATTTAGTAAATATGCAGCTTGTAAAGTATCTT
```

```
TATCAAGACCATAATCCCTATTAAAGTCTCCATTATTAACACTAATTATTAAATTAGAAGGTTTTATCT
TTTCAAATTCTTTAACTTGTTCTTTTGAAAATAATGCAATAATATTTAATACGTCACCATCATAGTCTCC
ACCTAATCCGGCAAGAACATTATTACATAGGCTTAGTGTTTTATCCGAAATATCCTTTTTAACTTTGGC
AATATTCATTAATAAGATACTTGAAGTGGATATTGAAGGATTTCGATTTAGTATAATATATAAACCACC
TTCAGTTTTATTAATCAATTCTTCCATATAACGATACATTTTTTATTAAATGTATTTTTAGTATCTATAT
GGAATTTTTCAGCTTCCACTAAAGAAATATTCTCTGAAGTTGAAATAAGATTAATTAATGGACCCTTAT
ATAATTCGTGAAAAGTAATATAATTCATATATACTTCATCCATTTTACATAATGGGTCTGGAGATATAA
CGTTTCTTGCAGAGTAGTTAATTCGAGTACCTAAAATCTGTTTACGAATTGTTCCTCTTTTACCTTTAAT
ATTATTTTTAATAATACTATCTACAATTTTTAACACGTCAATCTGTACTCGATACTGTAATTTTAACTTC
TGAATTTTAATATCTTCATAGATTTCTTCATCACTATTGACAATATCTTTTAACATATTTGTATGATTGA
TTAAGAAATTGTAGTCATTATTTATTTCAGAAAGCCGAAATAGATTTTCTGAAGCAATTAACTGAGCCG
GTCTCAATTTAGGACTAAATATTGGTAAGCAGTCAATAAACAATAATCCTTCAAAATACCAACGGATA
ATACGTTTATATTCTAATGAATTTTTCTGTTTTGTATCAACATACTTTTGGAGTAATTCAATAAATCTTT
CTTTAAATTCATCCAAACCGATATTCCGATCCTCAAATTCTTCATGCTCACTACCTTCTTCATCTTCTAA
ATCAACAATATTTCCATTTGCATCAATACGCTTATTATACATAATCATATCAATAAATTTAGTACCATC
AAATAATTTGATTAATCGATCAAACATAATAGGATTAACTACATAGTTATTCTTAAAATCTACATAACC
GAAGTTATCAATATTATCCCTTTCAACTTCAGGACCCATAGATTTCTTCAGAAAATATTCCATCAATAGA
ATATTTCTTTTCTTTTTTTGTTACTGGTTCATGGTTAGTAATAATTTTATCTTGTTCAATTAATTCCCTAA
AATCGATAATCCGTACTCTAGTCAAAAGTAATCAAGCATCCTTTCTAACACCTTTTAGGCTTTTATCAT
ATTCACGATTAATCATTACATCCACATATGAATAATTCTTAGCTTCCGCTTCAGATATCTCTTCTTCTGA
GAATCCTGAGTTGTAGATTGTTCTTTCTTCAACAATATTATCAATAATATCCTTTTTCTTTTTATTAAAT
TTTGTAATAATCTTCTGATAGAAGGAGGTTTTACTGATAAATGCAGAGATCACTGTAAAAACAATTATT
GTAATCATAATACATTCAAAAATAATAGTAAACATTTCCATCACCATTCTTTATTTATTTTTTTATTAAT
CATCATAATCAGTTAAGAAACCTTCAATATCAGGTTTCTTTTCAAAGAAGAATGTTCCTGAATTATTTG
GATCATATTTCTTACAGAAAGGTACTACGGTAAAAGAACTTCCAGGGTCTCCTGAACTAGTACTTACT
AAATCGATCTTTCCAACAAAGCTTGGATAAATACCCCTAGCGCTTACTGATAATCCATTAGCTGTTGCA
GATTGTGGACCCTTTACAGAACCTTTTAGATAACGAGTAAATAGATCCATAGAATTAACATTATTTGA
GAATCTTACTAATTCGCTGTTAGGAATATTATTTACTAAGTAATCTTCTTTAATATTGCTAAATAGTGTT
TTTAATTTACTTACATTATTATTTTTTGGTCCAACTAAGCGATATCCGCCTTTGGATAATTTTTGAGTTA
GATCATAAAATAGATATTCATTAACCCTTAAACGTTTATTGGATAAAGAGTGATTATCTACTTTTAAAA
TATTGTAATAGTTTGTAATCATATTTCTAACAATCGCATAAATATCTTCTTTATCTTCTGAACGTAATCT
TAAATTGGATCGAGTTGTATTATCTAGTAAACGTTCAAAGGAGGATAAGATAGATATAGCTTTATCAA
AAGTCATTGAATTATTATTTGTAAATACCGAACCTAGTTTTCTCTTCCAATAATCAGAATCAAAAGATT
TTTCATAATCAATTCGATTATATTTAAATAGATCTACTAAGGTTGCATTAATGTTGCATTAGATTTTTG
ATCGCTTTCAATCCATTCTCGATTAACTTTTAATGCAATACTTTTTGTCAACTGGAAGAAGTAATATTCT
GGACTAGTAATATCATGATCTTCAGTTTTAACGATTTCTACATAATTATGAATATTAAAGTATCTTAGA
GTTTCAACTACACCTTTTCCTGCAAAATAGTAGTTCATTACATTTACAGTTTTCTTAAATAATAGTGTCA
TTAACGCTCTAGTTTTTAATGGTTCACCATTATTAAAACGTTCATCAATATCAGATAGTACAACCTTTTT
ACCCTTAATCTTGATTGGCATAAACATTGTTTTCAATACAATAATTCCATCATTAGTACGATAATACTC
GGAGTCATTCATTTGGAATACTGGGAAAAATTCATTTCCGTTAATTAAGAAGTATTGTTGATCTAATAA
TTCAGGGAATAATAGTTTAATTTCTTTTTGGATTGTTTCTTTTCCATCAGAAAGTTCCATTGTAACTTTA
ATTCTAATAAATCTAGATTCCTCGATATTAACGGTTGGATGGTTAATCTTTCTAGCTTTACCTTTTTTAT
TTTCTTTCTTTTCTTCAGTAACTTGTTTTCTTTCCTTATAGATTTTCCGATCTGTATCAATTTCACATTTA
ACAAAACGAATACCTTCTACAAATTCAAGTCCTTTAAAAACATCTTCAACTAATTTTGGTAAGTTTTCT
TTAGATCTAAAGAAGATCACTTCCTCATTAAATGGAGCTTTTTCTTCCATTTTATTTTGAAGATCATTAA
AGAGTTTTCTTGACAAGTTTGGCACAAACAAACAACTCCAATCAAAATTTATTTTATAAATTTTTATAT
CGTATAAAAACAATTAACTATTATTAGATAAAAATTTGTTTTTATATAAAAATAAAAATTTAAGGATGT
GTATATACTATGTTGAGAAACGGTGAAGAATTTTTTAATGAATGGTCTGAAAGATCAGGAATACCTAA
ATATGAATTAAAACGTCAATGGAATATTATGGTAGAAATGGTTATGGATAGCATCATGGAAGAAGATT
TTACCAAAACAGTATTACCAAGCATAGGCGCTTTTGAAACTATTGTTAAACCTCCATATATTGCTAGAG
ATCCTAGAAATGAAAAAGTTGTTATTGCACAAGTTAGGAAGCGAATTAATTTTAGAATATATCGCAGA
TTTAAAAAAATAGTAACAGGATTGTTATAATTTTCGTAATACAGATATTTATTTCTGTATTACGAAAAT
CTTTTTAATTGTTATTTCTTTTAATAATCTGTTTTTCAATATAAATTCTATCTTCTTGAGATAGTCCATTA
TATATTTCTTCTAAAGATTCAATATCTTCATTATCATTAATTAATACATCAATATACCTATCTAAGATTT
CTTTAGGTACATTAGTTTTTAAATTATTGATATTATATGATAAATTGATCTTAGAATTAGTAAATTTATT
ATCAACAATCTTTACACTTAACTGATTTCCATCATTACTAATATTGATGCTTGAATTAGTACTTTCACTT
GTAATATTAAGTTCAATACTTTTTAATATTTTGTTAATTATATTTAAATCCAAGTTAAAACATCCTTTCT
ATTCTTATATATTGTACATTTATATAATATATAAGAATAATATTAGTTGATGAATCGAGATTTAGCTTC
TTCGATAGTCATAATTTCTTTTTGCATTTCCTTAGCTTTAACAATTTTTGAAGAAGTGGATTCTTTTATCT
TTACAAACTACAATATCAGTTTTTGAAGATACGCTACCTGTAACTTTATGACCGAGTAATTCTAATTTC
TGTTTAAATTCATTATCCCGAATTCCTGTAAAAACAATAACTTTAGATTCTTCAGAAGCATTATTAGAT
AATTCTTGTTTAATAGATTTTAGTTTAAATTCATTAATCAAGAATATCAATTCTTCTTCATTATTCGAGA
TACCGTTTAGTAATTTTCTGCCTTAATATCTGAAAATCCTTCAATATTAATAATATCTTCTTTCTTAGG
TAAAGATCCATTTACAAAGAATTCGTTAATTACTTCTTCCAAGATATATTCCTTACAGAATAGTTTAGA
GTTTTCAATACCTAATCCTTCAATACCTAATGAACCAAGAATTTGATAATCATATAGATCACGTTTGTT
ATTAATTGCATTCTTGATATTATCTAGTGATTTTCTACCTAACCCTTCAATAAAGTTATCATCAATACTA
TCATAATCTATACTATATAAGTCTGTGATTGAAGTCCATAATTTATTTTCATATAATTTACTAATAGTAG
ATTTGTCAATACCTTTAATGGCTAGTTTATCAAGATAGTTAGATATCTTTCCAATAACGTTTCCAGAAC
ATTCTGGATTATTACAGTATGCAAAGGTTTGATTATCATTAATAACTACACTTTCTTGCTGACATACGG
GACAATATTTGGTAAATTTGTCAGGAATAATATCTTTGTTATGATCACTATCTACTTTATCAATATATGT
TAGTGTATCATTCCTATATTGTACTAAAATTTCTGAACCAATACCTAAACCTAATTCTTCCGCTCTTGCA
AAATTATGGAGACTTTGTTTTGTATGCGTACTTCCATTTGAAAATGTAACTGGTTCAAAATGTACTAAT
TTAGTAATTCGTGAAAAAYYASSWAWKWSWTASCTAAAARTCAGTAMTMCACAYTWTTYKWYTGYWS
WTARRSTASYYTAWSWRCARWMRAAWARTGTKRWGTACYKWTWKKAGYYATYMMTWRGGTGATT
TTTCACGAWWWTCGTCATCTAAAATTTCAACGACAATACCATCAATCATAAATCCATAGTTATATCGA
TTATTAATAACTTCATTATAGAAATCATTAAATTCTTCAATGACTTTTTCTACTGAATTACTTTCACTAG
TAATACTGAATTCTTAACCGATTAAACTATTTGATCCTAAGATATTAAAACTATTATCTCGTTTAGATA
ATGTAATTTCGAATGGATAATTATCTTCATCGAGGAATTTAATATCTAGAGGGCAAGAGTTAAGAAT
TTAGAGAATTTATGAGCATCGTCCCTACCTAATATTCCAGAGGTTGCGGATCGTGGATTAACATAATTA
```

```
TTCTTTGTATAATCATTTAACTTTTCTAAATTATCATACGTAATAATAACTTCATTTCTAATTGCGAAAG
GTAGTTTGATATCATATTCTTGTAAAGGATCTTTAGCGATGCTCTTAAATACATTAGTGAGATCTAACC
CGATACCGTCTTTTCCACGAGTATACGCCTTATCAAACTTTCCATCTTTAAAAGTAGTAACTACTGAAT
TCCCATCAAACTTTAATGTAAATAGGAATGTCGGGAACTTAGAAAAAGGTTTAAGCTTATTAATCATT
CCTTGAATTACTTTTGGAAAATCATTAATATCTTTACATTTAAATAATGTTCCTGTCAGATTTTTATATT
CATGCTTCATATTAAGAATACCTTTATCCGTTTTCGGTAATGATCCTACAATTTCTTCACCAGTTAATTG
TAAGTATTGTTGATATAATTGGTCATATTCAAGATCAGACATAATTACTGTATCTGTATTATAATACAT
GCTTGATGCATTTTCTAAATATTCTTTTACTAAATTATATTTATCATGTTCTTTACTGTCTAAAATTCTTT
TTGATTCTGTATAATCCACATTTTTCAATATCCACACTTCTTTCTATATTATTATTTAATATTAATCTTTT
TTCCATTAATGGTAATATAGTTATATTCACTGTTATAAGATACATTTATAATGTCCATATCAGCATCAT
ATACTTCATCTATTTCTTTTTCATCAACATATATTTTTCCATTGTCTAATTTTATTTCATATAATCCATCA
CTTATAACTATAACATTATCTATCTTTTTATTATAAGTTTTAGATTTCTTACCATCAATATATATTTCAC
CATCTTTTAATAACACATTTAAACCATTATTATATATATTGGCATTTCTATTTTGAGGAAGAGTTTTATG
TTGATGAAAAATATTATTATATACTTTTTTAATTTTATTTATCACATCATCACAACCTTATTTAATCTTA
AGATATATCCTATCACACTATAAAAATGTGATAGGATACTTTTTATTTATTTTTATACTTATTAATATCA
AACTAGTCTTTATTATTGGTATATTCATTAAGCATGGATTCAATATCTTCATCACTTAATTTTTCGATAT
TATCAAAATCATTTTTATAATCTGGATCAGTATTAATTTCAACACCTATAGATTTAAAATATGAATTGA
TAATTTTATTATTATTACTAATAGTGTCTGATTTCTTAGGTAATTTAATGTCAAAAGGATTTCCGAGAA
GTTGAGCTTTTACTAAATTACTTCTATCTTCAGTATTATTTGAATAAGCATCAGTTAATCTTTCAATAGG
TTCTAAAGATCCTACTAATCCTGAATTGGTATATTCCATTTCCAATTACCTTCACATAGATTCGCAATTT
CTATGCAGTTCTCTTATGAACTTCTCTAAGTTTCCTTAGAAGTTGAGACTATATCTTTATCTTATTTAAA
ATTTCTTTTTGTTTTAAGATACTTCCCATTTCGCCTGTCATTTGCTTTACAGACTACATCAATAGTCGTTG
AACTTTCTTCCAATAATTGTTGGAAGCTTAGCTGCTGATTATCCATTATAATTGATACTTAGGAATATT
ATATTTATACCAGAATATAATATCTTTTTATCTCACCATATATCATTCCAATTATTTTTTCTATCTTTCGA
TAACATTCACGCTTATCATTACTGATTGCGTTTTAGTTAATTGGACTTTAGGAGTTTCCAGCAATTAAA
GAAATTTTCATCATATATCACTATATAATGCGGCAAAATTTACCGACTCTAATTGGAGTATTATTAGTA
ACATTATCAGAATTTTTCATATCTTTAGTTTTTGTTGGAAGATTCTGGAAGTTAGTATTACCTTCACTAC
GAATAGATGTTTTTTCAATAGGCTCATGTTTAAGTCTAAGCATATATAGTTGACCCATTTCAATAGGCT
TACTAATTCCACTTAGTTTATAACGATCGATATTGAATTTATCACGAATATCTTTAAGTTTAAAAATAT
CCATATCATTCCAGAATGGTGTAAATTGAATATAAATTCCATTCTTTATAGTATCTTCTAGATAATGAT
CCTTATCGCTATCACTTAATTGATCATATATACTGATTAATGATTTATACATATTTTCATCAATAGACTT
AATATATTCAGATAATAAATTAAACTTTTCTTCACGACTATCCATATGTTCCATTCGATATCGAATAAC
TTGAGACATCATATTGAATGTATGTTCAAATGATTGTGAAGGATTTAATCGGTTATTAACGCCAAAAG
GATTAAGAATAATATCCGCTCTATTTTCTAGGCAAGAATCTTTATCAAACTCCTCACCATCAATAGTTT
CAATTACAGGCATTTCTTCGTCCGGAAGAATTAATCCAATAATTCCTTTATTACCATATCGACCAGTTA
GTTTTGAACCTTTCACAAGAGGAATTCTTTCTAAGATTGTAAATACCGCTACAATACGGTCAAACACTC
TTCCCTCAGACTGAAATTTATTTGCAGGATCATTAAATGCTGCAATCTTATTATAAAATGCAGATAAAT
CACTACTGATATTATTTCTTTTACTAGATACAATAGGTTTTAAATATTCTACAACTTCAGAGTAATATTT
TGAGATAGAAATATATTCATTGTACATCTGATGATTATATTTTTGAGATCGTAACTTATCAAGACTTTC
GTTATTATAAATATCAATGTCAATAACAATACCTTCAGCATGTTTTACTGTGTCAGTAGCAAAGATCTT
TCTTAAATTGACATCTTTCATACTGAATCCCATATCATTATAATTAATTCGACGAATTCCCATTAACTTA
CCATCTTTAATTTCTTCACCAATACTAGGAAAAGTTCTATATGATTCATCATCGCCATATAGATTTAAT
AGTACATCATTGGTATTTAGATTGATCTTAACTTTCTTTATTAAATAGGAAGCCATCTTTTGAGCAGTA
CTCTCAGAAACAACAATAGAGTCTTCATTTGTGAATCCTTTGTATGGAATATATACCGCATTGAGATTT
TTACCATACTGAAAGTTCATATCTTCGTCATAATTTTGATCTCGATAAATTACTTTGTTTTCAAATTCTT
CATTTTCATTGATATTATCAATTACTTCATTATTGAATTTTAGTCCAAAGTGTTCTGTTAAATGTTTTGC
TTCTTTTCGTTCTACAATATGATAGAGTTCTTCTTCTTCATTAAATAATATTGCCGTGTAATTAAATTTA
TTCTTGTAAAATTTTTTAAGAAGTTTCCATCTACCATCAAGCTTTTTATATCCAGTAGAATATTTACCTA
CTTGATTTTCAAAACCAGTAAAAACTAATGGTGGATCAGCTTGTTCCAATTGAATATTTTGACTTAAAT
GAGAAGTAAACATTTGTGACCTATTAGAGTTAGTCTTATCTAAGTTTGGAATGAGTAATGTTTCGGCTA
AGAAATCAAATTTACCTTTATATTTTTCATCATTAATCTCTGTTAAATCCAAAGTATAACCACACTTTCT
TTTTTTTTTAATATACTAATCTATCCATTATATAAGAGTTATTATATTATACGCTTATTGGATAGATTA
GTACTTGTAATTATTAAGATTTATTTATCATTTTCTTTTTCGATTTCAATTAAATTCATGTCAGAGTCAT
AGTATCTTCCATCTGAACCAACCCAAATATCTTCATCTTTATTAACGCAGTCAATAAGAGTAACAATAT
TATCATTCTTGGTAGATTTTGGAATTGTTTTAAACACTTGATTTTCACCATAAGCGTCAAAAGCATTTCT
AAATTCTTCATTAGTATTATATAGTGTAACAAAATCTTTACGTTTAAATTTAACGTCTGGAAGAGTAGG
AATAGAGTATCCTCCTTGCGGTGAACCATCTAATAGTTTATTATCTTTAAGATAAGCAAACAGTGAAAT
ACCGTTAGAGAATCCATTAAGTTGATCAAAAACAGAATTAAATGAGTATCCTGAAGCCGAAATACGG
GACTTAACAATTAGTCCATCAACTTCTAAACCTTTATATCCAGTTTCCTCTTCCTTAACATTTTTACCCG
GATTCAATTTAACAAATGTATTAGATAAATATCCAAAGGCAGAACCACCTGGAATAGCTTCATCAATC
TTTAGATGATTCAGCGAAGCTTTAGTCTTAACTACTGGATTAATTTCAATCTTAGTAGTAATATGATTA
ATCGCAAATAACATGATATTTGCTTTTTCTAATGCACTTGAGCCAATTAATCGTTTAATCATCTGATTAT
TGTATTTTGCTTGTGCTGTTGCAGACATCTGTCCACTCATCTTTTCTTCTTCACTGATGTCTTTAGTATAC
ATAGCAGCAATAGAATCTAAGATAATAATTGTCGGATCGAACTCATAAATTGGTTTACCTGTAATTGG
ATCTAATTTACCTGTATCATGTTTAAGTTTATCGCCCCTGCTAAGTTTCTCTTTTTCAATAATTTTTACTA
AACCATAAAGAGTTTCTGTCGATATTCCTGAATTAAGAAGATTATACTTTTCAAGAATCTTTTCATCAT
CCCACCCAGTAATATTTTTAATACGAGCTAATGATCCGGCATGCTCATAATCTAGATGATAAATTTCAG
AATTTTCATAACGATCAACAATATTACATGCAATTTGTTGAATTAATGTTGATTTACCAGACCCGGATT
TACCTACAATGGTAAATAATTTACCGGCATCTAATCCCATCATTAATTCTCCCTTACTATCATAACTTG
CTAACTTTGCATCAATCTGACTGAAACCCGTTCTATAAGTTTCAGTAAAATTTTTGGATTCACCTAATC
CATCTTTCAATAACTCTTTTTTTAACTTCATCTGTAATTAATCCCATACATTTACTTCCTCCTTAGATATC
ATACATTATAAATCATTGTTATTACAATAAAATAATTTTTTATTTATAATAACATCATACTACAACATT
CCCTTCAGTATTTTTATTTTAACATATTTTTGACGTAAAGTGGAGATTTTTTTACCATCATAATTTATT
ATAAAATGCTATAATGAAGATTATACTTCTTCATTATAGCATCATTAATTCTAATACTTAGATAATATT
AATTTAACAACATCGTCAGTATTTATCATTTCAAATTTTGACATATTATCAATATAATCACGTAGTTTAT
CAGTATCAATCAAATTACAATAATCATTTCTTTTTACAATGTCTGTAACTATTTGTCTAAATCTAGTGTC
TGATATGATTACATTTACATCTTTTATAAATGTATCAATGAAAATTTTTATTGTATTTTTTGCAATATTA
GCTTTATCAACATCAAATATTTTATCGATAATTTTATCAATCTTGAATGCATAAAAAAGTAACATTTCA
TAGTTCATATCAGGTAATTTATTTTTTTGCATACATAATAAATACTTCGATAGGGTCTCGCTCAATTTCTT
```

-continued

```
CAGTTTTTAATAATAATTCATAAATATAGTCTCGGATAGATATTCGAGATAAAGCTTCTTGCATTTGAT
TAATAAAGACTGAAGTGTTATCTAATGATATTTTTTCTAATATTGTGATTAGTTCACTTGCCTGTTCATC
AACTAATCTTTTATAAATAGTATTATCACGCATATTATCTTCCTGAATTATCTTAAATTCATTTACAAAA
GTCAAAAATATTCCTCCTTTCTTCAATAGTAAATAATCACAAATATATAATATATATTTATTATTGAAT
TTTAAGATCGTTTATATTTGAGATGTTTTCTTCTTTAACATCAGCAAAATCTAAATTAAATGTATCGGA
ATCATCTAGTAAATCATTATCAATTCCTGCACCAGTAAGAAATTGGGATACGGTATTTAACGTACGCTT
ATCATTAATGCTTCCCGGTAAATCTTGTAATGAAGTATATCCATACATTGCAATATTTTTATACATTGT
AGATTTTGCGTCTTGTGAGTCCGCTCTAGGGCTTAAGAATTCTTTTAATGCATATTTAGCGTCAATAGC
ACTTAATGCAATAGTTTCTAAGTCACTGATCCGTGCAATCTTATCTTCGTTTGTTACTTGGTTGGTTCTT
AAACTACGTTTACTAATATCTAATGAGTAGGTATTCTTTTTCGATAAGGTTTGTTATACTGATAGGTAA
AGATATACTATAAACGTATTCTTTTTCCCCCAGTCCAAACCGTACGTGAGACTTTCATCTCATACGGCT
TTCCATCAAATTTATTTCATTACTTAGAATAAATACTTAATAAATAACTATTCTAATTAATGAAAATTA
GATTTGACTAAGAACTTTCTCTCCACTATTTATTATCATAGCTTCATCGATACTTCATTCTCTCTTACTC
CCTATAAATAGGGTATCAAACGTTCCCTTTAAATTAGGTATATAAATGTACTTAGGATCCACCTGTTAT
TTATAACAATACTTACATATAAGTATAATATGACAACCTATTAGTCATATTAGCTAATAAAGACTACA
ATTTTATTTCGCCTATTATAAATCATTAAAGTGATTCGTATTCCTATCCATATACATCTACCCTAACCGC
TATAAGTATTATTAGCGACTTCATCCAGCTTCACACATATTAATTACTCAATATGCATGTGGAATATCA
TTAATAGCAATTCATGACTATTATTTAGGTTAGTCACAGCTTATTCATTTAAAGAGTTAATTATATACG
CATATATAATCATGCAATCCTCAATATTTTTACATATCTTTCTGCATAACGTTTCGCACGTAGTCTCCTT
ACGGGAAGATAACCTAATGGTACTGGATATCTAGTTCTTAATGGATTATCTTTATTTCCATCATGACGA
TAATAGATATATTCTTCTAATGGTACATTCATAAAGTCTAGTGTTTCTTTAATATCTATCAGTTTTGGTT
CATTTTTATTCGGTAATACTTCTAAATAGAAATTATCATCACCATTAGTAAATTTTTTCATATACGATAA
AAATTGTTCGTCACTCATTTTATCGTAAATATCTTTATACTTTTTAGCATTAGAACCAGTTTTATCTAAT
TTATTGAATACGTCAATAATATACTTTTGAATTTTATTTCTTTTTTGTTTATTATTAGATACTTCTTCATT
TAATTCTACCGATTCATTGAGATTATCTTTTGTATCCATATAATATACTGATAATATTTTAAATAAATTA
ATCGAATTATCTTCAGAAATATCATACTTCTTAATGTTTTTATCTTTAAAAGGAAACTTGTCAATACTG
AATTCAATAATCTTTAGACCATCTAGATCACGGTTATCGTACTTATCAGTATATAACTTAGAAAGATAA
TTTGAACTAATTTCCCTAATTTGAGAAGTATTTGATAATCTAATAGATTCAGGATAACCAAACTCAGGA
TAATAATTAAATAATACATAACTATCATTTTCTTTGTAATAAGGAAGACTAATATAATCTATTAATTCT
TTATTTTTTTCATTATATAGACCCATTATCATAAGTTTTGTAAAAGGTTGAATGTTTCTTAGTATTAAGT
AAATAATAGTATTAATAACATTACTATTCAACTTGTGATAATCAGTAAGAGTATCACTATACTTGATGA
TATTGAATAGACTCATTTTTATACTACTATTATAACTTCGATTATTATCATTAAGTATAGATTCAATATA
CTTAATGATATCTTCTTTATTATTAATATCATTTCTAAATATAATATCCATTATATAATCATTAAAATCA
ATTTTTGTAATATCAATAACCGAATCCTCATCAATAGATATTACTCTTTTATATAATGATGATAATGGG
TATCTTACAATACCAGAACGGGTATATTTAGTAATTGATAATAATGAGGGATGAGATATTAACTGATC
TAATTTTATAGATGGATATAAATTTACTTTCTGAATCCCTGAGTTTAAATAATTCAATACCATAAGTTCTC
ATAATGGTCATAAATACGCTTACTAATTGAATTTCTCTTATAGTTGTTTTATTTCCTTCTGCACTTCTAA
TTATTAGATCATTATCCAAGTATTGATTATAATCTTTAATCTTATCAGAGAAAGTATTAAACTGATCTA
TAATATTAATATTATTTTTATCATAATATATAGGAAACTCAATTACCTCTGTAAACATATCAATATTCTT
TAACTTCTTTTCAAAATTGGATGTAAACTCAGATACTTCCATTTTTTCATCGTTATAATCAATTCCAAAT
ATTCTAGAATTATCATGACTATCTATTAACGCAATTTTACTTAGTCTATCTTTAGCAGAACCTATTACCC
TATCAATAATTAATGTAACTTCTAATTTACATTTATCCTCTGAAGGACTATTATCAAAAGGTATATATT
CATTATTATCTAGCATTAATGCATTATCTGTAAATTTTCTTTCATTCCCTAGGTACTCATTATATTTTTTA
TTCATATAATTATCCAACTATAATTCACTTCCTTTATATTATTCACTGGTATATCTATATGTTTATATTA
CTAGTTATTAAAATCTTTTATCAAAAAAAAAAAAAAATATTAATTATTAAATACATAGTATATAACAATT
TATTTGTTATATACTATGTATCTTTTTTTCCTTACATTATATTGATTAGAAATTTAAACCTAACCAGTAT
CTAGCAAACATAGATTTATATGAAACTAAATCTACAATAAATATTGATACGAAAATAACCAATGATAA
AGCAATTACCCAAGATAAGAATACAATTACTTTCTTAGATAAATTAAGATTAAGTAATCTTTCTTCAAA
TCTTTTTAGTGTAAAATTTTTCATGTTATCTTCTAAGAATAATAAGATTGTAATGCATTTTAATAGTTCA
TTAAAGATTCCCACAATTTTGTTACTACCATTATTTTTATTTACTATTACTGTTTGTTTTTCCACTTTCTC
CACACTCCTAATATTATTATTTTCATTTTATAAATTAAAAAGTTAACCTATCATCAGGATAATAAAAAT
ATCCAATGATAGGTTAACTCGTTTTTCTCTATATTTAAATAATATTTAAACTATTAAAAATTATAATCA
ATCTCAGACTTTTGAAATTCAGCTTTCATTCGTTTTAGTTCTTCTTTATCAATATTTTTTTCTGACCTAAT
AGTAGTACCTGTTGGCACTTTTATATTAGTAATCATTTTGCCTTGAACTGTTAGGATAATATTTAAAGT
AATCAATATAAGAGCCAAGAGCAATAATGAACCAATAATAAAAGATGAAATATATCTATCTACTTTCT
TTACATCTTCTTTATGTTTACTCTGGTTGGATTTATATTTCGTACTAAGATTATCCATTCTTATTTTCACT
TCCATTCATTTTATATTAGTAATAATAATTTATCTATATTACATAATGATAATATATAAACAAAATATGG
GTTATTACGCTTTTATAAAAATTTATAGTTAATGTATAATAATATTATATATTTTGGATCATAGAAAAA
TATATATGCTTTATAAGTATATATTAAATTTGTAGTAAAATAATTAATTATGGAGGATTAATATGAA
AGAATCTTTAAAGTTTAATGTCAAGGAAGTAAGAATTCTTAGCAAATCGCATCTAATGAATATGCTA
ATGAGGAAGTCGGTATGAAAGCTTTTTATCTAAATTGGAAACATTTAATAACTTTCGTTCAGGATTTT
TATATCTGTATCTAAAGAATCTTTCAGAAAGTGGATTAACTAAACAAGAATCTTTAAATAAGGCTATT
GATAAATATGTCAAATAATTCAATAAGATTTAGAATAATGGCAGATTTATTGTAATAATAAATTTAT
CAATGTTGAAGAATTAGAGTTCACTGGAACGAACGAAAGTAACGCAAGGAAACAATTAACTGGTTAC
CTTAATAGACTAACAAGAGAAAATAATAATGGTAGAATATACAGCTAAGAATATTAATATAATACCCAT
TAAATCCCAATTTCAAAACAATATTGAAAATCAAGAACAACTAAATCTTTTTAGTAATGATATTAATG
ATGATTTATAATCTAAGTAAATCATCATTAATTATCTTTAATAAATTATGAAAGTAGTGATATTTTTTTG
GCTAAATTAAAGAAAAGCAAAAGACGAGTATCCTTTGAAAACATTGTTAAAAGGGTTATTGAAAAAC
ATTTTCTTGAAAAGTATGATAAAGCAGAACTAGATTTAGATAACGAGGAAACGTATCAAATCGGGTTA
GGTTCTATTGATATTGATAAATACAATATCAATCCTGATGATTTCGAAACCTCTGGAATTTATTATTAC
AGTAAAGGGAAAATATCTTTAGATAAAGATTCATCTCCTTTACGAACAATGAATGTTAATGTAGGAAC
TGTTAAGCCTTTATATGACGTAATATATGAAATTGAAATTATTTCAAGGGTAGAACCAGAAATTAATA
ATTTAACAGTATTAGGATATTTTATTAAAGAATAGAATAGGATGGTGGTGAAATACATTGACAAGAACTT
ATTCTGGTGAAGATATTGATGTTTTAGAGGGTCTAGAGGCTATTCAGGTTAGACCGGATATGTATGTA
GGAAGTTCAGATGAAACAGTCAATCATCTTGTTAAAGAAGCAATTGATAATGGTGTAGATGAATTTCT
TAATAATTTTGGAACAAAGGTTATTGTTGACTTAGATACTGAAGAAAATATTATTACAGTTATTGATGA
TGGTCGAGGATTACCTACTGACATTCATCCTAAAAAGAAAATTCCAACAATGCAAGTATTGTTATCAG
AAGTACATTCTGGTGCAAAATTCCGTAAAGATTCTTTTAAAGTTTCTAGTGGTAAGAATGGCCGTTGGTA
TTAAAGCTGTTAATGCATTGTCTGAATATCTCCGAGTAATTTCTATTAGGGAAGGATACCAATATTCAA
```

```
TGGAATTCTCTAATGGTAAAGTTACTAAAGAATTTAAGAAAGAAAAGCAAAAAGAATACAAAGATAT
CAAGCATGGAACAATTATTGCATTTAAGCCTAATGGAGAATTTATCGATAATTATGACAAATTTGATC
CAGAATTCATTAAAGATAATTTAGAAAAGCGTGCATACAGTAATGCTAATCTTAAATTAATCTATAAA
GAAAAAGGTAAAGAAGTAGCTACGTATCATCATGAGAATGGTATTCGAGACTATATCACAATTCTTAA
TAATAATCCTTTTACTAGTAATCATTATTATAAAGAAGAATTAGAAAACGGCGACTTATACGAAGTAA
CTTTTGGATATAGTAACTCTTCAGACGAAAATATCTATAGTTTTGTTAATGGATTGAAAACTGCTCGTG
GTACGCATGAAACCGGATTCAAATGGCACTTACAAACTTAATGACTAATTATATTAAGAATAATAAA
ATGTTGCCAAAAAATATGCAAGCTAAGGCTATTACGGGTGAAGATATTCGTTCTGGATTAGTATGCGT
TATTAATCTTAAGTTGCAAAAAACATCATACAGGTCACAAACTAAAGATGAATTATCAAACCCTGAAG
TTTCTGGTATTATTAAGCGGATTACAAATTCAGCAGTAAAAGATATTATGGATACAAACCCTAGTGAA
TTTAAAAAGGTATGTAGTCGTATTATTGATTTTGCTAAAGGAAGAATTAATGCTTCTAAATATCGTGAA
AAGATTGTTAAAGATACGAATAATCTTACATTAAGTTCTAAATTTTCAGATTGCCTTTCTAAGGATCCT
TCTGAAAGAGAAATCTTTCTATGTGAAGGAGACTCTGCAAGCTCTGGAATTAAAGAATTCAGAATCTC
TCAAACTCAGGCAGTATTCCCATTAAAAGGTAAACCTAAGAACTCTTATGGTCTTTCTAGTAAAAGTTT
ATTAGGTAATGATGAATTTAATAATATCATTAAGATTATTTTTGGTACTAATGATATTAAAAATATTGA
TTATGATAAAGTCCGATATCATAAAATCATCTTTACTGCAGACTCAGATACTGATGGATTACACATTAA
TTCATTATTAGGGTTATTCTTTTATACGCATTTTAAAGAATTATTTGATAGAGGATATATTTATATCGCA
ATGCCACCTAAATATAGTACTTATGATAATGTTTCTAAGAAATTTATTTACTTTAAGAATGATAAAGAA
TTAAATACTTTTAAATTCAATAACATTAAGAAACGTATTAAGCTTAGTGATGATAGTGAATTTAAATTA
AAAGACTTTATTAATAATATGAGCGAATATCAAAATCAGTACAATATTGTTAAACAGAATAATAATAA
TATTTCCGATAGCGTTATTGATACATTCTTATTACATGGTCATGAAAGTAATTCCTTTATTGAAAAGAT
CCTTCTAGATAGGAATAACTACAGATTCAGTAAGAATAAAAACGGAATATTATTGGAATGCACGATA
ATGCTTGGCATGATATTAATATTGACTTATTAAATAATGATATTAGTCGTATTAAGAAAGTTATGAGCA
TTAGCGACTTGTTTGAATTTACAGATACCAAAACAAATGAAATTTATAGTAATGTAACATTAAAATTTC
TTATGGATTATATCAATAGTAAATTTACGTATAAACTTAACTATTTTAAGGGTCTTGGTGAAGCAAATC
CTGAAGAATTGTTTGATACTACCATTGATCCTGAAAAACGTGATTTAATTCAGGTTAGGATTGATCCTG
AAAATGAAGAATCAACCCAAGAAATTACAGATATATTCTTTAAAAATAATTCAACTCAAAGAAAAGA
ATATGTAAATAGTTGGTTTAATATTAAATAAAATTTTATACAATTCGGGTATTACTTAGAGTTAATCCC
GAATTGTATAATTAAATTAAAATAAAGGTGGTTCATACTTTTGGCTATTATTCAAAAACAACTTGTAAA
TATTCATGAAGAAAATATGGAAGAATACTTTGTTGAAATACTTACTAGTCGTTCAATTCCAGATATTAA
TGATTCATTAAAAACCCAGTCAACGAAGAATTATTTATTCTATGAATAAAGATCGAAGATTTAGTAATTT
ACCATTTACTAAATCTGCAATGATCGTAGGTTCTGCATTAATGATTCATGCCCATGGTGACGCATCATT
ATACAATACTGCAGTAAATTTAACTCGTAAATTTTCTAACATGCAACCATTAGTTGAAGGTCACGGATC
TTTTGGTAACGTATATGATCCTAGACCTGCTCAAATGAGATATACTCAAATGCGACTAAATAAGTTTAG
TGAAGAAGTTTTACTAGATAATATTAATGATAACTGCGTTGATTTCGTACCATCTTATGATGAATCTGA
ATTAGAACCTGTCGTTCTCCCATCAAAAATTCCAATGATTCTTATCAATGGTTCTTTTGGTATTGGTGG
AGCATATCGTTCATTTATTCCCCCTCATAATCCAAAAAATGTTATTAATTATACAATTGATTATATCAA
AAATCCAAATAAATCTGAAGAATCATTAATTAAAGATAATGAATTATATCCGAGTTTCCCTCTAGGTG
GTATTTTAGATAATAAAGATATTATTAAAAAAATATACGACTGGTGAAGGAAAATTGGTTCTACGTGCA
AAGATTATTAAGGATGAAAATAAATCTACTCTTACCATTGTACAATTACCATACATGAAAACTCAAGA
TATCATTATTGAAAATATACAAGAAGCAGTTAAAAAAGAATACATTAAAGATATTAAAGGTATTGATA
ATGGTTCTGAGCGTGGTAAGATTAAACTTATTATTAAATGTTTTAAGGGAACAGACCTAAACGTAGTA
GAAAGTCAATTATATAAGCATACCGGATTGCAAAGTACGTTACCATTAAGCTTTGTATTAGTAGATCA
AGGTGACTTTAAAAAATATAATGGAATTAAACATATTTATTTCTGATTGGGTTGAATTTAGAAGAACAA
CTATTCGAAGAATTAAAACGAACCTTATTAGTAAACTTGAAAGAAGGATTCATATATTAGAAGGATTA
CTAAAAGTATTAGATCCAAAAGTATTAACAAAACTTATTAAATTAATTCGTGAAGGAAATAGTCGTGA
TGGAATTAAACTAAGTATTCAAGATAAGTTTGATTTATCTGTAGAACAAGCTGAATATATTGTTGAAAT
GAAGATCTATCGACTAAGTAATATTGGTATTAATGATACAAAAAATGAATTAGCTGATAAAATGAGGG
AATTTGACGATCAATCCGAATTTATGAAAGATCCTAGTCGTATCGATAAATATATTATTGATGAACTAC
AATCAATCAGTAAATCTAAAAATCTTCGTAATGACTTTGAAATAACTACTTATGATGATAATATGAAT
GAATTGGATATAGAATCCCTGATTCCAGACGAAAATTATACGATTGTTGCTACAAAGGGAAACTATAT
CAAGAAATTCATTTCAGAAATGAAAGTACAAAAACGTGGCGGTAAAGGAATTAATATCGGCAAACTT
AAAGATAATGATATTCCTTTAGGAATTATCTCTGCTAATAGTAAAGACAATATTTTATTTATTACAGAT
AAAGGTAAGATTTATAACTATAAATGTTATAAATTACCAAACGCTTCTAGTATTAAGACGCTAGGTAA
TAATATTTCTAATCTTATTAAAAAGGAAAAGTTAGTATCGATTTTTAGCTTTACTGATGATCAATTAAA
TAATGATAAAAATTGCTTATTAGTAAGTACTATTGGTAATAATATTAAGTTAGTATCAATGACCGAACT
AAAAAGTATGAATGAATCTGGATTAATTTTATCTAAACTTAAAGATAATGATGAAGTAACAAGTGTTA
AATTAGTAGACATTACTGAATCTAGTAATGTAATTGGTATCCACTTCTGAAGGTATGGTTATTCGTACAG
ACATCTCAAATATTCCAGTTATTAAAAGAACTACACAAGGTAGTAACCTATTTAATAATAAAATATATT
ACAGAAAGTAATAAACTTGTATCGGTATCTCTAGAAACAAAAAAATACTACTGGTCTGTATATTATTAC
TAAATCAGGATTATCTAAACGTGTAAAGATTGATGAATTCAGTAAATATCCTAGAAGGGTAAAAGGTG
TAATGGGGATTAATCTAAAAGATACTGATGATAAAGTTGTATCTATGGAAACTTATGAAAATGTAGAT
GACCATAATCTTATCATTATCTCAAATCAGAAAGCAATTTCCATACCTCTTAGTGATATTTCTGAGTAT
AAGAGACCTGCAAAAGGACTAACACTTCAGAAGCTTGAAGATGACAACTATATTATTGATTCATGCTT
AATTTAGTATTAGAGGGTAAGCCATTGTTTATTGATGGCTTATCTTTTTTTTTTTTTCATTTATATATAAA
AATTAACCTTTTATATAACAATATTATATACTATTGAAAGGTTGTGGAAAATAAATGGCAAAAGAACT
TATTTTAGATGTTTCTCATCATCAAGATCCCAATAACTTTAACTGGGCTAAACTTAAAGATGAAATCGA
TCTAATACTAATTCGTGTACAATATGGATCAAATACTATTGACCGTCAATACAAGAAATTTGTTGAGCT
TGCTGAAAAACATAAAATTCCTTTTGGTCACTATGCTTATGGTGTATTTGTTAGTTCTAAAGATGCAGT
AGTTGAAGCTAATAACTTTTTAAAACGTGGTGATAGTGAAGCTACTGTATGGATTTTAGATGTAGAAT
CCGCACACTATTGAGTCATGTAAAAATTCTCCTCTAGGTGAAGCTTCTCAAGCATTTATCGATACTCTTA
GCAAAGCCGGAAAGAAAACTGGTTTTTTACTATGAACATCTTATATTGGAAAATATGGTTTAGATAATG
TTAAAGTCGATTTCCGCTGGATGCCACGCTATCAGGAAAAATGAGGTACTTTATCAGGAAGTGCTAAA
CCTGATATTTCTTGTGATTTATGGCAATATACTAGTACTGGTAAGCTAAAATCATATTCCGGTAGTGCT
TTAGACTTAAGTATTCTTAATGGTAAGAAGGATATTAAATACTTTACAGGTAAAGCATCATCAAATAA
ACCATCCACTGTTAAACCATCTAAGCCTTCTAAACCTAGTGATTCAAAAGATACTGTAAAAACTACTA
GTTATTATGTTACTGCAACTAAACTTAATATTCGTCAAAAACCTGATGCTGATAGTAAATCTTTAGGAA
CATTGGATCATAATGATCGTGTTCAAGTTATTTCAATTAGTAAAGGTTGGGCAAAATTAAAATCCGGT
AGTAAAGAAGTATATGTTTCTGAAAAATATATTTCTAAAAAAGCAAAATCAAATAAACCGAAACCAGT
```

```
AACCACTAAGACTTATACAGTCGTAAAAGGGGATACTCTTTCTGGTATTGGCAAAAAACTTGGAAAAG
ATTGGAAAGCATTAGCTTCTAAAAATAATATTAAAGGTCCAGCTTACGTAATTAAACCAGGACAAAAA
ATTAAATATTAAATATTTTATTCACCATACAAACAGATCATTATATTTAGTGATCACATATGTTTGTAT
GGTGATCTTTTTAAGAAAGAGGGTTTGAAAAGTTGACTAAACAATCAATATTATTAAATAGTTTTGAA
GAAAAAATTGAACAGGCATTTAAAAATAGTAGTAATGTAAATAAATTAGTAAAAATTGTAAGTCAAT
ATATTGATAAAAATAGTGATATATTAAATCATAATCACCTACATATCGACTAGTGTTTGCTCGTGAAG
GATATGATGCTGAAGTTATATATGATATAGTTAATATATATCCTGAAGAAATTAAAGAAGTTATTTCAC
AACTAACATTTATTCGAAAAGAATGGAAAGTAACCAATGAACCCTTTTCGGTATTAATGACTTTAATT
ATTCGATATTTTCATTTAAAAAATAATCGTAGAGCATTGCAATCTGCAATAATGTATCTTTCATTATCA
TTTTATTCATCGTTACATTTTAGATCATTTAGATATGAACCGAACGATAATATTATGCAGTATACAATT
AACCGTGTAAGTAATAAATTCTACTTTAAACAGTACGGTACAGTATTTAAAGCACTTAATGCTACTGCT
GACAAAGCAGATATGAATCTTAAAAACTCTTTAAAAAAGAATGATGACGAATTAATTATTGCATATAT
GACATCCCTAAGAAGTCGTCTTGCAAACCAATTAACTACTTTTGCCCAAGAGTTTTATAAAGACCATGC
AGCTAATAATTATTTAAATAAGGTATCGGATGTTTATGATGACGAAAACCATATTGAAAATACAAATG
TTTCTGGAATTGTGATGTCACAAACTAGTAAAGTATCTCTTAACTTTTATCAATCTAGACTTAATGAAA
AATATATTATGATATCTGCATCTACTTCTAAAGTTACGGCTAATGCAGTAAGAAATACATTAGAAGAT
GTTAAGGAACATGAACGAGAAAAAGTGGAAACGATTATTCGTAATACAATATCAATATATTTAAATGA
TCGAAAAAATTCGGTAAACTCAATCGGATCACAGAAATTTATCAATTATTGTATTGGAATATATACAA
AAAGTAATACAAAAGAAAAATTGGTATTAGAAATAAAATCAATATTAAACTATTTCTTAAAAGAATAC
TGTGATAAATATAACAGTACTGATAGGGAAGCTACTAAGAATAATTATCGTAAAGCTGTATTTCTTTA
CTTTATATTCTTAATCAGTGCAAATAACTAAAAAAAAAAAAATATTAAAGAATATATCCATATAACCAA
TAATAGGTTATATGGATATATTTTTATTGCTTATTTAAATTTCTTCAGTATCCCTTTTTATTTATTAATTCATTT
ACTTTTTCTGATATAAATATAGTGGATATTCCCATTGAAATCATTGTAATCAGCATAAGTGTTAATAAC
GCTAAAATTAAAATTTGCATAATAATCATTATAACCATCCTTTTAAATTTTATTTTTCAATTACAGTACT
TGTAATATTACCATCAGTATCGACTCCAGTCATTACAGTGTATGTATTAACTACAGCACCATCTGCAAA
TACGCCATCAGTTCCTTTAGATTTTACAAATACAATGTATGTATGTTCCCCATGAGGACCCATTTGTTC
ATTGTCTTCTGTAATATCATAATATAAATTACTAGTATTAATATTTCCATATTTTTTAGATACAATTGAA
GCTAGATCTTCATTAGATAATGTTGTTGACATATATACTTGTTGATAATTATTTAGATCAACTTTTTTAC
TATTTTTTACTTGTTCTTTCATTTCGCTTAATTTACTTTGTTTATAATCTACTTTATCAATAGATAATGTT
TTTGATTTAGTGTTATATTTAACCGTTTTATCTTTAATATTGAAAATAAGATTTCCATTTTTATCATCTTT
AGATTGATATTTGTCAAATTTATCATTCAATACTACATTATCATCTACATGACCGATTTCAACGCTAGT
ATAACTACCTAATACTAAATGATCTTTAGTTAATTTTACATATCCTTGAGTATCTTCATTATAATATTCC
CCAGTAACTGTATTGATATCTGGAGTCTTTTCTTTTTTAATTGTTACTTTCTTTTCTTTTTTCTTATTTTCT
TTAGAAGGAGTTTTAGTTTCAATTTTCTTAACGTCATTATCTTTCTTTCTTTACAAAAGTATAATTGGTTGACA
CAATCCCAACAAATATTCCAAGGGCAATAGCTACAGTAATAATTCCAGTTAGTATTAATTTCTTTTTCA
TGTTGATCCATCCTTTTCTTTTTTTTTTTATTTAAATGTCTAATACCGAATAGCTAATCGATATTAGACA
TAATTGAAAATTTATTATTTTTATTAATTTTTTTATTAATTAAATTTTGAATTTAATAACTTCTTTTTTA
AATTCTAAGTTTCTATCATCTATACCTTGGATAACTTTATCAAATTGATTATATCCAATAATATTTACAT
ATCCTTCTAGACCAGAACCTTTTATATCCTTATAACTGGATATAATAAATGATTTTGCATTACTTTTTAC
ATATAAATTTGAATTATATGAATTATTAGTTTTTCTAATTTTAATATATGATGATACCATTTTCTTAACT
TGTTTTTCATTCACAAATAATACTTTATATTTATCATTGATATATACTTCTTCAGGAATAATTCTTCTTTC
TAACATGTATGGAACACTTTTATTAAATGTAATTTCTGATGTATCATTATTATAAATAATATTATCATCT
TTACGAATATTAATATATTTATCAATATCTTTTACAGTATGAACTGCAGATAACTTATCGAAATTAATA
TCAAATTTTTCCATATAAATATAAATATCTAGTTCACCGCTAATATATTTACCGTTATCATATGTGATTA
TAGATACGGTAGTTTTCGTAGTTCCATTAAATTCAGATGTTTCGATATTATGCGTATTAAGAATTATAT
ACTTAAGATTATTATTATATAATTTTTTGATCTGTAAAAATAAGTCATTTACACTATACATTAGCATAA
TAGTTAATACCAACTTCCATTATTAATTTTTAATACTAGGATAATATCTATTAATTTAGATATTATCCTA
GTGATATTTTATTAATCTTCAAATACAACGAATCCGTAGATATTAATTGGATCTTCTACTTCAGTAATT
ACACTAAATGTATTTCCATTAGCACCACCATTATCTTCTACTACATAACCACTGTGACCCATCACTTCA
GTAATATTATTATCCTGTAGTTCTTTCATCTTACCATCATCAAAAAAGTCAGGATCAATTTCATCCACC
CCTAATGTATAACTTTCTGAAATGACTACATCTACACCATACACTTTTTTAATTTTTTTCCGTTAATTTAC
TTACGTCTAATGACATAATAAACACTTCCTTATTATTTATTTTATTTCATGATTATAATATATATTTGTA
AATGTCTTTATTACGGATTAATCGATATTCTTTTCCTTCAATAGTATTTATATTTAATGACATAGGATTA
ATATGTGGATGTAATACTACACGTTTATAACTGAATACCTGATTCATAAGTTCAATAATATTGTCAGCA
TCAAAATTATCGTTTATATATTCAATACTGTATATAATATTTTTATGCATTGAAACATTTAAACCAACA
TCAATATTATTCTTATCTAAATATTCTTTGATTAGATTAAGTCTATTTACGATATCATATTGGTCTGGAA
AACAGTTCATTAAATGGCTTGCCCTTCCTTGAATATTTTCTTCAATTATCATAATTTCTTTTATTTGTTCT
ATTATATTATCCAACTAATTCACTACCTTCTTTTAATATATTTGATAATTCTTTATAATATTTTCCTTCCA
ATGTAGTAATAATATTATCATCATTGTCTAGAAATATTAATGAGAATATCTGGCAACTATTTCTTGCAA
TAAATAATTTATTAACTTTTTCACCTTTTTCTAAGAATGTATTAAGTTTAATATCATAATACTTATAATA
AAGACTTCGCATAATCCAACCAATATCACGTTCTTCTTGAATATATAATGTATCATCATAATCTGGAAT
AATATCTAATTCATATATTTTTTCTGAATCATCATAATTGTATGAACTAAACTTATGTTCACTATTAATT
AAGGTATGTGGTCTATCAAAATAACATTTATCCTCTAGTATTGTACGATTAATATCATTACGTAAATAT
CCTAAGAATATCTTTTTATAATGAGTATTATTAGTAATCCAATCCGAAATAATACTAAAATCATTATTA
TTTAATAACTGGTTTGATTCAATATTATCCATTATTAAACAAATATCTATAGTTTTTGTTCTTGATTGA
ATATTCCAATTTCCCATACAAAACTAAACCAGATCTTTTTACCCATATATCCAGTCAATATTCCTGCAA
GAGGATTCTCTAGAGATATTTTTACTAAAGGTGCAGCCAATCCATTAGGAGTGAAACAACATTTTGTTT
TAACGCCAATATTCATTATTTCATCAACATCTTTAGAAAAGTAAATAAATTTATTACTATGATTATTGG
ATATATTCATTTTAGATTCAGATACATTATATTTTGTACCTGCACGAGCCAATAATACATTATTGATAT
ATTTATTCATTTCCTTATAATTTAGGTCAGATTTTCGAATTACTTCATAATTCATAAAAGGTAATAATTT
AATAAACTTATCATTATTATATTTAGATAATGAACTTTGAAGAAAATTATATGCTTCATCAATATAATT
ACTATTTACTTTTTTATTTGTAATATATTTATTAGTAACTTTATTAGGAAATTCACTAACAAATCGATGA
ATGGATATATTATTGACTACGCATTTATTTAAAAATATTCATTAACTGTTCATATGAAAATAAATTAAAC
ATACGATATAAACCATTTTTCTTTTTATATTTAACAAATTGTATGTCAAATAATTCAGGTTCTAATTTAT
TATCAAGATTATTATTGTACCAGTCCTTAATAAGCTTTATCATCTTATACATTCTTTTTTTTACCAAACTT
ATCATGCAAAAACAGTATTTCATGTTCTAATTTAAAATCAGTAATTGAAGCACCAATACCAATATTTAA
TTGATGTAATTTTTCAATTATTTTAATTTCATTATAGATTTCACTGTCAATTTGAGAAAGTGAAAGTACA
TCTTTATATAAGGATGCAATATATTCTTCATATAGTACATTATTATTCTTCAATTTTTTTCATCACCACGC
TTTATAGATTCAAATATATTAATATACTTATCATATAATTTTTCTAAATTTTCCAGTTTCATCAATATGCA
```

-continued

```
AATAGTATGACATCTTACCAAGTAATTCATAATCATCATAATAACAAGATCCGGTTTTCATATATGAAT
ATAAGTTATTACGCATATCATCATACTTTTCTGAACTTAATGTTAATTGATTTTTATGATTTATCGTAAT
CCCAGTAATATTACGCATATTCCCTTTAAGATAGACAGTTTTACTATCATTAATTTTAAATTTATCATTA
TATATCTTGAATGCCTGATTACATATCTTAATGATAAATTTTTTATTAAATAGTTTATTATTGTCAATAT
TTGTTGAAAAGTAATATCATCCGAATATGAAGAACAAATTATTCCATATTTATGGAATATGGTTTGTA
TATGATTAATAATATCTACCATAATAATATTCGATATTACGCCAGAAACTGGATTACCTAGAAACATTT
TATCATTTTCATCAACAAAACCTTTCTTTATAGTATCCATATATTTATCAGTAACGCCATGGAATAATA
GTAATATGAATCTACTATTAATTAATTTCCAATCAATACTAGGAAAATAATTAGATATATCTACTTTAA
TAATATATTTATTATTAAGGTGCATTAATGCATTATCTTTTATAGATACATTTTTTCGATAAGCCATAAT
ATTTGGATATTTCAAGTTTGATATTTTTCTATCTAATCTTTTATCGAGGATCTTAGAAATTTCTTTTAAT
GTATTTTTAATTTTTATATTTGGATCAATAACTTCACGTTCTTTACCATTTTTTTCTATCTTGATTTTCTT
AAATAATTCAATATTATTGTCCTCTAAGTCTTTAATGATACAATATAACTGAATTATTTCTAGAGACAT
TCTTCTTTTTAATAATAATTTTATATCACTGGCATATTTACTTTTAAGTTTATAAATTAGATATTTACTAT
TACTAATTTTAGAGTTGGGATATAATAATATATATCCTTTACTTACTGATACAAGAGGTGTAGATGAAA
AAGATCTATACATACTAAAGAATTCACTATATTCCCTCAGCTCAATAGAATTCTCTAATAAATATTTTT
TACTATAGTTAAAATCTATACTGTTGGATGTCTTATAATAATTCATAATCTTAATTAATAAGTCATAAC
TATCCTTAAATAGTATATTATTTAGCTGAACTAACTTTTTTTCTGAATTATCAAATCTTGATATTATTTT
AATATCTTTATCATATGGATAAAAGATCCCTTTATTAGTTAAAATTCTTAATGGATTCTTACTAATTATT
AATAAATCATTCAATATTTATCTTCACCTTTCTTTTTATTGTTTTCAAAAAAATTTAAAATGACCGAACA
TTCTTTATACTAATAATGTATAAAGAATGTTCGGCTAGTATATTTTAGATAGATGTATACTTTTACTACT
CAAATATAATAATACAAATTATGTTAGTACGAATATACAGTATACCGCACGCGCTGAGTGCGGTATAC
TAACACGCAACCGAAATCTATGAGGTGCGTGTTAGTATAATTAATATTACAGAGAATAGTGTTAAGTG
TTTGAATGCATATTAACGATACGTTAATGCTTATCAAATATTAAATGATATATTGAGAAAAACTAATAT
TATATTGATAGCTTAATATACATCTTATTAAAACCAAAATTATATTATATTATTTACATAAAATAATAAT
TTTTTATTATATATAAAATCAAAAAACAGGAATTTATTGACCGGGGTCCGAATAATGTCGATTTATCGC
ATGAATGGACCCGAAGCAATAAATTGCATGTATAATGGAAATAATTTTTTGACTAGTGACGATTACAT
CACATATTAATCATTTTATATATAATATATTAACTTATAAATTGTAAAATCCAAGAAATTTATGAAACC
GCAGCTCACGTCCCGAGTAATTTATAACTCAGAAATGTGAGCTGCTGGTTTTACTAAATGATAATGAT
AGAGACTTTTTTGATTAGTGAAGATTACATCCACATATTAATCATTTTACAATTTATAATTACGTAAATT
AAATAATATTTTGATTTACTGATTATTAATCAGTCTAAAATATTCCTTCAATATAATGATATATACTTA
AAATTTAAGTAAACTTTAAAAGCATATATTTGAGAAGGATACTTATAATTAATAGTAAATTGTAGAAT
CTAAACAAAAGAATTCAGCACTTCATTCGTACCTGACGTAACTAGTAAGGCAGGTACGGAAAGGATGT
GGAATTACTTTAATAATGATAGAAACTTTTTTGATTAGTGACGATTACATCCACATATTAATCATTCTAC
AATATACAATAAATATTAAAATTTAAGTAAGATTTAAAATCAGTGAAAACGATTTGTGAGATGTCGGAT
CGGATCGAGAAATACTTGTATGAAGCGATCAGATACTCTGATATCAAACAATCAATAAAATACGACAT
ATATTGATTAGTGACGATTACATCACATATTAATCATTTTATATCTACTTAAATTTATAAATTAATAAT
AATTTTTGCATCTTCTTTAATATTAACACTTTCCGGTCTAGAAGTTTTTAGAGAAGTTCTATCATTAAAT
CGAGTATCTTTAATAAATTCTAATCCATCAATATTAATTCTTTTCATAAACTGTTTAGAATTTTCATTAA
ATGATGATGAAATATATTTAATGTCATTATCAATAATAAATTTCTTTAGATCTTCAAAAATATACTTAA
TACTTGAGGTAATTTTTTTATTAAATGGAATTACAATGTCTTCAATATACAATAATTTACTATGGGTAT
CCGTATTAAAGCTTCTATTGTTAAATTGAACGCTCTCATTTTCCGGATCATAACCATAAATATTAGATA
TTAAATATCCATAAATATCATTGTTATCATTACGAATAATATATGATGGAGACTTCATTTTCCTAGCAA
TTTTCTTTAATTCAGAAATATCGCTATCTTGTTTCCAAACATTCTTTTCAACGTATAACATTCTATTGAA
CCAACCCGGTGATGCCTTTTCAATAATAACTTCACTATATGGAGAATATTTTTTAATAATATCTTTATTA
TCAGAACCAATATATTTAATATTATTTTTACGATCTAATACCGTAAATACATATCTTGAGTCGTCAAAT
GATGAATATCTATTGAAGTTATTTTCATAACAAATTAGCCCTTCACTAGAAGATCTTAATCTCTGAGTA
TATGAAACTTTATAATTACTATTAAATATCATTACGTAAATATCCTAAATATATTTTATTGTAGTCTGAAT
TAATATCAAGCCAGTTAATAATATATTCATATTCATTCATGTCTAAACTTTTTGACGATTCAATATTATC
TAGAATTAAATTGGTTTCATATGATTTAGTATCTTCATTATATTCAACAATCTCCCATACAAAACTAAA
CCACGTTTTAGTATCAAAAACGCCCTCAAGAATCCCTGCGATTGGACTTTCAATAGCGGGTTTTAATAA
TGATTTTGCAGCACCGTCTGGTCTGAAACAACATAATGTACGGAAACCAATTGAATTAATGTCTACTTT
TTCTTTAGTAAATTTAATCATATCATTATATTTACTATCGTCAAATAGCATTTCACCATTAGAAGTTTCC
CCATAGGATAATCCTTTTTTTGCGTTATCAATAATATTAACATACTTTCTTAGATCACTAATATTTTTAG
ATTCCCTAACACCTTGATAATTAATATAGTTTAATAGCTTAAGAAAGTCTTTACTTTTATAAATTCTTTT
AATATATGCTAATATCGTATCAATATATGTTTCATCATCATCCAGTCTTTCTATTGCAGTCTTTGGAAAA
TTCTCGATAAAGTTATGAAGATCTATTTTATTTTCAGAATTACCCTTATTATATGCATATGAGACAAAA
TTAAGAAGTTTAGTTGCATTATCATATGAGATTCGAATTAATAATGAATTTAATTTACTTCCATAATTA
CTATTTTTTTCTTTAAGATTTGATATAGTAAAGTTACTAGTATACTTATCCTTAAACATTTTTGGATTAA
TACCTAAATGTGACTCAGATATAAGATCTGTAATTTGGTAAACATCCTTTAATTGTTTAACAGGTTCTA
CTAGATTGATATTACTTCTTAAATCATTATTTAATTTATTTGTTATTTCTAAATCCATATTAAATTCATA
CTTATTAATGCGATCACTGAGAATACTATCTTCGCATGATAACATTAGCTTCATAATATTGATTGCTTTT
TTCTGACTGTTATATAATGCGGATAGATATATTAATGCACTAGTAAGTCTTTCACTATTGATTAATAAA
AATTCTGGAGGAATAACTCTAAATCTTCCAATGTCATGTAAAGAAGTAATATTATTTATTACCTGTAAT
AGATCAGAATTATCCATTGTATAGTTAAATTTAGAACAATAGTCTAGAAAATTAGAGAATATTTCATTT
AATTCGTTTAGATAATTTTTCATCATCTATATTATTGTAGTTGTCATATAAATACATATTATGATTCACT
TCCTTATTTATTAATCAACTTTAGGTTCATTAATTAATTTTAATTTAATTAACGTATTTGATATTCATTT
ACGAGATTTTCCATTTTATTAGTATTATCGATATAACGATAATAACTAATTCTACCTTTAAGTTCATTAA
ATGTCATTGAAATATTATTAATATTATTTTTATTCTTAGATAATTTAAAGAAAATAGTCTTTAGTAGTCT
ATACATTTTCCTATCTAATGTACATTGATCATTGTGATTAATTCGAATCCCTGTAATTCTTCTTTTGTTA
TTCGACATTTTAATAGTTTTTTCATCTTTAATAGATAAATTACTATAATTATATACTTCAAATGCCTTAT
TAAGAATGAACTTCAAATATTTTCTATTAAAGAATTCACTTTTCTCGTTTGATGAAAAAGTAATATCAT
CTGCATAAATAGAGAATGTAATACCACTATCAATTAATACATTTTTAAGATATTTTGCCACATTACTCA
TTAACAAGTTTGATAATGATCCAGAAGCAGGATTCCCCTGATATAATCCACCAGTCTCTGGATTAATA
AAGATTTCTTTGAATAACGTATCCATTACTGAATCTTTATTATTCTTCTTCTTAAAATTTTCTTTACCTA
ACACTAATAATTTAAAGTACTTACTAATATCTTCATATCTACAATTATCAAAGAATGAAGCAATATCCA
TTTTAATAATATATTTATTATTTTTATGAACTAATGCGTTATCTAGTATACCTTTTTTCTTTTGATAAGCA
AATAAATGTTTTTCAACACCTTTATTAGATAATTGAGTTTCTAACATTCCATTAAAGATATTATTAAATT
TTCTACTAATATCTTTAATATCATTATGTGGAGCATAGATATCTCTAATTTTTGTACCTTGATTAATCTT
GAAATGTTGATATAATTTTTCATTATTATTCTGAATTAATATTCTGGTTAATAGTAACTCTAGTAATAAT
```

```
GGTTTATTATTTGGTTGATCTGGCGATATACTTATATCTAATAAATATTTAATCATTTTAATCATTTCTT
TATCATCTGTGATTTTATAAATATTATATTTATTGTATATATCATTTGTATTTGTAATAATATAGAGATA
ACCATCATTCATTTCAATATATCTATGAGATATATTGAGATTTCTATAGGATAATTTTATACTGATATTA
TTAATAAACTCTGTAATTAAAGTTTTATCATAAGTAACAACTGGTAAATCGGGATATCCTTCATTAATA
CAAATTTCATCATTTGAGAGCAGATCATAAGTCTTAATAATTTTTCTATATTTTCTAGATGAATGTCAT
TAAATTCCTCGTTATTTTCAAATTTATTATTTTCTTCTAGATATGATATATCTTTTATTGATTGAATCAAT
TTATTACGGATATTATATTTAACTAATTTAGCTAATACCTTTTTATCAGAAATAATATTCTTTTTCATTC
GAATATCTATTTCTGATACAATCTCTCCATTTATATCGATTAATACATTATCGATTAATATTAGTGATAG
CAAATACTGTCACACCTTTCCTTTAATTATTAAATTATTACTACATAAATTTACTATTTAATATTCATTA
TATGATCCCACCTATTTATTTTATTTTACATTTTAATAATATATAAATAAAATTTAAATAAATATTCCCG
ATATCTCTATAATAGGAGATATCGGGAATATATTTTATTTAGTTACAGTTACGTTAATTTTTCTTTTCAT
GGAAGTAAAAGATTCAGGAACAACGGTAATAATTGTTTCACCTTCACTTACGCCAATAAGTTTAGATG
GATTATTCTCATCCACTTTAACGAGTTCTTCACCTTTTTCTAGAATTATCAGAACCTTATCACTAACGAG
ATTATCAGGAGTCATAGTTCCGATAATATCTTTACTTTCGCCTTCTTTTATAGTAAGATCTTCATCTACG
CTAAAACTTTCTGGTTTGGTAATTCTATCGTTAATTACAGATATTACGTCTATAGTATCAATAGGTGTA
TACCACGAAGAAACTTGTCCTGCAATACCTCTTGATTCATCTACTACTTCATCATAAATGATACAACCG
CTTACATCATCATACGTAAGTCGATGTCCAAAAGCTCTTGATGGAAAAATTTGAGATTGGGATGTTGTT
ACAATTGTGGAGATTAATAGTGGATCAGATAAATCATTATGACGATCGATAAATCCTTTTACAGTTTCA
ATAGCTATCATTTTTATTATTCATTCCTCTCTATTTTAACGAATATTTTTTCTGCGATTAAATTCAGCTTC
CTCTTTCTTTTCATTAAGGATTGTTAGATGAGTATCTATTCTATCTTGCTTTGCTTCCTTATCACTTTTAA
AAGTATTATTGTTAATAATACTTTCACTAAATACGTTTGGATGAGATATATTGCTTTTTTCATTAAATCC
ATCATTGAAGAAAATACTTTCATCAATATTTTTATTATCCATATTTATAAACATCCTTTCCTACATGATT
ATAAACCTTCAAAGAACTTCCACATATTCTCATCAACTTCTCCAGTAATAACCATATTAGATACCATTT
GTATTTTTCTTACATTATTATAAGTATCCTTATCATATATTCCTGAAACACTAGTTGTTGTAATTGCAAA
TTTACGTTTATTATCATTTATCTTTGTTTGAATAAATAATACGTCTGGTCCTTCCATAAGAGGATTACTA
TATTTAAGAACTCTTGTAAATTCAACAATAAGCGTATCAATAATATTTTTCCATGTTATGGGTCCAACA
ATTCCATCTTCAGTAAGATTATTTGAATGTTGAAATGATTTAACAATAGTTTCAGTAGAACTATCATAA
GAACCAGTAACCTCAATATCATATCTTAGTTTTGAAAGTTTATTTTGAAGCGTAATAATATCGTCACCT
ATCATCATTGGTGATTTATAACTAAGCATTCGATGATAGTTTGAATAGTCTTTAATATCATTTAATGCA
ATTATCAATTCATTAATTTTATCAAAGTCTTCTTTCTTCATTCTACCATCAACTTCTAGATTAAATGTTTT
TTGGAATATTCTTACCGAGTTATATGTGTATAAATCATAGATACCATTACGAATAGTGATTGGGATATT
AATCATAGATAAATATATTTGTAATAATTTAACGTCATTACCGATAACTGGTTTTTCTGGATCATAGTA
GAATTCCCTTTTACCAAAACTATAAGAAACAGTTCCTGCAGGATTGTCTACATACATCGGTAGAATAA
TAGAAAGAATTTGGGAACGAAGAACATTCATATCAACTAATGATCCTAGATTACTATATTTTGCATAA
TATTCATTTAATGAATGAATGTTTCTAATATTTCGATATCGACCACTAATATTAGCACATAGATTCTCT
AGAGATACATATTGGCTTTGAGTTAGGTCTTTAATCTCCGTATTTCCTTCAAGACATATAAAGATTTTA
CTAGAAGATACTGGATCAGTATTATCAATGAGTTCAATATCTTTTCCAGCAATATTTTCATTAAGATAC
ATTTTCCGCATTAGTAAGTCAATATTACAAGGTAATGCTCTTTCGGGTCTACCTGAAATAATATCCCCT
TTTTTAGTAATATAATAATGGAATGCAAACATCTTTAATCCTAACCCTTTATGAATTGATTCTAATGTA
TCATAATCCATACTAATATTATGACAATCTAAAATAACTATATTTGATGGATTATTCTTGTATATAAGA
TCTTTTACCGGGTCAGGAGTTGTATCTACATAGTTCTCATCAGTATTAGCATCCAGTAAAGATAACATG
TATGATATATGACTTCCCCACATATTATTCCATTGTTTTCCATCTACTGAAAAAGTTCCCGCTAAATCAT
TTTGATCATAAGAACCGCTTCTTGTAAATTTATTTAAGTATCTTAAACAACGGTTTAATAATGAATACG
TAGTAGATATTTCAATAGTGTCATTTATGATATTTAAATAACGGATACACGACTCTGCAAGAATGCTTG
CATAATAGGTATTATCTCTAGCACTGTTTGGTTCATATACACTATTAAATTTTGTGATTATCCCTTTATT
TTCAGAGTTCCATATAGTATTAATAGATTTTATAAATTTCATAATGATATTATTTACATTATTATTTACG
TAACCTTTTTCAAGAAGTCTAATTAATGAATTAATGATATTATATTTGAAACTCTCCCCAATCTCCTCTTT
GATCTAAACCTTCCCACCTAAAACTATTAGATGAAATATCAAAGATAGGTTTAAAGAAACCTTCTACA
CCTTTTTCATTATAATATTCTTTTTGAGATCGATCTAAAATATCAATAAGTTTAGTTAATTCATTAATCA
TTCCAAGGTCATATAATACTTCTGGTTTTTGATAACCTAGATATATGTCATCGTTCCAACTATCAAGCTT
ATTATTAATAGTTGTTATTGAGTTAGGTAGCATTATATTTTTCATATTATTAGAATAATTATCAACGCTT
TCGATATAATCGATATTTATAATACTAGGAATATCTTTTTCCTTTTCAATATAAAACTTATTAAATGTAC
GATCTAATGAATAATTTAATAATGATCCGATATATTGAAGCTCAATGAAAGAAGAAGTAACCTTACTT
TTAAATATTGCTTTGGTTAATGGAAATTTAACAGATTTTCCATCAGTATTAAAATTAACTTTAATACTA
TTAAATAAATCAACTGATTTAGGAAGATTTAATTTCCATTCTAACATTATTACTATCATAGATATATAAA
TCAATTCCATCACTAGCACGATAGCGAATTGTAGGGTTTGTTTTTGTATTTCGACTAAAAGGAATAACC
ATGTTTGACCAACCATCATAAGAACCATTATCATTACTTTCTTCATTAATCGTAAAGGTAGCTTTAATA
CTATTCCGAGTTTCATCATCAGTAGATTTCACTTCAATAATTTCAGAAATACTATTCGGAGAACTCTCT
GCAATATATAATGATTCTTCAGGAAGATTAAAATTATCCCAGATTACTTCACGGTAATCTTTTAACATT
TCAGGAGTCAATCAATATTTATTAAATTCATTATCTTTTACATTCGTCTTATAGAATCCAATATTATGAT
CTTTATCTTCAATAATAAATTTTAATACTTTATCATTATCGGTTTTAATTCTAGATTCTATATATGAAAT
ATCTTTAAGCGTAAATAATTTATTTACGCCAAAATGAATATCTTGATTAATTGAGATTGAATTTAGTAT
AACATTTCCATTAGTATCATCACGATAAATTAATACAGAATCTGAACTATCTTTATTAATAAAAGAGCC
ACTATCAGATAATGGATCCAAATTATTTATTTCAGAAGTGATCCATCTAGGTTTAATTGGCATATCTAA
TATAAATTTAATAGTATCTTTTGTAATATCCCTTGCCCTCATCCATTTACTATTCGGTAAAATATCATAA
AGATTACTATAACATTCATAAGAAAGCAATAAACTTTCAATACTGCATATATTTTTATTAGGATCCAGA
GTATGCCAATAATTTGTAGGATCATATTTCTGATTAGATTTAATAAAGTTATCATTATCTAATTGAGTA
TATACTAGTAATAGCGTGCTGTTAACATCTTTATCTTCTAATACAATCCTTACAGTATTATCTTTACGGA
TATAATACTCTTCAATATCATAGCTTATACCTATAATATTAGAAGCCGGATTATTTTCATCACTTAATTT
AGAACCAAAATCTCTAACACTAAATAATTTTTTAAAATTGCTATCCGTACTAAAAATTGCAATACCATT
AACAAATTCTGCCGATTCATTCAATATTAATTTTTCAGAATTAAAGGGTTCCGATGCATTATATGTAAA
ATGAGGAACCCATAAATTATCTTGAGAAAAACTAGTTGGAACATCATTTGGATATAAGGTATCAATGG
TTGCATTCATCGTAGATTCTATTAATTCTAAGGATATACTTACGCCAGAATTATACTGATATATAAGTG
AATTAATATATTGAAACTGCGAAGTAGATGTTCCTGAATTAATATTAATATAATCAAATAAGTAATCTT
CTTTTATATAATTTAATCTAGACATTGAATTAAGATTTATAGATAATGGACTAGTGTTTTTTGTATTTGC
ACTTACAAATTTATTATATTCAGATATCCATTTTCTAATATCTTTTAAATGAACATCTAATTTCTTTTCA
GAAAGATATTTTGTCAAATTTATCACCGCCATTCATATTATAACATTTTGTTTAATATCAATTTAACTTT
TTACCCAACCTTTAGTATTATTATATTTATATTTAACTGTAGTAATTTTAGTTTCATTAATAACTTTCTTA
AGACCTAATCTTAATACAAGTGAATCCCTATTAATAATATTCCGTGCAGAAACATATCTAACTTGTTTT
```

-continued

```
GTAATGAATGGAATTGTTCGTTGAACTGTAGAGAATGGACTACTTGAGTTGTCTCTACTCTTTGGTAAT
CTTTGAAGATTATCAGAGTTAAGCGTAGATATTCGATTAAGACCAGTAGGATCGATCTTCCATTTTTTA
CTTTTACCACCAAGATTAACTTTTTGTCGCCACGTTGCAGATCCTCCACCATACTTAACGCTCGGGTTA
GGTGAAAATCCATTAGACGATGTAGTAAATGTAGTTTTAGACGCAAATCCTGAAGGACTTTCATATAA
TGGCATTAGTAAATTAGATGGACTTCTAATGTATCCAATAGTATTTGCAGGACTGCTTGTTGTTCCAGT
TAATGGCAATCCTTCAAACATATCCCATGATAAATATCTATTCGATATTCTAGTTCCAGTAGTTTTATTT
ACTTTATTATAGAATCCTCGATAAAATACACCAGTACCTTCAGTAACACTATATTTTTCAAGAGTTAGA
GGATCAATTGCCGAACCTTGATAGAACCAATCAGAAAATCTAGATCTTAATCCAACACAAGCATCTAC
ATATTGGCTTTCTGAAGTATAATTCGAACTAGAGTAGTTAAATAATCTTCGATCCCAACGACAATCATA
TGCAGTTTTTTCATATGATACACTTTTTTGTAATTGCATTGTTCCTGAAAAACTTCCCATTTTAATTAAT
TTCTGATTTACTTCATCCATAAGTGTTTTAATATTATTCCATATCTGTAATAATTCAGTATTCTTACTATT
CGCATCATTACTAAATGCTTCAGTCAATGAATTATTACTAAGGTTATTGAATATATCAATCTGACTTTG
TATTAAGTCATTATATTGTCCTAAGTCTAGTCCGTCTAATTGTAATGATATATCACCTAATTGGTTTACA
TTATTCTTACTTATTTTACCTAGATATACTGTTTTGAGTCGGGCAGACTCCATATCAGAAAAAATATCT
AAACTTGTATCAAATATTTCTTCTTGTTTATTATATATTTCATTATATATATTATATAAATTATTAATCTT
TCCAGGTATTACATTCTTTCTTAATTTTATACCTTCCATATCATTCTCTAGGAAATCAATAATATTTTCT
CTAAGAACTTTAGTAATTGGTATTGGTAAGTTAATACCTTCCTCTGTAACGTATATGTCATGTTCTACT
AGATCAACTAATAACTCTCCAGTCTTCAGAGTATTAAAATATTTTTGAAGATAGTCTTGATACGACATT
GGTATATAAATATATCTTGACATTAAAATTACACCACCATTATTATATAATATGTTTAAATGTTATTGA
TTTAACCTTTTTATTACTTATCTTCCCTTTAGTCTTATTTACTAATGAAGTTACCCATGAATCATATGTTG
ATTGAAATGCACTAGAATCTACATTTTTCTCAACAGTAGTATATCTTGATCTCATATTAGTTAAATCAG
TTCCAGTTTTAGTCTTATAACCTTTTATAAAGTTGTATAGATATGTTAATTCAGATAATCTTCTTTGTAT
TGAAAATATTCCAGGAAGCTTTTCTACTACTTTTGGAATAATTGTTGCGATAATATCTACAAAACTCCA
TATATCTACGGTATTTTGTCTGATTTGATTTTCCAATGTATTTAATATTGCAATGATCTGAGCTAATAAT
TCTTTAAGACCGTTCATTCGATTATATAAATCATTTGTTTCAGATAATTTTGTCTGATAGAGTGCTTCCA
AATTAGATATCTCTGTTTCTAATAGAGTAATAATGCTCTTAAGAGTAGAGACTAGGTACTTCTGTGAAA
ATAACTCACCTTCAATATCCTTTGTAGCTGATTGATCATTAACAATTAAATGACCAGTACGAGTATTTA
CTAAAAGTTCTGAATCTTTCGATTCCAGTTTAGTTTTTTCAGTTAATGGCTGAACGTACAATCTATATGT
CATAACTTATTATCACTTCCATATCATTTTTAAATTTAAGTTAGCAGTTGATATATTAATTATACCAACT
GCTAACTATATTAGAAACTTGTAATAATATTTACAAGCTTAGTATAGAATCCTTCATGTTTATCTTTGA
ATGCATTATATTTAGTTGTTAATATCTTTTTATTAGCTTCGATTTCAACGCTTCGTAGATTGTAATAGTT
TCTACCAAGATTATCAATTACTGTAGTATATAGATCGGCATAATCTAATAAATCATTTCTTAATTTAGT
AATATTAGTACTTAGATTCATTAGCTTATTATAGTTTGTTAAGAAAGACCCATCTACATTATTTGTAAT
ACTTGTTATCTTATTACGAATATCAGTAATATCGGAAGTAGTTTTATCAACTTCAGCTTTTAATGCATC
AACCTGAGTTTTTAAATTATTTATTCCACCAACAACTGCATCTACAAAAGGTTTTAATAGATCATTATT
ACTGTCAATTTCAGATAAATTATCTCTTAACCAAGATAATTGATTTTTTATATAGATTTGTTACTTTAAAT
ATATCATATATAACTGTTGAGTTTAATGATAATAAGTTATTTAATTCTTTTGTAATTTCAATAATTTCAT
AACTACCAGTATCAGAATTTTTCGTATTAGATACAACGGATATATTTCCAGTATGTTCATCAATAATCA
GTTCTCCAGGAAATCTAAATAGATCATTTTCTCGACTAAACGGAATTAATACATTTCGATCAAGATCTA
CTGGAAGATTATAATTCTCAGTAACATTATTATCATGATCAATAATTCCGCTAGAGTAATTATTTACAT
CAATATAATAATAAGAACTATTATACATATTTATTTGACTGTTTTCTAGCGGTAATGATTAGTCGATATA
TACCATTTACACTACTGATATTCTTTAATAATGGGTCACCTATATTGATGATTGAATTATTAAGTGAAG
CAGTATATACAACTCCCGGTTCTTTATTAATAATATCCAATACAAAAGTTGAATCAATATTAATAATTT
TTCCATGACTAATATTCTTAGCAATTGGTTTTGAAGGAGGTATGGTATCAATAGTGATAGTTTTAGATG
AAGATGAACTTTTACCATTTAACTTACTAGTAGCTTTTACATTTAATGTAAATTTTCTAATAGATTTAAC
GTAATTATAGTTCTTAATAGGATCACCTAGAGTATACTGGTAAACCATTTATTGTAATTTCATAGGTAC
ACATTGGGATTCTTACAATATTAGGAATGATCAAACTATTTGTAAGGTTTCCTGAATTATCTGGAATAT
TAATTACTGGTAAATCTGGTACTGTAACATTTAACATGTCTGACGTAATTTCTAAATTATTTTCAAGAA
TCATATCATTATCCATTATTTTTCTAGCAGTGATGATGCAGGGTTCAGTAATTATAAATGGACCAGTAT
ACTCTTTCCAAGAATTGTTAATAGAAGTCTTATACAGTTTACTTTTAATGTGTTCTCTTTCAGACTCAAT
AAATACATATTCAATAGAAATATTATATGACTCGGAATAATATTTTTTATCATTATAATCTATTCTTGG
TGGAGTATAAATATAATTCTTAACAATATTAAATTTAAATGTAGTATAACTTAACGTATAATTATGTCT
ATCTGTAAATACTGCTAAGAATTCATGAGTCCCTCCCGAAGTGAATGTTGAACCAGAAGTATAATTGT
TTCCATCAATATAACAATTAAGCGTATAATTTGAATTATTATTCATTACAGTGATTGTTATATCATCAG
CACACTGAGATATATCTGCAGAACTCACATCAAAAGGAGTTAATGGTTTTAGATGATGATATTGATATT
GACGGATTAACTGGAACTGTAGTTTGATCCATTCCAGTAGTATTAATAGTCTGAGTTGCCATTAATTTA
TGTGAAGAATCAGAAACATTAGTGATATTACTTCCAGAAACTCAGCTAATCGTAACATCATCATGTAA
ATGGTTTCTAGTTGATGTAGCATATCTGTATAATTTAATAGTAGAATCAAAAAATATCGGCATATTATA
GTTAGGCATAATAAATTTTTTCTTACCATTATAATCCATAACATAACATAATTATTTTTATCAATTTTA
CTATCAGGCTTAAGAACAATATCATTAAATAATGGATTAGTATCACTAGATACTGAATCATGATATAT
AACAGTACTAATAATATCTCCAACTTGTTCTGGTATAATAACTACGTTTACGGAAATCTGTACTACATC
TGAATCTACACCATTGCTAACATTAATATCTAGATTATAATCTCCTTCATCTTTAAATGATAATTTTAGT
TTTGGATCATTCGTATTAGTGTCTAATGGTGTAGCGGTATATGTTTTGAAGGATCATCAGTATCTGTA
ACACTATAGGTATACGATGAATCTTTTTCAATATGAATTATAATATCAATTGATCCATCCCCATTAGTA
ATACTATCTACTATAGGTAAGATTAATGTTGCATTATCATCAGCAATAACTGAGAAAATTAAATCTTCA
GGGGGATTAATCGTATTTATAAAATTAACAATCATTAATTCGTCTGAATTGAATAGTTTATTTATATCG
ATTTTTCGATAAATATTAATCTCAGTATCAGTCTCATATAGCCCTAGATATGTGAGCATTGTATCTGAA
ACGTAATCGTTAACCTCTATAACGTCACCATCATCATTAGTTACCGTTATATTAGTAGATTCCTGTAAG
TCATTTACTAATTCATTCACATATACTTTAAACGTATACTGATCGGTACCTTTAGTTAGTTTAATATATA
CGTCATTATCTTCTGCAATTGTTATTGAAGTTGGTAATGATATACTAAACATGTTATAATTATTTGAGTC
TATTGTAATGTCATTATCAGTACCATTAATATTTAGTTTACCATTATAAATTCCAGTACCTTCAACGTGA
TATACTCCAGTAATATTAGAATCGCCAATATTAAATGTATCAATAGATAATTGTATATTTTCACTTCTA
ACTACTAGTACTTTCTGATTATCTGCAACTAATATACCCTTTGAGTTGTATATCTTAAATGATATCTCAT
CCGTATCTGAAGATATTCCTGTACTAGATGTTATTTTCATCATTTTATCATTTTTCGTATTACTAAATTT
AGTAACAGTTGATGTAGTTTCAACACCATTAATATACATAATAATATTATCTAATTCACCCTTATACTT
AGCAATAATCTCAGTTGGATTATTTCCATTAAAGAAGAAAGGATAAAAGTCTACTGCAGTATAATCAA
TATTTATTGCAACCTTATCATTAAATGTATCTACACTGTCTGGATCATCTGAGTCTTTTGGTATAGATGG
TTCATATGTGTCACTATATTTTACAATAGGATCTATAAAGTTGGTATATAATCCTGCAATTGAATCATT
CTTGACAATAGGTATATTTTCATTTCTGATTGATGTGTATGTTGATGGAATATCTACTCTATAAACATC
```

```
AATATTAGTACCATACGCAGAAGTATGTCTAATCGAGTCTGAATTGTAAAGATATTTATTAATATTCGA
TTTATCGATATATCCACTGAAAACATATATATCTGAAAATTCATCCATATTGAGAGTATATTCCGTTAC
CGTATCACTAATAAAATCTTCATCTTCTGATATTGATTGAAATGATTCAATTAAGCTTTCTTGAAGATC
ATTAATAAAATCTTCGTTAGATAGATCATCGTCATCGCCAATAGTTGAAGCACTTAACATAGTGATATT
ATTCTTACCAATAGAACCTTTTACAACTGAACCATTACCTCCTCCAATAATCTGCGATATATTATTATTT
ACATTAAATGATAAATTACTTACATCTTTTGGTAATCTAATTGCTTTATATAGGAAATTATCATTTATTC
CTTGAGTTAGTATAAATAGTTGATATAATATACTAGAATCATCAGAATAATCAGAAGTTCCTCCAAAA
TCATTTTCAATAATAACCCTAAATTTCAGTTGAGTTAATCCATTATATGCATTTGTACTATTATTAAAAT
CTTCGTCTCCAGTAATAAATCTTACTCTACTACCGTTACCGCCTGTGGGTGCTGTACTTTGTAATGTAA
AGACTTTATTGGTAGTACTCCAATTACTCCATTGATCCGATCTTTCATCTTTAACCGAATATTCTAGATA
TACTTTGTTAGCCCCAAATGATGGAATTGAACTTATAAAATCTTTATAATACTTTCCATAATTACTAAA
GTATGTTATATCTGCAGGTCTAGAATATAATGGATTAATACCGTTATCAATAAAGAAAGGATTTACATT
ATCTATCTTAATTGGATTTGGTTTAATCCCTTTCATATCATAATTCATTTTAAAATAAAATTTACGTGGA
TCAACTAATGATTTATTAGTTAAATCGTTAAACGCTTCTATTGTTAATTCAAATACTTTATTATGATAAT
TATTATATACTGCGTTTGGATTATCGCTTGCCAATGACAAAGTATATCCTGACGTATTCTCTTTATAAA
ACTTCTTAAGATCTGGATTATTAAGTGCTTTTATATTATATCGATAAATTACTGGTCGACCAGTTGAAT
CATTTACCCCTGAAAAACTAAAGGTATAATTAAGCTTATTTGCTTCACTAGTGTTTGCAGGAATCACTG
TAGGATTATTTGGATCATTACTCATAAATGTTAAAAATGATCGATCTTCATTTAACATACTAGCAGTAG
TAACTATCCCCAGTGCGCTCTTACTAATATTTATTACGTTTGGCATATTAGAAAGATTATTAAACACTT
CAGTATTATCCGGATCAATATTATCACTATATGATAGTACTGTATTAATTTTAGTTTCATCTGAAAAAT
AAAATGGATCAATATCAAGATAATATAAATCTCCAACTTTAGTATCATAGTTATCTTTAGATAATCTAA
ATTCGTGTAAACTACTCTGCGTTGTTACTTGGAAAAATAATATCAACAAAAGCAGAATCTTCCGTACCAT
TAATATTTTTATTTTCTAATTTTCCAAAAATAGAGAAACCGTTCTGATCTCCAACTATAGACTCATTTCC
TTCCGTACCGGACTCAACTTCTATATTTGTGTATGTTAATGCTTCTCCATATGGATTCTCTACAAAGAAT
GTTCTAGCAATTCCATAATCTGCAGGAGTCCAACTTTGTATGAATTGTATTAATTGTTCTCTAGTATGT
GCTATTACTGTCAAGAAATTTCACCACCTATATTTATAACTTCTTATAATTAATAGTTTAAAAATCCAT
ACTAAGAAATATTTAATTCCTTAGTATGGACGATATTTTTATATTATCGGATCAATAATATCCGCTTCA
GGATCATAGATTTTTTGAGGATTCATATCCAAAATAATATTCTGACTAATATATTTGTTATTTATTTCTT
CAGAATCTAATGAAATATCCCAACTTAATAGATCATTATTATTACAATTAATAATAGTTTTTCCACGTT
GACGCATATAGTCCATTAGAATTAATTTCCGGATACTACCTCTAGAATTATCATTTGTTATTCCAGTCA
ATATATCAAAATTACTAGTTTGTCTTACGTTATAGTATGAATGATAGTAATTATCGTTTAAATTCATTTT
ATCATACTTATACCAATCTAATATTAATTTAAGTTGAGTATGATCATCGTAGCTAAATCTAATCATTAC
ATTTATTAATGGATCAGCATAATCAATAATTTGAATACTTTTACCATTAAGTATTTTTACTTTACTAGAA
TCTATTCTTAAATTATTAACGTAAACTGTAAATGTGCCTTTAATAAATATTACTGAATCGTCATCTAAA
CTGAATACATCTGTTGTTCCTTCAGCCGGCTTACTAAAAGTTCTTATATAGTTGGAGTTTTCATTAAGA
AGATTTATTTCGATAGTAGATGTTTTAGGTACAATGCTTTTAAAAACAATTAATGACGGAATAGATTCA
AAGTCAGGATCAATAATGGTATAATCAATTCCAGGATATAATGTTAATCCATCGATATTAATATCGAT
ATCTTCAGGATTACTATTAATGTTTGTAAAAATATTTGAATCATCATCTAACGTAGCAAATGGTAAACA
ATCAATATCATATTCATTTAAGTCTAATTGATTGTAGTATAACGAGCCACTATTTGTACCACTAGTCAA
AAGATGTATTTCGGTACCTTCATCCATATAAGATGAACCATATACGATAAGTCTTACTGTATTATATTC
AGGTTCAATCTTAATATAATAATTGTATGGGTTAATTCTTCTAAAGAAATTCCAAGTTTTCTTCTTAATA
AAGACTCTTAATTGTGAAGGAGTAATTCCCGTTGGTAATGCAACATCCGTTAATAGTATACCAGTAGTT
CCTAACATATTAGTTTGATCTTCAAACGTATTATCAATTATATGAGTCTTAATTGTTTTCTCGGATTCAA
CAATCTTACGTTTATTACCAGAGACAATTACTTCATATTTATCCTGAAGACTAGAATTCCCATCTAAAA
CATCATTAGCATCATTCACATCAATATATTCTTTAATAAATCTTGAAGGCATGTATGCATATATTTTTCC
ATCTAAACTATCTTGTTGCTTAATCGATTTACGGAAAATATGTTTACCATTAATAAATATATCAGATAT
TAATGAATTTTGTTTCTTTTCATATGAACCATATTCCGAAGTAAAATCAATATAACCATACTGAGATTC
ATCATTAATAAAATTATTTATAAACGGATCTTTTGTAACTTTTATTTTAGAGTTATCCAACTTAGTTTCA
AATGAATTATGTCCCATTGTCTCTATAAATAATGTTTTATTACCTTGTTCTAATTCATTAACTAATGATT
TTTCAATCATCCGAATATCATTGTCTGTATTCTTATATAAGATATCAGTAACATTTCTTGGATCAATATC
CATTTGGAATGTTTTAGTCTCTATAAGTTGTTCTGAATTAGTTTAAATATACTAAAGGTTATATCTTTA
TTGGGGGTGAAATTAAGTTCATCAATCTGTAATCGATAGTACTTTTCTTCTAATTCTGGAAGATCGTCT
GGTTTATAATATACACGTTGATAATTATCATTACCAATGATATTAATTAAGTAGCTTGAAACATCATCA
TTACTCTCAGAAGAAGAGAATATCATATTTTTAATCTTTACAGTAAGCTTATAATAATCTTCGATTCTTT
TAAAATTATTAATGATGATAGTCTTTCCATCAATAGTTATTGTCATTATATATTCGGATGATAATAAAT
ATCTTAGTCTAAAATAGATTGATCCGTTCAGATAGTATGCATTCTTATATAGAATTTTATATATAATGT
CTTCTGGAGTGGCTTGAATATTTTTATTAGAATATCTAACATCTAAATCTTCATTAAGAACAGTATATC
TAATCATATCATTTCCTAAAGGTAGCATTAATTCTGATAATACTGTTTCTTTATCATCAAAAGGAATAT
ACATATTGGCACTTTGGTTTGCTTCAGGAAATATCCTACTAATAGAGTTCGATCTATAGTTTAGAGAAA
CATTATAGTTACTTTTATCTACAATATCTAAACTATGCATTAAATTAACATGAACATTTAAGAAAAATT
TACTATTTGTACTATTATTAAAACTGCGTTTTTCTATCCATGTATAATCAATACTTAAATCAGGAAGAT
ATTCTAATTTATAGAATGTGGTATCTCTACTAGAATTATTAACAATAACAAATAGATTGGTTGCTACAA
TATTTTCTGGATAGTTATCTAACTGAATATTTTCAATAATATTTCGCTTAGTATTAATTAATACTAATTG
ATTCATACTATCCATAAGAATAATATAATTTTTAACCAGTACTACTTTATCAATATTATTTCTAACGTTT
GCTAACCATGTTTTATTCGTCAAGTTATTATTAGCATACTTAAAACTATATATATTTCCACTATATGATG
ATACGTATAATGTAGATTTATCACTATCATATATCATAAAATTATTTGTCGATAATATTTTATCATTATA
ATCTGTCTGACTTAATGATACTTTTTCTACAATAGAGTTATCTACAGACTTAATAATATTAATATTAAA
ACTATCTTTTAATTCTAGTCCTATAAAATATTGTAAAGTCGATATTATTTCGATTCAGGAATGATTTCAAA
ACCAGAAATAAAATATGAAGCGGTATACAACACTTTTGTTGTATTCGTTATAGTATTTACTAGTATAAT
ATGTTGATACGTGGAGTAGTATATAAAATCATTAACAATCCTTAATTGATTTACTAATTCATACTCATA
TGGAGAAGTATTAGTTATTTTATTTATAGTTCCTGAGATATTTATACATTCCAGTAGTTGTATTTCTACTA
AAAGATACATAACTGATACCATTCTTATGAAACATATATATCTTATTATCGATAACTGTAAAATCGATT
ACTTCCTCATTAATATCAAATGAACCTACTTTTTTCTCCAGTACCAAAGTCTTTTATAAATATCAATTCGAT
TCTTAATAGAACCGGTAGGATATTTATATAATCTGAATAGTTCTTCTAAATATATACACATTGCAGGCA
TATATCCTGAATTAGCATATGATATAGAATGAAATAAGTCTAACCTATTACGTTTTTGATATTTATCTA
ATATATTCCCATTCAATGTTATAGTCAATACTTTCACCATCTTTCTTTTACAATTATAAGGAATCGAGA
ATAAAATATCCCGATTCCCAATTTATTTAAATAAGACTTGAAAAACTTGTAAATGTTTTTAGAGAGAAT
TTACCTAATGTATTTTCGATAATTGCTTCTCGATTAAGGTTAGCGCTTATAGATGATGACATTACCATA
TGCATAAATGCAGGAAGGTAATCAATAGCTAATACAGTAGAGTCTCCATACATTCTTACATAATTCTCT
```

-continued

```
AAATAAGAGCGTACTTGTAATTTCTCTAAACCTTTTATTTTCTTGAGGTTATCAAAAAGTGTAAAGATG
TCTTTATATAGTTCCTTCTCGCTTAGATTAAATCCTTCTTCCATTTCTTTAATTAAAGATAATGAAGAAC
CATTAAAGCAAGCTTTATAGGCAATATCGTCTATTGTATTATTATAATTCTTTTTAGCCATTGCTAATAG
ATAAAACTTTGATAGAATAAAGGATACAAAGTCTGATTTAAAATCATTTAGGTTTAATGAAAACATTT
TATCAAATATCTTTGAACCTAGTCTAGAATATGCAATAGATGAATTTTTCATTAATTCAGTATTACTTG
TAAATCGATTCCAATTTCCATTTAATTCATAAGTAATCATTGCTTGTTGCATTAGTCCGAATAATGTTTT
TGGTTGGATTTCTCCACCTGCATTAGTGTATCGTGAAACATCAACTAATACGTCACGTTGATTGTTATA
TCTTCTTTCAAATACAATCAAGTATGATGGAAATTTATTTGATTTATTTGATATAGGAATGATTTTTCCA
GAGTTATATAACCCAACAACTTTATTTTTAGTAGGATAATTAATTCGTCTATTAATAATATTTATATTTT
GATCTAATACATCTTTAGATAAAACATCTTTACTAGTGTTTATTTTATTAAGTTTTATTTTAAGATCATG
CTGAAAATTAGATGTATTGAAAATGGCGGAATCACTTAATTGTACCATTATTTCACTTTCCCTTCAATT
AATTTATATGATATTAATTTGTTCAATATATTAACATTTTTTACATTTATATATTATAAATTCGTATAAT
GGAAATATAATAAAATTTTCAGTTTATCGGTTAAAATATTATTATATTTATAAAATAAATGTGATAAGG
ATGGATTATATTATGAGTGATAAAAAAATGCTTAAAGTAGGATTTCTTAGCCCAAATGATGATAGGAT
TCGTTTTAAAGAAGTAGATTTTTCGAATAGTGAATCTTATGATAAAGAAATTGTGAGTGTTATTAGTCC
TACCGGAAATATTGATGCAGGAATCATGAATCTTAATGAAGATTTAGAAATTCATAACTTCTTAATTTT
ATTTGATAATGAAATGTCAACAAATAAAGGAGAATATAATTTTCACACATTCAATTAGTCCTCTTTTTGG
TGAAGTTGCTTTTGTAAAATTCGGTTATACTGGGGGATAATATGGAACCAGTAAGCATGTTAGATGATG
AAGCTGAGGTTCTCAGTGATATTATTTATCAAGAAAAAACTTCTGATCGAGCAATTGAATTTAAAGAA
AAAATTCTTGAAGAAGTAAGAATTTACGGTAAAGATGGATTTTTTACGTAAATATAATGAAAGTATTGA
AGAGGCGCAAAAAATGTATGAAGATAATTTTTTCAGAAGAAGAAGAAAAATAATTAAGAATGGATGGT
GGATTATAATTGTCTAATATAAACGTAGTTAGTATTGCAGATTTACATTTTGGCTAAGAAAGATGATAG
TCGACTAATGAATGAATTAACAACAATATTTATTCCACAGATTAAGAATATTCATGAATCTGATAAAA
TTGATTTGATTGTTATTGCTGGAGATCTATTTGACCGTATTCTTAAGTTTGATGAAGTTGGTGGAAAAT
TAGTATTGAATTTTATGCAAGAACTTATTGAATGGACAAATAAAAATAATATTTATTTTCGAATTATTC
AGGGAACTAAAACTCATGACTATAATCAATTAGCTGTGTTTAGAAAAGCAGAAGTTGATAATTATAAT
TTTAAAATTTATGAAACGGTATATAATGAAAAATTGACTATCAATGAAAAAGAATTTAATATTTTATAT
TTACCTGAAGAATATCCTGAAGATATGAATGATTATTATAAAGAATTCTTTGATGTTCAAGAAAATAC
GTATGATATGATTTTCGGTCATGGAATGATCGATTTTGTAGCTTTCACTGGTTATGAAGATGATACTGA
AAAAATTGTAAAGAAAGCACCAGTATTTGTTGCGGATGACTTAATTAAAATTACAAAAGGACCAATAT
GTTTTGGACATATTCACGACTATCATGAATATAAAAAACAAATATATTATTCAGGTTCATTCTCCAGAT
ATTCTCATGGCGATACTATGGATAAAGGATATTTATATATTAAGTTAAACAGTGAAGATACTTCTGAAT
ATGAAATTAGTTTCTATGTTAATGAATTAGCTCCAACATATGCCACTATTGATTTAGATAAAATCAAAT
ATGATAATATGGAAGATTTAGCATCATTAATTAATGATAGTCGTGAAGAAATTAACTTCATTCGAATT
AAATCAACAAATAATAATGATAGTTCTATTGTAAGAAAAGTTATTGAAAATAGTCCTAATATTAAAGT
TACTTTAAAGAATAAGAATAACGAAGAACAACAAGTTGATTCTAAATGGAACTTCATTCTTGATAGAG
AGCTTGATACTGACGACTCTATAAAGAAATTTATTAAAATTAAATATGATAAAGATATCGATATTAGT
AAGATTAAAGCAATTCTTAATCCAGAGATTGAAGATATTGATGATATTATTAAGAATATTTATGATAA
GAAAAAATAATTAATAATCTTTATTAAGAAGTGAATTATGAAAGGAATGTTTCATTGTGCCATTTATG
GATAATAGCGAACGTACAAGAGTCTTTAGATCTAGAATGGATGAATCTTCTCAACAAGAATTTCCATT
AAAGATTTCCGTATCATACTTATTTAGTTTAGCAAGATATGTGGTATATCCAAGTAAACTTATCACTAG
AACTAATTTACGGAATTTAGATACATTATTATCAGCAGTCGATATTGATAGATCTTATTTAGAAAATGA
AGTAATGGAAAAGAATGCATTTATATTCTTAAGAGAAATTAACCGTGTATTATTACATCAACAATCAA
CAATAGAAACATTGTTTGATTATATTGATGATGAATTAAAAGATAGAGAAATCTCTGAAGATGCTCTT
CAAGAATGTGTAAACAATATTGCAATGGTGTTTGATGATAATTTCATTCTTGATGATAGTGAAATATTA
AGCTTAACAAACTATGTAGAATCCAGATTAAAGATTATGGCACTATATCGTCAACGTGATAGAATGGA
AGGTATTTTAGAATTAATCAAAATGAATAAATCTCCAAACGAAATTAATACTGAATTTAAAGATTTTG
TTACGCAGAATGCATTACAATTAAGAAAGATTGAAACGAATAATCGAAGTTCAATGGACGATATTATG
TTTAGCAGAGATAATGATCGATCAGTAGATTCACTAGACTCTACTATTAGACAATTAAGAAGTCCTAG
TAATAAATTATTAACAGGATATAGTAAGTTTAATGAAATGATTAATGGTGGTTTAGAGGATGGTCGAC
TTTATTTACTCTTCGGCGTTCCTAAATCATTTAAGTCTGGTGTTATGTTAAATATTGGAATGTCAGTATG
TCATAATAACGCAGGATTTAAGACAAAAGATCCTAATAAAGAACCAACCGTTGTTTATTTATCTCAAG
AAAATACAATTATAGAAACAGTAGAACGATTATATGAATATATTACTGGTACTAGTATTAATGAATCA
CAAGCTACTACGCAAGATGTTTTAGAATTAATCATGCAATATACGTATGATTGTACTGGTATTTATTTA
AAAATTATGTATAGACCAAATAAAAGTATTGATACAAGTTATCTATAATAATATTTATGATGAGCTTAAT
GAAGAAGGTAAAGAATGCATCTTTTATGATTCAAGATTATACTCGAAGAATTAGACCTTCTGAAGGGCA
AAATCAAGATATTCGGATACAACTCGGTAATATATCTGATGAGTTCTGTACGTTTGCTAAGGAAAAAG
GTATCCCTGTAATGTCGGCGGGACAATTAAACCGTAATGCAAATGAAATTGTAGAGGATGCTCTTGTT
AAGAATCGTTCAGACTTTATTAATAAGTTAGGTCGCCATCATATTGCGACGGTCTGCAATGTTACTTGAA
AATGCTGATTATGGAATTATCATTGGTCGACAAGATTATCTTCCAGAGGGTGAAGACGAAATTAATCG
CAAAAGTTATATGTCATTTAAACTTATTGCTTCTCGTGGGAAAAATAAGGATAAAGATAGCAATATGT
TCTCTCAACCTTTTGAAAATGGATTTAAAATTGCAGAAGATATTAATCTAGCTGAACCATTAGCAAAAT
TAAGAATTAATGAACAACAGTCTCAACAAGATATGGAAAATAGTGCTGACGAAGTAATTACTTCAAG
AACTCCTAGATATAACAGTACTAGTAAATCTAGTAGTATAGTTCCGGGAATCAATACTGGTAAGAGAC
GAACAAATCTTTCATCAACAGCATTATTACAAGAAGATGATATTCCGTTCTAAATAATATTAATAACCT
AACATCCTTTTTTATAGGGATGTTAGGTTAATTTTTTTTTTTTTAGATAGATTCGGCTTTTTGACGTAATT
TACTAAAATCGATATTAAACATTTTAAGTGTATTCATACTTTCTAGTATAGTATAAGATATAATAGATT
CTACAATTGTCATTTCTGCAATATCTTCTTTTTTAGATTCTGATAGATCCATATTTTCCATTACGTATGA
TAAGCGTTCTTCACTAATTTTCATATATAATGATTTTTCATCTTTAACTTCTACATTATTTTCATTGCATT
TATCAACAAAGTTTTTGTATTTCTTCTCATAATCAATTACATTGATAACTTTATCTTCAATTACGTTTAC
TGCAGATTCAATTAATGATTTCTCCTCATCATGGATAGAAGATACAATATCTCCAACTTGGTCAAATGA
TAATTTCTCTTCATTTACATAATGACTGACTTTTGTCTTAACAAGACTTAATAAGTCACCAAAGGCACC
ATGCTCTTGAATATTGATTGATTTATTTTCTACAATAGTATTAAAAGCATTAATACATTCATTATAAAT
ATAATCAACATTCCCTTGTTTTTGAACTTCATCAATAGGAATAGCTCGGTATACAATACTTCCAAATAA
TGTTGGAGCTACTTCTTCAGCATGTTCATTAATTCGATTTTCCTTTTGAACCATCTTTTCACGTTCTTCA
GCTTCACGCTGAACCGTAATAGACGTTGTTCGTAGTAATTTACTCTTGTTTTCCATATCTAAATTTTCTT
GTAATGCTTTTTCTTCTTCTTTCTTTTTACGGAAATATTCAGTACGTGCATTATTTTCTTCTCTAAGATTT
CTTGAACTTTCACCAAAGATACTAAGTCTTGACATTAATTTTCACTCTCCTATAATTTTTGCTATATTAA
TTTGTTTGATAAGTTATATTAGCTACATGCTCATATTTTTTACCTAGATTGATAGTAGTGACTTTACCAT
```

```
TACTATCTGTCGTTTCTACAATATTATCAGAAAGTGTTTTCTTAATATTGATATATTCAGGAACATATTC
AATGATTTCTTGTTTTGAGAGATCATTAATATTTCTTGCATTGTTAAGGATTTTTTGATATTTATTAGAT
ATCTTTTCATCATAATTACCACTTAAACCGTTATATTCAATATAGCTAATGATCGCAAATTCTTCTTCTA
ACAATCTTAATAGATTAGATATAGGTACGATTCCATCAGTATTACAGGCTTCAATAAAGTCGGAAATA
AATTTCTTAATTGATAAGTCATCATTATCATTAACGGCTTCATATGTGTGAATAGTTAAATCAATTAGC
ATGTCAATGCGAGTAATAAGATCATACTTAACACTATCTCCATCCACTTCAGTATTTAAGTAATAATAT
TTAGATGGTTCCCAACTATTATAAAATTTCATATCAATTGTAGTATTATTTTCCAGTTTAGGAATAACA
TTGCTTAATATAGTGATATACGATTCAATTAATGTATATAAATAACTATATTCATATATAAAATATTGT
AAACTAATGAGCGGTATCATTTCAACTTTAAAATCCTTATTTGCGTCACTAACGTTTGAAGCACCTACT
CTAGTTACTGTACTTGTCATAATACTAGAAAGATTACGATATAACTTTACGGTAGAATTAGTAGTTACT
GATAATGCCAATACATAATTATCAATATTTCTATTAGCATCTGGAAACTCATCATCAAACAATTCAATT
TCATTATTATTCTTTGTACCAACAGTCTTATATGAATTATCTTTATAAAGAATTCCGATCTTAATATATA
GATCTTCATCAATAAATACATTATCTAGAACATCACCATTTTCATCATATAGCGAGTTTGATAATGATA
ATAATCCTTTATTAAATTTACGATTAGTTGATAATTTTGCAGTATAAGTAGACTCTGCTTGTTCTGGATT
TTCACGTTCAAATTCAAAGTAACCATACTTCTTATTAGAGTTTTTTGACATTAAGATACCTCGTACGCA
AATACGTTTATCTAAGTCGCCTATCGTTTCATTACTGTTTAGATCAAACTTAATAGTATAAGTATCGGA
ATCCAAAGTAGATTCAAAATCATGAATTTTTGTTATATTAAGTTTATTGATAATCATTGTTGTAGGAAT
TAAGTTATTAAGATAACTGTATGATGTATCGAATGTTTCATCAATATCCAGTTTATAATATTTAGCACT
TAATACAGGATCAATATCTATTTTAACTAAGAATGGATTAGTATATACAAGCGTATTTTTATCATTAAT
AGATTTTTTAATATCATCAGTATATCCATCGGGAAGATGTTTATATTTTTTATCAATATAATCATACTGA
ATTAATGAATGTTCCGGAATTACATATCCATTAATATCGTCACCTAACAGTTGATCTGTAAAATATTTC
TTAGAGAAAGTTACACTACTTGCAGTATTTGTAGGAATAACCTTTTTATCATTATCACGTAATAATAAA
AATGCATTATATAAACGCTGAAGAACATCATTTCGCTTTTTCATAAAGTTTATTGATGAGTCATTTAAG
CTTGATGCTCGATCAATATTTCGGAAATAGATATCTAAGTCAGTATCCATAATTAAATTATCTCTACCG
AGAGCAGTTTCAATAATTTTGTCTTTCATACCGCTAGTACTTAGTTTATCATTACCTCCTGAAGCAGAG
GTAATAGGAACTACTGTTGTGAGCATCTTTGAAAAGTTATTACTTGCTGAATTAGTAAAGTTAAATAAT
ACTTCTCCATCAAAAGTAAAGTTTCCTTCAGAACCTTTTGTAGTTAATATCTCAATGGTTATCTTACTAT
TATATCTAGGTCTAAAGTTATTAACTAATGAAGAAAAAGATATCTGTAATTTATTATCATCAACAAAC
GTATAATAACAGAATTTCTCATCAGGATTAGAAGGATTAAAGGTATTATTAAAGTATGCGTTTAATTTT
ACTTTTTCGCCCATATACGTATAATATATATTGAATCCTGCCAATTGATCGTCAAACTCTGCAGTATAG
AATAAATTATCACTAATATCTTCAGACAATATATCAAAGTCAAAAGAACTACTTTGAACTTGGTAAAT
ATCTAAATTTAGATACATATACTTTTCACCATCAAAGATAGATTGATAAACTTTTATCTCAGGAATACT
AAGTTCAATATATGGGAATGTACTTACTTCATCAATAAGATATCTAGCTGTAATCGTATAATCATTATT
CTGATTTTGTTTCATTAATATTTGTACGTCATAAGGTAACTGAATTTTAAATTTACCCACAGAAAATTC
AAATTCTCGATCTAATATGATCTGATAAGTTTTAAGAGCTTTAACTTTGATATATTGATCTTCGATAATT
TCTTCCCTTAATGGAGAATTTATTAAATCCTCTTTACGTATAACCATATTAACTAACATATGAGAAGGG
TTTGATAGTACTAATGGTACGTTATATAATTTTGCATAATTGAAGATACTATCTGGGAATGATGCACTA
TTTAAGAAGTGTTCATCATACAGTACATTACGATTATATACCGAGTTTTTAACCTCATGGGCTGCAATT
TCATTAAAGTATCCAAAGAAACCAGTTTTTAATAAGTTTAATGCAGCATTATTTCCTTCAGAACCAGTA
GCAATATTTGTATCATCAATATTAAAAATATGTGCTTGCCATTTTAAGCCAATGTTCATGTACGTCATAT
GACGTTTGATTTACTTTAACTACTGAACTTGTATCTTCTTTAGCATTCTTCATAAAAGAAGGTACATCTG
TTATATCGTTTGGATTATTTTTATTTGCCATTTATTCTCACGCCCAATCACTATTTAATTATCCAATACA
AATTTGAGTTTATATTTTTTCTTTTCATTATCACCATAGTTTTCAAGAACTACTGCAGGTCTATCTAATT
TTGTTAGGTCTAAGTCTGTAAAAAAGTCATTATATTTCTTAGCAGATCCTGGAGAAGTACTATATATAA
TACTTTCTGAATCTTTACTAGACGCTAATACTGGAGAGTCTAATGATACTGAATTAAAGTCCATTAATA
TTGCGGGATCCATATCTTCTTTATATGAATAAGCATAGTTAAAACTTAACTGAGCGATATCTTTTGAAG
CTCCAATATCACTATTCATTACGTCATATGGAACATTTGTTGGTGAACATCCAGTGTATTTAGTATAGT
ATAATATCGTTTCCATAACAAAATCTAATAAAAAGTAATATATGGAACTTGTATAATCAATATATCGA
TTCATAAATACTTGTGGATTAGGTTTCATTTGTCCTCTAGATACTGCTTCAATATAGTCAGTCCATAATT
TATGAATCTGTAGTATTGTACTATTTTTATCTTCTTCAAAAGTAACGCTAGTTTCATCAGCTACTACACT
ATTAATAAATGGTCCAGGAAGTAATTGCTTGTGACCATAAAACGTTTCATTAACTTCTTTAGTAATAGT
AGATATTCCTTTAAGTGACATGTTAATAAATCTATTAGTTAACGGTTTTATGAAAGAACTATTTGAACC
ATATATAGATCCTCCGCCAGTCTTACTGGTTGCGTTCCCACCATAATTAAGCATATTTAATATTTCAGG
GCGATTATCCCTCATATATTGAAAAAAAGAATTCACATTTATATTTTAATCCGTTAAGTTAAGTTTTGG
AGTAGTAACAAATACCATAGGGAATGCTTTAACCATCGGTTCATTTCTTAAGCTATTTTCCAATCTATA
TGGATTAAAATATTTATTCTCATTTATATTATAATTCCCTATAATCTTTTTTCTAATTTTCGTCTGACTTT
GACAAAAGTTTTCACCAACTTTCATATTAAGATCCTAGTATGTTATAAATTATTGTTAATGTATGCATG
AAAATATTAATTTATATTTTATTTATATATTATAAATTCGTAATAGATATAGTGATCATCCTTATAGAGT
AAGTTTAATAATTAATATTAAGAAAAATGATTTATATTACTGTCCATATAAATAAAATATGACCTCAC
ACCAGTAATATAAATTCTGTAAAATTATTTGGCTTAACTCTATCAGCGCTATATAAATTGAAATCATGC
ATATCGGAGAATATTAAATAATTCTTAGGGTTAGTCGATACAGTGAGAACTATATCTATTAAAAAAT
ATTATTGTCTTACATGGGGGCGTTCTTATGTGCTATATGATTGAATAAAAAGAAAAAATATGATTTAGA
AAAAACAGTAATAATACTTCTTAGTATTATTAATAAGATCCTATACTGAATAAAATTGAGGTATATGA
AAGCGCTCATAGGATTATTTATTAAAGATTATTAGAGTCACATTTCAATTAATTGATCTGTGACTCTAA
TAATCTTTATTTAATTTTTTTTTTTTTATAACGCTTCCTATGATAAAACAATAAAATATAAAGTAATATTA
ATTAGGTCATCTAAATTGAAAAGGAGAGAGCGTAAATGTCAAAAAGCGTATTGCTAAATTTGACTTCA
CTCTTTGGTGAAGTAGTTCTTAGTAAAAAAGGACAATCTGAATTAGATAAAAGTTATAAAGAATTAGT
TAAAAATAAATCTGCTAGTAATAGTTATCTAAATACAATTAAAGGAAAAGCAGAATCTGCTATTATGC
AATTTCCTTTAGTAATTTCTAATAATATATCTATCGGAGTTTTTAGATGGTATTCGTAGAAATATTGAAA
TTGAACGTGCTACGGAGTTCAGATTAGTATTGTCTAACGAACCAGTACAAAATGTTACAACTAATGCG
GAATTCATGAATAAATATCACACTAACTTTAGTCTTGGAGAAGATATTTCTTCAGCACATAATGAATTC
AATCAAGAGTCTAAATATATGGAAGAAAAATTAGAAATGCGTTCACTTAATGATTTTACAAGATCTCG
TCAATATCTTAGAGAAGAAGGCGAACAAGATTTTGTTAATGCTAAGATTGATAAGGATAAAGAAGAA
ATGAGTAGAGTTGAAAGAAGAATTCAGAATTCTCGTATAGTTTCTGATCGAAATGCAATCTCTCCATT
AATTGTAAACAGTCCTATTACTTATAGTATTTCTAAAGTCTTTAATAATGATGGAAAAGAAATTAAGGT
TGATCCTCCAAAAATTATTGAAGGTCAAATTCGTTTTGGAATTAAAGCGGTATCTCATTTAGTTAATAG
CGAAGATATTGTATTTTATCTTGGCGATGCCGCTAGACGTAGTAATTTCTTAGCAAAAGTAGTTCGGTT
TACTTCTGGCGAGCTTAAGTTTGGTAAGGATTTAATTCTAGCAAGTGAACGTAATAAACGTTTAGTACA
TGACCGTAAAGGTTCTGGTGCTATTTGGAGAAACATGAATTATATTTCTGAACTGAATAAATATTCGTGC
```

-continued

```
CAATGTAGGCAATGTAAATAAAATGCAAGTACCTACTATTACTTTAGCAATTAGTAAAGAAGAAGTAG
ATTCTATTGCAGAAAAGACAGGAATCAATTTTATCGATAATCCTAACGCTACAGAACGTTTGTTTAAA
GAATTTTACTTATTAGACTTCATGATCATTGATGAACTAAATGAAGTAGCATACAAATTTAATCGTACT
GGAAAAACATATGACCGTTTTAGCCTACGTTCTTTAGAGATTTCAGGATCTACTGAAAGTCAGTTAAA
GAAACCTATGGAATTCAGTCAATTAAATAAAATGATTAACTCTATGAGAAAATAAGAAAGGATAGGT
GAATAATTCAATGCGTGGATTTAATAATCGTTTAAAAAATAAACCAACATCTTCTAAAGATGCCTTAC
AACAGTTATTAGTTGAGAGTGGCGGATTAGAAATGAATAAATATAAATTACTTTCTGAAGAAGGTAAA
ATTGGTATTAGTGACCGAGTGTTAATTACTCTTATGAAATCAATTAAACCAAAATTAGAAAAACCGGT
ATTTAAGGATATTACTAAGTCTAAAGGTGATATTACTAAATATAAAGCTTATGATGATCTAGAAAAAG
TATTAAATAAAGTTCGTTCCGTTATTTCAAACAGTTCTAAACCTGTAGATAAAGACGTTAAAGAAAAT
ATGTCAAGCTTAGATACTGTTTATGATTTTGTTATTCGTGAAAAAGATGCATTTATGCGTGGATTTAGT
AATAAAGATTCTTTAGTAATGTCATTATATGTATCTTGTGTTTCGGTTATTGCAGAAGGATCATTAGTA
ATGTTTACAGATGCTTTAGAACCTACTTCCGATAACTTTGGAAATATTACAATTAATGTTAAAGATCGT
CCGAAATCAATGAATAAGAGTTTATTTATTGGACTAAGACAATTTTCTGATATGGTTAATGCTAAAAA
ATTAAAAGATATTATTAAAGGTGGACAAATTAACTTAGAAGAAGAACTAGGTGAAAGCTTTGTTGGAT
CTCTTTCAGTATTGGGTAAATTCTTTAATAAAGTAGCAGATAGTATGGATGATGCTAAAGAAAAAGCC
CATGATGATGCAGATTCTCCAAAAGGTGAAGATAGTGCAATGATTCGATTCTTCAAATCAAATAAATT
TGATAAAGCATCGGACGTTACTCGTAAGATTGGTAATCGAGTAATTCTACCGATTGTTGCATTATTATT
AGTATGTATGTTTATTCGCCTTGTAGTATTTATTATTTATCGTACTCGTGTAAACGTTGCAGACAATCTT
CGTAGTGCTGCTGAAGTTATTGATGAGAACTCTATTCGAATTCAAGATAAAAATGTACGTGAACGACA
AGAAAGTCTGCTAAACTATTCCGTAAACTAGCGGATAAAGTAGATGTAGACTTTAATGTGGCAGACT
CTGGTGCTGATAAGGATATTCGTCAACAAGATGAATTAATGGCTAAAGGTGCAGATGATATGATTAGT
TCATATCAAAATAATGCTAACGAGTTTGGTATCTAAAAAAAAAAATATCCCTATACATTCTAAAATTGA
ATGTATAGGGATATATATTATGAAATTTTACGTAATATAATTTGACCACCATTATCAGTAGTATTATTA
CTTTTAGTTGAAAATATTTCCGTCATTTTAAGAACCTGATAATCACCATTATATTTATTATAATATTCAG
AATCAAACGTTATAGTGAATTTTTTAAAACAGTCATCGATATTTATATCCATATTATTAAAACTAAATC
TTAGTATGGTATTATTTTCAGTTATTTGTTTAGTATATTCCTGTAGATTTTTATTATCATATTTATTTTCA
TATACAATTGTTTTATTAATAGTACCATTTCTATCCTTAATACTATCTATTTGATAACTGTCTTTTTCTAA
ACCTATCATGTCACGATTAAAAATAATATTATTTGTACCATATAATTCTGCATACAACTCAGTCTGATC
CATAATAACAACACTATTAATCTTAGTATTAATATACTTATCAGTTATTCCATTTAATTGATTAGTTTCA
CTATAAGTACCCATGATATTCTGGTCTTCAGGATTAGCATTAACTGGTATTTTAACGTCTATACGTATA
TTTCCAGACTCAACTATTTCCATAGAAGACATTGGAGTAATTACTAATTTATTATATGACATAAACACT
TTTAGACTATCATTATATATTCCGTAAGCATTATTAATGTGGCTAATATTAGTTAGAATATTTCCGGGT
ATTAAGGCTAATTGATCGTATATTTTTTGATTGTCTGGAGAAGATAGATATGTTCTTACTGGAAGAAGA
GTTAATAATCTAGTAATGACTTCAGTAACATTAGTATTTGAATATATACCGCTAGTATTATATTTATTA
ATAGATAGACATATTTCAGGGACGACATAAACATTCAAATTCTTCATACTGGTAATTTGTATCTGTTGTA
TCTTGGGTTAATCTATCACTAATATTAATCGCCCTCTTATCAATAATAAGCGGCTTTAGAATAATATCT
CCGAGAAATATATCATTAATATATGAGTTGGCAGTATCCGCATCAATGGATGAAGCTCCTAAACTTAC
TACAAATTTCTCAGAATCTTCTTGTAAACTTACCATAACAGATACTGGTAATTTATAGACTAATGATAT
CAGTGGCATTTTATAATTTTGAAAATCAATATCGATTTTAGTTAATCGAATATATTCAGAAGCATCAAA
CATATTTCCATCTGAGAATAAGAACTTACTACGTAGATTAAAAGTTTTTTTAGTTATACGAGAATAATC
CATTTATTATTTTTCACATCCATTTCATTCATTCAATATAGTAATATGTTTATTTATTAAAATAAATTTA
TAAGAATATATTTATAATAATAGATTATAATATATTTAGGGAGTTGTTTATATGGATTACGGAAATTATT
TTGGCTATGATACAGAAAATATCGAAAAGATTATGAACTCAAAGAAAGTTAAATATACAAAACTCATG
TCAATGGTAAAGAATTATGTAACGAGGGAATCTATTGGCAAGAATGTAAATATCTATATTGATATGAA
TACTATTTTAAAGCAGATATATAATAAGGATAATATTGAAATCTTTAATCATTTAAAGAGTGATAAAC
GTTTATTTATTACTGCTGAAATTATAAATATTATTGGTCACTATAGACATTTCTTTTCTTCAAGATTGAA
AATGTATACTACGTTTTATTTATTTACTTCTTTTGAAAAATCATCATATCATACAAATATATATCCTGAT
TATCGTAAAGAATATTACGAAAAAAGATTGGGTGATAGAGATTTTGTTTTTTCAAATATTAATAAGATT
ATTAAGGATAATATGAATATCGTTAAGAAGATTTTAAAGTATGTACCAAACGCATATTTGATTAATAC
AAAAGATAATGATCCTTCATTAGTACCTACTTATTTATTAAAATGATAATCGTTTTACTTTAGATACCGA
CTTGAATATTATTATTAGCAATGATAAACTTTTCAGACAAGATTTATTATATAGGGATAATACGCTTAT
CTTAGAGAATTAAAGGAAAGAATAATAAACGACTTATCGCTTATGAGGACGTTATCAATACTATTGTAG
ATAGTACTAAAGGTAAAAGGGTTTATTCAGACTATAACTTATTAACAGAATCCATTACACTTCTGGATC
CTCTTGTAAAGAATAAAGAATATAATATTAATTCAATTAAACGAACTAGATGAAATGAAAGCACTAGAC
ATTATTGAAAAAGGTATTAATGATAATATTATTTCTTCACAAAGCTATTATGACGTAGATGAAGCATAT
AATGATTTAGCTTTTTATCTTGGTGAAAATAATGAGGATGAATTTAAAAGAAATATGTCAATCGTTAAT
CATAAAATTGCAATGTCACATACTTTTAAAGATTTAGAACACGTTATACTTTCCCAAATAATTGATCTA
GAGGATGATAGAGGATTAATGAATTGAATGATAAGTTCTTTTCAAAATATCCTATTGTTATGGACTAT
CTTGGTGAAAGTTTCTATGATCCGAGATAAAAAAAAAAAATATCCCTAATGCTAATATTACTTAGCAT
TAGGGACTTATTATATACTTATTTTTTTTTTTTAGACTGATTTAATAAATTCAATAATTTCCATTGACAT
TAAAACTTTATCCATATCTTCGATAAATACTTCATTATCATTTTCATCAATATACATAAAATCATAATTA
TATGAGGTTGATAATGACATGATAAAGTTTTCACGTTGAACTAGATCAATAATACTGTCATACTCAGTA
AGAACTTCTCCATAGCTTTCTGATGTTACGATCTTATTATTAATCTTATTACTAATGCGATTTCTTTTTC
CAGAAGGAATAGTTTTACTTAGTAGAACTTTGGGTAAAAGTTTATAGTTATTCTTTTCAAGTTCTCTAA
TCATCGCAACTAGTAATACTAGTACTCTGGGTTCACGGAAGTTCTTAATGGCAAATCTTTTTGCAAAGT
ACATATTCATAAGTGAAATTTGGAATTCGTTTAAATGTTTAACATTACTACTTAAACGTACAATTTCTT
CATTAGTAATATTATATTTTAGATAGAGTCTCTCACATACTTATCGATAGATGCATCATTAATAACGC
TTGACATTTCATTATGTTTATGGTACTGAATTAAAGAAAATTTATCATTCTCATCTAGATCGTCATCTGA
ACTAGAAATCTTGATTACTTTGAATTGTAGTGCATAATTAGAACGGAAAGCATATTCAATCTTTCTTTT
AATAACTACGTCTAAATACGATATTGATGATTTATTAATAGAAAGTTTGCATATAATTGTACGTATAAT
TTCATCGGTAATTTTTTGGTTTAATATGTCTTCATCTACAGATATATTTTGCAAGAAGTACCAGATAACT
TTATCTTTGTATAACGTCTTTTTAATACGTGGTTCAACAATTTTGCTAATCTTAGTAAGAATATTAATCC
CTTTTTTTATTACTAAAATAGCGATTAATTAATTTAAAAGTCTTTAAGAATAGTTGTTCATTGTAAGGCTT
ATTTTTAGCATTACCTGAAGTAATAAGATATTCACATATAGTAGGAATTAACAAACGTTGCATGATTGC
AGAACGGATTAGTACTTTATTTGATTCATCAGTTACTTGTAGTTCAGGAACAATTTTATCAGAGTTAGT
TCTACTATAATCATCTAATGAAATCGTATATGTAGAATCAACTACTGCATCAATAGCTTGTAATAACTT
ATCAAATTTAATAAAATCTTCGAAATCTTCAATAAATTTACTTTCAGTATAATCTTCATCCATAAACAT
GTTTACTTTAAAAATTTAATAGTTTATAGGCAATTTCAGGAACTTCATTTAAAAAGTAGTTTAAATCATT
```

-continued

```
GTAAATAATATGATAGATATTTGAATAAATTGCTTGATGAATATTATATTCAAATAACTTTTCTTTACC
CTCTAAATTAGCATTCTCTAAAATAGAAGCAAAGTCTACAACTATCTTTTTGGGATGAGCATAGTTATC
TTCTGTAATATAAGTTGTAATGTCTTTACGATGTTCAACTTTTTCAATAGTTACCATTTCGTTTGGATCA
TTCTCACTTTTAGGTAAAGATACAGTTACTTCTTTTAATCCTTCAATAGATATATACTTATTTTTTAACT
TAAACTCTTCCTTCACACTATTACCCCTAACTTTTGTGTTATCAGACGTTATTGTCACTCAAAAACACCA
ACCATTCTCTTTTTATTTTTATTAATAATATAATTGGGATGAGATTAATTTTTCATCATATACATATCAA
CCTTTCTTATTTATATATACTATACCACACTTATATATAATATATAATTGAAAGTTATTAACGTTTATT
AATAGATGTTCTACGAGATTTAGATTTTTTATTACGATCAAAGATACTTTGTTTCTTAGGTTTATCGATA
TTTTTATTTTTAGGTTTTCCTTTACTTCTAATATCTTTTATCTTCTTGTTATGAAGTCTTCTATTCTTATAA
CGCTCAATTTCAACAAGCTTTCTTTCTGAAGCGGGTATATTTCTAGATACTTGTATTTTGTCAATAGGTT
TTAATCTTTCTAATGAGGGAAATGTTAATAGATTATTCTTTTCTAGATATATAAGGGCAAAATAAACAC
TTTTTTCAAATCCATAAATTTGGTTTGGGTTTCTTACTTTAGGTTCATCTACTAAAGATTTAATACTCAT
TTTATTCTTAAGCCAATCAATAATCAAACCATCTCGATTATAAATATATCCATACGTAAACATAAAGTT
AGGATTATTACTATAGAAACTGATATGCGAGTTTAGAATAGAAACGTTTGTATTATTTTTGTCTATTTT
AATTACTACGTCATAAACCATTTTTTCTWYWMTAWACGTYKCAKAWSRRWTTYTAWAKWMATART
MCWAACTTTATSTTTACRTMTKKAWATAYTTMTAMWCKARATGGTTTSAWTMTTGATTRGCTTWWK
WATAMAATGAGTATTAAATCGGTCATACATATTGGCGATAATCATATCCCGCCTAGCTAATCCTGCAG
AACCTTTTCCTGAAGGGTTTTGCATAAACTGTTTTACAGTGATCATTTCTAATATACACCCCCTATTTAT
TAATTATAACATAATTTTTTGTTAAATTTAAAATAAACTTTTTTATTTTAAAAAATTATTAACCCCTAAC
GTGAATGATAACTATCACGTTAGGGTCAACTTTATTATAAGCTAATTCGAATATATTGATTACTTGTAA
CCAGTAATCCAATTACTGAAAATGATGCTCTCATAATCTGAATATCCGTCATTACCGAGTTGATAATCT
TTGTTTCAGAGTCAGGAACATATTTCTTTTCTTTAAGATCATAAATCATTTTATTGTTAATACAACTCTC
AACAGTTTCATATACTTCTTCATCGCTAAATAATTGAGAGTTCTTTAATACAATTGCATATGTTTCTTTA
AATGCAGAATATACTAGTTGTAACAATACTTTATCTACTTCAGTTAAACTTTCTTCATTATCAATAATA
TCTTTAATTACTTTTGGAATTGAAATATTTCCTCCCGGAATATAACCGTAATCTAAAGCAGATCTACAT
GCAAAGATAGAATCTTCCAAGAGATATTTACGAGTATCACGTTCCAATTCAGATTTACCACCAATAAA
TAACGTAGCTACTTTAGAAAGTAATCTAGCTTTACGATTCTCTAATTTAAAGATTTCAGAATCTACACC
TTTTTGATATACGTCTAAATTCTTTAAATCTTGAATATTAAGGTCAATTAATTCAATTCGAGCATCTAAT
TCTTCTTGATGATACTCTCCCTTAATAAATTGAGTTGATCCACCAGTCATCGTTACTGTTTCACAACGAC
CAATATGTTCACCATAAAATTGAGCGTTATTTGTTTTACTTAAGATAAATAAGTCTTCAAAACCTTCTT
TACCTTTTTTAGTATTAATCTGAGTTCCTAAGTATATTGCTAAGTCTTCGAATTCTTCTTTACGAGTTCT
AGCGGGAAAGTCTGTAGCTGCAATTTCTAGGGATACTCTGGTATTATTGATCTTTTGAATCTTCATAAA
GTCAATAAATTCCGTTCTATATTCCTTCGCAACAATAACTAGACTTTTACCATTACCGCATACCTGACC
AATAAGATGGGCAAAGAAATCAATATCCGTCTTATCTAAACATGAATTCAGTAATAAATACATAAGGTT
CTTTGAACATTGCTTCAATCTTATTTGGTTTATTTGCAAAGATAGGGTCAACATACCCACGACTAGTTT
CAATACCATTTACAATTTCAAATGTATCCTCTTCAGAAGTAGATTTATCTAAATAAATAAATCCTCGTT
TACCAATTTGTTTATAGATATTATAAATAATATTTCCGTCTTTTTCATCATTGTTGTTAGATACGGTTGC
AATATTACGGAGAATCTCAAAGTTATCTTCATTAATAGGAATTGATTTTTCTTTTAATTTCTTTTCAATC
AGTTCACCAACATTATTTAATGAATTAATGATTTCTTTCTTAGGAAGCTTACCTAAGAATTGTGAACGA
TCATTAACCATTGGTTCTAATTGATTATATAATTCATTACTAACCACTACTGAAGAAGTTGATCCATCA
CCAACCTCTTGCACTAATGATCTTGAAATAGTCTTAATATTATTCAGAAAAGTAGTACTAATAGTATTG
TTAAAACGAATCTTGTCTAAAATTGTGAATCCATCTTTAGAGATCTTAGAACCATATAAATTATCTTCT
AGAATAGTTGTAGATCCATAATATCCTAAGGATTTAGAAAGAATATCACTAATACTATTAAGTGTTTCT
TTAGCAATTTTTTGATATACTTCATCAGAAATTACATTGCTTTCTACAATATCAATTTTTTCCTTAGGTT
CAAGAATTCTTGAAATTTGATCTTTAATAATATTGCTCATACACTTTTCCACGCTGCTATATAAATTAGT
GAATTTAATTTAATTCACAAGAATTTAATCAACTTCGTCAACAAGTTTCTTATAAATTCACAAAAAGTG
AAAATACAGAGGAAAACTCTCTTAAGTTATAATGGGTTTAGCCAACCCTTTCTGCATATATTTTTAAAT
TACATGCAGAATTATAATCTCTATCCATCACTTCATTACATTGATCACATGTATATAATCTATCCGAAA
GTTTCATTTTTTTATCATTTTCTTTTTTATATCAACAACAACTACAAATTTGAGTTGATGGAAACCATCT
ATCTGCAATAATTAAGGTATTTCCATATAAAATACTTTTTATATTGTAATTGAACTTTAAAACGATAAAA
TAAAGACCGTGATATAGATTTAGATATTTTTCGGTTAGATAACATTCCTTTAACATTTAAATCTTCTAT
ACATATAGTGTGATAATTTTTAATAACGTAAGAAGTAAACTTATGCAGCCAATCATCTTGTATATTTTG
TATTTTCAAATAAATATTTTGAAGTTTGATTTTCACTTTATTTATATTTATTCGAATTATTGACTTTTCTAG
ACAAGATTTTTTGGTATAAAGAAATTTTCTTATATAATGGAATTAAATTTTTTAAAGGACTATTAAATC
GGTGATTTTCTTCACTTATATCAAAATGACCAATATTTGCATCAATTCCAACTGTCGGAAGATTTTGAT
TTGAATGATACATACTATCATCAGTATCAATACAGAAAGAAGCAAAATACTGATTTGCTCTTTTTGTAA
TTGTACATATTTTAATATCACCATTAAATCGTATCGATTCAGACATTTTTACACCATATTTAAATTTAGG
TAAAAATAATCGATTATTAATAATCCTTATTGTACTTTCGGCTTTTCGATTAATCGTAAATGAACTTTTT
GCTTTTCGTTTATTTTTGAATTTAGGTTTACCTGAATTAGATGTAAAAAATCTCTTCCAACCATATGCCA
TATTTTTACAAGTATTATCAAAAATATTTGGGGGAAAATTATCCCATTCAGGTTTCAATTTCCTTTTATA
TTCGTCTCGCACTTTTCGTTCATTAGGTTTATTGCCGTTAATGTACATTTCATTCCATATATTCAAAGAC
ACATTATATGAATATCTTGAATAATTGAAAAAATCTTTAAATTGTAACTGCATTGTTTGTTAGGATAG
ATTCTGATTTTTTGACTTATTATCATCTAAATCATCCCTTAAAGTTTTTTATATTTTCGTAATCCGTATA
ATCGGCTAGAAAATACATGAATAATTGTCATAAGATCATCAACTAGTTCTTTTTCAGGAGAAGAACTT
TCTAAATTAATTACAGTTAGTGTTGTTCCATTAACTTTACATCTTTCTTCAATAAGTTCAAAACCAAAA
CGAGTTAGTCGATCTTTATATGTTATAATAAGTTCTGATACTTCTTTGTTTTCTATCATGTCAATTAATT
TTAAAAAATTCTTTCGTTTAAAATTAATTCCGGATGCAATATCTGAAAGATAAATATTAACAGGTTTTC
CACTATTAACTGAAAATGTTTCAATAGATTGTCGTTGGTTTTCAAGTCTTTCTTTTGGTTACTAGTTGA
AACTCGATAATATGCTACAATTTTTCTTTTTTCTTCAGGTTTGATATTATTAGTTAGTTCAAAATAATCA
TCAACCATTTCGTCAGTATAATACTTTAGGCGTCCTTTTCGAATAGGTTTAATTATTTTTTCCTTTTCTA
ATGTTTCTAGTTTTTTCTTTGATATACGTAATTTCATTCTAAATTCATCAGAACGCATAACCATTTAAAA
CACACTCCTTTTTAATTTATATTATATTGTTACATTAAAATATAAATTAAAGTGAAAAAGAGTGAAACT
AGATGATATTCATAATAAGTCGGCTAAATTAAATTCTTATTATAATTCCCAATTTTGTGTTTCCACATTG
GTTAAATAGCAGGACTATATCATAACCTATAATATTATAGGTCCCTCGTACTTCCCTTTCGGTACTCTA
CTTGCTTCGTATAGATATCTCAATCTATCTTATTCACCATATAGGTGTTACATTTATTATTTGCTTTCGA
TAGTCTCTGAACGTTCACCCATCAAGTGGGAGCTTCGCTGCTAGATTTTCCATTAGTCCACCCTTAGCA
CTACGTTTTCTAAGGTTCACATTATTACTTCACTTAGACACTGATAGGTTTTATTTCAGCTTAGGTAATC
TTAAAGAGTTTTTTCTGTCTTTCGACTGCATTCACGCTTACCGTTACCAGTTACGTTGTAGCCCTTTAAG
CTTTAGGAGTTTACAAGCAATTCACAAGGTTTCGCATACATCTTTACAGATATATGGGAGTTTTTGAATA
```

```
CAGGTTAATTTAATTTATATTTTAAACTAAACTCATTTAAAATCAATTAAACCATTACTGCTTCTTTTCT
CCACTTTTTTATTTTATTATAATTGAAAGTACATTGTCATTTTCAATAATACAATCGAATTCTTCGATAA
AGGTATACATCTTAATATAATCTTTACATGAATCAAGATCAATATAATTATTAAATTTTAAGGATACTT
TTTTAAATTGTCTAATTTCTTCATCTTTGGAAGTATTGTTAAATCCTTTGATGATATTAAATGAAAATTT
CTCTTCAAGATCATATAGTAGTAAATTAAGCTTTAATCCGAATTCAGAAT

SEQ ID NO: 2:. LPJP1.NL Recombinant Bacteriophage Genome Sequence >JG11_062520-1_
LPJP1.NL (224,658 bp):
TGACGAAAAAGCATGTCTTCTACATCTACCGGTACATCTGAAATATCTTTCTTACATTTACTACATGTT
AATCCATGAATTGCATAAGAAATACCATATTTATCAGATTGCTCACTAATCATTTCACTAAGACTCTTC
ATGTCACTAACTTCAAGATTACTAATGATCTTAAGAATTTGTTCTGGGTTTGTTACTTTTACAAATTTAA
GTTCTCCAGTTTTTTCCAATCTATCTAGGTCAGGAACCATTATTTTTTTAGTGAATAAAATTAGATCAAT
ATAATCTCTAACTTCATCATAGCTTTCAGGTTTAATATATGATAGTAATGTTAATTTATCTTTTAGTGAA
GGTATTTGAATATCGAATACCATTTTACTTAACGGCATTTGGGAACGAGTGATCTTATTTACTGCTGAA
TACTTTTTAATGACGCTTGGATCTTTAACTGTATCAGTAATTTGTTTTAAACGAGAATATGTTTCTTCAT
TCTTAACAACAATAAGATTCTCATTATAAGCTTTAACATTCCTCATAACGTTTCCACATGATCCACACT
TAATATCAAAAGAAGTTCCACGTGGGAATGTTTGACAGAATAGTCCGTAAATTAAAGTATCTAGATCA
TAGATAGATGTAATGTCAATGAATGTATCCCAATCTAATTTACCTAGTGTAGTGGAATTAATTTTACTA
AAGTATGTTTGATATTGACGTAATGTAGATTCATATGCAGAAGCGGTGCTTGATGAGATAGAAAGCAT
ATCATTCATACGTAGACTCTCTACATGAGCAATATATGCTGATTGATTTAATGTAACTTGATAAGTAGG
GCTTCCTGTTAATGCATATTTAAATTTATCAAAATTAATATCTTTAAATTTATCTTCATCATCAATAATT
AATGAGTCGATATCTTTTAAATTATCAATTTTTGCTTTATCAAGAATATCTTTAACTGAGTCTTTTTTAG
GTTCTTGTTTAATTTCAGTTAATGTTTCATCTACTTGTACGTTGTTAATATTTTCTTGATTAATTGGGTCT
TTAATAGGAATCTCATCACTTGGTTCTTCAAAAATTCCTTTAATCTCTTCTTCTTCTTTTTTCTCATTATC
AGGAACATCATCAGGTATTGGATTTCCATCTAAAGGCTCAATGTCTGATGGATTATACGCAAATTGTTC
TTCATTTTCTTGTGATTTTTGTTCATATTGATATTGTTGAGTCATTGCTTGTTCGGTATTTTCATTTTCTC
CAGTATTATTCGTTACTGAGGAATCTTCTTCTTTCTGGTAAACATCAATACCTGTACCAGAGAGAGATA
AGTTAGGATCAATATTCTCTTCTTTTTTAGCTTCTTCAGATTTTCTACGTTGCTCTGCTTCTAGAAATAA
TTTTGCTACATGTTGAGGATCTTCACCTACTACTTGGGCATGTAACATTGCTATTTCTAGATCGCTCATC
TTTTTATCGGGAATATTAATATTTGTAGGAATATTGTTATTTTCATTATTATCTGATTTTAATACCATTG
TATATTTTACCTCCACATAATTTATATTATTTTTAATTATACATTATTTTTTGATACAGTTGTATTTGTTTT
ATTATTGTATCCATATAATAATCCAAAGTTTAGATTAGTAGTAGTATTAGAATCTACTAAATTAATATC
TATATAAAACGTATTTACATTTACGTTTGAATTACTAGAAAGAACGTTTTTAACATTTTGTATATTAAT
CTTTACAACGATATCTTTGATGTACAATATATGATTCTATTTGATTTTCAATTTTACTTTGAAGTTCTAAT
CTAGTTTCCGTATCCAAGATTTCATATAAATATAATCCGATACCGATGCCCATATTAGGTGGTTCGGG
TACGTTCCTTGCTCTATTATAATTAAATTTTGGATCTGTTGTGCTAATGCTTCTAGGTTTTCTCTTAATAT
TGGTTGATTGAAGTCATCCCTCTCTAGTATAACTTCAGGTCTGAATGATATATTTGATTCATCCGCTTTA
AAGTCTGCCATAATTTTCACCACTTTCTATTTAAAGTATTCTATAAAAATCAATAGCTTTTAATTATAAT
TATATGTTGCAGTAAAAATTAACATTTTAAAAAATTATTTGTGAACAATATTATATATAAGTTTAGAAA
AATTTTTTTCTGGGTTTATATAATACTTAAATATCACTAAATTGTTTAAAATACTCGGGTTGTAGTTCAC
ATTGTTGACTAACCATTTAAATAATATAATTACATTTAGTGATATTATACATATCTTTCATCATAACATT
ATTCTAAAAAATAATGTTATGATGAATATTGTTTTAATGAACATATACTTATTATAGATATATTAATGC
AGAAAGAAGTGAATATTTTGAAACAATTTAAATGTCCATATGACAGAAAGAATATTTGTAAATAAAAAG
GCATTATATGATTATATGGAAAAGAATTATTCAGATCAATTAAATGGACTATCTCCGCTAATGCTTAT
TTTAATATCAAGTATAACAAAACACATGGTAGATGTATTGTATGCGGTAAGAATACACCATTTAACGA
AACTACTGAAAAGTATGATCGTTTATGTTCAGATAAATGTAAAATTAAATATAGAAAGCAGTTTGTAG
AGAGATGAAAAAAGTTCACGGAACAGATACTCTATTAAGAGATCCTGAAAATGCAGAAAAGAATGTT
AGCTAATCGTAAAATTGCAGGAGTATATACGTGGTCTGATGGTAGTAAATTTAAATATGTGGGTAGTT
ATGAGAAAGATGCGTTAGAATATATGGATAAGATATTAGGATTTCACTCTAAGGATATTATTGTTCCTT
CTCCAATAATCTTTGATTATACGCTTGATGGTAAAAAACATTTCTATATACCAGATATATTTATTGTTCC
TTTCAACATGGTGGTAGAAGTAAAAGGTACTAACAATCATTACCAAACTAGGGATAGCGTACTGAAG
ATGCTAAGGATAAAGCGGTTCTTAAGACAAAGTATCGTTATGCAAAATTAGTTGACAAGAAATATGAC
AAGTTCAATGACATTATTGAGAATCTTAAAGAATCAAAGGACGATAAAGTCCGTTAATATAAATAAAA
TTTTAAACCCTCATTTCAATAATATATTATAATTAAGATAATGTATATTATCATATTGAAATGAGGGGA
TTTTATTGGAAAATAAGAAACGTAAATTCTTGGCACTGTGTGGAATTAGTGGTTCGGGTAAGAATTCT
GTTGAATCTATACTTGATGGTTATTATGATAATGTTAATGGAGTGTTTTTTAAAAAACTAAATCAAGTA
ACAACTAGGAATATTCGAAATACTGATGAATTTAATAGTGGAATATATAGTTTTATAACTATAGATATT
TATAATCTAATAAAAGAAAATCTCATTGGAAAAACAGTTATCGATAATAAATATTATTATGGTACGCT
TGATACTAGTACTACAGATGGTTGTATTAATACTATTATTGTCAATGCAAAAGGATTATCTAATCTTAA
GAATGATCTTAATAATAAGTATGGTGAAGATAACTATGACCTATTTGTATTGCAGATTGCTAATAATAC
TCCTGTGGAAAGAAGAAATAGAGACGCAGAATTTATCAGAGGTGAATATAATGATTTAAAAGGATTG
TCTAACGCAACTCTTATAAATAATCCTAGTAAATGGTTAACTGTCTCTGACGTAATTAACTGTCTTAAG
AAAGAAGGTTTTTTGGATACATGACATTAGTTAGTCATACTAAGTTATATGAAAAACAAATTATCGT
AATAAAAGAATTAGCTATATTAAAAATACGTTGATTACTGAGTTTGATATAAAAAGTGCTGGTCTAAA
TATTCTATATGAAATGGAATATTTAGACCAAAATCAATATGAAAAATTATTATCAATGGAAAAGTATG
AAAGAAACGTTACAATCGGAAAGATATTAAGGTCTAATAAAGAAATGAATGAAGCATTATCATTTGGT
TTTTCAGAAGCGAGAAGATTATTTTTCGAATTAAATCAAATTGATGATTCAGAATTATTATCTATTAAG
AAGGATGCAATATTTCTTATAGGTAGAAATAATATAAAATATTAACGGTAATGTTTCTGAATTTATAAA
ATTTAGACCAAAGAAATCTTATACAACGTTTGTTGAAGTGTTAGACCGAGAACACTATTTGAACTTTG
AAAGCGAAGAAATAATTTATGATATTAAAGGATACTCTAGTGATATTAAAGATATTCATAATGAATAT
TTATTAAAGGATCTTCTTAATGTAATGAAGTTTGATTATGTTAATGATAAAGATAGAATATTTGAATAT
TTAGCAGTTCTTAAGGATGACCTAATTAAATATAGACTTCCAGTATCATACTATAATGATATTAAAGTA
GGAAAATATATTGTAGAAATGGGTAACGCATTATTTGATCTAGATAATATTAATGATAATATTAAGCA
ATATTGCCTGTTGTCTAATAATCTTAGTTTTATTTTAAATCTAATCAATAAGACTCTTTCATAAAAAAA
AAATAAATAATATATTAAGGTAACGATCATTAATTTGATCGTTACCTCTTTTTTTTTTTTCTATGATCCA
TAATATACTATATATTTACAGATTTTATTTTCTTGTCAATCGTTAATGATACTTCAGTCATGATAAGCAT
AATCTTGCTCATAACATATTCCTCAATATGTTCTTCTGAAATGATGGTAGAAACCCTATATTTTAAGTC
ACTAGACATTCTTTCTACAACTTCATTAGTACATGATATAACAGATTCTTCAAATTCATCTGTAGTTGT
ATCGATATCTATATCATCACTAAGTTCACTCTGATCTTCATCAATAGATGTTTCAGTAGTCGCAGTATTT
```

-continued

```
TCTACATATTCATTTCCTTCATTGTCATACTGAATATTCATACCATTAATTGCAGTAACTTCACTTAATC
TAGGAAGTATTCTATCAATACTTTCAGCAATTAAATTATTCTTTACAATCCGTATGCTAATATCAATAA
GAATATCTAATTCCTTTAGTGCTTTTTCACCATCAATATTATTATGCATCATTCTATTATTACGGTTAGA
TTTAATAATCAATCTTCCAATAATTATATGTGTAATAAATATAATTATTAGTATTGAAGGTACTGTAAT
GTAAAATAAATTTGTAGTCATCAAATAAACTTCCCCTATTCATTTATTATTTATATATAATTATTCATAC
TAAAAACTTGAATTTTATTTTCTTCTAAGAAAGATACAACTTCCTGAGAATTATCATATTCTTCTAAAT
AATATACTTTAGATATTCCTGAAGCAATAATCGTTTTGGCACAATTAAAGCATGGTGAATGAGTAATA
AACATTGATGCGCCTTCTGTATTTCCAGAGTTTCTAGCCACCTTAGATATTGCGTTTATTTCTGCATGTA
TTTCATATTTTAATGACCATTTATGATGAATTTCCATATCTTCACATAAATAAAATTTCTTTCCTTGACT
TTCAATATAATAATCTTTGCGACAAATGAATTCCGGATGTGAAGTATACCATAATCCTTCTTTCTTTAT
GAATATATCATTACAGTTAGCGTATCCACTAGGGGTTCCATTAATTCCTGAAGATATAATGGAGTTATT
CTTAACAATAATGCAGGAGACTTTCTTTGCAGAGCATTTACTTATTTCTGACATTCTTATTGCAATATTC
ATAAAGTTTACTTCGTTTGTCGTAATATAGTCATCCATATTATTATCTTCATTATCTATAAATATATCTA
CCACTATATAACCACCGATCTTATTCTAATTATAATAAATTATTTGAAATGATGCATTGTTTAAATACT
TTTAATTTTCCGAATGTTAATGTTAATATCAACACGATTTATAAAATTGTCAATTTCTGTATCTGTATTA
GAGAACATATTTTCAAAGATATCAAACTTTATAATTCGATAAAAGCTATCTTGACTTATATAATGTGCA
ATATTATTAACAATATTATCATTATCTGTAAGATAAAGATACTTCACAACAAGACTAAGCGTTGTTAAT
ATTAGTCTGTATATTTCTTTTATACGATAATCGTTTATATTTTTATCTATAATTAACGTATCATATGATT
CTGTCTGGAAGTTAAATTTATATGTTTCTTGAGAATTTACTTTCTTCATCAAACTAATTATAGATACTGC
GTTTGATGGCATTTTTTTCACTTTTGGAAATATCAATTCTTTATTATTTATTCTTCTTTTTGTATCTTTTAT
TAATTCATCAATAAATTTTGAAAATTCGGCATTATATAACTCATCATTACTTAGATCCATATTTTTTTGT
AGTTCAATATACATTTTAAATTCTAGTTCCAATCTATTTAATATATGAACTTCATGCTTTGATAATAAGT
TAATATATAATACGTTTATTGTAGGAAATTTAATATTGGATTTATCATCAGTATCTATATCAGTGGATT
CTATATAGTATGATGAGGGTGAAATATAATTTTTATATTTATACATATGCGTATATGAGTAAATAACTA
ATTCATTAGTATACGTAAAATTCATTAAATTATCATTATCATAATTATCCACTTCAATATAGTTGTTTAT
TATTGCATCTTTTCGACTGATTAACGATCTTTCTTTATTATATTTGTGCATTATAAAAGAGATATATCTA
TTATTATTTATATAATTAGATGAATCGATAAACATGTCATATTCTTGTAATTCTTCAAAACATAGTTCTA
AAATATTTGCAAGCAATATTTGAATTATATTTCTATTATCTTTTATTTTATTATAACCATAATAATTTTT
GTGACTTATCATAGGAATATCTGAAAATATGATGTAATTTTCAGAAGTAAGAAAAAAATTAGAATTAT
TTAAATCATTGAAGATACCAGTAATTTTACTGATATCTTCAAGACTTATATTTTTAAATTTTTCATAGTT
CCATAAATTTCTCACTTTAATATTATGGTTAGCATCAGTATAGAAATATTTAGTATCAATATTCATTAA
CTAATCACTATCCTTATATAATATTTTAGTATCGATATTTACTTTTGTTTTTAAAGTTAACGTCTCTTACT
GTTCCTGGAGGATTATTGATTGATAATCCTGCATTATTATTACTTTCTGTAAGAAGCCAGATAGTATAT
CCTTTAGGTTCTTACAATCAAGCGTATTCTCACCAAAACATCCGTAATAATAATATTAATATCTGAT
CGAATATTTTCATTAATATATTTAATTGGAGCAGTCAATGTAGTTCCACCATAAGCAGTTCTTTCAAAT
TTACGTAATCTATCTTTCTTAGATAACGGATATACATCATGAACCATTGTATCAAAGTGAATTACATAT
AGTTTACTTTTAATATTTGAAATAATCTGACGAATTTGATCAAAAGCCCAAGCCACTTCTTCGTCACTC
ATTGATCCTGACATGTCGATAGCTACGGTAATTTTAGATTCACGATCCGGCATTCTTCCTAATAAGTCA
CCACGATCTGGCATTCTTCTATTTCTACGGAGATTAGTTCTTTTATAAGGAACTTTTAAAGAACCAATC
TTCGTACGTAAGATTTGTTGCCAAGGAATAACTTTTTCCTTATTAATATTTTCTAGAAATTTATTAATAG
AAACAGGAACTGATCCGGCTAAAGATAGTCGTTCAATAGTATTTTCGATATTTTGTTTTATTGAACGTT
GAATGTCTTCTTCAGAATAATCGCCGTTTTTCCATTTTGAGTGAGAAGAATTAGCACTATTATTCATGT
TAATGCGTTCTTTCTTACCTTCTGAATCTAATTCATTACCTAGATCATTTTCATCTTTTCCGTATTCATGA
GATTTGCCAGTATTACCATTAGAAGAACCTTCTTCTTCATTTTCGCTGTCATTATCTCCACCATTATCAG
TATCAGATGAATCATCATCATTATTCCCACTTTGATTACTTGGCATTCCATTATTATTTTGACCGCTTTT
ATTATTTTCATTAGCTTCTAATAATGCATCCATATAGTATTCAAAAGATTTATCTTTTTCCAAATCCTTA
TTATTAGTTAACATTCTTACATAATCTAGTGTAATAGAACCTTCTGGAATATCATCAATATATTGATTA
ATAGAACAATCCATAGCAATATTTGCCATATGCATGAAGTCTTGATTTTTACTAATCGCCATATTCTTA
TATCGGAAAATATGATTATTTGAAATATGAAGTAATTCATGAGTAATAACTGCAATGAATTCTCGATC
ATTAAACATTAAAATTTTATATGGATTTAGATATAATGTAAATGTATCTTTAAATGTATTTTCAGCATA
GCTAACTGCTGCCGGAGCAAAGTTCGGATCATGAACAACTTCTTTAATCATATTAATTGTAAATAGAG
CAAAGAATTTGTCATCATTAATGTTATCACTAATTAAATTAGTGAATGTTAACTTAATATATGCTTCAA
ATGCTTTTTCTAACTTTTTTGAAGCTTCAAGAGGTAAAAGCTTCTCCTTACCATAATATTCAAGAAGAA
ACTTTTTTAATTCTTTTCTAGTCATACTATTAGAATTATAATTATCTAAAGTAGGCATTAATATCCTCCA
CCGATCTAATTATTTTAAACGTTTACTAATTTTTTGATTGATTGCGATATATTCATCATATTGATAAACT
CTGTTATAGAAATCATCTGCAGTATTATTTACTTGTCGATTAAACATTGCAAAAGTACTCATGATAACT
TCTTCTTCTCCCAAAGTATCTACAAATTTAATATAGTTCGCAGTCATTCTATCTAAATCTTTTTTATTTTT
TACTCGTTTACTATCGTTACCCATTTCACGAACAACATAATTAATTACATAACGACTAAGTAGTGTTTT
ACGTAAGTTTGTTTCCTCTTTAATTTGGGTCAATAGTTTTTCATCTTTAGATAAGTTTGGGTTATCGATA
ATCAATTCAGCTCGGATCATAGGGTTTGTTTTGTCTTTTAGGAAATTAAAGAATAATGAAGTAGCTTTC
GAACCTAGATTACCTTCAAACACTGCACGTAGTTTATGACTAATAGATACTGTATCTTCTGGGAATTGT
TTCATATGTTCATAATACGCATCAGAACTACGTTTCCATGAACGTGGAGTAGGTGACTTACCTAAGCTT
GAACTATCTACAAATGACAGCAACTCAGGATTTGTTGCAATAAATTCAGAAATATCTTCATGAATGTTT
GGTCGAATATATAGTGGAGTAGAAGTATTTGCATCTACATATTCAAATTCTTGAATAGCCCAATCTAAC
CATTCTTCTGGATCTGGATCTAGTCTAAGATCTGTAAATCGGTCACGTAGGGCATAGTTCATTGTGTTT
ACTTGATAATCAATACCGTCACTGTTTTCATCTGTAGGATTTCCTGCAGTAATAATATATAATTCTTCTG
GAAGAGAGTATTGATGAATTCTCCGATCAAGAATAATATTCATTAACTCTTGTTGAACAGCTAAATCT
GAACGGTTAAGTTCATCGATAAATAGTAATGGAATTTTTCCATTATCTGCAATCTTATATAGTTTACCA
ATTGTACTATGAATAGTATATTCATTTTCTTTAGGTTGTTCTTCATTTTTAAACCATGTTTTGATATTTGT
AAGTTTAAATTTATTTTTAGGTTCTGCAATATGAGGGATACCGGTAATTTCTCCTTCTTTAAGTAAGTTA
CCATCAAGCTTAACAAACTCAATTAAGTCACCATTTCTTTCATTATAACGTTCAACAAATAATTCAGCC
AAACTAGATTTTCCGATCCCTGCATGACCTTCAATAAATGGTACGCTTCCTGAAGCTACCACTACGCCT
ACTACATCTAACAAGTCTGACATTTTCATAAATAAATTCCACCAATCTATATTTTTATTTTATTACTAA
TTTATAATATATATTTATAAATTATTTATAATTGTGTTTGTCGCAGTACTAATTTTGGTTAATGTTTCTTC
AAGGTTTAAAAATACTTTCTTATCATCATTTTTTGCTTCTAATGCAAGATCGTCACATCGCTGATTATAT
TCAATAAAGTGAGGTAGTAATTCTTCTGGAATATGTCGATTTCTTTTTGATGTACCTTTTTTAAATGAAT
TAGTAGTATGTCCTTTAACCCACGTAAAATTAAATTCATATTGAGAAGAACTATTATTAATAATATTTA
CTAATAACTTCCACATCTCAGCATTCTTTACTGGTGTTCCTGAACTACTCATCCAGTTTCGATTAATCCA
TCCAGTCATATATTCTGTAATACCTCTGATAACGTATTGACTATCTGAAACAACACTAATATTAAACTT
```

```
TTCTTTATTACCATTCTTATAATTATCTCTCATAATATGCGCTATTCCATAAATAACGGCTAATAATTCA
TTTTGGTTAATTGTTGAATCATGAAAAGATCTTTTAATACTGTATAGCGTATTAAATTCGGTGTCAGTA
ATATAGCATCCAAATCCTCCATACATAGGCTTACTGGGGTCTTTCCTACCATTATTAAAGCTACTTGCA
TCCGTAAATAAATATATGTAATTTGTATTATCGTTGTCCAATATATTTTCACTCCCACGTTTAGTTATTT
CTTTTCGCCTATATTCTATTATTGTAATTCTAGAATAAAAAATTAATTATAATAAACAATATAATATAA
GCACTTCTATAAGAAAGGTCTGATATTTATGAAAGTTCCAAATAAGAATATAATAAATGATATTATAG
ATAAGGAACTAGAAGAAAATAAAACATTTGTAGTAGATACTAATGAATTTGATACTGAGAATATGATC
AATAGTGTTGTTCCTAGTGAAGAAAAATTTAATAAAGCTATTGAAAAAATTATTCGTAAGTCTAATGA
ATATCGTAGATATATCGGAATACTGAAAAATAATATTGATCTAACTTCTTGTAAATTTTTGAAACGTGT
TGATGTTTCTGAAATAAGAAGAGTTAATATTGAAATGCATCATTACCCATTTACTCTCTATGACATCGT
ATCTATGCATCGAGAACGTATCAAGCAAGATTTAGGTGAATTTTATTCATATGATACATTCACAATTGC
AGAAAATATTATGAAAATGCACTATGAGAATAAAATCGGTATTGTACCTTTATCATATACTGCTCATG
AATTAGCTCATTCCGGAAAACTAGTTATTCCTCTTAATAAAGATTATGTCTTTGGTAACTGGCAAGAAT
TAGAAAAAGAAGATATTATTATTACAGATAGTATGCGAAAGCAACTAGAAGTATTAGAACAAATGAC
AAATAGTATTGAGTCTGGAAGCCTTAACTCAAACGAAGATCTATTTAGTAATATTCAGACTGTAATCA
ATATGAAAGTTCTGGAATACCAAATAAGATTATAAAGGAAAAATCAATCATTGAGGATATTAATAAT
CCTGAAACTGATGAAGATATAAATATAATAAAAATCCCTTAACGTAATAATAATACTATACGTTAAGGGA
TATAATGTTATATTATGATTTTTTGCCATTAACTTGATCTAATAACTTATATATGAATAATTCTTTATAT
ACTTTCTGATCTCTATTATATTTATCAATAGTTGCTTTTTCATCATCAGAAATAACTTCTGTACTAAAGT
CTTTAACTTTAATAACCATATCTAACTCTGTGTTTAAAGATTCTGATTTTAATACGATATGGAATAAAT
TTATGAATTTAGTATTTTCACCTTCAATAAATTCATAATTATCTAATAAAGAAATTTTCTTATCAACATC
AGAAGAACTAAATATTTTTCCAAAGAAATCATCAATATATTGATTAATTGATAGTTTAATAATTTCTTC
TTCACTATAATTTTTATTAGTTGGAATATCCTGAGTGTACCAAATTTTTTGAATTTTATCATGGAGCAAT
ACATTAAATACGCCCGGAGAATTTACCATAATATTGCTAACAACAAAGCTAATACTAAACGTATATAC
CTTTGGCTTAGTTTCTAATTTATCATCTGAGTTACATGATCCTTCTGATGAAGTAAAGTTATAAAATGT
ATTAAATTCTTTTACAAACTGAGCATATAATCTTTCAATAAAATTATCTTCAAAAGGTCCAAAATCTGT
ACTTAATGGAAGTTCAAGGTCTCCACTCTCCATTAAATTAATTGCTTCTTGAATTGATTCAATTAATAT
ATCAATCTTACTATTTACTTCATTATCAATACGATCAGTTACACCTTTCGGACCATAGATATTTAACGTC
ATATATTCATTATTGTTATCATTCTTATTAAGTACGTCATATGTTACACTAGTAATAACTTCACAATTAC
GTGAAAAATCCAATTCTTTATCAGTGATATCATCTAAATCTTTGATATCACCAATAATTCTTAAACTAA
TAGCATCCTCAATATTAGGCATCCTAATTCCACATCCATTTCTTTTTATTTGATAATAATTTATTAATAA
ATAAATATAATTTTTTACATTCATTTACAAGATTATACATTCCCTATAACTATGATATATTCAATAGTTA
TAGGGAATGTATTTATAATTAATTAGTGCATTGTATTAATATATTGTATATACGATGAAGCGTTATCCT
TTATTACATTATCATGTTGTCTTATTTCATATTTCGTTAACATGAATTAATGAAGATATAAGTTATAAT
AAAGAATATATAACTAAGTATTAATAGTTTTAATAATAGTTTATTTTTAGTTCGATTATCTTGGTTTTCA
TCAGTATCTATATTTTTTCTTAAATTCTTCATTAAAAAGTCCCCCTTTTATTCTATATATTATATTGTTTT
TTAATAAAAGCGTAATAAACGAATATATAGACATATATTATAATTATGATAAAATAATAAATAATATA
AAGAAAAGGATGATATTATAATGAAAAAATTTGTACAAGTATTATTAGTAGGAGTTCTATTAGCAGTA
GCAGTAACAATTGTAACTATTAACGTTACAGAAAGTAATAACGGTACAATGCAAAAAGAATTATTACC
AAAAGAAATTTTAAATAGACAATAGTATAATTACTACTATTGTCTATTTTTTTTTTTTAGTTGATTAAGA
ATATTTTATCATAATCTAGATTATCGTTGAATTCTAAAAAGAAGTCCCCAACATTACTTACTGTACATT
TTCTAATAGAAGATACTCCTTCATCTATTGGTGTAGTATTATTTACTTCTAGCGCCATACTATTATCACT
ATAAACTCGGATAGATATTTTCCAAGAATAGATAACTTCTACATTTTCTTCATTTAATACTTTTTGTATC
ATGTATAAGTGATATATATTGTCATCATCCCTCTTCATATCGTTTGGGAAGATGTATCCAATAGTTTTAT
CATTCTTATCAAAATAAAAATTTTCCACAATAAATTCTTTGACAAGATTAGTATTCAGTAATTCAATAG
CGTTATTTAAGAAATCTTGTCTAAATAAACCTAAATTATGAATATTGATTTCTAGCATATTATAATCCA
CACCTTTTTCTTTTTCTTTTAAGATATTAATTCATTATTAAGATAAATGTTTACACTAAAGTCATCTTT
AGAAGTATTATTTATTTCTAACGTAATAATGTAATCATTGTTAGCACTATAAAAGATGTATTCTTTTAT
ATACCTAAAATTATGTTGTTTATCAATAAATGAATCAATCGTGTTTGATGTAATATCCCCCTTATAATC
TTTGATATAATTCTTATCAAAATATATTTTTGCTTTATATATCTTTTCTTTAATATATTCAAAAGATTCTT
TGTTATCTGCAGTAATTGTAACTTGATTATTTAGAAATTTGATTAATCAATATTAAGTATATTTACTTC
ATTATGATTATAACAAACGTTCCATGCAGTAAATATTTCTTTTGAAATAAACTCAAAAATATTATTATC
CCCACTGTTATTCATAATAAATTTCCCCCGATATATTTATTTGATATAGTAAGTTTTATTCTAATATTTA
TTTAAGTTTATAATGATATATTATAGATATGGCAAATATATAATATATATTTTAATTTTTCATTAACAAT
ATTTTAAGGAATAAGGAGTGCTGATTAATGTATAGATATATACGTACAAACGGTTCTATGCGAAATAA
ATTGAAAGAAATGAATATTGATAAGAATGACAGTATCTTTGAAAATACTGTTAAGATTATTAATGAAT
TAATAAATCATTTCTATTCAATAAGTGAAGTATTTAACTTCATAGAAAAAGAAAATATTCATATCAATA
ATGAAGTGATGCAATATTTAAGTTCTGATGAATTTTATAAATCTGCATATACTTCGAAAATAATGATGA
AGAATCATATGTCTAAACATTCATTTATTCGCATGATAAAAAATGATTTGTGTTATCGTAATATTAGTT
TTATTTTTAATGATTCATTATTTACTAATGATGATATTGCCACGATAATAGTTAGGAATGATCTAGCTG
AAATACCATTTGATATTATGGTTAAGGAAAATCCATTAAGCTTGAAAGATTTTAAGAAGACTTTAAGA
TATAATAATTTAAATGATCATGAAAAATCTATTTTAGAATTACGTAATATTTAAATTTATTAAGAAAAA
AAAAGATAACTATTGTAATTTTAATAGTTATCTTTTTTTCGGATCATAGAAATATTTTTATATATTATAT
AGGATAATCATATTATATATCTTTAATGATGATAATCTGTTGGCTAATTCTGGACTTCTTTTCTCTAATG
AATAGATATCGATAGCTTCAATAAGATTAATTACTTTAATAAATCCTAGATTTCGATATCTTTTATTTAT
TAAAACAAAATTAAGTAATTCTATGAATTGTATTAATCTTTCAGCATGATACAACGATTTTATTTTATA
TTTTTCTTCAACATCAGCGAGATCTAATCCATATTCTTTGTAGTAATTTTTCTTTAATAGCGGCTTCATC
CTACGTATCATGATACTAATATATCTTATTAAGTTCATTATAGGTAGTTTTAGTATTCTTATACACTGCCA
TTTTATGAGTTTTAAAGTAGTTATATAAGTAATCTATTATATCATTAAAGAAATATTCGTTTGCATAAA
TAATCTTTATAAAACTAGACTTTGGCATAATAATATCTAATATTTTAGGGTTAATCGTAATCCGAGTAT
TTTCAACCCTTGATAAGAATTTAATATATGTTTCAGTTATAAATTTATATACAACTTCTGATTCAATATT
AAACTTTTCACAAAAATTACATATGACATCATTGATATCATACTTATTATCACAACAGAAGACGTAAG
ACGAAATTGTATACAATAATAATATATTCAGTATTATTCATATTATTCATCATAATAT
CACTTATCATGATCATCATATTTTCAGGTTTAATATCATATAAATAGAATATATTTTGATAGTATGATA
ATATTTGTTGACTTTTACGTTTATTATTCTTTAATAAGTACGTAATAATATTCATAGGTAATAATGTAAC
CGATTCCGTATCTTTTTTATCTAATGCCCTATTATTACCTAAGTATGATAAGATATCGATAATATCACCA
AAGTTAGAAATATCATTGTATATATCTAGTATACTTTCAATGTTTTCATTTAATGACATTGGTTGTAATT
TATATTTATACGTTATCATAATTTGTCACCTGTATTCTTTTCAATGATATTTCTAATTTTATTATTAGTAT
ATTCATCATTTGAGTAAATTCTAGGTAATATCTTTGGTTTATTCTTATTAGAAGGAAGATTATCAATTAT
```

```
TGAAAAAATTGATATTACTTTATTAATAATATTTATAATATTGGTATTTTTAGATTTCAATAACTTATTA
ATGTCATATGATAATAATTCATTATCACTATCAAACTTCTTATAGAATGTAAAACCGTACATATTAATA
TTATTTTCTAGTAATATTAACGTATCCATAATATTATTATATCTTACGTCATCCAATTTATCTGAATACT
CCGTTCTCATAACAAAGCTTATTACTTTAACAATAAAATCAACTACGTTATATTTATTTTTATATCTACG
ATATATTCTAGGATAATTGAATATAGAATTGATAAAAGTTGATCTTTATACGTTATATAGGGATACTGA
TATAGAAGGGTCTCCGGTATCAATAATTCTAGTAATATTTTCATATTCATCATCAATTATATTATCATTG
TTAAGATATTTTAACAATATATATTCAATATATAGTAAATTCATATTTAAAAAAGGATCTAATATACAT
TGAATTTCATTAAAATTTTTAATATTTATATCATATCCCTCATACATTATAATATTTTCGATAAACCTTG
ATTTTTCAGTGCGAGAATAATCTTTAATTTTACAAATATTATTTTTTGTTAAGAGACATTTATACTTCAT
TGTATTGTTATTAATAACCATATCCCTAAAAATTTCTTTTGTATCTTTTGTAGGTTGATCTACATATTTA
GAAAATTTACGATTAAAATCAATTGTATCCCTTAATGATTTTGGATTATAGGTTCGTGAATTAATTTCT
AAATATTCTTGAATGTCTGTATTAATTGATATACTATTTGTCACGCTATATCACGTCCTATCATTTATTA
TATGCTTAACAAATTAATTCGGCTTTTCATTAACTTACATAATTCATCTATTCGTTTAATATTATTAAGA
GTGTTCTTTCTTATTAATGAATTATGATTATCCGCACTAACATTATCTTCATATCTTCTAAATAATTCAT
AATTATTATTAGTATAATCTATAGAATCCAAAATTTTAATACGTGCATTATTTTTTACGCTAGTCATTTT
ATTATTATTAAAATTAATATATAAGTTTAATAATTCAAAATAATGGATATTCTATCAATACTGCTTTC
AAATAATATTAGATCATCTTTATTGTTAAAATTAAGATATCTAGATATTCTTAATGCACTATGAGGGTC
TATTCCGATAATACTGTTAATTGCTTTTTTACTATTAAGTATTATATCTTTCTGATTATCTGTAAAAAAT
TTAGAATAACCACTACCATATATTGTATTGAATATTTTAGCCATTGATGATTTACTAATAAATTTTTTAA
AATGTTTATCATCAATATCTCTAACGCCATATATCGCACAGAATAGATTGGTTGAATATAGATTCATTT
TGTCAATCATAGTTAAATATTCATTATCTGTAATTGTAGAAGATTCTGAAATGCATGTTTTAAACTTTTC
AGATATCCTATTTCTTATACCGAAGTCAGGATCATCGTCATTGGATATATTGTTATATGTGTCAAATAG
TCTAAAAATAATTTTTCTAATGTATGAAGAGTTTATTTGTAAATTACTACTAGTATACTTATACTTCTTA
CTAGATGGTGATATAATAAAGTCAATTAAATCGTCAAACAGTACACTATACATGGAATTATTATTGAT
AAATGAATCATATAATTTGTCAATATTCTTCTTAGTAATTATATAATTACTATAATTCATACTTCTTTTC
GTATATATATGATTAATATTAACATATTGAGTATTATCCATAAAAGTACTAAACAGTTTATTGTATATT
ACGCTTGACCTAATACTATATTTAAACATAATGTAATCCTTTCTTAAATATTAATGTCCTTAATATAAT
GACGTAATAATTCCTCGGATATTCCTAGTTCCTTAGACATTACTTCAATAGGTTTGTTAAGATTCTTTTC
AATATAGTCTGTTATATATTGTTCTGAACTACGTGAATTACCTACCTTAATATCAGTAGTACTTAATGG
CATTTTAAACCCAATAGTTCTTGGGTTAGTAATTTTTTCAATATTCGGGAACTGGATCATTCTTAATAATA
TGGTCTGGTAGTTTCATATTATGTTTTTCTAGGCTACAATTATCCAATCTTTTAAGTTTATCTAATGATT
CATTAGTAATGATAATCATTAGATCGTTTCTACTTAGGTCTACTGACATTTCTTTCACATTTTCATCATA
AAGTAGTGTAGACATATGACTAATAATATCATGTGAATTTTCCAATGTAATATTTTGATCCATATATTT
TCTAATATATTCGACTAATTTTTTCTGCATATTCCGATTCCACCAATCTATATTATTTATTAGAGATTAT
ACGTATATCCATTCAATTGTTAGGTTGTTTAGAATTACCTTCATTTAGTTTTATATTTAATACATATTGA
ATATTGTTTCCTTTATTAAATTTAATGTAATACTTAGTCATATCACCAGTAGTATTATTAATAAGTCTAA
TTGAATAGGATTTCTTACTATGTTTATTAATATGAGTATATAGATTATCTTCATCCTCTATAATGATATT
CTTTTCTGTAAAGTAATCTAATATAGATTCTATTCGTTTTAATTTATTCATCCTTATCGAATAATAATATC
GATAAGGATGAGAATAATATAGTTAACATGATAAATATAATCATATATCCATCGTTCCTTCCATATCTA
TTTTATGGACATTCATTAAAGTAATATCATACTTTTTAACTTCAATATCAATTGCAGTATAGTTTACCAT
AAATGTATATCGATTCTTTCCAATTTTACTAAGACTATTATATATCTGGATTGAATATTCACGGATATTT
GGAGAAGTTATTATATTCGTATTCATTTTATTATCATATTCAGTTAATTTATCAATAATTGAGTATGATA
ACATGATTTTTTTATGTACAATAGATCTGTACACTATTGAGACTATAAAGATTATAATCATAATCGATA
ATAATAATATCATTTAAACATCCTTTCTTATATAGATTTATTTAATTTTTTGATTACTGATATACACAAC
TTCTTTAAAGTCTTCATCATATACTAATTCAAATTTATCGTTATTGTAGAAAAAAGTGTATGTATTATG
AGTCCTATTTAAAGATCTTTCACAGTGATATAACAGATCTTTAAATACATTTTCCGGATTTACATAAGA
TTCCTCCATAACATTTTCATATCCAGAAAGAATTAAATAATTTCTAATGTCTGGATAGACTTTTTCCTTA
AGAAACTTTGGATCCATTCTTTTTCTAAATTCAGCCCCAAGAATATAATCATTTATAGAATCCATTATC
TTATCAATAATTAAAAATCCGATTAACACTAAAGTAATACTCCTACAATATTAAATAATAACATAAA
TTTATCACTATCCTTTTCTTTTTATATATATATAAAAATCGATATCACTCCATTATAGTAACAATTATTG
GAGTGATATCGATTTAATTTTAAGTTATATACTAAGAATTATTTCGTGAGATAAATATTTCTTAGTATA
ATGAAATAAACATGCTTTAGACTAATAATAAGATAAATTGTCAAGGGGAATTTGATCTTTATACATTA
TTTTCATTTAATAACAAGTTTATTTATAATTCTAATTATTATATCAGAATTATAATATATTATTAAAATG
TAACTATAAATTTTTATAATTATACATTGATAATCATATCTACATTAATATTTTTCTGTTGAATCATTAG
ATTAGAATTCTTTAATGTATTATTAATTTTATTAATATTTAGGTTATCCGACTCAATATATTTGTTGATA
AATACATCAATGTATGCTTTTGGATTATTCATTGAATTAATAATCGTATCTTCCATATTATCAATAGGTT
TAGGAGATATGACCATATTGATAATAGATGACATTTCATTAGTCATTCCCGCTTCAATAGTAATCTTAT
CAAATATATTTTTTTCATCTTTCCATAAGGTATTATCAATATTCATTTTATTAATATTGAATTCTTCTAA
AATGAAACAATTGTTTTCTAATACATCTTTTATTTCATGAGTTAGAGTGATAACGTTTCTTAACCAAAA
GGAACACTGTTTATTAAGTTCTTCTAGAATTACATTCTTTTGAGATATATTTTCCCTTAATTCATCAATA
TCCTTGGTGTAGTTATCATATCTATTTTTATATAAATTATATTCATCCATATTGGATTCTTCTAATTTTAT
ATCCATAATTTCAGAAACAGCATTTTTTGCATCTATAAATTTAGATATCAATTTTTCAGATCGATTAAT
AGTGAAACCATTAAAATATTCTTTTGCCTTACTATTAATACATAAAATATGTATCATATAGGAAATTAAT
AGTTTTTTGTCTATTTTCCCTTAGCGTATTAAGATCTTTGTTATTCAATGATTTTCTAAATTTAACTGCTA
ATTCATAATCATTATCGATATTGTACCTTCAGTGCTGATGATATTATAATAAGTAGTAGTATTCTTTTT
TAAAGGTTTATTGATAATATTTAACTGAAATGTTCTAATTTCCTTCATACTTACTCCCACCACCATTATT
ATCTAAATATTTATCATACTAATAATATTATCTAATTTTTCACTTTTAACAATATTTTCATTTAATACTA
AAACATCATTTATATATGGAAAACATTCTGTAATGTGTTTAATTAAATACTCGACGTAATAGATCTTTT
GATTCATTAGTACTTCTTTATGATTTAATTTATACCAGTATATTTCAATAAAGTCAATTGACAACTTTTG
TCTTCTTGATATAATATCCCAACAATCATCATCAATATATACTGATATAAGTTCATATAGCGTTTTTTCA
TCAAGATTAGCATAATAGATATTCTTCTTCATATATTGGGAAAACTTTATTAAGAATTCCTTACTATAG
TTACAATGCATAACAATATGACTATCCCAAGGAATAAAATCTATATTTTGAGAGTATTCTTCAATTGTC
ATGTGTTTGTATATACTATGATCAAATATTCCCAAAATATTTTAGTTTGGTTTTTAGTAATAAATTTCA
TATACATTTTATTTATATTTCACCCGATAACTAAATCTAAACCATTCAGGATCATTTATATCTTCTTTTTT
AGTCATATCAAGATTAAATAAGACCCCAATAAATAATCTTAGTTGATTTATAAATCGCCCTTTATACGT
GTCCATTATATTCAAGTTATTCTTTTCCTTTCTTAATATAATTATATTCCATTTATATATTAACTATTTAT
TTTATACATATTAAAACCCAATAGATATATAGTAAATATCTATTGGGTTAGTGTTTTATTCAGAGATCT
TAACTGTACATACTAATGGATTATGCTGTAATTCACTAACTAATTTAGGAATAGTTGTAAGTTTATATC
TAATAGATGGATTTTGTTTTTCTTCTTCCAATATACTAATCGATTCATGAATTCGAATAAATTTCTTCACG
```

```
ACTAATTGGTTTAACAAATATTGCAGGCTTACCAGTATTAATATTGATTCCCTCAATAATATTCATTTC
ATCATGACTTGATAAGTAACCCACAATAATCTTAATATTTTTTAAATCTTTATACGTTAATCTTGTTTCT
AATAATGAATCATCTTTCATTACGCATAAACTTCCCTTCCAGTTTAAGTTTTATTTTATATAATTATTAG
TTAAACTAGTATATAAAAAATTAAACTGAATTATAGAATAATTTATTTAAAAGAATATAACGTACCTTT
CATATCATTATAATAACTATATTTAATCGATTTAAATTTATCCATACTATTGAAGAAGATAAATTCCGG
AGTATCTTTCTTAGGAGGATAGTTTACAATATCAATAATATGAGCGATAACTTGCATATCCATATCGGT
ATATTTAATATTAGATAGTTTTGTTTTTGATCGATTTACTGTAGTTTTTCTAGTCCTTTTATCAATGTAA
ATAGTAATTTCTTCGGGATTTTCAGTAAGTTCTTCATGAATTATATTGAGAAATTTACCGCTTCAAGA
TACGGTTCTAGCGATGTTTCCATTGTACTATTAAAGTTTTCTTCATTACTTTTAGAGTTGATCATATTTT
TAATATTTTTTAGTTTACCTATTGTTTTTAACATTATAATTTCCACCTTTAATTATTTATTTGTTGTTATC
ATATTAATAAAAAATGTATAGTCGATAAAATTAGACCCATTGTCTCTAATAATTTTTACATCATCTTTA
AAATTAACATATTCTTTAATAAAATCGAGATTATGGGTTTTTCCTTTAATCGATTTTGAGTCAATATCGT
TAATTGCAAGATTTCTTATAACGTATGGACTATCTTTAGAATCATAATACAAGTTATGGATTCTAAGAA
TAAATATACTATTATATAAATTTTCTTTTAAGAAAGATAAACTTTCAGTGAATCCTAATTCATGAGTCT
TATCATTATATCCAGTAATATGACCAGTGCTGACATGTCCATTACTATGGATAATTTCAACTTTATTATT
AATTAATGATTCAATATTCGTTTCGTTTGTATACTTATCAAAAATAGTATGATTAGACGCATTATAAAT
ATTAATATTCATATCGTCATCAATTGTATAAATATATTTTTTTGAGATAAGTTTATCGAGAATTAATTTT
AATGTATTTTTTCTTAATTTAAATAAACGCTCTTTTAGATAACATACTTTATCAATATCCGGATACTTTT
CTTTTAGTGAATAATCTTTATTGATAGTATTAACGTCAATATATGATATGTATTCAATATAATGAAGAT
TAATAATATCATTATCATTAAATGATGTTAATTTCTTTTTAATTGTAGTGATATTCATTACTTCATAGTA
AATATCATTATTAATCTTTTCTTTTAAACTAATAATCAATATTTCCTCAGACTTATCATTTGTAAATAAG
AAACCTAAATTGCTCATAGCACTTTCAATAAAAGAAATATTATTATCCATTTAGATTTACACCCTTTCT
AATCTATATATTCATTATAGTTAATGCATCTTTAAATTTTTGATCTTCATTCATATATTTAATTAAGTAT
GGATGTTCTTTAAATTCATTATCATACTTAGTTAATTTATTATAGTATCTAATAATAAATTTTTTTGGTA
AGTTTTCTTGACTTCTCGATATTTTGAACCATAAATTAGCATTATCTAAGGGTACAGTGCTTAGTATAT
ATTCAATTGATTCTATTGGTAATTGGTATCTTGAAATAGTCATTATAATTGTGTGCAAGTCAAAATATT
CTATATATTTTAGTATTACGCTTAATTCTAATTTATGGTTTGAAACGATAATATAATTCCAGAATAATTT
TGGAGCATATTTATCAAGAGAAATAATATTATCTATTGTTACATCATACTCAATATCGTATTGAGAGAA
TATTAATTCTGCAGTTATATTTTCCCAAATTTTAGTATTAATATCTATACTGTCTGCATACTTAATAAAT
AGATTAATATCGTACAGTAATAGTTTATAATTATATCCTATGGAAAAATCTATATTGTCAAGAATATTA
GGATTATTTCTCGATATATCTAATATTCTATTGCATATTTCAGGAATATTGTGATCATATTTATATGAGT
TAAATTGAGATTCAATAAAAGAAGGGTAGTAATTTTCTTCACCAGTATCATACTTTTTATCAATATCTA
TAACTAATTTAATTATATCGATTTTTTCATTCTTTTTAGAAATAATAATTTTTCTTATATCTTCGTTACTA
ATAGGCTCGGTATCAGTTCTAGACATAATATTCTAACAATCCTTTCTATTATTAAAAAATAAAATCTGA
GACTATAATTGATCATATAGTCTCAGAAATATTTTATATTAATCTTCTAAATTATTATTTAATATATTCA
TAGACATATTAAAAATACTTCTTGAACGTTTACCGATACGATTTATTGTTTTTTCAGATATATTTAAATA
ATCTTTAAATTTTATCGGAAAATACTTGAGGTACATAGAAATTTGTTCTGGATTATCAATAATATTGTT
ATCAATGATAGTTCGAACAACAGTATAAATTTGACCATTAAGTAATCGTCAATAGTTGTTTGGATCGT
ATGCTTGAATAATTCATCCTTTCTTAAATGTTGATGATCTTTATACTCCATTTTCATTCTAACTTTAATA
TAAGGATCGTTATAATCTTGATGATCATTAACTAGAGATTCAGGATGAAATATTTCATTAAATAATTTA
ATATCGTCATTTTTTCCATATTTTATAATAATATTTGTAATTAATAATCTCGAAATTTCACCAATTTCAT
TATAAGGAATTTCTGATTCTTCAAATTTTAATGTATAATTAATTTCTTTTAAATACTCATTATAGTATCG
GTATTTATAATTAGATGTTAATGCAAGAGAAGTTACAAAGTTAAGATTATTTTGATAACTTCCTACTAA
TCTAACTTCATTATAAAATACATTATCCTTTATAAGTTGATTAATGATTTTATAATATCTTTGCATTAAT
ACATTAAACTTATCGGTACTACAATTTTTTGGTTTAGTAATTGATTTAATTAATGATTGTTGGGTATTAA
TTAAATTTTCCATTTCGCTAAAGTCTGAAAGAACAAACTTGTCAGGATCAATATTCTTTAATAAGTTAT
ACGCATACATTAGAGTATTAACAATATCGTAATCACTACAAGAATAAATATTGGTTATTTCGCATAAAA
TTATACTTGAATTCATCACTAAATTTCAGTAATTTGGTATGGAATACCGTTATTAAGAAATGAAGTTATA
ATGTGTTTAACTTCTTGAACTGGTGAACCGGAATTAAATAATTTTTCAATACATTTAATTCCGTGATAA
CTGAATTCTAAGTCATCTATATCATTACAATAGTTCTTTTTAGGAACAATTGAATTCTTCGTAATATTCT
TATGAATATTACGAAATTCCCTATGAAGATCTTTAAAGTTCTTTTTGAATGTATCATTATTACTAGTTTC
TTTTAAATTAGCATAAATCTTAATTGTATTATTCATTATTTATCAATCCTTTAATATATTTTTATTTTTCA
ATATTAACTTTAAATTCTATTCCTTGATCTACCATATCATAATCAATATCAGCAACTCGACCAACGCTG
ATAATATATTGCTTGTACAATTCAGTATCTTTAAGATTATGACCAAGATATGCAGTATCATATCTGTCA
CTTTCAATCTCTCCTGGACTATATTGAACATTGGAGATCGGGTTATCATTTAGATCTTTTAATACGTTAT
ATTCTTTACGATCAGTATCAAAAAGCCTATTCATTGAACCTTCAAAAGCTACTTCACCATCACTAAAAT
TTTGTACGGATGAACTTACTGTTAAGAAATATAGTGAGTCAGTTGTTCTAACTTTATCATTAGGGTCAA
AATTAGATGGTTTTGGGTCATTATCAAACTTAACCCCTTTATTAGGAATAATATCCATACGAACTAGAG
CTACTGTATAATCAGTGGCTTGTACTGGTCCGATTGTAAACACATAATTTTTCAGGAGAATTACCGATAA
CTGTCATAATAATTTTATAATCATTATCATTAGTTACCCTATAGTCTCCTACCTCTGTAAGTTCATATTC
TTCTTCTTTTTTGGTTTTCATAAGAGGTTTAAGTTCTTGTATTTTTGATTGAACTGAATCTTTGTTAACAT
GATTACTATCATTATTTAATACAAAATAAATAACTACTGATAACCCTATTAATAATACTACAAATATTA
ATATTTTTTCATTTGAAAGTTCCTCCGTTTTCTAGATTTTTATTGATTTTATATATTACTTTTAAACCTT
TAGCAAATCTTTTAGATTTTACATCTTTCATACTAATTACATTACTTTTCTTAGCTACTTTTTTAATTTTC
ATAATTGATCCATCCTTTATATTTTATTTAATCATTATTATAATATATTAATGAAAATTATATTATTACG
CTAAAAAAAAAAAAATCCGTAATACTCATAAAAGAGTATTACGGGAATATTTATATTATTTAAAATCT
TTCACATATATGAAAACCATGATCAGTGGCTAATTTATAATCAAAGTTTAATCCTAGATTCATTAAATA
AAACTTATCAGCTTCTTCCTTACTGAATGTATTGATTAATGTTTCTAGTGACATATGACATTCTTTATCA
TAATCATAAGTTTCGCAAGAAGCATCATGATATATCTCATCAAAGTAACCTTGATGAATAAGACTTTC
AATATCATCACCGAAATTATTTGCGTCACCACTATAATATATTACTTTTTCATCAACCTTAATAATATAT
CCATACGTCATAATGCTCGGAGAATGTCCAACAGATACTGCTTTTATTTGAACGTTAGAGTCAATATGA
TAAAATTCATATTCTTCAATAAATTGTATTTTATAATCTACGTCTGCATGAACATCATTAATCTTTAATA
AATTAACGATATTTTCACCATATGATAAAAATAGATTAACTTTTATATTATGAATATGTTTAAAGTATC
TAATAAATGTTGGTAAGGAACCTATACGGTCAGCGTGAGTATGAGTAATAATTACATTAATGCTATCA
AAATTCTTTATCATACTATCCGTAAAATAATCATCAATTAATATATCAAACACCATACTTCCACAATCA
ATAAGATAAAAATTGTTATTATTAATAAAGTATGCAGACGTATTTCCTAATTCTGTATTAAATTCATTT
CCGGTTCCTATAAAATTTAGTAAATTATTATACATTTTATATACCGCCTTTATTTTTTTTTTTTTATTATTT
TTTCTAAAAAAAATATTGGATATTGTCATTTATTTGACAATATCCAATAAAATAAGGAAAGTGTAAACT
AGTTAGAATATTACACTTTTAGACGAAAGAGTAATATGGAGATAACAACTAGTCGTACGGGATTAGAG
```

```
ATAGTTATATTTAGGCATAAGATTTACCTAAATATAATATATTATTATCCAAAATATTAATTTTTTATTT
TTACAGTTTACGCATATAAATCTTCATTATAAGCGTATTGAATTCTTTATTGTATGAATTAATATCCGTA
ATATTATAATTATGACCAATAAGATTATCATTGTTAATATTAGAATTATATACGCTAATTGCATTATTA
TATAATGCTTCTAATTCATCATAATTTTCTAATAAACTATACTTGTAATGTATATATACAAAGTTACTTA
TAATCATATCGATAAATTTTGAATCGATATTTGCAAAATATATTTTACTAGAATTAGATATAAGCGTTG
GTATTGTAAAATTACCATGATACATTTCAGCATTAAAATAATTCTTCTTACATATTTCATAAATAACAG
TATCGTCATTACTATTTAGATATTCATTATACGTCATATTAATAAAATTTGCAAGATTGATTGGTTCTGT
TTTGATATTTGAATAGACGATATTATTTATATGATTTATAATCGTGTAGCGTAGATCGTAATACATTTTC
AGTAATTACACTATTACTACGAGAAAAATTTTCTTTATATTGAAAGTACTTTTCAATATTAATTCTTAA
GCAATTATTAACTTCTTCTAGATTAGATCTAGATTCATTATTCGAAGTATCAATAATATCTTCCTTAATA
TAATTTCGCAGACTTTTCTCATCAGGATTATTATGTAATATATCTACTATAATAATCGCAGTTTTAATTA
GTATATCCGTAGATTTTTTATCCGATCTATTTCCAAAATTAATAATATTTCTTAAGAAATAAATTAATAT
CTTTGGATCATAGTTATACATATTTATATATCATGCTGACAAATATATTGTTAATTCCAATTCTTCCATTA
AGAATATGTTCTATAAAATAATAATACTTATTTGTAGAATCTTCATTATATTTATTATTAGCAATATAC
GCTGATTGGTTGGATACACGAATAAAGCTTGAATATAATGCAGAGATATAACTATTATTAAAATAAAT
AGTTGGAACGATATTACAAAAGAAATCAGCTAATTCTTTAATATCTATAATATTTAGTATAGATTTTTT
ATAATACTTCATAAATTCTTTTGGCGTATATTGGAGATTATCAATCTTGATCTTTTCAGTGTCAAACATA
AGAGCGTGGGACTCATTTATAAATATATTAAAATCATATATATTTGAAGTGAATATATCTTTTAGGAAA
CTATATTTATCTTTGATTAATGAATACATTGTATTTCTAATCATATTTTGAAAATATATAATTCGTAGAT
TATTACTTTTTTTAGTATTGTCAGAATCGACTAATGATTTAATTTCTTTATAATATTTTGATAGATTAGA
TTTGGAAAAGTTTCGTTAAATTCTTTACAATCATCTAAAAATTTGTTATATACTTTATCGACAAGATC
ACTATTACTGATTTCATGAGTATCATATTTATTTTTTATTTTATCGATGAATTTTCGTCATAATAAATT
CTATCGATAAAACTACTAATTATCGGCATGTTGATGTATCACTTCTTTCCATTGATATAGTGCATAATG
TCAATATGTAACAAAATGCTCTTACTCTGATCTCTACTGGCATTACAATAATCAAATTCATGCTGATAA
TGATCCAATAACATTAATGCATCGTTATATTGATTTTGGATGATGCTTGAAATATTATTACTTAATTTAT
ATTCTAAATATTCAATAATATTTAGAACTTCATTGTCAATAGGATTAATTTTTTCATAATTATTTAATAA
GTAATGATATACATTTTTATAAATTTCGACAGAATCATTACTTATTTGAATGTCATTATTTATTGAAAA
ACAAAATAACGAATTAAAATCATTAGGATCAATTAATAGTTTTTCTAAAATAATCTTAGTCTTTTCACT
TTCTTTATATTCAATCCATCTTACAGGGATATATTCAGCTCTCTGCATGCTAATGAGAGATTTAAATAA
CTTAATTGAATTTTTCTTTTCTTGCAAACTATATTTACTAAAAATAATATTTATCATATTTTCTACAAAA
AGATTAATTCTACCAATAGTATGGTTTACTGTAGCCATGTTTGTTCCTTCAATAATATGATCTTTACTGC
TAACATTAATAATAAACATTCTTTATCATCCTTCACTGTTTTATTTTATTCACATTATTATAATATATAC
TTATCTTATTAGTAAAAAAAGAACTATCACATTTTATTATGTAATAGTTCTTCTATGGATTAATTGATG
AATTAATTTCTGTACTATTATTTATTCGGTTAATTTTATCTTCTAAAGATATCAACCTAATAACATTTTT
TTTTTTATTTGTCATATAAAATAAATCACTCTTTTATTCATAATTATTCTATTATCATATGCACTTCTTTA
TAAGATATATTTATAGAAACTGTATATTAATAACAGTTTCTATATTAATGATAGTTTAACTTTATCAAA
GATGTTTCTATGATTAAGAGAATTCTTAATAAGGTCATTAATAGTTATATTTATGTGGTAAGGTTTTAC
ATTATCTTCTGCATTATAAATCTGTAAATTTATATTGTATCCATTTACTACTATAAATTTAATAATACCGAA
ACATATTCTCTTGTTACTGGTTGCTTAAAACGGTCAGACGTAAAAGTATAATTAAATGTATAAGAATCA
ATATAACCATTATTAGTTGATAAATCACTGATATTATAAGTATATTCATCGATGTCTGATGGGTCAAGA
TCTGTATTATTTCTAATAAATTCATAGATCATACTTTTTAGGATTTCCGATAGATATGTGATAGTTAATA
TTGAAGAACTAAATCTTTTACTATTAAATTTTTCTTTTATATTGTAAGTATTATCATTATATTCAATATC
TTTTGATGGAATATTATAATTAGATGTAAACATTTCGTTAAATGTTTTTCGTTCTTCAGAAGTTAATTCA
TTTAATGTTTTAATTAATTCTTTGTCATTATATAATAAAAATGAATTAATTTATATGGTACGTAATATTCC
CATTAACATGTAAAGGTTTACTTAAAAATCCTAGAGATTTTACCATTAGATAATTTCCTTTCTTTTTTTT
TTTAATATTAATTTTAGATATTATACATTTTAATTCTATCATAATATTTGATATTCTACTTCTTTCCTTTA
TACTTATATGGATTCAAGAATCATTTTATCATATATTTTCATATGTTTCCCACAATCAAATAATAGATC
AATCATATTAATATTTTTGTTAAAAAATTTTATCATTAATGAAAAAATCAATATCTAATTCATTGCTATCT
TTATCCATACTAAATTTAATTTTGTCAGAAATAAATGTAAATTTAGTATAAGGATGATAATTCTCCATA
AATTTATATTCGGGTATATCTTGAATTCTTATTAGGGCAGAGACTTCAAATTTTAATATTAATGCTAAA
AATTTCTTAAAGAAATTAGATTCTAGTATATTCCAGACGCCAAAAAATATCATTCTCTCGATATTTACTA
AAACTAAATATACGCTCTAAGTTATCAATCATTTCCATATTATTTAGTTTTGTCAATTTTTCTTCTAAGT
CATCATAAATCTCAAATATTTGTACAATATCATTTTGATTTGTTTCGAAAATATACATAGATACTATTTC
CTCATACACGCTATTATCTATGTATGGAATAAATGAATTTTTAGCTGAATCTTTAATCGGTTTTATATTT
TTCATGTATACCATTCCTTTCATTCTTTAATTTCAAGAATATTATCGGTGGGAGAGATATCAATTAAAGATA
CCTTCCCACATAATATATGTAACGATTGTTTAGTACAACATATCACTATATTTATTCATAATATTCTTTG
TAAATATATAAAGGACTTGTTCAAATTCAATATCGGTCAAACATAATTTACCGTAGGCTTGACGATTAC
AAAATGATGAGATAGTTGATAATGAATTACCATGAAAAACCATTCTTTCAAGCACTCTGTTTTGATTGT
CATTAAGCTTATCATATTTTTCTTGGGAAGTGATCATTTTAGTAGGTCATACTTAATAGATCGCCTTCTAA
AGTATTAGGGAAAACATAATTACCTTCAGAATTTAAATAAAAATGGTTAAATCGATTTAATATTTCTTT
TTGATAATTTCTTTTGTTTTATTCAACACTATTAAAACCCCCATAACCAATTAGAATTATTTATATACT
ATATATTTATTTATTAGTATATCAATTTATTTTGAGTAATATGGAAAAAATTATTTTAAAATCCCTAAAT
AAACATATAAGTTTACTTAAGGATCATAGATATTTTTAATTCTTTATTTTATTAAATACTTTTTAATTTA
TTAATATCAATTAATTTCTTTTTCATACTTTCAGGTAATATTTCATCATGATACTTTAATATTAAAGGAA
TATTTAATTTATCAATATACGTATCAATAAATTCTAGTGATATATCTTGACATTTGCTAATAATATCCCA
ATTAACTTTATCTTGAAACTCAATAATAAAGTCTTCTGATAATGTCTGGTACCAACTAATAAAGTACCA
ATCTAAAGAATCTTTGAATCTACGAATAAAATCTTCTGATAATTTCTGTTGTGAACTAATATTATACCA
ATCTAATTCATCTTGGAACCTTTCAATAAATTCTTCTGATAATTCTCGATACCTACTGATGCTAAACCA
GTTTAATTTATCTTGAAACTTTTCAATGAATTCTTCTGATAACTCTTGATGTATGCTGATGCTAGACCAG
TTTAATTTATCTTGAAACTTTTCGATAAATTCTTCGGATAATTTCTGTTGTGAACTAATATTATACCAAT
CTATTTTATCCTGAAACTTCTCAATGAATTCTTCTGATAATGTCTGATTCCTACTGACATGATTCCTATT
AATGGTTATTTTTTCCATAAATAAGTATACCACCTTTTTGCTATATACTTTTTAATTTAATAATTTCTTTA
TGTTTATTAATAAATTCTCGTGATACATTTTGAATCGATTCAATAAATGCCAATTTACTTTATTCTGAA
ACTTCTCAATAAACTTTTCCGATAATTTCTGTTCTCTACTGATATAACTCCAATTTACTTTATCTTGAAA
TTTCTCGATGAATTCTTCTGATAGTTTTTGGTCAGACGATATATAGTCCCAATCTACTTTATCTTGAAAC
TCTTCGATGAATTTTTCGGATAATCTCTGATATATACTAATATGCTTCCAATTAACTTTATCTTGAAATT
TTCTAATTAATTCTTCTGATAATTTCTGGCATAAACCAATATAATGCCAATCTACTTTATCCTGAAACTT
CTCAATGAATTCTTCGGATAATTTATAATAATTCAGAGATACTACACCAATTAACTTTATCCTGAAACTT
TTCAATAAACTGCTCAGATAATTTCTGATACGCACTAATATTGTACCAAACTACTTTATCCTGATATTT
```

-continued

```
AGAAATAAAATTTTCTGATAAGTTCTTTTGATCCCTACTAATATTGTACCAAACTACTTTATCTTGAAA
CTCTTCAATAAACTGCTCAGATAATGTCTGATACCAACTAATATTGTACCAATTAACTTTATTCTGATA
TTTAGAAATAAAATTTTCTGATAAGTTCTTTTGATCCTTACTAATATAATACCAATCTACTTTATCCTGA
AACTTTTCAATGAATTCTTCGGATAATTTTTGATGTGAGCTAATAAATTTCCAATCTACTTTATCCTGAA
ACTTTTCAATGAATTCTTCGGATAATTTTTCTTCCAACTAATCTCAGTCCAATCTACTTTTACTGAATC
ATCAACGATTATTTTATCCATAGATAATATTACATCCTTTCTTTTTTCACTATATACTTTTTAATTTATCA
ATAGCAATCAATTTATCCATTGTTTCTTCAGATAGTGTATCTTCGTATCTATATATTAGATATTTAACGT
ATAATTTATGCATATATCTAATAATGAATTCTTCCGATAATTCTTGATGCATACTAATAGCTTTCCAATT
AATTTTATCCTGAAACTCTTCAATAAAATTTTCAGACAATGTCTGATATTTGCTAATTTCATTCCAATCT
ACCATATCCTGACAGTTACGAATAAAATCTTCTGATAAGTCTCGAACTGACGAAGAAGCATGCCGCCA
ATTAACATTTTCTGGAAATTTTAGAATAAGGTCATTAGATACATTTCTATTTAAGCAAAAATAATCCCA
ACATATCTTATCTTGAAATTTGGCAATAAATGATTCACTATTTAATTTCTGATGCATACTGATTTCATTC
CAATTAACTCTATCCTGAAACTCTTCAATGAATTCTTCTGATAGTTTTTGGTCAGACGATATATATTGCC
AATTAACTTTATCTTGATATTCACGAATAAATTTTTCCGATAATTTTTGGTATTGACTTATAATATTCCA
GTTTAATTTATCTTGATATTTAATGATAAACTTTTCAGGCAATTCTTCATTATATGCAATATATTCCCAG
TTAGGTTCAACAGTAAAATTATATTTTTCATTATACTTCATAGGAAACCCTCTTTCTTTTAAGCTATTAT
ATATTCTTCATTATAGTAATATTAGTCAGCTTATCTATAGTTTTCTGAGATAACGAGTTTTTATGAATTT
CAAGTACGAATTCAATATCCAAGCAATGAATATTCCTAAGAATAAAATCATCTGACAATTTCTGGTAT
TGGATAATAAAATCCCAGTACACTTTATTTCCAAAATTTTCAATGAATTCTTCTGATAATTTTTGATATT
GGGAAATATTATACCAATTAACTCTATCTTGAAACTCAATAATAAAGTCTTCTGATAATGTCTGGTACC
AACTAATTTCATTCCAATCTACTATATTCTGACAATTACGAATAAGATCTTCTGATAGCTTTTGGTTTAT
ACTGATGTAGTACCAATTAACTCTATCCTGAAACTTAATAATAAATGAATCAGATAATTCCTGAAATAT
ACTAATATATTTCCAATTAACCATGTCTTGATATTTATGGATAAGTTTTTCTGATAATTTCTGTTTTATA
CTAATAAAGTCCCAATCTAATTTGTCTTTAAAAGTATCAATAAATTTTTCATTCAACATTATGTTCTTAG
ATATGTATGTCCAATCAATTTTATCATCATTTATGTTAATATCATTAGTTTTAATGTACTCGTTAATATT
CATAAATTATAACCACCTTATTTTTCTTCTATATGTATAATATAATTTTAATTTATGTTAGATGTATA
AAAAAAAGGAAATGCGTATTTAATAAATGTATAATTCCTATATAATTATTATATTATATAAGAATTATA
CATTTAGTAGTTATATATGTCTTAATGCATCAATTTCCTCTAATCTATTTATGAATTCTTTAGATAATGA
TTCTGAATTATTATTTATTATTGAACTAATCGATACTTTATCAATATGATTATTAATAAATTCTTCTGAT
AATTGTTGCTCTCCACTAATAACGTTCCAATTAACTTTATCTTGAAATTTATCAATAAAAGATTCCGAT
AATGTCTGATATCTACTAATATAGTACCAACTAAGTTTATCTTGAAATTTCTCAATGAATTCTTCTGAT
AATTGTTGATCTGTACTAATAACATCCCAGTCTACTTTATCCTGATATTCACGAATAAATTTTTCCGATA
ATATTTGGTATTGACTTATAATATCCCAGTTTAATTTATCTTGAAATTTCTCAATGAATTCTTCTGATAA
TTTCTGTTGTGAACTAATAATGTACCAATCTATTTTATCTTGGAACCTTTCGATGAATTCTTCTGATAAT
TTTCGATACCTGCTGATGCTAGACCAGTTTAATTTATCTTGGAACTTCTCAATGAATTCCTCAGATAATT
CTTGATGTATACTGATGCTAGACCAGTTTAATTTATCTTGGAACTTCTCAATGAATTCCTCAGATAACT
TTTGATTTCTACTAATATCATACCAATCTAATTTATTTTTCAGATTATTAATAAAATCTTTATCATCTAA
GTTTTTATTTTTCATAAGTATATCAATCCTTTATACTAATATTTAAACATGTCTTAATTTATTAATTTCTT
TTAATTTATCTACAAATTCTTTAGATAATGATTTTGAATTGTATTGTAGTAATGCTTCAAGATTTAATTT
ATTTAGATATTTATGGATAAATGTCTTAGATAACTTTTGGTTTCTACTAATAGACTCCCAGTTTAATTTA
TCCTGAAACTTAATGATAAATTCTTCTGATAATACTTGACATGCACCAATATATTGCCAGTTAATCCTA
TTTTGGAACTTCTCAATGAATTCTTCTGATAATTGTTGCTCTTCACTAATAACGTCCCAATCAATTTTAT
CTTGAAATTTATCAATAAAAGTTTCAGATAATTTTTGGAACCGACTAATTAAGTACCAATTTACATTAC
TCTGAAACTCTTCAATAAATTCTTCTGATAACTTTTGATGTTCACAGATTAAAAGCCAATTTACATTAC
TCTGAAATTTACGAATAGATTCTTCAGATAATTTTTGAGATCGACTAACTTGACTCCAGATTAATTTAT
TTTGAAACTTACTAATAAATTCTCCTGACAGTTTTTGACATTGAGATATATAATACCAATCCAATTTAT
CTTGGAACTTCTCGATAAACTCTTCAGATAATTTTTGATATGTTACAATAAAATCCCAGTCAACAGTAT
TCTGAAACTTATCAATAAAAGTTTCAGATAATTTTTGATATATGCTGATATAAAACCAATTAACTTTAT
CTTGGAATTCTTCGATGAATTCTTCTGATAGTTTTTGGTATATACTGATATTTGACCATACTACTTTATC
TTGGAATTTTCTAATAAAGTCTTCAGATAATGTACGTTTTTCACATAATAACCCCCAATTAATCTTTTCG
GGGAATTCGCTTATAAACTCTTCGGTTAGGTTTTTATTCCACATAAAAGTATACCATTCCTTCTCTATAA
AGATATTTAGATACTTTTTATTTTATTAATTTGAATTAGTTTATTTAACAATTGAGGTGATAATAATTCT
GAATTGTACTGTATTAGGTGTTCAATATTTAATTTATTTAAATGATTATAGATAAACTTCTCAGATAAT
TTTTGATATCTGCTAATATAATCCCAATTAACTTTATCTTGGAACTTAATGATAAAGTTTTCTGATAGTT
TTTGATATTGACTTGTAGCATCCCAATCAAGCTTATTCTGAAAATCAGTGATGAATTCTTCCGATAATA
TTTGATATTGACTAACATCCTCCCAATCATTTATCATATCTTGAAACTTAATGATAAAGTTTTCTGACA
ATTTATGATAAATTACGACTAAGTACCAATTAAGTTTATATCTAAATTTTTCGATGAATTCTTCTGATA
GTTTTTGGTATCCGCTAATAGTATGCCAATCAATATTGTCCTGAAGTTCTTCGATGAATTCTTCGGATA
ATTCTTGATATTCACTAATATTAATCCAATTAACTTTATCTTTAAATCTAGCAATAAAGTCTTCTGATAA
TTTCTGATATTGGCTTATATTATACCAATCTACATTGTTTTGAAATTCTTCAATAAAGTCTTCCGATAAT
TCTTGATATCGACTAATAATATCCCATTTTAAATTATTCTGGAATTTGCGAATAAAGTCTTCCGATAAT
TCTTGATATCGACTAATAATATCCCATTTTACATTATTCTGGAATTTGCGAATAAAGTCTTCTGATAATT
TCTGATATTCACTAATATTAGTCCAGTCAACTTTATCTTGAAATTCGATAATAAATTTCTTTGATAGTTT
TTGATGTTTAGAAATACTGTGCCAATTTACTTTATCTTGAAACTCACGGATAAATTTTTCCGATAATTTT
TGATATTTACTAACGTCTGTCCATCTAATAATATCTTGATATTCACGGATAAAATCTTCAGGCAACTTA
ACACATGATACCGTAGTATACCAATCATAACCAAACCTTTCAAGTGTTACGTGACTTATATTATTATTG
ACTGTTTCCATAGTACTTAATTCCTCCTATAAATATCATTTTTAATCTTATTAAGAAATTAGACCAAGTTA
ATATCTAATTTTTTGAAGTATAAATTAATAAAATTCCTCTAATAGTTTTATGAAAATAAAATATATTCTC
AGTATATTTATTATGTGAAAAATCAGCACATATTCATCATATCATTAATAATACGCTTTCTCTCTTTTTT
TGATACAATGTAATACGTGTTATCAATATAATTAAATTCTTTAATAAAATCTTCCGATAATATTTGATA
TCGACTTATAATATCCCAGTTTACATTATCTTGAAACTCATGGATAAAATCTTCAGATAATTTTTGGTA
CATACTAATATAATCCCAATCTACTTTATCCTGAAATTCTCTAATAGAGTCTTCTGACAATCTTTGATAT
ATGCTAATATTTTCCCAGTCTACATTATCTTGGAATTCTTCAGAATTTTTTGATACCTTGAAGATTGAT
ACAAATTTGTAATTTTATTATATTCAATATTAATATCATTGTTATATTTGATATCGCTATCATGATTATC
ATTATTATTTAGTGATAACACATGATTTTTATCTTTTATAACATTATCATATTTTGGAATATACAATATT
AAGGGATCATTATTACTATTATCATCTAGATTTTTTGAAATTTCAATATTAGCGGAATTAGATTTAATTT
TATCAATATATACTTTATTTCTAAATTCTATAATAAACTTTTTGGATAGTTTTTGCGAATTGGATAATTT
TTGTGAAAATATAAGATGTTCCCAATATAATTCCGATTCATATTTTCTTATAAATTCTTCAGACAATCCT
CTGGTTCTATCAATCATGTTCCAATTTAAATTATATGGATTAAGTTCGACAATCTCTTCGACAGTATAA
```

-continued

```
TAACAATTAATATCCATAATAATCCCTCATTTCATTTATTATTTTAATATATGATGCATTTATACATTAT
AATTATAATATATATTTATCCTATAAGTTATAAAAAAAAAAATCAAACGTGATATATAATGATTATCA
CGTTTGATATGTAATTATTTTTTAAGAATGTTTAATAGTCTTAGAGAATATTCTAAATATTTAGATTGAT
TTTTTACATTGTAAGTTATTAATAATAATAATGAAGAGAGAAGGAACAGATCTCCTGATTTACAATAA
TCTTTTTGATATTTTCCATACATTACATTACATTTCAATAGCGTTAATAAGATCTAATTCTGCAATAAGC
TGACTTACTCGGTGATCTGATAGATTTTTCCTATTTTGAATTTCTTGTTCTTTTGCTTCATCTAAAATATT
ATTTAATGCTAACATAATTCTATCTAATAGAACCATCGATTCCTTATAAACTTTTACAGAATTTTCACG
ATTTTTAAGAATATTTATTAAATTACTGAGACTTAATTCATACTGTCTTATTTCTTCGCCATGATTATTG
ATTTTTGTAAGTTCAAGTTTTGCAATAAATAACCGAATAATATCAATATTCCTATCCCTATTATCCATTA
ATAGAATTATATTTTTTAGATTTTCGCAAATACCATCAACTGATACCATTATATTTCACCTTCTATTCTA
CTTTTAGTAAACATATTAAGTGCTTCTAATTCATTATTGATCATTTCCAAATTTACTTCTTGTAAATTCT
TTTCTTTCATTAATTTAATTTGTTCTTGATTTTCTTTTTCTTTTTCTACAGATTTAGTAATTACTTCTTCAA
TCTTAACAAGTAATGAATTTACTGTTGTATATACTTCATCTGAAAATATTGCACTATTTTCATTTAAGTG
TCCAATAATTATATCATTTATGCTTGATAAACTTAATCTAATTTTATCATGTGTATGGATATTGTATTTT
AATAGATTAGATACTTTTTTGTTTTTCATTAATGAATTAATAGTTCTTCTTAATCGATTATTATAGTTTTT
ATCTTTAAAGTATTGAATATACTCGATATTTTTATTAATGAATTTAATAAAATCAATAGCGTCCATATC
CGGAATATATTTTTCAGTTGAATAAATTATTGCATTATCATTATTATTTTTATATCTTAGTGAGTTTGAT
CTAGTTAAGTGCCTATTTATATATCTAAGATCATTTGTAGCTTGATCTATTTCACTGAAATTAACGGAA
TCATCTCTTACAATATCTTTATAGTCACGAAGTATTAAATATCCTGAACTAATAATACCTTTAGTTAAA
TGATTATTTTTAATGCGCATATAAGTCTCAATATTATTTTTAATAATATTGAGGCAACTTTGGATATTTA
ATGAATCAATATTATTTAAACTAATATATTCGATTTCATTAAACAATTTAGACAATTCTTTACTTCTAG
ATAAATTTTCTGAAAGTAAAAATTTATCTAAAAGATCATCATTCTTATTATTTTTTATTTTAATAAATTT
AAACATTCGATCACCATCCAGTTAATTATTATAATTCTTTCTAATCTTTGTTATATAAATTTATTATCAT
TTCGAAAATTCAGATATTTCTCAATTCTCTGATCTTAACTAATTTACGCTTTATTTTTATTAGATATTAGT
TTATCATGTGATATCAATAGATCAATATCTAATTTCTTGAAGAATATATTAATGAATTCTTCTGATAAA
TTTTCACAATATATAGATTTGCCCTTCCAGTTGATTGTACTATTATTTTCAATAGATAAGTATTAATCTT
CAGTTAGATCAATAATATCTTCAAGATGTGAACCAAAAGTAGAATAGTCTATTAACCATATTTCTTTTA
ATGGGTCTTCTTCAAGAAAGATTGCAATATCTTTTGCATGTTTCTTAATTTTATCCACAATATAATTATA
CGTTCGATCAGCACCACTAGGATTCTTAATGGATCTTAGAAAAACGTCATCATAAGATTCAGTTTCAAT
AATATGATATCCTTCATAAGTTTTATTTCCTTTTTGTAACGTCACCGATCTTAATACACTTTTTCGAGTT
TCTTTAATGCCAATTAGGTCAGCTAAATTAATTACTTCTTTTTTATTCAGATCAATTCCATTTTCTAGTA
CAAAAGGAACTGGTTGTAGGTTCTCGTATTCCTCATCATCAATATCACTTAGTGAATTAATATATTCTA
AAGCATCATTATATGATTTAAATACCTTATGTTTATTCTTTTCCGTATTAGTAATTTTATATTTGATTGT
CATAGACCATCAATCCCTTCATTTAGTTAATTTTTATTTTTAAATTCTAGTTTAATATTATTACTCTGAA
CCTTACGTAAATACGATAATATCGAATTCACCTTTACTTTCCATACATCATTCACAACAGAAAGTATTT
GCTTCATCCGATAATATATCTGATTATTATTATCGATGGCAAGAATTATACTCATATGCTGAGCCTGAA
TTACCTTATCAATCGTAATAATATCGTACAAGTTTCTTTCATTTCTACTTTTAATTAATTCTTCGCCATC
ATTATACTTAATTGGTCTTATCTTCATAAGTTCACTAACAGATTTAATAATTTCAGACGTATTTTATACAT
TCCATATTATCATTCAAAATTTCTTTTAAATATTGAATATTATTATCTGTCTGCTTAATATTATTTAATA
AGTATACTTCATATTCTGCGATAATAAATAAAATATCCTTATATTTTTCACGAACAGTACTAATCTCAC
GATTATTTCGAATATTATAGTCACTATCAATATTGGACATCATTCTCATAATAGTATCAGATTTTTCTTC
AATATAATTAATATACGTTTCATTATATGCGTAACGTATAATATCCTTTGATACTTGGTTATTTATTGAC
TGAAGTTTATGCGATATTTCAAAGATCTCTATTTTACGATTAACTACGTCATAATATATTCTTGAGCTT
CTTTCTTTTTATCCAGTGATAAGCTTGAATACGTAGGAACTTTATCATACATAGCAGGATGTATATACA
ATATATTATCTCCTTTCATTATTATTATTATTGTTGATTTATTAAATATATATTAATAATATATATGCATT
TTTATAATAAAGTTTAATATTATTCCCTAATACAAGAATTTACATTTATCTTGTATTAGGGAACAAATT
TATTTATTTTGATCTATATTAATAAAATATAATACCCAAAAAGACCATATTAACCCAAAGATGATTATT
AAAAATCTAAAAATTAATGAATCTATAAGCAATCCTAATATAATTAATATTAGTGACATTATGGTTAA
AATCATTAATACTATTTCTTTATGATCTTTTAATAAGTTAAATATTTTTTTCATAATAAAACCCCCATTA
TAATATAATAATTAAATGTATAAAAAAATTAAATCATAAAATTTAATTTATGTAACTTGTTAGGGGAG
AACGAGTTACGTCGTATCTCTTGCGTTATCAACAATATTTATAGTTGTTCATAAATATTATGACTTTTGT
ATTTTGCATTTTTGTTATTTCCAATAATTGTTATATAGTTTTGGTATATTAATCTATATATTATTTCATCA
TTACAATAGAACCAACCTTATAGTAAAAATTATATATAAAGAATAAAAAATCTATATAATTTACCTTC
GGTATAAGGATTGTTACATAGAAGGAAAGATCTACATATTTTTATTAAAAAGCATATATGGATTTATA
GTTAAGTCAGAACCAACCCTATAGTAAAAATTATATTAATAATTATTTTATTATGAGTTTAATGCTT
CGTTGTAAGAATCTTTACATGCACGGATAAATTATAGTTAATTGTTATGTATAATATATCCAAGCATGT
AAGGTTTCTTAGATTATTTTTATTTTTTATTATTTTAATAACTAATAAAGATATTAAACTTAATTTATTT
CGTTATATATAATATTAAAGTAATTATTTATCTATATGATTTACTTCTATAACTTTAATTTCTAGTTCTG
AAACTTCTTCGTGTTTTCTGAATACTGATGCAGTATTTCTTGTAACGTATATTTTATGTTTTCCGGGAAT
CCATTCAATATTGATTTAAGATTATCCTGAATCATTTTAATGAGCGTTAGTCTACTAGCTTTATTTACT
AATTCGCCCCAAAGGTAATATTCATTATAACCATTATTCCTAAGAATGTCTAATTCTTTTTTTGATAATT
TGTATTTTGTTTCATAAGTTATTTCCATGATTTATTAATTATCCACCTTTATTTATTATTTTTAAAGATCA
ATAATGTTATCTAGATGTAAAGATTCTTTATCTAATGAATTATTATCTGATAATATAGTTAATTCTTGATT
TAACGATGACGTCAGTTATTCTCTTAATTTCTTTAATGCAGGCACTATATAATTCATTCTTGTCTATTTT
TGTTATCTTTAAGGTAAGATCTTCAAGCTTTTCGTAATCAATTGGTTGTTCACGTCCATACATAATCCA
ACTTGTATATCCACTACTTACTTTTTTTCTTTTCAGTATTTCAGTGTTATAGTAATTTGTGATGGTAGAA
AAATATTTTTGCCTTTTTCTTTTAATACTTTTAAAGTATATTTTGTTGTCTGAATGAACGCAGAATTTTA
AGTTAAATGAATTGTTAATAAGAACTTCAAAATCTAAATCATCTAATACCATTTAATAATTCATTCCTT
TCATTTATTTAATTGTTTTATGCTCCAAAGAATATCTGATTTTAAGTCTTCTAGGAATTTTACCGTACTA
ATAATAGTGTTTTCGTGTAAGTAATCTTTTTCTAGTATCATTCTTTCTTTATATATTTCAATTAATTGGA
ATAATCTTTCTTTATGTTTAGAAAGATAAGCATAACCTAAGATTTCTGCTGAGAAGACGATATATTCAT
CATTCAAATTATCAATTCTTTTTTGAGACAGATTATTATCATTTTTATAAGACGTCATAATTTCAGAGAT
TAGATCATAAATATAAGTTACTTAATACTTTTATTGTCTTTTCTATTAACCTATTAAATTTTTCTGCTTTTT
CTTCTTGAATTAAAATAATCGTATCATTAATAGCATTATTATATAGGAATATTCTTCATTGCTGTAAAGAT
ATGTTTTCTTTTTATCTTCTAATTTCTTTTCTATTTCCTTAATAGTATTGATTTGTATTTTTATACTATTAA
TTGAATCATCATCGCTGATTGGGATATTGTCCATCTTTTTAATAAGAGACGTATCCGTTTTTAAATAATT
ATCTTTAGTATCAATCGCTACCTTATTACCATCTAATTCTTTTATTATACCTTCTTTTGTAACGCCATTAT
GCATTACTTTTACACGTTCACCTATCTCAAACTTTTCCATCATTTTCACCCCACATCTATTTCTTCAATA
GGAACTGCAAATTGCCAATAACGCTCATCTGATGACTTTATTTGTTCTTTTGTTAACTTAGTAGTAAAC
```

```
CCAGATGATATTTGAAAAGGAATAAGTTGTCTTTTTGCAAACATACCACTTACGCCTGTAGAAGGGTTT
ATCGCTAGATATAAATAATCATTAACTTTTTTAGAAACATTTTTATCCCATTTCAGTTCATTATTTTCAA
TAAATTGAACTTGTTCGTCTATTTCGAATTTCATAAATATGATTTCTTAAATTAATTATTTTTTCACTAA
TAGTCTTATCAATATTAATAATATTATTTTTCTTCTTTTTAAAAAACATATTCACCATTCCTTTAACTTAT
TCATTCTTTAATTTTTTGTTAATTGAATCTTTACTAATATTTCGAATAATTTCTAGTTCATCAGATAATA
TATCATCAATAGTATTATTCTTAGATATTTTAATATTTTTATCCATATCTTTATATACTTCGAATATTTTA
GAGAAATCGTTATAGATAGTAATTAATATTTCTTTAATTTTTTCATACATAGATTTGGTAATTATTCCTT
CAGTCTCTTGACCAATATTAATAATAATATTGTAAATATTATTAATTGTATCAATATACTGGGAGAGTT
CTTCAGTGAATTCATTTTTTTGTTGATTTAATATTGACATATTATCAGACTTAATAAGTATTTTATCGAT
TATATCTAAAAGTTTAACATGATAATTAGTTTTACCATTTACACCCATTACATAATCATATAACGGTTT
AGATCTATTAATATTTTCGTCAATTTCATTATCTGATAATCTATCGTAGTTATACAAACGATATCCACCT
TTTTTTAATATATTATACCTTTTTACATATGGATGAGATTTATTAATATTAATTTTGAAATCATATACTA
TATTTTTAATACTAAATTTATCATACATAATCTGATACTCATAACTAATAGTAGAACGTTCTCGGATGT
AGTATTTTTTATCCATAAAGATATTATCAAAGTATTCATAATATTCTTGGGGTGAAGGTAGTTTGTCTG
TAGTAATTTGAATTATTGATACCTTATGAATTGATTCAACTAAGGTATTAATAATTTGCTTTCTTAATTT
GATTAATTCATTATCGATAGTTATAACCGATTCTGTATCTGATAATTCATCAGTAATCACATCTTCAGG
TTCTTCATTATTTATTTTTTTATGTGATTTTCTTTTAAAAAACATGTTCATCATTCCTTTTCTATAATATT
TATTTAATTTATTAATAACAATAAAGTTTTTTCTTTAGTAACTATCTTTTTAAAATATTAGTTTATCATT
ACAGGAATAACTAATTTAATAGTTATTCCTGTAATAATTTTTCTTTTAATTTATATCTTCGTATATAATA
AGATACTGAATCATTTTTCATATGAACATTGGTTGAGATTTCAGAGATAGTTGCTTTTGGATTCTTTTTT
AGATATTCTAAGATACTATTGATTCTTGAATTAGTAGAATCATCATCACTATTTCGAATACCTTTAATTT
TTCGATTATATTTAATATTATTCTTTTTAATATATGACTGAATTGTGTGATATTCTACATTAAAATGTTT
TGCAATTTCTGTCATTGTTAAATTCGGATTTTCTTCAATAAATTTGGATAATCCTTCAATTTTTACTTTT
ATTTTCGGACCAATACCTTTTTTACTTACATATGGTAGATCATATTTTTTAATCTTTTCCCTTAATGTATT
TGGAACATAGTAAATTTTTTCAGATAATTCATTAACTGATAATTCGGGATTTTTCATAATGATATTTCTT
AGATATTCTTTTTCCTGAATTTGATCTTTAGAAAGTTTTTTGATCATTATATATACCTTCTTTGTTATATA
ATTTTTCTACTTTTATTAATTCGTCTAATATAATTATTAATTGTAGATACATTTGCATTAAAATGTTTAG
CAATCTTGCTTGCTGTAGCTTCAGGATATTTTATCATAAAATTAATAATTTCATTATCATCAAACATTTT
ATCCACCCTTTTTACTTTTATAGGGGATATTGTTTCTTTTAATTGTATTACCAATAAATGACTTTGATACA
TAAAAGTGTTTTGCAATTTTATCTAATGTTAAGTCAGGATTATCGCTAATATATTTAGAAAGGTCGTTA
ATATTGATAATATCTTCATAAATAACAGTATCGTTATCATAATTATATTGCATATTATATTCCTTAATAT
ATTTACGGATGGTTGGTGCAGAGTAACCAGTTCCTGATGCAATTTTCTTTATTGAATGAGTAGGGTTAC
TATTAATATATTCTTTAATAATATTAGGATCTACTTTTTTCAAAACTTTATTCACAACACTTTCATTTTA
TTTAGTATTCTTCTTTTCCTTAGCAAAGTATGCAATTAGTATGTATTATTATCATAGATATTAATGTTATT
ATATCTAAGACATATTCATTAATAGTTATTGCATTATGGTGTATTCCATATAAGAATGTATATATTGTG
GTATACACATTATTGAATATAAGGATTATTAGAGGTATATACCTCATTTTATAACGAAGTTTATATAGG
GATACTTCATGACTACTATATAGTAATAATCCAATAAGAAGATTAGCCGTTAATGCTAATGTATATGTT
ATTTTTTCAGACAATACTTCATTAGTAGTAAATAAATTTATTGTAAGAAATATAATCATAAAGAATATA
AATACGCTTGTTATTAGTCTAGTTCGAATATCAATTTTTTCATTATTAATACACGATATATAGACTAAT
AAAAAGATTACAAGATTTGTTAGTAACATATAATAATAATCCTACTTTCCATATACTTATAAGAAGAA
TCCCCATTAATAAAGGATTCTTCTTATAATCTAAATTTATTTTACATATACTTTATATGATTCAAGTAAT
TTATTTTTCTTTGATAGTTTAGTATTGATAAGTTTTCTGAAAAATAACTTTGTGTTGAAAGAGATTTGCG
TTAATTCTGTTTTATCTTCACCAAAATTAGTGCTTTCGTAAGATGCGGCTGATTTAATTACACCCCTATT
AATAAGATTTTCTTCAGAATATGTAGATAATTTACCGTTATTACCAATCATAACTACAAATTCAATTGA
TTCATCAATATTGCCGATAAAATGTTTTAAATTTTCAATAAAAATTCTTTTTTCATTAAATGTTCTAAGT
CTACGTTTTCTATCAATTTCAATAATAAATGCTTTCGGTTTCTTTTTGATATTATTAAATAGTTTAATAA
TATCTTCTTTAATAAATTTAGATTAGTATCACTGGTGATATAGTATTGTAAGTAATATTCTTCAGATTT
TAAATTATTTACTTTTTTGGTAATATCATAAAAAGTAGTAGTTTCAATTAATGGAATAATATAGTTACT
TTTAATACTCGTGATAGCAGTATTAATACCAGTGACATCTTTATCGCCAATCACAATTGTTTTTTTATTC
TTCTTAGCAAATTTTTCTAGATTATCAATCATTCTTGAGAAATCAGTTTTCTTAGTTTTTTTATTAGATCT
TAACAAACTTGCAACATTTAACATATAGTTTACCATCCTTTTATTTTTTAGGTTTTTTATTTACAAACA
GTAGAATAATAATGGCAACGCCAATTCCAATAATTGCAGGAAGTAAATCTTTAAATATATCCATGTCG
AATCACCTTTTATATTTTATTTTTTGTATACATATTCCGTATCATAATTTTCAATAATAAGTTTAACAGT
TCCATGAGAAACTCCAAGAGATCTTGCAATCTTAGCAATTGAAAATTCAGGATGTTCCATTATAATATT
ATTAACAGATTCTATAATTTTTTCATTAGTTAAAGAATTATTAGACATATTAACTTGGTTATACGTTGC
GATACTAAATTTATATTCTTCAAATAGACTAATAATATATTCTTCGGAGAATCCTGTATCTTCAGATAA
TCTTGCTGGAGTCATAATATCATTACTGTCTAATACAATTTTACTTAATCTTTTAAAGTCTGATAATCGT
GTATCAATCTTCATATCTGAAATGCTCATTTTTTGAAGTCTAATAGATGAAATATCTTTTCCTTCTTCTT
TCATAATTCTTCTAATAGTTGATTTTGCAATTGAAAATTCAACATTACATTTTTCAGCAATTTCTAATAT
TGTCATTTCAGGATTATTACGATAAGTATAAATAATATCTTTAGTCATCTTACTAAATTTATCATTATGC
TCATAAGTTTCTCTTCTCTCTTCTTTGTCTTCTTCTACTTTCTGCACTTGTTAAAACATTTTGACTCAT
TACCATGATAATCTTCCACCCTTTTTAATTAATTTAATAAATTGTATTAATATAAGATTATAAAGTATAT
CTATGATAGTTTAAATTAAATATATTGTAATCGTTTATCACATGCCTGAATTACAATAGCATCCCATAA
AGCATTATGTTTATCTTCATTTACTATGACATTAATATATTCACTAGCAAATTCTTCACGATTAATATCC
GGATCAATATTTTTAGTTCTAAATACTGTAGAAATATCATAATAGTACATGTCAACAAATTCTGGAATT
AATGTAGCATCTTTTCCTTTATTAATTAGATCCACAAATAACATCCAATCGTATGCCATTAAGTCACTA
ACAAATACTAGTTTTTCAGAACTATGCTTAGCATTATATGATAACCATTCGATAATTTTATCAGAAACT
TCATCTTTAGTTCCATATACTATAGTTGTCTTAGCATTATCCGATTTTGATGCTAATGCGTCATGTTTGT
TAAAAAATCGAAGTTTAGGAATAACATTATCATTCACCCAAACACTTGATTTCGTTGTATCAAAATTAG
ATACTTCCGCATAAAATAGTCTACCGTACGTATCTACCATTCCAATACTAATTAGGTCGGCATCTTTTG
TTAAATTTGTAAATTCTGTATCAAAATATATCTTATTATCCATAATGTACCAACTTTCTTTAATTTGTCT
ATATATTTCTCAATATAATACTTGATAAGAAATTATTGAATTCTTTTATTAATCGATCTAGCGCCTTATC
ATTAAGTAATGAATTTATATTTATAAAATATGGATTGATTATCAATAAATTTATTGATATCTTTTATATCT
ATAACAATTAAGAACTTACCATTATCATCTTTATATAAAGAACTATTGATTGATTCTAATTTTTTATTTA
TATATAACATTTTTACCATCAACAATAAATTTAGGGTTAGTATACACTAATTGAAACATACCATTAGAAC
ATTTCGATTCAATAGGTAAATATTTATACATCTTTATATTCATCTATAGATATAATATCAATAATGCATG
TAAACAAATATCTTTTAATGATTTTTCACCCCTATAATTTATAATTTTGATACTATAAAATAAATATCAT
ATTTTATAAATAATTATTATTCTAAAAAAATAAAAAATTCGATTAATGATATATGACATATCATTAATCG
AATATAATCTATTTAAGTATAGATACTGTTACGTTAGATGTCCCACTAGAACCTATTTGCGATTTATCA
```

```
ATTAATAAATCAATTTTATTCCCAATAATTGCGCTTCCCGTATCACATGCTTTAGCGATAAATGAATTA
CCATTAGGATATGTAATTCTTAAAATACTGTTCATTGGAATTACTGATGTATCTACAGCTACAATACGA
TGACCTTCTGGAGAATAAATAGTGTTACTCACTTTAGTTCCATTAGCAGTAATTCCTGTGCTTGGAGTA
TAATCATCCCCAACCGCATATACTGTCATACGAAAAGAACCAATTTTTCTGTATGAAGAATTTTCTTTA
GTTGAAACATTCCGTACAGTTTTTTTATTTTTTACTTTATGACCTTTGTTTAATTTTAATTTTCTTGATAAG
TTTAATATTATCATTCTTAATATTTTTAATAATTGTATCTTTATCTTTAATTTTCTTTGTAAGTTCTTTTAT
ATCAGTAGACATTTTATTACTTTTATTAACAATATTTTCATTTTGTTCTTCTAGATTATTATTGATTTTAT
TCTGTTTTAATATTAATTTTTCCTGACTTTGGATCATATGGTTTAGATTAGATTGATGAATCGTTTGAAA
TGCTGTTAACGATAGTAGTAGAATTACGATAATTGATACGCATGTAGTTTTAATATTCATTCGATTCAA
TTTCTTTTTCTTATGCATAGATTCCTCCATTTCTATTATAACATTAATACTATTTGCTATAGTAAAATTAT
ATATCAAAAAACCGTAGTATATTATTATTGTTTTAATATACTACGGTTTCTTATTTTATTTTATATTATT
TTTTAAACAATATTACTAAGAATTTTTGGCGTTTTTTCCACAAAATAAATTTCATCTGAATTGATCTCAA
TGATATTGGCAATTAGTTTTTTAATAAATCCAACAATATTACTGATATGGATAATTTTATTTTCGTTAAG
AATTGAGAAGTTATCTAGTAATCCATTAACTTTTAGATTGATATATGAATATGATTCTTTATCAATATA
AAATTCAATAAGGTCGGAATCGATAATCCTAACATTAACTATATTATACAAATTTGCTTTGTTTTTACT
ATTAATGTCACTAATAAGTTTATCATAATCATCTTTATCCGGAGTATGAAAATAATATGGATTTAAAAG
ATTAATAAAATTGATCTGATATTCTTTTCCTAAAATATTAAAAACTAATCCATTTTTTTCTGAAAATTTA
GTTGTAAGAACTTTATCTATAATCACTTTCTGTTCCATTTAAACCACACTCCTATACCATATTATTAGTA
TTAATAACTTATTGTATTAAGTTATTATAAAATACCCAATACGTTAAATAATAAACGTATTGGGAGTAT
TAATACTAATAATTATTGAATTCTATCTTTAATTACAACTATTGTTTTATGGAAATTACTAACAAATTTA
ATATTTGTGTCATAATATTTATTTCTAATATTATTAGGGATGTGACCAATAATATCACTATAAATAGTA
TCAATAGTCTTATCGATATTTTCAATATCCGTATATACATAATGAGATAAGTTATTTACAATAATTTTTC
CAATATCAATATATTCATTTTCAAACATATTAGTATATTCTTCAGGACGTAGTAAATTCCTAAATAGAT
TTTCAATATTATTAATAATTACATCAATATTTTCATCATTAATAATATCATCGATATCATTATTAATAAT
AATATCAACAATTTCATCTACATAATAATTAACATTGTCTTTTTGATTTTCAGTAATACCGATTAATCCG
TCAACTTGCTCTACTTTACCTGGATTATCATCATAGATATTACTATCCATTGATGTTGAAACGTTATCCA
TTTCATTAACGCTTGAATCTTCTTTATTCCTACCACTAAATAACTTATTAAATAATTTCTTAAACATACA
AATCTCTCCTTTTATACTATATTTTACTATTATTATAATATAAATAAAAAAATGATTAAATTAGTATA
TCTCCAATCAATTTATATTTTGATTAGAGATATACTAATTATTTTTAACTTATATAATCATCGATATTTA
TTTCTTTAAGTTTAATCGACATATCATGAAATGCTTTATATTGATAGGTAATTTTTTGAAGTTATCTCCA
AATTTTCCCCCAATCCAAACCGTACGTGAGACTTTCATCTCATACGGCTTTCCATCTACTAGGAATCTA
AACCTAATCTGTTATGTATCTTTCTTTTTAGTAGACTAAGGACTTTCCCTAATTTATATTTCTATAAATA
TTATCGGTATCTTATCCTCGCTTTCAATCCAAATAAAATTTCAGTTATAGTCCAGATTAGACTTTCCGA
GAAATAAGTATTATATTAATACTTTTGGATCTTCCCATGTTTCTATAGACTTAGGTTTATTATATAACTT
AGGACTTTTCTAGACCATATATCTTACTTCTTAACATGATAAGCTAATAAGGTTATTATCAATGATTAA
TAACTATTAGAAGATATATTTATACATTACTGTATAGGATTAAGTCATTATAGAAAATTCGTTAAATCT
ATCCATATTATACTACCCAAACCAAGATATCTTATCCTTTTTAATTAAAAGGACAATCTTCTTGACTTC
ATCCAGCTTCACACATAGTAATTACTTGCTATGCATGTGGAATATTATTTTCAGGAAAATCTTAGAATC
TTTGTTATCTAAGTCCTTGATCAGTCTATAAATTAAATTATATAAAAATATAATTCCTACAATCCCTCAT
ATTAAAATAATGATTTCTGTAGAACATGTCACACCATTGATAATCCAGTTAATGCATTCCCAATACCAT
TCGCAATTAGCCCAACATTCTTAATTCCCATTTGATAGTATAGTTCGCCTGCACATTTATTACAGATAT
GTTCAGACTTACAGTATAATGGACTACGCATTTCAACATTCTTATTAATAAATTTACCTTTATTTTCTTC
GGTAATTTGCGTTAATTTATCACCGTCTTTTACATAACGAGTAATAAATAAATTAATATTATTATTTGT
AAGTGTAATATTTAAATATTTTTTAGATTTACAATCACTTCCATGATCGCCAAGAATTATTGACTGAAA
TGCAGCGGCAAGTTTTTTCGCTTCATATCCACCATCTTGAGTACCAATAGCACGACTTGCACTAGCACT
TGTAATAATTTCTGCATATTGATATAGTTCGTCAGGAGGAATACCATCGTCTAGTGAAGCCATACTAAC
TCGAACATCATTTGGGTCCGCATAACTTTTAGTTACACCTCTAGCTACCGCTGTTTGTTTAAAGTTATTA
TTAAAACTTCCACGGCTTCCACTATCATAAATATCCATATCGGAAGCATCTTTAAGAATATCATGGGAT
AATGTTAATAATTCTTTTTCTATTTTAGATACAGTAACAATATCCCCAGAATCAATTGCCTTTTTATGCT
TAACAATCAGTTCTTCTTTACGAGATTTTACTTGAGGAGGAGTCATCATTAAAGTTGTACTAAGTGATG
TTGCAATGAATTTAGTTATACCAAAGCCCAGCCATTGCATCTTATCAATATAATTACTAAAATCAGCTA
CAGTAATTTTATCTTCTAATAAGAGAGTACTTAATTGTTTATCTAACTTACTAATAGCCCCACCATCCA
TTGGATGATTAATATATCCAATATATCTTCCTAATTTTGCATCAATAATTAATAGGTTAAAGATATATC
GACCTACTGTAGTAGTAATTTTATCTTTATTAAAATGAATATTTGATTCTAATTCAAAATAATCACTTG
GGTCAAACTTTGCATCTTCATTTTTGGTATATGCAAATAATTCTTGTAATTTTTCCATAGTGATATCATT
CTCTGAAAGATTAAGAATCTCAATCTTTCTAGCATCACTAATCTTTTTACCTTTATATGCTTTTTGCAAC
TATATTCACATCCTTTATAAATTATATCCTTTAATATAAATAAATGTTCTATTAGATAATAAAATTGTTA
GGATCATAGAAAAAAAAAATATAACCTAGATATCTAGGTTATATTTCTTAATATAATCTGACCATAA
AGAATTAATACTTTCCTTATCTTGAACGCTTATTATGTCTTTTAATTCAATTTTATTATTTTCTTCAAAGT
ATATATACGATAATATACTGGAGATTGCATCATAACCTTGTTCATCCGTATTAATATAAACGTTATCAT
CATTACCATAATCCATAAATGTATTATATGATCTTTTTGATTTTATTTGTACTGGTTGATGATTAATTAC
TACGTCTGTTCCATTCCTATCTAAATATGCAGAACATTCCATCCAAAATTTAATTTTCTTTTTATTAAAT
ATATTCTGAACTTTTCCTAGAATTCCCATTACTGCAATTTCTGCATAGTGACCTTCATTAAGCATTGGTG
GCAGTTTATCAATACATTTTCCGTTGAATCCTTCTTTTCTTGCTTGGTTCTTATAATAGTTCAATTCATTT
AAATTAATATACATCGTAATATTCCCCCACTAATCGTATTATTTATAGTATTATTATTTTTTCACAATTC
TTACATTTGGTTCGATAAATTTAATAAAACAAAATTTCATTGATAGCTTTATAATAGTATATGTAGTTG
CAATCATAAATACAATATTAATGAATATATTATTGTCATAGTTCCACAATACTACGTTTGAAGCAATAA
TTAATAGAATGGTCAGTATTACCGTTATCATAATTGAGATAAAGATTTGTTTTACTATACGATTATTCA
TATCATTTCCCTACCTTACTTTTACTTTTTATAAACATGTCTACTTTATTACGAGAATCCAAGTATTCAG
AGAACTGATCGATGAAAAGATTTATTGATATGTTATATGTTAAGTATGAGAATGAAATCGATACTAAT
AAGTCTAGGTAAATATTATTATTTCTAAAACATACTTCATTAATAAAAAGAAACCATAATGATGACGT
AATAATAATATTAAATATTACTTTGGTGATAAGATTTCTAAATAATTTATCACTAGAATAGATACTTAG
TATACTTTCCTCTCTCTCAAAATTAAATATAGCCATTACAGTTCTTAACATATTTTTTCTACTTTTAATTT
CGATATTCTTAATTAAAAAGTTGCATAAGAATAACACTGCTTTATTTATGTACATTATATAATCAACCC
TTCTTTTTTTTTATTTAATCATTATTATAATATATCATTAAAACTTGTATTATTACATTTTTTATAAATTAG
AGGGATATGACAAGTTATATGTCATATCCCTCTAATAAATATAATTTATGCTACGTAAATAATATATTC
CATTTCAATATTTGTAGATAATCCACTTAATGAGATAGAATCAAAAGTCAATCTTGATCCACAACTAAT
GTTTTCATAAGAGTTTTTAGTTTCATTGTATCTACCTAACCATAAACATAATTCATTGATCATTCCACCA
CGACATTCACTAGGGTCGATAGTTAATGATAGACTATATGAAACTTCTCCAGTAAATGTATTAATATTC
```

```
CAACCTTTAGAATTACCAAAAGGTTTTGAATTTGTAGCACCATTAAATCGTTTACCATAATATTTTACA
GTACCATCCGGATCAGCTTGTGGTAAATAATATTTCATTTTTTGTTCATCAGTAAGCTCTTTTACAATAG
AGGGATTATCTTGAGTTTCAGTATCATTATCCTTATCAGGGTCTACTGTAATAAAAGGAAATTTTTGAG
CTAATCCATTATCATTAAATTTTGGAGCAACTGGAGTGAATGGACTAGCATTAATATCCGCCCCTCCTT
CTCCTACTGAGAATAGACAGATTGATCTTGCAGGATCATAGACTTCGTTGTATGTTGATGGATGTTTTT
CTTTTAATAATGCTTCCATTACAAATACACGAGTTCTTTGTAAAATTAAATTATCTTGAATATTGATTAC
TTGTTTTGTATCTGCATTACGGAAAATAACTTTTCCTCGAATTCCTTTATCTGAATCTGCAGTACCAATA
TTATCTTCAAAAATTTCTTGAATGTTATTATCTTTAGACATAATGTGGATTACACTTCCTATTCATTTAT
TTTATAGATATCGATCTTAATCATTTGATTTAATAAATAATTTATCACTAAACGTTATATTATCATCAAG
ACGTTTTGTTAAGTTTAAACTATGAGAATCAATTATAGAAATATAATCCCTAAATAGTATTCCACCTAT
TTTAGTGACATCCATGGTATCAAACAATCTTATACTGTTATCCATTTTACTATCAAACTTATAAATAGA
ACTACTATAAACTGTATCGATAGTATAGGATTTAAATACTTTTATGAGGATATAAATATATGATTTTAC
ATAATCAGATAGACCAATCGTATTATTTTGAGTTAAGAAATCATATTCCCCTAGATTTAAATGATTATC
AATACTTTCAACAAGTTCAAATATTCTTTCACGATATATATCATCTTTACTTAATGAATCAATATCGTAT
ATATTAATATCTACTTCTGTATAGAAATATAAGTTTGGATCATTATCTTTTAAGTAATCTGTAAACGTA
TTATATTTTGAGAAAATATCCATATTTAAATCATTTGTAAATTTTTCATTCCATAATTTATTAAACAAAC
TATATAGTTTATAATCATTTGTATTAATAATTGTTTCTTCTAAGTCTTCCCTTAGTTTTTCATTATATCGG
TATATTTTTGCGAAGTCATTCATAGTATATCTTCTTTTATTATTGACTATTTCATCATATGAACCAAAAA
CATCTATAAATACCGATAAATTCTTATAGTTTATTAGCTGTTTTCGATAAATATATTCATTGACTGAAA
TAGCTTCATCAATAGCTGAAGGAATCATATCAATAACTTTTCTAAAGTTCTCAATAGTTTTATTTCGAT
TATATATATCAAAAACGGTACTTAACCTGTTAATACCAAGCTTATTTATAAAGTCTCGCATTTCAGACA
TTATTACCACGTTGTCCATACCAAACTGGAATATCTTATCAGTACTAATATATTTAATATCTACCTGAT
AATTAACAAATCTTGATAGTAATTGTTTCAATAGACTATATTCCGATATTATAGACATTGATATTTTTCT
ATTTTTATCAAGAAGATATTCATTAAGTATTCTAATCCATCATAAATATTACCATTCTTAATGTGATTT
TCTAATTTCTTAGAACCGTTAATACTTTGGATGTATTCTGAAGTGAACTGCATTTGGTTTTGGTAAACT
ATTGAAGAATTATACATTGCTACAATACTATCAAAATCTTGGTCTATATCTAAGTCAAATCCTTTCAAC
TTAAATCGATTTAGATAACCCATAATATTTTCCCATTCTCGTACTCTGAATTTTCGTTTATTCCAGAAAA
GATATTTTCTTTAATGAAATAATAATATCATTTACATTTTTATCAATATCATATCCGTAGGTATGTTCTAA
GAATGGAATTTTTCTAATTTTATCAGACCAATTCATTCTTTTTAATACCAGTGTTATTAATGCAACAATA
GCATCAAATATATGAATTTCACTATCAGAGATATTGCGGTTATTAAATTTAAAGTCAATATTCTCAAGA
TTAACTACTTTTGAAGCTTCTTGATAGGTAATATTATTATCACTAGCATATTTATTGATTATTGCTCTAT
TTTTAATTTCTAGGTCATTTAATAATCCATAAAAGTATGATAATTGTTTCGAATTATTAATCAGATCAA
GAACAATATCGACTGAAATATACTTTGTATTTATAATATTGAATGATTGTTCTAGTATATTTTTCTTTTC
AGCTCGCCAATAGGGATCACCTTCAGTAATTGCGTCATAATCTACCCTAGGATGAAGCGAAAAATTTA
ATTCTTCATCAATAGGAACTTTATAGAATTCTAGTGAGTCATCACCGCCTAGATTATTTTTCTTAGCAA
GCATATACCTATTTATCTGTACATTATCAAAAGAGAAAAGATTCTTTATGACATTGAATACATCATTAT
CTCCCTTGTTACGAATCATTTCATTTATTAATCGATAAATTCTTCGTTGATAATTTACTGGAACAGAATC
AAAATAATCTAATCCCCATGATATAAATCCATTTTTTAATTTTTTTCTATCATAAGTATCAATATTAAAG
TATCCTTCCATAGTCTTATTAATATAACGCATTATAGTCATAAATATTAGATATTCTCGATATACTTCAC
GATTATATGTTTGATTACTAAATGCTTCAGTAAACGTAACATTTAGGGAAATAATTAATCGATTCATAGT
AAGCTTCATTAAATAAACTTTTATGCCATTTATCTAATGTATTACTAGTTTCTTTAAGTATATAGAAATC
TTTTGCTCTTCTTGCTGAAGCATAATCAATATTATATCGATTAAATAAATCTTTATAATAAGGGTTTGAT
TCATTATATCCTTTAATGATATTTGATTTTTCTGATTCTGAAAGTTCCGAATCACTATCATATATAGCAC
TTAAATATCTACTAGAATTTAATAGTGATGAAGGAGTTTCATTTGCTTCTGCCAATTGAGTATCCTTAA
TTACTAGTCCACGAGCATAATTTATAACATCTTTTATTTCATTAATATCCGAGTCTTTAAATGCATTATA
AAAATAATATGGTGTATATTTTCTTAACATCTCTTCTTTAAATTCATTGACCAATTAAAAACGCCACCA
TTCTATTATTTTTATATTATAAAGAGTTGTTCATAAGTTATAATTCTTTTTAGTTTTGATATAGAA
ACAATATACTATATATTAAAATAAAGTTAGGGTGATTTATATATGAATATTAAAAAAATAAATAAGAA
TAAAACAGTAAGTAATATTGTATCTATCAGTAAAGATGGAAATATAATTCTTAAGGATAAGAATTATA
CAAGTGATAATTTTTTAGACTCATTCTATATAAAGTCACTGGATAGTAAATCTATGAATAAATTTATAA
AAAATATAGAATCATTAATTCGAACATCATTAGAGTATTCTAGATATATTGGGTATTTATCTACAGTTC
AAAATATCAATACAGATGCAATTATGGCAAATATTAATTCTGATGATGCCAGTCTAGAGTTTCATCATT
ATCCATTTACTCTTTATGATATTGTAGAAATTGTTATAAATAAAAATATTGCATTACAAGAAAATTTTA
CATCAATATCTATAGCTAGGGAAGTTTTAAAATTACATTATGATAATATGATAGGATTATCTAGAGTCA
GTAGAACGGTACATCAATTAGCTCATGCCGGCGAAATTTTTATTCCATTAGATAGTATATTTGGAAGG
GTTAATGATTTCGTTAATGATTTTTATGAATATATTTATCAAGAACACATTATTACGTATAATAAGATT
ATTGAAATTTATAATAATAAGAATTATGATAATGATATAACAAAATAATTTTTAGTTATATATTATAAT
TAAAATAATAACTATTATAGGTGGCGATTATATGAAAAAAGGAATAGACGATTATATTAATAAATATA
TAAGTGATGATCCAGAGACTCAAAAAGAAATAGATCTCATTGTAAGTAAAAATAAATGATTTTAATAAT
AATTGTATTGAATTGATGAATGATGAAAATATGATCTGTGAAGAAAATATTATTAATGGTACCATTAA
TGAAGTTAAAGACATTCTATTAACGTTATCAAATACATTTACATCTGTTTATATGGCGAACAGAGTTAT
TGAAAATATTGAATTATTTATAAATGGTGAAAATGACGAAGAGCTTCATGAATATATTTATATAATGC
AAGATTCAATTGAAGATTTTGATGATATTCCTTTATATGACAAAACGTTATTGTCTGAAGCGATTAATA
CCATTCAGCGAGCAGAATTTCTAAATATGATACTCAAAGAAATACATATCTCAATATATTTAGAAAAA
ACACTGAAATTATTAAACGATATTATGGATTATAATAGTGATAATTTGCCTTATGATATGTCTATAGAA
ATTAATGCATTACTGATGAGTTCTGAGTATACATTATCAGTTATATTAAGTCAATTTAATCATATTATA
ACTAAGTCATATACTAAATATCTAAAGATCGTTGACATTATCTAATTTTAAACCTAATACCATAATTTT
ATGGTATTAGGTTAATTTTTTTTTTTATTTTTTAAGGTTTAAACTACCTAGCACATTTGTTTTCTTTATTTC
TAATTCTTTCATCAACAGTATTTAATAATTTTAAATTACCATAAATTACTACTGCATAGGTTTTATTTTTC
TTCCGGATTTTTTGTTTTAACAATTAATTTATCAAAATCAACAGAATATTCATCTTCTGTAAGCATTCTG
TTATTTGCAAATATTTTTACTTCAATACATTTATCCATATTTCCATTATTTTTTTCAATTTCTTTAGCAAC
ACGAATTAGTCCTGAAGACATTATTGATTTAATATCCAATTCATCATATGCTACATTAAAGTCAGGAAT
AAATTCTGAGAAATATAAGATTTGCTTTTCATTAAGAGTTGGAGGTATTAAATCTTTTTGAGTTATAAT
ATTAAACTTAAATGTATCACTATTATCTATTTCTGGAATATCTTTTATAATATTTTCGTTTCGCATTTCT
AAAATAAATGATCCCGGCATCCATAATTCTGCAGTCATTGCATATCGCACTTCAGAATAAGAATTGAT
TAGATTATTCATTATTTTTGAGAATTTGCTAATCTGGATATCTTAACATGATATTTGCAGGATACTCG
CACATATAGGTAGGATTATTTGTAGACATATTTATTTTTTCTATAATTGGGTTTAGTGAATGAGATAAT
AAATATTCACGTAATTTATCTTTATCTTCTTCATTATCAAAATCTAAACCTAATACATTACATATATTCA
ATATAAATGATAATGGTATTTCATAAGGTATTCTAATATCATTAAGGTAATTTACTCCGTTATTCTCAA
```

```
AATTCTGATTTAAGAAATTTAAGTTATTCCAAGCAGAAAGTTCACTAGGGAGTTTCATGTATATATCAA
AACGTAATTTTATCCGATTAGGAATATAAAAAATACGAATATCATTTTCATGATCTTCAAATACCATTT
TGTATTCTTTGTGTTTATTACGATTTTTTATATAATATTGATGAGTAGACCAAAAAGGTAATATATCAA
TAAATGTATCACCTAACTCAAATTTAGGGGAGATTCCAATGTATGGTTTAGGCATATCAGTAAATAAC
CCTTTACCATTACTAAAATTAGTCGAATTTAATGATTCACCGATATATACCTTTTTAAAATATTTAGGT
GGAAATTTGCTTATAAAATAGTTTGATATGAATGATGATACGCCACTAATAACATTATGTATAGATGG
ACTAGCAGTACATAATGCTACACTATTATTATATTCAGATCTTGCAGGATCTAACATAAGAGAATCAC
GCCTTTCTATATAATGTTGTTCACAAAACAAAAAACCCCTATTACTATAGTTATATAGTAATAGGGTAA
AAGATCAGAGATTGTGGGATCTCTAAAAGTGTGGAGTACAGAAAGCATATACAATAGGTTAAAAAAT
AAAAGGTTAAAAAAATCCTATCGTATAATATATTATTTAGAAAATTACGCTTAAAAAAATAATATTAT
CTCTAGGTACTGATGCTCGAATTGTATACATGTTTGAAATGATGAATTTATCAAAGTCGAAATCTTCTC
CAACAATTTCTTCAAACTCTTCATTTCCTCTAATAAATTTATTAATGATAATAGTAGTTTTATTAATAAT
TTCGTTAGTCAAGATAACCTGTACTTTTTCTACATATTTATTCATGTTTTTATCATCATTTTGATTTTTAA
CTTCAGGAAAATTTTCATTTTCCGGTTTATTTAGTTTTAATACAAATTCAGGATTATCCTTATTAATAAA
GATTCTTGAATTATTATCTTTAAAATCAACTTTTTCTGATTCATCAATAATTTTTCTTAATTCATTAACT
AAATTTTCTTTACCGATAAAACTAATAATGTTATTTCGGATAGCAATTTCTTTTCTGAGTTTAATCAGTT
TTTCATCATCAATCATCTCATTTAGTCTTTTCTCATTTTCATTATAAATCATCTTGTATTTTCTTCCCTTC
TAATTCCTTTTCAGGATTATATGTTAATTCACTATTAATTTCATTATTTTTAATTTTCATTGCAAGATCTA
ATATGTCATCATCTAGTGTTTTTTTAAGTTCTTTACTTATGCGTATATTTTTTGAATTTGGGTTTTCTTTA
AATCTTATTATTAGATTTGTTTCTGGATGAGTATTATAACGTTTTTCAGATATTAACCGATATACTTGAT
TATCATCTTTCCATAGTATTTTATTTAATAAGTCCATTAATGTTTTTTGATAATTATCGATATCTGGTTTT
TTAATTCTTTTTTCCTGATTTGTCAACATTAGATATATTTTATAAAGGCTATTTCCAAACTTTGTTGGAA
TATTACTAAATATGGATTCTAATTCTATTGGACCTTCAAAAGCGTTTTCATTAAAAGGTATTTTATTCTT
ATGAACTGAATTATATTCGTTTATAGATTTAATTAATATTTTTCGAAATTCATTTTTATACCCACCTAAT
GGATCGTATGTGCTACCAATGATATTAAATCTATGTCGTTGATACGGTAATATTTCCCTATCAATATTA
ATATGTATTTCATTTTTATCAAATTTAATGATATCTATATTTGCATTTAAGATATACATCTTAAAATTTC
TCGATTTTGGTTTTTTAATTTTTATATCCAAAGGTTTTTCTTCACCATTAGGAATAGGTCTTTTTTTCATT
ACTGCTTCTCACCTCCAAAAGTATTAGTATATAAATAATTATTATTCAATAATTATAATTTTTTAAAGT
AAAAATATACTCATATCAATCATTTTAATATATCACGATATATGATAATTAATTAATTGATATGAGTAT
ATAAGTTATATAAAAATACTGATGCCATTATTAATATTAATGCAGTTACTATATAATATATTAACGCATT
ATTTTGCTTTTCAGATCTATTTATTCTAAACGTCATATTCATATGACGTTCTATTTCTTTAAATAATTTAT
CCATAAAGTTTTCAATATCAGAAGTAGTTTTCTTAATGGGTTTAATTTCTTTAATTATTTCATTAGTATA
TTTATTCGTTTCATCTGCTTGTTCTTTAATTGCATTTAAAACAGCATCAGTTTTCTTCTTATGTGCTTCAA
ATTCTTCTTTTGTAATATATTTTTCTTTATCAATATATTTATCGTTATCTTTTCTTTTAAAATATCCTTTTTA
GTAGTGCAGTGAACTTTTCCATCATCCTTAAACCCACCTTATTTTTATTTTAATAAAAGGTCGGGTACG
ATATTAATAGCTGAAACAATTATACCACTCAGAGCAGGTAACAATGCTAACCATATTTTATTTCTGCTT
TCACTATTATCTAATTTATGACTATGTGATAATTGTGTTGTTTCAAGATTCCCTATTCGTTCATCTGAAG
ATTTTGTAAATGAATCTATTTTTGTCCTAGTTTCATTTTTAACTTCCTCGATATTTGAATTAAATCTTTCA
CCAAGATCATCAATTTTATTAAAAAATTTGACTTGAGAAATCATCAAATTTTTCTTTAATATTATCTACAT
TTTGACTTATTTTAGCAATCTCTATATTTGTATCATTTAGTTTTGTTGAATTTTCATCAGTTTTCTTCTTA
ATATCTGAAGTAGTTTGATTATAGTTGTCGATAAAAAGTTTAAATTCATTTCTGGAAACTAGTTCTTTTT
CTGAGTTATTTGCCAAAACCTCACCCCCCCAGTTATAGTAGCCATACCGTTAAATACCGATATGATTAA
TAGACGGTTAAAGTTTGACTTAATGAGAGTATTTGTATCGTTTACTGCAGAAGCATAAATTATCCATGC
TATTGTTGCAAAGAAACATGATATCGCTATTATAATATATCTAGAGGGTTTCTTATAAGATATAAACGC
CGATATAATGAGTAATGAACCAGTAACAACAAAGATATATGACCATATAATTATGGGAAATACCCTAT
TTAACATAATATATGTTTCAGAAGTAAGTAATACACTAGATTCGGCAATATTAAAACTGATTCCCGTAC
TTAATGATAATAATCCTAATAGGATTAATAGAGATTGTTCCATCAAAAGAATATAATTAAATTCATTCA
TAAATTTTTTAATTATATTTTTCATTATAATAAACAATCCTTTCAGAAAATATTATACCATATACTTATA
ATTAAAATATATGGTATAATTATTCTCAATTAATAAATTTATACAAATTATTCGGATGGTGGTGAATCT
AATTTAGCTTCAATAGCACTTACCCGATTTAATAATTCATTCCACTGAGCTTCAGTCGGAAATCCATTA
TCACCTTTTGCACCTTTAAGACTAGCTAACCATTCAGCTTCCACTAAATCCAGATGCTTTTGCTA
GGTCGTAAGCAGACTTACCGTTATCACCAGTGCTTCCTTTATCGCCTTTATCACCTTTTGCGCCTTTAAT
ACTAGCTAACCATTGAGTTAATGTACCGTTAAATCCATCAGCAACTGCTAAGTCGTAAGCAGACTTAC
CGTTATCACCATTATCACCTTTTGCGCCTTTAAGACTAGCTAACCATTCAGCTTCAGTTCCACTAAATCC
AGCTAATTTTGCTAGTTCGTAAGCAGACTTACCGTTATCTCCAGTGCTTCCTTTATCACCTTTTGCACCT
TTAATACTAACTAACCATTCGGCTTCAGTTCCACTAAAGCCGGCTAATTTTGCTAGTTCGTAAGCAGAA
TTACCGTTATCACCAGTGCTTCCTTTATCGCCTTTGTCGCCTTTTGCACCTTTAAGACTAGCTAACCATT
CGGCTTCAGTTCCACTAAATCCATCTAATTTTGCTAGATCGTAAGCAGACTTACCCTCTTCACCATCAA
CTCCGGGATCACCCTTTGGTCCACGGTCACTATCGGAAACGGTATCATCTACGATATCTTCATTAGGTT
TATGATAGTTAACTTGAGATATTTCATCAATATTACTAATTACATTAGTAACTCTTCCCGCTTCAGAAT
ACGTTAATACAAGTTCATCACGATCATATTTTAATGTACCACTACGTTTAATATCTTTTACTAGTACTCG
ATGATCTGAGTATATTGATGTGATTATTATTTCATTTTTGTTATGTCTATCGATGTATTCTTCTATTCTAT
ATCCTATAGCCATTTTATTATATCATCCCTTTCGTATAAAGAAACCTTTATATAATTTTTTGTTTTATAT
ATTGGAGTTCTAAATATAAAAATTATTATGATTTGTATATATTAATAACATCTATAATTCTAAGCTGTG
CTTCTTGATATAATTTATTCTTCCAATCTTCACCTAAGTCAATAATTTTATTTTTTGGTAATGTTTCTAGT
AATTCAATCTTATTTTCACGTATATCGGTAGTAATTACATCATTATCGTCATATACGGTTAATGATTTAT
AATTATATTTATAAAATGATAATTCTATAAATCTACCTATATCGTTTATATTATTTTTTCCTATAACTAC
TAATTTAGGTATCATATAATCATTATAATCAACTTCAATAGCATTATCGTTATCAATATATTCAATAGT
TGTATGAATTTTATCATCTTCAGTAATTACTTCTGGAAGATTATATGGTTTAATACTGAAGTCAAAACC
ATATTTTTCAGAATAGTTATACGTATCTGTAATATTAACAGAATAGTTTCGTATTCCTTCATTTTGAATT
GAATTAATATCGTCTATATTATTAAATAAATAAATATTATCAATATTTGGTAGTTCTAAATAATGATAA
TTATTGAATTCTCTTTCTAGTACTGTTTCACTAAAGAACATTGAATCAAAAAGATAATCATCATCATTG
TTAGAAGTAATAATAAACGTATTAAATACCTTTATTAAGTTTAATTTTATTAGCATATTCGTAAACATTT
GTTTGTTCATTATAAATGCTTAATCGATCATGAGATATACCTTGACTATTATATTTATACGTATATGAC
AATCCGTTAATATTTACTTTTGCATTACGATTATATTTATCACTAGGATTATATCCAGTAATATATACAT
ATTTCTCAATATCATTTTCTAGGTTAATCTTAAATTCGATATTACCTTTATTTATCTTTACTAATTTATTA
GATAATAAGTTATTATAAGTATTATCAACAATCTCTGAAGTATTATCATCATTTACTGTTTTTAATGAA
GATGATAATTCATATCCTGTAATATTTCCATTAATTTTTATAGGATCGATGAAATGATTATATATTGGA
ACATGGTTAATAATTGCTTTTCTAAGAACTAAAATATTAAAAATCTACATTTTTTGTATTTCTAGGTTGAC
```

```
CTGACTTTAATAATATTTCTTCAATATAATCATTATGGTCAGCATTAATAATATTATTGTTGATTTGATT
CTGAGTATACATACTATACTGTTTAGGAGTTATATCTTGCCATACATTCTTGTTATTACCATTAGTTGTT
AAACTTCTTTCAATATTATTAATAAAGATTGAAGATGTTTTAGATGTCAGATTATTACTTCCCATATAT
ACCGTCATATTGTAATTATTCATTTCAGGAATAAATATCTTCATTCTTAAATACCCATCTTCTAATCGAA
CATAACCCTTTCCAAAATATTTTAAATAGTCAGAAGTCATTCGTGATCCAGAAGTTTTAGTATCTTCAT
ATTCAAATATTGTTCCATCATAACATTCATATACATAAGTACCGTCAGCTAGTATAGACGGATATATGA
CTCCATCATTATTGATATAACCATGAGTAATGATATCCTGATCAAAAATAATATCTTTTGGATAGTGTG
GATGACAATAACACTCTCCATTACAATTACACCCATTATCACAGTCATCATCATCGTCACCACCATTAT
TAGGTGGAGTAAATTTATTATTAATGTAATTTACCATTGTTATACTGGTAGGATCAACAATACTTTGAA
CTTTTCCATTCTTATCAGTAAAATTTATTTTAAAATCTTTATGTTCTAATAAGCCATCACGATTAATATC
TTTAATTAATGTCTTAACATTAGAATCGATTGATGTAATATCAATTAATCCTGAGTTATGATCATCAAT
CATTTCTTCAATACGATAAACTTTCATATTTTGTTTCACCTACTATCCGTTTAATATTATATTGTTATCTT
AAAAATTTTAGGACTTTTTGACCTATTCCATATTTAATATCTTTAAATTTATTATCTAATGACCTAAATG
ATAAAACTTGGACTGCTCTATCCCTAGTCATCAACAAGTTTGTTTTAATACGTTTCATTAGGTTTAATTC
ATCATAACGCATTCCTGCCATACACTCAATATATGATGTTAATCCAATATTATATCTTAATTGCTTAAT
ACGCTTAGAAGCCATTAGGTTAGGATATAAGTCACGTACTTGCATAGATACGGTTACTTCACGAGGAA
AGTTTTCAGCAGTCCATGTTTGTTCTTCGCCACGAACCATATTTATTGATGATATTACGCCACATTCAC
ATTCAAATCTTCCTGGACAAGACATTCTAACCAAGAAAGGTTGTTTATAACTATAATATGCGTCTTGTA
ACGGTAAACCTAATACCAGTAAAGATACAAATGGTACATATACATAATTGAATATCGCTCTAGGATCT
CCATAAGGAGTATAGAATCTAAATTCTAAATTATACGATCTATCGAAAGTAGAGTTTGACCATAAGTC
TGGATAGTATAACTGAGAACCATCTAGATTTTCAGTAAACGCACCAACTAAGCTACCCAATACCGGAA
TTGTTTCAATAACGTCTGTTATCATATCCTTGATTCCATCAGTAATAGCACCCAATAATCCTCCGCCGC
CAATTCCGGCAAGAGTTTTATTTTCTCTAATTCAGCCTGTTTACTATTAGATTCACTAGCTAAAGAAG
ACTGAGAATAATCATTAGATGAACTTTCTGATACGCTGGTTGATTTATTTGCATAGAAAGCAATGCCGT
AGTTATCACCATTATTATATTTACTAAAATCGAAAACACCTTCTAATCCCATAGAATGATATATATAGC
TTAGTATTGTTTGTACATATCGATAATACTCTTCGTAATTTTGTTTAAACGATATAAATCTTCCATCACT
AAACTTATTTGCATTAATCATTGGAAAGACATTATCTTCAATTTTCTCTCCAATACCGAAAAGATTAAA
AGTGTTTCCTGACATACTACCAAATAATTTCTTATTTAGTCTAGGTTTTCCGGGAGTAATAAATATTAC
TGGTAGATCATTTTCGAATGTATTTCGGTACACTCTAGAGTTTGCATCATCTAATGGACCATATTTAAG
TGGCATACCTAATACCCTTATATTATCTTTACCATATGAAGCATCAAACGTATCTATTTTAGTATTTCCA
AAAGCATTAATAGTTTCTCCCATTGCATTGACATATAGACCTTCATTATTAACTTGTGAAGGGTCAATA
TCATCTTCTTGCATTAGTGTGTCTCCCTCAACTCCACTGTCTGGTTTTACAATATAAAAATCATCATCTG
AATCCGTATTATTATTAGAATTTTTATTACTTACTAAATCAGGCATATTTTCACCACTTTCAAAATAAAT
TTTCCTTGAGACCAAATTTAATACATTTATGGTCTCAAGGAAATAAAATTTAATATCCCGCTAATATAG
GAGTTATACTATTAGGATCAAGTTTAAAGCTTGGTTGATCTAATTTATTATCTCTATCATTTTTATGATC
ATTTCTAGTTTGTTTTAAGATGTTATTCGTTTCATTAGTTAAGTTATTATTAGTTGCTTCTAGTCTACTAA
TATTTCTAATTTCACGAATTAAATCACTCAATTTGCTGATAGAATCTTTATCATTCTTATCAATTAATTT
ATACATCTTATCGAGAATATGATTTACTTTTTTAAGTTCATCATATTTTTCTTTATCATATTGGTAAGGT
TTATTAGGTTTAGCGGAACTTCCATTAGATCCATTTTTACCGTTAGAACCGTTAGCACCATTAGATCCG
TTTTTACCTCCGGAACCATTCTTTCCACCGCCGTTAGGTTTAGCGGAACTTCCATTAGATCCGTTTTTAC
CATTAAAACCGTTAGAACCATTACCATTAGAAGAACCACTAGAACCAGGACTATTATCTCCAGAATAT
CCACCCTTAGAGCCACCACTTTTAGAAGGTTCAGCGGTTGCTGAAGTTGAATTACTACCATCTTTACCA
TTAGAGAAGTCTTCATTATCTCCTTTTAGACCGTATTCTTTAGCATATTTACTGTTAATACGATCACCGA
TAGCTTTCTTTTCTTCTTCAGTTAGTTTAAAGTTAGCTCTTGATTTTTGTTCTTCAGTTTCTTCATTAACT
TCTCCAGTACCAGACAGTTCTGCACTACCATCAGCAGTACCTCCAGTGTTTCCACTAACTCTACCAAAT
CCTACTAATCTACCAAACCAATCTGCAGGCATATTTAATGCATCACTACGAATGTTTACACCTTTACTA
GATTCAGCATTGATCATTTTCCCTTCACTGATATAAATACCTACGTGGGAAATAGAACCATCTGGGTTT
GCTGAGAAGAATATCAAATCACCAATAGATAGTTCATCTTTTTTAATTCTTTTAGTAGCTTTATATTGTT
CTCTAGAAGTACGTGGAAGTTTCTTACCGACAGAATTGTATGCATTCATAACTAGACTAGAACAGTCA
AAGGTCTTAGTTTTACCTAAACCAGAACTTGGTCCCATTGAGTATGGAGTACCGATATACTTCTTAGCA
TATTCTACGGCTTTATATCCTATAGATTGTCCGTCAGTTTTATCAGAACTTCCATTATTGGACATTACAG
AACCTAAATTACTTCCAATATCTTTACCGGTATTTTTATTTTCTTTACTAGACGATACTTTTTGGTTTGT
AAGATCTTTTAGTTTTGCACCCTCTTCTTTAGCACGTCTTCTTAATCCCGCTTCTTGATTGGTTCCTGCAT
ATTGACCCATATATTGACTTAATCTTTGTTTTTGGACTAAATCAATAATTTGATTGTCTGATAGTTTACT
AATATTTTTTCCGGCTAATGCACGTTTAAATAGACTAGTTGCACCTCCAGCACCATGCTGTACTGAAGC
ACTTAAAATTAATTCTTGAATACCTCTAGATCGACCACTTAAATCAGTTCCCAGTGCTTTATTTATTTTA
GCTAGTCCTGGATTATAGAAGTCTTTTTGGAAGTATTCTTGTTGTGCTTCACCAAATGCTTTATTTTGTC
CTAATTTTTTCCAAGAAGCATCAAAGCTAGATGAACCTGGAGAACCACTAAGCTTTTTAGCAAGGTCT
GGATGAGCTGATCCTAACCATTTAACAAAATTAGCCAGTGATCCTTTAGTAGATGATAATTGGTAAAT
ACCGTAAGATTTACCGCCGGCATCTCCAACCCCACTAGAGATATATCCCGCACCACTAAAGTCTTCTTT
ACCAGTTTCATAAAATCTGGCTACTGAACCAAAGTCTTTTGAAAGATTCTTTCCAGCTCCGGAACCGCC
AGAGTTTCCACCAGTCGATGCAGCATTTGCATTAACGCTACCTAATCCTTTTACAATATCTTTTAATTTA
TCAGTAATTGATGAGAAGAAATTGCTTATTTTACCCCATACTGATTTAGATGGTTTATTTGGATCAAAT
CCATTTTCCGCCATATTATATAATGCTCCAACCGGAGTAAGACTGAATAAAGATTTAGCAAATGATTTA
GGATTCTTTTTCATATCTTGACCTACTCTAGATGACATTAATTTACTGTATTCAGAACCCATATTCATAA
CCATTCCTAATGGAGTAGCATCTAAAAAGTCTTTAAACTTACTTTGTTCTTTACCATCTTTACCTTTATC
ATCTTTCTTTTTCTTTCTAGCATCATTGAATTTTTCAGCAATACCCATTGGAGTTAATCCGTATAGTGCA
TCTTTAATCTTATTTTTACGTTCTTCGGATTTTTTCTCTTTAACTCTTTTTCTTTTCTTTTTCAGCTTTAT
CACCTTTAATTAAATCCCCAATAGAAGGTAATTTAGGAGTGCTTGCAGATTTACCTGATTTAGCACTCG
ACATTCCTTTTACAATTGATCCTACTAATATAGAACCTAATATTGCTGCACCGCCAACAGCTAATGCCG
GTCCGGCAATTGGAATTCCAGATACTAATGATAGTAATGCCCTTCCACCCATTTCCTGCAATCCTAAGAG
CTGATGAGATTCCAGATACTAATTTTTCTCTGGTTGCATTAAATATTGCAGTTCCTCTTTCAGTAACAGT
TCTAAATGCTTCAGTTTCACCTAGACTTTTCATTCGAAACATCATTCGAGCAATTATTCCTTTTTTACTT
TCTGCGGATTCTAGTGCAATATCTTTAGTTGCTGAAGCCATTCTCATTTTAGCTATTAGATTTTCAGTTT
TTTCACGAATGGAATTGATTGTACCCATTGGATCTTTTACTGATGAAACAATTGATCCTCCAACTTTTTT
AGCAGTATCCATAGCAAGACCGCCTGCATTTTTGACCATTCCACCAAATTTTGTATCTTTAACCATTCC
CCATACAGATCCGGCTGCATTAATGGCTCCAGATATAGTATCTTGGTTAATAATATTATCGGGTTCACC
GCTAATGATATCACCTTTAGTTTTATTATTAAACATATTCATACGATCTTTGGTTTTCTTGATTTTATCTT
GCATAGAATGATACTTGGATACAATTGAACTACCTAGTTTACTTGAAGGATTTTTAAATGCCGAGCTTG
```

-continued

```
CATCTTTAATTTTGGTTCTAGAGCCATAATCCTCACCGACTGAACTATCGATATTTACAGGGTCGCTTG
CGTCAGGAGTAACATCTTGACCATTCGCATTTTTTACAAAATCACTCCTAAGGTCTGATACGCTTGATG
CAATAATTGACAGATACCCTAGTTTCTTAGATATTTCAGTAAGAATATTTATCTTCTTCATATCATTATC
ATTATTTCCACTTGCAGAATTATATGATACCGTTGATCTATTATCGTCATCACGAGTTATATTTCCTGTA
GTTTCATTATCAAATAATCCAAATAATGCATTTTTTACTGATCCTAGAGGAGTCTCTGCTTGTAAATAT
CTTTGACCTTTTACTTGTGTCTTAAGAACATTTCTTGAAAAAGTTGCACTATTACCATCTATAATCTGTG
ATAATTTTTCATAGATGTCTCCATCAAACATGTCTTTGTTATTATCTAATGCAGTACGGTTTTTGATATT
ATTTTTAGATAATTTGATAATAGTATCTTTAATATTATCATTATCGATTCCTGCTTCACTCATCATAGAT
TCTAATGTTGCATTCTTACTAGATTTATTTAAAAGTATGCTGAGTGGAGATTTATTCTCCGTAGAGATT
GCTCTATCCATTCCAGAATTAAAGTTATCTTTAGCTTTACTAGGATCTAACCATTTTCCACTCTTATAAT
CATATACTAATTTTTGACCTGAAGAAGCTTCTAGCATTTTTGCTAAATAACCTGGAATTACCGTATTAA
TAGTATTATGAGTTTGAGCATCAAAGTTAACAGGTCTGTCTGCTGAAACTCTAGCCATAGAGCTTACTT
TTCCTAGATTAGCAGGACCAAATTGTCGATTGAGTGAAGTCATTAGTGGATTTTCACCAAAGATTTTCT
TAAATTGACCACTAATGATACTTTCGTCACCTTCAACAAGATTACCTAGTGCTGAATGTATTTTTCCGC
CAACTTTACCATTGGGATTAGTTCGATTAAGCGTACCTTTAACCATTCTGTCAATTAATCTTTCTTTATT
TTGGAATGGTCCAATTTCACCAGTAGATAATCTTTCAATAGTGTCATATATCGATGCAGGTATATTTGA
TACATTCTTATCAAAATAATTTTTTACTCTATCTCTTGCATATCTATTTGCTCGTTCGTTCATTAATATTTTTAG
AGATAGAATTTTTTGCATTTTTAAGTAAGTCTTTAGCGCTTGCATTTCCAGAATTTAGACTACTAAGTTT
AAACATTGATGATGTTATTTTACCTATTCCAAATATACCAGAAAGCATATCATCCATTAGACCCACATT
ATTGATACTTGCTTTAGCGCTTGCTTGAGATATTCTATTCATTTTTTCTAATAATGTAGTAGATTTAGAA
GATTGCTCGATTAATTGTGAATAGAATTTGATATTTGTTTGATTCATTTTATTTAAGGTATTATTTAACG
TAGAAAATCCTCTTGTATTTACCCCAACTACTGAACTTGCTGATACAATAGTAGATTCAACAATTTTAT
CAATATTTTGTTCTTCATTTACATCTTCATTATTGATATGATCATTATTATCTTGAGGAGATTCGGTATC
AATAATAACTTCAGAGTTAACGCTTGAAGTATTACTTGATTTTCGATTCATTTTATTTAATGATCTACTT
AGTATATCTAACGTGTTTTTACCATAAGCTTCAATACCCAAATTATCTTGGTTCATTGAATTATTTGAA
GTTCTATTATTCTTACTTTCCAGTTTATCGTCTAAATCTTTAGATATACTTCGGTATATATTATTAGCAG
ACATATTGGATGCAGGAATTCGATTATTTCCTTTTCCCCAATTTTTATTACCTTTATTCATATTGTCAAT
ATATTTACTTCCCTCTTTAAAAGTGCTATCAATACTTTTATCTGCCATTCTAGTGTCTCACCAACTTTCA
TATGTAGAGATTAAATCGCATTATTAATCTTCTTATATATTAATGTTTAAGAATAGTAAAAATCTGATA
ACTTTAGAAAAAAAAAAAATAACCATATAGAGATAAATATCTCTATATGGTAAATATAATTTAAAGATC
AATATTAAATTGTGATTTTTCAGTTATAAGAGTATTTAATTCTTCCGCACTATATTTACTATAACGTTTA
TTTATAGTACTGCTAATATATTTTAAAATATAAACTAGATTTAATAATACGCTAAATCTTCTTAATTCTT
TTTCATCTTTAGATAATTCTTTTAGTTTTTTATGATATTTCTTTCAGGATATTGCCTGCGAATATTAAG
GAAAGTATTTCTGAAATTACATCATTAAATTTATCTATTTGAAGCTTAGTTTTATATTCGCTAGGTAG
TTCTTCTAGAATAATCTTTTTAAAATGATCCTTGTTTAGATTATAATCTACAATAAGATGAGTAATGAC
TGAACCAATATATAAATATATATCCATAATTTCTAAGATAGCTAATTTTTCATTATCCATAGATTGATT
GTTTACTTCATATAAATATTCTTGTACTTCTTCCATTATCTGAGGGTAAAATCTTTCTAGCATTTTTACAT
TCTGTTTCTTCTGGAAATTTATACTTAGATATCATATGTTTTTGATTTTCAATAAGATTTTCTATAGAGA
ATGAGAAACTATTGTTTTCTTCCGTAATAATTGATTTAACTTTATAAGCCAAATTTACAACACCCACAA
TCTGTTTATTTATAAGTATTATTATCTAAAAGGGTCTTGGTATTAATCTAAATTCCTTAATATCTTCTTC
AGTATTAAGATTAAATTCAATTTCCCACTTATTTTTATTTAATATTTTTCGAATATTATAGTCAAAAAAG
AATTCGGCAGTATCTATAAAATTTCCTAAAATACTTGTTCTAAAGTTATACGTAAAAGATTTTCCAATA
ATAATCTTTTGATTTATACTGGTCGGTATTTTCCAAATTCCATTGATATCAATTCTGAAAAGATTATCTG
GATCATAGTAAATATTAGAAAAATAATCTAATATTGTTTTAATATCACCTATATTTCTATTATAAGGAA
TAATGCTTTTCTTAGTTTTCTTATGGATAATTTTTAATATACCGTCATAATTTTTTGTTTCCATAAGCGA
CATGCCTTTCAATTAATTTTATTAATAATTTATTTTTGAAAACTGATTTTTTAGATATAAATTTATTCTA
ATATTAGAGTTTTGTATTGAATGAGTTAGATCTATGATATTCTCATTACTATTACCAGAATTATTTAGTA
CATTTATAATTCTTAGTAAGTTTTGTTGACTTTCAGGAGTTACCTTCATACTCATATCATTAATTATATT
ATAATCTAAACTTTCTTTTGACATATTAATATCAATAGAATCAATAATATTAATATTTTCTAAAGATAT
ATCTTTCATTCTTTTATTATCCTCAATATCCGATATAATATAACTAAGATAGAATATTGTCCGTAGTTGA
TTTATTCGGTAAGTATTTTTATAATGAATGTTTGGATACGTTATCATGAATGGTGGTTCAATCTTATCTT
TATATTTAACATTATTATTGAATATTTCATCAATCTTATAAACAATATCCTGATACATTCCCCTATACAT
TATGTCTTTATTGTAACAAACACTGGAATAGTATACTAAATATACATTTATAATTAAAAACGAAAAAA
TATTTATCATTAGAAACATTTTTATTTCATGAATATTATAATAATTTATAAATGTACTAAAATTAAAAG
ATACTAGTAGTATACAAGTATTAATAGCTACTAGGTATAAAGGATTCTTATAAAATCTTACCAATA
GTAATAAATTTATATTTCTTTAACAATTTAGATCACTTCCATTTCTTTATATGACGTGAATATATTATTG
TATAGAAAAAATATAAATGTACAATAAATATTATAGTGCAGGTAGTTATATCTATAATAAAATAAATA
TAACTACCTACACTGATTCCCCGATTTAACTAATACAATAATAAAAAATTGTTATTGTTGTCTATGTTG
TTTGTATTTCTCTTCAAACTCAGAAGTGTATGATTCATTTAGTTTGGAGATATCATAATCTTTACCGTCA
TCTCCAGTGAACGTACCATCCCCATTATCTGTTCCACGAATCTTATCATAATTCATTACGCTTGCAAAC
ATACGAGTTCCTGGCATACACAATGTTTCAGTTTCACGGACTTTACCAATATGAGCATTTGTTTTCTTA
CGTGAAAATCCAGTAGAACCTACACGAACTCTTAGTCCATTTTTAAGAGTCTCATCTAAGATATCCCCA
AAGGCGGTAATCATATCAAATACTTTTCGTTTAGAAAGATCAATCTTCACTAAAAGATCCATCAGCAAT
CAGTTTATCATAAAGAAGATTTACTTGATCGTCCTTAATCAACATATCTAATTTTTCACCACTATCTGTC
TTTTGATCAATAAGTTTATTAAGAGTTAGATATTCACGAGATTCTTTTGGTTTCTCTTCTTTTTTCTTTTT
AGATTCTTTTTTAGGTTTATCCTCTTTTTTATCTTTTGTTGAATCTTTCTTGACTGATTTAGTAGTTTTAG
ATTTTTCTTTAGGTTCAACTTTTTCTTTATTAACTACTTCTTCTGAAGAAATCTTAGTAGGTTCACTTTCT
TCACTAGTTTTTTACCACTGGTTTAACAACACGTTTCTTGGGTGTTTCTTCTTTAGCTTTACTTTTTACCAC
TGGAACTACTTTTTTATTAAGTTCAACTTTTTCTTCACTAACTGCTTCTTCTGAAGAAGGTTTAACTGTA
CTCTTTCTTACTGCTCTTTTTACCATAGGACGAACGACTTTCTTCTTTTCTTCTGCCATTTAATTTACCAC
CTTTAATTTATTTTTTGAAATATTATTAAATTAGTTATTGAATAAAAATAATCTTTTAATTCTTAACTTT
ATTTAATATATACCCTATTTTATATTAATGTAACTACCTTATTGCCAACGATATTTAACAATATTTCACG
TTTATAATATATACTTATAATATAGGTTTAAATTTTAATTTTTAAAGAAAAATTTTCATAACATATTAA
TATTAAAAATTATATTAATTTGATTTTCTTATGGGACTCCGATGGGACTCGCAAAATCTGGACTGAGCC
TAGACTCCTTATTAAGATGCTTATTAATGGACTTTACTATTTTAAATCGAATTCCAACGTTTGTTAAAA
GGTGGACAAATAGAGGGTAAAGAGCTTGCGGTATAGTAGACGATGGTCTCACTGTAGATGTAAGTAA
GTTTGTAAAGATTCTTTATTATTTTACGTTTTATTCTTTTTTTTACTTCCCACACTTGAAGAGTGTTTAAAA
GGGGGGTTGGGGGGTTTATTGTTAGTTTAATTTTTTCATAAATAATTTTAAAATAAAAATTATTTTTATT
AAAAAATAATTTAGAGTGGGTGCTGGAATTTCAGCGCTCCGCACTTCATTCCGATAATAAACAAACCG
```

```
AGAACCTGAAGTTGAGTATTGTGTATCCAATTATCCTTAATATCAAAGAATGTTTATAATAAGTAATATAC
AGTAATTAAATAATAAATATTGTATATAGGAAATATAGTATGAATATTATTCAATATAATAATTAATG
ATTTGATAAATACTTTAATATAAAAAGTATTTATCAGTATAATATCTAATCAATATAAATATTCAATAA
TTAATAAAATTTTAAGTTAGATATTAAATATTTATATTAATATTAGAATAGTATAATAAATATTAAATAT
TAGAAATATCTAATAATTATTACATATAAGGTATATAGTATTTCAATTATATTAGTATTAATAAGTTTT
ATCAATATAATTTAAATAACAATTCTATATACTGAATGAATAAAAATAATTATTCAGAGAGGAGAGTA
TACTTTTGTTATATATCAGTGACCTAAAGAAGTATAGATTATATAAAGGTAATAAGCTTAATGGTATTA
ATAAGTTAAGTGAAAATAAAGATCCAAATAAAGGTCAATTAATATTACATTTAGGAAATAATGATACA
GATATTATCAGTTTCTTTAATTCAAGAATATTTAAGAATAATCTATTCAAAAGTTATTCTACAGCTAGA
AGATATAGAACTAATAATAAACGAAAAATGTATATTAAAGATCTTAAAGAACATTTTGCAAAGATAA
AGAAAGAAACAAAAGTTACATTATTTACTAAAGTAAATTATAAACAGTTTAAGGGTAATAACTTAGTA
TATGATATTACAGATCAATATAATATTGAAATTGAATCAATTAATAATAAAAAGAATGGTTTAATGGT
TTCTAATAACTTTATAAAGTTATTAGAAAAATCTCTGTTGGAAGAATATGATGATACAGTATTATTAAT
TAATATGAATACATTGAACGTAGATATGGATGATATATTCAATATTACTAAGTCTACTCATCCACTAAC
AGTTATTGATTTTATTATTAAAAAGAAATTGGATATTAGTAACTTAATTGACAAGAATATAACAATTGT
TGTATTTAATCCTAATAACAGATTATTTTATAGTTATCCATTAACTACAGAATTATATCCTAAAAGACA
GATCATCAATCAAAGATCTAAATCACTAATTAATTTGGAAGTTAATGAAATTGAAAGCAATGATGAGA
TGAGTAATATTCCAGACATTAATGATATTGATGATGCTAAAAGACAACTAGGTAATAATATGAGGTTA
GGTCGATTAAGGTCTAGAAGTAAGATACCTGTTAGTATAGACAATTCTGAAGTAAGTAATAATTCTTC
ACAAGAAGACTCAATAACAACTAAAAAATTAGATGATATTGATAAAGCTAATGAAATAAATGATAAG
GTTGAAGAAATTATTACCCTTACTAGTGATAATACTTTATTATCTTCAGAAGCTAAAAAACAATTATAT
ACAATAGCTCAAGATGAAATTAAAAATAATAAAGATTTAGTTAAGATGGATAGTGCTAAAGTTGTCTC
TATTCTTAATCGTAATGAAGAATTCAATAGAATAGTTTCAATGTCTTATAGATCATTTAATATTGGTGG
ATCGAACGCAAAAGAGCTTGCAAGAACAGCAGCACTACAAAAAAGACAGAATGAAATCCTTAATGAT
AAAAATATTTCGAATGTATTAGCTCATGCAAATGATAAAATGATTGATAAAGGAATTATTAAATCAAA
TAATATTAATGATGAAACATTATCAGAACTTTCTGTAAACTCTTTTGATAAGAGTTACATTGAGAAACA
ATTTAATGCCGATATTATTAATGTGTTAAAATCATTTAACGATAATGAGGATATTAGCGTATTCATCTC
AGACATATCTTCTGAAGACTCTTCAGACTTTCAGACAAAGAAACTACATTAAACGTTAAGCTTAAAG
ATACTAAAGGCGTTAATCATAAACTATCATTAGATATTCCTAAGATATATAACGGTAGATATATGATG
GTTAACGGTAGTAAAAAAATACTAACAAAACAGTTACTGTTAAACCTGTAGTAAAAACTGCCACCGG
ACACAGTACAAATAACTACTAACTACAATAAAATGTTTGTTAAGAGATTTGGTAGAAAAGATACTCCA
ATGTTAGCTTCTATCAAAGAAATCTTTAATAAATTTAAAATTGAAGATCATCTTCTTTCTGGTAAAAAC
ATTAAATATTCTTTAGGTAATTCATTATTAGTTAACTCAAAATATCTAACTTCAGTAGAATACAATAAT
ATTTCTAATTATTTACTAAGCTTTAGTTCTGGTAAAGATTATTACAATTTTAACCAAAAGTTATTATTAG
AATTCATTGATAATGATGATAAACTTAATTCACTAGAATATGATTCTACGTTATATTTCCCAGTAGGAT
ATACTTCAGATAAAAGTAAACTTATCTTAGCAAATTTTAAAGATTATCACGTTTATTATAAAGGTGCAA
CTAATAATTATGAATTTGTAGAAGAAAGTTTAAGTAGAATGATATTACTAAATATTTTGATGAGTGTTG
ATGATGAGGTTGCTAAGTTTATTGATAAGGGAATTAAAGCAAATGATAAACTAACATATACACGAGTA
AATATCATTAATAAAACAATTCCTCTAATAATATTATTGTCATATGAGAATGGATTAATCAATACATTG
AATCGATATAATATTGACTTTGAAGTATTAGATTCCAATCCTAAACTAAAGATTACTGATAATAAAGTT
AAACTTAAATTTAAGGATAAATATTTGGTATATGATAATACACTAATAAGAAATTCATTATTATTGTCA
GGTCTTCATATAATGGATATTAATGAATATAACTTAGATGAAATGGAAACCAAAGAACCATATTTAGA
TTTATTCCAAGAATTGTTTAATAGTCGGAATGTAGCTAAAGGTATTCATAATGCATTATCTCTCGCTAT
TGATCCTATCACCAAAGAAGTTTTAGAAGATCTGGGATTACCAACTAATATATTTGATGTCTTATTGTA
TTCAAATACATTATTAGAAGATATGTCTTATAATACTCCTAATGATATGAATGTCTATCGAATTCGTGG
GGCAGAGCAAATCTCTGGTATGATTTATAAGATAATTGCTGAATCATACAAGAACTATAAGGATTCTC
TAAATTCAAGAAATAGTGCTACTAGAATTACTGTACCAAAGGACATTCTTATAAAGACTCTTATGGAG
AGTCCTACGGTAGAGGAAAATTCTGAATTAAACCCAACATTAGAAGTTGAAGTTAGTGGTAAAGTATC
TTTATAAAGGACCAAATGGTCTTAACTTAAGTCAAGGTTATACTCCTGCAGTTCGTTCATATGACCGTTC
TATGAAAGGAATATTGTCGATGATATCACCAGACAGTAGTAAGATTGGTGAAGTTCGTCAATTAAGTT
ATAATCCTGCAATAGTTAGTACTCGTGGATATTTAGATGTAGATGCTTTAAACGGTAATGAATCTACAA
GCCTATATTCTCCTTCTGAACTTTTAAATAACTTTACAAGCTTACATGCTGATCCACCACGTATATCTAT
GCAAGTAACTCAACAAAAACATTTACTAACAACAAGAGTCAATAGTAAACCGCTTATCGGTACTGGTG
TAGAAAAATCATTAGCATATCAAATATCTGATACTTTTGCTACTAAAGCTAAATATGATGGTAAAGTA
GATAAGATAGATACTGTTAATAATTTAATGATGGTTTCTTACGATAACGGTAAAAAAGATATCATTGA
TATTGGAGTTGTAATGAATAAAAACTCCGGTGGAGGATTCTTTTTAGCACAATCTAAAGATATTATGTT
TAAAGAAGGTCAAAAGTTCAAGAATGGAGAAATTCTTGCAAAGAATCCTAACTTCTTTATTGGTGATA
AGCAAGGTGAAATCATATGCTATTGGTAAACTTTCTAAAGTAGCTTTAGCTCCATTAGACGGAACTT
ATGAAGATAGTTCTATGATATCATCATCTATGTCAGAGGATATGACTTCTAAAATTACAATGAAAAAA
GATTTAGTGTTAGGTACTTCGGCAAACTTATCTTATATTGTAAAAGAAGGTCAAAACGTTAAGACTGG
AGATTCATTAGCTGTATTTGAAAATGAATTTGATGATGATTCTATAAATCAGCTATTAAATACTATTGG
TGATAAATTTGAAGAAGAAATCCAAGAAATATCTAATAAAGTTGTAAAATCAAAGTATACTGGGGTA
GTCCAGAAGATTAATATTTATTTATAATCGAGAGATTGATGAATTTTCTCCTTCATTACAAAAGTTAATT
AAAGCTTATATTTCTAAATATGAAAAGAAAAATAAGATAATCTCAGATTATATGAAAGATAGCGATAT
TGATATATCATATGATATGAATATTCCTAGTATTACTAAAATGGATTCAGATAAGATTAAGGGTAATG
ATGTAGATGGATTATTAATTGAATTCTATATTGAATATGAGGATAATTTAAGTACTGGTGATAAAGTA
ACATATTATACGGCACTTAAAACGGTTATATCTGACGTATTCCCAGAAGGTGAAGAACCTTTTGCAGA
ATCAGACCCAGAAGAACATATTGAAGCAGTATTGTCTCCATTATCTGTTATTTCTCGTATGACTCAAGA
CGTTTATCTCAACATTATATACTAACAAAGCATTAATCAATCTGAAAAAACAAATTGGTGAAATGTTAA
AATAACTCACTCTTGAGAGAAACATATTAATATTATAGATGTGAAGGTTGCTTTGTGCAGCTTTCGCAT
CTATAATTTCTATCAAGAAAGTTGGTGAAACTAGTGGGTAAGTTAGTATCAAATAATAATAACGGGAA
TAATGTAAGTCCTATAGAAAAAGATATTGTAAATAACTATATAGGTAGTTATATTGAAGGTACTAGTG
CATATAGTAAACTATTAGAAAATGCTCCCAATTTTGTTACCTATTACTCTAAAAAATACTAGATCATCTA
ATGAAGATCCGGGTCTTGGAGGAACGGTTGAATACGTAGGTTCAGAATCTTCACTATTATATAACAAA
ATAAAGAATTTTCCAGTATTTTCCGTTAATGAAATAAATCCTACTTTTAATTTTGAAGAAGGCGTAGGA
CTGGATACTGAATTAGAAGTCAAGCAATAGTACTACCTAAAACTATTATACCTTTACCTGATGATTAT
TTGACATTTTCATATCATGAAAAAGGATATGAGTATTTTAAGACATATCGCATTAATAATGTTTCTACT
TCTTCAATAGGTAGTAACACCTACTATTCAATAACTTTTATTAATGATCCTATAGATATAAGGATTCTT
GAAGAAAGACAAGTAGATAAAAACTTATCGATTTGTTTATGAAAATGTAGGTACTACTGATAAAGTAAT
```

```
TATAGAAGAAGATGACATATTATTAATTGATAAAATTGAAAAGATATGTGGAGATATTAATGAAAGAT
ATATTAATAATTTCTACAATTCACAGTTAGGTATTTTATTATACGAAAATCTAGATGAAAGTTTATTAT
ATAGTCCTAATCTTCATTATTTTATAAATAAGAATCAGGTATTTATAAATAATCGAACTTTCATGAGAA
ACGTATATATAGAAGATATAACAAAAGTGAAGCTGAAAGATTATAACAAATCTTTATTTAGCATTATT
GATAATGGTTATAATAACATTAATATGTCTTATCAATATATAACTAGGGTTTTGGAAAATAATATTCTA
AAGAAAACTAGGGGTCTTTATGTTGAAGATTTAGAAATTATTGGATCTAGTTGTAATATTAAAATTCCG
AGAACTACGATTCATAATTATTTTTCAGTAGATATTAATGATTTGATAAATAACTATGATGGCGTAGAC
TCGTTAAATGGTATAGATGCGATAACATCAATTATAACAATTTATTTAGCACAACCAGAACAATTAAG
TATTAATACGTTATTTAATTTAGTTTCTAAATTAAATTATGATGACTATTCAATCAGTAATTATTTCTTT
ATACCATGCGTATTATCCATTATAAATATAATTACTAATAAAAAAATTACTATACATTCTGAAGAAGTA
TAGAACTGAGAGGAACGTGAATATAAATGTTTAAGAAAATAGAAGAAAAATCCATCAAAGAAATAT
GGAAGTTGAAGCTAGTAAAATTGTAAGTGAAGAATTAGAAGTTGTTGAACCAGAAGAAGAAAAAATT
ATTGCAGTACCTAATACTTCTGAAAACAATGAAGTTTTGGGTAATCCAGAACAAGATCCTGAAATTGG
TCAATTTATCGATAGCACTGATGAATACGATGATGAAGAAGATGCATTGATTGATGCTTTAGAAGATA
AAAATGACGATGAAGGTTTAGACGGTATTGTTGATAAAGATAATGAAGAAAAACCTGTAGAAACTTCT
GAAGTTACATTTAGTGAATCTAAAGATGATAAAAAAGAAGATAAGAAAGATGAGGACGAAAAAGAA
GATTCTGAAGATGAAGACAACGATGAATCTGAGGAAGCTGAAGAAGAAGATGGTGATGATGAGTCTG
AACTTGAAGAAGGAATCAGTTCCATGTTCTCTGGAATTTTTGACATCAATGAAGAAATTGAAGATGAT
ACTAATAATAATTTTAAATACACTAATCAGCGAAGAAGAAGATATCTTTATTTAAAGATGAAGAAGACGA
AAAAGATGATGAACCTATTGAAATTGATTTTATTGGTGATGATGAAAAAGATCAAGAAGATAAAGAA
ATCGAAGAATCTGATACTGATTATCTTAAAAAAGAATATCTAGGTGAAACAATACTTAATAAAATCTT
CGACAAATAATACTGTTAACATAATATTATTAAGGGTATATAAAATATAAATTATATAAAGGATGTGT
ATTTCAAAATGCCAAAAGTTGTTATAAAAGATAATAAATTTGTATTTGGTTTAGGTAAAGGACCATTTA
ATAATCCAGTTGAGATTAGTGATGAACTTTTACGTAAATTAAAAATCTCTGGATATACGGTAATTGAA
GTAAATGATCGTCATATCGTATATGAAACTCCAAATAATGAAGAAAAAGCTGAAGAAGTTAAAGAAG
ATCCTAAAGAAGAACTACACCAAGAAGAAGAGTCTGATGAATCCGTAGAAGCTACTGCAACTGAAGA
AGAAAATAAAGACGAAGAACATCAAGAAGAATCTAATGAAGAAAAAACCGAATCATCTAAAGAATCT
GATAACGAAAAAGTTGAAGATGATAGTGATGAAGAAGATTTCAAATCAATGAAGGTTGATGAACTTA
AAGAAATTCTAGAAGAACGTGGAATTGAATTCAAAGCTAATGATACTAAAAAAGTTCTCCTTTCAAAA
TTAGGTGTAAGTGAATAATATTTTTATATTATATTGATAGGTCTACTTGTTGAAATTATAGCAAGTAGA
CCTATTTTTTTCGATTATTATAAGTTAGATAAGAGGTGTTTATGTGTGCCAAAAGTAATTATATTAAAT
AATAAATATATACCAGATATTGGTAGTGGTCCAATACTAGAACCAATTGAAATCAGTAATGAAAAATA
CCATTATCTAATAGATAATGGTTTTAATATATATCAGATAGACGATAATGAAGATATTATGATTGATCC
ATCCATAACTACCATATTGAAAGGTAAAGTTAAGTCAGTATATGGAATGTTTCATGCAGATCAGAAAA
AACTTGATTCACTATTAATGTTTAATAGAACAAGCATATCTTCATTAAAAAAATGTTAATACTAAGAGTA
TTACAGAAAATAATAATATAATATATTGGAAATCAATAGATACCGATATTGCATATGTAAATTCTGAC
GGTTATATTGCTGCAAAAGAAAATGGTTCCACAATAGTTACTGGTTTTGATTCAAATAATACGCTTAAA
GCAATAATGTTCATAACGGTAATACCTAAACTTCCAATATTACCCAATGATATTAATGTTAATTTAGAA
AGCTATATGGAACTTAATAGATATGCAGAATTTCAATACTTAGTTGAATTACTTCCTAGCGAAGTAGAT
AATAATAAAGTAAGTATTACATCAAATAATATACAAATTGCAACTATTGATGAAAAGAATAAAAGAA
TTATTGCTGAAGAACCTGGATATGCTGTTATTAATGTTAAGAGTGCAGAAAACCCTGAAGTATCTCAT
AGTACGTTGCTAAAAGTTTTTCCTAATGATGATAGGAATAATCCTTCTAAATAAATGTAAATATTCCG
GACGAGATTACAATTAAGGTTGGAGAGGAAATTCCCTTTGAAGTAAAAATTACTCCTGAGTCGGCTAA
TAATCTAGGATATATGTCTTTCTCATCAAACGTTGGAATTGTATCTTTATTAGATAATAACCATATTCTT
GGTAATAGTATTGGCGTAGCAACCATAACTATTGTATCGAATAAAATATCATCATTATATAAAGAAAT
ACGAGTTAATGTTGAAGCACCAGACCCTAATGATATTATTGTAAATTTAACTGAAGTATCTCATTGAGA
AAGGTCAGACTAGAGGGTTTAATGTAACAGTTCTTCCAATATCAGCTAATGACAGAACTTACAGTAAT
AGTTCTTTAAATGAAAATATTGCGACTGTAACTCAGAATAATATTATTACCGGAGTTAATATTGGGGA
CACAAAAGTAAGAATAACATCTAATAAAAAGCCTGAATTATTTAGGGATATTATCGTGCATGTTACTC
CGCCAAGCCCTAAAGATATTATGACTGATCTTCCAGACGAGATTACAATTACTGATACCGAAACTAGA
AATTTTACAGTTCAAATTCTTCCTGAAGATACATTTAACAACAAATATGATATGGAAGTAACAATTCCG
GATATTATTGATCTTGATAAAGAAAATTTATCATTTAAAGGTAAAAAGATAGGTGTAACTAATTTAAG
AATTTTTTTCACAGTATAACCATGATATTTTTAAAAATGTTAAAATTAATGTAGTACCAAGTCCATTACC
TGATCCGACATCTTTTAAAGTTATTCGTAGAGATACTGGGGAAGAATTAAAAAATGGAGATACTGTAC
CTAGTAATAAAGATATACTTTTTGATGTTATAGTTTTACCAGAAAATGCCAATGATAAAAGTTATATAG
TATCATCTTCAGACGTAACGATTGCAAAAGTTAACTTAAATTCTATAATAGGAGTTTCTCCGGGTCAAG
TTAATATTAGAATAACATTAAACAAAGTTTCAACAATATTTAAAGTATTTCAACTTAATATTGAAGAAC
CTGTTCCTACATTAATTGATATTGATGTACCAAGCAATATTACTGTACAAACTATGCAAACACGTAATT
TCACTGCAACTATATATCCTGAAAATACTCCATACCAAAATTTCTTAACATCTGTTGAAAATCCTGATA
TAGTAACTATTTTAGATAATACAAATCCAAAAATACGTACGATTAAAGGAATAAAACAAGGTGTAACT
AAGGTTAAAGTGTATTCCGAATTTGATCCAACAATATTTAAAGAAATTAACGTTACAGTAGTTAATCCT
AATCCTAGTTCAATAGAAGTTTCTCCAAGAAGTATTTCAATGTTATTAAATGAAACTAAAGAATTGGA
TATTAATGTATTGCCAGAATATGCTAATGATAGAACATACACTATTAAACAAACAGGCTTAGGTATGG
TTTCTATTAATGGAAATAAGATTACTGGTGTGTTAAAAGGAAATGTAAGATTAGATATTATATCTAAC
AAAGTAAGTTCTCTTGGAACTACGGTATATGTTACTGTTGATAATCCTGACCCTGAAGTATGATTGTC
GATATACCTGACGAGATCGATATCAATGTAGATGAAAGAAGAAATTTTGGCGTAACATTTGTTCCAGA
AATAGTTAGTGATGATTCTATTATTATAACATCATCTAATTCTAGTATTGCTATAGGTAGTGCTGTACA
AAAATTTATTAATGGAGTTTCTGTTGGTACTGCAACATTAACTATTAGATCTAATAAAGTAGCTACTTT
ATTTAAAGAAGTTATCGTAAATGTTCATGAAGATAGACCTGACCCAACAAGTATCAATGTTGGAACTA
ATCCGCTTACTTTAGAATTAGGTACTACAACTCCAATAAATATTGCATATGAACCAGAAATTAATAGT
GGTGGTAAAATAATTGATGATTATTCCACATCAAACACTATTATTAGAATGGATCAATTTAAAAATTC
AATACAAGCTATTCGACTAGGATCTACTAGTATTAAATATACTTCTGAAAGATTTCCAAATATTACAAA
TACGCTAAATATTACAGTTTATTCCTCCTAGACCAAAAAGTATTAGTGATAACTTTTCATATAATAATTC
TTTAAATGTTAATGAAGCAACAAATAAATCGTTAATTGTTAGCTTTTTACCAAGCACGGCGGTAAACA
TTGGATACAATGTAGTTATTGATGATCCAACTGTTTTATTATTTAATACAAACTCTAAGAAATTTGAAG
CATTAAAAGAAGGAGAGACTATCGTTAAGGTGGTATCTACTGATAATTCTTCTCTATTTGTAGAACATA
AATTTAAAGTTAATAAAAATATTATTATCGATGACGGTGGTAACGGTAAAGATGATGATGGTAATGAA
GTTATAGTTCCAAAATCAATAACGTCAGATATAGTCACTGAAATGATAGTCGATAAGAACTATCGGGT
AAACGTAACAGTTTTACCAGATAATGCTATTGATAAAGGTTTTGAAGTTATAACTAGCGATAATAATG
```

```
CGTTTAATATAGTTCAAAACAGTGGATCATATTTTACTATTAAATCATTGGTTTCTGGAATGTATAATA
TTACGTTGCGATCTACATTAAATCCTAATATAAGCGTATCTTATGATATCGTGTCAGGCACTGAAGATG
AATTACATCCAATCTTACCAGAACAATAAATATTATAAATGCTACTGATGAAATGACTGTAGATGAA
GGTACATCTATGAATTTAGATATACAAGTTCTACCAGAAAATTCAACTAATAAAAATGTAACTGGTTA
CAGTAGTAATGAAGAATTAGCAACTATACCTAATAATAAAACTATAAGTTTTATTAAAGAAGGTTCAG
TAGACATTACAATTACATCAAATAAAGTACCTACATTAAGTAAAACAATTCACTTTATTATTAAAAAA
CCCGACCCTAAGAGAATTGAAATTAATGCACCCAACGCAGTAACTTTAAATATCGGTGAGTCTAAAGA
ATATCTGATAAGTGTAATTCCTGAAAATAGTATTGATAAAGAATATATTTCAGAAACACTAGATTCTA
GTATTGTTACTACTAATGGAAAAAATATTATTAAAGCGGTTAAAGAAGGAAACACTACAGTTGTGTTT
AGGTCTAAAACTTTTCCAGATATATTTACACGACTTAATGTTATTGTTCTTCCTCCTGAACCGAATGAA
ATAATTGTATCTCCATCCAATGAAACAATTAATATGATTAAGCTTGATGAATTAGTATTTGATGTAACG
ATTAATCCCTCAAACGCAATCGATTTAACATATAAGATTGAGTCAAGTGATACTAATATTGTAAAAAT
TAAAAATCAAGATACAGTGGTTGCAGTAAATCCCGGAGAAGCAAACGTGACTATATCGTCTAGACGG
AATGCTAATCTAAAAGTTATTAAAAAGATTATTGTAACTGCGCCTGACCCAGAATCTATAGATGTTATT
GGTTTTGGACCAGACGAAACAATGATTACAAATTCAACAACTAAGTCCGTTAATTTTATAGTCAATCC
GGCTAATGCTAAAGTATCTAACTTTACAGTAGTATCTTCTAGTGATTCGGTACAAATTAATATTCCGGA
TCAAACAAAATATGGATTTACTGTAAAACCTGTTAAAGAGGGTAATGCAATTATCACTATCCAATTAT
CATCATTCCCAGATATTATTTACAATATTAATGTAAGGGTGAATAACCCTGATCCTGAAAGCATAACTG
CAGGGATAACTAATCCTCCAAATATGCCTTCTGGAAATATTCCAGGAAAAGGAATTGCTATAGGAGAG
AAGGTTGTATTAAATGCTAAGATACTACCTGAATATGCTAATGATATAACTTACTCAATTAGTAGTAGC
GATAATGATGTCTTTGAGGTTCGAGATGATGGAATTTATGCATTAAAAGCCGGAACATCTAAAGTTAG
GGTATTCTCTAATAAAGTTCCAACAATATTTAAAGAATTTGATTTAGAATGTCTAGGTAATAATGTTAG
TGATATTGAACTGGATATTCAGTCACCATTCAATATGGTCGTTGGTAATACGAAACAAATAAGTATAA
ATATTCTTCCTACTGATGCTATTGATAAGAGGTATCAGCTTAAAACAGATGACGCTAATATTGTATCGG
TATTAGATAATAATACAATACGAGCTATATCTCCTGGGGTAAATGGTGAAGGATTTACGAATATACGA
ATAATATCTTTACGTAATAATTCTGTGGTTAAAGTAATACGAGTTAATGTAGAAAACTTAACGCCTCAA
AGTATTGATCTTGTTCCATCTGGACCCATAGAAATATATTCATTAACATCAACTACATTTAATGCATAT
GTAAGACCAGACACGGTAATTGATAGGGATACGGTAGTTAGTAGTTCAGACATTTCAATAGCTACGGT
TCAACAATCATATATAACTGAAGGTGGCATAAAAATTACTAGAGTTACCGTAAATGCACTTAAATCTG
GAAATGTTAATATTCGTGTATCATCTAATAATTATAGAAATATTTTTAAGATGATTAATATAAAATATTA
TTGACCCAGATCCGGAATCAATTACTGTAACTCCATTAACAATAAATATGGCTCAAGATACATCTACT
AATTTTAATGTAAATATTCTTCCAGAGAATGCTAATGATAGAACATTTAATACTGAGATTGCAGATCCT
ACAATTGTTTCTGTTAATGGAAATACAATTACTGGTCTTAAAACAGGAACGACTACAGTTAAAGTATC
TTCAAATAAAATACCATCATTAAATAAGACAATCACAGTCAATGTGAGTCTTCCTAATGTAAATAAAA
TTGAGATTACTACTGCATTAGTTGCGGGAACAGTTAATACTGTATATGAGGGCGAGTCTTATCCATTTC
TTATTAAGTTATTGCCAGAAGTTGCTGCAGATAAATCATTTACGATAAAATATTCTGCTAATGCTGATA
TGTCTGGTACTGCTGATTACTCATTTAATTTTGGGTATCGTAATGATTCATTAAATCCATCACTATATAT
ATCAGCTACAAGTTCATCTAGATATGTTCCACCTTTTGTTAGATATATTCAAGTGGTTTCAGCTAATGG
AATTACCTCGGATATATATGGTCTAAGTGTTGTACTTAAACCGATATATAAAATGGATAGTACATTTAC
ATTTTATAATGATCAGTACGCTTCTGCTAAAACTACTATATCTTTTGATAGTACTAATCCTAATTCTGAA
AATTATGTAATTAATGCCTATGCCGGAACAACAGCTAGAGACCCTAATATTAATACTGTTAATTTATAT
CCTCTTGAAGCAAAAGATACAAATTTAACAGTTACTATAAGTGATCCTACAAAAGCATCATATAATAG
TACAACTAAGACTTTTACCGCTCTTCAATATGATACTGAAACTACTGCAAAGATTGCATCCACAACTAG
CCCTGATGTATTTGTAATTGTTAAGATTAAATGTATGAGATCTAGAATAACGTCTGTACAAGTTACAGG
TCAGAATGGATTAAGATATAGTACTGGCGATGTCTTTGGAATAGTAGTAACAACTGGTCAGAAGGTG
CTATTGATACAAATGATTATACATTATCTTCAAGTAATGATACTATTATATCAATAAATAATGAAACTA
GAACTGGAGTTGCTTTAAAGGCAGGTTCATCAACTATTACCGCATTATTTAATAAAGCCGGCGTATCA
AATAGTGCTAGATTTACTATATCTGACGTACTTCCCACTTCAGTAGGTATTACTGACCCTCCAGGAGGT
TCTGAGCTAATTATTGGAAGATCCTATCCGATAACTCCAAGTGTATTGCCGACTAATACAACTAATAA
AGCGGTAACCTATTCTGGAAATAATTCAAGTTATTTAACATTGTCTAAAATAAATAATATTGATTATAT
TAATGTGGTGGGTAAAATTGCAACAAATACACCTATAACTATTCGATCAGTTGCTAGTACGGGAATTT
ACAGTACAGTTCAATATAAGACTGCGTATGAATACCCAACAAGCATTGATATATCCAAAATTAATGAC
TCATATAATTTAACTGAAACAATTGACTTATCTACTTTGATAAATATAATTCCATCAAATACCGATAAT
GATAATAATTATACAATAACAACTCAAGATACCGATAAAATAAATATTGATGGTAAGAAATTAACATT
TATTAAAGATGGTAGTGCAACTATTACAGTAACTCATAATAGAAATAATATTTCCGTTAATAAATTGAT
TAATATTGTATATAATGATTCAATTAAACCGAATATTGTATTTACTACTTCAAATATTATCATAAATAA
TAATGAATTTGATATTAAAAATAATATTACTAAAGATTTAACACTAGATGAATACCTCATTACTGGTGA
TCTTAATGGTTGGAGATATAATGGCAATAAGAAGTTTTCAGATAGTGGAGATTTTCAAATTAAATTTA
ATTATCCTATTAATATGCTTGAATTTGAAAGTATTAATGATCAATTTTCAAGTGAATTTATGTATAATTT
AAATAATCCGGATTCTAAAGTTGATCCACCCCAATATGTTGACCTTGATAGGGGGTAGTGATTTGATTAA
TGATCGATTATTTAGTATATTAGATACGTATACCATTTCTTCATATTTATAATAAACGAAGAAGTACTAG
TGGTAATGAAAGTCAATCATATATTGTAAGCGCTTCACCAGTAATAAATAATATATCTCCTGCAGGAG
AATATTTTTATAAAGTCTATGTAAAGAATGATCCTAATAATTATATTTATTATTAGAATTAAATATCGGTA
TTCATGGATCAAAACAATCCAGTAATTTGATATATAATGGATATCCTACTCTCATTAGTCCAGTATCAA
TATCTACTGATGATAATATAAACTATGAACTTAAAGTACAGCTGTATTTAAGATCTAAGTGGTTGAGTG
GGGACAAATCACCTTTATTATTTAATAATGAGTTAATTACTCATCGATTAATGCTTGATTCTTCATATA
ATAATAAAATAAATATTAATGGTATTGAATATAATAACATTAGTGATTTTATTGAAATTGATAATAGA
ATTATTAATCGAATAAGTAGACTAGGTGTAAATCGTGTAAATACTTACCGATACTGTCGCATCTATT
GATAGTGTGGTCGCAGCATATCCGGACAGGGTAAGTTATTTTATTAAAAGAAATCCTACTAAAAATGA
AGAATTTAGTATGGATATAAGATTAGTAAGTATTGAGGATTCGAATATCAAAATTCCAGTAACTTATA
CATTCACTACAATTAATAAATAATTCTTTCAAAGAAGCATATGATAAGATTCTTGAAAAGAAGATTAA
AAAAAAAAAAAAAATAAATCTCCCATAACCTATTAATTTAGGTTATGGGAGATTTTATGATTATTTA
TTAAACAGATCATCAATATTATTAGTATCGATATCTTCTTGAGTTTCTTCCTCATCATCTTCATCTAACG
GTACAAAATTGATAACTGGTTTATATCCTAATGCCTTTGCAATATCTGATAGACTGGAATAAGATGTCG
CACCTTTTTTCCGTAGTCTGTAAAAGATATTAGAAGCTCTTCCTTCATTATTAGGATTATCAAGATCAA
ACTTTTCAAAGAATTCTTCAAATGTTTTACCTTTTTCACCCTGCTCATTAATGAATTCTGCAGTAATTAA
TGCTAATTCTGTTTGATTTTCAATAGAATCCACATCAATATGCAATGGACCAGTTAATTTCTTTCGTTTA
GATTTCTCAGAAGGATCTTTAGAAGCCTTGATCATACTATCTTTCTTATCTAATTTATCCATATTTACAT
TATTTAGTTTTGAAAATAGATCATCGGACACGAGAATTTCACCTCATTTATTATTCATATTAGAAATCC
```

```
ATATCATCATTAGAAATTTCTTCAGAAGCACCAATCTCAGTTGATTTTGCAATTAATGATTTAAGATCT
TTTGATCCACCACTAGCTTGGATAATTTCTGTATCCACATCTTCTGTTTGTTTATCTGCAACTTTTTTCTC
GGATGATTTAAAGTTACTACCACTATTATTACTGTTATTAAATGTAGAACTTACATTTTTAGGTTCAGT
GGTTGTATCATTTTGTGATAGATTGTTATCATAAGGATGTTGAGTTGCGTTTGGATTCTTTCTAGTTACT
CGATTACTATTGAATCCACCACTTGTGTTTCCTGAACGATTGAATGGAGTTGTTGATGTAGGTCTATTA
AATCCACCAGTGTTTGGACGTTGACTAAATGAACCACTATTATTAGATTGACCTTGAGAATAATTTCCT
CCGCCCAAAATATTAATAACGTGATCTAATTTATTTTCTACAGTATATAATTTCGCTTGAATTTTCTGGA
ACTCTTGTAGAATATAAAGATCAATATTATTAATACAATCAATCATATTGAATAATTGTAGTGTAGTTA
GTTCTACTGAATATTCATCGCCATTTACGCATAAAATAAATCCTGGATAAGTAGTATCATCATTACGAT
GAATGATTGAAGGATAGATTAATAATTTTTTACCTTGACCACCAAACTCTGGAGAGAACCATTGTGGT
AATTCTGGAAGATCCCATACACGATTACCTGAATTATTACCTTCAATAATTTCATTAGCAACTTGGTTC
ATATATGATTTTAATGTTTCATGATGAGCCTGACTAACTACAACATTCTCACGAACGCTTTGATTAGTT
TCAGGATTAAATCGACTATAATCAAAACGTAAAAACACCGTTGCGCTGTTTTGAATACTAGTTAACGT
TTGAACATCGGAATATCGATCTGAAGTGTATTCTCTTGCATATTCAGCATCCCTACGTTTATCATTAGTT
GATGTTTTATTACCTAGTAATAAAGAACTTTCTAGTTTAAAATTGAAAGCACTAAATAGCGTTAGACCA
TGAGATTCTACTGGATTAAAATTTGACAAAATATGATTCCTCCTAATAATTTTATATATTACAATAATA
TAATATATGATTATAATTTATTTTAAATGATTATTCATTTGTATCTTGATTTAATGATAATGCAGTAAGT
CTGGAAAGCTTACTAACAAACTGACTTCGTATAATTGATGAGTACAATGCTTCTTCAGGAACATTAAA
CATTTCACCAATCTTACTGATACTGTCACCTGAAGTATAATCTAAGAATTGATATACACTAAAAATATT
GATAGGTTCAGGAATGATATATTCTGGAATTACTGGAATTTTATTTTTAAATAAGAAAGCTTTATCTAA
GAAATGAATCCAATCTATTGGATTATCTACCCAAAAAAGTATTTTATTTTTTCCTGAATTAGAAAGCTC
TAATAACAATGATTCAATATTATTGTATATTGTTGCATCTTCATCTTTCATAATTCTAATATTTTTGTTA
GCATCATAAGTATAAATCTTTTCAACATTATTCGCTAGTTGATTATTATATACTTTCATACTATCTTCTT
GGGATATAGCTGTAGCAATATCGTAATTTGTAAATTCATAATAGTAATTAGATATTACACCTTCTGCTT
CTTCTACACCCAAACACATATTCATGATGTTAGATGACGTACTAGACCCATCTAACATACATGATAAGT
AAATATTTACAATCTTAGTTCTTTCCATATTTTACCCATCCTTATTTAATTCTTTTTGTTTTTTCATTTCTT
TATTATAGAATATATCATGAGTTAATAAAAATTTGAAATTAAGTTCAGAATTAATACTATTGATAATAT
CTTTAATACTTTTATTAATAACTGCAGGGTTTGTTAAATCTTCAAGAATTTTCTTTTCCCTAATATCATT
ATTAATAGTTAAAGACATATCAAGTAGATCGTTTTTAATTTTATGATATTTTTCAAATTTAAGTTTACG
ATGTCTATAGAAAAAACCATCACTATTATTTTCACTATACATCTTTAAGAATGATGCATATTTATTAAA
TAAGTCTTCCCTTTGAATTTTAATTTCACCTTTTTGGAGTTCTAAAATTTCAATAGACCTTTTAATATGG
TTATTAATTTTTCTAAGTTGAGTTAATTCAATATCAATAATCTCTGTAACAAGATCAAAATTTACAATT
CCGATAATATTACCGTCAATATTAATATTAAATCTAAGAATATTAAAGTCTTCTGAAATTTTAGCACCA
ATTAATGAAAAGATATCTTCATCATACTGTCCAGTATTAACATTCTTTGTTAAAGAATATATAAAATCT
TTCTTAATACGATTCACAATCGTATTAAAGATATTTTTACTAGCGATTAATTCTTCAATGAATTTTGAA
GGATTTGTTTCTGAGAGGGAATAACGATCGTTAGATGCATACAAAATTTTCACCACTTTCCGCTATATA
ATTTCCAATTTAGATTCAATAATTTCTTTACATCTTTTACGATAAATTTTCTTTCTTTTAGTTAATTGACG
TTTACATTCATCAAAACCTGTATCAATGACATCAAAGTATAGACATTCTTTATTTTTTACCTTACGTAA
ACGACCCATAATTTGTATCAACCCTTCTTCAGAACCAGAAGGTACAGTATTTACTAATACTCGTAAAG
ATTGTTCATCTAAACCTTTACCGAAAGATTTATCCGTAGTAACAATAATATCTTTTTCAAACGCAGTAG
ATTTTTCATCTTTAGGAACGTCTGAATAAAATCTACTTACCGATATATCCCACTTATTATTTTCAATTTC
TACTAAGAAATCTTGGTAGAAAGCATTAACCATAATCTTATTTTTAAATAAGATTGCAGTCTTTCTTTT
ATTCTTACCTTTATCAAAGATAATATCGAAGATAATCTGATAAATATAGTTATAATATTCATCATGCTT
TTTATCAATAATATACTGAGAATAGCTTGGTACATTAAATCCATAACCTTTAGATTTCTTTCTAATTTCA
ACTAAATCTTCATTACTAGGTTTAGTATCTATTTTACAAATGATTGTTCTAATGTATCTATCACTATCAC
TAACTACAGTAGAGAATTTTGGAACGTTCATATACATATTCTGATAAACTTTATTTTCAATAGGATTAG
ATCTACTAGGAGTCGCAGTTAAATATAATGATGGACAGTCATAAGTAGAATCAATATTAAATACAGAA
ATATATTCAACGTGAGCTTCATCATAAACTTTAATTGATATTCCAATTCGATTAAATAACTTTACAACC
CTATCAGGATCAGACTGAATTAATTGGTTAACAGTCTTGTGAATAGATAAAAAGAATTTATACTTAGA
TATATCACGTTTAGTCATCTTTTCTAATTTTTCAATAGATTCTATTCCTGAAATAATATAAATATTATCT
AATGATACGTCTGTATATTCACTAATTCTATCCTTCCACTGTTCTAATAATGATTTCATATCAATAAAG
ATAATTGGTACTGCTTTGATTTTATTAATATAATTAATAGCACAAAAAGTTTTCCCTTCACCAGTCTTTA
ACGATAAAAACTTTTGATAATAATTATTATCATCATTAAGAAAATTCATTGCATCTTCTTGAATTTTATT
TTTAGGTTTATATTTCATTTTAAAATTATTTTTCCTAAGAATATTTTTATTTCTTTTATCATTAATATGAA
TATTAACATTTTGTCTTCTTCTTAAGTTACTAGATAAAGAATCAATATCAATACCAGAAGGAAATATTG
CTTTATCATCATCTATCTTGTATGCTTTAAAATCATACTTAAACCATTTAGCATTCCATACAGAAAGAC
TATTTTCTACAGCACTAGCCATTTTTTCGCTATAGTTATTAATAACTATCCTTGTTGGATAAATATCAAG
ATCCATTCATATATCACACCTTTATTAGTTTAAAATCAATAGAATGTATTATATAACTAAATAATACAT
TCTATTGATATATTTTAATTTAATATTCTTTAAAGAATAAGTGAGGAAAAGATTCAAAGAAATTAATAT
GGTTAAGTTCTTCAGGACTTTCAGCATCTGTAGCATTAATAATGTAACCAAAAATAGGGACTTTTGAA
GTGATATAATATTTACCTTCTTTAAATGGACCAACTGTCTTTTGACATTTATCCATTAAATATAATTCAC
CATCTAACTGGTATCCTACTGAAAGTTTATCACCTAGTTCATACATTGATAAAAAATCGGTATTATTAA
TAAATTCTGTAAATTCTTTTGGATTATTGGTATATCGTCTGATTCTAAATTTATTTTCATCTGGAATATT
ATCTAAACTAATAATAAATCTATTTTTTTCTACTTCTTCGGAATCAATTAAATTATCTTTGTCCATATTC
ATATATCTATATATCTCCCTTATAAATAAAATTATCTAAATACCCTATCGAATTCAGATTCAACATCTTT
ACCAAAAAGATCATTATAACTATCTGTCTTAAATTGTTTTTCAATATTTTGATATAATAGTGACATTGC
AGGACTTTTCTTACCGATAAGTATTGCATCACTTACATTATATATATTATATTTTGGTAATTCTTCAGCA
TTAGCAAATTCGGTTCTATCATTATTTTCTAGACTTACCATTTCCCTTACAATAGTTTCTACATGTACAG
AATCAATCATTGTTCCTGAATCCACTAATAAGTTTACAATTTCTTGTACAATGATAGAATAATCATTAT
TTGATACATTTCTAATAAAATGATTTTTTTCTAAGATATCTTTAATCTTTAGAAGTGGGTCTGCAATACC
ATCATTTTCCACAATAATATTAAACATATATTCATTATCAGGCATATATTTTAATGAGAATACATAATT
ATTTGTGGAATTATCATAATACTGTTCAATATCATCCGCAATCTCATTAGGAATAATTAAGCTTAATGG
AGTGTCAATTCTAATCTGAGTGTCTTTCCTACCTTTAACATAGATTGTTCTTGTTTGATATTTATTCTTTT
CAGAGTCTTCATTTTCCATAAGATCATCTTTATGAATATAGATTGTTTCATTATCAGAAATAGGACTAA
CCTTATCTTCAAATAATTGAAACTTAGATAAGAAATCTTTAGACCAGTTAGCATCCTTAATAATAACTT
CTAATAAATGCTTTGTTGATAAGATTTTTTGTGTTAATGGATTAGTAAGTTCTAAAGTTGCAGCAGTTC
CTACTTTAATGTGTTTATTAATCTTTTCTAATCTTCCATAACATCTAGGACATATACCTTTTGAATGTGC
GCATGTTATTGGACTAAATATCTTAATATCTTTACCAATAAGATGTGTATCATTCTTAGTTATTACGGT
AGTTTTATTAGTATCTTCATCATACATCCAACGATGATTATATAGTGATAACATGTCTTTATCTCTAATA
```

```
TGAATATTAATATAATGAGAAGTGTTACAACTATCTACATTATTTTCATCTTTGTGAAGTTCTTTATCTT
GTGGATCAATATCTAATGTGTATATTACTGAATCTTCAGTTAATATAGATATCTTTCGGTTAGTATATC
CAGACTGTTTTACTTGATCCTTTGCAGTGATAATTGCTTTTCTACCACCTACTGCATCAATAAAGAATTC
TGTTACATTTTTAATTCCCCTTACAAAAGAACTATTAATTGGAGTAGTAATAACTTTACCATATAGATC
GGGCTTATAACCAATTAATCCAAAATTTTGATTAAATTGTTTTATATTAATTCCTGCACCCGACATGAT
TAAATCTCTAGTAATATTATCTTTATCTTCTTTAATAATTTGAATCATTTTATCTTTGTTTTCTGCAATTT
TTTGATTATTTGTTCCAATATCATCTTTTAATTCTGGATCAAGTTCGAATTCTAAAGTTTTCTTAAATTC
TTCATTTCTATCCATAATATCGATTATATCAAATAAACTATAAGTCACTCCGCTCTGATATAATACGTTT
TGAGTACTAAATATTGATAGTTCATCTACTGACCACGCAATATCTTTTTTAATCAATTTTATCTTTTCAT
CACTAATATCATAATTATAAATTTTGTTAATAATCTTATCATAAAATACATTATGAAGATTAACATTAT
AATTACCCTTTTCATTACAATCTTTTAAGATAAATGTAAACTCTTCGGTAAATTCTTCTTCCAAACTCTT
AAAAGGTTTTGCCAAAATAAACGTTGTTAATAAATTTGACCTAGATATTTTTGATGTTCCAAATTGTAA
AATTTCTCTACGAGAATCCACATCTTCTACAATTTTCTTTCCTAATTCATCAATCTTCGAATAATACTTA
GTATCATCATGAAGAATTGAATTAAATAAAGATAGATCTAATACTGTACTCAATATCCTCCACACAAT
CCTTTCTGTAATATATTTAACCACAAATATATAATATATAATTGTAAGATAATTTAATAATCACAAACC
TATATTATGATTCTAACAGAATATTTCATTGTTGTAAATTAAAATTAACTTTTTATCTTATGAAACTTAA
TGTGGATCATAGAAAATTTAAACTATCAATAAAAATATATATTTATATATTTGCGAATAAAATCCCCTAT
CATATAATTATAACACAAATTTATATGATAGGGGAAATAAATTATTTATCTTCGACTTTTTTAGATTCT
GATTTAGCTTTACGTTTTTCTCCGAATTCACGAAGTTTTTGTTTTCCTTTGCTTGCATACTTAAGTTGAA
TTGCTCGGCGAGTTTCTCGGCGCAACTTAGAATATTTAACGTATTTACGGTAAAGTGGATCATTTGCTT
CTTTAGCGGAAATTAATACTGCTTGAGTATATAAACGTTTCTTAGCGGTACGTTTATCTAAACGAACAA
TATTGGCTTCTTCTAGATAGCTTAAAGATTCTTCCAAAGTTTGCATTGAACTTTCTTCATTATTATAATT
AAAAAATGTATCTTTCATATTGATTAAGCATCCCTTTCTCTAAATAAAATGGTTTAATAATTATATGTTT
ATCAATTCAATGCAGAAAAAATAATAATTTATTTTTATTCGTTAATAATGTTTTATATTATATAAAATA
TAGAAAGGAAAGATAATTTATGTATAGTTTTTAGTAGTAATATTCTCTTTAATTATATAAAAAATAAA
TTGGTGGTGTATTGTTTATATGAAGATTGAAGAAAAAGAACGTGAAATGAAACATATTGGTTACATGA
AGATATTACTTAATGTTGCTAAAGAAGAATTTCCAGATATGGAAGAAGATGTATTAAAAGAAAAGATT
AAAAATATTGTAAAGGATAACATGAAAAATCCAAAAGCAATGATTGATGATCGTGAAACAACATTAT
TAGGATTAGACAAATTTATCGTAACTGAGAAACCTATCATTACTGGTTTTGGATCAATGTATTTAACTC
ATGATAAGTTTGATAATCTATTAGCAAAATTGGTTGAATATATTATCAAAACTCGTAAAGTTTATAAAA
ATAAAATGTTCGAACACGTTAATGATGATGATCAAACACTGAGAAATATGTATGATATGTATCAACGT
ACCATGAAGATCCTAGCGAACTCATTTTACGGATCATTGATCCAAAGTAGCTTTATTTTGTATAATCCG
ATATCTGGTCCGTCAGTTACTTATTCTGGTGTTGATATTATCACTACTGCACTAAATAATTTTGAGAAA
TTCTTAGCAAATAATATCTATTTTAGAAATGTAGATGATATTATTGTATATATGAATAATATTAAATCT
GAAAATTATAGTATGGATAAAGTTAAATTTAAACAATCCCGTAGTAAAGATCAGATTATTGATTATTT
ATTTGATAAGACAGATAATTATATGGATGAAGATAGAATATTATTGATGACAATGATGAATAATTATA
CGGATGAAGATTTACTTAAGCTTTATTATAAAAATAACTTCATTGATTTATTAAAAGAATCTGATATTG
CAGATAATTATTTTAAAGAAATTCTAAGTTGCTATGAATTTACTGATCCAAACGATCCTCCTGCTAAAG
TTATCTCCACTAATGAAATTTGTACTATTAAAGGAAAAGATAACGGTAAAATTAAAGTTAAATTATCT
AATGGTGAAATTTCTCTAGAAGATCCTAGTAATATTTTAGATTATAGGGAAAAATTAGATAATTTATG
GAATATTATTAGAAATATTGTATTCTACAATTATCAAGATTTCTATCGTATGGAAAATTCTGAAGAAAG
ATTAAGAAAAACAGTGCTCGTGGTTAATGTATAGCCACACTTATATAGTAATATATAGGTTAAAAATT
CTATTAATTGCTGGAAAATCCTAAAGCTTATTTAACTACAACGGAATCAGTAATGATAAACGTGAATG
TTGTCGAAAGACTGAAAAAATAAATAAGATTAATACATGGTGAAATAAAAGTACTATAATATATAGTA
TCCTAAATATTAATTATAATGGATGATCAGCAGCAGTATTTCTTTAAGATTATAAATGAAAGAAAAAA
GAAATGTTGTTCAACGACTATCAAAAGATTATTATATAAATAATAATTTAGTAGAGTAGAGCCAAGCT
TTTGGGTTAGTATTTAAGAGATATTATCTTAATGTAAAACTATTAAATCGAAAAATAGAATTTATCCTTT
AGTAAGGATAAAGATATAGTCTGTTCTTTAAGGAAATCTTAAAGAAGTTCATAAGAGAACTGCATAAG
AATTAGCGCACTTATGTGAACACGAAAGTGATACCGACTCAAACTTCTTGTATCTCAATCACTTTGTCG
ATTTATTCTCAGAAATTTATCCAGATATTACGATGAAAGAAAATGATAAATCTATTGTATCTGCCATTA
ATACTATTATGTATATTGTTACTGAATGTATTAATGAAACGTATTACAAGTATGGAATGGAACTCGGTA
TTCCAGAAGATAAACGTGGACTAATTAATATGAAGAATGAATTTCTATATAAACGTTTAATGCTAACA
GACGCTCAAAAGAATTATGCTGGCGTAATTTTAATGCAAGAAGGAAATATTCTTCAGACTCCTAAGAT
TGATATTAAAGGATTAGCAATTAAGAAGACAAATACGAATAAACATGTACGTGAAGAATTTTCAGGA
ATTCTTAAAGATGTCATTCTTGAATCAGATAAGATTGATGGTTCTGAATTTATTACTAGATATAAGAAT
CTAGAAAAAGAAATTCGAAGATCTTTAATGAATAGTGAAATCACATTTACTCTCCCTAGAACTGCAAA
TATTAAAGAAAACTACGTAGCACCATATACGCAAGCACCATACAAAGGTGTATTAGTATGGAACACAT
TATATCCTGATAAAGAAATTAACTTACCAAACAAAGTTAATCTTATCAAGCTAAATATTGAAACTTTTG
ATGATATTGAAAGTAAAACTAATGATCAAGATCTAATTGAACGATTTAAGAAAGTTTATGAAGATGAG
GAATTGACAAAAAAAGGAATTACTTATATTGCTATTGAAGCAGAACAAAAACATATTCCTGAAGAAAT
CATTCCATTTATTGACATACCTGAAATGGTTAAGACTCATGTATCATCAGGATCCAAACTAATGACGTC
ATTAGGATTCAATCCATTAGTAATTAATGGATCATTATTCCCAACAAATATTATTAACTTTTAATGAAA
GTAGGAAATCTATTGGAAAATTTAAATATTGATATGAATGATCCAACCAAGAAAAAACATATTGTGGT
AGATTGTGATGAAGTATTATGCAATATTTCACCAAAATGGACATACTTAATACATCAAGAAAAAGACT
ATTTTGGTAAATATATGAATCTTATTGATAATTTTGATATTGATCTGCATTATAATATGGTTTTATCTAG
AAATAAGTTTTATCTAAATCAGTGGTTAATTAAAGATGAATCATATACGAATTATAGTGAAGACGAAA
TGGATGAAGTATTAAGACGTATGATGATGCTTTATGAAACTGAAGATTACTATGATAACTTAAAACCA
AATCCTATTGTAGAGTCATTAGCATTATCGATTCGTCAACCTATTTAGATAATCTATTGTAACA
AGAACAAACGCTAAAAATCTTAAGTCTAAAGAAAGATTTCTTAAGAATTGTTTTCAAGGTGTTATGAA
TAAAGTTGATATATACTTTGTAGAAAATGATGAAAATAAGTCTGATATTATTAAAGACTTAGGTGACG
GTATTGCAGCTATATATGAAGATGAAGTTAAAAATATTGTAGACATTTTAGATAACTGTAATAATCTTG
ATAAAAGCTTAATATATGTACCTAGTTATGGATATAATAACGCTAACCTTGATTTATATACTAAAGCAG
AAGAAAAAGGAACTCAATTAAGATATTATTCATATTAAAGGATGTGGACTTATTATGTATAATGGTAA
TTATGATATAAGTCTATATGAATATTTAAAAAGTAAACTTAAAGTATGCTATATCACAAGCAAAAAGG
ATGAAACTGTTATACGTTGTCCTTTTTGCGGTGATTCTGCAAAAAATCAGTATTCTGCACACTTATATA
TAAATAATAAACCACCTTATAAATATTATTGTCAAAAATGTAATTCAAATGGAATATTTAATGATAAG
ATACTTAATAATCTAAATATTTTTGATGCAAAACTAAATCAACAACTTAAAGTATCATACGAAAAATT
CATTAAAGATGCAGGAATAAAAATATGGAAAATCATTTTCATCACTATTTAATATGGATGAAACGGACA
TTCTTCCAAATAACTTTGGAATGTTAGAATTAAGAAAAAATAAAATACTATGAAGATAGATTGGGAATA
```

-continued

```
AAACTCAATGATGAATTATTAATTAAGTATAGAATTATTCTTAATCTTAGTGATTATATGGAAAATAAT
AAAATTCCAATAAAACAAGACAAATGGTATATTGAAAAATTAAAAATGATTAATGATAATTACATTAT
ATTCTTATCTAATGACAAGAATGTTATTAACTGCAGAAATATAACAAATGTTACTGAAAAAAAGAAAC
GTCATATTAAAATGAGACTATTTGAAGATTTTACTGATGAAAGTAGAAGTTTTTACTCAATAAAGAAT
AATATATCTCTTGATAAATCTTTATACAATATTCATTTAACAGAGGGTATATCTGATATTATATCCGTG
CATCATAATATATTTAAAGATCAGGAAAATAATAATGATATTTTTATATCTAGTAATGGTAAGGGTTAT
AATTCGGTATTACAATATTTATTATCAATTGGGATTACAAACGCAAATATTAATATATATGGTGATTCA
GATGTTAATCGTAATTATTATAATAGATTAAAGTATAATTTACTAGCTAAATATAATGGGGTTAATCTC
TATTTTAATATTGCTAAGGATCCTTATGGTAATGGATTTAAAGACTTTGGCGTAAGATCTGAAAATGTA
GAATTAAGTAAAAGCATTAAGATTTCTTTCTAACTTAATGGATCATAGAAATTTTCTAAAAAAAAAAA
AGACCCTAATAGATATTATATCTATTAGGGTTATATTTATTTAATTATTCTTTTTTTAATTGATAAGGAT
ACACATTAATATATTTACTATCTAATAAATCATACACATTAATTAACCGACCATACATATTAATCTTTG
AAATTACCACATCGTGAATTTTTCCTAAAGAATCAATAATATAAAAATCTTTTCCTACAATAATATTTC
TATTATAAATTTCTTTCATGAATTCATCTAATGAATTTTGGTCTAATTCAGTATTATACATATTAATCAT
TTATATTTCCTTCTTTCTTTTTTTTTTTTAATATATTTTCCATTTCATGATAAGGTATATTCATTATAATTG
ATACATCATTAGTACTATAATTATCATCTAGATATTTATCTATTAATCTTTTTCTTTCAGAGATGCATTT
ATTTTTAGCAGTATAATGATCATACTGTCGGTTAGCACTTTTAAGTTCTTTAAAGAATAAACTATTATT
GTTAATATATTTTTAATATTAGATTTATCTACTGATAATTCATTAGCTAATGAATAAACACTGCTGAT
ATTCTTCTTATTGATAATATCAAGAATATATGATAAACGAGAAATTCTTTTAACTATCAAATTGCAATC
TTTAACTTCCATATTAAAAATAATATCTACATATTTTTTCCATGATGGAGGATTATCGATAGATGTAGT
TTTATTATTTAATAGTGAATTAAGATATATGACAATATCTTTATTTAATTTGGTATTATTTATGATATCA
TCATATTTTCCTTCATCATAATTACGTTCTATATATTTTGTAAGGTATTTTATTTTTTCATCATCAAGACT
AAAATATGTCATATATTTCTTAAAGAAAGTATTTAACTTTAATTTAGTATATCTTCTTCGAATATTAAA
ACCATAAACAAACACATTAGTTACTGTGGTATCTATATCTTCCATAACAGTATTAACTTTAATATTATT
ATTAACAGTATTAACTTTAATATTATTATTCTTAATAAAATTATTCATGTTCTTTATTTCATCGATAGTA
TTAATGATAATATTTCTAGACAATAATTCTTCTTTTTTAAAATTATTAATAACTTCTGTATTATTTAAAG
ATAAAATGAAGGCATTTTTCATCTTTTTAATATTATTTCTAATAACTTTATTAATTATATTTATATCAAC
ACTATAAGTTTTTGATTTTATGTTATTAAATATATCTAGGTTAGTAATAATATCTTTTTTAGTAGATAAT
TTTAGATAAGTGTTGATTATAAATTCATCTATATCTTTAGGTATATATAATATACAATGCATCAACCATA
ACCTTATTATCATAGATAAGTTTAATTTTAATTGATAATTCTTTTTCTAGAATATTAATACAATTTTCAC
TAATTGATGTCTTAGTATTAATTTTTTTTACCATAATGGTAGTCATTTCGTATATCACATATTATTGAATG
TTCTAGATTAGTAATTATATAAATTTTATTATATAATTCTTTATTATTCTTTATAATATTATTAACACTAT
AAATATAACCAACGCCAATATCATAAAATATATCCATATTTGTAACAAAAGAAAATTTCTTTTTTAACT
GATTATATGACTTGATAATATTCTTTTCAATACTATCAGTACTTCCATCATTAAATATCAATTTATTATC
CTTTAGATATTCTTTAAATGAATCTAATATAGTATTATAGTTATCTAGATTCTTATTGAGTACTAAAGAT
ATAATATCAATGTCATTCATTTTTCGATAGTTCTTAATACTTTTGACAATACTTTTCTTTGTTGGAATTTT
TATATTGTTCTTTATATTTAATTCATTTATTGTATTAAATGGTATATTACAGTATAATAATATATCATCT
AAACTTAAATTTTCAATAAAAATTAATTGAATAAATTCATTATAGTTGATGTAATTATTTTTTAACTTTAT
TTTCTTCAGTAATTCGTATTCCTTTTAACATGGAATAAAGCTTTGACTGATCATAACTAAATCCTGATA
GTTCAGAGATTCTTCTAAGGTTACTTTATTAGGATTAAGTTTATTAATATTATTTAGGATAATATTATC
AACAATCTTAGCTTCTGAGATATTTTTGTTCTTCTTATTATTTTTAGTTTTATTATCATAACTAATTTTCA
TTTTTTATCAAATAGACCGGATTCATCAATATATAGATTTACTACACCTACTGGAACTTTATATTTCAT
ACATATTGACTTTAAATCAAAATTATCATTAAGATATGTACTATCTATTTCATGTTTTAATTCCTCGCTA
ATTCTTAACATCTAGTTATTCCACCTTTTAAATATTATTAAAGAAAAGGATAATGAAAATAAATTTCAT
TATCCATATAATTACAATGCAATAATCAAGTTTGTTTTAGCTCTAGTAATTCCAGTGTATAATTGTTGA
TGATATATGCTCTTATTATATATTTCATCAAACAGTAATACATTATCATATTCCGATCCCTGTGATTTAT
ATACGGTTGTTGCATAACCAAACTTAAACTTATTAATGATAACATGTGATTCTTCAAAAATATTTCTTC
GAAGAATTAATGACTTATACATTTCATTTTCATAAATTTGATCATCATTAGTTATTCCATCCGTAAAAT
ATAATGCATCTACATGCAATCTATTATAGATTCCAGTATCTGATGAAAATGTAGGTTTAAAGTCTAATT
CAAAAGTATCCAACCTTTTCTTATATTCATAGATATTTTCCACATAACCGATAATACCATTTGTTAAAT
ACTGTTGTGATCCATTATCTTCATACATTTCTAACCAGTTATTCTTAAGACATATTAATTTTTCACCAAC
ATATGGAAATGGTGAATTCAAATTAAGTATATTTTTTCTAATAAGAGAGTTTATCCTATCAACAGTTAT
ATTTTTTGAAGCTAGAATTTGATCTGCGCCAGTATACATATCATAGTCTACATCTTTTTTATTAATAATC
ATTACATTTTCACCGATAGGACCAATTCTTAATCTATTTTTCTTACGAACTTCATTAGCTAACCATATAA
TTGGATTATCCAGTGCTTGCCTTAATGGTTCATCTAGGAAGATATCTGGTCTTTTCATATATTTATTAAT
TCCACCTTTAACTGGTGGAAGCTGCATCGGGTCTCCAATCATAATGATTGGGACGTTAAATGTAATTAG
TTCTTCAATCATTGAATCTGTAACCATACTACCTTCGTCTACAATAATTAATTTAATATTTTTTGAAATA
CTTTCTTTTTTAATAAAGTTAAACTTATTCTTTTTTTCATCATAAACTACATTATACATTAACCTATGAA
TTGTTGAAGTGTTATTATTCCCTTTCCTATTAAGAACATTAGTAGCGGTTCCAGTATATGCAGAATATA
CTACCTGTTCATCGTTTAAATTGATTGCCGAAGTTATAAATTTTATAATTGTACTTTTACCTGTTCCGGC
TAATCCTGCTATTGTAAAAACTTTTTTAATATCTTTATTCCACCATTCAACTGCTCGCATAACAACCTCT
TCTTGTTTGTTTGTTAGCGTAATAATACTCATTATATACACCGCTTTCTATCCATTTTATTTACTATAATT
TTTTATTAACATTATAAATTACTTTTTCATTAATAATAATATAAATATAAACAACTTTCTTAAC
ATAACATTATAATAGTAAATAATGGCGGTGATAAAATGTCAATGAGAGATATGAATGGAAATCGTATT
ATGGACTCATTTAGCTTCGATAAAGAGTATGAAGGAATAGTATTAGATAATAACGATTTTGACGATAA
ACTATTTATTAAAGTATATATCTCTGAATTGTTTATTAATGATATTCCTGAGAAGGTTATCGATATTAAT
GAAAATATTGATCATACTAAAATAATTAATAATAATAAAATAAATTTTAAAAAATCTGTAGTACATAA
TAATTATTTGAAGTGCTATCCAATCATATATAATAATATGAATCTTGATATAATGAAACCAAAAATAG
GTTCAAAAGTTATTGTCAAATTTATTAATGGTAATCCAAAATTGCCATATTATGAGAATAAAGGATATT
ATACAGATATTATTATACCAATTCCTCCCGAAATTATAGATCCTCCTACTGATCCATCCACTAGTGATG
ATTATACTTCTTTTGGATACTATAGAATGATTAAACTTACTAATCCGGCTATGATTGGTCGAGATATAC
TAAAAATCCAAAAGAAATTAAAGACTCTTGGGTATACATTCACTATTGATACACTAGACGGTATATAT
GATTTAAGAAATGTTGAATTATATAAAAGATTTTCAATCTAAAAATAAACTAAGTGTAGATGGACAGAT
TGGTCCAATTACGTTTAGAACAATTATGCGTAAAAATATATAATTTTTAAATTCGAACATATATTTATA
GTAAGATAGTTTACTATAAATATATTTAATTGGGGTGGAAATTTTTATGGAACAAGTAACTTCTGGACT
ATTAATTTTGACAGTATTATCCGTAGTAATTCAGTATTTAGTTGAAAGAATTAAAGATATTTTTCCAAC
AAAAGTTATGGATAAACTAGCCAAACTATGTTAATCCTGCTTTCTGGTCTTTAATTGTATCTCTTCCTATT
GCTTTTGGTATAAATATTGATTTATTTGCAATTATCGGTTATAATATGCATCCAACATGGCTTGCAACA
TTATTTACTGGTTTTGCATTGAGTGGTGGAGCAACTGGTATTAATGAACTTATTAAAATCATTAAGTGCT
```

```
GTTAAAACTAATAATTTTACTCAAGCAGATTCGGTAAAAAATACTGATGAAGAAGAAATTAAAGTTGT
CGCTAAATCTAAAAAATAATATATATCCCTATAGTGTATAATTGCACTATAGGGAATTTTATTTACTAA
AATTATAAAATACATAATAAAATAACATTAAAATATATTTACATTAATATACAGAAATGGATGATTAA
ATATGAAATATCCGATACGTGAGGATCATAGAAAAAGAGTCAAGACAAATTACATTATTATTACTCAT
GCTAATAATCTTATAAAAAGGGGAACACATATAAATAATGCGTTAAGGCAGAGAACTTTTAAATACAC
TTGGGGAATATGGCAAGAATATTTAATGACTCACGTTAATAAAAGATATTTACCAATGCATTATTTTAT
TGAATTAATTGATAAAGATTATGCAGTATTGAAGGGTCTTTCTGACCATAAACCTTCTTACTTTATTAA
TGATTTAGTAGACGAAGGTGTAATAAAATATGTTTACCGAGATTCGATATTAATAGTCATTGGAGATA
ATTTTAGTATAAATAATCCTGATACTAGAATGATTGATCATTTAGCAACTAAAGTTATTCTTCCATTAA
TGAAAACGTATAATTTAAGTTGGAATAAAATACAATTTTTTGATGAGTGTTTAACTGACTCATTTATTA
ATAATATTGATAATGATGAAATAAAATATAATTACGAATATGAACCAATGTCTATGTTTGATATGAGT
ATTCTAAGAAATGCAGTACTTAGATATAAATCATAAATATAAAATAATAATTATAAGTATTGTGTGGT
GATAATTGGAAATGGATAATAATCAAAGACATAAGAATAGAAATTTTTTTAATATAATGATAATTATA
AATATTGTAATTATTGTTATAATAATTGTATCTTCAGTATATCTATATATACATATAAATTCAGGAAAC
AGTTATTCAAAAGAAACATATGCTAAAGTGAATAATGTGTATATGACATATGATAATGAAGATAAGGA
TATACAAGTAAGAATTGGTAAAAAGAAACTAATAATATTTAATAATGGTAAAATTAAAGAGATTATAT
TTAATAATTTTGAAGTATCAGTATATGATGAATATACTTTAATATACATTTCTGGAGATAATGATGAAG
TTAGTATTTCTGTAGACAATGATAAAGATTCCATTTCTGATATAGTCATAAATAATCAAAGTTTAATAG
AATAATTATATAGATATATAGAAGTGTGGAAAGAAGGTTACAATATATGCTCATATTAAAAATGAGAA
CTGACAAAAAAGTAGACTATAAAAAAATTATGGTTTATAAAACTTCATAGAAAATTAAATATTGAAATT
CATTATAATATAGAGGAAAATGGATTCTACTATATTGATAATAATAAAACATTAAAACTTAAAAAAGA
TTTTTCAAGAACAATTAGTATGATTCTTGATATTAAGAAAAGATTCAATTCGTTTAATACTGAAATGGA
TATAATTGATAATAATATTAATATGTATCTTAATGACGTTATAAATAACTTTGAAAAAGAAGAAATGC
TAAGAATTATACTAGGAACTTCGGAATATAATGTGAAGAATCTATATAATGATCTTACTGAATTAGGA
ATTAATATTGATCCAGACTTATTATATGTAAATTTATATAAAAATACAAAACATTCCGAATATAATGAT
GAAATAAAGAAATACATTTAAAAGAATTTGATAACCTGAATACTAATAATTAAAAATAGTATTCAGGTTA
TCAATTTTTATCGAGCAAAAAATATTTTTTTCCTTCTTGAATGTTTTAAGGCACCAATGCGCATTTTTTC
AACTAGTTCTTCTTTCTTATTTTTTCCATCAGCTAGATCTTCAATAAATAATTCTATACTGCCATACGTT
GTTTGAATATTTTGAAAGCGATGTCTAATTTGATATAATGATTCTTGAGTATCATATAGACATAATTGC
ATAAAATGTTCTTGAAGATTTACTGGTATGCTGTCAAAATGTTCACTATGAACTGCGTTTGCATATACT
AGAATTCCGTTTAATGTATATTGGGGAGCAATTTCAATTGGTTTGGATGAATAAACCGGAATGTTGA
AGGATTTATTTGACCTTGAATGTTACTCATCATCTGATTTTCAAATAAACTTCCAGAACCAGAACCAGC
TCTAGGAGTTCCTCCGATAATTGCACTATTACTACTATACATATCTAATCCAATTACACGATTAATATT
TAATACGGAAGTCTCTGTATCTAAATAATAACGATTCTCATATCCCGGAACAAGATCTTTATTAAATAC
TCGGATTTCTTCAATTCTTGGGAAATACTTACTAAACGTAATCAAACTTTCTGATCTTATTCCACTAAG
AATTTCTTCATGAGAAAGTTCTAATTGTGTAAATTTATATCCTAATTTTCGTTCTAAGAATCGAATAAC
CTCTGTAGGATTAATCATTTAGTTATCACTATCCTTCCAATAATAAAAATACAATACCACTTCCTAAAT
TTAATTAAGAAGTGGTATATTTTAAAACATATCTTGTATATATTTGCTTAAATCACGTTTAATTTCTTCT
TCGAGATAAATCCGGATAGTTTCGTTTGATTGTTTAATACTTAATGTTTGATCTTCAGTAAGAGTTACT
GAACCATTCTCGAGATTCATAGATATACCTAATGATTCTGCTAATGAATATACATTTTCAGATTTTTTA
GTAACAAACTCTAATAATTCAGAAACTTGATAAGGAACTACTTTACCTGAAAGATTATATGAGTTTGA
GCTTGCTGCTTCTAACAATCCTTGATAATCTTCTGAGAAGTCTTCATTAATCCGGTGAGTCATATATGA
GTTTGGATGGGATGGAATAACAACCCAATCATAGCAGCAAATCATTAAAGGTGAATGAACTCGTTGAT
ACTTCCCATCAGGCTTAATAATATTACCAATACCACGCATGGAGAATGCTGCCTTTGATCCTTGATTAA
TCAAACCTTTCATGTCTCTACCTACAGATGTATCTGCAGTTTCAACTCGTCCAATTAATCGATTCCCATC
AAACTTAGCTTCAGTTACAATATGCGAAATATTGCGTTGATCAATATATAATTGTCTACGATTATCAGT
ATTTAATGGATGACCTGCTTCTCCAAAGAATGTTCTATTTTTAATTTTTTCCTGAACAATTGGGTTTTGT
ATTGCTTCATCAATTGCACGTCTATCATAAATACGGTTATTACGGTTAGGTGCATCAGCTTCTTGCAAC
TCAGTCTCGAATAATACATTATTAAGTGTTTTATCTATAATTTTCGGTTTAGATTCAGTGACCGATTCCA
TTTATAATATAACCTTTTTCTTCAGTCATAATAGTAATACACGTCCTTTCTTAGTATATAAATAAAATTTA
TAATAAAATGTTTGATTAGATAATTATTTTTTTTAAACAACTTATTATAAAATATTCTTTTTATCATTTTT
GATAAAATATGTTTTAAATTTAAAGAATATTAAATTATAAAATAAAATGATAAGGTGGGAAATATAAA
ATGCCAAAACTTTTTTAGATGTAATCCTTGAAGATGCAGACGCATTTGAAGCTAGTAAATCTGTTGA
AGTGGTTGATAAAAATACTACTGAACCTGAAGTAGTCGCTAAAGATGAAAAAGCTGATGTAGAAGAA
CAAAAAGAAGTATGTGACGAAAAAGAAAAAGCTATTGAAAAAGAAAAAGAAGAATATACTAATGAT
GCAGAAGTTGAAATTACTAGTGACGTTTCATTAATGAATAATGTTGCTGATAAATTAGATAGTGGTAT
GTCTATTGAAGAATCATTCAATTCTCTAATCGAGGTTAATCTAGTTAAGAATGAATTTAAAAACATGG
GCTTGACTTCTGAAGAAATTAATCTTCTTGCTGAAGATGCTTCTAAAGAAAGAAAAGGAATTATACGT
GGATTGGCTAAAAAAATCGGTATCGATGATAGCGGTAATGTTGGTCTGTAAAATATGTTAATGCTCG
TAAAAAATTAGGCGTAAAACAAATTACTGCCGCAGTAACTTCTACGGTTGCTGCAAGTGCTGCTGCTG
GAGCTAGTAGCTATTATATTGAAACATCAAAAAGTAAAAGCGAAACTGTTAAAGGTGGAATCTTTTCA
GGTTTAACTGTAGGATTGGTCGTAGGTTATTGGGTTTCCCTTTTCTCATTTGTAGTTACTATTTTGCAAA
GTGCTAAAGTTAAAGGTCAAATGAAAAGTGATCCATCTATCTTAAGAAATGCTCTTGCTGAAAATAAA
AAAGATTTAGCTGAAGTTGTATCTTCTATGTCTAAAGTTAAAGAAGATGCTAAAGCAACCAAGCAATT
AGAACGTATTCAAAAAGCTTTACTTCGTGAAAAATCCAAATTATTGAAATTGCAAGAAAAATTAAATA
CAAAATAAGTTATATATGATCTCAATTCTGATTAATTTCAGAATTGAGATTTATTTAAACATTATTATA
TAAGAAAATATATATTGGTGGTGATTTCAATTGCATCTTGATGAGGAAAGTATTAGATACGCTATAAA
ATTTACAGAATCTTTAGAAAAAAATGATTTTGAATATGGTCAAACAATTCGTGAAGAAATTCAAAATG
AAAATAATTCATCTCAAATAAAAAATATTATGAATATGCTCAATATTAAAAATCCAAATACTATTACT
GTTGAAGAATATTTAAAGATACGTAGAAAAATTAAATTTTCGGGTCTTATTGGATTCTTAGCAGGTCTC
GGGAGGAAGCGTAATGTTTACTTCAGATATTATTATAAATAATGATCGGCTTAGAGACGATCCTCAAAA
TAGAGGAGTCGCTAATAGAAATAATCGTAGTAAGCTAAGTATGCTTAAGTCAACCTTATTTGCTTTAGT
TTCGGCTTTTGGTTCATTTGCTTTATCAGTATTATATAGTAAGAGCGTTAAGAAAACTTCAGTAGCTAA
TCCATCAATAGTTAGAAGTTTATTAGCTATTAATGCAAATGACTTAAGAATGGTAGAAAAAGCAAATA
ATAGTGTAGTTACTAAGTCTGACTTAAAATATATACGTAGAATAGAACGAATATTAATTAGGGAAAAA
AGGGATCTATTAAAATTGCAAGCATACGTTATAAAGAAAAATAAATGAAAGAAGTGAAAATTTTTATG
GAATATAATGATGTATTTTTAGAATATTTAAATTCTGAAGAAGATAATATTGAAAATATGGAAGAATT
CCTATCAAGCTACATTGGAATTAAACCAAGATATCTTGAAATTAGACCTACTGTATTTAGTGAAACAA
GAATTACTAATGATGGTATTAGTGATGAAGAAGATAATAGCGAAGAATCTGATCGTAAAAGATCTACT
```

-continued

```
GATGAAGTAAAAAAGATTAGTAGAGAAGTAATGGAAAAAGATAAGAAAAAGAATCTTAATCCACAA
AATAAAGCAAAAATTGCAACTATTAAACGTGAAATGGAAAAATCGATTAAAATGGATCCAAATAGTC
TTGGTAATGATACTAAACTTAAAAGACTTATGCGTGTAGGAATTACAATGTTAGTTTCTTTCGGGATTA
TTTTTGCTCCTGCAGTTGGTGTCTTAATAAAGATTATTGCTCTTATCGGAGTAGCTGCTACTGCAAAAC
ACGTTAATCGTAAAAAATTGGAAAATACTATTATATTACTAATGGATAAAATTAAATATATTGAAGAT
GAAATGGAAAAAGCATCAGACAATCCTAAAAAGAAATATGAATTAACAAGAGTAAAACGAGAACTCC
AAAGAACACTTATGAAGTATCAGTCTAGACTTCGGAATTTCCATTAATATATGATTTGTATAAGCGATG
TTGCAAAGGAGGTACTATTATATTGAAAGATGATTTCTTTAATTATTTATTTGAAGCAGATGATCCAGA
AGAAATAAGTAATATTGATCCTAATGAAGATAATACTGAAAATAATAACGAGGATACTCCTTCTAATG
AAGAAAGTTTACCAAACGAAAATAGTGATGAAAATGATTTAGAAAAGGATCCAGAAATAGAAGAACC
TGATAATGAAGAAGAAATAGAACCTAATGAAAATGAAGACCCGAATAATAATTTACGTATAAAGGAA
ATATTATTTGAGAATTTCTCTGGACTTAAAAATGCAATTAAACGATTATTTACTGACATTGAATCGGTA
ATACATATCGTAAAATCATATGATTCTAATAATGATAATCATAATTTAGAAAATACTGTGGATGGAAT
ATCTGAAAAAGGATATGACATTTTAAATAAAATTCAAACATTACAAAATGGTGTAATTCTTAATATAT
CAAACGATAAATTAAAAATCATATATAATGAATTAGAAATCAAGTAAGTGATATTATTAAGGAATAT
TCAAATAAAGTTGATGTAAAGTTGAAAAACAAGTATTAATAATATAAACAATTTAATATAAAAATTTT
AATTTATTTCTATGTAAGTTTCGTTTATTACTTTTTTTAAAGTAAGAATGATGAACAATTATATATAAATA
ATTTATAATATTATTTTTATAATCTATAATTTTATATAAGAAAAGGAGAGAAATTAAATTATGCGTAAT
TTTAAACGTATTACAAAGACTAATACAGATTCTTTTAGTACTCATCTAAGCGAAACTCAAGACTATTTC
GCTAATACTAAAGGAACAAATATTACTGGACAAGATATCGCTGCAATTATAGTGAATGAACAATATTT
TGATGAGTATGCAACTCGTCTATTAGAAGGTTTCGATGCTGACCTTAGTGAAGAACTAGGTGTTCTTTT
AGAAAACACTCGTAGCAACATTATGGAATCCTTGGGTGGAATTACTCCATTTGCTTCACTTTCAATGCC
TGTTTTGGTTAAACTTTGGGCTCGTTTGTCTATGGTAAATGCTATTCCTACTACTCCTGTTACTACTCCT
GCATTTGTAGTACCAACTATCAAACCATATACTATTGGTCCAGATGGTGAAAAATACTACCTACCAGA
AGCTATTAATACTATTCCTGAACACTTTGTAAGTCTTCGTCAACTTAAAGAAGATATCACTATTACTGG
TGGTCGTCTTCTGACTATGATCTATTTACAGGTGTATCAACTGCTGACCGTGCTAAAGGTGATCAAGT
AGACCGTAAATTCCAAATTGTTGCAGGAACATGGTCTGATTCTTATAATGTCGCTGATGCTGCTCTTGG
CGAATATGAACTTAAAGGTCAAGCTCTTAAAATGGATATTCATGGTAATATCTTTGGTAAAGTAACAT
ATACTACTGATGGTAATGGTGCTACTAATGAAGATACTATTATGGGACATGTTGATGTTGAAAAAGGT
CGTTTAGATTTAACTTCTCTTTCTGGTAAATTGACTGAGTTCAAAATTCAAGGTTTCGTTTCTTCTGAAA
TGCATACTGGTACAACTCAAGTTGGTTTTGATGTTGATGATCGTACAATCAACATTGGTACTGCTCCAC
ATATCGAAGGTATCCTACCTATCGAATCCGTACAAGATAGTAAAGCTATGTATGATATTGATGCAGCA
GCTGTTATTGTTGATACAATGTCTGCTACTTCTGCACAAAAAGTTGATACTGACTTGATTGAATTCTTG
TTACGTTCTTATGAAGGTACTAATGCTGCTTATCATAAAACTTTCGATGTACATCCAAATGGTGGATAC
AACATGCATCCGCATGAATGGCGCCGTGGTATTCGTGACGTTATTGACTGGATGTCTCAAGCAATGAA
AAATGATTACAAAACTTATGATGCTTACTTTGTAATTGTTGGTAATCCAATTGACACTCAATTGATTCC
TGACATTGAATGGGAATTCCAAGGAGCTACTGATGAAGTTGCGGGAATTAACGTTTCTTATAGCGTTG
GTGCTTCTTCTACAGTTAACCGTTATAAAGTTGTTTCTTCTGGGATTAGTACCTGCTGGAGATCTATTAAT
CTTTGCAGTTCCTACTCGTGAAGACTTCAAAACTTACGAATACTACCCATCACATTTCAATATCGTTAA
TAATTACAACAATGCTGTTAACCAAAGCGTTCCTAACATTATGCTTTCTCGCCGTTATACAGTTGAAGA
ATTTGTTCCAATTATCGGTAAAGTTACAATTAAAAACAACGATGCAACTCAATACGCTCGTTAAATAG
AGTATAAATTCTATTCAGTTTCGTATATTAATACTAGTAGATAGGAGGTGTTTCGAATGGTCTTCACAC
TCGAAGATTTCGTTGGGGACTGGCGACAGACAGCCGGCTACAACCTGGACCAAGTCCTTGAACAGGG
AGGTGTGTCCAGTTTGTTTCAGAATCTCGGGGTGTCCGTAACTCCGATCCAAAGGATTGTCCTGAGCGG
TGAAAATGGGCTGAAGATCGACATCCATGTCATCATCCCGTATGAAGGTCTGAGCGGCGACCAAATGG
GCCAGATCGAAAAAATTTTTAAGGTGGTGTACCCTGTGGATGATCATCACTTTAAGGTGATCCTGCACT
ATGGCACACTGGTAATCGACGGGGTTACGCCGAACATGATCGACTATTTCGGACGGCCGTATGAAGGC
ATCGCCGTGTTCGACGGCAAAAAGATCACTGTAACAGGGACCCTGTGGAACGGCAACAAAATTATCG
ACGAGCGCCTGATCAACCCCGACGGCTCCCTGCTGTTCCGAGTAACCATCAACGGAGTGACCGGCTGG
CGGCTGTGCGAACGCATTCTGGCGTAATAAATATTATGAACCTTTCAGAGACCTTTTGGTTTCTGAAAG
GTTATTATTTATAAAAATTTAAATTGGCGGTGCAACCATGCATATTGATTATGGATTGAAAAAGAATAT
ATCAAAGTACTTACATGAAGAATTACTAACTGAAGATATCTATAATCATCCTTTATTAAAAAAGATTG
ATGATGAATTTCAGAAAATATTAGATGAAGATAATATTAATGATACTAAACTACCAGTAACATCATAT
AAAAAAATTCAAAATATAATTAAATATGTCTCAACTATATTTAATATAAATTTAATTATAACGATTGAT
AACGATAAATATCCTTACTTATGGAATGATGACATTTATTCCGGTTAAAATCTAACAAAGATATCTAAT
AATATAAAGAAGATTGTACTTCAACCAAAAACTGGTTTTGAATATATTAAAACTGAAGTTATTGAAAT
TAAAATACAGAAAAAATTAATATCTTTCATTAAGGATCCAAACTTACTTATAAGAAATAATAAAGTTC
CAAAAAATTATACTCCTAGTGGAAGAATATTGACCAGTATACTTCTTCATGAAGTAGGTCATCATATAT
TCATTGGATTTGAAATTAAGAAATCTATTAAAAATGATAAACTTTTTTCAATTAACGGTGGTAATGGTA
AAGAAATAACTATACCTAGTAATGTTAATAATAATAAATATGTATTAACAAGCACTATATTATCTATAT
TAACGTTAAGTATTTCTATGCATAGTTATATGAGAAGTGAATACAATGCGGATAACCTACCAATACAA
TATGGTTATGGTAAAGAAGTATTTTATTTTTCAGAATTAATGGAAATATTAGAAAAACAAAAAAGAAA
TTCAATTCTATTAAAGATTAAAGGATTTCTAATGTTTGGTAAGAATAATTATTATAATCGTAAAAATAAA
GAATCAAGTAATTATTATGATGAAAAAAGAATTAAATAATGATAATAATAGTCCTAAAGATAAGGAA
ATTATTATAGATAATTTAAAAACTATAGAAAATCTTGAATAGATAATGTGGTATAACTTATTAATTAAT
AAGTTATACCATTAATACGCAAGTAACTATTAATTATAATAAAATAAAGAAATTGTGGTGATAAAAGT
ATGCTTAAGATTAATATTAAAGATAATCCTGAACTTAAAAAGAATATTACTTCAAAAAATAAAAAACT
CTTTTATGATTTCAATACAAATAATCAATCTTTCCTAGAATTAGCTATTGAATTAAAAAAGATTGGGAAT
CAGAAATAATAAGTTACATTTAGTTTTATATGATAAGAGTCTTTCCGGAGTAGATCCGTATGACCCGA
ACTTAACTGATAACGTAAAGGCAAGAATTGTTAAAGAGAGCATTATTAATTTTTGGTACTTTATTAGG
GAAGTAGTTCGTATTCCAGTTCCAGGATCTTCAGTCCATTTTGCTATTCATAGAGGGAACCTTGCAATG
TGTTTCTGTTTATTAAATAATTTAAATACCGTATTAATGTTACCTCGACAACATTATAAGACATATAGT
GCTGTAGGTTTTTATTTATGGATTGAATTATTAGTAGGTAGAAACTATCAAATGATCTTTTCACATAAA
TCATTAACGGATAGTATTGCCAATCTAAAAAGATTGACGGCTCTATTTGAACTATTACCGACATATATG
ACTGAACCTATCTTAAATAGTAAGAATGATAAGAATGCTGAAACTATTTTAACAATTGACTCAATAAA
TAATACCATTAGGACAATTGGTCCAAGCACAGATATTGCTTCAGCAGATAAGTCAGGTTAACTTAATT
TTTCGGCTTGACTATAAAACTTTTTTAATTGCTGGAACATCCTTAAGTCTATTAAACTACAACGTAACT
GGTAACGGTAAGCGTGAATGTTTGAAAATTAATAGAATTGGACAATCAGCAGCCAAGCTTCCAATGAT
TATTGGATGAAGGTTCAACGACTATCGAAAGGGTAAATTTATATTTTAAATTTAGAACTGAGTAGAGT
```

```
AGAGCCAAGACAAAAATTTGCAAGTTTACTTGGTTAGTAATTAAGTGACATTAACTTAATGTAATTCT
ATTAAATCGAAACGGAAAGTATAGAATAAAAATAAATATATATTATAATAATGATGAGATAATTTATA
TCTTCTTTAATTAAGATTATTAAAGAGGTGATTATTATGGTAAGAAAAACACAGAATTTGATCTAGTT
AATAGAATATCACAAAAATTCAGTAATAATGAATTTACCTATATTGAAGGGTTTAATAGAATGATAGA
TAAATGTAGATTTAAATGTAATAATTGTGGAAATGATAATTATTATACTTCGCCATCCATATTATTGGA
TAAAAATAAATCTATATACTGTAATCTATGTAATCCTGCAACTTTACGAAAAAATTCATTTATGGATAA
TGTTAATAAAAATTACACTGTTTTAGAAAAACCTAAAAATAATAAACAAAATATATCTGTAAAGTGTA
ATTTATGTGATTTCATATTTAAAACAAGGTCACAATATTTAACAGCTATGGACAAACCTAGTAAAACTC
GAAATTTGTGTCCTAAATGTAATGCATCAAATTCTGAAAAAATATTTGCAAAATTTCTTGATTCTCAAA
ATATTAATTATGAAATGCAGAAAAAGTTTAAAGAATGTATCGGTATTAATAATAGAGTCACTCCATTT
GATTTTTATATAGATTCAATGAATCTAATTGTTGAAATTGATGGAAAACAACACGATTCATTAAAATAT
GCATTCCATAGAGATATTAAAGAATATGAAAGAACTGTTGCTAATGACAATATTAAAAATAATTTTTG
TAGTGAAAATAATATTGGATTAATACGTTTAAGATATAATTGCAAAAGTAAAGAAATTGAATTCATGG
AATCAATTATTGATGCAAAATATATTCCAAACGTAAAATTATCCATAAATGCAAATCTTATTAAATATT
AGATATAAATCTCATCAATTTATAATTCTGACTCTTCAAATAAAATTTGGAGAGTTTATTTTTTTTTTTT
TTCTATAAAGATATAGTCTATGGGGAGAGAAATCTCTTAAACTTGTTATATTCTAAGCGAGGAATGAC
CGTTGTATGCGCCGTAATGAGTTTATAAAAACTCTAATCAATTTTGAGAATAACGGAATGATAGATAG
CAAATAATCTTGAAACGTTATATCTAATACTCCTACATGCATATATTTATTAAACGGACTATATGTGTG
AAGTTAGGTGAAGTCAGTTGAACCACTCCCCTATAACGGGAAACTTAAGTATTATATACTAAGAGTGT
ATAGACTGGGATGCGTTATAATATGGTAAGGATATTCTTTAAAAGAATTAGACGAATCAATGAATTAA
AACCGTTAAAAATTAATCTAACAGGTTAATGAATACTAATAGGGATGAGTAAGTGAGCGGTTATGAAA
ATCCTATTTAAGTTATGCTCTTAAATTATTATTAGTGCGGTAAGATTGGTACCTAAGTTATAACTATGC
TATCAAAATTGAAAAGGTGGAAACTAGGAAGATCGTAAAGATGTTTAATGTCTGATCTAATAAATAGG
AAATGATTTATGAATCTTAGTGGCAGCAGCCTGTAGTAGTGATGAAGCTCTTGTAATGAGAGTGGAGT
GAAGGGGCATAGTCAGAGATTATATTAACCAAATAATCTTTGATGGAACGCTGTATACGATGAAAGTC
GTACGTACAGTGTGAAGTGGGGGAAAATCCGGAGATAATTTCAAAGGATTACCTATCACTATCCGTTA
ATATGGTTAGATGAATATGCGTTTTTAAAATATAATGATACGGTATTTAAAGCAATGCGCCCTGCTTTT
ACAGAAGCAAGTAAAGCTGCAAGCATGAATGATACTCCGTATTCAATACTTATTACAACAACGCCTAG
TAATTTAGATTCCGATGAAGGAAATTCATGTTATAATCTTATACAAAATGCAGCTAGGTTTGATGAAA
AGATGTATGATTGGTACTATCAGTTTGGTCCAGAATACCTTCAATCATACTTGGATAAAAATCTCTGGTA
ATGATTTTATATATATTGAATTTAGTTATAAAGAATTAGGTAAAGATGATGAATGGTTAGAGAGTCAG
ATTCGGGCAATGTTAGGTGATAGACTTAAGGTTAAGATTGAATTATTATTAGAATGGGTTTCTAGTAGT
GAAGATTCAATCTTTAGTGAAGATATTATTGAATCTCTTGAAGGTAATATTATAAAAAGGGAAAATTA
TGCAGGATCCATATATTTATGTGATGGAACATATAAACTGATGTTATTAAAAATCCTATAAACTTATT
AACTAAAACATACGTTATATCAATAGATATTGCCGGAGGATTAGGTAAAGATAATACCGTTGTAACCG
TTATTGATCCAGTAGACCTTAATACGGTAATGGTATTTCAAAATAATAAAATTACTGTTCCGGAATTAG
AAGATCTTGTTACTGATCTAGTGTTAAATTATATTCCAAACGCAGTAGTTATTCCAGAACGAAACTATG
GTGGGGACAACTGATTGATTATATTATTAAACATAATTTAATATCTAAAAATCTTTTTTTATGTAACAA
AACAAATAACTACTGAAAAGACAATCTTACAAGAAAATAATGTTTTTAGAAAAAGAAGTAATAAAGT
TAGAAAAGAAAAAAGGGTATATGGTATATATACAACAACTAAGACTCGTGATATAATGATTAATACTA
TCCTTCCAATGATTGTTTATGAAAGACCCGAATTGGTAAATAATGCTTCCTTATTTAATGATATTAAAA
CGCTAGAAAGAAAAAGAAATGGTAAGATTGAACATAAGTCAAATCGCCATGATGATAATTTATTTTCA
TATCTGGTAGGATTATATGCACTATTATATGAACACTCGATCAGTAGGTTTGTGGATATTATTGATAAA
CCCGAGTTAAATAAGGAAGATGAATTAGTTGATAGCGGTAATAATACGGGTCAACATCGTTTAACTAG
TTCTCAAAAAGCATCAAGAACTATTAATAATTTAAGAAAAGTTAGTAAAAAACCAACAAGCAAATCA
ATTATTAATGCATCAATGAATATAAATAACGAAGATTCTAGTATTAATAATTCTATGAGTAAAAAACC
ACGAAGAGGACTAAATTTAGTCCGAAAATATAATAAAAAATAAATTAATTTTTTATATACTATCCTAA
AAAATATTATATAATAATTAAATATAATTGATTGGAAGTGGAAATTTTATTATGGTTATGTTAAATGCA
ACTGTAAATGAAGAATATAAACGTGAAAACGTAAATGAAATTATTACAAATATTAGTGAGGATATTAT
GATTGATAATATCTTATCTCAAATAAATGATACTGATATTCAGGATCTTTCTGAAGTAAGAAAATCATT
CTTTGAATACTTTGAAGAACGTTATAACTTTGTTAAGAAAAATTATAACGATGATGATGAAGCAATGC
AAAATTGCCGAGAAGTCTTTGATGATATTTTAAATCAAATTATTAAAGCAATCTCTGAAAAATACAGT
TTTGATCTTTTCTTTTCAGATATCCTATTATTCGATACAAAAGTAGAAATTACTAAAAGTCTATATTATT
TCTTTGTCATCAATATTCGGGAAAATATTGAAAATATGATTTATTATTTTATCATGAAAAATAGAAAAA
CATTAGTAAAAATGTTTAACACTATTAGTAAAGAAGAAAGAAAGAATTTAAGCTATATTAATCTTAGT
TCTGCAATCAATAATGATTATACGACAATGATATATCATTTAAGCATGATTATTGATAATATTGAAATT
CCTACTAATGAAGATATTATTGAATTAATGGTTGAAGATAATTCATATGAACTTTATAACTACGTAACT
GTTAATACATTAGTTCTTACAAATTTCTGCGAAGTAAATTATAATGAAAACTTTTACTCAATCTTTCTA
GATATTATTAAGAATTCTCCAATTATTGTAAGAAATGTTAGAAACTCACTTATTGACTCATTAAAATAA
TATTAATTACCCTATCCTTAAATAATTTAAGGATAGGGTTTTATTTAAACAATTTTTTATAAGAAATATT
TAAAGAGGGAGACGTTAATGGTTGACTAAAAAGATGAGCAGTTTAGACCGAATTAAAGATTCACTT
ATTTTTAAAGGTGAAATATTAGATATATACTTACCAAAATCTAATTTTGATAAAAATCTATCAACGTAT
AATGGTGAATATATAAATACTATGGGTATCTTTTCATTCATTGAAAAGAAAGCTGGACCTGAAGATAA
AACAACTAAAGGAACTTTACGTAAACTAGAATTACCTAATATGATTGACTTTCAATACGATTCAAGTT
ATTCTTTTAAGGGAAAATTATCGGATGAATTACCCTCTGACACATACGAAGTTTTTCGACTTACTACAG
GAAATCAATTTATTGCAAATGTATTTACAGAACAAAATGCTTCTAATGTTAAAAAATTTATATCGGCTC
TTCATGGTGGTAATATTCCGAGTTCAGTATCTTATGATAATATTATTAAACTATACTTAGATACTTTATC
AATTAATAAAGTTAGTTTACGTAGTCCATCAGTAATTTATGAATTGATTATCTCCGAATTATGTAGGTA
TAGTAAAGATATTAATGAACCTTTTAGAAAGATTATTGCTTCAAAAAATAATATTAGTCCCTATATGTA
TACAAATATTAATCTTAAGAAATTACCATCAATCAATTCTACTTTTGCGGCACTTAGTTTTGAAAATCC
AAATCAGCAATTATTGACAGTATTAATAAGAATATCAATGGTGAAAAAGAGAATGAATCTCCTATTG
AAAGGACTATTAAATACTAATATTTTAAAACAATAAAATATAATCTTAATAAGATGATTTATTTTTATG
TTTATTAAGTTTTTTATAAAAAAGATTATAATGAAAGGAATGAATTATAAATATGGCTAATGATGCAA
GTTTGACACAACTACATCCATCAGTTTCATCCGTTATCAATGCAAATCAGTCTAATTTTCTTACATCTA
ATGGTGTAGTTACTCTATTTGCTGCAGACACCTTTGCTAAAGGTAAAGATGGTGCAATTGATTTTGTTA
GTACTAAAGATGAATTTATTTTTAAATACGGTACTCCAGATTATTCCAAATACGGTCAATCAGCTTATA
ATATTGTAGAGTGGTTAGAAAATGGAGGTCAAGCATTTGTCCTACGTCTTCTTCCTGATGATGCTACCT
TCTCTCATGCAATTCTGAATGTACAAAGTAAAGTTGTATCTCAAGGTAAAAATGTTTTAACTACTGCAG
GAGAATTGGTTAAATTAGATGATGTTCATCTACGTCCTACTACTGCTTTTATTAAGAAAAATAATCGTG
```

```
ATAAGAATATGTTGATGTCTGAATTGACAAAAACTCGTTCTGATGAGAATACTGTTGATGGTTATACA
AATAACTTTGTATTGCTAGTATATCCAGAAGGTCGTGGAGAAGCTTACAATAATTTAGGTTTCCGTATG
ACTCTTAATGGTTCTTTCGATTCAGCAGTAAATAGTTCTCGTGTTTATAACTTCGAAGTAATTCAATAT
GATTCTGAATCTAATATGACTGTAGTTGAAGGACCATTTTATGTATCTTTCGATCGTACTGCAATCTCA
GCTTCTGGGGAATCTATGTTTATTGAAGATGTTATTAATCGCTATTCTAAACACGTTAATTGTGAATTT
AATGAAGAAAACTTTAACCGTTTGACTAAATCTATTAATCCTAATGTTAACCCAGGACATATTGATATT
CTTACTGGTAAATCTAAAGTTCTTCCTTCTGGTAAAGCTGAAACAGTTTATTCCGAAATTACTCGTGAT
AACGAAGATATTCATATTTCATTACAAAAATATAATGCTCGTGGAGAACTAGTAACTCAGAATGGTAA
TGCTGTGCTTAATATTCCAGACCCTACGGATACTGTTGAAGCAGCATTGATTAGTTTAGATAATGGATT
ACGTGAAAATATTTACAATCTAGACTCTAATAAACTTGCTTACATGAAAGAACAATTCCCTAAACTAA
AAACTGATAGTTCTAGCGAATTTAAATTGGCTATGAATCAAATTATCAATGTTCCAGGAGATGATTCTC
AACCTAAAACAGGTGAAGTGGTTACGCTTATTAATAATAACTTTGATTCATCTAATCCTAGCAGTCTTT
ATAGTAAATACCTTATTGCTAAAGAAGCTTATATTAGTGAAGATAGTGATGAAAATCTTTCTGCAGTAT
TATCATACGTAGATCGTTTGTCTGAAGTATTGAAGTCTCAATTTATTGATTATTCTACTAAAATGAATG
CTTCTTATACATTAACTCTTCATAATTCACCAAATCCTCAACTTCCGGCACAATATGCGCTTGAACTTA
ACTCTTTGACTGATCTTCTTAATAAGAAAGATCAAATCAATATCTTTACAGTTGAGCATCAAGGTAAAC
TATTTGATATTCAAGAAACAATCACTAAATATCGTTTAGGTACTGTTAGTGGAAGTTATTTGGAAGGAT
TGTCATTAATCCTAAACAATGTTGAGAATGAAATTAAATATGTATATGAAAGCTTACTTCCAGTAGCAT
ACAATGGTTATCAAAATGTACCTGTAGAGATTTCTGATAAATTTGATTCATCAAAACCAGAAAGCATT
ACAAGTCGTTATAACCGTATCTTAGATCTTCAAAGTGATATGCAATCAGGAATTATTGACAATACAGC
AACTAATCGTGATGAAATCACTTCAGTAGCTAATGATATTACTATTGATCTATTGGATGTTATTAATGA
AGTTACATTCACTTCTAGCACTACAAATATTGAAAGTGCATGTACAACTTCAGTATCTCATATTCTAGA
TAATATCGTTTCTTTCCATTCTGCAGTTCTTACAATGATTACACCTCAAGGTACTTATGACTTTGATGCA
ATCATTTCTAATGCTAGAACTCAAATTGAAACTGAAATTTCTAAAGTTTCTACATCTAACTCTAAATTC
TTTAATACAAATCTAATTGACTTTTCTAATCCAATTAAACTTCTTTTGGGTTCTGATGGTTCATTTACTT
ATGACCCAGATAATTTATCTGAAAGACGTGCTTCTATTAAACAATGGTTAATTAAAGCATATAGTGGA
TCAGTTGATTCTGATCTATTGAATAAAGATAAATATCCAATTGATATCATTTTGGATGCAAAATATGAT
AGTGATGTAAAAGCCGCTATCGGTAGTTTGGCAGCCAATATTCGCCGAGATTTCCAATTCTTTGCGGAT
GATGCGGGTGGTTCATTTAGTTCTTCTCCAGTAGATTCTCTATCATGGAGACAGACTTCTGCATTCAAT
ATTAGTTCTCTTAACGTTTCAATATTCTCTCAAGATTTAACTTACTATGATGAATATACTGGTAAAGAT
ATTCGCTTCACCGCTCCTTATCAACTAGCAAGTAAGATTCCTTACAACGCAGTACAATACGGATTGCAA
TATCCTTTAGCTGGACCACGTAGAGGTCTAATTAGTGGTCATAAAGCTATTTCTTGGGTTCCTAATGAA
GCTGAAAAGAAAAACTATATATTGCTAAAATCAATTATATTGAACAAGATACTAGACGTACTAAATT
TGGTTCACAATCCACTACAGAAACTGGTTATGGTGCATTATCTAATATTAATAATGTATTTACTATTCT
TAAAATGGAACGTGATGCTAAAGAACTTGTATCTAGTTACCAATTTGAATTCAATGATGAAGAAACTA
AAGATTCTCTTTATACTGAATTGAATTCTTACCTATCTAAATATACAAGTGACCGTAGCTGTGAGTCTG
TTGTAGCTACTGTTAGTGCTTCTGACTATGATAAACAACAACGTATCATTAAAGTAAATATTTCTGTTA
AGTTTAACGGAATTATTGAACGTGTTCAATTAAGCTTCGATGTAGCTAATTAATACTACAATATTTCTA
ACTAGAGGTAAATAATTTATACTTATTTTATTTATCTCTAGTATTTATTATAAACAATTATTACTTATAA
GAGAGGATGACAAACATAATGCTAAAACCGGGTTCTAGTGCTAGAGTCTTTGATAATGACTTAGCTAA
AGGTAAAAGCTTTTTTTACCGGATCAATGAATACACAAGAACTTCAGTTTGATCCATTTGTTACAGGATA
TGCATTTATCCTTTGGACTAAAGTTCCTACTTGGGTTGAAAAATCATTCCCAGGATTCCGTAGCCAAAC
TCAAAAGAATTTTAAAGAATTCTCAGGAATTTCAGATATGGAACTACAAACTGCTGAATATACGCATA
CTTTTAATAACAATGCTTATCGTTTTAATAGTGGTATTACTAAAAACAATACTGAGTTTACTCTAAGAC
ATCAAGAATTCTCAGGTAATCCAATTACAAATATGTATAACTTATGGGTTTCTGGTATCAGTGATCCAC
AAACTGGTATTGCTACTTATCCTAAAGAATATAATATGGAGTATGCTGCTAAGAATCATACAGGGGAA
CTTCTATATATTGTTACTCGTCCTGACGTAAATAACGTAGAACGTAATAATATTGAAAAAGCATTCTTC
TATACAGCAGTTATGCCTACTCGTATTGCATTAAATCATTTTAACTATACTTTAGGTACTCATGATGGT
GCTGAAGTTGAAATGCCATTTGCAGGAAACTTGCATATTGGTCCATTAGTTGATGATTATGCTAAAGA
AATGTTACGTAAAACATACTCCTTTAACGCTCAAGGTATGTTTAACCCTCAAGATGGTTCAATTGCTGG
TGAAAATATTGCTGTATTTAATGATAATGCAGGAGTTACTGGTTCTGGTCTAGGAGATATCTAATTAAA
TTAAATACCTATCACTATATTAATTTATGGTGATAGGTATTTTATATTTTAATTTTTTAGAGAAATTATA
GATATCTAACAATAATATATAAATGTATTTGGTTGTGAATCTTTATTATTTAAAATAATTTTTTAAATAT
TAGAATAACAATATAATATAATTTTACTTCTACGTGTCGGTATGCAAGCTGGTTAAAGCAGACGGACT
GTAACTCCGTTTCGAAAGATTCGAAGGTTCAAATCCTTCCCGGCACATCTTTATGGAAAGTTGTCTGAG
TGGTTTAAGGTCTCGGTCTTGAAAACCGATGAACGTTTATAGCGTTCCGTGGGTTCGAATCCCACACTT
TCCTCTTTTATATTATGGACTTTTAAAGTTTAGTGGCTTTAAGAGTCAGCCAATTGTTTGTTTTTCTTTCT
TTATTCCATATTTACTTTAGGGATATATCTTAAGGGGTTTTTGATATATCCCACTCCTTTTGACGTGTAG
CTCAATGGTAGAGCATCTGACTGTTAATCAGACGGTTGCAAGTTCGAGTCTTGCCACGTCAGCTTATTT
TATTAATACCTTATAATTAATTAATACCTTATAATTAATTAATATAAGGTATTAATAATCCTAATACGG
TTCTTTAGCTCAGTTGGTTAGAGCAGACGGCTCATAACCGTCCGGTCGATGGTTCGAGTCCATCAAGA
ACCATTTCTCTAAAAAAGATTATATAGAGAACAGTAATATTAAATTCAGTAATCTTATTCTAAGTTAAT
ATGTATATATTAATAAGATGATAATTAAAGAAATTAATTATTGCTGAATAATATTAAATTTCTTAATAA
ATAGATCAATTAACTTAAAAAAATATCATAACGATCCTTTTTAAAACCACACCTTCAAAAACCATGTAT
ATGATTGATCTATTTAATGAAGTCAAAAGTATTCTTGTATCCTCCTAATATGAATATTTAACCATTTT
TTTTTTTTTTTTTTGCAAGTTTATATTGGTTCTTGCAAACTCTTTTTTTCACGTATTATCTCTTAAATGAGGT
AATACGTGTTTTTATTATAAAAATAAATATATATTATAATGATGATTAAAATAATATATAGATTGGATT
GATGAGACGATGGCATACAATATTGATAACGTAAGGGAAACTAAGGCAAAGGTATTAAGAACGGCAA
TTAATTCTCTGATTGCTAGATATTATGAATCTAATGATCCAAATACTGCACTAGAGTATTTGGAGACAG
CTGCTAAAATGGAGGAATTTGTTGAGAATGACAATTATAATTATTTATTAGATTATAATATGAAGAGT
ACCCATCTAGTTAGACGAGTGACTAGTATTGATACAAATCTCAATAAATCAGAAACAAATGTTGGAAA
ACAAAAGATTAGATGTATGTATGAAAGAGAAAAGTCTGCATATATTTATAATATCAAAAACAAGAAA
GTTGAAAGTGTTTATAGAAATAATAAGAAATATTTCTAAGATCAATAAACCAAACTTTAATGAAGATGA
TATTGCATTAATGCGTAAGATTCTTGATTCCGAAGAGGGTAGTGCTATACATAGAAATCTTATTGGTTC
TTATGTATACAATCATCGAATTGGTAAATGTGGAGTGATTGTCGGAATTACTAAAGCGCATATGTATTA
TACACTTAGTGATAAGCATAATAATACTAAAACTAATGATACCAAGTTTGTTGTGAGATATCTAGACA
ATACTATGAACAACAAACAAACATCTATTGGTATCTGGCGTGCTACTAAATGTTCATTTAGTAAAGAA
ATTTCGGACTTTGCAACATATTATACTAGTTCAGAAAGTACGGAAGAGTATGATAAAGAATATGTTAT
TAATTCAATGAATCGTCTATATGAAATTGAGAAGAATTATACTCATAAATTCTTTGATACAGGACTAA
```

```
AGATTTAAAGAATATTAACGCTAATCATCCAATAATAAGGATGATTAGCGTTATTTTTTTTTTTTTTAAT
TTTTTCTAGATACGTTTATTGCCTTCATAACTATCTTATAGGAATCATATGCTATCTTTTCAGGAATTAC
GTTTGAATATTTATTATGGACATCCACTAATTTCTTACGTAGTTCTTCATCGCTAGTATTAATAATTAGC
TTCTGAAACATTCCAAAGATACTCATATGTTCTCGTAATCCACTATTACTAGAATTATATATTACCTTAT
TAAATTCGATCTTTTTTACTTTATTAGATCGGCAATATTCATTATCAATATTTTCTAATAGTTTATTAAG
GTCACTAATAGTCTTTATACCTTTTATTTTACTAATATCTTTATGATATTCAGATATAGATGCGTATATA
TTATTTTTAGAAAATATACTTATCTCATCTTTATTAAAATGTTTGTTTAAACCATCTTGATTTATAATAT
TAATTCCATTCCGAATATTTTCTTTATTTCGACTAATAATTTCAGTAATAGTACTTTGTCTATCTTTATGT
TTCTCAATAAGATTTTTTACTTTACGTAATATTGATTCATTAATTTGTGATTCTAATAAATCTTTAATAT
AATTATTATCCATATCTATATATCACCTTTGTCTTTACGATTATATTTATAGAATTCTATCAATTCAAGA
GAAAGATCACCAAAAATAGCTTGCATTGAAATTCCACCATTGATATTTACATTTTCCATATCCTTAAAG
TTTATTAGTGGGTTAAGGTAATCATAATTATTATTATTATCTGCAATAAATACTCGAATTCTATTATTTT
TTTTAATAACCTTAATTAATTTACTATCAAAGTTATAATCATAGGTATCTATAGTTTTAATATATAACGT
AGGATCATCTTTAAATATATTACGTTTAGTTCCATAGAATTGATCTATTTCTTTAAATCCGTTCGAAGC
AATATTTCCTACAGCTACAGAAACGCTATTATATGGTGGTAGATTACTATTTGTACTATCACTTTTAAT
AAAGAATCCATAACCAGAATTATCATTCTTATTGTAGTCGAGAGCAAATAATATCGCTCCGCCCTTAG
ATGGTGAAGTATGTTTTAGTTTAAATGTGATAATATATTCGTCTGGTAAAGTTAAATTTGTACTATACA
TATTTTTCCAAATATTATTCTTTGTTTCGTTATCCCTTGAACTTTTAATAATCACTGGATTAGATTTAATT
TTAACATTATTTTGAATTGTTTCTATAATTCTACCATTATTATATGATGGATTATTTGTGATAATTTCAC
TACCGTTTATTTCTTGTATGGTTGGATGAAAATATATTCCTTCAAAAGAATCTTTAGGGAAAATTTTAA
CACCTTTATCATCTATTGTCTTATAATTATATAATAGGTTTATATTATACCATCCAGAGGAAGGAACTG
TGAAACTAGTATATGAATCATTATTTGAATAGCTCTTAATATTAATAGATTTTGTTTTGATATATGCAG
TAGTATCCTTTTTTGCATTAATTATAACATTAACCGTAATTTTTTCAATACTTATTGATTTACTTTTAATA
ATACCCAACTTAAGGTAACTATTCTTTTTATTAGTATTAAAAATATCTGATCTTGGATGTAATGTAGTT
ACGCTTTCAGTAGTACTGTCTGTATAAGTAATAATCATTTCATAACCCATACTATCAATATCATCATTA
TTAAAACTACTTGAGTACTCTAAATTTGTAAAGAATAATCTATTATCTTTAATACGATTAATATCTCGA
TAGTTATTTACTGAGTCAGCAGTAAAATTTACCGATATAATATTATTCTTTCCTTTTTTTATTGTACTAT
CAAGAACATGCACATACCTACCTTGATCTTCATCATAAGAAACAAATGTTCCATTATACGAATTTACA
AACTTATCAAGATTATCATCTCTAAAATCGCTTAATAATTCCATTTCATTAGGATTAAAATCTTTATTA
ATATTTACAATATTTTTTGCAGTATCAAGGTTATTTATCATTAATCGTACATTTCCACTAAAGTTGTTGG
TCAATCCATATTTTTTACTTTTATCTAAGTATATTTTACCTGTAAATGATTTAGTATAACCTTTTTTAAA
ATAGTATGATGGTATACTAGTTAGACCTTTATCATCTAACGTAAAAGGATCTACATATCGACCATCATT
ATCTGTAACTTTACCCATTTCAACATCTATTGATGCTAGATTATAGTTTGCATTTAATATTTCATCTTTA
TTATCTGAAAAATCAGGAACTGTATGCCATGGAATTGTTTCATTGATATCAGTACCTAATAAATCTTTT
GATTTTTCATTTAATGGATGTAACATATGTTTTTTTTACATATCTTGGACTTTGTACGGTTGATTTCATAT
TTTTTTCCTGATTAATAATTTTATTGATTGTATTTAGAATAGTATCAGGGAATACTTTAATTGTTTTCTT
ATTAAATTTTTCAACAGTATCCATATCATTAACAAACATTAATAAGTACCATAAGTCAGTTGTTTCATA
TAATTCCTCAGATACATATTCCGGTCTATAAAATTGGTTTTCCGATATATCATAATCAATTAAGTTTGA
TTTAAAAATATTTTCATACTTTTTTAACAATGGAAAACCTAATACTATCTTTCCTTCTAATAAATAAAA
GTTAGATATATTACTAAGCAATATTTTATTAACGTTTATTGAATTTATTCCACCAACTAAGTCAACAAA
TCTTGAACTATCTAAACTATTTCTAGAATTATCTACTACTACCAAAATATATTCACCACTTTTCAAATTT
CATTATATAATTATATGTTACTATATTCTTTTTTATCAAAAAAAAAAAAAAAATGCCATAGTATATTATG
TAATATACTATGGCATAATAAATGTTACATCATTGGATCATTATTATCTTCAGAACTATTTTTAATATTA
GATATATTTAACTTATCTTTAGTTAAATCTTGATTTGTTTCGTTAAATAATGTATCAAACTTAGTCCAAT
CAAGAGTAGACATATATATTTCTGAAGCTAATTTTTTCCTAAACAATCTTTTCTTATTATCGGTATCCTC
ATTTTGTTCTGACTCTGTGAAATAATTACCTACAATAAAATCTATTGTCTGTGAAATATTATTAATTTGT
TCATTAACATTAGCAATATTCATAAATACTGGTGTAGGGAAATTAAATAGTGATTTCTTCAATTTTTACT
TCATCTTGGTTTTCGTTATAATCTTTTTCATCATTTGTTTTGTTCTTATCTTTACGATCTCGTTCACCATA
CTCATAACGATATAGCTCTTGAATTATCTTAGTAAAGAATTTACTAAACGTTTCTTGATATCCAATAAC
TCTTCGAACAAAATTACTATTCTGCATTGATAGATTTCTTGCAAAATCAACTTCATTAGTAGCATCAAT
ATAATTAATTGGAACACCTGTTCCATTAACTGCCGATTTCTGTAAGAATTCTAAGAAATCATCATTAAT
ATCAGCTTGTATACCTGGAATAACATCAATATCGAAAGGCTTATCTCCATTAACTGTTGGAATAAATGC
TTCTTCTGTAGCACCTAAAGTTTTAAGCATAGTAGATACACTATTTCCGGGACCAATACTATCCATTGA
AAATTCAGTAGTCTTTAAATCTCGGATAAGTTCTTCAATAGTTCCCTCAATATCAGAATCCATATCAGA
CTCTACGTAATATACTCTTCTATCTCTACCTTGATTAATTTTACCATTAAATTTGTAATTAATGTAGAA
AGATACATTTTAGCAAAAAATAGACTATTATTTAATCTAGATACACCATACTCGCTAGTGCTATCTAAA
GGTAGATGATACACCTGATTTGGTTCTAAGAATGTTATAGATATATCTTTATTGATAATATAGTCTTCT
CTGACCAATCTATATATTACATCTTTAAAATCTTGGTTATCTTCTAAAAAGTCTTTAGATATTTTATCAC
TAATTCCTTTTACAAATATATCAGTAATTATCTTTGTATTTTTCATTACTTAGTCACTCCTGAACCACTCTG
ATTTGATCTAGAGTTATAATACATTGTAATATCTCCATTAACACTAGAAGATCCTTGTGGGGCATTACC
GTTAAGAGTTCCTGCAATAGTACCTAATATTGAACTACCTTTAAATGAATTATTGCTACCATTCTTTTC
AATATACACGTATCCTAAACATACTCCATCAATAGATATTTTAATGATATCTTCCGGACTAAATATTTT
TAAGTAAGATCCGGTAATATTTAGATTTTGAATGTCTTTAGATTTTTTACTTGCTTTTCGAGATTCAGAT
ACAAGATTTAGAGGGTCTTTATAATATTTTACATTTTTAGATATAGACTCATATACCTCATTAGCAGTA
CTTTCTACTAAAATCTTTTCAATATCTTTAGGATTACTTTTAGAAAATCTTTTTCCATTTTTAATATTAG
ATGATTTAAATTCAATATTTTCATCATTCATAACACTTTCAATAAGATTTTCAATATTTCTATGATCCAC
GTTAAAAGATTCATTTAGATCATCTTCTTCAGAATCAATAAAGAGATTATTGGTATCTAATTCATTAAA
TTCATCTTCAGAAAGAATACTTTTAAATTGGCTTTCTAGATCGGTAACCATGATAAACAGATCACCCTC
AATTAATGTATTCCGAATAGAATTTCGAATAACTGTATTTAGATTATATTTTATCAATCAACTTAGACAT
ATTACCATTGAATTCTTTTTTATCCGTCTCCCCTAAGGTAGTATTTTCATTATTATAATAGTATGATATT
GATTGTTTGTTACATCGTCTGGAGCATAATAGAATCTACATACGTATCAATAGCTGTACCCAATTCC
GGAAAATACTGAGATATTAGTCTAAAATCATCATATCTTTGCCATCTTAGTTTTTCTTCAGCAAACTCT
CCTGATGAGAAACTACTTTCAACTTTTTCCTTAAAATAATTGTTGTATATCAGAACTTTTTTTATTTT
TCGTATTTTTCATTCCAGTATTCTTAACTTTATCTCTCTGTATGTCGGAGATAAATATCAATTATACTTCTT
CCTGAACTGTTATTATTACCGTTTCTTCGTTTAATCTTATTTAACATATCATGAAGATTACTTAATTTAT
CTTTTGGTATATCTTTCTGGTTCATAATACCGTATAGATTTTTATTAACGTTTGCATTATCTGCCATTAA
ACTTATCCACCTTTCTAAATTGATGAAAAAAAAAAATATCATAGGAAAAAATTTCCCTATGATATTCA
CTAATATTTATTTCATATCTACGAATATATATGATTGTTCCATAATATAAGTATCATTACAAACTTCAAT
TACAAGCATTTTTAATGATGAATCCTTGTTATGATTAAAGCATAAATATATTTATAGATGGATGTTTACT
```

```
ATATACTACTGGAATATAATCACTAAATTTTTCTTCTTTATATTTTTCATATGCTTCATTAATATCTTTTG
GATAGTTCAATGATCCGAGATTATCCTTAATATTTGTAAAATAAGGTATTTCAGTAAATTGGTCTATAT
CGACAATTAATGGTTCAGGATTCTTTTTACGAATATACTTAAAGCCTTTGATAAATTTAGTTGATACGG
TAACACTAATATAATCATCTAATTCAGGTTTAATCATATCATCATGGATAATAATATTATTATTATCAT
TTTTATCAATAACTATTGAGAATGTATATTTATTGTCAAATTCAAGTAATTTTATTACATCATCATCACT
AAGCGTTATCTTTGGAATATTTAATGAATTTTCACTAAAAGAATCTAATACAGGAACAATATGATCATT
ATACGCATTAATATCTTTTTCTTCTAAATACCATTTAATAAAAAAGTCTGATTGTCTAATAAACTTTATA
TAGTTATCGTTATAGTCTATTTCTATAGAGACAATTTTATCTGATTTATTTTTACGCATTTCAAAAAATT
CTATCATATGAATAGAAAATGTATTCTTTTGCATAAAATCATTTACTGTTTTCATTATACCTTTTTTATC
TAGTTTTCTTTCAATAAAAGTAGCATTGATATACTTTGGTAGTTGTTTTAGTAGTGCGTCATCGTTTAGT
GAGGGAAATGCAAAACCATTATTAAAAATCAACCTATCCCCAACATTAAGTACATTCCTAAATTGATC
TACCATTTCTTCAATAGAAACTACAATTTTTTGAGCTTCATTAGGATCATCTACAATAACTTTATTATTT
TCTTCAATATACAACTATAATTCACCTACTTCTTGCATACTTTCAGAATCTATTGATTCTCGAATCATAC
CCAAAGCATCTTTAATATTTGGTAGATTATAATATTTAATGCAAAATTGTAAAGGGTTATTACTATTAT
AATCATCAATAAATGATTCTGTAATATTCTTATTACCTTGTTTAAAAGTAATATTTCCGATAAGACTTTC
AGGACTAATATTTAACGCCATAATAATATGAGGGTATAGTGCAGTTAAGTCAATATCGGTTACATTAT
CGAAAATCATATTTGATTTTTTACCCATAATATCAATACCGATTGGATGAACTTTTGATGAGTCTGCTA
CAAACGCACCTTTAATTTTTCCATCAATCTTAGGATATAATGAACTATGATTATTCTAATTACAAACC
CACCATTATTATAAAAGATTTCTGTAAGGTTTCTTAAGCATATTGTTTTCTTAAGTGCTTTTGTTATTCG
AGTATGTGTTAACGAACTAATTTGATAAATTAGATCTAAGAATTTAGTTGCTTTTTCGATCATCATTAA
GAGAACTGTATCCTGAATGTTATATAGAATGAATTTATAGTAGTTTTTAATATATACGTTAGTGATGTC
TCCGTCACCCTCTTCAAACTCATCCTTTTGCATCCCTACTTCTTTTTCACCTATGTCGTTCAATTTGTAAG
AGTCTAAGACTCCCATAGATAGCGATAGGTAAGTATTTGATATTATCTCCAACTTTTCCCCCGCTTCAC
ACCGTACGTGAGACTTTCACCTCATCGGCGTTCCATCACTCAGTTTATATTGTCACCGATATATTAAT
GACAATAACTAGTCGTTAACTAAGTTTCTTAATTTAGTTAGTTGTGTTTTATTTACCCCGGTAGGAAAA
TCAGTACTATAGTGAATTAGATTATGTGAATAAACAGACAGTAATACAAGATTATCAAAACTATTTGA
CCCACCTTTTGATCTCGGCTTTTTATGATGTATAACTAAGTTATCTATTCCTATTTTATATAATGGTATA
TTAGTGATAGGATCCTTCTTCTGTTTTTTAACCAGACCGGGAAGATACATTTTATACCTTATATTGGGA
AAATTAGAACTATTTGTAAGCATATTAATAAATTTTAATATTAACTCATCGTTGTTCTTAGTTTTCATAA
TAGGCGTCCAATACTGTTTATTTATGAGATAATCTTTAGTATTTTTACTGGATTGTTTCCGCCACATCCA
TGTATTAAATATAATGTCTTTATACTTATAAATTTCAGTATCAGGTTTCTTATACATTTGACTTTGTCGA
CTCCAACTATATAAAATTCCGTTAACTAAGTTAATATAAGCTTGCATATTAGTAACTAAATTAAAATTA
TATATAGTTCCCAATATAATAGACATTACCTTTTGATAATGACCTTTTCTCAGTTCAGACCTTAATAATT
TTTTCTGATTATACCAAAACTTACTAAGATTTTTAAATGAGATCATCACATGTCCACTTGCAAATCGCA
TATACTTAAAACCTACAAAGTTAATTACAAAGTCCTGACCTTCTTTGATAATGATTTCACTAGTTTTATT
CCAGTTTAAAGAAACTTGATGTTTTGTACACCAAGAATCTAAAACAGGTTTAAATCTTTCTACATCCCA
AGGATTCGGACTAATTATTATAAAATCATCAGCATAACGAATCATTCTTATCTGCATTCGATTACCAAC
GGTTTTCAAATATTGATCTTTACCTTTTCGCCTATAATATGACATATTTAAAACTTATTATAAGGATGT
GTTTTGTGAAATTCAGATCCATTAGAAATAGCCTCATTATACATGTTTAAGTCATTGACTAAGATTTCT
AGATCATGTAATAAAACGTTAGCTAGTATAGGACCAAGTATAGAACCTTGAGCTAAACCAATCCCTTG
ATACTTTGTGTCTTTAGTATCTATAGACATAAGAAACTTTATAGATCTTAGTAGTTGCGTATCTCTAATT
TTGTGATTATACCTTAATTTATCAAGTACTATATCTAAATTAATAGTATCAAAATACTTAGATAAATCA
CAATCTAGTACTGATCCATTCTTTATTTCTTTAGTGTTATTTACTAAAGCTGACATGGCATGTTGAGTTG
AGAGATTACGTCTAAAACCATAAGAATCAGGATAAAATTGATATTCCAAAATAGGTTCTAAAATATTA
AGAATACATTGTTGTGCTATTCGATCTAATATATTAGTTATTCCAAGAGTTCTAAACGAACCATCCTCT
TTTGGAATGTCAACAAGTCTTGAATATGGTTTTATATCACCTTTTATTCGTTTCAATAATAGGCTTTTAA
TATCTTTGTAATCTTGTTTTAGTAAATCATCTAAAGTTTGACCATCTGGTCCCGGAGTATTTCTTCCATC
ATTAGACATTATCCGTTTAATAGCATATTGAATATTACTATCTTTAATAATATATCTAGATAAATGCGT
AAAAGATGGTTTACCATTTAAAACATCATTATACAATTTTATTTGGATTTTATTGAAATCAAAATATAT
AGAATGTAAACTTTTTGTGTCTATATTAACACACCTTCTTACAAAATCAAGCTCTGAATATAAATCAGG
CAATTATATATCATTGTTTTGAGTGACTTTGGGCTTTCCCATTAATGATACATTACATATCATATTATCG
GTTTCTACCCAAACTTTCAGTCTGTATTCATTTAACTTCACCGTGACTAGCAGCTAAACCGTTAAATTA
ATAATATAAAATTATCTACAGACCTTCCCACGTTCCCTCACATCATAGAATATAGTATACTTAGGTTCTT
CCTCTAGGCTCTGTGTGATTATAGAAATAATCTGGTTCCCATTATATACCATCCATCTACGCAACAAAC
AATACGTATTTGGAACACAAGTTTACTAGCATTTCTACTAGCACATACCTGTACATTCAGAAGTTCGTC
AGTCTTAAAAGACATACTAACCATATATACCTCCACCCGACCCATTTGAGAGGATTGTTTACCCTTTCG
TCAACTTAATGTTACGCTCTAAGTTAGCCGTCTTCACCCAGCTTCACACATAAATATCACTACTTATGC
ATGTGGGAGTATTAGTGTACATCTGATATAACTTTAGGGAGTTATATAGTGTATTTGATGTAGAGTTAT
TCAATATTATTATAATACTGAACTTTAGCACGCCTATGTGTATCATAGACTTTCTCTAAAAACATGTC
GCACGCTTATTGATATTGGCATATAACGCCATTTGATCTAAATATGTTGTATATCCAGCTACTTCATAT
ATGGAAGACTTATCTGCAGGATTATTGTGTTTTTCATCCATTTTATGATATACATATTTATATTTAAAAT
CATCAGGACACATTAATTCTTCAGGAATCGCATTATTCTTTAGAATTCGATTATATATTGTGATAAAGT
CAAAATCAGCATTCCACGCACTAGCAAAGTCAGGTCGATGAACTTCATTGATATAATGAAAGAAATCA
CTAATTAAATCAATTTCTTTATCATATTCATAAATATTAAACGTTAAGTCTAAATTATATTCTTTATATT
TGTTTTTTAGTTCATCCAATAATTTAGTTTTATCCAACATTGCGTCTTTATAACCATCATGATCATATTT
TAATGCAAAAGTTTCAACAGTAAGATTCCATTCATTTACAAGTGTAATAATATTAATCGGAGCTTCTGC
TTTCTTTTGATCTGGAAATCCAATAATATTTTGAGTATCTACTTCGATATCGTAAAAAGATTTCTTTAGT
CCAAAAAGATTATTATCAGGAGCATGTTTTTCTAAATAACGATGAATATAATTATCTTCAATATTCTTA
TCAGAACCATGAATTCGATAATCTAAATGCATTTTTTTAAGATTTCTTCTATCACGAAAATCTTCAGAC
TTCATAATATTATCATAGAATATTTTTACGCTAGGATCTTTTAACTCTGTAGCAATACTTTTAAATATAT
CTCTGTTATAACATCTTACTTGCCTTACTTTTTCTTTATCAATATAGTTTCTTACAACATTATCTTGAAAT
TCCGGTTTAGTAATATAATAATCCATCATTGGTTTTTCAATAATATGATGTTTTTTTTGTACCGTCCTCTT
CTTTAGTGACCATAATAAGTTTATCAAAATTATCTACTGCACCAGAATTTCTTGCATCTTTCTGGTTTAA
ATATGTTGTCTTAATTAGTTGACCCAAAATATACACCACCATCTAAATTTATATAATTCCTTGTTATTTT
TATTTTATAAAATTATATTCTAGTAAGATTAATGATATCAATAACTTTGTTATATCCATCGAATTTAAAT
AAATCTTTTCTACTTATAATAATATCTTTATCTAGATTTTTAGCATATTTAAGAAAGAATCTCATATCCA
TATCATGATAAGTACTAATCATTTCCCATTTTTTAGAATAATTTTTAGGATTATTCTTCATATGCCTATC
AATAAATTTAGTGGATAATTTTTTTCTTTTAAACATGTTTAAATTAAAATTATTACTTTTTCTACCGTTT
ATTATTGATAACAGTTTTTCTTCACTAATATTATTATTTTTCCGCCATTACTTCTTTTTTGTCTAACGGTAC
```

```
ATTTTTGAAATCTAATTTATCTTTATTATAAGCCAATAATTTACTATTTTTACTAATAAGATCAATATAT
TCATCATCCATGAAAACTGATGCGTTTGTTATAAAGTTTACAGTATCGTTAAATACATATATTTTTTCTT
TATTAGATGTATCACTACTACTATTATATTTACATATAGTATTTATTAGATACTTAATAGATTTAATACT
ATTAAGAGTATCATATTCCGCAATACGGAACATATATTTAAATACATAGGAAATATAACCAATACTAA
GATAATCAATATTTAACATTAACGTATCTATGAAACTGCATAAGACTTTATTAATATTCATATTATTTTT
CATATGACTTGACTTGATCATTAGATTAAGATGAATAATAGGTTCCACATCTTCGCTTTTATATGATTT
ATAATATTCAAAAATTTGCGGTATAATATAATCGCATAAAAATTCTTCATCTATATTCGAATTAGATAA
AATAAAATTTATATTATCGTATGAATATTCCATATAGTCACGAAATAATATTCTAATTATAGAACTATT
AAATTCCATAACTGACCGCACTGAAAGATAAGAATTTTTACTATTTACTATCTTATCAATATTCTTTAT
AAATATATGATTAGGTATTTTCATTTCATAATAATCTATATTATCAAAATTTTTTATAATAAAGTCAATC
ATCTTATCAGATATTCGGTGTCCGTAAAATGATACTAAATCTTTGATAAATTCTTCGCTGTATTCATAC
ATATATTTATCTAATTCTTCGTTCGGTATACTTATATAATTATCTGTAAATCTTAATAGTTTATCACCCA
AATTCCCATTACTAGGATCAATTTCTATTGTAAGTTTCTTCAATATACTTACCAACCTTTCTATAATTAT
ACTAGCTTTAGATCAATTACGCTTTTTTCAAATTCATTTAAATGTTTAGACCAATTGAATGATACTTCTT
TATACCTATTAATTTCATCAATAGTCATTAAGTTTATTGTATTAAAATCCAGCGATATCAATGAAAATA
CTTTATTCTTTAATGAACCGATAACATTTGTATTTATAAGTATATTATAAATTTCATAATATTTTTTAGA
TATATCTTTATTCATTTGTAATGAATTTTCACTAATAAAATTTCCACTATCTGATATCACATAATCAATA
AATACTGTATCATTTATTATATTAAAATATACTAACCGGATCAGATATGTCACGCATTATATTAGTCAAT
ATAGATTCAATATGTGAATTATCATTATTACCTTTATTATACTGATATAATAAAGGTAATATTTCTAAA
ACAAATATAGTTCTCTTAGACTTCCATAATGGAGGCTTATTTAAGTATAATGATACTTGGAATTTATCA
TCGATATCATAATAATTCTTTTTTAGTAAATCTATAAATGATATAATGAATTCATCATTATCAATAATCT
TTAGTGATTTAATTATATTATCATATAAGTTTAATTTTTTAATTATCTTCATGCTTAATTCAATATTTTTA
ATTCTAAGTATGTTCATTATAATATTGTCTGAATTTGATTTAAATATACATAGACTTAGAATTTTTATAT
AATGGAATATATACATATAATATCACGCTTCCTAATCATTCTTGCTTTTCATTATCGATTACTAAACTAT
GATTTTCTAAAGAACTTAGCCATGGATCATAGATATTATTGAATCTTTCTTTATCGCTAATATCTTTAGT
AAATATATTTAAGAATGATTTTTGATATTTCTTATCATTATCAAACCATGAAGATATAAACTCTTTTCC
ACTTTCTTTACTTAATTCAGTTAATGTAGTATATACTTGGATTGCAAAGAAAGAACTTAATCCTACTGC
ATCAACATCTAAATCATTATGTGAATCGTTATCAATAATAATATAGCGATTATCATCAACAGGAGTAT
ACTTATTCAGTGCAATCTTTTGAAACTCAATTTTAATATTACCATTAAAACTATATTCACCATCAATAT
AATTGTTAATAATATAAAAACTATTTGTAATAAGTTCCTCAATACATTTATCAGCTTCAGCAATAATTA
ATTCATTACTATATTTTTTGTAAATCTTCATAGTTTTGAATTCCTAAGGATTTAAGTCTTACAGCAATAAA
TCCTTCAGTAATTCCAGATAAAGAGATTAAAAATTTTGCAGGATTCAATGAATATACTAATTTATTAGT
ATTATTCTCAGTAATAATTTCAATACTATATGGAATTTCCATATATCGTTCAGAATTTTCAGTATATGTG
TTACTGTCTTCATCAGTAACCACCCATTTTTTTCTAGTTCTTCTATTAATTCTAGAAATTTTATTTTTCAT
TTCACCTACATTATTGCTGTTATTTAAGCTGATATTTACTAAGATAGTTTTTTCATTATCGTGAGAATTA
ATAATTCTAAAGTCATAATTATTTTTTTCGAAGATCACTTGTAACTTTCGGTAATTCATTATTTTTAACAT
CTAATTTTACGCTAAACATTTTTATCATCCATTCTATTTTTATTTTAACAATAATTCGACTACTAATATT
AATATTAGTAGTCGATATAATTTATTTTTCTGCATTAAAAATAAGTTTTATTTTCCATAAATACAGTA
TCTTCAATATCAATGCTTGGATTCTTCGTTAAAATTAAATCCACGTCAGAAGTATGGAATTCATCATTA
TGGCTAATCACAAATATTTGTTCCATATTTAAATAATCTGTTTGTAGATCCAATACTTCCATAAACTTA
CGTCTATTATTTGTATCTAATGTAGCATCAACTTCGTCTAAATATATAATGTTATACCCTGAAGATACG
GTTTCAATCATTGACAATGATAATGATAAACTAGTGATTGCAGTTTCACCTTGAGAACTTAACTTAATA
TCTGAAAGATCAGTTCCGTTATCTTTAAAGACCCTTATAAAGAAATCTTTTTCAGTGATATCAAAACGT
ATACTAAATGATTCACCGTAAGCAACTTTTAATAAGTTATTTGTATCAGACGCAATCTTTTTAAGATAA
TTATCAATAAATATTAATGGAATACCTTTCTTAGGATCTAATGATTCTTTAATAGTTTTAAAGTCATCAT
ATACTTTTTCAATACTAGATAGTTTATCGGTAATATTTGTTGCAATATTAAGTCTTTTTTCATTATCTTCT
AATTTATTCTTAACTTCAGATAATGCGTTATTATTAATATTGATAGACGTTTCAGTATTATTTAATAGAT
CATTATTATTTTCTAATGTTTTTAGTCTGGATGTAATATCATTATAAACTGAATCGTATACTTCTTTTTT
ATTAAGAATACTTTCATAGTTTGATCTCAGATCTTTAAGAATATTCAGTATATCCAATCGTTTAGATAC
TGTTTTAATATTCTTATCATATTGATCTATTGATTCATTATTATCTTTAATACTTGAAGATAATTTTTCTT
CTTCCAAAGTACTAGATTTCAATAGTTCTTCATACTCATTATATGATTCACGCATGATATTGTAATTTTC
AATAGACCCTTTAATATTATCAATAAGATTGGATACTTTGTCTCGGTTGTTGATATTATTAATTAGATC
AATATATAAATTAGGTAGTTTTACAAGACTATTTTCAATATGATCACGGTTTGGTAAAAATAAGTCATC
CTCATTTAAATTAATAATGCTTGCAATATTACGAATATTATTAAATTTAGGTAGAACTTCTTGACGATA
TTTATCAAAATATTTAATAATATTTGACAAATTACTGATATTATTTATTAGTTTCTATTCGATCTTTTTCT
AAATTACTTAAGGTATTTTCTAATTCATCCAACTTAGGATATTCATTCTCTTTATATTCTAAAGCAATTT
GAATAAAAGGACAACTATCAATATTACATGCTTCAGGTCTTCTATCTAGTGTTGTTAGTAAATTAGATC
TACTATTAATATCACTAATATTTTTATTGACTTCCAGAATTTGAGATTCGATATCATTCATTTTGGAATC
ATTAGATTTAAACATACTTAGATAATATTCGTAGTTGTCAAAAGTAATTATTATCGTCTTCAAAGTAAGT
ACTTTCATCCATACTCATAAGATTTCTTAGAGAGTCCAGAAGATTACCAGTTTGATGAATACTATTATA
CATATTATTGTCATTCATAATAGATTCAACATTTTCCATACTAGTTTCATTCAATAAAGAATTTATATTC
TTATTAACTTCAGTCAGATATTCTTCATTTTTTTCTAATTCGTCATAATACTTTTCAGGATTAAATTCTTT
AAACGAAGATATTTTATTACGGTAAAGACTAATATTTTCCCTAATTTTCTTTAATCGGTCTTCAGAATC
AGTATTTTTTTCCTTTAATGAATTTCTCGATGTTTCTTCTTTGATTAATTTTTCTGTAAATTGTTGATGTT
TATTATAAATATCATCACTTGTATATTTTTCTAATGCTGGAAATTGAGAATATATATTCTGTAATCCTTG
GTAAGATTCATCAAGACTCGTATTAATTGTATTAATAGTATTATTAAATTGGTCAATCGATTTATTAAT
ATCTATTTCATCAATAGGTAGATTTAGTTCATTTAATTTTTCTTTAATAAAAGAACTATCCATATCAATA
TTATATTTAGTAATTGTTCTTTGTTCGTTTAAACGTTCTTTTTCAGATTCTAATGATTTAATATTATTGGT
TAATCTTCTTTTATTTTCTTTTATAGTATTAATATCATCATACTTAGAAAGATCAGAATTTAATGTCTTA
AGATTTTTATCTAAAAAAGATAATTTATCTTTAATAACATTAAATCTTTCTAAATAATCATCCATAGAA
GGTATAAACTTATATAAATAATCCTTACGTTCGGCAGTTTTATAATCAATAAAGTTATTCATATTATTA
CCTAATCTAGCAACTGTCATATAATCTTTAGTAATTCCAAGCTCAGTACTTACAATTTCTTCAAAACCA
CGAATTCCACCATTTTCATTTAATTCCGTACCATTCTTAGAAATAAATGACTTATTATGAGAAGAATTA
TCACCATAATAATGTTTAATAATATACTTATCATTATAATTAATATAATGAATTTCTTTATATCCTTTAG
TATCTGGAATAATAATGTTATTTCTAGAGTCATTTGTACCACGGTAAGGATTCAATGCGGAAAGAATA
ACTGTTTTACCAGAACCATTAGAACCAATTAACATAATTATTTTATTTTTAGAATGGGAGAAATCAATT
TCAATTGACTCTTTTCCCATTCCAGCATATATTCCGATAAAGTTTACTAATTTTAAATATGTTATTTTCA
AGATATCACATCTTTCTAATTATTTAATCTTTTCTAGACAAACTAAAACTAAATTTAATCTTATTACTAG
CGGCATTATAAATAAAGTTTGTAATTACATCGTTAGGAGATTCATTATTCTTTTTACATGACTTAACAA
```

```
AATCTTCATAAATATCATATCTACAATTTAGTAATAGCGTTTCAGGAATGAAATCAATGATTTCCATAT
TCTGAATATTCATTTCTTCAGTAATACCATTATTATCAATATAATTTAGTATAAATAATTCAATAAGATT
ATAATCAGAGTTATTTAAGATTCCTGAATAAATTAGATCTTTTTCACGATTAGTATAATTATCAATATA
CTTCTTAGGAATAATAACCCTAATATTTTTTCTAGGTTTATCAAAAATAACTAAATTGATCTTTGTATTA
TCATGACCAAAAAGATTATTAGATTTTTCATAATCTACAACTTCTGTAAATTGCTGATATGACTTACAA
TGATAACAGTTAATTGTTTTGATATGATCAACCGCTTTATTGATCGATACTTTTCTTTGAATCATTACTT
TATTACCACAATTGTTACATATTAGAGTACATGGTTTTGTATTATATAATGAATTTGCGTTATTTTTTGT
CATGAGAAATCACCCATTCATCCATAACACTAATATAATCTTTATTCTTAATATCTAGAAATTCATTAT
ATAATTTATCAAAATCTGGATAAAATTCTTCTTTTTTACTTTTAACACGATTAATAACATCATTATAATT
TGGTGAAAATAATAGATCTCGAATATCCCTAAGACTATGATACGGCAAATTTTCTTTCTTTACGCTATT
ATACATTACTTGTGCCATGTTCATACTTCTTTCATGATTATAATCAATTTTTCGAATAATTCCAAATTTT
CTAGTCTTCAAATCAAAGCAAACCATATTTCGAATATGATTATTGTACTTAGTACTATATAACATATCT
TCTTTAACTTGTTCTGAAATAAAATCATTAGTTGTTAGTTTAATAGGTGCTTCTAAATCTTTTCTATCCA
CTACAATTTTATTTTTTTCAGATTGATAATAATTATATACGCCATAAGAATCATTTTTACCATAATTCGA
GATAGTTCTAATATTAAAAACCGCTCTTAATAATAAATTATCAGTACTGCTAAATTCATATGATAACTG
TAAATTGAAATCTCTTGCATTTTTTTCCACATCTGAAGCAAACTTTAAAAATTTTAGAGCTTCACCACT
AATATATGATGTAGTAGTTTTATCTCTAGCTTCATTATATCTATTTAAGTTTGCATTAATTGTGGATCTA
ATTATCTTTGATAATGTACCATTTACATCATTTACATTAAAATTTTTCATGAAAATCTCTCCATTCTATT
TTTTATAAATATTCATAATTGAGAATAATTCTTTTATTTCTTAAATCACTAATACGATCAATATTGATTC
CTAATCGGTTACAGTGTTCTAAGCTTGAAAGAATTCTAATATCTTTATTGATTGATTCGATATCTTTTAT
TGTAGTATTTTCTTTTCTGGAAGCATATAATAAAATTGATTCAGGGTCATTTGAAAAGATATTTTGATT
GATCCATCTATTATATCGATTATTAATAATATTGGACGTTGTATTCACAGTAGTAATAGATTCTTTGGA
ATCAATATTTCTTACAATACCTACTCTTTTTTGCGGAGAATTATAAGTAAAAACAATATCGTTACTAAT
ACTTTCTGGAGAAACTATTCTGCTATTATTAACAGTAAATTTACTATTAGTTCTACGTGTTAATAATTTA
TAACTATTCCGTTTATTTACGTTAGAATCTAAATCATCACTAATCTGAAATGATACATATGAAATTAAT
CCACCAATATTATTAAACGCAGGAATTAATAAGAGATCACTATATTCAGATGAAATCTTTCTTACGTTA
TTATCAATACGTCTTTTAATTGTTTCTAATGCTGAAATCGTTTCCCCTTTAGCGTATAATTTATAATACT
GCTTAATAAGAATGTTAATAAATTTGATTGTTTCTTTAATTTCAGTTGTAGGAATTAATAAATTATGAT
AATTATTATTCCTATAAGTTTTTCTTTCTTTAATACTAGTTGACATTAAAAATCATCCTTTCAAAATTAT
TATTATAATGACTATGTAATATTGACATAAATTAATTCTCATGTCATTACATAGTCATTATAATAATAT
ATAAATATAGTTAAAGTTGAAAGGTAATTTTTTATTCTTCTATTTCTACATAACTGAATTCTGAATTATC
AGAGAATATTACGCCTACTTCATTATCGTCTTCATCATAAAGAGATTCAATTATTCGGTTATTAGCTAA
ATATGAATCAATTACTTCATTATTCATTTCATTAGAAGAGTATACTGTTTGATCTTCATCTAAGAATATT
GGTTCTGAAGTATTAATATCTACGCACATTACATATCCAATACTTTCTAAAATAGTCCGCAAAGTTCTCG
GAATCATCTTCAACAATTACCACAGATTCAGTCTTTTTCCCTTTTTCGTTAACCGATTTTTTAGCATCAT
TATTCTTAATAGCATTTAGTCTTTCTTCAATGAGTTTATCATAATCTTGTTCTTCAACTTCATTTTCATTA
TCTTCGTTATTATCATTTTCTAAGTTTTCATCTACAACTTTTTGAAGGTCTTTTCGGTTTGTATTTAATAA
TTCATTTACAATTCCTTTAATAATTAAACTTTGATCCCCATTAATTCGTCTTTATTATTAATATTG
TATTCTTTAATCTTAATATCTGCCATTTTAACTTTAAGATCCGACATTGCTTTAATTAATTGCATCTTCA
TTGTCTTAAGACTAATCAGGTTAGATGTCTGGTCCGTAACAAACCTTGGGTCTGTCTTCATTCTAGAAT
TTTGTGCCTTACTTCCCCTATCAAAATAACCTTCAGAATAAGTATATAATTCATCAATAGATGATAATT
CTTTTTTAAGCATATTATATTCATCAATAAGTTCTGGATCTATTGAAAATTTAGGTTTATTTTGTTCTTC
CATATATTTAATTTCACCTACCTATTTTGTAAGAGTATATAGTGATAATACTGCTTCATTACCAACTTTA
CGTATCGATTCACCTTGTTGGGATAATATATTTGTTTTTGCATTAATCAATTGATCTGCTTCTTTATTTG
CTTCAGCACTGAATACCCCACGAATTGAAAGCGTATCCCCATCATAATCAGCACCTAGAGCAGCAGTT
AATGAGTTATTAATAACTAATGAATCAGTAAAATAATTTTCTGCTACTGGATAGTCTGGAAAAATGAT
TGGATAGTTTTCCAGATATCTATCTTCAATTTTTCGATATTCAGTATCATTAGTGCTTAGCACAACAATC
TTTGAAGGGAAGATGCTTTGATAATTATCTACTGGATATCGAGTACAATACACATGTTTATCAGAAGT
AATATCAATAGCTGCAATATACAATAAATCTGTTATTGTAAAGTTTCTATCAAGATCAGTATGAAATAC
TTCTACTGGATATTCATTACCTTTGTCGTCTTTAACCGTAATTGCTTTAAATCTAGCAGGTATATTCTTA
ATAAAGTTACTTACTAACTTATTAATATCTTTATCGGTAAATTGATTTTTTACATTATCAATAAAGACAT
CTTCACCTTTTTTATTCTTTACATTTGAAAATTCTTCAATATGGATATCAATAAAGTCATTAATATATTT
TACAAAGAATGGAAAGAATAATGCACATACCTGACTTAATGGAATGCCTACGGTCCCAAATTTTATTT
CTGTATCGTCCCATCTATTTGTGTTTGATCTAGGAGCAGAGATTACTGATCTAGTTGCATAATCAATGG
ATTTTCCTAATAGACCCCTATGCACTAAGCCGTTCTTACCAGAAATATAGTGATAAATGTTTTTATATA
CGTCATATATAATTGTCTGCATTTGAGATTCGGTATTTGTTCGGACAAAGCTAAACGATGATTCACCAT
CTAGACTAGAACCAAAACGAATTAGTTTAGCGTATAGATCATTAATCTCATCTACGTCTGCTATTCTTC
CGGCTTTTGATGTGTTTGGATTGAAGTCTCTTAAGAATGGGGGAATAACGATAAATTTATTTATAAATA
ATGTATCTTTATCAAATTTTTCAATAATATTTAGTTTACTATCACGTTGTAAACTTTCTGTTTTTTTTGAAT
GATAATTTTTCAAAATTATTGTATAAGAAACTTACACCGGTTTCTCCGTTTACATCATCCTCAACTAGTT
GACCATCTTTAATGGTAAAATATTTTAAACCACTAATACATTCTTCAATTCTTTTATCTAAAGATATGA
TTAATTTATATACTACTGGGTGAAATATTCTGGTATTTAAATCAATATATGCAAACTGATTTGATCTCG
ATTTAGACCCGATTTCTCCAAATATTTCATAACTAAACAATCCATCTTCAGTAGGATAATTCGATTGAT
TAAAAAATATTGGGTTTGTTATTTTTGGTAAGTTATTTTGTTTTACTACATTATCGATATCTAACAAATT
TATTTTCAAAGATAAACAACCACCTTTCTTTTTTAGGTATCACATTTTAAGATATAATAAATATTTGTTT
AATAATAGTATAAGTATTTAATTAAATGCAAGGATCTTAGAAAAAAAAAAATAAGAGAATAATATGT
CATTATATTATTCTCTTATATACTGATTTGTCTAGTGAATCAATATTCTTTAATGATATTATTATTTATA
AGATAACTTACAATAATATCGATATCAATGGCAAAATTTTCTTTATCATAAATATCTTTATTTAAAGAT
GTATATTCAATACATTTACTGATGATATCATCTTTACTGTATAATGATTTATCCTTATTCATTACAATCC
AGATGATATCTACATTATTTGAAGTATTTTCAAAATTTCCATTATTATTCAAATCAATTAACATTTTAAG
AATAATAACAATGTATTTAATAAATTCATTTACAATGTGACCATTAGTAATAATATCATTATTTATAATA
ATGTTGTTCGTATATTTCATAACTTTCATTAGATTCAATTTCATTAATAACAATCTTTCTAGGGTTTAGT
ACTTCTAGTGAAAATACATCCAATAAAAATTCTAGTCTTTTATTTAATACATGCCGATTAATTCTTGAA
TTCTGTTGTTGATGATTCTGAAGATCAATATTATAATATTGTTTTATCAAGTTATAAATAATATCTACAG
AGGTAGTATGAATTTTATTTCTTGAAAATTTTTCATTTTTTCGATATTTATATAGGTAACTTAAAACTTT
TGCATAACTGTCATCAACACCAGTCTTATTTTTCACATACAATATCTTTTAATTCAGATGAGCTAATTGTT
AACGATAACATATAATATACCCCTTTTCTTTATAGTTTTTATTTTAATCAATACAAAACACTTAGACATA
TCTAAATGGATATCATGAATATTATACTCAGATAAGGATTTTACAATATGATCTACAATAATGTGCATT
TCATTATCACTTAAGTATTTTTTATTATTTTTTCTAGATAATAGATTAATCTTTAATGTAAATAAATTTTT
```

-continued

```
ATAGAAATATTTTGAAGATTTAAATAATTCTGTATTAATTGATTCTTCTAAATATTGCACATAACTATT
ATTTAATAATTTTTTAGTATTAACTGTCATATATATTTGATCTTTATTAAAATTAATTTTATTTTTAAAAT
CTTTAAGTTTCATAATCATAGAATAATAAATCCATCCATTCGTATTTTTATTTAATGAATAAAATACTC
AACTAACATAAGAGTTAGTTGAGTATATATCCTAGTTATTTAGTAAATATGCAGCTTGTAAAGTATCTT
TATCAAGACCATAATCCCTATTAAAGTCTCCATTATTAACACTAATTATTAAATTAGAAGGTTTTATCT
TTTCAAATTCTTTAACTTGTTCTTTTGAAAATAATGCAATAATATTTAATACGTCACCATCATAGTCTCC
ACCTAATCCGGCAAGAACATTATTACATAGGCTTAGTGTTTTATCCGAAATATCCTTTTTAACTTTGGC
AATATTCATTAATAAGATACTTGAAGTGGATATTGAAGGATTTCGATTTAGTATAATATATAAACCACC
TTCAGTTTTATTAATCAATTCTTCCATATAACGATACATTTTTTTATTAAATGTATTTTTAGTATCTATAT
GGAATTTTTCAGCTTCCACTAAAGAAATATTCTCTGAAGTTGAAATAAGATTAATTAATGGACCCTTAT
ATAATTCGTGAAAAGTAATATAATTCATATATACTTCATCCATTTTACATAATGGGTCTGGAGATATAA
CGTTTCTTGCAGAGTAGTTAATTCGAGTACCTAAAATCTGTTTACGAATTGTTCCTCTTTTACCTTTAAT
ATTATTTTTAATAATACTATCTACAATTTTTAACACGTCAATCTGTACTCGATACTGTAATTTTAACTTC
TGAATTTTAATATCTTCATAGATTTCTTCATCACTATTGACAATATCTTTTAACATATTTGTATGATTGA
TTAAGAAATTGTAGTCATTATTTATTTCAGAAAGCCGAAATAGATTTTCTGAAGCAATTAACTGAGCCG
GTCTCAATTTAGGACTAAATATTGGTAAGCAGTCAATAAACAATAATCCTTCAAAATACCAACGGATA
ATACGTTTATATTCTAATGAATTTTTCTGTTTTGGATCAACATACTTTTGGAGTAATTCAATAAATCTTT
CTTTAAATTCATCCAAACCGATATTCCGATCCTCAAATTCTTCATGCTCACTACCTTCTTCATCTTCTAA
ATCAACAATATTTCCATTTGCATCAATACGCTTATTATACATAATCATATCAATAAATTTAGTACCATC
AAATAATTTGATTAATCGATCAAACATAATAGGATTAACTACATAGTTATTCTTAAAATCTACATAACC
GAAGTTATCAATATTATCCCTTTCAACTTCAGGACCATAGATTTCTTCAGAAAATATTCCATCAATAGA
ATATTTCTTTTCTTTTTTTGTTACTGGTTCATGGTTAGTAATAATTTTATCTTGTTCAATTAATTCCCTAA
AATCGATAATCCGTACTCTAGTCAAAAGTAATCAAGCATCCTTTCTAACACCTTTTAGGCTTTTATCAT
ATTCACGATTAATCATTACATCCACATATGAATAATTCTTAGCTTCCGCTTCAGATATCTCTTCTTCTGA
GAATCCTGAGTTGTAGATTGTTCTTTCTTCAACAATATTATCAATAATATCCTTTTTCTTTTTATTAAAT
TTTGTAATAATCTTCTGATAGAAGGAGGTTTTACTGATAAATGCAGAGATCACTGTAAAAACAATTATT
GTAATCATAATACATTCAAAAATAATAGTAAACATTTCCATCACCATTCTTTATTTATTTTTTTATTAAT
CATCATAATCAGTTAAGAAACCTTCAATATCAGGTTTCTTTTCAAAGAAGAATGTTCCTGAATTATTTG
GATCATATTTCTTACAGAAAGGTACTACGGTAAAAGAACTTCCAGGGTCTCCTGAACTAGTACTTACT
AAATCGATCTTTCCAACAAAGCTTGGATAAATACCCCTAGCGCTTACTGATAATCCATTAGCTGTTGCA
GATTGTGGACCCTTTACAGAACCTTTTAGATAACGAGTAAATAGATCCATAGAATTAACATTATTTGA
GAATCTTACTAATTCGCTGTTAGGAATATTATTTACTAAGTAATCTTCTTTAATATTGCTAAATAGTGTT
TTTAATTTACTTACATTATTATTTTTTGGTCCAACTAAGCGATATCCGCCTTTGGATAATTTTTGAGTTA
GATCATAAAATAGATATTCATTAACCCTTAAACGTTTATTGGATAAAAGAGTGATTATCTACTTTTAAAA
TATTGTAATAGTTTGTAATCATATTTCTAACAATCGCATAAATATCTTCTTTATCTTCTGAACGTAATCT
TAAATTGGATCGAGTTGTATTATCTAGTAAACGTTCAAAGGAGGATAAGATAGATATAGCTTTATCAA
AAGTCATTGAATTATTATTTGTAAATACCGAACCTAGTTTTCTCTTCCAATAATCAGAATCAAAAGATT
TTTCATAATCAATTCGATTATATTTAAATAGATCTACTAAGGTTGCAATTAATGTTGCATTAGATTTTTG
ATCGCTTTCAATCCATTCTCGATTAACTTTTAATGCAATACTTTTTGTCAACTGGAAGAAGTAATATTCT
GGACTAGTAATATCATGATCTTCAGTTTTAACGATTTCTACATAATTATGAATATTAAAGTATCTTAGA
GTTTCAACTACACCTTTTCCTGCAAAATAGTAGTTCATTACATTTACAGTTTTCTTAAATAATAGTGTCA
TTAACGCTCTAGTTTTTAATGGTTCACCATTATTAAAACGTTCATCAATATCAGATAGTACAACCTTTTT
ACCCTTAATCTTGATTGGCATAAACATTGTTTTCAATACAATAATTCCATCATTAGTACGATAATACTC
GGAGTCATTCATTTGGAATACTGGGAAAAATTCATTTCCGTTAATTAAGAAGTATTGTTGATCTAATAA
TTCAGGGAATAATAGTTTAATTTCTTTTTGGATTGTTTCTTTTCCATCAGAAAGTTCCATTGTAACTTTA
ATTCTAATAAATCTAGATTCCTCGATATTAACGGTTGGATGGTTAATCTTTCTAGCTTTACCTTTTTTAT
TTTCTTTCTTTTCTTCAGTAACTTGTTTTCTTTCCTTATAGATTTTCCGATCTGTATCAATTTCACATTTA
ACAAAACGAATACCTTCTACAAATTCAAGTCCTTTAAAAACATCTTCAACTAATTTTGGTAAGTTTTCT
TTAGATCTAAAGAAGATCACTTCCTCATTAAATGGAGCTTTTTCTTCCATTTTATTTTGAAGATCATTAA
AGAGTTTTCTTGACAAGTTTGGCACAAACAAACAACTCCAATCAAAATTTATTTTATAAATTTTTATAT
CGTATAAAAACAATTAACTATTATTAGATAAAAATTTGTTTTTATATAAAAATAAAAATTTAAGGATGT
GTATATACTATGTTGAGAAACGGTGAAGAATTTTTTAATGAATGGTCTGAAAGATCAGGAATACCTAA
ATATGAATTAAAACGTCAATGGAATATTATGGTAGAAATGGTTATGGATAGCATCATGGAAGAAGATT
TTACCAAAACAGTATTACCAAGCATAGGCGCTTTTGAAACTATTGTTAAACCTCCATATATTGCTAGAG
ATCCTAGAAATGAAAAAGTTGTTATTGCACAAGTTAGGAAGCGAATTAATTTTAGAAATATATCGCAGA
TTTAAAAAAAATAGTAACAGGATTGTTATAATTTTCGTAATACAGATATTTATTTCTGTATTACGAAAT
CTTTTTAATTGTTATTTCTTTTAATAATCTGTTTTTCAATATAAATTCTATCTTCTTGAGATAGTCCATTA
TATATTTCTTCTAAAGATTCAATATCTTCATTATCATTAATTAATACATCAATATACCTATCTAAGATTT
CTTTAGGTACATTAGTTTTTAAATTATTGATATTATATGATAAATTTGATCTTAGAATTAGTAAATTTATT
ATCAACAATCTTTACACTTAACTGATTTCCATCATTACTAATATTGATGCTTGAATTAGTACTTTCACTT
GTAATATTAAGTTCAATACTTTTTAATATTTTGTTAATTATATTTAAATCCAAGTTAAAACATCCTTTCT
ATTCTTATATATTGTACATTTATATAATATATAAGAATAATATTAGTTGATGAATCGAGATTTAGCTTC
TTCGATAGTCATAATTTCTTTTTGCATTTCCTTAGCTTTAACAATTTTTGAAGAAGTGGATTCTTTTATCT
TTACAAACTACAATATCAGTTTTTGAAGATACGCTACCTGTAACTTTATGACCGAGTAATTCTAATTTC
TGTTTAAATTCATTATCCCGAATTCCTGTAAAAACAATAACTTTAGATTCTTCAGAAGCATTATTAGAT
AATTCTTGTTTAATAGATTTTAGTTTAAATTCATTAATCAAGAATATCAATTCTTCTTCATTATTCGAGA
TACCGTTTAGTAATTTTTCTGCCTTAATATCTGAAAATCCTTCAATATTAATAATATCTTCTTTCTTAGG
TAAAGATCCATTTACAAAGAATTCGTTAATTACTTCTTCCAAGATAATTCCTTACAGAATAGTTTAGA
GTTTTCAATACCTAATCCTTCAATACCTAATGAACCAAGAATTTGATAATCATATAGATCACGTTTGTT
ATTAATTGCATTCTTGATATTATCTAGTGATTTTCTACCTAACCCTTCAATAAAGTTATCATCAATACTA
TCATAATCTATACTATATAAGTCTGTGATTGAAGTCCATAATTTATTTTCATATAATTTACTAATAGTAG
ATTTGTCAATACCTTTAATGGCTAGTTTATCAAGATAGTTAGATATCTTTCCAATAACGTTTCCAGAAC
ATTCTGGATTATTACAGTATGCAAAGGTTTGATTATCATTAATAACTACACTTTCTTGCTGACATACGG
GACAATATTTGGTAAATTTGTCAGGAATAATATCTTTGTTATGATCACTATCTACTTTATCAATATATGT
TAGTGTATCATTCCTATATTGTACTAAAAATTTCTGAACCAATACCTAAACCTAATTCTTCCGCTCTTGCA
AAATTATGGAGACTTTGTTTTGTATGCGTACTTCCATTTGAAAATGTAACTGGTTCAAAATGTACTAAT
TTAGTAATTCGTGAAAAATCACCTAATTGATAGCTAAAATCAGTAATAACACTTTTTTTCTGTTCATAG
GGTAGTTTAACTGCAATCGAATAATGTGGAGTACCTTTAGGAGTCATTCCTAGTTTTTCACGATAATCG
TCATCTAAAATTTCAACGACAATACCATCAATCATAAATCCATAGTTATATCGATTATTAATAACTTCA
```

```
TTATAGAAATCATTAAATTCTTCAATGACTTTTTCTACTGAATTACTTTCACTAGTAATACTGAATTCTG
AACCGATTAAACTATTTGATCCTAAGATATTAAAACTATTATCTCGTTTAGATAATGTAATTTCGAATG
GATAATTATCTTCATCGAGGAATTTAATATCTAGAGGGACAAGAGTTAAGAATTTAGAGAATTTATGA
GCATCGTCCCTACCTAATATTCCAGAGGTTGCGGATCGTGGATTAACATAATTATTCTTTGTATAATCA
TTTAACTTTTCTAAATTATCATACGTAATAATAACTTCATTTCTAATTGCGAAAGGTAGTTTGATATCAT
ATTCTTGTAAAGGATCTTTAGCGATGCTCTTAAATACATTAGTGAGATCTAACCCGATACCGTCTTTTC
CACGAGTATACGCCTTATCAAACTTTCCATCTTTAAAAGTAGTAACTACTGAATTCCCATCAAACTTTA
ATGTAAATAGGAATGTCGGGAACTTAGAAAAAGGTTTAAGCTTATTAATCATTCCTTGAATTACTTTTG
GAAAATCATTAATATCTTTACATTTAAATAATGTTCCTGTCAGATTTTTATATTCATGCTTCATATTAAG
AATACCTTTATCCGTTTTCGGTAATGATCCTACAATTTCTTCACCAGTTAATTGTAAGTATTGTTGATAT
AATTGGTCATATTCAAGATCAGACATAATTACTGTATCTGTATTATAATACATGCTTGATGCATTTTCT
AAATATTCTTTTACTAAATTATATTTATCATGTTCTTTACTGTCTAAAATTCTTTTTGATTCTGTATAATC
CACATTTTTCAATATCCACACTTCTTTCTATATTATTATTTAATATTAATCTTTTTTCCATTAATGGTAAT
ATAGTTATATTCACTGTTATAAGATACATTTATAATGTCCATATCAGCATCATATACTTCATCTATTTCT
TTTTCATTAACATATATTTTTCCATTGTCTAATTTTATTTCATATAATCCATCACTTATAACTATAACATT
ATCTATCTTTTTTATTATAAGTTTTAGATTTCTTACCATCAATATATATTTCACCATCTTTTAATAACACA
TTTAAACCATTATTATATATATTGGCATTTCTATTTTGAGGAAGAGTTTTATGTTGATGAAAAATATTAT
TATATACTTTTTTAATTTTATTTATCACATCATCACAACCTTATTTAATCTTAAGATATATCCTATCACA
CTATAAAAATGTGATAGGATACTTTTTATTTATTTTTATACTTATTAATATCAAACGAGTCTTTATTATT
GGTATATTCATTAAGCATGGATTCAATATCTTCATCACTTAATTTTTCGATATTATCAAAATCATTTTTA
TAATCTGGATCAGTATTAATTTCAACACCTATAGATTTAAAATATGAATTGATAATTTTATTATTATTA
CTAATAGTGTCTGATTTCTTAGGTAATTTAATGTCAAAAGGATTTCCGAGAAGTTGAGCTTTTACTAAA
TTACTTCTATCTTCAGTATTATTTGAATAAGCATCAGTTAATCTTTCAATAGGTTCTAAAGATCCTACTA
ATCCTGAATTGGTATATTCCATTTCCAATTACCTTCACATAGATTCGCAATTTCTATGCAGTTCTCCTTAT
GAACTTCTCTAAGTTTCCTTAGAAGTTGAGACTATATCTTTATCTTATTTAAAATTTCTTTTTGTTTTAA
GATACTTCCCATTTCGCCTGTCATTTGCTTACAGACTACATCAATAGTCGTTGAACTTTCTTCCAATAAT
TGTTGGAAGCTTAGCTGCTGATTATCCATTATAATTGATACTTAGGAATATTATATTTATACCAGAATA
TAATATCTTTTTATCTCACCATATATCATTCCAATTATTTTTTCTATCTTTCGATAACATTCACGCTTATC
ATTACTGATTGCGTTTTAGTTAATTGGACTTTAGGAGTTTCCAGCAATTAAAGAAATTTTCATCATATA
TCACTATATAATGCGGCAAAATTTACCGACTCTAATTGGAGTATTATTAGTAACATTATCAGAATTTTT
CATATCTTTAGTTTTTGTTGGAAGATTCTGGAAGTTAGTATTACCTTCACTACGAATAGATGTTTTTTCA
ATAGGCTCATGTTTAAGTCTAAGCATATATAGTTGACCCATTTCAATAGGCTTACTAATTCCACTTAGT
TTATAACGATCGATATTGAATTTATCACGAATATCTTTAAGTTTAAAAATATCCATATCATTCCAGAAT
GGTGTAAATTGAATATAAATTCCATTCTTTATAGTATCTTCTAGATAATGATCCTTATCGCTATCACTTA
ATTGATCATATATACTGATTAATGATTTATACATATTTTCATCAATAGACTTAATATATTCAGATAATA
AATTAAACTTTTCTTCACGACTATCCATATGTTCCATTCGATATCGAATAACTTGAGACATCATATTGA
ATGTATGTTCAAATGATTGTGAAGGATTTAATCGGTTATTAACGCCAAAAGGATTAAGAATAATATCC
GCTCTATTTTCTAGGCAAGAATCTTTATCAAACTCCTCACCATCAATAGTTTCAATTACAGGCATTTCTT
CGTCCGGAAGAATTAATCCAATAATTCCTTTATTACCATATCGACCAGTTAGTTTTGAACCTTTCACAA
GAGGAATTCTTTCTAAGATTGTAAATACCGCTACAATACGGTCAAACACTCTTCCCTCAGACTGAAATT
TATTTGCAGGATCATTAAATGCTGCAATCTTATTATAAAATGCAGATAAATCACTACTGATATTATTTC
TTTTACTAGATACAATAGGTTTTAAATATTCTACAACTTCAGAGTAATATTTTGAGATAGAAATATATT
CATTGTACATCTGATGATTATATTTTTGAGATCGTAACTTATCAAGACTTTCGTTATTATAAATATCAAT
GTCAATAACAATACCTTCAGCATGTTTTACTGTGTCAGTAGCAAAGATCTTTCTTAAATTGACATCTTT
CATACTGAATCCCATATCATTATAATTAATTCGACGAATTCCCATTAACTTACCATCTTTAATTTCTTCA
CCAATACTAGGAAAAGTTCTATATGATTCATCATCGCCATATAGATTTAATAGTACATCATTGGTATTT
AGATTGATCTTAACTTTCTTTATTAAATAGGAAGCCATCTTTTGAGCAGTACTCTCAGAAACAACAATA
GAGTCTTCATTTGTGAATCCTTTGTATGGAATATATACCGCATTGAGATTTTTACCATACTGAAAGTTC
ATATCTTCGTCATAATTTTGATCTCGATAAATTACTTTGTTTTCAAATTCTTCATTTTCATTGATATTATC
AATTACTTCATTATTGAATTTTAGTCCAAAGTGTTCTGTTAAATGTTTTGCTTCTTTTCGTTCTACAATA
TGATAGAGTTCTTCTTCTTCATTAAATAATATTGCCGTGTAATTAAATTTATTCTTGTAAAATTTTTTAA
GAAGTTTCCATCTACCATCAAGCTTTTTATATCCAGTAGAATATTTACCTACTTGATTTTCAAAACCAG
TAAAAACTAATGGTGGATCAGCTTGTTCCAATTGAATATTTTGACTTAAATGAGAAGTAAACATTTGTG
ACCTATTAGAGTTAGTCTTATCTAAGTTTGGAATGAGTAATGTTTCGGCTAAGAAATCAAATTTACCTT
TATATTTTTCATCATTAATCTCTGTTAAATCCAAAGTATAACCACACTTTCTTTTTTTTTTTTAATATACTA
ATCTATCCATTATATAAGAGTTATTATATTTATACGCTTATTGGATAGATTAGTACTTGTAATTATTAAG
ATTTATTTATCATTTTCTTTTTCGATTTCAATTAAATTCATGTCAGAGTCATAGTATCTTCCATCTGAAC
CAACCCAAATATCTTCATCTTTATTAACGCAGTCAATAAGAGTAACAATATTATCATTCTTGGTAGATT
TTGGAATTGTTTTAAACACTTGATTTTCACCATAAGCGTCAAAAGCATTTCTAAATTCTTCATTAGTATT
ATATAGTGTAACAAAATCTTTACGTTTAAATTTAACGTCTGGAAGAGTAGGAATAGAGTATCCTCCTTG
CGGTGAACCATCTAATAGTTTATTATCTTTAAGATAAGCAAACAGTGAAATACCGTTAGAGAATCCAT
TAAGTTGATCAAAAACAGAATTAAATGAGTATCCTGAAGCCGAAATACGGGACTTAACAATTAGTCCA
TCAACTTCTAAACCTTTATATCCAGTTTCCTCTTCCTTAACATTTTTACCCGGATTCAATTTAACAAATG
TATTAGATAAATATCCAAAGGCAGAACCACCTGGAATAGCTTCATCAATCTTTAGATGATTCAGCGAA
GCTTTAGTCTTAACTACTGGATTAATTTCAATCTTAGTAGTAATATGATTAATCGCAAATAACATGATA
TTTGCTTTTTCTAATGCACTTGAGCCAATTAATCGTTTAATCATCTGATTATTGTATTTTGCTTGTGCTGT
TGCAGACATCTGTCCACTCATCTTTTCTTCTTCACTGATGTCTTTAGTATACATAGCAGCAATAGAATCT
AAGATAATAATTGTCGGATCGAACTCATAAATTGGTTTACCTGTAATTGGATCTAATTTACCTGTATCA
TGTTTAAGTTTATCGCCCCTGCTAAGTTTCTCTTTTTCAATAATTTTTACTAAACCATAAAGAGTTTCTG
CCGATATTCCTGAATTAAGAAGATTATACTTTTCAAGAATCTTTTCATCAGCCCACCCAGTAATATTTT
TAATACGAGCTAATGATCCGGCATGCTCATAATCTAGATGATAAATTTCAGAATTTTCATAACGATCA
ACAATATTACATGCAATTTGTTGAATTAATGTTGATTTACCAGACCCGGATTTACCTACAATGGTAAAT
AATTTACCGGCATCTAATCCCATCATTAATTCTCCCTTACTATAACTTGCTAACTTTGCATCAATCT
GACTGAAACCCGTTCTATAAGTTTCAGTAAAATTTTTGGATTCACCTAATCCATCTTTCAATAACTCTTT
TTTAACTTCATCTGTAATTAATCCCATACATTTACTTCCTCCTTAGATATCATACATTATAAATCATTGT
TATTACAATAAAATAATTTTTTATTTATAATAACATCATACTACAACATTCCCTTCAGTATTTTTATTTTT
AACATATTTTTGACGTAAAGTGGAGATAATTTTTTACATCATAATTTATTATAAAATGCTATAATGAAG
ATTATACTTCTTCATTATAGCATCATTAATTCTAATACTTAGATAATATTAATTTAACAACATCGTCAGT
ATTTTATCATTTCAAATTTTGACATATTATCAATATAATCACGTAGTTTATCAGTATCAATCAAATTACA
```

```
ATAATCATTTCTTTTTACAATGTCTGTAACTATTTGTCTAAATCTAGTGTCTGATATGATTACATTTACA
TCTTTTATAAATGTATCAATGAAAATTTTTATTGTATTTTTTGCAATATTAGCTTTATCAACATCAAATA
TTTTATCGATAATTTTATCAATCTTGAATGCATAAAAAAGTAACATTTCATAGTTCATATCAGGTAATT
TATTTTTTGCATACATAATAAATACTTCGATAGGGTCTCGCTCAATTTCTTCAGTTTTTAATAATAATTC
ATAAATATAGTCTCGGATAGATATTCGAGATAAAGCTTCTTGCATTTGATTAATAAAGACTGAAGTGTT
ATCTAATGATATTTTTTCTAATATTGTGATTAGTTCACTTGCCTGTTCATCAACTAATCTTTTATAAATA
GTATTATCACGCATATTATCTTCCTGAATTATCTTAAATTCATTTACAAAAGTCAAAAATATTCCTCCTT
TCTTCAATAGTAAATAATCACAAATATATAATATATATTTATTATTGAATTTTAAGATCGTTTATATTTG
AGATGTTTTCTTCTTTAACATCAGCAAAATCTAAATTAAATGTATCGGAATCATCTAGTAAATCATTAT
CAATTCCTGCACCAGTAAGAAATTGGGATACGGTATTTAACGTACGCTTATCATTAATGCTTCCCGGTA
AATCTTGTAATGAAGTATATCCATACATTGCAATATTTTTATACATTGTAGATTTTGCGTCTTGTGAGTC
CGCTCTAGGGCTTAAGAATTCTTTTAATGCATATTTAGCGTCAATAGCACTTAATGCAATAGTTTCTAA
GTCACTGATCCGTGCAATCTTATCTTCGTTTGTTACTTGGTTGGTTCTTAAACTACGTTTACTAATATCT
AATGAGTAGGTATTCTTTTTCGATAAGGTTTGTTATACTGATAGGTAAAGATATACTATAAACGTATTC
TTTTTCCCCCAGTCCAAACCGTACGTGAGACTTTCATCTCATACGGCTTTCCATCAAATTTATTTCATTA
CTTAGAATAAATACTTAATAAATAACTATTCTAATTAATGAAAATTAGATTTGACTAAGAACTTTCTCT
CCACTATTTATTATCATAGCTTCATCGATACTTCATTCTCTCTTACTCCCTATAAATAGGGTATCAAACG
TTCCCTTTAAATTAGGTATATAAATGTACTTAGGATCCACCTGTTATTTATAACAATACTTACATATAA
GTATAAATATGACAACCTATTAGTCATATTAGCTAATAAAGACTACAATTTTATTTCGCCTATTATAAAT
CATTAAAGTGATTCGTATTCCTATCCATATACATCTACCCTAACCGCTATAAGTATTATTAGCGACTTC
ATCCAGCTTCACACATATTAATTACTCAATATGCATGTGGAATATCATTAATAGCAATTCATGACTATT
ATTTAGGTTAGTCACAGCTTATTCATTTAAAGAGTTAATTATATACGCATATATAATCATGCAATCCTC
AATATTTTTACATATCTTTCTGCATAACGTTTCGCACGTAGTCTCCTTACGGGAAGATAACCTAATGGT
ACTGGATATCTAGTTCTTAATGGATTATCTTTATTTCCATCATGACGATAATAGATATATTCTTCTAATG
GTACATTCATAAAGTCTAGTGTTTCTTTAATATCTATCAGTTTTGGTTCATTTTTATTCGGTAATACTTC
TAAATAGAAATTATCATCACCATTAGTAAATTTTTTCATATACGATAAAAATTGTTCGTCACTCATTTT
ATCGTAAATATCTTTATACTTTTTAGCATTAGAACCAGTTTTATCTAATTTATTGAATACGTCAATAATA
TACTTTTGAATTTTATTTCTTTTTTGTTTATTATTAGATACTTCTTCATTTAATTCTACCGATTCATTGAG
ATTATCTTTTGTATCCATATAATATACTGATAATATTTTAAATAAATTAATCGAATTATCTTCAGAAAT
ATCATACTTCTTAATGTTTTTATCTTTAAAAGGAAACTTGTCAATACTTGAATTCAATAATCTTTAGACC
ATCTAGATCACGGTTATCGTACTTATCAGTATATAACTTAGAAAGATAATTTGAACTAATTTCCCTAAT
TTGAGAAGTATTTGATAATCTAATAGATTCAGGATAACCAAACTCAGGATAATAATTAAATAATACAT
AACTATCATTTTCTTTGTAATAAGGAAGACTAATATAATCTATTAATTCTTTATTTTTTTCATTATATAG
ACCCATTATCATAAGTTTTGTAAAAGGTTGAATGTTTCTTAGTATTAAGTAAATAATAGTATTAATAAC
ATTACTATTCAACTTGTGATAATCAGTAAGAGTATCACTATACTTGATGATATTGAATAGACTCATTTT
TATACTACTATTATAACTTCGATTATTATCATTAAGTATAGATTCAATATACTTAATGATATCTTCTTTA
TTATTAATATCATTTCTAAATATAATATCCATTATATAATCATTAAAATCAATTTTTGTAATATCAATAA
CCGAATCCTCATCAATAGATATTACTCTTTTATATAATGATGATAATGGGTATCTTACAATACCAGAAC
GGGTATATTTAGTAATTGATAATAATGAGGGATGAGATATTAACTGATCTAATTTTATAGATGGATAT
AATTTACTTTCTGAATCCCTGAGTTTAAATAATTCAATACCATAAGTTCTCATAATGGTCATAAATACG
CTTACTAATTGAATTTCTCTTATAGTTGTTTTATTTCCTTCTGCACTTCTAATTATTAGATCATTATCCAA
GTATTGATTATAATCTTTAATCTTATCAGAGAAAGTATTAAACTGATCTATAATATTAATATTATTTTTA
TCATAATATATAGGAAACTCAATTACCTCTGTAAACATATCAATATTCTTTAACTTCTTTTCAAAATTG
GATGTAAACTCAGATACTTCCATTTTTTCATCGTTATAATCAATTCCAAATATTCTAGAATTATCATGA
CTATCTATTAACGCAATTTTACTTAGTCTATCTTTAGCAGAACCTATTACCCTATCAATAATTAATGTAA
CTTCTAATTTACATTTATCCTCTGAAGGACTATTATCAAAAGGTATATATTCATTATTATCTAGCATTAA
TGCATTATCTGTAAATTTTCTTTCATTCCCTAGGTACTCATTATATTTTTTTATTCATATAATTATCCAACT
ATAATTCACTTCCTTTATATTATTCACTGGTATATCTATATGTTTATATTACTAGTTATTAAAATCTTTTA
TCAAAAAAAAAAAAAATATTAATTATTAAATACATAGTATATAACAATTTATTTGTTATATACTATGTA
TCTTTTTTTCCTTACATTATATTGATTAGAAATTTAAACCTAACCAGTATCTAGCAAACATAGATTTATA
TGAAACTAAATCTACAATAAATATTGATACGAAAATAACCAATGATAAAGCAATTACCCAAGATAAG
AATACAATTACTTTCTTAGATAAATTAAGATTAAGTAATCTTTCTTCAAATCTTTTTAGTGTAAAATTTT
TCATGTTATCTTCTAAGAATAATAAGATTGTAATGCATTTTAATAGTTCATTAAAGATTCCCACAATTT
TGTTACTACCATTATTTTTATTTACTATTACTGTTTGTTTTTCCACTTTCTCCACACTCCTAATATTATTA
TTTTCATTTTATAAATTAAAAAGTTAACCTATCATCAGGATAATAAAATACCAATGATAGGTTAACT
CGTTTTTCTCTATATTTAAATAATATATTTAAACTATTAAAAATTATAATCAATCTCAGACTTTTGAAATTC
AGCTTTCATTCGTTTTAGTTCTTCTTTATCAATATTTTTTTCTGACCTAATAGTAGTACCTGTTGGCACTT
TTATATTAGTAATCATTTTGCCTTGAACTGTTAGGATAATATTTAAAGTAATCAATATAAGAGCCAAGA
GCAATAATGAACCAATAATAAAAGATGAAATATATCTATCTACTTTCTTTACATCTTCTTTATGTTTAC
TCTGGTTGGATTTATATTTCGTACTAAGATTATCCATTCTTATTTTCACTTCCATTCATTTTATATTAGTA
ATATAATTTATCTATATTACATAATGATAATATATAAACAAATATGGGTTATTACGCTTTTATAAAAA
TTTATAGTTAATGTATAATAATATTATATATTTTGGATCATAGAAAAATATATATGCTTTATAAGTATA
TATTATAAATTTGTAGTAAAATAATTAATTATGGAGGATTAATATGAAAGAATCTTTAAAGTTTAATGT
CAAGGAAGTAAGAATTCTTAGCAAAATCGCATCTAATGAATATGCTAATGAGGAAAGTCGGTATGAA
AGCTTTTTATCTAAATTGGAAACATTTAATAACTTTCGTTCAGGATTTTTATATCTGTATCTAAAGAATC
TTTCAGAAAGTGGATTAACTAAACAAGAATCTTTAAATAAGGCTATTGATAAATATGTCAAATAATTC
AATAAGATTTAGAATAATGGCAGATATTTATTGTAATAATAAATTTATCAATGTTGAAGAATTAGAGT
TCACTGGAACGAACGAAAGTAACGCAAGGAAACAATTAACTGGTTACCTTAATAGACTAACAAGAGA
AAATAATAATGGTAGATATACAGCTAAGAATATTAATATAATACCCATTAAATCCCAATTTCAAAACA
ATATTGAAAATCAAGAACAACTAAATCTTTTTAGTAATGATATTAATGATGATTTATAATCTAAGTAAA
TCATCATTAATTATCTTTAATAAATTATGAAGTAGTGATATTTTTTTGGCTAAATTAAAGAAAAGCAA
AAGACGAGTATCCTTTGAAACAATTGTTAAAAGGGTTATTGAAAAACATTTTCTTGAAAAGTATGATA
AAGCAGAACTAGATTTAGATAACGAGGAAACGTATCAAATCGGGTTAGGTTCTATTGATATTGATAAA
TACAATATCAATCCTGATGATTTCGAAACCTCTGGAATTTATTATTACAGTAAAGGGAAAATATCTTTA
GATAAAGATTCATCTCCTTTACGAACAATGAATGTTAATGTAGGAACTGTTAAGCCTTTATATGACGTA
ATATATGAAATTGAAATTATTTCAAGGGTAGAACCAGAAATTAATAATTTAACAGTATTAGGATATTT
TATTAAAGAATAGATATGGATGGTGAAATAACATTGACAAGAACTTATTCTGGTGAAGATATTGATGT
TTTAGAGGGTCTAGAGGCTATTCAGGTTAGACCGGATATGTATGTAGGAAGTTCAGATGAAACAGTCA
ATCATCTTGTTAAAGAAGCAATTGATAATGGTGTAGATGAATTTCTTAATAATTTTGGAACAAAGGTTA
```

-continued

```
TTGTTGACTTAGATACTGACGAAAATATTATTACAGTTATTGATGATGGTCGAGGATTACCTACTGACA
TTCATCCTAAAAAGAAAATTCCAACAATGCAAGTATTGTTATCAGAAGTACATTCTGGTGCAAAATTC
CGTAAAGATTCTTTTAAAGTTTCTAGTGGTAAGAATGGCGTTGGTATTAAAGCTGTTAATGCATTGTCT
GAATATCTCCGAGTAATTTCTATTAGGGAAGGATACCAATATTCAATGGAATTCTCTAATGGTAAAGTT
ACTAAAGAATTTAAGAAAGAAAAGCAAAAAGAATACAAAGATATCAAGCATGGAACAATTATTGCAT
TTAAGCCTAATGGAGAATTTATCGATAATTATGACAAATTTGATCCCGAATTCATTAAAGATAATTTAG
AAAAGCGTGCATACAGTAATGCTAATCTTAAATTAATCTATAAAGAAAAAGGTAAAGAAGTAGCTAC
GTATCATCATGAGAATGGTATTCGAGACTATATCACAATTCTTAATAATAATCCTTTTACTAGTAATCA
TTATTATAAAGAAGAATTAGAAAACGGCGACTTATACGAAGTAACTTTTGGATATAGTAACTCTTCAG
ACGAAAATATCTATAGTTTTGTTAATGGATTGAAAACTGCTCGTGGTACGCATGAAACCGGATTCAAA
ATGGCACTTACAAACTTAATGACTAATTATATTAAGAATAATAAAATGTTGCCAAAAAATATGCAAGC
TAAGGCTATTACGGGTGAAGATATTCGTTCTGGATTAGTATGCGTTATTAATCTTAAGTTGCAAAAAAC
ATCATACAGGTCACAAACTAAAGATGAATTATCAAACCCTGAAGTTTCTGGTATTATTAAGCGGATTA
CAAATTCAGCAGTAAAAGATATTATGGATACAAACCCTAGTGAATTTAAAAAGGTATGTAGTCGTATT
ATTGATTTTGCTAAAGGAAGAATTAATGCTTCTAAATATCGTGAAAAGATTGTTAAAGATACGAATAA
TCTTACATTAAGTTCTAAATTTTCAGATTGCCTTTCTAAGGATCCTTCTGAAAGAGAAATCTTTCTATGT
GAAGGAGACTCTGCAAGCTCTGGAATTAAAGAATTCAGAATCTCTCAAACTCAGGCAGTATTCCCATT
AAAAGGTAAACCTAAGAACTCTTATGGTCTTTCTAGTAAAAGTTTATTAGGTAATGATGAATTTAATA
ATATCATTAAGATTATTTTTGGTACTAATGATATTAAAAATATTGATTATGATAAAGTCCGATATCATA
AAATCATCTTTACTGCAGACGCAGATACTGATGGATTACACATTAATTCATTATTAGGGTTATTCTTTT
ATACGCATTTTAAAGAATTATTTGATAGAGGATATATTTATATCGCAATGCCACCTAAATATAGTACTT
ATGATAATGTTTCTAAGAAATTTATTTACTTTAAGAATGATAAAGAATTAAATACTTTTAAATTCAATA
ACATTAAGAAACGTATTAAGCTTAGTGATGATAGTGAATTTAAAATTAAAAGACTTTATTAATAATATG
AGCGAATATCAAATCAGTACAATATTGTTAAACAGAATAATAATAATATTTCCGATAGCGTTATTGA
TACATTCTTATTACATGGTCATGAAAGTAATTCCTTTATTGAAAAGATCCTTCTAGATAGGAATAACTA
CAGATTCAGTAAGAATAAAAACGGAAATATTATTGGAATGCACGATAATGCTTGGCATGATATTAATA
TTGACTTATTAAATAATGATATTAGTCGTATTAAGAAAGTTATGAGCATTAGCGACTTGTTTGAATTTA
CAGATACCAAAACAAATGAAATTTATAGTAATGTAACATTAAAATTTCTTATGGATTATATCAATAGT
AAATTTACGTATAAACTTAACTATTTTAAGGGTCTTGGTGAAGCAAATCCTGAAGAATTGTTTGATACT
ACCATTGATCCTGAAAAACGTGATTTAATTCAGGTTAGGATTGATCCTGAAAATGAAGAATCAACCCA
AGAAATTACAGATATATTCTTTAAAAATAATTCAACTCAAAGAAAAGAATATGTAAATAGTTGGTTTA
ATATTAAATAAAATTTTATACAATTCGGGTATTACTTAGAGTTAATCCCGAATTGTATAATTAAATTAA
AATAAAGGTGGTTCATACTTTTGGCTATTATTCAAAAACAACTTGTAAATATTCATGAAGAAAATATG
GAAGAATACTTTGTTGAAATACTTACTAGTCGTTCAATTCCAGATATTCAGGTTAGAGTCAGGTGACTTTAAAAACCCAGT
CAACGAAGAATTATTTATTCTATGAATAAAGATCGAAGATTTAGTAATTTACCATTTACTAAATCTGCA
ATGATCGTAGGTTCTGCATTAATGATTCATGCCCATGGTGACGCATCATTATACAATACTGCAGTAAAT
TTAACTCGTAAATTTTCTAACATGCAACCATTAGTTGAAGGTCACGGATCTTTTGGTAACGTATATGAT
CCTAGACCTGCTCAAATGAGATATACTCAAATGCGACTAAATAAGTTTAGTGAAGAAGTTTTACTAGA
TAATATTAATGATAACTGCGTTGATTTCGTACCATCTTATGATGAATCTGAATTAGAACCTGTCGTTCT
CCCATCAAAAATTCCAATGATTCTTATCAATGGTTCTTTTGGTATTGGTGGAGCATATCGTTCATTTATT
CCCCCTCATAATCCAAAAAATGTTATTAATTATACAATTGATTATATCAAAAATCCAAATAAATCTGAA
GAATCATTAATTAAAGATAATGAATTATATCCGAGTTTCCCTCTAGGTGGTATTTTAGATAATAAAGAT
ATTATTAAAAAATATACGACTGGTGAAGGAAAATTGGTTCTACGTGCAAAGATTATTAAGGATGAAAA
TAAATCTACTCTTACCATTGTACAATTACCATACATGAAAACTCAAGATATCATTATTGAAAATATACA
AGAAGCAGTTAAAAAGAATACATTAAAGATATTAAAGGTATTGATAATGGTTCTGAGCGTGGTAAG
ATTAAACTTATTATTAAATGTTTTAAGGGAACAGACCTAAACGTAGTAGAAAGTCAATTATATAAGCA
TACCGGATTGCAAAGTACGTTACCATTAAGCTTTGTATTAGTAGATCAAGGTGACTTTAAAAAATATA
ATGGAATTAAACATATTATTTCTGATTGGGTTGAATTTAGAAGAACAACTATTCGAAGAATTAAAACG
AACCTTATTAGTAAACTTGAAAGAAGGATTCATATATTAGAAGGATTACTAAAAGTATTAGATCCAAA
AGTATTAACAAAACTTATTAAATTAATTCGTGAAGGAAATAGTCGTGATGGAATTAAACTAAGTATTC
AAGATAAGTTTGATTTATCTGTAGAACAAGCTGAATATATTGTTGAAATGAAGATCTATCGACTAAGT
AATATTGGTATTAATGATACAAAAAATGAATTAGCTGATAAAATGAGGGAATTTGACGATCAATCCGA
ATTTATGAAAGATCCTAGTCGTATCGATAAATATATTATTGATGAACTACAATCAATCAGTAAATCTAA
AAATCTTCGTAATGACTTTGAAATAACTACTTATGATGATAATATGAATGAATTGGATATCGAATCCCT
GATTCCAGACGAAAATTATACGATTGTTGCTACAAAGGGAAACTATATCAAGAAATTCATTTCAGAAA
TGAAAGTACAAAAACGTGGCGGTAAAGGAATTAATATCGGCAAACTTAAAGATAATGATATTCCTTTA
GGAATTATCTCTGCTAATAGTAAAGACAATATTTTATTTATTACAGATAAAGGTAAGATTTATAACTAT
AAATGTTATAAATTACCAAACGCTTCTAGTATTAAGACGCTAGGTAATAATATTTCTAATCTTATTAAA
AAGGAAAAGTTAGTATCGATTATTAGCGTTACTGATGATCAATTAAATAATGATAAAAATTGCTTATT
AGTAAGTACTATTGGTAATAATATTAAGTTAGTATCAATGACCGAACTAAAAAGTATGAATGAATCTG
GATTAATTTTATCTAAACTTAAAGATAATGATGAAGTAACAAGTGTTAAATTAGTAGACATTACTGAA
TCTAGTAATGTAATTGGTATCACTTCTGAAGGTATGGTTATTCGTACAGACATCTCAAATATTCCAGTT
ATTAAAAGAACTACACAAGGTAGTAACCTATTTAATAATAAATATATTACAGAAAGTAATAAACTTGT
ATCGGTATCTCTAGAAACAAAAAATACTACTGGTCTGTATATTATTACTAAATCAGGATTATCTAAACG
TGTAAAGATTGATGAATTCAGTAAATATCCTAGAAGGGTAAAGGTGTAATGGGGATTAATCTAAAAG
ATACTGATGATAAAGTTGTATCTATGGAAACTTATGAAAATGTAGATGACCATAATCTTATCATTATCT
CAAATCAGAAAGCAATTTCCATACCTCTTAGTGATATTTCTGAGTATAAGAGACCTGCAAAAGGACTA
ACACTTCAGAAGCTTGAAGATGACAACTATATTATTGATTCATGCTTAATTTAGTATTAGAGGGTAAGC
CATTGTTTATTGATGGCTTATCTTTTTTTTTTTTTTTCATTTATATATAAAAATTAACCTTTTATATAACAAT
ATTATATACTATTGAAAGGTTGTGGAAAATAAATGGCAAAGAACTTATTTTAGATGTTTCTCATCATC
AAGATCCCAATAACTTTAACTGGGCTAAACTTAAAGATGAAATCGATCTAATACTAATTCGTGTACAA
TATGGATCAAATACTATTGACCGTCAATACAAGAAATTTGTTGAGCTTGCTAAAAAACATAAAATTCC
TTTTGGTCACTATGCTTATGGTGTATTTGTTAGTTCTAAAGATGCAGTAGTTGAAGCTAATAACTTTTA
AAACGTGGTGATAGTGAAGCTACTGTATGGGATTTTAGATGTAGAATCCGACACTATTGAGTCATGTAA
AAATTCTCCTCTAGGTGAAGCTTCTCAAGCATTTATCGTACTCTTAGCAAAGCCGGAAAGAAAACTG
GTTTTTACTATGAACATCGTTATATTGGAAAATATGGTTTAGATAATGTTAAAGCTGATTTCCGCTGGA
TGCCACGCTATGGAAAAAATGATGGTACTTTATCAGGAAGTGCTAAACCTGATATTTCTTGTGATTTAT
GGCAATATACTAGTACTGGTAAGCTAAAATCATATTCCGGTAGTGCTTTAGACTTAAGTATTCTTAATG
GTAAGAAGGATATTAAATACTTTACAGGTAAAGCATCATCAAATAAACCATCCACTGTTAAACCATCT
```

-continued

```
AAGCCTTCTAAACCTAGTGATTCAAAAGATACTGTAAAAACTACTAGTTATTATGTTACTGCAACTAA
ACTTAATATTCGTCAAAAACCTGATGCTGATAGTAAATCTTTAGGAACATTGGATCATAATGATCGTGT
TCAAGTTATTTCAATTAGTAAAGGTTGGGCAAAATTAAAATCCGGTAGTAAGAAGTATATGTTTCTG
AAAAATATATTTCTAAAAAAGCAAAATCAAATAAACCGAAACCAGTAACCACTAAGACTTATACAGT
CGTAAAAGGGGATACTCTTTCTGGTATTGGCAAAAAACTTGGAAAAGATTGGAAAGCATTAGCTTCTA
AAAATAATATTAAAGGTCCAGCTTACGTAATTAAACCAGGACAAAAAATTAAATATTAAATATTTTAT
TCACCATACAAACAGATCATTATATTTAGTGATCACATATGTTTGTATGGTGATCTTTTTAAGAAAGAG
GGTTTGAAAAGTTGACTAAACAATCAATATTATTAAATAGTTTTGAAGAAAAAATTGAACAGGCATTT
AAAAATAGTAGTAATGTAAATAAATTAGTAAAAATTGTAAGTCAATATATTGATAAAAATAGTGATAT
ATTAAATCATAATACACCTACATATCGACTAGTGTTTGCTCGTGAAGGATATGATGCTGAAGTTATATA
TGATATAGTTAATATATATCCTGAAGAAATTAAAGAAGTTATTTCACAACTAACATTTATTCGAAAAG
AATGGAAAGTAACCAATGAACCCTTTTCGGTATTAATGACTTTAATTATTCGATATTTTCATTTAAAAA
ATAATCGTAGAGCATTGCAATCTGCAATAATGTATCTTTCATTATCATTTTATTCATCGTTACATTTTAG
ATCATTTAGATATGAACCGAACGATAATATTATGCAGTATACAATTAACCGTGTAAGTAATAAATTCT
ACTTTAAACAGTACGGTACAGTATTTAAAGCACTTAATGCTACTGCTGACAAAGCAGATATGAATCTT
AAAAACTCTTTAAAAAAGAATGATGACGAATTAATTATTGCATATATGACATCCCTAAGAAGTCGTCT
TGCAAACCAATTAACTACTTTTGCCCAAGAGTTTTATAAAGACCATGCAGCTAATAATTATTTAAATAA
GGTATCGGATGTTTATGATGACGAAAACCATATTGAAAATACAAATGTTTCTGGAATTGTGATGTCAC
AAACTAGTAAAGTATCTCTTAACTTTTATCAATCTAGACTTAATGAAAAATATATTATGATATCTGCAT
CTACTTCTAAAGTTACGGCTAATGCAGTAAGAAATACATTAGAAGATGTTAAGGAACATGAACGAGA
AAAAGTGGAAACGATTATTCGTAATACAATATCAATATATTTAAATGATCGAAAAAATTCGGTAAACT
CAATCGGATCACAGAAATTTATCAATTATTGTATTGGAATATATACAAAAAGTAATACAAAAGAAAAA
TTGGTATTAGAAATAAAATCAATATTAAACTATTTCTTAAAAGAATACTGTGATAAATATAACAGTAC
TGATAGGGAAGCTACTAAGAATAATTATCGTAAAGCTGTATTTCTTTACTTTATATTCTTAATCAGTGC
AAATAACTAAAAAAAAAAAATATTAAAGAATATATCCATATAACCAATAATAGGTTATATGGATATAT
TTTTATTGCTTATTTAAATTTCTTCAGTATCCCTTTTTATTAATTCATTTACTTTTTTCTGATATAAATATA
GTGGATATTCCCATTGAAATCATTGTAATCAGCATAAGTGTTAATAACGCTAAAATTAAAATTTGCATA
ATAATCATTATAACCATCCTTTTAAATTTTATTTTTCAATTACAGTACTTGTAATATTACCATCAGTATC
GACTCCAGTCATTACAGTGTATGTATTAACTACAGCACCCTCTGCAAATACGCCATCAGTTCCTTTAGA
TTTTACAAATACAATGTATGTATGTTCCCCATGAGGACCCATTTGTTCATTGTCTTCTGTAATATCATAA
TATAAATTACTAGTATTAATATTTCCATATTTTTTAGATACAATTGAAGCTAGATCTTCATTAGATAAT
GTTGTTGACATATATACTTGTTGATAATTATTTAGATCAACTTTTTTACTATTTTTTACTTGTTCTTTCAT
TTCGCTTAATTTACTTTGTTTATAATCTACTTTATCAATAGATAATGTTTTTGATTTAGTGTTATATTTAA
CCGTTTTATCTTTAATATTGAAAATAAGATTTCCATTTTTATCATCTTTAGATTGATATTTGTCAAATTT
ATCATTCAATACTACATTATCATCTACATGACCGATTTCAACGCTAGTATAACTACCTAATACTAAATG
ATCTTTAGTTAATTTTACATATCCTTGAGTATCTTCATTATAATATTCCCCAGTAACTGTATTGATATCT
GGAGTCTTTTCTTTTTTAATTGTTACTTTCTTTTCTTTTTTCTTATTTTCTTTAGAAGGAGTTTTAGTTTCA
ATTTTCTTAACGTCATTATCTTTCTTTACAAAAGTATAATTGGTTGACACAATCCCAACAAATATTCCA
AGGGCAATAGCTACAGTAATAATTCCAGTTAGTATTAATTTCTTTTTCATGTTGATCCATCCTTTTCTTT
TTTTTTTTATTTAAATGTCTAATACCGAATAGCTAATCGATATTAGACATAATTGAAAATTTATTATTTT
TATTAATTTTTTTATTAATTAAATTTTGAATTTTAATAACTTCTTTTTTAAATTCTAAGTTTCTATCATCT
ATACCTTGGATAACTTTATCAAATTGATTATATCCAATAATATTTACATATCCTTCTAGACCAGAACCT
TTTATATCCTTATAACTGGATATAATAAATGATTTTGCATTACTTTTTTACATAAAATTTGAATTATATG
AATTATTAGTTTTTCTAATTTTAATATATGATGATACCATTTTCTTAACTTGTTTTTCATTCACAAATAA
TACTTTATATTTATCATTGATATATACTTCTTCAGGAATAATTCTTCTTTCTAACATGTATGGAACACTT
TTATTAAATGTAATTTCTGATGTATCATTATTATAAATAATATTATCATCTTTACGAATATTAATATATT
TATCAATATCTTTTACAGTATGAACTGCAGATAACTTATCGAAATTAATATCAAATTTTTCCATATAAA
TATAAATATCTAGTTCACCGCTAATATATTTACCGTTATCATATGTGATTATAGATACGGTAGTTTTCGT
AGTTCCATTAAATTCAGATGTTTCGATATTATGCGTATTAAGAATTATATACTTAAGATTATTATTATAT
AATTTTTTGATCTGTAAAAATAAGTCATTTACACTATACATTAGCATAATAGTTAATACCAACTTCCAT
TATTAATTTTTAATACTAGGATAATATCTATTAATTTAGATATTATCCTAGTGATATTTTATTAATCTTC
AAATACAACGAATCCGTAGATATTAATTGGATCTTCTACTTCAGTAATTACACTAAATGTATTTCCATT
AGCACCACCATTATCTTCTACTACATAACCACTGTGACCCATCACTTCAGTAATATTATTATCCTGTAG
TTCTTTCATCTTACCATCATCAAAAAAGTCAGGATCAATTTCATCCACCCCTAATGTATAACTTTCTGA
AATGACTACATCTACACCATACACTTTTTTAATTTTTTCCGTTAATTTTACGTCTAATGACATAATA
AACACTTCCTTATTATTTATTTTATTTCATGATTATAATATATATTTGTAAATGTCTTTATTACGGATTA
ATCGATATTCTTTTCCTTCAATAGTATTTATATTTAATGACATAGGATTAATATGTGGATGTAATACTAC
ACGTTTATAACTGAATACCTGATTCATAAGTTCAATAATATTGTCAGCATCAAAATTATCGTTTATATA
TTCAATACTGTATATAATATTTTTATGCATTGAAACATTTAAACCAACATCAATAATTATTCTTATCTAAA
TATTCTTTGATTAGATTAAGTCTATTTACGATATCATATTGGTCTGGAAAACAGTTCATTAAATGGCTT
GCCCTTCCTTGAATATTTTCTTCAATTATCATAATTTCTTTTATTTGTTCTATTATATTATCCAACTAATT
CACTACCTTCTTTTAATATATTTGATAATTCTTTATAATATTTTCCTTCCAATGTAGTAATAATATTATC
ATCATTGTCTAGAAATATTAATGAGAATATCTGGCAACTATTTCTTGCAATAAAAATAATTTATTAACTTT
TTCACCTTTTTCTAAGAATGTATTAAGTTTAATATCATAATACTTATAATAAAGACTTCGCATAATCCA
ACCAATATCACGTTCTTCTTGAATATATAATGTATCGTCATAATCTGGAATAATATCTAATTCATATAT
TTTTTCTGAATCATCATAATTGTATGAACTAAACTTATGTTCACTATTAATTAAGGTATGTGGTCTATCA
AAATAACATTTATCCTCTAGTATTGTACGATTAATATCATTACGTAAATATCCTAAGAATATCTTTTTAT
AATGAGTATTATTAGTAATCCAATCCGAAATAATACTAAAATCATTATTATTAATAACTGGTTTGATT
CAATATTATCCATTATTAAACAAATATCTATAGTTTTTGTTTCTTGATTGAATATTCCAATTTCCCATAC
AAAACTAAACCAGATCTTTTTACCCATATATCCAGTCAATATTCCTGCAAGAGGATTCTCTAGAGATAT
TTTTACTAAAGGTGCAGCCAATCCATTAGGAGTGAAACAACATTTTGTTTTAACGCCAATATTCATTAT
TTCATCAACATCTTTAGAAAAGTAAATAAATTTATTACTATGATTATTGGATATATTCATTTTAGATTC
AGATACATTATATTTTGTACCTGCACGAGCCAATAATACATTATTGATAAATACATTTTATTCATTTCCTTATAA
TTTAGGTCAGATTTTCGAATTACTTCATAATTCATAAAAGGTAATAATTTAATAAACTTATCATTATTA
TATTTAGATAATGAACTTTGAAGAAAATTATATGCTTCATCAATATAATTACTATTTACTTTTTTTATTTG
TAATATATTTATTAGTAACTTTATTAGGAAATTCACTAACAAATCGATGAATGGATATATTATTGACTA
CGCATTTATTTAAAATATTCATTAACTGTTCATATGAAAATAAATTAAACATACGATATAAACCATTTT
TCTTTTTATATTTAACAAATTGTATGTCAAATAATTCAGGTTCTAATTTATTATCAAGATTATTATTGTA
CCAGTCCTTAATAAGCTTTATCATCTTATACATTCTTTTTTTTTACCAAACTTATCATGCAAAAACAGTATT
```

-continued

```
TCATGTTCTAATTTAAAATCAGTAATTGAAGCACCAATACCAATATTTAATTGATGTAATTTTTCAATT
ATTTTAATTTCATTATAGATTTCACTGTCAATTTGAGAAAGTGAAAGTACATCTTTATATAAGGATGCA
ATATATTCTTCATATAGTACATTATTATTCTTCAATTTTTTCATCACCACGCTTTATAGATTCAAATATA
TTAATATACTTATCATATAATTTTCTAAATTTTCCAGTTTCATCAATATGCAAATAGTATGACATCTTAC
CAAGTAATTCATAATCATCATAATAACAAGATCCGGTTTTCATATATGAATATAAGTTATTACGCATAT
CATCATACTTTTCTGAACTTAATGTTAATTGATTTTTATGATTTATCGTAATCCCAGTAATATTACGCAT
ATTCCCTTTAAGATAGACAGTTTTACTATCATTAATTTTAAATTTATCATTATATATCTTGAATGCCTGA
TTACATATCTTAATGATAAATTTTTTATTAAATAGTTTATTATTGTCAATATTTGTTGAAAAAGTAATAT
CATCCGAATATGAAGAACAAATTATTCCATATTTATGGAATATGGTTTGTATATGATTAATAATATCTA
CCATAATAATATTCGATATTACGCCAGAAACTGGATTACCTAGAAACATTTTATCATTTTCATCAACAA
AACCTTTCTTTATAGTATCCATATATTTATCAGTAACGCCATGGAATAATAGTAATATGAATCTACTAT
TAATTAATTTCCAATCAATACTAGGAAAATAATTAGATATATCTACTTTAATAATATATTTATTATTAA
GGTGCATTAATGCATTATCTTTTATAGATACATTTTTTCGATAAGCCATAATATTTGGATATTTCAAGTT
TGATATTTTTCTATCTAATCTTTTATCGAGGATCTTAGAAATTTCTTTTAATGTATTTTTAATTTTTATAT
TTGGATCAATAACTTCACGTTCTTTACCATTTTTTTCTATCTTGATTTTCTTAAATAATTCAATATTATTG
TCCTCTAAGTCTTTAATGATACAATATAACTGAATTATTTCTAGAGACATTCTTCTTTTTAATAATAATT
TTATATCACTGGCATATTTACTTTTAAGTTTATAAATTAGATATTTACTATTACTAATTTTAGAGTTGGG
ATATAATAATATATATCCTTTACTTACTGATACAAGAGGTGTAGATGAAAAAGATCTATACATACTAA
AGAATTCACTATATTCCCTCAGCTCAATAGAATTCTCTAATAAATATTTTTACTATAGTTAAAATCTAT
ACTGTTGGATGTCTTATAATAATTCATAATCTTAATTAATAAGTCATAACTATCCTTAAATAGTATATT
ATTTAGCTGAACTAACTTTTTTTCTGAATTATCAAATCTTGATATTATTTTAATATCTTTATCATATGGA
TAAAAGATCCCTTTATTAGTTAAAATTCTTAATGGATTCTTACTAATTATTAATAAATCATTCAATATTT
ATCTTCACCTTTCTTTTTATTGTTTTCAAAAAAATTTAAAATGACCGAACATTCTTTATACTAATAATGT
ATAAAGAATGTTCGGCTAGTATATTTTAGATAGATGTATACTTTTACTACTCAAATATAATAATACAAA
TTACGTTAGTACGAATATACAGTATACCGCACGCGCTGAGTGCGGTATACTAACACGCAACCGAAATC
TATGAGGTGCGTGTTAGTATAATTAATATTACAGAGAATAGTGTTAAGTGTTTGAATGCATATTAACG
ATACGTTAATGCTTCTCAAATATTAAATGATATATTGAGAAAAACTAATATTATATTGATAGCTTAATA
TACATCTATTAAAACCAAAATTATATTATATTATTTACATAAAATAATAATTTTTTATTATATATAAAA
TCAAAAAACAGGAATTTATTGACCGGGGTCCGAATAATGTCGATTTATCGCATGAATGGACCCGAAGC
AATAAATTGCATGTATAATGGAAATAATTTTTTGACTAGTGACGATTACATCACATATTAATCATTTTA
TATATAATATATTAACTTATAAATTGTAAAATCCAAGAAATTTATGAAACCGCAGCTCACGTCCCGAG
TAATTTATAACTCGGAAATGTGAGCTGCTGGTTTTACTAAATGATAATGATAGAGACTTTTTTGATTAG
TGACGATTACATCACATATTAATCATTTTACAATTTATAATTACGTAAATTAAATAATATTTTGATTTAC
TGATTATTAATCAGTCTAAAATATTCCTTCAATATAATGATATATACTTAAAATTTAAGTAAACTTTAA
AAGCATATATTTGAGAAGGATACTTATAATTAATAGTAAATTGTAGAATCTAAACAAAAGAATTCAGC
ACTTCATTCGTACCTGACGTAACTAGTAAGGCAGGTACGGAAGGATGTGGAATTACTTTAATAATGA
TAGAAACTTTTTTGATTAGTGACGATTACATCACATATTAATCATTCTACAATATACAATAAATATTAA
AATTTAAGTAAGATTTAAAATCAGTGAAAAGATTTGTGAGATGTCGGATCGGATCGAGAAATACTTGT
ATGAAGCGATCAGATACTCTGATATCAAACAATCAATAAAATACGACATATATTGATTAGTGACGATT
ACATCACATATTAATCATTTTATATCTACTTAAATTTATAAATTAATAATAATTTTTGCATCTTCTTTAA
TATTAACACTTTCCGGTCTAGAAGTTTTTAGAGAAGTTCTATCATTAAATCGAGTATCTTTAATAAATT
CTAATCCATCAATATTAATTCTTTTCATAAACTGTTTAGAATTTTCATTAAATGATGATGAAATATATTT
AATGTCATTATCAATAATAAAATTTCTTTAGATCTTCAAAAATATACTTAATACTTGAGGTAATTTTTTTA
TTAAATGGAATTACAATGTCTTCAATATACAATAATTTACTATGGGTATCCGTATTAAAGCTTCTATTG
TTAAATTGAACGCTCTCATTTTCCGGATCATAACCATAAATATTAGATATTAAATATCCATAAATATCA
TTGTTATCATTACGAATAATATATGATGGAGACTTCATTTTCCTAGCAATTTTCTTTAATTCAGAAATAT
CGCTATCTTGTTTCCAAACATTCTTTTCAACGTATAACATTCTATTGAACCAACCCGGTGATGCCTTTTC
AATAATAACTTCACTATATGGAGAATATTTTTAATAATATCTTTATTATCAGAACCAATATATTTAAT
ATTATTTTTACGATCTAATACCGTAAATACATATCTTGAGTCGTCAAATGATGAATATCTATTGAAGTT
ATTTTCATAACAAATTAGCCCTTCACTAGAAGATCTTAATCTCTGAGTATATGAAACTTTATAATTACT
ATTAATATCATTACGTAAATATCCTAAATATATTTTATTGTAGTCTGAATTAATATCAAGCCAGTTAAT
AATATATTCATATTCATTCATGTCTAAACTTTTTGACGATTCAATATTATCTAGAATTAAATTGGTTTCA
TATGATTTAGTATCTTCATTATATTCAACAATCTCCCATACAAAACTAAACCACGTTTTAGTATCAAAA
ACGCCCTCAAGAATCCCTGCGATTGGACTTTCAATAGCGGGTTTTAATAATGATTTTGCAGCACCGTCT
GGTCTGAAACAACATAATGTACGGAAACCAATTGAATTAATGTCTACTTTTTCTTTAGTAAATTTAATC
ATATCATTATATTTACTATCGTCAAATAGCATTTCACCATTAGAAGTTTCCCCATAGGATAATCCTTTTT
TTGCGTTATCAATAATATTAACATACTTTCTTAGATCACTAATATTTTTAGATTCCCTAACACCTTGATA
ATTAATATAGTTTAATAGCTTAAGAAAGTCTTTACTTTTATAAATTCTTTTAATATATGCTAATATCGTA
TCAATATAGTTTCATCATCATCCAGTCTTTCTATTGCAGTCTTTGGAAAATTCTCGATAAAGTTATGAA
GATCTATTTTATTTTCAGAATTACCCTTATTATATGCATATGAGACAAAATTAAGAAGTTTAGTTGCAT
TATCATATGAGATTCGAATTAATAATGAATTTAATTTACTTCCATAATTACTATTTTTTTCTTTAAGATT
TGATATAGTAAAGTTACTAGTATACTTATCCTTAAACATTTTTGGATTAATACCTAAATGTGACTCAGA
TATAAGATCTGTAATTTGGTAAACATCCTTTAATTGTTTAACAGGTCTCACTAGATTGATATTACTTCTT
AAATCATTATTTAATTTATTTGTTATTTCTAAATCCATATTAAATTCATACTTATTAATGCGATCACTGA
GAATACTATCTTCGCATGATAACATTAGCTTCATAATATTGATTGCTTTTTTCTGACTGTTATATAATGC
GGATAGATATATTAATGCACTAGTAAGTCTTTCACTATTGATTAATAAAAATTCTGGAGGAATAACTCT
AAATCTTCCAATGTCATGTAAAGAAGTAATATTATTTATTACCTGTAATAGATCAGAATTATCCATTGT
ATAGTTAAATTTAGAACAATAGTCTAGAAAATTAGAGAATATTTCATTTATTCGTTTAGATAATTTTTC
ATCATCTATATTATTGTAGTTGTCATATAAATACATATTATGATTCACTTCCTTATTTATTAATCAACTT
TAGGTTCATTAATTAATTTTAATTTAATTAACGTATTTTGATATTCATTTACGAGATTTTCCATTTTATT
AGTATTATCGATATAACGATAATAACTAATTCTACCTTTAAGTTCATTAAATGTCATTGAAATATTATT
AATATTATTTTTATTCTTAGATAATTTAAAGAAAATAGTCTTTAGTAGTCTATACATTTTCCTATCTAAT
GTACATTGATCATTGTGATTAATTCGAATCCCTGTAATTCTTCTTTTGTTATTCGACATTTTAATAGTTT
TTTCATCTTTAATAGATAAATTACTATAATTATATACTTCAAATGCCTTATTAAGAATGAACTTCAAAT
ATTTTCTATTAAAGAATTCACTTTTCTCGTTTGATGAAAAGTAATATCATCTGCATAAATAGAGAATG
TAATACCCACTATCAATTAATACATTTTTAAGATATTTTGCCACATTACTCATTAACAAGTTTGATAATG
ATCCAGAAGCAGGATTCCCCTGATATAATCCACCAGTCTCTGGATTAATAAAGATTTCTTTGAATAACG
TATCCATTACTGAATCTTTATTATTCTTCTTCTTAAAATTTTCTTTACCTAACACTAATAATTTAAAGTA
CTTACTAATATCTTCATATCTACAATTATCAAAGAATGAAGCAATATCCATTTTAATAATATATTTATT
```

```
ATTTTTATGAACTAATGCGTTATCTAGTATACCTTTTTTCTTTTGATAAGCAAATAAATGTTTTTCAACA
CCTTTATTAGATAATTGAGTTTCTAACATTCCATTAAAGATATTATTAAATTTTCTACTAATATCTTTAA
TATCATTATGTGGAGCATAGATATCTCTAATTTTTGTACCTTGATTAATCTTGAAATGTTGATATAATTT
TTCATTATTATTCTGAATTAATATTCTGGTTAATAGTAACTCTAGTAATAATGGTTTATTATTTGGTTGA
TCTGGCGATATACTTATATCTAATAAATATTTAATCATTTTAATCATTTCTTTATCATCTGTGATTTTAT
AAATATTATATTTATTGTATATATCATTTGTATTTGTAATAATATAGAGATAACCATCATTCATTTCAAT
ATATCTATGAGATATATTGAGATTTCTATAGGATAATTTTATACTGATATTATTAATAAACTCTGTAAT
TAAAGTTTTATCATAAGTAACAACTGGTAAATCGGGATATCCTTCATTAATACAAATTTCATCATTTGA
GAGCAGATCATAAGTCTTAATAATTTTTTCTATATTTTCTAGATGAATGTCATTAAATTCCTCGTTATTT
TCAAATTTATTATTTTCTTCTAGATATGATATATCTTTTATTGATTGAATCAATTTATTACGGATATTAT
ATTTAACTAATTTAGCTAATACCTTTTTATCAGAAATAATATTCTTTTTCATTCGAATATCTATTTCTGA
TACAATCTCTCCATTTATATCGATTAATACATTATCGATTAATATTAGTGATAGCAAATACTGTCACAC
CTTTCCTTTAATTATTAAATTATTACTACATAAATTTACTATTTAATATTCATTATATGATCCCACCTAT
TTATTTTATTTTACATTTTAATAATATATAAATAAAATTTAAATAAATATTCCCGATATCTCTATAATAG
GAGATATCGGGAATATATTTTATTTAGTTACAGTTACGTTAATTTTTCTTTTCATGGAAGTAAAAGATT
CAGGAACAACGGTAATAATTGTTTCACCTTCACTTACGCCAATAAGTTTAGATGGATTATTCTCATCCA
CTTTAACGAGTTCTTCACCTTTTTCTAGAATTATCAGAACCTTATCACTAACGAGATTATCAGGAGTCA
TAGTTCCGATAATATCTTTACTTTCGCCTTCTTTTATAGTAAGATCTTCATCTACGCTAAAACTTTCTGG
TTTGGTAATTCTATCGTTAATTACAGATATTACGTCTATAGTATCAATAGGTGTATACCACGAAGAAAC
TTGTCCTGCAATACCTCTTGATTCATCTACTACTTCATCATAAATGATACAACCGCTTACATCATCATAC
GTAAGTCGATGTCCAAAAGCTCTTGATGGAAAAATTTGAGATTGGGATGTTGTTACAATTGTGGAGAT
TAATAGTGGATCAGATAAATCATTATGACGATCGATAAATCCTTTTACAGTTTCAATAGCTATCATTTT
TATTATTCATTCCTCTCTATTTTAACGAATATTTTTTCTGCGATTAAATTCAGCTTCCTCTTTCTTTTCAT
TAAGGATTGTTAGATGAGTATCTATTCTATCTTGCTTTGCTTCCTTATCACTTTTAAAAGTATTATTGTT
AATAATACTTTCACTAAATACGTTTGGATGAGATATATTGCTTTTTTCATTAAATCCATCATTGAAGAA
AATACTTTCATCAATATTTTATTATCCATATTTATAAACATCCTTTCCTACATGATTATAAACCTTCAA
AGAACTTCCACATATTCTCATCAACTTCTCCAGTAATAACCATATTAGATACCATTTGTATTTTTCTTAC
ATTATTATAAGTATCCTTATCATATATTCCTGAAACACTAGTTGTTGTAATTGCAAATTTACGTTTATTA
TCATTTATCTTTGTTTGAATAAATAATACGTCTGGTCCTTCCATAAGAGGATTACTATATTTAAGAACT
CTTGTAAATTCAACAATAAGCGTATCAATAATATTTTTCCATGTTATGGGTCCAACAATTCCATCTTCA
GTAAGATTATTTGAATGTTGAAATGATTTAACAATAGTTTCAGTAGAACTATCATAAGAACCAGTAAC
CTCAATATCATATCTTAGTTTTGAAAGTTTATTTTGAAGCGTAATAATATCGTCACCTATCATCATTGGT
GATTTATAACTAAGCATTCGATGATAGTTTGAATAGTCTTTAATATCATTTAATGCAATTATCAATTCA
TTAATTTTATCAAAGTCTTCTTTCTTCATTCTACCATCAACTTCTAGATTAAATGTTTTTTGGAATATTCT
TACCGAGTTATATGTGTATAAATCATAGATACCATTACGAATAGTGATTGGGATATTAATCATAGATA
AATATATTTGTAATAATTTAACGTCATTACCGATAACTGGTTTTTCTGGATCATAGTAGAATTCCCTTTT
ACCAAAACTATAAGAAACAGTTCCTGCAGGATTGTCTACATACATCGGTACAATAATAGAAAGAATTT
GGGAACGAAGAACATTCATATCAACTAATGATCCTAGATTACTATATTTTGCATAATATTCATTTAATG
AATGAATGTTTCTAATATTTCGATATCGACCACTAATATTAGCACATAGATTCTCTAGAGATACATATT
GGCTTTGAGTTAGGTCTTTAATCTCCGTATTTCCTTCAAGACATATAAAGATTTTACTAGAAGATACTG
GATCAGTATTATCAATGAGTTCAATATCTTTTCCAGCAATATTTTCATTAAGATACATTTTCCGCATTAG
TAAGTCAATATTACAAGGTAATGCTCTTTCGGGTCTACCTGAAATAATATCCCCTTTTTTAGTAATATA
ATAATGGAATGCAAACATCTTTAATCCTAACCCTTTATGAATTGATTCTAATGTATCATAATCCATACT
AATATTACGACAATCTAAAATAACTATATTTGATGGATTATTCTTGTATATAAGATCTTTTACCGGGTC
AGGAGTTGTATCTACATAGTTCTCATCAGTATTAGCATCCAGTAAAGATAACATGTATGATATATGACT
TCCCCACATATTATTCCATTGTTTTCCATCTACTGAAAAAGTTCCCGCTAAATCATTTTGATCATAAGA
ACCGCTTCTTGTAAATTTATTTAAGTATCTTAAACAACGGTTTAATAATGAATACGTAGTAGATATTTC
AATAGTGTCATTTATGATATTTAAATAACGGATACACGACTCTGCAAGAATGCTTGCATAATAGGTATT
ATCTCTAGCACTGTTTGGTTCATATACACTATTAAATTTTGTGATTATCCCTTTATTTTCAGAGTTCCAT
ATAGTATTAATAGATTTTATAAATTTCATAATGATATTATTTACATTATTATTTACGTAACCTTTTTCAA
GAAGTCTAATTAATGAATTAATGATTATATTGAAACTCTCCCCAATCTCCTCTTTGATCTAAACCTT
CCCACCTAAAACTATTAGATGAAATATCAAAGATAGGTTTAAAGAAACCTTCTACACCTTTTTCATTAT
AATATTCTTTTTGAGATCGATCTAAAATATCAATAAGTTTAGTTAATTCATTAATCATTCCAAGGTCAT
ATAATACTTCTGGTTTTTGATAACCTAGATATATGTCATCGTTCCAACTATCAAGCTTATTATTAATAGT
TGTTATTGAGTTAGGTAGCATTATATTTTTCATATTATTAGAATAATTATCAACGCTTTCGATAATAATCG
ATATTTATAATACTAGGAATATCTTTTTCCTTTTCAATATAAAACTTATTAAATGTACGATCTAATGAAT
AATTTAATAATGATCCGATATATTGAAGCTCAATGAAAGAAGAAGTAACCTTACTTTTAAATATTGCTT
TGGTTAATGGAAATTTAACAGATTTTCCATCAGTATTAAAATTAACTTTAATACTATTAAATAAATCAA
CTGATTTAGGAAGATTTAATTTCCATTCTACATTATTACTATCATAGATATATAAATCAATTCCATCACT
AGCACGATAGCGAATTGTAGGGTTTGTTTTTGTATTCGACTAAAAGGAATAACCATGTTTGACCAACC
ATCATAAGAACCATTATCATTACTTTCTTCATTAATCGTAAAGGTAGCTTTAATACTATTCCGAGTTTC
ATCATCAGTAGATTTCACTTCAATAATTTCAGAAATACTATTCGGAGAACTCTCTGCAATATATAATGA
TTCTTCAGGAAGATTAAAATTATCCCAGATTACTTCACGGTAATCTTTTAACATTTCAGGAGTCAATCG
ATATTTATTAAATTCATTATCTTTTACATTCGTCTTATAGAATCCAATATTATGATCTTTATCTTCAATA
ATAAATTTTAATACTTTATCATTATCGGTTTTAATTCTAGATTCTATATATGAAATATCTTTAAGCGTAA
ATAATTTATTTACGCCAAAATGAATATCTTGATTAATTGAGATTGAATTTAGTATAACATTTCCATTAG
TATCATCACGATAAATTAATACAGAATCTGAACTATCTTTATTAATAAAAGAGCCACTATCAGATAAT
GGATCCAAATTATTTATTTCAGAAGTGATCCATCTAGGTTTAATTGGCATATCTAATATAAATTTAATA
GTATCTTTTGTAATATCCCTTGCCCTCATCCATTTACTATTCGGTAAAATATCATAAAGATTACTATAAC
ATTCATAAGAAAGCAATAAACTTTCAATACTGCATATATTTTTATTAGGATCCAGAGTATGCCAATAAT
TTGTAGGATCATATTTCTGATTAGATTTAATAAAGTTATCATTATCTAATTGAGTATATACTAGTAATA
GCGTGCTGTTAACATCTTTATCTTCTAATACAATCCTTACAGTATTATCTTTACGGATATAATACTCTTC
AATATCATAGCTTATACCTATAATATTAGAAGCCGGATTATTTTCATCACTTAATTTAGAACCAAAATC
TCTAACACTAAATAATTTTTTAAAATTGCTATCCGTACTAAAAATTGCAATACCATTAACAAATTCTGC
CGATTCATTCAATATTAATTTTTCAGAATTAAAGGGTTCCGATGCATTATATGTAAAATGAGGAACCCA
TAAATTATCTTGAGAAAAACTAGTTGGAACATCATTTGGATATAAGGTATCAATGGTTGCATTCATCGT
AGATTCTATTAATTCTAAGGATATACTTACGCCAGAATTATACTGATATATAAGTGAATTAATATATTG
AAACTGCGAAGTAGATGTTCCTGAATTAATATTAATATAATCAAATAAGTAATCTTCTTTTATATAATT
TAATCTAGACATTGAATTAAGATTTATAGATAATGGACTAGTGTTTTTTGTATTTGCACTTACAAATTT
```

```
ATTATATTCAGATATCCATTTTCTAATATCTTTTAAATGAACATCTAATTTCTTTTCAGAAAGATATTTT
GTCAAATTTATCACCGCCATTCATATTATAACATTTTGTTTAATATCAATTTAACTTTTTACCCAACCTT
TAGTATTATTATATTTATATTTAACTGTAGTAATTTTAGTTTCATTAATAACTTTCTTAAGACCTAATCT
TAATACAAGTGAATCCCTATTAATAATATTCCGTGCAGAAACATATCTAACTTGTTTTGTAATGAATGG
AATTGTTCGTTGAACTGTAGAGAATGGACTACTTGAGTTGTCTCTACTCTTTGGTAATCTTTGAAGATT
ATCAGAGTTAAGCGTAGATATTCGATTAAGACCAGTAGGATCGATCTTCCATTTTTTACTTTTTACCACC
AAGATTAACTTTTTGTCGCCACGTTGCAGATCCTCCACCATACTTAACGCTCGGGTTAGGTGAAAATCC
ATTAGACGATGTAGTAAATGTAGTTTTAGACGCAAATCCTGAAGGACTTTCATATAATGGCATTAGTA
AATTAGATGGACTTCTAATGTATCCAATAGTATTTGCAGGACTGCTTGTTGTTCCAGTTAATGGCAATC
CTTCAAACATATCCCATGATAAATATCTATTCGATATTCTAGTTCCAGTAGTTTTATTTACTTTATTATA
GAATCCTCGATAAAATACACCAGTACCTTCAGTAACACTATATTTTTCACGAGTTAGAGGATCAATTGC
CGAACCTTGATAGAACCAATCAGAAAATCTAGATCTTAATCCAACACAAGCATCTACATATTGGCTTT
CTGAAGTATAATTCGAACTAGAGTAGTTAAATAATCTTCGATCCCAACGACAATCATATGCAGTTTTTT
CATATGATACACTTTTTTGTAATTGCATTGTTCCTGAAAAACTTCCCATTTTAATTAATTTCTGATTTAC
TTCATCCATAAGTGTTTTAATATTATTCCATATCTGTAATAATTCAGTATTCTTACTATTCGCATCATTA
CTAAATGCTTCAGTCAATGAATTATTACTAAGGTTATTGAATATATCAATCTGACTTTGTATTAAGTCA
TTATATTGTCCTAAGTCTAGTCCGTCTAATTGTAATGATATATCACCTAATTGGTTTACATTATTCTTAC
TTATTTTACCTAGATATACTGTTTTGAGTCGGGCAGACTCCCATATCAGAAAAAATATCTAAACTTGTAT
CAAATATTTCTTCTTGTTTATTATATATTTCATTATATATATTATATAAATTATTAATCTTTCCAGGTATT
ACATTCTTTCTTAATTTTATACCTTCCATATCATTCTCTAGGAAATCAATAATATTTTCTCTAAGAACTT
TAGTAATTGGTATTGGTAAGTTAATACCTTCCTCTGTAACGTATATGTCATGTTCTACTAGATCAACTA
ATAACTCTCCAGTCTTCAGAGTATTAAAATATTTTTGAAGATAGTCTTGATACGACATTGGTATATAAA
TATATCTTGACATTAAAATTACACCACCATTATTATATAATATGTTTAAATGTTATTGATTTAACCTTTT
TATTACTTATCTTCCCTTTAGTCTTATTTACTAATGAAGTTACCCATGAATCATATGTTGATTGAAATGC
ACGAGAATCTACATTTTTCTCAACAGTAGTATATCTTGATCTCATATTAGTTAAATCAGTTCCAGTTTTA
GTCTTATAACCTTTTATAAAGTTGTATAGATATGTTAATTCAGATATTCTTCTTTGTATTGAAAATATTC
CAGGAAGCTTTTCTACTACTTTTGGAATAATTGTTGCGATAATATCTACAAAACTCCATATATCTACGG
TATTTTGTCTGATTTGATTTTCCAATGTATTTAATATTGCAATGATCTGAGCTAATAATTCTTTAAGACC
GTTCATTCGATTATATAAATCATTTGTTTCAGATAATTTTGTCTGATAGAGTGCTTCCAAATTAGATATC
TCTGTTTCTAATAGAGTAATAATGCTCTTAAGAGTAGAGACTAGGTACTTCTGTGAAAATAACTCACCT
TCAATATCCTTTGTAGCTGATTGATCATTAACAATTAAATGACCAGTACGAGTATTTACTAAAAGTTCT
GAATCTTTCGATTCCAGTTTAGTTTTTTCAGTTAATGGCTGAACGTACAATCTATATGTCATAACTTATT
ATCACTTCCATATCATTTTTAAATTTAAGTTAGCAGTTGATATATTAATTATACCAACTGCTAACTATAT
TAGAAACTTGTAATAATATTTACAAGCTTAGTATAGAATCCTTCATGTTTATCTTTGAATGCATTATATT
TAGTTGTTAATATCTTTTTATTAGCTTCGATTTCAACGCTTCGTAGATTGTAATAGTTTCTACCAAGATT
ATCAATTACTGTAGTATATAGATCGGCATAATCTAATAAATCATTTCTTAATTTAGTAATATTAGTACT
TAGATTCATTAGCTTATTATAGTTTGTTAAGAAAGACCCATCTACATTATTTGTAATACTTGTTATCTTA
TTACGAATATCAGTAATATCGGAAGTAGTTTTATCAACTTCAGCTTTTAATGCATCAACCTGAGTTTTT
AAATTATTTATTCCACCAACAACTGCGTCTACAAAAGGTTTTAATAGATCATTATTACTGTCAATTTCA
GATAAATTATCTCTTAACCAAGATAATTGATTTTTATATAGATTTGTTACTTTAAATATATCATATATAA
CTGTTGAGTTTAATGATAATAAGTTATTTAATTCTTTTGTAATTTCAATAATTTCATAACTACCAGTATC
AGAATTTTTCGTATTAGATACAACGGATATATTTCCAGTATGTTCATCAATAATCAGTTCTCCAGGAAA
TCTAAATAGATCATTTTCTCGACTAAACGGAATTAATACATTTCGATCAAGATCTACTGGAAGATTATA
ATTCTCAGTAACATTATTATCATGATCAATAATTCCGCTAGAGTAATTATTTACATCAATATAATAATA
AGAACTATTATACATATTATTTGACTGTTTTCTAGCGGTAATGATTAGTCGATATATACCATTTACACT
ACTGATATTCTTTAATAATGGGTCACCTATATTGATGATTGAATTATTAAGTGAAGCAGTATATACAAC
TCCCGGTTCTTTATTAATAATATCCAATACAAAAGTTGAATCAATATTAATAATTTTTCCATGACTAAT
ATTCTTAGCAATTGGTTTTGAAGGAGGTATGGTATCAATAGTGATAGTTTTAGATGAAGATGAACTTTT
ACCATTTAACTTACTAGTAGCTTTTACATTTAATGTAAATTTTCTAATAGATTTAACGTAATTATAGTTC
GTAATAGGATCACCTAGAGTATACGGTAAACCATTTATTGTAATTTCATAGGTACACATTGGGATTCTT
ACAATATTAGGAATGATCAAACTATTTGTAAGGTTTCCTGAATTATCTGGAATATTAATTACTGGTAAG
TCTGGTACTGTAACATTTAACATGTCTGACGTAATTTCTAAATTATTTTCAAGAATCATATCATTATCCA
TTATTTTTCTAGCAGTGATGATGCAGGGTTCAGTAATTATAAATGGACCAGTATACTCTTTCCAAGAAT
TGTTAATAGAAGTCTTATACAGTTTACTTTTAATGTGTTCTCTTTCAGACTCAATAAATACATATTCAAT
AGAAATATTATATGACTCGGAATAATATTTTTTATCATTATAATCTATTCTTGGTGGAGTATAAAATATA
ATTCTTAACAATATTAAATTTAAATGTAGTATAACTTAACGTATAATTATGTCTATCTGTAAATACTGC
TAAGAATTCATGAGTCCCTCCCGAAGTGAATGTTGAACCAGAAGTATAATTGTTTCCATCAATATAAC
AATTAAGCGTATAATTTGAATTATTATTCATTACAGTGATTGTTATATCATCAGCACACTGAGATATAT
CTGCAGAACTCACATCAAAAGGAGTTAATGGTTTAGATGATGATATTGATATTGACGGATTAACTGGA
ACTGTAGTTTGATCCATTCCAGTAGTATTAATAGTCTGAGTTGCCATTAATTTATGTGAAGAATCAGAA
ACATTAGTGATATTACTTCCAGAAACTCCGCTAATCGTAACATCATCATGTAAATGGTTTCTCGTTGAT
GTAGCATATCTGTATAATTAATAGTAGAATCAAAAAATATCGGCATATTATAGTTAGGCATAATAAA
TTTTTTCTTACCATTATAATCCATAACATACATACTATTATCTTTATCAATTTTACTATCAGGCTTAAGA
ACAATATCATTAAATAATGGATTAGTATCACTAGATACTGAATCATGATATATAACAGTACTAATAAT
ATCTCCAACTTGTTCTGGTATAATAACTACGTTTACGGAAATCTGTACTACATCGAATCTACGCCATT
GCTAACATTAATATCTAGATTATAATCTCCTTCATCTTTAAATGATAATTTTAGTTTTGGATCATTCGTA
TTAGTGTCTAATGGTGTAGCGGTATATGTTTTTGAAGGATCATCAGTATCTGTAACACTATAGGTATAC
GATGAATCTTTTTCAATATGAATTATAATATCAATTGATCCATCCCCTAGTAATACTATCTTCACTGTA
GGTAAGATTAATGTTGCATTATCATCAGCAATAACTGAGAAAATTAAATCTTCAGGGGGATTAATCGT
ATTTATAAAATTAACAATCATTAATTCGTCTGAATTGAATAGTTTATTTATATCGATTTTTCGATAAATA
TTAATCTCAGTATCAGTCTCATATAGCCCTAGATATGTGAGCATTGTATCTGAAACGTAATCGTTAACC
TCTATAACGTCACCATCATCATTAGTTACCGTTATATTAGTAGATTCCTGTAAGTCATTTACTAATTCAT
TCACATATACTTTAAACGTATACTGATCGGTACCTTTAGTTAGTTTAATATATACGTCATTATCTTCTGC
AATTGTTATTGAAGTTGGTAATGATATACTAAACATGTTATAATTATTTGAGTCTATTGTAATGTCATT
ATCAGTACCATTAATATTTAGTTTACCATTATAAATTCCAGTACCTTCAACGTGATATACTCCAGTAAT
ATTAGAATCGCCAATATTAAATGTATCAATAGATAATTGTATATTTTCACTTCTAACTACTAGTACTTT
CTGATTATCTGCAACTAATATACCCTTTGAGTTGTATATCTTAAATGATATCTCATCCGTATCTGAAGA
TATTCCTGTACTAGATGTTATTTTCATCATTTTATCATTTTTCGTATTACTAAATTTAGTAACAGTTGAT
GTAGTTTCAACACCATTAATATACATAATAATATTATCTAATTCACCCTTATACTTAGCAATAATCTCA
```

```
GTTGGATTATTTCCATTAAAGAAGAAAGGATAAAAGTCTACTGCAGTATAATCAATATTTATTGCAAC
CTTATCATTAAATGTATCTACACTGTCTGGATCATCTGAGTCTTTTGGTATAGAGGGTTCATATGTGTC
ACTATATTTTACAATAGGATCTATAAAGTTGGTATATAATCCTGCAATTGAATCATTCTTGACAATAGG
TATATTTTCATTTCTGATTGATGTGTATGTTGATGGAATATCTACTCTATAAACATCAATATTAGTACCA
TACGCAGAAGTATGTCTAATCGAGTCTGAATTGTAAAGATATTTATTAATATTCGATTTATCGATATAT
CCACTGAAAACATATATATCTGAAAATTCATCCATATTGAGAGTATATTCCGTTACCGTATCACTAATA
AAATCTTCATCTTCTGATATTGATTGAAATGATTCAATTAAGCTTTCTTGAAGATCATTAATAAAATCT
TCGTTAGATAGATCATCGTCATCGCCAATAGTTGAAGCACTTAACATAGTGATATTATTCTTACCAATA
GAACCTTTTACAACTGAACCATTACCTCCGCCAATAATCTGCGATATATTATTATTTACATTAAATGAT
AAATTACTTACATCTTTTGGTAATCTAATTGCTTTATATAGGAAATTATCATTTATTCCTTGAGTTAGTA
TAAATAGTTGATATAATATACTAGAATCATCAGAATAATCAGAAGTTCCTCCAAAATCATTTTCAATA
ATAACCCTAAATTTCAGTTGAGTTAATCCATTATACGCATTTGTACTATTATTAAAATCTTCGTCTCCAG
TAATAAATCTTACTCTACTACCGTTACCGCCTGTGGGTGCTGTACTTTGTAATGTAAAGACTTTATTGG
TAGTACTCCAATTACTCCATTGATCCGATCTTTCATCTTTAACCGAATATTCTAGATATACTTTGTTAGC
CCCAAATGATGGAATTGAACTTATAAAATCTTTATAATACTTTCCATAATTACTAAAGTATGTTATATC
TGCAGGTCTAGAATATAATGGATTAATACCGTTATCAATAAAGAAAGGATTTACATTATCTATCTTAAT
TGGATTTGGTTTAATCCCTTTCATATCATAATTCATTTTAAAATAAAATTTACGTGGATCAACTAATGA
TTTATTAGTTAAATCGTTAAACGCTTCTATTGTTAATTCAAATACTTTATTATGATAATTATTATATACT
GCGTTTGGATTATCGCTTGCCAATGACAAAGTATATCCTGACGTATTCTCTTTATAAAACTTCTTAAGA
TCTGGATTATTAAGTGCTTTTATATTATATCGATAAATTACTGGTCGACCAGTTGAATCATTTACCCCTG
AAAAACTAAAGGTATAATTAAGCTTATTTGCTTCACTAGTGTTTGCAGGAATCACTGTAGGATTATTTG
GATCATTACTCATAAATGTTAAAAATGATCGATCTTCATTTAACATACTAGCAGTAGTAACTATCCCCG
GTGCGCTCTTACTAATATTTATTACGTTTGGCATATTAGAAAGATTATTAAACACTTCAGTATTATCCG
GATCAATATTATCACTATATGATAGTACTGTATTAATTTTAGTTTCATCTGAAAAATAAAATGGATCAA
TATCAAGATAATATAAATCTCCAACTTTAGTATCATAGTTATCTTTAGATAATCTAAATTCGTGTAAAC
TACTCTGCGTTGTTACTTGGAAAATAATATCGACAAAAGCAGAATCTTCCGTACCATTAATATTTTTAT
TTTCTAATTTTCCAAAAATAGAGAAACCGTTCTGATCTCCAACTATAGACTCATTTCCTTCCGTACCGG
ACTCAACTTCTATATTTGTGTATGTTAATGCTTCTCCATATGGATTCTCTACAAAGAATGTTCTAGCAAT
TCCATAATCTGCAGGAGTCCAACTTTGTATGAATTGTATTAATTGTTCTCTAGTATGTGCTATTACTGTC
AAGAAATTTCACCACCTATATTTATAACTTCTTATAATTAATAGTTTAAAAATCCATACTAAGAAATAT
TTAATTCCTTAGTATGGACGATATTTTTATATTATCGGATCAATAATATCCGCTTCAGGATCATAGATTT
TTTGAGGATTCATATCCAAAATAATATTCTGACTAATATATTTGTTATTTATTTCTTCAGAATCTAATGA
AATATCCCAACTTAATAGATCATTATTATTACAATTAATAATAGTTTTTCCACGTTGACGCATATAGTC
CATTAGAATTAATTTCCGGATACTACCTCTAGAATTATCATTTGTTATTCCAGTCAATATATCAAAATT
ACTAGTTTGTCTTACGTTATAGTATGAATGATAGTAATTATCGTTTAAATTCATTTTATCATACTTATAC
CAATCTAATATTAATTTAAGTTGAGTATGATCATCGTAGCTAAATCTAATCATTACATTTATTAATGGA
TCAGCATAATCAATAATTTGAATACTTTTACCATTAAGTATTTTTACTTTACTAGAATCTATTCTTAAAT
TATTAACGTAAACTGTAAATGTGCCTTTAATAAATATTACTGAATCGTCATCTAAACTGAATACATCTG
TTGTTCCTTCAGCCGGCTTACTAAAAGTTCTTATATAGTTGGAGTTTTCATTAAGAAGATTTATTTCGAT
AGTAGATGTTTTAGGTACAATGCTTTTAAAAACAATTAATGACGGAATAGATTCAAAGTCAGGATCAA
TAATGGTATAATCAATTCCAGGATATAATGTTAATCCATCGATATTAATATCGATATCTTCAGGATTAC
TATTAATGTTTGTAAAAATATTTGAATCATCATCTAACGTAGCAAATGGTAAACAATCAATATCATATT
CATTTAAGTCTAATTGATTGTAGTATAACGAGCCACTATTTGTACCACTAGTCAAAAGATGTATTTCGG
TACCTTCATCCATATAAGATGAACCATATACGATAAGTCTTACTGTATTATATTCAGGTTCAATCTTAA
TATAATAATTGTATGGGTTAATTCTTCTAAAGAAATTCCAAGTTTTCTTCTTAATAAAGACTCTTAATTG
TGAAGGAGTAATTCCCGTTGGTAATGCAACATCCGTTAATAGTATACCAGTAGTTCCTAACATATTAGT
TTGATCTTCAAACGTATTATCAATTATATGAGTCTTAATTGTTTTCTCGGATTCAACAATCTTACGTTTA
TTACCAGAGACAATTACTTCATATTTATCCGGAAGACTAGAATTCCCATCTAAAACATCATTAGCATCA
TTCACATCAATATATTCTTTAATAAATCTTGAAGGCATGTATGCATATATTTTTCCATCTAAACTATCTT
GTTGCTTAATCGATTTACGGAAAATATGTTTACCATTAATAAATATATCAGATATTAATGAATTTTGTT
TCTTTTCATATGAACCATATTCCGAAGTAAAATCAATATAACCATCTGAGATTCATCATTAATAAAAT
TATTTATAAACGGATCTTTTGTAACTTTTATTTTAGAGTTATCCAACTTAGTTTCAAATGAATTATGTCC
CATTGTCTCTATAAATAATGTTTTATTACCTTGTTCTAATTCATTAACTAATGATTTTTCAATCATCCGA
ATATCATTGTCTGTATTCTTATATAAGATATCAGTAACATTTCTTGGATCAATATCCATTTGGAATGTTT
TAGTCTCTATAAGTTGTTCTGAATTAGTATTAAATATACTAAAAGGTTATATCTTTATTGGGGGTGAAAT
TAAGTTCATCAATCTGTAATCGATAGTACTTTTCTTCTAATTCTGGAAGATCGTCTGGTTTATAATATAC
ACGTTGATAATTATCATTACCAATGATATTAATTAAGTCGCTTGAAACATCATCATTACTCTCAGAAGA
AGAGAATATCATATTTTTAATCTTTACAGTAAGCTTATAATAATCTTCGATTCTTTTAAAATTATTAATG
ATGATAGTCTTTCCATCAATAGTTATTGTCATTATATATTCGGATGATAATAAATCTTAGTCTAAAA
TAGATTGATCCGTTCAGATAGTATGCATTCTTATATAGAATTTTATATATAATGTCTTCTGGAGTGGCTT
GAATATTTTTATTAGAATATCTAACATCTAAATCTTCATTAAGAACAGTATATCTAATCATATCATTTC
CTAAAGGTAGCATTAATTCTGATAATACTGTTTCTTTATCATCAAAAGGAATATACATATTGGCACTTT
GGTTTGCTTCAGGAAATATCCTACTAATAGAGTTCGATCTATAGTTTAGAGAAACATTATAGTTACTTT
TATCTACAATATCTAAACTATGCATTAAATTAACATGAACATTTAAGAAAAAATTTACTATTTGTACTAT
TATTAAAACTGCGTTTTTCTATCCATGTATAATCAATACTTAAATCAGGAAGATATTCTAATTTATAGA
ATGTGGTATCTCTACTAGAATTATTAACAATAACAAATAGATTGGTTGCTACAATATTTTCTGGATAGT
TATCTAACTGAATATTTTCAATAATATTTCGCTTAGTATTAATTAATACTAATTGATTCATACTATCCAT
AAGAATAATATAATTTTTAACCAGTACTACTTTATCAATATTATTTCTAACGTTTGCTAACCATGTTTTA
TTCGTCAAGTTATTATTAGCATACTTAAAACTATATATATTTCCACTATATGATGATACGTATAATGTA
GATTTATCACTATCATATATCATAAAATTATTTGTCGATAATATTTTATCATTATAATCTGTCTGACTTA
ATGATACTTTTTCTACAATAGAGTTATCTACAGACTTAATAATATTAATATTAAAACTATCTTTTAATTC
TAGTCCTATAAATATTGTAAAGTCGATATTATTCGATTCAGGAATGATTTCAAAACCAGAAATAAAAT
ATGAAGCGGTATACAACACTTTTGTTGTATTCGTTATAGTATTTACTAGTATAATATGTTGATACGTAG
AGTAGTATATAAAATCATTAACAATCCTTAATTGATTTACTAATTCATACTCATATGGAGAAGTATTAG
TTATTTTATTTATAGTTCCTGAGATATTATACATTCCAGTAGTTGTATTTCTACTAAAAGATACATAACT
GATACCATTCTTATGAAACATATATATCTTATTATCGATAACTGTAAAATCGATTACTTCCTCATTAAT
ATCAAATGAACCTACTTTTTCTCCAGTACCAAAGTCTTTTATAATATCAATTCGATTCTTAATAGAACC
GGTAGGATATTTATATAATCTGAATAGTTCTTCTAAATATATACACATTGCAGGCATATATCCTGAATT
AGCATATGATATAGAATGAAATAAGTCTAACCTATTACGTTTTTGATATTTATCTAATATATTCCCATT
```

-continued

```
CAATGTTATAGTCAATACTTTCACCATCTTTCTTTTACAATTATAAGGAATCGAGAATAAAATATCCCG
ATTCCCAATTTATTTAAATAAGACTTGAAAAACTTGTAAATGTTTTTAGAGAGAATTTACCTAATGTAT
TTTCGATAATTGCTTCTCGATTAAGGTTAGCGCTTATAGATGATGACATTACCATATGCATAAATGCAG
GAAGGTAATCAATAGCTAATACAGTAGAGTCTCCATACATTCTTACATAATTCTCTAAATAAGAGCGT
ACTTGTAATTTCTCTAAACCTTTTATTTTCTTGAGGTTATCAAAAAGTGTAAAGATGTCTTTATATAGTT
CCTTCTCGCTTAGATTAAATCCTTCTTCCATTTCTTTAATTAAAGATAATGAAGAACCATTAAAGCAAG
CTTTATAGGCAATATCGTCTATTGTATTATTATAATTCTTTTTAGCCATTGCTAATAGATAAAACTTTGA
TAGAATAAAGGATACAAAGTCTGATTTAAAATCATTTAGGTTTAATGAAAACATTTTATCAAATATCTT
TGAACCTAGTCTAGAATATGCAATAGATGAATTTTTCATTAATTCAGTATTACTTGTAAATCGATTCCA
ATTTCCATTTAATTCATAAGTAATCATTGCTTGTTGCATTAGTCCGAATAATGTTTTTGGTTGGATTTCT
CCACCTGCATTAGTGTATCGTGAAACATCAACTAATACGTCACGTTGATTGTTATATCTTCTTTCAAAT
ACAATCAAGTATGATGGAAATTTATTTGATTTATTTGATATAGGAATGATTTTTCCAGAGTTATATAAC
CCAACAACTTTATTTTTAGTAGGATAATTAATTCGTCTATTAATAATATTTATATTTTGATCTAATACAT
CTTTAGATAAAACATCTTTACTAGTGTTTATTTTATTAAGTTTTATTTTAAGATCATGCTGAAAATTAGA
TGTATTGAAAATGGCGGAATCACTTAATTGTACCATTATTTCACTTTCCCTTCAATTAATTTATATGATA
TTAATTTGTTCAATATATTAACATTTTTTACATTTATATATTATAAATTCGTATAATGGAAATATAATAA
AATTTTCAGTTTATCGGTTAAAATATTTATTATATTATAAAATAAATGTGATAAGGATGGATTATATTAT
GAGTGATAAAAAAATGCTTAAAGTAGGGATTCTTAGCCCAAATGATGATAGGATTCGTTTTAAAGAAG
TAGATTTTTCGAATAGTGAATCTTATGATAAAGAAATTGTGAGTGTTATTAGTCCTACCGGAAATATTG
ATGCAGGAATCATGAATCTTAATGAAGATTTAGAAATTCGTAACTTCTTAATTTTATTTGATAATGAAA
TGTCAACAAATAAAGGAGAATATAATTTTACACATTCAATTAGTCCTCTTTTTGGTGAAGTTGCTTTTG
TAAAATTCGGTTATACTGGGGATAATATGGAACCAGTAAGCATGTTAGATGATGAAGCTGAGGTTCTC
AGTGATATTATTTATCAAGAAAAAACTTCTGATCGAGCAATTGAATTTAAAGAAAAAATTCTTGAAGA
AGTAAGAATTTACGGTAAAGATGGATTTTTACGTAAATATAATGAAAGTATTGAAGAGGCGCAAAAA
ATGTATGAAGATAATTTTTCAGAAGAAGAAGAAAAATAATTAAGAATGGATGGTGGATTATAATTGTC
TAATATAAACGTAGTTAGTATTGCAGATTTACATTTTGGTAAGAAAGATGATAGTCGACTAATGAATG
AATTAACAACAATATTTATTCCACAGATTAAGAATATTCATGAATCTGATAAAATTGATTTGATTGTTA
TTGCTGGAGATCTATTTGACCGTATTCTTAAGTTTGATGAAGTTGGTGGAAAATTAGTATTGAATTTTA
TGCAAGAACTTATTGAATGGACAAATAAAAATAATATTTATTTTCGAATTATTCAGGGAACTAAAACT
CATGACTATAATCAATTAGCTGTGTTTAGAAAAGCAGAAGTTGATAATTATAATTTTAAAATTTATGAA
ACGGTATATAATGAAAAATTGACTATCAATGAAAAAGAATTTAATATTTTATATTTACCTGAAGAATA
TCCTGAAGATATGAATGATTATTATAAAGAATTCTTTGATGTTCAAGAAAATACGTATGATATGATTTT
CGGTCATGGAATGATCGATTTTGTAGCTTTCACTGGTTATGAAGATGATACTGAAAAAAATTGTAAAGA
AAGCACCAGTATTTGTTGCGGATGACTTAATTAAAAATTACAAAAGGCAATATGTTTTGGACATATT
CACGACTATCATGAATATAAAAAACAAATATATTATTCAGGTTCATTCTCCAGATATTCTCATGGCGAT
ACTATGGATAAAGGATATTTATATATTAAGTTAAACAGTGAAGATACTTCTGAATATGAAATTAGTTTC
TATGTTAATGAATTAGCTCCAACATATGCCACTATTGATTTAGATAAAATCAAATATGATAATATGGA
AGATTTAGCATCATTAATTAATGATATTCGTGAAGAATATGACTTCATTCGAATTAAATCAACAAATA
ATAATCTTTATTAAGAAGTGAATTATGAAAGGAATGTTTCATTGTGCCATTTATGGATAATAGCGAAC
GTACAAGAGTCTTTAGATCTAGAATGGATGAATCTTCTCAACAAGAATTTCCATTAAAGATTTCCGTAT
CATACTTATTTAGTTTAGCAAGATATGTGGTATATCCAAGTAAACTTATCACTAGAACTAATTTACGGA
ATTTAGATACATTATTATCAGCAGTCGATATTGATAGATCTTATTTAGAAAATGAAGTAATGGAAAAG
AATGCATTTATATTCTTAAGAGAAATTAACCGTGTATTATTACATCAACAATCAACAATAGAAACATT
GTTTGATTATATTGATGATGAATTAAAAGATAGAGAAATCTCTGAAGATGCTCTTCAAGAATGTGTAA
ACAATATTGCAATGGTGTTTGATGATAATTTCATTCTTGATGATAGTGAAATATTAAGCTTAACAAACT
ATGTAGAATCCAGATTAAAGATTATGGCACTATATCGTCAACGTGATAGAATGGAAGGTATTTTAGAA
TTAATCAAAATGAATAAATCTCCAAACGAAATTAATACTGAATTTAAAGATTTTGTTACGCAGAATGC
ATTACAATTAAGAAAGATTGAAACGAATAATCGAAGTTCAATGGACGATATTATGTTTAGCAGAGATA
ATGATCGATCAGTAGATTCACTAGACTCTACTATTAGACAATTAAGAAGTCCTAGTAATAAATTATTA
ACAGGATATAGTAAGTTTAATGAAATGATTAATGGTGGTTTAGAGGATGGTCGACTTTATTTACTCTTC
GGCGTTCCTAAATCATTTAAGTCTGGTGTTATGTTAAAATATTGGAATGTCAGTATGTCATAATAACGCA
GGATTTAAGACAAAAGATCCTAATAAAGAACCAACCGTTGTTTATTTATCTCAAGAAAATACAATTAT
AGAAACAGTAGAACGATTATATGAATATATTACTGGTACTAGTATTAATGAATCACAAGCTACTACGC
AAGATGTTTTAGAATTAATCATGCAATATACGTATGATTGTACTGGTATTTATTTAAAAATTATGTATA
GACCAAATAAAAGTATTGATACAAGTTATCTATATAATATTTATGATGAGCTTAATGAAGAAGGTAAA
GAATGCATCTTTATGATTCAAGATTATACTCGAAGAATTAGACCTTCTGAAGGGCAAAATCAAGATAT
TCGGATACAACTCGGTAATATATCTGATGAGTTCTGTACGTTTGCTAAGGAAAAAGGTATCCCTGTAAT
GTCGGCGGGACAATTAAACCGTAATGCAAATGAAATTGTAGAGGATGCTCTTGTTAAGAATCGTTCAG
ACTTTATTAATAAGTTAGGTCGCCATCATATTGCAGAGTCTGCAATGTTACTTGAAAATGCTGATTATG
GAATTATCATTGGTCGACAAGATTATCTTCCAGAGGGTGAAGACGAAATTAATCGCAAAAGTTATATG
TCATTTAAACTTATTGCTTCTCGTGGGAAAAATAAGGATAAAGATAGCAATATGTTCTCTCAACCTTTT
GAAAATGGATTTAAAATTGCAGAAGATATTAATCTAGCTGAACCATTAGCAAAATTAAGAATTAATGA
ACAACAGTCTCAACAAGATATGGAAATAGTGCTGACGAAGTAATTACTTCAAGAACTCCTAGATATA
ACAGTACTAGTAAATCTAGTAGTATAGTTCCGGGAATCAATACTGGTAAGAGACGAACAAATCTTTCA
TCAACAGCATTATTACAAGAAGATGATATTCCGTTCTAAATAATATTAATAACCTAACATCCTTTTTTA
TAGGGATGTTAGGTTAATTTTTTTTTTTTTAGATAGATTCGGCTTTTTTGACGTAATTTACTAAAATCGATA
TTAAACATTTTAAGTGTATTCATACTTTCTAGTATAGTATAAGATATAATAGATTCTACAATTGTCATTT
CTGCAATATCTTCTTTTTTAGATTCTGATAGATCCATATTTTTCCATTACGTATGATAAGCGTTCTTCACT
AATTTTCATATATAATGATTTTTCATCTTTAACTTCTCACATTATTTCATTGCATTTATCAACAAAGTTTT
TGTATTTCTTCTCATAATCAATTACATTGATAACTTTATCTTCAATTACGTTTACTGCAGATTCAATTAA
TGATTTCTCCTCATCATGGATAGAAGATACAATATCTCCAACTTGGTCAAATGATAAATTTCTCTTCATTT
ACATAATGACTGACTTTTGTCTTAACAAGACTTAATAAGTCACCAAAGGCACCATGCTCTTGAATATTG
ATTGATTTATTTTCTACAATAGTATTAAAAGCATTAATACATTCATTATAAATATAATCAACATTCCCTT
GTTTTTGAACTTCATCAATAGGAATAGCTCGGTATACAATACTTCCAAATAATGTTGGAGCTACTTCTT
CAGCATGTTCATTAATTCGATTTTCCTTTTGAACCATCTTTTCACGTTCTTCAGCTTCACGCTGAACCGT
```

```
AATAGACGTTGTTCGTAGTAATTTACTCTTGTTTTCCATATCTAAATTTTCTTGTAATGCTTTTTCTTCTT
CTTTCTTTTTACGGAAATATTCAGTACGTGCATTATTTTCTTCTCTAAGATTTCTTGAACTTTCACCAAA
GATACTAAGTCTTGACATTAATTTTCACTCTCCTATAATTTTTGCTATATTAATTTGTTTGATAAGTTAT
ATTAGCTACATGCTCATATTTTTTACCTAGATTGATAGTAGTGACTTTACCATTACTATCGTCGTTTCT
ACAATATTATCAGAAAGTGTTTTCTTAATATTGATATATTCAGGAACATATTCAATGATTTCTTGTTTTG
AGAGATCATTAATATTTCTTGCATTGTTAAGGATTTTTTGATATTTATTAGATATCTTTTCATCATAATT
ACCACTTAAACCGTTATATTCAATATAGCTAATGATCGCAAATTCTTCTTCTAACAATCTTAATAGATT
AGATATAGGTACGATTCCATCAGTATTACAGGCTTCAATAAAGTCGGAAATAAATTTCTTAATTGATA
AGTCATCATTATCATTAACGGCTTCATATGTGTGAATAGTTAAATCAATTAGCATGTCAATGCGAGTAA
TAAGATCATACTTAACACTATCTCCATCCACTTCAGTATTTAAGTAATAATATTTAGATGGTCCCCAAC
TATTATAAAATTTCATATCAATTGTAGTATTATTTTCCAGTTTAGGAATAACATTGCTTAATATAGTGAT
ATACGATTCAATTAATGTATATAAATAACTATATTCATATATAAAATATTGTAAACTAATGAGCGGTAT
CATTTCAACTTTAAAATCCTTATTTGCGTCACTAACGTTTGAAGCACCTACTCTAGTTACTGTACTTGTC
ATAATACTAGAAAGATTACGATATAACTTTACGGTAGAATTAGTAGTTACTGATAATGCCAATACATA
ATTATCAATATTTCTATTAGCATCTGGAAACTCATCATCAAACAATTCAATTTCATTATTATTCTTTGTA
CCAACAGTCTTATATGAATTATCTTTATAAAGAATTCCGATCTTAATATATAGATCTTCATCAATAAAT
ACATTATCTAGAACATCACCATTTTCATCATATAGCGAGTTTGATAATGATAATAATCCTTTATTAAAT
TTACGATTAGTTGATAATTTTGCAGTATAAGTAGACTCTCGCTTGTTCTGGATTTTCACGTTCAAATTCAA
AGTAACCATACTTCTTATTAGAGTTTTTTGACATTAAGATACCTCGTACGCAAATACGTTTATCTAAGT
CGCCTATCGTTTCATTACTGTTTAGATCAAACTTAATAGTATACGTATCGGAATCCAAAGTAGATTCAA
AATCATGAATTTTTGTTATATTAAGTTTATTGATAATCATTGTTGTAGGAATTAAGTTATTAAGATAAC
TGTATGATGTATCGAATGTTTCATCAATATCCAGTTTATAATATTTAGCACTTAATACAGGATCAATAT
CTATTTTAACTAAGAATGGATTAGTATATACAAGCGTATTTTTATCATTAATAGATTTTTTAATATCATC
AGTATATCCATCGGGAAGATGTTTATATTTTTTATCAATATAATCATACTGAATTAATGAATGTTCCGG
AATTACATATCCATTAATATCGTCACCTAACAGTTGATCTGTAAAATATTTCTTAGAGAAAGTTACACT
ACTTGCAGTATTTGTAGGAATAACCTTTTTATCATTATCACGTAATAAAAATGCATTATATAAACG
CTGAAGAACATCATTTCGCTTTTTCATAAAGTTTATTGATGAGTCATTTAAGCTTGATGCTCGATCAAT
ATTTCGGAAATAGATATCTAAGTCAGTATCCATAATTAAATTATCTCTACCGAGAGCAGTTTCAATAAT
TTTGTCTTTCATACCGCTAGTACTTAGTTTATCATTACCTCCTGAAGCAGAGGTAATAGGAACTACTGT
TGTGAGCATCTTTGAAAAGTTATTACTTGCTGAATTAGTAAAGTTAAATAATACTTCTCCATCAAAAGT
AAAGTTTCCTTCAGAACCTTTTGTAGTTAATATCTCAATGGTTATCTTACTATTATATCTAGGTCTAAAG
TTATTAACTAATGAAGAAAAAGATATCTGTAATTTATTATCATCAACAAACGTATAATAACAGAATTT
CTCATCAGGATTAGAAGGATTAAAGGTATTATTAAAGTATGCGTTTAATTTTACTTTTTCGCCCATATA
CGTATAATATATATTGAATCCTGCCAATTGATCGTCAAACTCTGCAGTATAGAATAAATTATCACTAAT
ATCTTCAGACAATATATCAAAGTCAAAAGAACTACTTTGAACTTGGTAAATATCTAAATTTAGATACA
TATACTTTTCACCATCAAAGATAGATTGATAAACTTTTATCTCAGGAGTACTAAGTTCAATATATGGGA
ATGTACTTACTTCATCAATAAGATATCTAGCTGTAATCGTATAATCATTATTCTGATTTGTTTCATTAA
TATTTGTACGTCATAAGGTAACTGGAATTTAAATTTACCCACAGAAAATTCAAATTCTCGATCTAATAT
GATCTGATAAGTTTTAAGAGCTTTAACTTCGATATATTGATCTTCGATAATTCTTCCCTTAATGGAGA
ATTTATTAAATCCTCTTTACGTATAACCATATTAACTAACATATGAGAAGGGTTTGATAGTACTAATGG
TACGTTATATAATTTTGCATAATTGAAGATACTATCTGGGAATGATGCACTATTTAAGAAGTGTTCATC
ATACAGTACATTACGATGATATACCGAGTTTTTAACCTCATGGGCTGCAATTTCATTAAAGTATCCAAA
GAAACCAGTTTTTAATAAGTTTAATGCAGCATTATTTCCTTCAGAACCAGTAGCAATATTTGTATCATC
AATATTAAAATATGTGCTTGCCATTTTAAGCCAATGTTCATGTACGTCATATGACGTTTGATTTACTTTA
ACTACTGAACTTGTATCTTCTTTAGCATTCTTCATAAAAGAAGGTACATCTGTTATATCGTTTGGATTAT
TTTTATTTGCCATTTATTCTCACGCCCAATCACTATTTAATTATCCAATACAAATTTGAGTTTATATTTTT
TCTTTTCATTATCACCATAGTTTTCAAGAACTACTGCAGGTCTAATTTCTTTAGTAATAGTAGATATTGTTAGGTCTAAGTCTGT
AAAAAAGTCATTATATTTCTTAGCAGATCCCGGAGAAGTACTATATATAATACTTTCTGAATCTTTACT
AGACGCTAATACTGGAGAGTCTAATGATACTGAATTAAAGTCCATTAATATTGCGGGATCCATATCTT
CTTTATATGAATACGCATAGTTAAAACTTAACTGAGCGATATCTTTTGAACCTCCAATATCACTATTCA
TTACGTCATATGGAACATTTGTTGGTGAACATCCAGTGTATTTAGTAATAGTAGAATATCGTTTCCATAT
CAAAATCTAATAAAAAGTAATATATGGAACTTGTATAATCAATATATCGATTCATAAATACTTGTGGA
TTAGGTTTCATTTGTCCTCTAGATACTGCTTCAATATAGTCAGTCCATAATTTATGAATCGTGTAGTATTG
TACTATTTTTATCTTCTTCAAAAGTTACGCTAGTTTCATCAGCTACTACACTATTAATAAATGGTCCAGG
AAGTAATTGCTTGTGACCATAAAACGTTTCATTAACTTCTTTAGTAATAGTAGAATATTCCTTTAAGTGA
CATGTTAATAAATCTATTAGTTAACGGTTTTATGAAAGAACTATTTGAACCATATATAGATCCTCCGCC
AGTCTTACTGGTTGCGTTCCCACCATAATTAAGCATATTTAATATTTCAGGGCGATTATCCCTCATATA
TTGAAAAAAAGAATTCACATTTATATTTTCATCCGTTAAGTTAAGTTTTGGAGTAGTAACAAATACCAT
AGGGAATGCTTTAACCATCGGTTCATTTCTTAAGCTATTTTCCAATCTATATGGATTAAAATATTTATTC
TCATTTATATTATAATTCCCTATAATCTTTTTTCTAATTTCGTCTGACTTTGACAAAAGTTTTCACCAAC
TTTCATATTAAGATCCTAGTATGTTATAAATTATTGTTAATGTATGCATGAAAATATTAATTTATATTTT
ATTTATATATTATAAATTCGTAATAGATATAGTGATCATCCTTATAGAGTAAGTTTAATAATTAATATT
AAGAAAAATGATTTATATTACTGTCCATATTAAATAAAATATGACCTCACACCAGTAATATAAATTCT
GTAAAATTATTTGGCTTAACTCTATCAGCGCTATATAAATTGAAATCATGCATATCGGAGAATATTAAA
TAATTCTTAGGGTTAGTCGATACAGTGAGAAACTATATCTATTAAAAAAATATTATTGTCTTACATGGGG
GCGTTCTTATGTGCTATATGATTGAATAAAAAGAAAAAATATGATTTAGAAAAAACAGTAATAATACT
TCTTAGTATTATTAATAAGATCCTATACTGAATAAAATTGAGGTATATGAAAGCGCTCATAGGATTATT
TATTAAAGATTATTAGAGTCACATTTCATTAATTGATCTGTGACTCTAATAATCTTTATTTAATTTTTTT
TTTTTATAACGCTTCCTATGATAAAACAATAAAATATAAAGTAATATTAATTAGGTCATCTAAATTGAA
AAGGAGAGAGCGTAAATGTCAAAAAGCGTATTGCTAAATTTGACTTCACTCTTTGGTGAAGTAGTTCT
TAGTAAAAAAGGACAATCTGAATTAGATAAAAGTTATAAAGAATTAGTTAAAAATAAATCTGCTCGTA
ATAGTTATCTAAATACAATTAAAGGAAAAGCAGAATCTGCTATTATGCAATTTCCTTTAGTAATTTCTA
ATAATATCTATCGGAGTTTTAGATGGTATTCGTAGAAATATTGAAATTGAACGTGCTACGGAGTTCG
GATTAGTATTGTCTAACGAACCAGTACAAAATGTTACAACTAATGCGGAATTCATGAATAAATATCAC
ACTAACTTTAGTCTTGGAGAAGATATTTCTTCAGCACATAATGAATTCAATCAAGAGTCTAAATATATG
GAAGAAAAATTAGAAATGCGTTCACTTAATGATTTTACAAGATCTCGTCAATATCTTAGAGAAGAAGG
CGAACAAGATTTTGTTAATGCTAAGATTGATAAGGATAAAGAAGAAATGAGTAGAGTTGAAAGAAGA
ATTCAGAATTCTCGTATAGTTTCTGATCGAAATGCAATCTCTCCATTAATTGTAAACAGTCCTATTACTT
ATAGTATTTCTAAAGTCTTTAATAATGATGGAAAAGAAATTAAGGTTGATCCTCCAAAAAATTATTGAA
```

-continued

```
GGTCAAATTCGTTTTGGAATTAAAGCGGTATCTCATTTAGTTAATAGCGAAGATATTGTATTTTATCTT
GGCGATGCCGCTAGACGTAGTAATTTCTTAGCAAAAGTAGTTCGGTTTACTTCTGGCGAGCTTAAGTTT
GGTAAGGATTTAATTCTAGCAAGCGAACGTAATAAACGTTTAGTACATGACCGTAAAGGTTCTGGTGC
TATTTGGAGAAACATGAATTATATTTCTGAACTGAATAATATTCGTGCCAATGTAGGCAATGTAAATA
AAATGCAAGTACCTACTATTACTTTAGCAATTAGTAAAGAAGAAGTAGATTCTATTGCAGAAAAGACA
GGAATCAATTTTATCGATAATCCTAACGCTACAGAACGTTTGTTTAAAGAATTTTACTTATTAGACTTC
ATGATCATTGATGAACTAAATGAAGTAGCATACAAATTTAATCGTACTGGAAAAACATATGACCGTTT
TAGCCTACGTTCTTTAGAGATTTCAGGATCTACTGAAAGTCAGTTAAAGAAACCTATGGAATTCAGTC
AATTAAATAAAATGATTAACTCTATGAGAAAATAAGAAAGGATAGGTGAATAATTCAATGCGTGGATT
TAATAATCGTTTAAAAAATAAACCAACATCTTCTAAAGATGCCTTACAACAGTTATTAGTTGAGAGTG
GCGGATTAGAAATGAATAAATATAAATTACTTTCTGAAGAAGGTAAAATTGGTATTAGTGACCGAGTG
TTAATTACTCTTATGAAATCAATTAAACCAAAATTAGAAAAACCGGTATTTAAGGATATTACTAAGTCT
AAAGGTGATATTACTAAATATAAAGCTTATGATGATCTAGAAAAAGTATTAAATAAAGTTCGTTCCGT
TATTTCAAACAGTTCTAAACCTGTAGATAAAGACGTTAAAGAAAATATGTCAAGCTTAGATACTGTTT
ATGATTTTGTTATTCGTGAAAAAGATGCATTTATGCGTGGATTTAGTAATAAAGATTCTTTAGTAATGT
CATTATATGTATCTTGTGTTTCGGTTATTGCAGAAGGATCATTAGTAATGTTTACAGATGCTTTAGAAC
CTACTTCCGATAACTTTGGAAATATTACAATTAATGTTAAAGATCGTCCGAAATCAATGAATAAGAGT
TTATTTATTGGACTAAGACAATTTCTGATATGGTTAATGCTAAAAAATTAAAAGATATTATTAAAGGT
GGACAAATTAACTTAGAAGAAGAACTAGGTGAAAGCTTTGTTGGATCTCTTTCAGTATTGGGTAAATT
CTTTAATAAAGTAGCAGATAGTATGGATGATGCTAAAGAAAAAGCCCATGATGATGCAGATTCTCCAA
AAGGTGAAGATAGTGCAATGATTCGATTCTTCAAATCAAATAAATTTGATAAAGCATCGGACGTTACT
CGTAAGATTGGTACTCGAGTAATTCTACCGATTGTTGCATTATTATTAGTATGTATGTTTATTCGCCTTG
TAGTATTTATTATTTATCGTACTCGTGTAAACGTTGCAGACAATCTTCGTAGTGCTGCTGAAGTTATTG
ATGAGAACTCTATTCGAATTCAAGATAAAAATGTACGTGAACGACAAGAAAGTCTGCTAAACTATTC
CGTAAACTAGCGGATAAAGTAGATGTAGACTTTAATGTGGCAGACTCTGGTGCTGATAAGGATATTCG
TCAACAAGATGAATTAATGGCTAAAGGTGCAGATGATATGATTAGTTCATCACAAATAATGCTAACG
AGTTTGGTATCTAAAAAAAAATATCCCTATACATTCTAAAATTGAATGTATAGGGATATATATTATGA
AATTTTACGTAATATAATTTGACCACCATTATCAGTAGTATTATTACTTTTAGTTGAAAATATTTCCGTC
ATTTTAAGAACCTGATAATCACCATTATATTTTATTATAATATTCAGAATCAAACGTTATAGTGAATTTT
TTAAAACAGTCATCGATATTTATATCCATATTATTAAAACTAAATCTTAGTATGGTATTATTTTTCAGTTA
TTCGTTTAGTATATTCCTGTAGATTTTTATTATCATATTTATTTTCATATACAATTGTTTTATTAATAGTA
CCATTTCTATCCTTAATACTATCTATTTGATAACTGTCTTTTTCTAAACCTATCATGTCACGATTAAAAA
TAATATTATTTGTACCATATAATTCTGCATACAACTCAGTCTGATCCATAATAACAACACTATTAATCT
TAGTATTAATATACTTATCAGTTATTCCATTTAATTGATTAGTTTCACTATAAGTACCCATGATATTCTG
GTCTTCAGGATTAGCATTAACTGGTATTTTAACGTCTATACGTATATTTCCGGACTCAACTATTTCCATA
GAAGACATTGGAGTAATTACTAATTATTATATGACATAAACACTTTTAGACTATCATTATATATTCCG
TAAGCATTATTAATGTGGCTAATATTAGTTAGAATATTTCCGGGTATTAAGGCTAATTGATCGTATATT
TTTTGATTGTCTGGAGAAGATAGATATGTTCTTACTGGAAGAAGAGTTAATAATCTAGTAATGACTTCA
GTAACATTAGTATTTGAATATATACCGCTAGTATTATATTTATTAATAGATAGACATATTTCAGGGACG
CATAAACATTCAAATTCTTCATACTGGTAATTTGTATCTGTTGTATCTTGGGTTAATCTATCACTAATAT
TAATCGCCCTCTTATCAATAATAAGCGGCTTTAGAATAATATCTCCGAGAAATATATCATTAATATATG
AGTTGGTAGTATCCGCATCAATGGATGAAGCTCCTAAACTTACTACAAATTTCTCAGAATCTTCTTGTA
AACTTACCATAACAGATACTGGTAATTTATAGACTAATGATATCAGTGGCATTTTATAATTTTGAAAAT
CAATATCGATTTTAGTTAATCGAATATATTCAGAAGCATCAAACATATTTCCATCTGAGAATAAGAACT
TACTACGTAGATTAAAAGTTTTTTTAGTTATACGAGAATAATCCATTTATTATTTTTCACATCCATTTCA
TTCATTCAATATAGTAATATGTTTATTTATTAAAATAAATTTATAAGAATATATTATAATAATAGATTA
TAATATATTTAGGGAGTTGTTTATATGGATTACGGAAAATATTTTGGCTATGATGACAGAAAATATCGAA
AAGATTATGAACTCAAAGAAAGTTAAATATACAAAACTCATGTCAATGGTAAAGAATTATGTAACGA
GGGAATCTATTGGCAAGAATGTAAATATCTATATTGATATGAATACTATTTTAAAGCAGATATATAAT
AAGGATAATATTGAAATCTTTAATCATTTAAAGAGTGATAAACGTTTATTTATTACTGCTGAAATTATA
AATATTATTGGTCACTATAGACATTTCTTTTCTTCAAGATTGAAAATTGTATACTACGTTTTATTTATTTA
CTTCTTTTGAAAAATCATCATATCATACAAATATATATCCTGATTATCGTAAAGAATATTACGAAAAAA
GATTGGGTGATAGAGATTTTGTTTTTTCAAATATTAATAAGATTATTAAGGATAATATGAATATCGTTA
AGAAGATTTTAAAGTATGTACCAAACGCATATTTGATTAATACAAAAGATAATGATCCTTCATTAGTA
CCTACTTATTTATTAAATGATAATCGTTTTACTTTAGATACCGACTTTGAATATTTATTATTAGCAATGATGA
AACTTTTCAGACAAGATTTATTATATAGGGATAATACGCTTATCTTAGAAATTAAAGGAAAAGATAAT
AAACGACTTATCGCTTATGAGGACGTTATCAATACTATTGTAGATAGTACTAAAGGTAAAAGGGTTTA
TTCAGACTATAACTTATTAACAGAATCCATTACACTTCTGGATCCTCTTGTAAAGAATAAAGAATATAA
TATTAATTCAATTAAACGAACTAGTGAAATGAAAGCACTAGACATTATTGAAAAAGGTATTAATGATA
ATATTATTTCTTCACAAAGCTATTATGACGTAGATGAAGCATATAATGATTTAGCTTTTTATCTTGGTG
AAAATAATGAGGATGAATTAAAAGAAATATGTCAATCGTTAATCATAAAATTGCAATGTCACATACT
TTTAAAGATTTAGAACACGTTATACTTTCCCAAATAATTGATCTAGAGGATGATAGAGGATTAATGGA
ATTGAATGATAAGTTCTTTTCAAAATATCCTATTGTTATGGACTATCTTGGTGAAAGTTTCTATGATCC
GAGATAAAAAAAAAAATATCCCTAATGCTAATATTACTTAGCATTAGGGACTTATTATATACTTATTTT
TTTTTTTTAGACTGATTTAATAAATTCAATAATTTCCATTGACATTAAAACTTTATCCATATCTTCGATA
AATACTTCATTATCATTTTCATCAATATACATAAAATCATAATTATATGAGGTTGATAATGACATGATA
AAGTTTTCACGTTGAACTAGATCAATAATACTGTCATACTCAGTAAGAACTTCTCCATAGCTTTCTGAT
GTTACGATCTTATTATTAATCTTATTACTAATGCGATTTCTTTTTCCAGAAGGAATAGTTTTTACTTAGTA
GAACTTTGGGTAAAAGTTTATAGTTATTCTTTTCAAGTTCTCTAATCATCGCAACTAGTAATACTAGTA
CTCTGGGTTCACGGAAGTTCTTAATGGCAAATCTTTTTGCAAAGTACATATTCATAAGTGAAATTTGGA
ATTCGTTTAAATGTTTAACATTACTACTTAAACGTACAATTTCTTCATTAGTAATATTATATTTTTCGAT
AGAGTCTCTCACATACTTATCGATAGATGCATCATTAATAACGCTTGACATTTCATTATGTTTATGGTA
CTGAATTAAAGAAAATTTATCATTCTCATCTAGATCGTCATCTGAACTAGAAATCTTGATTACTTTGAA
TTGTAGTGCATAATTAGAACGGAAAGCATATTCAATCTTTCTTTTAATAACTACGTCTAAATACGATAT
TGATGATTTATTAATAGAAAGTTTGCATATAATTGTACGTATAATTTCATCGGTAATTTTTTGGTTTAAT
ATGTCTTCATCTACAGATATATTTGCAAGAAGTACCAGATAACTTTATCTTTGTATAACGTCTTTTTAA
TACGTGGTTCAACAATTTTGCTAATCTTAGTAAGAATATTAATCCCTTTTTGATTACTAAAATAGCGAT
TAATTAATTTAAAAGTCTTTAAGAATAGTTGTTCATTGTAAGGCTTATTTTTAGCATTACCTGAAGTAA
TAAGATATTCACATATAGTAGGAATTAACAAACGTTGCATGATTGCAGAACGGATTAGTACTTTATTT
```

```
GATTCATCAGTTACTTGTAGTTCAGGAACAATTTTATCAGAGTTAGTTCTACTATAATCATCTAATGAA
ATCGTATATGTAGAATCAACTACTGCATCAATAGCTTGTAATAACTTATCAAATTTAATAAAATCTTCG
AAATCTTCAATAAATTTACTTTCAGTATAATCTTCATCCATAAACATGTTTACTTTAAAATTTAATAGTT
TATAGGCAATTTCAGGAACTTCATTTAAAAAGTAGTTTAAATCATTGTAAATAATATGATAGATATTTG
AATAAATTGCTTGATGAATATTATATTCAAATAACTTTTCTTTACCCTCTAAATTAGCATTCTCTAAAAT
AGAAGCAAAGTCTACAACCATCTTTTTGGGATGAGCATAGTTATCTTCTGTAATATAAGTTGTAATGTC
TTTACGATGTTCAACTTTTTCAATAGTTACCATTTCGTTTGGATCATTCTCACTTTTAGGTAAAGATACA
GTTACTTCTTTTAATCCTTCAATAGATATATACTTATTTTTTAACTTAAACTCTTCCTTCACACTATTACC
CCTAACTTTTGTGTTATCAGACGTTATTGTCACTCAAAAACACCAACCATTCTCTTTTTATTTTTATTAA
TAATATAATTGGGATGAGATTAATTTTTCATCATATACATATCAACCTTTCTTATTTATATATACTATAC
CACACTTATATATAATATATAATTGAAAAGTTATTAACGTTTATTAATAGATGTTCTACGAGATTTAGA
TTTTTTATTACGATCAAAGATACTTTGTTTCTTAGGTTTATCGATATTTTTATTTTTAGGTTTTCCTTTAC
TTCTAATATCTTTTATCTTCTTGTTATGAAGTCTTCTATTCTTATAACGCTCAATTTCAACAAGCTTTCTT
TCTGAAGCGGGTATATTTCTAGATACTTGTATTTTGTCAATAGGTTTTAATCTTTCTAATGAGGGAAAT
GTTAATAGATTATTCTTTTCTAGATATATAAGGGCAAATAAACACTTTTTTCAAATCCATAAATTTGG
TTTGGGTTTCTTACTTTAGGTTCATCTACTAAAGATTTAATACTCATTTTATTCTTAAGCCAATCAATAA
TCAAACCATCTCGATTATAAATATATCCATACGTAAACATAAAGTTAGGATTATTACTATAGAAACTG
ATATGCGAGTTTAGAATAGAAACGTTTGTATTATTTTTGTCTATTTTAATTACTACGTCATAAACCATTT
TTTCTTCAATATACGTTTCAGAAGGAATTTTAAATACATAGTACAAACTATCTTCATCTTTAAATACTTC
TACACTAAACAATCTTTTAGCTTTTTTTATACAGAGTATTAAATCGGTCATACATATTGGCGATAATCAT
ATCCCGCCTAGCTAATCCTGCAGAACCTTTTCCTGAAGGGTTTTGCATAAACTGTTTTACAGTGATCAT
TTCTAATATACACCCCCTATTTATTAATTATAACATAATTTTTGTTAAATTTAAAATAAACTTTTTTAT
TTTAAAAAATTATTAACCCCTAACGTGAATGATAACTATCACGTTAGGGTCAACTTTATTATAAGCTAA
TTCGAATATATTGATTACTTGTAACCAGTAATCCAATTACTGAAAATGATGCTCTCATAATCTGAATAT
CCGTCATTACCGAGTTGATAATCTTTGTTTCAGAGTCAGGAACATATTTCTTTTCTTTAAGATCATAAAT
CATTTTATTGTTAATACAACTCTCAACAGTTTCATATACTTCTTCATCAGAAAGTAATAATTGAGAGTTCTTT
AATACAATTGCATATGTTTCTTTAAATGCAGAATATACTAGTTGTAACAATACTTTATCTACTTCAGTT
AAACTTTCTTCATTATCAATAATATCTTTAATTACTTTTGGAATTGAAATATTTCCTCCCGGAATATAAC
CGTAATCTAAAGCAGATCTACATGCAAAGATAGAATCTTCCAAGAGATATTTACGAGTATCACGTTCC
AATTCAGATTTACCACCAATAAATAACGTAGCTACTTTAGAAAGTAATCTAGCTTTACGATTCTCTAAT
TTAAAGATTTCAGAATCTACACCTTTTTGATATACGTCTAAATTCTTTAAATCTTGAATATTAAGGTCA
ATTAATTCAATTCGAGCATCTAATTCTTCTTGATGATACTCTCCCTTAATAAATTGAGTTGATCCACCA
GTCATCGTTACTGTTTCACAACGACCAATATGTTCACCATAAAATTGAGCGTTATTTGTTTTACTTAAG
ATAAATAAGTCTTCAAAACCTTCTTTACCTTTTTTAGTATTAATCTGAGTTCCTAAGTATATTGCTAAGT
CTTCGAATTCTTCTTTACGAGTTCTAGCGGGAAAGTCTGTAGCTGCAATTTCTAGGGATACTCTGGTAT
TATTGATCTTTTGAATCTTCATAAAGTCAATAAATTCCGGTCTATATTCCTTCGCAACAATAACTAGAC
TTTTACCATTACCGCATACCTGACCAATAAGATGGGCAAAGAAATCAATATCCGTCTTATCTAAACAT
GAATCAGTAATAAATACATAAGGTTCTTTGAACATTGCTTCAATCTTATTTGGTTTATTTGCAAAGATA
GGGTCAACATACCCACGACTAGTTTCAATACCATTTACAATTTCAAATGTATCCTCTTCAGAAGTAGAT
TTATCTAAATAAATAAATCCTCGTTTACCAATTTGTTTATAGATATTATAAATAATATTTCCGTCTTTTT
CATCATTGTTGTTAGATACGGTTGCAATATTACGGAGAATCTCAAAGTTATCTTCATTAATAGGAATTG
ATTTTTCTTTTAATTTCTTTTCAATCAGTTCACCAACATTATTTAATGAATTAATGATTTCTTTCTTAGGA
AGCTTACCTAAGAATTGTGAACGATCATTAACCATTGGTTCTAATTGATTATATAATTCATTACTAACC
ACTACTGAAGAAGTTGATCCATCACCAACCTCTTGCACTAATGATCTTGAAATAGTCTTAATATTATTC
AGAAAAGTAGTACTAATAGTATTGTTAAAACGAATCTTGTCTAAAATTGTGAATCCATCTTTAGAGAT
CTTAGAACCATATAAATTATCTTCTAGAATAGTTGTAGATCCATAATATCCTAAGGATTTAGAAAGAAT
ATCACTAATACTATTAAGTGTTTCTTTAGCAATTTTTTGATATACTTCATCAGAAATTACATTGCTTTCT
ACAATATCAATTTTTTCCTTAGGTTCAAGAATTCTTGAAATTTGATCTTTAATAATATTGCTCATACACT
TTTCCACGCTGCTATATAAATTAGTGAATTTAATTTAATTCACAAGAATTTAATCAACTTCGTCAACAA
GTTTCTTATAAATTCACAAAAAGTGAAAATACAGAGGAAAACTCTCTTAAGTTATAATGGGTTTAGCC
AACCCTTTCTGCATATATTTTTAAATTACATGCAGAATTATAATCTCTATCCATCACTTCATTACATTGA
TCACATGTATATAATCTATCCGAAAGTTTCATTTTTTTATCATTTTCTTTTTTATATCCACAACAACTAC
AAATTTGAGTTGATGGAAACCATCTATCTGCAATAATTAAGGTATTTCCATATAAAATACTTTTATATT
GTAATTGAACTTTAAAACGATAAAATAAAGACCGTGATATAGATTTAGATATTTTTCGGTTAGATAAC
ATTCCTTTAACATTTAAATCTTCTATACATATAGTGTGATAATTTCATCAGAATACTGAAGGTAAACTTA
TGCAGCCAATCATCTTGTATATTTTGTATTTTCAAATAAATATTTTGAAGTTTGATTTTCACTTTATTAT
ATTTATTCGAATTATTGACTTTTCTAGACAAGATTTTTTGGTATAAAGAAATTTTCTTATATAATGGAAT
TAAATTTTTTAAAGGACTATTAAATCGGTGATTTTCTTCACTTATATCAAAATGACCAATATTTGCATC
AATTCCAACTGTCGGAAGATTTTGATTTGAATGATACATACTATCATCAGTATCAATACAGAAAGAAG
CAAAATACTGATTTGCTCTTTTTGTAATTGTACATATTTTAATATCACCATTAAATCGTATCGATTCAGA
CATTTTTACACCATATTTAAATTTAGGTAAAAATAATCGATTATTAATAATCCTTATTGTACTTTCGGCT
TTTCGATTAATCGTAAATGAACTTTTTGCTTTTCGTTTATTTTTGAATTTAGGTTTACCTGAATTAGATG
TAAAAAATCTCTTCCAACCATATGCCATATTTTTACAAGCATTATCAAAAATATTTGGGGGAAAATTAT
CCCATTCAGGTTTCAATTTCCTTTTATATTCGTCTCGCACTTTTCGTTCATTAGGTTTATTGCCGTTAATG
TACATTTCATTCCATATATTCAAAGACACATTATATGAATATCTTGAATAATTGAAAAAATCTTTAAAT
TGTAACTGCATTGTTTTGTTAGGATAGATTCTGATTTTTTGACTTATTATCATCTAAATCATCCCTTAAA
GTTTTTTTATATTTTCGTAATCCGTATAATCGGCTAGAAAATACATGAATAATTGTCATAAGATCATCA
ACTAGTTCTTTTTCAGGAGAAGAACTTTCTAAATTAATTACAGTTGTTGTTCCATTAACTTTACATC
TTTCTTCAATAAGTTCAAAACCAAAACGAGTTAGTCGATCTTTATATGTTATAATAAGTTCTGATACTT
CTTGGTTTTCTATCATGTCAATTAATTTTAAAAAATTCTTTCGTTTAAAATTAATTCCGGATGCAATATC
TGAAAGATAAATATTAACAGGTTTTCCACTATTAACTGAAAATGTTTCAATAGATTGTCGTTGGTTTTC
AAGTTCTTTCTTTTGGTTACTAGTTGAAACTCGATAATATGCTACAATTTTTCTTTTTTCTTCAGGTTTG
ATATTATTAGTTAGTTCAAAATAATCATCAACCATTTCGTCAGTATAATACTTTAGGCGTCCTTTTCGA
ATAGGTTTAATTATTTTTTCCTTTTCTAATGTTTCTAGTTTTTTTCTTTGATATACGTAATTTCATTCTAAA
TTCATCAGAACGCATAACCATTTAAAACACACTCCTTTTTAATTTATATTATATTGTTACATTAAAATAT
AAATTAAAGTGAAAAGAGTGAAACTAGATGATATTCATAATAAGTCGGCTAAATTAAATTCTTATTA
TAATTCCCAATTTTGTGTTTCCACATTGGTTAAATAGCAGGACTATATCATAACCTATAATATTATAGG
TCCCTCGTACTTCCCTTTCGGTACTCTACTTGCTTCGTATAGATATCTCAATCTATCTTATTCACCTAT
AGGTGTTACATTTATTATTTGCTTTCGATAGTCTCTGAACGTTCACCCATCAAGTGGGAGCTTCGCTGC
```

-continued

```
TAGATTTTCCATTAGTCCACCCTTAGCACTACGTTTTCTAAGGTTCACATTATTACTTCACTTAGACACT
GATAGGTTTTATTTCAGCTTAGGTAATCTTAAAGAGTTTTTTCTGTCTTTCGACTGCATTCACGCTTACC
GTTACCAGTTACGTTGTAGCCCTTTAAGCTTTAGGAGTTTACAAGCAATTCACAAGGTTTCGCATACAT
CTTTACAGATATATGGGAGTTTTGAATACAGGTTAATTTAATTTATATTTTAAACTAAACTCATTTAAA
ATCAATTAAACCATTACTGCTTCTTTTCTCCACTTTTTTATTTTATTATAATTGAAAGTACATTGTCATTT
TCAATAATACAATCGAATTCTTCGATAAAGGTATACATCTTAATATAATCTTTACATGAATCAAGATCA
ATATAATTATTAAATTTTAAGGATACTTTTTTAAATTGTCTAATTTCTTCATCTTTGGAAGTATTGTTAA
ATCCTTTGATGATATTAAATGAAAATTTCTCTTCAAGATCATATAGTAGTAAATTAAGCTTTAATCCGA
ATTCAGAATGCTTAAGTGAATCATAATAATTGTCTTCATCATAATCCCCATTCTTTTCGGTAAGTTTATT
ATAAAATTTAAAATTATCGGTATTAATATTCATTAAACTTTCACCACGCTTTCTTAATTTGCCATAATA
ACTCAACTGGACTATTAGTATTTACCATTTATCGGACTTAGATATCCATGGTCTGGTTTACCTGTTGTAT
TTTCATTAGGAGAAGAAGAGGTTCCTCCATTATAGAGATTTCTCAGTTCAGCTTCTTGCCTTTTATGTTT
TTCAGCAATATCCTCTTCTTTAACTTCTCTAAGTCCTAATAATAGATACATTTCAGTGTTCATGATATCG
TTTAGACTTAATTTACCTTCAAATAACTCTAATAAATATAGTATATCTTTAGAATCATTCAATACTTTCT
TTTCGATAATCATTGAACCACTACTATTTTTCTCATCTACTGCTGAAGCTCCAGTTGAGTT
```

Example 10

Determining the Host Range of LPJP1.NL

The inclusivity of LPJP1.NL was determined using several commercially available *L. grayi* strains. Overnight cultures of each strain were diluted in BHI media to either a high burden ($OD_{600}$ of 0.2) or a low burden (1000 CFU/mL). 100 μL of each dilution was added to a well of a 96-well plate and infected with 10 μL of LPJP1.NL at $1.2 \times 10^7$ pfu/mL. As done previously, infected wells were incubated for 4 h at 30° C. before the addition of 65 μL of luciferase detection solution. RLU values were obtained for each sample on the GloMax Navigator as described above. Samples were evaluated using a threshold of 190 RLU, which was approximately twice the signal from background (BHI media control).

The exclusivity of LPJP1.NL was determined using both other *Listeria* species and a multitude of Gram-positive and Gram-negative genera. To assess the possibility of even minute signal production, a high bacterial burden was selected for testing. To this end, 100 μL of overnight culture was directly added to a 96-well plate and infected with 10 μL of LPJP1.NL at $1.2 \times 10^7$ pfu/mL. As done previously, infected wells were incubated for 4 h at 30° C. before the addition of 65 μL of luciferase detection solution. Luminescence was measured and analyzed as described above for inclusivity assays.

Example 11

Inclusivity of LPJP1.NL Detection

Based upon plaque formation and the limit of detection, LPJP1.NL was clearly capable of infecting the *L. grayi* subsp. *grayi* strain ATCC 19120. However, it was not known whether or not this bacteriophage could broadly infect other *L. grayi* strains. Although the number of strains commercially available for testing is limited, four additional strains of *L. grayi* were obtained, including members of the only other subspecies *L. grayi* subsp. *murrayi*. Cultures of each strain were diluted to a low burden (approximately 100 CFU) or a high burden ($OD_{600}$ of 0.2) and infected with LPJP1.NL for 4 h. A cutoff of 190 RLU, approximately two times background, was chosen to distinguish between positive and negative detection for all inclusivity and exclusivity testing. Using this method, all five *L. grayi* strains were successfully detected at both low and high burdens, indicating infection and subsequent NANOLUC® production (Table 4). As expected, the use of stationary phase bacterial cells resulted in reduced signal compared to the limit of detection assay results for 100 CFU. Despite this decrease, LPJP1.NL was capable of infecting and detecting low burdens of all tested *L. grayi* strains, including representatives of both known subspecies.

TABLE 4

| Inclusivity of LPJP1.NL Detection | | | |
| --- | --- | --- | --- |
| | | Signal (RLU) [3] | |
| Bacteria | ATCC [1] | Low Burden (100 CFU) [2] | High Burden ($OD_{600}$ of 0.2) [2] |
| *Listeria grayi* subsp. *grayi* | 19120 | 5755 (Pos.) | 274,905,152 (Pos.) |
| *Listeria grayi* subsp. *murrayi* | 25401 | 1129 (Pos.) | 76,794,888 (Pos.) |
| *Listeria grayi* subsp. *murrayi* | 25402 | 1242 (Pos.) | 278,885,856 (Pos.) |
| *Listeria grayi* subsp. *murrayi* | 25403 | 4399 (Pos.) | 176,249,632 (Pos.) |
| *Listeria grayi* | 700545 | 4743 (Pos.) | 58,170,464 (Pos.) |
| Summary (Positives/Total Strains) | | 5/5 | 5/5 |

[1] Strains were obtained from ATCC and each strains identification number is provided.

[2] Stationary phase cultures of each strain were diluted to the indicated colony forming unit (CFU) or optical density ($OD_{600}$) prior to a 4 h infection at 30° C. with LPJP1.NL.

[3] Detected luminometer signal as relative light units (RLU). Positive (Pos.) and negative (Neg.) detection was determined for each sample using a threshold of 190 RLU, approximately twice media background.

Example 12

Specificity of LPJP1.NL Detection Across Other *Listeria* Species

Many large characterized *Listera* phage of the Myoviridae family, such as P100 and A511, are capable of infecting multiple *Listeria* species, dependent on serovar (Klumpp, J.; et al., Bacteriophage 2013, 3, e26861; Habann, M., et al., *Mol Microbiol* 2014, 92, 84-99). While LPJP1.NL had demonstrated coverage across several *L. grayi* strains, the ability of this phage to infect other *Listeria* species was of significant interest. An exclusivity panel of 150 *Listeria* strains was assembled, consisting of 14 species and 12 different serovars. Due to commercial availability and the public health importance of *L. monocytogenes,* 106 strains of this species were included. In order to assess exclusivity, overnight stationary phase cultures of each strain were directly infected with LPJP1.NL for 4 h. This was expected to represent a significant bacterial burden and allow detection of even limited infection. Despite this burden, no strain in this *Listeria* panel yielded a positive result for NANO-LUC® production, as defined by the 190 RLU threshold (Table 5). RLU data and source of each strain are provided (Table 6). The lack of any substantial signal over background from these strains suggests that LPJP1.NL is incapable of infecting other *Listeria* species besides *L. grayi.*

TABLE 5

Exclusivity of LPJP1.NL in *Listeria* Species Besides *L. grayi*

| Bacteria [1] | Positives/Total Strains [2] |
|---|---|
| *Listeria aquatica* | 0/1 |
| *Listeria booriae* | 0/1 |
| *Listeria fleischmannii* | 0/1 |
| *Listeria floridensis* | 0/1 |
| *Listeria grandensis* | 0/1 |
| *Listeria innocua* | 0/21 |
| *Listeria ivanovii* | 0/6 |
| *Listeria marthii* | 0/2 |
| *Listeria monocytogenes* | 0/106 |
| *Listeria newyorkensis* | 0/1 |
| *Listeria riparia* | 0/1 |
| *Listeria seeligeri* | 0/4 |
| *Listeria welshimeri* | 0/4 |
| Summary | 0/150 |

[1] Stationary phase overnight cultures were infected for 4 h at 30° C. with LPJP1.NL.
[2] Positive detection was determined for each sample using a threshold of 190 relative light units (RLU). Individual RLU values and strain information are provided in (Table 6).

TABLE 6

RLU for Exclusivity of LPJP1.NL in *Listeria* Species Besides *L. grayi*

| Bacteria | Strain | Source [1] | Serovar [2] | RLU [3] |
|---|---|---|---|---|
| *Listeria aquatica* | FSL S10-1188 | FSL | | 64 |
| *Listeria booriae* | FSL A5-0281 | FSL | | 125 |
| *Listeria fleischmannii* | FSL F6-1016 | FSL | | 98 |
| *Listeria floridensis* | FSL S10-1187 | FSL | | 166 |
| *Listeria grandensis* | FSL F6-0971 | FSL | | 67 |
| *Listeria innocua* | 33090 | ATCC | 6a | 69 |
| *Listeria innocua* | BAA-680 | ATCC | 6a | 49 |
| *Listeria innocua* | 33091 | ATCC | 6b | 78 |
| *Listeria innocua* | 43547 | ATCC | 6b | 84 |
| *Listeria innocua* | 51742 | ATCC | | 50 |
| *Listeria innocua* | BAA-349 | ATCC | | 37 |
| *Listeria innocua* | 9 | UGA | | 73 |
| *Listeria innocua* | 15 | UGA | | 61 |
| *Listeria innocua* | 16 | UGA | | 69 |

TABLE 6-continued

RLU for Exclusivity of LPJP1.NL in *Listeria* Species Besides *L. grayi*

| Bacteria | Strain | Source [1] | Serovar [2] | RLU [3] |
|---|---|---|---|---|
| *Listeria innocua* | 18 | UGA | | 54 |
| *Listeria innocua* | 72 | UGA | | 56 |
| *Listeria innocua* | 80 | UGA | | 60 |
| *Listeria innocua* | 92 | UGA | | 81 |
| *Listeria innocua* | Silliker 9 | UGA | | 90 |
| *Listeria innocua* | Silliker 9 NAR | UGA | | 85 |
| *Listeria innocua* | Silliker 16 | UGA | | 61 |
| *Listeria innocua* | Silliker 16 NAR | UGA | | 58 |
| *Listeria innocua* | Silliker 23 NAR | UGA | | 90 |
| *Listeria innocua* | Silliker 24 | UGA | | 63 |
| *Listeria innocua* | Silliker 24 NAR | UGA | | 72 |
| *Listeria innocua* | Silliker106 NAR | UGA | | 56 |
| *Listeria ivanovii* | 19119 | ATCC | | 80 |
| *Listeria ivanovii* | 49953 | ATCC | | 87 |
| *Listeria ivanovii* | BAA-678 | ATCC | 5 | 92 |
| *Listeria ivanovii* | BAA-753 | ATCC | | 65 |
| *Listeria ivanovii* | 700402 | ATCC | | 66 |
| *Listeria ivanovii* | 49954 | ATCC | | 59 |
| *Listeria marthii* | FSL S4-120 | FSL | | 58 |
| *Listeria marthii* | FSL S4-965 | FSL | | 54 |
| *Listeria monocytogenes* | 19111 | ATCC | 1/2a | 35 |
| *Listeria monocytogenes* | 51772 | ATCC | 1/2a | 67 |
| *Listeria monocytogenes* | 51774 | ATCC | 1/2a | 71 |
| *Listeria monocytogenes* | 51775 | ATCC | 1/2a | 77 |
| *Listeria monocytogenes* | BAA-679 | ATCC | 1/2a | 70 |
| *Listeria monocytogenes* | BAA-2657 | ATCC | 1/2a | 52 |
| *Listeria monocytogenes* | BAA-2659 | ATCC | 1/2a | 55 |
| *Listeria monocytogenes* | BAA-2660 | ATCC | 1/2a | 74 |
| *Listeria monocytogenes* | F8369 | UGA | 1/2a | 60 |
| *Listeria monocytogenes* | FSL J2-020 | FSL | 1/2a | 53 |
| *Listeria monocytogenes* | FSL J2-066 | FSL | 1/2a | 65 |
| *Listeria monocytogenes* | FSL C1-056 | FSL | 1/2a | 57 |
| *Listeria monocytogenes* | FSL J2-031 | FSL | 1/2a | 34 |
| *Listeria monocytogenes* | FSL J2-054 | FSL | 1/2a | 50 |
| *Listeria monocytogenes* | FSL J2-063 | FSL | 1/2a | 51 |
| *Listeria monocytogenes* | BAA-751 | ATCC | 1/2b | 66 |
| *Listeria monocytogenes* | BAA-839 | ATCC | 1/2b | 73 |
| Listeria monocytogenes | 51780 | ATCC | 1/2b | 71 |
| *Listeria monocytogenes* | BAA-2658 | ATCC | 1/2b | 58 |
| *Listeria monocytogenes* | FSL J2-064 | FSL | 1/2b | 58 |
| *Listeria monocytogenes* | FSL J1-177 | FSL | 1/2b | 70 |
| *Listeria monocytogenes* | FSL J2-035 | FSL | 1/2b | 72 |
| *Listeria monocytogenes* | G6006 | UGA | 1/2b | 56 |
| *Listeria monocytogenes* | F8255 | UGA | 1/2b | 43 |
| *Listeria monocytogenes* | 51779 | ATCC | 1/2c | 51 |
| *Listeria monocytogenes* | FSL J1-094 | FSL | 1/2c | 48 |
| *Listeria monocytogenes* | 984 | ATCC | 1 | 44 |
| *Listeria monocytogenes* | 9525 | ATCC | 2 | 102 |
| *Listeria monocytogenes* | 19112 | ATCC | 2 | 38 |
| *Listeria monocytogenes* | 19113 | ATCC | 3 | 160 |
| *Listeria monocytogenes* | 51782 | ATCC | 3a | 89 |
| *Listeria monocytogenes* | FSL C1-115 | FSL | 3a | 56 |
| *Listeria monocytogenes* | FSL J1-169 | FSL | 3b | 55 |
| *Listeria monocytogenes* | FSL J1-049 | FSL | 3c | 45 |
| *Listeria monocytogenes* | 51781 | ATCC | 4 | 45 |
| *Listeria monocytogenes* | 19114 | ATCC | 4a | 55 |
| *Listeria monocytogenes* | FSL J1-031 | FSL | 4a | 67 |
| *Listeria monocytogenes* | FSL J1-168 | FSL | 4a | 67 |
| *Listeria monocytogenes* | FSL W1-112 | FSL | 4a | 62 |
| *Listeria monocytogenes* | 19115 | ATCC | 4b | 46 |
| *Listeria monocytogenes* | 13932 | ATCC | 4b | 55 |
| *Listeria monocytogenes* | 51776 | ATCC | 4b | 53 |
| *Listeria monocytogenes* | 51777 | ATCC | 4b | 76 |
| *Listeria monocytogenes* | 51778 | ATCC | 4b | 92 |
| *Listeria monocytogenes* | FSL J1-108 | FSL | 4b | 51 |
| *Listeria monocytogenes* | FSL J1-110 | FSL | 4b | 55 |
| *Listeria monocytogenes* | FSL J1-116 | FSL | 4b | 75 |
| *Listeria monocytogenes* | FSL J1-225 | FSL | 4b | 46 |
| *Listeria monocytogenes* | FSL J1-126 | FSL | 4b | 73 |
| *Listeria monocytogenes* | FSL J1-158 | FSL | 4b | 37 |
| *Listeria monocytogenes* | FSL C1-122 | FSL | 4b | 64 |
| *Listeria monocytogenes* | F2365 | UGA | 4b | 45 |
| *Listeria monocytogenes* | F2365-0770 | UGA | 4b | 38 |
| *Listeria monocytogenes* | F8027 | UGA | 4b | 48 |
| *Listeria monocytogenes* | G1091 | UGA | 4h | 74 |
| *Listeria monocytogenes* | FSL N1-225 | FSL | 4b | 53 |

TABLE 6-continued

RLU for Exclusivity of LPJP1.NL in *Listeria* Species Besides *L. grayi*

| Bacteria | Strain | Source [1] | Serovar [2] | RLU [3] |
|---|---|---|---|---|
| *Listeria monocytogenes* | FSL N1-227 | FSL | 4b | 86 |
| *Listeria monocytogenes* | FSL R2-500 | FSL | 4b | 72 |
| *Listeria monocytogenes* | FSL J1-129 | FSL | 4bx | 69 |
| *Listeria monocytogenes* | FSL W1-110 | FSL | 4c | 87 |
| *Listeria monocytogenes* | FSL W1-111 | FSL | 4c | 94 |
| *Listeria monocytogenes* | 19116 | ATCC | 4c | 30 |
| *Listeria monocytogenes* | 19117 | ATCC | 4d | 49 |
| *Listeria monocytogenes* | Li 2108 | UG | 4d | 89 |
| *Listeria monocytogenes* | FSL J1-107 | FSL | 4d | 58 |
| *Listeria monocytogenes* | 19118 | ATCC | 4e | 51 |
| *Listeria monocytogenes* | 23073 | ATCC | | 44 |
| *Listeria monocytogenes* | 23074 | ATCC | | 41 |
| *Listeria monocytogenes* | 7302 | ATCC | | 74 |
| *Listeria monocytogenes* | 7644 | ATCC | | 79 |
| *Listeria monocytogenes* | 43256 | ATCC | | 64 |
| *Listeria monocytogenes* | 15313 | ATCC | | 62 |
| *Listeria monocytogenes* | 35152 | ATCC | | 26 |
| *Listeria monocytogenes* | CWD 1554 | Q Labs | | 51 |
| *Listeria monocytogenes* | H7557 | UGA | | 52 |
| *Listeria monocytogenes* | H7738 | UGA | | 52 |
| *Listeria monocytogenes* | FSL M1-004 | FSL | | 51 |
| *Listeria monocytogenes* | Bilmar | UGA | | 28 |
| *Listeria monocytogenes* | Brie | UGA | | 47 |
| *Listeria monocytogenes* | Coleslaw | UGA | | 49 |
| *Listeria monocytogenes* | Jalisco | UGA | | 51 |
| *Listeria monocytogenes* | Jalisco GZ7 | UGA | | 71 |
| *Listeria monocytogenes* | Silliker 15 | UGA | | 62 |
| *Listeria monocytogenes* | Silliker 15 NAR | UGA | | 62 |
| *Listeria monocytogenes* | Silliker 17 | UGA | | 63 |
| *Listeria monocytogenes* | Silliker 17 NAR | UGA | | 76 |
| *Listeria monocytogenes* | Silliker 18 | UGA | | 48 |
| *Listeria monocytogenes* | Silliker 18 NAR | UGA | | 61 |
| *Listeria monocytogenes* | Silliker 32 NAR | UGA | | 135 |
| *Listeria monocytogenes* | Silliker 70 | UGA | | 52 |
| *Listeria monocytogenes* | Silliker 70 NAR | UGA | | 67 |
| *Listeria monocytogenes* | Silliker 72 NAR | UGA | | 73 |
| *Listeria monocytogenes* | Silliker 80 NAR | UGA | | 50 |
| *Listeria monocytogenes* | Silliker 106 | UGA | | 35 |
| *Listeria monocytogenes* | 2011L-2663 | UGA | | 60 |
| *Listeria monocytogenes* | 2011L-2626 | UGA | | 65 |
| *Listeria monocytogenes* | 2011L-2625 | UGA | | 121 |
| *Listeria monocytogenes* | 2011L-2624 | UGA | | 164 |
| *Listeria monocytogenes* | F6900 | UGA | | 43 |
| *Listeria monocytogenes* | SLR 516 | UGA | | 85 |
| *Listeria monocytogenes* | G3990 | UGA | | 54 |

TABLE 6-continued

RLU for Exclusivity of LPJP1.NL in *Listeria* Species Besides *L. grayi*

| Bacteria | Strain | Source [1] | Serovar [2] | RLU [3] |
|---|---|---|---|---|
| *Listeria monocytogenes* | LCDC | 81-861 | UGA | 72 |
| *Listeria monocytogenes* | 101M | UGA | | 48 |
| *Listeria monocytogenes* | 108 M | UGA | | 50 |
| *Listeria monocytogenes* | V7 | UGA | | 106 |
| *Listeria monocytogenes* | 1A1 | UGA | | 101 |
| *Listeria newyorkensis* | FSL M6-0635 | FSL | | 79 |
| *Listeria riparia* | FSL S10-1204 | FSL | | 65 |
| *Listeria seeligeri* | 35967 | ATCC | | 82 |
| *Listeria seeligeri* | 51334 | ATCC | | 65 |
| *Listeria seeligeri* | 51335 | ATCC | 4a | 45 |
| *Listeria seeligeri* | 2/25/04 | UGA | | 59 |
| *Listeria welshimeri* | 35897 | ATCC | 6b | 81 |
| *Listeria welshimeri* | 43549 | ATCC | 6b | 74 |
| *Listeria welshimeri* | 43551 | ATCC | 6a | 69 |
| *Listeria welshimeri* | 43550 | ATCC | 1/2b | 81 |

[1] Strains were obtained from either the American Type Culture Collection (ATCC, Manassas, VA, USA), the Food Safety Laboratory of Cornell University (FSL, Ithaca, NY, USA), the University of Georgia (UGA, Athens, GA, USA), or Q Laboratories (Q Labs, Cincinnati, OH, USA).
[2] Serovar of each strain is indicated when provided by source.
[3] RL

Example 13

Specificity of LPJP1.NL Detection Across Other Genera

To evaluate the specificity of LPJP1.NL for *Listeria*, an exclusivity panel of 26 Gram-negative and 19 Gram-positive strains was assembled. Representatives of 19 unique genera and 42 species were included. As done with *Listeria* species, overnight stationary phase cultures of each strain were infected with LPJP1.NL for 4 h. Unsurprisingly, no positive signal was detected from any of the 45 members of the exclusivity panel (Table 7). The absence of NANOLUC® production in these strains further supports the notion that LPJP1.NL is highly specific for *L. grayi*. LPJP1.NL was highly specific for *L. grayi* demonstrating no cross-reactivity with other *Listeria* species or bacterial genera (Tables 5,7). The narrow host range of LPJP1 may indicate a receptor unique to *L. grayi*.

TABLE 7

Exclusivity of LPJP1NANOLUC ® in other Genera (non-*Listeria*)

| Gram-Negative Bacteria | ATCC [1] | RLU [2] | Gram-Positive Bacteria | ATCC [1] | RLU [2] |
|---|---|---|---|---|---|
| *Acinetobacter baumannii* | 19606 | 48 (Neg.) | *Bacillus cereus* | 14579 | 48 (Neg.) |
| *Acinetobacter calcoaceticus* | 23055 | 95 (Neg.) | *Bacillus cereus* | 13061 | 108 (Neg.) |
| *Citrobacter braaki* | 51113 | 35 (Neg.) | *Bacillus circulans* | 61 | 88 (Neg.) |
| *Citrobacter freundii* | 8090 | 37 (Neg.) | *Bacillus coagulans* | 7050 | 108 (Neg.) |
| *Citrobacter koseri* | 25408 | 81 (Neg.) | *Bacillus licheniformis* | 9789 | 75 (Neg.) |
| *Cronobacter muytjensii* | 51329 | 69 (Neg.) | *Bacillus megaterium* | 14581 | 73 (Neg.) |
| *Cronobacter sakazakii* | 12868 | 65 (Neg.) | *Bacillus mycoides* | 6462 | 65 (Neg.) |
| *Escherichia coli* | 9637 | 48 (Neg.) | *Bacillus pumilus* | 700814 | 40 (Neg.) |
| *Escherichia fergusonii* | 35469 | 44 (Neg.) | *Bacillus subtilis* | 23857 | 49 (Neg.) |
| *Escherichia hermanii* | 33650 | 45 (Neg.) | *Bacillus subtilis* | 6051 | 101 (Neg.) |
| *Edwardsiella tarda* | 15947 | 40 (Neg.) | *Bacillus weihenstephanensis* | 12826 | 55 (Neg.) |
| *Enterobacter cloacae* | 13047 | 31 (Neg.) | *Enterococcus faecalis* | 19433 | 87 (Neg.) |
| *Enterobacter kobei* | BAA-260 | 26 (Neg.) | *Enterococcus faecalis* | 29212 | 35 (Neg.) |
| *Hafnia alevi* | 13337 | 25 (Neg.) | *Enterococcus faecium* | 19434 | 74 (Neg.) |
| *Klebsiella aerogenes* | 13048 | 50 (Neg.) | *Lactobacillus plantarum* | 14917 | 68 (Neg.) |
| *Klebsiella oxytoca* | 43165 | 36 (Neg.) | *Lactobacillus rhamnosus* | 7469 | 57 (Neg.) |
| *Klebsiella pneumoniae* | 4352 | 42 (Neg.) | *Staphylococcus aureus* | 27660 | 37 (Neg.) |
| *Morganella morganii* | 25830 | 25 (Neg.) | *Staphylococcus epidermidis* | 14990 | 44 (Neg.) |
| *Pluralibacter gergovi* | 33028 | 33 (Neg.) | *Staphylococcus haemolyticus* | 29970 | 26 (Neg.) |
| *Proteus mirabilis* | 43071 | 14 (Neg.) | | | |
| *Proteus vulgaris* | 33420 | 30 (Neg.) | | | |
| *Pseudomonas aeruginosa* | 27853 | 70 (Neg.) | | | |

TABLE 7-continued

| Exclusivity of LPJP1NANOLUC ® in other Genera (non-*Listeria*) | | | | | |
|---|---|---|---|---|---|
| Gram-Negative Bacteria | ATCC [1] | RLU [2] | Gram-Positive Bacteria | ATCC [1] | RLU [2] |
| *Serratia marcescens* | 13880 | 36 (Neg.) | | | |
| *Shigella flexneri* | 12022 | 45 (Neg.) | | | |
| *Shigella sonnei* | 9290 | 24 (Neg.) | | | |
| *Yersinia enterocolitica* | 23715 | 51 (Neg.) | | | |
| Summary (Positives/Total Strains) | | 0/26 | Summary (Positives/Total Strains) | | 0/19 |

[1] Strains were obtained from ATCC and each strain's identification number is provided.
[2] Stationary phase overnight cultures were infected for 4 h at 30° C. with LPJP1.NL. Detected luminometer signal as relative light units (RLU). Positive (Pos.) and negative (Neg.) detection was determined for each sample using a threshold of 190 RLU, approximately twice media background.

Example 15

Specificity of *Listeria*-Specific Phages

The inclusivity of A511-3A, LMA8, LP-ES1, and LPJP1 for *Listeria* was assessed using several commercially available *Listeria* strains. Overnight cultures of each strain were diluted in BHI media to either a high burden (OD60 of ~0.2) or a low burden (1000 CFU/mL). 100 µL of each dilution was added to a well of a 96-well plate and infected with 10 µL of either LMA8.NL, LP-ES1.NL, A511-3A.NL, or LPJP1.NL at 1.2×107 pfu/mL. As done previously, infected wells were incubated for 4 h at 30° C. before the addition of 65 µL of luciferase detection solution. RLU values were obtained for each sample on the GloMax Navigator as described above. Samples were evaluated using a threshold of 190 RLU, which was approximately twice the signal from background (BHI media control). The inclusivity data for LMA8.NL is shown in Table 8. The inclusivity data for LP-ES1.NL is shown in Table 9. The inclusivity data for LMA8.NL A511-3A.NL is shown in Table 10. The inclusivity data for LPJP1.NL is shown in Table 11.

TABLE 8

| | | | | | LMA8NANOLUC ® Inclusivity | | | |
|---|---|---|---|---|---|---|---|---|
| | Bacterial | | | | LM8NANOLUC ® | | | |
| # | Strains | Strain | Source | Serotype | RLU | OD600 | RLU | OD600 |
| 1 | *Listeria monocytogenes* | 7762 | ATCC | 4b | 201183 | 2.5 | 3694464 | 0.205 |
| 2 | *Listeria booriae* | A5-0281 | FSL | | 81452 | 3.56 | 133011168 | 0.209 |
| 3 | *Listeria monocytogenes* | ATCC 13932 | ATCC | 4b | 392535 | 2.57 | 112751536 | 0.257 |
| 4 | *Listeria monocytogenes* | ATCC 15313 | ATCC | 1/2a | 467188 | 1.86 | 38300472 | 0.186 |
| 5 | *Listeria monocytogenes* | ATCC 19111 | ATCC | 1/2a | 325959 | 2.56 | 104009944 | 0.256 |
| 6 | *Listeria monocytogenes* | ATCC 19112 | ATCC | 2 (1/2C) | 643630 | 2.63 | 9473955 | 0.263 |
| 7 | *Listeria monocytogenes* | ATCC 19113 | ATCC | 3a | 93 | 2.96 | 116 | 0.216 |
| 8 | *Listeria monocytogenes* | ATCC 19114 | ATCC | 4a | 1728 | 2.27 | 1119979 | 0.227 |
| 9 | *Listeria monocytogenes* | ATCC 19115 | ATCC | 4b | 247026 | 2.69 | 31892470 | 0.2 |
| 10 | *Listeria monocytogenes* | ATCC 19116 | ATCC | 4c | 1144115 | 2.09 | 56086620 | 0.209 |
| 11 | *Listeria monocytogenes* | ATCC 19117 | ATCC | 4d | 946509 | 1.99 | 8318137 | 0.199 |
| 12 | *Listeria monocytogenes* | ATCC 19118 | ATCC | 4e | 1215286 | 1.92 | 33015870 | 0.192 |
| 13 | *Listeria ivanovii* | ATCC 19119 | ATCC | | 560668 | 1.14 | 139484896 | 0.127 |
| 14 | *Listeria grayi* | ATCC 19120 | ATCC | | 101 | 2.53 | 94 | 0.225 |
| 15 | *Listeria monocytogenes* | ATCC 23073 | ATCC | | 974495 | 2.47 | 166638240 | 0.247 |
| 16 | *Listeria monocytogenes* | ATCC 23074 | ATCC | | 675752 | 2.09 | 15585736 | 0.209 |
| 17 | *Listeria grayi* | ATCC 25401 | ATCC | | 127 | 2.74 | 380 | 0.231 |
| 18 | *Listeria innocua* | ATCC 33090 | ATCC | 6a | 4773 | 2.28 | 89978 | 0.231 |
| 19 | *Listeria innocua* | ATCC 33091 | ATCC | 6b | 782 | 2.61 | 7940235 | 0.2 |
| 20 | *Listeria monocytogenes* | ATCC 35152 | ATCC | 1/2a | 176025 | 2.25 | 63048632 | 0.225 |
| 21 | *Listeria welshimeri* | ATCC 35897 | ATCC | 6b | 11924 | 2.38 | 3097106 | 0.23 |

TABLE 8-continued

| | | | | | LM8NANOLUC ® | | | |
|---|---|---|---|---|---|---|---|---|
| | Bacterial | | | | | | | |
| # | Strains | Strain | Source | Serotype | RLU | OD600 | RLU | OD600 |
| 22 | *Listeria seeligeri* | ATCC 35967 | ATCC | | 72823 | 1.97 | 481503680 | 0.21 |
| 23 | *Listeria monocytogenes* | ATCC 43256 | ATCC | | 8509 | 2.36 | 56072384 | 0.236 |
| 24 | *Listeria innocua* | ATCC 43547 | ATCC | 6b | 46528 | 2.67 | 75513832 | 0.206 |
| 25 | *Listeria welshimeri* | ATCC 43549 | ATCC | 6a | 10613 | 2.52 | 21210257 | 0.218 |
| 26 | *Listeria welshimeri* | ATCC 43550 | ATCC | 1/2b | 910046 | 0.46 | 62637188 | 0.215 |
| 27 | *Listeria welshimeri* | ATCC 43551 | ATCC | 6a | 2404 | 2.07 | 560743.5 | 0.207 |
| 28 | *Listeria ivanovii* | ATCC 49953 | ATCC | | 1306413 | 1.28 | 158548192 | 0.223 |
| 29 | *Listeria ivanovii, londoniensis* | ATCC 49954 | ATCC | | 25124 | 1.63 | 234277392 | 0.163 |
| 30 | *Listeria seeligeri* | ATCC 51334 | ATCC | | 192285 | 2.47 | 197103552 | 0.247 |
| 31 | *Listeria seeligeri* | ATCC 51335 | ATCC | 4a | 99 | 2.21 | 207 | 0.221 |
| 32 | *Listeria innocua* | ATCC 51742 | ATCC | | 146085 | 2.26 | 24802088 | 0.226 |
| 33 | *Listeria monocytogenes* | ATCC 51772 | ATCC | 1/2a | 2094 | 1.83 | 19229936 | 0.183 |
| 34 | *Listeria monocytogenes* | ATCC 51774 | ATCC | 1/2a | 34991 | 2.18 | 182480 | 0.218 |
| 35 | *Listeria monocytogenes* | ATCC 51775 | ATCC | 1/2a | 13537 | 2.78 | 83289544 | 0.278 |
| 36 | *Listeria monocytogenes* | ATCC 51776 | ATCC | 4b | 387054 | 2.15 | 204647040 | 0.215 |
| 37 | *Listeria monocytogenes* | ATCC 51777 | ATCC | 4b | 22722 | 1.94 | 79525872 | 0.194 |
| 38 | *Listeria monocytogenes* | ATCC 51778 | ATCC | 4b | 28283 | 2.28 | 116421808 | 0.228 |
| 39 | *Listeria monocytogenes* | ATCC 51779 | ATCC | 1/2c | 836579 | 2.55 | 18885666 | 0.255 |
| 40 | *Listeria monocytogenes* | ATCC 51780 | ATCC | 1/2b | 43236 | 2.43 | 70239432 | 0.243 |
| 41 | *Listeria monocytogenes* | ATCC 51781 | ATCC | 4 | 89953 | 2.14 | 55889052 | 0.214 |
| 42 | *Listeria monocytogenes* | ATCC 51782 | ATCC | 3a | 81 | 2.37 | 134 | 0.237 |
| 43 | *Listeria monocytogenes* | ATCC 700402 | ATCC | | 379973 | 1.75 | 27378515 | 0.2 |
| 44 | *Listeria grayi* | ATCC 700545 | ATCC | | 112 | 2.83 | 86 | 0.22 |
| 45 | *Listeria monocytogenes* | ATCC 7302 | ATCC | | 37065 | 2.24 | 288962688 | 0.224 |
| 46 | *Listeria monocytogenes* | ATCC 7644 | ATCC | | 1355416 | 2.15 | 238131152 | 0.215 |
| 47 | *Listeria monocytogenes* | ATCC 9525 | ATCC | 2 | 504969 | 2.35 | 39016790 | 0.2 |
| 48 | *Listeria monocytogenes* | ATCC 984 | ATCC | | 208196 | 2.65 | 94120536 | 0.265 |
| 49 | *Listeria monocytogenes* | ATCC BAA-2657 | ATCC | 1/2a | 219643 | 2.01 | 70258748 | 0.201 |
| 50 | *Listeria monocytogenes* | ATCC BAA-2658 | ATCC | | 6336 | 2.38 | 19042346 | 0.196 |
| 51 | *Listeria monocytogenes* | ATCC BAA-2659 | ATCC | 1/2a | 314716 | 2.31 | 42012014 | 0.231 |
| 52 | *Listeria monocytogenes* | ATCC BAA-2660 | ATCC | 1/2a | 81133 | 1.75 | 147021360 | 0.175 |
| 53 | *Listeria innocua* | ATCC BAA-349 | ATCC | | 1807000 | 2.56 | 58170000 | 0.256 |
| 54 | *Listeria ivanovii* | ATCC BAA-678 | ATCC | 5 | 181045 | 1.51 | 106635648 | 0.151 |
| 55 | *Listeria monocytogenes* | ATCC BAA-679 | ATCC | 1/2a | 691 | 2.67 | 160941600 | 0.205 |
| 56 | *Listeria innocua* | ATCC BAA-680 | ATCC | 6a | 244 | 2.94 | 19190 | 0.207 |
| 57 | *Listeria monocytogenes* | ATCC BAA-751 | ATCC | 1/2b | 345 | 2.29 | 72975 | 0.229 |

TABLE 8-continued

| | | | | | LM8NANOLUC ® | | | |
|---|---|---|---|---|---|---|---|---|
| | Bacterial | | | | | | | |
| # | Strains | Strain | Source | Serotype | RLU | OD600 | RLU | OD600 |
| 58 | *Listeria ivanovii* subsp. *londoniensis* | ATCC BAA-753 | ATCC | | 417150 | 1.6 | 164550000 | 0.16 |
| 59 | *Listeria monocytogenes* | ATCC BAA-839 | ATCC | 1/2b | 45166 | 2.22 | 50474760 | 0.222 |
| 60 | *Listeria monocytogenes* | C1-056 | FSL | | 5281 | 2.56 | 151693200 | 0.235 |
| 61 | *Listeria monocytogenes* | C1-115 | FSL | | 2071 | 2.9 | 44519308 | 0.2 |
| 62 | *Listeria monocytogenes* | C1-122 | FSL | 4b | 11661 | 2.88 | 37285228 | 0.208 |
| 63 | *Listeria monocytogenes* | CWD 1554 | Q Labs | | 77631 | 2.07 | 28014998 | 0.207 |
| 64 | *Listeria cornellensis* | F6-0969 | FSL | | 6075 | 1.89 | 3576594 | 0.189 |
| 65 | *Listeria grandensis* | F6-0971 | FSL | | 30501 | 2.85 | 39529188 | 0.211 |
| 66 | *Listeria fleischmannii* subsp. *coloradensis* | F6-1016 | FSL | | 16 | 3.24 | 55 | 0.209 |
| 67 | *Listeria monocytogenes* | J1-031 | FSL | | 3055 | 2.86 | 17211488 | 0.182 |
| 68 | *Listeria monocytogenes* | J1-049 | FSL | 3c | 66 | 2.59 | 3814 | 0.193 |
| 69 | *Listeria monocytogenes* | J1-094 | FSL | | 35367 | 2.9 | 55766904 | 0.212 |
| 70 | *Listeria monocytogenes* | J1-107 | FSL | | 120038 | 1.94 | 98064848 | 0.194 |
| 71 | *Listeria monocytogenes* | J1-108 | FSL | 4b | 484051 | 1.95 | 31781914 | 0.204 |
| 72 | *Listeria monocytogenes* | J1-110 | FSL | 4b | 15135 | 2.34 | 150981528 | 0.203 |
| 73 | *Listeria monocytogenes* | J1-116 | FSL | 4b | 828067 | 2.44 | 52092880 | 0.212 |
| 74 | *Listeria monocytogenes* | J1-126 | FSL | 4b | 724612 | 2.48 | 22148832 | 0.214 |
| 75 | *Listeria monocytogenes* | J1-129 | FSL | | 30904 | 2.12 | 46577832 | 0.212 |
| 76 | *Listeria monocytogenes* | J1-158 | FSL | 4b | 747310 | 2.37 | 8944823 | 0.207 |
| 77 | *Listeria monocytogenes* | J1-158 | FSL | | 25998 | 2.68 | 7153664 | 0.216 |
| 78 | *Listeria monocytogenes* | J1-168 | FSL | | 28187 | 2.75 | 37703144 | 0.203 |
| 79 | *Listeria monocytogenes* | J1-169 | FSL | 3b | 17638 | 2.61 | 7489451 | 0.211 |
| 80 | *Listeria monocytogenes* | J1-177 | FSL | 1/2b | 52 | 2.57 | 149 | 0.206 |
| 81 | *Listeria monocytogenes* | J1-225 | FSL | 4b | 19859 | 2.46 | 215210520 | 0.241 |
| 82 | *Listeria monocytogenes* | J2-020 | FSL | 1/2a | 244233 | 2.56 | 31195341 | 0.215 |
| 83 | *Listeria monocytogenes* | J2-020 | FSL | 1/2a | 8476 | 2.49 | 100771632 | 0.216 |
| 84 | *Listeria monocytogenes* | J2-031 | FSL | | 5433 | 2.78 | 109970440 | 0.223 |
| 85 | *Listeria monocytogenes* | J2-035 | FSL | 1/2b | 9351 | 2.14 | 61090432 | 0.214 |
| 86 | *Listeria monocytogenes* | J2-054 | FSL | | 17560 | 2.62 | 30626724 | 0.225 |
| 87 | *Listeria monocytogenes* | J2-063 | FSL | | 4550 | 2.7 | 23748378 | 0.209 |
| 88 | *Listeria monocytogenes* | J2-064 | FSL | 1/2b | 12308 | 2.5 | 99126764 | 0.223 |
| 89 | *Listeria monocytogenes* | J2-066 | FSL | 1/2a | 119213 | 2.43 | 462493 | 0.209 |
| 90 | *Listeria monocytogenes* | J2-066 | FSL | | 1896 | 3.09 | 1551655 | 0.216 |
| 91 | *Listeria monocytogenes* | M1-004 | FSL | | 75 | 2.61 | 198 | 0.217 |
| 92 | *Listeria newyorkensis* | M6-0635 | FSL | | 75889 | 4.09 | 32992518 | 0.221 |

TABLE 8-continued

| | | | | | LMA8NANOLUC ® Inclusivity | | | |
|---|---|---|---|---|---|---|---|---|
| | Bacterial | | | | LM8NANOLUC ® | | | |
| # | Strains | Strain | Source | Serotype | RLU | OD600 | RLU | OD600 |
| 93 | Listeria monocytogenes | N1-225 | FSL | 4b | 383176 | 2.55 | 4283739 | 0.208 |
| 94 | Listeria monocytogenes | N1-225 | FSL | 4b | 6913 | 2.93 | 382504 | 0.196 |
| 95 | Listeria monocytogenes | N1-227 | FSL | 4b | 152128 | 2.43 | 580291 | 0.2 |
| 96 | Listeria monocytogenes | R2-500 | FSL | 4b | 626800 | 2.19 | 87288832 | 0.216 |
| 97 | Listeria floridensis | S10-1187 | FSL | | 13929 | 1.79 | 17193370 | 0.179 |
| 98 | Listeria aquatica | S10-1188 | FSL | | 85 | 2.96 | 153 | 0.211 |
| 99 | Listeria riparia | S10-1204 | FSL | | 219806 | 3.09 | 163328736 | 0.213 |
| 100 | Listeria marthii | S4-120 | FSL | | 12064 | 2.69 | 83974656 | 0.215 |
| 101 | Listeria marthii | S4-965 | FSL | | 62 | 2.6 | 27292 | 0.195 |
| 102 | Listeria monocytogenes | Scott 1 | UGA | 4b | 765415 | 2.75 | 164051376 | 0.218 |
| 103 | Listeria monocytogenes | W1-110 | UGA | | 93 | 2.43 | 12717 | 0.214 |
| 104 | Listeria monocytogenes | W1-111 | UGA | | 22281 | 2.43 | 27923586 | 0.209 |
| 105 | Listeria monocytogenes | W1-112 | UGA | | 10374 | 2.57 | 30372276 | 0.217 |
| 106 | Listeria innocua | Silliker 9 | UGA | | 100 | 2.02 | 142 | 0.202 |
| 107 | Listeria monocytogenes | Silliker 17 | UGA | | 3645 | 2.33 | 71471160 | 0.233 |
| 108 | Listeria monocytogenes | Silliker 106 | UGA | | 1361853 | 2.27 | 56330156 | 0.227 |
| 109 | Listeria innocua | 15 | UGA | | 130 | 2.01 | 120 | 0.201 |
| 110 | Listeria innocua | 16 | UGA | | 19529 | 2.15 | 821112 | 0.215 |
| 111 | Listeria innocua | Silliker 24 | UGA | | 80 | 1.92 | 66 | 0.192 |
| 112 | Listeria monocytogenes | H7557 | UGA | | 273076 | 2.17 | 3214223 | 0.217 |
| 113 | Listeria innocua | 9 | UGA | | 70 | 2.3 | 58 | 0.23 |
| 114 | Listeria monocytogenes | 2011L-2663 | UGA | | 6387 | 2.3 | 120032968 | 0.23 |
| 115 | Listeria monocytogenes | H7738 | UGA | | 6838 | 2.39 | 1682729 | 0.239 |
| 116 | Listeria monocytogenes | Jalisco G278 | UGA | | 1995254 | 1.81 | 64005104 | 0.181 |
| 117 | Listeria monocytogenes | F2365 | UGA | 4b | 26800 | 2.51 | 46690608 | 0.251 |
| 118 | Listeria innocua | Silliker 23 NAR | UGA | | 13617 | 2.06 | 775426 | 0.206 |
| 119 | Listeria innocua | Silliker 16 NAR | UGA | | 87 | 2.46 | 143 | 0.246 |
| 120 | Listeria monocytogenes | Silliker 17NAR | UGA | | 26811 | 2.15 | 67068076 | 0.215 |
| 121 | Listeria innocua | Silliker 9 NAR | UGA | | 85 | 2.21 | 114 | 0.221 |
| 122 | Listeria innocua | Silliker 16 | UGA | | 103 | 2.32 | 298 | 0.232 |
| 123 | Listeria monocytogenes | F8027 | UGA | 4b | 16568 | 2.47 | 191940896 | 0.247 |
| 124 | Listeria innocua | 18 | UGA | | 5679 | 2.36 | 932619 | 0.236 |
| 125 | Listeria innocua | 72 | UGA | | 115 | 2.19 | 113 | 0.219 |
| 126 | Listeria innocua | Siliker 24 NAR | UGA | | 79 | 2 | 48 | 0.2 |
| 127 | Listeria innocua | 80 | UGA | | 13100 | 2.39 | 627243 | 0.239 |
| 128 | Listeria monocytogenes | G1091 | UGA | 4b | 17522 | 2.17 | 168322520 | 0.217 |
| 129 | Listeria monocytogenes | Silliker 70 | UGA | | 911 | 2.49 | 3412230 | 0.202 |

TABLE 8-continued

LMA8NANOLUC ® Inclusivity

| | Bacterial | | | | LM8NANOLUC ® | | | |
|---|---|---|---|---|---|---|---|---|
| # | Strains | Strain | Source | Serotype | RLU | OD600 | RLU | OD600 |
| 130 | *Listeria innocua* | Siliker 106 NAR | UGA | | 13338 | 2.69 | 66052424 | 0.207 |
| 131 | *Listeria monocytogenes* | F6900 | UGA | | 10702 | 2.72 | 61191720 | 0.21 |
| 132 | *Listeria monocytogenes* | F8639 | UGA | 1/2a | 3984 | 2.54 | 154929440 | 0.202 |
| 133 | *Listeria monocytogenes* | F2365-0770 | UGA | 4b | 65124 | 2.75 | 37817832 | 0.219 |
| 134 | *Listeria monocytogenes* | Li 2108 | UGA | 4d | 13915 | 2.5 | 3493041 | 0.202 |
| 135 | *Listeria monocytogenes* | 108 M | UGA | | 442765 | 2.28 | 338717856 | 0.207 |
| 136 | *Listeria monocytogenes* | 2011 L-2626 | UGA | | 12468 | 2.72 | 144002256 | 0.201 |
| 137 | *Listeria monocytogenes* | Silliker 32 NAR | UGA | | 10662 | 2.52 | 133726896 | 0.183 |
| 138 | *Listeria monocytogenes* | Silliker 70 NAR | UGA | | 2130 | 2.63 | 3414040 | 0.193 |
| 139 | *Listeria monocytogenes* | Silliker 72 NAR | UGA | | 464 | 3.07 | 204934 | 0.226 |
| 140 | *Listeria monocytogenes* | 2011L-2625 | UGA | | 1407 | 2.64 | 21277316 | 0.193 |
| 141 | *Listeria monocytogenes* | 2011L-2624 | UGA | | 11062 | 2.41 | 155413952 | 0.174 |
| 142 | *Listeria ivanovii* | # | UGA | | 480632 | 1.83 | 66060818 | 0.22 |
| 143 | *Listeria monocytogenes* | 101M | UGA | | 14256 | 2.66 | 4857065 | 0.187 |
| 144 | *Listeria monocytogenes* | SLR516 | UGA | | 56235 | 2.34 | 151878208 | 0.192 |
| 145 | *Listeria monocytogenes* | V7 | UGA | | 1977 | 2.41 | 110831072 | 0.189 |
| 146 | *Listeria innocua* | 92 | UGA | | 5275 | 2.26 | 359724 | 0.185 |
| 147 | *Listeria monocytogenes* | 1A1 | UGA | | 34902 | 2.68 | 159439280 | 0.199 |
| 148 | *Listeria monocytogenes* | Scotty A | UGA | | 1372842 | 2.19 | 70429392 | 0.219 |
| 149 | *Listeria monocytogenes* | G3990 | UGA | | 57043 | 2.35 | 158903968 | 0.236 |
| 150 | *Listeria monocytogenes* | Jalisco | UGA | | 5254 | 2.91 | 91889112 | 0.291 |
| 151 | *Listeria monocytogenes* | Coleslaw | UGA | | 3166676 | 2.69 | 152072416 | 0.269 |
| 152 | *Listeria monocytogenes* | LCDC 81-861 | UGA | | 27869 | 2.73 | 6063443 | 0.273 |
| 153 | *Listeria monocytogenes* | Bilmar | UGA | | 60 | 2.54 | 4138 | 0.254 |

TABLE 9

LP-ES1NAN0LUC ® Inclusivity

| | Bacterial | | | | LPES1NANOLUC ® | | | |
|---|---|---|---|---|---|---|---|---|
| # | Strains | Strain | Source | Serotype | RLU | OD600 | RLU | OD600 |
| 1 | *Listeria monocytogenes* | 7762 | ATCC | 4b | 6845 | 2.66 | 10422 | 0.209 |
| 2 | *Listeria booriae* | A5-0281 | FSL | | 194 | 3.56 | 851 | 0.209 |
| 3 | *Listeria monocytogenes* | ATCC 13932 | ATCC | 4b | 131 | 2.57 | 1125560 | 0.257 |
| 4 | *Listeria monocytogenes* | ATCC 15313 | ATCC | 1/2a | 56 | 1.54 | 101487392 | 0.203 |
| 5 | *Listeria monocytogenes* | ATCC 19111 | ATCC | 1/2a | 246 | 2.56 | 226709904 | 0.256 |
| 6 | *Listeria monocytogenes* | ATCC 19112 | ATCC | 2 (1/2C) | 61 | 2.99 | 2068 | 0.216 |
| 7 | *Listeria monocytogenes* | ATCC 19113 | ATCC | 3a | 42 | 2.56 | 289 | 0.197 |

TABLE 9-continued

| | | | | | LP-ES1NAN0LUC ® Inclusivity | | | |
|---|---|---|---|---|---|---|---|---|
| | Bacterial | | | | | LPES1NANOLUC ® | | |
| # | Strains | Strain | Source | Serotype | RLU | OD600 | RLU | OD600 |
| 8 | *Listeria monocytogenes* | ATCC 19114 | ATCC | 4a | 48 | 2.27 | 15835838 | 0.227 |
| 9 | *Listeria monocytogenes* | ATCC 19115 | ATCC | 4b | 231 | 2.8 | 795700 | 0.28 |
| 10 | *Listeria monocytogenes* | ATCC 19116 | ATCC | 4c | 141345 | 2.13 | 273572224 | 0.213 |
| 11 | *Listeria monocytogenes* | ATCC 19117 | ATCC | 4d | 9733 | 2.5 | 1290992 | 0.195 |
| 12 | *Listeria monocytogenes* | ATCC 19118 | ATCC | 4e | 38796 | 2.71 | 2688796 | 0.189 |
| 13 | *Listeria ivanovii* | ATCC 19119 | ATCC | | 479350 | 1.57 | 20550000 | 0.157 |
| 14 | *Listeria grayi* | ATCC 19120 | ATCC | | 73 | 2.73 | 62 | 0.273 |
| 15 | *Listeria monocytogenes* | ATCC 23073 | ATCC | | 1317014 | 2.11 | 112043832 | 0.211 |
| 16 | *Listeria monocytogenes* | ATCC 23074 | ATCC | | 160 | 2.86 | 1154689 | 0.217 |
| 17 | *Listeria grayi* | ATCC 25401 | ATCC | | 158 | 3.22 | 534 | 0.322 |
| 18 | *Listeria innocua* | ATCC 33090 | ATCC | 6a | 107 | 2.75 | 944950 | 0.275 |
| 19 | *Listeria innocua* | ATCC 33091 | ATCC | 6b | 126 | 2.61 | 420019040 | 0.2 |
| 20 | *Listeria monocytogenes* | ATCC 35152 | ATCC | 1/2a | 127 | 3.07 | 120403112 | 0.225 |
| 21 | *Listeria welshimeri* | ATCC 35897 | ATCC | 6b | 92 | 2.82 | 38380000 | 0.282 |
| 22 | *Listeria seeligeri* | ATCC 35967 | ATCC | | 88715 | 2.39 | 71270000 | 0.239 |
| 23 | *Listeria monocytogenes* | ATCC 43256 | ATCC | | 83 | 2.36 | 171450 | 0.236 |
| 24 | *Listeria innocua* | ATCC 43547 | ATCC | 6b | 888 | 2.67 | 27646752 | 0.206 |
| 25 | *Listeria welshimeri* | ATCC 43549 | ATCC | 6a | 68 | 2.52 | 12646106 | 0.218 |
| 26 | *Listeria welshimeri* | ATCC 43550 | ATCC | 1/2b | 209980 | 0.463 | 1095841 | 0.21 |
| 27 | *Listeria welshimeri* | ATCC 43551 | ATCC | 6a | 61 | 2.07 | 64016 | 0.207 |
| 28 | *Listeria ivanovii* | ATCC 49953 | ATCC | | 36880 | 1.17 | 1010157 | 0.236 |
| 29 | *Listeria ivanovii, Iondoniensis* | ATCC 49954 | ATCC | | 275 | 1.63 | 9447244 | 0.163 |
| 30 | *Listeria seeligeri* | ATCC 51334 | ATCC | | 2082 | 2.41 | 432200 | 0.241 |
| 31 | *Listeria seeligeri* | ATCC 51335 | ATCC | 4a | 121 | 2.7 | 275 | 0.195 |
| 32 | *Listeria innocua* | ATCC 51742 | ATCC | | 9653 | 3.2 | 1345200384 | 0.204 |
| 33 | *Listeria monocytogenes* | ATCC 51772 | ATCC | 1/2a | 83 | 1.83 | 968516 | 0.183 |
| 34 | *Listeria monocytogenes* | ATCC 51774 | ATCC | 1/2a | 86 | 2.8 | 4495321 | 0.233 |
| 35 | *Listeria monocytogenes* | ATCC 51775 | ATCC | 1/2a | 74 | 2.78 | 252496 | 0.278 |
| 36 | *Listeria monocytogenes* | ATCC 51776 | ATCC | 4b | 93 | 2.39 | 1941613 | 0.239 |
| 37 | *Listeria monocytogenes* | ATCC 51777 | ATCC | 4b | 106 | 1.94 | 1005797 | 0.194 |
| 38 | *Listeria monocytogenes* | ATCC 51778 | ATCC | 4b | 104 | 2.28 | 2043043 | 0.228 |
| 39 | *Listeria monocytogenes* | ATCC 51779 | ATCC | 1/2c | 110 | 2.64 | 23853 | 0.208 |
| 40 | *Listeria monocytogenes* | ATCC 51780 | ATCC | 1/2b | 124 | 2.43 | 204751 | 0.243 |
| 41 | *Listeria monocytogenes* | ATCC 51781 | ATCC | 4 | 146 | 2.28 | 34463296 | 0.228 |
| 42 | *Listeria monocytogenes* | ATCC 51782 | ATCC | 3a | | | | |
| 43 | *Listeria monocytogenes* | ATCC 700402 | ATCC | | 315415 | 2.56 | 45732240 | 0.201 |

TABLE 9-continued

LP-ES1NAN0LUC ® Inclusivity

| # | Bacterial Strains | Strain | Source | Serotype | LPES1NANOLUC ® | | | |
|---|---|---|---|---|---|---|---|---|
| | | | | | RLU | OD600 | RLU | OD600 |
| 44 | *Listeria grayi* | ATCC 700545 | ATCC | | 100 | 3.12 | 148 | 0.312 |
| 45 | *Listeria monocytogenes* | ATCC 7302 | ATCC | | 70 | 2.89 | 6226359 | 0.223 |
| 46 | *Listeria monocytogenes* | ATCC 7644 | ATCC | | 44065 | 2.32 | 28041706 | 0.214 |
| 47 | *Listeria monocytogenes* | ATCC 9525 | ATCC | 2 | 136631 | 2.91 | 289623584 | 0.202 |
| 48 | *Listeria monocytogenes* | ATCC 984 | ATCC | | 86 | 2.65 | 8757545 | 0.265 |
| 49 | *Listeria monocytogenes* | ATCC BAA-2657 | ATCC | 1/2a | 73 | 2.75 | 25269 | 0.228 |
| 50 | *Listeria monocytogenes* | ATCC BAA-2658 | ATCC | | 240 | 2.38 | 51232 | 0.196 |
| 51 | *Listeria monocytogenes* | ATCC BAA-2659 | ATCC | 1/2a | 88 | 3.13 | 1601153 | 0.239 |
| 52 | *Listeria monocytogenes* | ATCC BAA-2660 | ATCC | 1/2a | 128 | 1.75 | 5732 | 0.175 |
| 53 | *Listeria innocua* | ATCC BAA-349 | ATCC | | 4057 | 3.01 | 255050000 | 0.301 |
| 54 | *Listeria ivanovii* | ATCC BAA-678 | ATCC | 5 | 142 | 2.86 | 4196208 | 0.222 |
| 55 | *Listeria monocytogenes* | ATCC BAA-679 | ATCC | 1/2a | 60 | 2.67 | 1278569 | 0.205 |
| 56 | *Listeria innocua* | ATCC BAA-680 | ATCC | 6a | 130 | 2.94 | 8761 | 0.207 |
| 57 | *Listeria monocytogenes* | ATCC BAA-751 | ATCC | 1/2b | 205 | 2.85 | 1857 | 0.219 |
| 58 | *Listeria ivanovii* subsp. *Iondoniensis* | ATCC BAA-753 | ATCC | | 636 | 1.83 | 755300000 | 0.183 |
| 59 | *Listeria monocytogenes* | ATCC BAA-839 | ATCC | 1/2b | 98 | 2.22 | 3428299 | 0.222 |
| 60 | *Listeria monocytogenes* | C1-056 | FSL | | 116 | 2.56 | 530735 | 0.235 |
| 61 | *Listeria monocytogenes* | C1-115 | FSL | | 75 | 2.9 | 84105 | 0.2 |
| 62 | *Listeria monocytogenes* | C1-122 | FSL | 4b | 205 | 2.88 | 1046538 | 0.208 |
| 63 | *Listeria monocytogenes* | CWD 1554 | Q Labs | | 223 | 2.3 | 360329 | 0.23 |
| 64 | *Listeria cornellensis* | F6-0969 | FSL | | 72 | 1.89 | 72 | 0.189 |
| 65 | *Listeria grandensis* | F6-0971 | FSL | | 77 | 2.85 | 60 | 0.211 |
| 66 | *Listeria fleischmannii* subsp. *coloradensis* | F6-1016 | FSL | | 44 | 3.24 | 1274 | 0.209 |
| 67 | *Listeria monocytogenes* | J1-031 | FSL | | 79 | 2.86 | 39832488 | 0.182 |
| 68 | *Listeria monocytogenes* | J1-049 | FSL | 3c | 112 | 2.59 | 133 | 0.193 |
| 69 | *Listeria monocytogenes* | J1-094 | FSL | | 65 | 2.9 | 424265 | 0.212 |
| 70 | *Listeria monocytogenes* | J1-107 | FSL | | 212 | 1.94 | 2918723 | 0.194 |
| 71 | *Listeria monocytogenes* | J1-108 | FSL | 4b | 161 | 2.07 | 1732287 | 0.21 |
| 72 | *Listeria monocytogenes* | J1-110 | FSL | 4b | 158 | 2.34 | 535779 | 0.203 |
| 73 | *Listeria monocytogenes* | J1-116 | FSL | 4b | 22869 | 3.08 | 3771233 | 0.196 |
| 74 | *Listeria monocytogenes* | J1-126 | FSL | 4b | 84 | 2.74 | 315864 | 0.206 |
| 75 | *Listeria monocytogenes* | J1-129 | FSL | | 79 | 2.12 | 161762 | 0.212 |
| 76 | *Listeria monocytogenes* | J1-158 | FSL | 4b | 85 | 2.79 | 98101888 | 0.231 |
| 77 | *Listeria monocytogenes* | J1-158 | FSL | | 75 | 2.68 | 26395924 | 0.216 |
| 78 | *Listeria monocytogenes* | J1-168 | FSL | | 59 | 2.75 | 21604386 | 0.203 |

TABLE 9-continued

| | Bacterial | | | | LP-ES1NAN0LUC ® Inclusivity | | LPES1NANOLUC ® | |
|---|---|---|---|---|---|---|---|---|
| # | Strains | Strain | Source | Serotype | RLU | OD600 | RLU | OD600 |
| 79 | Listeria monocytogenes | J1-169 | FSL | 3b | 141 | 2.61 | 4571 | 0.211 |
| 80 | Listeria monocytogenes | J1-177 | FSL | 1/2b | 94 | 2.57 | 351 | 0.206 |
| 81 | Listeria monocytogenes | J1-225 | FSL | 4b | 114 | 2.46 | 1080567 | 0.241 |
| 82 | Listeria monocytogenes | J2-020 | FSL | 1/2a | 69 | 3.23 | 869289 | 0.224 |
| 83 | Listeria monocytogenes | J2-020 | FSL | 1/2a | 115 | 2.49 | 326665 | 0.216 |
| 84 | Listeria monocytogenes | J2-031 | FSL | | 96 | 2.78 | 1147302 | 0.223 |
| 85 | Listeria monocytogenes | J2-035 | FSL | 1/2b | 145 | 2.14 | 76325 | 0.214 |
| 86 | Listeria monocytogenes | J2-054 | FSL | | 101 | 2.62 | 982267 | 0.225 |
| 87 | Listeria monocytogenes | J2-063 | FSL | | 70 | 2.7 | 4175341 | 0.209 |
| 88 | Listeria monocytogenes | J2-064 | FSL | 1/2b | 113 | 2.5 | 5557 | 0.223 |
| 89 | Listeria monocytogenes | J2-066 | FSL | 1/2a | 99 | 3.11 | 1209872 | 0.24 |
| 90 | Listeria monocytogenes | J2-066 | FSL | | 203 | 3.09 | 860572 | 0.216 |
| 91 | Listeria monocytogenes | M1-004 | FSL | | 61 | 2.61 | 90 | 0.217 |
| 92 | Listeria newyorkensis | M6-0635 | FSL | | 80 | 4.09 | 59 | 0.221 |
| 93 | Listeria monocytogenes | N1-225 | FSL | 4b | 689 | 1.5 | 23077 | 0.216 |
| 94 | Listeria monocytogenes | N1-225 | FSL | 4b | 139 | 2.93 | 28939 | 0.196 |
| 95 | Listeria monocytogenes | N1-227 | FSL | 4b | 92 | 3.07 | 32997 | 0.209 |
| 96 | Listeria monocytogenes | R2-500 | FSL | 4b | 122 | 2.59 | 680695 | 0.212 |
| 97 | Listeria floridensis | S10-1187 | FSL | | 69 | 1.79 | 42558868 | 0.179 |
| 98 | Listeria aquatica | S10-1188 | FSL | | 105 | 2.96 | 92 | 0.211 |
| 99 | Listeria riparia | S10-1204 | FSL | | 97 | 3.09 | 66 | 0.213 |
| 100 | Listeria marthii | S4-120 | FSL | | 62 | 2.69 | 2288981 | 0.215 |
| 101 | Listeria marthii | S4-965 | FSL | | 52 | 2.6 | 7826588 | 0.195 |
| 102 | Listeria monocytogenes | Scott 1 | UGA | 4b | 161 | 2.62 | 1840881 | 0.214 |
| 103 | Listeria monocytogenes | W1-110 | UGA | | 78 | 2.43 | 1764091 | 0.214 |
| 104 | Listeria monocytogenes | W1-111 | UGA | | 59 | 2.43 | 699795 | 0.209 |
| 105 | Listeria monocytogenes | W1-112 | UGA | | 62 | 2.57 | 132653240 | 0.217 |
| 106 | Listeria innocua | Silliker 9 | UGA | | 63 | 2.52 | 140650 | 0.252 |
| 107 | Listeria monocytogenes | Silliker 17 | UGA | | 116946 | 2.13 | 2188523 | 0.213 |
| 108 | Listeria monocytogenes | Silliker 106 | UGA | | 87953 | 1.91 | 2194437 | 0.191 |
| 109 | Listeria innocua | 15 | UGA | | 199 | 2.51 | 215349 | 0.251 |
| 110 | Listeria innocua | 16 | UGA | | 73 | 2.33 | 37890 | 0.233 |
| 111 | Listeria innocua | Silliker 24 | UGA | | 374 | 2.42 | 197791 | 0.208 |
| 112 | Listeria monocytogenes | H7557 | UGA | | 372 | 2.98 | 31417 | 0.199 |
| 113 | Listeria innocua | 9 | UGA | | 134 | 2.52 | 147495 | 0.223 |
| 114 | Listeria monocytogenes | 2011L-2663 | UGA | | 118 | 2.3 | 5552 | 0.23 |
| 115 | Listeria monocytogenes | H7738 | UGA | | 986 | 3.2 | 48324 | 0.219 |

TABLE 9-continued

| | | | | | LPES1NANOLUC ® | | | |
|---|---|---|---|---|---|---|---|---|
| | Bacterial | | | | | | | |
| # | Strains | Strain | Source | Serotype | RLU | OD600 | RLU | OD600 |
| 116 | *Listeria monocytogenes* | Jalisco G278 | UGA | | 207 | 2.02 | 65238 | 0.202 |
| 117 | *Listeria monocytogenes* | F2365 | UGA | 4b | 10310 | 2.52 | 798134 | 0.187 |
| 118 | *Listeria innocua* | Silliker 23 NAR | UGA | | 176 | 2.33 | 10171 | 0.233 |
| 119 | *Listeria innocua* | Silliker 16 NAR | UGA | | 139 | 2.42 | 48361 | 0.242 |
| 120 | *Listeria monocytogenes* | Silliker 17NAR | UGA | | 125 | 2.81 | 1477184 | 0.216 |
| 121 | *Listeria innocua* | Silliker 9 NAR | UGA | | 142 | 2.57 | 167319 | 0.257 |
| 122 | *Listeria innocua* | Silliker 16 | UGA | | 185 | 2.38 | 63904 | 0.212 |
| 123 | *Listeria monocytogenes* | F8027 | UGA | 4b | 178 | 2.46 | 35378644 | 0.246 |
| 124 | *Listeria innocua* | 18 | UGA | | 103 | 2.29 | 43520 | 0.229 |
| 125 | *Listeria innocua* | 72 | UGA | | 133 | 2.53 | 76254 | 0.253 |
| 126 | *Listeria innocua* | Siliker 24 NAR | UGA | | 263 | 2.9 | 625088 | 0.29 |
| 127 | *Listeria innocua* | 80 | UGA | | 122 | 2.42 | 37525 | 0.242 |
| 128 | *Listeria monocytogenes* | G1091 | UGA | 4b | 5828 | 2.28 | 2341090 | 0.228 |
| 129 | *Listeria monocytogenes* | Silliker 70 | UGA | | 260 | 2.26 | 10931 | 0.226 |
| 130 | *Listeria innocua* | Siliker 106 NAR | UGA | | 107 | 2.49 | 591100 | 0.249 |
| 131 | *Listeria monocytogenes* | F6900 | UGA | | 76 | 2.9 | 1143405 | 0.219 |
| 132 | *Listeria monocytogenes* | F8639 | UGA | 1/2a | 582 | 2.54 | 11894014 | 0.21 |
| 133 | *Listeria monocytogenes* | F2365-0770 | UGA | 4b | 28675 | 2.03 | 699066 | 0.203 |
| 134 | *Listeria monocytogenes* | Li 2108 | UGA | 4d | 203 | 2.37 | 128415 | 0.237 |
| 135 | *Listeria monocytogenes* | 108 M | UGA | | 142 | 2.52 | 8943 | 0.213 |
| 136 | *Listeria monocytogenes* | 2011 L-2626 | UGA | | 121 | 2.56 | 464355 | 0.196 |
| 137 | *Listeria monocytogenes* | Silliker 32 NAR | UGA | | 102 | 1.98 | 917737 | 0.198 |
| 138 | *Listeria monocytogenes* | Silliker 70 NAR | UGA | | 83 | 2.15 | 13106 | 0.215 |
| 139 | *Listeria monocytogenes* | Silliker 72 NAR | UGA | | 65 | 2.32 | 8474 | 0.232 |
| 140 | *Listeria monocytogenes* | 2011L-2625 | UGA | | 107 | 2.36 | 688886 | 0.236 |
| 141 | *Listeria monocytogenes* | 2011L-2624 | UGA | | 147 | 2.36 | 3940 | 0.236 |
| 142 | *Listeria ivanovii* | # | UGA | | 5924 | 1.91 | 11820000 | 0.191 |
| 143 | *Listeria monocytogenes* | 101M | UGA | | 96 | 2.5 | 194929 | 0.224 |
| 144 | *Listeria monocytogenes* | SURA 16 | UGA | | 54282 | 2.39 | 2943150 | 0.239 |
| 145 | *Listeria monocytogenes* | V7 | UGA | | 2747 | 2.13 | 348994 | 0.213 |
| 146 | *Listeria innocua* | 92 | UGA | | 141 | 2.14 | 91855 | 0.214 |
| 147 | *Listeria monocytogenes* | 1A1 | UGA | | 1414 | 2.24 | 8927166 | 0.224 |
| 148 | *Listeria monocytogenes* | Scotty A | UGA | | 14907 | 2.35 | 937993 | 0.235 |
| 149 | *Listeria monocytogenes* | G3990 | UGA | | 7003 | 3.01 | 1080286 | 0.2 |
| 150 | *Listeria monocytogenes* | Jalisco | UGA | | 129 | 2.08 | 48819 | 0.202 |
| 151 | *Listeria monocytogenes* | Coleslaw | UGA | | 1128 | 2.78 | 1228403 | 0.204 |
| 152 | *Listeria monocytogenes* | LCDC 81-861 | UGA | | 79 | 2.05 | 71380 | 0.205 |

TABLE 9-continued

| | | | | | LPES1NANOLUC ® | | | |
|---|---|---|---|---|---|---|---|---|
| | Bacterial | | | | | | | |
| # | Strains | Strain | Source | Serotype | RLU | OD600 | RLU | OD600 |
| 153 | Listeria monocytogenes | Bilmar | UGA | | 136 | 2.66 | 159817 | 0.203 |

LP-ES1NAN0LUC ® Inclusivity

TABLE 10

A511-3ANANOLUC ® Inclusivity

| | | | | | A511-3ANANOLUC ® | | | |
|---|---|---|---|---|---|---|---|---|
| | Bacterial | | | | | | | |
| # | Strains | Strain | Source | Serotype | RLU | OD600 | RLU | OD600 |
| 1 | Listeria monocytogenes | 7762 | ATCC | 4b | 378754 | 2.66 | 416160 | 0.209 |
| 2 | Listeria booriae | A5-0281 | FSL | | 68902 | 3.56 | 113186552 | 0.209 |
| 3 | Listeria monocytogenes | ATCC 13932 | ATCC | 4b | 981266 | 2.39 | 291151040 | 0.239 |
| 4 | Listeria monocytogenes | ATCC 15313 | ATCC | 1/2a | 757 | 1.54 | 225358960 | 0.203 |
| 5 | Listeria monocytogenes | ATCC 19111 | ATCC | 1/2a | 992190 | 2.21 | 347133216 | 0.221 |
| 6 | Listeria monocytogenes | ATCC 19112 | ATCC | 2 (1/2C) | 97049 | 2.99 | 446091 | 0.216 |
| 7 | Listeria monocytogenes | ATCC 19113 | ATCC | 3a | 18605 | 2.56 | 286612128 | 0.197 |
| 8 | Listeria monocytogenes | ATCC 19114 | ATCC | 4a | | | | |
| 9 | Listeria monocytogenes | ATCC 19115 | ATCC | 4b | | | | |
| 10 | Listeria monocytogenes | ATCC 19116 | ATCC | 4c | 970099 | 2.13 | 212439536 | 0.213 |
| 11 | Listeria monocytogenes | ATCC 19117 | ATCC | 4d | 270443 | 2.5 | 130067528 | 0.195 |
| 12 | Listeria monocytogenes | ATCC 19118 | ATCC | 4e | 877948 | 2.71 | 149199712 | 0.189 |
| 13 | Listeria ivanovii | ATCC 19119 | ATCC | | 345499 | 1.22 | 226915856 | 0.202 |
| 14 | Listeria grayi | ATCC 19120 | ATCC | | 164 | 2.91 | 14684 | 0.21 |
| 15 | Listeria monocytogenes | ATCC 23073 | ATCC | | 1415339 | 2.11 | 333057344 | 0.211 |
| 16 | Listeria monocytogenes | ATCC 23074 | ATCC | | 27939 | 2.86 | 88750808 | 0.225 |
| 17 | Listeria grayi | ATCC 25401 | ATCC | | 132 | 3.46 | 401928 | 0.231 |
| 18 | Listeria innocua | ATCC 33090 | ATCC | 6a | 553 | 2.71 | 157372 | 0.213 |
| 19 | Listeria innocua | ATCC 33091 | ATCC | 6b | 32966 | 1.98 | 411075456 | 0.198 |
| 20 | Listeria monocytogenes | ATCC 35152 | ATCC | 1/2a | 15185 | 3.07 | 246787136 | 0.233 |
| 21 | Listeria welshimeri | ATCC 35897 | ATCC | 6b | 7170 | 2.98 | 561168 | 0.219 |
| 22 | Listeria seeligeri | ATCC 35967 | ATCC | | 3778 | 2.24 | 355317984 | 0.22 |
| 23 | Listeria monocytogenes | ATCC 43256 | ATCC | | | | | |
| 24 | Listeria innocua | ATCC 43547 | ATCC | 6b | 37682 | 2.09 | 242966112 | 0.209 |
| 25 | Listeria welshimeri | ATCC 43549 | ATCC | 6a | 30963 | 3.13 | 18794796 | 0.217 |
| 26 | Listeria welshimeri | ATCC 43550 | ATCC | 1/2b | 41591908 | 0.463 | 63387456 | 0.21 |
| 27 | Listeria welshimeri | ATCC 43551 | ATCC | 6a | 498 | 2.8 | 213243 | 0.209 |
| 28 | Listeria ivanovii | ATCC 49953 | ATCC | | 1582984 | 1.17 | 240627760 | 0.236 |
| 29 | Listeria ivanovii, Iondoniensis | ATCC 49954 | ATCC | | 87522 | 1.92 | 275119264 | 0.192 |

TABLE 10-continued

| | | | | | A511-3ANANOLUC ® | | | |
|---|---|---|---|---|---|---|---|---|
| | Bacterial | | | | | | | |
| # | Strains | Strain | Source | Serotype | RLU | OD600 | RLU | OD600 |
| 30 | Listeria seeligeri | ATCC 51334 | ATCC | | 3238 | 2.66 | 279581696 | 0.211 |
| 31 | Listeria seeligeri | ATCC 51335 | ATCC | 4a | 139 | 2.7 | 1020 | 0.195 |
| 32 | Listeria innocua | ATCC 51742 | ATCC | | | | | |
| 33 | Listeria monocytogenes | ATCC 51772 | ATCC | 1/2a | 1866 | 2.66 | 272003632 | 0.209 |
| 34 | Listeria monocytogenes | ATCC 51774 | ATCC | 1/2a | 589 | 2.8 | 7575342 | 0.214 |
| 35 | Listeria monocytogenes | ATCC 51775 | ATCC | 1/2a | | | | |
| 36 | Listeria monocytogenes | ATCC 51776 | ATCC | 4b | 14860 | 2.39 | 327121856 | 0.239 |
| 37 | Listeria monocytogenes | ATCC 51777 | ATCC | 4b | 25887 | 2.72 | 275524672 | 0.217 |
| 38 | Listeria monocytogenes | ATCC 51778 | ATCC | 4b | | | | |
| 39 | Listeria monocytogenes | ATCC 51779 | ATCC | 1/2c | 72222 | 2.64 | 231796912 | 0.208 |
| 40 | Listeria monocytogenes | ATCC 51780 | ATCC | 1/2b | 86004 | 2.38 | 189142016 | 0.238 |
| 41 | Listeria monocytogenes | ATCC 51781 | ATCC | 4 | 23698 | 2.28 | 279649792 | 0.228 |
| 42 | Listeria monocytogenes | ATCC 51782 | ATCC | 3a | 1021 | 3.26 | 262109392 | 0.207 |
| 43 | Listeria monocytogenes | ATCC 700402 | ATCC | | 4365543 | 1.5 | 92945744 | 0.201 |
| 44 | Listeria grayi | ATCC 700545 | ATCC | | 148 | 2.98 | 5920 | 0.208 |
| 45 | Listeria monocytogenes | ATCC 7302 | ATCC | | 191901 | 2.89 | 401095104 | 0.223 |
| 46 | Listeria monocytogenes | ATCC 7644 | ATCC | | 2295511 | 2.32 | 313680416 | 0.232 |
| 47 | Listeria monocytogenes | ATCC 9525 | ATCC | 2 | 622217 | 2.91 | 344576576 | 0.202 |
| 48 | Listeria monocytogenes | ATCC 984 | ATCC | | 1094441 | 2.35 | 373687712 | 0.235 |
| 49 | Listeria monocytogenes | ATCC BAA-2657 | ATCC | 1/2a | 17366 | 2.75 | 178098928 | 0.217 |
| 50 | Listeria monocytogenes | ATCC BAA-2658 | ATCC | | 3362 | 2.38 | 29346230 | 0.196 |
| 51 | Listeria monocytogenes | ATCC BAA-2659 | ATCC | 1/2a | 11895 | 3.13 | 283887776 | 0.228 |
| 52 | Listeria monocytogenes | ATCC BAA-2660 | ATCC | 1/2a | | | | |
| 53 | Listeria innocua | ATCC BAA-349 | ATCC | | 1522274 | 3.27 | 109447736 | 0.239 |
| 54 | Listeria ivanovii | ATCC BAA-678 | ATCC | 5 | 47602 | 2.86 | 262310976 | 0.222 |
| 55 | Listeria monocytogenes | ATCC BAA-679 | ATCC | 1/2a | 224112431 | 1.94 | 396430336 | 0.194 |
| 56 | Listeria innocua | ATCC BAA- 680 | ATCC | 6a | 18230 | 2.12 | 37960 | 0.212 |
| 57 | Listeria monocytogenes | ATCC BAA-751 | ATCC | 1/2b | 135 | 2.85 | 190535 | 0.219 |
| 58 | Listeria ivanovii subsp. Iondoniensis | ATCC BAA-753 | ATCC | | 44653 | 2.17 | 239830480 | 0.217 |
| 59 | Listeria monocytogenes | ATCC BAA-839 | ATCC | 1/2b | 49272 | 2.42 | 125631160 | 0.242 |
| 60 | Listeria monocytogenes | C1-056 | FSL | | 6253 | 2.56 | 306364544 | 0.235 |
| 61 | Listeria monocytogenes | C1-115 | FSL | | 1149 | 2.9 | 120531552 | 0.2 |
| 62 | Listeria monocytogenes | C1-122 | FSL | 4b | 12546 | 2.88 | 131960632 | 0.208 |
| 63 | Listeria monocytogenes | CWD 1554 | Q Labs | | 20393 | 2.3 | 126923976 | 0.23 |
| 64 | Listeria cornellensis | F6-0969 | FSL | | 5088 | 1.89 | 1754853 | 0.189 |
| 65 | Listeria grandensis | F6-0971 | FSL | | 40815 | 2.85 | 58876540 | 0.211 |

TABLE 10-continued

| | | | | | A511-3ANANOLUC ® Inclusivity | | | | |

| | Bacterial | | | | | A511-3ANANOLUC ® | | | |
|---|---|---|---|---|---|---|---|---|---|
| # | Strains | Strain | Source | Serotype | RLU | OD600 | RLU | OD600 |
| 66 | *Listeria fleischmannii subsp. coloradensis* | F6-1016 | FSL | | 45 | 3.24 | 90 | 0.209 |
| 67 | *Listeria monocytogenes* | J1-031 | FSL | | 1307 | 2.86 | 38236984 | 0.182 |
| 68 | *Listeria monocytogenes* | J1-049 | FSL | 3c | 14418 | 2.59 | 107394924 | 0.193 |
| 69 | *Listeria monocytogenes* | J1-094 | FSL | | 24883 | 2.9 | 89763696 | 0.212 |
| 70 | *Listeria monocytogenes* | J1-107 | FSL | | 64734 | 1.94 | 128972864 | 0.194 |
| 71 | *Listeria monocytogenes* | J1-108 | FSL | 4b | 36557 | 2.07 | 190108928 | 0.21 |
| 72 | *Listeria monocytogenes* | J1-110 | FSL | 4b | 24633 | 2.34 | 268195472 | 0.203 |
| 73 | *Listeria monocytogenes* | J1-116 | FSL | 4b | 889987 | 3.08 | 88391600 | 0.196 |
| 74 | *Listeria monocytogenes* | J1-126 | FSL | 4b | 6242 | 2.74 | 195367552 | 0.206 |
| 75 | *Listeria monocytogenes* | J1-129 | FSL | | 15674 | 2.12 | 67839480 | 0.212 |
| 76 | *Listeria monocytogenes* | J1-158 | FSL | 4b | 14203 | 2.79 | 8668546 | 0.231 |
| 77 | *Listeria monocytogenes* | J1-158 | FSL | | 15917 | 2.68 | 7539203 | 0.216 |
| 78 | *Listeria monocytogenes* | J1-168 | FSL | | 19073 | 2.75 | 86455832 | 0.203 |
| 79 | *Listeria monocytogenes* | J1-169 | FSL | 3b | 25346 | 2.61 | 20633603 | 0.211 |
| 80 | *Listeria monocytogenes* | J1-177 | FSL | 1/2b | 370 | 2.57 | 14923 | 0.206 |
| 81 | *Listeria monocytogenes* | J1-225 | FSL | 4b | 21005 | 2.46 | 312048272 | 0.241 |
| 82 | *Listeria monocytogenes* | J2-020 | FSL | 1/2a | 131462 | 3.23 | 201766480 | 0.224 |
| 83 | *Listeria monocytogenes* | J2-020 | FSL | 1/2a | 14892 | 2.49 | 348694688 | 0.216 |
| 84 | *Listeria monocytogenes* | J2-031 | FSL | | 4247 | 2.78 | 199728048 | 0.223 |
| 85 | *Listeria monocytogenes* | J2-035 | FSL | 1/2b | 15390 | 2.14 | 155024784 | 0.214 |
| 86 | *Listeria monocytogenes* | J2-054 | FSL | | 15220 | 2.62 | 92836128 | 0.225 |
| 87 | *Listeria monocytogenes* | J2-063 | FSL | | 3569 | 2.7 | 4828437 | 0.206 |
| 88 | *Listeria monocytogenes* | J2-064 | FSL | 1/2b | 12243 | 2.5 | 256161504 | 0.223 |
| 89 | *Listeria monocytogenes* | J2-066 | FSL | 1/2a | 653 | 3.11 | 484136 | 0.24 |
| 90 | *Listeria monocytogenes* | J2-066 | FSL | | 1172 | 3.09 | 1747958 | 0.216 |
| 91 | *Listeria monocytogenes* | M1-004 | FSL | | 1134 | 2.61 | 5553516 | 0.217 |
| 92 | *Listeria newyorkensis* | M6-0635 | FSL | | 73869 | 4.09 | 14520516 | 0.221 |
| 93 | *Listeria monocytogenes* | N1-225 | FSL | 4b | 335870 | 3.28 | 868073 | 0.216 |
| 94 | *Listeria monocytogenes* | N1-225 | FSL | 4b | 8211 | 2.93 | 997938 | 0.196 |
| 95 | *Listeria monocytogenes* | N1-227 | FSL | 4b | 4853 | 3.07 | 558970 | 0.209 |
| 96 | *Listeria monocytogenes* | R2-500 | FSL | 4b | 14631 | 2.59 | 208136352 | 0.212 |
| 97 | *Listeria floridensis* | S10-1187 | FSL | | 18864 | 1.79 | 82530600 | 0.179 |
| 98 | *Listeria aquatica* | S10-1188 | FSL | | 84 | 2.96 | 165 | 0.211 |
| 99 | *Listeria riparia* | S10-1204 | FSL | | 126161 | 3.09 | 160936768 | 0.213 |
| 100 | *Listeria marthii* | S4-120 | FSL | | 10566 | 2.69 | 65327340 | 0.215 |
| 101 | *Listeria marthii* | S4-965 | FSL | | 10856 | 2.6 | 90361976 | 0.195 |

TABLE 10-continued

<table>
<tr><td colspan="9" align="center">A511-3ANANOLUC ® Inclusivity</td></tr>
<tr><td></td><td>Bacterial</td><td></td><td></td><td></td><td colspan="4" align="center">A511-3ANANOLUC ®</td></tr>
<tr><td>#</td><td>Strains</td><td>Strain</td><td>Source</td><td>Serotype</td><td>RLU</td><td>OD600</td><td>RLU</td><td>OD600</td></tr>
<tr><td>102</td><td>Listeria monocytogenes</td><td>Scott 1</td><td>UGA</td><td>4b</td><td>19280</td><td>2.62</td><td>410805824</td><td>0.214</td></tr>
<tr><td>103</td><td>Listeria monocytogenes</td><td>W1-110</td><td>UGA</td><td></td><td>16597</td><td>2.43</td><td>112202608</td><td>0.214</td></tr>
<tr><td>104</td><td>Listeria monocytogenes</td><td>W1-111</td><td>UGA</td><td></td><td>13069</td><td>2.43</td><td>90069080</td><td>0.209</td></tr>
<tr><td>105</td><td>Listeria monocytogenes</td><td>W1-112</td><td>UGA</td><td></td><td>4499</td><td>2.57</td><td>72801704</td><td>0.217</td></tr>
<tr><td>106</td><td>Listeria innocua</td><td>Silliker 9</td><td>UGA</td><td></td><td>126</td><td>2.31</td><td>303</td><td>0.231</td></tr>
<tr><td>107</td><td>Listeria monocytogenes</td><td>Silliker 17</td><td>UGA</td><td></td><td>1612595</td><td>2.13</td><td>103956136</td><td>0.213</td></tr>
<tr><td>108</td><td>Listeria monocytogenes</td><td>Silliker 106</td><td>UGA</td><td></td><td>1209975</td><td>1.91</td><td>79406016</td><td>0.191</td></tr>
<tr><td>109</td><td>Listeria innocua</td><td>15</td><td>UGA</td><td></td><td>610719</td><td>2.5</td><td>1214580</td><td>0.192</td></tr>
<tr><td>110</td><td>Listeria innocua</td><td>16</td><td>UGA</td><td></td><td>73</td><td>1.98</td><td>205</td><td>0.198</td></tr>
<tr><td>111</td><td>Listeria innocua</td><td>Silliker 24</td><td>UGA</td><td></td><td>103</td><td>1.97</td><td>235</td><td>0.197</td></tr>
<tr><td>112</td><td>Listeria monocytogenes</td><td>H7557</td><td>UGA</td><td></td><td>460474</td><td>2.98</td><td>2369207</td><td>0.199</td></tr>
<tr><td>113</td><td>Listeria innocua</td><td>9</td><td>UGA</td><td></td><td>123</td><td>2.39</td><td>206</td><td>0.197</td></tr>
<tr><td>114</td><td>Listeria monocytogenes</td><td>2011L-2663</td><td>UGA</td><td></td><td>7830</td><td>2.3</td><td>112563264</td><td>0.23</td></tr>
<tr><td>115</td><td>Listeria monocytogenes</td><td>H7738</td><td>UGA</td><td></td><td>501794</td><td>3.2</td><td>1604713</td><td>0.219</td></tr>
<tr><td>116</td><td>Listeria monocytogenes</td><td>Jalisco G278</td><td>UGA</td><td></td><td>170781</td><td>2.02</td><td>184018304</td><td>0.202</td></tr>
<tr><td>117</td><td>Listeria monocytogenes</td><td>F2365</td><td>UGA</td><td>4b</td><td>756807</td><td>2.52</td><td>56226248</td><td>0.187</td></tr>
<tr><td>118</td><td>Listeria innocua</td><td>Silliker 23 NAR</td><td>UGA</td><td></td><td>3471</td><td>2.79</td><td>105456</td><td>0.202</td></tr>
<tr><td>119</td><td>Listeria innocua</td><td>Silliker 16 NAR</td><td>UGA</td><td></td><td>130</td><td>2.9</td><td>315</td><td>0.216</td></tr>
<tr><td>120</td><td>Listeria monocytogenes</td><td>Silliker 17NAR</td><td>UGA</td><td></td><td>15898</td><td>2.81</td><td>189137848</td><td>0.216</td></tr>
<tr><td>121</td><td>Listeria innocua</td><td>Silliker 9 NAR</td><td>UGA</td><td></td><td>115</td><td>2.7</td><td>115</td><td>0.221</td></tr>
<tr><td>122</td><td>Listeria innocua</td><td>Silliker 16</td><td>UGA</td><td></td><td></td><td></td><td>315</td><td>0.216</td></tr>
<tr><td>123</td><td>Listeria monocytogenes</td><td>F8027</td><td>UGA</td><td>4b</td><td>32976</td><td>2.46</td><td>314310720</td><td>0.246</td></tr>
<tr><td>124</td><td>Listeria innocua</td><td>18</td><td>UGA</td><td></td><td>825</td><td>2.51</td><td>1289845</td><td>0.187</td></tr>
<tr><td>125</td><td>Listeria innocua</td><td>72</td><td>UGA</td><td></td><td>112</td><td>2.04</td><td>149</td><td>0.204</td></tr>
<tr><td>126</td><td>Listeria innocua</td><td>Siliker 24 NAR</td><td>UGA</td><td></td><td>108</td><td>1.96</td><td>302</td><td>0.196</td></tr>
<tr><td>127</td><td>Listeria innocua</td><td>80</td><td>UGA</td><td></td><td>6551</td><td>2.03</td><td>1701315</td><td>0.203</td></tr>
<tr><td>128</td><td>Listeria monocytogenes</td><td>G1091</td><td>UGA</td><td>4b</td><td>1911676</td><td>2.28</td><td>178653136</td><td>0.228</td></tr>
<tr><td>129</td><td>Listeria monocytogenes</td><td>Silliker 70</td><td>UGA</td><td></td><td>227813</td><td>2.26</td><td>3045378</td><td>0.226</td></tr>
<tr><td>130</td><td>Listeria innocua</td><td>Siliker 106 NAR</td><td>UGA</td><td></td><td>8307</td><td>2.06</td><td>92752120</td><td>0.206</td></tr>
<tr><td>131</td><td>Listeria monocytogenes</td><td>F6900</td><td>UGA</td><td></td><td>12998</td><td>2.9</td><td>203527328</td><td>0.219</td></tr>
<tr><td>132</td><td>Listeria monocytogenes</td><td>F8639</td><td>UGA</td><td>1/2a</td><td>1072778</td><td>2.54</td><td>272927296</td><td>0.21</td></tr>
<tr><td>133</td><td>Listeria monocytogenes</td><td>F2365-0770</td><td>UGA</td><td>4b</td><td>1443452</td><td>2.03</td><td>58455628</td><td>0.203</td></tr>
<tr><td>134</td><td>Listeria monocytogenes</td><td>Li 2108</td><td>UGA</td><td>4d</td><td>11299</td><td>2.37</td><td>4949198</td><td>0.237</td></tr>
<tr><td>135</td><td>Listeria monocytogenes</td><td>108 M</td><td>UGA</td><td></td><td>80152</td><td>2.52</td><td>158713200</td><td>0.213</td></tr>
<tr><td>136</td><td>Listeria monocytogenes</td><td>2011 L-2626</td><td>UGA</td><td></td><td>9623</td><td>2.56</td><td>116665072</td><td>0.196</td></tr>
<tr><td>137</td><td>Listeria monocytogenes</td><td>Silliker 32 NAR</td><td>UGA</td><td></td><td>94689</td><td>1.98</td><td>112243336</td><td>0.198</td></tr>
</table>

TABLE 10-continued

| | Bacterial | | | | A511-3ANANOLUC ® | | | |
|---|---|---|---|---|---|---|---|---|
| # | Strains | Strain | Source | Serotype | RLU | OD600 | RLU | OD600 |
| 138 | *Listeria monocytogenes* | Silliker 70 NAR | UGA | | 2727 | 2.15 | 4661575 | 0.215 |
| 139 | *Listeria monocytogenes* | Silliker 72 NAR | UGA | | 513 | 2.32 | 828168 | 0.232 |
| 140 | *Listeria monocytogenes* | 2011L-2625 | UGA | | 550 | 2.36 | 19429948 | 0.236 |
| 141 | *Listeria monocytogenes* | 2011L-2624 | UGA | | 8934 | 2.36 | 84923400 | 0.236 |
| 142 | *Listeria ivanovii* | # | UGA | | 23867944 | 1.03 | 89709032 | 0.19 |
| 143 | *Listeria monocytogenes* | 101M | UGA | | 33669 | 2.5 | 1352686 | 0.224 |
| 144 | *Listeria monocytogenes* | SLR 516 | UGA | | 997826 | 2.39 | 167013936 | 0.239 |
| 145 | *Listeria monocytogenes* | V7 | UGA | | 59213 | 2.13 | 71193288 | 0.213 |
| 146 | *Listeria innocua* | 92 | UGA | | 6146 | 1.78 | 1186347 | 0.178 |
| 147 | *Listeria monocytogenes* | 1A1 | UGA | | 507228 | 2.24 | 171681744 | 0.224 |
| 148 | *Listeria monocytogenes* | Scotty A | UGA | | 1120860 | 2.35 | 298810496 | 0.235 |
| 149 | *Listeria monocytogenes* | G3990 | UGA | | 870479 | 3.01 | 251132672 | 0.2 |
| 150 | *Listeria monocytogenes* | Jalisco | UGA | | 43071 | 2.08 | 186783280 | 0.208 |
| 151 | *Listeria monocytogenes* | Coleslaw | UGA | | 18284 | 2.78 | 181046288 | 0.204 |
| 152 | *Listeria monocytogenes* | LCDC 81-861 | UGA | | 103 | 2.37 | 5269 | 0.237 |
| 153 | *Listeria monocytogenes* | Bilmar | UGA | | 825648 | 2.66 | 10408123 | 0.203 |

TABLE 11

LPJP1NANOLUC ® Inclusivity

| | Bacterial | | | | LPJP1NANOLUC ® | | | |
|---|---|---|---|---|---|---|---|---|
| # | Strains | Strain | Source | Serotype | RLU | OD600 | RLU | OD600 |
| 1 | *Listeria monocytogenes* | 7762 | ATCC | 4b | 80 | 3.04 | 108 | 0.202 |
| 2 | *Listeria booriae* | A5-0281 | FSL | | 125 | 4.33 | 83 | 0.216 |
| 3 | *Listeria monocytogenes* | ATCC 13932 | ATCC | 4b | 55 | 2.98 | 85 | 0.193 |
| 4 | *Listeria monocytogenes* | ATCC 15313 | ATCC | 1/2a | 62 | 2.08 | 63 | 0.208 |
| 5 | *Listeria monocytogenes* | ATCC 19111 | ATCC | 1/2a | 35 | 2.96 | 48 | 0.213 |
| 6 | *Listeria monocytogenes* | ATCC 19112 | ATCC | 2 (1/2C) | 38 | 3.7 | 88 | 0.206 |
| 7 | *Listeria monocytogenes* | ATCC 19113 | ATCC | 3a | 160 | 0.629 | 1271 | 0.225 |
| 8 | *Listeria monocytogenes* | ATCC 19114 | ATCC | 4a | 55 | 2.69 | 55 | 0.201 |
| 9 | *Listeria monocytogenes* | ATCC 19115 | ATCC | 4b | 46 | 2.67 | 56 | 0.227 |
| 10 | *Listeria monocytogenes* | ATCC 19116 | ATCC | 4c | 30 | 3.21 | 57 | 0.228 |
| 11 | *Listeria monocytogenes* | ATCC 19117 | ATCC | 4d | 49 | 3.18 | 69 | 0.173 |
| 12 | *Listeria monocytogenes* | ATCC 19118 | ATCC | 4e | 51 | 2.78 | 69 | 0.216 |
| 13 | *Listeria ivanovii* | ATCC 19119 | ATCC | | 80 | 1.16 | 92 | 0.192 |
| 14 | *Listeria grayi* | ATCC 19120 | ATCC | | 272 | 3.45 | 274905152 | 0.201 |
| 15 | *Listeria monocytogenes* | ATCC 23073 | ATCC | | 44 | 3.05 | 65 | 0.224 |

TABLE 11-continued

| | | | | | \multicolumn{2}{c}{LPJP1NANOLUC ®} | | |
| | Bacterial | | | | | | | |
| # | Strains | Strain | Source | Serotype | RLU | OD600 | RLU | OD600 |
|---|---|---|---|---|---|---|---|---|
| 16 | Listeria monocytogenes | ATCC 23074 | ATCC | | 41 | 2.87 | 84 | 0.21 |
| 17 | Listeria grayi | ATCC 25401 | ATCC | | 342 | 4.02 | 76794888 | 0.22 |
| 18 | Listeria innocua | ATCC 33090 | ATCC | 6a | 69 | 3.43 | 73 | 0.229 |
| 19 | Listeria innocua | ATCC 33091 | ATCC | 6b | 78 | 3.76 | 79 | 0.23 |
| 20 | Listeria monocytogenes | ATCC 35152 | ATCC | 1/2a | 26 | 2.44 | 52 | 0.214 |
| 21 | Listeria welshimeri | ATCC 35897 | ATCC | 6b | 81 | 3.48 | 88 | 0.197 |
| 22 | Listeria seeligeri | ATCC 35967 | ATCC | | 82 | 2.25 | 93 | 0.216 |
| 23 | Listeria monocytogenes | ATCC 43256 | ATCC | | 64 | 3.09 | 70 | 0.212 |
| 24 | Listeria innocua | ATCC 43547 | ATCC | 6b | 84 | 3.97 | 100 | 0.212 |
| 25 | Listeria welshimeri | ATCC 43549 | ATCC | 6a | 74 | 1.21 | 88 | 0.203 |
| 26 | Listeria welshimeri | ATCC 43550 | ATCC | 1/2b | 81 | 0.322 | 75 | 0.213 |
| 27 | Listeria welshimeri | ATCC 43551 | ATCC | 6a | 69 | 2.81 | 79 | 0.2 |
| 28 | Listeria ivanovii | ATCC 49953 | ATCC | | 87 | 0.224 | 73 | 0.224 |
| 29 | Listeria ivanovii, londoniensis | ATCC 49954 | ATCC | | 59 | 2.23 | 78 | 0.223 |
| 30 | Listeria seeligeri | ATCC 51334 | ATCC | | 65 | 3.29 | 84 | 0.207 |
| 31 | Listeria seeligeri | ATCC 51335 | ATCC | 4a | 45 | 0.94 | 60 | 0.211 |
| 32 | Listeria innocua | ATCC 51742 | ATCC | | 50 | 3.32 | 76 | 0.233 |
| 33 | Listeria monocytogenes | ATCC 51772 | ATCC | 1/2a | 67 | 3.15 | 69 | 0.195 |
| 34 | Listeria monocytogenes | ATCC 51774 | ATCC | 1/2a | 71 | 2.8 | 78 | 0.187 |
| 35 | Listeria monocytogenes | ATCC 51775 | ATCC | 1/2a | 77 | 3.4 | 104 | 0.208 |
| 36 | Listeria monocytogenes | ATCC 51776 | ATCC | 4b | 53 | 3.26 | 67 | 0.201 |
| 37 | Listeria monocytogenes | ATCC 51777 | ATCC | 4b | 76 | 3.07 | 76 | 0.2 |
| 38 | Listeria monocytogenes | ATCC 51778 | ATCC | 4b | 92 | 2.99 | 73 | 0.207 |
| 39 | Listeria monocytogenes | ATCC 51779 | ATCC | 1/2c | 51 | 3.58 | 57 | 0.219 |
| 40 | Listeria monocytogenes | ATCC 51780 | ATCC | 1/2b | 71 | 3.09 | 75 | 0.203 |
| 41 | Listeria monocytogenes | ATCC 51781 | ATCC | 4 | 45 | 3.62 | 98 | 0.209 |
| 42 | Listeria monocytogenes | ATCC 51782 | ATCC | 3a | 89 | 3.3 | 58 | 0.21 |
| 43 | Listeria monocytogenes | ATCC 700402 | ATCC | | 66 | 0.566 | 58 | 0.219 |
| 44 | Listeria grayi | ATCC 700545 | ATCC | | 349 | 3.71 | 58170464 | 0.208 |
| 45 | Listeria monocytogenes | ATCC 7302 | ATCC | | 74 | 2.87 | 699 | 0.186 |
| 46 | Listeria monocytogenes | ATCC 7644 | ATCC | | 79 | 0.235 | 1054 | 0.235 |
| 47 | Listeria monocytogenes | ATCC 9525 | ATCC | 2 | 102 | 3.43 | 129 | 0.215 |
| 48 | Listeria monocytogenes | ATCC 984 | ATCC | | 46 | 2.99 | 3077 | 0.209 |
| 49 | Listeria monocytogenes | ATCC BAA-2657 | ATCC | 1/2a | 52 | 3.05 | 84 | 0.206 |
| 50 | Listeria monocytogenes | ATCC BAA-2658 | ATCC | | 58 | 3.43 | 100 | 0.213 |
| 51 | Listeria monocytogenes | ATCC BAA-2659 | ATCC | 1/2a | 55 | 3.1 | 194 | 0.208 |

TABLE 11-continued

| | | | | | LPJP1NANOLUC ® Inclusivity | | | |
|---|---|---|---|---|---|---|---|---|
| | Bacterial | | | | | | LPJP1NANOLUC ® | |
| # | Strains | Strain | Source | Serotype | RLU | OD600 | RLU | OD600 |
| 52 | *Listeria monocytogenes* | ATCC BAA-2660 | ATCC | 1/2a | 74 | 3.3 | 78 | 0.206 |
| 53 | *Listeria innocua* | ATCC BAA-349 | ATCC | | 37 | 3.06 | 69 | 0.238 |
| 54 | *Listeria ivanovii* | ATCC BAA-678 | ATCC | 5 | 92 | 0.174 | 71 | 0.174 |
| 55 | *Listeria monocytogenes* | ATCC BAA-679 | ATCC | 1/2a | 70 | 3.71 | 78 | 0.209 |
| 56 | *Listeria innocua* | ATCC BAA-680 | ATCC | 6a | 49 | 3.92 | 89 | 0.222 |
| 57 | *Listeria monocytogenes* | ATCC BAA-751 | ATCC | 1/2b | 66 | 3.19 | 63 | 0.189 |
| 58 | *Listeria ivanovii* subsp. *Iondoniensis* | ATCC BAA-753 | ATCC | | 65 | 0.385 | 75 | 0.206 |
| 59 | *Listeria monocytogenes* | ATCC BAA-839 | ATCC | 1/2b | 73 | 3.11 | 80 | 0.207 |
| 60 | *Listeria monocytogenes* | C1-056 | FSL | | 57 | 3.52 | 72 | 0.219 |
| 61 | *Listeria monocytogenes* | C1-115 | FSL | | 56 | 3.23 | 108 | 0.188 |
| 62 | *Listeria monocytogenes* | C1-122 | FSL | 4b | 64 | 3.29 | 86 | 0.199 |
| 63 | *Listeria monocytogenes* | CWD 1554 | Q Labs | | 51 | 3.37 | 128 | 0.207 |
| 64 | *Listeria cornellensis* | F6-0969 | FSL | | | | | |
| 65 | *Listeria grandensis* | F6-0971 | FSL | | 67 | 1.06 | 62 | 0.21 |
| 66 | *Listeria fleischmannii* subsp. *coloradensis* | F6-1016 | FSL | | 98 | 3.2 | 60 | 0.218 |
| 67 | *Listeria monocytogenes* | J1-031 | FSL | | 67 | 3.75 | 70 | 0.212 |
| 68 | *Listeria monocytogenes* | J1-049 | FSL | 3c | 45 | 3.09 | 52 | 0.195 |
| 69 | *Listeria monocytogenes* | J1-094 | FSL | | 48 | 3 | 62 | 0.195 |
| 70 | *Listeria monocytogenes* | J1-107 | FSL | | 58 | 2.38 | 83 | 0.192 |
| 71 | *Listeria monocytogenes* | J1-108 | FSL | 4b | 51 | 2.58 | 60 | 0.209 |
| 72 | *Listeria monocytogenes* | J1-110 | FSL | 4b | 55 | 3.09 | 75 | 0.197 |
| 73 | *Listeria monocytogenes* | J1-116 | FSL | 4b | 75 | 2.93 | 75 | 0.201 |
| 74 | *Listeria monocytogenes* | J1-126 | FSL | 4b | 73 | 3.05 | 67 | 0.202 |
| 75 | *Listeria monocytogenes* | J1-129 | FSL | | 69 | 2.35 | 53 | 0.187 |
| 76 | *Listeria monocytogenes* | J1-158 | FSL | 4b | 37 | 3.49 | 63 | 0.208 |
| 77 | *Listeria monocytogenes* | J1-158 | FSL | | 50 | 3.11 | 74 | 0.195 |
| 78 | *Listeria monocytogenes* | J1-168 | FSL | | 67 | 3.64 | 73 | 0.204 |
| 79 | *Listeria monocytogenes* | J1-169 | FSL | 3b | 55 | 3.14 | 66 | 0.188 |
| 80 | *Listeria monocytogenes* | J1-177 | FSL | 1/2b | 70 | 2.97 | 70 | 0.203 |
| 81 | *Listeria monocytogenes* | J1-225 | FSL | 4b | 46 | 3.23 | 61 | 0.203 |
| 82 | *Listeria monocytogenes* | J2-020 | FSL | 1/2a | 53 | 3.11 | 53 | 0.212 |
| 83 | *Listeria monocytogenes* | J2-020 | FSL | 1/2a | 75 | 3.32 | 89 | 0.199 |
| 84 | *Listeria monocytogenes* | J2-031 | FSL | | 34 | 3.49 | 63 | 0.217 |
| 85 | *Listeria monocytogenes* | J2-035 | FSL | 1/2b | 72 | 2.68 | 77 | 0.194 |
| 86 | *Listeria monocytogenes* | J2-054 | FSL | | 50 | 3.54 | 123 | 0.222 |

TABLE 11-continued

| | | | | | LPJP1NANOLUC ® | | | |
|---|---|---|---|---|---|---|---|---|
| | Bacterial | | | | | | LPJP1NANOLUC ® | |
| # | Strains | Strain | Source | Serotype | RLU | OD600 | RLU | OD600 |
| 87 | *Listeria monocytogenes* | J2-063 | FSL | | 51 | 3.56 | 96 | 0.189 |
| 88 | *Listeria monocytogenes* | J2-064 | FSL | 1/2b | 58 | 3.4 | 72 | 0.2 |
| 89 | *Listeria monocytogenes* | J2-066 | FSL | 1/2a | 65 | 3.53 | 76 | 0.219 |
| 90 | *Listeria monocytogenes* | J2-066 | FSL | | 93 | 3.71 | 110 | 0.182 |
| 91 | *Listeria monocytogenes* | M1-004 | FSL | | 51 | 3.39 | 45 | 0.213 |
| 92 | *Listeria newyorkensis* | M6-0635 | FSL | | 79 | 3.77 | 80 | 0.225 |
| 93 | *Listeria monocytogenes* | N1-225 | FSL | 4b | 53 | 4 | 65 | 0.204 |
| 94 | *Listeria monocytogenes* | N1-225 | FSL | 4b | 79 | 3.88 | 86 | 0.201 |
| 95 | *Listeria monocytogenes* | N1-227 | FSL | 4b | 86 | 3.12 | 94 | 0.209 |
| 96 | *Listeria monocytogenes* | R2-500 | FSL | 4b | 72 | 3.24 | 67 | 0.208 |
| 97 | *Listeria floridensis* | S10-1187 | FSL | | 166 | 2.02 | 104 | 0.202 |
| 98 | *Listeria aquatica* | S10-1188 | FSL | | 64 | 4.08 | 66 | 0.218 |
| 99 | *Listeria riparia* | S10-1204 | FSL | | 65 | 3.83 | 86 | 0.223 |
| 100 | *Listeria marthii* | S4-120 | FSL | | 58 | 3.39 | 72 | 0.191 |
| 101 | *Listeria marthii* | S4-965 | FSL | | 54 | 3.05 | 100 | 0.183 |
| 102 | *Listeria monocytogenes* | Scott 1 | UGA | 4b | 31 | 3.21 | 60 | 0.21 |
| 103 | *Listeria monocytogenes* | W1-110 | UGA | | 87 | 3.29 | 94 | 0.205 |
| 104 | *Listeria monocytogenes* | W1-111 | UGA | | 94 | 2.95 | 103 | 0.206 |
| 105 | *Listeria monocytogenes* | W1-112 | UGA | | 62 | 3.33 | 85 | 0.211 |
| 106 | *Listeria innocua* | Silliker 9 | UGA | | 90 | 2.98 | 57 | 0.2 |
| 107 | *Listeria monocytogenes* | Silliker 17 | UGA | | 63 | 3.31 | 73 | 0.209 |
| 108 | *Listeria monocytogenes* | Silliker 106 | UGA | | 35 | 3.17 | 58 | 0.213 |
| 109 | *Listeria innocua* | 15 | UGA | | 61 | 3.01 | 71 | 0.211 |
| 110 | *Listeria innocua* | 16 | UGA | | 69 | 2.55 | 49 | 0.197 |
| 111 | *Listeria innocua* | Silliker 24 | UGA | | 63 | 3.15 | 54 | 0.211 |
| 112 | *Listeria monocytogenes* | H7557 | UGA | | 52 | 3.63 | 83 | 0.215 |
| 113 | *Listeria innocua* | 9 | UGA | | 73 | 3.41 | 66 | 0.179 |
| 114 | *Listeria monocytogenes* | 2011L-2663 | UGA | | 60 | 3.08 | 261 | 0.201 |
| 115 | *Listeria monocytogenes* | H7738 | UGA | | 52 | 3.54 | 93 | 0.216 |
| 116 | *Listeria monocytogenes* | Jalisco G278 | UGA | | 71 | 2.8 | 82 | 0.213 |
| 117 | *Listeria monocytogenes* | F2365 | UGA | 4b | 45 | 3.63 | 72 | 0.213 |
| 118 | *Listeria innocua* | Silliker 23 NAR | UGA | | 90 | 2.67 | 56 | 0.187 |
| 119 | *Listeria innocua* | Silliker 16 NAR | UGA | | 58 | 3.06 | 50 | 0.211 |
| 120 | *Listeria monocytogenes* | Silliker 17NAR | UGA | | 76 | 3.25 | 74 | 0.212 |
| 121 | *Listeria innocua* | Silliker 9 NAR | UGA | | 85 | 2.88 | 70 | 0.193 |
| 122 | *Listeria innocua* | Silliker 16 | UGA | | 61 | 3.33 | 62 | 0.209 |
| 123 | *Listeria monocytogenes* | F8027 | UGA | 4b | 48 | 3.18 | 60 | 0.223 |

TABLE 11-continued

| | | | | | LPJP1NANOLUC ® Inclusivity | | | |
|---|---|---|---|---|---|---|---|---|
| | Bacterial | | | | | | LPJP1NANOLUC ® | |
| # | Strains | Strain | Source | Serotype | RLU | OD600 | RLU | OD600 |
| 124 | *Listeria innocua* | 18 | UGA | | 54 | 3.2 | 66 | 0.178 |
| 125 | *Listeria innocua* | 72 | UGA | | 56 | 2.7 | 62 | 0.195 |
| 126 | *Listeria innocua* | Siliker 24 NAR | UGA | | 72 | 3.24 | 64 | 0.212 |
| 127 | *Listeria innocua* | 80 | UGA | | 60 | 3.32 | 72 | 0.2 |
| 128 | *Listeria monocytogenes* | G1091 | UGA | 4b | 74 | 2.22 | 67 | 0.221 |
| 129 | *Listeria monocytogenes* | Silliker 70 | UGA | | 52 | 3.84 | 49 | 0.215 |
| 130 | *Listeria innocua* | Siliker 106 NAR | UGA | | 56 | 3.33 | 57 | 0.212 |
| 131 | *Listeria monocytogenes* | F6900 | UGA | | 43 | 2.97 | 78 | 0.205 |
| 132 | *Listeria monocytogenes* | F8639 | UGA | 1/2a | 60 | 3.3 | 58 | 0.214 |
| 133 | *Listeria monocytogenes* | F2365-0770 | UGA | 4b | 38 | 3.67 | 72 | 0.214 |
| 134 | *Listeria monocytogenes* | Li 2108 | UGA | 4d | 89 | 3.37 | 65 | 0.199 |
| 135 | *Listeria monocytogenes* | 108 M | UGA | | 50 | 2.88 | 85 | 0.205 |
| 136 | *Listeria monocytogenes* | 2011 L-2626 | UGA | | 65 | 2.93 | 72 | 0.205 |
| 137 | *Listeria monocytogenes* | Silliker 32 NAR | UGA | | 135 | 3.1 | 68 | 0.213 |
| 138 | *Listeria monocytogenes* | Silliker 70 NAR | UGA | | 67 | 3.64 | 55 | 0.207 |
| 139 | *Listeria monocytogenes* | Silliker 72 NAR | UGA | | 73 | 4.03 | 62 | 0.213 |
| 140 | *Listeria monocytogenes* | 2011L-2625 | UGA | | 121 | 3.08 | 78 | 0.19 |
| 141 | *Listeria monocytogenes* | 2011L-2624 | UGA | | 164 | 2.89 | 227 | 0.204 |
| 142 | *Listeria ivanovii* | # | UGA | | 49 | 0.925 | 89 | 0.219 |
| 143 | *Listeria monocytogenes* | 101M | UGA | | 48 | 3.46 | 82 | 0.219 |
| 144 | *Listeria monocytogenes* | SLR516 | UGA | | 85 | 2.36 | 62 | 0.208 |
| 145 | *Listeria monocytogenes* | V7 | UGA | | 106 | 2.16 | 60 | 0.225 |
| 146 | *Listeria innocua* | 92 | UGA | | 81 | 2.69 | 82 | 0.213 |
| 147 | *Listeria monocytogenes* | 1A1 | UGA | | 101 | 2.57 | 59 | 0.205 |
| 148 | *Listeria monocytogenes* | Scotty A | UGA | | 48 | 3.3 | 44 | 0.21 |
| 149 | *Listeria monocytogenes* | G3990 | UGA | | 54 | 3.13 | 51 | 0.197 |
| 150 | *Listeria monocytogenes* | Jalisco | UGA | | 51 | 3.1 | 67 | 0.209 |
| 151 | *Listeria monocytogenes* | Coleslaw | UGA | | 49 | 2.52 | 61 | 0.196 |
| 152 | *Listeria monocytogenes* | LCDC 81-861 | UGA | | 72 | 2.75 | 64 | 0.191 |
| 153 | *Listeria monocytogenes* | Bilmar | UGA | | 28 | 2.77 | 60 | 0.23 |

Example 16

Specificity of *Listeria*-Specific Phage Cocktail

To evaluate the specificity of a phage cocktail (A511-3A, LMA8, LP-ES1, JP1) for *Listeria* spp., an exclusivity panel of 26 Gram-negative and 19 Gram-positive strains was assembled. Representatives of 19 unique genera and 42 species were included. As done with *Listeria* species, overnight stationary phase cultures of each strain were infected with the phage cocktail for 4 h. The results from the exclusivity panel are shown in Tables 12 and 13. A cutoff of 190 RLU, approximately two times background, was chosen to distinguish between positive and negative detection for all inclusivity and exclusivity testing.

TABLE 12

| | Gram Negative | | | A511-3A, LMA8, LPES1, LPJP1 | | | |
|---|---|---|---|---|---|---|---|
| # | Bacterial Strains | Strain | Gram +/− | RLU | OD600 | RLU | OD600 |
| 1 | *Acinetobacter baumannii* | ATCC 19606 | neg | 76 | 8.32 | 133 | 0.19 |
| 2 | *Acinetobacter calcoaceticus* | ATCC 23055 | neg | 174 | 0.762 | 138 | 0.198 |
| 3 | *Citrobacter braakii* | ATCC 51113 | neg | 53 | 5.22 | 97 | 0.209 |
| 4 | *Citrobacter freundii* | ATCC 8090 | neg | 91 | 5.52 | 150 | 0.187 |
| 5 | *Citrobacter koseri* | ATCC 25408 | neg | 118 | 4.31 | 103 | 0.214 |
| 6 | *Cronobacter muytjensii* | ATCC 51329 | neg | 122 | 3.67 | 108 | 0.219 |
| 7 | *Cronobacter sakazakii* | ATCC1 2868 | neg | 102 | 4.02 | 108 | 0.212 |
| 8 | *E. coli* | ATCC 9637 | neg | 76 | 5.22 | 99 | 0.208 |
| 9 | *Edwardsiella tarda* | ATCC 15947 | neg | 44 | 5.31 | 40 | 0.218 |
| 10 | *Enterobacter aerogenes* | ATCC 13048 | neg | 80 | 6.76 | 100 | 0.21 |
| 11 | *Enterobacter cloacae,* subsp *cloacae* | ATCC 13047 | neg | 78 | 7.53 | 77 | 0.209 |
| 12 | *Enterobacter kobei* | ATCC BAA-260 | neg | 91 | 4.18 | 86 | 0.217 |
| 13 | *Escherichia fergusonii* | ATCC 35469 | neg | 48 | 6.19 | 66 | 0.196 |
| 14 | *Escherichia hermanni* | ATCC 33650 | neg | 65 | 6.04 | 107 | 0.21 |
| 15 | *Hafnia alevi* | ATCC 33337 | neg | 66 | 3.45 | 125 | 0.202 |
| 16 | *Klebsiella oxytoca* | ATCC 43165 | neg | 54 | 6.5 | 139 | 0.24 |
| 17 | *Klebsiella pneumonia* | ATCC 4352 | neg | 73 | 5.2 | 129 | 0.223 |
| 18 | *Morganella morganii:* subsp. Maorganii M11 | ATCC 25830 | neg | 25 | 4.09 | 45 | 0.212 |
| 19 | *Pluralibacter gergoviae* | ATCC 33028 | neg | 69 | 5.23 | 119 | 0.234 |
| 20 | *Proteus mirabilis* | ATCC 43071 | neg | 27 | 5.27 | 34 | 0.204 |
| 21 | *Proteus vulgaris* | ATCC 33420 | neg | 28 | 5.1 | 44 | 0.216 |
| 22 | *Pseudomonas aeruginosa;* Strain Boston 41401 | ATCC 27853 | neg | 72 | 5.95 | 102 | 0.189 |
| 23 | *Serratia marcescens* | ATCC 13880 | neg | 36 | 1.094 | 49 | 0.214 |
| 24 | *Shigella flexneri* | ATCC 12022 | neg | 106 | 7.17 | 118 | 0.192 |
| 25 | *Shigella sonnei* | ATCC 9290 | neg | 55 | 7.39 | 124 | 0.218 |
| 26 | *Yersinia enterocolitica* | ATCC 23715 | neg | 122 | 2.92 | 114 | 0.211 |

TABLE 13

| | Gram Positive | | | A511-3A, LMA8, LPES1, JP1 | | | |
|---|---|---|---|---|---|---|---|
| # | Bacterial Strains | Strain | Gram +/− | RLU | OD600 | RLU | OD600 |
| 1 | *Bacillus cereus* | ATCC 14579 | pos | 88 | 6.45 | 133 | 0.196 |
| 2 | *Bacillus cereus* | ATCC 13061 | pos | 130 | 4.64 | 119 | 0.228 |
| 3 | *Bacillus circulans* | ATCC 61 | pos | 88 | 1.2 | 65 | 0.176 |
| 4 | *Bacillus coagulans* | ATCC 7050 | pos | 229 | 0.152 | 229 | 0.152 |
| 5 | *Bacillus licheniformis* | ATCC 9789 | pos | 122 | 2.85 | 128 | 0.211 |
| 6 | *Bacillus megaterium* | ATCC 14581 | pos | 73 | 3.26 | 76 | 0.188 |
| 7 | *Bacillus mycoides* | ATCC 6462 | pos | 65 | 0.469 | 65 | 0.215 |
| 8 | *Bacillus pumilus* | ATCC 700814 | pos | 40 | 4.78 | 67 | 0.216 |
| 9 | *Bacillus subtilis* | ATCC 23857 | pos | 80 | 3.56 | 149 | 0.22 |
| 10 | *Bacillus subtilis* subsp. *subtilis* | ATCC 6051 | pos | 143 | 5.35 | 166 | 0.204 |
| 11 | *Bacillus weihenstephanensis* | ATCC 12826 | pos | 118 | 3.84 | 123 | 0.172 |
| 12 | *Enteroccus faecalis* | ATCC 19433 | pos | 87 | 4.02 | 86 | 0.215 |
| 13 | *Enteroccus faeceum* | ATCC 19434 | pos | 100 | 2.85 | 137 | 0.192 |
| 14 | *Enterococcus faecalis* | ATCC 29212 | pos | 123 | 3.11 | 118 | 0.2 |
| 15 | *Lactobacillus plantarum* | ATCC 14917 | pos | 335 | 3.72 | 25853 | 0.203 |
| 16 | *Lactobacillus rhamnosus* | ATCC 7469 | pos | 112 | 1.91 | 172 | 0.191 |
| 17 | *Staphylococcus aureus* | ATCC 27660 | pos | 75 | 9.18 | 153 | 0.224 |
| 18 | *Staphylococcus epidermidis* | ATCC 14990 | pos | 119 | 8.61 | 133 | 0.232 |
| 19 | *Staphylococcus haemolyticus* | ATCC 29970 | pos | 67 | 9.33 | 154 | 0.24 |

Example 17

Specificity of *Listeria*-Specific Phage Cocktail

The *Listeria* assay was validated for the detection of *Listeria* spp. on glaze ceramic (4"×4" test area) and stainless steel (4"×4" test area) surfaces. The validation consisted of an inclusivity and exclusivity evaluation and a matrix study. The *Listeria* assay was compared to the 2017 U.S. Food and Drug Administration Bacteriological Analytical Manual, Chapter 10 "Detection of *Listeria monocytogenes* in Foods and Environmental samples, and Enumeration of *Listeria monocytogenes* in Foods" using an unpaired study design for ceramic (4"×4" test area) and stainless steel (4"×4" test area) surfaces. Final confirmation was obtained by Bruker MALDI Biotyper following AOAC OMA 2017.09. An alternate confirmation was also performed for all samples. This was performed by allowing the samples to continue enriching for a total of 24-28 hours at 35±1° C. The samples were thoroughly mixed and 100 μL of the sample was struck onto RAPID *L. mono* Agar and allowed to incubate for 24-28 hours at 37±1° C. The inclusivity and exclusivity evaluation evaluated two strains of *Listeria seeligeri*, two strains of *Listeria welshimeri*, one strain of *Enterococcus faecalis*, one strain of *Enterococcus faecium*, and one strain of *Streptococcus pyogenes*.

In the inclusivity study, four out of the four *Listeria* spp. strains evaluated were correctly detected, and all three exclusivity strains were correctly excluded. In the matrix study, the *Listeria* assay demonstrated no significant differences between presumptive and confirmed results or between candidate and reference method results for ceramic (4"×4" test area) and stainless steel (4"×4" test area) surfaces. The *Listeria* assay allowed for fast, reliable detection of *Listeria* on ceramic (4"×4" test area) and stainless steel (4"×4" test area) surfaces with instrument run time taking less than 10 minutes.

No statistical difference was detected between the *Listeria* assay and the reference culture method in the U.S. Food and Drug Administration Bacteriological Analytical Manual Chapter 10 "Detection of *Listeria* monocytogenes in Foods and Environmental samples, and Enumeration of *Listeria* monocytogenes in Foods" (FDA/BAM Chapter 10) for ceramic (4"×4") and stainless steel (4"×4") surfaces (1).

Sample Preparation

Ceramic (4"×4" test area) and stainless steel (4"×4" test area) environmental surfaces were swabbed with an EZ Reach Polyurethane Sponge Sample using firm and even pressure 10 times vertically and horizontally. The swabs were placed back into the sampler bag discarding the plastic handle and stored at room temperature (20-25° C.) for 2 hours. Following the 2 hour storage, the samples were enriched with 20 mL of pre-warmed (35±1° C.) BLEB, massaged by hand for 10-20 seconds, and incubated at 35±1° C. for 20-24 hours.

Sample Infection

Following incubation enriched samples were removed from the incubator and mixed thoroughly by massaging the sponge for 10-20 seconds. Using a single channel pipettor and clean tip for each sample, 150 µL of enriched sample was transferred into a well of the 96-well plate. One tube containing the recombinant phage solution was used for each 8 well strip. The tube was flicked or supun to collect all of the solution at the bottom of the tube. 10 µL of the recombinant phage solution was then added to each sample in the 96-well plate and mixed completely and gently by pipetting up and down. The plate was covered and sealed to prevent evaporation and placed in a 30±1° C. incubator for 4 hours.

Sample Lysis and Signal Reading

The substrate solution was prepared by transferring the entire contents of assay buffer (500 µL) and lysis buffer (150 µL) tubes to the substrate tube (10 µL) and mixing. 65 of freshly prepared lysis/luciferase master mix solution to each sample well and mix thoroughly by pipetting up and down. Once all the samples received the lysis/luciferase substrate master mix solution, the sample plate was placed in the luminometer and read.

Interpretation and Test Result Report

Samples having a reading value of 300 RLU or greater were considered positive for detection of *Listeria*. For a negative *Listeria* result, the reading value was less than 300 RLU.

Confirmation

Confirmation was also performed for all samples. For each surface test portion, the samples were allowed to continue enriching for a total of 24-28 hours at 35±1° C. The samples were thoroughly mixed and 100 µL of the sample was struck onto RAPID *L. mono* Agar and allowed to incubate for 24-28 hours at 37±1° C.

Inclusivity and Exclusivity Data

The inclusivity and exclusivity study evaluated two strains of *Listeria seeligeri*, two strains of *Listeria welshimeri*, one strain of *Enterococcus faecalis*, and one strain of *Enterococcus faecium*, and one strain of *Streptococcus pyogenes*. All cultures evaluated were propagated from a stock culture stored at −70° C. to trypticase soy agar with 5% sheep blood (SBA) and incubated for 24±2 hours at 35±1° C. After incubation of the target organisms, a single colony from SBA was transferred to a 9 mL aliquot of BLEB for 20-24 hours at 35±1° C. After incubation, each *Listeria* spp. strain was then diluted to 100 times the LOD50 of the *Listeria* assay. After incubation of the exclusivity organisms, each strain was transferred to a non-selective media and incubated under conditions for optimal growth. After incubation, each exclusivity organism was analyzed undiluted. All inclusivity and exclusivity strains were blind coded, randomized and analyzed using the *Listeria* assay follow package instructions. Test results were decoded and reported as either positive or negative.

The matrix study consisted of evaluating a total of 30 unpaired sample replicates of ceramic (4"×4") and stainless steel (4"×4") surface test areas. Within each sample set, there were 5 uninoculated samples (0 CFU/test portion), 20 low level inoculated samples (0.2-2 CFU/test portion) targeted to obtain fractional results, and 5 high level inoculated samples (2-10 CFU/test portion). All samples were analyzed by the PhageDx *Listeria* Assay following enrichment with pre-warmed (35±1° C.) BLEB and incubated for 20-24 hours at 35±1° C., analysis was conducted after 20 hours. Regardless of presumptive results, all samples were culturally confirmed by the FDA/BAM Chapter 10 reference method. In addition, all samples were confirmed following the alternative confirmation described previously in "Materials and Methods", subsection "Confirmation". Final confirmation for all samples were obtained by Bruker MALDI Biotyper following AOAC OMA 2017.10.

Organism Preparation and Inoculation

For ceramic surfaces, 4"×4" areas were inoculated with 0.25 mL of diluted *L. innocua* ATCC 43547 culture and sampled using sampling sponges premoistened in letheen broth. For stainless steel surfaces, 4"×4" areas were inoculated with 0.25 mL of diluted *L. monocytogenes* 4a CWD 1554. In addition to the *L. monocytogenes* culture, stainless steel surface was co-inoculated with a competitor organism, *Enterococcus faecalis* ATCC 29212, at 10× the level of the target organism. All cultures utilized were propagated from a stock culture stored at −70° C. to SBA and incubated for 24±2 hours at 35±1° C. After incubation, a single colony from SBA was transferred to a 9 mL aliquot of BHI broth for 20-24 hours at 35±1° C. Each culture was then diluted to the target concentration by performing serial dilutions as 0.1% peptone water as the diluent. For the uninoculated test portions, sterile 0.1% peptone water was applied to the test area. Each surface was dried for 16-24 hours at room temperature (24±2° C.) prior to sampling. To determine the inoculation level for the environmental surfaces, aliquots of each inoculum were plated onto Tryptic Soy agar (TSA) in triplicate.

For environmental samples, sponges were pre-moistened with 10 mL of D/E neutralizing broth. Following addition of D/E neutralizing broth surfaces were swabbed using firm and even pressure 10 times vertically and horizontally. All environmental samples were then stored at 22±2° C. for 2 h±15 minutes. Swabs were enriched with 90 mL of BLEB, massaged by hand for 2 minutes and incubated at 30±1° C. for 4 hours. Following 4 hours of incubation, selective supplements acriflavine (10 mg/L), sodium nalidixate (40 mg/L) and cycloheximide (50 mg/L) were added to each test portion and samples were re-incubated for 24-48 hours.

After 24 hours of total incubation, the enriched samples were streaked to MOX agar plates and incubated at 35±1° C. for 24-48 hours. In addition to MOX, each enriched sample was streaked to the chromogenic selective agar Brilliance *Listeria* Agar (BLA) and incubated at 37±1° C. for 24±2 hours. The enriched samples were re-incubated for an additional 24 hours at 30±1° C. and then streaked to a second MOX and BLA agar plate which was incubated for 24-48 hours at 35±1° C. and 37±1° C. for 24±2 hours, respectively. MOX and BLA agar plates were examined for suspect colonies, and if present, at least 5 colonies were streaked to Tryptic Soy Agar containing 0.6% yeast extract (TSA/YE). The TSA/YE plates were incubated at 35±1° C. for 24-48 hours and then examined for purity. Pure colonies were tested for catalase reactivity and a Gram stain was conducted. A pure *Listeria monocytogenes* colony was transferred to Trypticase Soy Broth containing 0.6% yeast extract (TSB/YE). The TSB/YE cultures were incubated at 25±1° C. overnight, or until the broth was turbid, indicating sufficient growth. Catalase-positive organisms were stabbed into SBA plates and incubated at 35±1° C. for 24-48 hours. The TSB/YE tubes incubated at 25±1° C. were used to prepare a wet mount slide to determine motility pattern. After incubation, the SBA plates were examined for hemolysis. Final confirmation was conducted using Bruker MALDI Biotyper following AOAC OMA 2017.10.

*Listeria* Assay

Ceramic (4"×4" test area) and stainless steel (4"×4" test area) surfaces were enriched and incubated according to the protocol described above. Following incubation, all samples were analyzed using the *Listeria* assay following product instructions. All sample regardless of presumptive results were culturally confirmed by the FDA/BAM Chapter 10 reference method. Final confirmation for all samples was obtained by Bruker MALDI Biotyper following AOAC OMA 2017.09.

For the inclusivity and exclusivity study of the four strains of *Listeria* spp. tested, all seven were correctly included, and for the three exclusivity strains all three were correctly excluded. A summary of the inclusivity exclusivity results are presented in Table 14. For ceramic (4"×4" test area) and stainless steel (4"×4" test area) environmental samples the inoculum recovered for the target *L. innocua* and *L. monocytogenes* stains fell withing the targeted levels, while the competitor organism was at a level at least 10 times higher.

TABLE 14

| Results of the Inclusivity and Exclusivity Study-*Listeria* Assay | | | |
|---|---|---|---|
| No. Organism | Source[a] | Origin | Result |
| 1 *Listeria grayi* | QL 030911.12 | Environmental Sample | Positive |
| 2 *Listeria grayi* serovar *Murrayi* | NCTC 10814 | Not Available | Positive |
| 3 *Listeria seeligeri* | QL 031011.2 | Creamer | Positive |
| 4 *Listeria seeligeri* | QL 031011.5 | Frozen Vegetables | Positive |
| 5 *Listeria seeligeri* | Cornell FSL-S4-035 | Not Available | Positive |
| 6 *Listeria welshimeri* | QL 030911.8 | Beef | Positive |
| 7 *Listeria welshimeri* | UVM LW001 | Not Available | Positive |
| 8 *Enterococcus faecalis* | ATCC 29212 | Urine | Negative |
| 9 *Enterococcus faecium* | ATCC 700221 | Human Feces | Negative |
| 10 *Streptococcus pyogenes* | ATCC 19615 | Pharynx of Child | Negative |

We claim:

1. A recombinant bacteriophage (i) comprising a bacteriophage LPJP1 having a phage genome of at least 200 kbp and (ii) comprising a genetic construct comprising an indicator gene, wherein the recombinant bacteriophage specifically infects *Listeria grayi.*

2. The recombinant bacteriophage of claim 1, wherein the recombinant bacteriophage comprises a wild-type bacteriophage LPJP1.

3. The recombinant bacteriophage of claim 1, wherein the recombinant bacteriophage comprises a mutant bacteriophage LPJP1.

4. The recombinant bacteriophage of claim 1, wherein bacteriophage has one or more mutations in the tail receptor of the bacteriophage genome.

5. The recombinant bacteriophage of claim 1, wherein the indicator gene is codon-optimized and encodes a soluble protein product that generates an intrinsic signal or a soluble enzyme that generates signal upon reaction with a substrate.

6. The recombinant bacteriophage of claim 5, further comprising an untranslated region upstream of the codon-optimized indicator gene, wherein the untranslated region includes a bacteriophage late gene promoter and a ribosomal entry site.

7. A cocktail composition comprising at least one recombinant bacteriophage according to claim 1.

8. The cocktail composition of claim 7, wherein at least one type of recombinant bacteriophage comprises a wild-type bacteriophage LPJP1 or a mutant bacteriophage LPJP1.

9. The cocktail composition of claim 7, wherein the cocktail further comprises at least one recombinant bacteriophage capable of infecting *Listeria innocua.*

10. The cocktail composition of claim 7, wherein the cocktail further comprises at least one recombinant bacteriophage capable of infecting serovar 3A of *Listeria monocytogenes.*

11. The cocktail composition of claim 7, wherein the cocktail comprises at least one recombinant bacteriophage comprising one or more mutations in the tail receptor of the bacteriophage genome.

12. A method of preparing a recombinant indicator bacteriophage comprising:

selecting a wild-type bacteriophage LPJP1 having a phage genome of at least 200 kbp that specifically infects *Listeria grayi;* preparing a homologous recombination plasmid/vector comprising an indicator gene;

transforming the homologous recombination plasmid/vector into target pathogenic bacteria;

infecting the transformed target pathogenic bacteria with the wild-type bacteriophage LPJP1, thereby allowing homologous recombination to occur between the plasmid/vector and the bacteriophage genome; and isolating a particular clone of recombinant bacteriophage comprising the indicator gene.

13. The method of claim 12, wherein preparing a homologous recombination plasmid/vector comprises:

determining the natural nucleotide sequence in the late region of the genome of the wild-type bacteriophage LPJP1;

annotating the genome and identifying the major capsid protein gene of the wild-type bacteriophage LPJP1;

designing a sequence for homologous recombination downstream of the major capsid protein gene, wherein the sequence comprises a codon-optimized indicator gene; and incorporating the sequence designed for homologous recombination into a plasmid/vector.

14. The method of claim 12, wherein isolating a particular clone of recombinant bacteriophage comprises a limiting dilution assay for isolating a clone that demonstrates expression of the indicator gene.

15. A method for detecting *Listeria grayi* in a sample comprising:

incubating the sample with a cocktail composition comprising at least the recombinant bacteriophage according to claim 1 and detecting an indicator protein product produced by the recombinant bacteriophage, wherein positive detection of the indicator protein product indicates that *Listeria grayi* is present in the sample.

16. The method of claim 15, wherein at least one type of recombinant bacteriophage comprises a wild-type bacteriophage LPJP1 or a mutant bacteriophage LPJP1.

17. The method of claim 15, wherein the cocktail comprises at least one recombinant bacteriophage comprising one or more mutations in the tail receptor of the bacteriophage genome.

18. The method of claim 15, wherein the sample is a food, environmental, water, or commercial sample.

19. The method of claim 15, wherein the method detects as few as 10, 9, 8, 7, 6, 5, 4, 3, 2, or a single bacterium in a sample of a standard size for the food safety industry.

20. The method of claim 19, wherein the food sample comprises meat, fish, vegetables, eggs, dairy products, dried food products, or powdered infant formula.

21. The method of claim 15, wherein the sample is first incubated in conditions favoring growth for an enrichment period of less than 24 hours, 23 hours, 22 hours, 21 hours, 20 hours, 19 hours, 18 hours, 17 hours, 16 hours, 15 hours, 14 hours, 13 hours, 12 hours, 11 hours, 10 hours, 9 hours, 8 hours, 7 hours, 6 hours, 5 hours, 4 hours, 3 hours, or 2 hours.

22. The method of claim 15, wherein the total time to results is less than 28 hours, 27 hours, 26 hours, 25 hours, 24 hours, 23 hours, 22 hours, 21 hours, 20 hours, 19 hours, 18 hours, 17 hours, 16 hours, 15 hours, 14 hours, 13 hours, 12 hours, 11 hours, 10 hours, 9 hours 8 hours, 7 hours, 6 hours, 5 hours, 4 hours, 3 hours, or 2 hours.

23. A kit for detecting *Listeria grayi* comprising the recombinant bacteriophage of claim 1.

24. The kit of claim 23 further comprising a substrate for reacting with a soluble protein product or a soluble enzyme encoded by the indicator gene to detect the soluble protein product or the soluble enzyme.

25. A system for detecting *Listeria grayi* comprising the recombinant bacteriophage of claim 1.

* * * * *